(12) United States Patent
Kyle et al.

(10) Patent No.: US 8,680,118 B2
(45) Date of Patent: *Mar. 25, 2014

(54) THERAPEUTIC AGENTS USEFUL FOR TREATING PAIN

(75) Inventors: Donald J. Kyle, Newton, PA (US); Qun Sun, Princeton, NJ (US); Laykea Tafesse, Robinsville, NJ (US)

(73) Assignee: Purdue Pharma L.P., Stamford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/525,950

(22) Filed: Jun. 18, 2012

(65) Prior Publication Data

US 2013/0012541 A1 Jan. 10, 2013

Related U.S. Application Data

(63) Continuation of application No. 12/706,571, filed on Feb. 16, 2010, now Pat. No. 8,227,467, which is a continuation of application No. 10/867,546, filed on Jun. 14, 2004, now Pat. No. 7,683,063.

(60) Provisional application No. 60/477,744, filed on Jun. 12, 2003.

(51) Int. Cl.
*C07D 401/04* (2006.01)
*A61K 31/444* (2006.01)

(52) U.S. Cl.
USPC ............ 514/318; 514/334; 546/194; 546/257

(58) Field of Classification Search
None
See application file for complete search history.

(56) References Cited

U.S. PATENT DOCUMENTS

| | | |
|---|---|---|
| 3,536,809 A | 10/1970 | Applezweig |
| 3,598,123 A | 8/1971 | Zaffaroni |
| 3,845,770 A | 11/1974 | Theeuwes et al. |
| 3,916,899 A | 11/1975 | Theeuwes et al. |
| 4,008,719 A | 2/1977 | Theeuwes et al. |
| 5,039,680 A | 8/1991 | Imperato et al. |
| 5,059,595 A | 10/1991 | Le Grazie |
| 5,073,543 A | 12/1991 | Marshall et al. |
| 5,075,341 A | 12/1991 | Mendelson et al. |
| 5,120,548 A | 6/1992 | McClelland et al. |
| 5,198,459 A | 3/1993 | Imperato et al. |
| 5,232,934 A | 8/1993 | Downs |
| 5,354,556 A | 10/1994 | Sparks et al. |
| 5,399,574 A | 3/1995 | Robertson et al. |
| 5,442,064 A | 8/1995 | Pieper et al. |
| 5,474,996 A | 12/1995 | Caille et al. |
| 5,556,837 A | 9/1996 | Nestler et al. |
| 5,556,838 A | 9/1996 | Mayer et al. |
| 5,574,052 A | 11/1996 | Rose et al. |
| 5,591,767 A | 1/1997 | Mohr et al. |
| 5,639,476 A | 6/1997 | Oshlack et al. |
| 5,674,533 A | 10/1997 | Santus et al. |
| 5,698,155 A | 12/1997 | Grosswald et al. |
| 5,733,566 A | 3/1998 | Lewis |
| 5,762,925 A | 6/1998 | Sagen |
| 6,063,930 A | 5/2000 | Dinsmore et al. |
| 6,136,839 A | 10/2000 | Isakson et al. |
| 6,166,038 A | 12/2000 | Fukami et al. |
| 6,204,284 B1 | 3/2001 | Beer et al. |
| 6,239,267 B1 | 5/2001 | Duckworth et al. |
| 6,335,180 B1 | 1/2002 | Julius et al. |
| 6,406,908 B1 | 6/2002 | McIntyre et al. |
| 6,635,657 B1 | 10/2003 | Beight et al. |
| 6,689,780 B1 | 2/2004 | Beight et al. |
| 6,703,362 B1 | 3/2004 | Alvarez et al. |
| 7,129,235 B2 | 10/2006 | Zheng et al. |
| 7,348,343 B2 | 3/2008 | Zheng et al. |
| 7,572,815 B2 | 8/2009 | Nakagawa et al. |
| 7,683,063 B2 | 3/2010 | Kyle et al. |

(Continued)

FOREIGN PATENT DOCUMENTS

| | | |
|---|---|---|
| JP | 62-089679 A | 4/1987 |
| JP | 2003-142681 | 5/2003 |

(Continued)

OTHER PUBLICATIONS

Office Action mailed Nov. 2, 2011, in U.S. Appl. No. 12/706,571, Kyle et al., filed Feb. 16, 2010.
Notice of Allowance mailed Mar. 7, 2012, in U.S. Appl. No. 12/706,571, Kyle et al., filed Feb. 16, 2010.
Office Action mailed Apr. 30, 2007, in U.S. Appl. No. 10/867,546, Kyle et al., filed Jun. 14, 2004.
Notice of Allowance mailed Jan. 17, 2008, in U.S. Appl. No. 10/867,546, Kyle et al., filed Jun. 14, 2004.

(Continued)

*Primary Examiner* — Zinna Northington Davis
(74) *Attorney, Agent, or Firm* — Sterne, Kessler, Goldstein & Fox P.L.L.C.

(57) ABSTRACT

A compound of formula:

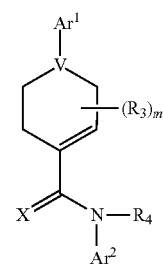

wherein $Ar^1$, $Ar^2$, V, X, $R_3$, $R_4$, and m are as disclosed herein or a pharmaceutically acceptable salt thereof (a "Cyclo(hetero)alkenyl Compound"); compositions comprising an effective amount of a Cyclo(hetero)alkenyl Compound; and methods for treating or preventing, e.g., pain, UI, an ulcer, IBD, or IBS in an animal, comprising administering to an animal in need thereof an effective amount of a Cyclo(hetero)alkenyl Compound are disclosed herein.

82 Claims, No Drawings

(56) References Cited

U.S. PATENT DOCUMENTS

| | | | |
|---|---|---|---|
| 8,168,827 B2 | 5/2012 | Nakagawa et al. | |
| 8,178,560 B2* | 5/2012 | Sun et al. | 514/333 |
| 8,227,467 B2 | 7/2012 | Kyle et al. | |
| 8,349,842 B2* | 1/2013 | Sun et al. | 514/255.05 |
| 8,389,549 B2* | 3/2013 | Tafesse | 514/340 |
| 2002/0091116 A1 | 7/2002 | Zhu et al. | |
| 2003/0087917 A1 | 5/2003 | Strack et al. | |
| 2004/0044003 A1 | 3/2004 | Kyle et al. | |
| 2004/0077628 A1 | 4/2004 | Ishihara et al. | |
| 2004/0152690 A1 | 8/2004 | Balan et al. | |
| 2004/0259931 A1 | 12/2004 | Goodfellow et al. | |
| 2005/0009841 A1 | 1/2005 | Zheng et al. | |
| 2006/0128717 A1 | 6/2006 | Sun et al. | |
| 2008/0153809 A1 | 6/2008 | Lee et al. | |
| 2009/0258900 A1 | 10/2009 | Nakagawa et al. | |

FOREIGN PATENT DOCUMENTS

| | | |
|---|---|---|
| JP | 2003-192673 A | 7/2003 |
| WO | WO 02/02549 A1 | 1/2002 |
| WO | WO 03/068749 A1 | 8/2003 |
| WO | WO 2004/089286 A2 | 10/2004 |
| WO | WO 2004/103954 A1 | 12/2004 |

OTHER PUBLICATIONS

Office Action mailed Dec. 8, 2008, in U.S. Appl. No. 10/867,546, Kyle et al., filed Jun. 14, 2004.

Notice of Allowance mailed Oct. 1, 2009, in U.S. Appl. No. 10/867,546, Kyle et al., filed Jun. 14, 2004.

English language abstract of Japanese Patent Application No. JP 2003-192673 A, European Patent Office, (2003).

Badham, N.F., et al., "A Practical Synthesis of the PDE4 Inhibitor, SB-207499, from a Cyclohexanone Precursor," *Org. Proc. Res. Dev.* 7(1): 101-8, American Chemical Society, United States (2003).

Barthó, L., et al., "Involvement of capsaicin-sensitive neurones in hyperalgesia and enhanced opioid antinociception in inflammation," *Naunyn Schmiedeberg's Arch Pharmacol.* 342(6): 666-70, Springer Verlag, Germany (Dec. 1990).

Buchwald, C., et al., "Observer variations in the evaluation of facial nerve function after acoustic neuroma surgery," *J. Laryngol. Otol.* 107(12): 1119-21, Cambridge University Press, England (Dec. 1993).

Chiamulera, C., et al., "Reinforcing and locomotor stimulant effects of cocaine are absent in mGluR5 null mutant mice," *Nat. Neurosci.* 4(9): 873-84, Nature Publishing Group, United States (Sep. 2001).

Cooke, R.D., "Glycopyrrolate in bladder dysfunction," *S. Afr. Med J.* 63(1): 3, South African Medical Association, South Africa (Jan. 1983).

Cope, A.C., et al., "Cyclic Polyolefins. VII. Structure of the Eight-membered Cyclic Dimer of Chloroprene," *J. Am. Chem. Soc.* 72(7): 3056-62, American Chemical Society, United States (Jul. 1950).

Cope, A.C. and Brown, M., "Proximity Effects. XV. The Reaction of Phenylmagnesium Bromide with Methyl Cyclooctene-1-carboxylate," *J. Am. Chem. Soc.* 80(11): 2859-64, American Chemical Society, United States (Jun. 1958).

D' Amour, F.E. and Smith, D.L., "A Method for Determining Loss of Pain Sensation," *J. Pharmacol. Exp. Ther.* 72(1): 74-79, American Society for Pharmacology and Experimental Therapeutics, United States (May 1941).

Di Marzo, V., et al. "Endovanilloid signaling in pain," *Curr. Opin. Neurobiol.* 12(4): 372-89, Current Biology, England (Aug. 2002).

Dogrul, A., et al., "Peripheral and spinal antihyperalgesic activity of SIB-1757, a metabotropic glutamate receptor (mGLUR$_5$) antagonist, in experimental neuropathic pain in rats," *Neurosci. Lett.* 292(2): 115-28, Elsevier Scientific Publishers Ireland, Ireland (Oct. 2000).

During, M.J., et al., "Controlled release of dopamine from a polymeric brain implant: in vivo characterization," *Ann. Neurol.* 25(4): 351-6, American Neurological Association, United States (Apr. 1989).

Foley, K.M., "Pain", in *Cecil Textbook of Medicine*, 20th Edition, pp. 100-107, Plum, F., Bennett, J.C. and Cecil, R.L. (eds.), W.B. Saunders Company, United States (1996).

Fundytus, M.E., et al., "Knockdown of spinal metabotropic glutamate receptor 1 (mGluR(1)) alleviates pain and restores opioid efficacy after nerve injury in rats," *Br. J. Pharmacol.* 132(1): 354-67, Nature Publishing Group, England (Jan. 2001).

Fundytus, M.E., et al., "In vivo antinociceptive activity of anti-rat mGluR$_1$ and mGluR$_5$ antibodies in rats," *Neuroreport.* 9(4): 731-35, Rapid Science Publishers, England (Mar. 1998).

Fundytus, M.E., et al., "Antisense oligonucleotide knockdown of mGluR1 alleviates hyperalgesia and allodynia associated with chronic inflammation," *Pharmacol. Biochem. Behav.* 73(2): 401-10, Elsevier Science Inc., United States (Sep. 2002).

Fundytus, M.E., "Glutamate receptors and nociception: implications for the drug treatment of pain," *CNS Drugs* 15(1): 29-58, Adis International Limited, New Zealand (Jan. 2001).

Brunton, L.L., "Agents for Control of Gastric Acidity and Treatment of Peptic Ulcers," in *Goodman and Gilman's The Pharmacological Basis of Therapeutics*, 9th Edition, pp. 901-915, Hardman, J.G., Limbird, L.E., Milinoff, P.B., Ruddon,R.W., and Gilman, A.G. (Eds.), New York: McGraw-Hill, United States (1996).

Goodson, J.M., "Dental Applications," in *Medical Applications of Controlled Release*, vol. 2, Chapter 6, pp. 115-138, Langer, R.S. and Wise, D.L. (Eds.), CRC Press, Boca Raton, Florida, United States (1984).

Grupp, I.L., et al., "Protection against hypoxia-reoxygenation in the absence of poly(ADP-ribose) synthetase in isolated working hearts," *J. Mol. Cell Cardiol.* 31(1): 297-303, *Academic Press*, England (Jan. 1999).

Hanson, G.R., "Analgesic, Antipyretic and Anti-Inflammatory Drugs" in *Remington:The Science and Practice of Pharmacy vol. II*, 19th Edition, pp. 1196-1221, Gennaro, A.R. (Ed.), Mack Pub. Co., Easton, Pensylvania, United States (1995).

Hargreaves, K., et al., "A new and sensitive method for measuring thermal nociception in cutaneous hyperalgesia," *Pain* 32(1): 77-88, Elsevier/North-Holland, Netherlands (Jan. 1988).

Howard, M.A. III, et al., "Intracerebral drug delivery in rats with lesion-induced memory deficits," *J. Neurosurg.* 71(1): 105-12, American Association of Neurological Surgeons, United States (Jul. 1989).

Insel, P.A., "Analgesic-Antipyretic and Anti-inflammatory Agents and Drugs Employed in the Treatment of Gout", in *Goodman & Gilman's The Pharmacological Basis of Therapeutics, 9th Edition*, pp. 617-657, Hardman, J.G., Limbird, L.E., Molinoff, P.B., Ruddon, R.W., and Gilman, A.G. (Eds.), New York: McGraw-Hill, United States (1996).

Wright. M.E. and Pulley S.R., "Vinyl triflates: a mechanistic study on their formation from carbonyl compounds and triflic anhydride," *J. Org. Chem.* 54(12): 2886-89, American Chemical Society, United States (Jun. 1989).

Wong, L.T.L., et al., "New Synthesis of Nitroxyl Radicals of the Piperidine and Tetrahydropyridine Series," *Can. J. Chem.* 52(19): 3381-83, NRC Canada, Canada (1974).

Kaiho, T., et al., "Cardiotonic agents. 1-Methyl-7-(4-pyridyl)-5,6,7,8-tetrahydro-3 (2H)-isoquinolinones and related compounds. Synthesis and activity," *J. Med. Chem.* 32(2): 251-7, American Chemical Society, United States (Feb. 1989).

Kim, S.H. and Chung, J.M., "An experimental model for peripheral neuropathy produced by segmental spinal nerve ligation in the rat," *Pain* 50(3): 355-63, Elsevier North-Holland, Netherlands (Sep. 1992).

Langer, R., "New methods for drug delivery," *Science* 249(4976): 1527-33, American Association for the Advancement of Science, United States (Sep. 1990).

Levin, R.M. and Wein, A.J., "Direct measurement of the anticholingeric activity of a series of pharmacological compounds on the canine and rabbit urinary bladder," *J. Urol.* 128(2): 396-8, The Williams & Wilkins Co., United States (Aug. 1982).

Levy, R.J., et al., "Inhibition of calcification of bioprosthetic heart valves by local controlled-release diphosphonate," *Science* 228(4696): 190-2, American Association for the Advancement of Science, United States (Apr. 1985).

(56) References Cited

OTHER PUBLICATIONS

Masu, M., et al., "Sequence and expression of a metabotropic glutamate receptor," *Nature* 349(6312): 760-5, Nature Publishing Group, England (Feb. 1991).

Miller, S., et al., "Growth factor upregulation of a phosphoinositide-coupled metabotropic glutamate receptor in cortical astrocytes," *J. Neurosci.* 15(9): 6103-9, Society for Neuroscience, United States (Sep. 1995).

Mirakhur, R.K. and Dundee, J.W., "Glycopyrrolate: pharmacology and clinical use," *Anaesthesia* 38(12): 1195-204, The Association of Anaesthetists of Great Britain and Ireland, England (Dec. 1983).

Scott, W.J., et al., "Palladium-Catalyzed Coupling of Vinyl Triflates with Organostannanes: 4-tert-Butyl-1-Vinylcyclohexene and 1-(4-tert-Butylcyclohexen-1-YL)-2-Propen-1-One," *Organic Syntheses* 68: 116-29 (Collective vol. 8, p. 97 (1993)), Wiley, United States (1980).

Ossowska, K., et al., "Blockade of the metabotropic glutamate receptor subtype 5 (mGluR5) produces antiparkinsonian-like effects in rats," *Neuropharmacology* 41(4): 413-20, Elsevier Science Ltd., England (Sep. 2001).

Langer, R. and Peppas, N., "Chemical and Physical Structure of Polymers as Carriers for Controlled Release of Bioactive Agents: A Review," *Macromol. Sci. Rev. Macromol. Chem.* 23(1): 61-126, Marcel Dekker, Inc., United States (1983).

Radebaugh, G.W and Ravin, L.J., "Preformulation", in *Remington:The Science and Practice of Pharmacy*, 19th Edition, pp. 1447-1676, Gennaro, A.R. (Ed.), Mack Pub. Co., Easton Pensylvania, United States (1995).

Saudek, C.D., et al., "A preliminary trial of the programmable implantable medication system for insulin delivery," *N. Engl. J. Med.* 321(9): 574-9, Massachusetts Medical Society, United States (Aug. 1989).

Sefton, M.V., "Implantable pumps," *Crit. Rev. Biomed. Eng.* 14(3): 201-40, Begell House, United States (1987).

Stein, C., et al., "Unilateral inflammation of the hindpaw in rats as a model of prolonged noxious stimulation: Alterations in behavior and nociceptive thresholds," *Pharmcol. Biochem. Behavior* 31(2): 445-51, Pergamon Press PLC, United States (Oct. 1988).

Tatarczyńska, E., et al., "Potential anxiolytic- and antidepressant-like effects of MPEP, a potent, selective and systemically active mGlu5 receptor antagonist," *Br. J. Pharmacol.* 132(7): 1423-30, Nature Publishing Group, England (Apr. 2001).

Meyers, A.I., et al., "The synthesis of chiral α,β-unsaturated and aryl oxazolines from ketones and arols via their triflates and pd-catalyzed CO and amino alcohol coupling," *Tetrahedron Letters* 33(9): 1181-84, Pergamon Press PLC, England (Feb. 1992).

Berkow, R. et al. (Eds), "Seizure Disorder," *The Merck Manual of Medical Information*, Home Edition, pp. 345-350, Merck Research Laboratories, Whitehouse Station, N.J., United States (1997).

Berkow, R. et al. (Eds), "Stroke," *The Merck Manual of Medical Information*, Home Edition, pp. 352-355, Merck Research Laboratories, Whitehouse Station, N.J., United States (1997).

Berkow, R. et al. (Eds), "Peptic Ulcer," *The Merck Manual of Medical Information*, Home Edition, pp. 496-500, Merck Research Laboratories, Whitehouse Station, N.J., United States (1997).

Berkow, R. et al. (Eds), "Irritable Bowel Syndrome," *The Merck Manual of Medical Information*, Home Edition, pp. 525-526, Merck Research Laboratories, Whitehouse Station, N.J., United States (1997).

Berkow, R. et al. (Eds), "Crohn's Disease," *The Merck Manual of Medical Information*, Home Edition, pp. 528-530, Merck Research Laboratories, Whitehouse Station, N.J., United States (1997).

Berkow, R. et al. (Eds), "Ulcerative Colitis," *The Merck Manual of Medical Information*, Home Edition, pp. 530-532, Merck Research Laboratories, Whitehouse Station, N.J., United States (1997).

Berkow, R. et al. (Eds), "Urinary Incontinence," *The Merck Manual of Medical Information*, Home Edition, pp. 631-634, Merck Research Laboratories, Whitehouse Station, N.J., United States (1997).

Treat, J., et al., "Liposome Encapsulated Doxorubicin: Preliminary Results of Phase I and Phase II Trials," in *Liposomes in the Therapy of infectious Disease and Cancer: Proceedings of a Ciba-Geigy-Squibb-UCLA Colloquium*, Held at Lake Tahoe, California, Feb. 16-20, 1988, pp. 317-327 and 353-365, by Lopez-Berestein, G. et al., Alan R. Liss, Inc., United States (Jan. 1989).

Treit, D., "Animal models for the study of anti-anxiety agents: a review," *Neurosci. Biobehav. Rev.* 9(2): 203-22, Ankho International Inc., United States (1985).

Walker, K, et al., "Metabotropic glutamate receptor subtype 5 (mGlu5) and nociceptive function. I. Selective blockade of mGlu5 receptors in models of acute, persistent and chronic pain," *Neuropharmacology* 40(1): 1-9, Elsevier Science Ltd., England (2001).

Weinm A.J., "Pharmacology of incontinence," *Urol. Clin. North. Am.* 22(3): 557-77, Saunders, United States (Aug. 1995).

Spooren, W.P., et al., "Novel allosteric antagonists shed light on mglu$_5$ receptors and CNS disorders," *Trends. Pharmacol. Sci.* 22(7): 331-7, Elsevier Science Ltd., England (Jul. 2001).

English language translation of Japanese Patent Publication No. JP 62-089679 A, Patent Bureau of Japan, Official Gazette of Unexamined Patents, (1987).

English language translation of Japenese Patent Application No. JP 2003-142681, Japanese Patent Office, (2003).

English language translation of International Patent Publication No. WO 2004/103954 A1, International Bureau of World Intellectual Property Organization, (2004).

\* cited by examiner

THERAPEUTIC AGENTS USEFUL FOR TREATING PAIN

This application is a continuation of Ser. No. 12/706,571 filed Feb. 16, 2010, now U.S. Pat. No. 8,227,467, which is a continuation of Ser. No. 10/867,546 filed Jun. 14, 2004, now U.S. Pat. No. 7,683,063, which claims the benefit of U.S. Provisional application No. 60/477,744, filed Jun. 12, 2003, the disclosure of which is incorporated by reference herein in its entirety.

REFERENCE TO SEQUENCE LISTING SUBMITTED ELECTRONICALLY

The content of the electronically submitted Sequence Listing (Name: 1861_2160004_SequenceListing_ascii.txt; Size: 790 bytes; and Date of Creation: Aug. 28, 2012) filed herewith is incorporated herein by reference in its entirety.

1. FIELD OF THE INVENTION

The present invention relates to Cyclo(hetero)alkenyl Compounds, compositions comprising an effective amount of a Cyclo(hetero)alkenyl Compound and methods for treating or preventing a condition such as pain comprising administering to an animal in need thereof an effective amount of a Cyclo(hetero)alkenyl Compound.

2. BACKGROUND OF THE INVENTION

Pain is the most common symptom for which patients seek medical advice and treatment. Pain can be acute or chronic. While acute pain is usually self-limited, chronic pain persists for 3 months or longer and can lead to significant changes in a patient's personality, lifestyle, functional ability and overall quality of life (K. M. Foley, Pain, in *Cecil Textbook of Medicine* 100-107 (J. C. Bennett and F. Plum eds., 20th ed. 1996)).

Moreover, chronic pain can be classified as either nociceptive or neuropathic. Nociceptive pain includes tissue injury-induced pain and inflammatory pain such as that associated with arthritis. Neuropathic pain is caused by damage to the peripheral or central nervous system and is maintained by aberrant somatosensory processing. There is a large body of evidence relating activity at both Group I metabotropic glutamate receptors (mGluR1 and mGluR5) (M. E. Fundytus, *CNS Drugs* 15:29-58 (2001)) and vanilloid receptors (VR1) (V. Di Marzo et al., *Current Opinion in Neurobiology* 12:372-379 (2002)) to pain processing. Inhibiting mGluR1 or mGluR5 reduces pain, as shown by in vivo treatment with antibodies selective for either mGluR1 or mGluR5, where neuropathic pain in rats was attenuated (M. E. Fundytus et al., *NeuroReport* 9:731-735 (1998)). It has also been shown that antisense oligonucleotide knockdown of mGluR1 alleviates both neuropathic and inflammatory pain (M. E. Fundytus et al., *Brit. J. Pharmacol.* 132:354-367 (2001); M. E. Fundytus et al., *Pharmacol., Biochem. & Behavior* 73:401-410 (2002)). Small molecule antagonists for mGluR5-attenuated pain in in vivo animal models are disclosed in, e.g., K. Walker et al., *Neuropharmacol.* 40:1-9 (2000) and A. Dogrul et al., *Neurosci. Let.* 292:115-118 (2000)).

Nociceptive pain has been traditionally managed by administering non-opioid analgesics, such as acetylsalicylic acid, choline magnesium trisalicylate, acetaminophen, ibuprofen, fenoprofen, diflusinal, and naproxen; or opioid analgesics, including morphine, hydromorphone, methadone, levorphanol, fentanyl, oxycodone, and oxymorphone. Id. In addition to the above-listed treatments, neuropathic pain, which can be difficult to treat, has also been treated with anti-epileptics (e.g., gabapentin, carbamazepine, valproic acid, topiramate, phenyloin), NMDA antagonists (e.g., ketamine, dextromethorphan), topical lidocaine (for post-herpetic neuralgia), and tricyclic antidepressants (e.g., fluoxetine, sertraline and amitriptyline).

UI is uncontrollable urination, generally caused by bladder-detrusor-muscle instability. UI affects people of all ages and levels of physical health, both in health care settings and in the community at large. Physiologic bladder contraction results in large part from acetylcholine-induced stimulation of post-ganglionic muscarinic-receptor sites on bladder smooth muscle. Treatments for UI include the administration of drugs having bladder-relaxant properties, which help to control bladder-detrusor-muscle overactivity. For example, anticholinergics such as propantheline bromide and glycopyrrolate, and combinations of smooth-muscle relaxants such as a combination of racemic oxybutynin and dicyclomine or an anticholinergic, have been used to treat UI (See, e.g., A. J. Wein, *Urol. Clin. N. Am.* 22:557-577 (1995); Levin et al., *J. Urol.* 128:396-398 (1982); Cooke et al., *S. Afr. Med. J.* 63:3 (1983); R. K. Mirakhur et al., *Anaesthesia* 38:1195-1204 (1983)). These drugs are not effective, however, in all patients having uninhibited bladder contractions.

None of the existing commercial drug treatments for UI has achieved complete success in all classes of UI patients, nor has treatment occurred without significant adverse side effects. For example, drowsiness, dry mouth, constipation, blurred vision, headaches, tachycardia, and cardiac arrhythmia, which are related to the anticholinergic activity of traditional anti-UI drugs, can occur frequently and adversely affect patient compliance. Yet despite the prevalence of unwanted anticholinergic effects in many patients, anticholinergic drugs are currently prescribed for patients having UI. *The Merck Manual of Medical Information* 631-634 (R. Berkow ed., 1997).

Ulcers are sores occurring where the lining of the digestive tract has been eroded by stomach acids or digestive juices. The sores are typically well-defined round or oval lesions primarily occurring in the stomach and duodenum. About 1 in 10 people develop an ulcer. Ulcers develop as a result of an imbalance between acid-secretory factors, also known as "aggressive factors," such as stomach acid, pepsin, and *Helicobacter pylori* infection, and local mucosal-protective factors, such as secretion of bicarbonate, mucus, and prostaglandins.

Treatment of ulcers typically involves reducing or inhibiting the aggressive factors. For example, antacids such as aluminum hydroxide, magnesium hydroxide, sodium bicarbonate, and calcium bicarbonate can be used to neutralize stomach acids. Antacids, however, can cause alkalosis, leading to nausea, headache, and weakness. Antacids can also interfere with the absorption of other drugs into the blood stream and cause diarrhea.

$H_2$ antagonists, such as cimetidine, ranitidine, famotidine, and nizatidine, are also used to treat ulcers. $H_2$ antagonists promote ulcer healing by reducing gastric acid and digestive-enzyme secretion elicited by histamine and other $H_2$ agonists in the stomach and duodenum. $H_2$ antagonists, however, can cause breast enlargement and impotence in men, mental changes (especially in the elderly), headache, dizziness, nausea, myalgia, diarrhea, rash, and fever.

$H^+$, $K^+$-ATPase inhibitors such as omeprazole and lansoprazole are also used to treat ulcers. $H^+$, $K^+$-ATPase inhibitors inhibit the production of enzymes used by the stomach to secrete acid. Side effects associated with $H^+$, $K^+$-ATPase inhibitors include nausea, diarrhea, abdominal colic, headache, dizziness, somnolence, skin rashes, and transient elevations of plasma activities of aminotransferases.

Sucraflate is also used to treat ulcers. Sucraflate adheres to epithelial cells and is believed to form a protective coating at the base of an ulcer to promote healing. Sucraflate, however, can cause constipation, dry mouth, and interfere with the absorption of other drugs.

Antibiotics are used when *Helicobacter pylori* is the underlying cause of the ulcer. Often antibiotic therapy is coupled with the administration of bismuth compounds such as bismuth subsalicylate and colloidal bismuth citrate. The bismuth compounds are believed to enhance secretion of mucous and $HCO_3^-$, inhibit pepsin activity, and act as an antibacterial against *H. pylori*. Ingestion of bismuth compounds, however, can lead to elevated plasma concentrations of $Bi^{+3}$ and can interfere with the absorption of other drugs.

Prostaglandin analogues, such as misoprostal, inhibit secretion of acid and stimulate the secretion of mucous and bicarbonate and are also used to treat ulcers, especially ulcers in patients who require nonsteroidal anti-inflammatory drugs. Effective oral doses of prostaglandin analogues, however, can cause diarrhea and abdominal cramping. In addition, some prostaglandin analogues are abortifacients.

Carbenoxolone, a mineral corticoid, can also be used to treat ulcers. Carbenoxolone appears to alter the composition and quantity of mucous, thereby enhancing the mucosal barrier. Carbenoxolone, however, can lead to $Na^+$ and fluid retention, hypertension, hypokalemia, and impaired glucose tolerance.

Muscarinic cholinergic antagonists such as pirenzapine and telenzapine can also be used to reduce acid secretion and treat ulcers. Side effects of muscarinic cholinergic antagonists include dry mouth, blurred vision, and constipation. *The Merck Manual of Medical Information* 496-500 (R. Berkow ed., 1997) and *Goodman and Gilman's The Pharmacological Basis of Therapeutics* 901-915 (J. Hardman and L. Limbird eds., 9$^{th}$ ed. 1996).

Inflammatory-bowel disease ("IBD") is a chronic disorder in which the bowel becomes inflamed, often causing recurring abdominal cramps and diarrhea. The two types of IBD are Crohn's disease and ulcerative colitis.

Crohn's disease, which can include regional enteritis, granulomatous ileitis, and ileocolitis, is a chronic inflammation of the intestinal wall. Crohn's disease occurs equally in both sexes and is more common in Jews of eastern-European ancestry. Most cases of Crohn's disease begin before age 30 and the majority start between the ages of 14 and 24. The disease typically affects the full thickness of the intestinal wall. Generally the disease affects the lowest portion of the small intestine (ileum) and the large intestine, but can occur in any part of the digestive tract.

Early symptoms of Crohn's disease are chronic diarrhea, crampy abdominal pain, fever, loss of appetite, and weight loss. Complications associated with Crohn's disease include the development of intestinal obstructions, abnormal connecting channels (fistulas), and abscesses. The risk of cancer of the large intestine is increased in people who have Crohn's disease. Often Crohn's disease is associated with other disorders such as gallstones, inadequate absorption of nutrients, amyloidosis, arthritis, episcleritis, aphthous stomatitis, erythema nodosum, pyoderma gangrenosum, ankylosing spondylitis, sacroilitis, uveitis, and primary sclerosing cholangitis. There is no known cure for Crohn's disease.

Cramps and diarrhea, side effects associated with Crohn's disease, can be relieved by anticholinergic drugs, diphenoxylate, loperamide, deodorized opium tincture, or codeine. Generally, the drug is taken orally before a meal.

Broad-spectrum antibiotics are often administered to treat the symptoms of Crohn's disease. The antibiotic metronidazole is often administered when the disease affects the large intestine or causes abscesses and fistulas around the anus. Long-term use of metronidazole, however, can damage nerves, resulting in pins-and-needles sensations in the arms and legs. Sulfasalazine and chemically related drugs can suppress mild inflammation, especially in the large intestine. These drugs, however, are less effective in sudden, severe flare-ups. Corticosteroids, such as prednisone, reduce fever and diarrhea and relieve abdominal pain and tenderness. Long-term corticosteroid therapy, however, invariably results in serious side effects such as high blood-sugar levels, increased risk of infection, osteoporosis, water retention, and fragility of the skin. Drugs such as azathioprine and mercaptourine can compromise the immune system and are often effective for Crohn's disease in patients that do not respond to other drugs. These drugs, however, usually need 3 to 6 months before they produce benefits and can cause serious side effects such as allergy, pancreatitis, and low white-blood-cell count.

When Crohn's disease causes the intestine to be obstructed or when abscesses or fistulas do not heal, surgery can be necessary to remove diseased sections of the intestine. Surgery, however, does not cure the disease, and inflammation tends to recur where the intestine is rejoined. In almost half of the cases a second operation is needed. *The Merck Manual of Medical Information* 528-530 (R. Berkow ed., 1997).

Ulcerative colitis is a chronic disease in which the large intestine becomes inflamed and ulcerated, leading to episodes of bloody diarrhea, abdominal cramps, and fever. Ulcerative colitis usually begins between ages 15 and 30; however, a small group of people have their first attack between ages 50 and 70. Unlike Crohn's disease, ulcerative colitis never affects the small intestine and does not affect the full thickness of the intestine. The disease usually begins in the rectum and the sigmoid colon and eventually spreads partially or completely throughout the large intestine. The cause of ulcerative colitis is unknown.

Treatment of ulcerative colitis is directed to controlling inflammation, reducing symptoms, and replacing lost fluids and nutrients. Anticholinergic drugs and low doses of diphenoxylate or loperamide are administered for treating mild diarrhea. For more intense diarrhea higher doses of diphenoxylate or loperamide, or deodorized opium tincture or codeine are administered. Sulfasalazine, olsalazine, prednisone, or mesalamine can be used to reduce inflammation. Azathioprine and mercaptopurine have been used to maintain remissions in ulcerative-colitis patients who would otherwise need long-term corticosteroid treatment. In severe cases of ulcerative colitis the patient is hospitalized and given corticosteroids intravenously. People with severe rectal bleeding can require transfusions and intravenous fluids. If toxic colitis develops and treatments fail, surgery to remove the large intestine can be necessary. Non-emergency surgery can be performed if cancer is diagnosed, precancerous lesions are detected, or unremitting chronic disease would otherwise make the person an invalid or dependent on high doses of corticosteroids. Complete removal of the large intestine and rectum permanently cures ulcerative colitis. *The Merck Manual of Medical Information* 530-532 (R. Berkow ed., 1997) and *Goodman and Gilman's The Pharmacological Basis of Therapeutics* (J. Hardman and L. Limbird eds., 9$^{th}$ ed. 1996).

Irritable-bowel syndrome ("IBS") is a disorder of motility of the entire gastrointestinal tract, causing abdominal pain, constipation, and/or diarrhea. IBS affects three-times more women than men. In IBS stimuli such as stress, diet, drugs, hormones, or irritants can cause the gastrointestinal tract to contract abnormally. During an episode of IBS, contractions of the gastrointestinal tract become stronger and more frequent, resulting in the rapid transit of food and feces through the small intestine, often leading to diarrhea. Cramps result from the strong contractions of the large intestine and increased sensitivity of pain receptors in the large intestine.

There are two major types of IBS. The first type, spastic-colon type, is commonly triggered by eating, and usually produces periodic constipation and diarrhea with pain. Mucous often appears in the stool. The pain can come in bouts of continuous dull aching pain or cramps, usually in the lower abdomen. The person suffering from spastic-colon type IBS can also experience bloating, gas, nausea, headache, fatigue, depression, anxiety, and difficulty concentrating. The second type of IBS usually produces painless diarrhea or constipation. The diarrhea can begin suddenly and with extreme urgency. Often the diarrhea occurs soon after a meal and can sometimes occur immediately upon awakening.

Treatment of IBS typically involves modification of an IBS-patient's diet. Often it is recommended that an IBS patient avoid beans, cabbage, sorbitol, and fructose. A low-fat, high-fiber diet can also help some IBS patients. Regular physical activity can also help keep the gastrointestinal tract functioning properly. Drugs such as propantheline that slow the function of the gastrointestinal tract are generally not effective for treating IBS. Antidiarrheal drugs, such as diphenoxylate and loperamide, help with diarrhea. *The Merck Manual of Medical Information* 525-526 (R. Berkow ed., 1997).

Certain pharmaceutical agents have been administered for treating addiction. U.S. Pat. No. 5,556,838 to Mayer et al. discloses the use of nontoxic NMDA-blocking agents co-administered with an addictive substance to prevent the development of tolerance or withdrawal symptoms. U.S. Pat. No. 5,574,052 to Rose et al. discloses co-administration of an addictive substance with an antagonist to partially block the pharmacological effects of the addictive substance. U.S. Pat. No. 5,075,341 to Mendelson et al. discloses the use of a mixed opiate agonist/antagonist to treat cocaine and opiate addiction. U.S. Pat. No. 5,232,934 to Downs discloses administration of 3-phenoxypyridine to treat addiction. U.S. Pat. Nos. 5,039,680 and 5,198,459 to Imperato et al. disclose using a serotonin antagonist to treat chemical addiction. U.S. Pat. No. 5,556,837 to Nestler et. al. discloses infusing BDNF or NT-4 growth factors to inhibit or reverse neurological adaptive changes that correlate with behavioral changes in an addicted individual. U.S. Pat. No. 5,762,925 to Sagan discloses implanting encapsulated adrenal medullary cells into an animal's central nervous system to inhibit the development of opioid tolerance. U.S. Pat. No. 6,204,284 to Beer et al. discloses racemic (±)-1-(3,4-dichlorophenyl)-3-azabicyclo[3.1.0]hexane for use in the prevention or relief of a withdrawal syndrome resulting from addiction to drugs and for the treatment of chemical dependencies.

Without treatment, Parkinson's disease progresses to a rigid akinetic state in which patients are incapable of caring for themselves. Death frequently results from complications of immobility, including aspiration pneumonia or pulmonary embolism. Drugs commonly used for the treatment of Parkinson's disease include carbidopa/levodopa, pergolide, bromocriptine, selegiline, amantadine, and trihexyphenidyl hydrochloride. There remains, however, a need for drugs useful for the treatment of Parkinson's disease and having an improved therapeutic profile.

Currently, benzodiazepines are the most commonly used anti-anxiety agents for generalized anxiety disorder. Benzodiazepines, however, carry the risk of producing impairment of cognition and skilled motor functions, particularly in the elderly, which can result in confusion, delerium, and falls with fractures. Sedatives are also commonly prescribed for treating anxiety. The azapirones, such as buspirone, are also used to treat moderate anxiety. The azapirones, however, are less useful for treating severe anxiety accompanied with panic attacks.

Examples of drugs for treating a seizure and epilepsy include carbamazepine, ethosuximide, gabapentin, lamotrigine, phenobarbital, phenyloin, primidone, valproic acid, trimethadione, benzodiazepines, γ-vinyl GABA, acetazolamide, and felbamate. Anti-seizure drugs, however, can have side effects such as drowsiness; hyperactivity; hallucinations; inability to concentrate; central and peripheral nervous system toxicity, such as nystagmus, ataxia, diplopia, and vertigo; gingival hyperplasia; gastrointestinal disturbances such as nausea, vomiting, epigastric pain, and anorexia; endocrine effects such as inhibition of antidiuretic hormone, hyperglycemia, glycosuria, osteomalacia; and hypersensitivity such as scarlatiniform rash, morbilliform rash, Stevens-Johnson syndrome, systemic lupus erythematosus, and hepatic necrosis; and hematological reactions such as red-cell aplasia, agranulocytosis, thrombocytopenia, aplastic anemia, and megaloblastic anemia. *The Merck Manual of Medical Information* 345-350 (R. Berkow ed., 1997).

Symptoms of strokes vary depending on what part of the brain is affected. Symptoms include loss or abnormal sensations in an arm or leg or one side of the body, weakness or paralysis of an arm or leg or one side of the body, partial loss of vison or hearing, double vision, dizziness, slurred speech, difficulty in thinking of the appropriate word or saying it, inability to recognize parts of the body, unusual movements, loss of bladder control, imbalance, and falling, and fainting. The symptoms can be permanent and can be associated with coma or stupor. Examples of drugs for treating strokes include anticoagulants such as heparin, drugs that break up clots such as streptokinase or tissue plasminogen activator, and drugs that reduce swelling such as mannitol or corticosteroids. *The Merck Manual of Medical Information* 352-355 (R. Berkow ed., 1997).

Pruritus is an unpleasant sensation that prompts scratching. Conventionally, pruritus is treated by phototherapy with ultraviolet B or PUVA or with therapeutic agents such as naltrexone, nalmefene, danazol, tricyclics, and antidepressants.

Selective antagonists of the metabotropic glutamate receptor 5 ("mGluR5") have been shown to exert analgesic activity in in vivo animal models (K. Walker et al., *Neuropharmacol.* 40:1-9 (2000) and A. Dogrul et al., *Neurosci. Let.* 292(2): 115-118 (2000)).

Selective antagonists of the mGluR5 receptor have also been shown to exert anxiolytic and anti-depressant activity in in vivo animal models (E. Tatarczynska et al., *Brit. J. Pharmacol.* 132(7):1423-1430 (2001) and P. J. M. Will et al., *Trends in Pharmacological Sci.* 22(7):331-37 (2001)).

Selective antagonists of the mGluR5 receptor have also been shown to exert anti-Parkinson activity in vivo (K. J. Ossowska et al., *Neuropharmacol.* 41(4):413-20 (2001) and P. J. M. Will et al., *Trends in Pharmacological Sci.* 22(7):331-37 (2001)).

Selective antagonists of the mGluR5 receptor have also been shown to exert anti-dependence activity in vivo (C. Chiamulera et al., *Nature Neurosci.* 4(9):873-74 (2001)).

U.S. published patent application no. US 2002/0091116 to Zhu et al. describes a class of compounds useful as selective inhibitors of isolated factor Xa or useful when assembled in the prothrombinase complex.

U.S. Pat. No. 5,474,996 to Caille et al. describes a class of pyrimidine derivatives having angiotensin II inhibiting activity.

U.S. Pat. No. 6,063,930 to Dinsmore et al. describes a class of compounds that are useful for inhibiting farnesyl-protein transferase and for the farnesylation of Ras, an oncogene protein.

Citation of any reference in Section 2 of this application is not to be construed as an admission that such reference is prior art to the present application.

3. SUMMARY OF THE INVENTION

The present invention encompasses compounds of formula:

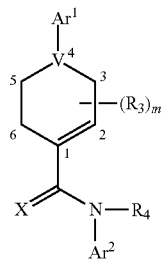
(I)

and pharmaceutically acceptable salts thereof, wherein
$Ar^1$ is

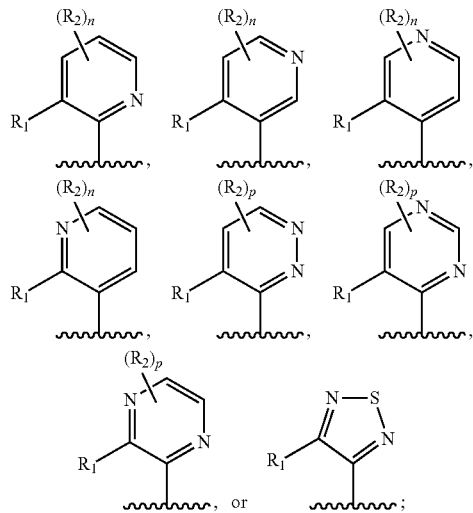

$Ar^2$ is

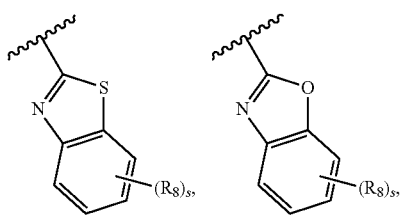

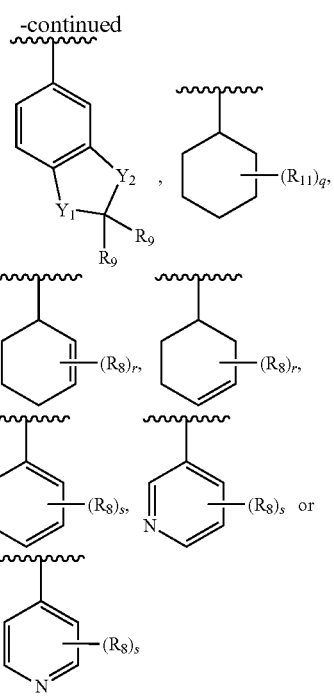

V is N or CH;
X is O or S;
$R_1$ is —H, -halo, —$(C_1-C_4)$alkyl, —$NO_2$, —CN, —OH, —$OCH_3$, —$NH_2$, C(halo)$_3$, —CH(halo)$_2$, or —$CH_2$(halo);
each $R_2$ is independently:
(a) -halo, —CN, —OH, —$NO_2$, or —$NH_2$,
(b) —$(C_1-C_{10})$alkyl, —$(C_2-C_{10})$alkenyl, —$(C_2-C_{10})$alkynyl, —$(C_3-C_{10})$cycloalkyl, —$(C_8-C_{14})$bicycloalkyl, —$(C_8-C_{14})$tricycloalkyl, —$(C_5-C_{10})$cycloalkenyl, —$(C_5-C_{14})$bicycloalkenyl, —$(C_8-C_{14})$tricycloalkenyl, -(3- to 7-membered)heterocycle, or -(7- to 10-membered)bicycloheterocycle, each of which is unsubstituted or substituted with one or more $R_5$ groups, or
(c) -phenyl, -naphthyl, —$(C_{14})$aryl or -(5- to 10-membered)heteroaryl, each of which is unsubstituted or substituted with one or more $R_6$ groups;
each $R_3$ is independently:
(a) -halo, —CN, —OH, —$NO_2$, or —$NH_2$,
(b) —$(C_1-C_{10})$alkyl, —$(C_2-C_{10})$alkenyl, —$(C_2-C_{10})$alkynyl, —$(C_3-C_{10})$cycloalkyl, —$(C_8-C_{14})$bicycloalkyl, —$(C_8-C_{14})$tricycloalkyl, —$(C_5-C_{10})$cycloalkenyl, —$(C_8-C_{14})$bicycloalkenyl, —$(C_8-C_{14})$tricycloalkenyl, -(3- to 7-membered)heterocycle, or -(7- to 10-membered)bicycloheterocycle, each of which is unsubstituted or substituted with one or more $R_5$ groups, or
(c) -phenyl, -naphthyl, —$(C_{14})$aryl or -(5- to 10-membered) heteroaryl, each of which is unsubstituted or substituted with one or more $R_6$ groups;
$R_4$ is —H or —$(C_1-C_6)$alkyl;
each $R_5$ is independently —CN, —OH, —$(C_1-C_6)$alkyl, —$(C_2-C_6)$alkenyl, —$(C_2-C_6)$alkynyl, -halo, —$N_3$, —$NO_2$, —$N(R_7)_2$, —CH=$NR_7$, —$NR_7$OH, —$OR_7$, —$COR_7$, —$C(O)OR_7$, —$OC(O)R_7$, —$OC(O)OR_7$, —$SR_7$, —$S(O)R_7$, or —$S(O)_2R_7$;
each $R_6$ is independently —$(C_1-C_6)$alkyl, —$(C_2-C_6)$alkenyl, —$(C_2-C_6)$alkynyl, —$(C_3-C_8)$cycloalkyl, —$(C_5-C_8)$cycloalkenyl, -phenyl, -(3- to 5-membered)heterocycle, —C(halo)$_3$, —CH(halo)$_2$, —$CH_2$(halo), —CN, —OH, -halo, —$N_3$, —$NO_2$, —$N(R_7)_2$, —$CH=NR_7$, —$NR_7OH$, —$OR_7$, —$COR_7$, —$C(O)OR_7$, —$OC(O)R_7$, —$OC(O)OR_7$, —$SR_7$, —$S(O)R_7$, or —$S(O)_2R_7$;

each $R_7$ is independently —H, —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, -(3- to 5-membered)heterocycle, —C(halo)$_3$, —CH(halo)$_2$, or $CH_2$(halo);

each $R_8$ is independently —($C_1$-$C_{10}$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, —C(halo)$_3$, —CH(halo)$_2$, —$CH_2$(halo), —CN, —OH, -halo, —$N_3$, —$NO_2$, —$N(R_7)_2$, —$CH=NR_7$, —$NR_7OH$, —$OR_7$, —$COR_7$, —$C(O)OR_7$, —$OC(O)R_7$, —$OC(O)OR_7$, —$SR_7$, —$S(O)R_7$, —$S(O)_2R_7$, —$R_7OR_7$, —$R_7COR_7$, —$R_7C(O)OR_7$, —$R_7OC(O)R_7$, —$R_7OC(O)OR_7$, —$R_7SR_7$, —$R_7S(O)R_7$, —$R_7S(O)_2R_7$, —C(halo)$_2$C(halo)$_3$, —C(halo)$_2$CH(halo)$_2$, —CH(C(halo)$_3$)$_2$, —CH(C(halo)$_3$)(CH$_3$), —OC(halo)$_2$C(halo)$_3$, —OC(halo)$_2$CH(halo)$_2$, —OCH(C(halo)$_3$)$_2$, —OCH(C(halo)$_3$)(CH$_3$), —C(OH)(CF$_3$)$_2$, —($C_1$-$C_{10}$)alkyl, or -(3- to 7-membered)heterocycle;

each $R_9$ is independently —H, -halo, or —($C_1$-$C_6$)alkyl;

each $R_{11}$ is independently —CN, —OH, —($C_1$-$C_6$)alkyl, —($C_2$-$C_6$)alkenyl, —($C_2$-$C_6$)alkynyl, -halo, —$N_3$, —$NO_2$, —$N(R_7)_2$, —$CH=NR_7$, —$NR_7OH$, —$OR_7$, —$COR_7$, —$C(O)OR_7$, —$OC(O)R_7$, or —$OC(O)OR_7$;

$Y_1$ and $Y_2$ are —$CH_2$— and —$CH_2$—, —O— and —O—, —NH— and —NH—, —S— and —S—, —$CH_2$— and —O—, —$CH_2$— and —NH—, —$CH_2$— and —S—, —O— and —$CH_2$—, —NH— and —$CH_2$—, —S— and —$CH_2$—, —O— and —NH—, —NH— and —O—, —S— and —NH—, or —NH— and —S— respectively; each halo is independently —F, —Cl, —Br, or —I;

m is 0 or 1 and when m is 1, $R_3$ is attached to the 2-, 3-, 5-, or 6-position of the cyclo(hetero)alkenyl ring;

n is an integer ranging from 0 to 3;

p is an integer ranging from 0 to 2;

q is an integer ranging from 0 to 6;

r is an integer ranging from 0 to 5; and s is an integer ranging from 0 to 4.

The present invention encompasses compounds of formula:

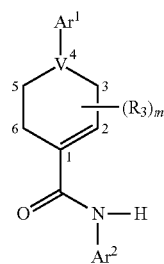

(IA)

and pharmaceutically acceptable salts thereof, wherein Ar$^1$ is

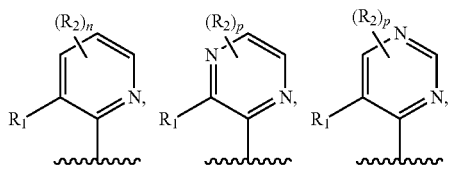

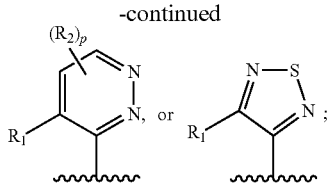

Ar$^2$ is

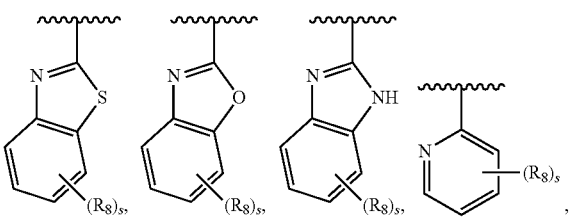

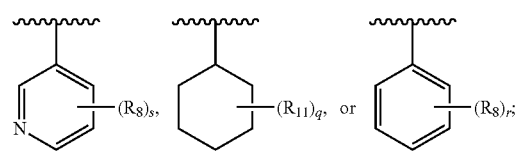

V is N or CH;

$R_1$ is —H, -halo, —$CH_3$, —$NO_2$, —CN, —OH, —$OCH_3$, —$NH_2$, C(halo)$_3$, —CH(halo)$_2$, or —$CH_2$(halo);

each $R_2$ is independently:

(a) -halo, —CN, —OH, —$NO_2$, or —$NH_2$, (b) —($C_1$-$C_{10}$)alkyl, —($C_2$-$C_{10}$)alkenyl, —($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle, or -(7- to 10-membered)bicycloheterocycle, each of which is unsubstituted or substituted with one or more $R_5$ groups, or (c) -phenyl, -naphthyl, —($C_{14}$)aryl or -(5- to 10-membered)heteroaryl, each of which is unsubstituted or substituted with one or more $R_6$ groups;

each $R_3$ is independently:

(a) -halo, —CN, —OH, —$NO_2$, or —$NH_2$, (b) —($C_1$-$C_{10}$)alkyl, —($C_2$-$C_{10}$)alkenyl, —($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle, or -(7- to 10-membered)bicycloheterocycle, each of which is unsubstituted or substituted with one or more $R_5$ groups, or (c) -phenyl, -naphthyl, —($C_{14}$)aryl or -(5- to 10-membered) heteroaryl, each of which is unsubstituted or substituted with one or more $R_6$ groups;

each $R_5$ is independently —CN, —OH, —($C_1$-$C_6$)alkyl, —($C_2$-$C_6$)alkenyl, —($C_2$-$C_6$)alkynyl, -halo, —$N_3$, —$NO_2$, —$N(R_7)_2$, —$CH=NR_7$, —$NR_7OH$, —$OR_7$, —$COR_7$, —$C(O)OR_7$, —$OC(O)R_7$, —$OC(O)OR_7$, —$SR_7$, —$S(O)R_7$, or —$S(O)_2R_7$;

each $R_6$ is independently —$(C_1$-$C_6)$alkyl, —$(C_2$-$C_6)$alkenyl, —$(C_2$-$C_6)$alkynyl, —$(C_3$-$C_8)$cycloalkyl, —$(C_5$-$C_8)$cycloalkenyl, -phenyl, -(3- to 5-membered)heterocycle, —$C(halo)_3$, —$CH(halo)_2$, —$CH_2(halo)$, —CN, —OH, -halo, —$N_3$, —$NO_2$, —$N(R_7)_2$, —CH=$NR_7$, —$NR_7OH$, —$OR_7$, —$COR_7$, —$C(O)OR_7$, —$OC(O)R_7$, —$OC(O)OR_7$, —$SR_7$, —$S(O)R_7$, or —$S(O)_2R_7$;

each $R_7$ is independently —H, —$(C_1$-$C_6)$alkyl, —$(C_2$-$C_6)$alkenyl, —$(C_2$-$C_6)$alkynyl, —$(C_3$-$C_8)$cycloalkyl, —$(C_5$-$C_8)$cycloalkenyl, -phenyl, -(3- to 5-membered)heterocycle, —$C(halo)_3$, —$CH(halo)_2$, or $CH_2(halo)$;

each $R_8$ is independently —$(C_1$-$C_6)$alkyl, —$(C_2$-$C_6)$alkenyl, —$(C_2$-$C_6)$alkynyl, —$(C_3$-$C_8)$cycloalkyl, —$(C_5$-$C_8)$cycloalkenyl, -phenyl, —$C(halo)_3$, —$CH(halo)_2$, —$CH_2(halo)$, —CN, —OH, -halo, —$N_3$, —$NO_2$, —$N(R_7)_2$, —CH=$NR_7$, —$NR_7OH$, —$OR_7$, —$COR_7$, —$C(O)OR_7$, —$OC(O)R_7$, —$OC(O)OR_7$, —$SR_7$, —$S(O)R_7$, or —$S(O)_2R_7$;

each $R_{11}$ is independently —CN, —OH, —$(C_1$-$C_6)$alkyl, —$(C_2$-$C_6)$alkenyl, —$(C_2$-$C_6)$alkynyl, -halo, —$N_3$, —$NO_2$, —$N(R_7)_2$, —CH=$NR_7$, —$NR_7OH$, —$OR_7$, —$COR_7$, —$C(O)OR_7$, —$OC(O)R_7$, or —$OC(O)OR_7$;

each halo is independently —F, —Cl, —Br, or —I;

m is 0 or 1 and when m is 1, $R_3$ is attached to the 2-, 3-, 5-, or 6-position of the cyclo(hetero)alkenyl ring;

n is an integer ranging from 0 to 3;

p is an integer ranging from 0 to 2;

q is an integer ranging from 0 to 6;

r is an integer ranging from 0 to 5; and s is an integer ranging from 0 to 4.

A Compound of Formula (I) or (IA) or a pharmaceutically acceptable salt thereof (a "Cyclo(hetero)alkenyl Compound"), is useful for treating or preventing pain, UI, an ulcer, IBD, IBS, an addictive disorder, Parkinson's disease, parkinsonism, anxiety, epilepsy, stroke, a seizure, a pruritic condition, psychosis, a cognitive disorder, a memory deficit, restricted brain function, Huntington's chorea, ALS, dementia, retinopathy, a muscle spasm, a migraine, vomiting, dyskinesia, or depression (each being a "Condition") in an animal.

The invention also relates to compositions comprising an effective amount of a Cyclo(hetero)alkenyl Compound and a pharmaceutically acceptable carrier or excipient. The compositions are useful for treating or preventing a Condition in an animal.

The invention further relates to methods for treating a Condition, comprising administering to an animal in need thereof an effective amount of a Cyclo(hetero)alkenyl Compound.

The invention further relates to methods for preventing a Condition, comprising administering to an animal in need thereof an effective amount of a Cyclo(hetero)alkenyl Compound.

The invention still further relates to methods for inhibiting Vanilloid Receptor 1 ("VR1") function in a cell, comprising contacting a cell capable of expressing VR1 with an effective amount of a Cyclo(hetero)alkenyl Compound.

The invention still further relates to a method for preparing a composition, comprising the step of admixing a Cyclo(hetero)alkenyl Compound and a pharmaceutically acceptable carrier or excipient.

The invention still further relates to a kit comprising a container containing an effective amount of a Cyclo(hetero)alkenyl Compound. The kit may further comprise printed instructions for using the Cyclo(hetero)alkenyl Compound to treat any of the aforementioned Conditions.

The present invention can be understood more fully by reference to the following detailed description and illustrative examples, which are intended to exemplify non-limiting embodiments of the invention.

4. DETAILED DESCRIPTION OF THE INVENTION

4.1 Cyclo(Hetero)Alkenyl Compounds

4.1.1 Cyclo(Hetero)Alkenyl Compounds of Formula (I)

The present invention encompasses Compounds of Formula (I)

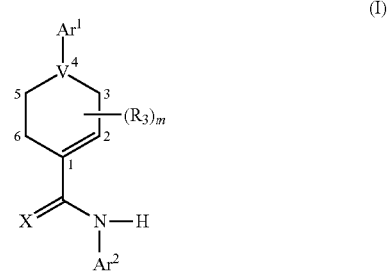

(I)

and pharmaceutically acceptable salts thereof, where V, X, $Ar^1$, $Ar^2$, $R_3$, $R_4$, and m are defined above for the Cyclo(hetero)alkenyl Compounds of Formula (I).

In one embodiment, each $R_8$ is independently —$(C_1$-$C_6)$alkyl, —$(C_2$-$C_6)$alkenyl, —$(C_2$-$C_6)$alkynyl, —$(C_3$-$C_8)$cycloalkyl, —$(C_5$-$C_8)$cycloalkenyl, -phenyl, —$C(halo)_3$, —$CH(halo)_2$, —$CH_2(halo)$, —CN, —OH, -halo, —$N_3$, —$NO_2$, —$N(R_7)_2$, —CH=$NR_7$, —$NR_7OH$, —$OR_7$, —$COR_7$, —$C(O)OR_7$, —$OC(O)R_7$, —$OC(O)OR_7$, —$SR_7$, —$S(O)R_7$, —$S(O)_2R_7$, —$R_7OR_7$, —$R_7COR_7$, —$R_7C(O)OR_7$, —$R_7OC(O)R_7$, —$R_7OC(O)OR_7$, —$R_7SR_7$, —$R_7S(O)R_7$, —$R_7S(O)_2R_7$, —$C(halo)_2C(halo)_3$, —$C(halo)_2CH(halo)_2$, —$CH(C(halo)_3)_2$, —$CH(C(halo)_3)(CH_3)$, —$OC(halo)_2C(halo)_3$, —$OC(halo)_2CH(halo)_2$, —$OCH(C(halo)_3)_2$, —$OCH(C(halo)_3)(CH_3)$, —$C(OH)(CF_3)_2$, —$(C_1$-$C_{10})$alkyl, or -(3- to 7-membered)heterocycle.

In another embodiment, $R_1$ is —H, -halo, —$CH_3$, —$NO_2$, —CN, —OH, —$OCH_3$, —$NH_2$, $C(halo)_3$, —$CH(halo)_2$, or —$CH_2(halo)$.

In another embodiment, $Ar^2$ is

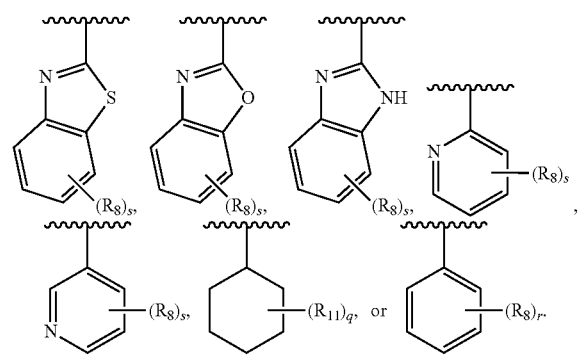

In another embodiment, $Ar^1$ is

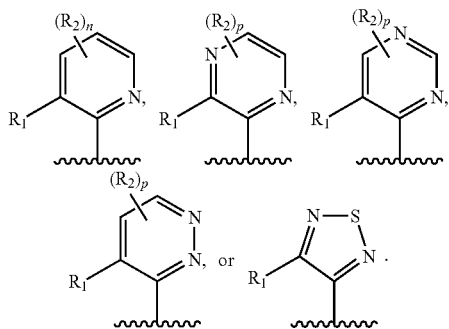

In another embodiment, $Ar^2$ is

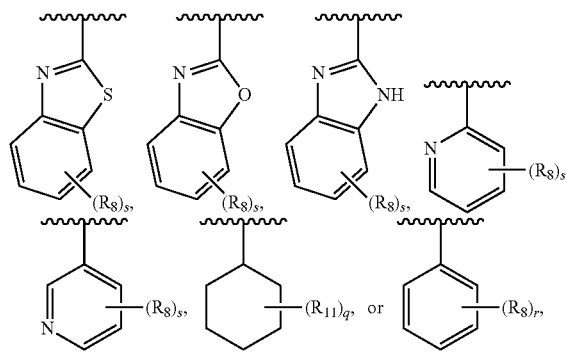

and $Ar^1$ is

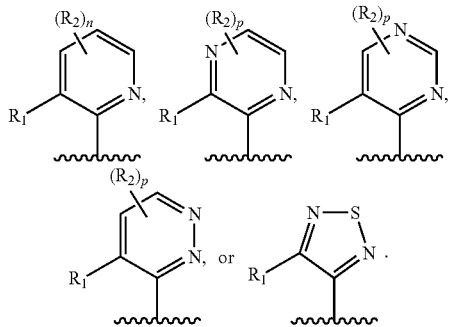

In another embodiment, each $R_8$ is independently —$(C_1$-$C_6)$alkyl, —$(C_2$-$C_6)$alkenyl, —$(C_2$-$C_6)$alkynyl, —$(C_3$-$C_8)$cycloalkyl, —$(C_5$-$C_8)$cycloalkenyl, -phenyl, —$C(halo)_3$, —$CH(halo)_2$, —$CH_2(halo)$, —CN, —OH, -halo, —$N_3$, —$NO_2$, —$N(R_7)_2$, —$CH=NR_7$, —$NR_7OH$, —$OR_7$, —$COR_7$, —$C(O)OR_7$, —$OC(O)R_7$, —$OC(O)OR_7$, —$SR_7$, —$S(O)R_7$, or —$S(O)_2R_7$.

In another embodiment, $Ar^2$ is

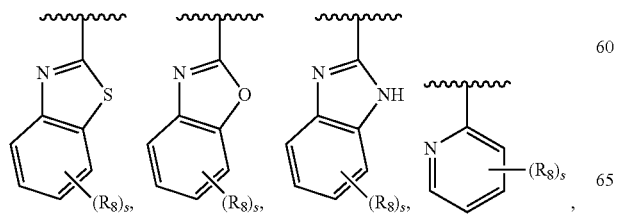

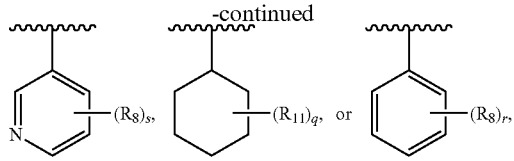

and each $R_8$ is independently —$(C_1$-$C_6)$alkyl, —$(C_2$-$C_6)$alkenyl, —$(C_2$-$C_6)$alkynyl, —$(C_3$-$C_8)$cycloalkyl, —$(C_5$-$C_8)$cycloalkenyl, -phenyl, —$C(halo)_3$, —$CH(halo)_2$, —$CH_2(halo)$, —CN, —OH, -halo, —$N_3$, —$NO_2$, —$N(R_7)_2$, —$CH=NR_7$, —$NR_7OH$, —$OR_7$, —$COR_7$, —$C(O)OR_7$, —$OC(O)R_7$, —$OC(O)OR_7$, —$SR_7$, —$S(O)R_7$, or —$S(O)_2R_7$.

In another embodiment, $Ar^1$ is

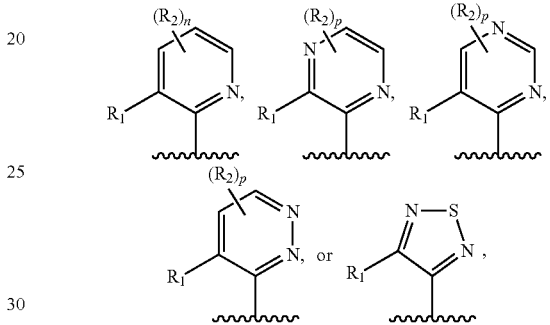

and each $R_8$ is independently —$(C_1$-$C_6)$alkyl, —$(C_2$-$C_6)$alkenyl, —$(C_2$-$C_6)$alkynyl, —$(C_3$-$C_8)$cycloalkyl, —$(C_5$-$C_8)$cycloalkenyl, -phenyl, —$C(halo)_3$, —$CH(halo)_2$, —$CH_2(halo)$, —CN, —OH, -halo, —$N_3$, —$NO_2$, —$N(R_7)_2$, —$CH=NR_7$, —$NR_7OH$, —$OR_7$, —$COR_7$, —$C(O)OR_7$, —$OC(O)R_7$, —$OC(O)OR_7$, —$SR_7$, —$S(O)R_7$, or —$S(O)_2R_7$.

In another embodiment, $Ar^2$ is

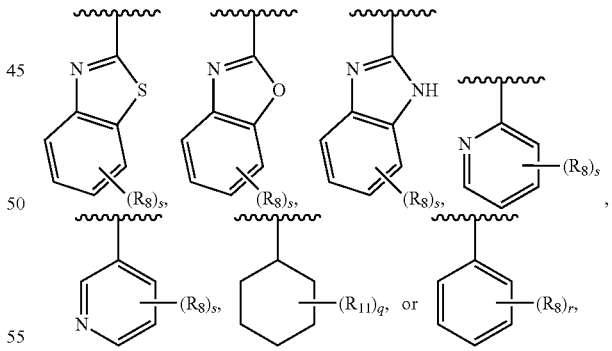

$Ar^1$ is

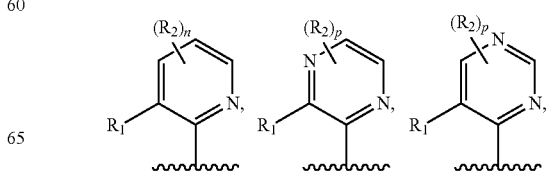

-continued

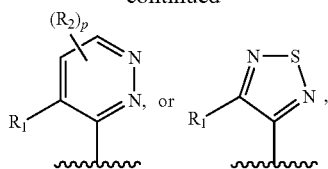

and each $R_8$ is independently —$(C_1-C_6)$alkyl, —$(C_2-C_6)$alkenyl, —$(C_2-C_6)$alkynyl, —$(C_3-C_8)$cycloalkyl, —$(C_5-C_8)$cycloalkenyl, -phenyl, —C(halo)$_3$, —CH(halo)$_2$, —CH$_2$(halo), —CN, —OH, -halo, —N$_3$, —NO$_2$, —N(R$_7$)$_2$, —CH=NR$_7$, —NR$_7$OH, —OR$_7$, —COR$_7$, —C(O)OR$_7$, —OC(O)R$_7$, —OC(O)OR$_7$, —SR$_7$, —S(O)R$_7$, or —S(O)$_2$R$_7$.

In another embodiment, $R_4$ is —H.

In another embodiment, $Ar^2$ is

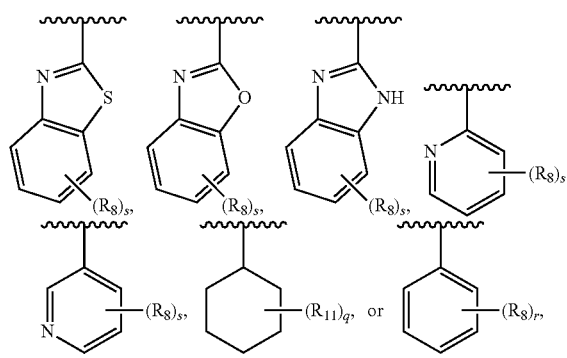

and $R_4$ is —H.

In another embodiment, $Ar^1$ is

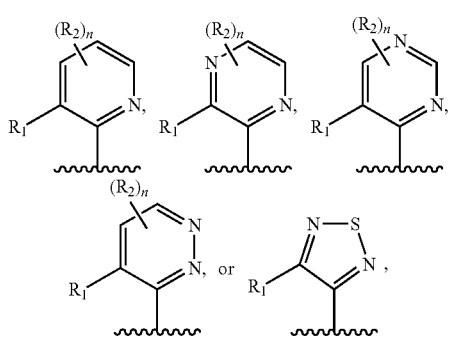

and $R_4$ is —H.

In another embodiment, $Ar^2$ is

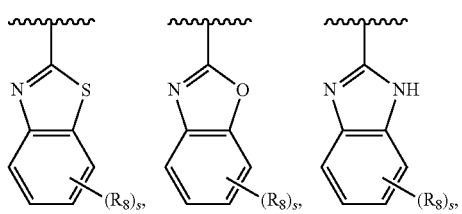

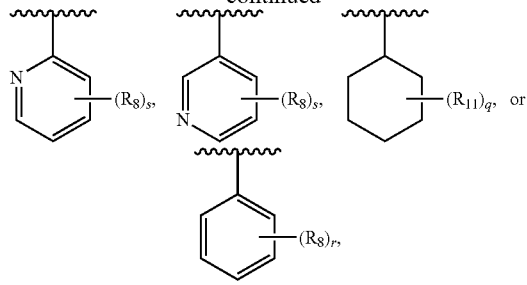

$Ar^1$ is

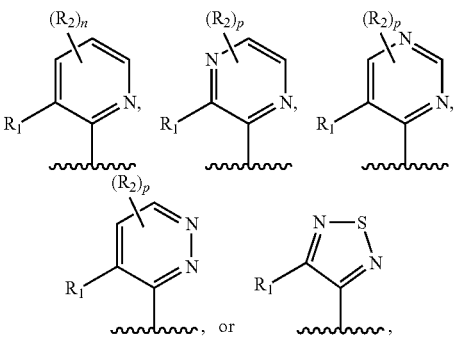

and $R_4$ is —H.

In another embodiment, $R_4$ is —H and each $R_8$ is independently —$(C_1-C_6)$alkyl, —$(C_2-C_6)$alkenyl, —$(C_2-C_6)$alkynyl, —$(C_3-C_8)$cycloalkyl, —$(C_5-C_8)$cycloalkenyl, -phenyl, —C(halo)$_3$, —CH(halo)$_2$, —CH$_2$(halo), —CN, —OH, -halo, —N$_3$, —NO$_2$, —N(R$_7$)$_2$, —CH=NR$_7$, —NR$_7$OH, —OR$_7$, —COR$_7$, —C(O)OR$_7$, —OC(O)R$_7$, —OC(O)OR$_7$, —SR$_7$, —S(O)R$_7$, or —S(O)$_2$R$_7$.

In another embodiment, $Ar^2$ is

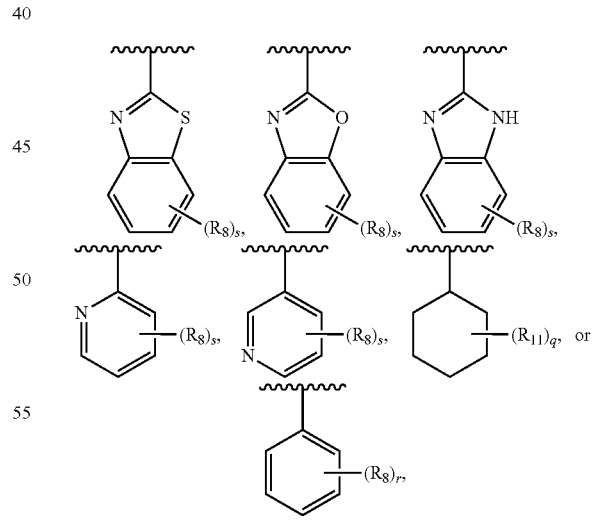

each $R_8$ is independently —$(C_1-C_6)$alkyl, —$(C_2-C_6)$alkenyl, —$(C_2-C_6)$alkynyl, —$(C_3-C_8)$cycloalkyl, —$(C_5-C_8)$cycloalkenyl, -phenyl, —C(halo)$_3$, —CH(halo)$_2$, —CH$_2$(halo), —CN, —OH, -halo, —N$_3$, —NO$_2$, —N(R$_7$)$_2$, —CH=NR$_7$, —NR$_7$OH, —OR$_7$, —COR$_7$, —C(O)OR$_7$, —OC(O)R$_7$, —OC(O)OR$_7$, —SR$_7$, —S(O)R$_7$, or —S(O)$_2$R$_7$, and $R_4$ is —H.

In another embodiment, $Ar^1$ is

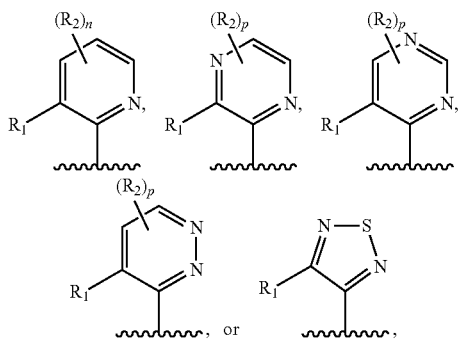

or, each $R_8$ is independently —$(C_1\text{-}C_6)$alkyl, —$(C_2\text{-}C_6)$alkenyl, —$(C_2\text{-}C_6)$alkynyl, —$(C_3\text{-}C_8)$cycloalkyl, —$(C_5\text{-}C_8)$cycloalkenyl, -phenyl, —C(halo)$_3$, —CH(halo)$_2$, —CH$_2$(halo), —CN, —OH, -halo, —N$_3$, —NO$_2$, —N(R$_7$)$_2$, —CH=NR$_7$, —NR$_7$OH, —OR$_7$, —COR$_7$, —C(O)OR$_7$, —OC(O)R$_7$, —OC(O)OR$_7$, —SR$_7$, —S(O)R$_7$, or —S(O)$_2$R$_7$, and $R_4$ is —H.

In another embodiment, $Ar^2$ is

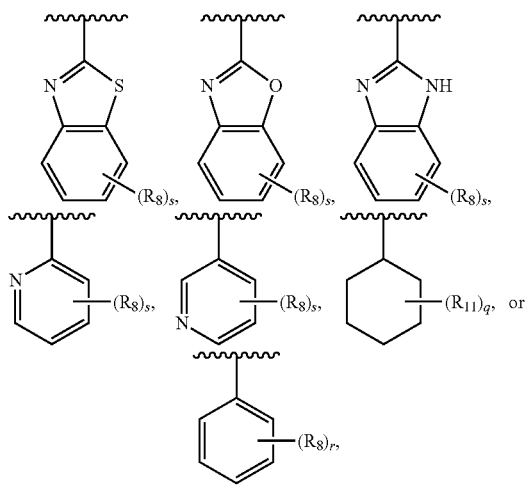

$Ar^1$ is

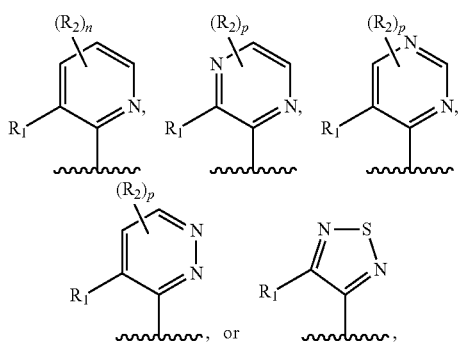

or, each $R_8$ is independently —$(C_1\text{-}C_6)$alkyl, —$(C_2\text{-}C_6)$alkenyl, —$(C_2\text{-}C_6)$alkynyl, —$(C_3\text{-}C_8)$cycloalkyl, —$(C_5\text{-}C_8)$cycloalkenyl, -phenyl, —C(halo)$_3$, —CH(halo)$_2$, —CH$_2$(halo), —CN, —OH, -halo, —N$_3$, —NO$_2$, —N(R$_7$)$_2$, —CH=NR$_7$, —NR$_7$OH, —OR$_7$, —COR$_7$, —C(O)OR$_7$, —OC(O)R$_7$, —OC(O)OR$_7$, —SR$_7$, —S(O)R$_7$, or —S(O)$_2$R$_7$, and $R_4$ is —H.

In another embodiment, $R_1$ is —H, -halo, —CH$_3$, —NO$_2$, —CN, —OH, —OCH$_3$, —NH$_2$, C(halo)$_3$, —CH(halo)$_2$, or —CH$_2$(halo); and $Ar^2$ is

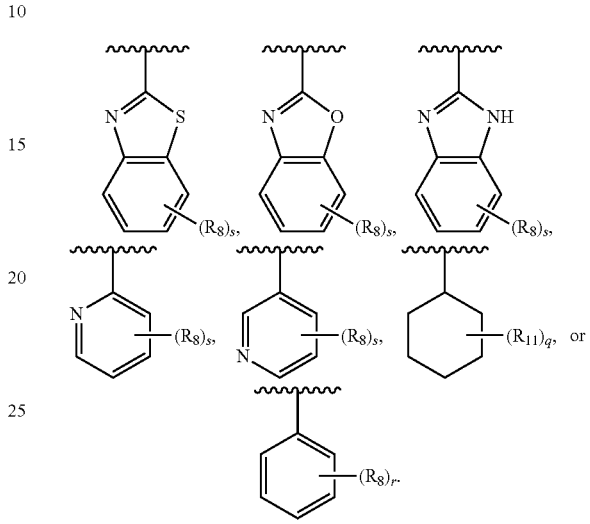

In another embodiment, $Ar^1$ is

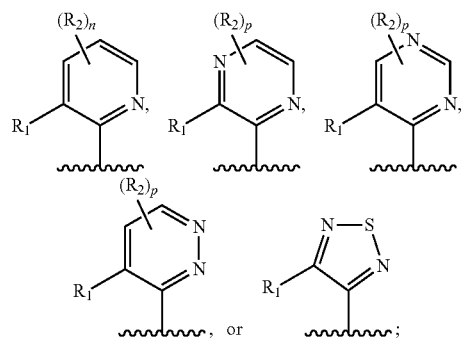

or;

and $R_1$ is —H, -halo, —CH$_3$, —NO$_2$, —CN, —OH, —OCH$_3$, —NH$_2$, C(halo)$_3$, —CH(halo)$_2$, or —CH$_2$(halo).

In another embodiment, $Ar^2$ is

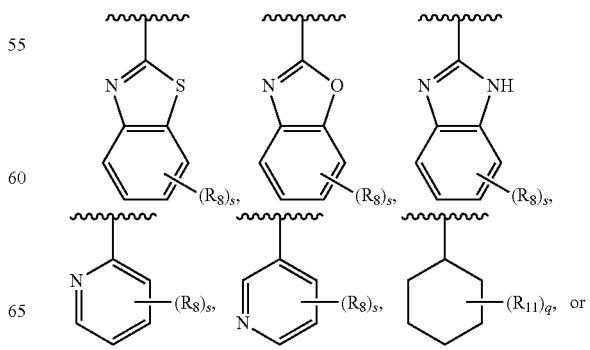

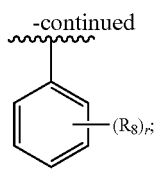

$Ar^1$ is

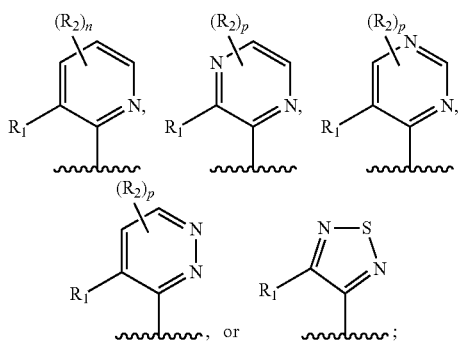

and $R_1$ is —H, -halo, —$CH_3$, —$NO_2$, —CN, —OH, —$OCH_3$, —$NH_2$, C(halo)$_3$, —CH(halo)$_2$, or —$CH_2$(halo).

In another embodiment, $R_1$ is —H, -halo, —$CH_3$, —$NO_2$, —CN, —OH, —$OCH_3$, —$NH_2$, C(halo)$_3$, —CH(halo)$_2$, or —$CH_2$(halo); and each $R_8$ is independently —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, —C(halo)$_3$, —CH(halo)$_2$, —$CH_2$(halo), —CN, —OH, -halo, —$N_3$, —$NO_2$, —N($R_7$)$_2$, —CH=$NR_7$, —$NR_7$OH, —$OR_7$, —$COR_7$, —C(O)$OR_7$, —OC(O)$R_7$, —OC(O)$OR_7$, —$SR_7$, —S(O)$R_7$, or —S(O)$_2R_7$.

In another embodiment, $Ar^2$ is

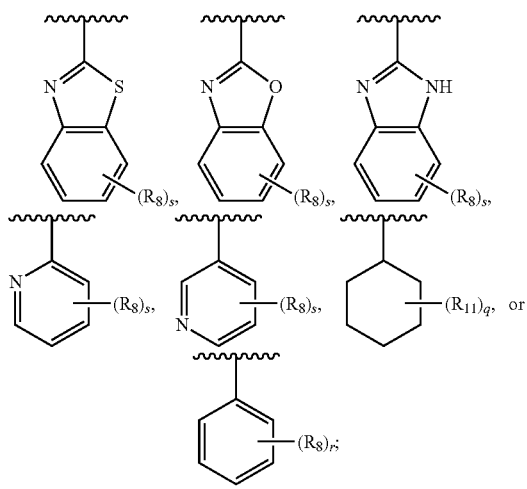

each $R_8$ is independently —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, —C(halo)$_3$, —CH(halo)$_2$, —$CH_2$(halo), —CN, —OH, -halo, —$N_3$, —$NO_2$, —N($R_7$)$_2$, —CH=$NR_7$, —$NR_7$OH, —$OR_7$, —$COR_7$, —C(O)$OR_7$, —OC(O)$R_7$, —OC(O)$OR_7$, —$SR_7$, —S(O)$R_7$, or —S(O)$_2R_7$; and $R_1$ is —H, -halo, —$CH_3$, —$NO_2$, —CN, —OH, —$OCH_3$, —$NH_2$, C(halo)$_3$, —CH(halo)$_2$, or —$CH_2$(halo).

In another embodiment, $Ar^1$ is

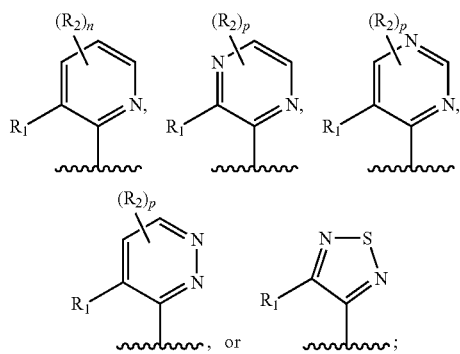

$R_1$ is —H, -halo, —$CH_3$, —$NO_2$, —CN, —OH, —$OCH_3$, —$NH_2$, C(halo)$_3$, —CH(halo)$_2$, or —$CH_2$(halo); and each $R_8$ is independently —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, —C(halo)$_3$, —CH(halo)$_2$, —$CH_2$(halo), —CN, —OH, -halo, —$N_3$, —$NO_2$, —N($R_7$)$_2$, —CH=$NR_7$, —$NR_7$OH, —$OR_7$, —$COR_7$, —C(O)$OR_7$, —OC(O)$R_7$, —OC(O)$OR_7$, —$SR_7$, —S(O)$R_7$, or —S(O)$_2R_7$.

In another embodiment, $Ar^2$ is

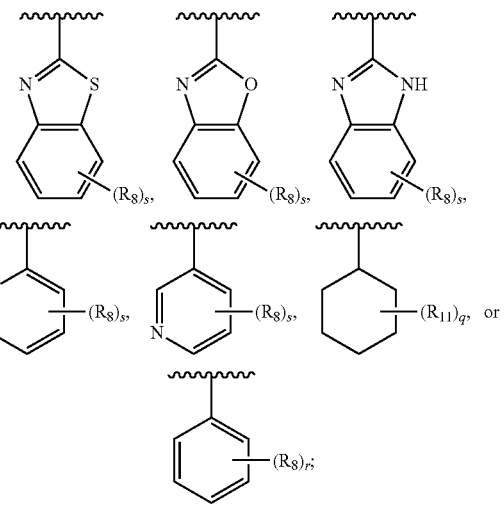

each $R_8$ is independently —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, —C(halo)$_3$, —CH(halo)$_2$, —$CH_2$(halo), —CN, —OH, -halo, —N3, —$NO_2$, —N($R_7$)$_2$, —CH=$NR_7$, —$NR_7$OH, —$OR_7$, —$COR_7$, —C(O)$OR_7$, —OC(O)$R_7$, —OC(O)$OR_7$, —$SR_7$, —S(O)$R_7$, or —S(O)$_2R_7$; $Ar^1$ is

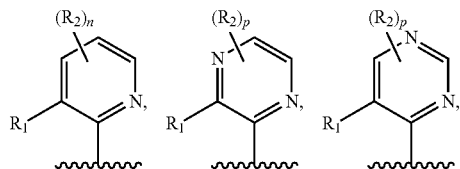

-continued

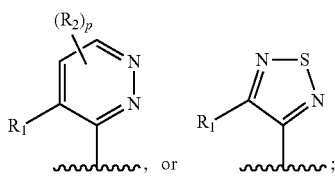

and R₁ is —H, -halo, —CH₃, —NO₂, —CN, —OH, —OCH₃, —NH₂, C(halo)₃, —CH(halo)₂, or —CH₂(halo).

In another embodiment, R is —H, -halo, —CH₃, —NO₂, —CN, —OH, —OCH₃, —NH₂, C(halo)₃, —CH(halo)₂, or —C$_H$2 (halo); and R₄ is —H.

In another embodiment, Ar² is

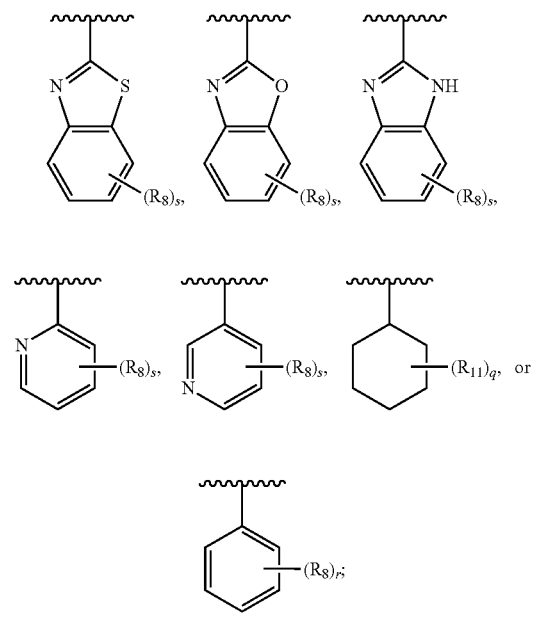

$R_1$ is —H, -halo, —CH₃, —NO₂, —CN, —OH, —OCH₃, —NH₂, C(halo)₃, —CH(halo)₂, or —CH₂(halo); and R₄ is —H.

In another embodiment, Ar¹ is

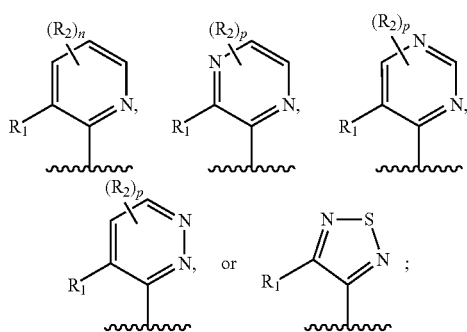

$R_1$ is —H, -halo, —CH₃, —NO₂, —CN, —OH, —OCH₃, —NH₂, C(halo)₃, —CH(halo)₂, or —CH₂(halo); and R₄ is —H.

In another embodiment, Ar² is

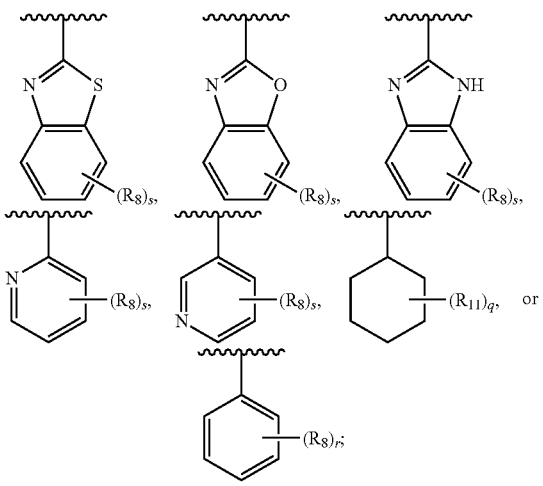

Ar¹ is

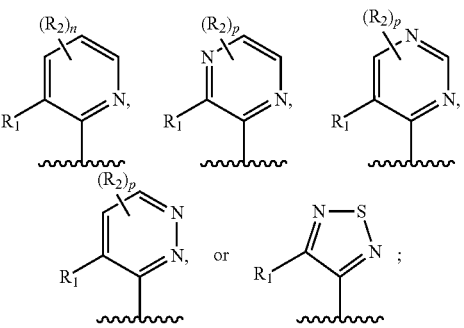

$R_1$ is —H, -halo, —CH₃, —NO₂, —CN, —OH, —OCH₃, —NH₂, C(halo)₃, —CH(halo)₂, or —CH₂(halo); and R₄ is —H.

In another embodiment, R₁ is —H, -halo, —CH₃, —NO₂, —CN, —OH, —OCH₃, —NH₂, C(halo)₃, —CH(halo)₂, or —CH₂(halo); R₄ is —H; and each R₈ is independently —(C₁-C₆)alkyl, —(C₂-C₆)alkenyl, —(C₂-C₆)alkynyl, —(C₃-C₈)cycloalkyl, —(C₅-C₈)cycloalkenyl, -phenyl, —C(halo)₃, —CH(halo)₂, —CH₂(halo), —CN, —OH, -halo, —N₃, —NO₂, —N(R₇)₂, —CH=NR₇, —NR₇OH, —OR₇, —COR₇, —C(O)OR₇, —OC(O)R₇, —OC(O)OR₇, —SR₇, —S(O)R₇, or —S(O)₂R₇.

In another embodiment, Ar² is

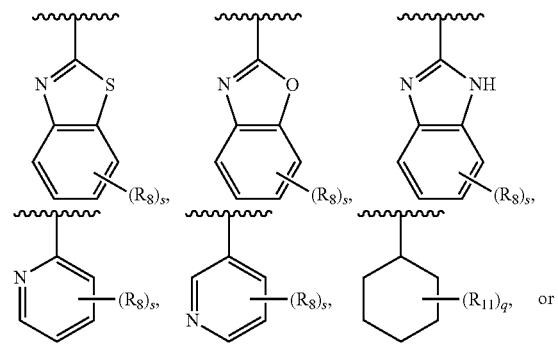

-continued

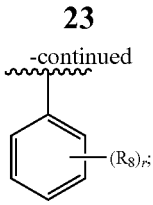

each $R_8$ is independently —$(C_1\text{-}C_6)$alkyl, —$(C_2\text{-}C_6)$alkenyl, —$(C_2\text{-}C_6)$alkynyl, —$(C_3\text{-}C_8)$cycloalkyl, —$(C_5\text{-}C_8)$cycloalkenyl, -phenyl, —$C(halo)_3$, —$CH(halo)_2$, —$CH_2(halo)$, —CN, —OH, -halo, —$N_3$, —$NO_2$, —$N(R_7)_2$, —$CH\!=\!NR_7$, —$NR_7OH$, —$OR_7$, —$COR_7$, —$C(O)OR_7$, —$OC(O)R_7$, —$OC(O)OR_7$, —$SR_7$, —$S(O)R_7$, or —$S(O)_2R_7$; $R_1$ is —H, -halo, —$CH_3$, —$NO_2$, —CN, —OH, —$OCH_3$, —$NH_2$, $C(halo)_3$, —$CH(halo)_2$, or —$CH_2(halo)$; and $R_4$ is —H.

In another embodiment, $Ar^1$ is

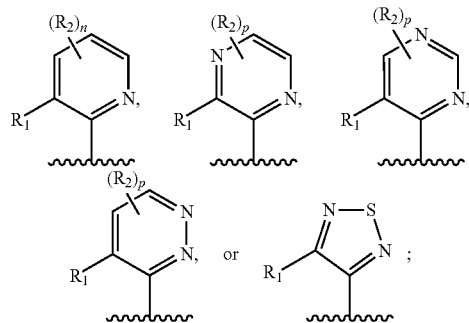

$R_1$ is —H, -halo, —$CH_3$, —$NO_2$, —CN, —OH, —$OCH_3$, —$NH_2$, $C(halo)_3$, —$CH(halo)_2$, or —$CH_2(halo)$; each $R_8$ is independently —$(C_1\text{-}C_6)$alkyl, —$(C_2\text{-}C_6)$alkenyl, —$(C_2\text{-}C_6)$alkynyl, —$(C_3\text{-}C_8)$cycloalkyl, —$(C_5\text{-}C_8)$cycloalkenyl, -phenyl, —$C(halo)_3$, —$CH(halo)_2$, —$CH_2(halo)$, —CN, —OH, -halo, —$N_3$, —$NO_2$, —$N(R_7)_2$, —$CH\!=\!NR_7$, —$NR_7OH$, —$OR_7$, —$COR_7$, —$C(O)OR_7$, —$OC(O)R_7$, —$OC(O)OR_7$, —$SR_7$, —$S(O)R_7$, or —$S(O)_2R_7$, and $R_4$ is —H.

In another embodiment, $Ar^2$ is

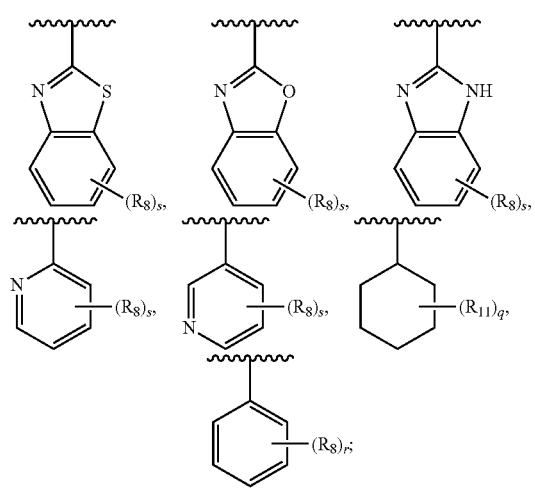

each $R_8$ is independently —$(C_1\text{-}C_6)$alkyl, —$(C_2\text{-}C_6)$alkenyl, —$(C_2\text{-}C_6)$alkynyl, —$(C_3\text{-}C_8)$cycloalkyl, —$(C_5\text{-}C_8)$cycloalkenyl, -phenyl, —$C(halo)_3$, —$CH(halo)_2$, —$CH_2(halo)$, —CN, —OH, -halo, —$N_3$, —$NO_2$, —$N(R_7)_2$, —$CH\!=\!NR_7$, —$NR_7OH$, —$OR_7$, —$COR_7$, —$C(O)OR_7$, —$OC(O)R_7$, —$OC(O)OR_7$, —$SR_7$, —$S(O)R_7$, or —$S(O)_2R_7$; $Ar^1$ is

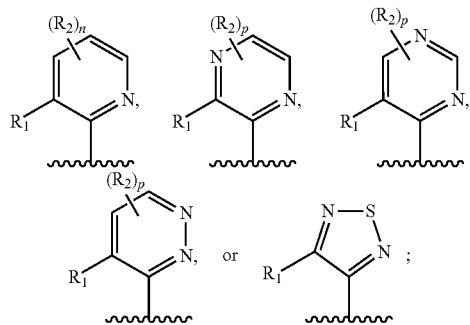

and $R_1$ is —H, -halo, —$CH_3$, —$NO_2$, —CN, —OH, —$OCH_3$, —$NH_2$, $C(halo)_3$, —$CH(halo)_2$, or —$CH_2(halo)$.

In one embodiment, $Ar^1$ is a pyridyl group.
In another embodiment, $Ar^1$ is a pyrimidyl group
In another embodiment, $Ar^1$ is a pyrazinyl group.
In another embodiment, $Ar^1$ is a pyridazinyl group.
In another embodiment, $Ar^1$ is a thiadiazolyl group.
In another embodiment, $Ar^1$ is

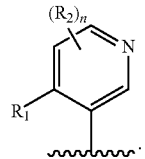

In another embodiment, $Ar^1$ is

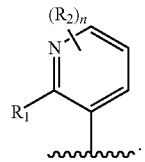

In another embodiment, $Ar^1$ is

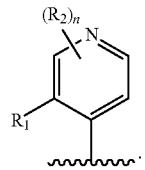

In another embodiment, V is N.
In another embodiment, V is CH.
In another embodiment, $Ar^2$ is a benzoimidazolyl group.
In another embodiment, $Ar^2$ is a benzothiazolyl group.
In another embodiment, $Ar^2$ is a benzooxazolyl group.
In another embodiment, $Ar^2$ is a 5-benzodioxolyl group, a 5-benzodithiolyl group, a 5-dihydroindenyl group, a 5-dihydrobenzoimidazolyl group, a 6-dihydrobenzofuranyl group, a 5-dihydrobenzofuranyl group, a 6-indolinyl group, a 5-indolinyl group, a 6-dihydrobenzothiopheneyl group, a 5-dihydrobenzothiopheneyl group, a 5-dihydrobenzooxazolyl group, a 6-dihydrobenzooxazolyl group, a 5-dihydrobenzothiazolyl group, or a 6-dihydrobenzothiazolyl group.

In another embodiment, Ar² is a 5-benzodioxolyl group, a 5-benzodithiolyl group, a 5-dihydroindenyl group, a 5-dihydrobenzoimidazolyl group, a 6-dihydrobenzofuranyl group, a 5-dihydrobenzofuranyl group, a 6-indolinyl group, a 5-indolinyl group, a 6-dihydrobenzothiopheneyl group, or a 5-dihydrobenzothiopheneyl group.

In another embodiment, Ar² is a 5-dihydroindenyl group, a 5-dihydrobenzoimidazolyl group, a 5-benzodioxolyl group, or a 5-benzodithiolyl group.

In another embodiment, Ar² is a 5-benzodioxolyl group or a 5-benzodithiolyl group.

In another embodiment, Ar² is a 5-benzodioxolyl group.

In another embodiment, Ar² is a 5-benzodithiolyl group.

In another embodiment, Ar² is

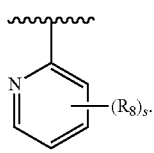

In another embodiment, Ar² is

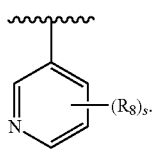

In another embodiment, Ar² is

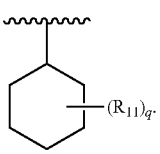

In another embodiment, Ar² is

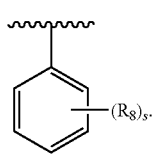

In another embodiment, Ar² is

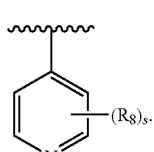

In another embodiment, Ar² is

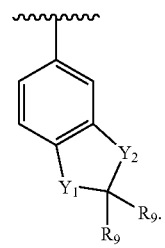

In another embodiment, p or n is 0.
In another embodiment, p or n is 1.
In another embodiment, m is 0.
In another embodiment, m is 0 and V is N.
In another embodiment, m is 0 and V is CH.
In another embodiment, m is 1.
In another embodiment, m is 1 and V is N.
In another embodiment, m is 1 and V is CH.
In another embodiment, Ar² is

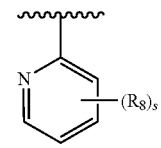

and s is 0.
In another embodiment, Ar² is

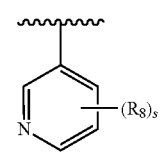

and s is 1.
In another embodiment, Ar² is

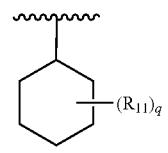

and q is 0.
In another embodiment, Ar² is

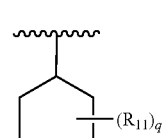

and q is 1.

In another embodiment, Ar² is

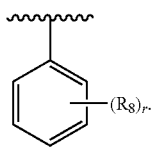

and r is 0.

In another embodiment, Ar² is

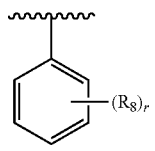

and r is 0.

In another embodiment, Ar² is a benzothiazolyl group and s is 0.

In another embodiment, Ar² is a benzoimidazolyl group and s is 0.

In another embodiment, Ar² is a benzooxazolyl group and s is 0.

In another embodiment, Ar² is a benzothiazolyl group and s is 1.

In another embodiment, Ar² is a benzoimidazolyl group and s is 1.

In another embodiment, Ar² is a benzooxazolyl group and s is 1.

In another embodiment, Ar² is a 5-benzodioxolyl group and each $R_9$ is —H.

In another embodiment, Ar² is a 5-benzodioxolyl group and each $R_9$ is —F.

In another embodiment, $R_1$ is —H.

In another embodiment, $R_2$ is -halo.

In another embodiment, $R_1$ is —$(C_1$-$C_4)$alkyl.

In another embodiment, $R_1$ is —$CH_3$ or —$CH_2CH_3$.

In another embodiment, $R_1$ is —$CH_2CH_3$.

In another embodiment, $R_1$ is —$CH_3$.

In another embodiment, $R_1$ is —$NO_2$.

In another embodiment, $R_1$ is —CN.

In another embodiment, $R_1$ is —OH.

In another embodiment, $R_1$ is —$OCH_3$.

In another embodiment, $R_1$ is —$NH_2$.

In another embodiment, $R_1$ is —$C(halo)_3$.

In another embodiment, $R_1$ is —$CH(halo)_2$.

In another embodiment, $R_1$ is —$CH_2(halo)$.

In another embodiment, n or p is 1 and $R_2$ is -halo, —CN, —OH, —$NO_2$, or —$NH_2$.

In another embodiment, n or p is 1 and $R_2$ is —$(C_1$-$C_{10})$alkyl, —$(C_2$-$C_{10})$alkenyl, —$(C_2$-$C_{10})$alkynyl, —$(C_3$-$C_{10})$cycloalkyl, —$(C_8$-$C_{14})$bicycloalkyl, —$(C_8$-$C_{14})$tricycloalkyl, —$(C_5$-$C_{10})$cycloalkenyl, —$(C_8$-$C_{14})$bicycloalkenyl, —$(C_8$-$C_{14})$tricycloalkenyl, -(3- to 7-membered)heterocycle, or -(7- to 10-membered)bicycloheterocycle, each of which is unsubstituted or substituted with one or more $R_5$ groups.

In another embodiment, n or p is 1 and $R_2$ is -phenyl, -naphthyl, —$(C_{14})$aryl or -(5- to 10-membered)heteroaryl, each of which is unsubstituted or substituted with one or more $R_6$ groups.

In another embodiment, m is 1, $R_3$ is attached to the 2-, 3-, 5-, or 6-position of the cyclo(hetero)alkenyl ring, and $R_3$ is -halo, —CN, —OH, —$NO_2$, or —$NH_2$;

In another embodiment, m is 1, $R_3$ is attached to the 2-, 3-, 5-, or 6-position of the cyclo(hetero)alkenyl ring, and $R_3$ is —$(C_1$-$C_{10})$alkyl, —$(C_2$-$C_{10})$alkenyl, —$(C_2$-$C_{10})$alkynyl, —$(C_3$-$C_{10})$cycloalkyl, —$(C_8$-$C_{14})$bicycloalkyl, —$(C_8$-$C_{14})$tricycloalkyl, —$(C_5$-$C_{10})$cycloalkenyl, —$(C_8$-$C_{14})$bicycloalkenyl, —$(C_8$-$C_{14})$tricycloalkenyl, -(3- to 7-membered)heterocycle, or -(7- to 10-membered)bicycloheterocycle, each of which is unsubstituted or substituted with one or more $R_5$ groups.

In another embodiment, m is 1, $R_3$ is attached to the 2-, 3-, 5-, or 6-position of the cyclo(hetero)alkenyl ring, and $R_3$ is -phenyl, -naphthyl, —$(C_{14})$aryl or -(5- to 10-membered)heteroaryl, each of which is unsubstituted or substituted with one or more $R_6$ groups.

In another embodiment, m is 1, $R_3$ is attached to the 2-, 3-, 5-, or 6-position of the cyclo(hetero)alkenyl ring, and $R_3$ is —$CH_3$.

In another embodiment, $R_4$ is —H.

In another embodiment, $R_4$ is —$(C_1$-$C_6)$alkyl.

In another embodiment, $R_4$ is ethyl.

In another embodiment, $R_4$ is methyl.

In another embodiment, $R_4$ is —H or methyl.

In another embodiment, each $R_8$ is independently —$(C_1$-$C_{10})$alkyl, —$(C_2$-$C_6)$alkenyl, —$(C_2$-$C_6)$alkynyl, —$(C_3$-$C_8)$cycloalkyl, —$(C_5$-$C_8)$cycloalkenyl, -(3- to 7-membered)heterocycle, -phenyl, —$C(halo)_3$, —$CH(halo)_2$, —$CH_2(halo)$, —CN, —OH, -halo, —$N_3$, —$NO_2$, —$N(R_7)_2$, —CH=$NR_7$, —$NR_7OH$, —$OR_7$, —$COR_7$, —$C(O)OR_7$, —$R_7C(O)OR_7$, —$OC(O)R_7$, —$R_7OC(O)R_7$, —$OC(O)OR_7$, —$R_7OC(O)OR_7$, —$SR_7$, —$S(O)R_7$, or —$S(O)_2R_7$.

In another embodiment, each $R_8$ is independently —$(C_1$-$C_6)$alkyl, —$(C_2$-$C_6)$alkenyl, —$(C_2$-$C_6)$alkynyl, —$(C_3$-$C_8)$cycloalkyl, —$(C_5$-$C_8)$cycloalkenyl, -phenyl, —$C(halo)_3$, —$CH(halo)_2$, —$CH_2(halo)$, —CN, —OH, -halo, —N3, —$NO_2$, —$N(R_7)_2$, —CH=$NR_7$, —$NR_7OH$, —$OR_7$, —$COR_7$, —$C(O)OR_7$, —$OC(O)R_7$, —$OC(O)OR_7$, —$SR_7$, —$S(O)R_7$, —$S(O)_2R_7$, or —$C(halo)_2C(halo)_3$.

In another embodiment, Ar² is a benzothiazolyl group, benzoimidazolyl group, or benzooxazolyl group and each $R_8$ is independently —H, halo, —$(C_1$-$C_6)$alkyl, —$O(C_1$-$C_6)$alkyl, —$C(halo)_3$, —$CH(halo)_2$, or —$CH_2(halo)$.

In another embodiment, Ar² is

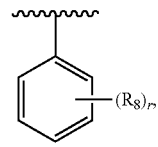

and each $R_8$ is independently —$(C_1$-$C_6)$alkyl, —$(C_2$-$C_6)$alkenyl, —$(C_2$-$C_6)$alkynyl, —$(C_3$-$C_8)$cycloalkyl, —$(C_5$-$C_8)$cycloalkenyl, -phenyl, —$C(halo)_3$, —$CH(halo)_2$, —$CH_2(halo)$, —CN, —OH, -halo, —$N_3$, —$NO_2$, —$N(R_7)_2$, —CH=$NR_7$, —$NR_7OH$, —$OR_7$, —$COR_7$, —$C(O)OR_7$, —$OC(O)R_7$, —$OC(O)OR_7$, —$SR_7$, —$S(O)R_7$, —$S(O)_2R_7$, —$C(halo)_2C(halo)_3$, —$C(halo)_2CH(halo)_2$, —$CH(C(halo)_3)_2$, —$CH(C(halo)_3)(CH_3)$, —$OC(halo)_2C(halo)_3$, —$OC(halo)_2CH(halo)_2$, —$OCH(C(halo)_3)_2$, —$OCH(C(halo)_3)(CH_3)$, or —$C(OH)(CF_3)_2$.

In another embodiment, Ar² is $$\text{[pyridyl structure with (R}_8\text{)}_s\text{, N at position 1, attachment at position 4]}$$

and each $R_8$ is independently —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, —C(halo)$_3$, —CH(halo)$_2$, —CH$_2$(halo), —CN, —OH, -halo, —N$_3$, —NO$_2$, —N(R$_7$)$_2$, —CH=NR$_7$, —NR$_7$OH, —OR$_7$, —COR$_7$, —C(O)OR$_7$, —OC(O)R$_7$, —OC(O)OR$_7$, —SR$_7$, —S(O)R$_7$, —S(O)$_2$R$_7$, —C(halo)$_2$C(halo)$_3$, —C(halo)$_2$CH(halo)$_2$, —CH(C(halo)$_3$)$_2$, —CH(C(halo)$_3$)(CH$_3$), —OC(halo)$_2$C(halo)$_3$, —OC(halo)$_2$CH(halo)$_2$, —OCH(C(halo)$_3$)$_2$, —OCH(C(halo)$_3$)(CH$_3$), or —C(OH)(CF$_3$)$_2$.

In another embodiment, Ar² is $$\text{[pyridyl structure with (R}_8\text{)}_s\text{, N at position 1, attachment at position 2]}$$

and each $R_8$ is independently —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, —C(halo)$_3$, —CH(halo)$_2$, —CH$_2$(halo), —CN, —OH, -halo, —N$_3$, —NO$_2$, —N(R$_7$)$_2$, —CH=NR$_7$, —NR$_7$OH, —OR$_7$, —COR$_7$, —C(O)OR$_7$, —OC(O)R$_7$, —OC(O)OR$_7$, —SR$_7$, —S(O)R$_7$, —S(O)$_2$R$_7$, —C(halo)$_2$C(halo)$_3$, —C(halo)$_2$CH(halo)$_2$, —CH(C(halo)$_3$)$_2$, —CH(C(halo)$_3$)(CH$_3$), —OC(halo)$_2$C(halo)$_3$, —OC(halo)$_2$CH(halo)$_2$, —OCH(C(halo)$_3$)$_2$, —OCH(C(halo)$_3$)(CH$_3$), or —C(OH)(CF$_3$)$_2$.

In another embodiment, Ar² is $$\text{[cyclohexyl structure with (R}_{11}\text{)}_q\text{]}$$

and each $R_{11}$ is independently —CN, —OH, —($C_1$-$C_6$)alkyl, —($C_2$-$C_6$)alkenyl, —($C_2$-$C_6$)alkynyl, -halo, —N$_3$, —NO$_2$, —N(R$_7$)$_2$, —CH=NR$_7$, —NR$_7$OH, —OR$_7$, —COR$_7$, —C(O)OR$_7$, —OC(O)R$_7$, or —OC(O)OR$_7$.

In another embodiment, Ar¹ is a pyridyl group; V is N; m is 0, and Ar² is a benzothiazolyl group.

In another embodiment, Ar¹ is a pyridyl group; V is N; n is 0; m is 0; $R_1$ is —F, —Cl, —Br, or —I; Ar² is a benzothiazolyl group; and s is 0.

In another embodiment, Ar¹ is a pyridyl group; V is N; n is 0; m is 0; $R_1$ is —F; Ar² is a benzothiazolyl group; and s is 0.

In another embodiment, Ar¹ is a pyridyl group; V is N; n is 0; m is 0; $R_1$ is —Cl; Ar² is a benzothiazolyl group; and s is 0.

In another embodiment, Ar¹ is a pyridyl group; V is N; n is 0; m is 0; $R_1$ is —Br; Ar² is a benzothiazolyl group; and s is 0.

In another embodiment, Ar¹ is a pyridyl group; V is N; n is 0; m is 0; $R_1$ is —I; Ar² is a benzothiazolyl group; and s is 0.

In another embodiment, Ar¹ is a pyridyl group; V is N; n is 0; m is 0; $R_1$ is —CH$_3$; Ar² is a benzothiazolyl group; and s is 0.

In another embodiment, Ar¹ is a pyridyl group; V is N; n is 0; m is 0; $R_1$ is —CF$_3$; Ar² is a benzothiazolyl group; and s is 0.

In another embodiment, Ar¹ is a pyridyl group; V is N; n is 0; m is 0; $R_1$ is —F, —Cl —Br, or —I; Ar² is a benzothiazolyl group; s is 1; and $R_8$ is -halo.

In another embodiment, Ar¹ is a pyridyl group; V is N; n is 0; m is 0; $R_1$ is —F; Ar² is a benzothiazolyl group; s is 1; and $R_8$ is -halo.

In another embodiment, Ar¹ is a pyridyl group; V is N; n is 0; m is 0; $R_1$ is —Cl; Ar² is a benzothiazolyl group; s is 1; and $R_8$ is -halo.

In another embodiment, Ar¹ is a pyridyl group; V is N; n is 0; m is 0; $R_1$ is —Br; Ar² is a benzothiazolyl group; s is 1; and $R_8$ is -halo.

In another embodiment, Ar¹ is a pyridyl group; V is N; n is 0; m is 0; $R_1$ is —I; Ar² is a benzothiazolyl group; $R_8$ s is 1; and $R_8$ is -halo.

In another embodiment, Ar¹ is a pyridyl group; V is N; n is 0; m is 0; $R_1$ is —CH$_3$; Ar² is a benzothiazolyl group; s is 1; and $R_8$ is -halo.

In another embodiment, Ar¹ is a pyridyl group; V is N; n is 0; m is 0; $R_1$ is —CF$_3$; Ar² is a benzothiazolyl group; s is 1; and $R_8$ is -halo.

In another embodiment, Ar¹ is a pyridyl group; V is N; n is 0; m is 0; $R_1$ is —F, —Cl, —Br, or —I; Ar² is a benzothiazolyl group; s is 1; and $R_8$ is —Br.

In another embodiment, Ar¹ is a pyridyl group; V is N; n is 0; m is 0; $R_1$ is —F; Ar² is a benzothiazolyl group; s is 1; and $R_8$ is —Br.

In another embodiment, Ar¹ is a pyridyl group; V is N; n is 0; m is 0; $R_1$ is —Cl; Ar² is a benzothiazolyl group; s is 1; and $R_8$ is —Br.

In another embodiment, Ar¹ is a pyridyl group; V is N; n is 0; m is 0; $R_1$ is —Br; Ar² is a benzothiazolyl group; s is 1; and $R_8$ is —Br.

In another embodiment, Ar¹ is a pyridyl group; V is N; n is 0; m is 0; $R_1$ is —I; Ar² is a benzothiazolyl group; s is 1; and $R_8$ is —Br.

In another embodiment, Ar¹ is a pyridyl group; V is N; n is 0; m is 0; $R_1$ is —CH$_3$; Ar² is a benzothiazolyl group; s is 1; and $R_8$ is —Br.

In another embodiment, Ar¹ is a pyridyl group; V is N; n is 0; m is 0; $R_1$ is —CF$_3$; Ar² is a benzothiazolyl group; s is 1; and $R_8$ is —Br.

In another embodiment, Ar¹ is a pyridyl group; V is N; n is 0; m is 0; $R_1$ is —Cl, —F —Br, or —I; Ar² is a benzothiazolyl group; s is 1; and $R_8$ is —F.

In another embodiment, Ar¹ is a pyridyl group; V is N; n is 0; m is 0; $R_1$ is —F; Ar² is a benzothiazolyl group; s is 1; and $R_8$ is —F.

In another embodiment, Ar¹ is a pyridyl group; V is N; n is 0; m is 0; $R_1$ is —Cl; Ar² is a benzothiazolyl group; s is 1; and $R_8$ is —F.

In another embodiment, Ar¹ is a pyridyl group; V is N; n is 0; m is 0; $R_1$ is —Br; Ar² is a benzothiazolyl group; s is 1; and $R_8$ is —F.

In another embodiment, Ar¹ is a pyridyl group; V is N; n is 0; m is 0; $R_1$ is —I; Ar² is a benzothiazolyl group; s is 1; and $R_8$ is —F.

In another embodiment, Ar¹ is a pyridyl group; V is N; n is 0; m is 0; $R_1$ is —CH$_3$; Ar² is a benzothiazolyl group; s is 1; and $R_8$ is —F.

In another embodiment, Ar¹ is a pyridyl group; V is N; n is 0; m is 0; $R_1$ is —CF$_3$; Ar² is a benzothiazolyl group; s is 1; and $R_8$ is —F.

In another embodiment, $Ar^1$ is a pyridyl group; V is N; n is 0; m is 0; $R_1$ is —Cl, —F —Br, or —I; $Ar^2$ is a benzothiazolyl group; s is 1; and $R_8$ is —Cl.

In another embodiment, $Ar^1$ is a pyridyl group; V is N; n is 0; m is 0; $R_1$ is —F; $Ar^2$ is a benzothiazolyl group; s is 1; and $R_8$ is —Cl.

In another embodiment, $Ar^1$ is a pyridyl group; V is N; n is 0; m is 0; $R_1$ is —Cl; $Ar^2$ is a benzothiazolyl group; s is 1; and $R_8$ is —Cl.

In another embodiment, $Ar^1$ is a pyridyl group; V is N; n is 0; m is 0; $R_1$ is —Br; $Ar^2$ is a benzothiazolyl group; s is 1; and $R_8$ is —Cl.

In another embodiment, $Ar^1$ is a pyridyl group; V is N; n is 0; m is 0; $R_1$ is —I; $Ar^2$ is a benzothiazolyl group; s is 1; and $R_8$ is —Cl.

In another embodiment, $Ar^1$ is a pyridyl group; V is N; n is 0; m is 0; $R_1$ is —$CH_3$; $Ar^2$ is a benzothiazolyl group; s is 1; and $R_8$ is —Cl.

In another embodiment, $Ar^1$ is a pyridyl group; V is N; n is 0; m is 0; $R_1$ is —$CF_3$; $Ar^2$ is a benzothiazolyl group s is 1; and $R_8$ is —Cl.

In another embodiment, $Ar^1$ is a pyridyl group; V is N; n is 0; m is 0; $R_1$ is —Cl, —F, —Br, or —I; $Ar^2$ is a benzothiazolyl group; s is 1; and $R_8$ is —I.

In another embodiment, $Ar^1$ is a pyridyl group; V is N; n is 0; m is 0; $R_1$ is —F; $Ar^2$ is a benzothiazolyl group; s is 1; and $R_8$ is —I.

In another embodiment, $Ar^1$ is a pyridyl group; V is N; n is 0; m is 0; $R_1$ is —Cl; $Ar^2$ is a benzothiazolyl group; s is 1; and $R_8$ is —I.

In another embodiment, $Ar^1$ is a pyridyl group; V is N; n is 0; m is 0; $R_1$ is —Br; $Ar^2$ is a benzothiazolyl group; s is 1; and $R_8$ is —I.

In another embodiment, $Ar^1$ is a pyridyl group; V is N; n is 0; m is 0; $R_1$ is —I; $Ar^2$ is a benzothiazolyl group; s is 1; and $R_8$ is —I.

In another embodiment, $Ar^1$ is a pyridyl group; V is N; n is 0; m is 0; $R_1$ is —$CH_3$; $Ar^2$ is a benzothiazolyl group; s is 1; and $R_8$ is —I.

In another embodiment, $Ar^1$ is a pyridyl group; V is N; n is 0; m is 0; $R_1$ is —$CF_3$; $Ar^2$ is a benzothiazolyl group; s is 1; and $R_8$ is —I.

In another embodiment, $Ar^1$ is a pyridyl group; V is N; n is 0; m is 0; $R_1$ is —F, —Cl, —Br, or —I; $Ar^2$ is a benzothiazolyl group; s is 1; and $R_8$ is —$CH_3$.

In another embodiment, $Ar^1$ is a pyridyl group; V is N; n is 0; m is 0; $R_1$ is —F; $Ar^2$ is a benzothiazolyl group; s is 1; and $R_8$ is —$CH_3$.

In another embodiment, $Ar^1$ is a pyridyl group; V is N; n is 0; m is 0; $R_1$ is —Cl; $Ar^2$ is a benzothiazolyl group; s is 1; and $R_8$ is —$CH_3$.

In another embodiment, $Ar^1$ is a pyridyl group; V is N; n is 0; m is 0; $R_1$ is —Br; $Ar^2$ is a benzothiazolyl group; s is 1; and $R_8$ is —$CH_3$.

In another embodiment, $Ar^1$ is a pyridyl group; V is N; n is 0; m is 0; $R_1$ is —I; $Ar^2$ is a benzothiazolyl group; s is 1; and $R_8$ is —$CH_3$.

In another embodiment, $Ar^1$ is a pyridyl group; V is N; n is 0; m is 0; $R_1$ is —$CH_3$; $Ar^2$ is a benzothiazolyl group; s is 1; and $R_8$ is —$CH_3$.

In another embodiment, $Ar^1$ is a pyridyl group; V is N; n is 0; m is 0; $R_1$ is —$CF_3$; $Ar^2$ is a benzothiazolyl group; s is 1; and $R_8$ is —$CH_3$.

In another embodiment, $Ar^1$ is a pyridyl group; V is N; n is 0; m is 0; $R_1$ is —F, —Cl, —Br, or —I; $Ar^2$ is a benzothiazolyl group; s is 1; and $R_8$ is —$CF_3$.

In another embodiment, $Ar^1$ is a pyridyl group; V is N; n is 0; m is 0; $R_1$ is —F; $Ar^2$ is a benzothiazolyl group; s is 1; and $R_8$ is —$CF_3$.

In another embodiment, $Ar^1$ is a pyridyl group; V is N; n is 0; m is 0; $R_1$ is —Cl; $Ar^2$ is a benzothiazolyl group; s is 1; and $R_8$ is —$CF_3$.

In another embodiment, $Ar^1$ is a pyridyl group; V is N; n is 0; m is 0; $R_1$ is —Br; $Ar^2$ is a benzothiazolyl group; s is 1; and $R_8$ is —$CF_3$.

In another embodiment, $Ar^1$ is a pyridyl group; V is N; n is 0; m is 0; $R_1$ is —I; $Ar^2$ is a benzothiazolyl group; s is 1; and $R_8$ is —$CF_3$.

In another embodiment, $Ar^1$ is a pyridyl group; V is N; n is 0; m is 0; $R_1$ is —$CH_3$; $Ar^2$ is a benzothiazolyl group; s is 1; and $R_8$ is —$CF_3$.

In another embodiment, $Ar^1$ is a pyridyl group; V is N; n is 0; m is 0; $R_1$ is —$CF_3$; $Ar^2$ is a benzothiazolyl group; s is 1; and $R_8$ is —$CF_3$.

In another embodiment, $Ar^1$ is a pyridyl group; V is N; n is 0; m is 0; $R_1$ is —F, —Cl —Br, or —I; $Ar^2$ is a benzothiazolyl group; s is 1; and $R_8$ is —$OCH_2CH_3$.

In another embodiment, $Ar^1$ is a pyridyl group; V is N; n is 0; m is 0; $R_1$ is —F; $Ar^2$ is a benzothiazolyl group; s is 1; and $R_8$ is —$OCH_2CH_3$.

In another embodiment, $Ar^1$ is a pyridyl group; V is N; n is 0; m is 0; $R_1$ is —Cl; $Ar^2$ is a benzothiazolyl group; s is 1; and $R_8$ is —$OCH_2CH_3$.

In another embodiment, $Ar^1$ is a pyridyl group; V is N; n is 0; m is 0; $R_1$ is —Br; $Ar^2$ is a benzothiazolyl group; s is 1; and $R_8$ is —$OCH_2CH_3$.

In another embodiment, $Ar^1$ is a pyridyl group; V is N; n is 0; m is 0; $R_1$ is —I; $Ar^2$ is a benzothiazolyl group; s is 1; and $R_8$ is —$OCH_2CH_3$.

In another embodiment, $Ar^1$ is a pyridyl group; V is N; n is 0; m is 0; $R_1$ is —$CH_3$; $Ar^2$ is a benzothiazolyl group; s is 1; and $R_8$ is —$OCH_2CH_3$.

In another embodiment, $Ar^1$ is a pyridyl group; V is N; n is 0; m is 0; $R_1$ is —$CF_3$; $Ar^2$ is a benzothiazolyl group; s is 1; and $R_8$ is —$OCH_2CH_3$.

In another embodiment, $Ar^1$ is a pyridyl group; V is N; n is 0; m is 0; $R_1$ is —F, —Cl —Br, or —I; $Ar^2$ is a benzothiazolyl group; $R_8$ is -tert-butyl.

In another embodiment, $Ar^1$ is a pyridyl group; V is N; n is 0; m is 0; $R_1$ is —F; $Ar^2$ is a benzothiazolyl group; s is 1; and $R_8$ is -tert-butyl.

In another embodiment, $Ar^1$ is a pyridyl group; V is N; n is 0; m is 0; $R_1$ is —Cl; $Ar^2$ is a benzothiazolyl group; s is 1; and $R_8$ is -tert-butyl.

In another embodiment, $Ar^1$ is a pyridyl group; V is N; n is 0; m is 0; $R_1$ is —Br; $Ar^2$ is a benzothiazolyl group; s is 1; and $R_8$ is -tert-butyl.

In another embodiment, $Ar^1$ is a pyridyl group; V is N; n is 0; m is 0; $R_1$ is —I; $Ar^2$ is a benzothiazolyl group; s is 1; and $R_8$ is -tert-butyl.

In another embodiment, $Ar^1$ is a pyridyl group; V is N; n is 0; m is 0; $R_1$ is —$CH_3$; $Ar^2$ is a benzothiazolyl group; s is 1; and $R_8$ is -tert-butyl.

In another embodiment, $Ar^1$ is a pyridyl group; V is N; n is 0; m is 0; $R_1$ is —$CF_3$; $Ar^2$ is a benzothiazolyl group; s is 1; and $R_8$ is -tert-butyl.

In another embodiment, $Ar^1$ is a pyridyl group; V is N; n is 0; m is 1; $R_3$ is —$CH_3$; $R_1$ is —F, —Cl, —Br, or —I; $Ar^2$ is a benzothiazolyl group; and s is 0. In another embodiment, the $R_3$ group is attached to the 3-, 5- or 6-position of the cyclo (hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl rig.

In another embodiment, $Ar^1$ is a pyridyl group; V is N; n is 0; m is 1; $R_3$ is —$CH_3$; $R_1$ is —F; $Ar^2$ is a benzothiazolyl group; and s is 0. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, Art is a pyridyl group; V is N; n is 0; m is 1; $R_3$ is —$CH_3$; $R_1$ is —Cl; $Ar^2$ is a benzothiazolyl group; and s is 0. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Br; $Ar^2$ is a benzothiazolyl group; and s is 0. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —I; $Ar^2$ is a benzothiazolyl group; and s is 0. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CH_3$; $Ar^2$ is a benzothiazolyl group; and s is 0. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CF_3$; $Ar^2$ is a benzothiazolyl group; and s is 1. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —F, —Cl, —Br, or —I; $Ar^2$ is a benzothiazolyl group; s is 1; and $R_8$ is -halo. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —F; $Ar^2$ is a benzothiazolyl group; s is 1; and $R_8$ is -halo. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Cl; $Ar^2$ is a benzothiazolyl group; s is 1; and $R_8$ is -halo. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Br; $Ar^2$ is a benzothiazolyl group; s is 1; and $R_8$ is -halo. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —I; $Ar^2$ is a benzothiazolyl group; s is 1; and $R_8$ is -halo. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CH_3$; $Ar^2$ is a benzothiazolyl group; s is 1; and $R_8$ is -halo. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CF_3$; $Ar^2$ is a benzothiazolyl group; s is 1; and $R_8$ is -halo. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —F, —Cl, —Br, or —I; $Ar^2$ is a benzothiazolyl group; s is 1; and $R_8$ is —Br. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —F; $Ar^2$ is a benzothiazolyl group; s is 1; and $R_8$ is —Br. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Cl; $Ar^2$ is a benzothiazolyl group; s is 1; and $R_8$ is —Br. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Br; $Ar^2$ is a benzothiazolyl group; s is 1; and $R_8$ is —Br. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —I; $Ar^2$ is a benzothiazolyl group; s is 1; and $R_8$ is —Br. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CH_3$; $Ar^2$ is a benzothiazolyl group; s is 1; and $R_8$ is —Br. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CF_3$; $Ar^2$ is a benzothiazolyl group; s is 1; and $R_8$ is —Br. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Cl; —F —Br, or —I; $Ar^2$ is a benzothiazolyl group; s is 1; and $R_8$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —F; $Ar^2$ is a benzothiazolyl group; s is 1; and $R_8$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Cl; $Ar^2$ is a benzothiazolyl group; s is 1; and $R_8$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Br; $Ar^2$ is a benzothiazolyl group; s is 1; and $R_8$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —I; $Ar^2$ is a benzothiazolyl group; s is 1; and $R_8$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CH_3$; $Ar^2$ is a benzothiazolyl group; s is 1; and $R_8$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CF_3$; $Ar^2$ is a benzothiazolyl group; s is 1; and $R_8$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is $CH_3$; $R_1$ is —Cl, —F —Br, or —I; $Ar^2$ is a benzothiazolyl group; s is 1; and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —F; $Ar^2$ is a benzothiazolyl group; s is 1; and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Cl; $Ar^2$ is a benzothiazolyl group; s is 1; and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Br; $Ar^2$ is a benzothiazolyl group; s is 1; and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —I; $Ar^2$ is a benzothiazolyl group; s is 1; and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CH_3$; $Ar^2$ is a benzothiazolyl group; s is 1; and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CF_3$; $Ar^2$ is a benzothiazolyl group; s is 1; and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Cl, —F, —Br, or —I, $Ar^2$ is a benzothiazolyl group; s is 1; and $R_8$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —F; $Ar^2$ is a benzothiazolyl group; s is 1; and $R_8$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Cl; $Ar^2$ is a benzothiazolyl group; s is 1; and $R_8$ is —I. In another embodiment, the $R_3$ group is attached to the 3-, 5- or 6-position of the cyclo (hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Br; $Ar^2$ is a benzothiazolyl group; s is 1; and $R_8$ is —I. In another embodiment, the $R_3$ group is attached to the 3-, 5- or 6-position of the cyclo (hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —I; $Ar^2$ is a benzothiazolyl group; s is 1; and $R_8$ is —I. In another embodiment, the $R_3$ group is attached to the 3-, 5- or 6-position of the cyclo (hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CH_3$; $Ar^2$ is a benzothiazolyl group; s is 1; and $R_8$ is —I. In another embodiment, the $R_3$ group is attached to the 3-, 5- or 6-position of the cyclo (hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CF_3$; $Ar^2$ is a benzothiazolyl group; s is 1; and $R_8$ is —I. In another embodiment, the $R_3$ group is attached to the 3-, 5- or 6-position of the cyclo (hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —F, —Cl, —Br, or —I; $Ar^2$ is a benzothiazolyl group; s is 1; and $R_8$ is —$CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —F; $Ar^2$ is a benzothiazolyl group; s is 1; and $R_8$ is —$CH_3$. In another embodiment, the $R_3$ group is attached to the 3-, 5- or 6-position of the cyclo (hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Cl; $Ar^2$ is a benzothiazolyl group; s is 1; and $R_8$ is —$CH_3$. In another embodiment, the $R_3$ group is attached to the 3-, 5- or 6-position of the cyclo (hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Br; $Ar^2$ is a benzothiazolyl group; s is 1; and $R_8$ is —$CH_3$. In another embodiment, the $R_3$ group is attached to the 3-, 5- or 6-position of the cyclo (hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —I; $Ar^2$ is a benzothiazolyl group; s is 1; and $R_8$ is —$CH_3$. In another embodiment, the $R_3$ group is attached to the 3-, 5- or 6-position of the cyclo (hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CH_3$; $Ar^2$ is a benzothiazolyl group; s is 1; and $R_8$ is —$CH_3$. In another embodiment, the $R_3$ group is attached to the 3-, 5- or 6-position of the cyclo (hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CF_3$; $Ar^2$ is a benzothiazolyl group; s is 1; and $R_8$ is —$CH_3$. In another embodiment, the $R_3$ group is attached to the 3-, 5- or 6-position of the cyclo (hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —F, —Cl, —Br, or —I; $Ar^2$ is a benzothiazolyl group; s is 1; and $R_8$ is —$CF_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —F; $Ar^2$ is a benzothiazolyl group; s is 1; and $R_8$ is —$CF_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Cl; $Ar^2$ is a benzothiazolyl group; s is 1; and $R_8$ is —$CF_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Br; $Ar^2$ is a benzothiazolyl group; s is 1; and $R_8$ is —$CF_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —I; $Ar^2$ is a benzothiazolyl group; s is 1; and $R_8$ is —$CF_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CH_3$; $Ar^2$ is a benzothiazolyl group; s is 1; and $R_8$ is —$CF_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CF_3$; $Ar^2$ is a benzothiazolyl group; s is 1; and $R_8$ is —$CF_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —F, —Cl, —Br, or —I; $Ar^2$ is a benzothiazolyl group; s is 1; and $R_8$ is —$OCH_2CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —F; $Ar^2$ is a benzothiazolyl group; s is 1; and $R_8$ is —$OCH_2CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Cl; $Ar^2$ is a benzothiazolyl group; s is 1; and $R_8$ is —$OCH_2CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Br; $Ar^2$ is a benzothiazolyl group; s is 1; and $R_8$ is —$OCH_2CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —I; $Ar^2$ is a benzothiazolyl group; s is 1; and $R_8$ is —$OCH_2CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CH_3$; $Ar^2$ is a benzothiazolyl group; s is 1; and $R_8$ is —$OCH_2CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CF_3$; $Ar^2$ is a benzothiazolyl group; s is 1; and $R_8$ is —$OCH_2CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —F, —Cl, —Br, or —I; $Ar^2$ is a benzothiazolyl group; s is 1; and $R_8$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —F; $Ar^2$ is a benzothiazolyl group; s is 1; and $R_8$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Cl; $Ar^2$ is a benzothiazolyl group; s is 1; and $R_8$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Br; $Ar^2$ is a benzothiazolyl group; s is 1; and $R_8$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —I; $Ar^2$ is a benzothiazolyl group; s is 1; and $R_8$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CH_3$; $Ar^2$ is a benzothiazolyl group; s is 1; and $R_8$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CF_3$; $Ar^2$ is a benzothiazolyl group; s is 1; and $R_8$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group, V is CH; m is 0, and $Ar^2$ is a benzothiazolyl group.

In another embodiment, $Ar^1$ is a pyridyl group; V is CH; n is 0; m is 0; $R_1$ is —F, —Cl, —Br, or —I; $Ar^2$ is a benzothiazolyl group; and s is 0.

In another embodiment, $Ar^1$ is a pyridyl group; V is CH; n is 0; m is 0; $R_1$ is —F; $Ar^2$ is a benzothiazolyl group; and s is 0.

In another embodiment, $Ar^1$ is a pyridyl group; V is CH; n is 0; m is 0; $R_1$ is —Cl; $Ar^2$ is a benzothiazolyl group; and s is 0.

In another embodiment, $Ar^1$ is a pyridyl group; V is CH; n is 0; m is 0; $R_1$ is —Br; $Ar^2$ is a benzothiazolyl group; and s is 0.

In another embodiment, $Ar^1$ is a pyridyl group; V is CH; n is 0; m is 0; $R_1$ is —I; $Ar^2$ is a benzothiazolyl group; and s is 0.

In another embodiment, $Ar^1$ is a pyridyl group; V is CH; n is 0; m is 0; $R_1$ is —$CH_3$; $Ar^2$ is a benzothiazolyl group; and s is 0.

In another embodiment, $Ar^1$ is a pyridyl group; V is CH; n is 0; m is 0; $R_1$ is —$CF_3$; $Ar^2$ is a benzothiazolyl group; and s is 0.

In another embodiment, $Ar^1$ is a pyridyl group; V is CH; n is 0; m is 0; $R_1$ is —F, —Cl, —Br, or —I; $Ar^2$ is a benzothiazolyl group; s is 1; and $R_8$ is -halo.

In another embodiment, $Ar^1$ is a pyridyl group; V is CH; n is 0; m is 0; $R_1$ is —F; $Ar^2$ is a benzothiazolyl group; s is 1; and $R_8$ is -halo.

In another embodiment, $Ar^1$ is a pyridyl group; V is CH; n is 0; m is 0; $R_1$ is —Cl; $Ar^2$ is a benzothiazolyl group; s is 1; and $R_8$ is -halo.

In another embodiment, $Ar^1$ is a pyridyl group; V is CH; n is 0; m is 0; $R_1$ is —Br; $Ar^2$ is a benzothiazolyl group; s is 1; and $R_8$ is -halo.

In another embodiment, $Ar^1$ is a pyridyl group; V is CH; n is 0; m is 0; $R_1$ is —I; $Ar^2$ is a benzothiazolyl group; $R_8$ s is 1; and $R_8$ is -halo.

In another embodiment, $Ar^1$ is a pyridyl group; V is CH; n is 0; m is 0; $R_1$ is —CH$_3$; $Ar^2$ is a benzothiazolyl group; s is 1; and $R_8$ is -halo.

In another embodiment, $Ar^1$ is a pyridyl group; V is CH; n is 0; m is 0; $R_1$ is —CF$_3$; $Ar^2$ is a benzothiazolyl group; s is 1; and $R_8$ is -halo.

In another embodiment, $Ar^1$ is a pyridyl group; V is CH; n is 0; m is 0; $R_1$ is —F, —Cl, —Br, or —I; $Ar^2$ is a benzothiazolyl group; s is 1; and $R_8$ is —Br.

In another embodiment, $Ar^1$ is a pyridyl group; V is CH; n is 0; m is 0; $R_1$ is —F; $Ar^2$ is a benzothiazolyl group; s is 1; and $R_8$ is —Br.

In another embodiment, $Ar^1$ is a pyridyl group; V is CH; n is 0; m is 0; $R_1$ is —Cl; $Ar^2$ is a benzothiazolyl group; s is 1; and $R_8$ is —Br.

In another embodiment, $Ar^1$ is a pyridyl group; V is CH; n is 0; m is 0; $R_1$ is —Br; $Ar^2$ is a benzothiazolyl group; s is 1; and $R_8$ is —Br.

In another embodiment, $Ar^1$ is a pyridyl group; V is CH; n is 0; m is 0; $R_1$ is —I; $Ar^2$ is a benzothiazolyl group; s is 1; and $R_8$ is —Br.

In another embodiment, $Ar^1$ is a pyridyl group; V is CH; n is 0; m is 0; $R_1$ is —CH$_3$; $Ar^2$ is a benzothiazolyl group; s is 1; and $R_8$ is —Br.

In another embodiment, $Ar^1$ is a pyridyl group; V is CH; n is 0; m is 0; $R_1$ is —CF$_3$; $Ar^2$ is a benzothiazolyl group; s is 1; and $R_8$ is —Br.

In another embodiment, $Ar^1$ is a pyridyl group; V is CH; n is 0; m is 0; $R_1$ is —Cl, —F —Br, or —I; $Ar^2$ is a benzothiazolyl group; s is 1; and $R_8$ is —F.

In another embodiment, $Ar^1$ is a pyridyl group; V is CH; n is 0; m is 0; $R_1$ is —F; $Ar^2$ is a benzothiazolyl group; s is 1; and $R_8$ is —F.

In another embodiment, $Ar^1$ is a pyridyl group; V is CH; n is 0; m is 0; $R_1$ is —Cl; $Ar^2$ is a benzothiazolyl group; s is 1; and $R_8$ is —F.

In another embodiment, $Ar^1$ is a pyridyl group; V is CH; n is 0; m is 0; $R_1$ is —Br; $Ar^2$ is a benzothiazolyl group; s is 1; and $R_8$ is —F.

In another embodiment, $Ar^1$ is a pyridyl group; V is CH; n is 0; m is 0; $R_1$ is —I; $Ar^2$ is a benzothiazolyl group; s is 1; and $R_8$ is —F.

In another embodiment, $Ar^1$ is a pyridyl group; V is CH; n is 0; m is 0; $R_1$ is —CH$_3$; $Ar^2$ is a benzothiazolyl group; s is 1; and $R_8$ is —F.

In another embodiment, $Ar^1$ is a pyridyl group; V is CH; n is 0; m is 0; $R_1$ is —CF$_3$; $Ar^2$ is a benzothiazolyl group; s is 1; and $R_8$ is —F.

In another embodiment, $Ar^1$ is a pyridyl group; V is CH; n is 0; m is 0; $R_1$ is —Cl, —F—Br, or —I; $Ar^2$ is a benzothiazolyl group; s is 1; and $R_8$ is —Cl.

In another embodiment, $Ar^1$ is a pyridyl group; V is CH; n is 0; m is 0; $R_1$ is —F; $Ar^2$ is a benzothiazolyl group; s is 1; and $R_8$ is —Cl.

In another embodiment, $Ar^1$ is a pyridyl group; V is CH; n is 0; m is 0; $R_1$ is —Cl; $Ar^2$ is a benzothiazolyl group; s is 1; and $R_8$ is —Cl.

In another embodiment, $Ar^1$ is a pyridyl group; V is CH; n is 0; m is 0; $R_1$ is —Br; $Ar^2$ is a benzothiazolyl group; s is 1; and $R_8$ is —Cl.

In another embodiment, $Ar^1$ is a pyridyl group; V is CH; n is 0; m is 0; $R_1$ is —I; $Ar^2$ is a benzothiazolyl group; s is 1; and $R_8$ is —Cl.

In another embodiment, $Ar^1$ is a pyridyl group; V is CH; n is 0; m is 0; $R_1$ is —CH$_3$; $Ar^2$ is a benzothiazolyl group; s is 1; and $R_8$ is —Cl.

In another embodiment, $Ar^1$ is a pyridyl group; V is CH; n is 0; m is 0; $R_1$ is —CF$_3$; $Ar^2$ is a benzothiazolyl group s is 1; and $R_8$ is —Cl.

In another embodiment, $Ar^1$ is a pyridyl group; V is CH; n is 0; m is 0; $R_1$ is —Cl, —F, —Br, or —I, $Ar^2$ is a benzothiazolyl group; s is 1; and $R_8$ is —I.

In another embodiment, $Ar^1$ is a pyridyl group; V is CH; n is 0; m is 0; $R_1$ is —F; $Ar^2$ is a benzothiazolyl group; s is 1; and $R_8$ is —I.

In another embodiment, $Ar^1$ is a pyridyl group; V is CH; n is 0; m is 0; $R_1$ is —Cl; $Ar^2$ is a benzothiazolyl group; s is 1; and $R_8$ is —I.

In another embodiment, $Ar^1$ is a pyridyl group; V is CH; n is 0; m is 0; $R_1$ is —Br; $Ar^2$ is a benzothiazolyl group; s is 1; and $R_8$ is —I.

In another embodiment, $Ar^1$ is a pyridyl group; V is CH; n is 0; m is 0; $R_1$ is —I; $Ar^2$ is a benzothiazolyl group; s is 1; and $R_8$ is —I.

In another embodiment, $Ar^1$ is a pyridyl group; V is CH; n is 0; m is 0; $R_1$ is —CH$_3$; $Ar^2$ is a benzothiazolyl group; s is 1; and $R_8$ is —I.

In another embodiment, $Ar^1$ is a pyridyl group; V is CH; n is 0; m is 0; $R_1$ is —CF$_3$; $Ar^2$ is a benzothiazolyl group; s is 1; and $R_8$ is —I.

In another embodiment, $Ar^1$ is a pyridyl group; V is CH; n is 0; m is 0; $R_1$ is —F, —Cl, —Br, or —I; $Ar^2$ is a benzothiazolyl group; s is 1; and $R_8$ is —CH$_3$.

In another embodiment, $Ar^1$ is a pyridyl group; V is CH; n is 0; m is 0; $R_1$ is —F; $Ar^2$ is a benzothiazolyl group; s is 1; and $R_8$ is —CH$_3$.

In another embodiment, $Ar^1$ is a pyridyl group; V is CH; n is 0; m is 0; $R_1$ is —Cl; $Ar^2$ is a benzothiazolyl group; s is 1; and $R_8$ is —CH$_3$.

In another embodiment, $Ar^1$ is a pyridyl group; V is CH; n is 0; m is 0; $R_1$ is —Br; $Ar^2$ is a benzothiazolyl group; s is 1; and $R_8$ is —CH$_3$.

In another embodiment, $Ar^1$ is a pyridyl group; V is CH; n is 0; m is 0; $R_1$ is —I; $Ar^2$ is a benzothiazolyl group; s is 1; and $R_8$ is —CH$_3$.

In another embodiment, $Ar^1$ is a pyridyl group; V is CH; n is 0; m is 0; $R_1$ is —CH$_3$; $Ar^2$ is a benzothiazolyl group; s is 1; and $R_8$ is —CH$_3$.

In another embodiment, $Ar^1$ is a pyridyl group; V is CH; n is 0; m is 0; $R_1$ is —CF$_3$; $Ar^2$ is a benzothiazolyl group; s is 1; and $R_8$ is —CH$_3$.

In another embodiment, $Ar^1$ is a pyridyl group; V is CH; n is 0; m is 0; $R_1$ is —F, —Cl, —Br, or —I; $Ar^2$ is a benzothiazolyl group; s is 1; and $R_8$ is —CF$_3$.

In another embodiment, $Ar^1$ is a pyridyl group; V is CH; n is 0; m is 0; $R_1$ is —F; $Ar^2$ is a benzothiazolyl group; s is 1; and $R_8$ is —CF$_3$.

In another embodiment, $Ar^1$ is a pyridyl group; V is CH; n is 0; m is 0; $R_1$ is —Cl; $Ar^2$ is a benzothiazolyl group; s is 1; and $R_8$ is —CF$_3$.

In another embodiment, $Ar^1$ is a pyridyl group; V is CH; n is 0; m is 0; $R_1$ is —Br; $Ar^2$ is a benzothiazolyl group; s is 1; and $R_8$ is —CF$_3$.

In another embodiment, $Ar^1$ is a pyridyl group; V is CH; n is 0; m is 0; $R_1$ is —I; $Ar^2$ is a benzothiazolyl group; s is 1; and $R_8$ is —CF$_3$.

In another embodiment, $Ar^1$ is a pyridyl group; V is CH; n is 0; m is 0; $R_1$ is —$CH_3$; $Ar^2$ is a benzothiazolyl group; s is 1; and $R_8$ is —$CF_3$.

In another embodiment, $Ar^1$ is a pyridyl group; V is CH; n is 0; m is 0; $R_1$ is —$CF_3$; $Ar^2$ is a benzothiazolyl group; s is 1; and $R_8$ is —$CF_3$.

In another embodiment, $Ar^1$ is a pyridyl group; V is CH; n is 0; m is 0; $R_1$ is —F, —Cl, —Br, or —I; $Ar^2$ is a benzothiazolyl group; s is 1; and $R_8$ is —$OCH_2CH_3$.

In another embodiment, $Ar^1$ is a pyridyl group; V is CH; n is 0; m is 0; $R_1$ is —F; $Ar^2$ is a benzothiazolyl group; s is 1; and $R_8$ is —$OCH_2CH_3$.

In another embodiment, $Ar^1$ is a pyridyl group; V is CH; n is 0; m is 0; $R_1$ is —Cl; $Ar^2$ is a benzothiazolyl group; s is 1; and $R_8$ is —$OCH_2CH_3$.

In another embodiment, $Ar^1$ is a pyridyl group; V is CH; n is 0; m is 0; $R_1$ is —Br; $Ar^2$ is a benzothiazolyl group; s is 1; and $R_8$ is —$OCH_2CH_3$.

In another embodiment, $Ar^1$ is a pyridyl group; V is CH; n is 0; m is 0; $R_1$ is —I; $Ar^2$ is a benzothiazolyl group; s is 1; and $R_8$ is —$OCH_2CH_3$.

In another embodiment, $Ar^1$ is a pyridyl group; V is CH; n is 0; m is 0; $R_1$ is —$CH_3$; $Ar^2$ is a benzothiazolyl group; s is 1; and $R_8$ is —$OCH_2CH_3$.

In another embodiment, $Ar^1$ is a pyridyl group; V is CH; n is 0; m is 0; $R_1$ is —$CF_3$; $Ar^2$ is a benzothiazolyl group; s is 1; and $R_8$ is —$OCH_2CH_3$.

In another embodiment, $Ar^1$ is a pyridyl group; V is CH; n is 0; m is 0; $R_1$ is —F, —Cl, —Br, or —I; $Ar^2$ is a benzothiazolyl group; $R_8$ is -tert-butyl.

In another embodiment, $Ar^1$ is a pyridyl group; V is CH; n is 0; m is 0; $R_1$ is —F; $Ar^2$ is a benzothiazolyl group; s is 1; and $R_8$ is -tert-butyl.

In another embodiment, $Ar^1$ is a pyridyl group; V is CH; n is 0; m is 0; $R_1$ is —Cl; $Ar^2$ is a benzothiazolyl group; s is 1; and $R_8$ is -tert-butyl.

In another embodiment, $Ar^1$ is a pyridyl group; V is CH; n is 0; m is 0; $R_1$ is —Br; $Ar^2$ is a benzothiazolyl group; s is 1; and $R_8$ is -tert-butyl.

In another embodiment, $Ar^1$ is a pyridyl group; V is CH; n is 0; m is 0; $R_1$ is —I; $Ar^2$ is a benzothiazolyl group; s is 1; and $R_8$ is -tert-butyl.

In another embodiment, $Ar^1$ is a pyridyl group; V is CH; n is 0; m is 0; $R_1$ is —$CH_3$; $Ar^2$ is a benzothiazolyl group; s is 1; and $R_8$ is -tert-butyl.

In another embodiment, $Ar^1$ is a pyridyl group; V is CH; n is 0; m is 0; $R_1$ is —$CF_3$; $Ar^2$ is a benzothiazolyl group; s is 1; and $R_8$ is -tert-butyl.

In another embodiment, $Ar^1$ is a pyridyl group; V is CH; n is 0; m is 1; $R_3$ is —$CH_3$; $R_1$ is —F, —Cl, —Br, or —I; $Ar^2$ is a benzothiazolyl group; and s is 0. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F; $Ar^2$ is a benzothiazolyl group; and s is 0. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Cl; $Ar^2$ is a benzothiazolyl group; and s is 0. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Br; $Ar^2$ is a benzothiazolyl group; and s is 0. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —I; $Ar^2$ is a benzothiazolyl group; and s is 0. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CH_3$; $Ar^2$ is a benzothiazolyl group; and s is 0. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CF_3$; $Ar^2$ is a benzothiazolyl group; and s is 1. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F, —Cl, —Br, or —I; $Ar^2$ is a benzothiazolyl group; s is 1; and $R_8$ is -halo. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F; $Ar^2$ is a benzothiazolyl group; s is 1; and $R_8$ is -halo. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Cl; $Ar^2$ is a benzothiazolyl group; s is 1; and $R_8$ is -halo. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Br; $Ar^2$ is a benzothiazolyl group; s is 1; and $R_8$ is -halo. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —I; $Ar^2$ is a benzothiazolyl group; s is 1; and $R_8$ is -halo. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CH_3$; $Ar^2$ is a benzothiazolyl group; s is 1; and $R_8$ is -halo. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CF_3$; $Ar^2$ is a benzothiazolyl group; s is 1; and $R_8$ is -halo. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F, —Cl, —Br, or —I; $Ar^2$ is a benzothiazolyl group; s is 1; and $R_8$ is —Br. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F; $Ar^2$ is a benzothiazolyl group; s is 1; and $R_8$ is —Br. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Cl; $Ar^2$ is a benzothiazolyl group; s is 1; and $R_8$ is —Br. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Br; $Ar^2$ is a benzothiazolyl group; s is 1; and $R_8$ is —Br. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —I; $Ar^2$ is a benzothiazolyl group; s is 1; and $R_8$ is —Br. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CH_3$; $Ar^2$ is a benzothiazolyl group; s is 1; and $R_8$ is —Br. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CF_3$; $Ar^2$ is a benzothiazolyl group; s is 1; and $R_8$ is —Br. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Cl, —F —Br, or —I; $Ar^2$ is a benzothiazolyl group; s is 1; and $R_8$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F; $Ar^2$ is a benzothiazolyl group; s is 1; and $R_8$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Cl; $Ar^2$ is a benzothiazolyl group; s is 1; and $R_8$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment the $R_3$ group in attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Br; $Ar^2$ is a benzothiazolyl group; s is 1; and $R_8$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —I; $Ar^2$ is a benzothiazolyl group; s is 1; and $R_8$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CH_3$; $Ar^2$ is a benzothiazolyl group; s is 1; and $R_8$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CF_3$; $Ar^2$ is a benzothiazolyl group; s is 1; and $R_8$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is $CH_3$; $R_1$ is —Cl, —F —Br, or —I; $Ar^2$ is a benzothiazolyl group; s is 1; and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F; $Ar^2$ is a benzothiazolyl group; s is 1; and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Cl; $Ar^2$ is a benzothiazolyl group; s is 1; and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Br; $Ar^2$ is a benzothiazolyl group; s is 1; and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —I; $Ar^2$ is a benzothiazolyl group; s is 1; and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CH_3$; $Ar^2$ is a benzothiazolyl group; s is 1; and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CF_3$; $Ar^2$ is a benzothiazolyl group; s is 1; and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Cl, —F, —Br, or —I, $Ar^2$ is a benzothiazolyl group; s is 1; and $R_8$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F; $Ar^2$ is a benzothiazolyl group; s is 1; and $R_8$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Cl; $Ar^2$ is a benzothiazolyl group; s is 1; and $R_8$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Br; $Ar^2$ is a benzothiazolyl group; s is 1; and $R_8$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —I; $Ar^2$ is a benzothiazolyl group; s is 1; and $R_8$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CH_3$; $Ar^2$ is a benzothiazolyl group; s is 1; and $R_8$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CF_3$; $Ar^2$ is a benzothiazolyl group; s is 1; and $R_8$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F, —Cl, —Br, or —I; $Ar^2$ is a benzothiazolyl group; s is 1; and $R_8$ is —$CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F; $Ar^2$ is a benzothiazolyl group; s is 1; and $R_8$ is —$CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Cl; $Ar^2$ is a benzothiazolyl group; s is 1; and $R_8$ is —$CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Br; $Ar^2$ is a benzothiazolyl group; s is 1; and $R_8$ is —$CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —I; $Ar^2$ is a benzothiazolyl group; s is 1; and $R_8$ is —$CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CH_3$; $Ar^2$ is a benzothiazolyl group; s is 1; and $R_8$ is —$CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CF_3$; $Ar^2$ is a benzothiazolyl group; s is 1; and $R_8$ is —$CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F, —Cl, —Br, or —I; $Ar^2$ is a benzothiazolyl group; s is 1; and $R_8$ is —$CF_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F; $Ar^2$ is a benzothiazolyl group; s is 1; and $R_8$ is —$CF_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Cl; $Ar^2$ is a benzothiazolyl group; s is 1; and $R_8$ is —$CF_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Br; $Ar^2$ is a benzothiazolyl group; s is 1; and $R_8$ is —$CF_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —I; $Ar^2$ is a benzothiazolyl group; s is 1; and $R_8$ is —$CF_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CH_3$; $Ar^2$ is a benzothiazolyl group; s is 1; and $R_8$ is —$CF_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CF_3$; $Ar^2$ is a benzothiazolyl group; s is 1; and $R_8$ is —$CF_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F, —Cl, —Br, or —I; $Ar^2$ is a benzothiazolyl group; s is 1; and $R_8$ is —$OCH_2CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F; $Ar^2$ is a benzothiazolyl group; s is 1; and $R_8$ is —$OCH_2CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Cl; $Ar^2$ is a benzothiazolyl group; s is 1; and $R_8$ is —$OCH_2CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Br; $Ar^2$ is a benzothiazolyl group; s is 1; and $R_8$ is —$OCH_2CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —I; $Ar^2$ is a benzothiazolyl group; s is 1; and $R_8$ is —$OCH_2CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CH_3$; $Ar^2$ is a benzothiazolyl group; s is 1; and $R_8$ is —$OCH_2CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CF_3$; $Ar^2$ is a benzothiazolyl group; s is 1; and $R_8$ is —$OCH_2CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F, —Cl, —Br, or —I; $Ar^2$ is a benzothiazolyl group; s is 1; and $R_8$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F; $Ar^2$ is a benzothiazolyl group; s is 1; and $R_8$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Cl; $Ar^2$ is a benzothiazolyl group; s is 1; and $R_8$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Br; $Ar^2$ is a benzothiazolyl group; s is 1; and $R_8$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —I; $Ar^2$ is a benzothiazolyl group; s is 1; and $R_8$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CH_3$; $Ar^2$ is a benzothiazolyl group; s is 1; and $R_8$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CF_3$; $Ar^2$ is a benzothiazolyl group; s is 1; and $R_8$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group, V is N; m is 0, and $Ar^2$ is a benzoimidazolyl group.

In another embodiment, $Ar^1$ is a pyridyl group; V is N; n is 0; m is 0; $R_1$ is —F, —Cl, —Br, or —I; $Ar^2$ is a benzoimidazolyl group; and s is 0.

In another embodiment, $Ar^1$ is a pyridyl group; V is N; n is 0; m is 0; $R_1$ is —F; $Ar^2$ is a benzoimidazolyl group; and s is 0.

In another embodiment, $Ar^1$ is a pyridyl group; V is N; n is 0; m is 0; $R_1$ is —Cl; $Ar^2$ is a benzoimidazolyl group; and s is 0.

In another embodiment, $Ar^1$ is a pyridyl group; V is N; n is 0; m is 0; $R_1$ is —Br; $Ar^2$ is a benzoimidazolyl group; and s is 0.

In another embodiment, $Ar^1$ is a pyridyl group; V is N; n is 0; m is 0; $R_1$ is —I; $Ar^2$ is a benzoimidazolyl group; and s is 0.

In another embodiment, $Ar^1$ is a pyridyl group; V is N; n is 0; m is 0; $R_1$ is —$CH_3$; $Ar^2$ is a benzoimidazolyl group; and s is 0.

In another embodiment, $Ar^1$ is a pyridyl group; V is N; n is 0; m is 0; $R_1$ is —$CF_3$; $Ar^2$ is a benzoimidazolyl group; and s is 0.

In another embodiment, $Ar^1$ is a pyridyl group; V is N; n is 0; m is 0; $R_1$ is —F, —Cl —Br, or —I; $Ar^2$ is a benzoimidazolyl group; s is 1; and $R_8$ is -halo.

In another embodiment, $Ar^1$ is a pyridyl group; V is N; n is 0; m is 0; $R_1$ is —F; $Ar^2$ is a benzoimidazolyl group; s is 1; and $R_8$ is -halo.

In another embodiment, $Ar^1$ is a pyridyl group; V is N; n is 0; m is 0; $R_1$ is —Cl; $Ar^2$ is a benzoimidazolyl group; s is 1; and $R_8$ is -halo.

In another embodiment, $Ar^1$ is a pyridyl group; V is N; n is 0; m is 0; $R_1$ is —Br; $Ar^2$ is a benzoimidazolyl group; s is 1; and $R_8$ is -halo.

In another embodiment, $Ar^1$ is a pyridyl group; V is N; n is 0; m is 0; $R_1$ is —I; $Ar^2$ is a benzoimidazolyl group; $R_8$ s is 1; and $R_8$ is -halo.

In another embodiment, $Ar^1$ is a pyridyl group; V is N; n is 0; m is 0; $R_1$ is —$CH_3$; $Ar^2$ is a benzoimidazolyl group; s is 1; and $R_8$ is -halo.

In another embodiment, $Ar^1$ is a pyridyl group; V is N; n is 0; m is 0; $R_1$ is —$CF_3$; $Ar^2$ is a benzoimidazolyl group; s is 1; and $R_8$ is -halo.

In another embodiment, $Ar^1$ is a pyridyl group; V is N; n is 0; m is 0; $R_1$ is —F, —Cl, —Br, or —I; $Ar^2$ is a benzoimidazolyl group; s is 1; and $R_8$ is —Br.

In another embodiment, $Ar^1$ is a pyridyl group; V is N; n is 0; m is 0; $R_1$ is —F; $Ar^2$ is a benzoimidazolyl group; s is 1; and $R_8$ is —Br.

In another embodiment, $Ar^1$ is a pyridyl group; V is N; n is 0; m is 0; $R_1$ is —Cl; $Ar^2$ is a benzoimidazolyl group; s is 1; and $R_8$ is —Br.

In another embodiment, $Ar^1$ is a pyridyl group; V is N; n is 0; m is 0; $R_1$ is —Br; $Ar^2$ is a benzoimidazolyl group; s is 1; and $R_8$ is —Br.

In another embodiment, $Ar^1$ is a pyridyl group; V is N; n is 0; m is 0; $R_1$ is —I; $Ar^2$ is a benzoimidazolyl group; s is 1; and $R_8$ is —Br.

In another embodiment, $Ar^1$ is a pyridyl group; V is N; n is 0; m is 0; $R_1$ is —$CH_3$; $Ar^2$ is a benzoimidazolyl group; s is 1; and $R_8$ is —Br.

In another embodiment, $Ar^1$ is a pyridyl group; V is N; n is 0; m is 0; $R_1$ is —$CF_3$; $Ar^2$ is a benzoimidazolyl group; s is 1; and $R_8$ is —Br.

In another embodiment, $Ar^1$ is a pyridyl group; V is N; n is 0; m is 0; $R_1$ is —Cl, —F —Br, or —I; $Ar^2$ is a benzoimidazolyl group; s is 1; and $R_8$ is —F.

In another embodiment, $Ar^1$ is a pyridyl group; V is N; n is 0; m is 0; $R_1$ is —F; $Ar^2$ is a benzoimidazolyl group; s is 1; and $R_8$ is —F.

In another embodiment, $Ar^1$ is a pyridyl group; V is N; n is 0; m is 0; $R_1$ is —Cl; $Ar^2$ is a benzoimidazolyl group; s is 1; and $R_8$ is —F.

In another embodiment, $Ar^1$ is a pyridyl group; V is N; n is 0; m is 0; $R_1$ is —Br; $Ar^2$ is a benzoimidazolyl group; s is 1; and $R_8$ is —F.

In another embodiment, $Ar^1$ is a pyridyl group; V is N; n is 0; m is 0; $R_1$ is —I; $Ar^2$ is a benzoimidazolyl group; s is 1; and $R_8$ is —F.

In another embodiment, $Ar^1$ is a pyridyl group; V is N; n is 0; m is 0; $R_1$ is —$CH_3$; $Ar^2$ is a benzoimidazolyl group; s is 1; and $R_8$ is —F.

In another embodiment, $Ar^1$ is a pyridyl group; V is N; n is 0; m is 0; $R_1$ is —$CF_3$; $Ar^2$ is a benzoimidazolyl group; s is 1; and $R_8$ is —F.

In another embodiment, $Ar^1$ is a pyridyl group; V is N; n is 0; m is 0; $R_1$ is —Cl, —F —Br, or —I; $Ar^2$ is a benzoimidazolyl group; s is 1; and $R_8$ is —Cl.

In another embodiment, $Ar^1$ is a pyridyl group; V is N; n is 0; m is 0; $R_1$ is —F; $Ar^2$ is a benzoimidazolyl group; s is 1; and $R_8$ is —Cl.

In another embodiment, $Ar^1$ is a pyridyl group; V is N; n is 0; m is 0; $R_1$ is —Cl; $Ar^2$ is a benzoimidazolyl group; s is 1; and $R_8$ is —Cl.

In another embodiment, $Ar^1$ is a pyridyl group; V is N; n is 0; m is 0; $R_1$ is —Br; $Ar^2$ is a benzoimidazolyl group; s is 1; and $R_8$ is —Cl.

In another embodiment, $Ar^1$ is a pyridyl group; v is N; n is 0; m is 0; $R_1$ is —I; $Ar^2$ is a benzoimidazolyl group; s is 1; and $R_8$ is —Cl.

In another embodiment, $Ar^1$ is a pyridyl group; V is N; n is 0; m is 0; $R_1$ is —$CH_3$; $Ar^2$ is a benzoimidazolyl group; s is 1; and $R_8$ is —Cl.

In another embodiment, $Ar^1$ is a pyridyl group; V is N; n is 0; m is 0; $R_1$ is —$CF_3$; $Ar^2$ is a benzoimidazolyl group s is 1; and $R_8$ is —Cl.

In another embodiment, $Ar^1$ is a pyridyl group; V is N; n is 0; m is 0; $R_1$ is —Cl, —F, —Br, or —I, $Ar^2$ is a benzoimidazolyl group; s is 1; and $R_8$ is —I.

In another embodiment, $Ar^1$ is a pyridyl group; V is N; n is 0; m is 0; $R_1$ is —F; $Ar^2$ is a benzoimidazolyl group; s is 1; and $R_8$ is —I.

In another embodiment, $Ar^1$ is a pyridyl group; V is N; n is 0; m is 0; $R_1$ is —Cl; $Ar^2$ is a benzoimidazolyl group; s is 1; and $R_8$ is —I.

In another embodiment, $Ar^1$ is a pyridyl group; V is N; n is 0; m is 0; $R_1$ is —Br; $Ar^2$ is a benzoimidazolyl group; s is 1; and $R_8$ is —I.

In another embodiment, $Ar^1$ is a pyridyl group; V is N; n is 0; m is 0; $R_1$ is —I; $Ar^2$ is a benzoimidazolyl group; s is 1; and $R_8$ is —I.

In another embodiment, $Ar^1$ is a pyridyl group; V is N; n is 0; m is 0; $R_1$ is —CH$_3$; $Ar^2$ is a benzoimidazolyl group; s is 1; and $R_8$ is —I.

In another embodiment, $Ar^1$ is a pyridyl group; V is N; n is 0; m is 0; $R_1$ is —CF$_3$; $Ar^2$ is a benzoimidazolyl group; s is 1; and $R_8$ is —I.

In another embodiment, $Ar^1$ is a pyridyl group; V is N; n is 0; m is 0; $R_1$ is —F, —Cl, —Br, or —I; $Ar^2$ is a benzoimidazolyl group; s is 1; and $R_8$ is —CH$_3$.

In another embodiment, $Ar^1$ is a pyridyl group; V is N; n is 0; m is 0; $R_1$ is —F; $Ar^2$ is a benzoimidazolyl group; s is 1; and $R_8$ is —CH$_3$.

In another embodiment, $Ar^1$ is a pyridyl group; V is N; n is 0; m is 0; $R_1$ is —Cl; $Ar^2$ is a benzoimidazolyl group; s is 1; and $R_8$ is —CH$_3$.

In another embodiment, $Ar^1$ is a pyridyl group; V is N; n is 0; m is 0; $R_1$ is —Br; $Ar^2$ is a benzoimidazolyl group; s is 1; and $R_8$ is —CH$_3$.

In another embodiment, $Ar^1$ is a pyridyl group; V is N; n is 0; m is 0; $R_1$ is —I; $Ar^2$ is a benzoimidazolyl group; s is 1; and $R_8$ is —CH$_3$.

In another embodiment, $Ar^1$ is a pyridyl group; V is N; n is 0; m is 0; $R_1$ is —CH$_3$; $Ar^2$ is a benzoimidazolyl group; s is 1; and $R_8$ is —CH$_3$.

In another embodiment, $Ar^1$ is a pyridyl group; V is N; n is 0; m is 0; $R_1$ is —CF$_3$; $Ar^2$ is a benzoimidazolyl group; s is 1; and $R_8$ is —CH$_3$.

In another embodiment, $Ar^1$ is a pyridyl group; V is N; n is 0; m is 0; $R_1$ is —F, —Cl, —Br, or —I; $Ar^2$ is a benzoimidazolyl group; s is 1; and $R_8$ is —CF$_3$.

In another embodiment, $Ar^1$ is a pyridyl group; V is N; n is 0; m is 0; $R_1$ is —F; $Ar^2$ is a benzoimidazolyl group; s is 1; and $R_8$ is —CF$_3$.

In another embodiment, $Ar^1$ is a pyridyl group; V is N; n is 0; m is 0; $R_1$ is —Cl; $Ar^2$ is a benzoimidazolyl group; s is 1; and $R_8$ is —CF$_3$.

In another embodiment, $Ar^1$ is a pyridyl group; V is N; n is 0; m is 0; $R_1$ is —Br; $Ar^2$ is a benzoimidazolyl group; s is 1; and $R_8$ is —CF$_3$.

In another embodiment, $Ar^1$ is a pyridyl group; V is N; n is 0; m is 0; $R_1$ is —I; $Ar^2$ is a benzoimidazolyl group; s is 1; and $R_8$ is —CF$_3$.

In another embodiment, $Ar^1$ is a pyridyl group; V is N; n is 0; m is 0; $R_1$ is —CH$_3$; $Ar^2$ is a benzoimidazolyl group; s is 1; and $R_8$ is —CF$_3$.

In another embodiment, $Ar^1$ is a pyridyl group; V is N; n is 0; m is 0; $R_1$ is —CF$_3$; $Ar^2$ is a benzoimidazolyl group; s is 1; and $R_8$ is —CF$_3$.

In another embodiment, $Ar^1$ is a pyridyl group; V is N; n is 0; m is 0; $R_1$ is —F, —Cl —Br, or —I; $Ar^2$ is a benzoimidazolyl group; s is 1; and $R_8$ is —OCH$_2$CH$_3$.

In another embodiment, $Ar^1$ is a pyridyl group; V is N; n is 0; m is 0; $R_1$ is —F; $Ar^2$ is a benzoimidazolyl group; s is 1; and $R_8$ is —OCH$_2$CH$_3$.

In another embodiment, $Ar^1$ is a pyridyl group; V is N; n is 0; m is 0; $R_1$ is —Cl; $Ar^2$ is a benzoimidazolyl group; s is 1; and $R_8$ is —OCH$_2$CH$_3$.

In another embodiment, $Ar^1$ is a pyridyl group; V is N; n is 0; m is 0; $R_1$ is —Br; $Ar^2$ is a benzoimidazolyl group; s is 1; and $R_8$ is —OCH$_2$CH$_3$.

In another embodiment, $Ar^1$ is a pyridyl group; V is N; n is 0; m is 0; $R_1$ is —I; $Ar^2$ is a benzoimidazolyl group; s is 1; and $R_8$ is —OCH$_2$CH$_3$.

In another embodiment, $Ar^1$ is a pyridyl group; V is N; n is 0; m is 0; $R_1$ is —CH$_3$; $Ar^2$ is a benzoimidazolyl group; s is 1; and $R_8$ is —OCH$_2$CH$_3$.

In another embodiment, $Ar^1$ is a pyridyl group; V is N; n is 0; m is 0; $R_1$ is —CF$_3$; $Ar^2$ is a benzoimidazolyl group; s is 1; and $R_8$ is —OCH$_2$CH$_3$.

In another embodiment, $Ar^1$ is a pyridyl group; V is N; n is 0; m is 0; $R_1$ is —F, —Cl, —Br, or —I; $Ar^2$ is a benzoimidazolyl group; $R_8$ is -tert-butyl.

In another embodiment, $Ar^1$ is a pyridyl group; V is N; n is 0; m is 0; $R_1$ is —F; $Ar^2$ is a benzoimidazolyl group; s is 1; and $R_8$ is -tert-butyl.

In another embodiment, $Ar^1$ is a pyridyl group; V is N; n is 0; m is 0; $R_1$ is —Cl; $Ar^2$ is a benzoimidazolyl group; s is 1; and $R_8$ is -tert-butyl.

In another embodiment, $Ar^1$ is a pyridyl group; V is N; n is 0; m is 0; $R_1$ is —Br; $Ar^2$ is a benzoimidazolyl group; s is 1; and $R_8$ is -tert-butyl.

In another embodiment, $Ar^1$ is a pyridyl group; V is N; n is 0; m is 0; $R_1$ is —I; $Ar^2$ is a benzoimidazolyl group; s is 1; and $R_8$ is -tert-butyl.

In another embodiment, $Ar^1$ is a pyridyl group; V is N; n is 0; m is 0; $R_1$ is —CH$_3$; $Ar^2$ is a benzoimidazolyl group; s is 1; and $R_8$ is -tert-butyl.

In another embodiment, $Ar^1$ is a pyridyl group; V is N; n is 0; m is 0; $R_1$ is —CF$_3$; $Ar^2$ is a benzoimidazolyl group; s is 1; and $R_8$ is -tert-butyl.

In another embodiment, $Ar^1$ is a pyridyl group; V is N; n is 0; m is 1; $R_3$ is —CH$_3$; $R_1$ is —F, —Cl, —Br, or —I; $Ar^2$ is a benzoimidazolyl group; and s is 0. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —CH$_3$; $R_1$ is —F; $Ar^2$ is a benzoimidazolyl group; and s is 0. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —CH$_3$; $R_1$ is —Cl; $Ar^2$ is a benzoimidazolyl group; and s is 0. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Br; $Ar^2$ is a benzoimidazolyl group; and s is 0. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —I; $Ar^2$ is a benzoimidazolyl group; and s is 0. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CH_3$; $Ar^2$ is a benzoimidazolyl group; and s is 0. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CF_3$; $Ar^2$ is a benzoimidazolyl group; and s is 1. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —F, —Cl, —Br, or —I; $Ar^2$ is a benzoimidazolyl group; s is 1; and $R_8$ is -halo. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —F; $Ar^2$ is a benzoimidazolyl group; s is 1; and $R_8$ is -halo. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Cl; $Ar^2$ is a benzoimidazolyl group; s is 1; and $R_8$ is -halo. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Br; $Ar^2$ is a benzoimidazolyl group; s is 1; and $R_8$ is -halo. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —I; $Ar^2$ is a benzoimidazolyl group; s is 1; and $R_8$ is -halo. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CH_3$; $Ar^2$ is a benzoimidazolyl group; s is 1; and $R_8$ is -halo. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CF_3$; $Ar^2$ is a benzoimidazolyl group; s is 1; and $R_8$ is -halo. In another embodiment, the $R_3$ group is attached to the 3-, 5- or 6-position of the cyclo(hetero)alkenyl ring and the carbon atom to which the $R_3$ group is attached has the (R) configuration. In other embodiments, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —F, —Cl, —Br, or —I; $Ar^2$ is a benzoimidazolyl group; s is 1; and $R_8$ is —Br. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —F; $Ar^2$ is a benzoimidazolyl group; s is 1; and $R_8$ is —Br. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Cl; $Ar^2$ is a benzoimidazolyl group; s is 1; and $R_8$ is —Br. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Br; $Ar^2$ is a benzoimidazolyl group; s is 1; and $R_8$ is —Br. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —I; $Ar^2$ is a benzoimidazolyl group; s is 1; and $R_8$ is —Br. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CH_3$; $Ar^2$ is a benzoimidazolyl group; s is 1; and $R_8$ is —Br. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CF_3$; $Ar^2$ is a benzoimidazolyl group; s is 1; and $R_8$ is —Br. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Cl, —F —Br, or —I; $Ar^2$ is a benzoimidazolyl group; s is 1; and $R_8$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —F; $Ar^2$ is a benzoimidazolyl group; s is 1; and $R_8$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Cl; $Ar^2$ is a benzoimidazolyl group; s is 1; and $R_8$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Br; $Ar^2$ is a benzoimidazolyl group; s is 1; and $R_8$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —I; $Ar^2$ is a benzoimidazolyl group; s is 1; and $R_8$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CH_3$; $Ar^2$ is a benzoimidazolyl group; s is 1; and $R_8$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CF_3$; $Ar^2$ is a benzoimidazolyl group; s is 1; and $R_8$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is $CH_3$; $R_1$ is —Cl, —F —Br, or —I; $Ar^2$ is a benzoimidazolyl group; s is 1; and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —F; $Ar^2$ is a benzoimidazolyl group; s is 1; and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Cl; $Ar^2$ is a benzoimidazolyl group; s is 1; and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Br; $Ar^2$ is a benzoimidazolyl group; s is 1; and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —I; $Ar^2$ is a benzoimidazolyl group; s is 1; and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CH_3$; $Ar^2$ is a benzoimidazolyl group; s is 1; and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CF_3$; $Ar^2$ is a benzoimidazolyl group; s is 1; and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Cl, —F, —Br, or —I, $Ar^2$ is a benzoimidazolyl group; s is 1; and $R_8$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —F; $Ar^2$ is a benzoimidazolyl group; s is 1; and $R_8$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Cl; $Ar^2$ is a benzoimidazolyl group; s is 1; and $R_8$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Br; $Ar^2$ is a benzoimidazolyl group; s is 1; and $R_8$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —I; $Ar^2$ is a benzoimidazolyl group; s is 1; and $R_8$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CH_3$; $Ar^2$ is a benzoimidazolyl group; s is 1; and $R_8$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CF_3$; $Ar^2$ is a benzoimidazolyl group; s is 1; and $R_8$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —F, —Cl, —Br, or —I; $Ar^2$ is a benzoimidazolyl group; s is 1; and $R_8$ is —$CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —F; $Ar^2$ is a benzoimidazolyl group; s is 1; and $R_8$ is —$CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Cl; $Ar^2$ is a benzoimidazolyl group; s is 1; and $R_8$ is —$CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Br; $Ar^2$ is a benzoimidazolyl group; s is 1; and $R_8$ is —$CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —I; $Ar^2$ is a benzoimidazolyl group; s is 1; and $R_8$ is —$CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CH_3$; $Ar^2$ is a benzoimidazolyl group; s is 1; and $R_8$ is —$CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CF_3$; $Ar^2$ is a benzoimidazolyl group; s is 1; and $R_8$ is —$CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —F, —Cl, —Br, or —I; $Ar^2$ is a benzoimidazolyl group; s is 1; and $R_8$ is —$CF_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —F; $Ar^2$ is a benzoimidazolyl group; s is 1; and $R_8$ is —$CF_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Cl; $Ar^2$ is a benzoimidazolyl group; s is 1; and $R_8$ is —$CF_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Br; $Ar^2$ is a benzoimidazolyl group; s is 1; and $R_8$ is —$CF_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —I; $Ar^2$ is a benzoimidazolyl group; s is 1; and $R_8$ is —$CF_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CH_3$; $Ar^2$ is a benzoimidazolyl group; s is 1; and $R_8$ is —$CF_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CF_3$; $Ar^2$ is a benzoimidazolyl group; s is 1; and $R_8$ is —$CF_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —F, —Cl, —Br, or —I; $Ar^2$ is a benzoimidazolyl group; s is 1; and $R_8$ is —$OCH_2CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —F; $Ar^2$ is a benzoimidazolyl group; s is 1; and $R_8$ is —$OCH_2CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Cl; $Ar^2$ is a benzoimidazolyl group; s is 1; and $R_8$ is —$OCH_2CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Br; $Ar^2$ is a benzoimidazolyl group; s is 1; and $R_8$ is —$OCH_2CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —I; $Ar^2$ is a benzoimidazolyl group; s is 1; and $R_8$ is —$OCH_2CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CH_3$; $Ar^2$ is a benzoimidazolyl group; s is 1; and $R_8$ is —$OCH_2CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CF_3$; $Ar^2$ is a benzoimidazolyl group; s is 1; and $R_8$ is —$OCH_2CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —F, —Cl, —Br, or —I; $Ar^2$ is a benzoimidazolyl group; s is 1; and $R_8$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —F; $Ar^2$ is a benzoimidazolyl group; s is 1; and $R_8$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Cl; $Ar^2$ is a benzoimidazolyl group; s is 1; and $R_8$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Br; $Ar^2$ is a benzoimidazolyl group; s is 1; and $R_8$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —I; $Ar^2$ is a benzoimidazolyl group; s is 1; and $R_8$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CH_3$; $Ar^2$ is a benzoimidazolyl group; s is 1; and $R_8$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CF_3$; $Ar^2$ is a benzoimidazolyl group; s is 1; and $R_8$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group, V is CH; m is 0, and $Ar^2$ is a benzoimidazolyl group.

In another embodiment, $Ar^1$ is a pyridyl group; V is CH; n is 0; m is 0; $R_1$ is —F, —Cl, —Br, or —I; $Ar^2$ is a benzoimidazolyl group; and s is 0.

In another embodiment, $Ar^1$ is a pyridyl group; V is CH; n is 0; m is 0; $R_1$ is —F; $Ar^2$ is a benzoimidazolyl group; and s is 0.

In another embodiment, $Ar^1$ is a pyridyl group; V is CH; n is 0; m is 0; $R_1$ is —Cl; $Ar^2$ is a benzoimidazolyl group; and s is 0.

In another embodiment, $Ar^1$ is a pyridyl group; V is CH; n is 0; m is 0; $R_1$ is —Br; $Ar^2$ is a benzoimidazolyl group; and s is 0.

In another embodiment, $Ar^1$ is a pyridyl group; V is CH; n is 0; m is 0; $R_1$ is —I; $Ar^2$ is a benzoimidazolyl group; and s is 0.

In another embodiment, $Ar^1$ is a pyridyl group; V is CH; n is 0; m is 0; $R_1$ is —$CH_3$; $Ar^2$ is a benzoimidazolyl group; and s is 0.

In another embodiment, $Ar^1$ is a pyridyl group; V is CH; n is 0; m is 0; $R_1$ is —$CF_3$; $Ar^2$ is a benzoimidazolyl group; and s is 0.

In another embodiment, $Ar^1$ is a pyridyl group; V is CH; n is 0; m is 0; $R_1$ is —F, —Cl, —Br, or —I; $Ar^2$ is a benzoimidazolyl group; s is 1; and $R_8$ is -halo.

In another embodiment, $Ar^1$ is a pyridyl group; V is CH; n is 0; m is 0; $R_1$ is —F; $Ar^2$ is a benzoimidazolyl group; s is 1; and $R_8$ is -halo.

In another embodiment, $Ar^1$ is a pyridyl group; V is CH; n is 0; m is 0; $R_1$ is —Cl; $Ar^2$ is a benzoimidazolyl group; s is 1; and $R_8$ is -halo.

In another embodiment, $Ar^1$ is a pyridyl group; V is CH; n is 0; m is 0; $R_1$ is —Br; $Ar^2$ is a benzoimidazolyl group; s is 1; and $R_8$ is -halo.

In another embodiment, $Ar^1$ is a pyridyl group; V is CH; n is 0; m is 0; $R_1$ is —I; $Ar^2$ is a benzoimidazolyl group; $R_8$ s is 1; and $R_8$ is -halo.

In another embodiment, $Ar^1$ is a pyridyl group; V is CH; n is 0; m is 0; $R_1$ is —$CH_3$; $Ar^2$ is a benzoimidazolyl group; s is 1; and $R_8$ is -halo.

In another embodiment, $Ar^1$ is a pyridyl group; V is CH; n is 0; m is 0; $R_1$ is —$CF_3$; $Ar^2$ is a benzoimidazolyl group; s is 1; and $R_8$ is -halo.

In another embodiment, $Ar^1$ is a pyridyl group; V is CH; n is 0; m is 0; $R_1$ is —F, —Cl, —Br, or —I; $Ar^2$ is a benzoimidazolyl group; s is 1; and $R_8$ is —Br.

In another embodiment, $Ar^1$ is a pyridyl group; V is CH; n is 0; m is 0; $R_1$ is —F; $Ar^2$ is a benzoimidazolyl group; s is 1; and $R_8$ is —Br.

In another embodiment, $Ar^1$ is a pyridyl group; V is CH; n is 0; m is 0; $R_1$ is —Cl; $Ar^2$ is a benzoimidazolyl group; s is 1; and $R_8$ is —Br.

In another embodiment, Ar$^1$ is a pyridyl group; V is CH; n is 0; m is 0; R$_1$ is —Br; Ar$^2$ is a benzoimidazolyl group; s is 1; and R$_8$ is —Br.

In another embodiment, Ar$^1$ is a pyridyl group; V is CH; n is 0; m is 0; R$_1$ is —I; Ar$^2$ is a benzoimidazolyl group; s is 1; and R$_8$ is —Br.

In another embodiment, Ar$^1$ is a pyridyl group; V is CH; n is 0; m is 0; R$_1$ is —CH$_3$; Ar$^2$ is a benzoimidazolyl group; s is 1; and R$_8$ is —Br.

In another embodiment, Ar$^1$ is a pyridyl group; V is CH; n is 0; m is 0; R$_1$ is —CF$_3$; Ar$^2$ is a benzoimidazolyl group; s is 1; and R$_8$ is —Br.

In another embodiment, Ar$^1$ is a pyridyl group; V is CH; n is 0; m is 0; R$_1$ is —Cl, —F —Br, or —I; Ar$^2$ is a benzoimidazolyl group; s is 1; and R$_8$ is —F.

In another embodiment, Ar$^1$ is a pyridyl group; V is CH; n is 0; m is 0; R$_1$ is —F; Ar$^2$ is a benzoimidazolyl group; s is 1; and R$_8$ is —F.

In another embodiment, Ar$^1$ is a pyridyl group; V is CH; n is 0; m is 0; R$_1$ is —Cl; Ar$^2$ is a benzoimidazolyl group; s is 1; and R$_8$ is —F.

In another embodiment, Ar$^1$ is a pyridyl group; V is CH; n is 0; m is 0; R$_1$ is —Br; Ar$^2$ is a benzoimidazolyl group; s is 1; and R$_8$ is —F.

In another embodiment, Ar$^1$ is a pyridyl group; V is CH; n is 0; m is 0; R$_1$ is —I; Ar$^2$ is a benzoimidazolyl group; s is 1; and R$_8$ is —F.

In another embodiment, Ar$^1$ is a pyridyl group; V is CH; n is 0; m is 0; R$_1$ is —CH$_3$; Ar$^2$ is a benzoimidazolyl group; s is 1; and R$_8$ is —F.

In another embodiment, Ar$^1$ is a pyridyl group; V is CH; n is 0; m is 0; R$_1$ is —CF$_3$; Ar$^2$ is a benzoimidazolyl group; s is 1; and R$_8$ is —F.

In another embodiment, Ar$^1$ is a pyridyl group; V is CH; n is 0; m is 0; R$_1$ is —Cl, —F —Br, or —I; Ar$^2$ is a benzoimidazolyl group; s is 1; and R$_8$ is —Cl.

In another embodiment, Ar$^1$ is a pyridyl group; V is CH; n is 0; m is 0; R$_1$ is —F; Ar$^2$ is a benzoimidazolyl group; s is 1; and R$_8$ is —Cl.

In another embodiment, Ar$^1$ is a pyridyl group; V is CH; n is 0; m is 0; R$_1$ is —Cl; Ar$^2$ is a benzoimidazolyl group; s is 1; and R$_8$ is —Cl.

In another embodiment, Ar$^1$ is a pyridyl group; V is CH; n is 0; m is 0; R$_1$ is —Br; Ar$^2$ is a benzoimidazolyl group; s is 1; and R$_8$ is —Cl.

In another embodiment, Ar$^1$ is a pyridyl group; V is CH; n is 0; m is 0; R$_1$ is —I; Ar$^2$ is a benzoimidazolyl group; s is 1; and R$_8$ is —Cl.

In another embodiment, Ar$^1$ is a pyridyl group; V is CH; n is 0; m is 0; R$_1$ is —CH$_3$; Ar$^2$ is a benzoimidazolyl group; s is 1; and R$_8$ is —Cl.

In another embodiment, Ar$^1$ is a pyridyl group; V is CH; n is 0; m is 0; R$_1$ is —CF$_3$; Ar$^2$ is a benzoimidazolyl group s is 1; and R$_8$ is —Cl.

In another embodiment, Ar$^1$ is a pyridyl group; V is CH; n is 0; m is 0; R$_1$ is —Cl, —F, —Br, or —I, Ar$^2$ is a benzoimidazolyl group; s is 1; and R$_8$ is —I.

In another embodiment, Ar$^1$ is a pyridyl group; V is CH; n is 0; m is 0; R$_1$ is —F; Ar$^2$ is a benzoimidazolyl group; s is 1; and R$_8$ is —I.

In another embodiment, Ar$^1$ is a pyridyl group; V is CH; n is 0; m is 0; R$_1$ is —Cl; Ar$^2$ is a benzoimidazolyl group; s is 1; and R$_8$ is —I.

In another embodiment, Ar$^1$ is a pyridyl group; V is CH; n is 0; m is 0; R$_1$ is —Br; Ar$^2$ is a benzoimidazolyl group; s is 1; and R$_8$ is —I.

In another embodiment, Ar$^1$ is a pyridyl group; V is CH; n is 0; m is 0; R$_1$ is —I; Ar$^2$ is a benzoimidazolyl group; s is 1; and R$_8$ is —I.

In another embodiment, Ar$^1$ is a pyridyl group; V is CH; n is 0; m is 0; R$_1$ is —CH$_3$; Ar$^2$ is a benzoimidazolyl group; s is 1; and R$_8$ is —I.

In another embodiment, Ar$^1$ is a pyridyl group; V is CH; n is 0; m is 0; R$_1$ is —CF$_3$; Ar$^2$ is a benzoimidazolyl group; s is 1; and R$_8$ is —I.

In another embodiment, Ar$^1$ is a pyridyl group; V is CH; n is 0; m is 0; R$_1$ is —F, —Cl, —Br, or —I; Ar$^2$ is a benzoimidazolyl group; s is 1; and R$_8$ is —CH$_3$.

In another embodiment, Ar$^1$ is a pyridyl group; V is CH; n is 0; m is 0; R$_1$ is —F; Ar$^2$ is a benzoimidazolyl group; s is 1; and R$_8$ is —CH$_3$.

In another embodiment, Ar$^1$ is a pyridyl group; V is CH; n is 0; m is 0; R$_1$ is —Cl; Ar$^2$ is a benzoimidazolyl group; s is 1; and R$_8$ is —CH$_3$.

In another embodiment, Ar$^1$ is a pyridyl group; V is CH; n is 0; m is 0; R$_1$ is —Br; Ar$^2$ is a benzoimidazolyl group; s is 1; and R$_8$ is —CH$_3$.

In another embodiment, Ar$^1$ is a pyridyl group; V is CH; n is 0; m is 0; R$_1$ is —I; Ar$^2$ is a benzoimidazolyl group; s is 1; and R$_8$ is —CH$_3$.

In another embodiment, Ar$^1$ is a pyridyl group; V is CH; n is 0; m is 0; R$_1$ is —CH$_3$; Ar$^2$ is a benzoimidazolyl group; s is 1; and R$_8$ is —CH$_3$.

In another embodiment, Ar$^1$ is a pyridyl group; V is CH; n is 0; m is 0; R$_1$ is —CF$_3$; Ar$^2$ is a benzoimidazolyl group; s is 1; and R$_8$ is —CH$_3$.

In another embodiment, Ar$^1$ is a pyridyl group; V is CH; n is 0; m is 0; R$_1$ is —F, —Cl, —Br, or —I; Ar$^2$ is a benzoimidazolyl group; s is 1; and R$_8$ is —CF$_3$.

In another embodiment, Ar$^1$ is a pyridyl group; V is CH; n is 0; m is 0; R$_1$ is —F; Ar$^2$ is a benzoimidazolyl group; s is 1; and R$_8$ is —CF$_3$.

In another embodiment, Ar$^1$ is a pyridyl group; V is CH; n is 0; m is 0; R$_1$ is —Cl; Ar$^2$ is a benzoimidazolyl group; s is 1; and R$_8$ is —CF$_3$.

In another embodiment, Ar$^1$ is a pyridyl group; V is CH; n is 0; m is 0; R$_1$ is —Br; Ar$^2$ is a benzoimidazolyl group; s is 1; and R$_8$ is —CF$_3$.

In another embodiment, Ar$^1$ is a pyridyl group; V is CH; n is 0; m is 0; R$_1$ is —I; Ar$^2$ is a benzoimidazolyl group; s is 1; and R$_8$ is —CF$_3$.

In another embodiment, Ar$^1$ is a pyridyl group; V is CH; n is 0; m is 0; R$_1$ is —CH$_3$; Ar$^2$ is a benzoimidazolyl group; s is 1; and R$_8$ is —CF$_3$.

In another embodiment, Ar$^1$ is a pyridyl group; V is CH; n is 0; m is 0; R$_1$ is —CF$_3$; Ar$^2$ is a benzoimidazolyl group; s is 1; and R$_8$ is —CF$_3$.

In another embodiment, Ar$^1$ is a pyridyl group; V is CH; n is 0; m is 0; R$_1$ is —F, —Cl, —Br, or —I; Ar$^2$ is a benzoimidazolyl group; s is 1; and R$_8$ is —OCH$_2$CH$_3$.

In another embodiment, Ar$^1$ is a pyridyl group; V is CH; n is 0; m is 0; R$_1$ is —F; Ar$^2$ is a benzoimidazolyl group; s is 1; and R$_8$ is —OCH$_2$CH$_3$.

In another embodiment, Ar$^1$ is a pyridyl group; V is CH; n is 0; m is 0; R$_1$ is —Cl; Ar$^2$ is a benzoimidazolyl group; s is 1; and R$_8$ is —OCH$_2$CH$_3$.

In another embodiment, Ar$^1$ is a pyridyl group; V is CH; n is 0; m is 0; R$_1$ is —Br; Ar$^2$ is a benzoimidazolyl group; s is 1; and R$_8$ is —OCH$_2$CH$_3$.

In another embodiment, Ar$^1$ is a pyridyl group; V is CH; n is 0; m is 0; R$_1$ is —I; Ar$^2$ is a benzoimidazolyl group; s is 1; and R$_8$ is —OCH$_2$CH$_3$.

In another embodiment, $Ar^1$ is a pyridyl group; V is CH; n is 0; m is 0; $R_1$ is —$CH_3$; $Ar^2$ is a benzoimidazolyl group; s is 1; and $R_8$ is —$OCH_2CH_3$.

In another embodiment, $Ar^1$ is a pyridyl group; V is CH; n is 0; m is 0; $R_1$ is —$CF_3$; $Ar^2$ is a benzoimidazolyl group; s is 1; and $R_8$ is —$OCH_2CH_3$.

In another embodiment, $Ar^1$ is a pyridyl group; V is CH; n is 0; m is 0; $R_1$ is —F, —Cl, —Br, or —I; $Ar^2$ is a benzoimidazolyl group; $R_8$ is -tert-butyl.

In another embodiment, $Ar^1$ is a pyridyl group; V is CH; n is 0; m is 0; $R_1$ is —F; $Ar^2$ is a benzoimidazolyl group; s is 1; and $R_8$ is -tert-butyl.

In another embodiment, $Ar^1$ is a pyridyl group; V is CH; n is 0; m is 0; $R_1$ is —Cl; $Ar^2$ is a benzoimidazolyl group; s is 1; and $R_8$ is -tert-butyl.

In another embodiment, $Ar^1$ is a pyridyl group; V is CH; n is 0; m is 0; $R_1$ is —Br; $Ar^2$ is a benzoimidazolyl group; s is 1; and $R_8$ is -tert-butyl.

In another embodiment, $Ar^1$ is a pyridyl group; V is CH; n is 0; m is 0; $R_1$ is —I; $Ar^2$ is a benzoimidazolyl group; s is 1; and $R_8$ is -tert-butyl.

In another embodiment, $Ar^1$ is a pyridyl group; V is CH; n is 0; m is 0; $R_1$ is —$CH_3$; $Ar^2$ is a benzoimidazolyl group; s is 1; and $R_8$ is -tert-butyl.

In another embodiment, $Ar^1$ is a pyridyl group; V is CH; n is 0; m is 0; $R_1$ is —$CF_3$; $Ar^2$ is a benzoimidazolyl group; s is 1; and $R_8$ is -tert-butyl.

In another embodiment, $Ar^1$ is a pyridyl group; V is CH; n is 0; m is 1; $R_3$ is —$CH_3$; $R_1$ is —F, —Cl, —Br, or —I; $Ar^2$ is a benzoimidazolyl group; and s is 0. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F; $Ar^2$ is a benzoimidazolyl group; and s is 0. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Cl; $Ar^2$ is a benzoimidazolyl group; and s is 0. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Br; $Ar^2$ is a benzoimidazolyl group; and s is 0. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —I; $Ar^2$ is a benzoimidazolyl group; and s is 0. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CH_3$; $Ar^2$ is a benzoimidazolyl group; and s is 0. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CF_3$; $Ar^2$ is a benzoimidazolyl group; and s is 1. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F, —Cl, —Br, or —I; $Ar^2$ is a benzoimidazolyl group; s is 1; and $R_8$ is -halo. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F; $Ar^2$ is a benzoimidazolyl group; s is 1; and $R_8$ is -halo. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Cl; $Ar^2$ is a benzoimidazolyl group; s is 1; and $R_8$ is -halo. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Br; $Ar^2$ is a benzoimidazolyl group; s is 1; and $R_8$ is -halo. In another embodiment, the $R_3$ group is attached to the 3-, 5- or 6-position of the cyclo (hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —I; $Ar^2$ is a benzoimidazolyl group; s is 1; and $R_8$ is -halo. In another embodiment, the $R_3$ group is attached to the 3-, 5- or 6-position of the cyclo (hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CH_3$; $Ar^2$ is a benzoimidazolyl group; s is 1; and $R_8$ is -halo. In another embodiment, the $R_3$ group is attached to the 3-, 5- or 6-position of the cyclo (hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CF_3$; $Ar^2$ is a benzoimidazolyl group; s is 1; and $R_8$ is -halo. In another embodiment, the $R_3$ group is attached to the 3-, 5- or 6-position of the cyclo (hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F, —Cl, —Br, or —I; $Ar^2$ is a benzoimidazolyl group; s is 1; and $R_8$ is —Br. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F; $Ar^2$ is a benzoimidazolyl group; s is 1; and $R_8$ is —Br. In another embodiment, the $R_3$ group is attached to the 3-, 5- or 6-position of the cyclo (hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Cl; $Ar^2$ is a benzoimidazolyl group; s is 1; and $R_8$ is —Br. In another embodiment, the $R_3$ group is attached to the 3-, 5- or 6-position of the cyclo (hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Br; $Ar^2$ is a benzoimidazolyl group; s is 1; and $R_8$ is —Br. In another embodiment, the $R_3$ group is attached to the 3-, 5- or 6-position of the cyclo (hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —I; $Ar^2$ is a benzoimidazolyl group; s is 1; and $R_8$ is —Br. In another embodiment, the $R_3$ group is attached to the 3-, 5- or 6-position of the cyclo (hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CH_3$; $Ar^2$ is a benzoimidazolyl group; s is 1; and $R_8$ is —Br. In another embodiment, the $R_3$ group is attached to the 3-, 5- or 6-position of the cyclo (hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CF_3$; $Ar^2$ is a benzoimidazolyl group; s is 1; and $R_8$ is —Br. In another embodiment, the $R_3$ group is attached to the 3-, 5- or 6-position of the cyclo (hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Cl, —F —Br, or —I; $Ar^2$ is a benzoimidazolyl group; s is 1; and $R_8$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F; $Ar^2$ is a benzoimidazolyl group; s is 1; and $R_8$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Cl; $Ar^2$ is a benzoimidazolyl group; s is 1; and $R_8$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Br; $Ar^2$ is a benzoimidazolyl group; s is 1; and $R_8$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —I; $Ar^2$ is a benzoimidazolyl group; s is 1; and $R_8$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CH_3$; $Ar^2$ is a benzoimidazolyl group; s is 1; and $R_8$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CF_3$; $Ar^2$ is a benzoimidazolyl group; s is 1; and $R_8$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is $CH_3$; $R_1$ is —Cl, —F —Br, or —I; $Ar^2$ is a benzoimidazolyl group; s is 1; and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F; $Ar^2$ is a benzoimidazolyl group; s is 1; and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Cl; $Ar^2$ is a benzoimidazolyl group; s is 1; and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Br; $Ar^2$ is a benzoimidazolyl group; s is 1; and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —I; $Ar^2$ is a benzoimidazolyl group; s is 1; and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CH_3$; $Ar^2$ is a benzoimidazolyl group; s is 1; and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CF_3$; $Ar^2$ is a benzoimidazolyl group; s is 1; and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Cl, —F, —Br, or —I, $Ar^2$ is a benzoimidazolyl group; s is 1; and $R_8$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F; $Ar^2$ is a benzoimidazolyl group; s is 1; and $R_8$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Cl; $Ar^2$ is a benzoimidazolyl group; s is 1; and $R_8$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Br; $Ar^2$ is a benzoimidazolyl group; s is 1; and $R_8$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —I; $Ar^2$ is a benzoimidazolyl group; s is 1; and $R_8$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CH_3$; $Ar^2$ is a benzoimidazolyl group; s is 1; and $R_8$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CF_3$; $Ar^2$ is a benzoimidazolyl group; s is 1; and $R_8$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F, —Cl, —Br, or —I; $Ar^2$ is a benzoimidazolyl group; s is 1; and $R_8$ is —$CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F; $Ar^2$ is a benzoimidazolyl group; s is 1; and $R_8$ is —$CH_3$. In another embodiment, the $R_3$ is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Cl; $Ar^2$ is a benzoimidazolyl group; s is 1; and $R_8$ is —$CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Br; $Ar^2$ is a benzoimidazolyl group; s is 1; and $R_8$ is —$CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —I; $Ar^2$ is a benzoimidazolyl group; s is 1; and $R_8$ is —$CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CH_3$; $Ar^2$ is a benzoimidazolyl group; s is 1; and $R_8$ is —$CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CF_3$; $Ar^2$ is a benzoimidazolyl group; s is 1; and $R_8$ is —$CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F, —Cl, —Br, or —I; $Ar^2$ is a benzoimidazolyl group; s is 1; and $R_8$ is —$CF_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F; $Ar^2$ is a benzoimidazolyl group; s is 1; and $R_8$ is —$CF_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Cl; $Ar^2$ is a benzoimidazolyl group; s is 1; and $R_8$ is —$CF_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Br; $Ar^2$ is a benzoimidazolyl group; s is 1; and $R_8$ is —$CF_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —I; $Ar^2$ is a benzoimidazolyl group; s is 1; and $R_8$ is —$CF_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CH_3$; $Ar^2$ is a benzoimidazolyl group; s is 1; and $R_8$ is —$CF_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CF_3$; $Ar^2$ is a benzoimidazolyl group; s is 1; and $R_8$ is —$CF_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F, —Cl, —Br, or —I; $Ar^2$ is a benzoimidazolyl group; s is 1; and $R_8$ is —$OCH_2CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F; $Ar^2$ is a benzoimidazolyl group; s is 1; and $R_8$ is —$OCH_2CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Cl; $Ar^2$ is a benzoimidazolyl group; s is 1; and $R_8$ is —$OCH_2CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Br; $Ar^2$ is a benzoimidazolyl group; s is 1; and $R_8$ is —$OCH_2CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —I; $Ar^2$ is a benzoimidazolyl group; s is 1; and $R_8$ is —$OCH_2CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CH_3$; $Ar^2$ is a benzoimidazolyl group; s is 1; and $R_8$ is —$OCH_2CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CF_3$; $Ar^2$ is a benzoimidazolyl group; s is 1; and $R_8$ is —$OCH_2CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F, —Cl, —Br, or —I; $Ar^2$ is a benzoimidazolyl group; s is 1; and $R_8$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F; $Ar^2$ is a benzoimidazolyl group; s is 1; and $R_8$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Cl; $Ar^2$ is a benzoimidazolyl group; s is 1; and $R_8$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Br; $Ar^2$ is a benzoimidazolyl group; s is 1; and $R_8$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —I; $Ar^2$ is a benzoimidazolyl group; s is 1; and $R_8$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CH_3$; $Ar^2$ is a benzoimidazolyl group; s is 1; and $R_8$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CF_3$; $Ar^2$ is a benzoimidazolyl group; s is 1; and $R_8$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group, V is N; m is 0, and $Ar^2$ is a benzooxazolyl group.

In another embodiment, $Ar^1$ is a pyridyl group; V is N; n is 0; m is 0; $R_1$ is —F, —Cl, —Br, or —I; $Ar^2$ is a benzooxazolyl group; and s is 0.

In another embodiment, $Ar^1$ is a pyridyl group; V is N; n is 0; m is 0; $R_1$ is —F; $Ar^2$ is a benzooxazolyl group; and s is 0.

In another embodiment, $Ar^1$ is a pyridyl group; V is N; n is 0; m is 0; $R_1$ is —Cl; $Ar^2$ is a benzooxazolyl group; and s is 0.

In another embodiment, $Ar^1$ is a pyridyl group; V is N; n is 0; m is 0; $R_1$ is —Br; $Ar^2$ is a benzooxazolyl group; and s is 0.

In another embodiment, $Ar^1$ is a pyridyl group; V is N; n is 0; m is 0; $R_1$ is —I; $Ar^2$ is a benzooxazolyl group; and s is 0.

In another embodiment, $Ar^1$ is a pyridyl group; V is N; n is 0; m is 0; $R_1$ is —$CH_3$; $Ar^2$ is a benzooxazolyl group; and s is 0.

In another embodiment, $Ar^1$ is a pyridyl group; V is N; n is 0; m is 0; $R_1$ is —$CF_3$; $Ar^2$ is a benzooxazolyl group; and s is 0.

In another embodiment, $Ar^1$ is a pyridyl group; V is N; n is 0; m is 0; $R_1$ is —F, —Cl, —Br, or —I; $Ar^2$ is a benzooxazolyl group; s is 1; and $R_8$ is -halo.

In another embodiment, $Ar^1$ is a pyridyl group; V is N; n is 0; m is 0; $R_1$ is —F; $Ar^2$ is a benzooxazolyl group; s is 1; and $R_8$ is -halo.

In another embodiment, $Ar^1$ is a pyridyl group; V is N; n is 0; m is 0; $R_1$ is —Cl; $Ar^2$ is a benzooxazolyl group; s is 1; and $R_8$ is -halo.

In another embodiment, $Ar^1$ is a pyridyl group; V is N; n is 0; m is 0; $R_1$ is —Br; $Ar^2$ is a benzooxazolyl group; s is 1; and $R_8$ is -halo.

In another embodiment, $Ar^1$ is a pyridyl group; V is N; n is 0; m is 0; $R_1$ is —I; $Ar^2$ is a benzooxazolyl group; $R_8$ s is 1; and $R_8$ is -halo.

In another embodiment, $Ar^1$ is a pyridyl group; V is N; n is 0; m is 0; $R_1$ is —$CH_3$; $Ar^2$ is a benzooxazolyl group; s is 1; and $R_8$ is -halo.

In another embodiment, $Ar^1$ is a pyridyl group; V is N; n is 0; m is 0; $R_1$ is —$CF_3$; $Ar^2$ is a benzooxazolyl group; s is 1; and $R_8$ is -halo.

In another embodiment, $Ar^1$ is a pyridyl group; V is N; n is 0; m is 0; $R_1$ is —F, —Cl, —Br, or —I; $Ar^2$ is a benzooxazolyl group; s is 1; and $R_8$ is —Br.

In another embodiment, $Ar^1$ is a pyridyl group; V is N; n is 0; m is 0; $R_1$ is —F; $Ar^2$ is a benzooxazolyl group; s is 1; and $R_8$ is —Br.

In another embodiment, $Ar^1$ is a pyridyl group; V is N; n is 0; m is 0; $R_1$ is —Cl; $Ar^2$ is a benzooxazolyl group; s is 1; and $R_8$ is —Br.

In another embodiment, $Ar^1$ is a pyridyl group; V is N; n is 0; m is 0; $R_1$ is —Br; $Ar^2$ is a benzooxazolyl group; s is 1; and $R_8$ is —Br.

In another embodiment, $Ar^1$ is a pyridyl group; V is N; n is 0; m is 0; $R_1$ is —I; $Ar^2$ is a benzooxazolyl group; s is 1; and $R_8$ is —Br.

In another embodiment, $Ar^1$ is a pyridyl group; V is N; n is 0; m is 0; $R_1$ is —$CH_3$; $Ar^2$ is a benzooxazolyl group; s is 1; and $R_8$ is —Br.

In another embodiment, $Ar^1$ is a pyridyl group; V is N; n is 0; m is 0; $R_1$ is —$CF_3$; $Ar^2$ is a benzooxazolyl group; s is 1; and $R_8$ is —Br.

In another embodiment, $Ar^1$ is a pyridyl group; V is N; n is 0; m is 0; $R_1$ is —Cl, —F —Br, or —I; $Ar^2$ is a benzooxazolyl group; s is 1; and $R_8$ is —F.

In another embodiment, $Ar^1$ is a pyridyl group; V is N; n is 0; m is 0; $R_1$ is —F; $Ar^2$ is a benzooxazolyl group; s is 1; and $R_8$ is —F.

In another embodiment, $Ar^1$ is a pyridyl group; V is N; n is 0; m is 0; $R_1$ is —Cl; $Ar^2$ is a benzooxazolyl group; s is 1; and $R_8$ is —F.

In another embodiment, $Ar^1$ is a pyridyl group; V is N; n is 0; m is 0; $R_1$ is —Br; $Ar^2$ is a benzooxazolyl group; s is 1; and $R_8$ is —F.

In another embodiment, $Ar^1$ is a pyridyl group; V is N; n is 0; m is 0; $R_1$ is —I; $Ar^2$ is a benzooxazolyl group; s is 1; and $R_8$ is —F.

In another embodiment, $Ar^1$ is a pyridyl group; V is N; n is 0; m is 0; $R_1$ is —$CH_3$; $Ar^2$ is a benzooxazolyl group; s is 1; and $R_8$ is —F.

In another embodiment, $Ar^1$ is a pyridyl group; V is N; n is 0; m is 0; $R_1$ is —$CF_3$; $Ar^2$ is a benzooxazolyl group; s is 1; and $R_8$ is —F.

In another embodiment, $Ar^1$ is a pyridyl group; V is N; n is 0; m is 0; $R_1$ is —Cl, —F —Br, or —I; $Ar^2$ is a benzooxazolyl group; s is 1; and $R_8$ is —Cl.

In another embodiment, $Ar^1$ is a pyridyl group; V is N; n is 0; m is 0; $R_1$ is —F; $Ar^2$ is a benzooxazolyl group; s is 1; and $R_8$ is —Cl.

In another embodiment, $Ar^1$ is a pyridyl group; V is N; n is 0; m is 0; $R_1$ is —Cl; $Ar^2$ is a benzooxazolyl group; s is 1; and $R_8$ is —Cl.

In another embodiment, $Ar^1$ is a pyridyl group; V is N; n is 0; m is 0; $R_1$ is —Br; $Ar^2$ is a benzooxazolyl group; s is 1; and $R_8$ is —Cl.

In another embodiment, $Ar^1$ is a pyridyl group; V is N; n is 0; m is 0; $R_1$ is —I; $Ar^2$ is a benzooxazolyl group; s is 1; and $R_8$ is —Cl.

In another embodiment, $Ar^1$ is a pyridyl group; V is N; n is 0; m is 0; $R_1$ is —$CH_3$; $Ar^2$ is a benzooxazolyl group; s is 1; and $R_8$ is —Cl.

In another embodiment, $Ar^1$ is a pyridyl group; V is N; n is 0; m is 0; $R_1$ is —$CF_3$; $Ar^2$ is a benzooxazolyl group s is 1; and $R_8$ is —Cl.

In another embodiment, $Ar^1$ is a pyridyl group; V is N; n is 0; m is 0; $R_1$ is —Cl, —F, —Br, or —I, $Ar^2$ is a benzooxazolyl group; s is 1; and $R_8$ is —I.

In another embodiment, $Ar^1$ is a pyridyl group; V is N; n is 0; m is 0; $R_1$ is —F; $Ar^2$ is a benzooxazolyl group; s is 1; and $R_8$ is —I.

In another embodiment, $Ar^1$ is a pyridyl group; V is N; n is 0; m is 0; $R_1$ is —Cl; $Ar^2$ is a benzooxazolyl group; s is 1; and $R_8$ is —I.

In another embodiment, $Ar^1$ is a pyridyl group; V is N; n is 0; m is 0; $R_1$ is —Br; $Ar^2$ is a benzooxazolyl group; s is 1; and $R_8$ is —I.

In another embodiment, Art is a pyridyl group; V is N; n is 0; m is 0; $R_1$ is —I; $Ar^2$ is a benzooxazolyl group; s is 1; and $R_8$ is —I.

In another embodiment, $Ar^1$ is a pyridyl group; V is N; n is 0; m is 0; $R_1$ is —$CH_3$; $Ar^2$ is a benzooxazolyl group; s is 1; and $R_8$ is —I.

In another embodiment, $Ar^1$ is a pyridyl group; V is N; n is 0; m is 0; $R_1$ is —$CF_3$; $Ar^2$ is a benzooxazolyl group; s is 1; and $R_8$ is —I.

In another embodiment, $Ar^1$ is a pyridyl group; V is N; n is 0; m is 0; $R_1$ is —F, —Cl, —Br, or —I; $Ar^2$ is a benzooxazolyl group; s is 1; and $R_8$ is —$CH_3$.

In another embodiment, $Ar^1$ is a pyridyl group; V is N; n is 0; m is 0; $R_1$ is —F; $Ar^2$ is a benzooxazolyl group; s is 1; and $R_8$ is —$CH_3$.

In another embodiment, $Ar^1$ is a pyridyl group; V is N; n is 0; m is 0; $R_1$ is —Cl; $Ar^2$ is a benzooxazolyl group; s is 1; and $R_8$ is —$CH_3$.

In another embodiment, $Ar^1$ is a pyridyl group; V is N; n is 0; m is 0; $R_1$ is —Br; $Ar^2$ is a benzooxazolyl group; s is 1; and $R_8$ is —$CH_3$.

In another embodiment, $Ar^1$ is a pyridyl group; V is N; n is 0; m is 0; $R_1$ is —I; $Ar^2$ is a benzooxazolyl group; s is 1; and $R_8$ is —$CH_3$.

In another embodiment, $Ar^1$ is a pyridyl group; V is N; n is 0; m is 0; $R_1$ is —$CH_3$; $Ar^2$ is a benzooxazolyl group; s is 1; and $R_8$ is —$CH_3$.

In another embodiment, $Ar^1$ is a pyridyl group; V is N; n is 0; m is 0; $R_1$ is —$CF_3$; $Ar^2$ is a benzooxazolyl group; s is 1; and $R_8$ is —$CH_3$.

In another embodiment, $Ar^1$ is a pyridyl group; V is N; n is 0; m is 0; $R_1$ is —F, —Cl, —Br, or —I; $Ar^2$ is a benzooxazolyl group; s is 1; and $R_8$ is —$CF_3$.

In another embodiment, $Ar^1$ is a pyridyl group; V is N; n is 0; m is 0; $R_1$ is —F; $Ar^2$ is a benzooxazolyl group; s is 1; and $R_8$ is —$CF_3$.

In another embodiment, $Ar^1$ is a pyridyl group; V is N; n is 0; m is 0; $R_1$ is —Cl; $Ar^2$ is a benzooxazolyl group; s is 1; and $R_8$ is —$CF_3$.

In another embodiment, $Ar^1$ is a pyridyl group; V is N; n is 0; m is 0; $R_1$ is —Br; $Ar^2$ is a benzooxazolyl group; s is 1; and $R_8$ is —$CF_3$.

In another embodiment, $Ar^1$ is a pyridyl group; V is N; n is 0; m is 0; $R_1$ is —I; $Ar^2$ is a benzooxazolyl group; s is 1; and $R_8$ is —$CF_3$.

In another embodiment, $Ar^1$ is a pyridyl group; V is N; n is 0; m is 0; $R_1$ is —$CH_3$; $Ar^2$ is a benzooxazolyl group; s is 1; and $R_8$ is —$CF_3$.

In another embodiment, $Ar^1$ is a pyridyl group; V is N; n is 0; m is 0; $R_1$ is —$CF_3$; $Ar^2$ is a benzooxazolyl group; s is 1; and $R_8$ is —$CF_3$.

In another embodiment, $Ar^1$ is a pyridyl group; V is N; n is 0; m is 0; $R_1$ is —F, —Cl, —Br, or —I; $Ar^2$ is a benzooxazolyl group; s is 1; and $R_8$ is —$OCH_2CH_3$.

In another embodiment, $Ar^1$ is a pyridyl group; V is N; n is 0; m is 0; $R_1$ is —F; $Ar^2$ is a benzooxazolyl group; s is 1; and $R_8$ is —$OCH_2CH_3$.

In another embodiment, $Ar^1$ is a pyridyl group; V is N; n is 0; m is 0; $R_1$ is —Cl; $Ar^2$ is a benzooxazolyl group; s is 1; and $R_8$ is —$OCH_2CH_3$.

In another embodiment, $Ar^1$ is a pyridyl group; V is N; n is 0; m is 0; $R_1$ is —Br; $Ar^2$ is a benzooxazolyl group; s is 1; and $R_8$ is —$OCH_2CH_3$.

In another embodiment, $Ar^1$ is a pyridyl group; V is N; n is 0; m is 0; $R_1$ is —I; $Ar^2$ is a benzooxazolyl group; s is 1; and $R_8$ is —$OCH_2CH_3$.

In another embodiment, $Ar^1$ is a pyridyl group; V is N; n is 0; m is 0; $R_1$ is —$CH_3$; $Ar^2$ is a benzooxazolyl group; s is 1; and $R_8$ is —$OCH_2CH_3$.

In another embodiment, $Ar^1$ is a pyridyl group; V is N; n is 0; m is 0; $R_1$ is —$CF_3$; $Ar^2$ is a benzooxazolyl group; s is 1; and $R_8$ is —$OCH_2CH_3$.

In another embodiment, $Ar^1$ is a pyridyl group; V is N; n is 0; m is 0; $R_1$ is —F, —Cl —Br, or —I; $Ar^2$ is a benzooxazolyl group; $R_8$ is -tert-butyl.

In another embodiment, $Ar^1$ is a pyridyl group; V is N; n is 0; m is 0; $R_1$ is —F; $Ar^2$ is a benzooxazolyl group; s is 1; and $R_8$ is -tert-butyl.

In another embodiment, $Ar^1$ is a pyridyl group; V is N; n is 0; m is 0; $R_1$ is —Cl; $Ar^2$ is a benzooxazolyl group; s is 1; and $R_8$ is -tert-butyl.

In another embodiment, $Ar^1$ is a pyridyl group; V is N; n is 0; m is 0; $R_1$ is —Br; $Ar^2$ is a benzooxazolyl group; s is 1; and $R_8$ is -tert-butyl.

In another embodiment, $Ar^1$ is a pyridyl group; V is N; n is 0; m is 0; $R_1$ is —I; $Ar^2$ is a benzooxazolyl group; s is 1; and $R_8$ is -tert-butyl.

In another embodiment, $Ar^1$ is a pyridyl group; V is N; n is 0; m is 0; $R_1$ is —$CH_3$; $Ar^2$ is a benzooxazolyl group; s is 1; and $R_8$ is -tert-butyl.

In another embodiment, $Ar^1$ is a pyridyl group; V is N; n is 0; m is 0; $R_1$ is —$CF_3$; $Ar^2$ is a benzooxazolyl group; s is 1; and $R_8$ is -tert-butyl.

In another embodiment, $Ar^1$ is a pyridyl group; V is N; n is 0; m is 1; $R_3$ is —$CH_3$; $R_1$ is —F, —Cl, —Br, or —I; $Ar^2$ is a benzooxazolyl group; and s is 0. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —F; $Ar^2$ is a benzooxazolyl group; and s is 0. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Cl; $Ar^2$ is a benzooxazolyl group; and s is 0. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Br; $Ar^2$ is a benzooxazolyl group; and s is 0. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —I; $Ar^2$ is a benzooxazolyl group; and s is 0. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CH_3$; $Ar^2$ is a benzooxazolyl group; and s is 0. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CF_3$; $Ar^2$ is a benzooxazolyl group; and s is 1. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —F, —Cl, —Br, or —I; $Ar^2$ is a benzooxazolyl group; s is 1; and $R_8$ is -halo. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —F; $Ar^2$ is a benzooxazolyl group; s is 1; and $R_8$ is -halo. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Cl; $Ar^2$ is a benzooxazolyl group; s is 1; and $R_8$ is -halo. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Br; $Ar^2$ is a benzooxazolyl group; s is 1; and $R_8$ is -halo. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —I; $Ar^2$ is a benzooxazolyl group; s is 1; and $R_8$ is -halo. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CH_3$; $Ar^2$ is a benzooxazolyl group; s is 1; and $R_8$ is -halo. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CF_3$; $Ar^2$ is a benzooxazolyl group; s is 1; and $R_8$ is -halo. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —F, —Cl, —Br, or —I; $Ar^2$ is a benzooxazolyl group; s is 1; and $R_8$ is —Br. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —F; $Ar^2$ is a benzooxazolyl group; s is 1; and $R_8$ is —Br. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Cl; $Ar^2$ is a benzooxazolyl group; s is 1; and $R_8$ is —Br. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Br; $Ar^2$ is a benzooxazolyl group; s is 1; and $R_8$ is —Br. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —I; $Ar^2$ is a benzooxazolyl group; s is 1; and $R_8$ is —Br. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CH_3$; $Ar^2$ is a benzooxazolyl group; s is 1; and $R_8$ is —Br. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CF_3$; $Ar^2$ is a benzooxazolyl group; s is 1; and $R_8$ is —Br. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Cl, —F —Br, or —I; $Ar^2$ is a benzooxazolyl group; s is 1; and $R_8$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —F; $Ar^2$ is a benzooxazolyl group; s is 1; and $R_8$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Cl; $Ar^2$ is a benzooxazolyl group; s is 1; and $R_8$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Br; $Ar^2$ is a benzooxazolyl group; s is 1; and $R_8$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —I; $Ar^2$ is a benzooxazolyl group; s is 1; and $R_8$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CH_3$; $Ar^2$ is a benzooxazolyl group; s is 1; and $R_8$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CF_3$; $Ar^2$ is a benzooxazolyl group; s is 1; and $R_8$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is $CH_3$; $R_1$ is —Cl, —F —Br, or —I; $Ar^2$ is a benzooxazolyl group; s is 1; and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —F; $Ar^2$ is a benzooxazolyl group; s is 1; and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Cl; $Ar^2$ is a benzooxazolyl group; s is 1; and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Br; $Ar^2$ is a benzooxazolyl group; s is 1; and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —I; $Ar^2$ is a benzooxazolyl group; s is 1; and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CH_3$; $Ar^2$ is a benzooxazolyl group; s is 1; and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CF_3$; $Ar^2$ is a benzooxazolyl group; s is 1; and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Cl, —F, —Br, or —I, $Ar^2$ is a benzooxazolyl group; s is 1; and $R_8$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —F; $Ar^2$ is a benzooxazolyl group; s is 1; and $R_8$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Cl; $Ar^2$ is a benzooxazolyl group; s is 1; and $R_8$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Br; $Ar^2$ is a benzooxazolyl group; s is 1; and $R_8$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —I; $Ar^2$ is a benzooxazolyl group; s is 1; and $R_8$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CH_3$; $Ar^2$ is a benzooxazolyl group; s is 1; and $R_8$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, Ar$^1$ is a pyridyl group; V is N; n is 0; m is 1; R$_3$ is —CH$_3$; R$_1$ is —CF$_3$; Ar$^2$ is a benzooxazolyl group; s is 1; and R$_8$ is —I. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring.

In another embodiment, Ar$^1$ is a pyridyl group; V is N; n is 0; m is 1; R$_3$ is —CH$_3$; R$_1$ is —F, —Cl, —Br, or —I; Ar$^2$ is a benzooxazolyl group; s is 1; and R$_8$ is —CH$_3$. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring.

In another embodiment, Ar$^1$ is a pyridyl group; V is N; n is 0; m is 1; R$_3$ is —CH$_3$; R$_1$ is —F; Ar$^2$ is a benzooxazolyl group; s is 1; and R$_8$ is —CH$_3$. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring.

In another embodiment, Ar$^1$ is a pyridyl group; V is N; n is 0; m is 1; R$_3$ is —CH$_3$; R$_1$ is —Cl; Ar$^2$ is a benzooxazolyl group; s is 1; and R$_8$ is —CH$_3$. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring.

In another embodiment, Ar$^1$ is a pyridyl group; V is N; n is 0; m is 1; R$_3$ is —CH$_3$; R$_1$ is —Br; Ar$^2$ is a benzooxazolyl group; s is 1; and R$_8$ is —CH$_3$. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring.

In another embodiment, Ar$^1$ is a pyridyl group; V is N; n is 0; m is 1; R$_3$ is —CH$_3$; R$_1$ is —I; Ar$^2$ is a benzooxazolyl group; s is 1; and R$_8$ is —CH$_3$. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring.

In another embodiment, Ar$^1$ is a pyridyl group; V is N; n is 0; m is 1; R$_3$ is —CH$_3$; R$_1$ is —CH$_3$; Ar$^2$ is a benzooxazolyl group; s is 1; and R$_8$ is —CH$_3$. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring.

In another embodiment, Ar$^1$ is a pyridyl group; V is N; n is 0; m is 1; R$_3$ is —CH$_3$; R$_1$ is —CF$_3$; Ar$^2$ is a benzooxazolyl group; s is 1; and R$_8$ is —CH$_3$. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring.

In another embodiment, Ar$^1$ is a pyridyl group; V is N; n is 0; m is 1; R$_3$ is —CH$_3$; R$_1$ is —F, —Cl, —Br, or —I; Ar$^2$ is a benzooxazolyl group; s is 1; and R$_8$ is —CF$_3$. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring.

In another embodiment, Ar$^1$ is a pyridyl group; V is N; n is 0; m is 1; R$_3$ is —CH$_3$; R$_1$ is —F; Ar$^2$ is a benzooxazolyl group; s is 1; and R$_8$ is —CF$_3$. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring.

In another embodiment, Ar$^1$ is a pyridyl group; V is N; n is 0; m is 1; R$_3$ is —CH$_3$; R$_1$ is —Cl; Ar$^2$ is a benzooxazolyl group; s is 1; and R$_8$ is —CF$_3$. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring.

In another embodiment, Ar$^1$ is a pyridyl group; V is N; n is 0; m is 1; R$_3$ is —CH$_3$; R$_1$ is —Br; Ar$^2$ is a benzooxazolyl group; s is 1; and R$_8$ is —CF$_3$. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —I; $Ar^2$ is a benzooxazolyl group; s is 1; and $R_8$ is —$CF_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CH_3$; $Ar^2$ is a benzooxazolyl group; s is 1; and $R_8$ is —$CF_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CF_3$; $Ar^2$ is a benzooxazolyl group; s is 1; and $R_8$ is —$CF_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —F, —Cl, —Br, or —I; $Ar^2$ is a benzooxazolyl group; s is 1; and $R_8$ is —$OCH_2CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —F; $Ar^2$ is a benzooxazolyl group; s is 1; and $R_8$ is —$OCH_2CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Cl; $Ar^2$ is a benzooxazolyl group; s is 1; and $R_8$ is —$OCH_2CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Br; $Ar^2$ is a benzooxazolyl group; s is 1; and $R_8$ is —$OCH_2CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —I; $Ar^2$ is a benzooxazolyl group; s is 1; and $R_8$ is —$OCH_2CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CH_3$; $Ar^2$ is a benzooxazolyl group; s is 1; and $R_8$ is —$OCH_2CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CF_3$; $Ar^2$ is a benzooxazolyl group; s is 1; and $R_8$ is —$OCH_2CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —F, —Cl, —Br, or —I; $Ar^2$ is a benzooxazolyl group; s is 1; and $R_8$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —F; $Ar^2$ is a benzooxazolyl group; s is 1; and $R_8$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Cl; $Ar^2$ is a benzooxazolyl group; s is 1; and $R_8$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Br; $Ar^2$ is a benzooxazolyl group; s is 1; and $R_8$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —I; $Ar^2$ is a benzooxazolyl group; s is 1; and $R_8$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CH_3$; $Ar^2$ is a benzooxazolyl group; s is 1; and $R_8$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CF_3$; $Ar^2$ is a benzooxazolyl group; s is 1; and $R_8$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group, V is CH; m is 0, and $Ar^2$ is a benzooxazolyl group.

In another embodiment, $Ar^1$ is a pyridyl group; V is CH; n is 0; m is 0; $R_1$ is —F, —Cl, —Br, or —I; $Ar^2$ is a benzooxazolyl group; and s is 0.

In another embodiment, $Ar^1$ is a pyridyl group; V is CH; n is 0; m is 0; $R_1$ is —F; $Ar^2$ is a benzooxazolyl group; and s is 0.

In another embodiment, $Ar^1$ is a pyridyl group; V is CH; n is 0; m is 0; $R_1$ is —Cl; $Ar^2$ is a benzooxazolyl group; and s is 0.

In another embodiment, $Ar^1$ is a pyridyl group; V is CH; n is 0; m is 0; $R_1$ is —Br; $Ar^2$ is a benzooxazolyl group; and s is 0.

In another embodiment, $Ar^1$ is a pyridyl group; V is CH; n is 0; m is 0; $R_1$ is —I; $Ar^2$ is a benzooxazolyl group; and s is 0.

In another embodiment, $Ar^1$ is a pyridyl group; V is CH; n is 0; m is 0; $R_1$ is —$CH_3$; $Ar^2$ is a benzooxazolyl group; and s is 0.

In another embodiment, $Ar^1$ is a pyridyl group; V is CH; n is 0; m is 0; $R_1$ is —$CF_3$; $Ar^2$ is a benzooxazolyl group; and s is 0.

In another embodiment, $Ar^1$ is a pyridyl group; V is CH; n is 0; m is 0; $R_1$ is —F, —Cl, —Br, or —I; $Ar^2$ is a benzooxazolyl group; s is 1; and $R_8$ is -halo.

In another embodiment, $Ar^1$ is a pyridyl group; V is CH; n is 0; m is 0; $R_1$ is —F; $Ar^2$ is a benzooxazolyl group; s is 1; and $R_8$ is -halo.

In another embodiment, $Ar^1$ is a pyridyl group; V is CH; n is 0; m is 0; $R_1$ is —Cl; $Ar^2$ is a benzooxazolyl group; s is 1; and $R_8$ is -halo.

In another embodiment, $Ar^1$ is a pyridyl group; V is CH; n is 0; m is 0; $R_1$ is —Br; $Ar^2$ is a benzooxazolyl group; s is 1; and $R_8$ is -halo.

In another embodiment, $Ar^1$ is a pyridyl group; V is CH; n is 0; m is 0; $R_1$ is —I; $Ar^2$ is a benzooxazolyl group; $R_8$ s is 1; and $R_8$ is -halo.

In another embodiment, $Ar^1$ is a pyridyl group; V is CH; n is 0; m is 0; $R_1$ is —$CH_3$; $Ar^2$ is a benzooxazolyl group; s is 1; and $R_8$ is -halo.

In another embodiment, $Ar^1$ is a pyridyl group; V is CH; n is 0; m is 0; $R_1$ is —$CF_3$; $Ar^2$ is a benzooxazolyl group; s is 1; and $R_8$ is -halo.

In another embodiment, $Ar^1$ is a pyridyl group; V is CH; n is 0; m is 0; $R_1$ is —F, —Cl, —Br, or —I; $Ar^2$ is a benzooxazolyl group; s is 1; and $R_8$ is —Br.

In another embodiment, $Ar^1$ is a pyridyl group; V is CH; n is 0; m is 0; $R_1$ is —F; $Ar^2$ is a benzooxazolyl group; s is 1; and $R_8$ is —Br.

In another embodiment, $Ar^1$ is a pyridyl group; V is CH; n is 0; m is 0; $R_1$ is —Cl; $Ar^2$ is a benzooxazolyl group; s is 1; and $R_8$ is —Br.

In another embodiment, $Ar^1$ is a pyridyl group; V is CH; n is 0; m is 0; $R_1$ is —Br; $Ar^2$ is a benzooxazolyl group; s is 1; and $R_8$ is —Br.

In another embodiment, $Ar^1$ is a pyridyl group; V is CH; n is 0; m is 0; $R_1$ is —I; $Ar^2$ is a benzooxazolyl group; s is 1; and $R_8$ is —Br.

In another embodiment, $Ar^1$ is a pyridyl group; V is CH; n is 0; m is 0; $R_1$ is —$CH_3$; $Ar^2$ is a benzooxazolyl group; s is 1; and $R_8$ is —Br.

In another embodiment, $Ar^1$ is a pyridyl group; V is CH; n is 0; m is 0; $R_1$ is —$CF_3$; $Ar^2$ is a benzooxazolyl group; s is 1; and $R_8$ is —Br.

In another embodiment, $Ar^1$ is a pyridyl group; V is CH; n is 0; m is 0; $R_1$ is —Cl, —F —Br, or —I; $Ar^2$ is a benzooxazolyl group; s is 1; and $R_8$ is —F.

In another embodiment, $Ar^1$ is a pyridyl group; V is CH; n is 0; m is 0; $R_1$ is —F; $Ar^2$ is a benzooxazolyl group; s is 1; and $R_8$ is —F.

In another embodiment, $Ar^1$ is a pyridyl group; V is CH; n is 0; m is 0; $R_1$ is —Cl; $Ar^2$ is a benzooxazolyl group; s is 1; and $R_8$ is —F.

In another embodiment, $Ar^1$ is a pyridyl group; V is CH; n is 0; m is 0; $R_1$ is —Br; $Ar^2$ is a benzooxazolyl group; s is 1; and $R_8$ is —F.

In another embodiment, $Ar^1$ is a pyridyl group; V is CH; n is 0; m is 0; $R_1$ is —I; $Ar^2$ is a benzooxazolyl group; s is 1; and $R_8$ is —F.

In another embodiment, $Ar^1$ is a pyridyl group; V is CH; n is 0; m is 0; $R_1$ is —$CH_3$; $Ar^2$ is a benzooxazolyl group; s is 1; and $R_8$ is —F.

In another embodiment, Art is a pyridyl group; V is CH; n is 0; m is 0; $R_1$ is —$CF_3$; $Ar^2$ is a benzooxazolyl group; s is 1; and $R_8$ is —F.

In another embodiment, $Ar^1$ is a pyridyl group; V is CH; n is 0; m is 0; $R_1$ is —Cl, —F —Br, or —I; $Ar^2$ is a benzooxazolyl group; s is 1; and $R_8$ is —Cl.

In another embodiment, $Ar^1$ is a pyridyl group; V is CH; n is 0; m is 0; $R_1$ is —F; $Ar^2$ is a benzooxazolyl group; s is 1; and $R_8$ is —Cl.

In another embodiment, $Ar^1$ is a pyridyl group; V is CH; n is 0; m is 0; $R_1$ is —Cl; $Ar^2$ is a benzooxazolyl group; s is 1; and $R_8$ is —Cl.

In another embodiment, $Ar^1$ is a pyridyl group; V is CH; n is 0; m is 0; $R_1$ is —Br; $Ar^2$ is a benzooxazolyl group; s is 1; and $R_8$ is —Cl.

In another embodiment, $Ar^1$ is a pyridyl group; V is CH; n is 0; m is 0; $R_1$ is —I; $Ar^2$ is a benzooxazolyl group; s is 1; and $R_8$ is —Cl.

In another embodiment, $Ar^1$ is a pyridyl group; V is CH; n is 0; m is 0; $R_1$ is —$CH_3$; $Ar^2$ is a benzooxazolyl group; s is 1; and $R_8$ is —Cl.

In another embodiment, $Ar^1$ is a pyridyl group; V is CH; n is 0; m is 0; $R_1$ is —$CF_3$; $Ar^2$ is a benzooxazolyl group s is 1; and $R_8$ is —Cl.

In another embodiment, $Ar^1$ is a pyridyl group; V is CH; n is 0; m is 0; $R_1$ is —Cl, —F, —Br, or —I, $Ar^2$ is a benzooxazolyl group; s is 1; and $R_8$ is —I.

In another embodiment, $Ar^1$ is a pyridyl group; V is CH; n is 0; m is 0; $R_1$ is —F; $Ar^2$ is a benzooxazolyl group; s is 1; and $R_8$ is —I.

In another embodiment, $Ar^1$ is a pyridyl group; V is CH; n is 0; m is 0; $R_1$ is —Cl; $Ar^2$ is a benzooxazolyl group; s is 1; and $R_8$ is —I.

In another embodiment, $Ar^1$ is a pyridyl group; V is CH; n is 0; m is 0; $R_1$ is —Br; $Ar^2$ is a benzooxazolyl group; s is 1; and $R_8$ is —I.

In another embodiment, $Ar^1$ is a pyridyl group; V is CH; n is 0; m is 0; $R_1$ is —I; $Ar^2$ is a benzooxazolyl group; s is 1; and $R_8$ is —I.

In another embodiment, $Ar^1$ is a pyridyl group; V is CH; n is 0; m is 0; $R_1$ is —$CH_3$; $Ar^2$ is a benzooxazolyl group; s is 1; and $R_8$ is —I.

In another embodiment, $Ar^1$ is a pyridyl group; V is CH; n is 0; m is 0; $R_1$ is —$CF_3$; $Ar^2$ is a benzooxazolyl group; s is 1; and $R_8$ is —I.

In another embodiment, $Ar^1$ is a pyridyl group; V is CH; n is 0; m is 0; $R_1$ is —F, —Cl, —Br, or —I; $Ar^2$ is a benzooxazolyl group; s is 1; and $R_8$ is —$CH_3$.

In another embodiment, $Ar^1$ is a pyridyl group; V is CH; n is 0; m is 0; $R_1$ is —F; $Ar^2$ is a benzooxazolyl group; s is 1; and $R_8$ is —$CH_3$.

In another embodiment, $Ar^1$ is a pyridyl group; V is CH; n is 0; m is 0; $R_1$ is —Cl; $Ar^2$ is a benzooxazolyl group; s is 1; and $R_8$ is —$CH_3$.

In another embodiment, $Ar^1$ is a pyridyl group; V is CH; n is 0; m is 0; $R_1$ is —Br; $Ar^2$ is a benzooxazolyl group; s is 1; and $R_8$ is —$CH_3$.

In another embodiment, $Ar^1$ is a pyridyl group; V is CH; n is 0; m is 0; $R_1$ is —I; $Ar^2$ is a benzooxazolyl group; s is 1; and $R_8$ is —$CH_3$.

In another embodiment, $Ar^1$ is a pyridyl group; V is CH; n is 0; m is 0; $R_1$ is —$CH_3$; $Ar^2$ is a benzooxazolyl group; s is 1; and $R_8$ is —$CH_3$.

In another embodiment, $Ar^1$ is a pyridyl group; V is CH; n is 0; m is 0; $R_1$ is —$CF_3$; $Ar^2$ is a benzooxazolyl group; s is 1; and $R_8$ is —$CH_3$.

In another embodiment, $Ar^1$ is a pyridyl group; V is CH; n is 0; m is 0; $R_1$ is —F, —Cl, —Br, or —I; $Ar^2$ is a benzooxazolyl group; s is 1; and $R_8$ is —$CF_3$.

In another embodiment, $Ar^1$ is a pyridyl group; V is CH; n is 0; m is 0; $R_1$ is —F; $Ar^2$ is a benzooxazolyl group; s is 1; and $R_8$ is —$CF_3$.

In another embodiment, $Ar^1$ is a pyridyl group; V is CH; n is 0; m is 0; $R_1$ is —Cl; $Ar^2$ is a benzooxazolyl group; s is 1; and $R_8$ is —$CF_3$.

In another embodiment, $Ar^1$ is a pyridyl group; V is CH; n is 0; m is 0; $R_1$ is —Br; $Ar^2$ is a benzooxazolyl group; s is 1; and $R_8$ is —$CF_3$.

In another embodiment, $Ar^1$ is a pyridyl group; V is CH; n is 0; m is 0; $R_1$ is —I; $Ar^2$ is a benzooxazolyl group; s is 1; and $R_8$ is —$CF_3$.

In another embodiment, $Ar^1$ is a pyridyl group; V is CH; n is 0; m is 0; $R_1$ is —$CH_3$; $Ar^2$ is a benzooxazolyl group; s is 1; and $R_8$ is —$CF_3$.

In another embodiment, $Ar^1$ is a pyridyl group; V is CH; n is 0; m is 0; $R_1$ is —$CF_3$; $Ar^2$ is a benzooxazolyl group; s is 1; and $R_8$ is —$CF_3$.

In another embodiment, $Ar^1$ is a pyridyl group; V is CH; n is 0; m is 0; $R_1$ is —F, —Cl, —Br, or —I; $Ar^2$ is a benzooxazolyl group; s is 1; and $R_8$ is —$OCH_2CH_3$.

In another embodiment, $Ar^1$ is a pyridyl group; V is CH; n is 0; m is 0; $R_1$ is —F; $Ar^2$ is a benzooxazolyl group; s is 1; and $R_8$ is —$OCH_2CH_3$.

In another embodiment, $Ar^1$ is a pyridyl group; V is CH; n is 0; m is 0; $R_1$ is —Cl; $Ar^2$ is a benzooxazolyl group; s is 1; and $R_8$ is —$OCH_2CH_3$.

In another embodiment, $Ar^1$ is a pyridyl group; V is CH; n is 0; m is 0; $R_1$ is —Br; $Ar^2$ is a benzooxazolyl group; s is 1; and $R_8$ is —$OCH_2CH_3$.

In another embodiment, $Ar^1$ is a pyridyl group; V is CH; n is 0; m is 0; $R_1$ is —I; $Ar^2$ is a benzooxazolyl group; s is 1; and $R_8$ is —$OCH_2CH_3$.

In another embodiment, $Ar^1$ is a pyridyl group; V is CH; n is 0; m is 0; $R_1$ is —$CH_3$; $Ar^2$ is a benzooxazolyl group; s is 1; and $R_8$ is —$OCH_2CH_3$.

In another embodiment, $Ar^1$ is a pyridyl group; V is CH; n is 0; m is 0; $R_1$ is —$CF_3$; $Ar^2$ is a benzooxazolyl group; s is 1; and $R_8$ is —$OCH_2CH_3$.

In another embodiment, $Ar^1$ is a pyridyl group; V is CH; n is 0; m is 0; $R_1$ is —F, —Cl, —Br, or —I; $Ar^2$ is a benzooxazolyl group; $R_8$ is -tert-butyl.

In another embodiment, $Ar^1$ is a pyridyl group; V is CH; n is 0; m is 0; $R_1$ is —F; $Ar^2$ is a benzooxazolyl group; s is 1; and $R_8$ is -tert-butyl.

In another embodiment, $Ar^1$ is a pyridyl group; V is CH; n is 0; m is 0; $R_1$ is —Cl; $Ar^2$ is a benzooxazolyl group; s is 1; and $R_8$ is -tert-butyl.

In another embodiment, $Ar^1$ is a pyridyl group; V is CH; n is 0; m is 0; $R_1$ is —Br; $Ar^2$ is a benzooxazolyl group; s is 1; and $R_8$ is -tert-butyl.

In another embodiment, $Ar^1$ is a pyridyl group; V is CH; n is 0; m is 0; $R_1$ is –1; $Ar^2$ is a benzooxazolyl group; s is 1; and $R_8$ is -tert-butyl.

In another embodiment, $Ar^1$ is a pyridyl group; V is CH; n is 0; m is 0; $R_1$ is —$CH_3$; $Ar^2$ is a benzooxazolyl group; s is 1; and $R_8$ is -tert-butyl.

In another embodiment, $Ar^1$ is a pyridyl group; V is CH; n is 0; m is 0; $R_1$ is —$CF_3$; $Ar^2$ is a benzooxazolyl group; s is 1; and $R_8$ is -tert-butyl.

In another embodiment, $Ar^1$ is a pyridyl group; V is CH; n is 0; m is 1; $R_3$ is —$CH_3$; $R_1$ is —F, —Cl, —Br, or —I; $Ar^2$ is a benzooxazolyl group; and s is 0. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F; $Ar^2$ is a benzooxazolyl group; and s is 0. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Cl; $Ar^2$ is a benzooxazolyl group; and s is 0. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Br; $Ar^2$ is a benzooxazolyl group; and s is 0. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —I; $Ar^2$ is a benzooxazolyl group; and s is 0. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CH_3$; $Ar^2$ is a benzooxazolyl group; and s is 0. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CF_3$; $Ar^2$ is a benzooxazolyl group; and s is 1. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F, —Cl, —Br, or —I; $Ar^2$ is a benzooxazolyl group; s is 1; and $R_8$ is -halo. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F; $Ar^2$ is a benzooxazolyl group; s is 1; and $R_8$ is -halo. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Cl; $Ar^2$ is a benzooxazolyl group; s is 1; and $R_8$ is -halo. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Br; $Ar^2$ is a benzooxazolyl group; s is 1; and $R_8$ is -halo. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —I; $Ar^2$ is a benzooxazolyl group; s is 1; and $R_8$ is -halo. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CH_3$; $Ar^2$ is a benzooxazolyl group; s is 1; and $R_8$ is -halo. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CF_3$; $Ar^2$ is a benzooxazolyl group; s is 1; and $R_8$ is -halo. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F, —Cl, —Br, or —I; $Ar^2$ is a benzooxazolyl group; s is 1; and $R_8$ is —Br. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F; $Ar^2$ is a benzooxazolyl group; s is 1; and $R_8$ is —Br. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Cl; $Ar^2$ is a benzooxazolyl group; s is 1; and $R_8$ is —Br. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Br; $Ar^2$ is a benzooxazolyl group; s is 1; and $R_8$ is —Br. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —I; $Ar^2$ is a benzooxazolyl group; s is 1; and $R_8$ is —Br. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CH_3$; $Ar^2$ is a benzooxazolyl group; s is 1; and $R_8$ is —Br. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CF_3$; $Ar^2$ is a benzooxazolyl group; s is 1; and $R_8$ is —Br. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Cl, —F —Br, or —I; $Ar^2$ is a benzooxazolyl group; s is 1; and $R_8$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F; $Ar^2$ is a benzooxazolyl group; s is 1; and $R_8$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Cl; $Ar^2$ is a benzooxazolyl group; s is 1; and $R_8$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Br; $Ar^2$ is a benzooxazolyl group; s is 1; and $R_8$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —I; $Ar^2$ is a benzooxazolyl group; s is 1; and $R_8$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CH_3$; $Ar^2$ is a benzooxazolyl group; s is 1; and $R_8$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CF_3$; $Ar^2$ is a benzooxazolyl group; s is 1; and $R_8$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is $CH_3$; $R_1$ is —Cl, —F —Br, or —I; $Ar^2$ is a benzooxazolyl group; s is 1; and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F; $Ar^2$ is a benzooxazolyl group; s is 1; and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Cl; $Ar^2$ is a benzooxazolyl group; s is 1; and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Br; $Ar^2$ is a benzooxazolyl group; s is 1; and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —I; $Ar^2$ is a benzooxazolyl group; s is 1; and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CH_3$; $Ar^2$ is a benzooxazolyl group; s is 1; and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CF_3$; $Ar^2$ is a benzooxazolyl group; s is 1; and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Cl, —F, —Br, or —I, $Ar^2$ is a benzooxazolyl group; s is 1; and $R_8$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F; $Ar^2$ is a benzooxazolyl group; s is 1; and $R_8$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Cl; $Ar^2$ is a benzooxazolyl group; s is 1; and $R_8$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Br; $Ar^2$ is a benzooxazolyl group; s is 1; and $R_8$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —I; $Ar^2$ is a benzooxazolyl group; s is 1; and $R_8$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CH_3$; $Ar^2$ is a benzooxazolyl group; s is 1; and $R_8$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CF_3$; $Ar^2$ is a benzooxazolyl group; s is 1; and $R_8$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F, —Cl, —Br, or —I; $Ar^2$ is a benzooxazolyl group; s is 1; and $R_8$ is —$CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F; $Ar^2$ is a benzooxazolyl group; s is 1; and $R_8$ is —$CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Cl; $Ar^2$ is a benzooxazolyl group; s is 1; and $R_8$ is —$CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Br; $Ar^2$ is a benzooxazolyl group; s is 1; and $R_8$ is —$CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —I; $Ar^2$ is a benzooxazolyl group; s is 1; and $R_8$ is —$CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CH_3$; $Ar^2$ is a benzooxazolyl group; s is 1; and $R_8$ is —$CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CF_3$; $Ar^2$ is a benzooxazolyl group; s is 1; and $R_8$ is —$CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F, —Cl, —Br, or —I; $Ar^2$ is a benzooxazolyl group; s is 1; and $R_8$ is —$CF_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F; $Ar^2$ is a benzooxazolyl group; s is 1; and $R_8$ is —$CF_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Cl; $Ar^2$ is a benzooxazolyl group; s is 1; and $R_8$ is —$CF_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Br; $Ar^2$ is a benzooxazolyl group; s is 1; and $R_8$ is —$CF_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —I; $Ar^2$ is a benzooxazolyl group; s is 1; and $R_8$ is —$CF_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CH_3$; $Ar^2$ is a benzooxazolyl group; s is 1; and $R_8$ is —$CF_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CF_3$; $Ar^2$ is a benzooxazolyl group; s is 1; and $R_8$ is —$CF_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the . . . cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F, —Cl, —Br, or —I; $Ar^2$ is a benzooxazolyl group; s is 1; and $R_8$ is —$OCH_2CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F; $Ar^2$ is a benzooxazolyl group; s is 1; and $R_8$ is —$OCH_2CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Cl; $Ar^2$ is a benzooxazolyl group; s is 1; and $R_8$ is —$OCH_2CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Br; $Ar^2$ is a benzooxazolyl group; s is 1; and $R_8$ is —$OCH_2CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —I; $Ar^2$ is a benzooxazolyl group; s is 1; and $R_8$ is —$OCH_2CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CH_3$; $Ar^2$ is a benzooxazolyl group; s is 1; and $R_8$ is —$OCH_2CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CF_3$; $Ar^2$ is a benzooxazolyl group; s is 1; and $R_8$ is —$OCH_2CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F, —Cl, —Br, or —I; $Ar^2$ is a benzooxazolyl group; s is 1; and $R_8$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F; $Ar^2$ is a benzooxazolyl group; s is 1; and $R_8$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Cl; $Ar^2$ is a benzooxazolyl group; s is 1; and $R_8$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Br; $Ar^2$ is a benzooxazolyl group; s is 1; and $R_8$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —I; $Ar^2$ is a benzooxazolyl group; s is 1; and $R_8$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CH_3$; $Ar^2$ is a benzooxazolyl group; s is 1; and $R_8$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CF_3$; $Ar^2$ is a benzooxazolyl group; s is 1; and $R_8$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, V is N, $Ar^1$ is a pyridyl group, m is 0, and $Ar^2$ is

In another embodiment, $Ar^1$ is a pyridyl group; V is N; n is 0; m is 0; $R_1$ is —F, —Cl, —Br, or —I; $Ar^2$ is and r is 0.

In another embodiment, $Ar^1$ is a pyridyl group; V is N; n is 0; m is 0; $R_1$ is —F; $Ar^2$ is

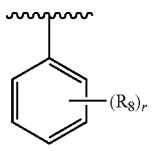

and r is 0.

In another embodiment, $Ar^1$ is a pyridyl group; V is N; n is 0; m is 0; $R_1$ is —Cl; $Ar^2$ is

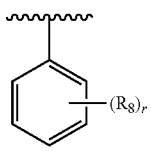

and r is 0.

In another embodiment, $Ar^1$ is a pyridyl group; V is N; n is 0; m is 0; $R_1$ is —Br; $Ar^2$ is

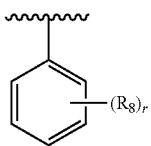

and r is 0.

In another embodiment, $Ar^1$ is a pyridyl group; V is N; n is 0; m is 0; $R_1$ is —I; $Ar^2$ is

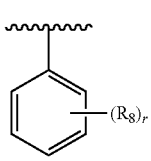

and r is 0.

In another embodiment, $Ar^1$ is a pyridyl group; V is N; n is 0; m is 0; $R_1$ is —$CH_3$; $Ar^2$ is

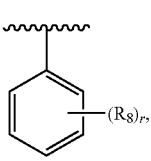

and r is 0.

In another embodiment, $Ar^1$ is a pyridyl group; V is N; n is 0; m is 0; $R_1$ is —$CF_3$; $Ar^2$ is

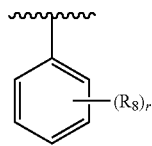

and r is 0.

In another embodiment, $Ar^1$ is a pyridyl group; V is N; n is 0; m is 0; $R_1$ is —F, —Cl —Br, or —I; $Ar^2$ is

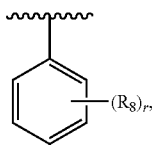

r is 1 and $R_8$ is -halo. In another embodiment, $R_8$ is at the 4-position of the phenyl ring.

In another embodiment, $Ar^1$ is a pyridyl group; V is N; n is 0; m is 0; $R_1$ is —F; $Ar^2$ is

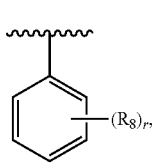

r is 1 and $R_8$ is -halo.

In another embodiment, $Ar^1$ is a pyridyl group; V is N; n is 0; m is 0; $R_1$ is —Cl; $Ar^2$ is

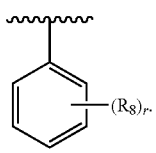

r is 1 and $R_8$ is -halo. In another embodiment, $R_8$ is at the 4-position of the phenyl ring.

In another embodiment, $Ar^1$ is a pyridyl group; V is N; n is 0; m is 0; $R_1$ is —Br; $Ar^2$ is

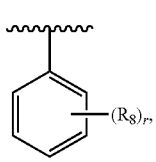

r is 1 and $R_8$ is -halo. In another embodiment, $R_8$ is at the 4-position of the phenyl ring.

In another embodiment, $Ar^1$ is a pyridyl group; V is N; n is 0; m is 0; $R_1$ is —I; $Ar^2$ is

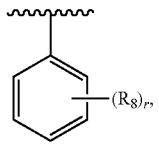

r is 1 and $R_8$ is -halo. In another embodiment, $R_8$ is at the 4-position of the phenyl ring.

In another embodiment, $Ar^1$ is a pyridyl group; V is N; n is 0; m is 0; $R_1$ is —$CH_3$; $Ar^2$ is

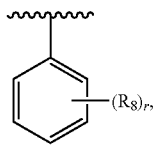

r is 1 and $R_8$ is -halo. In another embodiment, $R_8$ is at the 4-position of the phenyl ring.

In another embodiment, $Ar^1$ is a pyridyl group; V is N; n is 0; m is 0; $R_1$ is —$CF_3$; $Ar^2$ is

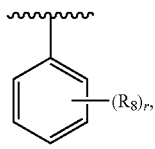

r is 1 and $R_8$ is -halo. In another embodiment, $R_8$ is at the 4-position of the phenyl ring.

In another embodiment, $Ar^1$ is a pyridyl group; V is N; n is 0; m is 0; $R_1$ is —F, —Cl, —Br, or —I; $Ar^2$ is

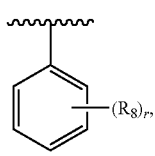

r is 1 and $R_8$ is —Br. In another embodiment, $R_8$ is at the 4-position of the phenyl ring.

In another embodiment, $Ar^1$ is a pyridyl group; V is N; n is 0; m is 0; $R_1$ is —F; $Ar^2$ is

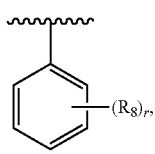

r is 1 and $R_8$ is —Br. In another embodiment, $R_8$ is at the 4-position of the phenyl ring.

In another embodiment, $Ar^1$ is a pyridyl group; V is N; n is 0; m is 0; $R_1$ is —Cl; $Ar^2$ is

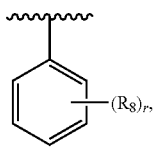

r is 1 and $R_8$ is —Br. In another embodiment, $R_8$ is at the 4-position of the phenyl ring.

In another embodiment, $Ar^1$ is a pyridyl group; V is N; n is 0; m is 0; $R_1$ is —Br; $Ar^2$ is

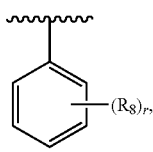

r is 1 and $R_8$ is —Br. In another embodiment, $R_8$ is at the 4-position of the phenyl ring.

In another embodiment, $Ar^1$ is a pyridyl group; V is N; n is 0; m is 0; $R_1$ is —I; $Ar^2$ is

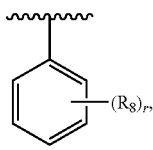

r is 1 and $R_8$ is —Br. In another embodiment, $R_8$ is at the 4-position of the phenyl ring.

In another embodiment, $Ar^1$ is a pyridyl group; V is N; n is 0; m is 0; $R_1$ is —$CH_3$; $Ar^2$ is

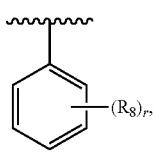

r is 1 and $R_8$ is —Br. In another embodiment, $R_8$ is at the 4-position of the phenyl ring.

In another embodiment, $Ar^1$ is a pyridyl group; V is N; n is 0; m is 0; $R_1$ is —$CF_3$; $Ar^2$ is

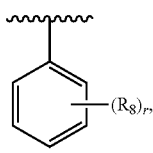

r is 1 and $R_8$ is —Br. In another embodiment, $R_8$ is at the 4-position of the phenyl ring.

In another embodiment, $Ar^1$ is a pyridyl group; V is N; n is 0; m is 0; $R_1$ is —Cl, —F —Br, or —I; $Ar^2$ is

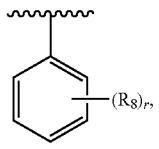

r is 1 and $R_8$ is —F. In another embodiment, $R_8$ is at the 4-position of the phenyl ring.

In another embodiment, $Ar^1$ is a pyridyl group; V is N; n is 0; m is 0; $R_1$ is —F; $Ar^2$ is

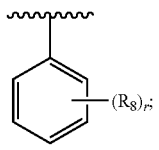

r is 1 and $R_8$ is —F. In another embodiment, $R_8$ is at the 4-position of the phenyl ring In another embodiment, $Ar^1$ is a pyridyl group; V is N; n is 0; m is 0; $R_1$ is —Cl; $Ar^2$ is

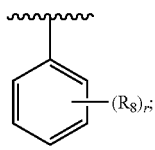

r is 1 and $R_8$ is —F. In another embodiment, $R_8$ is at the 4-position of the phenyl ring.

In another embodiment, $Ar^1$ is a pyridyl group; V is N; n is 0; m is 0; $R_1$ is —Br; $Ar^2$ is

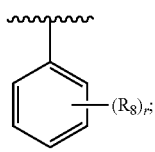

r is 1 and $R_8$ is —F. In another embodiment, $R_8$ is at the 4-position of the phenyl ring.

In another embodiment, $Ar^1$ is a pyridyl group; V is N; n is 0; m is 0; $R_1$ is —I; $Ar^2$ is

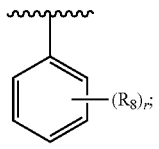

r is 1 and $R_8$ is —F. In another embodiment, $R_8$ is at the 4-position of the phenyl ring.

In another embodiment, $Ar^1$ is a pyridyl group; V is N; n is 0; m is 0; $R_1$ is —$CH_3$; $Ar^2$ is

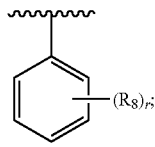

r is 1 and $R_8$ is —F. In another embodiment, $R_8$ is at the 4-position of the phenyl ring.

In another embodiment, $Ar^1$ is a pyridyl group; V is N; n is 0; m is 0; $R_1$ is —$CF_3$; $Ar^2$ is

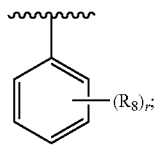

r is 1 and $R_8$ is —F. In another embodiment, $R_8$ is at the 4-position of the phenyl ring.

In another embodiment, $Ar^1$ is a pyridyl group; V is N; n is 0; m is 0; $R_1$ is —Cl, —F —Br, or —I; $Ar^2$ is

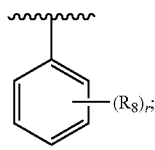

r is 1 and $R_8$ is —Cl. In another embodiment, $R_8$ is at the 4-position of the phenyl ring.

In another embodiment, $Ar^1$ is a pyridyl group; V is N; n is 0; m is 0; $R_1$ is —F; $Ar^2$ is

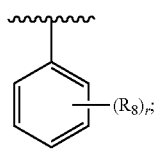

r is 1 and $R_8$ is —Cl. In another embodiment, $R_8$ is at the 4-position of the phenyl ring.

In another embodiment, $Ar^1$ is a pyridyl group; V is N; n is 0; m is 0; $R_1$ is —Cl; $Ar^2$ is

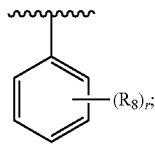

r is 1 and $R_8$ is —Cl. In another embodiment, $R_8$ is at the 4-position of the phenyl ring.

In another embodiment, Ar$^1$ is a pyridyl group; V is N; n is 0; m is 0; R$_1$ is —Br; Ar$^2$ is

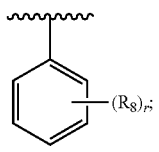

r is 1 and R$_8$ is —Cl. In another embodiment, R$_8$ is at the 4-position of the phenyl ring.

In another embodiment, Ar$^1$ is a pyridyl group; V is N; n is 0; m is 0; R$_1$ is —I; Ar$^2$ is

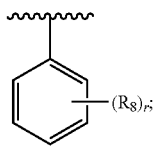

r is 1 and R$_8$ is —Cl. In another embodiment, R$_8$ is at the 4-position of the phenyl ring.

In another embodiment, Ar$^1$ is a pyridyl group; V is N; n is 0; m is 0; R$_1$ is —CH$_3$; Ar$^2$ is

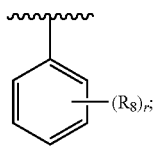

r is 1 and R$_8$ is —Cl. In another embodiment, R$_8$ is at the 4-position of the phenyl ring.

In another embodiment, Ar$^1$ is a pyridyl group; V is N; n is 0; m is 0; R$_1$ is —CF$_3$; Ar$^2$ is

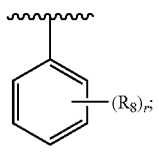

r is 1 and R$_8$ is chloro. In another embodiment, R$_8$ is at the 4-position of the phenyl ring.

In another embodiment, Ar$^1$ is a pyridyl group; V is N; n is 0; m is 0; R$_1$ is —Cl, —F, —Br, or —I, Ar$^2$ is

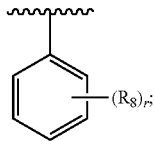

r is 1 and R$_8$ is —I. In another embodiment, R$_8$ is at the 4-position of the phenyl ring.

In another embodiment, Ar$^1$ is a pyridyl group; V is N; n is 0; m is 0; R$_1$ is —F; Ar$^2$ is

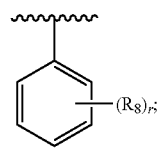

r is 1 and R$_8$ is —I. In another embodiment, R$_8$ is at the 4-position of the phenyl ring.

In another embodiment, Ar$^1$ is a pyridyl group; V is N; n is 0; m is 0; R$_1$ is —Cl; Ar$^2$ is

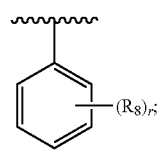

r is 1 and R$_8$ is —I. In another embodiment, R$_8$ is at the 4-position of the phenyl ring.

In another embodiment, Ar$^1$ is a pyridyl group; V is N; n is 0; m is 0; R$_1$ is —Br; Ar$^2$ is

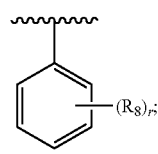

r is 1 and R$_8$ is —I. In another embodiment, R$_8$ is at the 4-position of the phenyl ring.

In another embodiment, Ar$^1$ is a pyridyl group; V is N; n is 0; m is 0; R$_1$ is —I; Ar$^2$ is

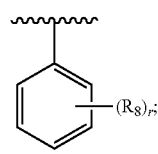

r is 1 and R$_8$ is —I. In another embodiment, R$_8$ is at the 4-position of the phenyl ring.

In another embodiment, Ar$^1$ is a pyridyl group; V is N; n is 0; m is 0; R$_1$ is —CH$_3$; Ar$^2$ is

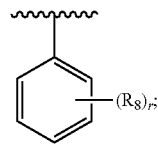

r is 1 and R$_8$ is —I. In another embodiment, R$_8$ is at the 4-position of the phenyl ring.

In another embodiment, $Ar^1$ is a pyridyl group; V is N; n is 0; m is 0; $R_1$ is —$CF_3$; $Ar^2$ is

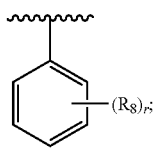

r is 1 and $R_8$ is —I. In another embodiment, $R_8$ is at the 4-position of the phenyl ring.

In another embodiment, $Ar^1$ is a pyridyl group; V is N; n is 0; m is 0; $R_1$ is —F, —Cl, —Br, or —I; $Ar^2$ is

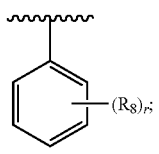

r is 1 and $R_8$ is —$CH_3$. In another embodiment, $R_8$ is at the 4-position of the phenyl ring.

In another embodiment, $Ar^1$ is a pyridyl group; V is N; n is 0; m is 0; $R_1$ is —F; $Ar^2$ is

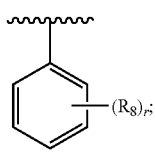

r is 1 and $R_8$ is —$CH_3$. In another embodiment, $R_8$ is at the 4-position of the phenyl ring.

In another embodiment, $Ar^1$ is a pyridyl group; V is N; n is 0; m is 0; $R_1$ is —Cl; $Ar^2$ is

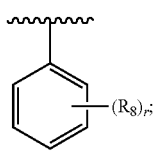

r is 1 and $R_8$ is —$CH_3$. In another embodiment, $R_8$ is at the 4-position of the phenyl ring.

In another embodiment, $Ar^1$ is a pyridyl group; V is N; n is 0; m is 0; $R_1$ is —Br; $Ar^2$ is

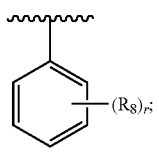

r is 1 and $R_8$ is —$CH_3$. In another embodiment, $R_8$ is at the 4-position of the phenyl ring.

In another embodiment, $Ar^1$ is a pyridyl group; V is N; n is 0; m is 0; $R_1$ is —I; $Ar^2$ is

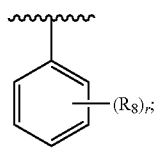

r is 1 and $R_8$ is —$CH_3$. In another embodiment, $R_8$ is at the 4-position of the phenyl ring.

In another embodiment, $Ar^1$ is a pyridyl group; V is N; n is 0; m is 0; $R_1$ is —$CH_3$; $Ar^2$ is

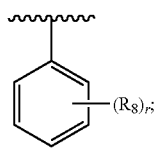

r is 1 and $R_8$ is —$CH_3$. In another embodiment, $R_8$ is at the 4-position of the phenyl ring.

In another embodiment, $Ar^1$ is a pyridyl group; V is N; n is 0; m is 0; $R_1$ is —$CF_3$; $Ar^2$ is

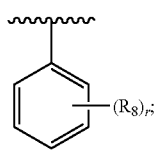

r is 1 and $R_8$ is —$CH_3$. In another embodiment, $R_8$ is at the 4-position of the phenyl ring.

In another embodiment, $Ar^1$ is a pyridyl group; V is N; n is 0; m is 0; $R_1$ is —F, —Cl —Br, or —I; $Ar^2$ is

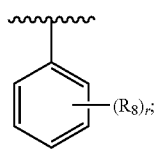

r is 1 and $R_8$ is —$CF_3$. In another embodiment, $R_8$ is at the 4-position of the phenyl ring.

In another embodiment, $Ar^1$ is a pyridyl group; V is N; n is 0; m is 0; $R_1$ is —F; $Ar^2$ is

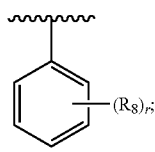

r is 1 and $R_8$ is —$CF_3$. In another embodiment, $R_8$ is at the 4-position of the phenyl ring.

In another embodiment, Ar$^1$ is a pyridyl group; V is N; n is 0; m is 0; R$_1$ is —Cl; Ar$^2$ is

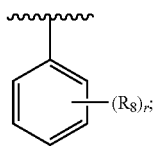

r is 1 and R$_8$ is —CF$_3$. In another embodiment, R$_8$ is at the 4-position of the phenyl ring.

In another embodiment, Ar$^1$ is a pyridyl group; V is N; n is 0; m is 0; R$_1$ is —Br; Ar$^2$ is

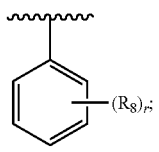

r is 1 and R$_8$ is —CF$_3$. In another embodiment, R$_8$ is at the 4-position of the phenyl ring.

In another embodiment, Ar$^1$ is a pyridyl group; V is N; n is 0; m is 0; R$_1$ is —I; Ar$^2$ is

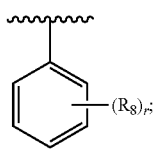

r is 1 and R$_8$ is —CF$_3$. In another embodiment, R$_8$ is at the 4-position of the phenyl ring.

In another embodiment, Ar$^1$ is a pyridyl group; V is N; n is 0; m is 0; R$_1$ is —CH$_3$; Ar$^2$ is

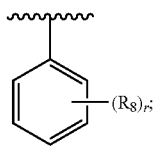

r is 1 and R$_8$ is —CF$_3$. In another embodiment, R$_8$ is at the 4-position of the phenyl ring.

In another embodiment, Ar$^1$ is a pyridyl group; V is N; n is 0; m is 0; R$_1$ is —CF$_3$; Ar$^2$ is

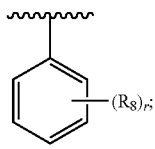

r is 1 and R$_8$ is —CF$_3$. In another embodiment, R$_8$ is at the 4-position of the phenyl ring.

In another embodiment, Ar$^1$ is a pyridyl group; V is N; n is 0; m is 0; R$_1$ is —F, —Cl —Br, or —I; Ar$^2$ is

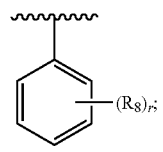

r is 1 and R$_8$ is —OCH$_2$CH$_3$. In another embodiment, R$_8$ is at the 4-position of the phenyl ring.

In another embodiment, Ar$^1$ is a pyridyl group; V is N; n is 0; m is 0; R$_1$ is —F; Ar$^2$ is

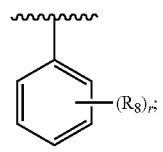

r is 1 and R$_8$ is —OCH$_2$CH$_3$. In another embodiment, R$_8$ is at the 4-position of the phenyl ring.

In another embodiment, Ar$^1$ is a pyridyl group; V is N; n is 0; m is 0; R$_1$ is —Cl; Ar$^2$ is

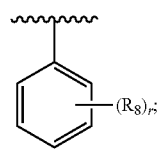

r is 1 and R$_8$ is —OCH$_2$CH$_3$. In another embodiment, R$_8$ is at the 4-position of the phenyl ring.

In another embodiment, Ar$^1$ is a pyridyl group; V is N; n is 0; m is 0; R$_1$ is —Br; Ar$^2$ is

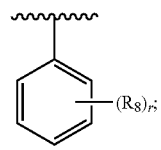

r is 1 and R$_8$ is —OCH$_2$CH$_3$. In another embodiment, R$_8$ is at the 4-position of the phenyl ring.

In another embodiment, Ar$^1$ is a pyridyl group; V is N; n is 0; m is 0; R$_1$ is —I; Ar$^2$ is

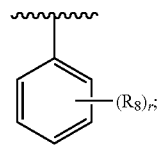

r is 1 and R$_8$ is —OCH$_2$CH$_3$. In another embodiment, R$_8$ is at the 4-position of the phenyl ring.

In another embodiment, $Ar^1$ is a pyridyl group; V is N; n is 0; m is 0; $R_1$ is —$CH_3$; $Ar^2$ is

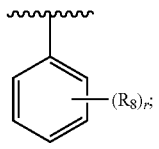

r is 1 and $R_8$ is —$OCH_2CH_3$. In another embodiment, $R_8$ is at the 4-position of the phenyl ring.

In another embodiment, $Ar^1$ is a pyridyl group; V is N; n is 0; m is 0; $R_1$ is —$CF_3$; $Ar^2$ is

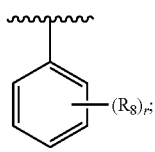

r is 1 and $R_8$ is —$OCH_2CH_3$. In another embodiment, $R_8$ is at the 4-position of the phenyl ring.

In another embodiment, $Ar^1$ is a pyridyl group; V is N; n is 0; m is 0; $R_1$ is —F, —Cl —Br, or —I; $Ar^2$ is

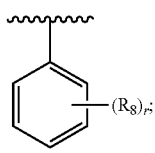

r is 1 and $R_8$ is -tert-butyl. In another embodiment, $R_8$ is at the 4-position of the phenyl ring.

In another embodiment, $Ar^1$ is a pyridyl group; V is N; n is 0; m is 0; $R_1$ is —F; $Ar^2$ is

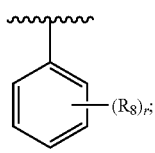

r is 1 and $R_8$ is -tert-butyl. In another embodiment, $R_8$ is at the 4-position of the phenyl ring.

In another embodiment, $Ar^1$ is a pyridyl group; V is N; n is 0; m is 0; $R_1$ is —Cl; $Ar^2$ is

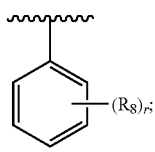

r is 1 and $R_8$ is -tert-butyl. In another embodiment, $R_8$ is at the 4-position of the phenyl ring.

In another embodiment, $Ar^1$ is a pyridyl group; V is N; n is 0; m is 0; $R_1$ is —Br; $Ar^2$ is

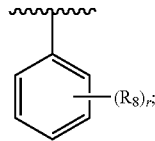

r is 1 and $R_8$ is -tert-butyl. In another embodiment, $R_8$ is at the 4-position of the phenyl ring.

In another embodiment, $Ar^1$ is a pyridyl group; V is N; n is 0; m is 0; $R_1$ is —I; $Ar^2$ is

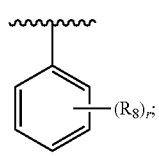

r is 1 and $R_8$ is -tert-butyl. In another embodiment, $R_8$ is at the 4-position of the phenyl ring.

In another embodiment, $Ar^1$ is a pyridyl group; V is N; n is 0; m is 0; $R_1$ is —$CH_3$; $Ar^2$ is

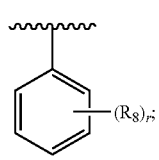

r is 1 and $R_8$ is -tert-butyl. In another embodiment, $R_8$ is at the 4-position of the phenyl ring.

In another embodiment, $Ar^1$ is a pyridyl group; V is N; n is 0; m is 0; $R_1$ is —$CF_3$; $Ar^2$ is

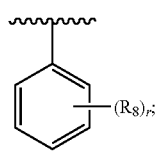

r is 1 and $R_8$ is -tert-butyl. In another embodiment, $R_8$ is at the 4-position of the phenyl ring.

In another embodiment, $Ar^1$ is a pyridyl group; V is N; n is 0; m is 1; $R_3$ is —$CH_3$; $R_1$ is —F, —Cl, —Br, or —I; $Ar^2$ is

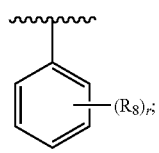

and r is 0. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 4-position of the phenyl ring.

In another embodiment, $Ar^1$ is a pyridyl group; V is N; n is 0; m is 1; $R_3$ is —$CH_3$; $R_1$ is —F; $Ar^2$ is $(R_8)_r$;

and r is 0. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 4-position of the phenyl ring.

In another embodiment, $Ar^1$ is a pyridyl group; V is N; n is 0; m is 1; $R_3$ is —$CH_3$; $R_1$ is —Cl; $Ar^2$ is $(R_8)_r$;

and r is 0. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 4-position of the phenyl ring.

In another embodiment, $Ar^1$ is a pyridyl group; V is N; n is 0; m is 1; $R_3$ is —$CH_3$; $R_1$ is —Br; $Ar^2$ is $(R_8)_r$;

and r is 0. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 4-position of the phenyl ring.

In another embodiment, $Ar^1$ is a pyridyl group; V is N; n is 0; m is 1; $R_3$ is —$CH_3$; $R_1$ is —I; $Ar^2$ is $(R_8)_r$;

and r is 0. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 4-position of the phenyl ring.

In another embodiment, $Ar^1$ is a pyridyl group; V is N; n is 0; m is 1; $R_3$ is —$CH_3$; $R_1$ is —$CH_3$; $Ar^2$ is $(R_8)_r$;

and r is 0. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 4-position of the phenyl ring.

In another embodiment, $Ar^1$ is a pyridyl group; V is N; n is 0; m is 1; $R_3$ is —$CH_3$; $R_1$ is —$CF_3$; $Ar^2$ is $(R_8)_r$;

and r is 0. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 4-position of the phenyl ring.

In another embodiment, $Ar^1$ is a pyridyl group; V is N; n is 0; m is 1; $R_3$ is —$CH_3$; $R_1$ is —F, —Cl —Br, or —I; $Ar^2$ is

[Structure: phenyl ring with (R₈)ᵣ substituent]

r is 1 and R₈ is -halo. In another embodiment, the R₃ group is attached to the 3-, 5- or 6-position of the cyclo(hetero)alkenyl ring and the carbon atom to which the R₃ group is attached has the (R) configuration. In another embodiment, the R₃ group is attached to the 3-, 5- or 6-position of the cyclo(hetero)alkenyl ring and the carbon atom to which the R₃ group is attached has the (S) configuration. In yet another embodiment, the R₃ group is attached to the 2-position of the cyclo(hetero)alkenyl ring.

In another embodiment, $Ar^1$ is a pyridyl group; V is N; n is 0; m is 1; R₃ is —CH₃; R₁ is —F; $Ar^2$ is

[Structure: phenyl ring with (R₈)ᵣ substituent]

r is 1 and R₈ is -halo. In another embodiment, the R₃ group is attached to the 3-, 5- or 6-position of the cyclo(hetero)alkenyl ring and the carbon atom to which the R₃ group is attached has the (R) configuration. In another embodiment, the R₃ group is attached to the 3-, 5- or 6-position of the cyclo(hetero)alkenyl ring and the carbon atom to which the R₃ group is attached has the (S) configuration. In yet another embodiment, the R₃ group is attached to the 2-position of the cyclo(hetero)alkenyl ring. In another embodiment, R₈ is at the 4-position of the phenyl ring.

In another embodiment, $Ar^1$ is a pyridyl group; V is N; n is 0; m is 1; R₃ is —CH₃; R₁ is —Cl; $Ar^2$ is

[Structure: phenyl ring with (R₈)ᵣ substituent]

r is 1 and R₈ is -halo. In another embodiment, the R₃ group is attached to the 3-, 5- or 6-position of the cyclo(hetero)alkenyl ring and the carbon atom to which the R₃ group is attached has the (R) configuration. In another embodiment, the R₃ group is attached to the 3-, 5- or 6-position of the cyclo(hetero)alkenyl ring and the carbon atom to which the R₃ group is attached has the (S) configuration. In yet another embodiment, the R₃ group is attached to the 2-position of the cyclo(hetero)alkenyl ring. In another embodiment, R₈ is at the 4-position of the phenyl ring.

In another embodiment, $Ar^1$ is a pyridyl group; V is N; n is 0; m is 1; R₃ is —CH₃; R₁ is —Br; $Ar^2$ is

[Structure: phenyl ring with (R₈)ᵣ substituent]

r is 1 and R₈ is -halo. In another embodiment, the R₃ group is attached to the 3-, 5- or 6-position of the cyclo(hetero)alkenyl ring and the carbon atom to which the R₃ group is attached has the (R) configuration. In another embodiment, the R₃ group is attached to the 3-, 5- or 6-position of the cyclo(hetero)alkenyl ring and the carbon atom to which the R₃ group is attached has the (S) configuration. In yet another embodiment, the R₃ group is attached to the 2-position of the cyclo(hetero)alkenyl ring. In another embodiment, R₈ is at the 4-position of the phenyl ring.

In another embodiment, $Ar^1$ is a pyridyl group; V is N; n is 0; m is 1; R₃ is —CH₃; R₁ is —I; $Ar^2$ is

[Structure: phenyl ring with (R₈)ᵣ substituent]

r is 1 and R₈ is -halo. In another embodiment, the R₃ group is attached to the 3-, 5- or 6-position of the cyclo(hetero)alkenyl ring and the carbon atom to which the R₃ group is attached has the (R) configuration. In another embodiment, the R₃ group is attached to the 3-, 5- or 6-position of the cyclo(hetero)alkenyl ring and the carbon atom to which the R₃ group is attached has the (S) configuration. In yet another embodiment, the R₃ group is attached to the 2-position of the cyclo(hetero)alkenyl ring. In another embodiment, R₈ is at the 4-position of the phenyl ring.

In another embodiment, $Ar^1$ is a pyridyl group; V is N; n is 0; m is 1; R₃ is —CH₃; R₁ is —CH₃; $Ar^2$ is

[Structure: phenyl ring with (R₈)ᵣ substituent]

r is 1 and R₈ is -halo. In another embodiment, the R₃ group is attached to the 3-, 5- or 6-position of the cyclo(hetero)alkenyl ring and the carbon atom to which the R₃ group is attached has the (R) configuration. In another embodiment, the R₃ group is attached to the 3-, 5- or 6-position of the cyclo(hetero)alkenyl ring and the carbon atom to which the R₃ group is attached has the (S) configuration. In yet another embodiment, the R₃ group is attached to the 2-position of the cyclo(hetero)alkenyl ring. In another embodiment, R₈ is at the 4-position of the phenyl ring.

In another embodiment, Ar$^1$ is a pyridyl group; V is N; n is 0; m is 1; R$_3$ is —CH$_3$; R$_1$ is —CF$_3$; Ar$^2$ is

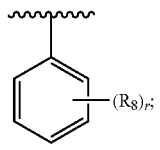

r is 1 and R$_8$ is -halo. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 4-position of the phenyl ring.

In another embodiment, Ar$^1$ is a pyridyl group; V is N; n is 0; m is 1; R$_3$ is —CH$_3$; R$_1$ is —F, —Cl, —Br, or —I; Ar$^2$ is

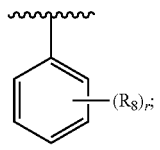

r is 1 and R$_8$ is —Br. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 4-position of the phenyl ring.

In another embodiment, Ar$^1$ is a pyridyl group; V is N; n is 0; m is 1; R$_3$ is —CH$_3$; R$_1$ is —F; Ar$^2$ is

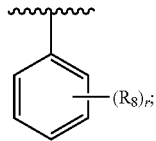

r is 1 and R$_8$ is —Br. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 4-position of the phenyl ring.

In another embodiment, Ar$^1$ is a pyridyl group; V is N; n is 0; m is 1; R$_3$ is —CH$_3$; R$_1$ is —Cl; Ar$^2$ is

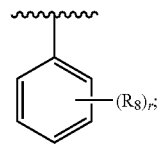

r is 1 and R$_8$ is —Br. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 4-position of the phenyl ring.

In another embodiment, Ar$^1$ is a pyridyl group; V is N; n is 0; m is 1; R$_3$ is —CH$_3$; R$_1$ is —Br; Ar$^2$ is

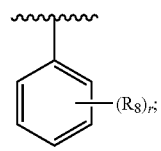

r is 1 and R$_8$ is —Br. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 4-position of the phenyl ring.

In another embodiment, Ar$^1$ is a pyridyl group; V is N; n is 0; m is 1; R$_3$ is —CH$_3$; R$_1$ is —I; Ar$^2$ is

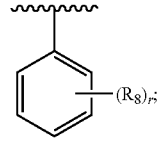

r is 1 and R$_8$ is —Br. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 4-position of the phenyl ring.

In another embodiment, Ar¹ is a pyridyl group; V is N; n is 0; m is 1; R₃ is —CH₃; R₁ is —CH₃; Ar² is

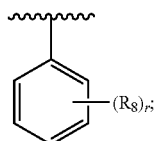

r is 1 and R₈ is —Br. In another embodiment, the R₃ group is attached to the 3-, 5- or 6-position of the cyclo(hetero)alkenyl ring and the carbon atom to which the R₃ group is attached has the (R) configuration. In another embodiment, the R₃ group is attached to the 3-, 5- or 6-position of the cyclo(hetero)alkenyl ring and the carbon atom to which the R₃ group is attached has the (S) configuration. In yet another embodiment, the R₃ group is attached to the 2-position of the cyclo(hetero)alkenyl ring. In another embodiment, R₈ is at the 4-position of the phenyl ring.

In another embodiment, Ar¹ is a pyridyl group; V is N; n is 0; m is 1; R₃ is —CH₃; R₁ is —CF₃; Ar² is

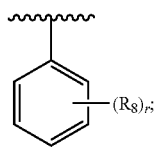

r is 1 and R₈ is —Br. In another embodiment, the R₃ group is attached to the 3-, 5- or 6-position of the cyclo(hetero)alkenyl ring and the carbon atom to which the R₃ group is attached has the (R) configuration. In another embodiment, the R₃ group is attached to the 3-, 5- or 6-position of the cyclo(hetero)alkenyl ring and the carbon atom to which the R₃ group is attached has the (S) configuration. In yet another embodiment, the R₃ group is attached to the 2-position of the cyclo(hetero)alkenyl ring. In another embodiment, R₈ is at the 4-position of the phenyl ring.

In another embodiment, Ar¹ is a pyridyl group; V is N; n is 0; m is 1; R₃ is —CH₃; R₁ is —Cl, —F —Br, or —I; Ar² is

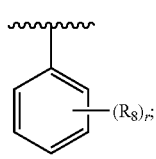

r is 1 and R₈ is —F. In another embodiment, the R₃ group is attached to the 3-, 5- or 6-position of the cyclo(hetero)alkenyl ring and the carbon atom to which the R₃ group is attached has the (R) configuration. In another embodiment, the R₃ group is attached to the 3-, 5- or 6-position of the cyclo(hetero)alkenyl ring and the carbon atom to which the R₃ group is attached has the (S) configuration. In yet another embodiment, the R₃ group is attached to the 2-position of the cyclo(hetero)alkenyl ring. In another embodiment, R₈ is at the 4-position of the phenyl ring.

In another embodiment, Ar¹ is a pyridyl group; V is N; n is 0; m is 1; R₃ is —CH₃; R₁ is —F; Ar² is

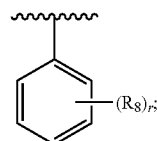

r is 1 and R₈ is —F. In another embodiment, the R₃ group is attached to the 3-, 5- or 6-position of the cyclo(hetero)alkenyl ring and the carbon atom to which the R₃ group is attached has the (R) configuration. In another embodiment, the R₃ group is attached to the 3-, 5- or 6-position of the cyclo(hetero)alkenyl ring and the carbon atom to which the R₃ group is attached has the (S) configuration. In yet another embodiment, the R₃ group is attached to the 2-position of the cyclo(hetero)alkenyl ring. In another embodiment, R₈ is at the 4-position of the phenyl ring.

In another embodiment, Ar¹ is a pyridyl group; V is N; n is 0; m is 1; R₃ is —CH₃; R₁ is —Cl; Ar² is

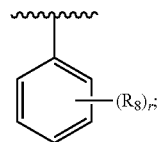

r is 1 and R₈ is —F. In another embodiment, the R₃ group is attached to the 3-, 5- or 6-position of the cyclo(hetero)alkenyl ring and the carbon atom to which the R₃ group is attached has the (R) configuration. In another embodiment, the R₃ group is attached to the 3-, 5- or 6-position of the cyclo(hetero)alkenyl ring and the carbon atom to which the R₃ group is attached has the (S) configuration. In yet another embodiment, the R₃ group is attached to the 2-position of the cyclo(hetero)alkenyl ring. In another embodiment, R₈ is at the 4-position of the phenyl ring.

In another embodiment, Ar¹ is a pyridyl group; V is N; n is 0; m is 1; R₃ is —CH₃; R₁ is —Br; Ar² is

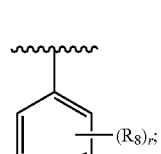

r is 1 and R₈ is —F. In another embodiment, the R₃ group is attached to the 3-, 5- or 6-position of the cyclo(hetero)alkenyl ring and the carbon atom to which the R₃ group is attached has the (R) configuration. In another embodiment, the R₃ group is attached to the 3-, 5- or 6-position of the cyclo(hetero)alkenyl ring and the carbon atom to which the R₃ group is attached has the (S) configuration. In yet another embodiment, the R₃ group is attached to the 2-position of the cyclo(hetero)alkenyl ring. In another embodiment, R₈ is at the 4-position of the phenyl ring.

In another embodiment, Ar$^1$ is a pyridyl group; V is N; n is 0; m is 1; R$_3$ is —CH$_3$; R$_1$ is —I; Ar$^2$ is

[structure: phenyl with (R$_8$)$_r$]

r is 1 and R$_8$ is —F. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 4-position of the phenyl ring.

In another embodiment, Ar$^1$ is a pyridyl group; V is N; n is 0; m is 1; R$_3$ is —CH$_3$; R$_1$ is —CH$_3$, Ar$^2$ is

[structure: phenyl with (R$_8$)$_r$]

r is 1 and R$_8$ is —F. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 4-position of the phenyl ring.

In another embodiment, Ar$^1$ is a pyridyl group; V is N; n is 0; m is 1; R$_3$ is —CH$_3$; R$_1$ is —CF$_3$; Ar$^2$ is

[structure: phenyl with (R$_8$)$_r$]

r is 1 and R$_8$ is —F. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 4-position of the phenyl ring.

In another embodiment, Ar$^1$ is a pyridyl group; V is N; n is 0; m is 1; R$_3$ is CH$_3$; R$_1$ is —Cl, —F —Br, or —I; Ar$^2$ is

[structure: phenyl with (R$_8$)$_r$]

r is 1 and R$_8$ is —Cl. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 4-position of the phenyl ring.

In another embodiment, Ar$^1$ is a pyridyl group; V is N; n is 0; m is 1; R$_3$ is —CH$_3$; R$_1$ is —F; Ar$^2$ is

[structure: phenyl with (R$_8$)$_r$]

r is 1 and R$_8$ is —Cl. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 4-position of the phenyl ring.

In another embodiment, Ar$^1$ is a pyridyl group; V is N; n is 0; m is 1; R$_3$ is —CH$_3$; R$_1$ is —Cl; Ar$^2$ is

[structure: phenyl with (R$_8$)$_r$]

r is 1 and R$_8$ is —Cl. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 4-position of the phenyl ring.

In another embodiment, $Ar^1$ is a pyridyl group; V is N; n is 0; m is 1; $R_3$ is —$CH_3$; $R_1$ is —Br; $Ar^2$ is

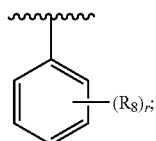

r is 1 and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 4-position of the phenyl ring.

In another embodiment, $Ar^1$ is a pyridyl group; V is N; n is 0; m is 1; $R_3$ is —$CH_3$; $R_1$ is —I; $Ar^2$ is

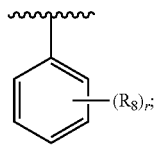

r is 1 and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 4-position of the phenyl ring.

In another embodiment, $Ar^1$ is a pyridyl group; V is N; n is 0; m is 1; $R_3$ is —$CH_3$; $R_1$ is —$CH_3$, $Ar^2$ is

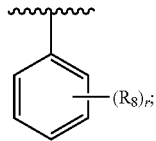

r is 1 and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 4-position of the phenyl ring.

In another embodiment, $Ar^1$ is a pyridyl group; V is N; n is 0; m is 1; $R_3$ is —$CH_3$; $R_1$ is —$CF_3$; $Ar^2$ is

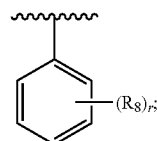

r is 1 and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 4-position of the phenyl ring.

In another embodiment, $Ar^1$ is a pyridyl group; V is N; n is 0; m is 1; $R_3$ is —$CH_3$; $R_1$ is —Cl, —F, —Br, or —I, $Ar^2$ is

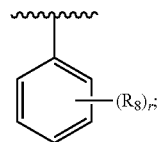

r is 1; and $R_8$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 4-position of the phenyl ring.

In another embodiment, $Ar^1$ is a pyridyl group; V is N; n is 0; m is 1; $R_3$ is —$CH_3$; $R_1$ is —F; $Ar^2$ is

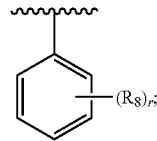

r is 1 and $R_8$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 4-position of the phenyl ring.

In another embodiment, Ar$^1$ is a pyridyl group; V is N; n is 0; m is 1; R$_3$ is —CH$_3$; R$_1$ is —Cl; Ar$^2$ is

[structure: phenyl ring with (R$_8$)$_r$ substituent]

r is 1 and R$_8$ is —I. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 4-position of the phenyl ring.

In another embodiment, Ar$^1$ is a pyridyl group; V is N; n is 0; m is 1; R$_3$ is —CH$_3$; R$_1$ is —Br; Ar$^2$ is

[structure: phenyl ring with (R$_8$)$_r$ substituent]

r is 1 and R$_8$ is —I. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 4-position of the phenyl ring.

In another embodiment, Ar$^1$ is a pyridyl group; V is N; n is 0; m is 1; R$_3$ is —CH$_3$; R$_1$ is —I; Ar$^2$ is

[structure: phenyl ring with (R$_8$)$_r$ substituent]

r is 1 and R$_8$ is —I. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 4-position of the phenyl ring.

In another embodiment, Ar$^1$ is a pyridyl group; V is N; n is 0; m is 1; R$_3$ is —CH$_3$; R$_1$ is —CH$_3$; Ar$^2$ is

[structure: phenyl ring with (R$_8$)$_r$ substituent]

r is 1 and R$_8$ is —I. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 4-position of the phenyl ring.

In another embodiment, Ar$^1$ is a pyridyl group; V is N; n is 0; m is 1; R$_3$ is —CH$_3$; R$_1$ is —CF$_3$; Ar$^2$ is

[structure: phenyl ring with (R$_8$)$_r$ substituent]

r is 1 and R$_8$ is —I. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 4-position of the phenyl ring.

In another embodiment, Ar$^1$ is a pyridyl group; V is N; n is 0; m is 1; R$_3$ is —CH$_3$; R$_1$ is —F, —Cl, —Br, or —I; Ar$^2$ is

[structure: phenyl ring with (R$_8$)$_r$ substituent]

r is 1 and R$_8$ is —CH$_3$. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 4-position of the phenyl ring.

In another embodiment, Ar$^1$ is a pyridyl group; V is N; n is 0; m is 1; R$_3$ is —CH$_3$; R$_1$ is —F; Ar$^2$ is

[structure: phenyl with (R$_8$)$_r$ substituent]

r is 1 and R$_8$ is —CH$_3$. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 4-position of the phenyl ring.

In another embodiment, Ar$^1$ is a pyridyl group; V is N; n is 0; m is 1; R$_3$ is —CH$_3$; R$_1$ is —Cl; Ar$^2$ is

[structure: phenyl with (R$_8$)$_r$ substituent]

r is 1 and R$_8$ is —CH$_3$. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 4-position of the phenyl ring.

In another embodiment, Ar$^1$ is a pyridyl group; V is N; n is 0; m is 1; R$_3$ is —CH$_3$; R$_1$ is —Br; Ar$^2$ is

[structure: phenyl with (R$_8$)$_r$ substituent]

r is 1 and R$_8$ is —CH$_3$. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 4-position of the phenyl ring.

In another embodiment, Ar$^1$ is a pyridyl group; V is N; n is 0; m is 1; R$_3$ is —CH$_3$; R$_1$ is —I; Ar$^2$ is

[structure: phenyl with (R$_8$)$_r$ substituent]

r is 1 and R$_8$ is —CH$_3$. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 4-position of the phenyl ring.

In another embodiment, Ar$^1$ is a pyridyl group; V is N; n is 0; m is 1; R$_3$ is —CH$_3$; R$_1$ is —CH$_3$; Ar$^2$ is

[structure: phenyl with (R$_8$)$_r$ substituent]

r is 1 and R$_8$ is —CH$_3$. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 4-position of the phenyl ring.

In another embodiment, Ar$^1$ is a pyridyl group; V is N; n is 0; m is 1; R$_3$ is —CH$_3$; R$_1$ is —CF$_3$; Ar$^2$ is

[structure: phenyl with (R$_8$)$_r$ substituent]

r is 1 and R$_8$ is —CH$_3$. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 4-position of the phenyl ring.

In another embodiment, Ar$^1$ is a pyridyl group; V is N; n is 0; m is 1; R$_3$ is —CH$_3$; R$_1$ is —F, —Cl, —Br, or —I; Ar$^2$ is

[structure: phenyl ring with (R$_8$)$_r$ substituent]

r is 1 and R$_8$ is —CF$_3$. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 4-position of the phenyl ring.

In another embodiment, Ar$^1$ is a pyridyl group; V is N; n is 0; m is 1; R$_3$ is —CH$_3$; R$_1$ is —F; Ar$^2$ is

[structure: phenyl ring with (R$_8$)$_r$ substituent]

r is 1 and R$_8$ is —CF$_3$. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 4-position of the phenyl ring.

In another embodiment, Ar$^1$ is a pyridyl group; V is N; n is 0; m is 1; R$_3$ is —CH$_3$; R$_1$ is —Cl; Ar$^2$ is

[structure: phenyl ring with (R$_8$)$_r$ substituent]

r is 1 and R$_8$ is —CF$_3$. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 4-position of the phenyl ring.

In another embodiment, Ar$^1$ is a pyridyl group; V is N; n is 0; m is 1; R$_3$ is —CH$_3$; R$_1$ is —Br; Ar$^2$ is

[structure: phenyl ring with (R$_8$)$_r$ substituent]

r is 1 and R$_8$ is —CF$_3$. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 4-position of the phenyl ring.

In another embodiment, Ar$^1$ is a pyridyl group; V is N; n is 0; m is 1; R$_3$ is —CH$_3$; R$_1$ is —I; Ar$^2$ is

[structure: phenyl ring with (R$_8$)$_r$ substituent]

r is 1 and R$_8$ is —CF$_3$. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 4-position of the phenyl ring.

In another embodiment, Ar$^1$ is a pyridyl group; V is N; n is 0; m is 1; R$_3$ is —CH$_3$; R$_1$ is —CH$_3$; Ar$^2$ is

[structure: phenyl ring with (R$_8$)$_r$ substituent]

r is 1 and R$_8$ is —CF$_3$. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 4-position of the phenyl ring.

In another embodiment, Ar$^1$ is a pyridyl group; V is N; n is 0; m is 1; R$_3$ is —CH$_3$; R$_1$ is —CF$_3$; Ar$^2$ is

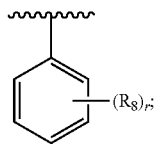

r is 1 and R$_8$ is —CF$_3$. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 4-position of the phenyl ring.

In another embodiment, Ar$^1$ is a pyridyl group; V is N; n is 0; m is 1; R$_3$ is —CH$_3$; R$_1$ is —F, —Cl —Br, or —I; Ar$^2$ is

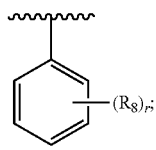

r is 1 and R$_8$ is —OCH$_2$CH$_3$. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 4-position of the phenyl ring.

In another embodiment, Ar$^1$ is a pyridyl group; V is N; n is 0; m is 1; R$_3$ is —CH$_3$; R$_1$ is —F; Ar$^2$ is

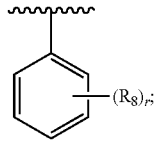

r is 1 and R$_8$ is —OCH$_2$CH$_3$. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 4-position of the phenyl ring.

In another embodiment, Ar$^1$ is a pyridyl group; V is N; n is 0; m is 1; R$_3$ is —CH$_3$; R$_1$ is —Cl; Ar$^2$ is

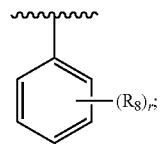

r is 1 and R$_8$ is —OCH$_2$CH$_3$. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 4-position of the phenyl ring.

In another embodiment, Ar$^1$ is a pyridyl group; V is N; n is 0; m is 1; R$_3$ is —CH$_3$; R$_1$ is —Br; Ar$^2$ is

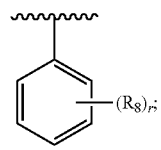

r is 1 and R$_8$ is —OCH$_2$CH$_3$. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 4-position of the phenyl ring.

In another embodiment, Ar$^1$ is a pyridyl group; V is N; n is 0; m is 1; R$_3$ is —CH$_3$; R$_1$ is —I; Ar$^2$ is

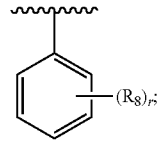

r is 1 and R$_8$ is —OCH$_2$CH$_3$. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 4-position of the phenyl ring.

In another embodiment, $Ar^1$ is a pyridyl group; V is N; n is 0; m is 1; $R_3$ is —$CH_3$; $R_1$ is —$CH_3$; $Ar^2$ is

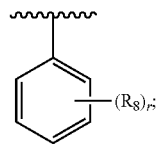

r is 1 and $R_8$ is —$OCH_2CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 4-position of the phenyl ring.

In another embodiment, $Ar^1$ is a pyridyl group; V is N; n is 0; m is 1; $R_3$ is —$CH_3$; $R_1$ is —$CF_3$; $Ar^2$ is

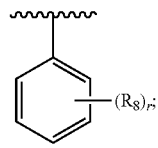

r is 1 and $R_8$ is —$OCH_2CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 4-position of the phenyl ring.

In another embodiment, $Ar^1$ is a pyridyl group; V is N; n is 0; m is 1; $R_3$ is —$CH_3$; $R_1$ is —F, —Cl —Br, or —I; $Ar^2$ is

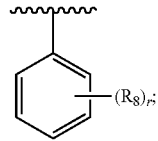

r is 1 and $R_8$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 4-position of the phenyl ring.

In another embodiment, $Ar^1$ is a pyridyl group; V is N; n is 0; m is 1; $R_3$ is —$CH_3$; $R_1$ is —F; $Ar^2$ is

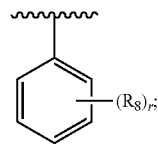

r is 1 and $R_8$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 4-position of the phenyl ring.

In another embodiment, $Ar^1$ is a pyridyl group; V is N; n is 0; m is 1; $R_3$ is —$CH_3$; $R_1$ is —Cl; $Ar^2$ is

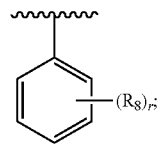

r is 1 and $R_8$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 4-position of the phenyl ring.

In another embodiment, $Ar^1$ is a pyridyl group; V is N; n is 0; m is 1; $R_3$ is —$CH_3$; $R_1$ is —Br; $Ar^2$ is

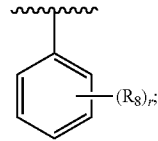

r is 1 and $R_8$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 4-position of the phenyl ring.

In another embodiment, $Ar^1$ is a pyridyl group; V is N; n is 0; m is 1; $R_3$ is —$CH_3$; $R_1$ is —I; $Ar^2$ is

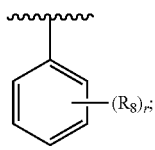

r is 1 and $R_8$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 4-position of the phenyl ring.

In another embodiment, $Ar^1$ is a pyridyl group; V is N; n is 0; m is 1; $R_3$ is —$CH_3$; $R_1$ is —$CH_3$; $Ar^2$ is

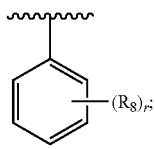

r is 1 and $R_8$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 4-position of the phenyl ring.

In another embodiment, $Ar^1$ is a pyridyl group; V is N; n is 0; m is 1; $R_3$ is —$CH_3$; $R_1$ is —$CF_3$; $Ar^2$ is

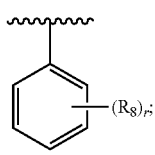

r is 1 and $R_8$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 4-position of the phenyl ring.

In another embodiment, V is CH, $Ar^1$ is a pyridyl group, m is 0, and $Ar^2$ is

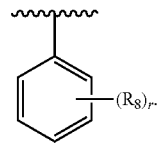

In another embodiment, $Ar^1$ is a pyridyl group; V is CH; n is 0; m is 0; $R_1$ is —F, —Cl, —Br, or —I; $Ar^2$ is

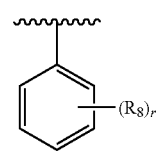

and r is 0.

In another embodiment, $Ar^1$ is a pyridyl group; V is CH; n is 0; m is 0; $R_1$ is —F; $Ar^2$ is

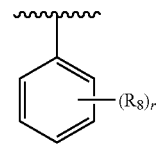

and r is 0.

In another embodiment, $Ar^1$ is a pyridyl group; V is CH; n is 0; m is 0; $R_1$ is —Cl; $Ar^2$ is

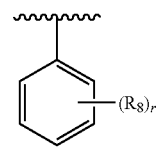

and r is 0.

In another embodiment, $Ar^1$ is a pyridyl group; V is CH; n is 0; m is 0; $R_1$ is —Br; $Ar^2$ is

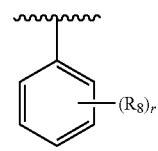

and r is 0.

In another embodiment, $Ar^1$ is a pyridyl group; V is CH; n is 0; m is 0; $R_1$ is —I; $Ar^2$ is

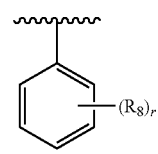

and r is 0.

In another embodiment, $Ar^1$ is a pyridyl group; V is CH; n is 0; m is 0; $R_1$ is —$CH_3$; $Ar^2$ is

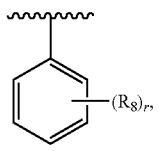

and r is 0.

In another embodiment, $Ar^1$ is a pyridyl group; V is CH; n is 0; m is 0; $R_1$ is —$CF_3$; $Ar^2$ is

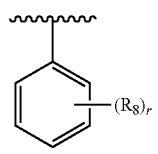

and r is 0.

In another embodiment, $Ar^1$ is a pyridyl group; V is CH; n is 0; m is 0; $R_1$ is —F, —Cl, —Br, or —I; $Ar^2$ is

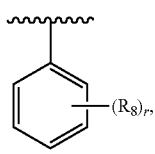

r is 1 and $R_8$ is -halo. In another embodiment, $R_8$ is at the 4-position of the phenyl ring.

In another embodiment, $Ar^1$ is a pyridyl group; V is CH; n is 0; m is 0; $R_1$ is —F; $Ar^2$ is

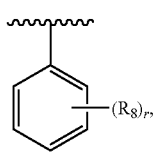

r is 1 and $R_8$ is -halo.

In another embodiment, $Ar^1$ is a pyridyl group; V is CH; n is 0; m is 0; $R_1$ is —Cl; $Ar^2$ is

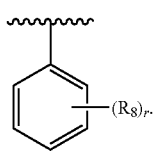

r is 1 and $R_8$ is -halo. In another embodiment, $R_8$ is at the 4-position of the phenyl ring.

In another embodiment, $Ar^1$ is a pyridyl group; V is CH; n is 0; m is 0; $R_1$ is —Br; $Ar^2$ is

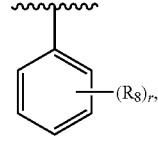

r is 1 and $R_8$ is -halo. In another embodiment, $R_8$ is at the 4-position of the phenyl ring.

In another embodiment, $Ar^1$ is a pyridyl group; V is CH; n is 0; m is 0; $R_1$ is —I; $Ar^2$ is

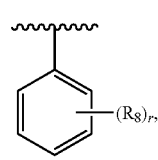

r is 1 and $R_8$ is -halo. In another embodiment, $R_8$ is at the 4-position of the phenyl ring.

In another embodiment, $Ar^1$ is a pyridyl group; V is CH; n is 0; m is 0; $R_1$ is —$CH_3$; $Ar^2$ is

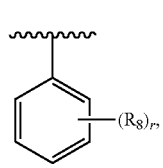

r is 1 and $R_8$ is -halo. In another embodiment, $R_8$ is at the 4-position of the phenyl ring.

In another embodiment, $Ar^1$ is a pyridyl group; V is CH; n is 0; m is 0; $R_1$ is —$CF_3$; $Ar^2$ is

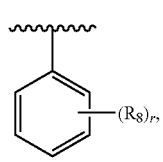

r is 1 and $R_8$ is -halo. In another embodiment, $R_8$ is at the 4-position of the phenyl ring.

In another embodiment, $Ar^1$ is a pyridyl group; V is CH; n is 0; m is 0; $R_1$ is —F, —Cl, —Br, or —I; $Ar^2$ is $(R_8)_r$

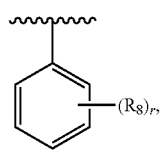

r is 1 and $R_8$ is —Br. In another embodiment, $R_8$ is at the 4-position of the phenyl ring.

In another embodiment, $Ar^1$ is a pyridyl group; V is CH; n is 0; m is 0; $R_1$ is —F; $Ar^2$ is

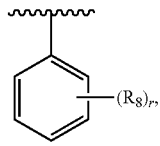

r is 1 and $R_8$ is —Br. In another embodiment, $R_8$ is at the 4-position of the phenyl ring.

In another embodiment, $Ar^1$ is a pyridyl group; V is CH; n is 0; m is 0; $R_1$ is —Cl; $Ar^2$ is

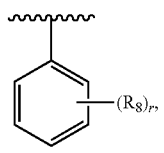

r is 1 and $R_8$ is —Br. In another embodiment, $R_8$ is at the 4-position of the phenyl ring.

In another embodiment, $Ar^1$ is a pyridyl group; V is CH; n is 0; m is 0; $R_1$ is —Br; $Ar^2$ is

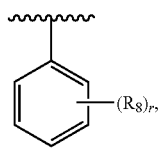

r is 1 and $R_8$ is —Br. In another embodiment, $R_8$ is at the 4-position of the phenyl ring.

In another embodiment, $Ar^1$ is a pyridyl group; V is CH; n is 0; m is 0; $R_1$ is —I; $Ar^2$ is

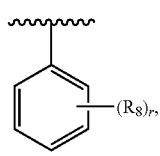

r is 1 and $R_8$ is —Br. In another embodiment, $R_8$ is at the 4-position of the phenyl ring.

In another embodiment, $Ar^1$ is a pyridyl group; V is CH; n is 0; m is 0; $R_1$ is —$CH_3$; $Ar^2$ is

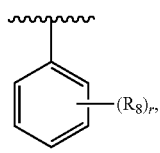

r is 1 and $R_8$ is —Br. In another embodiment, $R_8$ is at the 4-position of the phenyl ring.

In another embodiment, $Ar^1$ is a pyridyl group; V is CH; n is 0; m is 0; $R_1$ is —$CF_3$; $Ar^2$ is

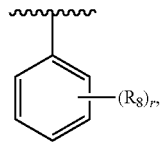

r is 1 and $R_8$ is —Br. In another embodiment, $R_8$ is at the 4-position of the phenyl ring.

In another embodiment, $Ar^1$ is a pyridyl group; V is CH; n is 0; m is 0; $R_1$ is —Cl, —F —Br, or —I; $Ar^2$ is

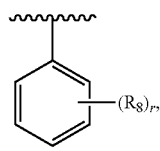

r is 1 and $R_8$ is —F. In another embodiment, $R_8$ is at the 4-position of the phenyl ring.

In another embodiment, $Ar^1$ is a pyridyl group; V is CH; n is 0; m is 0; $R_1$ is —F; $Ar^2$ is

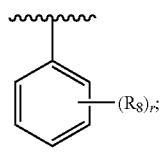

r is 1 and $R_8$ is —F. In another embodiment, $R_8$ is at the 4-position of the phenyl ring In another embodiment, $Ar^1$ is a pyridyl group; V is CH; n is 0; m is 0; $R_1$ is —Cl; $Ar^2$ is

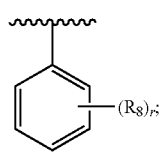

r is 1 and $R_8$ is —F. In another embodiment, $R_8$ is at the 4-position of the phenyl ring.

In another embodiment, $Ar^1$ is a pyridyl group; V is CH; n is 0; m is 0; $R_1$ is —Br; $Ar^2$ is

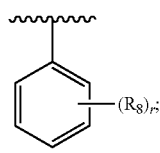

r is 1 and $R_8$ is —F. In another embodiment, $R_8$ is at the 4-position of the phenyl ring.

In another embodiment, $Ar^1$ is a pyridyl group; V is CH; n is 0; m is 0; $R_1$ is —I; $Ar^2$ is

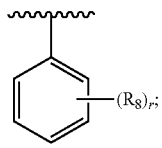

r is 1 and $R_8$ is —F. In another embodiment, $R_8$ is at the 4-position of the phenyl ring.

In another embodiment, $Ar^1$ is a pyridyl group; V is CH; n is 0; m is 0; $R_1$ is —$CH_3$; $Ar^2$ is

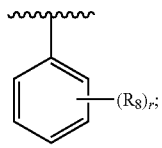

r is 1 and $R_8$ is —F. In another embodiment, $R_8$ is at the 4-position of the phenyl ring.

In another embodiment, $Ar^1$ is a pyridyl group; V is CH; n is 0; m is 0; $R_1$ is —$CF_3$; $Ar^2$ is

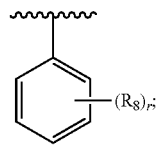

r is 1 and $R_8$ is —F. In another embodiment, $R_8$ is at the 4-position of the phenyl ring.

In another embodiment, $Ar^1$ is a pyridyl group; V is CH; n is 0; m is 0; $R_1$ is —Cl, —F —Br, or —I; $Ar^2$ is

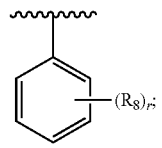

r is 1 and $R_8$ is —Cl. In another embodiment, $R_8$ is at the 4-position of the phenyl ring.

In another embodiment, $Ar^1$ is a pyridyl group; V is CH; n is 0; m is 0; $R_1$ is —F; $Ar^2$ is

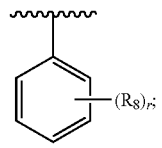

r is 1 and $R_8$ is —Cl. In another embodiment, $R_8$ is at the 4-position of the phenyl ring.

In another embodiment, $Ar^1$ is a pyridyl group; V is CH; n is 0; m is 0; $R_1$ is —Cl; $Ar^2$ is

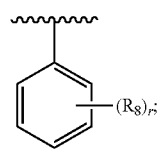

r is 1 and $R_8$ is —Cl. In another embodiment, $R_8$ is at the 4-position of the phenyl ring.

In another embodiment, $Ar^1$ is a pyridyl group; V is CH; n is 0; m is 0; $R_1$ is —Br; $Ar^2$ is

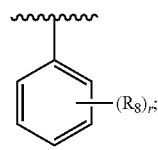

r is 1 and $R_8$ is —Cl. In another embodiment, $R_8$ is at the 4-position of the phenyl ring.

In another embodiment, $Ar^1$ is a pyridyl group; V is CH; n is 0; m is 0; $R_1$ is —I; $Ar^2$ is

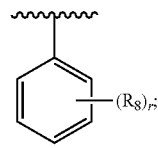

r is 1 and $R_8$ is —Cl. In another embodiment, $R_8$ is at the 4-position of the phenyl ring.

In another embodiment, $Ar^1$ is a pyridyl group; V is CH; n is 0; m is 0; $R_1$ is —$CH_3$; $Ar^2$ is

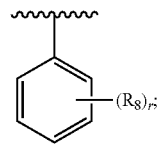

r is 1 and $R_8$ is —Cl. In another embodiment, $R_8$ is at the 4-position of the phenyl ring.

In another embodiment, $Ar^1$ is a pyridyl group; V is CH; n is 0; m is 0; $R_1$ is —$CF_3$; $Ar^2$ is

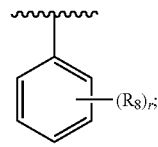

r is 1 and $R_8$ is chloro. In another embodiment, $R_8$ is at the 4-position of the phenyl ring.

In another embodiment, $Ar^1$ is a pyridyl group; V is CH; n is 0; m is 0; $R_1$ is —Cl, —F, —Br, or —I, $Ar^2$ is

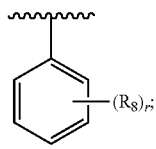

r is 1 and $R_8$ is —I. In another embodiment, $R_8$ is at the 4-position of the phenyl ring.

In another embodiment, $Ar^1$ is a pyridyl group; V is CH; n is 0; m is 0; $R_1$ is —F; $Ar^2$ is

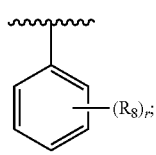

r is 1 and $R_8$ is —I. In another embodiment, $R_8$ is at the 4-position of the phenyl ring.

In another embodiment, $Ar^1$ is a pyridyl group; V is CH; n is 0; m is 0; $R_1$ is —Cl; $Ar^2$ is

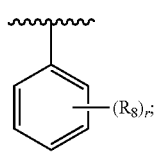

r is 1 and $R_8$ is —I. In another embodiment, $R_8$ is at the 4-position of the phenyl ring.

In another embodiment, $Ar^1$ is a pyridyl group; V is CH; n is 0; m is 0; $R_1$ is —Br; $Ar^2$ is

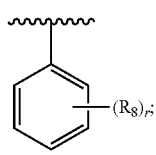

r is 1 and $R_8$ is —I. In another embodiment, $R_8$ is at the 4-position of the phenyl ring.

In another embodiment, $Ar^1$ is a pyridyl group; V is CH; n is 0; m is 0; $R_1$ is —I; $Ar^2$ is

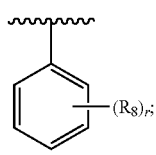

r is 1 and $R_8$ is —I. In another embodiment, $R_8$ is at the 4-position of the phenyl ring.

In another embodiment, $Ar^1$ is a pyridyl group; V is CH; n is 0; m is 0; $R_1$ is —$CH_3$; $Ar^2$ is

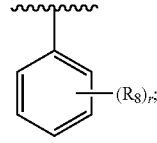

r is 1 and $R_8$ is —I. In another embodiment, $R_8$ is at the 4-position of the phenyl ring.

In another embodiment, $Ar^1$ is a pyridyl group; V is CH; n is 0; m is 0; $R_1$ is —$CF_3$; $Ar^2$ is

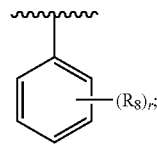

r is 1 and $R_8$ is —I. In another embodiment, $R_8$ is at the 4-position of the phenyl ring.

In another embodiment, $Ar^1$ is a pyridyl group; V is CH; n is 0; m is 0; $R_1$ is —F, —Cl, —Br, or —I; $Ar^2$ is

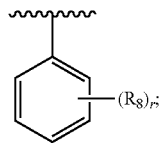

r is 1 and $R_8$ is —$CH_3$. In another embodiment, $R_8$ is at the 4-position of the phenyl ring.

In another embodiment, $Ar^1$ is a pyridyl group; V is CH; n is 0; m is 0; $R_1$ is —F; $Ar^2$ is

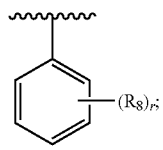

r is 1 and $R_8$ is —$CH_3$. In another embodiment, $R_8$ is at the 4-position of the phenyl ring.

In another embodiment, $Ar^1$ is a pyridyl group; V is CH; n is 0; m is 0; $R_1$ is —Cl; $Ar^2$ is

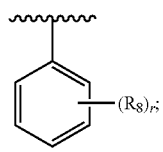

r is 1 and $R_8$ is —$CH_3$. In another embodiment, $R_8$ is at the 4-position of the phenyl ring.

In another embodiment, Ar¹ is a pyridyl group; V is CH; n is 0; m is 0; $R_1$ is —Br; $Ar^2$ is

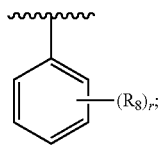

r is 1 and $R_8$ is —CH₃. In another embodiment, $R_8$ is at the 4-position of the phenyl ring.

In another embodiment, Ar¹ is a pyridyl group; V is CH; n is 0; m is 0; $R_1$ is —I; $Ar^2$ is

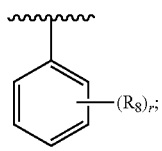

r is 1 and $R_8$ is —CH₃. In another embodiment, $R_8$ is at the 4-position of the phenyl ring.

In another embodiment, Ar¹ is a pyridyl group; V is CH; n is 0; m is 0; $R_1$ is —CH₃; $Ar^2$ is

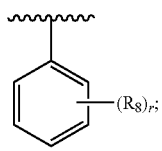

r is 1 and $R_8$ is —CH₃. In another embodiment, $R_8$ is at the 4-position of the phenyl ring.

In another embodiment, Ar¹ is a pyridyl group; V is CH; n is 0; m is 0; $R_1$ is —CF₃; $Ar^2$ is

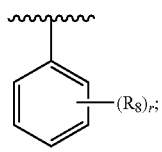

r is 1 and $R_8$ is —CH₃. In another embodiment, $R_8$ is at the 4-position of the phenyl ring.

In another embodiment, Ar¹ is a pyridyl group; V is CH; n is 0; m is 0; $R_1$ is —F, —Cl, —Br, or —I; $Ar^2$ is

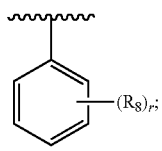

r is 1 and $R_8$ is —CF₃. In another embodiment, $R_8$ is at the 4-position of the phenyl ring.

In another embodiment, Ar¹ is a pyridyl group; V is CH; n is 0; m is 0; $R_1$ is —F; $Ar^2$ is

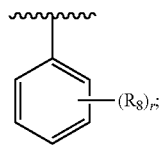

r is 1 and $R_8$ is —CF₃. In another embodiment, $R_8$ is at the 4-position of the phenyl ring.

In another embodiment, Ar¹ is a pyridyl group; V is CH; n is 0; m is 0; $R_1$ is —Cl; $Ar^2$ is

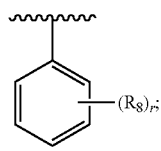

r is 1 and $R_8$ is —CF₃. In another embodiment, $R_8$ is at the 4-position of the phenyl ring.

In another embodiment, Ar¹ is a pyridyl group; V is CH; n is 0; m is 0; $R_1$ is —Br; $Ar^2$ is

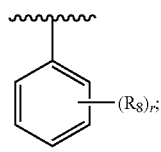

r is 1 and $R_8$ is —CF₃. In another embodiment, $R_8$ is at the 4-position of the phenyl ring.

In another embodiment, Ar¹ is a pyridyl group; V is CH; n is 0; m is 0; $R_1$ is —I; $Ar^2$ is

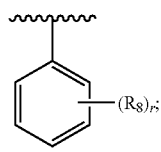

r is 1 and $R_8$ is —CF₃. In another embodiment, $R_8$ is at the 4-position of the phenyl ring.

In another embodiment, Ar¹ is a pyridyl group; V is CH; n is 0; m is 0; $R_1$ is —CH₃; $Ar^2$ is

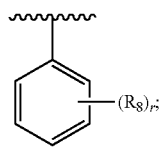

r is 1 and $R_8$ is —CF₃. In another embodiment, $R_8$ is at the 4-position of the phenyl ring.

In another embodiment, $Ar^1$ is a pyridyl group; V is CH; n is 0; m is 0; $R_1$ is —$CF_3$; $Ar^2$ is

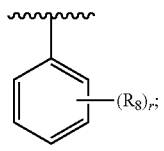

r is 1 and $R_8$ is —$CF_3$. In another embodiment, $R_8$ is at the 4-position of the phenyl ring.

In another embodiment, $Ar^1$ is a pyridyl group; V is CH; n is 0; m is 0; $R_1$ is —F, —Cl —Br, or —I; $Ar^2$ is

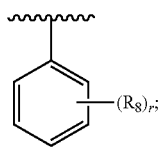

r is 1 and $R_8$ is —$OCH_2CH_3$. In another embodiment, $R_8$ is at the 4-position of the phenyl ring.

In another embodiment, $Ar^1$ is a pyridyl group; V is CH; n is 0; m is 0; $R_1$ is —F; $Ar^2$ is

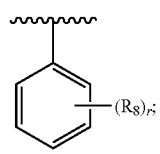

r is 1 and $R_8$ is —$OCH_2CH_3$. In another embodiment, $R_8$ is at the 4-position of the phenyl ring.

In another embodiment, $Ar^1$ is a pyridyl group; V is CH; n is 0; m is 0; $R_1$ is —Cl; $Ar^2$ is

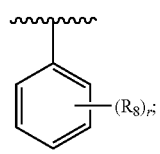

r is 1 and $R_8$ is —$OCH_2CH_3$. In another embodiment, $R_8$ is at the 4-position of the phenyl ring.

In another embodiment, $Ar^1$ is a pyridyl group; V is CH; n is 0; m is 0; $R_1$ is —Br; $Ar^2$ is

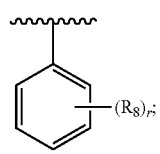

r is 1 and $R_8$ is —$OCH_2CH_3$. In another embodiment, $R_8$ is at the 4-position of the phenyl ring.

In another embodiment, $Ar^1$ is a pyridyl group; V is CH; n is 0; m is 0; $R_1$ is —I; $Ar^2$ is

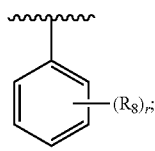

r is 1 and $R_8$ is —$OCH_2CH_3$. In another embodiment, $R_8$ is at the 4-position of the phenyl ring.

In another embodiment, $Ar^1$ is a pyridyl group; V is CH; n is 0; m is 0; $R_1$ is —$CH_3$; $Ar^2$ is

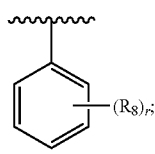

r is 1 and $R_8$ is —$OCH_2CH_3$. In another embodiment, $R_8$ is at the 4-position of the phenyl ring.

In another embodiment, $Ar^1$ is a pyridyl group; V is CH; n is 0; m is 0; $R_1$ is —$CF_3$; $Ar^2$ is

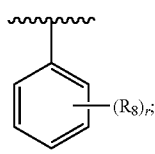

r is 1 and $R_8$ is —$OCH_2CH_3$. In another embodiment, $R_8$ is at the 4-position of the phenyl ring.

In another embodiment, $Ar^1$ is a pyridyl group; V is CH; n is 0; m is 0; $R_1$ is —F, —Cl, —Br, or —I; $Ar^2$ is

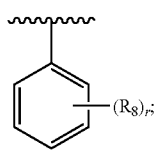

r is 1 and $R_8$ is -tert-butyl. In another embodiment, $R_8$ is at the 4-position of the phenyl ring.

In another embodiment, $Ar^1$ is a pyridyl group; V is CH; n is 0; m is 0; $R_1$ is —F; $Ar^2$ is

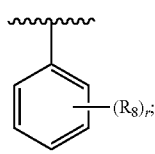

r is 1 and $R_8$ is -tert-butyl. In another embodiment, $R_8$ is at the 4-position of the phenyl ring.

In another embodiment, $Ar^1$ is a pyridyl group; V is CH; n is 0; m is 0; $R_1$ is —Cl; $Ar^2$ is

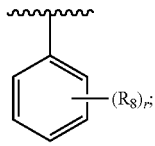

r is 1 and $R_8$ is -tert-butyl. In another embodiment, $R_8$ is at the 4-position of the phenyl ring.

In another embodiment, $Ar^1$ is a pyridyl group; V is CH; n is 0; m is 0; $R_1$ is —Br; $Ar^2$ is

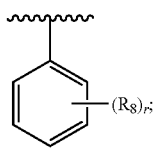

r is 1 and $R_8$ is -tert-butyl. In another embodiment, $R_8$ is at the 4-position of the phenyl ring.

In another embodiment, $Ar^1$ is a pyridyl group; V is CH; n is 0; m is 0; $R_1$ is —I; $Ar^2$ is

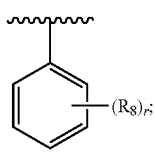

r is 1 and $R_8$ is -tert-butyl. In another embodiment, $R_8$ is at the 4-position of the phenyl ring.

In another embodiment, $Ar^1$ is a pyridyl group; V is CH; n is 0; m is 0; $R_1$ is —$CH_3$; $Ar^2$ is

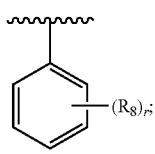

r is 1 and $R_8$ is -tert-butyl. In another embodiment, $R_8$ is at the 4-position of the phenyl ring.

In another embodiment, $Ar^1$ is a pyridyl group; V is CH; n is 0; m is 0; $R_1$ is —$CF_3$; $Ar^2$ is

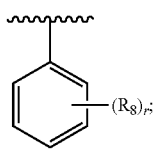

r is 1 and $R_8$ is -tert-butyl. In another embodiment, $R_8$ is at the 4-position of the phenyl ring.

In another embodiment, $Ar^1$ is a pyridyl group; V is CH; n is 0; m is 1; $R_3$ is —$CH_3$; $R_1$ is —F, —Cl, —Br, or —I; $Ar^2$ is

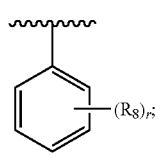

and r is 0. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 4-position of the phenyl ring.

In another embodiment, $Ar^1$ is a pyridyl group; V is CH; n is 0; m is 1; $R_3$ is —$CH_3$; $R_1$ is —F; $Ar^2$ is

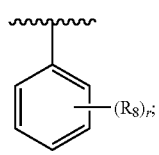

and r is 0. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 4-position of the phenyl ring.

In another embodiment, $Ar^1$ is a pyridyl group; V is CH; n is 0; m is 1; $R_3$ is —$CH_3$; $R_1$ is —Cl; $Ar^2$ is

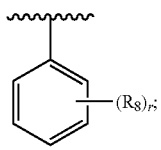

and r is 0. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 4-position of the phenyl ring.

In another embodiment, $Ar^1$ is a pyridyl group; V is CH; n is 0; m is 1; $R_3$ is —$CH_3$; $R_1$ is —Br; $Ar^2$ is

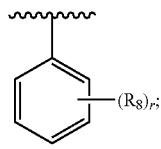

and r is 0. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 4-position of the phenyl ring.

In another embodiment, $Ar^1$ is a pyridyl group; V is CH; n is 0; m is 1; $R_3$ is —$CH_3$; $R_1$ is —I; $Ar^2$ is

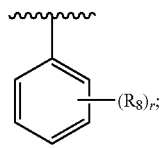

and r is 0. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 4-position of the phenyl ring.

In another embodiment, $Ar^1$ is a pyridyl group; V is CH; n is 0; m is 1; $R_3$ is —$CH_3$; $R_1$ is —$CH_3$; $Ar^2$ is

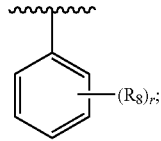

and r is 0. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 4-position of the phenyl ring.

In another embodiment, $Ar^1$ is a pyridyl group; V is CH; n is 0; m is 1; $R_3$ is —$CH_3$; $R_1$ is —$CF_3$; $Ar^2$ is

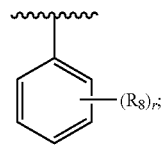

and r is 0. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 4-position of the phenyl ring.

In another embodiment, $Ar^1$ is a pyridyl group; V is CH; n is 0; m is 1; $R_3$ is —$CH_3$; $R_1$ is —F, —Cl, —Br, or —I; $Ar^2$ is

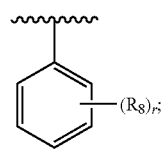

r is 1 and $R_8$ is -halo. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F; $Ar^2$ is

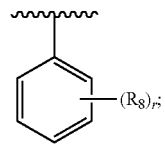

r is 1 and $R_8$ is -halo. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 4-position of the phenyl ring.

In another embodiment, Ar$^1$ is a pyridyl group; V is CH; n is 0; m is 1; R$_3$ is —CH$_3$; R$_1$ is —Cl; Ar$^2$ is

[structure: phenyl with (R$_8$)$_r$]

r is 1 and R$_8$ is -halo. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 4-position of the phenyl ring.

In another embodiment, Ar$^1$ is a pyridyl group; V is CH; n is 0; m is 1; R$_3$ is —CH$_3$; R$_1$ is —Br; Ar$^2$ is

[structure: phenyl with (R$_8$)$_r$]

r is 1 and R$_8$ is -halo. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 4-position of the phenyl ring.

In another embodiment, Ar$^1$ is a pyridyl group; V is CH; n is 0; m is 1; R$_3$ is —CH$_3$; R$_1$ is —I; Ar$^2$ is

[structure: phenyl with (R$_8$)$_r$]

r is 1 and R$_8$ is -halo. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 4-position of the phenyl ring.

In another embodiment, Ar$^1$ is a pyridyl group; V is CH; n is 0; m is 1; R$_3$ is —CH$_3$; —R$_1$ is —CH$_3$; Ar$^2$ is

[structure: phenyl with (R$_8$)$_r$]

r is 1 and R$_8$ is -halo. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 4-position of the phenyl ring.

In another embodiment, Ar$^1$ is a pyridyl group; V is CH; n is 0; m is 1; R$_3$ is —CH$_3$; R$_1$ is —CF$_3$; Ar$^2$ is

[structure: phenyl with (R$_8$)$_r$]

r is 1 and R$_8$ is -halo. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 4-position of the phenyl ring.

In another embodiment, Ar$^1$ is a pyridyl group; V is CH; n is 0; m is 1; R$_3$ is —CH$_3$; R$_1$ is —F, —Cl, —Br, or —I; Ar$^2$ is

[structure: phenyl with (R$_8$)$_r$]

r is 1 and R$_8$ is —Br. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 4-position of the phenyl ring.

In another embodiment, Ar$^1$ is a pyridyl group; V is CH; n is 0; m is 1; R$_3$ is —CH$_3$; R$_1$ is —F; Ar$^2$ is

[Structure: phenyl ring with (R$_8$)$_r$ substituent]

r is 1 and R$_8$ is —Br. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 4-position of the phenyl ring.

In another embodiment, Ar$^1$ is a pyridyl group; V is CH; n is 0; m is 1; R$_3$ is —CH$_3$; R$_1$ is —Cl; Ar$^2$ is

[Structure: phenyl ring with (R$_8$)$_r$ substituent]

r is 1 and R$_8$ is —Br. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 4-position of the phenyl ring.

In another embodiment, Ar$^1$ is a pyridyl group; V is CH; n is 0; m is 1; R$_3$ is —CH$_3$; R$_1$ is —Br; Ar$^2$ is

[Structure: phenyl ring with (R$_8$)$_r$ substituent]

r is 1 and R$_8$ is —Br. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 4-position of the phenyl ring.

In another embodiment, Ar$^1$ is a pyridyl group; V is CH; n is 0; m is 1; R$_3$ is —CH$_3$; R$_1$ is —I; Ar$^2$ is

[Structure: phenyl ring with (R$_8$)$_r$ substituent]

r is 1 and R$_8$ is —Br. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 4-position of the phenyl ring.

In another embodiment, Ar$^1$ is a pyridyl group; V is CH; n is 0; m is 1; R$_3$ is —CH$_3$; R$_1$ is —CH$_3$; Ar$^2$ is

[Structure: phenyl ring with (R$_8$)$_r$ substituent]

r is 1 and R$_8$ is —Br. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 4-position of the phenyl ring.

In another embodiment, Ar$^1$ is a pyridyl group; V is CH; n is 0; m is 1; R$_3$ is —CH$_3$; R$_1$ is —CF$_3$; Ar$^2$ is

[Structure: phenyl ring with (R$_8$)$_r$ substituent]

r is 1 and R$_8$ is —Br. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 4-position of the phenyl ring.

In another embodiment, $Ar^1$ is a pyridyl group; V is CH; n is 0; m is 1; $R_3$ is —$CH_3$; $R_1$ is —Cl, —F —Br, or —I; $Ar^2$ is

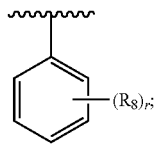

r is 1 and $R_8$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 4-position of the phenyl ring.

In another embodiment, $Ar^1$ is a pyridyl group; V is CH; n is 0; m is 1; $R_3$ is —$CH_3$; $R_1$ is —F; $Ar^2$ is

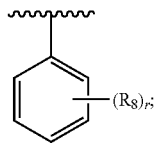

r is 1 and $R_8$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 4-position of the phenyl ring.

In another embodiment, $Ar^1$ is a pyridyl group; V is CH; n is 0; m is 1; $R_3$ is —$CH_3$; $R_1$ is —Cl; $Ar^2$ is

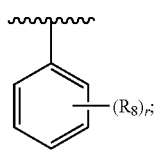

r is 1 and $R_8$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 4-position of the phenyl ring.

In another embodiment, $Ar^1$ is a pyridyl group; V is CH; n is 0; m is 1; $R_3$ is —$CH_3$; $R_1$ is —Br; $Ar^2$ is

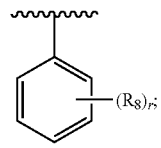

r is 1 and $R_8$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 4-position of the phenyl ring.

In another embodiment, $Ar^1$ is a pyridyl group; V is CH; n is 0; m is 1; $R_3$ is —$CH_3$; $R_1$ is —I; $Ar^2$ is

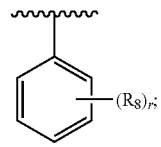

r is 1 and $R_8$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 4-position of the phenyl ring.

In another embodiment, Art is a pyridyl group; V is CH; n is 0; m is 1; $R_3$ is —$CH_3$; $R_1$ is —$CH_3$; $Ar^2$ is

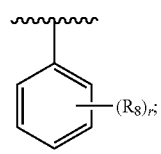

r is 1 and $R_8$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 4-position of the phenyl ring.

In another embodiment, $Ar^1$ is a pyridyl group; V is CH; n is 0; m is 1; $R_3$ is —$CH_3$; $R_1$ is —$CF_3$; $Ar^2$ is

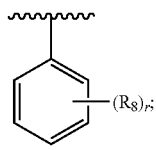

r is 1 and $R_8$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 4-position of the phenyl ring.

In another embodiment, $Ar^1$ is a pyridyl group; V is CH; n is 0; m is 1; $R_3$ is $CH_3$; $R_1$ is —Cl, —F —Br, or —I; $Ar^2$ is

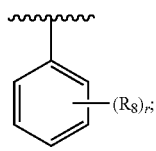

r is 1 and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 4-position of the phenyl ring.

In another embodiment, $Ar^1$ is a pyridyl group; V is CH; n is 0; m is 1; $R_3$ is —$CH_3$; $R_1$ is —F; $Ar^2$ is

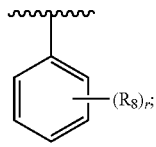

r is 1 and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 4-position of the phenyl ring.

In another embodiment, $Ar^1$ is a pyridyl group; V is CH; n is 0; m is 1; $R_3$ is —$CH_3$; $R_1$ is —Cl; $Ar^2$ is

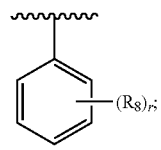

r is 1 and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 4-position of the phenyl ring.

In another embodiment, $Ar^1$ is a pyridyl group; V is CH; n is 0; m is 1; $R_3$ is —$CH_3$; $R_1$ is —Br; $Ar^2$ is

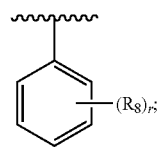

r is 1 and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 4-position of the phenyl ring.

In another embodiment, $Ar^1$ is a pyridyl group; V is CH; n is 0; m is 1; $R_3$ is —$CH_3$; $R_1$ is —I; $Ar^2$ is

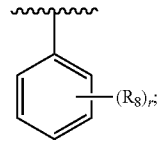

r is 1 and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 4-position of the phenyl ring.

In another embodiment, $Ar^1$ is a pyridyl group; V is CH; n is 0; m is 1; $R_3$ is —$CH_3$; $R_1$ is —$CH_3$; $Ar^2$ is

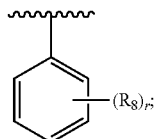

r is 1 and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 4-position of the phenyl ring.

In another embodiment, $Ar^1$ is a pyridyl group; V is CH; n is 0; m is 1; $R_3$ is —$CH_3$; $R_1$ is —$CF_3$; $Ar^2$ is

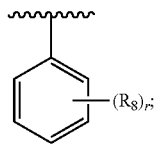

r is 1 and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 4-position of the phenyl ring.

In another embodiment, $Ar^1$ is a pyridyl group; V is CH; n is 0; m is 1; $R_3$ is —$CH_3$; $R_1$ is —Cl, —F, —Br, or —I, $Ar^2$ is

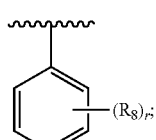

r is 1; and $R_8$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 4-position of the phenyl ring.

In another embodiment, $Ar^1$ is a pyridyl group; V is CH; n is 0; m is 1; $R_3$ is —$CH_3$; $R_1$ is —F; $Ar^2$ is

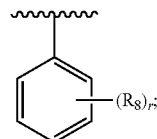

r is 1 and $R_8$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 4-position of the phenyl ring.

In another embodiment, $Ar^1$ is a pyridyl group; V is CH; n is 0; m is 1; $R_3$ is —$CH_3$; $R_1$ is —Cl; $Ar^2$ is

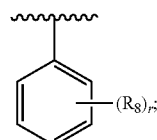

r is 1 and $R_8$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 4-position of the phenyl ring.

In another embodiment, $Ar^1$ is a pyridyl group; V is CH; n is 0; m is 1; $R_3$ is —$CH_3$; $R_1$ is —Br; $Ar^2$ is

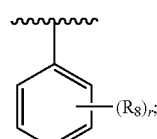

r is 1 and $R_8$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 4-position of the phenyl ring.

In another embodiment, Ar$^1$ is a pyridyl group; V is CH; n is 0; m is 1; R$_3$ is —CH$_3$; R$_1$ is —I; Ar$^2$ is

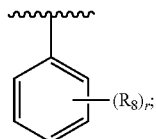

r is 1 and R$_8$ is —I. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 4-position of the phenyl ring.

In another embodiment, Ar$^1$ is a pyridyl group; V is CH; n is 0; m is 1; R$_3$ is —CH$_3$; R$_1$ is —CH$_3$; Ar$^2$ is

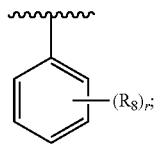

r is 1 and R$_8$ is —I. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 4-position of the phenyl ring.

In another embodiment, Ar$^1$ is a pyridyl group; V is CH; n is 0; m is 1; R$_3$ is —CH$_3$; R$_1$ is —CF$_3$; Ar$^2$ is

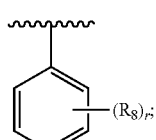

r is 1 and R$_8$ is —I. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 4-position of the phenyl ring.

In another embodiment, Ar$^1$ is a pyridyl group; V is CH; n is 0; m is 1; R$_3$ is —CH$_3$; R$_1$ is —F, —Cl, —Br, or —I; Ar$^2$ is

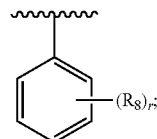

r is 1 and R$_8$ is —CH$_3$. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 4-position of the phenyl ring.

In another embodiment, Ar$^1$ is a pyridyl group; V is CH; n is 0; m is 1; R$_3$ is —CH$_3$; R$_1$ is —F; Ar$^2$ is

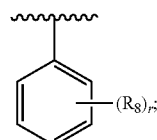

r is 1 and R$_8$ is —CH$_3$. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 4-position of the phenyl ring.

In another embodiment, Ar$^1$ is a pyridyl group; V is CH; n is 0; m is 1; R$_3$ is —CH$_3$; R$_1$ is —Cl; Ar$^2$ is

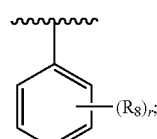

r is 1 and R$_8$ is —CH$_3$. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 4-position of the phenyl ring.

In another embodiment, $Ar^1$ is a pyridyl group; V is CH; n is 0; m is 1; $R_3$ is —$CH_3$; $R_1$ is —Br; $Ar^2$ is

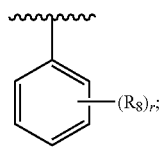

r is 1 and $R_8$ is —$CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 4-position of the phenyl ring.

In another embodiment, $Ar^1$ is a pyridyl group; V is CH; n is 0; m is 1; $R_3$ is —$CH_3$; $R_1$ is —I; $Ar^2$ is

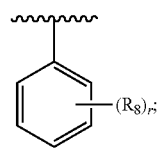

r is 1 and $R_8$ is —$CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 4-position of the phenyl ring.

In another embodiment, $Ar^1$ is a pyridyl group; V is CH; n is 0; m is 1; $R_3$ is —$CH_3$; $R_1$ is —$CH_3$; $Ar^2$ is

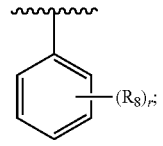

r is 1 and $R_8$ is —$CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 4-position of the phenyl ring.

In another embodiment, $Ar^1$ is a pyridyl group; V is CH; n is 0; m is 1; $R_3$ is —$CH_3$; $R_1$ is —$CF_3$; $Ar^2$ is

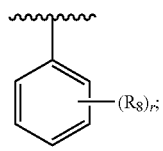

r is 1 and $R_8$ is —$CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 4-position of the phenyl ring.

In another embodiment, $Ar^1$ is a pyridyl group; V is CH; n is 0; m is 1; $R_3$ is —$CH_3$; $R_1$ is —F, —Cl, —Br, or —I; $Ar^2$ is

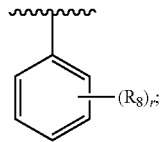

r is 1 and $R_8$ is —$CF_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 4-position of the phenyl ring.

In another embodiment, $Ar^1$ is a pyridyl group; V is CH; n is 0; m is 1; $R_3$ is —$CH_3$; $R_1$ is —F; $Ar^2$ is

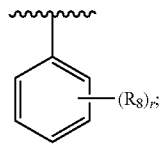

r is 1 and $R_8$ is —$CF_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 4-position of the phenyl ring.

In another embodiment, Ar$^1$ is a pyridyl group; V is CH; n is 0; m is 1; R$_3$ is —CH$_3$; R$_1$ is —Cl; Ar$^2$ is

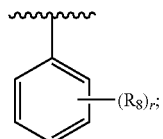

r is 1 and R$_8$ is —CF$_3$. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 4-position of the phenyl ring.

In another embodiment, Ar$^1$ is a pyridyl group; V is CH; n is 0; m is 1; R$_3$ is —CH$_3$; R$_1$ is —Br; Ar$^2$ is

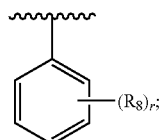

r is 1 and R$_8$ is —CF$_3$. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 4-position of the phenyl ring.

In another embodiment, Ar$^1$ is a pyridyl group; V is CH; n is 0; m is 1; R$_3$ is —CH$_3$; R$_1$ is —I; Ar$^2$ is

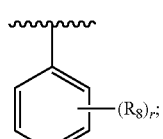

r is 1 and R$_8$ is —CF$_3$. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 4-position of the phenyl ring.

In another embodiment, Ar$^1$ is a pyridyl group; V is CH; n is 0; m is 1; R$_3$ is —CH$_3$; R$_1$ is —CH$_3$; Ar$^2$ is

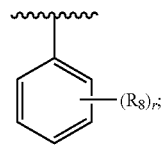

r is 1 and R$_8$ is —CF$_3$. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 4-position of the phenyl ring.

In another embodiment, Ar$^1$ is a pyridyl group; V is CH; n is 0; m is 1; R$_3$ is —CH$_3$; R$_1$ is —CF$_3$; Ar$^2$ is

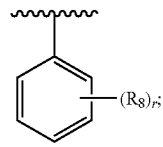

r is 1 and R$_8$ is —CF$_3$. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 4-position of the phenyl ring.

In another embodiment, Ar$^1$ is a pyridyl group; V is CH; n is 0; m is 1; R$_3$ is —CH$_3$; R$_1$ is —F, —Cl, —Br, or —I; Ar$^2$ is

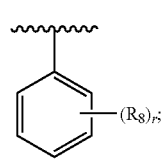

r is 1 and R$_8$ is —OCH$_2$CH$_3$. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 4-position of the phenyl ring.

In another embodiment, $Ar^1$ is a pyridyl group; V is CH; n is 0; m is 1; $R_3$ is —$CH_3$; $R_1$ is —F; $Ar^2$ is

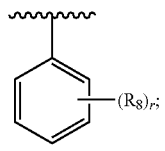

r is 1 and $R_8$ is —$OCH_2CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 4-position of the phenyl ring.

In another embodiment, $Ar^1$ is a pyridyl group; V is CH; n is 0; m is 1; $R_3$ is —$CH_3$; $R_1$ is —Cl; $Ar^2$ is

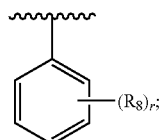

r is 1 and $R_8$ is —$OCH_2CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 4-position of the phenyl ring.

In another embodiment, $Ar^1$ is a pyridyl group; V is CH; n is 0; m is 1; $R_3$ is —$CH_3$; $R_1$ is —Br; $Ar^2$ is

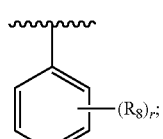

r is 1 and $R_8$ is —$OCH_2CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 4-position of the phenyl ring.

In another embodiment, $Ar^1$ is a pyridyl group; V is CH; n is 0; m is 1; $R_3$ is —$CH_3$; $R_1$ is —I; $Ar^2$ is

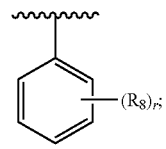

r is 1 and $R_8$ is —$OCH_2CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 4-position of the phenyl ring.

In another embodiment, $Ar^1$ is a pyridyl group; V is CH; n is 0; m is 1; $R_3$ is —$CH_3$; $R_1$ is —$CH_3$; $Ar^2$ is

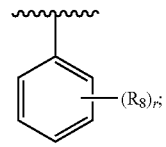

r is 1 and $R_8$ is —$OCH_2CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 4-position of the phenyl ring.

In another embodiment, $Ar^1$ is a pyridyl group; V is CH; n is 0; m is 1; $R_3$ is —$CH_3$; $R_1$ is —$CF_3$; $Ar^2$ is

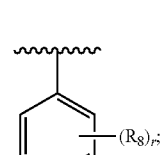

r is 1 and $R_8$ is —$OCH_2CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 4-position of the phenyl ring.

In another embodiment, Ar¹ is a pyridyl group; V is CH; n is 0; m is 1; R₃ is —CH₃; R₁ is —F, —Cl, —Br, or —I; Ar² is

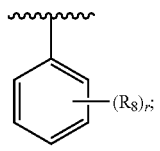

r is 1 and R₈ is -tert-butyl. In another embodiment, the R₃ group is attached to the 3-, 5- or 6-position of the cyclo(hetero)alkenyl ring and the carbon atom to which the R₃ group is attached has the (R) configuration. In another embodiment, the R₃ group is attached to the 3-, 5- or 6-position of the cyclo(hetero)alkenyl ring and the carbon atom to which the R₃ group is attached has the (S) configuration. In yet another embodiment, the R₃ group is attached to the 2-position of the cyclo(hetero)alkenyl ring. In another embodiment, R₈ is at the 4-position of the phenyl ring.

In another embodiment, Ar¹ is a pyridyl group; V is CH; n is 0; m is 1; R₃ is —CH₃; R₁ is —F Ar² is

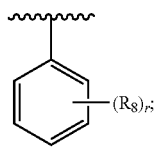

r is 1 and R₈ is -tert-butyl. In another embodiment, the R₃ group is attached to the 3-, 5- or 6-position of the cyclo(hetero)alkenyl ring and the carbon atom to which the R₃ group is attached has the (R) configuration. In another embodiment, the R₃ group is attached to the 3-, 5- or 6-position of the cyclo(hetero)alkenyl ring and the carbon atom to which the R₃ group is attached has the (S) configuration. In yet another embodiment, the R₃ group is attached to the 2-position of the cyclo(hetero)alkenyl ring. In another embodiment, R₈ is at the 4-position of the phenyl ring.

In another embodiment, Ar¹ is a pyridyl group; V is CH; n is 0; m is 1; R₃ is —CH₃; R₁ is —Cl; Ar² is

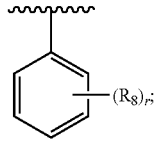

r is 1 and R₈ is -tert-butyl. In another embodiment, the R₃ group is attached to the 3-, 5- or 6-position of the cyclo(hetero)alkenyl ring and the carbon atom to which the R₃ group is attached has the (R) configuration. In another embodiment, the R₃ group is attached to the 3-, 5- or 6-position of the cyclo(hetero)alkenyl ring and the carbon atom to which the R₃ group is attached has the (S) configuration. In yet another embodiment, the R₃ group is attached to the 2-position of the cyclo(hetero)alkenyl ring. In another embodiment, R₈ is at the 4-position of the phenyl ring.

In another embodiment, Ar¹ is a pyridyl group; V is CH; n is 0; m is 1; R₃ is —CH₃; R₁ is —Br; Ar² is

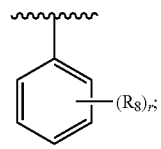

r is 1 and R₈ is -tert-butyl. In another embodiment, the R₃ group is attached to the 3-, 5- or 6-position of the cyclo(hetero)alkenyl ring and the carbon atom to which the R₃ group is attached has the (R) configuration. In another embodiment, the R₃ group is attached to the 3-, 5- or 6-position of the cyclo(hetero)alkenyl ring and the carbon atom to which the R₃ group is attached has the (S) configuration. In yet another embodiment, the R₃ group is attached to the 2-position of the cyclo(hetero)alkenyl ring. In another embodiment, R₈ is at the 4-position of the phenyl ring.

In another embodiment, Ar¹ is a pyridyl group; V is CH; n is 0; m is 1; R₃ is —CH₃; R₁ is —I; Ar² is

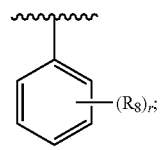

r is 1 and R₈ is -tert-butyl. In another embodiment, the R₃ group is attached to the 3-, 5- or 6-position of the cyclo(hetero)alkenyl ring and the carbon atom to which the R₃ group is attached has the (R) configuration. In another embodiment, the R₃ group is attached to the 3-, 5- or 6-position of the cyclo(hetero)alkenyl ring and the carbon atom to which the R₃ group is attached has the (S) configuration. In yet another embodiment, the R₃ group is attached to the 2-position of the cyclo(hetero)alkenyl ring. In another embodiment, R₈ is at the 4-position of the phenyl ring.

In another embodiment, Ar¹ is a pyridyl group; V is CH; n is 0; m is 1; R₃ is —CH₃; R₁ is —CH₃; Ar² is

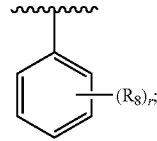

r is 1 and R₈ is -tert-butyl. In another embodiment, the R₃ group is attached to the 3-, 5- or 6-position of the cyclo(hetero)alkenyl ring and the carbon atom to which the R₃ group is attached has the (R) configuration. In another embodiment, the R₃ group is attached to the 3-, 5- or 6-position of the cyclo(hetero)alkenyl ring and the carbon atom to which the R₃ group is attached has the (S) configuration. In yet another embodiment, the R₃ group is attached to the 2-position of the cyclo(hetero)alkenyl ring. In another embodiment, R₈ is at the 4-position of the phenyl ring.

In another embodiment, Ar$^1$ is a pyridyl group; V is CH; n is 0; m is 1; R$_3$ is —CH$_3$; R$_1$ is —CF$_3$; Ar$^2$ is

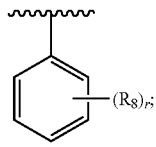

r is 1 and R$_8$ is -tert-butyl. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 4-position of the phenyl ring.

In another embodiment, V is N, Ar$^1$ is a pyridyl group, m is 0, and Ar$^2$ is

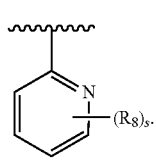

In another embodiment, Ar$^1$ is a pyridyl group; V is N; n is 0; m is 0; R$_1$ is —F, —Cl, —Br, or —I; Ar$^2$ is

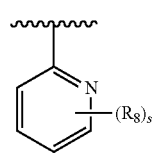

and s is 0.

In another embodiment, Ar$^1$ is a pyridyl group; V is N; n is 0; m is 0; R$_1$ is —F; Ar$^2$ is

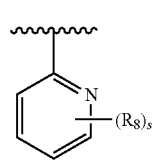

and s is 0.

In another embodiment, Ar$^1$ is a pyridyl group; V is N; n is 0; m is 0; R$_1$ is —Cl; Ar$^2$ is

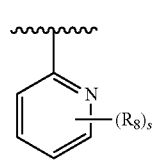

and s is 0.

In another embodiment, Ar$^1$ is a pyridyl group; V is N; n is 0; m is 0; R$_1$ is —Br; Ar$^2$ is

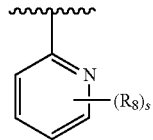

and s is 0.

In another embodiment, Ar$^1$ is a pyridyl group; V is N; n is 0; m is 0; R$_1$ is —I; Ar$^2$ is

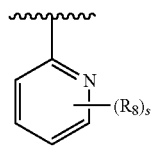

and s is 0.

In another embodiment, Ar$^1$ is a pyridyl group; V is N; n is 0; m is 0; R$_1$ is —CH$_3$; Ar$^2$ is

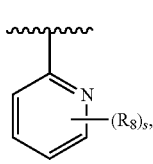

and s is 0.

In another embodiment, Ar$^1$ is a pyridyl group; V is N; n is 0; m is 0; R$_1$ is —CF$_3$; Ar$^2$ is

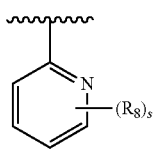

and s is 0.

In another embodiment, Ar$^1$ is a pyridyl group; V is N; n is 0; m is 0; R$_1$ is —F, —Cl —Br, or —I; Ar$^2$ is

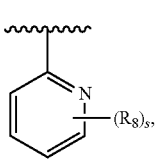

s is 1 and R$_8$ is -halo. In another embodiment, R$_8$ is at the 5-position of the Ar$^2$ pyridyl ring.

In another embodiment, $Ar^1$ is a pyridyl group; V is N; n is 0; m is 0; $R_1$ is —F; $Ar^2$ is

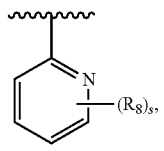

s is 1 and $R_8$ is -halo.

In another embodiment, $Ar^1$ is a pyridyl group; V is N; n is 0; m is 0; $R_1$ is —Cl; $Ar^2$ is

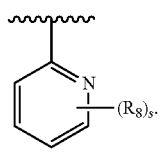

s is 1 and $R_8$ is -halo. In another embodiment, $R_8$ is at the 5-position of the $Ar^2$ pyridyl ring.

In another embodiment, $Ar^1$ is a pyridyl group; V is N; n is 0; m is 0; $R_1$ is —Br; $Ar^2$ is

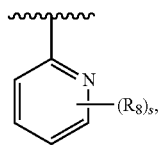

s is 1 and $R_8$ is -halo. In another embodiment, $R_8$ is at the 5-position of the $Ar^2$ pyridyl ring.

In another embodiment, $Ar^1$ is a pyridyl group; V is N; n is 0; m is 0; $R_1$ is —I; $Ar^2$ is

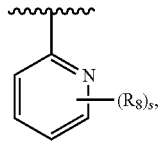

s is 1 and $R_8$ is -halo. In another embodiment, $R_8$ is at the 5-position of the $Ar^2$ pyridyl ring.

In another embodiment, $Ar^1$ is a pyridyl group; V is N; n is 0; m is 0; $R_1$ is —CH$_3$; $Ar^2$ is

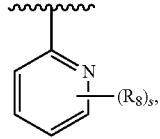

s is 1 and $R_8$ is -halo. In another embodiment, $R_8$ is at the 5-position of the $Ar^2$ pyridyl ring.

In another embodiment, $Ar^1$ is a pyridyl group; V is N; n is 0; m is 0; $R_1$ is —CF$_3$; $Ar^2$ is

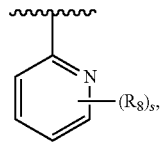

s is 1 and $R_8$ is -halo. In another embodiment, $R_8$ is at the 5-position of the $Ar^2$ pyridyl ring.

In another embodiment, $Ar^1$ is a pyridyl group; V is N; n is 0; m is 0; $R_1$ is —F, —Cl, —Br, or —I; $Ar^2$ is

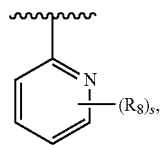

s is 1 and $R_8$ is —Br. In another embodiment, $R_8$ is at the 5-position of the $Ar^2$ pyridyl ring.

In another embodiment, $Ar^1$ is a pyridyl group; V is N; n is 0; m is 0; $R_1$ is —F; $Ar^2$ is

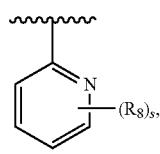

s is 1 and $R_8$ is —Br. In another embodiment, $R_8$ is at the 5-position of the $Ar^2$ pyridyl ring.

In another embodiment, $Ar^1$ is a pyridyl group; V is N; n is 0; m is 0, $R_1$ is —Cl; $Ar^2$ is

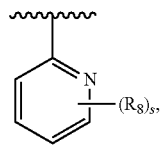

s is 1 and $R_8$ is —Br. In another embodiment, $R_8$ is at the 5-position of the $Ar^2$ pyridyl ring.

In another embodiment, $Ar^1$ is a pyridyl group; V is N; n is 0; m is 0; $R_1$ is —Br; $Ar^2$ is

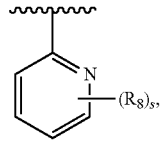

s is 1 and $R_8$ is —Br. In another embodiment, $R_8$ is at the 5-position of the $Ar^2$ pyridyl ring.

In another embodiment, Ar$^1$ is a pyridyl group; V is N; n is 0; m is 0; R$_1$ is —I; Ar$^2$ is

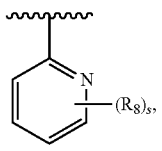

s is 1 and R$_8$ is —Br. In another embodiment, R$_8$ is at the 5-position of the Ar$^2$ pyridyl ring.

In another embodiment, Ar$^1$ is a pyridyl group; V is N; n is 0; m is 0; R$_1$ is —CH$_3$; Ar$^2$ is

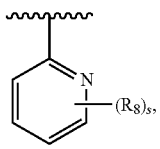

s is 1 and R$_8$ is —Br. In another embodiment, R$_8$ is at the 5-position of the Ar$^2$ pyridyl ring.

In another embodiment, Ar$^1$ is a pyridyl group; V is N; n is 0; m is 0; R$_1$ is —CF$_3$; Ar$^2$ is

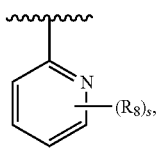

s is 1 and R$_8$ is —Br. In another embodiment, R$_8$ is at the 5-position of the Ar$^2$ pyridyl ring.

In another embodiment, Ar$^1$ is a pyridyl group; V is N; n is 0; m is 0; R$_1$ is —Cl, —F —Br, or —I; Ar$^2$ is

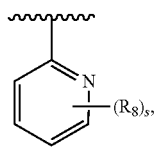

s is 1 and R$_8$ is —F. In another embodiment, R$_8$ is at the 5-position of the Ar$^2$ pyridyl ring.

In another embodiment, Ar$^1$ is a pyridyl group; V is N; n is 0; m is 0; R$_1$ is —F; Ar$^2$ is

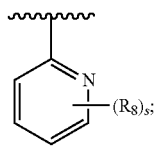

s is 1 and R$_8$ is —F. In another embodiment, R$_8$ is at the 5-position of the Ar$^2$ pyridyl ring In another embodiment, Ar$^1$ is a pyridyl group; V is N; n is 0; m is 0; R$_1$ is —Cl; Ar$^2$ is

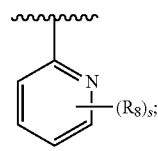

s is 1 and R$_8$ is —F. In another embodiment, R$_8$ is at the 5-position of the Ar$^2$ pyridyl ring.

In another embodiment, Ar$^1$ is a pyridyl group; V is N; n is 0; m is 0; R$_1$ is —Br; Ar$^2$ is

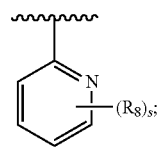

s is 1 and R$_8$ is —F. In another embodiment, R$_8$ is at the 5-position of the Ar$^2$ pyridyl ring.

In another embodiment, Ar$^1$ is a pyridyl group; V is N; n is 0; m is 0; R$_1$ is —I; Ar$^2$ is

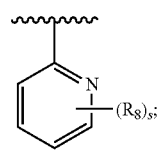

s is 1 and R$_8$ is —F. In another embodiment, R$_8$ is at the 5-position of the Ar$^2$ pyridyl ring.

In another embodiment, Ar$^1$ is a pyridyl group; V is N; n is 0; m is 0; R$_1$ is —CH$_3$; Ar$^2$ is

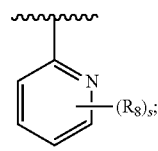

s is 1 and R$_8$ is —F. In another embodiment, R$_8$ is at the 5-position of the Ar$^2$ pyridyl ring.

In another embodiment, Ar$^1$ is a pyridyl group; V is N; n is 0; m is 0; R$_1$ is —CF$_3$; Ar$^2$ is

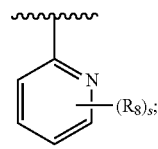

s is 1 and R$_8$ is —F. In another embodiment, R$_8$ is at the 5-position of the Ar$^2$ pyridyl ring.

In another embodiment, Ar$^1$ is a pyridyl group; V is N; n is 0; m is 0; R$_1$ is —Cl, —F —Br, or —I; Ar$^2$ is

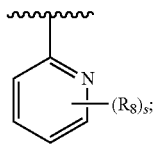

s is 1 and R$_8$ is —Cl. In another embodiment, R$_8$ is at the 5-position of the Ar$^2$ pyridyl ring.

In another embodiment, Ar$^1$ is a pyridyl group; V is N; n is 0; m is 0; R$_1$ is —F; Ar$^2$ is

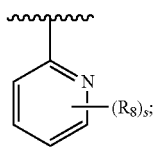

s is 1 and R$_8$ is —Cl. In another embodiment, R$_8$ is at the 5-position of the Ar$^2$ pyridyl ring.

In another embodiment, Ar$^1$ is a pyridyl group; V is N; n is 0; m is 0; R$_1$ is —Cl; Ar$^2$ is

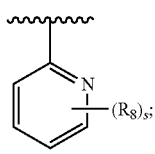

s is 1 and R$_8$ is —Cl. In another embodiment, R$_8$ is at the 5-position of the Ar$^2$ pyridyl ring.

In another embodiment, Ar$^1$ is a pyridyl group; V is N; n is 0; m is 0; R$_1$ is —Br; Ar$^2$ is

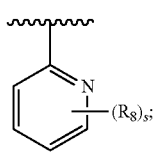

s is 1 and R$_8$ is —Cl. In another embodiment, R$_8$ is at the 5-position of the Ar$^2$ pyridyl ring.

In another embodiment, Ar$^1$ is a pyridyl group; V is N; n is 0; m is 0; R$_1$ is —I; Ar$^2$ is

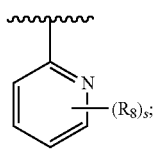

s is 1 and R$_8$ is —Cl. In another embodiment, R$_8$ is at the 5-position of the Ar$^2$ pyridyl ring.

In another embodiment, Ar$^1$ is a pyridyl group; V is N; n is 0; m is 0; R$_1$ is —CH$_3$; Ar$^2$ is

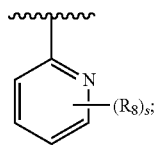

s is 1 and R$_8$ is —Cl. In another embodiment, R$_8$ is at the 5-position of the Ar$^2$ pyridyl ring.

In another embodiment, Ar$^1$ is a pyridyl group; V is N; n is 0; m is 0; R$_1$ is —CF$_3$; Ar$^2$ is

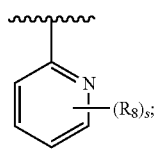

s is 1 and R$_8$ is chloro. In another embodiment, R$_8$ is at the 5-position of the Ar$^2$ pyridyl ring.

In another embodiment, Ar$^1$ is a pyridyl group; V is N; n is 0; m is 0; R$_1$ is —Cl, —F, —Br, or —I, Ar$^2$ is

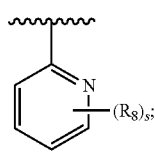

s is 1 and R$_8$ is —I. In another embodiment, R$_8$ is at the 5-position of the Ar$^2$ pyridyl ring.

In another embodiment, Ar$^1$ is a pyridyl group; V is N; n is 0; m is 0; R$_1$ is —F; Ar$^2$ is

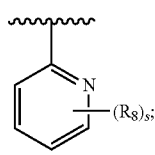

s is 1 and R$_8$ is —I. In another embodiment, R$_8$ is at the 5-position of the Ar$^2$ pyridyl ring.

In another embodiment, Ar$^1$ is a pyridyl group; V is N; n is 0; m is 0; R$_1$ is —Cl; Ar$^2$ is

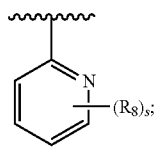

s is 1 and R$_8$ is —I. In another embodiment, R$_8$ is at the 5-position of the Ar$^2$ pyridyl ring.

In another embodiment, $Ar^1$ is a pyridyl group; V is N; n is 0; m is 0; $R_1$ is —Br; $Ar^2$ is

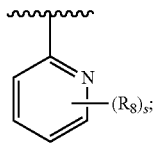

s is 1 and $R_8$ is —I. In another embodiment, $R_8$ is at the 5-position of the $Ar^2$ pyridyl ring.

In another embodiment, $Ar^1$ is a pyridyl group; V is N; n is 0; m is 0; $R_1$ is —I; $Ar^2$ is

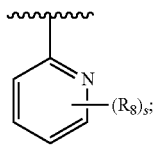

s is 1 and $R_8$ is —I. In another embodiment, $R_8$ is at the 5-position of the $Ar^2$ pyridyl ring.

In another embodiment, $Ar^1$ is a pyridyl group; V is N; n is 0; m is 0; $R_1$ is —$CH_3$; $Ar^2$ is

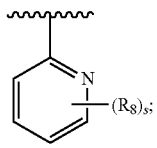

s is 1 and $R_8$ is —I. In another embodiment, $R_8$ is at the 5-position of the $Ar^2$ pyridyl ring.

In another embodiment, $Ar^1$ is a pyridyl group; V is N; n is 0; m is 0; $R_1$ is —$CF_3$; $Ar^2$ is

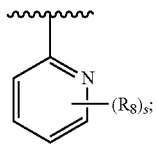

s is 1 and $R_8$ is —I. In another embodiment, $R_8$ is at the 5-position of the $Ar^2$ pyridyl ring.

In another embodiment, $Ar^1$ is a pyridyl group; V is N; n is 0; m is 0; $R_1$ is —F, —Cl, —Br, or —I; $Ar^2$ is

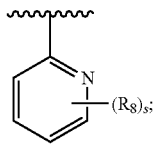

s is 1 and $R_8$ is —$CH_3$. In another embodiment, $R_8$ is at the 5-position of the $Ar^2$ pyridyl ring.

In another embodiment, $Ar^1$ is a pyridyl group; V is N; n is 0; m is 0; $R_1$ is —F; $Ar^2$ is

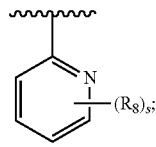

s is 1 and $R_8$ is —$CH_3$. In another embodiment, $R_8$ is at the 5-position of the $Ar^2$ pyridyl ring.

In another embodiment, $Ar^1$ is a pyridyl group; V is N; n is 0; m is 0; $R_1$ is —Cl; $Ar^2$ is

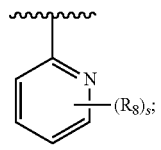

s is 1 and $R_8$ is —$CH_3$. In another embodiment, $R_8$ is at the 5-position of the $Ar^2$ pyridyl ring.

In another embodiment, $Ar^1$ is a pyridyl group; V is N; n is 0; m is 0; $R_1$ is —Br; $Ar^2$ is

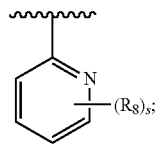

s is 1 and $R_8$ is —$CH_3$. In another embodiment, $R_8$ is at the 5-position of the $Ar^2$ pyridyl ring.

In another embodiment, $Ar^1$ is a pyridyl group; V is N; n is 0; m is 0; $R_1$ is —I; $Ar^2$ is

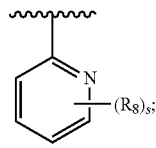

s is 1 and $R_8$ is —$CH_3$. In another embodiment, $R_8$ is at the 5-position of the $Ar^2$ pyridyl ring.

In another embodiment, $Ar^1$ is a pyridyl group; V is N; n is 0; m is 0; $R_1$ is —$CH_3$; $Ar^2$ is

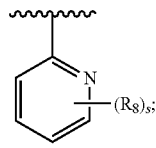

s is 1 and $R_8$ is —$CH_3$. In another embodiment, $R_8$ is at the 5-position of the $Ar^2$ pyridyl ring.

In another embodiment, $Ar^1$ is a pyridyl group; V is N; n is 0; m is 0; $R_1$ is —$CF_3$; $Ar^2$ is

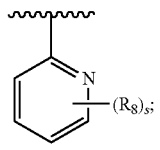

s is 1 and $R_8$ is —$CH_3$. In another embodiment, $R_8$ is at the 5-position of the $Ar^2$ pyridyl ring.

In another embodiment, $Ar^1$ is a pyridyl group; V is N; n is 0; m is 0; $R_1$ is —F, —Cl —Br, or —I; $Ar^2$ is

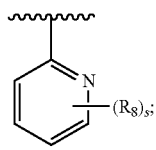

s is 1 and $R_8$ is —$CF_3$. In another embodiment, $R_8$ is at the 5-position of the $Ar^2$ pyridyl ring.

In another embodiment, $Ar^1$ is a pyridyl group; V is N; n is 0; m is 0; $R_1$ is —F; $Ar^2$ is

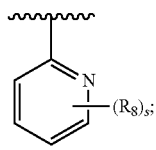

s is 1 and $R_8$ is —$CF_3$. In another embodiment, $R_8$ is at the 5-position of the $Ar^2$ pyridyl ring.

In another embodiment, $Ar^1$ is a pyridyl group; V is N; n is 0; m is 0; $R_1$ is —Cl; $Ar^2$ is

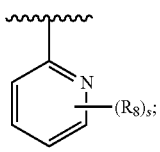

s is 1 and $R_8$ is —$CF_3$. In another embodiment, $R_8$ is at the 5-position of the $Ar^2$ pyridyl ring.

In another embodiment, $Ar^1$ is a pyridyl group; V is N; n is 0; m is 0; $R_1$ is —Br; $Ar^2$ is

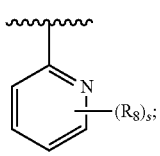

s is 1 and $R_8$ is —$CF_3$. In another embodiment, $R_8$ is at the 5-position of the $Ar^2$ pyridyl ring.

In another embodiment, $Ar^1$ is a pyridyl group; V is N; n is 0; m is 0; $R_1$ is —I; $Ar^2$ is

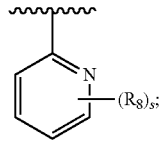

s is 1 and $R_8$ is —$CF_3$. In another embodiment, $R_8$ is at the 5-position of the $Ar^2$ pyridyl ring.

In another embodiment, $Ar^1$ is a pyridyl group; V is N; n is 0; m is 0; $R_1$ is —$CH_3$; $Ar^2$ is

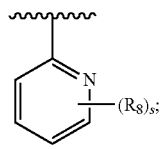

s is 1 and $R_8$ is —$CF_3$. In another embodiment, $R_8$ is at the 5-position of the $Ar^2$ pyridyl ring.

In another embodiment, $Ar^1$ is a pyridyl group; V is N; n is 0; m is 0; $R_1$ is —$CF_3$; $Ar^2$ is

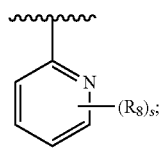

s is 1 and $R_8$ is —$CF_3$. In another embodiment, $R_8$ is at the 5-position of the $Ar^2$ pyridyl ring.

In another embodiment, $Ar^1$ is a pyridyl group; V is N; n is 0; m is 0; $R_1$ is —F, —Cl —Br, or —I; $Ar^2$ is

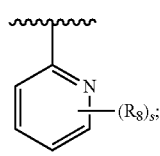

s is 1 and $R_8$ is —$CH_2CF_3$. In another embodiment, $R_8$ is at the 5-position of the $Ar^2$ pyridyl ring.

In another embodiment, $Ar^1$ is a pyridyl group; V is N; n is 0; m is 0; $R_1$ is —F; $Ar^2$ is

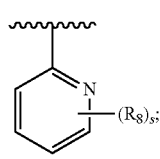

s is 1 and $R_8$ is —$CH_2CF_3$. In another embodiment, $R_8$ is at the 5-position of the $Ar^2$ pyridyl ring.

In another embodiment, $Ar^1$ is a pyridyl group; V is N; n is 0; m is 0; $R_1$ is —Cl; $Ar^2$ is

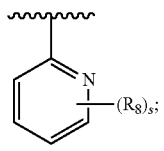

s is 1 and $R_8$ is —CH$_2$CF$_3$. In another embodiment, $R_8$ is at the 5-position of the $Ar^2$ pyridyl ring.

In another embodiment, $Ar^1$ is a pyridyl group; V is N; n is 0; m is 0; $R_1$ is —Br; $Ar^2$ is

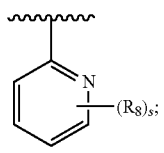

s is 1 and $R_8$ is —CH$_2$CF$_3$. In another embodiment, $R_8$ is at the 5-position of the $Ar^2$ pyridyl ring.

In another embodiment, $Ar^1$ is a pyridyl group; V is N; n is 0; m is 0; $R_1$ is —I; $Ar^2$ is

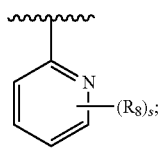

s is 1 and $R_8$ is —CH$_2$CF$_3$. In another embodiment, $R_8$ is at the 5-position of the $Ar^2$ pyridyl ring.

In another embodiment, $Ar^1$ is a pyridyl group; V is N; n is 0; m is 0; $R_1$ is —CH$_3$; $Ar^2$ is

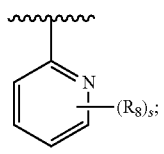

s is 1 and $R_8$ is —CH$_2$CF$_3$. In another embodiment, $R_8$ is at the 5-position of the $Ar^2$ pyridyl ring.

In another embodiment, $Ar^1$ is a pyridyl group; V is N; n is 0; m is 0; $R_1$ is —CF$_3$; $Ar^2$ is

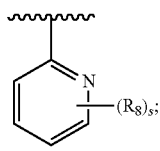

s is 1 and $R_8$ is —CH$_2$CF$_3$. In another embodiment, $R_8$ is at the 5-position of the $Ar^2$ pyridyl ring.

In another embodiment, $Ar^1$ is a pyridyl group; V is N; n is 0; m is 0; $R_1$ is —F, —Cl —Br, or —I; $Ar^2$ is

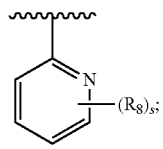

s is 1 and $R_8$ is -tert-butyl. In another embodiment, $R_8$ is at the 5-position of the $Ar^2$ pyridyl ring.

In another embodiment, $Ar^1$ is a pyridyl group; V is N; n is 0; m is 0; $R_1$ is —F; $Ar^2$ is

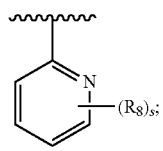

s is 1 and $R_8$ is -tert-butyl. In another embodiment, $R_8$ is at the 5-position of the $Ar^2$ pyridyl ring.

In another embodiment, $Ar^1$ is a pyridyl group; V is N; n is 0; m is 0; $R_1$ is —Cl; $Ar^2$ is

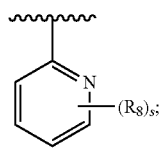

s is 1 and $R_8$ is -tert-butyl. In another embodiment, $R_8$ is at the 5-position of the $Ar^2$ pyridyl ring.

In another embodiment, $Ar^1$ is a pyridyl group; V is N; n is 0; m is 0; $R_1$ is —Br; $Ar^2$ is

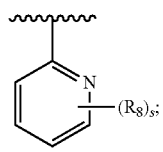

s is 1 and $R_8$ is -tert-butyl. In another embodiment, $R_8$ is at the 5-position of the $Ar^2$ pyridyl ring.

In another embodiment, $Ar^1$ is a pyridyl group; V is N; n is 0; m is 0; $R_1$ is —I; $Ar^2$ is

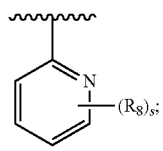

s is 1 and $R_8$ is -tert-butyl. In another embodiment, $R_8$ is at the 5-position of the $Ar^2$ pyridyl ring.

In another embodiment, $Ar^1$ is a pyridyl group; V is N; n is 0; m is 0; $R_1$ is —$CH_3$; $Ar^2$ is

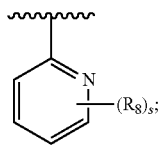

s is 1 and $R_8$ is -tert-butyl. In another embodiment, $R_8$ is at the 5-position of the $Ar^2$ pyridyl ring.

In another embodiment, $Ar^1$ is a pyridyl group; V is N; n is 0; m is 0; $R_1$ is —$CF_3$; $Ar^2$ is

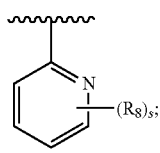

s is 1 and $R_8$ is -tert-butyl. In another embodiment, $R_8$ is at the 5-position of the $Ar^2$ pyridyl ring.

In another embodiment, $Ar^1$ is a pyridyl group; V is N; n is 0; m is 1; $R_3$ is —$CH_3$; $R_1$ is —F, —Cl, —Br, or —I; $Ar^2$ is

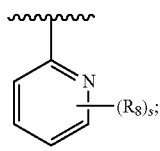

and s is 0. In another embodiment, the $R_3$ group is attached to the 3-, 5- or 6-position of the cyclo(hetero)alkenyl ring and the carbon atom to which the $R_3$ group is attached has the (P) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is N; n is 0; m is 1; $R_3$ is —$CH_3$; $R_1$ is —F; $Ar^2$ is

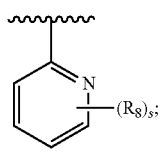

and s is 0. In another embodiment, the $R_3$ group is attached to the 3-, 5- or 6-position of the cyclo(hetero)alkenyl ring and the carbon atom to which the $R_3$ group is attached has the (P) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is N; n is 0; m is 1; $R_3$ is —$CH_3$; $R_1$ is —Cl; $Ar^2$ is

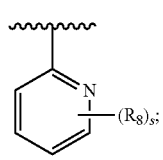

and s is 0. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is N; n is 0; m is 1; $R_3$ is —$CH_3$; $R_1$ is —Br; $Ar^2$ is

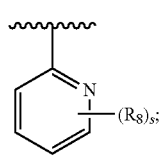

and s is 0. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is N; n is 0; m is 1; $R_3$ is —$CH_3$; $R_1$ is —I; $Ar^2$ is

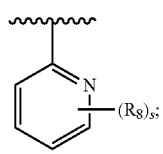

and s is 0. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, Ar$^1$ is a pyridyl group; V is N; n is 0; m is 1; R$_3$ is —CH$_3$; R$_1$ is —CH$_3$; Ar$^2$ is $$\text{[pyridyl structure with (R}_8\text{)}_s\text{];}$$

and s is 0. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 5-position of the Ar$^2$ pyridyl ring.

In another embodiment, Ar$^1$ is a pyridyl group; V is N; n is 0; m is 1; R$_3$ is —CH$_3$; R$_1$ is —CF$_3$; Ar$^2$ is $$\text{[pyridyl structure with (R}_8\text{)}_s\text{];}$$

and s is 0. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 5-position of the Ar$^2$ pyridyl ring.

In another embodiment, Ar$^1$ is a pyridyl group; V is N; n is 0; m is 1; R$_3$ is —CH$_3$; R$_1$ is —F, —Cl, —Br, or —I; Ar$^2$ is $$\text{[pyridyl structure with (R}_8\text{)}_s\text{];}$$

s is 1 and R$_8$ is -halo. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring.

In another embodiment, Ar$^1$ is a pyridyl group; V is N; n is 0; m is 1; R$_3$ is —CH$_3$; R$_1$ is —F; Ar$^2$ is $$\text{[pyridyl structure with (R}_8\text{)}_s\text{];}$$

s is 1 and R$_8$ is -halo. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 5-position of the Ar$^2$ pyridyl ring.

In another embodiment, Ar$^1$ is a pyridyl group; V is N; n is 0; m is 1; R$_3$ is —CH$_3$; R$_1$ is —Cl; Ar$^2$ is $$\text{[pyridyl structure with (R}_8\text{)}_s\text{];}$$

s is 1 and R$_8$ is -halo. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 5-position of the Ar$^2$ pyridyl ring.

In another embodiment, Ar$^1$ is a pyridyl group; V is N; n is 0; m is 1; R$_3$ is —CH$_3$; R$_1$ is —Br; Ar$^2$ is $$\text{[pyridyl structure with (R}_8\text{)}_s\text{];}$$

s is 1 and R$_8$ is -halo. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 5-position of the Ar$^2$ pyridyl ring.

In another embodiment, Ar$^1$ is a pyridyl group; V is N; n is 0; m is 1; R$_3$ is —CH$_3$; R$_1$ is —I; Ar$^2$ is

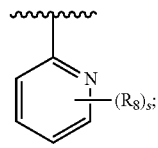

s is 1 and R$_8$ is -halo. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 5-position of the Ar$^2$ pyridyl ring.

In another embodiment, Ar$^1$ is a pyridyl group; V is N; n is 0; m is 1; R$_3$ is —CH$_3$; R$_1$ is —CH$_3$; Ar$^2$ is

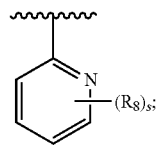

s is 1 and R$_8$ is -halo. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 5-position of the Ar$^2$ pyridyl ring.

In another embodiment, Ar$^1$ is a pyridyl group; V is N; n is 0; m is 1; R$_3$ is —CH$_3$; R$_1$ is —CF$_3$; Ar$^2$ is

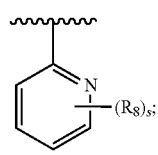

s is 1 and R$_8$ is -halo. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 5-position of the Ar$^2$ pyridyl ring.

In another embodiment, Ar$^1$ is a pyridyl group; V is N; n is 0; m is 1; R$_3$ is —CH$_3$; R$_1$ is —F, —Cl, —Br, or —I; Ar$^2$ is

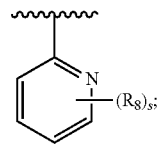

s is 1 and R$_8$ is —Br. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 5-position of the Ar$^2$ pyridyl ring.

In another embodiment, Ar$^1$ is a pyridyl group; V is N; n is 0; m is 1; R$_3$ is —CH$_3$; R$_1$ is —F; Ar$^2$ is

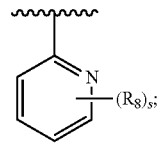

s is 1 and R$_8$ is —Br. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 5-position of the Ar$^2$ pyridyl ring.

In another embodiment, Ar$^1$ is a pyridyl group; V is N; n is 0; m is 1; R$_3$ is —CH$_3$; R$_1$ is —Cl; Ar$^2$ is

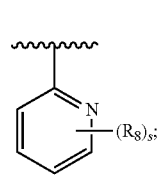

s is 1 and R$_8$ is —Br. In another embodiment, the R$_3$ group is attached to the 3-, 5- or 6-position of the cyclo(hetero)alkenyl ring and the carbon atom to which the R$_3$ group is attached has the (R) configuration. In another embodiment the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 5-position of the Ar$^2$ pyridyl ring.

In another embodiment, Ar$^1$ is a pyridyl group; V is N; n is 0; m is 1; R$_3$ is —CH$_3$; R$_1$ is —Br; Ar$^2$ is

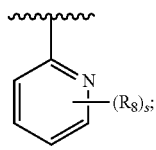

s is 1 and R$_8$ is —Br. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 5-position of the Ar$^2$ pyridyl ring.

In another embodiment, Ar$^1$ is a pyridyl group; V is N; n is 0; m is 1; R$_3$ is —CH$_3$; R$_1$ is —I; Ar$^2$ is

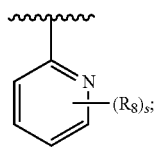

s is 1 and R$_8$ is —Br. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 5-position of the Ar$^2$ pyridyl ring.

In another embodiment, Ar$^1$ is a pyridyl group; V is N; n is 0; m is 1; R$_3$ is —CH$_3$; R$_1$ is —CH$_3$; Ar$^2$ is

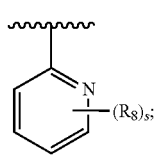

s is 1 and R$_8$ is —Br. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 5-position of the Ar$^2$ pyridyl ring.

In another embodiment, Ar$^1$ is a pyridyl group; V is N; n is 0; m is 1; R$_3$ is —CH$_3$; R$_1$ is —CF$_3$; Ar$^2$ is

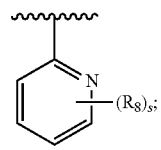

s is 1 and R$_8$ is —Br. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 5-position of the Ar$^2$ pyridyl ring.

In another embodiment, Ar$^1$ is a pyridyl group; V is N; n is 0; m is 1; R$_3$ is —CH$_3$; R$_1$ is —Cl, —F —Br, or —I; Ar$^2$ is

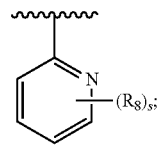

s is 1 and R$_8$ is —F. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 5-position of the Ar$^2$ pyridyl ring.

In another embodiment, Ar$^1$ is a pyridyl group; V is N; n is 0; m is 1; R$_3$ is —CH$_3$; R$_1$ is —F; Ar$^2$ is

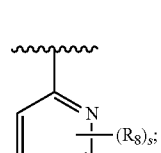

s is 1 and R$_8$ is —F. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 5-position of the Ar$^2$ pyridyl ring.

In another embodiment, $Ar^1$ is a pyridyl group; V is N; n is 0; m is 1; $R_3$ is —$CH_3$; $R_1$ is —Cl; $Ar^2$ is

[chemical structure: pyridine with $(R_8)_s$]

s is 1 and $R_8$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is N; n is 0; m is 1; $R_3$ is —$CH_3$; $R_1$ is —Br; $Ar^2$ is

[chemical structure: pyridine with $(R_8)_s$]

s is 1 and $R_8$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is N; n is 0; m is 1; $R_3$ is —$CH_3$; $R_1$ is —I; $Ar^2$ is

[chemical structure: pyridine with $(R_8)_s$]

s is 1 and $R_8$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is N; n is 0; m is 1; $R_3$ is —$CH_3$, $R_1$ is —$CH_3$, $Ar^2$ is

[chemical structure: pyridine with $(R_8)_s$]

s is 1 and $R_8$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is N; n is 0; m is 1; $R_3$ is —$CH_3$; $R_1$ is —$CF_3$; $Ar^2$ is

[chemical structure: pyridine with $(R_8)_s$]

s is 1 and $R_8$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is N; n is 0; m is 1; $R_3$ is $CH_3$; $R_1$ is —Cl, —F —Br, or —I; $Ar^2$ is

[chemical structure: pyridine with $(R_8)_s$]

s is 1 and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is N; n is 0; m is 1; $R_3$ is —$CH_3$; $R_1$ is —F; $Ar^2$ is

[chemical structure: pyridine with $(R_8)_s$]

s is 1 and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is N; n is 0; m is 1; $R_3$ is —$CH_3$; $R_1$ is —Cl; $Ar^2$ is s is 1 and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is N; n is 0; m is 1; $R_3$ is —$CH_3$; $R_1$ is —Br; $Ar^2$ is s is 1 and $R_8$ is —Cl. In another embodiment, the $R_3$ group is attached to the 3-, 5- or 6-position of the cyclo(hetero)alkenyl ring and the carbon atom to which the $R_3$ group is attached has the ($R_1$) configuration. In another embodiment, the $R_3$ group is attached to the 3-, 5- or 6-position of the cyclo(hetero) alkenyl ring and the carbon atom to which the $R_3$ group is attached has the (S) configuration. In yet another embodiment, the $R_3$ group is attached to the 2-position of the cyclo (hetero)alkenyl ring. In another embodiment, $R_8$ is at the 5-position of the $Ar^2$ pyridyl ring.

In another embodiment, $Ar^1$ is a pyridyl group; V is N; n is 0; m is 1; $R_3$ is —$CH_3$; $R_1$ is —I; $Ar^2$ is s is 1 and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is N; n is 0; m is 1; $R_3$ is —$CH_3$; $R_1$ is —$CH_3$, $Ar^2$ is s is 1 and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is N; n is 0; m is 1; $R_3$ is —$CH_3$; $R_1$ is —$CF_3$; $Ar^2$ is s is 1 and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is N; n is 0; m is 1; $R_3$ is —$CH_3$; $R_1$ is —Cl, —F, —Br, or —I, $Ar^2$ is s is 1; and $R_8$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is N; n is 0; m is 1; $R_3$ is —$CH_3$; $R_1$ is —F; $Ar^2$ is s is 1 and $R_8$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is N; n is 0; m is 1; $R_3$ is —$CH_3$; $R_1$ is —Cl; $Ar^2$ is s is 1 and $R_8$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is N; n is 0; m is 1; $R_3$ is —$CH_3$; $R_1$ is —Br; $Ar^2$ is s is 1 and $R_8$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is N; n is 0; m is 1; $R_3$ is —$CH_3$; $R_1$ is —I; $Ar^2$ is s is 1 and $R_8$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is N; n is 0; m is 1; $R_3$ is —$CH_3$; $R_1$ is —$CH_3$; $Ar^2$ is s is 1 and $R_8$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is N; n is 0; m is 1; $R_3$ is —$CH_3$; $R_1$ is —$CF_3$; $Ar^2$ is s is 1 and $R_8$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, Ar$^1$ is a pyridyl group; V is N; n is 0; m is 1; R$_3$ is —CH$_3$; R$_1$ is —F, —Cl, —Br, or —I; Ar$^2$ is

[Structure: pyridyl ring with (R$_8$)$_s$ substituent]

s is 1 and R$_8$ is —CH$_3$. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 5-position of the Ar$^2$ pyridyl ring.

In another embodiment, Ar$^1$ is a pyridyl group; V is N; n is 0; m is 1; R$_3$ is —CH$_3$; R$_1$ is —F; Ar$^2$ is

[Structure: pyridyl ring with (R$_8$)$_s$ substituent]

s is 1 and R$_8$ is —CH$_3$. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 5-position of the Ar$^2$ pyridyl ring.

In another embodiment, Ar$^1$ is a pyridyl group; V is N; n is 0; m is 1; R$_3$ is —CH$_3$; R$_1$ is —Cl; Ar$^2$ is

[Structure: pyridyl ring with (R$_8$)$_s$ substituent]

s is 1 and R$_8$ is —CH$_3$. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 5-position of the Ar$^2$ pyridyl ring.

In another embodiment, Ar$^1$ is a pyridyl group; V is N; n is 0; m is 1; R$_3$ is —CH$_3$; R$_1$ is —Br; Ar$^2$ is

[Structure: pyridyl ring with (R$_8$)$_s$ substituent]

s is 1 and R$_8$ is —CH$_3$. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 5-position of the Ar$^2$ pyridyl ring.

In another embodiment, Ar$^1$ is a pyridyl group; V is N; n is 0; m is 1; R$_3$ is —CH$_3$; R$_1$ is —I; Ar$^2$ is

[Structure: pyridyl ring with (R$_8$)$_s$ substituent]

s is 1 and R$_8$ is —CH$_3$. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 5-position of the Ar$^2$ pyridyl ring.

In another embodiment, Ar$^1$ is a pyridyl group; V is N; n is 0; m is 1; R$_3$ is —CH$_3$; R$_1$ is —CH$_3$; Ar$^2$ is

[Structure: pyridyl ring with (R$_8$)$_s$ substituent]

s is 1 and R$_8$ is —CH$_3$. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 5-position of the Ar$^2$ pyridyl ring.

In another embodiment, Ar$^1$ is a pyridyl group; V is N; n is 0; m is 1; R$_3$ is —CH$_3$; R$_1$ is —CF$_3$; Ar$^2$ is $$\text{pyridyl ring with }(R_8)_s;$$

s is 1 and R$_8$ is —CH$_3$. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 5-position of the Ar$^2$ pyridyl ring.

In another embodiment, Ar$^1$ is a pyridyl group; V is N; n is 0; m is 1; R$_3$ is —CH$_3$; R$_1$ is —F, —Cl, —Br, or —I; Ar$^2$ is $$\text{pyridyl ring with }(R_8)_s;$$

s is 1 and R$_8$ is —CF$_3$. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 5-position of the Ar$^2$ pyridyl ring.

In another embodiment, Ar$^1$ is a pyridyl group; V is N; n is 0; m is 1; R$_3$ is —CH$_3$; R$_1$ is —F; Ar$^2$ is $$\text{pyridyl ring with }(R_8)_s;$$

s is 1 and R$_8$ is —CF$_3$. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 5-position of the Ar$^2$ pyridyl ring.

In another embodiment, Ar$^1$ is a pyridyl group; V is N; n is 0; m is 1; R$_3$ is —CH$_3$; R$_1$ is —Cl; Ar$^2$ is $$\text{pyridyl ring with }(R_8)_s;$$

s is 1 and R$_8$ is —CF$_3$. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 5-position of the Ar$^2$ pyridyl ring.

In another embodiment, Ar$^1$ is a pyridyl group; V is N; n is 0; m is 1; R$_3$ is —CH$_3$; R$_1$ is —Br; Ar$^2$ is $$\text{pyridyl ring with }(R_8)_s;$$

s is 1 and R$_8$ is —CF$_3$. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 5-position of the Ar$^2$ pyridyl ring.

In another embodiment, Ar$^1$ is a pyridyl group; V is N; n is 0; m is 1; R$_3$ is —CH$_3$; R$_1$ is —I; Ar$^2$ is $$\text{pyridyl ring with }(R_8)_s;$$

s is 1 and R$_8$ is —CF$_3$. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 5-position of the Ar$^2$ pyridyl ring.

In another embodiment, Ar$^1$ is a pyridyl group; V is N; n is 0; m is 1; R$_3$ is —CH$_3$; R$_1$ is —CH$_3$; Ar$^2$ is

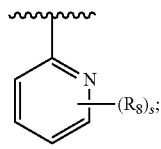

s is 1 and R$_8$ is —CF$_3$. In another embodiment, the R$_3$ group is attached to the 3-, 5- or 6-position of the cyclo(hetero) alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 5-position of the Ar$^2$ pyridyl ring.

In another embodiment, Ar$^1$ is a pyridyl group; V is N; n is 0; m is 1; R$_3$ is —CH$_3$; R$_1$ is —CF$_3$; Ar$^2$ is

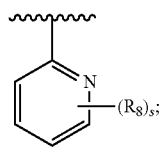

s is 1 and R$_8$ is —CF$_3$. In another embodiment, the R$_3$ group is attached to the 3-, 5- or 6-position of the cyclo(hetero) alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 5-position of the Ar$^2$ pyridyl ring.

In another embodiment, Ar$^1$ is a pyridyl group; V is N; n is 0; m is 1; R$_3$ is —CH$_3$; R$_1$ is —F, —Cl, —Br, or —I; Ar$^2$ is

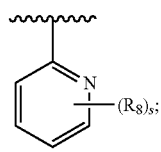

s is 1 and R$_8$ is —CH$_2$CF$_3$. In another embodiment, the R$_3$ group is attached to the 3-, 5- or 6-position of the cyclo (hetero)alkenyl ring and the carbon atom to which the R$_3$ group is attached has the (R) configuration. In another embodiment the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 5-position of the Ar$^2$ pyridyl ring.

In another embodiment, Ar$^1$ is a pyridyl group; V is N; n is 0; m is 1; R$_3$ is —CH$_3$; R$_1$ is —F; Ar$^2$ is

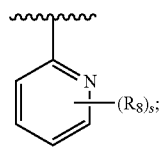

s is 1 and R$_8$ is —CH$_2$CF$_3$. In another embodiment, the R$_3$ group is attached to the 3-, 5- or 6-position of the cyclo (hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 5-position of the Ar$^2$ pyridyl ring.

In another embodiment, Ar$^1$ is a pyridyl group; V is N; n is 0; m is 1; R$_3$ is —CH$_3$; R$_1$ is —Cl; Ar$^2$ is

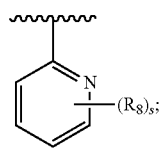

s is 1 and R$_8$ is —CH$_2$CF$_3$. In another embodiment, the R$_3$ group is attached to the 3-, 5- or 6-position of the cyclo (hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 5-position of the Ar$^2$ pyridyl ring.

In another embodiment, Ar$^1$ is a pyridyl group; V is N; n is 0; m is 1; R$_3$ is —CH$_3$; R$_1$ is —Br; Ar$^2$ is

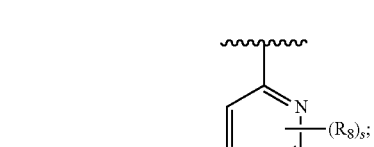

s is 1 and R$_8$ is —CH$_2$CF$_3$. In another embodiment, the R$_3$ group is attached to the 3-, 5- or 6-position of the cyclo (hetero)alkenyl ring and the carbon atom to which the R$_3$ group is attached has the (R) configuration. In another embodiment, the R$_3$ group is attached to the 3-, 5- or 6-posi-tion of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 5-position of the Ar$^2$ pyridyl ring.

In another embodiment, Ar¹ is a pyridyl group; V is N; n is 0; m is 1; R₃ is —CH₃; R₁ is —I; Ar² is

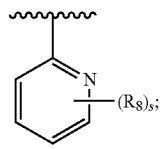

s is 1 and R₈ is —CH₂CF₃. In another embodiment, the R₃ group is attached to the 3-, 5- or 6-position of the cyclo(hetero)alkenyl ring and the carbon atom to which the R₃ group is attached has the (R) configuration. In another embodiment, the R₃ group is attached to the 3-, 5- or 6-position of the cyclo(hetero)alkenyl ring and the carbon atom to which the R₃ group is attached has the (S) configuration. In yet another embodiment, the R₃ group is attached to the 2-position of the cyclo(hetero)alkenyl ring. In another embodiment, R₈ is at the 5-position of the Ar² pyridyl ring.

In another embodiment, Ar¹ is a pyridyl group; V is N; n is 0; m is 1; R₃ is —CH₃; R₁ is —CH₃; Ar² is

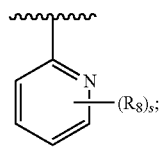

s is 1 and R₈ is —CH₂CF₃. In another embodiment, the R₃ group is attached to the 3-, 5- or 6-position of the cyclo(hetero)alkenyl ring and the carbon atom to which the R₃ group is attached has the (R) configuration. In another embodiment, the R₃ group is attached to the 3-, 5- or 6-position of the cyclo(hetero)alkenyl ring and the carbon atom to which the R₃ group is attached has the (S) configuration. In yet another embodiment, the R₃ group is attached to the 2-position of the cyclo(hetero)alkenyl ring. In another embodiment, R₈ is at the 5-position of the Ar² pyridyl ring.

In another embodiment, Ar¹ is a pyridyl group; V is N; n is 0; m is 1; R₃ is —CH₃; R₁ is —CF₃; Ar² is

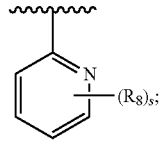

s is 1 and R₈ is —CH₂CF₃. In another embodiment, the R₃ group is attached to the 3-, 5- or 6-position of the cyclo(hetero)alkenyl ring and the carbon atom to which the R₃ group is attached has the (R) configuration. In another embodiment, the R₃ group is attached to the 3-, 5- or 6-position of the cyclo(hetero)alkenyl ring and the carbon atom to which the R₃ group is attached has the (S) configuration. In yet another embodiment, the R₃ group is attached to the 2-position of the cyclo(hetero)alkenyl ring. In another embodiment, R₈ is at the 5-position of the Ar² pyridyl ring.

In another embodiment, Ar¹ is a pyridyl group; V is N; n is 0; m is 1; R₃ is —CH₃; R₁ is —F, —Cl, —Br, or —I; Ar² is

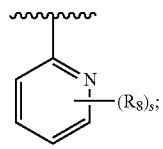

s is 1 and R₈ is -tert-butyl. In another embodiment, the R₃ group is attached to the 3-, 5- or 6-position of the cyclo(hetero)alkenyl ring and the carbon atom to which the R₃ group is attached has the (R) configuration. In another embodiment, the R₃ group is attached to the 3-, 5- or 6-position of the cyclo(hetero)alkenyl ring and the carbon atom to which the R₃ group is attached has the (S) configuration. In yet another embodiment, the R₃ group is attached to the 2-position of the cyclo(hetero)alkenyl ring. In another embodiment, R₈ is at the 5-position of the Ar² pyridyl ring.

In another embodiment, Ar¹ is a pyridyl group; V is N; n is 0; m is 1; R₃ is —CH₃; R₁ is —F; Ar² is

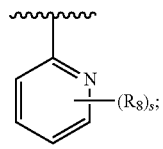

s is 1 and R₈ is -tert-butyl. In another embodiment, the R₃ group is attached to the 3-, 5- or 6-position of the cyclo(hetero)alkenyl ring and the carbon atom to which the R₃ group is attached has the (R) configuration. In another embodiment, the R₃ group is attached to the 3-, 5- or 6-position of the cyclo(hetero)alkenyl ring and the carbon atom to which the R₃ group is attached has the (S) configuration. In yet another embodiment, the R₃ group is attached to the 2-position of the cyclo(hetero)alkenyl ring. In another embodiment, R₈ is at the 5-position of the Ar² pyridyl ring.

In another embodiment, Ar¹ is a pyridyl group; V is N; n is 0; m is 1; R₃ is —CH₃; R₁ is —Cl; Ar² is

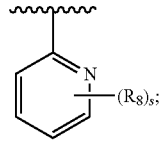

s is 1 and R₈ is -tert-butyl. In another embodiment, the R₃ group is attached to the 3-, 5- or 6-position of the cyclo(hetero)alkenyl ring and the carbon atom to which the R₃ group is attached has the (R) configuration. In another embodiment, the R₃ group is attached to the 3-, 5- or 6-position of the cyclo(hetero)alkenyl ring and the carbon atom to which the R₃ group is attached has the (S) configuration. In yet another embodiment, the R₃ group is attached to the 2-position of the cyclo(hetero)alkenyl ring. In another embodiment, R₈ is at the 5-position of the Ar² pyridyl ring.

In another embodiment, $Ar^1$ is a pyridyl group; V is N; n is 0; m is 1; $R_3$ is —$CH_3$; $R_1$ is —Br; $Ar^2$ is

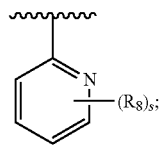

s is 1 and $R_8$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is N; n is 0; m is 1; $R_3$ is —$CH_3$; $R_1$ is —I; $Ar^2$ is

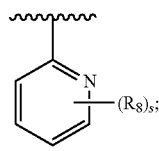

s is 1 and $R_8$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is N; n is 0; m is 1; $R_3$ is —$CH_3$; $R_1$ is —$CH_3$; $Ar^2$ is

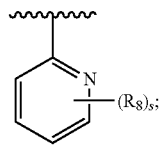

s is 1 and $R_8$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is N; n is 0; m is 1; $R_3$ is —$CH_3$; $R_1$ is —$CF_3$; $Ar^2$ is

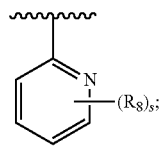

s is 1 and $R_8$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, V is CH, $Ar^1$ is a pyridyl group, m is 0, and $Ar^2$ is

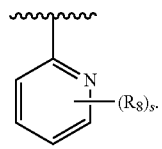

In another embodiment, $Ar^1$ is a pyridyl group; V is CH; n is 0; m is 0; $R_1$ is —F, —Cl, —Br, or —I; $Ar^2$ is

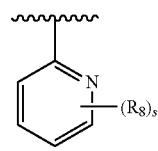

and s is 0.

In another embodiment, $Ar^1$ is a pyridyl group; V is CH; n is 0; m is 0; $R_1$ is —F; $Ar^2$ is

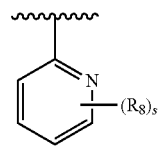

and s is 0.

In another embodiment, $Ar^1$ is a pyridyl group; V is CH; n is 0; m is 0; $R_1$ is —Cl; $Ar^2$ is

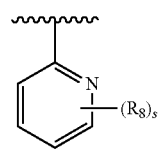

and s is 0.

In another embodiment, $Ar^1$ is a pyridyl group; V is CH; n is 0; m is 0; $R_1$ is —Br; $Ar^2$ is

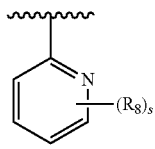

and s is 0.

In another embodiment, $Ar^1$ is a pyridyl group; V is CH; n is 0; m is 0; $R_1$ is —I; $Ar^2$ is

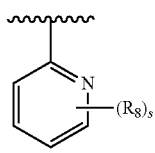

and s is 0.

In another embodiment, $Ar^1$ is a pyridyl group; V is CH; n is 0; m is 0; $R_1$ is —$CH_3$; $Ar^2$ is

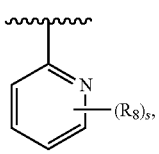

and s is 0.

In another embodiment, $Ar^1$ is a pyridyl group; V is CH; n is 0; m is 0; $R_1$ is —$CF_3$; $Ar^2$ is

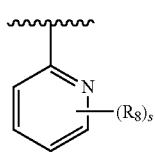

and s is 0.

In another embodiment, $Ar^1$ is a pyridyl group; V is CH; n is 0; m is 0; $R_1$ is —F, —Cl, —Br, or —I; $Ar^2$ is

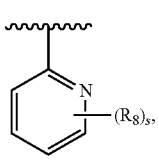

s is 1 and $R_8$ is -halo. In another embodiment, $R_8$ is at the 5-position of the $Ar^2$ pyridyl ring.

In another embodiment, $Ar^1$ is a pyridyl group; V is CH; n is 0; m is 0; $R_1$ is —F; $Ar^2$ is

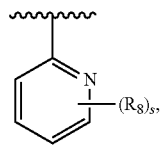

s is 1 and $R_8$ is -halo.

In another embodiment, $Ar^1$ is a pyridyl group; V is CH; n is 0; m is 0; $R_1$ is —Cl; $Ar^2$ is

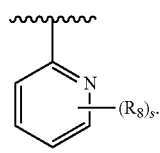

s is 1 and $R_8$ is -halo. In another embodiment, $R_8$ is at the 5-position of the $Ar^2$ pyridyl ring.

In another embodiment, $Ar^1$ is a pyridyl group; V is CH; n is 0; m is 0; $R_1$ is —Br; $Ar^2$ is

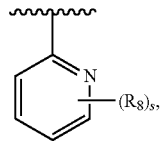

s is 1 and $R_8$ is -halo. In another embodiment, $R_8$ is at the 5-position of the $Ar^2$ pyridyl ring.

In another embodiment, $Ar^1$ is a pyridyl group; V is CH; n is 0; m is 0; $R_1$ is —I; $Ar^2$ is

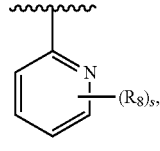

s is 1 and $R_8$ is -halo. In another embodiment, $R_8$ is at the 5-position of the $Ar^2$ pyridyl ring.

In another embodiment, $Ar^1$ is a pyridyl group; V is CH; n is 0; m is 0; $R_1$ is —$CH_3$; $Ar^2$ is

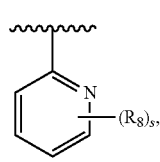

s is 1 and $R_8$ is -halo. In another embodiment, $R_8$ is at the 5-position of the $Ar^2$ pyridyl ring.

In another embodiment, $Ar^1$ is a pyridyl group; V is CH; n is 0; m is 0; $R_1$ is —$CF_3$; $Ar^2$ is

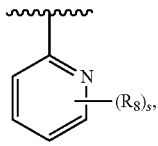

s is 1 and $R_8$ is -halo. In another embodiment, $R_8$ is at the 5-position of the $Ar^2$ pyridyl ring.

In another embodiment, $Ar^1$ is a pyridyl group; V is CH; n is 0; m is 0; $R_1$ is —F, —Cl, —Br, or —I; $Ar^2$ is

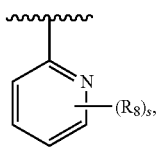

s is 1 and $R_8$ is —Br. In another embodiment, $R_8$ is at the 5-position of the $Ar^2$ pyridyl ring.

In another embodiment, $Ar^1$ is a pyridyl group; V is CH; n is 0; m is 0; $R_1$ is —F; $Ar^2$ is

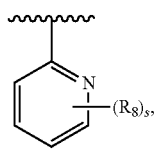

s is 1 and $R_8$ is —Br. In another embodiment, $R_8$ is at the 5-position of the $Ar^2$ pyridyl ring.

In another embodiment, $Ar^1$ is a pyridyl group; V is CH; n is 0; m is 0; $R_1$ is —Cl; $Ar^2$ is

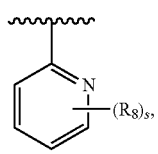

s is 1 and $R_8$ is —Br. In another embodiment, $R_8$ is at the 5-position of the $Ar^2$ pyridyl ring.

In another embodiment, $Ar^1$ is a pyridyl group; V is CH; n is 0; m is 0; $R_1$ is —Br; $Ar^2$ is

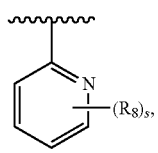

s is 1 and $R_8$ is —Br. In another embodiment, $R_8$ is at the 5-position of the $Ar^2$ pyridyl ring.

In another embodiment, $Ar^1$ is a pyridyl group; V is CH; n is 0; m is 0; $R_1$ is —I; $Ar^2$ is

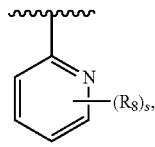

s is 1 and $R_8$ is —Br. In another embodiment, $R_8$ is at the 5-position of the $Ar^2$ pyridyl ring.

In another embodiment, $Ar^1$ is a pyridyl group; V is CH; n is 0; m is 0; $R_1$ is —$CH_3$; $Ar^2$ is

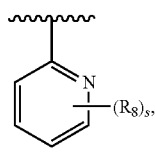

s is 1 and $R_8$ is —Br. In another embodiment, $R_8$ is at the 5-position of the $Ar^2$ pyridyl ring.

In another embodiment, $Ar^1$ is a pyridyl group; V is CH; n is 0; m is 0; $R_1$ is —$CF_3$; $Ar^2$ is

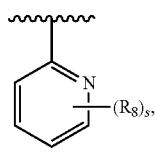

s is 1 and $R_8$ is —Br. In another embodiment, $R_8$ is at the 5-position of the $Ar^2$ pyridyl ring.

In another embodiment, $Ar^1$ is a pyridyl group; V is CH; n is 0; m is 0; $R_1$ is —Cl, —F —Br, or —I; $Ar^2$ is

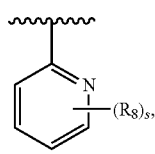

s is 1 and $R_8$ is —F. In another embodiment, $R_8$ is at the 5-position of the $Ar^2$ pyridyl ring.

In another embodiment, $Ar^1$ is a pyridyl group; V is CH; n is 0; m is 0; $R_1$ is —F; $Ar^2$ is

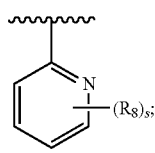

s is 1 and $R_8$ is —F. In another embodiment, $R_8$ is at the 5-position of the $Ar^2$ pyridyl ring.

In another embodiment, $Ar^1$ is a pyridyl group; V is CH; n is 0; m is 0; $R_1$ is —Cl; $Ar^2$ is

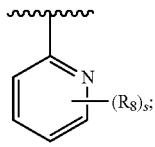

s is 1 and $R_8$ is —F. In another embodiment, $R_8$ is at the 5-position of the $Ar^2$ pyridyl ring.

In another embodiment, $Ar^1$ is a pyridyl group; V is CH; n is 0; m is 0; $R_1$ is —Br; $Ar^2$ is

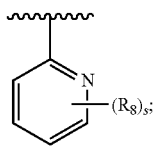

s is 1 and $R_8$ is —F. In another embodiment, $R_8$ is at the 5-position of the $Ar^2$ pyridyl ring.

In another embodiment, $Ar^1$ is a pyridyl group; V is CH; n is 0; m is 0; $R_1$ is —I; $Ar^2$ is

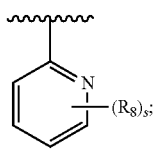

s is 1 and $R_8$ is —F. In another embodiment, $R_8$ is at the 5-position of the $Ar^2$ pyridyl ring.

In another embodiment, $Ar^1$ is a pyridyl group; V is CH; n is 0; m is 0; $R_1$ is —$CH_3$; $Ar^2$ is

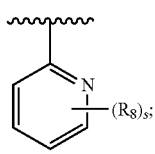

s is 1 and $R_8$ is —F. In another embodiment, $R_8$ is at the 5-position of the $Ar^2$ pyridyl ring.

In another embodiment, $Ar^1$ is a pyridyl group; V is CH; n is 0; m is 0; $R_1$ is —$CF_3$; $Ar^2$ is

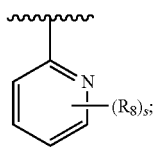

s is 1 and $R_8$ is —F. In another embodiment, $R_8$ is at the 5-position of the $Ar^2$ pyridyl ring.

In another embodiment, $Ar^1$ is a pyridyl group; V is CH; n is 0; m is 0; $R_1$ is —Cl, —F —Br, or —I; $Ar^2$ is

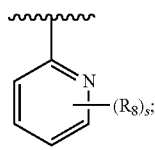

s is 1 and $R_8$ is —Cl. In another embodiment, $R_8$ is at the 5-position of the $Ar^2$ pyridyl ring.

In another embodiment, $Ar^1$ is a pyridyl group; V is CH; n is 0; m is 0; $R_1$ is —F; $Ar^2$ is

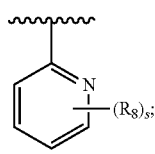

s is 1 and $R_8$ is —Cl. In another embodiment, $R_8$ is at the 5-position of the $Ar^2$ pyridyl ring.

In another embodiment, $Ar^1$ is a pyridyl group; V is CH; n is 0; m is 0; $R_1$ is —Cl; $Ar^2$ is

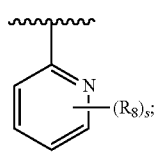

s is 1 and $R_8$ is —Cl. In another embodiment, $R_8$ is at the 5-position of the $Ar^2$ pyridyl ring.

In another embodiment, $Ar^1$ is a pyridyl group; V is CH; n is 0; m is 0; $R_1$ is —Br; $Ar^2$ is

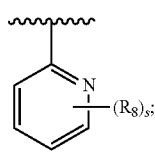

s is 1 and $R_8$ is —Cl. In another embodiment, $R_8$ is at the 5-position of the $Ar^2$ pyridyl ring.

In another embodiment, $Ar^1$ is a pyridyl group; V is CH; n is 0; m is 0; $R_1$ is —I; $Ar^2$ is

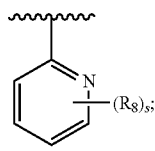

s is 1 and $R_8$ is —Cl. In another embodiment, $R_8$ is at the 5-position of the $Ar^2$ pyridyl ring.

In another embodiment, $Ar^1$ is a pyridyl group; V is CH; n is 0; m is 0; $R_1$ is —$CH_3$; $Ar^2$ is

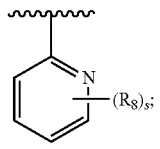

s is 1 and $R_8$ is —Cl. In another embodiment, $R_8$ is at the 5-position of the $Ar^2$ pyridyl ring.

In another embodiment, $Ar^1$ is a pyridyl group; V is CH; n is 0; m is 0; $R_1$ is —$CF_3$; $Ar^2$ is

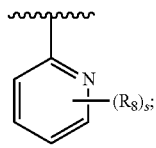

s is 1 and $R_8$ is chloro. In another embodiment, $R_8$ is at the 5-position of the $Ar^2$ pyridyl ring.

In another embodiment, $Ar^1$ is a pyridyl group; V is CH; n is 0; m is 0; $R_1$ is —Cl, —F, —Br, or —I, $Ar^2$ is

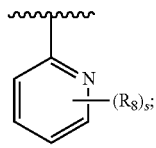

s is 1 and $R_8$ is —I. In another embodiment, $R_8$ is at the 5-position of the $Ar^2$ pyridyl ring.

In another embodiment, $Ar^1$ is a pyridyl group; V is CH; n is 0; m is 0; $R_1$ is —F; $Ar^2$ is

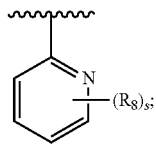

s is 1 and $R_8$ is —I. In another embodiment, $R_8$ is at the 5-position of the $Ar^2$ pyridyl ring.

In another embodiment, $Ar^1$ is a pyridyl group; V is CH; n is 0; m is 0; $R_1$ is —Cl; $Ar^2$ is

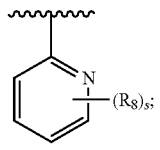

s is 1 and $R_8$ is —I. In another embodiment, $R_8$ is at the 5-position of the $Ar^2$ pyridyl ring.

In another embodiment, $Ar^1$ is a pyridyl group; V is CH; n is 0; m is 0; $R_1$ is —Br; $Ar^2$ is

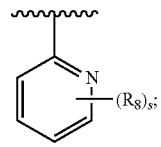

s is 1 and $R_8$ is —I. In another embodiment, $R_8$ is at the 5-position of the $Ar^2$ pyridyl ring.

In another embodiment, $Ar^1$ is a pyridyl group; V is CH; n is 0; m is 0; $R_1$ is —I; $Ar^2$ is

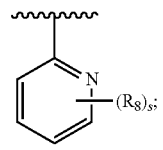

s is 1 and $R_8$ is —I. In another embodiment, $R_8$ is at the 5-position of the $Ar^2$ pyridyl ring.

In another embodiment, $Ar^1$ is a pyridyl group; V is CH; n is 0; m is 0; $R_1$ is —$CH_3$; $Ar^2$ is

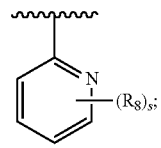

s is 1 and $R_8$ is —I. In another embodiment, $R_8$ is at the 5-position of the $Ar^2$ pyridyl ring.

In another embodiment, $Ar^1$ is a pyridyl group; V is CH; n is 0; m is 0; $R_1$ is —$CF_3$; $Ar^2$ is

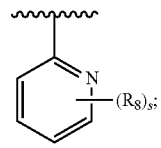

s is 1 and $R_8$ is —I. In another embodiment, $R_8$ is at the 5-position of the $Ar^2$ pyridyl ring.

In another embodiment, $Ar^1$ is a pyridyl group; V is CH; n is 0; m is 0; $R_1$ is —F, —Cl, —Br, or —I; $Ar^2$ is

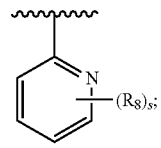

s is 1 and $R_8$ is —$CH_3$. In another embodiment, $R_8$ is at the 5-position of the $Ar^2$ pyridyl ring.

In another embodiment, $Ar^1$ is a pyridyl group; V is CH; n is 0; m is 0; $R_1$ is —F; $Ar^2$ is

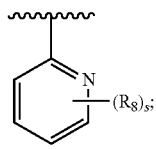

s is 1 and $R_8$ is —CH$_3$. In another embodiment, $R_8$ is at the 5-position of the $Ar^2$ pyridyl ring.

In another embodiment, $Ar^1$ is a pyridyl group; V is CH; n is 0; m is 0; $R_1$ is —Cl; $Ar^2$ is

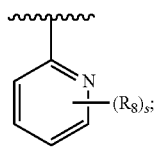

s is 1 and $R_8$ is —CH$_3$. In another embodiment, $R_8$ is at the 5-position of the $Ar^2$ pyridyl ring.

In another embodiment, $Ar^1$ is a pyridyl group; V is CH; n is 0; m is 0; $R_1$ is —Br; $Ar^2$ is

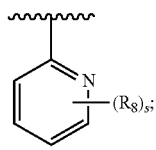

s is 1 and $R_8$ is —CH$_3$. In another embodiment, $R_8$ is at the 5-position of the $Ar^2$ pyridyl ring.

In another embodiment, $Ar^1$ is a pyridyl group; V is CH; n is 0; m is 0; $R_1$ is —I; $Ar^2$ is

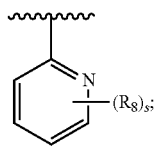

s is 1 and $R_8$ is —CH$_3$. In another embodiment, $R_8$ is at the 5-position of the $Ar^2$ pyridyl ring.

In another embodiment, $Ar^1$ is a pyridyl group; V is CH; n is 0; m is 0; $R_1$ is —CH$_3$; $Ar^2$ is

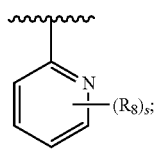

s is 1 and $R_8$ is —CH$_3$. In another embodiment, $R_8$ is at the 5-position of the $Ar^2$ pyridyl ring.

In another embodiment, $Ar^1$ is a pyridyl group; V is CH; n is 0; m is 0; $R_1$ is —CF$_3$; $Ar^2$ is

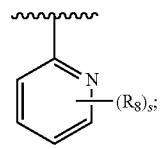

s is 1 and $R_8$ is —CH$_3$. In another embodiment, $R_8$ is at the 5-position of the $Ar^2$ pyridyl ring.

In another embodiment, $Ar^1$ is a pyridyl group; V is CH; n is 0; m is 0; $R_1$ is —F, —Cl, —Br, or —I; $Ar^2$ is

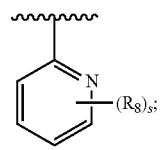

s is 1 and $R_8$ is —CF$_3$. In another embodiment, $R_8$ is at the 5-position of the $Ar^2$ pyridyl ring.

In another embodiment, $Ar^1$ is a pyridyl group; V is CH; n is 0; m is 0; $R_1$ is —F; $Ar^2$ is

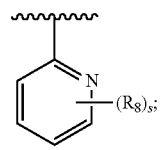

s is 1 and $R_8$ is —CF$_3$. In another embodiment, $R_8$ is at the 5-position of the $Ar^2$ pyridyl ring.

In another embodiment, $Ar^1$ is a pyridyl group; V is CH; n is 0; m is 0; $R_1$ is —Cl; $Ar^2$ is

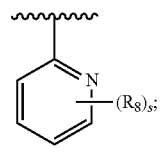

s is 1 and $R_8$ is —CF$_3$. In another embodiment, $R_8$ is at the 5-position of the $Ar^2$ pyridyl ring.

In another embodiment, $Ar^1$ is a pyridyl group; V is CH; n is 0; m is 0; $R_1$ is —Br; $Ar^2$ is

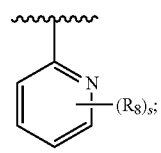

s is 1 and $R_8$ is —CF$_3$. In another embodiment, $R_8$ is at the 5-position of the $Ar^2$ pyridyl ring.

In another embodiment, $Ar^1$ is a pyridyl group; V is CH; n is 0; m is 0; $R_1$ is —I; $Ar^2$ is

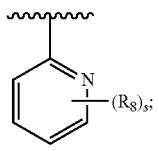

s is 1 and $R_8$ is —$CF_3$. In another embodiment, $R_8$ is at the 5-position of the $Ar^2$ pyridyl ring.

In another embodiment, $Ar^1$ is a pyridyl group; V is CH; n is 0; m is 0; $R_1$ is —$CH_3$; $Ar^2$ is

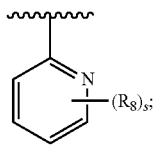

s is 1 and $R_8$ is —$CF_3$. In another embodiment, $R_8$ is at the 5-position of the $Ar^2$ pyridyl ring.

In another embodiment, $Ar^1$ is a pyridyl group; V is CH; n is 0; m is 0; $R_1$ is —$CF_3$; $Ar^2$ is

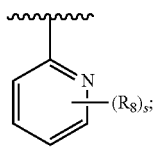

s is 1 and $R_8$ is —$CF_3$. In another embodiment, $R_8$ is at the 5-position of the $Ar^2$ pyridyl ring.

In another embodiment, $Ar^1$ is a pyridyl group; V is CH; n is 0; m is 0; $R_1$ is —F, —Cl, —Br, or —I; $Ar^2$ is

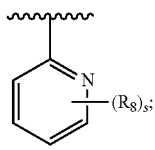

s is 1 and $R_8$ is —$CH_2CF_3$. In another embodiment, $R_8$ is at the 5-position of the $Ar^2$ pyridyl ring.

In another embodiment, $Ar^1$ is a pyridyl group; V is CH; n is 0; m is 0; $R_1$ is —F; $Ar^2$ is

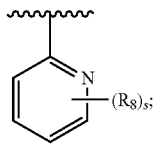

s is 1 and $R_8$ is —$CH_2CF_3$. In another embodiment, $R_8$ is at the 5-position of the $Ar^2$ pyridyl ring.

In another embodiment, $Ar^1$ is a pyridyl group; V is CH; n is 0; m is 0; $R_1$ is —Cl; $Ar^2$ is

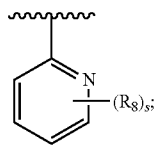

s is 1 and $R_8$ is —$CH_2CF_3$. In another embodiment, $R_8$ is at the 5-position of the $Ar^2$ pyridyl ring.

In another embodiment, $Ar^1$ is a pyridyl group; V is CH; n is 0; m is 0; $R_1$ is —Br; $Ar^2$ is

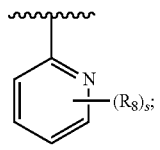

s is 1 and $R_8$ is —$CH_2CF_3$. In another embodiment, $R_8$ is at the 5-position of the $Ar^2$ pyridyl ring.

In another embodiment, $Ar^1$ is a pyridyl group; V is CH; n is 0; m is 0; $R_1$ is —I; $Ar^2$ is

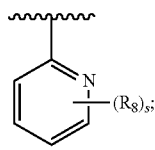

s is 1 and $R_8$ is —$CH_2CF_3$. In another embodiment, $R_8$ is at the 5-position of the $Ar^2$ pyridyl ring.

In another embodiment, $Ar^1$ is a pyridyl group; V is CH; n is 0; m is 0; $R_1$ is —$CH_3$; $Ar^2$ is

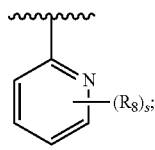

s is 1 and $R_8$ is —$CH_2CF_3$. In another embodiment, $R_8$ is at the 5-position of the $Ar^2$ pyridyl ring.

In another embodiment, $Ar^1$ is a pyridyl group; V is CH; n is 0; m is 0; $R_1$ is —$CF_3$; $Ar^2$ is

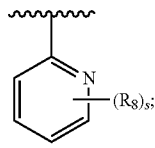

s is 1 and $R_8$ is —$CH_2CF_3$. In another embodiment, $R_8$ is at the 5-position of the $Ar^2$ pyridyl ring.

In another embodiment, Ar¹ is a pyridyl group; V is CH; n is 0; m is 0; R₁ is —F, —Cl, —Br, or —I; Ar² is

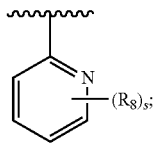

s is 1 and R₈ is -tert-butyl. In another embodiment, R₈ is at the 5-position of the Ar² pyridyl ring.

In another embodiment, Ar¹ is a pyridyl group; V is CH; n is 0; m is 0; R₁ is —F; Ar² is

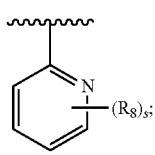

s is 1 and R₈ is -tert-butyl. In another embodiment, R₈ is at the 5-position of the Ar² pyridyl ring.

In another embodiment, Ar¹ is a pyridyl group; V is CH; n is 0; m is 0; R₁ is —Cl; Ar² is

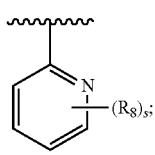

s is 1 and R₈ is -tert-butyl. In another embodiment, R₈ is at the 5-position of the Ar² pyridyl ring.

In another embodiment, Ar¹ is a pyridyl group; V is CH; n is 0; m is 0; R₁ is —Br; Ar² is

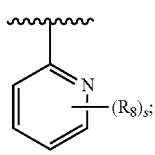

s is 1 and R₈ is -tert-butyl. In another embodiment, R₈ is at the 5-position of the Ar² pyridyl ring.

In another embodiment, Ar¹ is a pyridyl group; V is CH; n is 0; m is 0; R₁ is —I; Ar² is

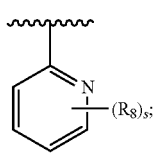

s is 1 and R₈ is -tert-butyl. In another embodiment, R₈ is at the 5-position of the Ar² pyridyl ring.

In another embodiment, Ar¹ is a pyridyl group; V is CH; n is 0; m is 0; R₁ is —CH₃; Ar² is

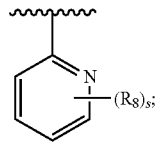

s is 1 and R₈ is -tert-butyl. In another embodiment, R₈ is at the 5-position of the Ar² pyridyl ring.

In another embodiment, Ar¹ is a pyridyl group; V is CH; n is 0; m is 0; R₁ is —CF₃; Ar² is

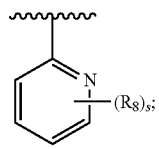

s is 1 and R₈ is -tert-butyl. In another embodiment, R₈ is at the 5-position of the Ar² pyridyl ring.

In another embodiment, Ar¹ is a pyridyl group; V is CH; n is 0; m is 1; R₃ is —CH₃; R₁ is —F, —Cl, —Br, or —I; Ar² is

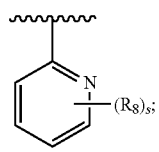

and s is 0. In another embodiment, the R₃ group is attached to the 3-, 5- or 6-position of the cyclo(hetero)alkenyl ring and the carbon atom to which the R₃ group is attached has the (R) configuration. In another embodiment, the R₃ group is attached to the 3-, 5- or 6-position of the cyclo(hetero)alkenyl ring and the carbon atom to which the R₃ group is attached has the (S) configuration. In yet another embodiment, the R₃ group is attached to the 2-position of the cyclo(hetero)alkenyl ring. In another embodiment, R₈ is at the 5-position of the Ar² pyridyl ring.

In another embodiment, Ar¹ is a pyridyl group; V is CH; n is 0; m is 1; R₃ is —CH₃; R₁ is —F; Ar² is

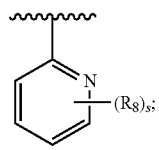

and s is 0. In another embodiment, the R₃ group is attached to the 3-, 5- or 6-position of the cyclo(hetero)alkenyl ring and the carbon atom to which the R₃ group is attached has the (R) configuration. In another embodiment, the R₃ group is attached to the 3-, 5- or 6-position of the cyclo(hetero)alkenyl ring and the carbon atom to which the R₃ group is attached has the (S) configuration. In yet another embodiment, the R₃ group is attached to the 2-position of the cyclo(hetero)alkenyl ring. In another embodiment, R₈ is at the 5-position of the Ar² pyridyl ring.

In another embodiment, $Ar^1$ is a pyridyl group; V is CH; n is 0; m is 1; $R_3$ is —$CH_3$; $R_1$ is —Cl; $Ar^2$ is and s is 0. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is CH; n is 0; m is 1; $R_3$ is —$CH_3$; $R_1$ is —Br; $Ar^2$ is and s is 0. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is CH; n is 0; m is 1; $R_3$ is —$CH_3$; $R_1$ is —I; $Ar^2$ is and s is 0. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is CH; n is 0; m is 1; $R_3$ is —$CH_3$; $R_1$ is —$CH_3$; $Ar^2$ is and s is 0. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is CH; n is 0; m is 1; $R_3$ is —$CH_3$; $R_1$ is —$CF_3$; $Ar^2$ is and s is 0. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is CH; n is 0; m is 1; $R_3$ is —$CH_3$; $R_1$ is —F, —Cl, —Br, or —I; $Ar^2$ is s is 1 and $R_8$ is -halo. In another embodiment, the $R_3$ group is attached to the 3-, 5- or 6-position of the cyclo(hetero)alkenyl ring and the carbon atom to which the $R_3$ group is attached has the (R) configuration. In another embodiment the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F; $Ar^2$ is s is 1 and $R_8$ is -halo. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is CH; n is 0; m is 1; $R_3$ is —$CH_3$; $R_1$ is —Cl; $Ar^2$ is s is 1 and $R_8$ is -halo. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is CH; n is 0; m is 1; $R_3$ is —$CH_3$; $R_1$ is —Br; $Ar^2$ is s is 1 and $R_8$ is -halo. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is CH; n is 0; m is 1; $R_3$ is —$CH_3$; $R_1$ is —I; $Ar^2$ is s is 1 and $R_8$ is -halo. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is CH; n is 0; m is 1; $R_3$ is —$CH_3$; $R_1$ is —$CH_3$; $Ar^2$ is s is 1 and $R_8$ is -halo. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is CH; n is 0; m is 1; $R_3$ is —$CH_3$; $R_1$ is —$CF_3$; $Ar^2$ is s is 1 and $R_8$ is -halo. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is CH; n is 0; m is 1; $R_3$ is —$CH_3$; $R_1$ is —F, —Cl, —Br, or —I; $Ar^2$ is s is 1 and $R_8$ is —Br. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, Ar$^1$ is a pyridyl group; V is CH; n is 0; m is 1; R$_3$ is —CH$_3$; R$_1$ is —F; Ar$^2$ is

[structure: pyridyl with (R$_8$)$_s$]

s is 1 and R$_8$ is —Br. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 5-position of the Ar$^2$ pyridyl ring.

In another embodiment, Ar$^1$ is a pyridyl group; V is CH; n is 0; m is 1; R$_3$ is —CH$_3$; R$_1$ is —Cl; Ar$^2$ is

[structure: pyridyl with (R$_8$)$_s$]

s is 1 and R$_8$ is —Br. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 5-position of the Ar$^2$ pyridyl ring.

In another embodiment, Ar$^1$ is a pyridyl group; V is CH; n is 0; m is 1; R$_3$ is —CH$_3$; R$_1$ is —Br; Ar$^2$ is

[structure: pyridyl with (R$_8$)$_s$]

s is 1 and R$_8$ is —Br. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 5-position of the Ar$^2$ pyridyl ring.

In another embodiment, Ar$^1$ is a pyridyl group; V is CH; n is 0; m is 1; R$_3$ is —CH$_3$; R$_1$ is —I; Ar$^2$ is

[structure: pyridyl with (R$_8$)$_s$]

s is 1 and R$_8$ is —Br. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 5-position of the Ar$^2$ pyridyl ring.

In another embodiment, Ar$^1$ is a pyridyl group; V is CH; n is 0; m is 1; R$_3$ is —CH$_3$; R$_1$ is —CH$_3$; Ar$^2$ is

[structure: pyridyl with (R$_8$)$_s$]

s is 1 and R$_8$ is —Br. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 5-position of the Ar$^2$ pyridyl ring.

In another embodiment, Ar$^1$ is a pyridyl group; V is CH; n is 0; m is 1; R$_3$ is —CH$_3$; R$_1$ is —CF$_3$; Ar$^2$ is

[structure: pyridyl with (R$_8$)$_s$]

s is 1 and R$_8$ is —Br. In another embodiment, the R$_3$ group is attached to the 3-, 5- or 6-position of the cyclo(hetero)alkenyl ring and the carbon atom to which the R$_3$ group is attached has the (R) configuration. In another embodiment, the R$_3$ group is attached to the 3-, 5- or 6-position of the cyclo(hetero)alkenyl ring and the carbon atom to which the R$_3$ group is attached has the (S) configuration. In yet another embodiment, the R$_3$ group is attached to the 2-position of the cyclo(hetero)alkenyl ring. In another embodiment, R$_8$ is at the 5-position of the Ar$^2$ pyridyl ring.

In another embodiment, $Ar^1$ is a pyridyl group; V is CH; n is 0; m is 1; $R_3$ is —$CH_3$; $R_1$ is —Cl, —F —Br, or —I; $Ar^2$ is

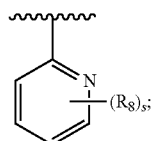

s is 1 and $R_8$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is CH; n is 0; m is 1; $R_3$ is —$CH_3$; $R_1$ is —F; $Ar^2$ is

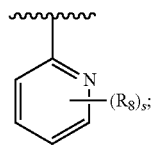

s is 1 and $R_8$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is CH; n is 0; m is 1; $R_3$ is —$CH_3$; $R_1$ is —Cl; $Ar^2$ is

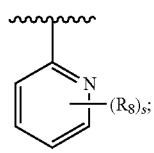

s is 1 and $R_8$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is CH; n is 0; m is 1; $R_3$ is —$CH_3$; $R_1$ is —Br; $Ar^2$ is

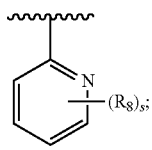

s is 1 and $R_8$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is CH; n is 0; m is 1; $R_3$ is —$CH_3$; $R_1$ is —I; $Ar^2$ is s is 1 and $R_8$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is CH; n is 0; m is 1; $R_3$ is —$CH_3$; $R_1$ is —$CH_3$; $Ar^2$ is s is 1 and $R_8$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is CH; n is 0; m is 1; $R_3$ is —$CH_3$; $R_1$ is —$CF_3$; $Ar^2$ is

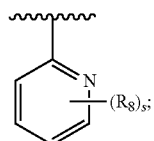

s is 1 and $R_8$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is CH; n is 0; m is 1; $R_3$ is $CH_3$; $R_1$ is —Cl, —F —Br, or —I; $Ar^2$ is

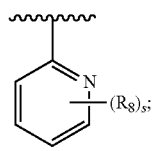

s is 1 and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is CH; n is 0; m is 1; $R_3$ is —$CH_3$; $R_1$ is —F; $Ar^2$ is

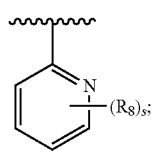

s is 1 and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is CH; n is 0; m is 1; $R_3$ is —$CH_3$; $R_1$ is —Cl; $Ar^2$ is

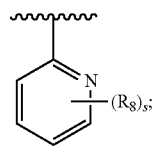

s is 1 and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is CH; n is 0; m is 1; $R_3$ is —$CH_3$; $R_1$ is —Br; $Ar^2$ is

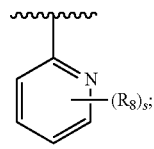

s is 1 and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is CH; n is 0; m is 1; $R_3$ is —$CH_3$; $R_1$ is —I; $Ar^2$ is

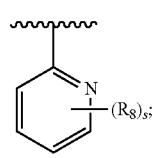

s is 1 and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is CH; n is 0; m is 1; $R_3$ is —$CH_3$; $R_1$ is —$CH_3$; $Ar^2$ is

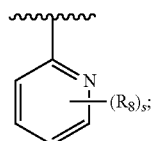

s is 1 and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is CH; n is 0; m is 1; $R_3$ is —$CH_3$; $R_1$ is —$CF_3$; $Ar^2$ is

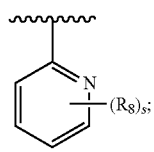

s is 1 and $R_8$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is CH; n is 0; m is 1; $R_3$ is —$CH_3$; $R_1$ is —Cl, —F, —Br, or —I, $Ar^2$ is

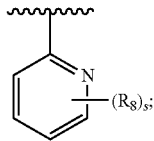

s is 1; and $R_8$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is CH; n is 0; m is 1; $R_3$ is —$CH_3$; $R_1$ is —F; $Ar^2$ is

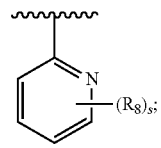

s is 1 and $R_8$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is CH; n is 0; m is 1; $R_3$ is —$CH_3$; $R_1$ is —Cl; $Ar^2$ is

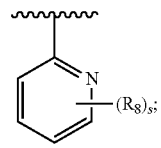

s is 1 and $R_8$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is CH; n is 0; m is 1; $R_3$ is —$CH_3$; $R_1$ is —Br; $Ar^2$ is

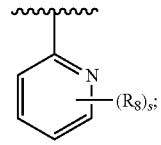

s is 1 and $R_8$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is CH; n is 0; m is 1; $R_3$ is —$CH_3$; $R_1$ is —I; $Ar^2$ is

[chemical structure: pyridyl ring with $(R_8)_s$];

s is 1 and $R_8$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is CH; n is 0; m is 1; $R_3$ is —$CH_3$; $R_1$ is —$CH_3$; $Ar^2$ is

[chemical structure: pyridyl ring with $(R_8)_s$];

s is 1 and $R_8$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is CH; n is 0; m is 1; $R_3$ is —$CH_3$; $R_1$ is —$CF_3$; $Ar^2$ is

[chemical structure: pyridyl ring with $(R_8)_s$];

s is 1 and $R_8$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is CH; n is 0; m is 1; $R_3$ is —$CH_3$; $R_1$ is —F, —Cl, —Br, or —I; $Ar^2$ is

[chemical structure: pyridyl ring with $(R_8)_s$];

s is 1 and $R_8$ is —$CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is CH; n is 0; m is 1; $R_3$ is —$CH_3$; $R_1$ is —F; $Ar^2$ is

[chemical structure: pyridyl ring with $(R_8)_s$];

s is 1 and $R_8$ is —$CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is CH; n is 0; m is 1; $R_3$ is —$CH_3$; $R_1$ is —Cl; $Ar^2$ is

[chemical structure: pyridyl ring with $(R_8)_s$];

s is 1 and $R_8$ is —$CH_3$. In another embodiment, the $R_3$ group is attached to the 3-, 5- or 6-position of the cyclo(hetero) alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is CH; n is 0; m is 1; $R_3$ is —$CH_3$; $R_1$ is —Br; $Ar^2$ is

[chemical structure: pyridyl ring with $(R_8)_s$];

s is 1 and $R_8$ is —$CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is CH; n is 0; m is 1; $R_3$ is —$CH_3$; $R_1$ is —I; $Ar^2$ is s is 1 and $R_8$ is —$CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is CH; n is 0; m is 1; $R_3$ is —$CH_3$; $R_1$ is —$CH_3$; $Ar^2$ is s is 1 and $R_8$ is —$CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is CH; n is 0; m is 1; $R_3$ is —$CH_3$; $R_1$ is —$CF_3$; $Ar^2$ is s is 1 and $R_8$ is —$CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is CH; n is 0; m is 1; $R_3$ is —$CH_3$; $R_1$ is —F, —Cl, —Br, or —I; $Ar^2$ is is 1 and $R_8$ is —$CF_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is CH; n is 0; m is 1; $R_3$ is —$CH_3$; $R_1$ is —F; $Ar^2$ is s is 1 and $R_8$ is —$CF_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is CH; n is 0; m is 1; $R_3$ is —$CH_3$; $R_1$ is —Cl; $Ar^2$ is s is 1 and $R_8$ is —$CF_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is CH; n is 0; m is 1; $R_3$ is —$CH_3$; $R_1$ is —Br; $Ar^2$ is

[structure: pyridyl with $(R_8)_s$]

s is 1 and $R_8$ is —$CF_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is CH; n is 0; m is 1; $R_3$ is —$CH_3$; $R_1$ is —I; $Ar^2$ is

[structure: pyridyl with $(R_8)_s$]

s is 1 and $R_8$ is —$CF_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is CH; n is 0; m is 1; $R_3$ is —$CH_3$; $R_1$ is —$CH_3$; $Ar^2$ is

[structure: pyridyl with $(R_8)_s$]

s is 1 and $R_8$ is —$CF_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is CH; n is 0; m is 1; $R_3$ is —$CH_3$; $R_1$ is —$CF_3$; $Ar^2$ is

[structure: pyridyl with $(R_8)_s$]

s is 1 and $R_8$ is —$CF_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is CH; n is 0; m is 1; $R_3$ is —$CH_3$; $R_1$ is —F, —Cl, —Br, or —I; $Ar^2$ is

[structure: pyridyl with $(R_8)_s$]

s is 1 and $R_8$ is —$CH_2CF_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is CH; n is 0; m is 1; $R_3$ is —$CH_3$; $R_1$ is —F; $Ar^2$ is

[structure: pyridyl with $(R_8)_s$]

s is 1 and $R_8$ is —$CH_2CF_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is CH; n is 0; m is 1; $R_3$ is —$CH_3$; $R_1$ is —Cl; $Ar^2$ is

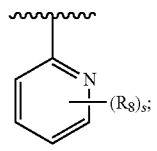

s is 1 and $R_8$ is —$CH_2CF_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is CH; n is 0; m is 1; $R_3$ is —$CH_3$; $R_1$ is —Br; $Ar^2$ is

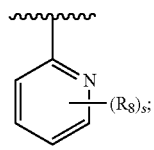

s is 1 and $R_8$ is —$CH_2CF_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is CH; n is 0; m is 1; $R_3$ is —$CH_3$; $R_1$ is —I; $Ar^2$ is

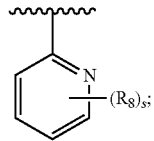

s is 1 and $R_8$ is —$CH_2CF_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is CH; n is 0; m is 1; $R_3$ is —$CH_3$; $R_1$ is —$CH_3$; $Ar^2$ is

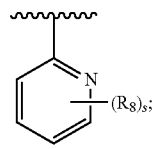

s is 1 and $R_8$ is —$CH_2CF_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is CH; n is 0; m is 1; $R_3$ is —$CH_3$; $R_1$ is —$CF_3$; $Ar^2$ is

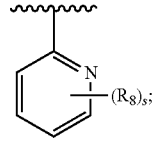

s is 1 and $R_8$ is —$CH_2CF_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is CH; n is 0; m is 1; $R_3$ is —$CH_3$; $R_1$ is —F, —Cl, —Br, or —I; $Ar^2$ is

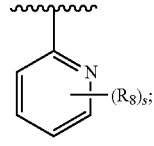

s is 1 and $R_8$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is CH; n is 0; m is 1; $R_3$ is —$CH_3$; $R_1$ is —F; $Ar^2$ is

[Structure: pyridyl group with $(R_8)_s$]

s is 1 and $R_8$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is CH; n is 0; m is 1; $R_3$ is —$CH_3$; $R_1$ is —Cl; $Ar^2$ is

[Structure: pyridyl group with $(R_8)_s$]

s is 1 and $R_8$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is CH; n is 0; m is 1; $R_3$ is —$CH_3$; $R_1$ is —Br; $Ar^2$ is

[Structure: pyridyl group with $(R_8)_s$]

s is 1 and $R_8$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is CH; n is 0; m is 1; $R_3$ is —$CH_3$; $R_1$ is —I; $Ar^2$ is

[Structure: pyridyl group with $(R_8)_s$]

s is 1 and $R_8$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is CH; n is 0; m is 1; $R_3$ is —$CH_3$; $R_1$ is —$CH_3$; $Ar^2$ is

[Structure: pyridyl group with $(R_8)_s$]

s is 1 and $R_8$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is CH; n is 0; m is 1; $R_3$ is —$CH_3$; $R_1$ is —$CF_3$; $Ar^2$ is

[Structure: pyridyl group with $(R_8)_s$]

s is 1 and $R_8$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring. In another embodiment, $R_8$ is at the 5-position of the $Ar^2$ pyridyl ring.

In another embodiment, $Ar^1$ is a pyridyl group; V is N; m is 0, and $Ar^2$ is a 5-benzodioxolyl group.

In another embodiment, $Ar^1$ is a pyridyl group; V is N; n is 0; m is 0; $R_1$ is —F, —Cl, —Br, or —I; and $Ar^2$ is a 5-benzodioxolyl group.

In another embodiment, $Ar^1$ is a pyridyl group; V is N; n is 0; m is 0; $R_1$ is —F; and $Ar^2$ is a 5-benzodioxolyl group.

In another embodiment, $Ar^1$ is a pyridyl group; V is N; n is 0; m is 0; $R_1$ is —Cl; and $Ar^2$ is a 5-benzodioxolyl group.

In another embodiment, $Ar^1$ is a pyridyl group; V is N; n is 0; m is 0; $R_1$ is —Br; and $Ar^2$ is a 5-benzodioxolyl group.

In another embodiment, $Ar^1$ is a pyridyl group; V is N; n is 0; m is 0; $R_1$ is —I; and $Ar^2$ is a 5-benzodioxolyl group.

In another embodiment, $Ar^1$ is a pyridyl group; V is N; n is 0; m is 0; $R_1$ is —CH$_3$; and $Ar^2$ is a 5-benzodioxolyl group.

In another embodiment, $Ar^1$ is a pyridyl group; V is N; n is 0; m is 0; $R_1$ is —CF$_3$; and $Ar^2$ is a 5-benzodioxolyl group.

In another embodiment, $Ar^1$ is a pyridyl group; V is N; n is 0; m is 0; $R_1$ is —F, —Cl —Br, or —I; $Ar^2$ is a 5-benzodioxolyl group; and each $R_9$ is -halo.

In another embodiment, $Ar^1$ is a pyridyl group; V is N; n is 0; m is 0; $R_1$ is —F; $Ar^2$ is a 5-benzodioxolyl group; and each $R_9$ is -halo.

In another embodiment, $Ar^1$ is a pyridyl group; V is N; n is 0; m is 0; $R_1$ is —Cl; $Ar^2$ is a 5-benzodioxolyl group; and each $R_9$ is -halo.

In another embodiment, $Ar^1$ is a pyridyl group; V is N; n is 0; m is 0; $R_1$ is —Br; $Ar^2$ is a 5-benzodioxolyl group; and each $R_9$ is -halo.

In another embodiment, $Ar^1$ is a pyridyl group; V is N; n is 0; m is 0; $R_1$ is —I; $Ar^2$ is a 5-benzodioxolyl group; and each $R_9$ is -halo.

In another embodiment, $Ar^1$ is a pyridyl group; V is N; n is 0; m is 0; $R_1$ is —CH$_3$; $Ar^2$ is a 5-benzodioxolyl group; and each $R_9$ is -halo.

In another embodiment, $Ar^1$ is a pyridyl group; V is N; n is 0; m is 0; $R_1$ is —CF$_3$; $Ar^2$ is a 5-benzodioxolyl group; and each $R_9$ is -halo.

In another embodiment, $Ar^1$ is a pyridyl group; V is N; n is 0; m is 0; $R_1$ is —F, —Cl, —Br, or —I; $Ar^2$ is a 5-benzodioxolyl group; and each $R_9$ is —Br.

In another embodiment, $Ar^1$ is a pyridyl group; V is N; n is 0; m is 0; $R_1$ is —F; $Ar^2$ is a 5-benzodioxolyl group; and each $R_9$ is —Br.

In another embodiment, $Ar^1$ is a pyridyl group; V is N; n is 0; m is 0; $R_1$ is —Cl; $Ar^2$ is a 5-benzodioxolyl group; and each $R_9$ is —Br.

In another embodiment, $Ar^1$ is a pyridyl group; V is N; n is 0; m is 0; $R_1$ is —Br; $Ar^2$ is a 5-benzodioxolyl group; and each $R_9$ is —Br.

In another embodiment, $Ar^1$ is a pyridyl group; V is N; n is 0; m is 0; $R_1$ is —I; $Ar^2$ is a 5-benzodioxolyl group; and each $R_9$ is —Br.

In another embodiment, $Ar^1$ is a pyridyl group; V is N; n is 0; m is 0; $R_1$ is —CH$_3$; $Ar^2$ is a 5-benzodioxolyl group; and each $R_9$ is —Br.

In another embodiment, $Ar^1$ is a pyridyl group; V is N; n is 0; m is 0; $R_1$ is —CF$_3$; $Ar^2$ is a 5-benzodioxolyl group; and each $R_9$ is —Br.

In another embodiment, $Ar^1$ is a pyridyl group; V is N; n is 0; m is 0; $R_1$ is —Cl, —F —Br, or —I; $Ar^2$ is a 5-benzodioxolyl group; and each $R_9$ is —F.

In another embodiment, $Ar^1$ is a pyridyl group; V is N; n is 0; m is 0; $R_1$ is —F; $Ar^2$ is a 5-benzodioxolyl group; and each $R_9$ is —F.

In another embodiment, $Ar^1$ is a pyridyl group; V is N; n is 0; m is 0; $R_1$ is —Cl; $Ar^2$ is a 5-benzodioxolyl group; and each $R_9$ is —F.

In another embodiment, $Ar^1$ is a pyridyl group; V is N; n is 0; m is 0; $R_1$ is —Br; $Ar^2$ is a 5-benzodioxolyl group; and each $R_9$ is —F.

In another embodiment, $Ar^1$ is a pyridyl group; V is N; n is 0; m is 0; $R_1$ is —I; $Ar^2$ is a 5-benzodioxolyl group; and each $R_9$ is —F.

In another embodiment, $Ar^1$ is a pyridyl group; V is N; n is 0; m is 0; $R_1$ is —CH$_3$; $Ar^2$ is a 5-benzodioxolyl group; and each $R_9$ is —F.

In another embodiment, $Ar^1$ is a pyridyl group; V is N; n is 0; m is 0; $R_1$ is —CF$_3$; $Ar^2$ is a 5-benzodioxolyl group; and each $R_9$ is —F.

In another embodiment, $Ar^1$ is a pyridyl group; V is N; n is 0; m is 0; $R_1$ is —Cl, —F, —Br, or —I; $Ar^2$ is a 5-benzodioxolyl group; and each $R_9$ is —Cl.

In another embodiment, $Ar^1$ is a pyridyl group; V is N; n is 0; m is 0; $R_1$ is —F; $Ar^2$ is a 5-benzodioxolyl group; and each $R_9$ is —Cl.

In another embodiment, $Ar^1$ is a pyridyl group; V is N; n is 0; m is 0; $R_1$ is —Cl; $Ar^2$ is a 5-benzodioxolyl group; and each $R_9$ is —Cl.

In another embodiment, $Ar^1$ is a pyridyl group; V is N; n is 0; m is 0; $R_1$ is —Br; $Ar^2$ is a 5-benzodioxolyl group; and each $R_9$ is —Cl.

In another embodiment, $Ar^1$ is a pyridyl group; V is N; n is 0; m is 0; $R_1$ is —I; $Ar^2$ is a 5-benzodioxolyl group; and each $R_9$ is —Cl.

In another embodiment, $Ar^1$ is a pyridyl group; V is N; n is 0; m is 0; $R_1$ is —CH$_3$; $Ar^2$ is a 5-benzodioxolyl group; and each $R_9$ is —Cl.

In another embodiment, $Ar^1$ is a pyridyl group; V is N; n is 0; m is 0; $R_1$ is —CF$_3$; $Ar^2$ is a 5-benzodioxolyl group and each $R_9$ is —Cl.

In another embodiment, $Ar^1$ is a pyridyl group; V is N; n is 0; m is 0; $R_1$ is —Cl, —F, —Br, or —I; $Ar^2$ is a 5-benzodioxolyl group; and each $R_9$ is —I.

In another embodiment, $Ar^1$ is a pyridyl group; V is N; n is 0; m is 0; $R_1$ is —F; $Ar^2$ is a 5-benzodioxolyl group; and each $R_9$ is —I.

In another embodiment, $Ar^1$ is a pyridyl group; V is N; n is 0; m is 0; $R_1$ is —Cl; $Ar^2$ is a 5-benzodioxolyl group; and each $R_9$ is —I.

In another embodiment, $Ar^1$ is a pyridyl group; V is N; n is 0; m is 0; $R_1$ is —Br; $Ar^2$ is a 5-benzodioxolyl group; and each $R_9$ is —I.

In another embodiment, $Ar^1$ is a pyridyl group; V is N; n is 0; m is 0; $R_1$ is —I; $Ar^2$ is a 5-benzodioxolyl group; and each $R_9$ is —I.

In another embodiment, $Ar^1$ is a pyridyl group; V is N; n is 0; m is 0; $R_1$ is —CH$_3$; $Ar^2$ is a 5-benzodioxolyl group; and each $R_9$ is —I.

In another embodiment, $Ar^1$ is a pyridyl group; V is N; n is 0; m is 0; $R_1$ is —CF$_3$; $Ar^2$ is a 5-benzodioxolyl group; and each $R_9$ is —I.

In another embodiment, $Ar^1$ is a pyridyl group; V is N; n is 0; m is 0; $R_1$ is —F, —Cl, —Br, or —I; $Ar^2$ is a 5-benzodioxolyl group; and each $R_9$ is —CH$_3$.

In another embodiment, $Ar^1$ is a pyridyl group; V is N; n is 0; m is 0; $R_1$ is —F; $Ar^2$ is a 5-benzodioxolyl group; and each $R_9$ is —CH$_3$.

In another embodiment, $Ar^1$ is a pyridyl group; V is N; n is 0; m is 0; $R_1$ is —Cl; $Ar^2$ is a 5-benzodioxolyl group; and each $R_9$ is —CH$_3$.

In another embodiment, $Ar^1$ is a pyridyl group; V is N; n is 0; m is 0; $R_1$ is —Br; $Ar^2$ is a 5-benzodioxolyl group; and each $R_9$ is —CH$_3$.

In another embodiment, $Ar^1$ is a pyridyl group; V is N; n is 0; m is 0; $R_1$ is —I; $Ar^2$ is a 5-benzodioxolyl group; and each $R_9$ is —CH$_3$.

In another embodiment, $Ar^1$ is a pyridyl group; V is N; n is 0; m is 0; $R_1$ is —CH$_3$; $Ar^2$ is a 5-benzodioxolyl group; and each $R_9$ is —CH$_3$.

In another embodiment, $Ar^1$ is a pyridyl group; V is N; n is 0; m is 0; $R_1$ is —$CF_3$; $Ar^2$ is a 5-benzodioxolyl group; and each $R_9$ is —$CH_3$.

In another embodiment, $Ar^1$ is a pyridyl group; V is N; n is 0; m is 0; $R_1$ is —F, —Cl —Br, or —I; $Ar^2$ is a 5-benzodioxolyl group; and each $R_9$ is -ethyl.

In another embodiment, $Ar^1$ is a pyridyl group; V is N; n is 0; m is 0; $R_1$ is —F; $Ar^2$ is a 5-benzodioxolyl group; and each $R_9$ is -ethyl.

In another embodiment, $Ar^1$ is a pyridyl group; V is N; n is 0; m is 0; $R_1$ is —Cl; $Ar^2$ is a 5-benzodioxolyl group; and each $R_9$ is -ethyl.

In another embodiment, $Ar^1$ is a pyridyl group; V is N; n is 0; m is 0; $R_1$ is —Br; $Ar^2$ is a 5-benzodioxolyl group; and each $R_9$ is -ethyl.

In another embodiment, $Ar^1$ is a pyridyl group; V is N; n is 0; m is 0; $R_1$ is —I; $Ar^2$ is a 5-benzodioxolyl group; and each $R_9$ is -ethyl.

In another embodiment, $Ar^1$ is a pyridyl group; V is N; n is 0; m is 0; $R_1$ is —$CH_3$; $Ar^2$ is a 5-benzodioxolyl group; and each $R_9$ is -ethyl.

In another embodiment, $Ar^1$ is a pyridyl group; V is N; n is 0; m is 0; $R_1$ is —$CF_3$; $Ar^2$ is a 5-benzodioxolyl group; and each $R_9$ is -ethyl.

In another embodiment, $Ar^1$ is a pyridyl group; V is N; n is 0; m is 0; $R_1$ is —F, —Cl, —Br, or —I; $Ar^2$ is a 5-benzodioxolyl group; and each $R_9$ is -isopropyl.

In another embodiment, $Ar^1$ is a pyridyl group; V is N; n is 0; m is 0; $R_1$ is —F; $Ar^2$ is a 5-benzodioxolyl group; and each $R_9$ is -isopropyl.

In another embodiment, $Ar^1$ is a pyridyl group; V is N; n is 0; m is 0; $R_1$ is —Cl; $Ar^2$ is a 5-benzodioxolyl group; and each $R_9$ is -isopropyl.

In another embodiment, $Ar^1$ is a pyridyl group; V is N; n is 0; m is 0; $R_1$ is —Br; $Ar^2$ is a 5-benzodioxolyl group; and each $R_9$ is -isopropyl.

In another embodiment, $Ar^1$ is a pyridyl group; V is N; n is 0; m is 0; $R_1$ is —I; $Ar^2$ is a 5-benzodioxolyl group; and each $R_9$ is -isopropyl.

In another embodiment, $Ar^1$ is a pyridyl group; V is N; n is 0; m is 0; $R_1$ is —$CH_3$; $Ar^2$ is a 5-benzodioxolyl group; and each $R_9$ is -isopropyl.

In another embodiment, $Ar^1$ is a pyridyl group; V is N; n is 0; m is 0; $R_1$ is —$CF_3$; $Ar^2$ is a 5-benzodioxolyl group; and each $R_9$ is -isopropyl.

In another embodiment, $Ar^1$ is a pyridyl group; V is N; n is 0; m is 0; $R_1$ is —F, —Cl —Br, or —I; $Ar^2$ is a 5-benzodioxolyl group; $R_9$ is -tert-butyl.

In another embodiment, $Ar^1$ is a pyridyl group; V is N; n is 0; m is 0; $R_1$ is —F; $Ar^2$ is a 5-benzodioxolyl group; and each $R_9$ is -tert-butyl.

In another embodiment, $Ar^1$ is a pyridyl group; V is N; n is 0; m is 0; $R_1$ is —Cl; $Ar^2$ is a 5-benzodioxolyl group; and each $R_9$ is -tert-butyl.

In another embodiment, $Ar^1$ is a pyridyl group; V is N; n is 0; m is 0; $R_1$ is —Br; $Ar^2$ is a 5-benzodioxolyl group; and each $R_9$ is -tert-butyl.

In another embodiment, $Ar^1$ is a pyridyl group; V is N; n is 0; m is 0; $R_1$ is —I; $Ar^2$ is a 5-benzodioxolyl group; and each $R_9$ is -tert-butyl.

In another embodiment, $Ar^1$ is a pyridyl group; V is N; n is 0; m is 0; $R_1$ is —$CH_3$; $Ar^2$ is a 5-benzodioxolyl group; and each $R_9$ is -tert-butyl.

In another embodiment, $Ar^1$ is a pyridyl group; V is N; n is 0; m is 0; $R_1$ is —$CF_3$; $Ar^2$ is a 5-benzodioxolyl group; and each $R_9$ is -tert-butyl.

In another embodiment, $Ar^1$ is a pyridyl group; V is N; n is 0; m is 1; $R_3$ is —$CH_3$; $R_1$ is —F, —Cl, —Br, or —I; and $Ar^2$ is a 5-benzodioxolyl group. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —F; and $Ar^2$ is a 5-benzodioxolyl group. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Cl; and $Ar^2$ is a 5-benzodioxolyl group. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Br; and $Ar^2$ is a 5-benzodioxolyl group. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —I; and $Ar^2$ is a 5-benzodioxolyl group. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CH_3$; and $Ar^2$ is a 5-benzodioxolyl group. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CF_3$; and $Ar^2$ is a 5-benzodioxolyl group. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —F, —Cl, —Br, or —I; $Ar^2$ is a 5-benzodioxolyl group; and each $R_9$ is -halo. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —F; $Ar^2$ is a 5-benzodioxolyl group; and each $R_9$ is -halo. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Cl; $Ar^2$ is a 5-benzodioxolyl group; and each $R_9$ is -halo. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Br; $Ar^2$ is a 5-benzodioxolyl group; and each $R_9$ is -halo. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —I; $Ar^2$ is a 5-benzodioxolyl group; and each $R_9$ is -halo. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CH_3$; $Ar^2$ is a 5-benzodioxolyl group; and each $R_9$ is -halo. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CF_3$; $Ar^2$ is a 5-benzodioxolyl group; and each $R_9$ is -halo. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —F, —Cl, —Br, or —I; $Ar^2$ is a 5-benzodioxolyl group; and each $R_9$ is —Br. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —F; $Ar^2$ is a 5-benzodioxolyl group; and each $R_9$ is —Br. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Cl; $Ar^2$ is a 5-benzodioxolyl group; and each $R_9$ is —Br. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Br; $Ar^2$ is a 5-benzodioxolyl group; and each $R_9$ is —Br. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —I; $Ar^2$ is a 5-benzodioxolyl group; and each $R_9$ is —Br. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CH_3$; $Ar^2$ is a 5-benzodioxolyl group; and each $R_9$ is —Br. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CF_3$; $Ar^2$ is a 5-benzodioxolyl group; and each $R_9$ is —Br. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Cl; —F —Br, or —I; $Ar^2$ is a 5-benzodioxolyl group; and each $R_9$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —F; $Ar^2$ is a 5-benzodioxolyl group; and each $R_9$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, Art is a pyridyl group; V is N; n is 0; m is 1; $R_3$ is —$CH_3$; $R_1$ is —Cl; $Ar^2$ is a 5-benzodioxolyl group; and each $R_9$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Br; $Ar^2$ is a 5-benzodioxolyl group; and each $R_9$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —I; $Ar^2$ is a 5-benzodioxolyl group; and each $R_9$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CH_3$; $Ar^2$ is a 5-benzodioxolyl group; and each $R_9$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CF_3$; $Ar^2$ is a 5-benzodioxolyl group; and each $R_9$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is $CH_3$; $R_1$ is —Cl, —F —Br, or —I; $Ar^2$ is a 5-benzodioxolyl group; and each $R_9$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —F; $Ar^2$ is a 5-benzodioxolyl group; and each $R_9$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Cl; $Ar^2$ is a 5-benzodioxolyl group; and each $R_9$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Br; $Ar^2$ is a 5-benzodioxolyl group; and each $R_9$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —I; $Ar^2$ is a 5-benzodioxolyl group; and each $R_9$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CH_3$; $Ar^2$ is a 5-benzodioxolyl group; and each $R_9$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CF_3$; $Ar^2$ is a 5-benzodioxolyl group; and each $R_9$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Cl, —F, —Br, or —I, $Ar^2$ is a 5-benzodioxolyl group; and each $R_9$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —F; $Ar^2$ is a 5-benzodioxolyl group; and each $R_9$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Cl; $Ar^2$ is a 5-benzodioxolyl group; and each $R_9$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Br; $Ar^2$ is a 5-benzodioxolyl group; and each $R_9$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —I; $Ar^2$ is a 5-benzodioxolyl group; and each $R_9$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CH_3$; $Ar^2$ is a 5-benzodioxolyl group; and each $R_9$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CF_3$; $Ar^2$ is a 5-benzodioxolyl group; and each $R_9$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —F, —Cl, —Br, or —I; $Ar^2$ is a 5-benzodioxolyl group; and each $R_9$ is —$CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —F; $Ar^2$ is a 5-benzodioxolyl group; and each $R_9$ is —$CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Cl; $Ar^2$ is a 5-benzodioxolyl group; and each $R_9$ is —$CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Br; $Ar^2$ is a 5-benzodioxolyl group; and each $R_9$ is —$CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —I; $Ar^2$ is a 5-benzodioxolyl group; and each $R_9$ is —$CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CH_3$; $Ar^2$ is a 5-benzodioxolyl group; and each $R_9$ is —$CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CF_3$; $Ar^2$ is a 5-benzodioxolyl group; and each $R_9$ is —$CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —F, —Cl, —Br, or —I; $Ar^2$ is a 5-benzodioxolyl group; and each $R_9$ is -ethyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —F; $Ar^2$ is a 5-benzodioxolyl group; and each $R_9$ is -ethyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Cl; $Ar^2$ is a 5-benzodioxolyl group; and each $R_9$ is -ethyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Br; $Ar^2$ is a 5-benzodioxolyl group; and each $R_9$ is -ethyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —I; $Ar^2$ is a 5-benzodioxolyl group; and each $R_9$ is -ethyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CH_3$; $Ar^2$ is a 5-benzodioxolyl group; and each $R_9$ is -ethyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CF_3$; $Ar^2$ is a 5-benzodioxolyl group; and each $R_9$ is -ethyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —F, —Cl, —Br, or —I; $Ar^2$ is a 5-benzodioxolyl group; and each $R_9$ is -isopropyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —F; $Ar^2$ is a 5-benzodioxolyl group; and each $R_9$ is -isopropyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Cl; $Ar^2$ is a 5-benzodioxolyl group; and each $R_9$ is -isopropyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Br; $Ar^2$ is a 5-benzodioxolyl group; and each $R_9$ is -isopropyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —I; $Ar^2$ is a 5-benzodioxolyl group; and each $R_9$ is -isopropyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CH_3$; $Ar^2$ is a 5-benzodioxolyl group; and each $R_9$ is -isopropyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CF_3$; $Ar^2$ is a 5-benzodioxolyl group; and each $R_9$ is -isopropyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —F, —Cl, —Br, or —I; $Ar^2$ is a 5-benzodioxolyl group; and each $R_9$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —F; $Ar^2$ is a 5-benzodioxolyl group; and each $R_9$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Cl; $Ar^2$ is a 5-benzodioxolyl group; and each $R_9$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —Br; $Ar^2$ is a 5-benzodioxolyl group; and each $R_9$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —I; $Ar^2$ is a 5-benzodioxolyl group; and each $R_9$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CH_3$; $Ar^2$ is a 5-benzodioxolyl group; and each $R_9$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is N; n is 0; m is 1; $R_3$ is —$CH_3$; $R_1$ is —$CF_3$; $Ar^2$ is a 5-benzodioxolyl group; and each $R_9$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group, V is CH; m is 0, and $Ar^2$ is a 5-benzodioxolyl group.

In another embodiment, $Ar^1$ is a pyridyl group; V is CH; n is 0; m is 0; $R_1$ is —F, —Cl, —Br, or —I; and $Ar^2$ is a 5-benzodioxolyl group.

In another embodiment, $Ar^1$ is a pyridyl group; V is CH; n is 0; m is 0; $R_1$ is —F; and $Ar^2$ is a 5-benzodioxolyl group.

In another embodiment, $Ar^1$ is a pyridyl group; V is CH; n is 0; m is 0; $R_1$ is —Cl; and $Ar^2$ is a 5-benzodioxolyl group.

In another embodiment, $Ar^1$ is a pyridyl group; V is CH; n is 0; m is 0; $R_1$ is —Br; and $Ar^2$ is a 5-benzodioxolyl group.

In another embodiment, $Ar^1$ is a pyridyl group; V is CH; n is 0; m is 0; $R_1$ is —I; and $Ar^2$ is a 5-benzodioxolyl group.

In another embodiment, $Ar^1$ is a pyridyl group; V is CH; n is 0; m is 0; $R_1$ is —$CH_3$; and $Ar^2$ is a 5-benzodioxolyl group.

In another embodiment, $Ar^1$ is a pyridyl group; V is CH; n is 0; m is 0; $R_1$ is —$CF_3$; and $Ar^2$ is a 5-benzodioxolyl group.

In another embodiment, $Ar^1$ is a pyridyl group; V is CH; n is 0; m is 0; $R_1$ is —F, —Cl, —Br, or —I; $Ar^2$ is a 5-benzodioxolyl group; and each $R_9$ is -halo.

In another embodiment, $Ar^1$ is a pyridyl group; V is CH; n is 0; m is 0; $R_1$ is —F; $Ar^2$ is a 5-benzodioxolyl group; and each $R_9$ is -halo.

In another embodiment, $Ar^1$ is a pyridyl group; V is CH; n is 0; m is 0; $R_1$ is —Cl; $Ar^2$ is a 5-benzodioxolyl group; and each $R_9$ is -halo.

In another embodiment, $Ar^1$ is a pyridyl group; V is CH; n is 0; m is 0; $R_1$ is —Br; $Ar^2$ is a 5-benzodioxolyl group; and each $R_9$ is -halo.

In another embodiment, $Ar^1$ is a pyridyl group; V is CH; n is 0; m is 0; $R_1$ is —I; $Ar^2$ is a 5-benzodioxolyl group; and each $R_9$ is -halo.

In another embodiment, $Ar^1$ is a pyridyl group; V is CH; n is 0; m is 0; $R_1$ is —$CH_3$; and $Ar^2$ is a 5-benzodioxolyl group.

In another embodiment, $Ar^1$ is a pyridyl group; V is CH; n is 0; m is 0; $R_1$ is —$CF_3$; $Ar^2$ is a 5-benzodioxolyl group; and each $R_9$ is -halo.

In another embodiment, $Ar^1$ is a pyridyl group; V is CH; n is 0; m is 0; $R_1$ is —F, —Cl, —Br, or —I; $Ar^2$ is a 5-benzodioxolyl group; and each $R_9$ is —Br.

In another embodiment, $Ar^1$ is a pyridyl group; V is CH; n is 0; m is 0; $R_1$ is —F; $Ar^2$ is a 5-benzodioxolyl group; and each $R_9$ is —Br.

In another embodiment, $Ar^1$ is a pyridyl group; V is CH; n is 0; m is 0; $R_1$ is —Cl; $Ar^2$ is a 5-benzodioxolyl group; and each $R_9$ is —Br.

In another embodiment, $Ar^1$ is a pyridyl group; V is CH; n is 0; m is 0; $R_1$ is —Br; $Ar^2$ is a 5-benzodioxolyl group; and each $R_9$ is —Br.

In another embodiment, $Ar^1$ is a pyridyl group; V is CH; n is 0; m is 0; $R_1$ is —I; $Ar^2$ is a 5-benzodioxolyl group; and each $R_9$ is —Br.

In another embodiment, $Ar^1$ is a pyridyl group; V is CH; n is 0; m is 0; $R_1$ is —$CH_3$; $Ar^2$ is a 5-benzodioxolyl group; and each $R_9$ is —Br.

In another embodiment, $Ar^1$ is a pyridyl group; V is CH; n is 0; m is 0; $R_1$ is —$CF_3$; $Ar^2$ is a 5-benzodioxolyl group; and each $R_9$ is —Br.

In another embodiment, $Ar^1$ is a pyridyl group; V is CH; n is 0; m is 0; $R_1$ is —Cl, —F —Br, or —I; $Ar^2$ is a 5-benzodioxolyl group; and each $R_9$ is —F.

In another embodiment, $Ar^1$ is a pyridyl group; V is CH; n is 0; m is 0; $R_1$ is —F; $Ar^2$ is a 5-benzodioxolyl group; and each $R_9$ is —F.

In another embodiment, $Ar^1$ is a pyridyl group; V is CH; n is 0; m is 0; $R_1$ is —Cl; $Ar^2$ is a 5-benzodioxolyl group; and each $R_9$ is —F.

In another embodiment, $Ar^1$ is a pyridyl group; V is CH; n is 0; m is 0; $R_1$ is —Br; $Ar^2$ is a 5-benzodioxolyl group; and each $R_9$ is —F.

In another embodiment, $Ar^1$ is a pyridyl group; V is CH; n is 0; m is 0; $R_1$ is —I; $Ar^2$ is a 5-benzodioxolyl group; and each $R_9$ is —F.

In another embodiment, $Ar^1$ is a pyridyl group; V is CH; n is 0; m is 0; $R_1$ is —$CH_3$; $Ar^2$ is a 5-benzodioxolyl group; and each $R_9$ is —F.

In another embodiment, $Ar^1$ is a pyridyl group; V is CH; n is 0; m is 0; $R_1$ is —$CF_3$; $Ar^2$ is a 5-benzodioxolyl group; and each $R_9$ is —F.

In another embodiment, $Ar^1$ is a pyridyl group; V is CH; n is 0; m is 0; $R_1$ is —Cl, —F —Br, or —I; $Ar^2$ is a 5-benzodioxolyl group; and each $R_9$ is —Cl.

In another embodiment, $Ar^1$ is a pyridyl group; V is CH; n is 0; m is 0; $R_1$ is —F; $Ar^2$ is a 5-benzodioxolyl group; and each $R_9$ is —Cl.

In another embodiment, $Ar^1$ is a pyridyl group; V is CH; n is 0; m is 0; $R_1$ is —Cl; $Ar^2$ is a 5-benzodioxolyl group; and each $R_9$ is —Cl.

In another embodiment, $Ar^1$ is a pyridyl group; V is CH; n is 0; m is 0; $R_1$ is —Br; $Ar^2$ is a 5-benzodioxolyl group; and each $R_9$ is —Cl.

In another embodiment, $Ar^1$ is a pyridyl group; V is CH; n is 0; m is 0; $R_1$ is —I; $Ar^2$ is a 5-benzodioxolyl group; and each $R_9$ is —Cl.

In another embodiment, $Ar^1$ is a pyridyl group; V is CH; n is 0; m is 0; $R_1$ is —CH$_3$; $Ar^2$ is a 5-benzodioxolyl group; and each $R_9$ is —Cl.

In another embodiment, $Ar^1$ is a pyridyl group; V is CH; n is 0; m is 0; $R_1$ is —CF$_3$; $Ar^2$ is a 5-benzodioxolyl group and each $R_9$ is —Cl.

In another embodiment, $Ar^1$ is a pyridyl group; V is CH; n is 0; m is 0; $R_1$ is —Cl, —F, —Br, or —I, $Ar^2$ is a 5-benzodioxolyl group; and each $R_9$ is —I.

In another embodiment, $Ar^1$ is a pyridyl group; V is CH; n is 0; m is 0; $R_1$ is —F; $Ar^2$ is a 5-benzodioxolyl group; and each $R_9$ is —I.

In another embodiment, $Ar^1$ is a pyridyl group; V is CH; n is 0; m is 0; $R_1$ is —Cl; $Ar^2$ is a 5-benzodioxolyl group; and each $R_9$ is —I.

In another embodiment, $Ar^1$ is a pyridyl group; V is CH; n is 0; m is 0; $R_1$ is —Br; $Ar^2$ is a 5-benzodioxolyl group; and each $R_9$ is —I.

In another embodiment, $Ar^1$ is a pyridyl group; V is CH; n is 0; m is 0; $R_1$ is —I; $Ar^2$ is a 5-benzodioxolyl group; and each $R_9$ is —I.

In another embodiment, $Ar^1$ is a pyridyl group; V is CH; n is 0; m is 0; $R_1$ is —CH$_3$; and $Ar^2$ is a 5-benzodioxolyl group.

In another embodiment, $Ar^1$ is a pyridyl group; V is CH; n is 0; m is 0; $R_1$ is —CF$_3$; $Ar^2$ is a 5-benzodioxolyl group; and each $R_9$ is —I.

In another embodiment, $Ar^1$ is a pyridyl group; V is CH; n is 0; m is 0; $R_1$ is —F, —Cl, —Br, or —I; $Ar^2$ is a 5-benzodioxolyl group; and each $R_9$ is —CH$_3$.

In another embodiment, $Ar^1$ is a pyridyl group; V is CH; n is 0; m is 0; $R_1$ is —F; $Ar^2$ is a 5-benzodioxolyl group; and each $R_9$ is —CH$_3$.

In another embodiment, $Ar^1$ is a pyridyl group; V is CH; n is 0; m is 0; $R_1$ is —Cl; $Ar^2$ is a 5-benzodioxolyl group; and each $R_9$ is —CH$_3$.

In another embodiment, $Ar^1$ is a pyridyl group; V is CH; n is 0; m is 0; $R_1$ is —Br; $Ar^2$ is a 5-benzodioxolyl group; and each $R_9$ is —CH$_3$.

In another embodiment, $Ar^1$ is a pyridyl group; V is CH; n is 0; m is 0; $R_1$ is —I; $Ar^2$ is a 5-benzodioxolyl group; and each $R_9$ is —CH$_3$.

In another embodiment, $Ar^1$ is a pyridyl group; V is CH; n is 0; m is 0; $R_1$ is —CH$_3$; $Ar^2$ is a 5-benzodioxolyl group; and each $R_9$ is —CH$_3$.

In another embodiment, $Ar^1$ is a pyridyl group; V is CH; n is 0; m is 0; $R_1$ is —CF$_3$; $Ar^2$ is a 5-benzodioxolyl group; and each $R_9$ is —CH$_3$.

In another embodiment, $Ar^1$ is a pyridyl group; V is CH; n is 0; m is 0; $R_1$ is —F, —Cl, —Br, or —I; $Ar^2$ is a 5-benzodioxolyl group; and each $R_9$ is -ethyl.

In another embodiment, $Ar^1$ is a pyridyl group; V is CH; n is 0; m is 0; $R_1$ is —F; $Ar^2$ is a 5-benzodioxolyl group; and each $R_9$ is -ethyl.

In another embodiment, $Ar^1$ is a pyridyl group; V is CH; n is 0; m is 0; $R_1$ is —Cl; $Ar^2$ is a 5-benzodioxolyl group; and each $R_9$ is -ethyl.

In another embodiment, $Ar^1$ is a pyridyl group; V is CH; n is 0; m is 0; $R_1$ is —Br; $Ar^2$ is a 5-benzodioxolyl group; and each $R_9$ is -ethyl.

In another embodiment, $Ar^1$ is a pyridyl group; V is CH; n is 0; m is 0; $R_1$ is —I; $Ar^2$ is a 5-benzodioxolyl group; and each $R_9$ is -ethyl.

In another embodiment, $Ar^1$ is a pyridyl group; V is CH; n is 0; m is 0; $R_1$ is —CH$_3$; $Ar^2$ is a 5-benzodioxolyl group; and each $R_9$ is -ethyl.

In another embodiment, $Ar^1$ is a pyridyl group; V is CH; n is 0; m is 0; $R_1$ is —CF$_3$; $Ar^2$ is a 5-benzodioxolyl group; and each $R_9$ is -ethyl.

In another embodiment, $Ar^1$ is a pyridyl group; V is CH; n is 0; m is 0; $R_1$ is —F, —Cl, —Br, or —I; $Ar^2$ is a 5-benzodioxolyl group; and each $R_9$ is -isopropyl.

In another embodiment, $Ar^1$ is a pyridyl group; V is CH; n is 0; m is 0; $R_1$ is —F; $Ar^2$ is a 5-benzodioxolyl group; and each $R_9$ is -isopropyl.

In another embodiment, $Ar^1$ is a pyridyl group; V is CH; n is 0; m is 0; $R_1$ is —Cl; $Ar^2$ is a 5-benzodioxolyl group; and each $R_9$ is -isopropyl.

In another embodiment, $Ar^1$ is a pyridyl group; V is CH; n is 0; m is 0; $R_1$ is —Br; $Ar^2$ is a 5-benzodioxolyl group; and each $R_9$ is -isopropyl.

In another embodiment, $Ar^1$ is a pyridyl group; V is CH; n is 0; m is 0; $R_1$ is —I; $Ar^2$ is a 5-benzodioxolyl group; and each $R_9$ is -isopropyl.

In another embodiment, $Ar^1$ is a pyridyl group; V is CH; n is 0; m is 0; $R_1$ is —CH$_3$; $Ar^2$ is a 5-benzodioxolyl group; and each $R_9$ is -isopropyl.

In another embodiment, $Ar^1$ is a pyridyl group; V is CH; n is 0; m is 0; $R_1$ is —CF$_3$; $Ar^2$ is a 5-benzodioxolyl group; and each $R_9$ is -isopropyl.

In another embodiment, $Ar^1$ is a pyridyl group; V is CH; n is 0; m is 0; $R_1$ is —F, —Cl, —Br, or —I; $Ar^2$ is a 5-benzodioxolyl group; each $R_9$ is -tert-butyl.

In another embodiment, $Ar^1$ is a pyridyl group; V is CH; n is 0; m is 0; $R_1$ is —F; $Ar^2$ is a 5-benzodioxolyl group; and each $R_9$ is -tert-butyl.

In another embodiment, $Ar^1$ is a pyridyl group; V is CH; n is 0; m is 0; $R_1$ is —Cl; $Ar^2$ is a 5-benzodioxolyl group; and each $R_9$ is -tert-butyl.

In another embodiment, $Ar^1$ is a pyridyl group; V is CH; n is 0; m is 0; $R_1$ is —Br; $Ar^2$ is a 5-benzodioxolyl group; and each $R_9$ is -tert-butyl.

In another embodiment, $Ar^1$ is a pyridyl group; V is CH; n is 0; m is 0; $R_1$ is —I; $Ar^2$ is a 5-benzodioxolyl group; and each $R_9$ is -tert-butyl.

In another embodiment, $Ar^1$ is a pyridyl group; V is CH; n is 0; m is 0; $R_1$ is —CH$_3$; $Ar^2$ is a 5-benzodioxolyl group; and each $R_9$ is -tert-butyl.

In another embodiment, $Ar^1$ is a pyridyl group; V is CH; n is 0; m is 0; $R_1$ is —CF$_3$; $Ar^2$ is a 5-benzodioxolyl group; and each $R_9$ is -tert-butyl.

In another embodiment, $Ar^1$ is a pyridyl group; V is CH; n is 0; m is 1; $R_3$ is —CH$_3$; $R_1$ is —F, —Cl, —Br, or —I; and $Ar^2$ is a 5-benzodioxolyl group. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —CH$_3$; $R_1$ is —F; and $Ar^2$ is a 5-benzodioxolyl group. In another embodiment, the $R_3$ group is attached to the 3-, 5- or 6-position of the cyclo(hetero)alkenyl ring and the carbon atom to which the $R_3$ group is attached has the (R)

configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Cl; and $Ar^2$ is a 5-benzodioxolyl group. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Br; and $Ar^2$ is a 5-benzodioxolyl group. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —I; and $Ar^2$ is a 5-benzodioxolyl group. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CH_3$; and $Ar^2$ is a 5-benzodioxolyl group. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CF_3$; and $Ar^2$ is a 5-benzodioxolyl group. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F, —Cl, —Br, or —I; $Ar^2$ is a 5-benzodioxolyl group; and each $R_9$ is -halo. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F; $Ar^2$ is a 5-benzodioxolyl group; and each $R_9$ is -halo. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Cl; $Ar^2$ is a 5-benzodioxolyl group; and each $R_9$ is -halo. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Br; $Ar^2$ is a 5-benzodioxolyl group; and each $R_9$ is -halo. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —I; $Ar^2$ is a 5-benzodioxolyl group; and each $R_9$ is -halo. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CH_3$; $Ar^2$ is a 5-benzodioxolyl group; and each $R_9$ is -halo. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CF_3$; $Ar^2$ is a 5-benzodioxolyl group; and each $R_9$ is -halo. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F, —Cl, —Br, or —I; $Ar^2$ is a 5-benzodioxolyl group; and each $R_9$ is —Br. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F; $Ar^2$ is a 5-benzodioxolyl group; and each $R_9$ is —Br. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Cl; $Ar^2$ is a 5-benzodioxolyl group; and each $R_9$ is —Br. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Br; $Ar^2$ is a 5-benzodioxolyl group; and each $R_9$ is —Br. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —I; $Ar^2$ is a 5-benzodioxolyl group; and each $R_9$ is —Br. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CH_3$; $Ar^2$ is a 5-benzodioxolyl group; and each $R_9$ is —Br. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CF_3$; $Ar^2$ is a 5-benzodioxolyl group; and each $R_9$ is —Br. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Cl, —F —Br, or —I; $Ar^2$ is a 5-benzodioxolyl group; and each $R_9$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F; $Ar^2$ is a 5-benzodioxolyl group; and each $R_9$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Cl; $Ar^2$ is a 5-benzodioxolyl group; and each $R_9$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Br; $Ar^2$ is a 5-benzodioxolyl group; and each $R_9$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —I; $Ar^2$ is a 5-benzodioxolyl group; and each $R_9$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CH_3$; $Ar^2$ is a 5-benzodioxolyl group; and each $R_9$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CF_3$; $Ar^2$ is a 5-benzodioxolyl group; and each $R_9$ is —F. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is $CH_3$; $R_1$ is —Cl, —F —Br, or —I; $Ar^2$ is a 5-benzodioxolyl group; and each $R_9$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F; $Ar^2$ is a 5-benzodioxolyl group; and each $R_9$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Cl; $Ar^2$ is a 5-benzodioxolyl group; and each $R_9$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Br; $Ar^2$ is a 5-benzodioxolyl group; and each $R_9$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —I; $Ar^2$ is a 5-benzodioxolyl group; and each $R_9$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CH_3$; $Ar^2$ is a 5-benzodioxolyl group; and each $R_9$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CF_3$; $Ar^2$ is a 5-benzodioxolyl group; and each $R_9$ is —Cl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Cl, —F, —Br, or —I, $Ar^2$ is a 5-benzodioxolyl group; and each $R_9$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F; $Ar^2$ is a 5-benzodioxolyl group; and each $R_9$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Cl; $Ar^2$ is a 5-benzodioxolyl group; and each $R_9$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Br; $Ar^2$ is a 5-benzodioxolyl group; and each $R_9$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —I; $Ar^2$ is a 5-benzodioxolyl group; and each $R_9$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CH_3$; $Ar^2$ is a 5-benzodioxolyl group; and each $R_9$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CF_3$; $Ar^2$ is a 5-benzodioxolyl group; and each $R_9$ is —I. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F, —Cl, —Br, or —I; $Ar^2$ is a 5-benzodioxolyl group; and each $R_9$ is —$CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F; $Ar^2$ is a 5-benzodioxolyl group; and each $R_9$ is —$CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Cl; $Ar^2$ is a 5-benzodioxolyl group; and each $R_9$ is —$CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Br; $Ar^2$ is a 5-benzodioxolyl group; and each $R_9$ is —$CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —I; $Ar^2$ is a 5-benzodioxolyl group; and each $R_9$ is —$CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CH_3$; $Ar^2$ is a 5-benzodioxolyl group; and each $R_9$ is —$CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CF_3$; $Ar^2$ is a 5-benzodioxolyl group; and each $R_9$ is —$CH_3$. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F, —Cl, —Br, or —I; $Ar^2$ is a 5-benzodioxolyl group; and each $R_9$ is -ethyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F; $Ar^2$ is a 5-benzodioxolyl group; and each $R_9$ is -ethyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Cl; $Ar^2$ is a 5-benzodioxolyl group; and each $R_9$ is -ethyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Br; $Ar^2$ is a 5-benzodioxolyl group; and each $R_9$ is -ethyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —I; $Ar^2$ is a 5-benzodioxolyl group; and each $R_9$ is -ethyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CH_3$; $Ar^2$ is a 5-benzodioxolyl group; and each $R_9$ is -ethyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CF_3$; $Ar^2$ is a 5-benzodioxolyl group; and each $R_9$ is -ethyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F, —Cl, —Br, or —I; $Ar^2$ is a 5-benzodioxolyl group; and each $R_9$ is -isopropyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F; $Ar^2$ is a 5-benzodioxolyl group; and each $R_9$ is -isopropyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Cl; $Ar^2$ is a 5-benzodioxolyl group; and each $R_9$ is -isopropyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Br; $Ar^2$ is a 5-benzodioxolyl group; and each $R_9$ is -isopropyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —I; $Ar^2$ is a 5-benzodioxolyl group; and each $R_9$ is -isopropyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CH_3$; $Ar^2$ is a 5-benzodioxolyl group; and each $R_9$ is -isopropyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CF_3$; $Ar^2$ is a 5-benzodioxolyl group; and each $R_9$ is -isopropyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F, —Cl, —Br, or —I; $Ar^2$ is a 5-benzodioxolyl group; and each $R_9$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —F; $Ar^2$ is a 5-benzodioxolyl group; and each $R_9$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Cl; $Ar^2$ is a 5-benzodioxolyl group; and each $R_9$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —Br; $Ar^2$ is a 5-benzodioxolyl group; and each $R_9$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —I; $Ar^2$ is a 5-benzodioxolyl group; and each $R_9$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CH_3$; $Ar^2$ is a 5-benzodioxolyl group; and each $R_9$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In another embodiment, $Ar^1$ is a pyridyl group; V is CH; n is 0; m is 1; $R_3$ is —$CH_3$; $R_1$ is —$CF_3$; $Ar^2$ is a 5-benzodioxolyl group; and each $R_9$ is -tert-butyl. In another embodiment, the $R_3$ group is attached to the 3-, 5- or 6-position of the cyclo(hetero)alkenyl ring and the carbon atom to which the $R_3$ group is attached has the (R) configuration. In another embodiment, the $R_3$ group is attached to the 3-, 5- or 6-position of the cyclo(hetero)alkenyl ring and the carbon atom to which the $R_3$ group is attached has the (S) configuration. In yet another embodiment, the $R_3$ group is attached to the 2-position of the cyclo(hetero)alkenyl ring.

In the Cyclo(hetero)alkenyl Compounds that have an $R_3$ group, the $R_3$ group can be attached to the carbon at the 2-, 3-, 5- or 6-position of the cyclo(hetero)alkenyl ring. In one embodiment, the $R_3$ group is attached to the carbon at the 3-position of the cyclo(hetero)alkenyl ring. In another embodiment, the $R_3$ group is attached to the carbon at the 5-position of the cyclo(hetero)alkenyl ring. In another embodiment, the $R_3$ group is attached to the carbon at the 6-position of the cyclo(hetero)alkenyl ring. In another embodiment, the $R_3$ group is attached to the carbon at the 2-position of the In one embodiment, the Cyclo(hetero)alkenyl Compound has an $R_3$ group; the carbon atom to which the $R_3$ group is attached is at the 3-, 5- or 6-position of the tetrahydropiperidine ring; and the carbon atom to which the $R_3$ group is attached has the (R) configuration. In another embodiment, the Cyclo(hetero)alkenyl Compound has an $R_3$ group; the carbon atom to which the $R_3$ group is attached is at the 3-, 5- or 6-position of the tetrahydropiperidine ring; and the carbon atom to which the $R_3$ group is attached has the (S) configuration.

In another embodiment, the Cyclo(hetero)alkenyl Compound has an $R_3$ group, the $R_3$ group is attached to the carbon that is at the 3-position of the tetrahydropiperidine ring, and the carbon to which the $R_3$ group is attached is in the (R) configuration. In another embodiment, the Cyclo(hetero)alkenyl Compound has an $R_3$ group, the $R_3$ group is attached to the carbon that is at the 3-position of the tetrahydropiperidine ring, the carbon to which the $R_3$ group is attached is in the (R) configuration, and $R_3$ is —($C_1$-$C_4$)alkyl unsubstituted or substituted with one or more halo groups. In another embodiment, the Cyclo(hetero)alkenyl Compound has an $R_3$ group, the $R_3$ group is attached to the carbon that is at the 3-position of the tetrahydropiperidine ring, the carbon to which the $R_3$ group is attached is in the (R) configuration, and $R_3$ is —$CH_3$. In another embodiment, the Cyclo(hetero)alkenyl Compound has an $R_3$ group, the $R_3$ group is attached to the carbon that is at the 3-position of the tetrahydropiperidine ring, the carbon to which the $R_3$ group is attached is in the (R) configuration, and $R_3$ is —$CF_3$. In another embodiment, the Cyclo(hetero)alkenyl Compound has an $R_3$ group, the $R_3$ group is attached to the carbon that is at the 3-position of the tetrahydropiperidine ring, the carbon to which the $R_3$ group is attached is in the (R) configuration, and $R_3$ is —$CH_2CH_3$.

In another embodiment, the Cyclo(hetero)alkenyl Compound has an $R_3$ group, the $R_3$ group is attached to the carbon atom at the 6-position of the tetrahydropiperidine ring, and the carbon to which the $R_3$ group is attached is in the (R) configuration. In another embodiment, the Cyclo(hetero)alkenyl Compound has an $R_3$ group, the $R_3$ group is attached to the carbon atom at the 6-position of the tetrahydropiperidine ring, the carbon to which the $R_3$ group is attached is in the (R) configuration, and $R_3$ is —$(C_1$-$C_4)$alkyl unsubstituted or substituted with one or more halo groups. In another embodiment, the Cyclo(hetero)alkenyl Compound has an $R_3$ group, the $R_3$ group is attached to the carbon atom at the 6-position of the tetrahydropiperidine ring, the carbon to which the $R_3$ group is attached is in the (R) configuration, and $R_3$ is —$CH_3$. In another embodiment, the Cyclo(hetero)alkenyl Compound has an $R_3$ group, the $R_3$ group is attached to the carbon atom at the 6-position of the tetrahydropiperidine ring, the carbon to which the $R_3$ group is attached is in the (R) configuration, and $R_3$ is —$CF_3$. In another embodiment, the Cyclo(hetero)alkenyl Compound has an $R_3$ group, the $R_3$ group is attached to the carbon atom at the 6-position of the tetrahydropiperidine ring, the carbon to which the $R_3$ group is attached is in the (R) configuration, and $R_3$ is —$CH_2CH_3$.

In another embodiment, the Cyclo(hetero)alkenyl Compound has an $R_3$ group, the $R_3$ group is attached to the carbon atom at the 5-position of the tetrahydropiperidine ring, and the carbon to which the $R_3$ group is attached is in the (R) configuration. In another embodiment, the Cyclo(hetero)alkenyl Compound has an $R_3$ group, the $R_3$ group is attached to the carbon atom at the 5-position of the tetrahydrorpiperidine ring, the carbon to which the $R_3$ group is attached is in the (R) configuration, and $R_3$ is —$(C_1$-$C_4)$alkyl unsubstituted or substituted with one or more halo groups. In another embodiment, the Cyclo(hetero)alkenyl Compound has an $R_3$ group, the $R_3$ group is attached to the carbon atom at the 5-position of the tetrahydropiperidine ring, the carbon to which the $R_3$ group is attached is in the (R) configuration, and $R_3$ is —$CH_3$. In another embodiment, the Cyclo(hetero)alkenyl Compound has an $R_3$ group, the $R_3$ group is attached to the carbon atom at the 5-position of the tetrahydropiperidine ring, the carbon to which the $R_3$ group is attached is in the (R) configuration, and $R_3$ is —$CF_3$. In another embodiment, the Cyclo(hetero)alkenyl Compound has an $R_3$ group, the $R_3$ group is attached to the carbon atom at the 5-position of the tetrahydropiperidine ring. The $R_3$ group is in the (R) configuration, and $R_3$ is —$CH_2CH_3$.

In another embodiment, the Cyclo(hetero)alkenyl Compound has an $R_3$ group, the $R_3$ group is attached to the carbon that is at the 3-position of the tetrahydropiperidine ring, and the carbon to which the $R_3$ group is attached is in the (S) configuration. In another embodiment, the Cyclo(hetero)alkenyl Compound has an $R_3$ group, the $R_3$ group is attached to the carbon that is at the 3-position of the tetrahydropiperidine ring, the carbon to which the $R_3$ group is attached is in the (S) configuration, and $R_3$ is —$(C_1$-$C_4)$alkyl unsubstituted or substituted with one or more halo groups. In another embodiment, the Cyclo(hetero)alkenyl Compound has an $R_3$ group, the $R_3$ group is attached to the carbon that is at the 3-position of the tetrahydropiperidine ring, the carbon to which the $R_3$ group is attached is in the (S) configuration, and $R_3$ is —$CH_3$. In another embodiment, the Cyclo(hetero)alkenyl Compound has an $R_3$ group, the $R_3$ group is attached to the carbon that is at the 3-position of the tetrahydropiperidine ring, the carbon to which the $R_3$ group is attached is in the (S) configuration, and $R_3$ is —$CF_3$. In another embodiment, the Cyclo(hetero) alkenyl Compound has an $R_3$ group, the $R_3$ group is attached to the carbon that is at the 3-position of the tetrahydropiperidine ring, the carbon to which the $R_3$ group is attached is in the (S) configuration, and $R_3$ is —$CH_2CH_3$.

In another embodiment, the Cyclo(hetero)alkenyl Compound has an $R_3$ group, the $R_3$ group is attached to the carbon atom at the 6-position of the tetrahydropiperidine ring, and the carbon to which the $R_3$ group is attached is in the (S) configuration. In another embodiment, the Cyclo(hetero)alkenyl Compound has an $R_3$ group, the $R_3$ group is attached to the carbon atom at the 6-position of the tetrahydropiperidine ring, the carbon to which the $R_3$ group is attached is in the (S) configuration, and $R_3$ is —$(C_1$-$C_4)$alkyl unsubstituted or substituted with one or more halo groups. In another embodiment, the Cyclo(hetero)alkenyl Compound has an $R_3$ group, the $R_3$ group is attached to the carbon atom at the 6-position of the tetrahydropiperidine ring, the carbon to which the $R_3$ group is attached is in the (S) configuration, and $R_3$ is —$CH_3$. In another embodiment, the Cyclo(hetero)alkenyl Compound has an $R_3$ group, the $R_3$ group is attached to the carbon atom at the 6-position of the tetrahydropiperidine ring, the carbon to which the $R_3$ group is attached is in the (S) configuration, and $R_3$ is —$CF_3$. In another embodiment, the Cyclo(hetero) alkenyl Compound has an $R_3$ group, the $R_3$ group is attached to the carbon atom at the 6-position of the tetrahydropiperidine ring, the carbon to which the $R_3$ group is attached is in the (S) configuration, and $R_3$ is —$CH_2CH_3$.

In another embodiment, the Cyclo(hetero)alkenyl Compound has an $R_3$ group, the $R_3$ group is attached to the carbon atom at the 5-position of the tetrahydropiperidine ring, and the carbon to which the $R_3$ group is attached is in the (S) configuration. In another embodiment, the Cyclo(hetero)alkenyl Compound has an $R_3$ group, the $R_3$ group is attached to the carbon atom at the 5-position of the tetrahydropiperidine ring, the carbon to which the $R_3$ group is attached is in the (S) configuration, and $R_3$ is —$(C_1$-$C_4)$alkyl unsubstituted or substituted with one or more halo groups. In another embodiment, the Cyclo(hetero)alkenyl Compound has an $R_3$ group, the $R_3$ group is attached to the carbon atom at the 5-position of the tetrahydropiperidine ring, the carbon to which the $R_3$ group is attached is in the (S) configuration, and $R_3$ is —$CH_3$. In another embodiment, the Cyclo(hetero)alkenyl Compound has an $R_3$ group, the $R_3$ group is attached to the carbon atom at the 5-position of the tetrahydropiperidine ring, the carbon to which the $R_3$ group is attached is in the (S) configuration, and $R_3$ is —$CF_3$. In another embodiment, the Cyclo(hetero) alkenyl Compound has an $R_3$ group, the $R_3$ group is attached to the carbon atom at the 5-position of the tetrahydropiperidine ring, the carbon atom to which the $R_3$ group is attached is in the (S) configuration, and $R_3$ is —$CH_2CH_3$.

In another embodiment, the Cyclo(hetero)alkenyl Compound has an $R_3$ group, the $R_3$ group is attached to the carbon atom at the 2-position of the cyclo(hetero)alkenyl ring and $R_3$ is —$(C_1$-$C_4)$ alkyl unsubstituted or substituted with one or more halo groups. In another embodiment, the Cyclo(hetero) alkenyl Compound has an $R_3$ group, the $R_3$ group is attached to the carbon atom at the 2-position of the cyclo(hetero) alkenyl ring and $R_3$ is —$CH_3$. In another embodiment, the Cyclo(hetero)alkenyl Compound has an $R_3$ group, the $R_3$ group is attached to the carbon atom at the 2-position of the cyclo(hetero)alkenyl ring and $R_3$ is —$CF_3$. In another embodiment, the Cyclo(hetero)alkenyl Compound has an $R_3$ group, the $R_3$ group is attached to the carbon atom at the 2-position of the cyclo(hetero)alkenyl ring and $R_3$ is —$CH_2CH_3$.

4.1.2 Cyclo(Hetero)Alkenyl Compounds of Formula (IA)

The present invention encompasses Compounds of Formula (IA)

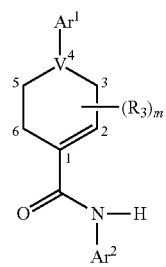

(IA)

and pharmaceutically acceptable salts thereof, where V, Ar¹, Ar², R₃, and m are defined above for the Cyclo(hetero)alkenyl Compounds of Formula (IA).

Illustrative Cyclo(hetero)alkenyl Compounds are listed below in Tables 1-27.

For the chemical structure depicted, e.g., at the head of each of Tables 1, 3, 5, 7, 9, 13-19, 21, 22, 24, 25 and 27, a is independently 0 or 1. When a=0, the group at the "a" position is —H. When a=1, the group at the "a" position ($R_{8a}$) is other than —H, i.e., is $R_8$.

For the chemical structure depicted, e.g., at the head of each of Tables 2, 4, 6, 8, 10, 20, 23 and 26, a is independently 0 or 1. When a=0, the group at the "a" position is —H. When a=1, the group at the "a" position (($R_8)_a$) is other than —H, i.e., is $R_8$.

For the chemical structure depicted, e.g., at the head of each of Tables 2, 4, 6, 8, 10, 20, 23 and 26, b is independently 0 or 1. When b=0, the group at the "b" position is —H. When b=1, the group at the "b" position (($R_8)_b$) is other than —H, i.e., is $R_8$.

TABLE 1

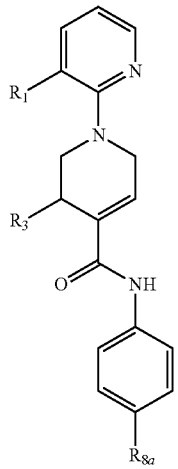

(Ia)

and pharmaceutically acceptable salts thereof, wherein:

| Compound | $R_1$ | $R_{8a}$ |
|---|---|---|
| A01 (a and b) | —H | —H |
| A02 (a and b) | —H | -tert-butyl |

TABLE 1-continued

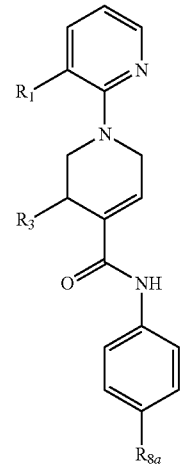

(Ia)

and pharmaceutically acceptable salts thereof, wherein:

| Compound | $R_1$ | $R_{8a}$ |
|---|---|---|
| A03 (a and b) | —H | -iso-butyl |
| A04 (a and b) | —H | -sec-butyl |
| A05 (a and b) | —H | -iso-propyl |
| A06 (a and b) | —H | -n-propyl |
| A07 (a and b) | —H | -cyclohexyl |
| A08 (a and b) | —H | -tert-butoxy |
| A09 (a and b) | —H | -isopropoxy |
| A10 (a and b) | —H | —$CF_3$ |
| A11 (a and b) | —H | —$CH_2CF_3$ |
| A12 (a and b) | —H | —$OCF_3$ |
| A13 (a and b) | —H | —Cl |
| A14 (a and b) | —H | —Br |
| A15 (a and b) | —H | —I |
| A16 (a and b) | —H | -n-butyl |
| A17 (a and b) | —H | —$CH_3$ |
| A18 (a and b) | —H | —$SCF_3$ |
| A19 (a and b) | —H | —$N(CH_2CH_3)_2$ |
| A20 (a and b) | —H | —$OCF_2CHF_2$ |
| A21 (a and b) | —H | —$C(OH)(CF_3)_2$ |
| A22 (a and b) | —H | -(1,1-dimethyl-pentyl) |
| A23 (a and b) | —H | -(1,1-dimethyl-acetic acid) ethyl ester |
| A24 (a and b) | —H | —N-piperidinyl |
| A25 (a and b) | —Cl | —H |
| A26 (a and b) | —Cl | -tert-butyl |
| A27 (a and b) | —Cl | -iso-butyl |
| A28 (a and b) | —Cl | -sec-butyl |
| A29 (a and b) | —Cl | -iso-propyl |
| A30 (a and b) | —Cl | -n-propyl |
| A31 (a and b) | —Cl | -cyclohexyl |
| A32 (a and b) | —Cl | -tert-butoxy |
| A33 (a and b) | —Cl | -isopropoxy |
| A34 (a and b) | —Cl | —$CF_3$ |
| A35 (a and b) | —Cl | —$CH_2CF_3$ |
| A36 (a and b) | —Cl | —$OCF_3$ |
| A37 (a and b) | —Cl | —Cl |
| A38 (a and b) | —Cl | —Br |
| A39 (a and b) | —Cl | —I |
| A40 (a and b) | —Cl | -n-butyl |
| A41 (a and b) | —Cl | —$CH_3$ |
| A42 (a and b) | —Cl | —$SCF_3$ |
| A43 (a and b) | —Cl | —$N(CH_2CH_3)_2$ |
| A44 (a and b) | —Cl | —$OCF_2CHF_2$ |
| A45 (a and b) | —Cl | —$C(OH)(CF_3)_2$ |
| A46 (a and b) | —Cl | -(1,1-dimethyl-pentyl) |
| A47 (a and b) | —Cl | -(1,1-dimethyl-acetic acid) ethyl ester |
| A48 (a and b) | —Cl | —N-piperidinyl |
| A49 (a and b) | —F | —H |
| A50 (a and b) | —F | -tert-butyl |
| A51 (a and b) | —F | -iso-butyl |
| A52 (a and b) | —F | -sec-butyl |

TABLE 1-continued

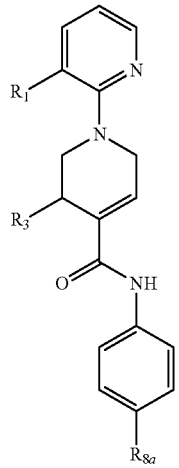

(Ia)

and pharmaceutically acceptable salts thereof, wherein:

| Compound | $R_1$ | $R_{8a}$ |
|---|---|---|
| A53 (a and b) | —F | -iso-propyl |
| A54 (a and b) | —F | -n-propyl |
| A55 (a and b) | —F | -cyclohexyl |
| A56 (a and b) | —F | -tert-butoxy |
| A57 (a and b) | —F | -isopropoxy |
| A58 (a and b) | —F | —CF$_3$ |
| A59 (a and b) | —F | —CH$_2$CF$_3$ |
| A60 (a and b) | —F | —OCF$_3$ |
| A61 (a and b) | —F | —Cl |
| A62 (a and b) | —F | —Br |
| A63 (a and b) | —F | —I |
| A64 (a and b) | —F | -n-butyl |
| A65 (a and b) | —F | —CH$_3$ |
| A66 (a and b) | —F | —SCF$_3$ |
| A67 (a and b) | —F | —N(CH$_2$CH$_3$)$_2$ |
| A68 (a and b) | —F | —OCF$_2$CHF$_2$ |
| A69 (a and b) | —F | —C(OH)(CF$_3$)$_2$ |
| A70 (a and b) | —F | -(1,1-dimethyl-pentyl) |
| A71 (a and b) | —F | -(1,1-dimethyl-acetic acid) ethyl ester |
| A72 (a and b) | —F | —N-piperidinyl |
| A73 (a and b) | —CH$_3$ | —H |
| A74 (a and b) | —CH$_3$ | -iso-butyl |
| A75 (a and b) | —CH$_3$ | -tert-butyl |
| A76 (a and b) | —CH$_3$ | -sec-butyl |
| A77 (a and b) | —CH$_3$ | -iso-propyl |
| A78 (a and b) | —CH$_3$ | -n-propyl |
| A79 (a and b) | —CH$_3$ | -cyclohexyl |
| A80 (a and b) | —CH$_3$ | -tert-butoxy |
| A81 (a and b) | —CH$_3$ | -isopropoxy |
| A82 (a and b) | —CH$_3$ | —CF$_3$ |
| A83 (a and b) | —CH$_3$ | —CH$_2$CF$_3$ |
| A84 (a and b) | —CH$_3$ | —OCF$_3$ |
| A85 (a and b) | —CH$_3$ | —Cl |
| A86 (a and b) | —CH$_3$ | —Br |
| A87 (a and b) | —CH$_3$ | —I |
| A88 (a and b) | —CH$_3$ | -n-butyl |
| A89 (a and b) | —CH$_3$ | —CH$_3$ |
| A90 (a and b) | —CH$_3$ | —SCF$_3$ |
| A91 (a and b) | —CH$_3$ | —N(CH$_2$CH$_3$)$_2$ |
| A92 (a and b) | —CH$_3$ | —OCF$_2$CHF$_2$ |
| A93 (a and b) | —CH$_3$ | —C(OH)(CF$_3$)$_2$ |
| A94 (a and b) | —CH$_3$ | -(1,1-dimethyl-pentyl) |
| A95 (a and b) | —CH$_3$ | -(1,1-dimethyl-acetic acid) ethyl ester |
| A96 (a and b) | —CH$_3$ | —N-piperidinyl |
| A97 (a and b) | —CF$_3$ | —H |
| A98 (a and b) | —CF$_3$ | -tert-butyl |
| A99 (a and b) | —CF$_3$ | -iso-butyl |
| A100 (a and b) | —CF$_3$ | -sec-butyl |
| A101 (a and b) | —CF$_3$ | -iso-propyl |
| A102 (a and b) | —CF$_3$ | -n-propyl |

TABLE 1-continued

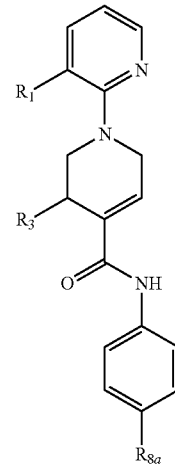

(Ia)

and pharmaceutically acceptable salts thereof, wherein:

| Compound | $R_1$ | $R_{8a}$ |
|---|---|---|
| A103 (a and b) | —CF$_3$ | -cyclohexyl |
| A104 (a and b) | —CF$_3$ | -tert-butoxy |
| A105 (a and b) | —CF$_3$ | -isopropoxy |
| A106 (a and b) | —CF$_3$ | —CF$_3$ |
| A107 (a and b) | —CF$_3$ | —CH$_2$CF$_3$ |
| A108 (a and b) | —CF$_3$ | —OCF$_3$ |
| A109 (a and b) | —CF$_3$ | —Cl |
| A110 (a and b) | —CF$_3$ | —Br |
| A111 (a and b) | —CF$_3$ | —I |
| A112 (a and b) | —CF$_3$ | -n-butyl |
| A113 (a and b) | —CF$_3$ | —CH$_3$ |
| A114 (a and b) | —CF$_3$ | —SCF$_3$ |
| A115 (a and b) | —CF$_3$ | —N(CH$_2$CH$_3$)$_2$ |
| A116 (a and b) | —CF$_3$ | —OCF$_2$CHF$_2$ |
| A117 (a and b) | —CF$_3$ | —C(OH)(CF$_3$)$_2$ |
| A118 (a and b) | —CF$_3$ | -(1,1-dimethyl-pentyl) |
| A119 (a and b) | —CF$_3$ | -(1,1-dimethyl-acetic acid) ethyl ester |
| A120 (a and b) | —CF$_3$ | —N-piperidinyl |
| A121 (a and b) | —CHF$_2$ | -tert-butyl |
| A122 (a and b) | —CHF$_2$ | —H |
| A123 (a and b) | —CHF$_2$ | -iso-butyl |
| A124 (a and b) | —CHF$_2$ | -sec-butyl |
| A125 (a and b) | —CHF$_2$ | -iso-propyl |
| A126 (a and b) | —CHF$_2$ | -n-propyl |
| A127 (a and b) | —CHF$_2$ | -cyclohexyl |
| A128 (a and b) | —CHF$_2$ | -tert-butoxy |
| A129 (a and b) | —CHF$_2$ | -isopropoxy |
| A130 (a and b) | —CHF$_2$ | —CF$_3$ |
| A131 (a and b) | —CHF$_2$ | —CH$_2$CF$_3$ |
| A132 (a and b) | —CHF$_2$ | —OCF$_3$ |
| A133 (a and b) | —CHF$_2$ | —Cl |
| A134 (a and b) | —CHF$_2$ | —Br |
| A135 (a and b) | —CHF$_2$ | —I |
| A136 (a and b) | —CHF$_2$ | -n-butyl |
| A137 (a and b) | —CHF$_2$ | —CH$_3$ |
| A138 (a and b) | —CHF$_2$ | —SCF$_3$ |
| A139 (a and b) | —CHF$_2$ | —N(CH$_2$CH$_3$)$_2$ |
| A140 (a and b) | —CHF$_2$ | —OCF$_2$CHF$_2$ |
| A141 (a and b) | —CHF$_2$ | —C(OH)(CF$_3$)$_2$ |
| A142 (a and b) | —CHF$_2$ | -(1,1-dimethyl-pentyl) |
| A143 (a and b) | —CHF$_2$ | -(1,1-dimethyl-acetic acid) ethyl ester |
| A144 (a and b) | —CHF$_2$ | —N-piperidinyl |
| A145 (a and b) | —OH | —H |
| A146 (a and b) | —OH | -tert-butyl |
| A147 (a and b) | —OH | -iso-butyl |
| A148 (a and b) | —OH | -sec-butyl |
| A149 (a and b) | —OH | -iso-propyl |
| A150 (a and b) | —OH | -n-propyl |
| A151 (a and b) | —OH | -cyclohexyl |
| A152 (a and b) | —OH | -tert-butoxy |

TABLE 1-continued

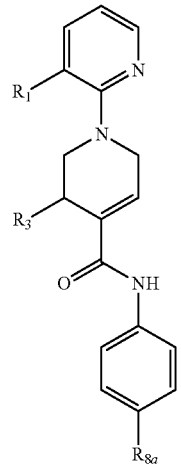

(Ia)

and pharmaceutically acceptable salts thereof, wherein:

| Compound | $R_1$ | $R_{8a}$ |
|---|---|---|
| A153 (a and b) | —OH | -isopropoxy |
| A154 (a and b) | —OH | —CF$_3$ |
| A155 (a and b) | —OH | —CH$_2$CF$_3$ |
| A156 (a and b) | —OH | —OCF$_3$ |
| A157 (a and b) | —OH | —Cl |
| A158 (a and b) | —OH | —Br |
| A159 (a and b) | —OH | —I |
| A160 (a and b) | —OH | -n-butyl |
| A161 (a and b) | —OH | —CH$_3$ |
| A162 (a and b) | —OH | —SCF$_3$ |
| A163 (a and b) | —OH | —N(CH$_2$CH$_3$)$_2$ |
| A164 (a and b) | —OH | —OCF$_2$CHF$_2$ |
| A165 (a and b) | —OH | —C(OH)(CF$_3$)$_2$ |
| A166 (a and b) | —OH | -(1,1-dimethyl-pentyl) |
| A167 (a and b) | —OH | -(1,1-dimethyl-acetic acid) ethyl ester |
| A168 (a and b) | —OH | —N-piperidinyl |
| A169 (a and b) | —NO$_2$ | —H |
| A170 (a and b) | —NO$_2$ | -tert-butyl |
| A171 (a and b) | —NO$_2$ | -iso-butyl |
| A172 (a and b) | —NO$_2$ | -sec-butyl |
| A173 (a and b) | —NO$_2$ | -iso-propyl |
| A174 (a and b) | —NO$_2$ | -n-propyl |
| A175 (a and b) | —NO$_2$ | -cyclohexyl |
| A176 (a and b) | —NO$_2$ | -tert-butoxy |
| A177 (a and b) | —NO$_2$ | -isopropoxy |
| A178 (a and b) | —NO$_2$ | —CF$_3$ |
| A179 (a and b) | —NO$_2$ | —CH$_2$CF$_3$ |
| A180 (a and b) | —NO$_2$ | —OCF$_3$ |
| A181 (a and b) | —NO$_2$ | —Cl |
| A182 (a and b) | —NO$_2$ | —Br |
| A183 (a and b) | —NO$_2$ | —I |
| A184 (a and b) | —NO$_2$ | -n-butyl |
| A185 (a and b) | —NO$_2$ | —CH$_3$ |
| A186 (a and b) | —NO$_2$ | —SCF$_3$ |
| A187 (a and b) | —NO$_2$ | —N(CH$_2$CH$_3$)$_2$ |
| A188 (a and b) | —NO$_2$ | —OCF$_2$CHF$_2$ |
| A189 (a and b) | —NO$_2$ | —C(OH)(CF$_3$)$_2$ |
| A190 (a and b) | —NO$_2$ | -(1,1-dimethyl-pentyl) |
| A191 (a and b) | —NO$_2$ | -(1,1-dimethyl-acetic acid) ethyl ester |
| A192 (a and b) | —NO$_2$ | —N-piperidinyl |
| A193 (a and b) | —CN | —H |
| A194 (a and b) | —CN | -tert-butyl |
| A195 (a and b) | —CN | -iso-butyl |
| A196 (a and b) | —CN | -sec-butyl |
| A197 (a and b) | —CN | -iso-propyl |
| A198 (a and b) | —CN | -n-propyl |
| A199 (a and b) | —CN | -cyclohexyl |
| A200 (a and b) | —CN | -tert-butoxy |
| A201 (a and b) | —CN | -isopropoxy |
| A202 (a and b) | —CN | —CF$_3$ |

TABLE 1-continued

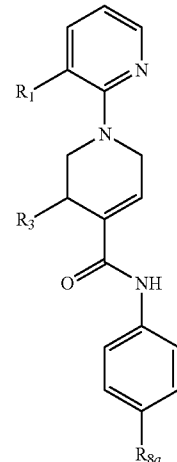

(Ia)

and pharmaceutically acceptable salts thereof, wherein:

| Compound | $R_1$ | $R_{8a}$ |
|---|---|---|
| A203 (a and b) | —CN | —CH$_2$CF$_3$ |
| A204 (a and b) | —CN | —OCF$_3$ |
| A205 (a and b) | —CN | —Cl |
| A206 (a and b) | —CN | —Br |
| A207 (a and b) | —CN | —I |
| A208 (a and b) | —CN | -n-butyl |
| A209 (a and b) | —CN | —CH$_3$ |
| A210 (a and b) | —CN | —SCF$_3$ |
| A211 (a and b) | —CN | —N(CH$_2$CH$_3$)$_2$ |
| A212 (a and b) | —CN | —OCF$_2$CHF$_2$ |
| A213 (a and b) | —CN | —C(OH)(CF$_3$)$_2$ |
| A214 (a and b) | —CN | -(1,1-dimethyl-pentyl) |
| A215 (a and b) | —CN | -(1,1-dimethyl-acetic acid) ethyl ester |
| A216 (a and b) | —CN | —N-piperidinyl |
| A217 (a and b) | —Br | —H |
| A218 (a and b) | —Br | -tert-butyl |
| A219 (a and b) | —Br | -iso-butyl |
| A220 (a and b) | —Br | -sec-butyl |
| A221 (a and b) | —Br | -iso-propyl |
| A222 (a and b) | —Br | -n-propyl |
| A223 (a and b) | —Br | -cyclohexyl |
| A224 (a and b) | —Br | -tert-butoxy |
| A225 (a and b) | —Br | -isopropoxy |
| A226 (a and b) | —Br | —CF$_3$ |
| A227 (a and b) | —Br | —CH$_2$CF$_3$ |
| A228 (a and b) | —Br | —OCF$_3$ |
| A229 (a and b) | —Br | —Cl |
| A230 (a and b) | —Br | —Br |
| A231 (a and b) | —Br | —I |
| A232 (a and b) | —Br | -n-butyl |
| A233 (a and b) | —Br | —CH$_3$ |
| A234 (a and b) | —Br | —SCF$_3$ |
| A235 (a and b) | —Br | —N(CH$_2$CH$_3$)$_2$ |
| A236 (a and b) | —Br | —OCF$_2$CHF$_2$ |
| A237 (a and b) | —Br | —C(OH)(CF$_3$)$_2$ |
| A238 (a and b) | —Br | -(1,1-dimethyl-pentyl) |
| A239 (a and b) | —Br | -(1,1-dimethyl-acetic acid) ethyl ester |
| A240 (a and b) | —Br | —N-piperidinyl |
| A241 (a and b) | —I | -tert-butyl |
| A242 (a and b) | —I | —H |
| A243 (a and b) | —I | -iso-butyl |
| A244 (a and b) | —I | -sec-butyl |
| A245 (a and b) | —I | -iso-propyl |
| A246 (a and b) | —I | -n-propyl |
| A247 (a and b) | —I | -cyclohexyl |
| A248 (a and b) | —I | -tert-butoxy |
| A249 (a and b) | —I | -isopropoxy |
| A250 (a and b) | —I | —CF$_3$ |
| A251 (a and b) | —I | —CH$_2$CF$_3$ |
| A252 (a and b) | —I | —OCF$_3$ |

TABLE 1-continued

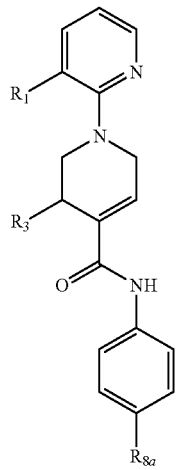

(Ia)

and pharmaceutically acceptable salts thereof, wherein:

| Compound | $R_1$ | $R_{8a}$ |
|---|---|---|
| A253 (a and b) | —I | —Cl |
| A254 (a and b) | —I | —Br |
| A255 (a and b) | —I | —I |
| A256 (a and b) | —I | -n-butyl |
| A257 (a and b) | —I | —CH$_3$ |
| A258 (a and b) | —I | —SCF$_3$ |
| A259 (a and b) | —I | —N(CH$_2$CH$_3$)$_2$ |
| A260 (a and b) | —I | —OCF$_2$CHF$_2$ |
| A261 (a and b) | —I | —C(OH)(CF$_3$)$_2$ |
| A262 (a and b) | —I | -(1,1-dimethyl-pentyl) |
| A263 (a and b) | —I | -(1,1-dimethyl-acetic acid) ethyl ester |
| A264 (a and b) | —I | —N-piperidinyl |

(a) means that $R_3$ is —H.
(b) means that $R_3$ is —CH$_3$.

TABLE 2

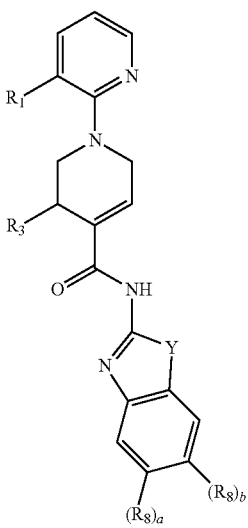

(Ib)

and pharmaceutically acceptable salts thereof, wherein:

| Compound | Y | $R_1$ | $(R_8)_a$ | $(R_8)_b$ |
|---|---|---|---|---|
| B1 (a and b) | S | —H | —Cl | —H |
| B2 (a and b) | S | —H | —Br | —H |
| B3 (a and b) | S | —H | —F | —H |

TABLE 2-continued

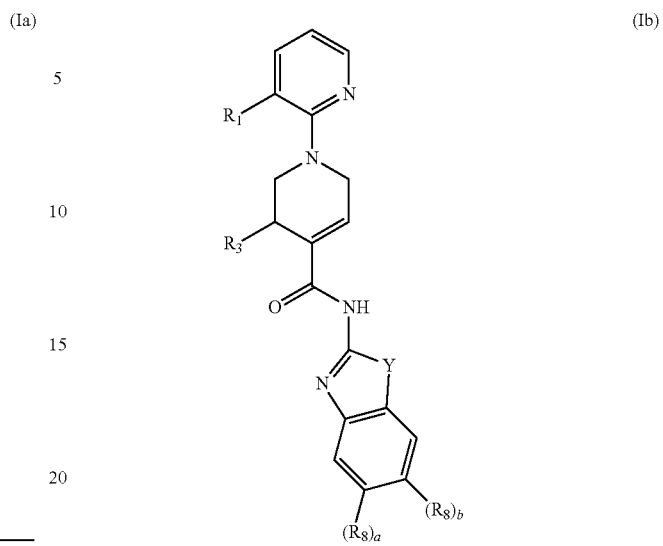

(Ib)

and pharmaceutically acceptable salts thereof, wherein:

| Compound | Y | $R_1$ | $(R_8)_a$ | $(R_8)_b$ |
|---|---|---|---|---|
| B4 (a and b) | S | —H | —CH$_3$ | —H |
| B5 (a and b) | S | —H | —CF$_3$ | —H |
| B6 (a and b) | S | —H | —OCH$_3$ | —H |
| B7 (a and b) | S | —H | —OCH$_2$CH$_3$ | —H |
| B8 (a and b) | S | —H | —OCF$_3$ | —H |
| B9 (a and b) | S | —H | -tert-butyl | —H |
| B10 (a and b) | S | —H | -iso-propyl | —H |
| B11 (a and b) | S | —H | —CH$_3$ | —CH$_3$ |
| B12 (a and b) | S | —H | —H | —H |
| B13 (a and b) | S | —H | —H | —Cl |
| B14 (a and b) | S | —H | —H | —Br |
| B15 (a and b) | S | —H | —H | —F |
| B16 (a and b) | S | —H | —H | —CH$_3$ |
| B17 (a and b) | S | —H | —H | —CF$_3$ |
| B18 (a and b) | S | —H | —H | —OCH$_3$ |
| B19 (a and b) | S | —H | —H | —OCH$_2$CH$_3$ |
| B20 (a and b) | S | —H | —H | —OCF$_3$ |
| B21 (a and b) | S | —H | —H | -tert-butyl |
| B22 (a and b) | S | —H | —H | -iso-propyl |
| B23 (a and b) | S | —Cl | —Cl | —H |
| B24 (a and b) | S | —Cl | —Br | —H |
| B25 (a and b) | S | —Cl | —F | —H |
| B26 (a and b) | S | —Cl | —CH$_3$ | —H |
| B27 (a and b) | S | —Cl | —CF$_3$ | —H |
| B28 (a and b) | S | —Cl | —OCH$_3$ | —H |
| B29 (a and b) | S | —Cl | —OCH$_2$CH$_3$ | —H |
| B30 (a and b) | S | —Cl | —OCF$_3$ | —H |
| B31 (a and b) | S | —Cl | -tert-butyl | —H |
| B32 (a and b) | S | —Cl | -iso-propyl | —H |
| B33 (a and b) | S | —Cl | —CH$_3$ | —CH$_3$ |
| B34 (a and b) | S | —Cl | —H | —H |
| B35 (a and b) | S | —Cl | —H | —Cl |
| B36 (a and b) | S | —Cl | —H | —Br |
| B37 (a and b) | S | —Cl | —H | —F |
| B38 (a and b) | S | —Cl | —H | —CH$_3$ |
| B39 (a and b) | S | —Cl | —H | —CF$_3$ |
| B40 (a and b) | S | —Cl | —H | —OCH$_3$ |
| B41 (a and b) | S | —Cl | —H | —OCH$_2$CH$_3$ |
| B42 (a and b) | S | —Cl | —H | —OCF$_3$ |
| B43 (a and b) | S | —Cl | —H | -tert-butyl |
| B44 (a and b) | S | —Cl | —H | -iso-propyl |
| B45 (a and b) | S | —Cl | —H | —OCF$_3$ |
| B46 (a and b) | S | —Cl | —H | -tert-butyl |
| B47 (a and b) | S | —Cl | —H | -iso-propyl |
| B48 (a and b) | S | —CH$_3$ | —Cl | —H |
| B49 (a and b) | S | —CH$_3$ | —Br | —H |
| B50 (a and b) | S | —CH$_3$ | —F | —H |

TABLE 2-continued

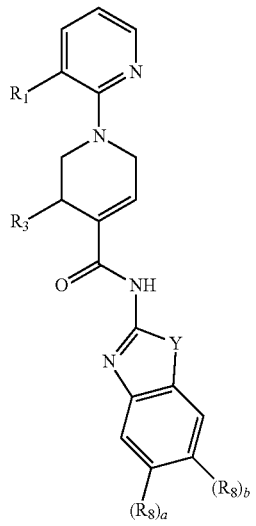

(Ib)

and pharmaceutically acceptable salts thereof, wherein:

| Compound | Y | $R_1$ | $(R_8)_a$ | $(R_8)_b$ |
|---|---|---|---|---|
| B51 (a and b) | S | —$CH_3$ | —$CH_3$ | —H |
| B52 (a and b) | S | —$CH_3$ | —$CF_3$ | —H |
| B53 (a and b) | S | —$CH_3$ | —$OCH_3$ | —H |
| B54 (a and b) | S | —$CH_3$ | —$OCH_2CH_3$ | —H |
| B55 (a and b) | S | —$CH_3$ | —$OCF_3$ | —H |
| B56 (a and b) | S | —$CH_3$ | -tert-butyl | —H |
| B57 (a and b) | S | —$CH_3$ | -iso-propyl | —H |
| B58 (a and b) | S | —$CH_3$ | —$CH_3$ | —$CH_3$ |
| B59 (a and b) | S | —$CH_3$ | —H | —H |
| B60 (a and b) | S | —$CH_3$ | —H | —Cl |
| B61 (a and b) | S | —$CH_3$ | —H | —Br |
| B62 (a and b) | S | —$CH_3$ | —H | —F |
| B63 (a and b) | S | —$CH_3$ | —H | —$CH_3$ |
| B64 (a and b) | S | —$CH_3$ | —H | —$CF_3$ |
| B65 (a and b) | S | —$CH_3$ | —H | —$OCH_3$ |
| B66 (a and b) | S | —$CH_3$ | —H | —$OCH_2CH_3$ |
| B67 (a and b) | S | —$CH_3$ | —H | —$OCF_3$ |
| B68 (a and b) | S | —$CH_3$ | —H | -tert-butyl |
| B69 (a and b) | S | —$CH_3$ | —H | -iso-propyl |
| B70 (a and b) | S | —$CF_3$ | —Cl | —H |
| B71 (a and b) | S | —$CF_3$ | —Br | —H |
| B72 (a and b) | S | —$CF_3$ | —F | —H |
| B73 (a and b) | S | —$CF_3$ | —$CH_3$ | —H |
| B74 (a and b) | S | —$CF_3$ | —$CF_3$ | —H |
| B75 (a and b) | S | —$CF_3$ | —$OCH_3$ | —H |
| B76 (a and b) | S | —$CF_3$ | —$OCH_2CH_3$ | —H |
| B77 (a and b) | S | —$CF_3$ | —$OCF_3$ | —H |
| B78 (a and b) | S | —$CF_3$ | -tert-butyl | —H |
| B79 (a and b) | S | —$CF_3$ | -iso-propyl | —H |
| B80 (a and b) | S | —$CF_3$ | —$CH_3$ | —$CH_3$ |
| B81 (a and b) | S | —$CF_3$ | —H | —H |
| B82 (a and b) | S | —$CF_3$ | —H | —Cl |
| B83 (a and b) | S | —$CF_3$ | —H | —Br |
| B84 (a and b) | S | —$CF_3$ | —H | —F |
| B85 (a and b) | S | —$CF_3$ | —H | —$CH_3$ |
| B86 (a and b) | S | —$CF_3$ | —H | —$CF_3$ |
| B87 (a and b) | S | —$CF_3$ | —H | —$OCH_3$ |
| B88 (a and b) | S | —$CF_3$ | —H | —$OCH_2CH_3$ |
| B89 (a and b) | S | —$CF_3$ | —H | —$OCF_3$ |
| B90 (a and b) | S | —$CF_3$ | —H | -tert-butyl |
| B91 (a and b) | S | —$CF_3$ | —H | -iso-propyl |
| B92 (a and b) | S | —$CHF_2$ | —Cl | —H |
| B93 (a and b) | S | —$CHF_2$ | —Br | —H |
| B94 (a and b) | S | —$CHF_2$ | —F | —H |
| B95 (a and b) | S | —$CHF_2$ | —$CH_3$ | —H |
| B96 (a and b) | S | —$CHF_2$ | —$CF_3$ | —H |
| B97 (a and b) | S | —$CHF_2$ | —$OCH_3$ | —H |
| B98 (a and b) | S | —$CHF_2$ | —$OCH_2CH_3$ | —H |
| B99 (a and b) | S | —$CHF_2$ | —$OCF_3$ | —H |
| B100 (a and b) | S | —$CHF_2$ | -tert-butyl | —H |
| B101 (a and b) | S | —$CHF_2$ | -iso-propyl | —H |
| B102 (a and b) | S | —$CHF_2$ | —$CH_3$ | —$CH_3$ |
| B103 (a and b) | S | —$CHF_2$ | —H | —H |
| B104 (a and b) | S | —$CHF_2$ | —H | —Cl |
| B105 (a and b) | S | —$CHF_2$ | —H | —Br |
| B106 (a and b) | S | —$CHF_2$ | —H | —F |
| B107 (a and b) | S | —$CHF_2$ | —H | —$CH_3$ |
| B108 (a and b) | S | —$CHF_2$ | —H | —$CF_3$ |
| B109 (a and b) | S | —$CHF_2$ | —H | —$OCH_3$ |
| B110 (a and b) | S | —$CHF_2$ | —H | —$OCH_2CH_3$ |
| B111 (a and b) | S | —$CHF_2$ | —H | —$OCF_3$ |
| B112 (a and b) | S | —$CHF_2$ | —H | -tert-butyl |
| B113 (a and b) | S | —$CHF_2$ | —H | -iso-propyl |
| B114 (a and b) | S | —OH | —Cl | —H |
| B115 (a and b) | S | —OH | —Br | —H |
| B116 (a and b) | S | —OH | —F | —H |
| B117 (a and b) | S | —OH | —$CH_3$ | —H |
| B118 (a and b) | S | —OH | —$CF_3$ | —H |
| B119 (a and b) | S | —OH | —$OCH_3$ | —H |
| B120 (a and b) | S | —OH | —$OCH_2CH_3$ | —H |
| B121 (a and b) | S | —OH | —$OCF_3$ | —H |
| B122 (a and b) | S | —OH | -tert-butyl | —H |
| B123 (a and b) | S | —OH | -iso-propyl | —H |
| B124 (a and b) | S | —OH | —$CH_3$ | —$CH_3$ |
| B125 (a and b) | S | —OH | —H | —H |
| B126 (a and b) | S | —OH | —H | —Cl |
| B127 (a and b) | S | —OH | —H | —Br |
| B128 (a and b) | S | —OH | —H | —F |
| B129 (a and b) | S | —OH | —H | —$CH_3$ |
| B130 (a and b) | S | —OH | —H | —$CF_3$ |
| B131 (a and b) | S | —OH | —H | —$OCH_3$ |
| B132 (a and b) | S | —OH | —H | —$OCH_2CH_3$ |
| B133 (a and b) | S | —OH | —H | —$OCF_3$ |
| B134 (a and b) | S | —OH | —H | -tert-butyl |
| B135 (a and b) | S | —OH | —H | -iso-propyl |
| B136 (a and b) | S | —$NO_2$ | —Cl | —H |
| B137 (a and b) | S | —$NO_2$ | —Br | —H |
| B138 (a and b) | S | —$NO_2$ | —F | —H |
| B139 (a and b) | S | —$NO_2$ | —$CH_3$ | —H |
| B140 (a and b) | S | —$NO_2$ | —$CF_3$ | —H |
| B141 (a and b) | S | —$NO_2$ | —$OCH_3$ | —H |
| B142 (a and b) | S | —$NO_2$ | —$OCH_2CH_3$ | —H |
| B143 (a and b) | S | —$NO_2$ | —$OCF_3$ | —H |
| B144 (a and b) | S | —$NO_2$ | -tert-butyl | —H |
| B145 (a and b) | S | —$NO_2$ | -iso-propyl | —H |
| B146 (a and b) | S | —$NO_2$ | —$CH_3$ | —$CH_3$ |
| B147 (a and b) | S | —$NO_2$ | —H | —H |
| B148 (a and b) | S | —$NO_2$ | —H | —Cl |

TABLE 2-continued

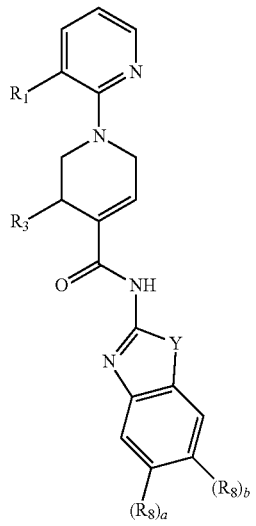

(Ib)

and pharmaceutically acceptable salts thereof, wherein:

| Compound | Y | R$_1$ | (R$_8$)$_a$ | (R$_8$)$_b$ |
|---|---|---|---|---|
| B149 (a and b) | S | —NO$_2$ | —H | —Br |
| B150 (a and b) | S | —NO$_2$ | —H | —F |
| B151 (a and b) | S | —NO$_2$ | —H | —CH$_3$ |
| B152 (a and b) | S | —NO$_2$ | —H | —CF$_3$ |
| B153 (a and b) | S | —NO$_2$ | —H | —OCH$_3$ |
| B154 (a and b) | S | —NO$_2$ | —H | —OCH$_2$CH$_3$ |
| B155 (a and b) | S | —NO$_2$ | —H | —OCF$_3$ |
| B156 (a and b) | S | —NO$_2$ | —H | -tert-butyl |
| B157 (a and b) | S | —NO$_2$ | —H | -iso-propyl |
| B158 (a and b) | S | —CN | —Br | —H |
| B159 (a and b) | S | —CN | —Cl | —H |
| B160 (a and b) | S | —CN | —F | —H |
| B161 (a and b) | S | —CN | —CH$_3$ | —H |
| B162 (a and b) | S | —CN | —CF$_3$ | —H |
| B163 (a and b) | S | —CN | —OCH$_3$ | —H |
| B164 (a and b) | S | —CN | —OCH$_2$CH$_3$ | —H |
| B165 (a and b) | S | —CN | —OCF$_3$ | —H |
| B166 (a and b) | S | —CN | -tert-butyl | —H |
| B167 (a and b) | S | —CN | -iso-propyl | —H |
| B168 (a and b) | S | —CN | —CH$_3$ | —CH$_3$ |
| B169 (a and b) | S | —CN | —H | —H |
| B170 (a and b) | S | —CN | —H | —Cl |
| B171 (a and b) | S | —CN | —H | —Br |
| B172 (a and b) | S | —CN | —H | —F |
| B173 (a and b) | S | —CN | —H | —CH$_3$ |
| B174 (a and b) | S | —CN | —H | —CF$_3$ |
| B175 (a and b) | S | —CN | —H | —OCH$_3$ |
| B176 (a and b) | S | —CN | —H | —OCH$_2$CH$_3$ |
| B177 (a and b) | S | —CN | —H | —OCF$_3$ |
| B178 (a and b) | S | —CN | —H | -tert-butyl |
| B179 (a and b) | S | —CN | —H | -iso-propyl |
| B180 (a and b) | S | —Br | —Br | —H |
| B181 (a and b) | S | —Br | —Cl | —H |
| B182 (a and b) | S | —Br | —F | —H |
| B183 (a and b) | S | —Br | —CH$_3$ | —H |
| B184 (a and b) | S | —Br | —CF$_3$ | —H |
| B185 (a and b) | S | —Br | —OCH$_3$ | —H |
| B186 (a and b) | S | —Br | —OCH$_2$CH$_3$ | —H |
| B187 (a and b) | S | —Br | —OCF$_3$ | —H |
| B188 (a and b) | S | —Br | -tert-butyl | —H |
| B189 (a and b) | S | —Br | -iso-propyl | —H |
| B190 (a and b) | S | —Br | —CH$_3$ | —CH$_3$ |
| B191 (a and b) | S | —Br | —H | —H |
| B192 (a and b) | S | —Br | —H | —Cl |
| B193 (a and b) | S | —Br | —H | —Br |
| B194 (a and b) | S | —Br | —H | —F |
| B195 (a and b) | S | —Br | —H | —CH$_3$ |
| B196 (a and b) | S | —Br | —H | —CF$_3$ |
| B197 (a and b) | S | —Br | —H | —OCH$_3$ |

TABLE 2-continued

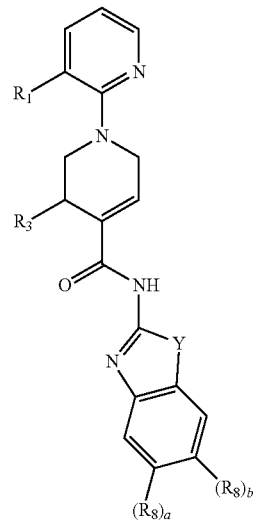

(Ib)

and pharmaceutically acceptable salts thereof, wherein:

| Compound | Y | R$_1$ | (R$_8$)$_a$ | (R$_8$)$_b$ |
|---|---|---|---|---|
| B198 (a and b) | S | —Br | —H | —OCH$_2$CH$_3$ |
| B199 (a and b) | S | —Br | —H | —OCF$_3$ |
| B200 (a and b) | S | —Br | —H | -tert-butyl |
| B201 (a and b) | S | —Br | —H | -iso-propyl |
| B202 (a and b) | S | —I | —Cl | —H |
| B203 (a and b) | S | —I | —Br | —H |
| B204 (a and b) | S | —I | —F | —H |
| B205 (a and b) | S | —I | —CH$_3$ | —H |
| B206 (a and b) | S | —I | —CF$_3$ | —H |
| B207 (a and b) | S | —I | —OCH$_3$ | —H |
| B208 (a and b) | S | —I | —OCH$_2$CH$_3$ | —H |
| B209 (a and b) | S | —I | —OCF$_3$ | —H |
| B210 (a and b) | S | —I | -tert-butyl | —H |
| B211 (a and b) | S | —I | -iso-propyl | —H |
| B212 (a and b) | S | —I | —CH$_3$ | —CH$_3$ |
| B213 (a and b) | S | —I | —H | —H |
| B214 (a and b) | S | —I | —H | —Cl |
| B215 (a and b) | S | —I | —H | —Br |
| B216 (a and b) | S | —I | —H | —F |
| B217 (a and b) | S | —I | —H | —CH$_3$ |
| B218 (a and b) | S | —I | —H | —CF$_3$ |
| B219 (a and b) | S | —I | —H | —OCH$_3$ |
| B220 (a and b) | S | —I | —H | —OCH$_2$CH$_3$ |
| B221 (a and b) | S | —I | —H | —OCF$_3$ |
| B222 (a and b) | S | —I | —H | -tert-butyl |
| B223 (a and b) | S | —I | —H | -iso-propyl |
| B224 (a and b) | O | —H | —Cl | —H |
| B225 (a and b) | O | —H | —Br | —H |
| B226 (a and b) | O | —H | —F | —H |
| B227 (a and b) | O | —H | —CH$_3$ | —H |
| B228 (a and b) | O | —H | —CF$_3$ | —H |
| B229 (a and b) | O | —H | —OCH$_3$ | —H |
| B230 (a and b) | O | —H | —OCH$_2$CH$_3$ | —H |
| B231 (a and b) | O | —H | —OCF$_3$ | —H |
| B232 (a and b) | O | —H | -tert-butyl | —H |
| B233 (a and b) | O | —H | -iso-propyl | —H |
| B234 (a and b) | O | —H | —CH$_3$ | —CH$_3$ |
| B235 (a and b) | O | —H | —H | —H |
| B236 (a and b) | O | —H | —H | —Cl |
| B237 (a and b) | O | —H | —H | —Br |
| B238 (a and b) | O | —H | —H | —F |
| B239 (a and b) | O | —H | —H | —CH$_3$ |
| B240 (a and b) | O | —H | —H | —CF$_3$ |
| B241 (a and b) | O | —H | —H | —OCH$_3$ |
| B242 (a and b) | O | —H | —H | —OCH$_2$CH$_3$ |
| B243 (a and b) | O | —H | —H | —OCF$_3$ |
| B244 (a and b) | O | —H | —H | -tert-butyl |
| B245 (a and b) | O | —H | —H | -iso-propyl |
| B246 (a and b) | O | —Cl | —Cl | —H |

TABLE 2-continued

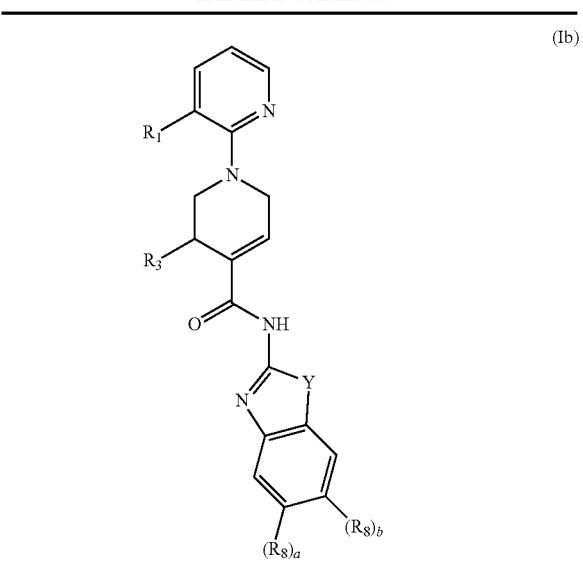

(Ib)

and pharmaceutically acceptable salts thereof, wherein:

| Compound | Y | R$_1$ | (R$_8$)$_a$ | (R$_8$)$_b$ |
|---|---|---|---|---|
| B247 (a and b) | O | —Cl | —Br | —H |
| B248 (a and b) | O | —Cl | —F | —H |
| B249 (a and b) | O | —Cl | —CH$_3$ | —H |
| B250 (a and b) | O | —Cl | —CF$_3$ | —H |
| B251 (a and b) | O | —Cl | —OCH$_3$ | —H |
| B252 (a and b) | O | —Cl | —OCH$_2$CH$_3$ | —H |
| B253 (a and b) | O | —Cl | —OCF$_3$ | —H |
| B254 (a and b) | O | —Cl | -tert-butyl | —H |
| B255 (a and b) | O | —Cl | -iso-propyl | —H |
| B256 (a and b) | O | —Cl | —CH$_3$ | —CH$_3$ |
| B257 (a and b) | O | —Cl | —H | —H |
| B258 (a and b) | O | —Cl | —H | —CH$_3$ |
| B259 (a and b) | O | —Cl | —H | —Cl |
| B260 (a and b) | O | —Cl | —H | —Br |
| B261 (a and b) | O | —Cl | —H | —F |
| B262 (a and b) | O | —Cl | —H | —CF$_3$ |
| B263 (a and b) | O | —Cl | —H | —OCH$_3$ |
| B264 (a and b) | O | —Cl | —H | —OCH$_2$CH$_3$ |
| B265 (a and b) | O | —Cl | —H | —OCF$_3$ |
| B266 (a and b) | O | —Cl | —H | -tert-butyl |
| B267 (a and b) | O | —Cl | —H | -iso-propyl |
| B268 (a and b) | O | —Cl | —H | —OCF$_3$ |
| B269 (a and b) | O | —Cl | —H | -tert-butyl |
| B270 (a and b) | O | —Cl | —H | -iso-propyl |
| B271 (a and b) | O | —CH$_3$ | —Cl | —H |
| B272 (a and b) | O | —CH$_3$ | —Br | —H |
| B273 (a and b) | O | —CH$_3$ | —F | —H |
| B274 (a and b) | O | —CH$_3$ | —CH$_3$ | —H |
| B275 (a and b) | O | —CH$_3$ | —CF$_3$ | —H |
| B276 (a and b) | O | —CH$_3$ | —OCH$_3$ | —H |
| B277 (a and b) | O | —CH$_3$ | —OCH$_2$CH$_3$ | —H |
| B278 (a and b) | O | —CH$_3$ | —OCF$_3$ | —H |
| B279 (a and b) | O | —CH$_3$ | -tert-butyl | —H |
| B280 (a and b) | O | —CH$_3$ | -iso-propyl | —H |
| B281 (a and b) | O | —CH$_3$ | —CH$_3$ | —CH$_3$ |
| B282 (a and b) | O | —CH$_3$ | —H | —H |
| B283 (a and b) | O | —CH$_3$ | —H | —Cl |
| B284 (a and b) | O | —CH$_3$ | —H | —Br |
| B285 (a and b) | O | —CH$_3$ | —H | —F |
| B286 (a and b) | O | —CH$_3$ | —H | —CH$_3$ |
| B287 (a and b) | O | —CH$_3$ | —H | —CF$_3$ |
| B288 (a and b) | O | —CH$_3$ | —H | —OCH$_3$ |
| B289 (a and b) | O | —CH$_3$ | —H | —OCH$_2$CH$_3$ |
| B290 (a and b) | O | —CH$_3$ | —H | —OCF$_3$ |
| B291 (a and b) | O | —CH$_3$ | —H | -tert-butyl |
| B292 (a and b) | O | —CH$_3$ | —H | -iso-propyl |
| B293 (a and b) | O | —CF$_3$ | —Cl | —H |
| B294 (a and b) | O | —CF$_3$ | —Br | —H |
| B295 (a and b) | O | —CF$_3$ | —F | —H |

TABLE 2-continued

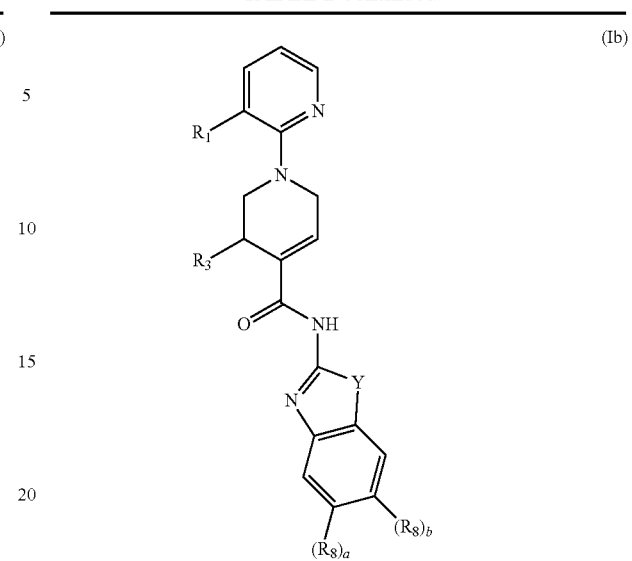

(Ib)

and pharmaceutically acceptable salts thereof, wherein:

| Compound | Y | R$_1$ | (R$_8$)$_a$ | (R$_8$)$_b$ |
|---|---|---|---|---|
| B296 (a and b) | O | —CF$_3$ | —CH$_3$ | —H |
| B297 (a and b) | O | —CF$_3$ | —CF$_3$ | —H |
| B298 (a and b) | O | —CF$_3$ | —OCH$_3$ | —H |
| B299 (a and b) | O | —CF$_3$ | —OCH$_2$CH$_3$ | —H |
| B300 (a and b) | O | —CF$_3$ | —OCF$_3$ | —H |
| B301 (a and b) | O | —CF$_3$ | -tert-butyl | —H |
| B302 (a and b) | O | —CF$_3$ | -iso-propyl | —H |
| B303 (a and b) | O | —CF$_3$ | —CH$_3$ | —CH$_3$ |
| B304 (a and b) | O | —CF$_3$ | —H | —H |
| B305 (a and b) | O | —CF$_3$ | —H | —Cl |
| B306 (a and b) | O | —CF$_3$ | —H | —Br |
| B307 (a and b) | O | —CF$_3$ | —H | —F |
| B308 (a and b) | O | —CF$_3$ | —H | —CH$_3$ |
| B309 (a and b) | O | —CF$_3$ | —H | —CF$_3$ |
| B310 (a and b) | O | —CF$_3$ | —H | —OCH$_3$ |
| B311 (a and b) | O | —CF$_3$ | —H | —OCH$_2$CH$_3$ |
| B312 (a and b) | O | —CF$_3$ | —H | —OCF$_3$ |
| B313 (a and b) | O | —CF$_3$ | —H | -tert-butyl |
| B314 (a and b) | O | —CF$_3$ | —H | -iso-propyl |
| B315 (a and b) | O | —CHF$_2$ | —Cl | —H |
| B316 (a and b) | O | —CHF$_2$ | —Br | —H |
| B317 (a and b) | O | —CHF$_2$ | —F | —H |
| B318 (a and b) | O | —CHF$_2$ | —CH$_3$ | —H |
| B319 (a and b) | O | —CHF$_2$ | —CF$_3$ | —H |
| B320 (a and b) | O | —CHF$_2$ | —OCH$_3$ | —H |
| B321 (a and b) | O | —CHF$_2$ | —OCH$_2$CH$_3$ | —H |
| B322 (a and b) | O | —CHF$_2$ | —OCF$_3$ | —H |
| B323 (a and b) | O | —CHF$_2$ | -tert-butyl | —H |
| B324 (a and b) | O | —CHF$_2$ | -iso-propyl | —H |
| B325 (a and b) | O | —CHF$_2$ | —CH$_3$ | —CH$_3$ |
| B326 (a and b) | O | —CHF$_2$ | —H | —H |
| B327 (a and b) | O | —CHF$_2$ | —H | —Cl |
| B328 (a and b) | O | —CHF$_2$ | —H | —Br |
| B329 (a and b) | O | —CHF$_2$ | —H | —F |
| B330 (a and b) | O | —CHF$_2$ | —H | —CH$_3$ |
| B331 (a and b) | O | —CHF$_2$ | —H | —CF$_3$ |
| B332 (a and b) | O | —CHF$_2$ | —H | —OCH$_3$ |
| B333 (a and b) | O | —CHF$_2$ | —H | —OCH$_2$CH$_3$ |
| B334 (a and b) | O | —CHF$_2$ | —H | —OCF$_3$ |
| B335 (a and b) | O | —CHF$_2$ | —H | -tert-butyl |
| B336 (a and b) | O | —CHF$_2$ | —H | -iso-propyl |
| B337 (a and b) | O | —OH | —Cl | —H |
| B338 (a and b) | O | —OH | —Br | —H |
| B339 (a and b) | O | —OH | —F | —H |
| B340 (a and b) | O | —OH | —CH$_3$ | —H |
| B341 (a and b) | O | —OH | —CF$_3$ | —H |
| B342 (a and b) | O | —OH | —OCH$_3$ | —H |
| B343 (a and b) | O | —OH | —OCH$_2$CH$_3$ | —H |
| B344 (a and b) | O | —OH | —OCF$_3$ | —H |

TABLE 2-continued

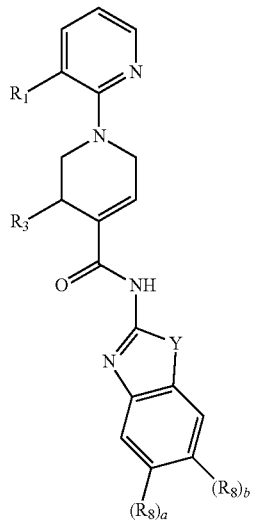

(Ib)

and pharmaceutically acceptable salts thereof, wherein:

| Compound | Y | $R_1$ | $(R_8)_a$ | $(R_8)_b$ |
|---|---|---|---|---|
| B345 (a and b) | O | —OH | -tert-butyl | —H |
| B346 (a and b) | O | —OH | -iso-propyl | —H |
| B347 (a and b) | O | —OH | —CH$_3$ | —CH$_3$ |
| B348 (a and b) | O | —OH | —H | —H |
| B349 (a and b) | O | —OH | —H | —Cl |
| B350 (a and b) | O | —OH | —H | —Br |
| B351 (a and b) | O | —OH | —H | —F |
| B352 (a and b) | O | —OH | —H | —CH$_3$ |
| B353 (a and b) | O | —OH | —H | —CF$_3$ |
| B354 (a and b) | O | —OH | —H | —OCH$_3$ |
| B355 (a and b) | O | —OH | —H | —OCH$_2$CH$_3$ |
| B356 (a and b) | O | —OH | —H | —OCF$_3$ |
| B357 (a and b) | O | —OH | —H | -tert-butyl |
| B358 (a and b) | O | —OH | —H | -iso-propyl |
| B359 (a and b) | O | —NO$_2$ | —Cl | —H |
| B360 (a and b) | O | —NO$_2$ | —Br | —H |
| B361 (a and b) | O | —NO$_2$ | —F | —H |
| B362 (a and b) | O | —NO$_2$ | —CH$_3$ | —H |
| B363 (a and b) | O | —NO$_2$ | —CF$_3$ | —H |
| B364 (a and b) | O | —NO$_2$ | —OCH$_3$ | —H |
| B365 (a and b) | O | —NO$_2$ | —OCH$_2$CH$_3$ | —H |
| B366 (a and b) | O | —NO$_2$ | —OCF$_3$ | —H |
| B367 (a and b) | O | —NO$_2$ | -tert-butyl | —H |
| B368 (a and b) | O | —NO$_2$ | -iso-propyl | —H |
| B369 (a and b) | O | —NO$_2$ | —CH$_3$ | —CH$_3$ |
| B370 (a and b) | O | —NO$_2$ | —H | —H |
| B371 (a and b) | O | —NO$_2$ | —H | —Cl |
| B372 (a and b) | O | —NO$_2$ | —H | —Br |
| B373 (a and b) | O | —NO$_2$ | —H | —F |
| B374 (a and b) | O | —NO$_2$ | —H | —CH$_3$ |
| B375 (a and b) | O | —NO$_2$ | —H | —CF$_3$ |
| B376 (a and b) | O | —NO$_2$ | —H | —OCH$_3$ |
| B377 (a and b) | O | —NO$_2$ | —H | —OCH$_2$CH$_3$ |
| B378 (a and b) | O | —NO$_2$ | —H | —OCF$_3$ |
| B379 (a and b) | O | —NO$_2$ | —H | -tert-butyl |
| B380 (a and b) | O | —NO$_2$ | —H | -iso-propyl |
| B381 (a and b) | O | —CN | —Br | —H |
| B382 (a and b) | O | —CN | —Cl | —H |
| B383 (a and b) | O | —CN | —F | —H |
| B384 (a and b) | O | —CN | —CH$_3$ | —H |
| B385 (a and b) | O | —CN | —CF$_3$ | —H |
| B386 (a and b) | O | —CN | —OCH$_3$ | —H |
| B387 (a and b) | O | —CN | —OCH$_2$CH$_3$ | —H |
| B388 (a and b) | O | —CN | —OCF$_3$ | —H |
| B389 (a and b) | O | —CN | -tert-butyl | —H |
| B390 (a and b) | O | —CN | -iso-propyl | —H |
| B391 (a and b) | O | —CN | —CH$_3$ | —CH$_3$ |
| B392 (a and b) | O | —CN | —H | —H |
| B393 (a and b) | O | —CN | —H | —Cl |

TABLE 2-continued

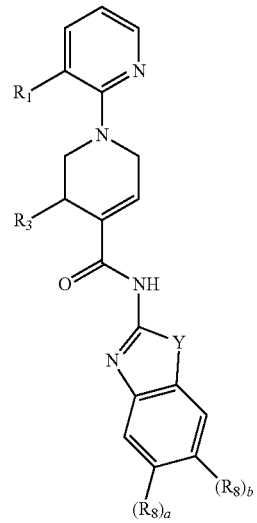

(Ib)

and pharmaceutically acceptable salts thereof, wherein:

| Compound | Y | $R_1$ | $(R_8)_a$ | $(R_8)_b$ |
|---|---|---|---|---|
| B394 (a and b) | O | —CN | —H | —Br |
| B395 (a and b) | O | —CN | —H | —F |
| B396 (a and b) | O | —CN | —H | —CH$_3$ |
| B397 (a and b) | O | —CN | —H | —CF$_3$ |
| B398 (a and b) | O | —CN | —H | —OCH$_3$ |
| B399 (a and b) | O | —CN | —H | —OCH$_2$CH$_3$ |
| B400 (a and b) | O | —CN | —H | —OCF$_3$ |
| B401 (a and b) | O | —CN | —H | -tert-butyl |
| B402 (a and b) | O | —CN | —H | -iso-propyl |
| B403 (a and b) | O | —Br | —Br | —H |
| B404 (a and b) | O | —Br | —Cl | —H |
| B405 (a and b) | O | —Br | —F | —H |
| B406 (a and b) | O | —Br | —CH$_3$ | —H |
| B407 (a and b) | O | —Br | —CF$_3$ | —H |
| B408 (a and b) | O | —Br | —OCH$_3$ | —H |
| B409 (a and b) | O | —Br | —OCH$_2$CH$_3$ | —H |
| B410 (a and b) | O | —Br | —OCF$_3$ | —H |
| B411 (a and b) | O | —Br | -tert-butyl | —H |
| B412 (a and b) | O | —Br | -iso-propyl | —H |
| B413 (a and b) | O | —Br | —CH$_3$ | —CH$_3$ |
| B414 (a and b) | O | —Br | —H | —H |
| B415 (a and b) | O | —Br | —H | —Cl |
| B416 (a and b) | O | —Br | —H | —Br |
| B417 (a and b) | O | —Br | —H | —F |
| B418 (a and b) | O | —Br | —H | —CH$_3$ |
| B419 (a and b) | O | —Br | —H | —CF$_3$ |
| B420 (a and b) | O | —Br | —H | —OCH$_3$ |
| B421 (a and b) | O | —Br | —H | —OCH$_2$CH$_3$ |
| B422 (a and b) | O | —Br | —H | —OCF$_3$ |
| B423 (a and b) | O | —Br | —H | -tert-butyl |
| B424 (a and b) | O | —Br | —H | -iso-propyl |
| B425 (a and b) | O | —I | —Cl | —H |
| B426 (a and b) | O | —I | —Br | —H |
| B427 (a and b) | O | —I | —F | —H |
| B428 (a and b) | O | —I | —CH$_3$ | —H |
| B429 (a and b) | O | —I | —CF$_3$ | —H |
| B430 (a and b) | O | —I | —OCH$_3$ | —H |
| B431 (a and b) | O | —I | —OCH$_2$CH$_3$ | —H |
| B432 (a and b) | O | —I | —OCF$_3$ | —H |
| B433 (a and b) | O | —I | -tert-butyl | —H |
| B434 (a and b) | O | —I | -iso-propyl | —H |
| B435 (a and b) | O | —I | —CH$_3$ | —CH$_3$ |
| B436 (a and b) | O | —I | —H | —H |
| B437 (a and b) | O | —I | —H | —Cl |
| B438 (a and b) | O | —I | —H | —Br |
| B439 (a and b) | O | —I | —H | —F |
| B440 (a and b) | O | —I | —H | —CH$_3$ |
| B441 (a and b) | O | —I | —H | —CF$_3$ |
| B442 (a and b) | O | —I | —H | —OCH$_3$ |

TABLE 2-continued

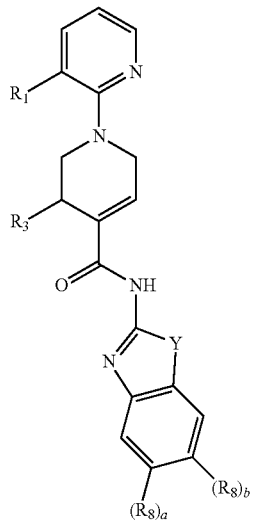

(Ib)

and pharmaceutically acceptable salts thereof, wherein:

| Compound | Y | R₁ | (R₈)ₐ | (R₈)ᵦ |
|---|---|---|---|---|
| B443 (a and b) | O | —I | —H | —OCH₂CH₃ |
| B444 (a and b) | O | —I | —H | —OCF₃ |
| B445 (a and b) | O | —I | —H | -tert-butyl |
| B446 (a and b) | O | —I | —H | -iso-propyl |
| B447 (a and b) | NH | —H | —Cl | —H |
| B448 (a and b) | NH | —H | —Br | —H |
| B449 (a and b) | NH | —H | —F | —H |
| B450 (a and b) | NH | —H | —CH₃ | —H |
| B451 (a and b) | NH | —H | —CF₃ | —H |
| B452 (a and b) | NH | —H | —OCH₃ | —H |
| B453 (a and b) | NH | —H | —OCH₂CH₃ | —H |
| B454 (a and b) | NH | —H | —OCF₃ | —H |
| B455 (a and b) | NH | —H | -tert-butyl | —H |
| B456 (a and b) | NH | —H | -iso-propyl | —H |
| B457 (a and b) | NH | —H | —CH₃ | —CH₃ |
| B458 (a and b) | NH | —H | —H | —H |
| B459 (a and b) | NH | —H | —H | —Cl |
| B460 (a and b) | NH | —H | —H | —Br |
| B461 (a and b) | NH | —H | —H | —F |
| B462 (a and b) | NH | —H | —H | —CH₃ |
| B463 (a and b) | NH | —H | —H | —CF₃ |
| B464 (a and b) | NH | —H | —H | —OCH₃ |
| B465 (a and b) | NH | —H | —H | —OCH₂CH₃ |
| B466 (a and b) | NH | —H | —H | —OCF₃ |
| B467 (a and b) | NH | —H | —H | -tert-butyl |
| B468 (a and b) | NH | —H | —H | -iso-propyl |
| B469 (a and b) | NH | —Cl | —Cl | —H |
| B470 (a and b) | NH | —Cl | —Br | —H |
| B471 (a and b) | NH | —Cl | —F | —H |
| B472 (a and b) | NH | —Cl | —CH₃ | —H |
| B473 (a and b) | NH | —Cl | —CF₃ | —H |
| B474 (a and b) | NH | —Cl | —OCH₃ | —H |
| B475 (a and b) | NH | —Cl | —OCH₂CH₃ | —H |
| B476 (a and b) | NH | —Cl | —OCF₃ | —H |
| B477 (a and b) | NH | —Cl | -tert-butyl | —H |
| B478 (a and b) | NH | —Cl | -iso-propyl | —H |
| B479 (a and b) | NH | —Cl | —CH₃ | —CH₃ |
| B480 (a and b) | NH | —Cl | —H | —H |
| B481 (a and b) | NH | —Cl | —H | —CH₃ |
| B482 (a and b) | NH | —Cl | —H | —Cl |
| B483 (a and b) | NH | —Cl | —H | —Br |
| B484 (a and b) | NH | —Cl | —H | —F |
| B485 (a and b) | NH | —Cl | —H | —CF₃ |
| B486 (a and b) | NH | —Cl | —H | —OCH₃ |
| B487 (a and b) | NH | —Cl | —H | —OCH₂CH₃ |
| B488 (a and b) | NH | —Cl | —H | —OCF₃ |
| B489 (a and b) | NH | —Cl | —H | -tert-butyl |
| B490 (a and b) | NH | —Cl | —H | -iso-propyl |
| B491 (a and b) | NH | —Cl | —H | —OCF₃ |

TABLE 2-continued

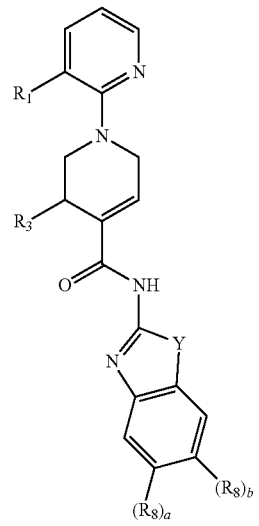

(Ib)

and pharmaceutically acceptable salts thereof, wherein:

| Compound | Y | R₁ | (R₈)ₐ | (R₈)ᵦ |
|---|---|---|---|---|
| B492 (a and b) | NH | —Cl | —H | -tert-butyl |
| B493 (a and b) | NH | —Cl | —H | -iso-propyl |
| B494 (a and b) | NH | —CH₃ | —Cl | —H |
| B495 (a and b) | NH | —CH₃ | —Br | —H |
| B496 (a and b) | NH | —CH₃ | —F | —H |
| B497 (a and b) | NH | —CH₃ | —CH₃ | —H |
| B498 (a and b) | NH | —CH₃ | —CF₃ | —H |
| B499 (a and b) | NH | —CH₃ | —OCH₃ | —H |
| B500 (a and b) | NH | —CH₃ | —OCH₂CH₃ | —H |
| B501 (a and b) | NH | —CH₃ | —OCF₃ | —H |
| B502 (a and b) | NH | —CH₃ | -tert-butyl | —H |
| B503 (a and b) | NH | —CH₃ | -iso-propyl | —H |
| B504 (a and b) | NH | —CH₃ | —CH₃ | —CH₃ |
| B505 (a and b) | NH | —CH₃ | —H | —H |
| B506 (a and b) | NH | —CH₃ | —H | —Cl |
| B507 (a and b) | NH | —CH₃ | —H | —Br |
| B508 (a and b) | NH | —CH₃ | —H | —F |
| B509 (a and b) | NH | —CH₃ | —H | —CH₃ |
| B510 (a and b) | NH | —CH₃ | —H | —CF₃ |
| B511 (a and b) | NH | —CH₃ | —H | —OCH₃ |
| B512 (a and b) | NH | —CH₃ | —H | —OCH₂CH₃ |
| B513 (a and b) | NH | —CH₃ | —H | —OCF₃ |
| B514 (a and b) | NH | —CH₃ | —H | -tert-butyl |
| B515 (a and b) | NH | —CH₃ | —H | -iso-propyl |
| B516 (a and b) | NH | —CF₃ | —Cl | —H |
| B517 (a and b) | NH | —CF₃ | —Br | —H |
| B518 (a and b) | NH | —CF₃ | —F | —H |
| B519 (a and b) | NH | —CF₃ | —CH₃ | —H |
| B520 (a and b) | NH | —CF₃ | —CF₃ | —H |
| B521 (a and b) | NH | —CF₃ | —OCH₃ | —H |
| B522 (a and b) | NH | —CF₃ | —OCH₂CH₃ | —H |
| B523 (a and b) | NH | —CF₃ | —OCF₃ | —H |
| B524 (a and b) | NH | —CF₃ | -tert-butyl | —H |
| B525 (a and b) | NH | —CF₃ | -iso-propyl | —H |
| B526 (a and b) | NH | —CF₃ | —CH₃ | —CH₃ |
| B527 (a and b) | NH | —CF₃ | —H | —H |
| B528 (a and b) | NH | —CF₃ | —H | —Cl |
| B529 (a and b) | NH | —CF₃ | —H | —Br |
| B530 (a and b) | NH | —CF₃ | —H | —F |
| B531 (a and b) | NH | —CF₃ | —H | —CH₃ |
| B532 (a and b) | NH | —CF₃ | —H | —CF₃ |
| B533 (a and b) | NH | —CF₃ | —H | —OCH₃ |
| B534 (a and b) | NH | —CF₃ | —H | —OCH₂CH₃ |
| B535 (a and b) | NH | —CF₃ | —H | —OCF₃ |
| B536 (a and b) | NH | —CF₃ | —H | -tert-butyl |
| B537 (a and b) | NH | —CF₃ | —H | -iso-propyl |
| B538 (a and b) | NH | —CHF₂ | —Cl | —H |
| B539 (a and b) | NH | —CHF₂ | —Br | —H |
| B540 (a and b) | NH | —CHF₂ | —F | —H |

TABLE 2-continued

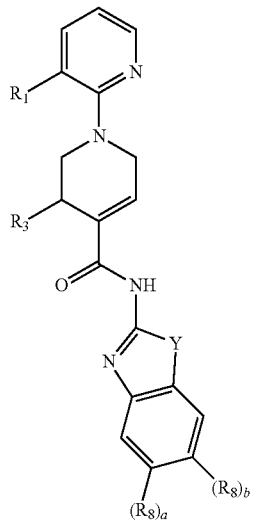

(Ib)

and pharmaceutically acceptable salts thereof, wherein:

| Compound | Y | R₁ | (R₈)ₐ | (R₈)ᵦ |
|---|---|---|---|---|
| B541 (a and b) | NH | —CHF₂ | —CH₃ | —H |
| B542 (a and b) | NH | —CHF₂ | —CF₃ | —H |
| B543 (a and b) | NH | —CHF₂ | —OCH₃ | —H |
| B544 (a and b) | NH | —CHF₂ | —OCH₂CH₃ | —H |
| B545 (a and b) | NH | —CHF₂ | —OCF₃ | —H |
| B546 (a and b) | NH | —CHF₂ | -tert-butyl | —H |
| B547 (a and b) | NH | —CHF₂ | -iso-propyl | —H |
| B548 (a and b) | NH | —CHF₂ | —CH₃ | —CH₃ |
| B549 (a and b) | NH | —CHF₂ | —H | —H |
| B550 (a and b) | NH | —CHF₂ | —H | —Cl |
| B551 (a and b) | NH | —CHF₂ | —H | —Br |
| B552 (a and b) | NH | —CHF₂ | —H | —F |
| B553 (a and b) | NH | —CHF₂ | —H | —CH₃ |
| B554 (a and b) | NH | —CHF₂ | —H | —CF₃ |
| B555 (a and b) | NH | —CHF₂ | —H | —OCH₃ |
| B556 (a and b) | NH | —CHF₂ | —H | —OCH₂CH₃ |
| B557 (a and b) | NH | —CHF₂ | —H | —OCF₃ |
| B558 (a and b) | NH | —CHF₂ | —H | -tert-butyl |
| B559 (a and b) | NH | —CHF₂ | —H | -iso-propyl |
| B560 (a and b) | NH | —OH | —Cl | —H |
| B561 (a and b) | NH | —OH | —Br | —H |
| B562 (a and b) | NH | —OH | —F | —H |
| B563 (a and b) | NH | —OH | —CH₃ | —H |
| B564 (a and b) | NH | —OH | —CF₃ | —H |
| B565 (a and b) | NH | —OH | —OCH₃ | —H |
| B566 (a and b) | NH | —OH | —OCH₂CH₃ | —H |
| B567 (a and b) | NH | —OH | —OCF₃ | —H |
| B568 (a and b) | NH | —OH | -tert-butyl | —H |
| B569 (a and b) | NH | —OH | -iso-propyl | —H |
| B570 (a and b) | NH | —OH | —CH₃ | —CH₃ |
| B571 (a and b) | NH | —OH | —H | —H |
| B572 (a and b) | NH | —OH | —H | —Cl |
| B573 (a and b) | NH | —OH | —H | —Br |
| B574 (a and b) | NH | —OH | —H | —F |
| B575 (a and b) | NH | —OH | —H | —CH₃ |
| B576 (a and b) | NH | —OH | —H | —CF₃ |
| B577 (a and b) | NH | —OH | —H | —OCH₃ |
| B578 (a and b) | NH | —OH | —H | —OCH₂CH₃ |
| B579 (a and b) | NH | —OH | —H | —OCF₃ |
| B580 (a and b) | NH | —OH | —H | -tert-butyl |
| B581 (a and b) | NH | —OH | —H | -iso-propyl |
| B582 (a and b) | NH | —NO₂ | —Cl | —H |
| B583 (a and b) | NH | —NO₂ | —Br | —H |
| B584 (a and b) | NH | —NO₂ | —F | —H |
| B585 (a and b) | NH | —NO₂ | —CH₃ | —H |
| B586 (a and b) | NH | —NO₂ | —CF₃ | —H |
| B587 (a and b) | NH | —NO₂ | —OCH₃ | —H |
| B588 (a and b) | NH | —NO₂ | —OCH₂CH₃ | —H |
| B589 (a and b) | NH | —NO₂ | —OCF₃ | —H |

TABLE 2-continued

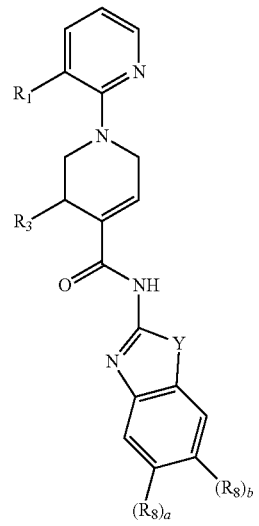

(Ib)

and pharmaceutically acceptable salts thereof, wherein:

| Compound | Y | R₁ | (R₈)ₐ | (R₈)ᵦ |
|---|---|---|---|---|
| B590 (a and b) | NH | —NO₂ | -tert-butyl | —H |
| B591 (a and b) | NH | —NO₂ | -iso-propyl | —H |
| B592 (a and b) | NH | —NO₂ | —CH₃ | —CH₃ |
| B593 (a and b) | NH | —NO₂ | —H | —H |
| B594 (a and b) | NH | —NO₂ | —H | —Cl |
| B595 (a and b) | NH | —NO₂ | —H | —Br |
| B596 (a and b) | NH | —NO₂ | —H | —F |
| B597 (a and b) | NH | —NO₂ | —H | —CH₃ |
| B598 (a and b) | NH | —NO₂ | —H | —CF₃ |
| B599 (a and b) | NH | —NO₂ | —H | —OCH₃ |
| B600 (a and b) | NH | —NO₂ | —H | —OCH₂CH₃ |
| B601 (a and b) | NH | —NO₂ | —H | —OCF₃ |
| B602 (a and b) | NH | —NO₂ | —H | -tert-butyl |
| B603 (a and b) | NH | —NO₂ | —H | -iso-propyl |
| B604 (a and b) | NH | —CN | —Br | —H |
| B605 (a and b) | NH | —CN | —Cl | —H |
| B606 (a and b) | NH | —CN | —F | —H |
| B607 (a and b) | NH | —CN | —CH₃ | —H |
| B608 (a and b) | NH | —CN | —CF₃ | —H |
| B609 (a and b) | NH | —CN | —OCH₃ | —H |
| B610 (a and b) | NH | —CN | —OCH₂CH₃ | —H |
| B611 (a and b) | NH | —CN | —OCF₃ | —H |
| B612 (a and b) | NH | —CN | -tert-butyl | —H |
| B613 (a and b) | NH | —CN | -iso-propyl | —H |
| B614 (a and b) | NH | —CN | —CH₃ | —CH₃ |
| B615 (a and b) | NH | —CN | —H | —H |
| B616 (a and b) | NH | —CN | —H | —Cl |
| B617 (a and b) | NH | —CN | —H | —Br |
| B618 (a and b) | NH | —CN | —H | —F |
| B619 (a and b) | NH | —CN | —H | —CH₃ |
| B620 (a and b) | NH | —CN | —H | —CF₃ |
| B621 (a and b) | NH | —CN | —H | —OCH₃ |
| B622 (a and b) | NH | —CN | —H | —OCH₂CH₃ |
| B623 (a and b) | NH | —CN | —H | —OCF₃ |
| B624 (a and b) | NH | —CN | —H | -tert-butyl |
| B625 (a and b) | NH | —CN | —H | -iso-propyl |
| B626 (a and b) | NH | —Br | —Br | —H |
| B627 (a and b) | NH | —Br | —Cl | —H |
| B628 (a and b) | NH | —Br | —F | —H |
| B629 (a and b) | NH | —Br | —CH₃ | —H |
| B630 (a and b) | NH | —Br | —CF₃ | —H |
| B631 (a and b) | NH | —Br | —OCH₃ | —H |
| B632 (a and b) | NH | —Br | —OCH₂CH₃ | —H |
| B633 (a and b) | NH | —Br | —OCF₃ | —H |
| B634 (a and b) | NH | —Br | -tert-butyl | —H |
| B635 (a and b) | NH | —Br | -iso-propyl | —H |
| B636 (a and b) | NH | —Br | —CH₃ | —CH₃ |
| B637 (a and b) | NH | —Br | —H | —H |
| B638 (a and b) | NH | —Br | —H | —Cl |

TABLE 2-continued

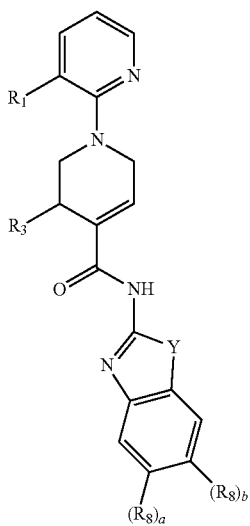

(Ib)

and pharmaceutically acceptable salts thereof, wherein:

| Compound | Y | R₁ | (R₈)ₐ | (R₈)ᵦ |
|---|---|---|---|---|
| B639 (a and b) | NH | —Br | —H | —Br |
| B640 (a and b) | NH | —Br | —H | —F |
| B641 (a and b) | NH | —Br | —H | —CH₃ |
| B642 (a and b) | NH | —Br | —H | —CF₃ |
| B643 (a and b) | NH | —Br | —H | —OCH₃ |
| B644 (a and b) | NH | —Br | —H | —OCH₂CH₃ |
| B645 (a and b) | NH | —Br | —H | —OCF₃ |
| B646 (a and b) | NH | —Br | —H | -tert-butyl |
| B647 (a and b) | NH | —Br | —H | -iso-propyl |
| B648 (a and b) | NH | —I | —Cl | —H |
| B649 (a and b) | NH | —I | —Br | —H |
| B650 (a and b) | NH | —I | —F | —H |
| B651 (a and b) | NH | —I | —CH₃ | —H |
| B652 (a and b) | NH | —I | —CF₃ | —H |
| B653 (a and b) | NH | —I | —OCH₃ | —H |
| B654 (a and b) | NH | —I | —OCH₂CH₃ | —H |
| B655 (a and b) | NH | —I | —OCF₃ | —H |
| B656 (a and b) | NH | —I | -tert-butyl | —H |
| B657 (a and b) | NH | —I | -iso-propyl | —H |
| B658 (a and b) | NH | —I | —CH₃ | —CH₃ |
| B659 (a and b) | NH | —I | —H | —H |
| B660 (a and b) | NH | —I | —H | —Cl |
| B661 (a and b) | NH | —I | —H | —Br |
| B662 (a and b) | NH | —I | —H | —F |
| B663 (a and b) | NH | —I | —H | —CH₃ |
| B664 (a and b) | NH | —I | —H | —CF₃ |
| B665 (a and b) | NH | —I | —H | —OCH₃ |
| B666 (a and b) | NH | —I | —H | —OCH₂CH₃ |
| B667 (a and b) | NH | —I | —H | —OCF₃ |
| B668 (a and b) | NH | —I | —H | -tert-butyl |
| B669 (a and b) | NH | —I | —H | -iso-propyl |

(a) means that R₃ is —H.
(b) means that R₃ is —CH₃.

TABLE 3

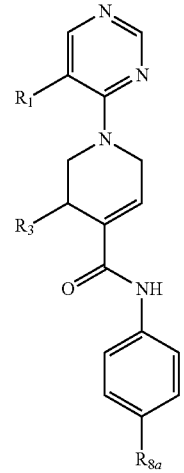

(Ic)

and pharmaceutically acceptable salts thereof, wherein:

| Compound | R₁ | R₈ₐ |
|---|---|---|
| C01 (a and b) | —H | —H |
| C02 (a and b) | —H | -tert-butyl |
| C03 (a and b) | —H | -iso-butyl |
| C04 (a and b) | —H | -sec-butyl |
| C05 (a and b) | —H | -iso-propyl |
| C06 (a and b) | —H | -n-propyl |
| C07 (a and b) | —H | -cyclohexyl |
| C08 (a and b) | —H | -tert-butoxy |
| C09 (a and b) | —H | -isopropoxy |
| C10 (a and b) | —H | —CF₃ |
| C11 (a and b) | —H | —CH₂CF₃ |
| C12 (a and b) | —H | —OCF₃ |
| C13 (a and b) | —H | —Cl |
| C14 (a and b) | —H | —Br |
| C15 (a and b) | —H | —I |
| C16 (a and b) | —H | -n-butyl |
| C17 (a and b) | —H | —CH₃ |
| C18 (a and b) | —H | —SCF₃ |
| C19 (a and b) | —H | —N(CH₂CH₃)₂ |
| C20 (a and b) | —H | —OCF₂CHF₂ |
| C21 (a and b) | —H | —C(OH)(CF₃)₂ |
| C22 (a and b) | —H | -(1,1-dimethyl-pentyl) |
| C23 (a and b) | —H | -(1,1-dimethyl-acetic acid) ethyl ester |
| C24 (a and b) | —H | —N-piperidinyl |
| C25 (a and b) | —Cl | —H |
| C26 (a and b) | —Cl | -tert-butyl |
| C27 (a and b) | —Cl | -iso-butyl |
| C28 (a and b) | —Cl | -sec-butyl |
| C29 (a and b) | —Cl | -iso-propyl |
| C30 (a and b) | —Cl | -n-propyl |
| C31 (a and b) | —Cl | -cyclohexyl |
| C32 (a and b) | —Cl | -tert-butoxy |
| C33 (a and b) | —Cl | -isopropoxy |
| C34 (a and b) | —Cl | —CF₃ |
| C35 (a and b) | —Cl | —CH₂CF₃ |
| C36 (a and b) | —Cl | —OCF₃ |
| C37 (a and b) | —Cl | —Cl |
| C38 (a and b) | —Cl | —Br |
| C39 (a and b) | —Cl | —I |
| C40 (a and b) | —Cl | -n-butyl |
| C41 (a and b) | —Cl | —CH₃ |
| C42 (a and b) | —Cl | —SCF₃ |
| C43 (a and b) | —Cl | —N(CH₂CH₃)₂ |
| C44 (a and b) | —Cl | —OCF₂CHF₂ |
| C45 (a and b) | —Cl | —C(OH)(CF₃)₂ |
| C46 (a and b) | —Cl | -(1,1-dimethyl-pentyl) |
| C47 (a and b) | —Cl | -(1,1-dimethyl-acetic acid) ethyl ester |
| C48 (a and b) | —Cl | —N-piperidinyl |
| C49 (a and b) | —F | —H |
| C50 (a and b) | —F | -tert-butyl |
| C51 (a and b) | —F | -iso-butyl |
| C52 (a and b) | —F | -sec-butyl |

TABLE 3-continued (Ic)

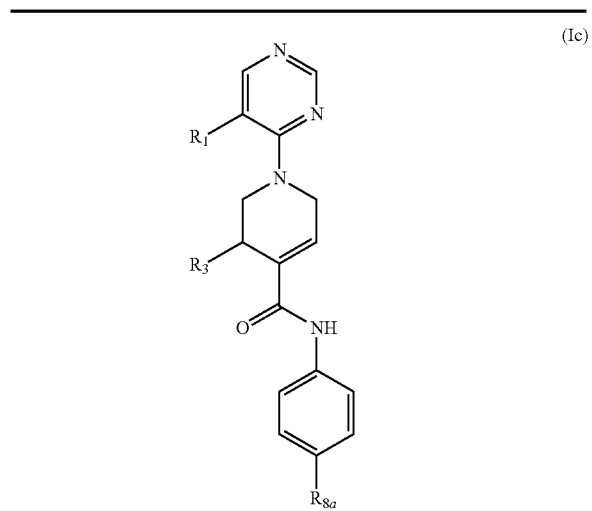

and pharmaceutically acceptable salts thereof, wherein:

| Compound | $R_1$ | $R_{8a}$ |
|---|---|---|
| C53 (a and b) | —F | -iso-propyl |
| C54 (a and b) | —F | -n-propyl |
| C55 (a and b) | —F | -cyclohexyl |
| C56 (a and b) | —F | -tert-butoxy |
| C57 (a and b) | —F | -isopropoxy |
| C58 (a and b) | —F | —$CF_3$ |
| C59 (a and b) | —F | —$CH_2CF_3$ |
| C60 (a and b) | —F | —$OCF_3$ |
| C61 (a and b) | —F | —Cl |
| C62 (a and b) | —F | —Br |
| C63 (a and b) | —F | —I |
| C64 (a and b) | —F | -n-butyl |
| C65 (a and b) | —F | —$CH_3$ |
| C66 (a and b) | —F | —$SCF_3$ |
| C67 (a and b) | —F | —$N(CH_2CH_3)_2$ |
| C68 (a and b) | —F | —$OCF_2CHF_2$ |
| C69 (a and b) | —F | —$C(OH)(CF_3)_2$ |
| C70 (a and b) | —F | -(1,1-dimethyl-pentyl) |
| C71 (a and b) | —F | -(1,1-dimethyl-acetic acid) ethyl ester |
| C72 (a and b) | —F | —N-piperidinyl |
| C73 (a and b) | —$CH_3$ | —H |
| C74 (a and b) | —$CH_3$ | -iso-butyl |
| C75 (a and b) | —$CH_3$ | -tert-butyl |
| C76 (a and b) | —$CH_3$ | -sec-butyl |
| C77 (a and b) | —$CH_3$ | -iso-propyl |
| C78 (a and b) | —$CH_3$ | -n-propyl |
| C79 (a and b) | —$CH_3$ | -cyclohexyl |
| C80 (a and b) | —$CH_3$ | -tert-butoxy |
| C81 (a and b) | —$CH_3$ | -isopropoxy |
| C82 (a and b) | —$CH_3$ | —$CF_3$ |
| C83 (a and b) | —$CH_3$ | —$CH_2CF_3$ |
| C84 (a and b) | —$CH_3$ | —$OCF_3$ |
| C85 (a and b) | —$CH_3$ | —Cl |
| C86 (a and b) | —$CH_3$ | —Br |
| C87 (a and b) | —$CH_3$ | —I |
| C88 (a and b) | —$CH_3$ | -n-butyl |
| C89 (a and b) | —$CH_3$ | —$CH_3$ |
| C90 (a and b) | —$CH_3$ | —$SCF_3$ |
| C91 (a and b) | —$CH_3$ | —$N(CH_2CH_3)_2$ |
| C92 (a and b) | —$CH_3$ | —$OCF_2CHF_2$ |
| C93 (a and b) | —$CH_3$ | —$C(OH)(CF_3)_2$ |
| C94 (a and b) | —$CH_3$ | -(1,1-dimethyl-pentyl) |
| C95 (a and b) | —$CH_3$ | -(1,1-dimethyl-acetic acid) ethyl ester |
| C96 (a and b) | —$CH_3$ | —N-piperidinyl |
| C97 (a and b) | —$CF_3$ | —H |
| C98 (a and b) | —$CF_3$ | -tert-butyl |
| C99 (a and b) | —$CF_3$ | -iso-butyl |
| C100 (a and b) | —$CF_3$ | -sec-butyl |
| C101 (a and b) | —$CF_3$ | -iso-propyl |
| C102 (a and b) | —$CF_3$ | -n-propyl |
| C103 (a and b) | —$CF_3$ | -cyclohexyl |
| C104 (a and b) | —$CF_3$ | -tert-butoxy |

TABLE 3-continued (Ic)

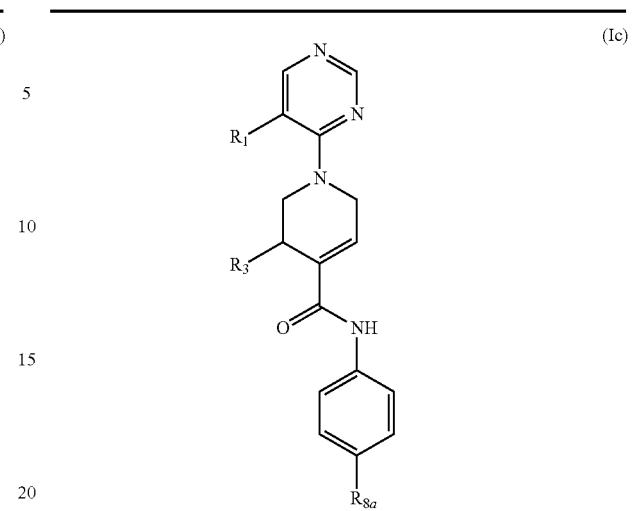

and pharmaceutically acceptable salts thereof, wherein:

| Compound | $R_1$ | $R_{8a}$ |
|---|---|---|
| C105 (a and b) | —$CF_3$ | -isopropoxy |
| C106 (a and b) | —$CF_3$ | —$CF_3$ |
| C107 (a and b) | —$CF_3$ | —$CH_2CF_3$ |
| C108 (a and b) | —$CF_3$ | —$OCF_3$ |
| C109 (a and b) | —$CF_3$ | —Cl |
| C110 (a and b) | —$CF_3$ | —Br |
| C111 (a and b) | —$CF_3$ | —I |
| C112 (a and b) | —$CF_3$ | -n-butyl |
| C113 (a and b) | —$CF_3$ | —$CH_3$ |
| C114 (a and b) | —$CF_3$ | —$SCF_3$ |
| C115 (a and b) | —$CF_3$ | —$N(CH_2CH_3)_2$ |
| C116 (a and b) | —$CF_3$ | —$OCF_2CHF_2$ |
| C117 (a and b) | —$CF_3$ | —$C(OH)(CF_3)_2$ |
| C118 (a and b) | —$CF_3$ | -(1,1-dimethyl-pentyl) |
| C119 (a and b) | —$CF_3$ | -(1,1-dimethyl-acetic acid) ethyl ester |
| C120 (a and b) | —$CF_3$ | —N-piperidinyl |
| C121 (a and b) | —$CHF_2$ | -tert-butyl |
| C122 (a and b) | —$CHF_2$ | —H |
| C123 (a and b) | —$CHF_2$ | -iso-butyl |
| C124 (a and b) | —$CHF_2$ | -sec-butyl |
| C125 (a and b) | —$CHF_2$ | -iso-propyl |
| C126 (a and b) | —$CHF_2$ | -n-propyl |
| C127 (a and b) | —$CHF_2$ | -cyclohexyl |
| C128 (a and b) | —$CHF_2$ | -tert-butoxy |
| C129 (a and b) | —$CHF_2$ | -isopropoxy |
| C130 (a and b) | —$CHF_2$ | —$CF_3$ |
| C131 (a and b) | —$CHF_2$ | —$CH_2CF_3$ |
| C132 (a and b) | —$CHF_2$ | —$OCF_3$ |
| C133 (a and b) | —$CHF_2$ | —Cl |
| C134 (a and b) | —$CHF_2$ | —Br |
| C135 (a and b) | —$CHF_2$ | —I |
| C136 (a and b) | —$CHF_2$ | -n-butyl |
| C137 (a and b) | —$CHF_2$ | —$CH_3$ |
| C138 (a and b) | —$CHF_2$ | —$SCF_3$ |
| C139 (a and b) | —$CHF_2$ | —$N(CH_2CH_3)_2$ |
| C140 (a and b) | —$CHF_2$ | —$OCF_2CHF_2$ |
| C141 (a and b) | —$CHF_2$ | —$C(OH)(CF_3)_2$ |
| C142 (a and b) | —$CHF_2$ | -(1,1-dimethyl-pentyl) |
| C143 (a and b) | —$CHF_2$ | -(1,1-dimethyl-acetic acid) ethyl ester |
| C144 (a and b) | —$CHF_2$ | —N-piperidinyl |
| C145 (a and b) | —OH | —H |
| C146 (a and b) | —OH | -tert-butyl |
| C147 (a and b) | —OH | -iso-butyl |
| C148 (a and b) | —OH | -sec-butyl |
| C149 (a and b) | —OH | -iso-propyl |
| C150 (a and b) | —OH | -n-propyl |
| C151 (a and b) | —OH | -cyclohexyl |
| C152 (a and b) | —OH | -tert-butoxy |
| C153 (a and b) | —OH | -isopropoxy |
| C154 (a and b) | —OH | —$CF_3$ |
| C155 (a and b) | —OH | —$CH_2CF_3$ |
| C156 (a and b) | —OH | —$OCF_3$ |

TABLE 3-continued

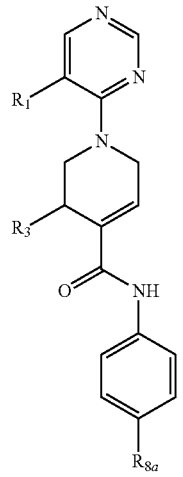

(Ic)

and pharmaceutically acceptable salts thereof, wherein:

| Compound | $R_1$ | $R_{8a}$ |
|---|---|---|
| C157 (a and b) | —OH | —Cl |
| C158 (a and b) | —OH | —Br |
| C159 (a and b) | —OH | —I |
| C160 (a and b) | —OH | -n-butyl |
| C161 (a and b) | —OH | —CH$_3$ |
| C162 (a and b) | —OH | —SCF$_3$ |
| C163 (a and b) | —OH | —N(CH$_2$CH$_3$)$_2$ |
| C164 (a and b) | —OH | —OCF$_2$CHF$_2$ |
| C165 (a and b) | —OH | —C(OH)(CF$_3$)$_2$ |
| C166 (a and b) | —OH | -(1,1-dimethyl-pentyl) |
| C167 (a and b) | —OH | -(1,1-dimethyl-acetic acid) ethyl ester |
| C168 (a and b) | —OH | —N-piperidinyl |
| C169 (a and b) | —NO$_2$ | —H |
| C170 (a and b) | —NO$_2$ | -tert-butyl |
| C171 (a and b) | —NO$_2$ | -iso-butyl |
| C172 (a and b) | —NO$_2$ | -sec-butyl |
| C173 (a and b) | —NO$_2$ | -iso-propyl |
| C174 (a and b) | —NO$_2$ | -n-propyl |
| C175 (a and b) | —NO$_2$ | -cyclohexyl |
| C176 (a and b) | —NO$_2$ | -tert-butoxy |
| C177 (a and b) | —NO$_2$ | -isopropoxy |
| C178 (a and b) | —NO$_2$ | —CF$_3$ |
| C179 (a and b) | —NO$_2$ | —CH$_2$CF$_3$ |
| C180 (a and b) | —NO$_2$ | —OCF$_3$ |
| C181 (a and b) | —NO$_2$ | —Cl |
| C182 (a and b) | —NO$_2$ | —Br |
| C183 (a and b) | —NO$_2$ | —I |
| C184 (a and b) | —NO$_2$ | -n-butyl |
| C185 (a and b) | —NO$_2$ | —CH$_3$ |
| C186 (a and b) | —NO$_2$ | —SCF$_3$ |
| C187 (a and b) | —NO$_2$ | —N(CH$_2$CH$_3$)$_2$ |
| C188 (a and b) | —NO$_2$ | —OCF$_2$CHF$_2$ |
| C189 (a and b) | —NO$_2$ | —C(OH)(CF$_3$)$_2$ |
| C190 (a and b) | —NO$_2$ | -(1,1-dimethyl-pentyl) |
| C191 (a and b) | —NO$_2$ | -(1,1-dimethyl-acetic acid) ethyl ester |
| C192 (a and b) | —NO$_2$ | —N-piperidinyl |
| C193 (a and b) | —CN | —H |
| C194 (a and b) | —CN | -tert-butyl |
| C195 (a and b) | —CN | -iso-butyl |
| C196 (a and b) | —CN | -sec-butyl |
| C197 (a and b) | —CN | -iso-propyl |
| C198 (a and b) | —CN | -n-propyl |
| C199 (a and b) | —CN | -cyclohexyl |
| C200 (a and b) | —CN | -tert-butoxy |
| C201 (a and b) | —CN | -isopropoxy |
| C202 (a and b) | —CN | —CF$_3$ |
| C203 (a and b) | —CN | —CH$_2$CF$_3$ |
| C204 (a and b) | —CN | —OCF$_3$ |
| C205 (a and b) | —CN | —Cl |
| C206 (a and b) | —CN | —Br |
| C207 (a and b) | —CN | —I |
| C208 (a and b) | —CN | -n-butyl |

TABLE 3-continued

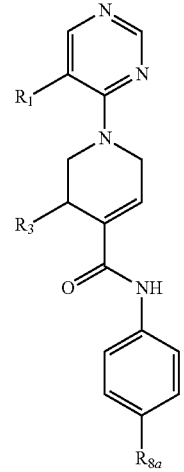

(Ic)

and pharmaceutically acceptable salts thereof, wherein:

| Compound | $R_1$ | $R_{8a}$ |
|---|---|---|
| C209 (a and b) | —CN | —CH$_3$ |
| C210 (a and b) | —CN | —SCF$_3$ |
| C211 (a and b) | —CN | —N(CH$_2$CH$_3$)$_2$ |
| C212 (a and b) | —CN | —OCF$_2$CHF$_2$ |
| C213 (a and b) | —CN | —C(OH)(CF$_3$)$_2$ |
| C214 (a and b) | —CN | -(1,1-dimethyl-pentyl) |
| C215 (a and b) | —CN | -(1,1-dimethyl-acetic acid) ethyl ester |
| C216 (a and b) | —CN | —N-piperidinyl |
| C217 (a and b) | —Br | —H |
| C218 (a and b) | —Br | -tert-butyl |
| C219 (a and b) | —Br | -iso-butyl |
| C220 (a and b) | —Br | -sec-butyl |
| C221 (a and b) | —Br | -iso-propyl |
| C222 (a and b) | —Br | -n-propyl |
| C223 (a and b) | —Br | -cyclohexyl |
| C224 (a and b) | —Br | -tert-butoxy |
| C225 (a and b) | —Br | -isopropoxy |
| C226 (a and b) | —Br | —CF$_3$ |
| C227 (a and b) | —Br | —CH$_2$CF$_3$ |
| C228 (a and b) | —Br | —OCF$_3$ |
| C229 (a and b) | —Br | —Cl |
| C230 (a and b) | —Br | —Br |
| C231 (a and b) | —Br | —I |
| C232 (a and b) | —Br | -n-butyl |
| C233 (a and b) | —Br | —CH$_3$ |
| C234 (a and b) | —Br | —SCF$_3$ |
| C235 (a and b) | —Br | —N(CH$_2$CH$_3$)$_2$ |
| C236 (a and b) | —Br | —OCF$_2$CHF$_2$ |
| C237 (a and b) | —Br | —C(OH)(CF$_3$)$_2$ |
| C238 (a and b) | —Br | -(1,1-dimethyl-pentyl) |
| C239 (a and b) | —Br | -(1,1-dimethyl-acetic acid) ethyl ester |
| C240 (a and b) | —Br | —N-piperidinyl |
| C241 (a and b) | —I | -tert-butyl |
| C242 (a and b) | —I | —H |
| C243 (a and b) | —I | -iso-butyl |
| C244 (a and b) | —I | -sec-butyl |
| C245 (a and b) | —I | -iso-propyl |
| C246 (a and b) | —I | -n-propyl |
| C247 (a and b) | —I | -cyclohexyl |
| C248 (a and b) | —I | -tert-butoxy |
| C249 (a and b) | —I | -isopropoxy |
| C250 (a and b) | —I | —CF$_3$ |
| C251 (a and b) | —I | —CH$_2$CF$_3$ |
| C252 (a and b) | —I | —OCF$_3$ |
| C253 (a and b) | —I | —Cl |
| C254 (a and b) | —I | —Br |
| C255 (a and b) | —I | —I |
| C256 (a and b) | —I | -n-butyl |
| C257 (a and b) | —I | —CH$_3$ |
| C258 (a and b) | —I | —SCF$_3$ |
| C259 (a and b) | —I | —N(CH$_2$CH$_3$)$_2$ |
| C260 (a and b) | —I | —OCF$_2$CHF$_2$ |

TABLE 3-continued

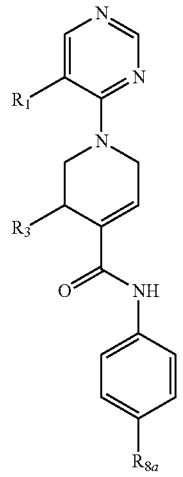

(Ic)

and pharmaceutically acceptable salts thereof, wherein:

| Compound | R₁ | R₈ₐ |
|---|---|---|
| C261 (a and b) | —I | —C(OH)(CF₃)₂ |
| C262 (a and b) | —I | -(1,1-dimethyl-pentyl) |
| C263 (a and b) | —I | -(1,1-dimethyl-acetic acid) ethyl ester |
| C264 (a and b) | —I | —N-piperidinyl |

(a) means that R₃ is —H.
(b) means that R₃ is —CH₃.

TABLE 4

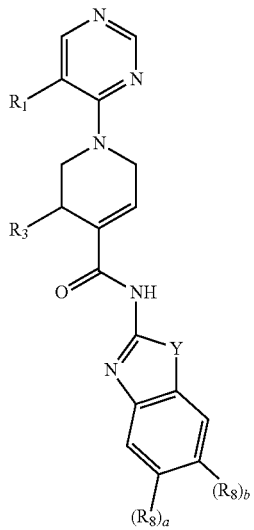

(Id)

and pharmaceutically acceptable salts thereof, wherein:

| Compound | Y | R₁ | (R₈)ₐ | (R₈)ᵦ |
|---|---|---|---|---|
| D01 (a and b) | S | —H | —Cl | —H |
| D02 (a and b) | S | —H | —Br | —H |
| D03 (a and b) | S | —H | —F | —H |
| D04 (a and b) | S | —H | —CH₃ | —H |
| D05 (a and b) | S | —H | —CF₃ | —H |
| D06 (a and b) | S | —H | —OCH₃ | —H |
| D07 (a and b) | S | —H | —OCH₂CH₃ | —H |
| D08 (a and b) | S | —H | —OCF₃ | —H |
| D09 (a and b) | S | —H | -tert-butyl | —H |
| D10 (a and b) | S | —H | -iso-propyl | —H |

TABLE 4-continued

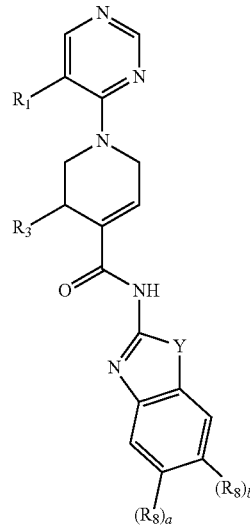

(Id)

and pharmaceutically acceptable salts thereof, wherein:

| Compound | Y | R₁ | (R₈)ₐ | (R₈)ᵦ |
|---|---|---|---|---|
| D11 (a and b) | S | —H | —CH₃ | —CH₃ |
| D12 (a and b) | S | —H | —H | —H |
| D13 (a and b) | S | —H | —H | —Cl |
| D14 (a and b) | S | —H | —H | —Br |
| D15 (a and b) | S | —H | —H | —F |
| D16 (a and b) | S | —H | —H | —CH₃ |
| D17 (a and b) | S | —H | —H | —CF₃ |
| D18 (a and b) | S | —H | —H | —OCH₃ |
| D19 (a and b) | S | —H | —H | —OCH₂CH₃ |
| D20 (a and b) | S | —H | —H | —OCF₃ |
| D21 (a and b) | S | —H | —H | -tert-butyl |
| D22 (a and b) | S | —H | —H | -iso-propyl |
| D23 (a and b) | S | —Cl | —Cl | —H |
| D24 (a and b) | S | —Cl | —Br | —H |
| D25 (a and b) | S | —Cl | —F | —H |
| D26 (a and b) | S | —Cl | —CH₃ | —H |
| D27 (a and b) | S | —Cl | —CF₃ | —H |
| D28 (a and b) | S | —Cl | —OCH₃ | —H |
| D29 (a and b) | S | —Cl | —OCH₂CH₃ | —H |
| D30 (a and b) | S | —Cl | —OCF₃ | —H |
| D31 (a and b) | S | —Cl | -tert-butyl | —H |
| D32 (a and b) | S | —Cl | -iso-propyl | —H |
| D33 (a and b) | S | —Cl | —CH₃ | —CH₃ |
| D34 (a and b) | S | —Cl | —H | —H |
| D35 (a and b) | S | —Cl | —H | —CH₃ |
| D36 (a and b) | S | —Cl | —H | —Cl |
| D37 (a and b) | S | —Cl | —H | —Br |
| D38 (a and b) | S | —Cl | —H | —F |
| D39 (a and b) | S | —Cl | —H | —CF₃ |
| D40 (a and b) | S | —Cl | —H | —OCH₃ |
| D41 (a and b) | S | —Cl | —H | —OCH₂CH₃ |
| D42 (a and b) | S | —Cl | —H | —OCF₃ |
| D43 (a and b) | S | —Cl | —H | -tert-butyl |
| D44 (a and b) | S | —Cl | —H | -iso-propyl |
| D45 (a and b) | S | —Cl | —H | —OCF₃ |
| D46 (a and b) | S | —Cl | —H | -tert-butyl |
| D47 (a and b) | S | —Cl | —H | -iso-propyl |
| D48 (a and b) | S | —CH₃ | —Cl | —H |
| D49 (a and b) | S | —CH₃ | —Br | —H |
| D50 (a and b) | S | —CH₃ | —F | —H |
| D51 (a and b) | S | —CH₃ | —CH₃ | —H |
| D52 (a and b) | S | —CH₃ | —CF₃ | —H |
| D53 (a and b) | S | —CH₃ | —OCH₃ | —H |
| D54 (a and b) | S | —CH₃ | —OCH₂CH₃ | —H |
| D55 (a and b) | S | —CH₃ | —OCF₃ | —H |
| D56 (a and b) | S | —CH₃ | -tert-butyl | —H |
| D57 (a and b) | S | —CH₃ | -iso-propyl | —H |
| D58 (a and b) | S | —CH₃ | —CH₃ | —CH₃ |
| D59 (a and b) | S | —CH₃ | —H | —H |

TABLE 4-continued

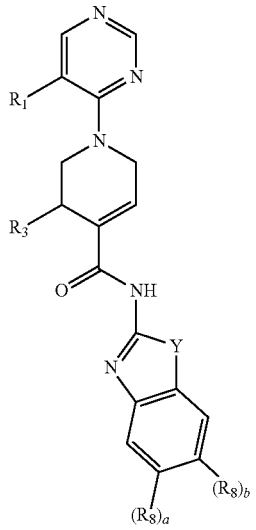

(Id)

and pharmaceutically acceptable salts thereof, wherein:

| Compound | Y | $R_1$ | $(R_8)_a$ | $(R_8)_b$ |
|---|---|---|---|---|
| D60 (a and b) | S | —$CH_3$ | —H | —Cl |
| D61 (a and b) | S | —$CH_3$ | —H | —Br |
| D62 (a and b) | S | —$CH_3$ | —H | —F |
| D63 (a and b) | S | —$CH_3$ | —H | —$CH_3$ |
| D64 (a and b) | S | —$CH_3$ | —H | —$CF_3$ |
| D65 (a and b) | S | —$CH_3$ | —H | —$OCH_3$ |
| D66 (a and b) | S | —$CH_3$ | —H | —$OCH_2CH_3$ |
| D67 (a and b) | S | —$CH_3$ | —H | —$OCF_3$ |
| D68 (a and b) | S | —$CH_3$ | —H | -tert-butyl |
| D69 (a and b) | S | —$CH_3$ | —H | -iso-propyl |
| D70 (a and b) | S | —$CF_3$ | —Cl | —H |
| D71 (a and b) | S | —$CF_3$ | —Br | —H |
| D72 (a and b) | S | —$CF_3$ | —F | —H |
| D73 (a and b) | S | —$CF_3$ | —$CH_3$ | —H |
| D74 (a and b) | S | —$CF_3$ | —$CF_3$ | —H |
| D75 (a and b) | S | —$CF_3$ | —$OCH_3$ | —H |
| D76 (a and b) | S | —$CF_3$ | —$OCH_2CH_3$ | —H |
| D77 (a and b) | S | —$CF_3$ | —$OCF_3$ | —H |
| D78 (a and b) | S | —$CF_3$ | -tert-butyl | —H |
| D79 (a and b) | S | —$CF_3$ | -iso-propyl | —H |
| D80 (a and b) | S | —$CF_3$ | —$CH_3$ | —$CH_3$ |
| D81 (a and b) | S | —$CF_3$ | —H | —H |
| D82 (a and b) | S | —$CF_3$ | —H | —Cl |
| D83 (a and b) | S | —$CF_3$ | —H | —Br |
| D84 (a and b) | S | —$CF_3$ | —H | —F |
| D85 (a and b) | S | —$CF_3$ | —H | —$CH_3$ |
| D86 (a and b) | S | —$CF_3$ | —H | —$CF_3$ |
| D87 (a and b) | S | —$CF_3$ | —H | —$OCH_3$ |
| D88 (a and b) | S | —$CF_3$ | —H | —$OCH_2CH_3$ |
| D89 (a and b) | S | —$CF_3$ | —H | —$OCF_3$ |
| D90 (a and b) | S | —$CF_3$ | —H | -tert-butyl |
| D91 (a and b) | S | —$CF_3$ | —H | -iso-propyl |
| D92 (a and b) | S | —$CHF_2$ | —Cl | —H |
| D93 (a and b) | S | —$CHF_2$ | —Br | —H |
| D94 (a and b) | S | —$CHF_2$ | —F | —H |
| D95 (a and b) | S | —$CHF_2$ | —$CH_3$ | —H |
| D96 (a and b) | S | —$CHF_2$ | —$CF_3$ | —H |
| D97 (a and b) | S | —$CHF_2$ | —$OCH_3$ | —H |
| D98 (a and b) | S | —$CHF_2$ | —$OCH_2CH_3$ | —H |
| D99 (a and b) | S | —$CHF_2$ | —$OCF_3$ | —H |
| D100 (a and b) | S | —$CHF_2$ | -tert-butyl | —H |
| D101 (a and b) | S | —$CHF_2$ | -iso-propyl | —H |
| D102 (a and b) | S | —$CHF_2$ | —$CH_3$ | —$CH_3$ |
| D103 (a and b) | S | —$CHF_2$ | —H | —H |
| D104 (a and b) | S | —$CHF_2$ | —H | —Cl |
| D105 (a and b) | S | —$CHF_2$ | —H | —Br |
| D106 (a and b) | S | —$CHF_2$ | —H | —F |
| D107 (a and b) | S | —$CHF_2$ | —H | —$CH_3$ |
| D108 (a and b) | S | —$CHF_2$ | —H | —$CF_3$ |

TABLE 4-continued

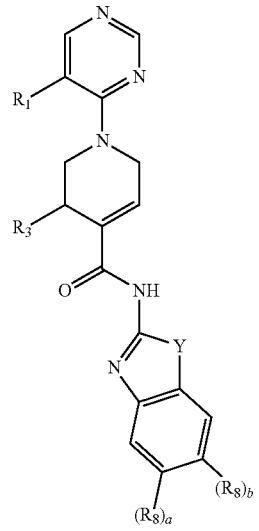

(Id)

and pharmaceutically acceptable salts thereof, wherein:

| Compound | Y | $R_1$ | $(R_8)_a$ | $(R_8)_b$ |
|---|---|---|---|---|
| D109 (a and b) | S | —$CHF_2$ | —H | —$OCH_3$ |
| D110 (a and b) | S | —$CHF_2$ | —H | —$OCH_2CH_3$ |
| D111 (a and b) | S | —$CHF_2$ | —H | —$OCF_3$ |
| D112 (a and b) | S | —$CHF_2$ | —H | -tert-butyl |
| D113 (a and b) | S | —$CHF_2$ | —H | -iso-propyl |
| D114 (a and b) | S | —OH | —Cl | —H |
| D115 (a and b) | S | —OH | —Br | —H |
| D116 (a and b) | S | —OH | —F | —H |
| D117 (a and b) | S | —OH | —$CH_3$ | —H |
| D118 (a and b) | S | —OH | —$CF_3$ | —H |
| D119 (a and b) | S | —OH | —$OCH_3$ | —H |
| D120 (a and b) | S | —OH | —$OCH_2CH_3$ | —H |
| D121 (a and b) | S | —OH | —$OCF_3$ | —H |
| D122 (a and b) | S | —OH | -tert-butyl | —H |
| D123 (a and b) | S | —OH | -iso-propyl | —H |
| D124 (a and b) | S | —OH | —$CH_3$ | —$CH_3$ |
| D125 (a and b) | S | —OH | —H | —H |
| D126 (a and b) | S | —OH | —H | —Cl |
| D127 (a and b) | S | —OH | —H | —Br |
| D128 (a and b) | S | —OH | —H | —F |
| D129 (a and b) | S | —OH | —H | —$CH_3$ |
| D130 (a and b) | S | —OH | —H | —$CF_3$ |
| D131 (a and b) | S | —OH | —H | —$OCH_3$ |
| D132 (a and b) | S | —OH | —H | —$OCH_2CH_3$ |
| D133 (a and b) | S | —OH | —H | —$OCF_3$ |
| D134 (a and b) | S | —OH | —H | -tert-butyl |
| D135 (a and b) | S | —OH | —H | -iso-propyl |
| D136 (a and b) | S | —$NO_2$ | —Cl | —H |
| D137 (a and b) | S | —$NO_2$ | —Br | —H |
| D138 (a and b) | S | —$NO_2$ | —F | —H |
| D139 (a and b) | S | —$NO_2$ | —$CH_3$ | —H |
| D140 (a and b) | S | —$NO_2$ | —$CF_3$ | —H |
| D141 (a and b) | S | —$NO_2$ | —$OCH_3$ | —H |
| D142 (a and b) | S | —$NO_2$ | —$OCH_2CH_3$ | —H |
| D143 (a and b) | S | —$NO_2$ | —$OCF_3$ | —H |
| D144 (a and b) | S | —$NO_2$ | -tert-butyl | —H |
| D145 (a and b) | S | —$NO_2$ | -iso-propyl | —H |
| D146 (a and b) | S | —$NO_2$ | —$CH_3$ | —$CH_3$ |
| D147 (a and b) | S | —$NO_2$ | —H | —H |
| D148 (a and b) | S | —$NO_2$ | —H | —Cl |
| D149 (a and b) | S | —$NO_2$ | —H | —Br |
| D150 (a and b) | S | —$NO_2$ | —H | —F |
| D151 (a and b) | S | —$NO_2$ | —H | —$CH_3$ |
| D152 (a and b) | S | —$NO_2$ | —H | —$CF_3$ |
| D153 (a and b) | S | —$NO_2$ | —H | —$OCH_3$ |
| D154 (a and b) | S | —$NO_2$ | —H | —$OCH_2CH_3$ |
| D155 (a and b) | S | —$NO_2$ | —H | —$OCF_3$ |
| D156 (a and b) | S | —$NO_2$ | —H | -tert-butyl |
| D157 (a and b) | S | —$NO_2$ | —H | -iso-propyl |

TABLE 4-continued

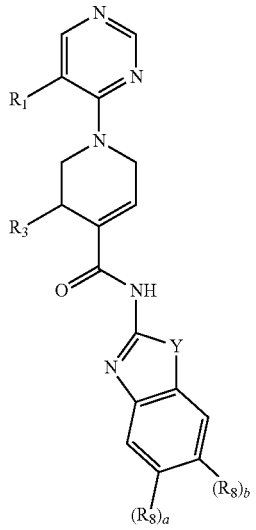

(Id)

and pharmaceutically acceptable salts thereof, wherein:

| Compound | Y | R₁ | (R₈)ₐ | (R₈)ᵦ |
|---|---|---|---|---|
| D158 (a and b) | S | —CN | —Br | —H |
| D159 (a and b) | S | —CN | —Cl | —H |
| D160 (a and b) | S | —CN | —F | —H |
| D161 (a and b) | S | —CN | —CH₃ | —H |
| D162 (a and b) | S | —CN | —CF₃ | —H |
| D163 (a and b) | S | —CN | —OCH₃ | —H |
| D164 (a and b) | S | —CN | —OCH₂CH₃ | —H |
| D165 (a and b) | S | —CN | —OCF₃ | —H |
| D166 (a and b) | S | —CN | -tert-butyl | —H |
| D167 (a and b) | S | —CN | -iso-propyl | —H |
| D168 (a and b) | S | —CN | —CH₃ | —CH₃ |
| D169 (a and b) | S | —CN | —H | —H |
| D170 (a and b) | S | —CN | —H | —Cl |
| D171 (a and b) | S | —CN | —H | —Br |
| D172 (a and b) | S | —CN | —H | —F |
| D173 (a and b) | S | —CN | —H | —CH₃ |
| D174 (a and b) | S | —CN | —H | —CF₃ |
| D175 (a and b) | S | —CN | —H | —OCH₃ |
| D176 (a and b) | S | —CN | —H | —OCH₂CH₃ |
| D177 (a and b) | S | —CN | —H | —OCF₃ |
| D178 (a and b) | S | —CN | —H | -tert-butyl |
| D179 (a and b) | S | —CN | —H | -iso-propyl |
| D180 (a and b) | S | —Br | —Br | —H |
| D181 (a and b) | S | —Br | —Cl | —H |
| D182 (a and b) | S | —Br | —F | —H |
| D183 (a and b) | S | —Br | —CH₃ | —H |
| D184 (a and b) | S | —Br | —CF₃ | —H |
| D185 (a and b) | S | —Br | —OCH₃ | —H |
| D186 (a and b) | S | —Br | —OCH₂CH₃ | —H |
| D187 (a and b) | S | —Br | —OCF₃ | —H |
| D188 (a and b) | S | —Br | -tert-butyl | —H |
| D189 (a and b) | S | —Br | -iso-propyl | —H |
| D190 (a and b) | S | —Br | —CH₃ | —CH₃ |
| D191 (a and b) | S | —Br | —H | —H |
| D192 (a and b) | S | —Br | —H | —Cl |
| D193 (a and b) | S | —Br | —H | —Br |
| D194 (a and b) | S | —Br | —H | —F |
| D195 (a and b) | S | —Br | —H | —CH₃ |
| D196 (a and b) | S | —Br | —H | —CF₃ |
| D197 (a and b) | S | —Br | —H | —OCH₃ |
| D198 (a and b) | S | —Br | —H | —OCH₂CH₃ |
| D199 (a and b) | S | —Br | —H | —OCF₃ |
| D200 (a and b) | S | —Br | —H | -tert-butyl |
| D201 (a and b) | S | —Br | —H | -iso-propyl |
| D202 (a and b) | S | —I | —Cl | —H |
| D203 (a and b) | S | —I | —Br | —H |
| D204 (a and b) | S | —I | —F | —H |
| D205 (a and b) | S | —I | —CH₃ | —H |
| D206 (a and b) | S | —I | —CF₃ | —H |

TABLE 4-continued

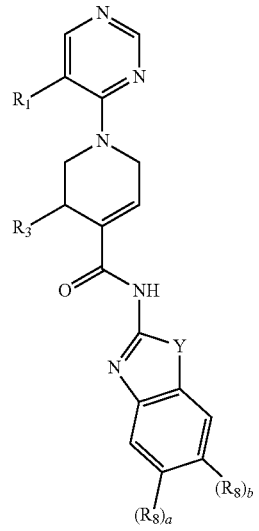

(Id)

and pharmaceutically acceptable salts thereof, wherein:

| Compound | Y | R₁ | (R₈)ₐ | (R₈)ᵦ |
|---|---|---|---|---|
| D207 (a and b) | S | —I | —OCH₃ | —H |
| D208 (a and b) | S | —I | —OCH₂CH₃ | —H |
| D209 (a and b) | S | —I | —OCF₃ | —H |
| D210 (a and b) | S | —I | -tert-butyl | —H |
| D211 (a and b) | S | —I | -iso-propyl | —H |
| D212 (a and b) | S | —I | —CH₃ | —CH₃ |
| D213 (a and b) | S | —I | —H | —H |
| D214 (a and b) | S | —I | —H | —Cl |
| D215 (a and b) | S | —I | —H | —Br |
| D216 (a and b) | S | —I | —H | —F |
| D217 (a and b) | S | —I | —H | —CH₃ |
| D218 (a and b) | S | —I | —H | —CF₃ |
| D219 (a and b) | S | —I | —H | —OCH₃ |
| D220 (a and b) | S | —I | —H | —OCH₂CH₃ |
| D221 (a and b) | S | —I | —H | —OCF₃ |
| D222 (a and b) | S | —I | —H | -tert-butyl |
| D223 (a and b) | S | —I | —H | -iso-propyl |
| D224 (a and b) | O | —H | —Cl | —H |
| D225 (a and b) | O | —H | —Br | —H |
| D226 (a and b) | O | —H | —F | —H |
| D227 (a and b) | O | —H | —CH₃ | —H |
| D228 (a and b) | O | —H | —CF₃ | —H |
| D229 (a and b) | O | —H | —OCH₃ | —H |
| D230 (a and b) | O | —H | —OCH₂CH₃ | —H |
| D231 (a and b) | O | —H | —OCF₃ | —H |
| D232 (a and b) | O | —H | -tert-butyl | —H |
| D233 (a and b) | O | —H | -iso-propyl | —H |
| D234 (a and b) | O | —H | —CH₃ | —CH₃ |
| D235 (a and b) | O | —H | —H | —H |
| D236 (a and b) | O | —H | —H | —Cl |
| D237 (a and b) | O | —H | —H | —Br |
| D238 (a and b) | O | —H | —H | —F |
| D239 (a and b) | O | —H | —H | —CH₃ |
| D240 (a and b) | O | —H | —H | —CF₃ |
| D241 (a and b) | O | —H | —H | —OCH₃ |
| D242 (a and b) | O | —H | —H | —OCH₂CH₃ |
| D243 (a and b) | O | —H | —H | —OCF₃ |
| D244 (a and b) | O | —H | —H | -tert-butyl |
| D245 (a and b) | O | —H | —H | -iso-propyl |
| D246 (a and b) | O | —Cl | —Cl | —H |
| D247 (a and b) | O | —Cl | —Br | —H |
| D248 (a and b) | O | —Cl | —F | —H |
| D249 (a and b) | O | —Cl | —CH₃ | —H |
| D250 (a and b) | O | —Cl | —CF₃ | —H |
| D251 (a and b) | O | —Cl | —OCH₃ | —H |
| D252 (a and b) | O | —Cl | —OCH₂CH₃ | —H |
| D253 (a and b) | O | —Cl | —OCF₃ | —H |
| D254 (a and b) | O | —Cl | -tert-butyl | —H |
| D255 (a and b) | O | —Cl | -iso-propyl | —H |

TABLE 4-continued (Id)

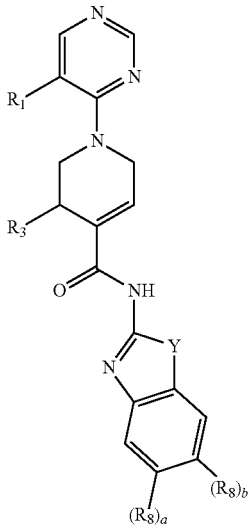

and pharmaceutically acceptable salts thereof, wherein:

| Compound | Y | R$_1$ | (R$_8$)$_a$ | (R$_8$)$_b$ |
|---|---|---|---|---|
| D256 (a and b) | O | —Cl | —CH$_3$ | —CH$_3$ |
| D257 (a and b) | O | —Cl | —H | —H |
| D258 (a and b) | O | —Cl | —H | —CH$_3$ |
| D259 (a and b) | O | —Cl | —H | —Cl |
| D260 (a and b) | O | —Cl | —H | —Br |
| D261 (a and b) | O | —Cl | —H | —F |
| D262 (a and b) | O | —Cl | —H | —CF$_3$ |
| D263 (a and b) | O | —Cl | —H | —OCH$_3$ |
| D264 (a and b) | O | —Cl | —H | —OCH$_2$CH$_3$ |
| D265 (a and b) | O | —Cl | —H | —OCF$_3$ |
| D266 (a and b) | O | —Cl | —H | -tert-butyl |
| D267 (a and b) | O | —Cl | —H | -iso-propyl |
| D268 (a and b) | O | —Cl | —H | —OCF$_3$ |
| D269 (a and b) | O | —Cl | —H | -tert-butyl |
| D270 (a and b) | O | —Cl | —H | -iso-propyl |
| D271 (a and b) | O | —CH$_3$ | —Cl | —H |
| D272 (a and b) | O | —CH$_3$ | —Br | —H |
| D273 (a and b) | O | —CH$_3$ | —F | —H |
| D274 (a and b) | O | —CH$_3$ | —CH$_3$ | —H |
| D275 (a and b) | O | —CH$_3$ | —CF$_3$ | —H |
| D276 (a and b) | O | —CH$_3$ | —OCH$_3$ | —H |
| D277 (a and b) | O | —CH$_3$ | —OCH$_2$CH$_3$ | —H |
| D278 (a and b) | O | —CH$_3$ | —OCF$_3$ | —H |
| D279 (a and b) | O | —CH$_3$ | -tert-butyl | —H |
| D280 (a and b) | O | —CH$_3$ | -iso-propyl | —H |
| D281 (a and b) | O | —CH$_3$ | —CH$_3$ | —CH$_3$ |
| D282 (a and b) | O | —CH$_3$ | —H | —H |
| D283 (a and b) | O | —CH$_3$ | —H | —Cl |
| D284 (a and b) | O | —CH$_3$ | —H | —Br |
| D285 (a and b) | O | —CH$_3$ | —H | —F |
| D286 (a and b) | O | —CH$_3$ | —H | —CH$_3$ |
| D287 (a and b) | O | —CH$_3$ | —H | —CF$_3$ |
| D288 (a and b) | O | —CH$_3$ | —H | —OCH$_3$ |
| D289 (a and b) | O | —CH$_3$ | —H | —OCH$_2$CH$_3$ |
| D290 (a and b) | O | —CH$_3$ | —H | —OCF$_3$ |
| D291 (a and b) | O | —CH$_3$ | —H | -tert-butyl |
| D292 (a and b) | O | —CH$_3$ | —H | -iso-propyl |
| D293 (a and b) | O | —CF$_3$ | —Cl | —H |
| D294 (a and b) | O | —CF$_3$ | —Br | —H |
| D295 (a and b) | O | —CF$_3$ | —F | —H |
| D296 (a and b) | O | —CF$_3$ | —CH$_3$ | —H |
| D297 (a and b) | O | —CF$_3$ | —CF$_3$ | —H |
| D298 (a and b) | O | —CF$_3$ | —OCH$_3$ | —H |
| D299 (a and b) | O | —CF$_3$ | —OCH$_2$CH$_3$ | —H |
| D300 (a and b) | O | —CF$_3$ | —OCF$_3$ | —H |
| D301 (a and b) | O | —CF$_3$ | -tert-butyl | —H |
| D302 (a and b) | O | —CF$_3$ | -iso-propyl | —H |
| D303 (a and b) | O | —CF$_3$ | —CH$_3$ | —CH$_3$ |
| D304 (a and b) | O | —CF$_3$ | —H | —H |

TABLE 4-continued (Id)

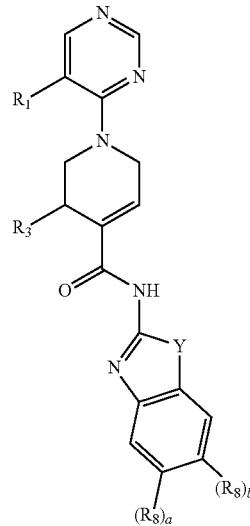

and pharmaceutically acceptable salts thereof, wherein:

| Compound | Y | R$_1$ | (R$_8$)$_a$ | (R$_8$)$_b$ |
|---|---|---|---|---|
| D305 (a and b) | O | —CF$_3$ | —H | —Cl |
| D306 (a and b) | O | —CF$_3$ | —H | —Br |
| D307 (a and b) | O | —CF$_3$ | —H | —F |
| D308 (a and b) | O | —CF$_3$ | —H | —CH$_3$ |
| D309 (a and b) | O | —CF$_3$ | —H | —CF$_3$ |
| D310 (a and b) | O | —CF$_3$ | —H | —OCH$_3$ |
| D311 (a and b) | O | —CF$_3$ | —H | —OCH$_2$CH$_3$ |
| D312 (a and b) | O | —CF$_3$ | —H | —OCF$_3$ |
| D313 (a and b) | O | —CF$_3$ | —H | -tert-butyl |
| D314 (a and b) | O | —CF$_3$ | —H | -iso-propyl |
| D315 (a and b) | O | —CHF$_2$ | —Cl | —H |
| D316 (a and b) | O | —CHF$_2$ | —Br | —H |
| D317 (a and b) | O | —CHF$_2$ | —F | —H |
| D318 (a and b) | O | —CHF$_2$ | —CH$_3$ | —H |
| D319 (a and b) | O | —CHF$_2$ | —CF$_3$ | —H |
| D320 (a and b) | O | —CHF$_2$ | —OCH$_3$ | —H |
| D321 (a and b) | O | —CHF$_2$ | —OCH$_2$CH$_3$ | —H |
| D322 (a and b) | O | —CHF$_2$ | —OCF$_3$ | —H |
| D323 (a and b) | O | —CHF$_2$ | -tert-butyl | —H |
| D324 (a and b) | O | —CHF$_2$ | -iso-propyl | —H |
| D325 (a and b) | O | —CHF$_2$ | —CH$_3$ | —CH$_3$ |
| D326 (a and b) | O | —CHF$_2$ | —H | —H |
| D327 (a and b) | O | —CHF$_2$ | —H | —Cl |
| D328 (a and b) | O | —CHF$_2$ | —H | —Br |
| D329 (a and b) | O | —CHF$_2$ | —H | —F |
| D330 (a and b) | O | —CHF$_2$ | —H | —CH$_3$ |
| D331 (a and b) | O | —CHF$_2$ | —H | —CF$_3$ |
| D332 (a and b) | O | —CHF$_2$ | —H | —OCH$_3$ |
| D333 (a and b) | O | —CHF$_2$ | —H | —OCH$_2$CH$_3$ |
| D334 (a and b) | O | —CHF$_2$ | —H | —OCF$_3$ |
| D335 (a and b) | O | —CHF$_2$ | —H | -tert-butyl |
| D336 (a and b) | O | —CHF$_2$ | —H | -iso-propyl |
| D337 (a and b) | O | —OH | —Cl | —H |
| D338 (a and b) | O | —OH | —Br | —H |
| D339 (a and b) | O | —OH | —F | —H |
| D340 (a and b) | O | —OH | —CH$_3$ | —H |
| D341 (a and b) | O | —OH | —CF$_3$ | —H |
| D342 (a and b) | O | —OH | —OCH$_3$ | —H |
| D343 (a and b) | O | —OH | —OCH$_2$CH$_3$ | —H |
| D344 (a and b) | O | —OH | —OCF$_3$ | —H |
| D345 (a and b) | O | —OH | -tert-butyl | —H |
| D346 (a and b) | O | —OH | -iso-propyl | —H |
| D347 (a and b) | O | —OH | —CH$_3$ | —CH$_3$ |
| D348 (a and b) | O | —OH | —H | —H |
| D349 (a and b) | O | —OH | —H | —Cl |
| D350 (a and b) | O | —OH | —H | —Br |
| D351 (a and b) | O | —OH | —H | —F |
| D352 (a and b) | O | —OH | —H | —CH$_3$ |
| D353 (a and b) | O | —OH | —H | —CF$_3$ |

TABLE 4-continued (Id)

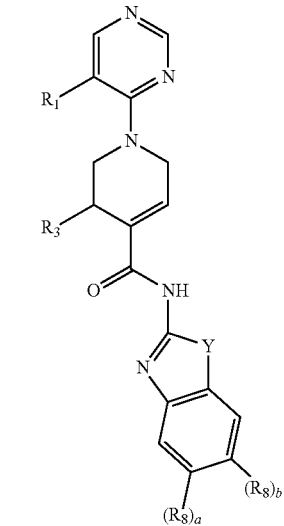

and pharmaceutically acceptable salts thereof, wherein:

| Compound | Y | R₁ | (R₈)ₐ | (R₈)ᵦ |
|---|---|---|---|---|
| D354 (a and b) | O | —OH | —H | —OCH₃ |
| D355 (a and b) | O | —OH | —H | —OCH₂CH₃ |
| D356 (a and b) | O | —OH | —H | —OCF₃ |
| D357 (a and b) | O | —OH | —H | -tert-butyl |
| D358 (a and b) | O | —OH | —H | -iso-propyl |
| D359 (a and b) | O | —NO₂ | —Cl | —H |
| D360 (a and b) | O | —NO₂ | —Br | —H |
| D361 (a and b) | O | —NO₂ | —F | —H |
| D362 (a and b) | O | —NO₂ | —CH₃ | —H |
| D363 (a and b) | O | —NO₂ | —CF₃ | —H |
| D364 (a and b) | O | —NO₂ | —OCH₃ | —H |
| D365 (a and b) | O | —NO₂ | —OCH₂CH₃ | —H |
| D366 (a and b) | O | —NO₂ | —OCF₃ | —H |
| D367 (a and b) | O | —NO₂ | -tert-butyl | —H |
| D368 (a and b) | O | —NO₂ | -iso-propyl | —H |
| D369 (a and b) | O | —NO₂ | —CH₃ | —CH₃ |
| D370 (a and b) | O | —NO₂ | —H | —H |
| D371 (a and b) | O | —NO₂ | —H | —Cl |
| D372 (a and b) | O | —NO₂ | —H | —Br |
| D373 (a and b) | O | —NO₂ | —H | —F |
| D374 (a and b) | O | —NO₂ | —H | —CH₃ |
| D375 (a and b) | O | —NO₂ | —H | —CF₃ |
| D376 (a and b) | O | —NO₂ | —H | —OCH₃ |
| D377 (a and b) | O | —NO₂ | —H | —OCH₂CH₃ |
| D378 (a and b) | O | —NO₂ | —H | —OCF₃ |
| D379 (a and b) | O | —NO₂ | —H | -tert-butyl |
| D380 (a and b) | O | —NO₂ | —H | -iso-propyl |
| D381 (a and b) | O | —CN | —Br | —H |
| D382 (a and b) | O | —CN | —Cl | —H |
| D383 (a and b) | O | —CN | —F | —H |
| D384 (a and b) | O | —CN | —CH₃ | —H |
| D385 (a and b) | O | —CN | —CF₃ | —H |
| D386 (a and b) | O | —CN | —OCH₃ | —H |
| D387 (a and b) | O | —CN | —OCH₂CH₃ | —H |
| D388 (a and b) | O | —CN | —OCF₃ | —H |
| D389 (a and b) | O | —CN | -tert-butyl | —H |
| D390 (a and b) | O | —CN | -iso-propyl | —H |
| D391 (a and b) | O | —CN | —CH₃ | —CH₃ |
| D392 (a and b) | O | —CN | —H | —H |
| D393 (a and b) | O | —CN | —H | —Cl |
| D394 (a and b) | O | —CN | —H | —Br |
| D395 (a and b) | O | —CN | —H | —F |
| D396 (a and b) | O | —CN | —H | —CH₃ |
| D397 (a and b) | O | —CN | —H | —CF₃ |
| D398 (a and b) | O | —CN | —H | —OCH₃ |
| D399 (a and b) | O | —CN | —H | —OCH₂CH₃ |
| D400 (a and b) | O | —CN | —H | —OCF₃ |
| D401 (a and b) | O | —CN | —H | -tert-butyl |
| D402 (a and b) | O | —CN | —H | -iso-propyl |

TABLE 4-continued (Id)

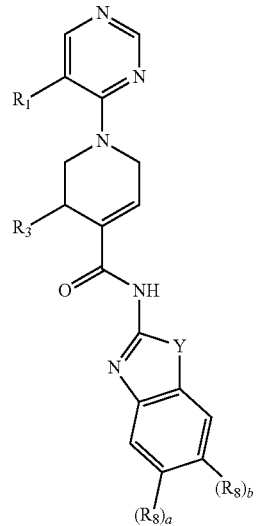

and pharmaceutically acceptable salts thereof, wherein:

| Compound | Y | R₁ | (R₈)ₐ | (R₈)ᵦ |
|---|---|---|---|---|
| D403 (a and b) | O | —Br | —Br | —H |
| D404 (a and b) | O | —Br | —Cl | —H |
| D405 (a and b) | O | —Br | —F | —H |
| D406 (a and b) | O | —Br | —CH₃ | —H |
| D407 (a and b) | O | —Br | —CF₃ | —H |
| D408 (a and b) | O | —Br | —OCH₃ | —H |
| D409 (a and b) | O | —Br | —OCH₂CH₃ | —H |
| D410 (a and b) | O | —Br | —OCF₃ | —H |
| D411 (a and b) | O | —Br | -tert-butyl | —H |
| D412 (a and b) | O | —Br | -iso-propyl | —H |
| D413 (a and b) | O | —Br | —CH₃ | —CH₃ |
| D414 (a and b) | O | —Br | —H | —H |
| D415 (a and b) | O | —Br | —H | —Cl |
| D416 (a and b) | O | —Br | —H | —Br |
| D417 (a and b) | O | —Br | —H | —F |
| D418 (a and b) | O | —Br | —H | —CH₃ |
| D419 (a and b) | O | —Br | —H | —CF₃ |
| D420 (a and b) | O | —Br | —H | —OCH₃ |
| D421 (a and b) | O | —Br | —H | —OCH₂CH₃ |
| D422 (a and b) | O | —Br | —H | —OCF₃ |
| D423 (a and b) | O | —Br | —H | -tert-butyl |
| D424 (a and b) | O | —Br | —H | -iso-propyl |
| D425 (a and b) | O | —I | —Cl | —H |
| D426 (a and b) | O | —I | —Br | —H |
| D427 (a and b) | O | —I | —F | —H |
| D428 (a and b) | O | —I | —CH₃ | —H |
| D429 (a and b) | O | —I | —CF₃ | —H |
| D430 (a and b) | O | —I | —OCH₃ | —H |
| D431 (a and b) | O | —I | —OCH₂CH₃ | —H |
| D432 (a and b) | O | —I | —OCF₃ | —H |
| D433 (a and b) | O | —I | -tert-butyl | —H |
| D434 (a and b) | O | —I | -iso-propyl | —H |
| D435 (a and b) | O | —I | —CH₃ | —CH₃ |
| D436 (a and b) | O | —I | —H | —H |
| D437 (a and b) | O | —I | —H | —Cl |
| D438 (a and b) | O | —I | —H | —Br |
| D439 (a and b) | O | —I | —H | —F |
| D440 (a and b) | O | —I | —H | —CH₃ |
| D441 (a and b) | O | —I | —H | —CF₃ |
| D442 (a and b) | O | —I | —H | —OCH₃ |
| D443 (a and b) | O | —I | —H | —OCH₂CH₃ |
| D444 (a and b) | O | —I | —H | —OCF₃ |
| D445 (a and b) | O | —I | —H | -tert-butyl |
| D446 (a and b) | O | —I | —H | -iso-propyl |
| D447 (a and b) | NH | —H | —Cl | —H |
| D448 (a and b) | NH | —H | —Br | —H |
| D449 (a and b) | NH | —H | —F | —H |
| D450 (a and b) | NH | —H | —CH₃ | —H |
| D451 (a and b) | NH | —H | —CF₃ | —H |

TABLE 4-continued

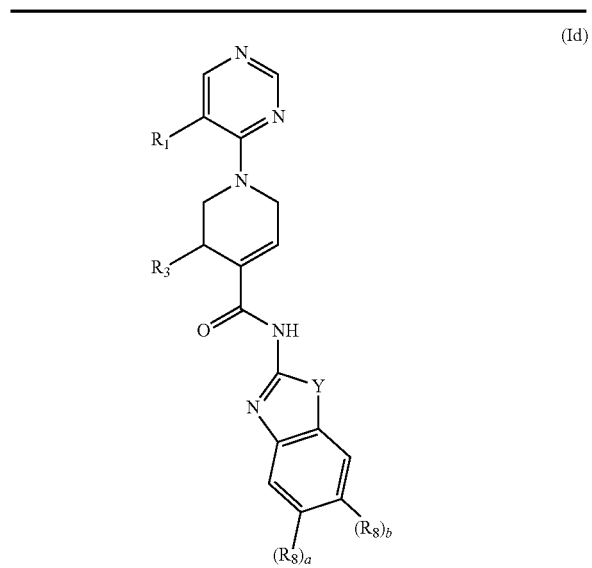

(Id)

and pharmaceutically acceptable salts thereof, wherein:

| Compound | Y | R₁ | (R₈)ₐ | (R₈)ᵦ |
|---|---|---|---|---|
| D452 (a and b) | NH | —H | —OCH₃ | —H |
| D453 (a and b) | NH | —H | —OCH₂CH₃ | —H |
| D454 (a and b) | NH | —H | —OCF₃ | —H |
| D455 (a and b) | NH | —H | -tert-butyl | —H |
| D456 (a and b) | NH | —H | -iso-propyl | —H |
| D457 (a and b) | NH | —H | —CH₃ | —CH₃ |
| D458 (a and b) | NH | —H | —H | —H |
| D459 (a and b) | NH | —H | —H | —Cl |
| D460 (a and b) | NH | —H | —H | —Br |
| D461 (a and b) | NH | —H | —H | —F |
| D462 (a and b) | NH | —H | —H | —CH₃ |
| D463 (a and b) | NH | —H | —H | —CF₃ |
| D464 (a and b) | NH | —H | —H | —OCH₃ |
| D465 (a and b) | NH | —H | —H | —OCH₂CH₃ |
| D466 (a and b) | NH | —H | —H | —OCF₃ |
| D467 (a and b) | NH | —H | —H | -tert-butyl |
| D468 (a and b) | NH | —H | —H | -iso-propyl |
| D469 (a and b) | NH | —Cl | —Cl | —H |
| D470 (a and b) | NH | —Cl | —Br | —H |
| D471 (a and b) | NH | —Cl | —F | —H |
| D472 (a and b) | NH | —Cl | —CH₃ | —H |
| D473 (a and b) | NH | —Cl | —CF₃ | —H |
| D474 (a and b) | NH | —Cl | —OCH₃ | —H |
| D475 (a and b) | NH | —Cl | —OCH₂CH₃ | —H |
| D476 (a and b) | NH | —Cl | —OCF₃ | —H |
| D477 (a and b) | NH | —Cl | -tert-butyl | —H |
| D478 (a and b) | NH | —Cl | -iso-propyl | —H |
| D479 (a and b) | NH | —Cl | —CH₃ | —CH₃ |
| D480 (a and b) | NH | —Cl | —H | —H |
| D481 (a and b) | NH | —Cl | —H | —Cl |
| D482 (a and b) | NH | —Cl | —H | —Br |
| D483 (a and b) | NH | —Cl | —H | —F |
| D484 (a and b) | NH | —Cl | —H | —CH₃ |
| D485 (a and b) | NH | —Cl | —H | —CF₃ |
| D486 (a and b) | NH | —Cl | —H | —OCH₃ |
| D487 (a and b) | NH | —Cl | —H | —OCH₂CH₃ |
| D488 (a and b) | NH | —Cl | —H | —OCF₃ |
| D489 (a and b) | NH | —Cl | —H | -tert-butyl |
| D490 (a and b) | NH | —Cl | —H | -iso-propyl |
| D491 (a and b) | NH | —Cl | —H | —OCF₃ |
| D492 (a and b) | NH | —Cl | —H | -tert-butyl |
| D493 (a and b) | NH | —Cl | —H | -iso-propyl |
| D494 (a and b) | NH | —CH₃ | —Cl | —H |
| D495 (a and b) | NH | —CH₃ | —Br | —H |
| D496 (a and b) | NH | —CH₃ | —F | —H |
| D497 (a and b) | NH | —CH₃ | —CH₃ | —H |
| D498 (a and b) | NH | —CH₃ | —CF₃ | —H |
| D499 (a and b) | NH | —CH₃ | —OCH₃ | —H |
| D500 (a and b) | NH | —CH₃ | —OCH₂CH₃ | —H |
| D501 (a and b) | NH | —CH₃ | —OCF₃ | —H |
| D502 (a and b) | NH | —CH₃ | -tert-butyl | —H |
| D503 (a and b) | NH | —CH₃ | -iso-propyl | —H |
| D504 (a and b) | NH | —CH₃ | —CH₃ | —CH₃ |
| D505 (a and b) | NH | —CH₃ | —H | —H |
| D506 (a and b) | NH | —CH₃ | —H | —Cl |
| D507 (a and b) | NH | —CH₃ | —H | —Br |
| D508 (a and b) | NH | —CH₃ | —H | —F |
| D509 (a and b) | NH | —CH₃ | —H | —CH₃ |
| D510 (a and b) | NH | —CH₃ | —H | —CF₃ |
| D511 (a and b) | NH | —CH₃ | —H | —OCH₃ |
| D512 (a and b) | NH | —CH₃ | —H | —OCH₂CH₃ |
| D513 (a and b) | NH | —CH₃ | —H | —OCF₃ |
| D514 (a and b) | NH | —CH₃ | —H | -tert-butyl |
| D515 (a and b) | NH | —CH₃ | —H | -iso-propyl |
| D516 (a and b) | NH | —CF₃ | —Cl | —H |
| D517 (a and b) | NH | —CF₃ | —Br | —H |
| D518 (a and b) | NH | —CF₃ | —F | —H |
| D519 (a and b) | NH | —CF₃ | —CH₃ | —H |
| D520 (a and b) | NH | —CF₃ | —CF₃ | —H |
| D521 (a and b) | NH | —CF₃ | —OCH₃ | —H |
| D522 (a and b) | NH | —CF₃ | —OCH₂CH₃ | —H |
| D523 (a and b) | NH | —CF₃ | —OCF₃ | —H |
| D524 (a and b) | NH | —CF₃ | -tert-butyl | —H |
| D525 (a and b) | NH | —CF₃ | -iso-propyl | —H |
| D526 (a and b) | NH | —CF₃ | —CH₃ | —CH₃ |
| D527 (a and b) | NH | —CF₃ | —H | —H |
| D528 (a and b) | NH | —CF₃ | —H | —Cl |
| D529 (a and b) | NH | —CF₃ | —H | —Br |
| D530 (a and b) | NH | —CF₃ | —H | —F |
| D531 (a and b) | NH | —CF₃ | —H | —CH₃ |
| D532 (a and b) | NH | —CF₃ | —H | —CF₃ |
| D533 (a and b) | NH | —CF₃ | —H | —OCH₃ |
| D534 (a and b) | NH | —CF₃ | —H | —OCH₂CH₃ |
| D535 (a and b) | NH | —CF₃ | —H | —OCF₃ |
| D536 (a and b) | NH | —CF₃ | —H | -tert-butyl |
| D537 (a and b) | NH | —CF₃ | —H | -iso-propyl |
| D538 (a and b) | NH | —CHF₂ | —Cl | —H |
| D539 (a and b) | NH | —CHF₂ | —Br | —H |
| D540 (a and b) | NH | —CHF₂ | —F | —H |
| D541 (a and b) | NH | —CHF₂ | —CH₃ | —H |
| D542 (a and b) | NH | —CHF₂ | —CF₃ | —H |
| D543 (a and b) | NH | —CHF₂ | —OCH₃ | —H |
| D544 (a and b) | NH | —CHF₂ | —OCH₂CH₃ | —H |
| D545 (a and b) | NH | —CHF₂ | —OCF₃ | —H |
| D546 (a and b) | NH | —CHF₂ | -tert-butyl | —H |
| D547 (a and b) | NH | —CHF₂ | -iso-propyl | —H |
| D548 (a and b) | NH | —CHF₂ | —CH₃ | —CH₃ |
| D549 (a and b) | NH | —CHF₂ | —H | —H |

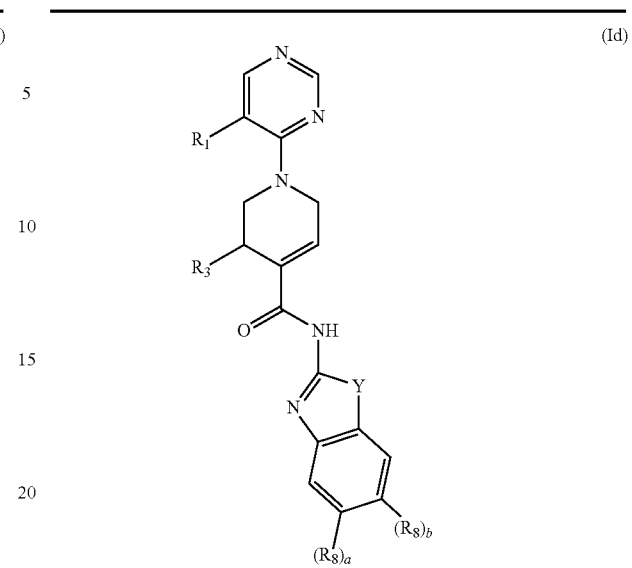

TABLE 4-continued (Id)

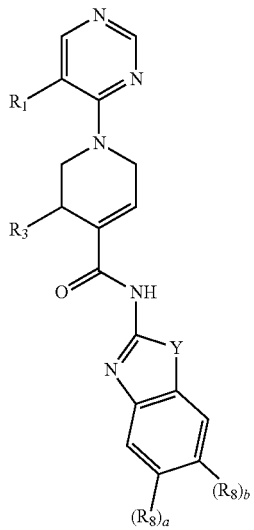

and pharmaceutically acceptable salts thereof, wherein:

| Compound | Y | $R_1$ | $(R_8)_a$ | $(R_8)_b$ |
|---|---|---|---|---|
| D550 (a and b) | NH | —CHF$_2$ | —H | —Cl |
| D551 (a and b) | NH | —CHF$_2$ | —H | —Br |
| D552 (a and b) | NH | —CHF$_2$ | —H | —F |
| D553 (a and b) | NH | —CHF$_2$ | —H | —CH$_3$ |
| D554 (a and b) | NH | —CHF$_2$ | —H | —CF$_3$ |
| D555 (a and b) | NH | —CHF$_2$ | —H | —OCH$_3$ |
| D556 (a and b) | NH | —CHF$_2$ | —H | —OCH$_2$CH$_3$ |
| D557 (a and b) | NH | —CHF$_2$ | —H | —OCF$_3$ |
| D558 (a and b) | NH | —CHF$_2$ | —H | -tert-butyl |
| D559 (a and b) | NH | —CHF$_2$ | —H | -iso-propyl |
| D560 (a and b) | NH | —OH | —Cl | —H |
| D561 (a and b) | NH | —OH | —Br | —H |
| D562 (a and b) | NH | —OH | —F | —H |
| D563 (a and b) | NH | —OH | —CH$_3$ | —H |
| D564 (a and b) | NH | —OH | —CF$_3$ | —H |
| D565 (a and b) | NH | —OH | —OCH$_3$ | —H |
| D566 (a and b) | NH | —OH | —OCH$_2$CH$_3$ | —H |
| D567 (a and b) | NH | —OH | —OCF$_3$ | —H |
| D568 (a and b) | NH | —OH | -tert-butyl | —H |
| D569 (a and b) | NH | —OH | -iso-propyl | —H |
| D570 (a and b) | NH | —OH | —CH$_3$ | —CH$_3$ |
| D571 (a and b) | NH | —OH | —H | —H |
| D572 (a and b) | NH | —OH | —H | —Cl |
| D573 (a and b) | NH | —OH | —H | —Br |
| D574 (a and b) | NH | —OH | —H | —F |
| D575 (a and b) | NH | —OH | —H | —CH$_3$ |
| D576 (a and b) | NH | —OH | —H | —CF$_3$ |
| D577 (a and b) | NH | —OH | —H | —OCH$_3$ |
| D578 (a and b) | NH | —OH | —H | —OCH$_2$CH$_3$ |
| D579 (a and b) | NH | —OH | —H | —OCF$_3$ |
| D580 (a and b) | NH | —OH | —H | -tert-butyl |
| D581 (a and b) | NH | —OH | —H | -iso-propyl |
| D582 (a and b) | NH | —NO$_2$ | —Cl | —H |
| D583 (a and b) | NH | —NO$_2$ | —Br | —H |
| D584 (a and b) | NH | —NO$_2$ | —F | —H |
| D585 (a and b) | NH | —NO$_2$ | —CH$_3$ | —H |
| DS86 (a and b) | NH | —NO$_2$ | —CF$_3$ | —H |
| D587 (a and b) | NH | —NO$_2$ | —OCH$_3$ | —H |
| D588 (a and b) | NH | —NO$_2$ | —OCH$_2$CH$_3$ | —H |
| D589 (a and b) | NH | —NO$_2$ | —OCF$_3$ | —H |
| D590 (a and b) | NH | —NO$_2$ | -tert-butyl | —H |
| D591 (a and b) | NH | —NO$_2$ | -iso-propyl | —H |
| D592 (a and b) | NH | —NO$_2$ | —CH$_3$ | —CH$_3$ |

TABLE 4-continued (Id)

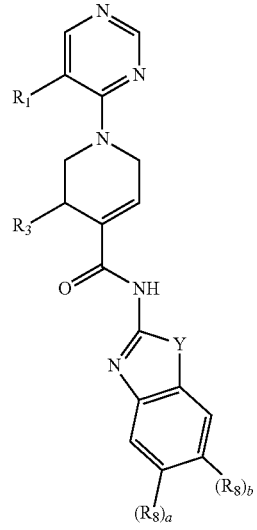

and pharmaceutically acceptable salts thereof, wherein:

| Compound | Y | $R_1$ | $(R_8)_a$ | $(R_8)_b$ |
|---|---|---|---|---|
| D593 (a and b) | NH | —NO$_2$ | —H | —H |
| D594 (a and b) | NH | —NO$_2$ | —H | —Cl |
| D595 (a and b) | NH | —NO$_2$ | —H | —Br |
| D596 (a and b) | NH | —NO$_2$ | —H | —F |
| D597 (a and b) | NH | —NO$_2$ | —H | —CH$_3$ |
| D598 (a and b) | NH | —NO$_2$ | —H | —CF$_3$ |
| D599 (a and b) | NH | —NO$_2$ | —H | —OCH$_3$ |
| D600 (a and b) | NH | —NO$_2$ | —H | —OCH$_2$CH$_3$ |
| D601 (a and b) | NH | —NO$_2$ | —H | —OCF$_3$ |
| D602 (a and b) | NH | —NO$_2$ | —H | -tert-butyl |
| D603 (a and b) | NH | —NO$_2$ | —H | -iso-propyl |
| D604 (a and b) | NH | —CN | —Br | —H |
| D605 (a and b) | NH | —CN | —Cl | —H |
| D606 (a and b) | NH | —CN | —F | —H |
| D607 (a and b) | NH | —CN | —CH$_3$ | —H |
| D608 (a and b) | NH | —CN | —CF$_3$ | —H |
| D609 (a and b) | NH | —CN | —OCH$_3$ | —H |
| D610 (a and b) | NH | —CN | —OCH$_2$CH$_3$ | —H |
| D611 (a and b) | NH | —CN | —OCF$_3$ | —H |
| D612 (a and b) | NH | —CN | -tert-butyl | —H |
| D613 (a and b) | NH | —CN | -iso-propyl | —H |
| D614 (a and b) | NH | —CN | —CH$_3$ | —CH$_3$ |
| D615 (a and b) | NH | —CN | —H | —H |
| D616 (a and b) | NH | —CN | —H | —Cl |
| D617 (a and b) | NH | —CN | —H | —Br |
| D618 (a and b) | NH | —CN | —H | —F |
| D619 (a and b) | NH | —CN | —H | —CH$_3$ |
| D620 (a and b) | NH | —CN | —H | —CF$_3$ |
| D621 (a and b) | NH | —CN | —H | —OCH$_3$ |
| D622 (a and b) | NH | —CN | —H | —OCH$_2$CH$_3$ |
| D623 (a and b) | NH | —CN | —H | —OCF$_3$ |
| D624 (a and b) | NH | —CN | —H | -tert-butyl |
| D625 (a and b) | NH | —CN | —H | -iso-propyl |
| D626 (a and b) | NH | —Br | —Br | —H |
| D627 (a and b) | NH | —Br | —Cl | —H |
| D628 (a and b) | NH | —Br | —F | —H |
| D629 (a and b) | NH | —Br | —CH$_3$ | —H |
| D630 (a and b) | NH | —Br | —CF$_3$ | —H |
| D631 (a and b) | NH | —Br | —OCH$_3$ | —H |
| D632 (a and b) | NH | —Br | —OCH$_2$CH$_3$ | —H |
| D633 (a and b) | NH | —Br | —OCF$_3$ | —H |
| D634 (a and b) | NH | —Br | -tert-butyl | —H |
| D635 (a and b) | NH | —Br | -iso-propyl | —H |
| D636 (a and b) | NH | —Br | —CH$_3$ | —CH$_3$ |
| D637 (a and b) | NH | —Br | —H | —H |
| D638 (a and b) | NH | —Br | —H | —Cl |
| D639 (a and b) | NH | —Br | —H | —Br |
| D640 (a and b) | NH | —Br | —H | —F |
| D641 (a and b) | NH | —Br | —H | —CH$_3$ |

TABLE 4-continued

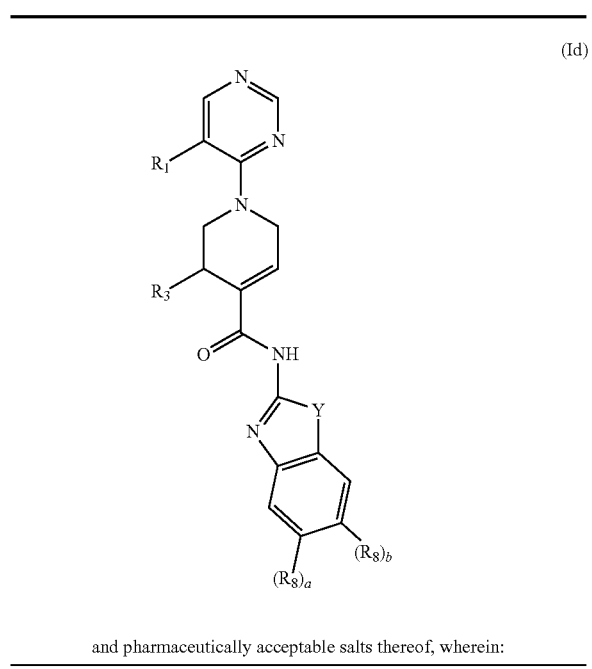

(Id)

and pharmaceutically acceptable salts thereof, wherein:

| Compound | Y | R₁ | (R₈)ₐ | (R₈)ᵦ |
|---|---|---|---|---|
| D642 (a and b) | NH | —Br | —H | —CF₃ |
| D643 (a and b) | NH | —Br | —H | —OCH₃ |
| D644 (a and b) | NH | —Br | —H | —OCH₂CH₃ |
| D645 (a and b) | NH | —Br | —H | —OCF₃ |
| D646 (a and b) | NH | —Br | —H | -tert-butyl |
| D647 (a and b) | NH | —Br | —H | -iso-propyl |
| D648 (a and b) | NH | —I | —Cl | —H |
| D649 (a and b) | NH | —I | —Br | —H |
| D650 (a and b) | NH | —I | —F | —H |
| D651 (a and b) | NH | —I | —CH₃ | —H |
| D652 (a and b) | NH | —I | —CF₃ | —H |
| D653 (a and b) | NH | —I | —OCH₃ | —H |
| D654 (a and b) | NH | —I | —OCH₂CH₃ | —H |
| D655 (a and b) | NH | —I | —OCF₃ | —H |
| D656 (a and b) | NH | —I | -tert-butyl | —H |
| D657 (a and b) | NH | —I | -iso-propyl | —H |
| D658 (a and b) | NH | —I | —CH₃ | —CH₃ |
| D659 (a and b) | NH | —I | —H | —H |
| D660 (a and b) | NH | —I | —H | —Cl |
| D661 (a and b) | NH | —I | —H | —Br |
| D662 (a and b) | NH | —I | —H | —F |
| D663 (a and b) | NH | —I | —H | —CH₃ |
| D664 (a and b) | NH | —I | —H | —CF₃ |
| D665 (a and b) | NH | —I | —H | —OCH₃ |
| D666 (a and b) | NH | —I | —H | —OCH₂CH₃ |
| D667 (a and b) | NH | —I | —H | —OCF₃ |
| D668 (a and b) | NH | —I | —H | -tert-butyl |
| D669 (a and b) | NH | —I | —H | -iso-propyl |

(a) means that R₃ is —H.
(b) means that R₃ is —CH₃.

TABLE 5

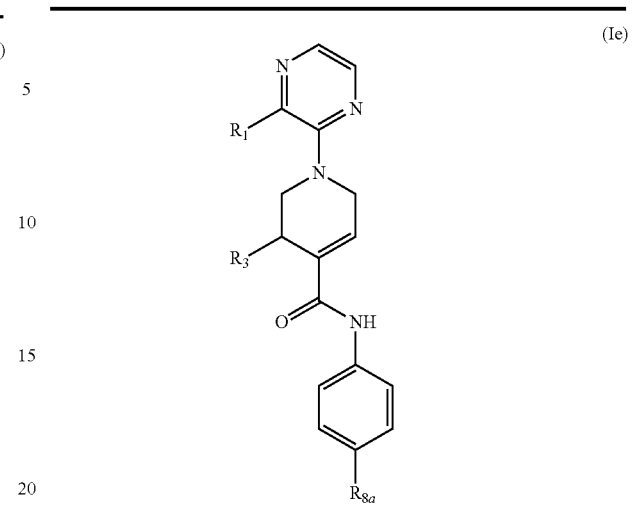

(Ie)

and pharmaceutically acceptable salts thereof, wherein:

| Compound | R₁ | R₈ₐ |
|---|---|---|
| E01 (a and b) | —H | —H |
| E02 (a and b) | —H | -tert-butyl |
| E03 (a and b) | —H | -iso-butyl |
| E04 (a and b) | —H | -sec-butyl |
| E05 (a and b) | —H | -iso-propyl |
| E06 (a and b) | —H | -n-propyl |
| E07 (a and b) | —H | -cyclohexyl |
| E08 (a and b) | —H | -tert-butoxy |
| E09 (a and b) | —H | -isopropoxy |
| E10 (a and b) | —H | —CF₃ |
| E11 (a and b) | —H | —CH₂CF₃ |
| E12 (a and b) | —H | —OCF₃ |
| E13 (a and b) | —H | —Cl |
| E14 (a and b) | —H | —Br |
| E15 (a and b) | —H | —I |
| E16 (a and b) | —H | -n-butyl |
| E17 (a and b) | —H | —CH₃ |
| E18 (a and b) | —H | —SCF₃ |
| E19 (a and b) | —H | —N(CH₂CH₃)₂ |
| E20 (a and b) | —H | —OCF₂CHF₂ |
| E21 (a and b) | —H | —C(OH)(CF₃)₂ |
| E22 (a and b) | —H | -(1,1-dimethyl-pentyl) |
| E23 (a and b) | —H | -(1,1-dimethyl-acetic acid) ethyl ester |
| E24 (a and b) | —H | —N-piperidinyl |
| E25 (a and b) | —Cl | —H |
| E26 (a and b) | —Cl | -tert-butyl |
| E27 (a and b) | —Cl | -iso-butyl |
| E28 (a and b) | —Cl | -sec-butyl |
| E29 (a and b) | —Cl | -iso-propyl |
| E30 (a and b) | —Cl | -n-propyl |
| E31 (a and b) | —Cl | -cyclohexyl |
| E32 (a and b) | —Cl | -tert-butoxy |
| E33 (a and b) | —Cl | -isopropoxy |
| E34 (a and b) | —Cl | —CF₃ |
| E35 (a and b) | —Cl | —CH₂CF₃ |
| E36 (a and b) | —Cl | —OCF₃ |
| E37 (a and b) | —Cl | —Cl |
| E38 (a and b) | —Cl | —Br |
| E39 (a and b) | —Cl | —I |
| E40 (a and b) | —Cl | -n-butyl |
| E41 (a and b) | —Cl | —CH₃ |
| E42 (a and b) | —Cl | —SCF₃ |
| E43 (a and b) | —Cl | —N(CH₂CH₃)₂ |
| E44 (a and b) | —Cl | —OCF₂CHF₂ |
| E45 (a and b) | —Cl | —C(OH)(CF₃)₂ |

TABLE 5-continued

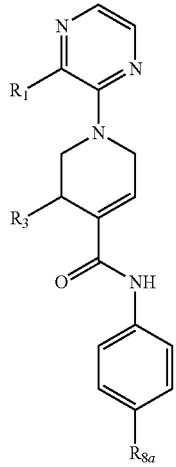

(Ie)

and pharmaceutically acceptable salts thereof, wherein:

| Compound | $R_1$ | $R_{8a}$ |
|---|---|---|
| E46 (a and b) | —Cl | -(1,1-dimethyl-pentyl) |
| E47 (a and b) | —Cl | -(1,1-dimethyl-acetic acid) ethyl ester |
| E48 (a and b) | —Cl | —N-piperidinyl |
| E49 (a and b) | —F | —H |
| E50 (a and b) | —F | -tert-butyl |
| E51 (a and b) | —F | -iso-butyl |
| E52 (a and b) | —F | -sec-butyl |
| E53 (a and b) | —F | -iso-propyl |
| E54 (a and b) | —F | -n-propyl |
| E55 (a and b) | —F | -cyclohexyl |
| E56 (a and b) | —F | -tert-butoxy |
| E57 (a and b) | —F | -isopropoxy |
| E58 (a and b) | —F | —$CF_3$ |
| E59 (a and b) | —F | —$CH_2CF_3$ |
| E60 (a and b) | —F | —$OCF_3$ |
| E61 (a and b) | —F | —Cl |
| E62 (a and b) | —F | —Br |
| E63 (a and b) | —F | —I |
| E64 (a and b) | —F | -n-butyl |
| E65 (a and b) | —F | —$CH_3$ |
| E66 (a and b) | —F | —$SCF_3$ |
| E67 (a and b) | —F | —$N(CH_2CH_3)_2$ |
| E68 (a and b) | —F | —$OCF_2CHF_2$ |
| E69 (a and b) | —F | —$C(OH)(CF_3)_2$ |
| E70 (a and b) | —F | -(1,1-dimethyl-pentyl) |
| E71 (a and b) | —F | -(1,1-dimethyl-acetic acid) ethyl ester |
| E72 (a and b) | —F | —N-piperidinyl |
| E73 (a and b) | —$CH_3$ | —H |
| E74 (a and b) | —$CH_3$ | -iso-butyl |
| E75 (a and b) | —$CH_3$ | -tert-butyl |
| E76 (a and b) | —$CH_3$ | -sec-butyl |
| E77 (a and b) | —$CH_3$ | -iso-propyl |
| E78 (a and b) | —$CH_3$ | -n-propyl |
| E79 (a and b) | —$CH_3$ | -cyclohexyl |
| E80 (a and b) | —$CH_3$ | -tert-butoxy |
| E81 (a and b) | —$CH_3$ | -isopropoxy |
| E82 (a and b) | —$CH_3$ | —$CF_3$ |
| E83 (a and b) | —$CH_3$ | —$CH_2CF_3$ |
| E84 (a and b) | —$CH_3$ | —$OCF_3$ |
| E85 (a and b) | —$CH_3$ | —Cl |
| E86 (a and b) | —$CH_3$ | —Br |
| E87 (a and b) | —$CH_3$ | —I |
| E88 (a and b) | —$CH_3$ | -n-butyl |
| E89 (a and b) | —$CH_3$ | —$CH_3$ |
| E90 (a and b) | —$CH_3$ | —$SCF_3$ |
| E91 (a and b) | —$CH_3$ | —$N(CH_2CH_3)_2$ |
| E92 (a and b) | —$CH_3$ | —$OCF_2CHF_2$ |
| E93 (a and b) | —$CH_3$ | —$C(OH)(CF_3)_2$ |
| E94 (a and b) | —$CH_3$ | -(1,1-dimethyl-pentyl) |
| E95 (a and b) | —$CH_3$ | -(1,1-dimethyl-acetic acid) ethyl ester |
| E96 (a and b) | —$CH_3$ | —N-piperidinyl |
| E97 (a and b) | —$CF_3$ | —H |
| E98 (a and b) | —$CF_3$ | -tert-butyl |
| E99 (a and b) | —$CF_3$ | -iso-butyl |
| E100 (a and b) | —$CF_3$ | -sec-butyl |
| E101 (a and b) | —$CF_3$ | -iso-propyl |
| E102 (a and b) | —$CF_3$ | -n-propyl |
| E103 (a and b) | —$CF_3$ | -cyclohexyl |
| E104 (a and b) | —$CF_3$ | -tert-butoxy |
| E105 (a and b) | —$CF_3$ | -isopropoxy |
| E106 (a and b) | —$CF_3$ | —$CF_3$ |
| E107 (a and b) | —$CF_3$ | —$CH_2CF_3$ |
| E108 (a and b) | —$CF_3$ | —$OCF_3$ |
| E109 (a and b) | —$CF_3$ | —Cl |
| E110 (a and b) | —$CF_3$ | —Br |
| E111 (a and b) | —$CF_3$ | —I |
| E112 (a and b) | —$CF_3$ | -n-butyl |
| E113 (a and b) | —$CF_3$ | —$CH_3$ |
| E114 (a and b) | —$CF_3$ | —$SCF_3$ |
| E115 (a and b) | —$CF_3$ | —$N(CH_2CH_3)_2$ |
| E116 (a and b) | —$CF_3$ | —$OCF_2CHF_2$ |
| E117 (a and b) | —$CF_3$ | —$C(OH)(CF_3)_2$ |
| E118 (a and b) | —$CF_3$ | -(1,1-dimethyl-pentyl) |
| E119 (a and b) | —$CF_3$ | -(1,1-dimethyl-acetic acid) ethyl ester |
| E120 (a and b) | —$CF_3$ | —N-piperidinyl |
| E121 (a and b) | —$CHF_2$ | -tert-butyl |
| E122 (a and b) | —$CHF_2$ | —H |
| E123 (a and b) | —$CHF_2$ | -iso-butyl |
| E124 (a and b) | —$CHF_2$ | -sec-butyl |
| E125 (a and b) | —$CHF_2$ | -iso-propyl |
| E126 (a and b) | —$CHF_2$ | -n-propyl |
| E127 (a and b) | —$CHF_2$ | -cyclohexyl |
| E128 (a and b) | —$CHF_2$ | -tert-butoxy |
| E129 (a and b) | —$CHF_2$ | -isopropoxy |
| E130 (a and b) | —$CHF_2$ | —$CF_3$ |
| E131 (a and b) | —$CHF_2$ | —$CH_2CF_3$ |
| E132 (a and b) | —$CHF_2$ | —$OCF_3$ |
| E133 (a and b) | —$CHF_2$ | —Cl |
| E134 (a and b) | —$CHF_2$ | —Br |
| E135 (a and b) | —$CHF_2$ | —I |
| E136 (a and b) | —$CHF_2$ | -n-butyl |
| E137 (a and b) | —$CHF_2$ | —$CH_3$ |
| E138 (a and b) | —$CHF_2$ | —$SCF_3$ |
| E139 (a and b) | —$CHF_2$ | —$N(CH_2CH_3)_2$ |
| E140 (a and b) | —$CHF_2$ | —$OCF_2CHF_2$ |
| E141 (a and b) | —$CHF_2$ | —$C(OH)(CF_3)_2$ |
| E142 (a and b) | —$CHF_2$ | -(1,1-dimethyl-pentyl) |
| E143 (a and b) | —$CHF_2$ | -(1,1-dimethyl-acetic acid) ethyl ester |
| E144 (a and b) | —$CHF_2$ | —N-piperidinyl |

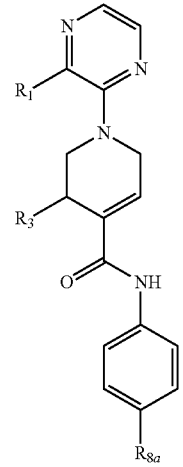

TABLE 5-continued

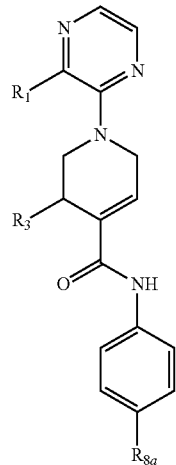

(Ie)

and pharmaceutically acceptable salts thereof, wherein:

| Compound | $R_1$ | $R_{8a}$ |
|---|---|---|
| E145 (a and b) | —OH | —H |
| E146 (a and b) | —OH | -tert-butyl |
| E147 (a and b) | —OH | -iso-butyl |
| E148 (a and b) | —OH | -sec-butyl |
| E149 (a and b) | —OH | -iso-propyl |
| E150 (a and b) | —OH | -n-propyl |
| E151 (a and b) | —OH | -cyclohexyl |
| E152 (a and b) | —OH | -tert-butoxy |
| E153 (a and b) | —OH | -isopropoxy |
| E154 (a and b) | —OH | —$CF_3$ |
| E155 (a and b) | —OH | —$CH_2CF_3$ |
| E156 (a and b) | —OH | —$OCF_3$ |
| E157 (a and b) | —OH | —Cl |
| E158 (a and b) | —OH | —Br |
| E159 (a and b) | —OH | —I |
| E160 (a and b) | —OH | -n-butyl |
| E161 (a and b) | —OH | —$CH_3$ |
| E162 (a and b) | —OH | —$SCF_3$ |
| E163 (a and b) | —OH | —$N(CH_2CH_3)_2$ |
| E164 (a and b) | —OH | —$OCF_2CHF_2$ |
| E165 (a and b) | —OH | —$C(OH)(CF_3)_2$ |
| E166 (a and b) | —OH | -(1,1-dimethyl-pentyl) |
| E167 (a and b) | —OH | -(1,1-dimethyl-acetic acid) ethyl ester |
| E168 (a and b) | —OH | —N-piperidinyl |
| E169 (a and b) | —$NO_2$ | —H |
| E170 (a and b) | —$NO_2$ | -tert-butyl |
| E171 (a and b) | —$NO_2$ | -iso-butyl |
| E172 (a and b) | —$NO_2$ | -sec-butyl |
| E173 (a and b) | —$NO_2$ | -iso-propyl |
| E174 (a and b) | —$NO_2$ | -n-propyl |
| E175 (a and b) | —$NO_2$ | -cyclohexyl |
| E176 (a and b) | —$NO_2$ | -tert-butoxy |
| E177 (a and b) | —$NO_2$ | -isopropoxy |
| E178 (a and b) | —$NO_2$ | —$CF_3$ |
| E179 (a and b) | —$NO_2$ | —$CH_2CF_3$ |
| E180 (a and b) | —$NO_2$ | —$OCF_3$ |
| E181 (a and b) | —$NO_2$ | —Cl |
| E182 (a and b) | —$NO_2$ | —Br |
| E183 (a and b) | —$NO_2$ | —I |
| E184 (a and b) | —$NO_2$ | -n-butyl |
| E185 (a and b) | —$NO_2$ | —$CH_3$ |
| E186 (a and b) | —$NO_2$ | —$SCF_3$ |
| E187 (a and b) | —$NO_2$ | —$N(CH_2CH_3)_2$ |
| E188 (a and b) | —$NO_2$ | —$OCF_2CHF_2$ |
| E189 (a and b) | —$NO_2$ | —$C(OH)(CF_3)_2$ |

TABLE 5-continued

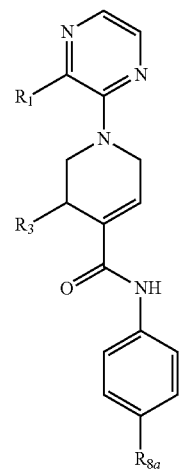

(Ie)

and pharmaceutically acceptable salts thereof, wherein:

| Compound | $R_1$ | $R_{8a}$ |
|---|---|---|
| E190 (a and b) | —$NO_2$ | -(1,1-dimethyl-pentyl) |
| E191 (a and b) | —$NO_2$ | -(1,1-dimethyl-acetic acid) ethyl ester |
| E192 (a and b) | —$NO_2$ | —N-piperidinyl |
| E193 (a and b) | —CN | —H |
| E194 (a and b) | —CN | -tert-butyl |
| E195 (a and b) | —CN | -iso-butyl |
| E196 (a and b) | —CN | -sec-butyl |
| E197 (a and b) | —CN | -iso-propyl |
| E198 (a and b) | —CN | -n-propyl |
| E199 (a and b) | —CN | -cyclohexyl |
| E200 (a and b) | —CN | -tert-butoxy |
| E201 (a and b) | —CN | -isopropoxy |
| E202 (a and b) | —CN | —$CF_3$ |
| E203 (a and b) | —CN | —$CH_2CF_3$ |
| E204 (a and b) | —CN | —$OCF_3$ |
| E205 (a and b) | —CN | —Cl |
| E206 (a and b) | —CN | —Br |
| E207 (a and b) | —CN | —I |
| E208 (a and b) | —CN | -n-butyl |
| E209 (a and b) | —CN | —$CH_3$ |
| E210 (a and b) | —CN | —$SCF_3$ |
| E211 (a and b) | —CN | —$N(CH_2CH_3)_2$ |
| E212 (a and b) | —CN | —$OCF_2CHF_2$ |
| E213 (a and b) | —CN | —$C(OH)(CF_3)_2$ |
| E214 (a and b) | —CN | -(1,1-dimethyl-pentyl) |
| E215 (a and b) | —CN | -(1,1-dimethyl-acetic acid) ethyl ester |
| E216 (a and b) | —CN | —N-piperidinyl |
| E217 (a and b) | —Br | —H |
| E218 (a and b) | —Br | -tert-butyl |
| E219 (a and b) | —Br | -iso-butyl |
| E220 (a and b) | —Br | -sec-butyl |
| E221 (a and b) | —Br | -iso-propyl |
| E222 (a and b) | —Br | -n-propyl |
| E223 (a and b) | —Br | -cyclohexyl |
| E224 (a and b) | —Br | -tert-butoxy |
| E225 (a and b) | —Br | -isopropoxy |
| E226 (a and b) | —Br | —$CF_3$ |
| E227 (a and b) | —Br | —$CH_2CF_3$ |
| E228 (a and b) | —Br | —$OCF_3$ |
| E229 (a and b) | —Br | —Cl |
| E230 (a and b) | —Br | —Br |
| E231 (a and b) | —Br | —I |
| E232 (a and b) | —Br | -n-butyl |

TABLE 5-continued

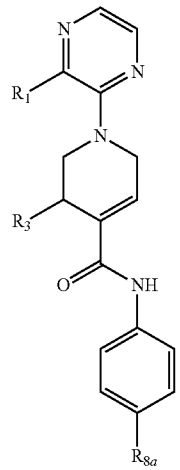

(Ie)

and pharmaceutically acceptable salts thereof, wherein:

| Compound | R₁ | R₈ₐ |
|---|---|---|
| E233 (a and b) | —Br | —CH₃ |
| E234 (a and b) | —Br | —SCF₃ |
| E235 (a and b) | —Br | —N(CH₂CH₃)₂ |
| E236 (a and b) | —Br | —OCF₂CHF₂ |
| E237 (a and b) | —Br | —C(OH)(CF₃)₂ |
| E238 (a and b) | —Br | -(1,1-dimethyl-pentyl) |
| E239 (a and b) | —Br | -(1,1-dimethyl-acetic acid) ethyl ester |
| E240 (a and b) | —Br | —N-piperidinyl |
| E241 (a and b) | —I | -tert-butyl |
| E242 (a and b) | —I | —H |
| E243 (a and b) | —I | -iso-butyl |
| E244 (a and b) | —I | -sec-butyl |
| E245 (a and b) | —I | -iso-propyl |
| E246 (a and b) | —I | -n-propyl |
| E247 (a and b) | —I | -cyclohexyl |
| E248 (a and b) | —I | -tert-butoxy |
| E249 (a and b) | —I | -isopropoxy |
| E250 (a and b) | —I | —CF₃ |
| E251 (a and b) | —I | —CH₂CF₃ |
| E252 (a and b) | —I | —OCF₃ |
| E253 (a and b) | —I | —Cl |
| E254 (a and b) | —I | —Br |
| E255 (a and b) | —I | —I |
| E256 (a and b) | —I | -n-butyl |
| E257 (a and b) | —I | —CH₃ |
| E258 (a and b) | —I | —SCF₃ |
| E259 (a and b) | —I | —N(CH₂CH₃)₂ |
| E260 (a and b) | —I | —OCF₂CHF₂ |
| E261 (a and b) | —I | —C(OH)(CF₃)₂ |
| E262 (a and b) | —I | -(1,1-dimethyl-pentyl) |
| E263 (a and b) | —I | -(1,1-dimethyl-acetic acid) ethyl ester |
| E264 (a and b) | —I | —N-piperidinyl |

(a) means that R₃ is —H.
(b) means that R₃ is —CH₃.

TABLE 6

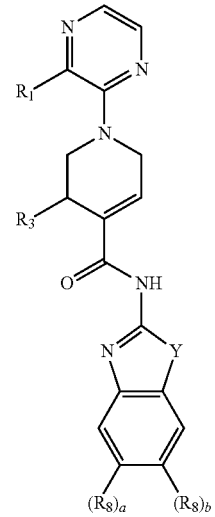

(If)

and pharmaceutically acceptable salts thereof, wherein:

| Compound | Y | R₁ | (R₈)ₐ | (R₈)ᵦ |
|---|---|---|---|---|
| F01 (a and b) | S | —H | —Cl | —H |
| F02 (a and b) | S | —H | —Br | —H |
| F03 (a and b) | S | —H | —F | —H |
| F04 (a and b) | S | —H | —CH₃ | —H |
| F05 (a and b) | S | —H | —CF₃ | —H |
| F06 (a and b) | S | —H | —OCH₃ | —H |
| F07 (a and b) | S | —H | —OCH₂CH₃ | —H |
| F08 (a and b) | S | —H | —OCF₃ | —H |
| F09 (a and b) | S | —H | -tert-butyl | —H |
| F10 (a and b) | S | —H | -iso-propyl | —H |
| F11 (a and b) | S | —H | —CH₃ | —CH₃ |
| F12 (a and b) | S | —H | —H | —H |
| F13 (a and b) | S | —H | —H | —Cl |
| F14 (a and b) | S | —H | —H | —Br |
| F15 (a and b) | S | —H | —H | —F |
| F16 (a and b) | S | —H | —H | —CH₃ |
| F17 (a and b) | S | —H | —H | —CF₃ |
| F18 (a and b) | S | —H | —H | —OCH₃ |
| F19 (a and b) | S | —H | —H | —OCH₂CH₃ |
| F20 (a and b) | S | —H | —H | —OCF₃ |
| F21 (a and b) | S | —H | —H | -tert-butyl |
| F22 (a and b) | S | —H | —H | -iso-propyl |
| F23 (a and b) | S | —Cl | —Cl | —H |
| F24 (a and b) | S | —Cl | —Br | —H |
| F25 (a and b) | S | —Cl | —F | —H |
| F26 (a and b) | S | —Cl | —CH₃ | —H |
| F27 (a and b) | S | —Cl | —CF₃ | —H |
| F28 (a and b) | S | —Cl | —OCH₃ | —H |
| F29 (a and b) | S | —Cl | —OCH₂CH₃ | —H |
| F30 (a and b) | S | —Cl | —OCF₃ | —H |
| F31 (a and b) | S | —Cl | -tert-butyl | —H |
| F32 (a and b) | S | —Cl | -iso-propyl | —H |
| F33 (a and b) | S | —Cl | —CH₃ | —CH₃ |
| F34 (a and b) | S | —Cl | —H | —H |
| F35 (a and b) | S | —Cl | —H | —Cl |
| F36 (a and b) | S | —Cl | —H | —Br |
| F37 (a and b) | S | —Cl | —H | —F |
| F38 (a and b) | S | —Cl | —H | —CH₃ |
| F39 (a and b) | S | —Cl | —H | —CF₃ |
| F40 (a and b) | S | —Cl | —H | —OCH₃ |
| F41 (a and b) | S | —Cl | —H | —OCH₂CH₃ |
| F42 (a and b) | S | —Cl | —H | —OCF₃ |
| F43 (a and b) | S | —Cl | —H | -tert-butyl |
| F44 (a and b) | S | —Cl | —H | -iso-propyl |
| F45 (a and b) | S | —Cl | —H | —OCF₃ |
| F46 (a and b) | S | —Cl | —H | -tert-butyl |
| F47 (a and b) | S | —Cl | —H | -iso-propyl |
| F48 (a and b) | S | —CH₃ | —Cl | —H |
| F49 (a and b) | S | —CH₃ | —Br | —H |
| F50 (a and b) | S | —CH₃ | —F | —H |

TABLE 6-continued (If)

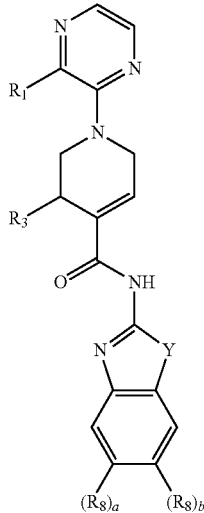

and pharmaceutically acceptable salts thereof, wherein:

| Compound | Y | R₁ | (R₈)ₐ | (R₈)ᵦ |
|---|---|---|---|---|
| F51 (a and b) | S | —CH₃ | —CH₃ | —H |
| F52 (a and b) | S | —CH₃ | —CF₃ | —H |
| F53 (a and b) | S | —CH₃ | —OCH₃ | —H |
| F54 (a and b) | S | —CH₃ | —OCH₂CH₃ | —H |
| F55 (a and b) | S | —CH₃ | —OCF₃ | —H |
| F56 (a and b) | S | —CH₃ | -tert-butyl | —H |
| F57 (a and b) | S | —CH₃ | -iso-propyl | —H |
| F58 (a and b) | S | —CH₃ | —CH₃ | —CH₃ |
| F59 (a and b) | S | —CH₃ | —H | —H |
| F60 (a and b) | S | —CH₃ | —H | —Cl |
| F61 (a and b) | S | —CH₃ | —H | —Br |
| F62 (a and b) | S | —CH₃ | —H | —F |
| F63 (a and b) | S | —CH₃ | —H | —CH₃ |
| F64 (a and b) | S | —CH₃ | —H | —CF₃ |
| F65 (a and b) | S | —CH₃ | —H | —OCH₃ |
| F66 (a and b) | S | —CH₃ | —H | —OCH₂CH₃ |
| F67 (a and b) | S | —CH₃ | —H | —OCF₃ |
| F68 (a and b) | S | —CH₃ | —H | -tert-butyl |
| F69 (a and b) | S | —CH₃ | —H | -iso-propyl |
| F70 (a and b) | S | —CF₃ | —Cl | —H |
| F71 (a and b) | S | —CF₃ | —Br | —H |
| F72 (a and b) | S | —CF₃ | —F | —H |
| F73 (a and b) | S | —CF₃ | —CH₃ | —H |
| F74 (a and b) | S | —CF₃ | —CF₃ | —H |
| F75 (a and b) | S | —CF₃ | —OCH₃ | —H |
| F76 (a and b) | S | —CF₃ | —OCH₂CH₃ | —H |
| F77 (a and b) | S | —CF₃ | —OCF₃ | —H |
| F78 (a and b) | S | —CF₃ | -tert-butyl | —H |
| F79 (a and b) | S | —CF₃ | -iso-propyl | —H |
| F80 (a and b) | S | —CF₃ | —CH₃ | —CH₃ |
| F81 (a and b) | S | —CF₃ | —H | —H |
| F82 (a and b) | S | —CF₃ | —H | —Cl |
| F83 (a and b) | S | —CF₃ | —H | —Br |
| F84 (a and b) | S | —CF₃ | —H | —F |
| F85 (a and b) | S | —CF₃ | —H | —CH₃ |
| F86 (a and b) | S | —CF₃ | —H | —CF₃ |
| F87 (a and b) | S | —CF₃ | —H | —OCH₃ |
| F88 (a and b) | S | —CF₃ | —H | —OCH₂CH₃ |
| F89 (a and b) | S | —CF₃ | —H | —OCF₃ |
| F90 (a and b) | S | —CF₃ | —H | -tert-butyl |
| F91 (a and b) | S | —CF₃ | —H | -iso-propyl |
| F92 (a and b) | S | —CHF₂ | —Cl | —H |
| F93 (a and b) | S | —CHF₂ | —Br | —H |
| F94 (a and b) | S | —CHF₂ | —F | —H |
| F95 (a and b) | S | —CHF₂ | —CH₃ | —H |
| F96 (a and b) | S | —CHF₂ | —CF₃ | —H |
| F97 (a and b) | S | —CHF₂ | —OCH₃ | —H |
| F98 (a and b) | S | —CHF₂ | —OCH₂CH₃ | —H |
| F99 (a and b) | S | —CHF₂ | —OCF₃ | —H |
| F100 (a and b) | S | —CHF₂ | -tert-butyl | —H |
| F101 (a and b) | S | —CHF₂ | -iso-propyl | —H |
| F102 (a and b) | S | —CHF₂ | —CH₃ | —CH₃ |
| F103 (a and b) | S | —CHF₂ | —H | —H |
| F104 (a and b) | S | —CHF₂ | —H | —Cl |
| F105 (a and b) | S | —CHF₂ | —H | —Br |
| F106 (a and b) | S | —CHF₂ | —H | —F |
| F107 (a and b) | S | —CHF₂ | —H | —CH₃ |
| F108 (a and b) | S | —CHF₂ | —H | —CF₃ |
| F109 (a and b) | S | —CHF₂ | —H | —OCH₃ |
| F110 (a and b) | S | —CHF₂ | —H | —OCH₂CH₃ |
| F111 (a and b) | S | —CHF₂ | —H | —OCF₃ |
| F112 (a and b) | S | —CHF₂ | —H | -tert-butyl |
| F113 (a and b) | S | —CHF₂ | —H | -iso-propyl |
| F114 (a and b) | S | —OH | —Cl | —H |
| F115 (a and b) | S | —OH | —Br | —H |
| F116 (a and b) | S | —OH | —F | —H |
| F117 (a and b) | S | —OH | —CH₃ | —H |
| F118 (a and b) | S | —OH | —CF₃ | —H |
| F119 (a and b) | S | —OH | —OCH₃ | —H |
| F120 (a and b) | S | —OH | —OCH₂CH₃ | —H |
| F121 (a and b) | S | —OH | —OCF₃ | —H |
| F122 (a and b) | S | —OH | -tert-butyl | —H |
| F123 (a and b) | S | —OH | -iso-propyl | —H |
| F124 (a and b) | S | —OH | —CH₃ | —CH₃ |
| F125 (a and b) | S | —OH | —H | —H |
| F126 (a and b) | S | —OH | —H | —Cl |
| F127 (a and b) | S | —OH | —H | —Br |
| F128 (a and b) | S | —OH | —H | —F |
| F129 (a and b) | S | —OH | —H | —CH₃ |
| F130 (a and b) | S | —OH | —H | —CF₃ |
| F131 (a and b) | S | —OH | —H | —OCH₃ |
| F132 (a and b) | S | —OH | —H | —OCH₂CH₃ |
| F133 (a and b) | S | —OH | —H | —OCF₃ |
| F134 (a and b) | S | —OH | —H | -tert-butyl |
| F135 (a and b) | S | —OH | —H | -iso-propyl |
| F136 (a and b) | S | —NO₂ | —Cl | —H |
| F137 (a and b) | S | —NO₂ | —Br | —H |
| F138 (a and b) | S | —NO₂ | —F | —H |
| F139 (a and b) | S | —NO₂ | —CH₃ | —H |
| F140 (a and b) | S | —NO₂ | —CF₃ | —H |
| F141 (a and b) | S | —NO₂ | —OCH₃ | —H |
| F142 (a and b) | S | —NO₂ | —OCH₂CH₃ | —H |
| F143 (a and b) | S | —NO₂ | —OCF₃ | —H |
| F144 (a and b) | S | —NO₂ | -tert-butyl | —H |
| F145 (a and b) | S | —NO₂ | -iso-propyl | —H |
| F146 (a and b) | S | —NO₂ | —CH₃ | —CH₃ |
| F147 (a and b) | S | —NO₂ | —H | —H |
| F148 (a and b) | S | —NO₂ | —H | —Cl |
| F149 (a and b) | S | —NO₂ | —H | —Br |
| F150 (a and b) | S | —NO₂ | —H | —F |

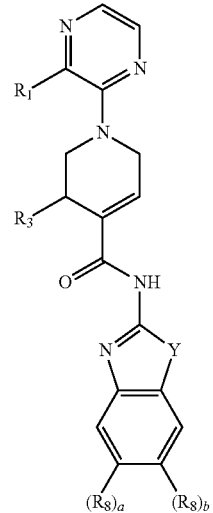

TABLE 6-continued (If)

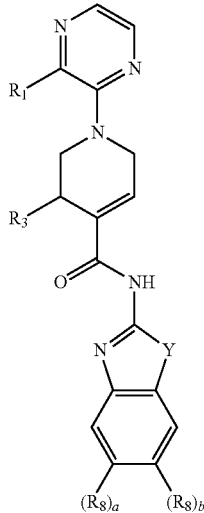

and pharmaceutically acceptable salts thereof, wherein:

| Compound | Y | $R_1$ | $(R_8)_a$ | $(R_8)_b$ |
|---|---|---|---|---|
| F151 (a and b) | S | —NO$_2$ | —H | —CH$_3$ |
| F152 (a and b) | S | —NO$_2$ | —H | —CF$_3$ |
| F153 (a and b) | S | —NO$_2$ | —H | —OCH$_3$ |
| F154 (a and b) | S | —NO$_2$ | —H | —OCH$_2$CH$_3$ |
| F155 (a and b) | S | —NO$_2$ | —H | -OCF3 |
| F156 (a and b) | S | —NO$_2$ | —H | -tert-butyl |
| F157 (a and b) | S | —NO$_2$ | —H | -iso-propyl |
| F158 (a and b) | S | —CN | —Br | —H |
| F159 (a and b) | S | —CN | —Cl | —H |
| F160 (a and b) | S | —CN | —F | —H |
| F161 (a and b) | S | —CN | —CH$_3$ | —H |
| F162 (a and b) | S | —CN | —CF$_3$ | —H |
| F163 (a and b) | S | —CN | —OCH$_3$ | —H |
| F164 (a and b) | S | —CN | —OCH$_2$CH$_3$ | —H |
| F165 (a and b) | S | —CN | —OCF$_3$ | —H |
| F166 (a and b) | S | —CN | -tert-butyl | —H |
| F167 (a and b) | S | —CN | -iso-propyl | —H |
| F168 (a and b) | S | —CN | —CH$_3$ | —CH$_3$ |
| F169 (a and b) | S | —CN | —H | —H |
| F170 (a and b) | S | —CN | —H | —Cl |
| F171 (a and b) | S | —CN | —H | —Br |
| F172 (a and b) | S | —CN | —H | —F |
| F173 (a and b) | S | —CN | —H | —CH$_3$ |
| F174 (a and b) | S | —CN | —H | —CF$_3$ |
| F175 (a and b) | S | —CN | —H | —OCH$_3$ |
| F176 (a and b) | S | —CN | —H | —OCH$_2$CH$_3$ |
| F177 (a and b) | S | —CN | —H | —OCF$_3$ |
| F178 (a and b) | S | —CN | —H | -tert-butyl |
| F179 (a and b) | S | —CN | —H | -iso-propyl |
| F180 (a and b) | S | —Br | —Br | —H |
| F181 (a and b) | S | —Br | —Cl | —H |
| F182 (a and b) | S | —Br | —F | —H |
| F183 (a and b) | S | —Br | —CH$_3$ | —H |
| F184 (a and b) | S | —Br | —CF$_3$ | —H |
| F185 (a and b) | S | —Br | —OCH$_3$ | —H |
| F186 (a and b) | S | —Br | —OCH$_2$CH$_3$ | —H |
| F187 (a and b) | S | —Br | —OCF$_3$ | —H |
| F188 (a and b) | S | —Br | -tert-butyl | —H |
| F189 (a and b) | S | —Br | -iso-propyl | —H |
| F190 (a and b) | S | —Br | —CH$_3$ | —CH$_3$ |
| F191 (a and b) | S | —Br | —H | —H |
| F192 (a and b) | S | —Br | —H | —Cl |
| F193 (a and b) | S | —Br | —H | —Br |
| F194 (a and b) | S | —Br | —H | —F |
| F195 (a and b) | S | —Br | —H | —CH$_3$ |
| F196 (a and b) | S | —Br | —H | —CF$_3$ |
| F197 (a and b) | S | —Br | —H | —OCH$_3$ |
| F198 (a and b) | S | —Br | —H | —OCH$_2$CH$_3$ |
| F199 (a and b) | S | —Br | —H | —OCF$_3$ |
| F200 (a and b) | S | —Br | —H | -tert-butyl |

TABLE 6-continued (If)

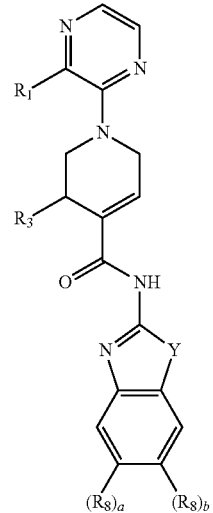

and pharmaceutically acceptable salts thereof, wherein:

| Compound | Y | $R_1$ | $(R_8)_a$ | $(R_8)_b$ |
|---|---|---|---|---|
| F201 (a and b) | S | —Br | —H | -iso-propyl |
| F202 (a and b) | S | —I | —Cl | —H |
| F203 (a and b) | S | —I | —Br | —H |
| F204 (a and b) | S | —I | —F | —H |
| F205 (a and b) | S | —I | —CH$_3$ | —H |
| F206 (a and b) | S | —I | —CF$_3$ | —H |
| F207 (a and b) | S | —I | —OCH$_3$ | —H |
| F208 (a and b) | S | —I | —OCH$_2$CH$_3$ | —H |
| F209 (a and b) | S | —I | —OCF$_3$ | —H |
| F210 (a and b) | S | —I | -tert-butyl | —H |
| F211 (a and b) | S | —I | -iso-propyl | —H |
| F212 (a and b) | S | —I | —CH$_3$ | —CH$_3$ |
| F213 (a and b) | S | —I | —H | —H |
| F214 (a and b) | S | —I | —H | —Cl |
| F215 (a and b) | S | —I | —H | —Br |
| F216 (a and b) | S | —I | —H | —F |
| F217 (a and b) | S | —I | —H | —CH$_3$ |
| F218 (a and b) | S | —I | —H | —CF$_3$ |
| F219 (a and b) | S | —I | —H | —OCH$_3$ |
| F220 (a and b) | S | —I | —H | —OCH$_2$CH$_3$ |
| F221 (a and b) | S | —I | —H | —OCF$_3$ |
| F222 (a and b) | S | —I | —H | -tert-butyl |
| F223 (a and b) | S | —I | —H | -iso-propyl |
| F224 (a and b) | O | —H | —Cl | —H |
| F225 (a and b) | O | —H | —Br | —H |
| F226 (a and b) | O | —H | —F | —H |
| F227 (a and b) | O | —H | —CH$_3$ | —H |
| F228 (a and b) | O | —H | —CF$_3$ | —H |
| F229 (a and b) | O | —H | —OCH$_3$ | —H |
| F230 (a and b) | O | —H | —OCH$_2$CH$_3$ | —H |
| F231 (a and b) | O | —H | —OCF$_3$ | —H |
| F232 (a and b) | O | —H | -tert-butyl | —H |
| F233 (a and b) | O | —H | -iso-propyl | —H |
| F234 (a and b) | O | —H | —CH$_3$ | —CH$_3$ |
| F235 (a and b) | O | —H | —H | —H |
| F236 (a and b) | O | —H | —H | —Cl |
| F237 (a and b) | O | —H | —H | —Br |
| F238 (a and b) | O | —H | —H | —F |
| F239 (a and b) | O | —H | —H | —CH$_3$ |
| F240 (a and b) | O | —H | —H | —CF$_3$ |
| F241 (a and b) | O | —H | —H | —OCH$_3$ |
| F242 (a and b) | O | —H | —H | —OCH$_2$CH$_3$ |
| F243 (a and b) | O | —H | —H | —OCF$_3$ |
| F244 (a and b) | O | —H | —H | -tert-butyl |
| F245 (a and b) | O | —H | —H | -iso-propyl |
| F246 (a and b) | O | —Cl | —Cl | —H |
| F247 (a and b) | O | —Cl | —Br | —H |
| F248 (a and b) | O | —Cl | —F | —H |
| F249 (a and b) | O | —Cl | —CH$_3$ | —H |
| F250 (a and b) | O | —Cl | —CF$_3$ | —H |

TABLE 6-continued (If)

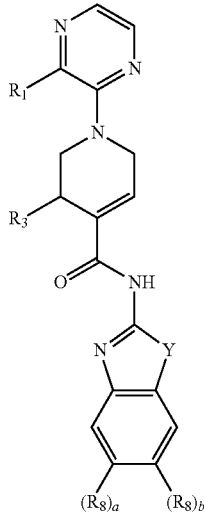

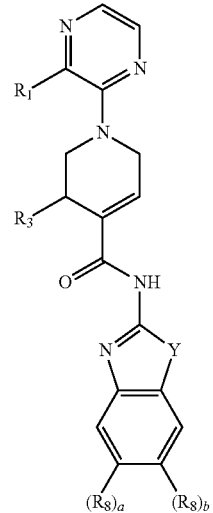

and pharmaceutically acceptable salts thereof, wherein:

| Compound | Y | R$_1$ | (R$_8$)$_a$ | (R$_8$)$_b$ |
|---|---|---|---|---|
| F251 (a and b) | O | —Cl | —OCH$_3$ | —H |
| F252 (a and b) | O | —Cl | —OCH$_2$CH$_3$ | —H |
| F253 (a and b) | O | —Cl | —OCF$_3$ | —H |
| F254 (a and b) | O | —Cl | -tert-butyl | —H |
| F255 (a and b) | O | —Cl | -iso-propyl | —H |
| F256 (a and b) | O | —Cl | —CH$_3$ | —CH$_3$ |
| F257 (a and b) | O | —Cl | —H | —H |
| F258 (a and b) | O | —Cl | —H | —Cl |
| F259 (a and b) | O | —Cl | —H | —Br |
| F260 (a and b) | O | —Cl | —H | —F |
| F261 (a and b) | O | —Cl | —H | —CH$_3$ |
| F262 (a and b) | O | —Cl | —H | —CF$_3$ |
| F263 (a and b) | O | —Cl | —H | —OCH$_3$ |
| F264 (a and b) | O | —Cl | —H | —OCH$_2$CH$_3$ |
| F265 (a and b) | O | —Cl | —H | —OCF$_3$ |
| F266 (a and b) | O | —Cl | —H | -tert-butyl |
| F267 (a and b) | O | —Cl | —H | -iso-propyl |
| F268 (a and b) | O | —Cl | —H | —OCF$_3$ |
| F269 (a and b) | O | —Cl | —H | -tert-butyl |
| F270 (a and b) | O | —Cl | —H | -iso-propyl |
| F271 (a and b) | O | —CH$_3$ | —Cl | —H |
| F272 (a and b) | O | —CH$_3$ | —Br | —H |
| F273 (a and b) | O | —CH$_3$ | —F | —H |
| F274 (a and b) | O | —CH$_3$ | —CH$_3$ | —H |
| F275 (a and b) | O | —CH$_3$ | —CF$_3$ | —H |
| F276 (a and b) | O | —CH$_3$ | —OCH$_3$ | —H |
| F277 (a and b) | O | —CH$_3$ | —OCH$_2$CH$_3$ | —H |
| F278 (a and b) | O | —CH$_3$ | —OCF$_3$ | —H |
| F279 (a and b) | O | —CH$_3$ | -tert-butyl | —H |
| F280 (a and b) | O | —CH$_3$ | -iso-propyl | —H |
| F281 (a and b) | O | —CH$_3$ | —CH$_3$ | —CH$_3$ |
| F282 (a and b) | O | —CH$_3$ | —H | —H |
| F283 (a and b) | O | —CH$_3$ | —H | —Cl |
| F284 (a and b) | O | —CH$_3$ | —H | —Br |
| F285 (a and b) | O | —CH$_3$ | —H | —F |
| F286 (a and b) | O | —CH$_3$ | —H | —CH$_3$ |
| F287 (a and b) | O | —CH$_3$ | —H | —CF$_3$ |
| F288 (a and b) | O | —CH$_3$ | —H | —OCH$_3$ |
| F289 (a and b) | O | —CH$_3$ | —H | —OCH$_2$CH$_3$ |
| F290 (a and b) | O | —CH$_3$ | —H | —OCF$_3$ |
| F291 (a and b) | O | —CH$_3$ | —H | -tert-butyl |
| F292 (a and b) | O | —CH$_3$ | —H | -iso-propyl |
| F293 (a and b) | O | —CF$_3$ | —Cl | —H |
| F294 (a and b) | O | —CF$_3$ | —Br | —H |
| F295 (a and b) | O | —CF$_3$ | —F | —H |
| F296 (a and b) | O | —CF$_3$ | —CH$_3$ | —H |
| F297 (a and b) | O | —CF$_3$ | —CF$_3$ | —H |
| F298 (a and b) | O | —CF$_3$ | —OCH$_3$ | —H |
| F299 (a and b) | O | —CF$_3$ | —OCH$_2$CH$_3$ | —H |
| F300 (a and b) | O | —CF$_3$ | —OCF$_3$ | —H |
| F301 (a and b) | O | —CF$_3$ | -tert-butyl | —H |
| F302 (a and b) | O | —CF$_3$ | -iso-propyl | —H |
| F303 (a and b) | O | —CF$_3$ | —CH$_3$ | —CH$_3$ |
| F304 (a and b) | O | —CF$_3$ | —H | —H |
| F305 (a and b) | O | —CF$_3$ | —H | —Cl |
| F306 (a and b) | O | —CF$_3$ | —H | —Br |
| F307 (a and b) | O | —CF$_3$ | —H | —F |
| F308 (a and b) | O | —CF$_3$ | —H | —CH$_3$ |
| F309 (a and b) | O | —CF$_3$ | —H | —CF$_3$ |
| F310 (a and b) | O | —CF$_3$ | —H | —OCH$_3$ |
| F311 (a and b) | O | —CF$_3$ | —H | —OCH$_2$CH$_3$ |
| F312 (a and b) | O | —CF$_3$ | —H | —OCF$_3$ |
| F313 (a and b) | O | —CF$_3$ | —H | -tert-butyl |
| F314 (a and b) | O | —CF$_3$ | —H | -iso-propyl |
| F315 (a and b) | O | —CHF$_2$ | —Cl | —H |
| F316 (a and b) | O | —CHF$_2$ | —Br | —H |
| F317 (a and b) | O | —CHF$_2$ | —F | —H |
| F318 (a and b) | O | —CHF$_2$ | —CH$_3$ | —H |
| F319 (a and b) | O | —CHF$_2$ | —CF$_3$ | —H |
| F320 (a and b) | O | —CHF$_2$ | —OCH$_3$ | —H |
| F321 (a and b) | O | —CHF$_2$ | —OCH$_2$CH$_3$ | —H |
| F322 (a and b) | O | —CHF$_2$ | —OCF$_3$ | —H |
| F323 (a and b) | O | —CHF$_2$ | -tert-butyl | —H |
| F324 (a and b) | O | —CHF$_2$ | -iso-propyl | —H |
| F325 (a and b) | O | —CHF$_2$ | —CH$_3$ | —CH$_3$ |
| F326 (a and b) | O | —CHF$_2$ | —H | —H |
| F327 (a and b) | O | —CHF$_2$ | —H | —Cl |
| F328 (a and b) | O | —CHF$_2$ | —H | —Br |
| F329 (a and b) | O | —CHF$_2$ | —H | —F |
| F330 (a and b) | O | —CHF$_2$ | —H | —CH$_3$ |
| F331 (a and b) | O | —CHF$_2$ | —H | —CF$_3$ |
| F332 (a and b) | O | —CHF$_2$ | —H | —OCH$_3$ |
| F333 (a and b) | O | —CHF$_2$ | —H | —OCH$_2$CH$_3$ |
| F334 (a and b) | O | —CHF$_2$ | —H | —OCF$_3$ |
| F335 (a and b) | O | —CHF$_2$ | —H | -tert-butyl |
| F336 (a and b) | O | —CHF$_2$ | —H | -iso-propyl |
| F337 (a and b) | O | —OH | —Cl | —H |
| F338 (a and b) | O | —OH | —Br | —H |
| F339 (a and b) | O | —OH | —F | —H |
| F340 (a and b) | O | —OH | —CH$_3$ | —H |
| F341 (a and b) | O | —OH | —CF$_3$ | —H |
| F342 (a and b) | O | —OH | —OCH$_3$ | —H |
| F343 (a and b) | O | —OH | —OCH$_2$CH$_3$ | —H |
| F344 (a and b) | O | —OH | —OCF$_3$ | —H |
| F345 (a and b) | O | —OH | -tert-butyl | —H |
| F346 (a and b) | O | —OH | -iso-propyl | —H |
| F347 (a and b) | O | —OH | —CH$_3$ | —CH$_3$ |
| F348 (a and b) | O | —OH | —H | —H |
| F349 (a and b) | O | —OH | —H | —Cl |
| F350 (a and b) | O | —OH | —H | —Br |

TABLE 6-continued

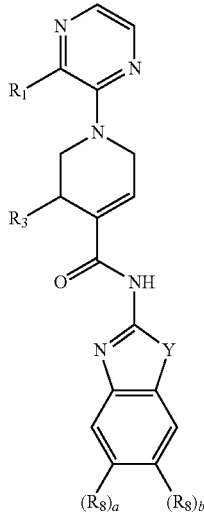

(If)

and pharmaceutically acceptable salts thereof, wherein:

| Compound | Y | $R_1$ | $(R_8)_a$ | $(R_8)_b$ |
|---|---|---|---|---|
| F351 (a and b) | O | —OH | —H | —F |
| F352 (a and b) | O | —OH | —H | —CH$_3$ |
| F353 (a and b) | O | —OH | —H | —CF$_3$ |
| F354 (a and b) | O | —OH | —H | —OCH$_3$ |
| F355 (a and b) | O | —OH | —H | —OCH$_2$CH$_3$ |
| F356 (a and b) | O | —OH | —H | —OCF$_3$ |
| F357 (a and b) | O | —OH | —H | -tert-butyl |
| F358 (a and b) | O | —OH | —H | -iso-propyl |
| F359 (a and b) | O | —NO$_2$ | —Cl | —H |
| F360 (a and b) | O | —NO$_2$ | —Br | —H |
| F361 (a and b) | O | —NO$_2$ | —F | —H |
| F362 (a and b) | O | —NO$_2$ | —CH$_3$ | —H |
| F363 (a and b) | O | —NO$_2$ | —CF$_3$ | —H |
| F364 (a and b) | O | —NO$_2$ | —OCH$_3$ | —H |
| F365 (a and b) | O | —NO$_2$ | —OCH$_2$CH$_3$ | —H |
| F366 (a and b) | O | —NO$_2$ | —OCF$_3$ | —H |
| F367 (a and b) | O | —NO$_2$ | -tert-butyl | —H |
| F368 (a and b) | O | —NO$_2$ | -iso-propyl | —H |
| F369 (a and b) | O | —NO$_2$ | —CH$_3$ | —CH$_3$ |
| F370 (a and b) | O | —NO$_2$ | —H | —H |
| F371 (a and b) | O | —NO$_2$ | —H | —Cl |
| F372 (a and b) | O | —NO$_2$ | —H | —Br |
| F373 (a and b) | O | —NO$_2$ | —H | —F |
| F374 (a and b) | O | —NO$_2$ | —H | —CH$_3$ |
| F375 (a and b) | O | —NO$_2$ | —H | —CF$_3$ |
| F376 (a and b) | O | —NO$_2$ | —H | —OCH$_3$ |
| F377 (a and b) | O | —NO$_2$ | —H | —OCH$_2$CH$_3$ |
| F378 (a and b) | O | —NO$_2$ | —H | —OCF$_3$ |
| F379 (a and b) | O | —NO$_2$ | —H | -tert-butyl |
| F380 (a and b) | O | —NO$_2$ | —H | -iso-propyl |
| F381 (a and b) | O | —CN | —Br | —H |
| F382 (a and b) | O | —CN | —Cl | —H |
| F383 (a and b) | O | —CN | —F | —H |
| F384 (a and b) | O | —CN | —CH$_3$ | —H |
| F385 (a and b) | O | —CN | —CF$_3$ | —H |
| F386 (a and b) | O | —CN | —OCH$_3$ | —H |
| F387 (a and b) | O | —CN | —OCH$_2$CH$_3$ | —H |
| F388 (a and b) | O | —CN | —OCF$_3$ | —H |
| F389 (a and b) | O | —CN | -tert-butyl | —H |
| F390 (a and b) | O | —CN | -iso-propyl | —H |
| F391 (a and b) | O | —CN | —CH$_3$ | —CH$_3$ |
| F392 (a and b) | O | —CN | —H | —H |
| F393 (a and b) | O | —CN | —H | —Cl |
| F394 (a and b) | O | —CN | —H | —Br |
| F395 (a and b) | O | —CN | —H | —F |
| F396 (a and b) | O | —CN | —H | —CH$_3$ |
| F397 (a and b) | O | —CN | —H | —CF$_3$ |
| F398 (a and b) | O | —CN | —H | —OCH$_3$ |
| F399 (a and b) | O | —CN | —H | —OCH$_2$CH$_3$ |
| F400 (a and b) | O | —CN | —H | —OCF$_3$ |

TABLE 6-continued

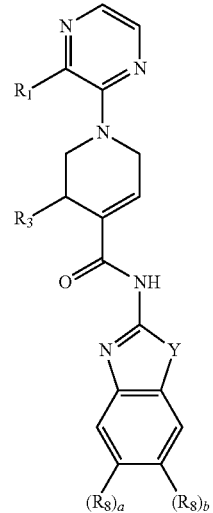

(If)

and pharmaceutically acceptable salts thereof, wherein:

| Compound | Y | $R_1$ | $(R_8)_a$ | $(R_8)_b$ |
|---|---|---|---|---|
| F401 (a and b) | O | —CN | —H | -tert-butyl |
| F402 (a and b) | O | —CN | —H | -iso-propyl |
| F403 (a and b) | O | —Br | —Br | —H |
| F404 (a and b) | O | —Br | —Cl | —H |
| F405 (a and b) | O | —Br | —F | —H |
| F406 (a and b) | O | —Br | —CH$_3$ | —H |
| F407 (a and b) | O | —Br | —CF$_3$ | —H |
| F408 (a and b) | O | —Br | —OCH$_3$ | —H |
| F409 (a and b) | O | —Br | —OCH$_2$CH$_3$ | —H |
| F410 (a and b) | O | —Br | —OCF$_3$ | —H |
| F411 (a and b) | O | —Br | -tert-butyl | —H |
| F412 (a and b) | O | —Br | -iso-propyl | —H |
| F413 (a and b) | O | —Br | —CH$_3$ | —CH$_3$ |
| F414 (a and b) | O | —Br | —H | —H |
| F415 (a and b) | O | —Br | —H | —Cl |
| F416 (a and b) | O | —Br | —H | —Br |
| F417 (a and b) | O | —Br | —H | —F |
| F418 (a and b) | O | —Br | —H | —CH$_3$ |
| F419 (a and b) | O | —Br | —H | —CF$_3$ |
| F420 (a and b) | O | —Br | —H | —OCH$_3$ |
| F421 (a and b) | O | —Br | —H | —OCH$_2$CH$_3$ |
| F422 (a and b) | O | —Br | —H | —OCF$_3$ |
| F423 (a and b) | O | —Br | —H | -tert-butyl |
| F424 (a and b) | O | —Br | —H | -iso-propyl |
| F425 (a and b) | O | —I | —Cl | —H |
| F426 (a and b) | O | —I | —Br | —H |
| F427 (a and b) | O | —I | —F | —H |
| F428 (a and b) | O | —I | —CH$_3$ | —H |
| F429 (a and b) | O | —I | —CF$_3$ | —H |
| F430 (a and b) | O | —I | —OCH$_3$ | —H |
| F431 (a and b) | O | —I | —OCH$_2$CH$_3$ | —H |
| F432 (a and b) | O | —I | —OCF$_3$ | —H |
| F433 (a and b) | O | —I | -tert-butyl | —H |
| F434 (a and b) | O | —I | -iso-propyl | —H |
| F435 (a and b) | O | —I | —CH$_3$ | —CH$_3$ |
| F436 (a and b) | O | —I | —H | —H |
| F437 (a and b) | O | —I | —H | —Cl |
| F438 (a and b) | O | —I | —H | —Br |
| F439 (a and b) | O | —I | —H | —F |
| F440 (a and b) | O | —I | —H | —CH$_3$ |
| F441 (a and b) | O | —I | —H | —CF$_3$ |
| F442 (a and b) | O | —I | —H | —OCH$_3$ |
| F443 (a and b) | O | —I | —H | —OCH$_2$CH$_3$ |
| F444 (a and b) | O | —I | —H | —OCF$_3$ |
| F445 (a and b) | O | —I | —H | -tert-butyl |
| F446 (a and b) | O | —I | —H | -iso-propyl |
| F447 (a and b) | NH | —H | —Cl | —H |
| F448 (a and b) | NH | —H | —Br | —H |
| F449 (a and b) | NH | —H | —F | —H |
| F450 (a and b) | NH | —H | —CH$_3$ | —H |

TABLE 6-continued (If)

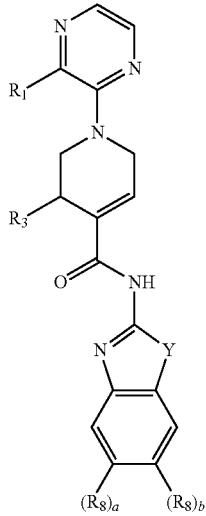

and pharmaceutically acceptable salts thereof, wherein:

| Compound | Y | R$_1$ | (R$_8$)$_a$ | (R$_8$)$_b$ |
|---|---|---|---|---|
| F451 (a and b) | NH | —H | —CF$_3$ | —H |
| F452 (a and b) | NH | —H | —OCH$_3$ | —H |
| F453 (a and b) | NH | —H | —OCH$_2$CH$_3$ | —H |
| F454 (a and b) | NH | —H | —OCF$_3$ | —H |
| F455 (a and b) | NH | —H | -tert-butyl | —H |
| F456 (a and b) | NH | —H | -iso-propyl | —H |
| F457 (a and b) | NH | —H | —CH$_3$ | —CH$_3$ |
| F458 (a and b) | NH | —H | —H | —H |
| F459 (a and b) | NH | —H | —H | —Cl |
| F460 (a and b) | NH | —H | —H | —Br |
| F461 (a and b) | NH | —H | —H | —F |
| F462 (a and b) | NH | —H | —H | —CH$_3$ |
| F463 (a and b) | NH | —H | —H | —CF$_3$ |
| F464 (a and b) | NH | —H | —H | —OCH$_3$ |
| F465 (a and b) | NH | —H | —H | —OCH$_2$CH$_3$ |
| F466 (a and b) | NH | —H | —H | —OCF$_3$ |
| F467 (a and b) | NH | —H | —H | -tert-butyl |
| F468 (a and b) | NH | —H | —H | -iso-propyl |
| F469 (a and b) | NH | —Cl | —Cl | —H |
| F470 (a and b) | NH | —Cl | —Br | —H |
| F471 (a and b) | NH | —Cl | —F | —H |
| F472 (a and b) | NH | —Cl | —CH$_3$ | —H |
| F473 (a and b) | NH | —Cl | —CF$_3$ | —H |
| F474 (a and b) | NH | —Cl | —OCH$_3$ | —H |
| F475 (a and b) | NH | —Cl | —OCH$_2$CH$_3$ | —H |
| F476 (a and b) | NH | —Cl | —OCF$_3$ | —H |
| F477 (a and b) | NH | —Cl | -tert-butyl | —H |
| F478 (a and b) | NH | —Cl | -iso-propyl | —H |
| F479 (a and b) | NH | —Cl | —CH$_3$ | —CH$_3$ |
| F480 (a and b) | NH | —Cl | —H | —H |
| F481 (a and b) | NH | —Cl | —H | —Cl |
| F482 (a and b) | NH | —Cl | —H | —Br |
| F483 (a and b) | NH | —Cl | —H | —F |
| F484 (a and b) | NH | —Cl | —H | —CH$_3$ |
| F485 (a and b) | NH | —Cl | —H | —CF$_3$ |
| F486 (a and b) | NH | —Cl | —H | —OCH$_3$ |
| F487 (a and b) | NH | —Cl | —H | —OCH$_2$CH$_3$ |
| F488 (a and b) | NH | —Cl | —H | —OCF$_3$ |
| F489 (a and b) | NH | —Cl | —H | -tert-butyl |
| F490 (a and b) | NH | —Cl | —H | -iso-propyl |
| F491 (a and b) | NH | —Cl | —H | —OCF$_3$ |
| F492 (a and b) | NH | —Cl | —H | -tert-butyl |
| F493 (a and b) | NH | —Cl | —H | -iso-propyl |
| F494 (a and b) | NH | —CH$_3$ | —Cl | —H |
| F495 (a and b) | NH | —CH$_3$ | —Br | —H |
| F496 (a and b) | NH | —CH$_3$ | —F | —H |
| F497 (a and b) | NH | —CH$_3$ | —CH$_3$ | —H |
| F498 (a and b) | NH | —CH$_3$ | —CF$_3$ | —H |
| F499 (a and b) | NH | —CH$_3$ | —OCH$_3$ | —H |
| F500 (a and b) | NH | —CH$_3$ | —OCH$_2$CH$_3$ | —H |

TABLE 6-continued (If)

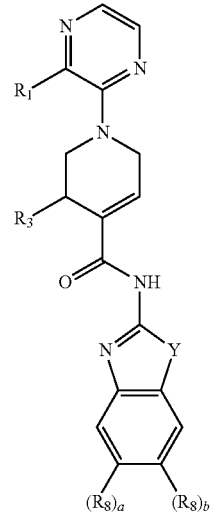

and pharmaceutically acceptable salts thereof, wherein:

| Compound | Y | R$_1$ | (R$_8$)$_a$ | (R$_8$)$_b$ |
|---|---|---|---|---|
| F501 (a and b) | NH | —CH$_3$ | —OCF$_3$ | —H |
| F502 (a and b) | NH | —CH$_3$ | -tert-butyl | —H |
| F503 (a and b) | NH | —CH$_3$ | -iso-propyl | —H |
| F504 (a and b) | NH | —CH$_3$ | —CH$_3$ | —CH$_3$ |
| F505 (a and b) | NH | —CH$_3$ | —H | —H |
| F506 (a and b) | NH | —CH$_3$ | —H | —Cl |
| F507 (a and b) | NH | —CH$_3$ | —H | —Br |
| F508 (a and b) | NH | —CH$_3$ | —H | —F |
| F509 (a and b) | NH | —CH$_3$ | —H | —CH$_3$ |
| F510 (a and b) | NH | —CH$_3$ | —H | —CF$_3$ |
| F511 (a and b) | NH | —CH$_3$ | —H | —OCH$_3$ |
| F512 (a and b) | NH | —CH$_3$ | —H | —OCH$_2$CH$_3$ |
| F513 (a and b) | NH | —CH$_3$ | —H | —OCF$_3$ |
| F514 (a and b) | NH | —CH$_3$ | —H | -tert-butyl |
| F515 (a and b) | NH | —CH$_3$ | —H | -iso-propyl |
| F516 (a and b) | NH | —CF$_3$ | —Cl | —H |
| F517 (a and b) | NH | —CF$_3$ | —Br | —H |
| F518 (a and b) | NH | —CF$_3$ | —F | —H |
| F519 (a and b) | NH | —CF$_3$ | —CH$_3$ | —H |
| F520 (a and b) | NH | —CF$_3$ | —CF$_3$ | —H |
| F521 (a and b) | NH | —CF$_3$ | —OCH$_3$ | —H |
| F522 (a and b) | NH | —CF$_3$ | —OCH$_2$CH$_3$ | —H |
| F523 (a and b) | NH | —CF$_3$ | —OCF$_3$ | —H |
| F524 (a and b) | NH | —CF$_3$ | -tert-butyl | —H |
| F525 (a and b) | NH | —CF$_3$ | -iso-propyl | —H |
| F526 (a and b) | NH | —CF$_3$ | —CH$_3$ | —CH$_3$ |
| F527 (a and b) | NH | —CF$_3$ | —H | —H |
| F528 (a and b) | NH | —CF$_3$ | —H | —Cl |
| F529 (a and b) | NH | —CF$_3$ | —H | —Br |
| F530 (a and b) | NH | —CF$_3$ | —H | —F |
| F531 (a and b) | NH | —CF$_3$ | —H | —CH$_3$ |
| F532 (a and b) | NH | —CF$_3$ | —H | —CF$_3$ |
| F533 (a and b) | NH | —CF$_3$ | —H | —OCH$_3$ |
| F534 (a and b) | NH | —CF$_3$ | —H | —OCH$_2$CH$_3$ |
| F535 (a and b) | NH | —CF$_3$ | —H | —OCF$_3$ |
| F536 (a and b) | NH | —CF$_3$ | —H | -tert-butyl |
| F537 (a and b) | NH | —CF$_3$ | —H | -iso-propyl |
| F538 (a and b) | NH | —CHF$_2$ | —Cl | —H |
| F539 (a and b) | NH | —CHF$_2$ | —Br | —H |
| F540 (a and b) | NH | —CHF$_2$ | —F | —H |
| F541 (a and b) | NH | —CHF$_2$ | —CH$_3$ | —H |
| F542 (a and b) | NH | —CHF$_2$ | —CF$_3$ | —H |
| F543 (a and b) | NH | —CHF$_2$ | —OCH$_3$ | —H |
| F544 (a and b) | NH | —CHF$_2$ | —OCH$_2$CH$_3$ | —H |
| F545 (a and b) | NH | —CHF$_2$ | —OCF$_3$ | —H |
| F546 (a and b) | NH | —CHF$_2$ | -tert-butyl | —H |
| F547 (a and b) | NH | —CHF$_2$ | -iso-propyl | —H |
| F548 (a and b) | NH | —CHF$_2$ | —CH$_3$ | —CH$_3$ |
| F549 (a and b) | NH | —CHF$_2$ | —H | —H |
| F550 (a and b) | NH | —CHF$_2$ | —H | —Cl |

TABLE 6-continued

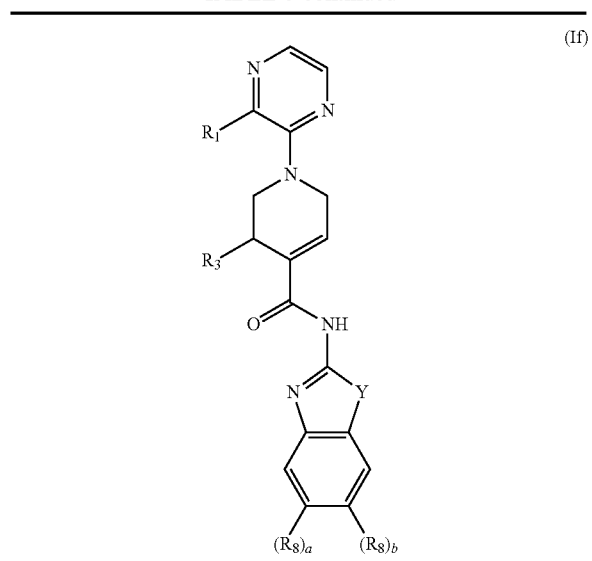

(If)

and pharmaceutically acceptable salts thereof, wherein:

| Compound | Y | $R_1$ | $(R_8)_a$ | $(R_8)_b$ |
|---|---|---|---|---|
| F551 (a and b) | NH | —$CHF_2$ | —H | —Br |
| F552 (a and b) | NH | —$CHF_2$ | —H | —F |
| F553 (a and b) | NH | —$CHF_2$ | —H | —$CH_3$ |
| F554 (a and b) | NH | —$CHF_2$ | —H | —$CF_3$ |
| F555 (a and b) | NH | —$CHF_2$ | —H | —$OCH_3$ |
| F556 (a and b) | NH | —$CHF_2$ | —H | —$OCH_2CH_3$ |
| F557 (a and b) | NH | —$CHF_2$ | —H | —$OCF_3$ |
| F558 (a and b) | NH | —$CHF_2$ | —H | -tert-butyl |
| F559 (a and b) | NH | —$CHF_2$ | —H | -iso-propyl |
| F560 (a and b) | NH | —OH | —Cl | —H |
| F561 (a and b) | NH | —OH | —Br | —H |
| F562 (a and b) | NH | —OH | —F | —H |
| F563 (a and b) | NH | —OH | —$CH_3$ | —H |
| F564 (a and b) | NH | —OH | —$CF_3$ | —H |
| F565 (a and b) | NH | —OH | —$OCH_3$ | —H |
| F566 (a and b) | NH | —OH | —$OCH_2CH_3$ | —H |
| F567 (a and b) | NH | —OH | —$OCF_3$ | —H |
| F568 (a and b) | NH | —OH | -tert-butyl | —H |
| F569 (a and b) | NH | —OH | -iso-propyl | —H |
| F570 (a and b) | NH | —OH | —$CH_3$ | —$CH_3$ |
| F571 (a and b) | NH | —OH | —H | —H |
| F572 (a and b) | NH | —OH | —H | —Cl |
| F573 (a and b) | NH | —OH | —H | —Br |
| F574 (a and b) | NH | —OH | —H | —F |
| F575 (a and b) | NH | —OH | —H | —$CH_3$ |
| F576 (a and b) | NH | —OH | —H | —$CF_3$ |
| F577 (a and b) | NH | —OH | —H | —$OCH_3$ |
| F578 (a and b) | NH | —OH | —H | —$OCH_2CH_3$ |
| F579 (a and b) | NH | —OH | —H | —$OCF_3$ |
| F580 (a and b) | NH | —OH | —H | -tert-butyl |
| F581 (a and b) | NH | —OH | —H | -iso-propyl |
| F582 (a and b) | NH | —$NO_2$ | —Cl | —H |
| F583 (a and b) | NH | —$NO_2$ | —Br | —H |
| F584 (a and b) | NH | —$NO_2$ | —F | —H |
| F585 (a and b) | NH | —$NO_2$ | —$CH_3$ | —H |
| F586 (a and b) | NH | —$NO_2$ | —$CF_3$ | —H |
| F587 (a and b) | NH | —$NO_2$ | —$OCH_3$ | —H |
| F588 (a and b) | NH | —$NO_2$ | —$OCH_2CH_3$ | —H |
| F589 (a and b) | NH | —$NO_2$ | —$OCF_3$ | —H |
| F590 (a and b) | NH | —$NO_2$ | -tert-butyl | —H |
| F591 (a and b) | NH | —$NO_2$ | -iso-propyl | —H |
| F592 (a and b) | NH | —$NO_2$ | —$CH_3$ | —$CH_3$ |
| F593 (a and b) | NH | —$NO_2$ | —H | —H |
| F594 (a and b) | NH | —$NO_2$ | —H | —Cl |
| F595 (a and b) | NH | —$NO_2$ | —H | —Br |
| F596 (a and b) | NH | —$NO_2$ | —H | —F |
| F597 (a and b) | NH | —$NO_2$ | —H | —$CH_3$ |
| F598 (a and b) | NH | —$NO_2$ | —H | —$CF_3$ |
| F599 (a and b) | NH | —$NO_2$ | —H | —$OCH_3$ |
| F600 (a and b) | NH | —$NO_2$ | —H | —$OCH_2CH_3$ |

TABLE 6-continued

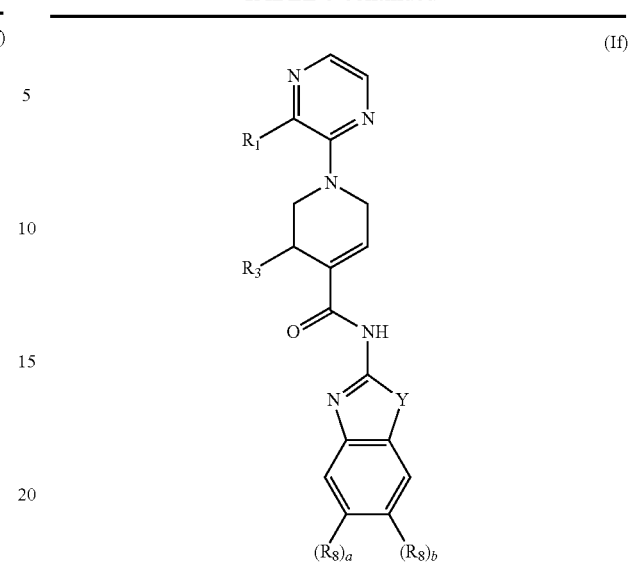

(If)

and pharmaceutically acceptable salts thereof, wherein:

| Compound | Y | $R_1$ | $(R_8)_a$ | $(R_8)_b$ |
|---|---|---|---|---|
| F601 (a and b) | NH | —$NO_2$ | —H | —$OCF_3$ |
| F602 (a and b) | NH | —$NO_2$ | —H | -tert-butyl |
| F603 (a and b) | NH | —$NO_2$ | —H | -iso-propyl |
| F604 (a and b) | NH | —CN | —Br | —H |
| F605 (a and b) | NH | —CN | —Cl | —H |
| F606 (a and b) | NH | —CN | —F | —H |
| F607 (a and b) | NH | —CN | —$CH_3$ | —H |
| F608 (a and b) | NH | —CN | —$CF_3$ | —H |
| F609 (a and b) | NH | —CN | —$OCH_3$ | —H |
| F610 (a and b) | NH | —CN | —$OCH_2CH_3$ | —H |
| F611 (a and b) | NH | —CN | —$OCF_3$ | —H |
| F612 (a and b) | NH | —CN | -tert-butyl | —H |
| F613 (a and b) | NH | —CN | -iso-propyl | —H |
| F614 (a and b) | NH | —CN | —$CH_3$ | —$CH_3$ |
| F615 (a and b) | NH | —CN | —H | —H |
| F616 (a and b) | NH | —CN | —H | —Cl |
| F617 (a and b) | NH | —CN | —H | —Br |
| F618 (a and b) | NH | —CN | —H | —F |
| F619 (a and b) | NH | —CN | —H | —$CH_3$ |
| F620 (a and b) | NH | —CN | —H | —$CF_3$ |
| F621 (a and b) | NH | —CN | —H | —$OCH_3$ |
| F622 (a and b) | NH | —CN | —H | —$OCH_2CH_3$ |
| F623 (a and b) | NH | —CN | —H | —$OCF_3$ |
| F624 (a and b) | NH | —CN | —H | -tert-butyl |
| F625 (a and b) | NH | —CN | —H | -iso-propyl |
| F626 (a and b) | NH | —Br | —Br | —H |
| F627 (a and b) | NH | —Br | —Cl | —H |
| F628 (a and b) | NH | —Br | —F | —H |
| F629 (a and b) | NH | —Br | —$CH_3$ | —H |
| F630 (a and b) | NH | —Br | —$CF_3$ | —H |
| F631 (a and b) | NH | —Br | —$OCH_3$ | —H |
| F632 (a and b) | NH | —Br | —$OCH_2CH_3$ | —H |
| F633 (a and b) | NH | —Br | —$OCF_3$ | —H |
| F634 (a and b) | NH | —Br | -tert-butyl | —H |
| F635 (a and b) | NH | —Br | -iso-propyl | —H |
| F636 (a and b) | NH | —Br | —$CH_3$ | —$CH_3$ |
| F637 (a and b) | NH | —Br | —H | —H |
| F638 (a and b) | NH | —Br | —H | —Cl |
| F639 (a and b) | NH | —Br | —H | —Br |
| F640 (a and b) | NH | —Br | —H | —F |
| F641 (a and b) | NH | —Br | —H | —$CH_3$ |

TABLE 6-continued

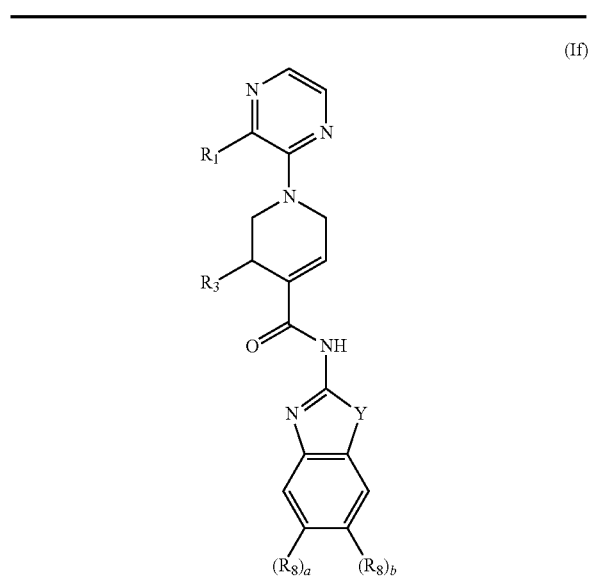

(If)

and pharmaceutically acceptable salts thereof, wherein:

| Compound | Y | $R_1$ | $(R_8)_a$ | $(R_8)_b$ |
|---|---|---|---|---|
| F642 (a and b) | NH | —Br | —H | —CF$_3$ |
| F643 (a and b) | NH | —Br | —H | —OCH$_3$ |
| F644 (a and b) | NH | —Br | —H | —OCH$_2$CH$_3$ |
| F645 (a and b) | NH | —Br | —H | —OCF$_3$ |
| F646 (a and b) | NH | —Br | —H | -tert-butyl |
| F647 (a and b) | NH | —Br | —H | -iso-propyl |
| F648 (a and b) | NH | —I | —Cl | —H |
| F649 (a and b) | NH | —I | —Br | —H |
| F650 (a and b) | NH | —I | —F | —H |
| F651 (a and b) | NH | —I | —CH$_3$ | —H |
| F652 (a and b) | NH | —I | —CF$_3$ | —H |
| F653 (a and b) | NH | —I | —OCH$_3$ | —H |
| F654 (a and b) | NH | —I | —OCH$_2$CH$_3$ | —H |
| F655 (a and b) | NH | —I | —OCF$_3$ | —H |
| F656 (a and b) | NH | —I | -tert-butyl | —H |
| F657 (a and b) | NH | —I | -iso-propyl | —H |
| F658 (a and b) | NH | —I | —CH$_3$ | —CH$_3$ |
| F659 (a and b) | NH | —I | —H | —H |
| F660 (a and b) | NH | —I | —H | —Cl |
| F661 (a and b) | NH | —I | —H | —Br |
| F662 (a and b) | NH | —I | —H | —F |
| F663 (a and b) | NH | —I | —H | —CH$_3$ |
| F664 (a and b) | NH | —I | —H | —CF$_3$ |
| F665 (a and b) | NH | —I | —H | —OCH$_3$ |
| F666 (a and b) | NH | —I | —H | —OCH$_2$CH$_3$ |
| F667 (a and b) | NH | —I | —H | —OCF$_3$ |
| F668 (a and b) | NH | —I | —H | -tert-butyl |
| F669 (a and b) | NH | —I | —H | -iso-propyl |

(a) means that $R_3$ is —H.
(b) means that $R_3$ is —CH$_3$.

TABLE 7

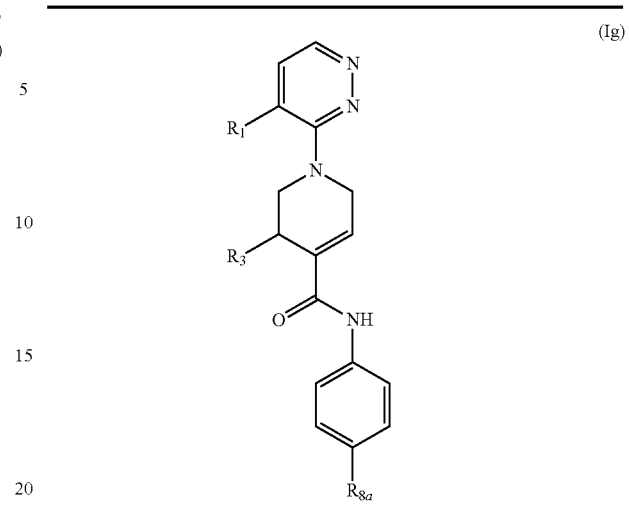

(Ig)

and pharmaceutically acceptable salts thereof, wherein:

| Compound | $R_1$ | $R_{8a}$ |
|---|---|---|
| G01 (a and b) | —H | —H |
| G02 (a and b) | —H | -tert-butyl |
| G03 (a and b) | —H | -iso-butyl |
| G04 (a and b) | —H | -sec-butyl |
| G05 (a and b) | —H | -iso-propyl |
| G06 (a and b) | —H | -n-propyl |
| G07 (a and b) | —H | -cyclohexyl |
| G08 (a and b) | —H | -tert-butoxy |
| G09 (a and b) | —H | -isopropoxy |
| G10 (a and b) | —H | —CF$_3$ |
| G11 (a and b) | —H | —CH$_2$CF$_3$ |
| G12 (a and b) | —H | —OCF$_3$ |
| G13 (a and b) | —H | —Cl |
| G14 (a and b) | —H | —Br |
| G15 (a and b) | —H | —I |
| G16 (a and b) | —H | -n-butyl |
| G17 (a and b) | —H | —CH$_3$ |
| G18 (a and b) | —H | —SCF$_3$ |
| G19 (a and b) | —H | —N(CH$_2$CH$_3$)$_2$ |
| G20 (a and b) | —H | —OCF$_2$CHF$_2$ |
| G21 (a and b) | —H | —C(OH)(CF$_3$)$_2$ |
| G22 (a and b) | —H | -(1,1-dimethyl-pentyl) |
| G23 (a and b) | —H | -(1,1-dimethyl-acetic acid) ethyl ester |
| G24 (a and b) | —H | —N-piperidinyl |
| G25 (a and b) | —Cl | —H |
| G26 (a and b) | —Cl | -tert-butyl |
| G27 (a and b) | —Cl | -iso-butyl |
| G28 (a and b) | —Cl | -sec-butyl |
| G29 (a and b) | —Cl | -iso-propyl |
| G30 (a and b) | —Cl | -n-propyl |
| G31 (a and b) | —Cl | -cyclohexyl |
| G32 (a and b) | —Cl | -tert-butoxy |
| G33 (a and b) | —Cl | -isopropoxy |
| G34 (a and b) | —Cl | —CF$_3$ |
| G35 (a and b) | —Cl | —CH$_2$CF$_3$ |
| G36 (a and b) | —Cl | —OCF$_3$ |
| G37 (a and b) | —Cl | —Cl |
| G38 (a and b) | —Cl | —Br |
| G39 (a and b) | —Cl | —I |
| G40 (a and b) | —Cl | -n-butyl |
| G41 (a and b) | —Cl | —CH$_3$ |
| G42 (a and b) | —Cl | —SCF$_3$ |
| G43 (a and b) | —Cl | —N(CH$_2$CH$_3$)$_2$ |
| G44 (a and b) | —Cl | —OCF$_2$CHF$_2$ |
| G45 (a and b) | —Cl | —C(OH)(CF$_3$)$_2$ |
| G46 (a and b) | —Cl | -(1,1-dimethyl-pentyl) |
| G47 (a and b) | —Cl | -(1,1-dimethyl-acetic acid) ethyl ester |
| G48 (a and b) | —Cl | —N-piperidinyl |
| G49 (a and b) | —F | —H |
| G50 (a and b) | —F | -tert-butyl |
| G51 (a and b) | —F | -iso-butyl |
| G52 (a and b) | —F | -sec-butyl |

TABLE 7-continued

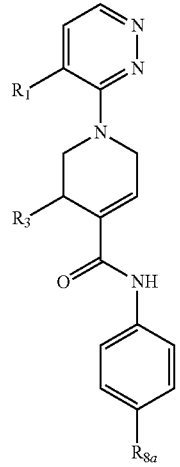

(Ig)

and pharmaceutically acceptable salts thereof, wherein:

| Compound | $R_1$ | $R_{8a}$ |
|---|---|---|
| G53 (a and b) | —F | -iso-propyl |
| G54 (a and b) | —F | -n-propyl |
| G55 (a and b) | —F | -cyclohexyl |
| G56 (a and b) | —F | -tert-butoxy |
| G57 (a and b) | —F | -isopropoxy |
| G58 (a and b) | —F | —$CF_3$ |
| G59 (a and b) | —F | —$CH_2CF_3$ |
| G60 (a and b) | —F | —$OCF_3$ |
| G61 (a and b) | —F | —Cl |
| G62 (a and b) | —F | —Br |
| G63 (a and b) | —F | —I |
| G64 (a and b) | —F | -n-butyl |
| G65 (a and b) | —F | —$CH_3$ |
| G66 (a and b) | —F | —$SCF_3$ |
| G67 (a and b) | —F | —$N(CH_2CH_3)_2$ |
| G68 (a and b) | —F | —$OCF_2CHF_2$ |
| G69 (a and b) | —F | —$C(OH)(CF_3)_2$ |
| G70 (a and b) | —F | -(1,1-dimethyl-pentyl) |
| G71 (a and b) | —F | -(1,1-dimethyl-acetic acid) ethyl ester |
| G72 (a and b) | —F | —N-piperidinyl |
| G73 (a and b) | —$CH_3$ | —H |
| G74 (a and b) | —$CH_3$ | -iso-butyl |
| G75 (a and b) | —$CH_3$ | -tert-butyl |
| G76 (a and b) | —$CH_3$ | -sec-butyl |
| G77 (a and b) | —$CH_3$ | -iso-propyl |
| G78 (a and b) | —$CH_3$ | -n-propyl |
| G79 (a and b) | —$CH_3$ | -cyclohexyl |
| G80 (a and b) | —$CH_3$ | -tert-butoxy |
| G81 (a and b) | —$CH_3$ | -isopropoxy |
| G82 (a and b) | —$CH_3$ | —$CF_3$ |
| G83 (a and b) | —$CH_3$ | —$CH_2CF_3$ |
| G84 (a and b) | —$CH_3$ | —$OCF_3$ |
| G85 (a and b) | —$CH_3$ | —Cl |
| G86 (a and b) | —$CH_3$ | —Br |
| G87 (a and b) | —$CH_3$ | —I |
| G88 (a and b) | —$CH_3$ | -n-butyl |
| G89 (a and b) | —$CH_3$ | —$CH_3$ |
| G90 (a and b) | —$CH_3$ | —$SCF_3$ |
| G91 (a and b) | —$CH_3$ | —$N(CH_2CH_3)_2$ |
| G92 (a and b) | —$CH_3$ | —$OCF_2CHF_2$ |
| G93 (a and b) | —$CH_3$ | —$C(OH)(CF_3)_2$ |
| G94 (a and b) | —$CH_3$ | -(1,1-dimethyl-pentyl) |
| G95 (a and b) | —$CH_3$ | -(1,1-dimethyl-acetic acid) ethyl ester |
| G96 (a and b) | —$CH_3$ | —N-piperidinyl |
| G97 (a and b) | —$CF_3$ | —H |
| G98 (a and b) | —$CF_3$ | -tert-butyl |
| G99 (a and b) | —$CF_3$ | -iso-butyl |
| G100 (a and b) | —$CF_3$ | -sec-butyl |
| G101 (a and b) | —$CF_3$ | -iso-propyl |
| G102 (a and b) | —$CF_3$ | -n-propyl |
| G103 (a and b) | —$CF_3$ | -cyclohexyl |
| G104 (a and b) | —$CF_3$ | -tert-butoxy |

TABLE 7-continued

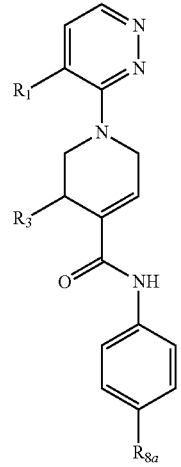

(Ig)

and pharmaceutically acceptable salts thereof, wherein:

| Compound | $R_1$ | $R_{8a}$ |
|---|---|---|
| G105 (a and b) | —$CF_3$ | -isopropoxy |
| G106 (a and b) | —$CF_3$ | —$CF_3$ |
| G107 (a and b) | —$CF_3$ | —$CH_2CF_3$ |
| G108 (a and b) | —$CF_3$ | —$OCF_3$ |
| G109 (a and b) | —$CF_3$ | —Cl |
| G110 (a and b) | —$CF_3$ | —Br |
| G111 (a and b) | —$CF_3$ | —I |
| G112 (a and b) | —$CF_3$ | -n-butyl |
| G113 (a and b) | —$CF_3$ | —$CH_3$ |
| G114 (a and b) | —$CF_3$ | —$SCF_3$ |
| G115 (a and b) | —$CF_3$ | —$N(CH_2CH_3)_2$ |
| G116 (a and b) | —$CF_3$ | —$OCF_2CHF_2$ |
| G117 (a and b) | —$CF_3$ | —$C(OH)(CF_3)_2$ |
| G118 (a and b) | —$CF_3$ | -(1,1-dimethyl-pentyl) |
| G119 (a and b) | —$CF_3$ | -(1,1-dimethyl-acetic acid) ethyl ester |
| G120 (a and b) | —$CF_3$ | —N-piperidinyl |
| G121 (a and b) | —$CHF_2$ | -tert-butyl |
| G122 (a and b) | —$CHF_2$ | —H |
| G123 (a and b) | —$CHF_2$ | -iso-butyl |
| G124 (a and b) | —$CHF_2$ | -sec-butyl |
| G125 (a and b) | —$CHF_2$ | -iso-propyl |
| G126 (a and b) | —$CHF_2$ | -n-propyl |
| G127 (a and b) | —$CHF_2$ | -cyclohexyl |
| G128 (a and b) | —$CHF_2$ | -tert-butoxy |
| G129 (a and b) | —$CHF_2$ | -isopropoxy |
| G130 (a and b) | —$CHF_2$ | —$CF_3$ |
| G131 (a and b) | —$CHF_2$ | —$CH_2CF_3$ |
| G132 (a and b) | —$CHF_2$ | —$OCF_3$ |
| G133 (a and b) | —$CHF_2$ | —Cl |
| G134 (a and b) | —$CHF_2$ | —Br |
| G135 (a and b) | —$CHF_2$ | —I |
| G136 (a and b) | —$CHF_2$ | -n-butyl |
| G137 (a and b) | —$CHF_2$ | —$CH_3$ |
| G138 (a and b) | —$CHF_2$ | —$SCF_3$ |
| G139 (a and b) | —$CHF_2$ | —$N(CH_2CH_3)_2$ |
| G140 (a and b) | —$CHF_2$ | —$OCF_2CHF_2$ |
| G141 (a and b) | —$CHF_2$ | —$C(OH)(CF_3)_2$ |
| G142 (a and b) | —$CHF_2$ | -(1,1-dimethyl-pentyl) |
| G143 (a and b) | —$CHF_2$ | -(1,1-dimethyl-acetic acid) ethyl ester |
| G144 (a and b) | —$CHF_2$ | —N-piperidinyl |
| G145 (a and b) | —OH | —H |
| G146 (a and b) | —OH | -tert-butyl |
| G147 (a and b) | —OH | -iso-butyl |
| G148 (a and b) | —OH | -sec-butyl |
| G149 (a and b) | —OH | -iso-propyl |
| G150 (a and b) | —OH | -n-propyl |
| G151 (a and b) | —OH | -cyclohexyl |
| G152 (a and b) | —OH | -tert-butoxy |
| G153 (a and b) | —OH | -isopropoxy |
| G154 (a and b) | —OH | —$CF_3$ |
| G155 (a and b) | —OH | —$CH_2CF_3$ |
| G156 (a and b) | —OH | —$OCF_3$ |

TABLE 7-continued (Ig)

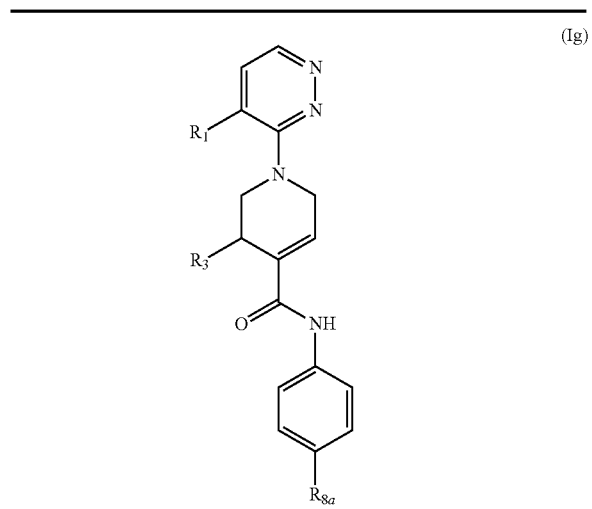

and pharmaceutically acceptable salts thereof, wherein:

| Compound | $R_1$ | $R_{8a}$ |
|---|---|---|
| G157 (a and b) | —OH | —Cl |
| G158 (a and b) | —OH | —Br |
| G159 (a and b) | —OH | —I |
| G160 (a and b) | —OH | -n-butyl |
| G161 (a and b) | —OH | —CH$_3$ |
| G162 (a and b) | —OH | —SCF$_3$ |
| G163 (a and b) | —OH | —N(CH$_2$CH$_3$)$_2$ |
| G164 (a and b) | —OH | —OCF$_2$CHF$_2$ |
| G165 (a and b) | —OH | —C(OH)(CF$_3$)$_2$ |
| G166 (a and b) | —OH | -(1,1-dimethyl-pentyl) |
| G167 (a and b) | —OH | -(1,1-dimethyl-acetic acid) ethyl ester |
| G168 (a and b) | —OH | —N-piperidinyl |
| G169 (a and b) | —NO$_2$ | —H |
| G170 (a and b) | —NO$_2$ | -tert-butyl |
| G171 (a and b) | —NO$_2$ | -iso-butyl |
| G172 (a and b) | —NO$_2$ | -sec-butyl |
| G173 (a and b) | —NO$_2$ | -iso-propyl |
| G174 (a and b) | —NO$_2$ | -n-propyl |
| G175 (a and b) | —NO$_2$ | -cyclohexyl |
| G176 (a and b) | —NO$_2$ | -tert-butoxy |
| G177 (a and b) | —NO$_2$ | -isopropoxy |
| G178 (a and b) | —NO$_2$ | —CF$_3$ |
| G179 (a and b) | —NO$_2$ | —CH$_2$CF$_3$ |
| G180 (a and b) | —NO$_2$ | —OCF$_3$ |
| G181 (a and b) | —NO$_2$ | —Cl |
| G182 (a and b) | —NO$_2$ | —Br |
| G183 (a and b) | —NO$_2$ | —I |
| G184 (a and b) | —NO$_2$ | -n-butyl |
| G185 (a and b) | —NO$_2$ | —CH$_3$ |
| G186 (a and b) | —NO$_2$ | —SCF$_3$ |
| G187 (a and b) | —NO$_2$ | —N(CH$_2$CH$_3$)$_2$ |
| G188 (a and b) | —NO$_2$ | —OCF$_2$CHF$_2$ |
| G189 (a and b) | —NO$_2$ | —C(OH)(CF$_3$)$_2$ |
| G190 (a and b) | —NO$_2$ | -(1,1-dimethyl-pentyl) |
| G191 (a and b) | —NO$_2$ | -(1,1-dimethyl-acetic acid) ethyl ester |
| G192 (a and b) | —NO$_2$ | —N-piperidinyl |
| G193 (a and b) | —CN | —H |
| G194 (a and b) | —CN | -tert-butyl |
| G195 (a and b) | —CN | -iso-butyl |
| G196 (a and b) | —CN | -sec-butyl |
| G197 (a and b) | —CN | -iso-propyl |
| G198 (a and b) | —CN | -n-propyl |
| G199 (a and b) | —CN | -cyclohexyl |
| G200 (a and b) | —CN | -tert-butoxy |
| G201 (a and b) | —CN | -isopropoxy |
| G202 (a and b) | —CN | —CF$_3$ |
| G203 (a and b) | —CN | —CH$_2$CF$_3$ |
| G204 (a and b) | —CN | —OCF$_3$ |
| G205 (a and b) | —CN | —Cl |
| G206 (a and b) | —CN | —Br |
| G207 (a and b) | —CN | —I |
| G208 (a and b) | —CN | -n-butyl |

TABLE 7-continued (Ig)

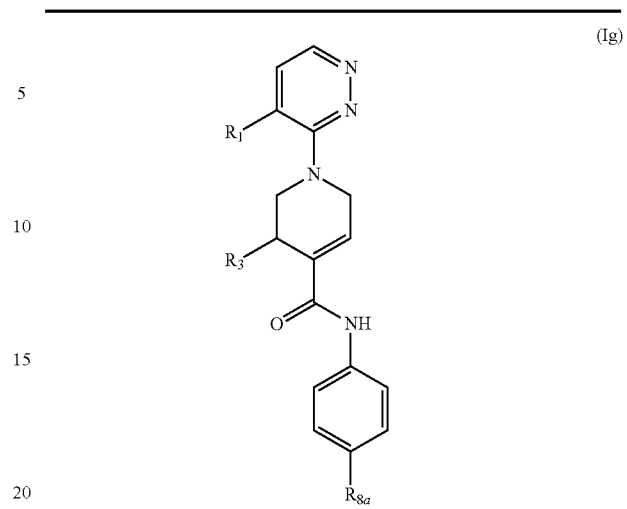

and pharmaceutically acceptable salts thereof, wherein:

| Compound | $R_1$ | $R_{8a}$ |
|---|---|---|
| G209 (a and b) | —CN | —CH$_3$ |
| G210 (a and b) | —CN | —SCF$_3$ |
| G211 (a and b) | —CN | —N(CH$_2$CH$_3$)$_2$ |
| G212 (a and b) | —CN | —OCF$_2$CHF$_2$ |
| G213 (a and b) | —CN | —C(OH)(CF$_3$)$_2$ |
| G214 (a and b) | —CN | -(1,1-dimethyl-pentyl) |
| G215 (a and b) | —CN | -(1,1-dimethyl-acetic acid) ethyl ester |
| G216 (a and b) | —CN | —N-piperidinyl |
| G217 (a and b) | —Br | —H |
| G218 (a and b) | —Br | -tert-butyl |
| G219 (a and b) | —Br | -iso-butyl |
| G220 (a and b) | —Br | -sec-butyl |
| G221 (a and b) | —Br | -iso-propyl |
| G222 (a and b) | —Br | -n-propyl |
| G223 (a and b) | —Br | -cyclohexyl |
| G224 (a and b) | —Br | -tert-butoxy |
| G225 (a and b) | —Br | -isopropoxy |
| G226 (a and b) | —Br | —CF$_3$ |
| G227 (a and b) | —Br | —CH$_2$CF$_3$ |
| G228 (a and b) | —Br | —OCF$_3$ |
| G229 (a and b) | —Br | —Cl |
| G230 (a and b) | —Br | —Br |
| G231 (a and b) | —Br | —I |
| G232 (a and b) | —Br | -n-butyl |
| G233 (a and b) | —Br | —CH$_3$ |
| G234 (a and b) | —Br | —SCF$_3$ |
| G235 (a and b) | —Br | —N(CH$_2$CH$_3$)$_2$ |
| G236 (a and b) | —Br | —OCF$_2$CHF$_2$ |
| G237 (a and b) | —Br | —C(OH)(CF$_3$)$_2$ |
| G238 (a and b) | —Br | -(1,1-dimethyl-pentyl) |
| G239 (a and b) | —Br | -(1,1-dimethyl-acetic acid) ethyl ester |
| G240 (a and b) | —Br | —N-piperidinyl |
| G241 (a and b) | —I | -tert-butyl |
| G242 (a and b) | —I | —H |
| G243 (a and b) | —I | -iso-butyl |
| G244 (a and b) | —I | -sec-butyl |
| G245 (a and b) | —I | -iso-propyl |
| G246 (a and b) | —I | -n-propyl |
| G247 (a and b) | —I | -cyclohexyl |
| G248 (a and b) | —I | -tert-butoxy |
| G249 (a and b) | —I | -isopropoxy |
| G250 (a and b) | —I | —CF$_3$ |
| G251 (a and b) | —I | —CH$_2$CF$_3$ |
| G252 (a and b) | —I | —OCF$_3$ |
| G253 (a and b) | —I | —Cl |
| G254 (a and b) | —I | —Br |
| G255 (a and b) | —I | —I |
| G256 (a and b) | —I | -n-butyl |
| G257 (a and b) | —I | —CH$_3$ |
| G258 (a and b) | —I | —SCF$_3$ |
| G259 (a and b) | —I | —N(CH$_2$CH$_3$)$_2$ |
| G260 (a and b) | —I | —OCF$_2$CHF$_2$ |

TABLE 7-continued

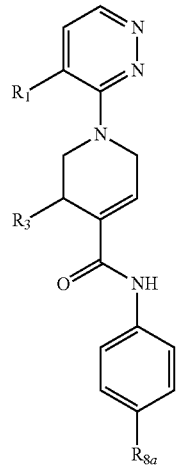

(Ig)

and pharmaceutically acceptable salts thereof, wherein:

| Compound | R₁ | R₈ₐ |
|---|---|---|
| G261 (a and b) | —I | —C(OH)(CF₃)₂ |
| G262 (a and b) | —I | -(1,1-dimethyl-pentyl) |
| G263 (a and b) | —I | -(1,1-dimethyl-acetic acid) ethyl ester |
| G264 (a and b) | —I | —N-piperidinyl |

(a) means that R₃ is —H.
(b) means that R₃ is —CH₃.

TABLE 8

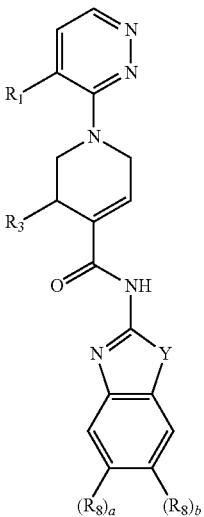

(Ih)

and pharmaceutically acceptable salts thereof, wherein:

| Compound | Y | R₁ | (R₈)ₐ | (R₈)ᵦ |
|---|---|---|---|---|
| H01 (a and b) | S | —H | —Cl | —H |
| H02 (a and b) | S | —H | —Br | —H |
| H03 (a and b) | S | —H | —F | —H |
| H04 (a and b) | S | —H | —CH₃ | —H |
| H05 (a and b) | S | —H | —CF₃ | —H |
| H06 (a and b) | S | —H | —OCH₃ | —H |
| H07 (a and b) | S | —H | —OCH₂CH₃ | —H |
| H08 (a and b) | S | —H | —OCF₃ | —H |
| H09 (a and b) | S | —H | -tert-butyl | —H |
| H10 (a and b) | S | —H | -iso-propyl | —H |

TABLE 8-continued

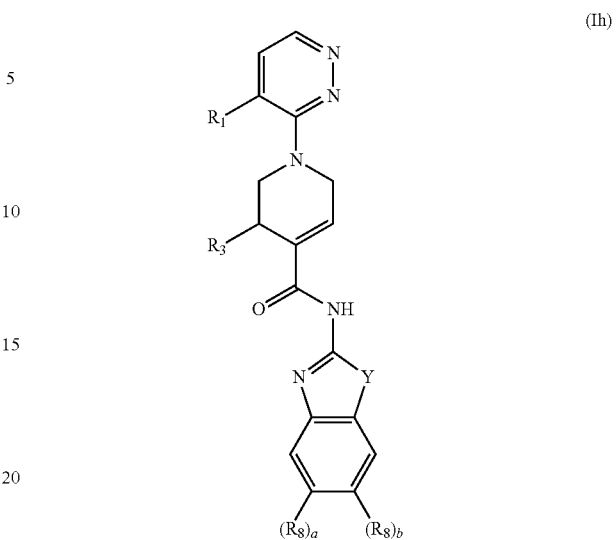

(Ih)

and pharmaceutically acceptable salts thereof, wherein:

| Compound | Y | R₁ | (R₈)ₐ | (R₈)ᵦ |
|---|---|---|---|---|
| H11 (a and b) | S | —H | —CH₃ | —CH₃ |
| H12 (a and b) | S | —H | —H | —H |
| H13 (a and b) | S | —H | —H | —Cl |
| H14 (a and b) | S | —H | —H | —Br |
| H15 (a and b) | S | —H | —H | —F |
| H16 (a and b) | S | —H | —H | —CH₃ |
| H17 (a and b) | S | —H | —H | —CF₃ |
| H18 (a and b) | S | —H | —H | —OCH₃ |
| H19 (a and b) | S | —H | —H | —OCH₂CH₃ |
| H20 (a and b) | S | —H | —H | —OCF₃ |
| H21 (a and b) | S | —H | —H | -tert-butyl |
| H22 (a and b) | S | —H | —H | -iso-propyl |
| H23 (a and b) | S | —Cl | —Cl | —H |
| H24 (a and b) | S | —Cl | —Br | —H |
| H25 (a and b) | S | —Cl | —F | —H |
| H26 (a and b) | S | —Cl | —CH₃ | —H |
| H27 (a and b) | S | —Cl | —CF₃ | —H |
| H28 (a and b) | S | —Cl | —OCH₃ | —H |
| H29 (a and b) | S | —Cl | —OCH₂CH₃ | —H |
| H30 (a and b) | S | —Cl | —OCF₃ | —H |
| H31 (a and b) | S | —Cl | -tert-butyl | —H |
| H32 (a and b) | S | —Cl | -iso-propyl | —H |
| H33 (a and b) | S | —Cl | —CH₃ | —CH₃ |
| H34 (a and b) | S | —Cl | —H | —H |
| H35 (a and b) | S | —Cl | —H | —Cl |
| H36 (a and b) | S | —Cl | —H | —Br |
| H37 (a and b) | S | —Cl | —H | —F |
| H38 (a and b) | S | —Cl | —H | —CH₃ |
| H39 (a and b) | S | —Cl | —H | —CF₃ |
| H40 (a and b) | S | —Cl | —H | —OCH₃ |
| H41 (a and b) | S | —Cl | —H | —OCH₂CH₃ |
| H42 (a and b) | S | —Cl | —H | —OCF₃ |
| H43 (a and b) | S | —Cl | —H | -tert-butyl |
| H44 (a and b) | S | —Cl | —H | -iso-propyl |
| H45 (a and b) | S | —Cl | —H | —OCF₃ |
| H46 (a and b) | S | —Cl | —H | -tert-butyl |
| H47 (a and b) | S | —Cl | —H | -iso-propyl |
| H48 (a and b) | S | —CH₃ | —Cl | —H |
| H49 (a and b) | S | —CH₃ | —Br | —H |
| H50 (a and b) | S | —CH₃ | —F | —H |
| H51 (a and b) | S | —CH₃ | —CH₃ | —H |
| H52 (a and b) | S | —CH₃ | —CF₃ | —H |
| H53 (a and b) | S | —CH₃ | —OCH₃ | —H |
| H54 (a and b) | S | —CH₃ | —OCH₂CH₃ | —H |
| H55 (a and b) | S | —CH₃ | —OCF₃ | —H |
| H56 (a and b) | S | —CH₃ | -tert-butyl | —H |
| H57 (a and b) | S | —CH₃ | -iso-propyl | —H |
| H58 (a and b) | S | —CH₃ | —CH₃ | —CH₃ |
| H59 (a and b) | S | —CH₃ | —H | —H |

TABLE 8-continued (Ih)

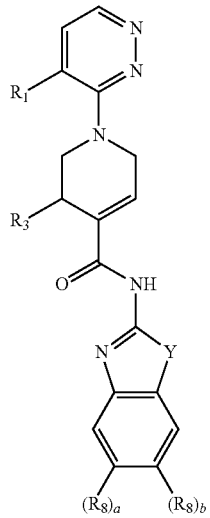

and pharmaceutically acceptable salts thereof, wherein:

| Compound | Y | R₁ | (R₈)ₐ | (R₈)ᵦ |
|---|---|---|---|---|
| H60 (a and b) | S | —CH₃ | —H | —Cl |
| H61 (a and b) | S | —CH₃ | —H | —Br |
| H62 (a and b) | S | —CH₃ | —H | —F |
| H63 (a and b) | S | —CH₃ | —H | —CH₃ |
| H64 (a and b) | S | —CH₃ | —H | —CF₃ |
| H65 (a and b) | S | —CH₃ | —H | —OCH₃ |
| H66 (a and b) | S | —CH₃ | —H | —OCH₂CH₃ |
| H67 (a and b) | S | —CH₃ | —H | —OCF₃ |
| H68 (a and b) | S | —CH₃ | —H | -tert-butyl |
| H69 (a and b) | S | —CH₃ | —H | -iso-propyl |
| H70 (a and b) | S | —CF₃ | —Cl | —H |
| H71 (a and b) | S | —CF₃ | —Br | —H |
| H72 (a and b) | S | —CF₃ | —F | —H |
| H73 (a and b) | S | —CF₃ | —CH₃ | —H |
| H74 (a and b) | S | —CF₃ | —CF₃ | —H |
| H75 (a and b) | S | —CF₃ | —OCH₃ | —H |
| H76 (a and b) | S | —CF₃ | —OCH₂CH₃ | —H |
| H77 (a and b) | S | —CF₃ | —OCF₃ | —H |
| H78 (a and b) | S | —CF₃ | -tert-butyl | —H |
| H79 (a and b) | S | —CF₃ | -iso-propyl | —H |
| H80 (a and b) | S | —CF₃ | —CH₃ | —CH₃ |
| H81 (a and b) | S | —CF₃ | —H | —H |
| H82 (a and b) | S | —CF₃ | —H | —Cl |
| H83 (a and b) | S | —CF₃ | —H | —Br |
| H84 (a and b) | S | —CF₃ | —H | —F |
| H85 (a and b) | S | —CF₃ | —H | —CH₃ |
| H86 (a and b) | S | —CF₃ | —H | —CF₃ |
| H87 (a and b) | S | —CF₃ | —H | —OCH₃ |
| H88 (a and b) | S | —CF₃ | —H | —OCH₂CH₃ |
| H89 (a and b) | S | —CF₃ | —H | —OCF₃ |
| H90 (a and b) | S | —CF₃ | —H | -tert-butyl |
| H91 (a and b) | S | —CF₃ | —H | -iso-propyl |
| H92 (a and b) | S | —CHF₂ | —Cl | —H |
| H93 (a and b) | S | —CHF₂ | —Br | —H |
| H94 (a and b) | S | —CHF₂ | —F | —H |
| H95 (a and b) | S | —CHF₂ | —CH₃ | —H |
| H96 (a and b) | S | —CHF₂ | —CF₃ | —H |
| H97 (a and b) | S | —CHF₂ | —OCH₃ | —H |
| H98 (a and b) | S | —CHF₂ | —OCH₂CH₃ | —H |
| H99 (a and b) | S | —CHF₂ | —OCF₃ | —H |
| H100 (a and b) | S | —CHF₂ | -tert-butyl | —H |
| H101 (a and b) | S | —CHF₂ | -iso-propyl | —H |
| H102 (a and b) | S | —CHF₂ | —CH₃ | —CH₃ |
| H103 (a and b) | S | —CHF₂ | —H | —H |
| H104 (a and b) | S | —CHF₂ | —H | —Cl |
| H105 (a and b) | S | —CHF₂ | —H | —Br |
| H106 (a and b) | S | —CHF₂ | —H | —F |
| H107 (a and b) | S | —CHF₂ | —H | —CH₃ |
| H108 (a and b) | S | —CHF₂ | —H | —CF₃ |
| H109 (a and b) | S | —CHF₂ | —H | —OCH₃ |
| H110 (a and b) | S | —CHF₂ | —H | —OCH₂CH₃ |
| H111 (a and b) | S | —CHF₂ | —H | —OCF₃ |
| H112 (a and b) | S | —CHF₂ | —H | -tert-butyl |
| H113 (a and b) | S | —CHF₂ | —H | -iso-propyl |
| H114 (a and b) | S | —OH | —Cl | —H |
| H115 (a and b) | S | —OH | —Br | —H |
| H116 (a and b) | S | —OH | —F | —H |
| H117 (a and b) | S | —OH | —CH₃ | —H |
| H118 (a and b) | S | —OH | —CF₃ | —H |
| H119 (a and b) | S | —OH | —OCH₃ | —H |
| H120 (a and b) | S | —OH | —OCH₂CH₃ | —H |
| H121 (a and b) | S | —OH | —OCF₃ | —H |
| H122 (a and b) | S | —OH | -tert-butyl | —H |
| H123 (a and b) | S | —OH | -iso-propyl | —H |
| H124 (a and b) | S | —OH | —CH₃ | —CH₃ |
| H125 (a and b) | S | —OH | —H | —H |
| H126 (a and b) | S | —OH | —H | —Cl |
| H127 (a and b) | S | —OH | —H | —Br |
| H128 (a and b) | S | —OH | —H | —F |
| H129 (a and b) | S | —OH | —H | —CH₃ |
| H130 (a and b) | S | —OH | —H | —CF₃ |
| H131 (a and b) | S | —OH | —H | —OCH₃ |
| H132 (a and b) | S | —OH | —H | —OCH₂CH₃ |
| H133 (a and b) | S | —OH | —H | —OCF₃ |
| H134 (a and b) | S | —OH | —H | -tert-butyl |
| H135 (a and b) | S | —OH | —H | -iso-propyl |
| H136 (a and b) | S | —NO₂ | —Cl | —H |
| H137 (a and b) | S | —NO₂ | —Br | —H |
| H138 (a and b) | S | —NO₂ | —F | —H |
| H139 (a and b) | S | —NO₂ | —CH₃ | —H |
| H140 (a and b) | S | —NO₂ | —CF₃ | —H |
| H141 (a and b) | S | —NO₂ | —OCH₃ | —H |
| H142 (a and b) | S | —NO₂ | —OCH₂CH₃ | —H |
| H143 (a and b) | S | —NO₂ | —OCF₃ | —H |
| H144 (a and b) | S | —NO₂ | -tert-butyl | —H |
| H145 (a and b) | S | —NO₂ | -iso-propyl | —H |
| H146 (a and b) | S | —NO₂ | —CH₃ | —CH₃ |
| H147 (a and b) | S | —NO₂ | —H | —H |
| H148 (a and b) | S | —NO₂ | —H | —Cl |
| H149 (a and b) | S | —NO₂ | —H | —Br |
| H150 (a and b) | S | —NO₂ | —H | —F |
| H151 (a and b) | S | —NO₂ | —H | —CH₃ |
| H152 (a and b) | S | —NO₂ | —H | —CF₃ |
| H153 (a and b) | S | —NO₂ | —H | —OCH₃ |
| H154 (a and b) | S | —NO₂ | —H | —OCH₂CH₃ |
| H155 (a and b) | S | —NO₂ | —H | —OCF₃ |
| H156 (a and b) | S | —NO₂ | —H | -tert-butyl |
| H157 (a and b) | S | —NO₂ | —H | -iso-propyl |

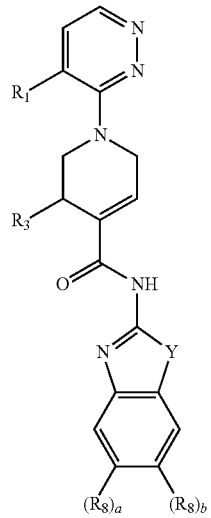

TABLE 8-continued (Ih)

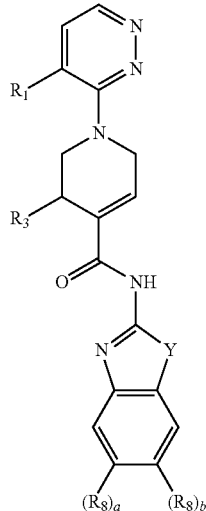

and pharmaceutically acceptable salts thereof, wherein:

| Compound | Y | $R_1$ | $(R_8)_a$ | $(R_8)_b$ |
|---|---|---|---|---|
| H158 (a and b) | S | —CN | —Br | —H |
| H159 (a and b) | S | —CN | —Cl | —H |
| H160 (a and b) | S | —CN | —F | —H |
| H161 (a and b) | S | —CN | —CH$_3$ | —H |
| H162 (a and b) | S | —CN | —CF$_3$ | —H |
| H163 (a and b) | S | —CN | —OCH$_3$ | —H |
| H164 (a and b) | S | —CN | —OCH$_2$CH$_3$ | —H |
| H165 (a and b) | S | —CN | —OCF$_3$ | —H |
| H166 (a and b) | S | —CN | -tert-butyl | —H |
| H167 (a and b) | S | —CN | -iso-propyl | —H |
| H168 (a and b) | S | —CN | —CH$_3$ | —CH$_3$ |
| H169 (a and b) | S | —CN | —H | —H |
| H170 (a and b) | S | —CN | —H | —Cl |
| H171 (a and b) | S | —CN | —H | —Br |
| H172 (a and b) | S | —CN | —H | —F |
| H173 (a and b) | S | —CN | —H | —CH$_3$ |
| H174 (a and b) | S | —CN | —H | —CF$_3$ |
| H175 (a and b) | S | —CN | —H | —OCH$_3$ |
| H176 (a and b) | S | —CN | —H | —OCH$_2$CH$_3$ |
| H177 (a and b) | S | —CN | —H | —OCF$_3$ |
| H178 (a and b) | S | —CN | —H | -tert-butyl |
| H179 (a and b) | S | —CN | —H | -iso-propyl |
| H180 (a and b) | S | —Br | —Br | —H |
| H181 (a and b) | S | —Br | —Cl | —H |
| H182 (a and b) | S | —Br | —F | —H |
| H183 (a and b) | S | —Br | —CH$_3$ | —H |
| H184 (a and b) | S | —Br | —CF$_3$ | —H |
| H185 (a and b) | S | —Br | —OCH$_3$ | —H |
| H186 (a and b) | S | —Br | —OCH$_2$CH$_3$ | —H |
| H187 (a and b) | S | —Br | —OCF$_3$ | —H |
| H188 (a and b) | S | —Br | -tert-butyl | —H |
| H189 (a and b) | S | —Br | -iso-propyl | —H |
| H190 (a and b) | S | —Br | —CH$_3$ | —CH$_3$ |
| H191 (a and b) | S | —Br | —H | —H |
| H192 (a and b) | S | —Br | —H | —Cl |
| H193 (a and b) | S | —Br | —H | —Br |
| H194 (a and b) | S | —Br | —H | —F |
| H195 (a and b) | S | —Br | —H | —CH$_3$ |
| H196 (a and b) | S | —Br | —H | —CF$_3$ |
| H197 (a and b) | S | —Br | —H | —OCH$_3$ |
| H198 (a and b) | S | —Br | —H | —OCH$_2$CH$_3$ |
| H199 (a and b) | S | —Br | —H | —OCF$_3$ |
| H200 (a and b) | S | —Br | —H | -tert-butyl |
| H201 (a and b) | S | —Br | —H | -iso-propyl |
| H202 (a and b) | S | —I | —Cl | —H |
| H203 (a and b) | S | —I | —Br | —H |
| H204 (a and b) | S | —I | —F | —H |
| H205 (a and b) | S | —I | —CH$_3$ | —H |
| H206 (a and b) | S | —I | —CF$_3$ | —H |

TABLE 8-continued (Ih)

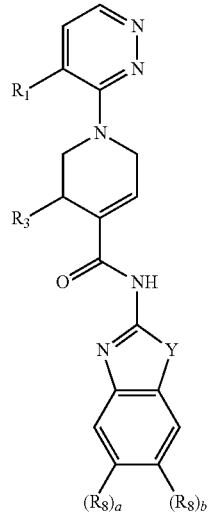

and pharmaceutically acceptable salts thereof, wherein:

| Compound | Y | $R_1$ | $(R_8)_a$ | $(R_8)_b$ |
|---|---|---|---|---|
| H207 (a and b) | S | —I | —OCH$_3$ | —H |
| H208 (a and b) | S | —I | —OCH$_2$CH$_3$ | —H |
| H209 (a and b) | S | —I | —OCF$_3$ | —H |
| H210 (a and b) | S | —I | -tert-butyl | —H |
| H211 (a and b) | S | —I | -iso-propyl | —H |
| H212 (a and b) | S | —I | —CH$_3$ | —CH$_3$ |
| H213 (a and b) | S | —I | —H | —H |
| H214 (a and b) | S | —I | —H | —Cl |
| H215 (a and b) | S | —I | —H | —Br |
| H216 (a and b) | S | —I | —H | —F |
| H217 (a and b) | S | —I | —H | —CH$_3$ |
| H218 (a and b) | S | —I | —H | —CF$_3$ |
| H219 (a and b) | S | —I | —H | —OCH$_3$ |
| H220 (a and b) | S | —I | —H | —OCH$_2$CH$_3$ |
| H221 (a and b) | S | —I | —H | —OCF$_3$ |
| H222 (a and b) | S | —I | —H | -tert-butyl |
| H223 (a and b) | S | —I | —H | -iso-propyl |
| H224 (a and b) | O | —H | —Cl | —H |
| H225 (a and b) | O | —H | —Br | —H |
| H226 (a and b) | O | —H | —F | —H |
| H227 (a and b) | O | —H | —CH$_3$ | —H |
| H228 (a and b) | O | —H | —CF$_3$ | —H |
| H229 (a and b) | O | —H | —OCH$_3$ | —H |
| H230 (a and b) | O | —H | —OCH$_2$CH$_3$ | —H |
| H231 (a and b) | O | —H | —OCF$_3$ | —H |
| H232 (a and b) | O | —H | -tert-butyl | —H |
| H233 (a and b) | O | —H | -iso-propyl | —H |
| H234 (a and b) | O | —H | —CH$_3$ | —CH$_3$ |
| H235 (a and b) | O | —H | —H | —H |
| H236 (a and b) | O | —H | —H | —Cl |
| H237 (a and b) | O | —H | —H | —Br |
| H238 (a and b) | O | —H | —H | —F |
| H239 (a and b) | O | —H | —H | —CH$_3$ |
| H240 (a and b) | O | —H | —H | —CF$_3$ |
| H241 (a and b) | O | —H | —H | —OCH$_3$ |
| H242 (a and b) | O | —H | —H | —OCH$_2$CH$_3$ |
| H243 (a and b) | O | —H | —H | —OCF$_3$ |
| H244 (a and b) | O | —H | —H | -tert-butyl |
| H245 (a and b) | O | —H | —H | -iso-propyl |
| H246 (a and b) | O | —Cl | —Cl | —H |
| H247 (a and b) | O | —Cl | —Br | —H |
| H248 (a and b) | O | —Cl | —F | —H |
| H249 (a and b) | O | —Cl | —CH$_3$ | —H |
| H250 (a and b) | O | —Cl | —CF$_3$ | —H |
| H251 (a and b) | O | —Cl | —OCH$_3$ | —H |
| H252 (a and b) | O | —Cl | —OCH$_2$CH$_3$ | —H |
| H253 (a and b) | O | —Cl | —OCF$_3$ | —H |
| H254 (a and b) | O | —Cl | -tert-butyl | —H |
| H255 (a and b) | O | —Cl | -iso-propyl | —H |

TABLE 8-continued (Ih)

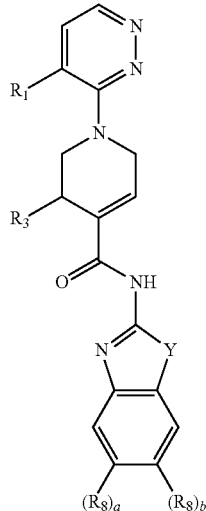

and pharmaceutically acceptable salts thereof, wherein:

| Compound | Y | $R_1$ | $(R_8)_a$ | $(R_8)_b$ |
|---|---|---|---|---|
| H256 (a and b) | O | —Cl | —$CH_3$ | —$CH_3$ |
| H257 (a and b) | O | —Cl | —H | —H |
| H258 (a and b) | O | —Cl | —H | —Cl |
| H259 (a and b) | O | —Cl | —H | —Br |
| H260 (a and b) | O | —Cl | —H | —F |
| H261 (a and b) | O | —Cl | —H | —$CH_3$ |
| H262 (a and b) | O | —Cl | —H | —$CF_3$ |
| H263 (a and b) | O | —Cl | —H | —$OCH_3$ |
| H264 (a and b) | O | —Cl | —H | —$OCH_2CH_3$ |
| H265 (a and b) | O | —Cl | —H | —$OCF_3$ |
| H266 (a and b) | O | —Cl | —H | -tert-butyl |
| H267 (a and b) | O | —Cl | —H | -iso-propyl |
| H268 (a and b) | O | —Cl | —H | —$OCF_3$ |
| H269 (a and b) | O | —Cl | —H | -tert-butyl |
| H270 (a and b) | O | —Cl | —H | -iso-propyl |
| H271 (a and b) | O | —$CH_3$ | —Cl | —H |
| H272 (a and b) | O | —$CH_3$ | —Br | —H |
| H273 (a and b) | O | —$CH_3$ | —F | —H |
| H274 (a and b) | O | —$CH_3$ | —$CH_3$ | —H |
| H275 (a and b) | O | —$CH_3$ | —$CF_3$ | —H |
| H276 (a and b) | O | —$CH_3$ | —$OCH_3$ | —H |
| H277 (a and b) | O | —$CH_3$ | —$OCH_2CH_3$ | —H |
| H278 (a and b) | O | —$CH_3$ | —$OCF_3$ | —H |
| H279 (a and b) | O | —$CH_3$ | -tert-butyl | —H |
| H280 (a and b) | O | —$CH_3$ | -iso-propyl | —H |
| H281 (a and b) | O | —$CH_3$ | —$CH_3$ | —$CH_3$ |
| H282 (a and b) | O | —$CH_3$ | —H | —H |
| H283 (a and b) | O | —$CH_3$ | —H | —Cl |
| H284 (a and b) | O | —$CH_3$ | —H | —Br |
| H285 (a and b) | O | —$CH_3$ | —H | —F |
| H286 (a and b) | O | —$CH_3$ | —H | —$CH_3$ |
| H287 (a and b) | O | —$CH_3$ | —H | —$CF_3$ |
| H288 (a and b) | O | —$CH_3$ | —H | —$OCH_3$ |
| H289 (a and b) | O | —$CH_3$ | —H | —$OCH_2CH_3$ |
| H290 (a and b) | O | —$CH_3$ | —H | —$OCF_3$ |
| H291 (a and b) | O | —$CH_3$ | —H | -tert-butyl |
| H292 (a and b) | O | —$CH_3$ | —H | -iso-propyl |
| H293 (a and b) | O | —$CF_3$ | —Cl | —H |
| H294 (a and b) | O | —$CF_3$ | —Br | —H |
| H295 (a and b) | O | —$CF_3$ | —F | —H |
| H296 (a and b) | O | —$CF_3$ | —$CH_3$ | —H |
| H297 (a and b) | O | —$CF_3$ | —$CF_3$ | —H |
| H298 (a and b) | O | —$CF_3$ | —$OCH_3$ | —H |
| H299 (a and b) | O | —$CF_3$ | —$OCH_2CH_3$ | —H |
| H300 (a and b) | O | —$CF_3$ | —$OCF_3$ | —H |
| H301 (a and b) | O | —$CF_3$ | -tert-butyl | —H |
| H302 (a and b) | O | —$CF_3$ | -iso-propyl | —H |
| H303 (a and b) | O | —$CF_3$ | —$CH_3$ | —$CH_3$ |
| H304 (a and b) | O | —$CF_3$ | —H | —H |

TABLE 8-continued (Ih)

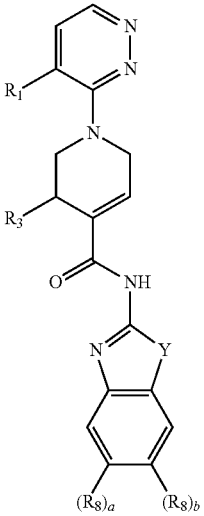

and pharmaceutically acceptable salts thereof, wherein:

| Compound | Y | $R_1$ | $(R_8)_a$ | $(R_8)_b$ |
|---|---|---|---|---|
| H305 (a and b) | O | —$CF_3$ | —H | —Cl |
| H306 (a and b) | O | —$CF_3$ | —H | —Br |
| H307 (a and b) | O | —$CF_3$ | —H | —F |
| H308 (a and b) | O | —$CF_3$ | —H | —$CH_3$ |
| H309 (a and b) | O | —$CF_3$ | —H | —$CF_3$ |
| H310 (a and b) | O | —$CF_3$ | —H | —$OCH_3$ |
| H311 (a and b) | O | —$CF_3$ | —H | —$OCH_2CH_3$ |
| H312 (a and b) | O | —$CF_3$ | —H | —$OCF_3$ |
| H313 (a and b) | O | —$CF_3$ | —H | -tert-butyl |
| H314 (a and b) | O | —$CF_3$ | —H | -iso-propyl |
| H315 (a and b) | O | —$CHF_2$ | —Cl | —H |
| H316 (a and b) | O | —$CHF_2$ | —Br | —H |
| H317 (a and b) | O | —$CHF_2$ | —F | —H |
| H318 (a and b) | O | —$CHF_2$ | —$CH_3$ | —H |
| H319 (a and b) | O | —$CHF_2$ | —$CF_3$ | —H |
| H320 (a and b) | O | —$CHF_2$ | —$OCH_3$ | —H |
| H321 (a and b) | O | —$CHF_2$ | —$OCH_2CH_3$ | —H |
| H322 (a and b) | O | —$CHF_2$ | —$OCF_3$ | —H |
| H323 (a and b) | O | —$CHF_2$ | -tert-butyl | —H |
| H324 (a and b) | O | —$CHF_2$ | -iso-propyl | —H |
| H325 (a and b) | O | —$CHF_2$ | —$CH_3$ | —$CH_3$ |
| H326 (a and b) | O | —$CHF_2$ | —H | —H |
| H327 (a and b) | O | —$CHF_2$ | —H | —Cl |
| H328 (a and b) | O | —$CHF_2$ | —H | —Br |
| H329 (a and b) | O | —$CHF_2$ | —H | —F |
| H330 (a and b) | O | —$CHF_2$ | —H | —$CH_3$ |
| H331 (a and b) | O | —$CHF_2$ | —H | —$CF_3$ |
| H332 (a and b) | O | —$CHF_2$ | —H | —$OCH_3$ |
| H333 (a and b) | O | —$CHF_2$ | —H | —$OCH_2CH_3$ |
| H334 (a and b) | O | —$CHF_2$ | —H | —$OCF_3$ |
| H335 (a and b) | O | —$CHF_2$ | —H | -tert-butyl |
| H336 (a and b) | O | —$CHF_2$ | —H | -iso-propyl |
| H337 (a and b) | O | —OH | —Cl | —H |
| H338 (a and b) | O | —OH | —Br | —H |
| H339 (a and b) | O | —OH | —F | —H |
| H340 (a and b) | O | —OH | —$CH_3$ | —H |
| H341 (a and b) | O | —OH | —$CF_3$ | —H |
| H342 (a and b) | O | —OH | —$OCH_3$ | —H |
| H343 (a and b) | O | —OH | —$OCH_2CH_3$ | —H |
| H344 (a and b) | O | —OH | —$OCF_3$ | —H |
| H345 (a and b) | O | —OH | -tert-butyl | —H |
| H346 (a and b) | O | —OH | -iso-propyl | —H |
| H347 (a and b) | O | —OH | —$CH_3$ | —$CH_3$ |
| H348 (a and b) | O | —OH | —H | —H |
| H349 (a and b) | O | —OH | —H | —Cl |
| H350 (a and b) | O | —OH | —H | —Br |
| H351 (a and b) | O | —OH | —H | —F |
| H352 (a and b) | O | —OH | —H | —$CH_3$ |
| H353 (a and b) | O | —OH | —H | —$CF_3$ |

TABLE 8-continued (Ih)

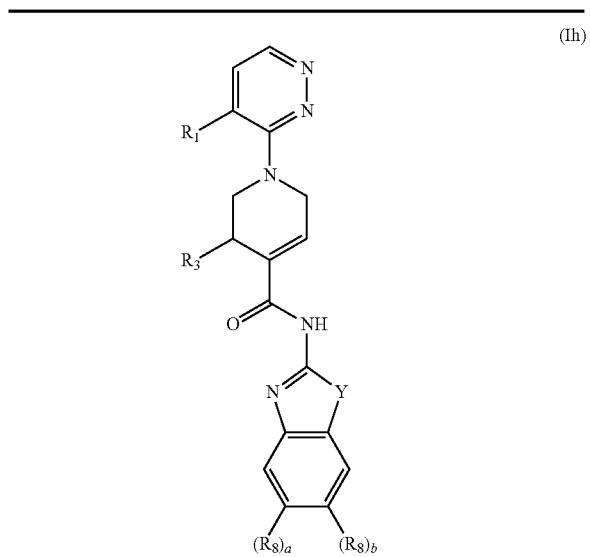

and pharmaceutically acceptable salts thereof, wherein:

| Compound | Y | R₁ | (R₈)ₐ | (R₈)ᵦ |
|---|---|---|---|---|
| H354 (a and b) | O | —OH | —H | —OCH₃ |
| H355 (a and b) | O | —OH | —H | —OCH₂CH₃ |
| H356 (a and b) | O | —OH | —H | —OCF₃ |
| H357 (a and b) | O | —OH | —H | -tert-butyl |
| H358 (a and b) | O | —OH | —H | -iso-propyl |
| H359 (a and b) | O | —NO₂ | —Cl | —H |
| H360 (a and b) | O | —NO₂ | —Br | —H |
| H361 (a and b) | O | —NO₂ | —F | —H |
| H362 (a and b) | O | —NO₂ | —CH₃ | —H |
| H363 (a and b) | O | —NO₂ | —CF₃ | —H |
| H364 (a and b) | O | —NO₂ | —OCH₃ | —H |
| H365 (a and b) | O | —NO₂ | —OCH₂CH₃ | —H |
| H366 (a and b) | O | —NO₂ | —OCF₃ | —H |
| H367 (a and b) | O | —NO₂ | -tert-butyl | —H |
| H368 (a and b) | O | —NO₂ | -iso-propyl | —H |
| H369 (a and b) | O | —NO₂ | —CH₃ | —CH₃ |
| H370 (a and b) | O | —NO₂ | —H | —H |
| H371 (a and b) | O | —NO₂ | —H | —Cl |
| H372 (a and b) | O | —NO₂ | —H | —Br |
| H373 (a and b) | O | —NO₂ | —H | —F |
| H374 (a and b) | O | —NO₂ | —H | —CH₃ |
| H375 (a and b) | O | —NO₂ | —H | —CF₃ |
| H376 (a and b) | O | —NO₂ | —H | —OCH₃ |
| H377 (a and b) | O | —NO₂ | —H | —OCH₂CH₃ |
| H378 (a and b) | O | —NO₂ | —H | —OCF₃ |
| H379 (a and b) | O | —NO₂ | —H | -tert-butyl |
| H380 (a and b) | O | —NO₂ | —H | -iso-propyl |
| H381 (a and b) | O | —CN | —Br | —H |
| H382 (a and b) | O | —CN | —Cl | —H |
| H383 (a and b) | O | —CN | —F | —H |
| H384 (a and b) | O | —CN | —CH₃ | —H |
| H385 (a and b) | O | —CN | —CF₃ | —H |
| H386 (a and b) | O | —CN | —OCH₃ | —H |
| H387 (a and b) | O | —CN | —OCH₂CH₃ | —H |
| H388 (a and b) | O | —CN | —OCF₃ | —H |
| H389 (a and b) | O | —CN | -tert-butyl | —H |
| H390 (a and b) | O | —CN | -iso-propyl | —H |
| H391 (a and b) | O | —CN | —CH₃ | —CH₃ |
| H392 (a and b) | O | —CN | —H | —H |
| H393 (a and b) | O | —CN | —H | —Cl |
| H394 (a and b) | O | —CN | —H | —Br |
| H395 (a and b) | O | —CN | —H | —F |
| H396 (a and b) | O | —CN | —H | —CH₃ |
| H397 (a and b) | O | —CN | —H | —CF₃ |
| H398 (a and b) | O | —CN | —H | —OCH₃ |
| H399 (a and b) | O | —CN | —H | —OCH₂CH₃ |
| H400 (a and b) | O | —CN | —H | —OCF₃ |
| H401 (a and b) | O | —CN | —H | -tert-butyl |
| H402 (a and b) | O | —CN | —H | -iso-propyl |

TABLE 8-continued (Ih)

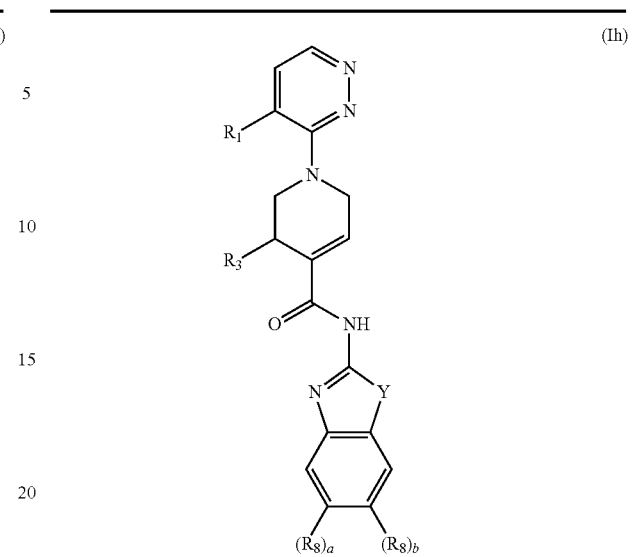

and pharmaceutically acceptable salts thereof, wherein:

| Compound | Y | R₁ | (R₈)ₐ | (R₈)ᵦ |
|---|---|---|---|---|
| H403 (a and b) | O | —Br | —Br | —H |
| H404 (a and b) | O | —Br | —Cl | —H |
| H405 (a and b) | O | —Br | —F | —H |
| H406 (a and b) | O | —Br | —CH₃ | —H |
| H407 (a and b) | O | —Br | —CF₃ | —H |
| H408 (a and b) | O | —Br | —OCH₃ | —H |
| H409 (a and b) | O | —Br | —OCH₂CH₃ | —H |
| H410 (a and b) | O | —Br | —OCF₃ | —H |
| H411 (a and b) | O | —Br | -tert-butyl | —H |
| H412 (a and b) | O | —Br | -iso-propyl | —H |
| H413 (a and b) | O | —Br | —CH₃ | —CH₃ |
| H414 (a and b) | O | —Br | —H | —H |
| H415 (a and b) | O | —Br | —H | —Cl |
| H416 (a and b) | O | —Br | —H | —Br |
| H417 (a and b) | O | —Br | —H | —F |
| H418 (a and b) | O | —Br | —H | —CH₃ |
| H419 (a and b) | O | —Br | —H | —CF₃ |
| H420 (a and b) | O | —Br | —H | —OCH₃ |
| H421 (a and b) | O | —Br | —H | —OCH₂CH₃ |
| H422 (a and b) | O | —Br | —H | —OCF₃ |
| H423 (a and b) | O | —Br | —H | -tert-butyl |
| H424 (a and b) | O | —Br | —H | -iso-propyl |
| H425 (a and b) | O | —I | —Cl | —H |
| H426 (a and b) | O | —I | —Br | —H |
| H427 (a and b) | O | —I | —F | —H |
| H428 (a and b) | O | —I | —CH₃ | —H |
| H429 (a and b) | O | —I | —CF₃ | —H |
| H430 (a and b) | O | —I | —OCH₃ | —H |
| H431 (a and b) | O | —I | —OCH₂CH₃ | —H |
| H432 (a and b) | O | —I | —OCF₃ | —H |
| H433 (a and b) | O | —I | -tert-butyl | —H |
| H434 (a and b) | O | —I | -iso-propyl | —H |
| H435 (a and b) | O | —I | —CH₃ | —CH₃ |
| H436 (a and b) | O | —I | —H | —H |
| H437 (a and b) | O | —I | —H | —Cl |
| H438 (a and b) | O | —I | —H | —Br |
| H439 (a and b) | O | —I | —H | —F |
| H440 (a and b) | O | —I | —H | —CH₃ |
| H441 (a and b) | O | —I | —H | —CF₃ |
| H442 (a and b) | O | —I | —H | —OCH₃ |
| H443 (a and b) | O | —I | —H | —OCH₂CH₃ |
| H444 (a and b) | O | —I | —H | —OCF₃ |
| H445 (a and b) | O | —I | —H | -tert-butyl |
| H446 (a and b) | O | —I | —H | -iso-propyl |
| H447 (a and b) | NH | —H | —Cl | —H |
| H448 (a and b) | NH | —H | —Br | —H |
| H449 (a and b) | NH | —H | —F | —H |
| H450 (a and b) | NH | —H | —CH₃ | —H |
| H451 (a and b) | NH | —H | —CF₃ | —H |

TABLE 8-continued (Ih)

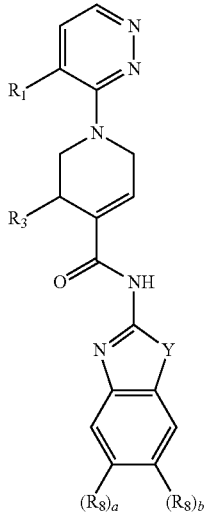

and pharmaceutically acceptable salts thereof, wherein:

| Compound | Y | $R_1$ | $(R_8)_a$ | $(R_8)_b$ |
|---|---|---|---|---|
| H452 (a and b) | NH | —H | —OCH$_3$ | —H |
| H453 (a and b) | NH | —H | —OCH$_2$CH$_3$ | —H |
| H454 (a and b) | NH | —H | —OCF$_3$ | —H |
| H455 (a and b) | NH | —H | -tert-butyl | —H |
| H456 (a and b) | NH | —H | -iso-propyl | —H |
| H457 (a and b) | NH | —H | —CH$_3$ | —CH$_3$ |
| H458 (a and b) | NH | —H | —H | —H |
| H459 (a and b) | NH | —H | —H | —Cl |
| H460 (a and b) | NH | —H | —H | —Br |
| H461 (a and b) | NH | —H | —H | —F |
| H462 (a and b) | NH | —H | —H | —CH$_3$ |
| H463 (a and b) | NH | —H | —H | —CF$_3$ |
| H464 (a and b) | NH | —H | —H | —OCH$_3$ |
| H465 (a and b) | NH | —H | —H | —OCH$_2$CH$_3$ |
| H466 (a and b) | NH | —H | —H | —OCF$_3$ |
| H467 (a and b) | NH | —H | —H | -tert-butyl |
| H468 (a and b) | NH | —H | —H | -iso-propyl |
| H469 (a and b) | NH | —Cl | —Cl | —H |
| H470 (a and b) | NH | —Cl | —Br | —H |
| H471 (a and b) | NH | —Cl | —F | —H |
| H472 (a and b) | NH | —Cl | —CH$_3$ | —H |
| H473 (a and b) | NH | —Cl | —CF$_3$ | —H |
| H474 (a and b) | NH | —Cl | —OCH$_3$ | —H |
| H475 (a and b) | NH | —Cl | —OCH$_2$CH$_3$ | —H |
| H476 (a and b) | NH | —Cl | —OCF$_3$ | —H |
| H477 (a and b) | NH | —Cl | -tert-butyl | —H |
| H478 (a and b) | NH | —Cl | -iso-propyl | —H |
| H479 (a and b) | NH | —Cl | —CH$_3$ | —CH$_3$ |
| H480 (a and b) | NH | —Cl | —H | —H |
| H481 (a and b) | NH | —Cl | —H | —Cl |
| H482 (a and b) | NH | —Cl | —H | —Br |
| H483 (a and b) | NH | —Cl | —H | —F |
| H484 (a and b) | NH | —Cl | —H | —CH$_3$ |
| H485 (a and b) | NH | —Cl | —H | —CF$_3$ |
| H486 (a and b) | NH | —Cl | —H | —OCH$_3$ |
| H487 (a and b) | NH | —Cl | —H | —OCH$_2$CH$_3$ |
| H488 (a and b) | NH | —Cl | —H | —OCF$_3$ |
| H489 (a and b) | NH | —Cl | —H | -tert-butyl |
| H490 (a and b) | NH | —Cl | —H | -iso-propyl |
| H491 (a and b) | NH | —Cl | —H | —OCF$_3$ |
| H492 (a and b) | NH | —Cl | —H | -tert-butyl |
| H493 (a and b) | NH | —Cl | —H | -iso-propyl |
| H494 (a and b) | NH | —CH$_3$ | —Cl | —H |
| H495 (a and b) | NH | —CH$_3$ | —Br | —H |
| H496 (a and b) | NH | —CH$_3$ | —F | —H |
| H497 (a and b) | NH | —CH$_3$ | —CH$_3$ | —H |
| H498 (a and b) | NH | —CH$_3$ | —CF$_3$ | —H |
| H499 (a and b) | NH | —CH$_3$ | —OCH$_3$ | —H |
| H500 (a and b) | NH | —CH$_3$ | —OCH$_2$CH$_3$ | —H |

TABLE 8-continued (Ih)

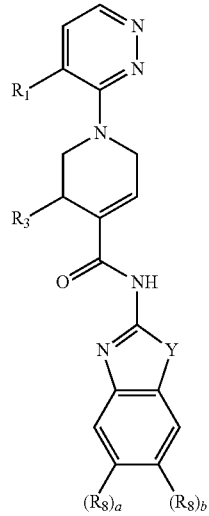

and pharmaceutically acceptable salts thereof, wherein:

| Compound | Y | $R_1$ | $(R_8)_a$ | $(R_8)_b$ |
|---|---|---|---|---|
| H501 (a and b) | NH | —CH$_3$ | —OCF$_3$ | —H |
| H502 (a and b) | NH | —CH$_3$ | -tert-butyl | —H |
| H503 (a and b) | NH | —CH$_3$ | -iso-propyl | —H |
| H504 (a and b) | NH | —CH$_3$ | —CH$_3$ | —CH$_3$ |
| H505 (a and b) | NH | —CH$_3$ | —H | —H |
| H506 (a and b) | NH | —CH$_3$ | —H | —Cl |
| H507 (a and b) | NH | —CH$_3$ | —H | —Br |
| H508 (a and b) | NH | —CH$_3$ | —H | —F |
| H509 (a and b) | NH | —CH$_3$ | —H | —CH$_3$ |
| H510 (a and b) | NH | —CH$_3$ | —H | —CF$_3$ |
| H511 (a and b) | NH | —CH$_3$ | —H | —OCH$_3$ |
| H512 (a and b) | NH | —CH$_3$ | —H | —OCH$_2$CH$_3$ |
| H513 (a and b) | NH | —CH$_3$ | —H | —OCF$_3$ |
| H514 (a and b) | NH | —CH$_3$ | —H | -tert-butyl |
| H515 (a and b) | NH | —CH$_3$ | —H | -iso-propyl |
| H516 (a and b) | NH | —CF$_3$ | —Cl | —H |
| H517 (a and b) | NH | —CF$_3$ | —Br | —H |
| H518 (a and b) | NH | —CF$_3$ | —F | —H |
| H519 (a and b) | NH | —CF$_3$ | —CH$_3$ | —H |
| H520 (a and b) | NH | —CF$_3$ | —CF$_3$ | —H |
| H521 (a and b) | NH | —CF$_3$ | —OCH$_3$ | —H |
| H522 (a and b) | NH | —CF$_3$ | —OCH$_2$CH$_3$ | —H |
| H523 (a and b) | NH | —CF$_3$ | —OCF$_3$ | —H |
| H524 (a and b) | NH | —CF$_3$ | -tert-butyl | —H |
| H525 (a and b) | NH | —CF$_3$ | -iso-propyl | —H |
| H526 (a and b) | NH | —CF$_3$ | —CH$_3$ | —CH$_3$ |
| H527 (a and b) | NH | —CF$_3$ | —H | —H |
| H528 (a and b) | NH | —CF$_3$ | —H | —Cl |
| H529 (a and b) | NH | —CF$_3$ | —H | —Br |
| H530 (a and b) | NH | —CF$_3$ | —H | —F |
| H531 (a and b) | NH | —CF$_3$ | —H | —CH$_3$ |
| H532 (a and b) | NH | —CF$_3$ | —H | —CF$_3$ |
| H533 (a and b) | NH | —CF$_3$ | —H | —OCH$_3$ |
| H534 (a and b) | NH | —CF$_3$ | —H | —OCH$_2$CH$_3$ |
| H535 (a and b) | NH | —CF$_3$ | —H | —OCF$_3$ |
| H536 (a and b) | NH | —CF$_3$ | —H | -tert-butyl |
| H537 (a and b) | NH | —CF$_3$ | —H | -iso-propyl |
| H538 (a and b) | NH | —CHF$_2$ | —Cl | —H |
| H539 (a and b) | NH | —CHF$_2$ | —Br | —H |
| H540 (a and b) | NH | —CHF$_2$ | —F | —H |
| H541 (a and b) | NH | —CHF$_2$ | —CH$_3$ | —H |
| H542 (a and b) | NH | —CHF$_2$ | —CF$_3$ | —H |
| H543 (a and b) | NH | —CHF$_2$ | —OCH$_3$ | —H |
| H544 (a and b) | NH | —CHF$_2$ | —OCH$_2$CH$_3$ | —H |
| H545 (a and b) | NH | —CHF$_2$ | —OCF$_3$ | —H |
| H546 (a and b) | NH | —CHF$_2$ | -tert-butyl | —H |
| H547 (a and b) | NH | —CHF$_2$ | -iso-propyl | —H |
| H548 (a and b) | NH | —CHF$_2$ | —CH$_3$ | —CH$_3$ |
| H549 (a and b) | NH | —CHF$_2$ | —H | —H |

TABLE 8-continued (Ih)

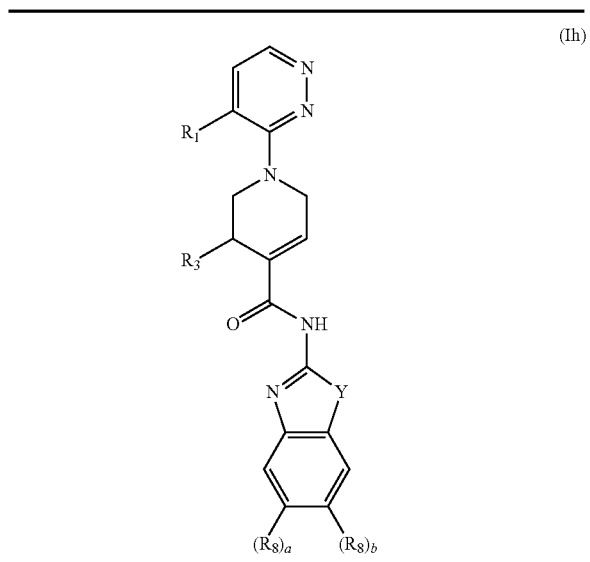

and pharmaceutically acceptable salts thereof, wherein:

| Compound | Y | $R_1$ | $(R_8)_a$ | $(R_8)_b$ |
|---|---|---|---|---|
| H550 (a and b) | NH | —CHF$_2$ | —H | —Cl |
| H551 (a and b) | NH | —CHF$_2$ | —H | —Br |
| H552 (a and b) | NH | —CHF$_2$ | —H | —F |
| H553 (a and b) | NH | —CHF$_2$ | —H | —CH$_3$ |
| H554 (a and b) | NH | —CHF$_2$ | —H | —CF$_3$ |
| H555 (a and b) | NH | —CHF$_2$ | —H | —OCH$_3$ |
| H556 (a and b) | NH | —CHF$_2$ | —H | —OCH$_2$CH$_3$ |
| H557 (a and b) | NH | —CHF$_2$ | —H | —OCF$_3$ |
| H558 (a and b) | NH | —CHF$_2$ | —H | -tert-butyl |
| H559 (a and b) | NH | —CHF$_2$ | —H | -iso-propyl |
| H560 (a and b) | NH | —OH | —Cl | —H |
| H561 (a and b) | NH | —OH | —Br | —H |
| H562 (a and b) | NH | —OH | —F | —H |
| H563 (a and b) | NH | —OH | —CH$_3$ | —H |
| H564 (a and b) | NH | —OH | —CF$_3$ | —H |
| H565 (a and b) | NH | —OH | —OCH$_3$ | —H |
| H566 (a and b) | NH | —OH | —OCH$_2$CH$_3$ | —H |
| H567 (a and b) | NH | —OH | —OCF$_3$ | —H |
| H568 (a and b) | NH | —OH | -tert-butyl | —H |
| H569 (a and b) | NH | —OH | -iso-propyl | —H |
| H570 (a and b) | NH | —OH | —CH$_3$ | —CH$_3$ |
| H571 (a and b) | NH | —OH | —H | —H |
| H572 (a and b) | NH | —OH | —H | —Cl |
| H573 (a and b) | NH | —OH | —H | —Br |
| H574 (a and b) | NH | —OH | —H | —F |
| H575 (a and b) | NH | —OH | —H | —CH$_3$ |
| H576 (a and b) | NH | —OH | —H | —CF$_3$ |
| H577 (a and b) | NH | —OH | —H | —OCH$_3$ |
| H578 (a and b) | NH | —OH | —H | —OCH$_2$CH$_3$ |
| H579 (a and b) | NH | —OH | —H | —OCF$_3$ |
| H580 (a and b) | NH | —OH | —H | -tert-butyl |
| H581 (a and b) | NH | —OH | —H | -iso-propyl |
| H582 (a and b) | NH | —NO$_2$ | —Cl | —H |
| H583 (a and b) | NH | —NO$_2$ | —Br | —H |
| H584 (a and b) | NH | —NO$_2$ | —F | —H |
| H585 (a and b) | NH | —NO$_2$ | —CH$_3$ | —H |
| H586 (a and b) | NH | —NO$_2$ | —CF$_3$ | —H |
| H587 (a and b) | NH | —NO$_2$ | —OCH$_3$ | —H |
| H588 (a and b) | NH | —NO$_2$ | —OCH$_2$CH$_3$ | —H |
| H589 (a and b) | NH | —NO$_2$ | —OCF$_3$ | —H |
| H590 (a and b) | NH | —NO$_2$ | -tert-butyl | —H |
| H591 (a and b) | NH | —NO$_2$ | -iso-propyl | —H |
| H592 (a and b) | NH | —NO$_2$ | —CH$_3$ | —CH$_3$ |
| H593 (a and b) | NH | —NO$_2$ | —H | —H |
| H594 (a and b) | NH | —NO$_2$ | —H | —Cl |
| H595 (a and b) | NH | —NO$_2$ | —H | —Br |
| H596 (a and b) | NH | —NO$_2$ | —H | —F |
| H597 (a and b) | NH | —NO$_2$ | —H | —CH$_3$ |
| H598 (a and b) | NH | —NO$_2$ | —H | —CF$_3$ |

TABLE 8-continued (Ih)

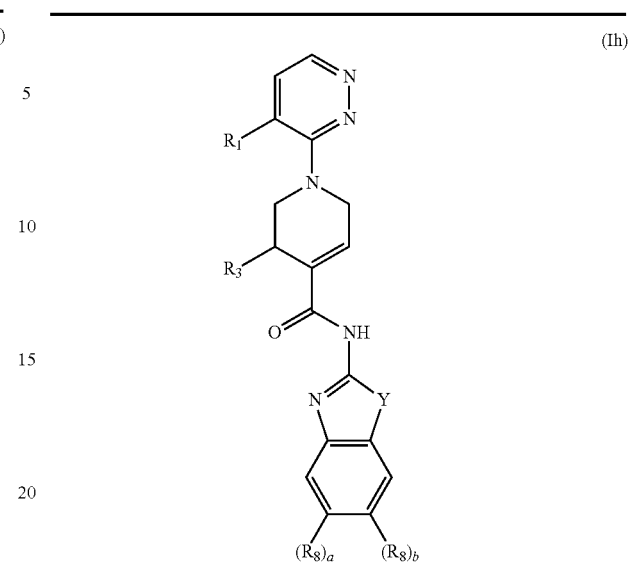

and pharmaceutically acceptable salts thereof, wherein:

| Compound | Y | $R_1$ | $(R_8)_a$ | $(R_8)_b$ |
|---|---|---|---|---|
| H599 (a and b) | NH | —NO$_2$ | —H | —OCH$_3$ |
| H600 (a and b) | NH | —NO$_2$ | —H | —OCH$_2$CH$_3$ |
| H601 (a and b) | NH | —NO$_2$ | —H | —OCF$_3$ |
| H602 (a and b) | NH | —NO$_2$ | —H | -tert-butyl |
| H603 (a and b) | NH | —NO$_2$ | —H | -iso-propyl |
| H604 (a and b) | NH | —CN | —Br | —H |
| H605 (a and b) | NH | —CN | —Cl | —H |
| H606 (a and b) | NH | —CN | —F | —H |
| H607 (a and b) | NH | —CN | —CH$_3$ | —H |
| H608 (a and b) | NH | —CN | —CF$_3$ | —H |
| H609 (a and b) | NH | —CN | —OCH$_3$ | —H |
| H610 (a and b) | NH | —CN | —OCH$_2$CH$_3$ | —H |
| H611 (a and b) | NH | —CN | —OCF$_3$ | —H |
| H612 (a and b) | NH | —CN | -tert-butyl | —H |
| H613 (a and b) | NH | —CN | -iso-propyl | —H |
| H614 (a and b) | NH | —CN | —CH$_3$ | —CH$_3$ |
| H615 (a and b) | NH | —CN | —H | —H |
| H616 (a and b) | NH | —CN | —H | —Cl |
| H617 (a and b) | NH | —CN | —H | —Br |
| H618 (a and b) | NH | —CN | —H | —F |
| H619 (a and b) | NH | —CN | —H | —CH$_3$ |
| H620 (a and b) | NH | —CN | —H | —CF$_3$ |
| H621 (a and b) | NH | —CN | —H | —OCH$_3$ |
| H622 (a and b) | NH | —CN | —H | —OCH$_2$CH$_3$ |
| H623 (a and b) | NH | —CN | —H | —OCF$_3$ |
| H624 (a and b) | NH | —CN | —H | -tert-butyl |
| H625 (a and b) | NH | —CN | —H | -iso-propyl |
| H626 (a and b) | NH | —Br | —Br | —H |
| H627 (a and b) | NH | —Br | —Cl | —H |
| H628 (a and b) | NH | —Br | —F | —H |
| H629 (a and b) | NH | —Br | —CH$_3$ | —H |
| H630 (a and b) | NH | —Br | —CF$_3$ | —H |
| H631 (a and b) | NH | —Br | —OCH$_3$ | —H |
| H632 (a and b) | NH | —Br | —OCH$_2$CH$_3$ | —H |
| H633 (a and b) | NH | —Br | —OCF$_3$ | —H |
| H634 (a and b) | NH | —Br | -tert-butyl | —H |
| H635 (a and b) | NH | —Br | -iso-propyl | —H |
| H636 (a and b) | NH | —Br | —CH$_3$ | —CH$_3$ |
| H637 (a and b) | NH | —Br | —H | —H |
| H638 (a and b) | NH | —Br | —H | —Cl |
| H639 (a and b) | NH | —Br | —H | —Br |
| H640 (a and b) | NH | —Br | —H | —F |

TABLE 8-continued

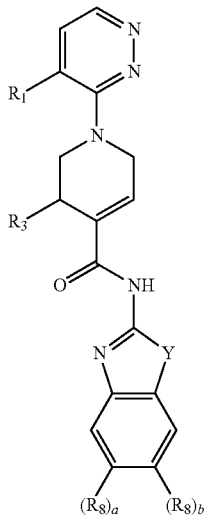

(Ih)

and pharmaceutically acceptable salts thereof, wherein:

| Compound | Y | R$_1$ | (R$_8$)$_a$ | (R$_8$)$_b$ |
|---|---|---|---|---|
| H641 (a and b) | NH | —Br | —H | —CH$_3$ |
| H642 (a and b) | NH | —Br | —H | —CF$_3$ |
| H643 (a and b) | NH | —Br | —H | —OCH$_3$ |
| H644 (a and b) | NH | —Br | —H | —OCH$_2$CH$_3$ |
| H645 (a and b) | NH | —Br | —H | —OCF$_3$ |
| H646 (a and b) | NH | —Br | —H | -tert-butyl |
| H647 (a and b) | NH | —Br | —H | -iso-propyl |
| H648 (a and b) | NH | —I | —Cl | —H |
| H649 (a and b) | NH | —I | —Br | —H |
| H650 (a and b) | NH | —I | —F | —H |
| H651 (a and b) | NH | —I | —CH$_3$ | —H |
| H652 (a and b) | NH | —I | —CF$_3$ | —H |
| H653 (a and b) | NH | —I | —OCH$_3$ | —H |
| H654 (a and b) | NH | —I | —OCH$_2$CH$_3$ | —H |
| H655 (a and b) | NH | —I | —OCF$_3$ | —H |
| H656 (a and b) | NH | —I | -tert-butyl | —H |
| H657 (a and b) | NH | —I | -iso-propyl | —H |
| H658 (a and b) | NH | —I | —CH$_3$ | —CH$_3$ |
| H659 (a and b) | NH | —I | —H | —H |
| H660 (a and b) | NH | —I | —H | —Cl |
| H661 (a and b) | NH | —I | —H | —Br |
| H662 (a and b) | NH | —I | —H | —F |
| H663 (a and b) | NH | —I | —H | —CH$_3$ |
| H664 (a and b) | NH | —I | —H | —CF$_3$ |
| H665 (a and b) | NH | —I | —H | —OCH$_3$ |
| H666 (a and b) | NH | —I | —H | —OCH$_2$CH$_3$ |
| H667 (a and b) | NH | —I | —H | —OCF$_3$ |
| H668 (a and b) | NH | —I | —H | -tert-butyl |
| H669 (a and b) | NH | —I | —H | -iso-propyl |

(a) means that R$_3$ is —H.
(b) means that R$_3$ is —CH$_3$.

TABLE 9

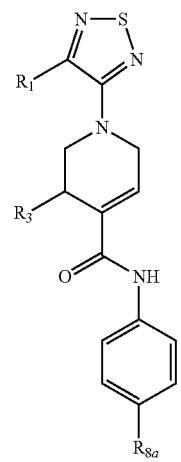

(Ii)

and pharmaceutically acceptable salts thereof, wherein:

| Compound | R$_1$ | R$_{8a}$ |
|---|---|---|
| I01 (a and b) | —H | —H |
| I02 (a and b) | —H | -tert-butyl |
| I03 (a and b) | —H | -iso-butyl |
| I04 (a and b) | —H | -sec-butyl |
| I05 (a and b) | —H | -iso-propyl |
| I06 (a and b) | —H | -n-propyl |
| I07 (a and b) | —H | -cyclohexyl |
| I08 (a and b) | —H | -tert-butoxy |
| I09 (a and b) | —H | -isopropoxy |
| I10 (a and b) | —H | —CF$_3$ |
| I11 (a and b) | —H | —CH$_2$CF$_3$ |
| I12 (a and b) | —H | —OCF$_3$ |
| I13 (a and b) | —H | —Cl |
| I14 (a and b) | —H | —Br |
| I15 (a and b) | —H | —I |
| I16 (a and b) | —H | -n-butyl |
| I17 (a and b) | —H | —CH$_3$ |
| I18 (a and b) | —H | —SCF$_3$ |
| I19 (a and b) | —H | —N(CH$_2$CH$_3$)$_2$ |
| I20 (a and b) | —H | —OCF$_2$CHF$_2$ |
| I21 (a and b) | —H | —C(OH)(CF$_3$)$_2$ |
| I22 (a and b) | —H | -(1,1-dimethyl-pentyl) |
| I23 (a and b) | —H | -(1,1-dimethyl-acetic acid) ethyl ester |
| I24 (a and b) | —H | —N-piperidinyl |
| I25 (a and b) | —Cl | —H |
| I26 (a and b) | —Cl | -tert-butyl |
| I27 (a and b) | —Cl | -iso-butyl |
| I28 (a and b) | —Cl | -sec-butyl |
| I29 (a and b) | —Cl | -iso-propyl |
| I30 (a and b) | —Cl | -n-propyl |
| I31 (a and b) | —Cl | -cyclohexyl |
| I32 (a and b) | —Cl | -tert-butoxy |
| I33 (a and b) | —Cl | -isopropoxy |
| I34 (a and b) | —Cl | —CF$_3$ |
| I35 (a and b) | —Cl | —CH$_2$CF$_3$ |
| I36 (a and b) | —Cl | —OCF$_3$ |
| I37 (a and b) | —Cl | —Cl |
| I38 (a and b) | —Cl | —Br |
| I39 (a and b) | —Cl | —I |
| I40 (a and b) | —Cl | -n-butyl |
| I41 (a and b) | —Cl | —CH$_3$ |
| I42 (a and b) | —Cl | —SCF$_3$ |
| I43 (a and b) | —Cl | —N(CH$_2$CH$_3$)$_2$ |
| I44 (a and b) | —Cl | —OCF$_2$CHF$_2$ |
| I45 (a and b) | —Cl | —C(OH)(CF$_3$)$_2$ |
| I46 (a and b) | —Cl | -(1,1-dimethyl-pentyl) |
| I47 (a and b) | —Cl | -(1,1-dimethyl-acetic acid) ethyl ester |
| I48 (a and b) | —Cl | —N-piperidinyl |
| I49 (a and b) | —F | —H |
| I50 (a and b) | —F | -tert-butyl |

TABLE 9-continued

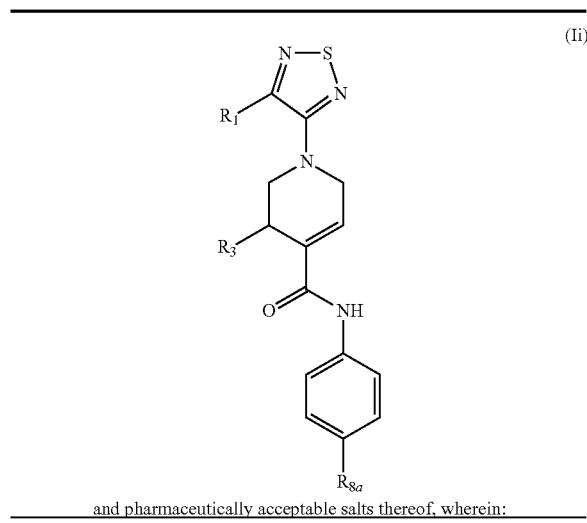

(Ii)

and pharmaceutically acceptable salts thereof, wherein:

| Compound | R₁ | R₈ₐ |
|---|---|---|
| I51 (a and b) | —F | -iso-butyl |
| I52 (a and b) | —F | -sec-butyl |
| I53 (a and b) | —F | -iso-propyl |
| I54 (a and b) | —F | -n-propyl |
| I55 (a and b) | —F | -cyclohexyl |
| I56 (a and b) | —F | -tert-butoxy |
| I57 (a and b) | —F | -isopropoxy |
| I58 (a and b) | —F | —CF₃ |
| I59 (a and b) | —F | —CH₂CF₃ |
| I60 (a and b) | —F | —OCF₃ |
| I61 (a and b) | —F | —Cl |
| I62 (a and b) | —F | —Br |
| I63 (a and b) | —F | —I |
| I64 (a and b) | —F | -n-butyl |
| I65 (a and b) | —F | —CH₃ |
| I66 (a and b) | —F | —SCF₃ |
| I67 (a and b) | —F | —N(CH₂CH₃)₂ |
| I68 (a and b) | —F | —OCF₂CHF₂ |
| I69 (a and b) | —F | —C(OH)(CF₃)₂ |
| I70 (a and b) | —F | -(1,1-dimethyl-pentyl) |
| I71 (a and b) | —F | -(1,1-dimethyl-acetic acid) ethyl ester |
| I72 (a and b) | —F | —N-piperidinyl |
| I73 (a and b) | —CH₃ | —H |
| I74 (a and b) | —CH₃ | -iso-butyl |
| I75 (a and b) | —CH₃ | -tert-butyl |
| I76 (a and b) | —CH₃ | -sec-butyl |
| I77 (a and b) | —CH₃ | -iso-propyl |
| I78 (a and b) | —CH₃ | -n-propyl |
| I79 (a and b) | —CH₃ | -cyclohexyl |
| I80 (a and b) | —CH₃ | -tert-butoxy |
| I81 (a and b) | —CH₃ | -isopropoxy |
| I82 (a and b) | —CH₃ | —CF₃ |
| I83 (a and b) | —CH₃ | —CH₂CF₃ |
| I84 (a and b) | —CH₃ | —OCF₃ |
| I85 (a and b) | —CH₃ | —Cl |
| I86 (a and b) | —CH₃ | —Br |
| I87 (a and b) | —CH₃ | —I |
| I88 (a and b) | —CH₃ | -n-butyl |
| I89 (a and b) | —CH₃ | —CH₃ |
| I90 (a and b) | —CH₃ | —SCF₃ |
| I91 (a and b) | —CH₃ | —N(CH₂CH₃)₂ |
| I92 (a and b) | —CH₃ | —OCF₂CHF₂ |
| I93 (a and b) | —CH₃ | —C(OH)(CF₃)₂ |
| I94 (a and b) | —CH₃ | -(1,1-dimethyl-pentyl) |
| I95 (a and b) | —CH₃ | -(1,1-dimethyl-acetic acid) ethyl ester |
| I96 (a and b) | —CH₃ | —N-piperidinyl |
| I97 (a and b) | —CF₃ | —H |
| I98 (a and b) | —CF₃ | -tert-butyl |
| I99 (a and b) | —CF₃ | -iso-butyl |
| I100 (a and b) | —CF₃ | -sec-butyl |

TABLE 9-continued

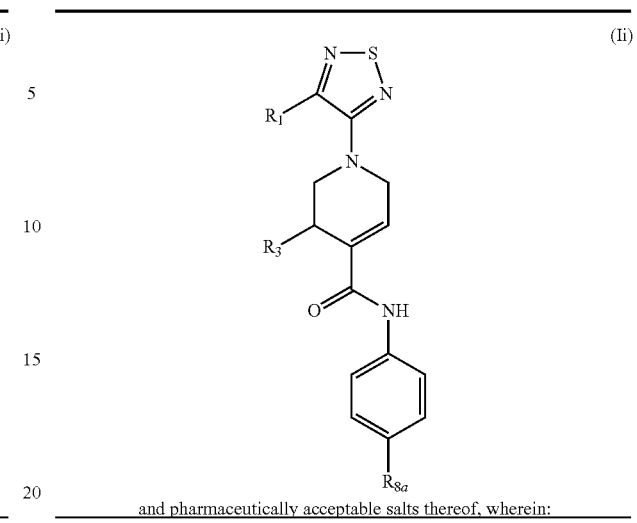

(Ii)

and pharmaceutically acceptable salts thereof, wherein:

| Compound | R₁ | R₈ₐ |
|---|---|---|
| I101 (a and b) | —CF₃ | -iso-propyl |
| I102 (a and b) | —CF₃ | -n-propyl |
| I103 (a and b) | —CF₃ | -cyclohexyl |
| I104 (a and b) | —CF₃ | -tert-butoxy |
| I105 (a and b) | —CF₃ | -isopropoxy |
| I106 (a and b) | —CF₃ | —CF₃ |
| I107 (a and b) | —CF₃ | —CH₂CF₃ |
| I108 (a and b) | —CF₃ | —OCF₃ |
| I109 (a and b) | —CF₃ | —Cl |
| I110 (a and b) | —CF₃ | —Br |
| I111 (a and b) | —CF₃ | —I |
| I112 (a and b) | —CF₃ | -n-butyl |
| I113 (a and b) | —CF₃ | —CH₃ |
| I114 (a and b) | —CF₃ | —SCF₃ |
| I115 (a and b) | —CF₃ | —N(CH₂CH₃)₂ |
| I116 (a and b) | —CF₃ | —OCF₂CHF₂ |
| I117 (a and b) | —CF₃ | —C(OH)(CF₃)₂ |
| I118 (a and b) | —CF₃ | -(1,1-dimethyl-pentyl) |
| I119 (a and b) | —CF₃ | -(1,1-dimethyl-acetic acid) ethyl ester |
| I120 (a and b) | —CF₃ | —N-piperidinyl |
| I121 (a and b) | —CHF₂ | -tert-butyl |
| I122 (a and b) | —CHF₂ | —H |
| I123 (a and b) | —CHF₂ | -iso-butyl |
| I124 (a and b) | —CHF₂ | -sec-butyl |
| I125 (a and b) | —CHF₂ | -iso-propyl |
| I126 (a and b) | —CHF₂ | -n-propyl |
| I127 (a and b) | —CHF₂ | -cyclohexyl |
| I128 (a and b) | —CHF₂ | -tert-butoxy |
| I129 (a and b) | —CHF₂ | -isopropoxy |
| I130 (a and b) | —CHF₂ | —CF₃ |
| I131 (a and b) | —CHF₂ | —CH₂CF₃ |
| I132 (a and b) | —CHF₂ | —OCF₃ |
| I133 (a and b) | —CHF₂ | —Cl |
| I134 (a and b) | —CHF₂ | —Br |
| I135 (a and b) | —CHF₂ | —I |
| I136 (a and b) | —CHF₂ | -n-butyl |
| I137 (a and b) | —CHF₂ | —CH₃ |
| I138 (a and b) | —CHF₂ | —SCF₃ |
| I139 (a and b) | —CHF₂ | —N(CH₂CH₃)₂ |
| I140 (a and b) | —CHF₂ | —OCF₂CHF₂ |
| I141 (a and b) | —CHF₂ | —C(OH)(CF₃)₂ |
| I142 (a and b) | —CHF₂ | -(1,1-dimethyl-pentyl) |
| I143 (a and b) | —CHF₂ | -(1,1-dimethyl-acetic acid) ethyl ester |
| I144 (a and b) | —CHF₂ | —N-piperidinyl |
| I145 (a and b) | —OH | —H |
| I146 (a and b) | —OH | -tert-butyl |
| I147 (a and b) | —OH | -iso-butyl |
| I148 (a and b) | —OH | -sec-butyl |
| I149 (a and b) | —OH | -iso-propyl |
| I150 (a and b) | —OH | -n-propyl |

TABLE 9-continued

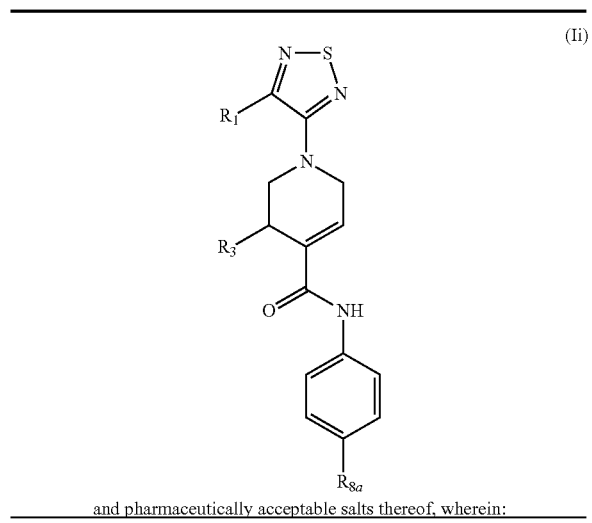

(Ii)

and pharmaceutically acceptable salts thereof, wherein:

| Compound | $R_1$ | $R_{8a}$ |
|---|---|---|
| I151 (a and b) | —OH | -cyclohexyl |
| I152 (a and b) | —OH | -tert-butoxy |
| I153 (a and b) | —OH | -isopropoxy |
| I154 (a and b) | —OH | —CF$_3$ |
| I155 (a and b) | —OH | —CH$_2$CF$_3$ |
| I156 (a and b) | —OH | —OCF$_3$ |
| I157 (a and b) | —OH | —Cl |
| I158 (a and b) | —OH | —Br |
| I159 (a and b) | —OH | —I |
| I160 (a and b) | —OH | -n-butyl |
| I161 (a and b) | —OH | —CH$_3$ |
| I162 (a and b) | —OH | —SCF$_3$ |
| I163 (a and b) | —OH | —N(CH$_2$CH$_3$)$_2$ |
| I164 (a and b) | —OH | —OCF$_2$CHF$_2$ |
| I165 (a and b) | —OH | —C(OH)(CF$_3$)$_2$ |
| I166 (a and b) | —OH | -(1,1-dimethyl-pentyl) |
| I167 (a and b) | —OH | -(1,1-dimethyl-acetic acid) ethyl ester |
| I168 (a and b) | —OH | —N-piperidinyl |
| I169 (a and b) | —NO$_2$ | —H |
| I170 (a and b) | —NO$_2$ | -tert-butyl |
| I171 (a and b) | —NO$_2$ | -iso-butyl |
| I172 (a and b) | —NO$_2$ | -sec-butyl |
| I173 (a and b) | —NO$_2$ | -iso-propyl |
| I174 (a and b) | —NO$_2$ | -n-propyl |
| I175 (a and b) | —NO$_2$ | -cyclohexyl |
| I176 (a and b) | —NO$_2$ | -tert-butoxy |
| I177 (a and b) | —NO$_2$ | -isopropoxy |
| I178 (a and b) | —NO$_2$ | —CF$_3$ |
| I179 (a and b) | —NO$_2$ | —CH$_2$CF$_3$ |
| I180 (a and b) | —NO$_2$ | —OCF$_3$ |
| I181 (a and b) | —NO$_2$ | —Cl |
| I182 (a and b) | —NO$_2$ | —Br |
| I183 (a and b) | —NO$_2$ | —I |
| I184 (a and b) | —NO$_2$ | -n-butyl |
| I185 (a and b) | —NO$_2$ | —CH$_3$ |
| I186 (a and b) | —NO$_2$ | —SCF$_3$ |
| I187 (a and b) | —NO$_2$ | —N(CH$_2$CH$_3$)$_2$ |
| I188 (a and b) | —NO$_2$ | —OCF$_2$CHF$_2$ |
| I189 (a and b) | —NO$_2$ | —C(OH)(CF$_3$)$_2$ |
| I190 (a and b) | —NO$_2$ | -(1,1-dimethyl-pentyl) |
| I191 (a and b) | —NO$_2$ | -(1,1-dimethyl-acetic acid) ethyl ester |
| I192 (a and b) | —NO$_2$ | —N-piperidinyl |
| I193 (a and b) | —CN | —H |
| I194 (a and b) | —CN | -tert-butyl |
| I195 (a and b) | —CN | -iso-butyl |
| I196 (a and b) | —CN | -sec-butyl |
| I197 (a and b) | —CN | -iso-propyl |
| I198 (a and b) | —CN | -n-propyl |
| I199 (a and b) | —CN | -cyclohexyl |
| I200 (a and b) | —CN | -tert-butoxy |

TABLE 9-continued

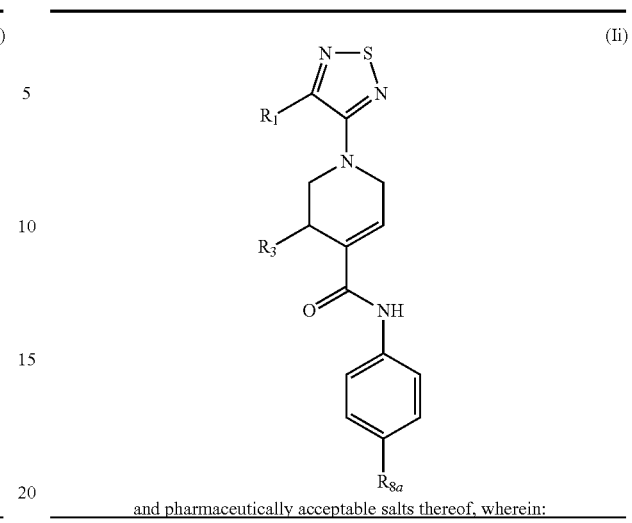

(Ii)

and pharmaceutically acceptable salts thereof, wherein:

| Compound | $R_1$ | $R_{8a}$ |
|---|---|---|
| I201 (a and b) | —CN | -isopropoxy |
| I202 (a and b) | —CN | —CF$_3$ |
| I203 (a and b) | —CN | —CH$_2$CF$_3$ |
| I204 (a and b) | —CN | —OCF$_3$ |
| I205 (a and b) | —CN | —Cl |
| I206 (a and b) | —CN | —Br |
| I207 (a and b) | —CN | —I |
| I208 (a and b) | —CN | -n-butyl |
| I209 (a and b) | —CN | —CH$_3$ |
| I210 (a and b) | —CN | —SCF$_3$ |
| I211 (a and b) | —CN | —N(CH$_2$CH$_3$)$_2$ |
| I212 (a and b) | —CN | —OCF$_2$CHF$_2$ |
| I213 (a and b) | —CN | —C(OH)(CF$_3$)$_2$ |
| I214 (a and b) | —CN | -(1,1-dimethyl-pentyl) |
| I215 (a and b) | —CN | -(1,1-dimethyl-acetic acid) ethyl ester |
| I216 (a and b) | —CN | —N-piperidinyl |
| I217 (a and b) | —Br | —H |
| I218 (a and b) | —Br | -tert-butyl |
| I219 (a and b) | —Br | -iso-butyl |
| I220 (a and b) | —Br | -sec-butyl |
| I221 (a and b) | —Br | -iso-propyl |
| I222 (a and b) | —Br | -n-propyl |
| I223 (a and b) | —Br | -cyclohexyl |
| I224 (a and b) | —Br | -tert-butoxy |
| I225 (a and b) | —Br | -isopropoxy |
| I226 (a and b) | —Br | —CF$_3$ |
| I227 (a and b) | —Br | —CH$_2$CF$_3$ |
| I228 (a and b) | —Br | —OCF$_3$ |
| I229 (a and b) | —Br | —Cl |
| I230 (a and b) | —Br | —Br |
| I231 (a and b) | —Br | —I |
| I232 (a and b) | —Br | -n-butyl |
| I233 (a and b) | —Br | —CH$_3$ |
| I234 (a and b) | —Br | —SCF$_3$ |
| I235 (a and b) | —Br | —N(CH$_2$CH$_3$)$_2$ |
| I236 (a and b) | —Br | —OCF$_2$CHF$_2$ |
| I237 (a and b) | —Br | —C(OH)(CF$_3$)$_2$ |
| I238 (a and b) | —Br | -(1,1-dimethyl-pentyl) |
| I239 (a and b) | —Br | -(1,1-dimethyl-acetic acid) ethyl ester |
| I240 (a and b) | —Br | —N-piperidinyl |
| I241 (a and b) | —I | -tert-butyl |
| I242 (a and b) | —I | —H |
| I243 (a and b) | —I | -iso-butyl |
| I244 (a and b) | —I | -sec-butyl |
| I245 (a and b) | —I | -iso-propyl |
| I246 (a and b) | —I | -n-propyl |
| I247 (a and b) | —I | -cyclohexyl |
| I248 (a and b) | —I | -tert-butoxy |
| I249 (a and b) | —I | -isopropoxy |
| I250 (a and b) | —I | —CF$_3$ |

TABLE 9-continued

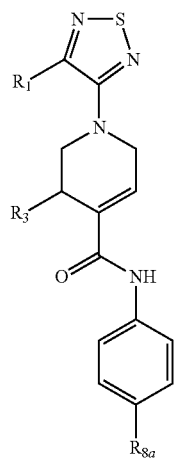

(Ii)

and pharmaceutically acceptable salts thereof, wherein:

| Compound | $R_1$ | $R_{8a}$ |
|---|---|---|
| I251 (a and b) | —I | —CH$_2$CF$_3$ |
| I252 (a and b) | —I | —OCF$_3$ |
| I253 (a and b) | —I | —Cl |
| I254 (a and b) | —I | —Br |
| I255 (a and b) | —I | —I |
| I256 (a and b) | —I | -n-butyl |
| I257 (a and b) | —I | —CH$_3$ |
| I258 (a and b) | —I | —SCF$_3$ |
| I259 (a and b) | —I | —N(CH$_2$CH$_3$)$_2$ |
| I260 (a and b) | —I | —OCF$_2$CHF$_2$ |
| I261 (a and b) | —I | —C(OH)(CF$_3$)$_2$ |
| I262 (a and b) | —I | -(1,1-dimethyl-pentyl) |
| I263 (a and b) | —I | -(1,1-dimethyl-acetic acid) ethyl ester |
| I264 (a and b) | —I | —N-piperidinyl |

(a) means that $R_3$ is —H.
(b) means that $R_3$ is —CH$_3$.

TABLE 10

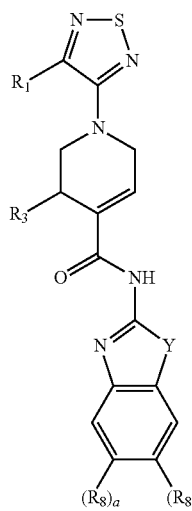

(Ij)

and pharmaceutically acceptable salts thereof, wherein:

| Compound | Y | $R_1$ | $(R_8)_a$ | $(R_8)_b$ |
|---|---|---|---|---|
| J1 (a and b) | S | —H | —Cl | —H |
| J2 (a and b) | S | —H | —Br | —H |
| J3 (a and b) | S | —H | —F | —H |
| J4 (a and b) | S | —H | —CH$_3$ | —H |
| J5 (a and b) | S | —H | —CF$_3$ | —H |
| J6 (a and b) | S | —H | —OCH$_3$ | —H |
| J7 (a and b) | S | —H | —OCH$_2$CH$_3$ | —H |
| J8 (a and b) | S | —H | —OCF$_3$ | —H |
| J9 (a and b) | S | —H | -tert-butyl | —H |
| J10 (a and b) | S | —H | -iso-propyl | —H |
| J11 (a and b) | S | —H | —CH$_3$ | —CH$_3$ |
| J12 (a and b) | S | —H | —H | —H |
| J13 (a and b) | S | —H | —H | —Cl |
| J14 (a and b) | S | —H | —H | —Br |
| J15 (a and b) | S | —H | —H | —F |
| J16 (a and b) | S | —H | —H | —CH$_3$ |
| J17 (a and b) | S | —H | —H | —CF$_3$ |
| J18 (a and b) | S | —H | —H | —OCH$_3$ |
| J19 (a and b) | S | —H | —H | —OCH$_2$CH$_3$ |
| J20 (a and b) | S | —H | —H | —OCF$_3$ |
| J21 (a and b) | S | —H | —H | -tert-butyl |
| J22 (a and b) | S | —H | —H | -iso-propyl |
| J23 (a and b) | S | —Cl | —Cl | —H |
| J24 (a and b) | S | —Cl | —Br | —H |
| J25 (a and b) | S | —Cl | —F | —H |
| J26 (a and b) | S | —Cl | —CH$_3$ | —H |
| J27 (a and b) | S | —Cl | —CF$_3$ | —H |
| J28 (a and b) | S | —Cl | —OCH$_3$ | —H |
| J29 (a and b) | S | —Cl | —OCH$_2$CH$_3$ | —H |
| J30 (a and b) | S | —Cl | —OCF$_3$ | —H |
| J31 (a and b) | S | —Cl | -tert-butyl | —H |
| J32 (a and b) | S | —Cl | -iso-propyl | —H |
| J33 (a and b) | S | —Cl | —CH$_3$ | —CH$_3$ |
| J34 (a and b) | S | —Cl | —H | —H |
| J35 (a and b) | S | —Cl | —H | —Cl |
| J36 (a and b) | S | —Cl | —H | —Br |
| J37 (a and b) | S | —Cl | —H | —F |
| J38 (a and b) | S | —Cl | —H | —CH$_3$ |
| J39 (a and b) | S | —Cl | —H | —CF$_3$ |
| J40 (a and b) | S | —Cl | —H | —OCH$_3$ |
| J41 (a and b) | S | —Cl | —H | —OCH$_2$CH$_3$ |
| J42 (a and b) | S | —Cl | —H | —OCF$_3$ |
| J43 (a and b) | S | —Cl | —H | -tert-butyl |
| J44 (a and b) | S | —Cl | —H | -iso-propyl |
| J45 (a and b) | S | —Cl | —H | —OCF$_3$ |
| J46 (a and b) | S | —Cl | —H | -tert-butyl |
| J47 (a and b) | S | —Cl | —H | -iso-propyl |
| J48 (a and b) | S | —CH$_3$ | —Cl | —H |
| J49 (a and b) | S | —CH$_3$ | —Br | —H |
| J50 (a and b) | S | —CH$_3$ | —F | —H |
| J51 (a and b) | S | —CH$_3$ | —CH$_3$ | —H |

TABLE 10-continued (Ij)

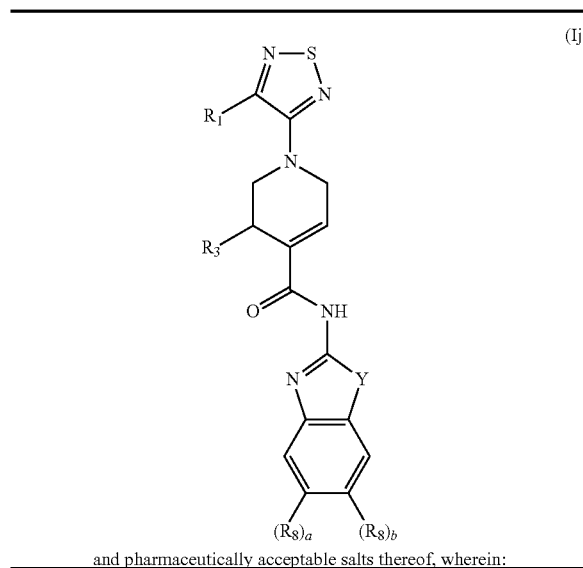

and pharmaceutically acceptable salts thereof, wherein:

| Compound | Y | $R_1$ | $(R_8)_a$ | $(R_8)_b$ |
|---|---|---|---|---|
| J52 (a and b) | S | —CH$_3$ | —CF$_3$ | —H |
| J53 (a and b) | S | —CH$_3$ | —OCH$_3$ | —H |
| J54 (a and b) | S | —CH$_3$ | —OCH$_2$CH$_3$ | —H |
| J55 (a and b) | S | —CH$_3$ | —OCF$_3$ | —H |
| J56 (a and b) | S | —CH$_3$ | -tert-butyl | —H |
| J57 (a and b) | S | —CH$_3$ | -iso-propyl | —H |
| J58 (a and b) | S | —CH$_3$ | —CH$_3$ | —CH$_3$ |
| J59 (a and b) | S | —CH$_3$ | —H | —H |
| J60 (a and b) | S | —CH$_3$ | —H | —Cl |
| J61 (a and b) | S | —CH$_3$ | —H | —Br |
| J62 (a and b) | S | —CH$_3$ | —H | —F |
| J63 (a and b) | S | —CH$_3$ | —H | —CH$_3$ |
| J64 (a and b) | S | —CH$_3$ | —H | —CF$_3$ |
| J65 (a and b) | S | —CH$_3$ | —H | —OCH$_3$ |
| J66 (a and b) | S | —CH$_3$ | —H | —OCH$_2$CH$_3$ |
| J67 (a and b) | S | —CH$_3$ | —H | —OCF$_3$ |
| J68 (a and b) | S | —CH$_3$ | —H | -tert-butyl |
| J69 (a and b) | S | —CH$_3$ | —H | -iso-propyl |
| J70 (a and b) | S | —CF$_3$ | —Cl | —H |
| J71 (a and b) | S | —CF$_3$ | —Br | —H |
| J72 (a and b) | S | —CF$_3$ | —F | —H |
| J73 (a and b) | S | —CF$_3$ | —CH$_3$ | —H |
| J74 (a and b) | S | —CF$_3$ | —CF$_3$ | —H |
| J75 (a and b) | S | —CF$_3$ | —OCH$_3$ | —H |
| J76 (a and b) | S | —CF$_3$ | —OCH$_2$CH$_3$ | —H |
| J77 (a and b) | S | —CF$_3$ | —OCF$_3$ | —H |
| J78 (a and b) | S | —CF$_3$ | -tert-butyl | —H |
| J79 (a and b) | S | —CF$_3$ | -iso-propyl | —H |
| J80 (a and b) | S | —CF$_3$ | —CH$_3$ | —CH$_3$ |
| J81 (a and b) | S | —CF$_3$ | —H | —H |
| J82 (a and b) | S | —CF$_3$ | —H | —Cl |
| J83 (a and b) | S | —CF$_3$ | —H | —Br |
| J84 (a and b) | S | —CF$_3$ | —H | —F |
| J85 (a and b) | S | —CF$_3$ | —H | —CH$_3$ |
| J86 (a and b) | S | —CF$_3$ | —H | —CF$_3$ |
| J87 (a and b) | S | —CF$_3$ | —H | —OCH$_3$ |
| J88 (a and b) | S | —CF$_3$ | —H | —OCH$_2$CH$_3$ |
| J89 (a and b) | S | —CF$_3$ | —H | —OCF$_3$ |
| J90 (a and b) | S | —CF$_3$ | —H | -tert-butyl |
| J91 (a and b) | S | —CF$_3$ | —H | -iso-propyl |
| J92 (a and b) | S | —CHF$_2$ | —Cl | —H |
| J93 (a and b) | S | —CHF$_2$ | —Br | —H |
| J94 (a and b) | S | —CHF$_2$ | —F | —H |
| J95 (a and b) | S | —CHF$_2$ | —CH$_3$ | —H |
| J96 (a and b) | S | —CHF$_2$ | —CF$_3$ | —H |
| J97 (a and b) | S | —CHF$_2$ | —OCH$_3$ | —H |
| J98 (a and b) | S | —CHF$_2$ | —OCH$_2$CH$_3$ | —H |
| J99 (a and b) | S | —CHF$_2$ | —OCF$_3$ | —H |
| J100 (a and b) | S | —CHF$_2$ | -tert-butyl | —H |
| J101 (a and b) | S | —CHF$_2$ | -iso-propyl | —H |
| J102 (a and b) | S | —CHF$_2$ | —CH$_3$ | —CH$_3$ |
| J103 (a and b) | S | —CHF$_2$ | —H | —H |
| J104 (a and b) | S | —CHF$_2$ | —H | —Cl |
| J105 (a and b) | S | —CHF$_2$ | —H | —Br |
| J106 (a and b) | S | —CHF$_2$ | —H | —F |
| J107 (a and b) | S | —CHF$_2$ | —H | —CH$_3$ |
| J108 (a and b) | S | —CHF$_2$ | —H | —CF$_3$ |
| J109 (a and b) | S | —CHF$_2$ | —H | —OCH$_3$ |
| J110 (a and b) | S | —CHF$_2$ | —H | —OCH$_2$CH$_3$ |
| J111 (a and b) | S | —CHF$_2$ | —H | —OCF$_3$ |
| J112 (a and b) | S | —CHF$_2$ | —H | -tert-butyl |
| J113 (a and b) | S | —CHF$_2$ | —H | -iso-propyl |
| J114 (a and b) | S | —OH | —Cl | —H |
| J115 (a and b) | S | —OH | —Br | —H |
| J116 (a and b) | S | —OH | —F | —H |
| J117 (a and b) | S | —OH | —CH$_3$ | —H |
| J118 (a and b) | S | —OH | —CF$_3$ | —H |
| J119 (a and b) | S | —OH | —OCH$_3$ | —H |
| J120 (a and b) | S | —OH | —OCH$_2$CH$_3$ | —H |
| J121 (a and b) | S | —OH | —OCF$_3$ | —H |
| J122 (a and b) | S | —OH | -tert-butyl | —H |
| J123 (a and b) | S | —OH | -iso-propyl | —H |
| J124 (a and b) | S | —OH | —CH$_3$ | —CH$_3$ |
| J125 (a and b) | S | —OH | —H | —H |
| J126 (a and b) | S | —OH | —H | —Cl |
| J127 (a and b) | S | —OH | —H | —Br |
| J128 (a and b) | S | —OH | —H | —F |
| J129 (a and b) | S | —OH | —H | —CH$_3$ |
| J130 (a and b) | S | —OH | —H | —CF$_3$ |
| J131 (a and b) | S | —OH | —H | —OCH$_3$ |
| J132 (a and b) | S | —OH | —H | —OCH$_2$CH$_3$ |
| J133 (a and b) | S | —OH | —H | —OCF$_3$ |
| J134 (a and b) | S | —OH | —H | -tert-butyl |
| J135 (a and b) | S | —OH | —H | -iso-propyl |
| J136 (a and b) | S | —NO$_2$ | —Cl | —H |
| J137 (a and b) | S | —NO$_2$ | —Br | —H |
| J138 (a and b) | S | —NO$_2$ | —F | —H |
| J139 (a and b) | S | —NO$_2$ | —CH$_3$ | —H |
| J140 (a and b) | S | —NO$_2$ | —CF$_3$ | —H |
| J141 (a and b) | S | —NO$_2$ | —OCH$_3$ | —H |
| J142 (a and b) | S | —NO$_2$ | —OCH$_2$CH$_3$ | —H |
| J143 (a and b) | S | —NO$_2$ | —OCF$_3$ | —H |
| J144 (a and b) | S | —NO$_2$ | -tert-butyl | —H |
| J145 (a and b) | S | —NO$_2$ | -iso-propyl | —H |
| J146 (a and b) | S | —NO$_2$ | —CH$_3$ | —CH$_3$ |
| J147 (a and b) | S | —NO$_2$ | —H | —H |
| J148 (a and b) | S | —NO$_2$ | —H | —Cl |
| J149 (a and b) | S | —NO$_2$ | —H | —Br |
| J150 (a and b) | S | —NO$_2$ | —H | —F |
| J151 (a and b) | S | —NO$_2$ | —H | —CH$_3$ |

TABLE 10-continued

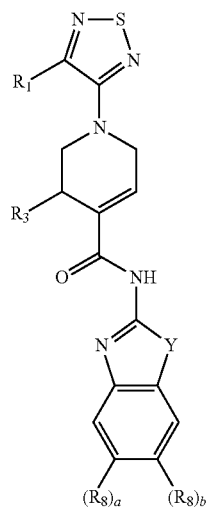

(Ij)

and pharmaceutically acceptable salts thereof, wherein:

| Compound | Y | R$_1$ | (R$_8$)$_a$ | (R$_8$)$_b$ |
|---|---|---|---|---|
| J152 (a and b) | S | —NO$_2$ | —H | —CF$_3$ |
| J153 (a and b) | S | —NO$_2$ | —H | —OCH$_3$ |
| J154 (a and b) | S | —NO$_2$ | —H | —OCH$_2$CH$_3$ |
| J155 (a and b) | S | —NO$_2$ | —H | —OCF$_3$ |
| J156 (a and b) | S | —NO$_2$ | —H | -tert-butyl |
| J157 (a and b) | S | —NO$_2$ | —H | -iso-propyl |
| J158 (a and b) | S | —CN | —Br | —H |
| J159 (a and b) | S | —CN | —Cl | —H |
| J160 (a and b) | S | —CN | —F | —H |
| J161 (a and b) | S | —CN | —CH$_3$ | —H |
| J162 (a and b) | S | —CN | —CF$_3$ | —H |
| J163 (a and b) | S | —CN | —OCH$_3$ | —H |
| J164 (a and b) | S | —CN | —OCH$_2$CH$_3$ | —H |
| J165 (a and b) | S | —CN | —OCF$_3$ | —H |
| J166 (a and b) | S | —CN | -tert-butyl | —H |
| J167 (a and b) | S | —CN | -iso-propyl | —H |
| J168 (a and b) | S | —CN | —CH$_3$ | —CH$_3$ |
| J169 (a and b) | S | —CN | —H | —H |
| J170 (a and b) | S | —CN | —H | —Cl |
| J171 (a and b) | S | —CN | —H | —Br |
| J172 (a and b) | S | —CN | —H | —F |
| J173 (a and b) | S | —CN | —H | —CH$_3$ |
| J174 (a and b) | S | —CN | —H | —CF$_3$ |
| J175 (a and b) | S | —CN | —H | —OCH$_3$ |
| J176 (a and b) | S | —CN | —H | —OCH$_2$CH$_3$ |
| J177 (a and b) | S | —CN | —H | —OCF$_3$ |
| J178 (a and b) | S | —CN | —H | -tert-butyl |
| J179 (a and b) | S | —CN | —H | -iso-propyl |
| J180 (a and b) | S | —Br | —Br | —H |
| J181 (a and b) | S | —Br | —Cl | —H |
| J182 (a and b) | S | —Br | —F | —H |
| J183 (a and b) | S | —Br | —CH$_3$ | —H |
| J184 (a and b) | S | —Br | —CF$_3$ | —H |
| J185 (a and b) | S | —Br | —OCH$_3$ | —H |
| J186 (a and b) | S | —Br | —OCH$_2$CH$_3$ | —H |
| J187 (a and b) | S | —Br | —OCF$_3$ | —H |
| J188 (a and b) | S | —Br | -tert-butyl | —H |
| J189 (a and b) | S | —Br | -iso-propyl | —H |
| J190 (a and b) | S | —Br | —CH$_3$ | —CH$_3$ |
| J191 (a and b) | S | —Br | —H | —H |
| J192 (a and b) | S | —Br | —H | —Cl |
| J193 (a and b) | S | —Br | —H | —Br |
| J194 (a and b) | S | —Br | —H | —F |
| J195 (a and b) | S | —Br | —H | —CH$_3$ |
| J196 (a and b) | S | —Br | —H | —CF$_3$ |
| J197 (a and b) | S | —Br | —H | —OCH$_3$ |
| J198 (a and b) | S | —Br | —H | —OCH$_2$CH$_3$ |
| J199 (a and b) | S | —Br | —H | —OCF$_3$ |
| J200 (a and b) | S | —Br | —H | -tert-butyl |
| J201 (a and b) | S | —Br | —H | -iso-propyl |
| J202 (a and b) | S | —I | —Cl | —H |
| J203 (a and b) | S | —I | —Br | —H |
| J204 (a and b) | S | —I | —F | —H |
| J205 (a and b) | S | —I | —CH$_3$ | —H |
| J206 (a and b) | S | —I | —CF$_3$ | —H |
| J207 (a and b) | S | —I | —OCH$_3$ | —H |
| J208 (a and b) | S | —I | —OCH$_2$CH$_3$ | —H |
| J209 (a and b) | S | —I | —OCF$_3$ | —H |
| J210 (a and b) | S | —I | -tert-butyl | —H |
| J211 (a and b) | S | —I | -iso-propyl | —H |
| J212 (a and b) | S | —I | —CH$_3$ | —CH$_3$ |
| J213 (a and b) | S | —I | —H | —H |
| J214 (a and b) | S | —I | —H | —Cl |
| J215 (a and b) | S | —I | —H | —Br |
| J216 (a and b) | S | —I | —H | —F |
| J217 (a and b) | S | —I | —H | —CH$_3$ |
| J218 (a and b) | S | —I | —H | —CF$_3$ |
| J219 (a and b) | S | —I | —H | —OCH$_3$ |
| J220 (a and b) | S | —I | —H | —OCH$_2$CH$_3$ |
| J221 (a and b) | S | —I | —H | —OCF$_3$ |
| J222 (a and b) | S | —I | —H | -tert-butyl |
| J223 (a and b) | S | —I | —H | -iso-propyl |
| J224 (a and b) | O | —H | —Cl | —H |
| J225 (a and b) | O | —H | —Br | —H |
| J226 (a and b) | O | —H | —F | —H |
| J227 (a and b) | O | —H | —CH$_3$ | —H |
| J228 (a and b) | O | —H | —CF$_3$ | —H |
| J229 (a and b) | O | —H | —OCH$_3$ | —H |
| J230 (a and b) | O | —H | —OCH$_2$CH$_3$ | —H |
| J231 (a and b) | O | —H | —OCF$_3$ | —H |
| J232 (a and b) | O | —H | -tert-butyl | —H |
| J233 (a and b) | O | —H | -iso-propyl | —H |
| J234 (a and b) | O | —H | —CH$_3$ | —CH$_3$ |
| J235 (a and b) | O | —H | —H | —H |
| J236 (a and b) | O | —H | —H | —Cl |
| J237 (a and b) | O | —H | —H | —Br |
| J238 (a and b) | O | —H | —H | —F |
| J239 (a and b) | O | —H | —H | —CH$_3$ |
| J240 (a and b) | O | —H | —H | —CF$_3$ |
| J241 (a and b) | O | —H | —H | —OCH$_3$ |
| J242 (a and b) | O | —H | —H | —OCH$_2$CH$_3$ |
| J243 (a and b) | O | —H | —H | —OCF$_3$ |
| J244 (a and b) | O | —H | —H | -tert-butyl |
| J245 (a and b) | O | —H | —H | -iso-propyl |
| J246 (a and b) | O | —Cl | —Cl | —H |
| J247 (a and b) | O | —Cl | —Br | —H |
| J248 (a and b) | O | —Cl | —F | —H |
| J249 (a and b) | O | —Cl | —CH$_3$ | —H |
| J250 (a and b) | O | —Cl | —CF$_3$ | —H |
| J251 (a and b) | O | —Cl | —OCH$_3$ | —H |

TABLE 10-continued

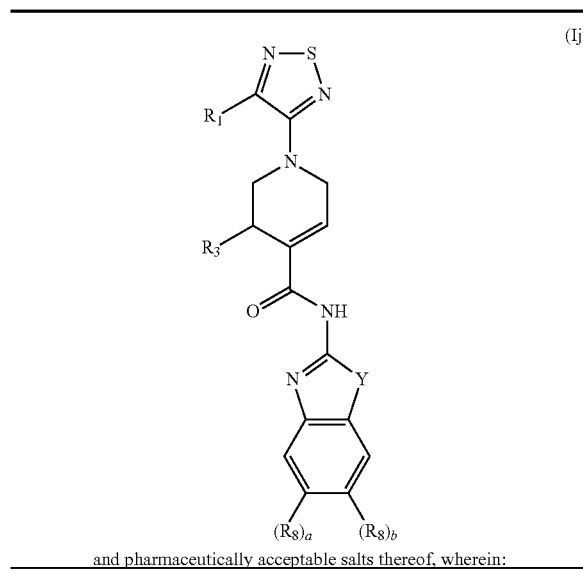

and pharmaceutically acceptable salts thereof, wherein:

| Compound | Y | $R_1$ | $(R_8)_a$ | $(R_8)_b$ |
|---|---|---|---|---|
| J252 (a and b) | O | —Cl | —OCH$_2$CH$_3$ | —H |
| J253 (a and b) | O | —Cl | —OCF$_3$ | —H |
| J254 (a and b) | O | —Cl | -tert-butyl | —H |
| J255 (a and b) | O | —Cl | -iso-propyl | —H |
| J256 (a and b) | O | —Cl | —CH$_3$ | —CH$_3$ |
| J257 (a and b) | O | —Cl | —H | —H |
| J258 (a and b) | O | —Cl | —H | —Cl |
| J259 (a and b) | O | —Cl | —H | —Br |
| J260 (a and b) | O | —Cl | —H | —F |
| J261 (a and b) | O | —Cl | —H | —CH$_3$ |
| J262 (a and b) | O | —Cl | —H | —CF$_3$ |
| J263 (a and b) | O | —Cl | —H | —OCH$_3$ |
| J264 (a and b) | O | —Cl | —H | —OCH$_2$CH$_3$ |
| J265 (a and b) | O | —Cl | —H | —OCF$_3$ |
| J266 (a and b) | O | —Cl | —H | -tert-butyl |
| J267 (a and b) | O | —Cl | —H | -iso-propyl |
| J268 (a and b) | O | —Cl | —H | —OCF$_3$ |
| J269 (a and b) | O | —Cl | —H | -tert-butyl |
| J270 (a and b) | O | —Cl | —H | -iso-propyl |
| J271 (a and b) | O | —CH$_3$ | —Cl | —H |
| J272 (a and b) | O | —CH$_3$ | —Br | —H |
| J273 (a and b) | O | —CH$_3$ | —F | —H |
| J274 (a and b) | O | —CH$_3$ | —CH$_3$ | —H |
| J275 (a and b) | O | —CH$_3$ | —CF$_3$ | —H |
| J276 (a and b) | O | —CH$_3$ | —OCH$_3$ | —H |
| J277 (a and b) | O | —CH$_3$ | —OCH$_2$CH$_3$ | —H |
| J278 (a and b) | O | —CH$_3$ | —OCF$_3$ | —H |
| J279 (a and b) | O | —CH$_3$ | -tert-butyl | —H |
| J280 (a and b) | O | —CH$_3$ | -iso-propyl | —H |
| J281 (a and b) | O | —CH$_3$ | —CH$_3$ | —CH$_3$ |
| J282 (a and b) | O | —CH$_3$ | —H | —H |
| J283 (a and b) | O | —CH$_3$ | —H | —Cl |
| J284 (a and b) | O | —CH$_3$ | —H | —Br |
| J285 (a and b) | O | —CH$_3$ | —H | —F |
| J286 (a and b) | O | —CH$_3$ | —H | —CH$_3$ |
| J287 (a and b) | O | —CH$_3$ | —H | —CF$_3$ |
| J288 (a and b) | O | —CH$_3$ | —H | —OCH$_3$ |
| J289 (a and b) | O | —CH$_3$ | —H | —OCH$_2$CH$_3$ |
| J290 (a and b) | O | —CH$_3$ | —H | —OCF$_3$ |
| J291 (a and b) | O | —CH$_3$ | —H | -tert-butyl |
| J292 (a and b) | O | —CH$_3$ | —H | -iso-propyl |
| J293 (a and b) | O | —CF$_3$ | —Cl | —H |
| J294 (a and b) | O | —CF$_3$ | —Br | —H |
| J295 (a and b) | O | —CF$_3$ | —F | —H |
| J296 (a and b) | O | —CF$_3$ | —CH$_3$ | —H |
| J297 (a and b) | O | —CF$_3$ | —CF$_3$ | —H |
| J298 (a and b) | O | —CF$_3$ | —OCH$_3$ | —H |
| J299 (a and b) | O | —CF$_3$ | —OCH$_2$CH$_3$ | —H |
| J300 (a and b) | O | —CF$_3$ | —OCF$_3$ | —H |
| J301 (a and b) | O | —CF$_3$ | -tert-butyl | —H |

TABLE 10-continued

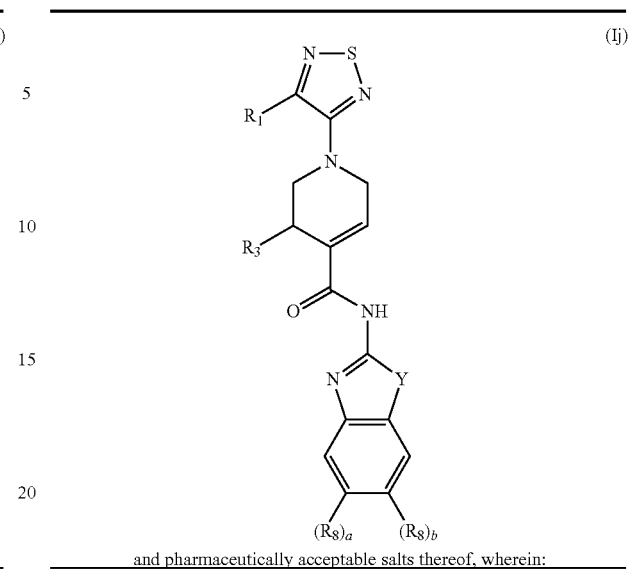

and pharmaceutically acceptable salts thereof, wherein:

| Compound | Y | $R_1$ | $(R_8)_a$ | $(R_8)_b$ |
|---|---|---|---|---|
| J302 (a and b) | O | —CF$_3$ | -iso-propyl | —H |
| J303 (a and b) | O | —CF$_3$ | —CH$_3$ | —CH$_3$ |
| J304 (a and b) | O | —CF$_3$ | —H | —H |
| J305 (a and b) | O | —CF$_3$ | —H | —Cl |
| J306 (a and b) | O | —CF$_3$ | —H | —Br |
| J307 (a and b) | O | —CF$_3$ | —H | —F |
| J308 (a and b) | O | —CF$_3$ | —H | —CH$_3$ |
| J309 (a and b) | O | —CF$_3$ | —H | —CF$_3$ |
| J310 (a and b) | O | —CF$_3$ | —H | —OCH$_3$ |
| J311 (a and b) | O | —CF$_3$ | —H | —OCH$_2$CH$_3$ |
| J312 (a and b) | O | —CF$_3$ | —H | —OCF$_3$ |
| J313 (a and b) | O | —CF$_3$ | —H | -tert-butyl |
| J314 (a and b) | O | —CF$_3$ | —H | -iso-propyl |
| J315 (a and b) | O | —CHF$_2$ | —Cl | —H |
| J316 (a and b) | O | —CHF$_2$ | —Br | —H |
| J317 (a and b) | O | —CHF$_2$ | —F | —H |
| J318 (a and b) | O | —CHF$_2$ | —CH$_3$ | —H |
| J319 (a and b) | O | —CHF$_2$ | —CF$_3$ | —H |
| J320 (a and b) | O | —CHF$_2$ | —OCH$_3$ | —H |
| J321 (a and b) | O | —CHF$_2$ | —OCH$_2$CH$_3$ | —H |
| J322 (a and b) | O | —CHF$_2$ | —OCF$_3$ | —H |
| J323 (a and b) | O | —CHF$_2$ | -tert-butyl | —H |
| J324 (a and b) | O | —CHF$_2$ | -iso-propyl | —H |
| J325 (a and b) | O | —CHF$_2$ | —CH$_3$ | —CH$_3$ |
| J326 (a and b) | O | —CHF$_2$ | —H | —H |
| J327 (a and b) | O | —CHF$_2$ | —H | —Cl |
| J328 (a and b) | O | —CHF$_2$ | —H | —Br |
| J329 (a and b) | O | —CHF$_2$ | —H | —F |
| J330 (a and b) | O | —CHF$_2$ | —H | —CH$_3$ |
| J331 (a and b) | O | —CHF$_2$ | —H | —CF$_3$ |
| J332 (a and b) | O | —CHF$_2$ | —H | —OCH$_3$ |
| J333 (a and b) | O | —CHF$_2$ | —H | —OCH$_2$CH$_3$ |
| J334 (a and b) | O | —CHF$_2$ | —H | —OCF$_3$ |
| J335 (a and b) | O | —CHF$_2$ | —H | -tert-butyl |
| J336 (a and b) | O | —CHF$_2$ | —H | -iso-propyl |
| J337 (a and b) | O | —OH | —Cl | —H |
| J338 (a and b) | O | —OH | —Br | —H |
| J339 (a and b) | O | —OH | —F | —H |
| J340 (a and b) | O | —OH | —CH$_3$ | —H |
| J341 (a and b) | O | —OH | —CF$_3$ | —H |
| J342 (a and b) | O | —OH | —OCH$_3$ | —H |
| J343 (a and b) | O | —OH | —OCH$_2$CH$_3$ | —H |
| J344 (a and b) | O | —OH | —OCF$_3$ | —H |
| J345 (a and b) | O | —OH | -tert-butyl | —H |
| J346 (a and b) | O | —OH | -iso-propyl | —H |
| J347 (a and b) | O | —OH | —CH$_3$ | —CH$_3$ |
| J348 (a and b) | O | —OH | —H | —H |
| J349 (a and b) | O | —OH | —H | —Cl |
| J350 (a and b) | O | —OH | —H | —Br |
| J351 (a and b) | O | —OH | —H | —F |

TABLE 10-continued

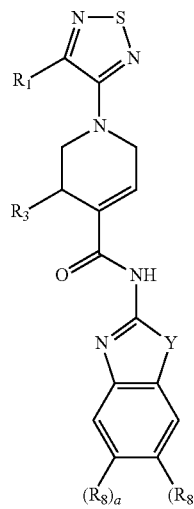

(Ij)

and pharmaceutically acceptable salts thereof, wherein:

| Compound | Y | $R_1$ | $(R_8)_a$ | $(R_8)_b$ |
|---|---|---|---|---|
| J352 (a and b) | O | —OH | —H | —CH₃ |
| J353 (a and b) | O | —OH | —H | —CF₃ |
| J354 (a and b) | O | —OH | —H | —OCH₃ |
| J355 (a and b) | O | —OH | —H | —OCH₂CH₃ |
| J356 (a and b) | O | —OH | —H | —OCF₃ |
| J357 (a and b) | O | —OH | —H | -tert-butyl |
| J358 (a and b) | O | —OH | —H | -iso-propyl |
| J359 (a and b) | O | —NO₂ | —Cl | —H |
| J360 (a and b) | O | —NO₂ | —Br | —H |
| J361 (a and b) | O | —NO₂ | —F | —H |
| J362 (a and b) | O | —NO₂ | —CH₃ | —H |
| J363 (a and b) | O | —NO₂ | —CF₃ | —H |
| J364 (a and b) | O | —NO₂ | —OCH₃ | —H |
| J365 (a and b) | O | —NO₂ | —OCH₂CH₃ | —H |
| J366 (a and b) | O | —NO₂ | —OCF₃ | —H |
| J367 (a and b) | O | —NO₂ | -tert-butyl | —H |
| J368 (a and b) | O | —NO₂ | -iso-propyl | —H |
| J369 (a and b) | O | —NO₂ | —CH₃ | —CH₃ |
| J370 (a and b) | O | —NO₂ | —H | —H |
| J371 (a and b) | O | —NO₂ | —H | —Cl |
| J372 (a and b) | O | —NO₂ | —H | —Br |
| J373 (a and b) | O | —NO₂ | —H | —F |
| J374 (a and b) | O | —NO₂ | —H | —CH₃ |
| J375 (a and b) | O | —NO₂ | —H | —CF₃ |
| J376 (a and b) | O | —NO₂ | —H | —OCH₃ |
| J377 (a and b) | O | —NO₂ | —H | —OCH₂CH₃ |
| J378 (a and b) | O | —NO₂ | —H | —OCF₃ |
| J379 (a and b) | O | —NO₂ | —H | -tert-butyl |
| J380 (a and b) | O | —NO₂ | —H | -iso-propyl |
| J381 (a and b) | O | —CN | —Br | —H |
| J382 (a and b) | O | —CN | —Cl | —H |
| J383 (a and b) | O | —CN | —F | —H |
| J384 (a and b) | O | —CN | —CH₃ | —H |
| J385 (a and b) | O | —CN | —CF₃ | —H |
| J386 (a and b) | O | —CN | —OCH₃ | —H |
| J387 (a and b) | O | —CN | —OCH₂CH₃ | —H |
| J388 (a and b) | O | —CN | —OCF₃ | —H |
| J389 (a and b) | O | —CN | -tert-butyl | —H |
| J390 (a and b) | O | —CN | -iso-propyl | —H |
| J391 (a and b) | O | —CN | —CH₃ | —CH₃ |
| J392 (a and b) | O | —CN | —H | —H |
| J393 (a and b) | O | —CN | —H | —Cl |
| J394 (a and b) | O | —CN | —H | —Br |
| J395 (a and b) | O | —CN | —H | —F |
| J396 (a and b) | O | —CN | —H | —CH₃ |
| J397 (a and b) | O | —CN | —H | —CF₃ |
| J398 (a and b) | O | —CN | —H | —OCH₃ |
| J399 (a and b) | O | —CN | —H | —OCH₂CH₃ |
| J400 (a and b) | O | —CN | —H | —OCF₃ |
| J401 (a and b) | O | —CN | —H | -tert-butyl |
| J402 (a and b) | O | —CN | —H | -iso-propyl |
| J403 (a and b) | O | —Br | —Br | —H |
| J404 (a and b) | O | —Br | —Cl | —H |
| J405 (a and b) | O | —Br | —F | —H |
| J406 (a and b) | O | —Br | —CH₃ | —H |
| J407 (a and b) | O | —Br | —CF₃ | —H |
| J408 (a and b) | O | —Br | —OCH₃ | —H |
| J409 (a and b) | O | —Br | —OCH₂CH₃ | —H |
| J410 (a and b) | O | —Br | —OCF₃ | —H |
| J411 (a and b) | O | —Br | -tert-butyl | —H |
| J412 (a and b) | O | —Br | -iso-propyl | —H |
| J413 (a and b) | O | —Br | —CH₃ | —CH₃ |
| J414 (a and b) | O | —Br | —H | —H |
| J415 (a and b) | O | —Br | —H | —Cl |
| J416 (a and b) | O | —Br | —H | —Br |
| J417 (a and b) | O | —Br | —H | —F |
| J418 (a and b) | O | —Br | —H | —CH₃ |
| J419 (a and b) | O | —Br | —H | —CF₃ |
| J420 (a and b) | O | —Br | —H | —OCH₃ |
| J421 (a and b) | O | —Br | —H | —OCH₂CH₃ |
| J422 (a and b) | O | —Br | —H | —OCF₃ |
| J423 (a and b) | O | —Br | —H | -tert-butyl |
| J424 (a and b) | O | —Br | —H | -iso-propyl |
| J425 (a and b) | O | —I | —Cl | —H |
| J426 (a and b) | O | —I | —Br | —H |
| J427 (a and b) | O | —I | —F | —H |
| J428 (a and b) | O | —I | —CH₃ | —H |
| J429 (a and b) | O | —I | —CF₃ | —H |
| J430 (a and b) | O | —I | —OCH₃ | —H |
| J431 (a and b) | O | —I | —OCH₂CH₃ | —H |
| J432 (a and b) | O | —I | —OCF₃ | —H |
| J433 (a and b) | O | —I | -tert-butyl | —H |
| J434 (a and b) | O | —I | -iso-propyl | —H |
| J435 (a and b) | O | —I | —CH₃ | —CH₃ |
| J436 (a and b) | O | —I | —H | —H |
| J437 (a and b) | O | —I | —H | —Cl |
| J438 (a and b) | O | —I | —H | —Br |
| J439 (a and b) | O | —I | —H | —F |

TABLE 10-continued

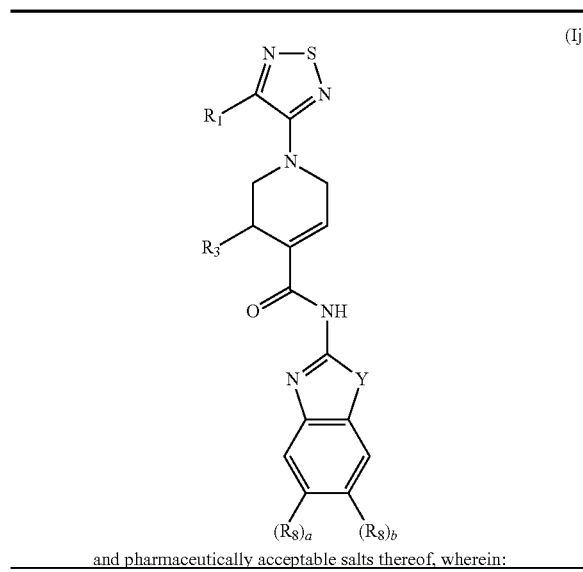

(Ij)

and pharmaceutically acceptable salts thereof, wherein:

| Compound | Y | $R_1$ | $(R_8)_a$ | $(R_8)_b$ |
|---|---|---|---|---|
| J440 (a and b) | O | —I | —H | —$CH_3$ |
| J441 (a and b) | O | —I | —H | —$CF_3$ |
| J442 (a and b) | O | —I | —H | —$OCH_3$ |
| J443 (a and b) | O | —I | —H | —$OCH_2CH_3$ |
| J444 (a and b) | O | —I | —H | —$OCF_3$ |
| J445 (a and b) | O | —I | —H | -tert-butyl |
| J446 (a and b) | O | —I | —H | -iso-propyl |
| J447 (a and b) | NH | —H | —Cl | —H |
| J448 (a and b) | NH | —H | —Br | —H |
| J449 (a and b) | NH | —H | —F | —H |
| J450 (a and b) | NH | —H | —$CH_3$ | —H |
| J451 (a and b) | NH | —H | —$CF_3$ | —H |
| J452 (a and b) | NH | —H | —$OCH_3$ | —H |
| J453 (a and b) | NH | —H | —$OCH_2CH_3$ | —H |
| J454 (a and b) | NH | —H | —$OCF_3$ | —H |
| J455 (a and b) | NH | —H | -tert-butyl | —H |
| J456 (a and b) | NH | —H | -iso-propyl | —H |
| J457 (a and b) | NH | —H | —$CH_3$ | —$CH_3$ |
| J458 (a and b) | NH | —H | —H | —H |
| J459 (a and b) | NH | —H | —H | —Cl |
| J460 (a and b) | NH | —H | —H | —Br |
| J461 (a and b) | NH | —H | —H | —F |
| J462 (a and b) | NH | —H | —H | —$CH_3$ |
| J463 (a and b) | NH | —H | —H | —$CF_3$ |
| J464 (a and b) | NH | —H | —H | —$OCH_3$ |
| J465 (a and b) | NH | —H | —H | —$OCH_2CH_3$ |
| J466 (a and b) | NH | —H | —H | —$OCF_3$ |
| J467 (a and b) | NH | —H | —H | -tert-butyl |
| J468 (a and b) | NH | —H | —H | -iso-propyl |
| J469 (a and b) | NH | —Cl | —Cl | —H |
| J470 (a and b) | NH | —Cl | —Br | —H |
| J471 (a and b) | NH | —Cl | —F | —H |
| J472 (a and b) | NH | —Cl | —$CH_3$ | —H |
| J473 (a and b) | NH | —Cl | —$CF_3$ | —H |
| J474 (a and b) | NH | —Cl | —$OCH_3$ | —H |
| J475 (a and b) | NH | —Cl | —$OCH_2CH_3$ | —H |
| J476 (a and b) | NH | —Cl | —$OCF_3$ | —H |
| J477 (a and b) | NH | —Cl | -tert-butyl | —H |
| J478 (a and b) | NH | —Cl | -iso-propyl | —H |
| J479 (a and b) | NH | —Cl | —$CH_3$ | —$CH_3$ |
| J480 (a and b) | NH | —Cl | —H | —H |
| J481 (a and b) | NH | —Cl | —H | —Cl |
| J482 (a and b) | NH | —Cl | —H | —Br |
| J483 (a and b) | NH | —Cl | —H | —F |
| J484 (a and b) | NH | —Cl | —H | —$CH_3$ |
| J485 (a and b) | NH | —Cl | —H | —$CF_3$ |
| J486 (a and b) | NH | —Cl | —H | —$OCH_3$ |
| J487 (a and b) | NH | —Cl | —H | —$OCH_2CH_3$ |
| J488 (a and b) | NH | —Cl | —H | —$OCF_3$ |
| J489 (a and b) | NH | —Cl | —H | -tert-butyl |
| J490 (a and b) | NH | —Cl | —H | -iso-propyl |
| J491 (a and b) | NH | —Cl | —H | —$OCF_3$ |
| J492 (a and b) | NH | —Cl | —H | -tert-butyl |
| J493 (a and b) | NH | —Cl | —H | -iso-propyl |
| J494 (a and b) | NH | —$CH_3$ | —Cl | —H |
| J495 (a and b) | NH | —$CH_3$ | —Br | —H |
| J496 (a and b) | NH | —$CH_3$ | —F | —H |
| J497 (a and b) | NH | —$CH_3$ | —$CH_3$ | —H |
| J498 (a and b) | NH | —$CH_3$ | —$CF_3$ | —H |
| J499 (a and b) | NH | —$CH_3$ | —$OCH_3$ | —H |
| J500 (a and b) | NH | —$CH_3$ | —$OCH_2CH_3$ | —H |
| J501 (a and b) | NH | —$CH_3$ | —$OCF_3$ | —H |
| J502 (a and b) | NH | —$CH_3$ | -tert-butyl | —H |
| J503 (a and b) | NH | —$CH_3$ | -iso-propyl | —H |
| J504 (a and b) | NH | —$CH_3$ | —$CH_3$ | —$CH_3$ |
| J505 (a and b) | NH | —$CH_3$ | —H | —H |
| J506 (a and b) | NH | —$CH_3$ | —H | —Cl |
| J507 (a and b) | NH | —$CH_3$ | —H | —Br |
| J508 (a and b) | NH | —$CH_3$ | —H | —F |
| J509 (a and b) | NH | —$CH_3$ | —H | —$CH_3$ |
| J510 (a and b) | NH | —$CH_3$ | —H | —$CF_3$ |
| J511 (a and b) | NH | —$CH_3$ | —H | —$OCH_3$ |
| J512 (a and b) | NH | —$CH_3$ | —H | —$OCH_2CH_3$ |
| J513 (a and b) | NH | —$CH_3$ | —H | —$OCF_3$ |
| J514 (a and b) | NH | —$CH_3$ | —H | -tert-butyl |
| J515 (a and b) | NH | —$CH_3$ | —H | -iso-propyl |
| J516 (a and b) | NH | —$CF_3$ | —Cl | —H |
| J517 (a and b) | NH | —$CF_3$ | —Br | —H |
| J518 (a and b) | NH | —$CF_3$ | —F | —H |
| J519 (a and b) | NH | —$CF_3$ | —$CH_3$ | —H |
| J520 (a and b) | NH | —$CF_3$ | —$CF_3$ | —H |
| J521 (a and b) | NH | —$CF_3$ | —$OCH_3$ | —H |
| J522 (a and b) | NH | —$CF_3$ | —$OCH_2CH_3$ | —H |
| J523 (a and b) | NH | —$CF_3$ | —$OCF_3$ | —H |
| J524 (a and b) | NH | —$CF_3$ | -tert-butyl | —H |
| J525 (a and b) | NH | —$CF_3$ | -iso-propyl | —H |
| J526 (a and b) | NH | —$CF_3$ | —$CH_3$ | —$CH_3$ |
| J527 (a and b) | NH | —$CF_3$ | —H | —H |
| J528 (a and b) | NH | —$CF_3$ | —H | —Cl |
| J529 (a and b) | NH | —$CF_3$ | —H | —Br |
| J530 (a and b) | NH | —$CF_3$ | —H | —F |
| J531 (a and b) | NH | —$CF_3$ | —H | —$CH_3$ |
| J532 (a and b) | NH | —$CF_3$ | —H | —$CF_3$ |
| J533 (a and b) | NH | —$CF_3$ | —H | —$OCH_3$ |
| J534 (a and b) | NH | —$CF_3$ | —H | —$OCH_2CH_3$ |
| J535 (a and b) | NH | —$CF_3$ | —H | —$OCF_3$ |
| J536 (a and b) | NH | —$CF_3$ | —H | -tert-butyl |
| J537 (a and b) | NH | —$CF_3$ | —H | -iso-propyl |
| J538 (a and b) | NH | —$CHF_2$ | —Cl | —H |
| J539 (a and b) | NH | —$CHF_2$ | —Br | —H |

TABLE 10-continued

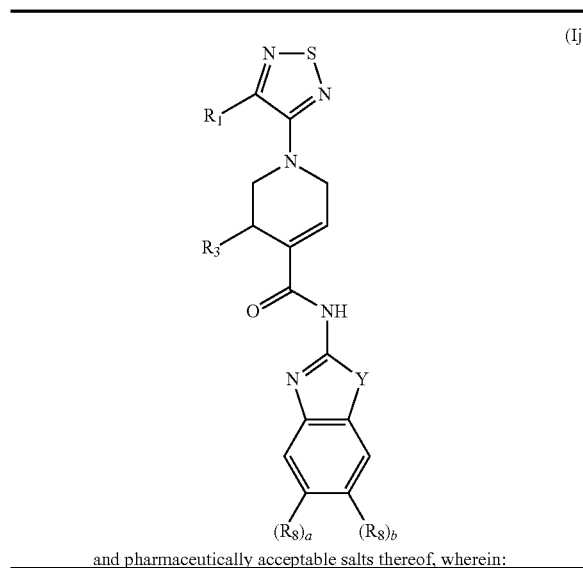

(Ij)

and pharmaceutically acceptable salts thereof, wherein:

| Compound | Y | R₁ | (R₈)ₐ | (R₈)ᵦ |
|---|---|---|---|---|
| J540 (a and b) | NH | —CHF₂ | —F | —H |
| J541 (a and b) | NH | —CHF₂ | —CH₃ | —H |
| J542 (a and b) | NH | —CHF₂ | —CF₃ | —H |
| J543 (a and b) | NH | —CHF₂ | —OCH₃ | —H |
| J544 (a and b) | NH | —CHF₂ | —OCH₂CH₃ | —H |
| J545 (a and b) | NH | —CHF₂ | —OCF₃ | —H |
| J546 (a and b) | NH | —CHF₂ | -tert-butyl | —H |
| J547 (a and b) | NH | —CHF₂ | -iso-propyl | —H |
| J548 (a and b) | NH | —CHF₂ | —CH₃ | —CH₃ |
| J549 (a and b) | NH | —CHF₂ | —H | —H |
| J550 (a and b) | NH | —CHF₂ | —H | —Cl |
| J551 (a and b) | NH | —CHF₂ | —H | —Br |
| J552 (a and b) | NH | —CHF₂ | —H | —F |
| J553 (a and b) | NH | —CHF₂ | —H | —CH₃ |
| J554 (a and b) | NH | —CHF₂ | —H | —CF₃ |
| J555 (a and b) | NH | —CHF₂ | —H | —OCH₃ |
| J556 (a and b) | NH | —CHF₂ | —H | —OCH₂CH₃ |
| J557 (a and b) | NH | —CHF₂ | —H | —OCF₃ |
| J558 (a and b) | NH | —CHF₂ | —H | -tert-butyl |
| J559 (a and b) | NH | —CHF₂ | —H | -iso-propyl |
| J560 (a and b) | NH | —OH | —Cl | —H |
| J561 (a and b) | NH | —OH | —Br | —H |
| J562 (a and b) | NH | —OH | —F | —H |
| J563 (a and b) | NH | —OH | —CH₃ | —H |
| J564 (a and b) | NH | —OH | —CF₃ | —H |
| J565 (a and b) | NH | —OH | —OCH₃ | —H |
| J566 (a and b) | NH | —OH | —OCH₂CH₃ | —H |
| J567 (a and b) | NH | —OH | —OCF₃ | —H |
| J568 (a and b) | NH | —OH | -tert-butyl | —H |
| J569 (a and b) | NH | —OH | -iso-propyl | —H |
| J570 (a and b) | NH | —OH | —CH₃ | —CH₃ |
| J571 (a and b) | NH | —OH | —H | —H |
| J572 (a and b) | NH | —OH | —H | —Cl |
| J573 (a and b) | NH | —OH | —H | —Br |
| J574 (a and b) | NH | —OH | —H | —F |
| J575 (a and b) | NH | —OH | —H | —CH₃ |
| J576 (a and b) | NH | —OH | —H | —CF₃ |
| J577 (a and b) | NH | —OH | —H | —OCH₃ |
| J578 (a and b) | NH | —OH | —H | —OCH₂CH₃ |
| J579 (a and b) | NH | —OH | —H | —OCF₃ |
| J580 (a and b) | NH | —OH | —H | -tert-butyl |
| J581 (a and b) | NH | —OH | —H | -iso-propyl |
| J582 (a and b) | NH | —NO₂ | —Cl | —H |
| J583 (a and b) | NH | —NO₂ | —Br | —H |
| J584 (a and b) | NH | —NO₂ | —F | —H |
| J585 (a and b) | NH | —NO₂ | —CH₃ | —H |
| J586 (a and b) | NH | —NO₂ | —CF₃ | —H |
| J587 (a and b) | NH | —NO₂ | —OCH₃ | —H |
| J588 (a and b) | NH | —NO₂ | —OCH₂CH₃ | —H |
| J589 (a and b) | NH | —NO₂ | —OCF₃ | —H |

TABLE 10-continued

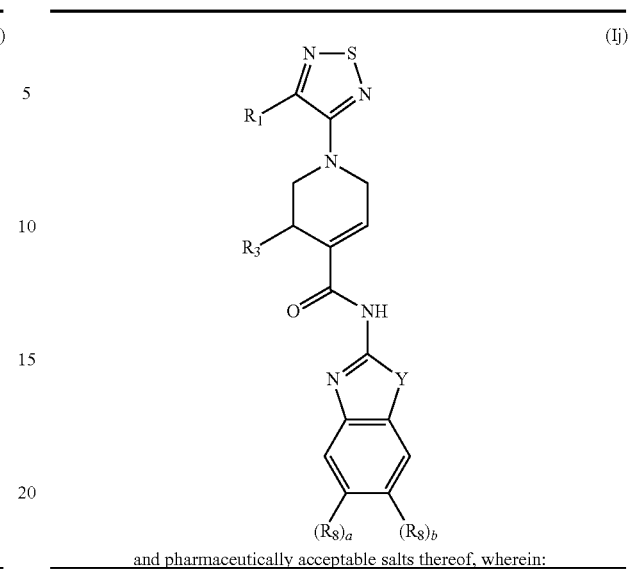

(Ij)

and pharmaceutically acceptable salts thereof, wherein:

| Compound | Y | R₁ | (R₈)ₐ | (R₈)ᵦ |
|---|---|---|---|---|
| J590 (a and b) | NH | —NO₂ | -tert-butyl | —H |
| J591 (a and b) | NH | —NO₂ | -iso-propyl | —H |
| J592 (a and b) | NH | —NO₂ | —CH₃ | —CH₃ |
| J593 (a and b) | NH | —NO₂ | —H | —H |
| J594 (a and b) | NH | —NO₂ | —H | —Cl |
| J595 (a and b) | NH | —NO₂ | —H | —Br |
| J596 (a and b) | NH | —NO₂ | —H | —F |
| J597 (a and b) | NH | —NO₂ | —H | —CH₃ |
| J598 (a and b) | NH | —NO₂ | —H | —CF₃ |
| J599 (a and b) | NH | —NO₂ | —H | —OCH₃ |
| J600 (a and b) | NH | —NO₂ | —H | —OCH₂CH₃ |
| J601 (a and b) | NH | —NO₂ | —H | —OCF₃ |
| J602 (a and b) | NH | —NO₂ | —H | -tert-butyl |
| J603 (a and b) | NH | —NO₂ | —H | -iso-propyl |
| J604 (a and b) | NH | —CN | —Br | —H |
| J605 (a and b) | NH | —CN | —Cl | —H |
| J606 (a and b) | NH | —CN | —F | —H |
| J607 (a and b) | NH | —CN | —CH₃ | —H |
| J608 (a and b) | NH | —CN | —CF₃ | —H |
| J609 (a and b) | NH | —CN | —OCH₃ | —H |
| J610 (a and b) | NH | —CN | —OCH₂CH₃ | —H |
| J611 (a and b) | NH | —CN | —OCF₃ | —H |
| J612 (a and b) | NH | —CN | -tert-butyl | —H |
| J613 (a and b) | NH | —CN | -iso-propyl | —H |
| J614 (a and b) | NH | —CN | —CH₃ | —CH₃ |
| J615 (a and b) | NH | —CN | —H | —H |
| J616 (a and b) | NH | —CN | —H | —Cl |
| J617 (a and b) | NH | —CN | —H | —Br |
| J618 (a and b) | NH | —CN | —H | —F |
| J619 (a and b) | NH | —CN | —H | —CH₃ |
| J620 (a and b) | NH | —CN | —H | —CF₃ |
| J621 (a and b) | NH | —CN | —H | —OCH₃ |
| J622 (a and b) | NH | —CN | —H | —OCH₂CH₃ |
| J623 (a and b) | NH | —CN | —H | —OCF₃ |
| J624 (a and b) | NH | —CN | —H | -tert-butyl |
| J625 (a and b) | NH | —CN | —H | -iso-propyl |
| J626 (a and b) | NH | —Br | —Br | —H |
| J627 (a and b) | NH | —Br | —Cl | —H |
| J628 (a and b) | NH | —Br | —F | —H |
| J629 (a and b) | NH | —Br | —CH₃ | —H |
| J630 (a and b) | NH | —Br | —CF₃ | —H |
| J631 (a and b) | NH | —Br | —OCH₃ | —H |
| J632 (a and b) | NH | —Br | —OCH₂CH₃ | —H |
| J633 (a and b) | NH | —Br | —OCF₃ | —H |
| J634 (a and b) | NH | —Br | -tert-butyl | —H |
| J635 (a and b) | NH | —Br | -iso-propyl | —H |
| J636 (a and b) | NH | —Br | —CH₃ | —CH₃ |
| J637 (a and b) | NH | —Br | —H | —H |
| J638 (a and b) | NH | —Br | —H | —Cl |
| J639 (a and b) | NH | —Br | —H | —Br |

TABLE 10-continued

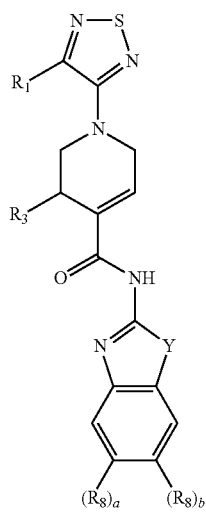

(Ij)

and pharmaceutically acceptable salts thereof, wherein:

| Compound | Y | R$_1$ | (R$_8$)$_a$ | (R$_8$)$_b$ |
|---|---|---|---|---|
| J640 (a and b) | NH | —Br | —H | —F |
| J641 (a and b) | NH | —Br | —H | —CH$_3$ |
| J642 (a and b) | NH | —Br | —H | —CF$_3$ |
| J643 (a and b) | NH | —Br | —H | —OCH$_3$ |
| J644 (a and b) | NH | —Br | —H | —OCH$_2$CH$_3$ |
| J645 (a and b) | NH | —Br | —H | —OCF$_3$ |
| J646 (a and b) | NH | —Br | —H | -tert-butyl |
| J647 (a and b) | NH | —Br | —H | -iso-propyl |
| J648 (a and b) | NH | —I | —Cl | —H |
| J649 (a and b) | NH | —I | —Br | —H |
| J650 (a and b) | NH | —I | —F | —H |
| J651 (a and b) | NH | —I | —CH$_3$ | —H |
| J652 (a and b) | NH | —I | —CF$_3$ | —H |
| J653 (a and b) | NH | —I | —OCH$_3$ | —H |
| J654 (a and b) | NH | —I | —OCH$_2$CH$_3$ | —H |
| J655 (a and b) | NH | —I | —OCF$_3$ | —H |
| J656 (a and b) | NH | —I | -tert-butyl | —H |
| J657 (a and b) | NH | —I | -iso-propyl | —H |
| J658 (a and b) | NH | —I | —CH$_3$ | —CH$_3$ |
| J659 (a and b) | NH | —I | —H | —H |
| J660 (a and b) | NH | —I | —H | —Cl |
| J661 (a and b) | NH | —I | —H | —Br |
| J662 (a and b) | NH | —I | —H | —F |
| J663 (a and b) | NH | —I | —H | —CH$_3$ |
| J664 (a and b) | NH | —I | —H | —CF$_3$ |
| J665 (a and b) | NH | —I | —H | —OCH$_3$ |
| J666 (a and b) | NH | —I | —H | —OCH$_2$CH$_3$ |
| J667 (a and b) | NH | —I | —H | —OCF$_3$ |
| J668 (a and b) | NH | —I | —H | -tert-butyl |
| J669 (a and b) | NH | —I | —H | -iso-propyl |

(a) means that R$_3$ is —H.
(b) means that R$_3$ is —CH$_3$.

TABLE 11

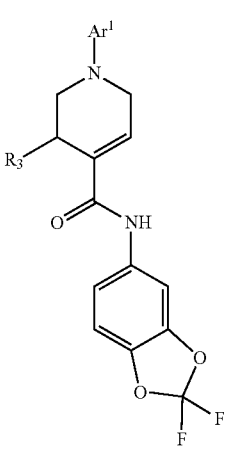

(Ik)

and pharmaceutically acceptable salts thereof, wherein:

| Compound | Ar$^1$ |
|---|---|
| K1 (a and b) | -2-(3-chloropyridyl) |
| K2 (a and b) | -2-(3-fluoropyridyl) |
| K3 (a and b) | -2-(3-methylpyridyl) |
| K4 (a and b) | -2-(3-CF$_3$-pyridyl) |
| K5 (a and b) | -2-(3-CHF$_2$-pyridyl) |
| K6 (a and b) | -2-(3-hydroxypyridyl) |
| K7 (a and b) | -2-(3-nitropyridyl) |
| K8 (a and b) | -2-(3-cyanopyridyl) |
| K9 (a and b) | -2-(3-bromopyridyl) |
| K10 (a and b) | -2-(3-iodopyridyl) |
| K11 (a and b) | -4-(5-chloropyrimidinyl) |
| K12 (a and b) | -4-(5-methylpyrimidinyl) |
| K13 (a and b) | -4-(5-fluoropyrimidinyl) |
| K14 (a and b) | -2-(3-chloropyrazinyl) |
| K15 (a and b) | -2-(3-methylpyrazinyl) |
| K16 (a and b) | -2-(3-fluoropyrazinyl) |
| K17 (a and b) | -3-(4-chloropyridazinyl) |
| K18 (a and b) | -3-(4-methylpyridazinyl) |
| K19 (a and b) | -3-(4-fluoropyridazinyl) |
| K20 (a and b) | -5-(4-chlorothiadiazolyl) |
| K21 (a and b) | -5-(4-methylthiadiazolyl) |
| K22 (a and b) | -5-(4-fluorothiadiazolyl) |

(a) means that R$_3$ is —H.
(b) means that R$_3$ is —CH$_3$.

TABLE 12

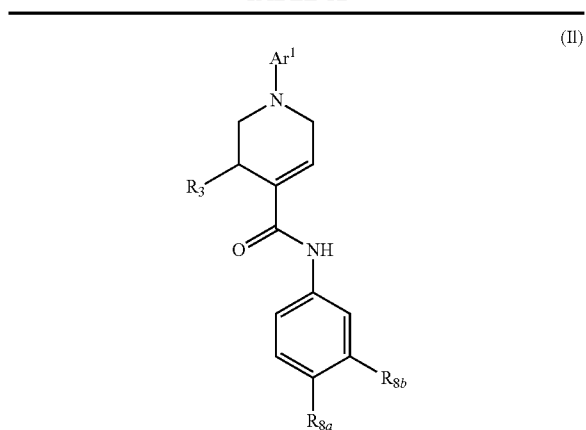

and pharmaceutically acceptable salts thereof, wherein:

| Compound | Ar¹ | $R_{8a}$ | $R_{8b}$ |
|---|---|---|---|
| L1 (a and b) | -2-(3-chloropyridyl) | —Cl | —CF$_3$ |
| L2 (a and b) | -2-(3-chloropyridyl) | —CF$_3$ | —Cl |
| L3 (a and b) | -2-(3-chloropyridyl) | —CH$_3$ | —CF$_3$ |
| L4 (a and b) | -2-(3-chloropyridyl) | —SCF$_3$ | —Cl |
| L5 (a and b) | -2-(3-chloropyridyl) | —F | —CF$_3$ |
| L6 (a and b) | -2-(3-chloropyridyl) | —CF$_3$ | —F |
| L7 (a and b) | -2-(3-chloropyridyl) | —CN | —CF$_3$ |
| L8 (a and b) | -2-(3-chloropyridyl) | —OCF$_3$ | —Cl |
| L9 (a and b) | -2-(3-fluoropyridyl) | —Cl | —CF$_3$ |
| L10 (a and b) | -2-(3-fluoropyridyl) | —CF$_3$ | —Cl |
| L11 (a and b) | -2-(3-fluoropyridyl) | —CH$_3$ | —CF$_3$ |
| L12 (a and b) | -2-(3-fluoropyridyl) | —SCF$_3$ | —Cl |
| L13 (a and b) | -2-(3-fluoropyridyl) | —F | —CF$_3$ |
| L14 (a and b) | -2-(3-fluoropyridyl) | —CF$_3$ | —F |
| L15 (a and b) | -2-(3-fluoropyridyl) | —CN | —CF$_3$ |
| L16 (a and b) | -2-(3-fluoropyridyl) | —OCF$_3$ | —Cl |
| L17 (a and b) | -2-(3-methylpyridyl) | —Cl | —CF$_3$ |
| L18 (a and b) | -2-(3-methylpyridyl) | —CF$_3$ | —Cl |
| L19 (a and b) | -2-(3-methylpyridyl) | —CH$_3$ | —CF$_3$ |
| L20 (a and b) | -2-(3-methylpyridyl) | —SCF$_3$ | —Cl |
| L21 (a and b) | -2-(3-methylpyridyl) | —F | —CF$_3$ |
| L22 (a and b) | -2-(3-methylpyridyl) | —CF$_3$ | —F |
| L23 (a and b) | -2-(3-methylpyridyl) | —CN | —CF$_3$ |
| L24 (a and b) | -2-(3-methylpyridyl) | —OCF$_3$ | —Cl |
| L25 (a and b) | -2-(3-CF$_3$-pyridyl) | —Cl | —CF$_3$ |
| L26 (a and b) | -2-(3-CF$_3$-pyridyl) | —CF$_3$ | —Cl |
| L27 (a and b) | -2-(3-CF$_3$-pyridyl) | —CH$_3$ | —CF$_3$ |
| L28 (a and b) | -2-(3-CF$_3$-pyridyl) | —SCF$_3$ | —Cl |
| L29 (a and b) | -2-(3-CF$_3$-pyridyl) | —F | —CF$_3$ |
| L30 (a and b) | -2-(3-CF$_3$-pyridyl) | —CF$_3$ | —F |
| L31 (a and b) | -2-(3-CF$_3$-pyridyl) | —CN | —CF$_3$ |
| L32 (a and b) | -2-(3-CF$_3$-pyridyl) | —OCF$_3$ | —Cl |
| L33 (a and b) | -2-(3-CHF$_2$-pyridyl) | —Cl | —CF$_3$ |
| L34 (a and b) | -2-(3-CHF$_2$-pyridyl) | —CF$_3$ | —Cl |
| L35 (a and b) | -2-(3-CHF$_2$-pyridyl) | —CH$_3$ | —CF$_3$ |
| L36 (a and b) | -2-(3-CHF$_2$-pyridyl) | —SCF$_3$ | —Cl |
| L37 (a and b) | -2-(3-CHF$_2$-pyridyl) | —F | —CF$_3$ |
| L38 (a and b) | -2-(3-CHF$_2$-pyridyl) | —CF$_3$ | —F |
| L39 (a and b) | -2-(3-CHF$_2$-pyridyl) | —CN | —CF$_3$ |
| L40 (a and b) | -2-(3-CHF$_2$-pyridyl) | —OCF$_3$ | —Cl |
| L41 (a and b) | -2-(3-hydroxypyridyl) | —Cl | —CF$_3$ |
| L42 (a and b) | -2-(3-hydroxypyridyl) | —CF$_3$ | —Cl |
| L43 (a and b) | -2-(3-hydroxypyridyl) | —CH$_3$ | —CF$_3$ |
| L44 (a and b) | -2-(3-hydroxypyridyl) | —SCF$_3$ | —Cl |
| L45 (a and b) | -2-(3-hydroxypyridyl) | —F | —CF$_3$ |
| L46 (a and b) | -2-(3-hydroxypyridyl) | —CF$_3$ | —F |
| L47 (a and b) | -2-(3-hydroxypyridyl) | —CN | —CF$_3$ |
| L48 (a and b) | -2-(3-hydroxypyridyl) | —OCF$_3$ | —Cl |
| L49 (a and b) | -2-(3-nitropyridyl) | —Cl | —CF$_3$ |
| L50 (a and b) | -2-(3-nitropyridyl) | —CF$_3$ | —Cl |
| L51 (a and b) | -2-(3-nitropyridyl) | —CH$_3$ | —CF$_3$ |
| L52 (a and b) | -2-(3-nitropyridyl) | —SCF$_3$ | —Cl |
| L53 (a and b) | -2-(3-nitropyridyl) | —F | —CF$_3$ |
| L54 (a and b) | -2-(3-nitropyridyl) | —CF$_3$ | —F |
| L55 (a and b) | -2-(3-nitropyridyl) | —CN | —CF$_3$ |

TABLE 12-continued

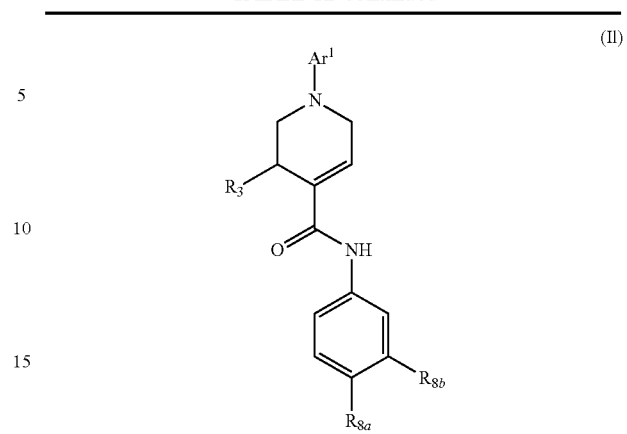

and pharmaceutically acceptable salts thereof, wherein:

| Compound | Ar¹ | $R_{8a}$ | $R_{8b}$ |
|---|---|---|---|
| L56 (a and b) | -2-(3-nitropyridyl) | —OCF$_3$ | —Cl |
| L57 (a and b) | -2-(3-cyanopyridyl) | —Cl | —CF$_3$ |
| L58 (a and b) | -2-(3-cyanopyridyl) | —CF$_3$ | —Cl |
| L59 (a and b) | -2-(3-cyanopyridyl) | —CH$_3$ | —CF$_3$ |
| L60 (a and b) | -2-(3-cyanopyridyl) | —SCF$_3$ | —Cl |
| L61 (a and b) | -2-(3-cyanopyridyl) | —F | —CF$_3$ |
| L62 (a and b) | -2-(3-cyanopyridyl) | —CF$_3$ | —F |
| L63 (a and b) | -2-(3-cyanopyridyl) | —CN | —CF$_3$ |
| L64 (a and b) | -2-(3-cyanopyridyl) | —OCF$_3$ | —Cl |
| L65 (a and b) | -2-(3-bromopyridyl) | —Cl | —CF$_3$ |
| L66 (a and b) | -2-(3-bromopyridyl) | —CF$_3$ | —Cl |
| L67 (a and b) | -2-(3-bromopyridyl) | —CH$_3$ | —CF$_3$ |
| L68 (a and b) | -2-(3-bromopyridyl) | —SCF$_3$ | —Cl |
| L69 (a and b) | -2-(3-bromopyridyl) | —F | —CF$_3$ |
| L70 (a and b) | -2-(3-bromopyridyl) | —CF$_3$ | —F |
| L71 (a and b) | -2-(3-bromopyridyl) | —CN | —CF$_3$ |
| L72 (a and b) | -2-(3-bromopyridyl) | —OCF$_3$ | —Cl |
| L73 (a and b) | -2-(3-iodopyridyl) | —Cl | —CF$_3$ |
| L74 (a and b) | -2-(3-iodopyridyl) | —CF$_3$ | —Cl |
| L75 (a and b) | -2-(3-iodopyridyl) | —CH$_3$ | —CF$_3$ |
| L76 (a and b) | -2-(3-iodopyridyl) | —SCF$_3$ | —Cl |
| L77 (a and b) | -2-(3-iodopyridyl) | —F | —CF$_3$ |
| L78 (a and b) | -2-(3-iodopyridyl) | —CF$_3$ | —F |
| L79 (a and b) | -2-(3-iodopyridyl) | —CN | —CF$_3$ |
| L80 (a and b) | -2-(3-iodopyridyl) | —OCF$_3$ | —Cl |
| L81 (a and b) | -4-(5-chloropyrimidinyl) | —Cl | —CF$_3$ |
| L82 (a and b) | -4-(5-chloropyrimidinyl) | —CF$_3$ | —Cl |
| L83 (a and b) | -4-(5-chloropyrimidinyl) | —CH$_3$ | —CF$_3$ |
| L84 (a and b) | -4-(5-chloropyrimidinyl) | —SCF$_3$ | —Cl |
| L85 (a and b) | -4-(5-chloropyrimidinyl) | —F | —CF$_3$ |
| L86 (a and b) | -4-(5-chloropyrimidinyl) | —CF$_3$ | —F |
| L87 (a and b) | -4-(5-chloropyrimidinyl) | —CN | —CF$_3$ |
| L88 (a and b) | -4-(5-chloropyrimidinyl) | —OCF$_3$ | —Cl |
| L89 (a and b) | -4-(5-methylpyrimidinyl) | —Cl | —CF$_3$ |
| L90 (a and b) | -4-(5-methylpyrimidinyl) | —CF$_3$ | —Cl |
| L91 (a and b) | -4-(5-methylpyrimidinyl) | —CH$_3$ | —CF$_3$ |
| L92 (a and b) | -4-(5-methylpyrimidinyl) | —SCF$_3$ | —Cl |
| L93 (a and b) | -4-(5-methylpyrimidinyl) | —F | —CF$_3$ |
| L94 (a and b) | -4-(5-methylpyrimidinyl) | —CF$_3$ | —F |
| L95 (a and b) | -4-(5-methylpyrimidinyl) | —CN | —CF$_3$ |
| L96 (a and b) | -4-(5-methylpyrimidinyl) | —OCF$_3$ | —Cl |
| L97 (a and b) | -4-(5-fluoropyrimidinyl) | —Cl | —CF$_3$ |
| L98 (a and b) | -4-(5-fluoropyrimidinyl) | —CF$_3$ | —Cl |
| L99 (a and b) | -4-(5-fluoropyrimidinyl) | —CH$_3$ | —CF$_3$ |
| L100 (a and b) | -4-(5-fluoropyrimidinyl) | —SCF$_3$ | —Cl |
| L101 (a and b) | -4-(5-fluoropyrimidinyl) | —F | —CF$_3$ |
| L102 (a and b) | -4-(5-fluoropyrimidinyl) | —CF$_3$ | —F |
| L103 (a and b) | -4-(5-fluoropyrimidinyl) | —CN | —CF$_3$ |
| L104 (a and b) | -4-(5-fluoropyrimidinyl) | —OCF$_3$ | —Cl |
| L105 (a and b) | -2-(3-chloropyrazinyl) | —Cl | —CF$_3$ |
| L106 (a and b) | -2-(3-chloropyrazinyl) | —CF$_3$ | —Cl |
| L107 (a and b) | -2-(3-chloropyrazinyl) | —CH$_3$ | —CF$_3$ |
| L108 (a and b) | -2-(3-chloropyrazinyl) | —SCF$_3$ | —Cl |
| L109 (a and b) | -2-(3-chloropyrazinyl) | —F | —CF$_3$ |
| L110 (a and b) | -2-(3-chloropyrazinyl) | —CF$_3$ | —F |

TABLE 12-continued (II)

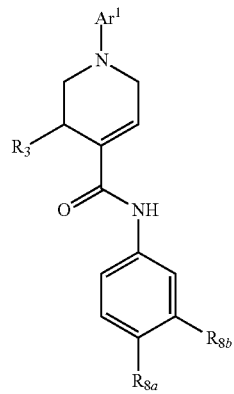

and pharmaceutically acceptable salts thereof, wherein:

| Compound | Ar¹ | $R_{8a}$ | $R_{8b}$ |
|---|---|---|---|
| L111 (a and b) | -2-(3-chloropyrazinyl) | —CN | —CF₃ |
| L112 (a and b) | -2-(3-chloropyrazinyl) | —OCF₃ | —Cl |
| L113 (a and b) | -2-(3-methylpyrazinyl) | —Cl | —CF₃ |
| L114 (a and b) | -2-(3-methylpyrazinyl) | —CF₃ | —Cl |
| L115 (a and b) | -2-(3-methylpyrazinyl) | —CH₃ | —CF₃ |
| L116 (a and b) | -2-(3-methylpyrazinyl) | —SCF₃ | —Cl |
| L117 (a and b) | -2-(3-methylpyrazinyl) | —F | —CF₃ |
| L118 (a and b) | -2-(3-methylpyrazinyl) | —CF₃ | —F |
| L119 (a and b) | -2-(3-methylpyrazinyl) | —CN | —CF₃ |
| L120 (a and b) | -2-(3-methylpyrazinyl) | —OCF₃ | —Cl |
| L121 (a and b) | -2-(3-fluoropyrazinyl) | —Cl | —CF₃ |
| L122 (a and b) | -2-(3-fluoropyrazinyl) | —CF₃ | —Cl |
| L123 (a and b) | -2-(3-fluoropyrazinyl) | —CH₃ | —CF₃ |
| L124 (a and b) | -2-(3-fluoropyrazinyl) | —SCF₃ | —Cl |
| L125 (a and b) | -2-(3-fluoropyrazinyl) | —F | —CF₃ |
| L126 (a and b) | -2-(3-fluoropyrazinyl) | —CF₃ | —F |
| L127 (a and b) | -2-(3-fluoropyrazinyl) | —CN | —CF₃ |
| L128 (a and b) | -2-(3-fluoropyrazinyl) | —OCF₃ | —Cl |
| L129 (a and b) | -3-(4-chloropyridazinyl) | —Cl | —CF₃ |
| L130 (a and b) | -3-(4-chloropyridazinyl) | —CF₃ | —Cl |
| L131 (a and b) | -3-(4-chloropyridazinyl) | —CH₃ | —CF₃ |
| L132 (a and b) | -3-(4-chloropyridazinyl) | —SCF₃ | —Cl |
| L133 (a and b) | -3-(4-chloropyridazinyl) | —F | —CF₃ |
| L134 (a and b) | -3-(4-chloropyridazinyl) | —CF₃ | —F |
| L135 (a and b) | -3-(4-chloropyridazinyl) | —CN | —CF₃ |
| L136 (a and b) | -3-(4-chloropyridazinyl) | —OCF₃ | —Cl |
| L137 (a and b) | -3-(4-methylpyridazinyl) | —Cl | —CF₃ |
| L138 (a and b) | -3-(4-methylpyridazinyl) | —CF₃ | —Cl |
| L139 (a and b) | -3-(4-methylpyridazinyl) | —CH₃ | —CF₃ |
| L140 (a and b) | -3-(4-methylpyridazinyl) | —SCF₃ | —Cl |
| L141 (a and b) | -3-(4-methylpyridazinyl) | —F | —CF₃ |
| L142 (a and b) | -3-(4-methylpyridazinyl) | —CF₃ | —F |
| L143 (a and b) | -3-(4-methylpyridazinyl) | —CN | —CF₃ |
| L144 (a and b) | -3-(4-methylpyridazinyl) | —OCF₃ | —Cl |
| L145 (a and b) | -3-(4-fluoropyridazinyl) | —Cl | —CF₃ |
| L146 (a and b) | -3-(4-fluoropyridazinyl) | —CF₃ | —Cl |
| L147 (a and b) | -3-(4-fluoropyridazinyl) | —CH₃ | —CF₃ |
| L148 (a and b) | -3-(4-fluoropyridazinyl) | —SCF₃ | —Cl |
| L149 (a and b) | -3-(4-fluoropyridazinyl) | —F | —CF₃ |
| L150 (a and b) | -3-(4-fluoropyridazinyl) | —CF₃ | —F |
| L151 (a and b) | -3-(4-fluoropyridazinyl) | —CN | —CF₃ |
| L152 (a and b) | -3-(4-fluoropyridazinyl) | —OCF₃ | —Cl |
| L153 (a and b) | -5-(4-chlorothiadiazolyl) | —Cl | —CF₃ |
| L154 (a and b) | -5-(4-chlorothiadiazolyl) | —CF₃ | —Cl |
| L155 (a and b) | -5-(4-chlorothiadiazolyl) | —CH₃ | —CF₃ |
| L156 (a and b) | -5-(4-chlorothiadiazolyl) | —SCF₃ | —Cl |
| L157 (a and b) | -5-(4-chlorothiadiazolyl) | —F | —CF₃ |
| L158 (a and b) | -5-(4-chlorothiadiazolyl) | —CF₃ | —F |
| L159 (a and b) | -5-(4-chlorothiadiazolyl) | —CN | —CF₃ |
| L160 (a and b) | -5-(4-chlorothiadiazolyl) | —OCF₃ | —Cl |
| L161 (a and b) | -5-(4-methylthiadiazolyl) | —Cl | —CF₃ |
| L162 (a and b) | -5-(4-methylthiadiazolyl) | —CF₃ | —Cl |
| L163 (a and b) | -5-(4-methylthiadiazolyl) | —CH₃ | —CF₃ |
| L164 (a and b) | -5-(4-methylthiadiazolyl) | —SCF₃ | —Cl |
| L165 (a and b) | -5-(4-methylthiadiazolyl) | —F | —CF₃ |

TABLE 12-continued (II)

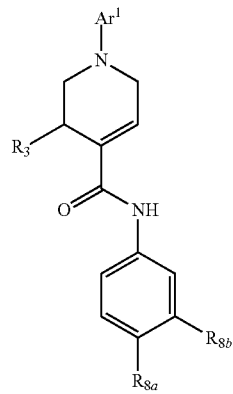

and pharmaceutically acceptable salts thereof, wherein:

| Compound | Ar¹ | $R_{8a}$ | $R_{8b}$ |
|---|---|---|---|
| L166 (a and b) | -5-(4-methylthiadiazolyl) | —CF₃ | —F |
| L167 (a and b) | -5-(4-methylthiadiazolyl) | —CN | —CF₃ |
| L168 (a and b) | -5-(4-methylthiadiazolyl) | —OCF₃ | —Cl |
| L169 (a and b) | -5-(4-fluorothiadiazolyl) | —Cl | —CF₃ |
| L170 (a and b) | -5-(4-fluorothiadiazolyl) | —CF₃ | —Cl |
| L171 (a and b) | -5-(4-fluorothiadiazolyl) | —CH₃ | —CF₃ |
| L172 (a and b) | -5-(4-fluorothiadiazolyl) | —SCF₃ | —Cl |
| L173 (a and b) | -5-(4-fluorothiadiazolyl) | —F | —CF₃ |
| L174 (a and b) | -5-(4-fluorothiadiazolyl) | —CF₃ | —F |
| L175 (a and b) | -5-(4-fluorothiadiazolyl) | —CN | —CF₃ |
| L176 (a and b) | -5-(4-fluorothiadiazolyl) | —OCF₃ | —Cl |

(a) means that $R_3$ is —H.
(b) means that $R_3$ is —CH₃.

TABLE 13

(Im)

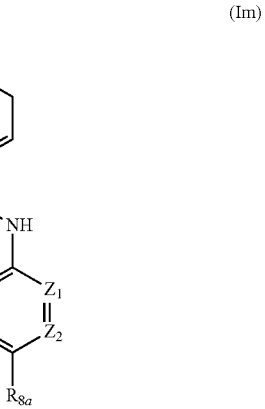

and pharmaceutically acceptable salts thereof, wherein:

| Compound | Ar¹ | $Z_1$ | $Z_2$ | $R_{8a}$ |
|---|---|---|---|---|
| M1 (a and b) | -2-(3-chloropyridyl) | N | CH | —CF₃ |
| M2 (a and b) | -2-(3-fluoropyridyl) | N | CH | —CF₃ |
| M3 (a and b) | -2-(3-methylpyridyl) | N | CH | —CF₃ |
| M4 (a and b) | -2-(3-CF₃-pyridyl) | N | CH | —CF₃ |
| M5 (a and b) | -2-(3-CHF₂-pyridyl) | N | CH | —CF₃ |
| M6 (a and b) | -2-(3-hydroxypyridyl) | N | CH | —CF₃ |
| M7 (a and b) | -2-(3-nitropyridyl) | N | CH | —CF₃ |
| M8 (a and b) | -2-(3-cyanopyridyl) | N | CH | —CF₃ |
| M9 (a and b) | -2-(3-bromopyridyl) | N | CH | —CF₃ |
| M10 (a and b) | -2-(3-iodopyridyl) | N | CH | —CF₃ |
| M11 (a and b) | -4-(5-chloropyrimidinyl) | N | CH | —CF₃ |
| M12 (a and b) | -4-(5-methylpyrimidinyl) | N | CH | —CF₃ |
| M13 (a and b) | -4-(5-fluoropyrimidinyl) | N | CH | —CF₃ |

TABLE 13-continued

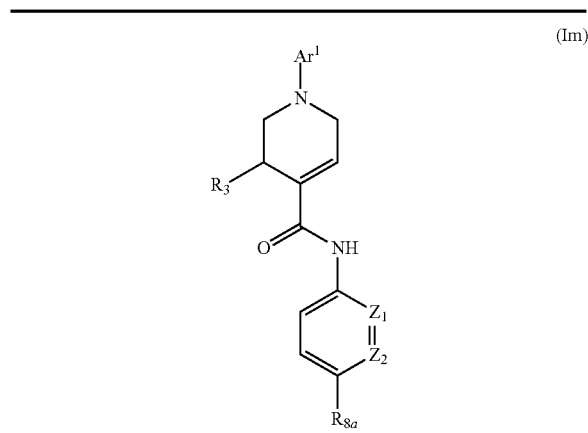

(Im)

and pharmaceutically acceptable salts thereof, wherein:

| Compound | Ar$^1$ | Z$_1$ | Z$_2$ | R$_{8a}$ |
|---|---|---|---|---|
| M14 (a and b) | -2-(3-chloropyrazinyl) | N | CH | —CF$_3$ |
| M15 (a and b) | -2-(3-methylpyrazinyl) | N | CH | —CF$_3$ |
| M16 (a and b) | -2-(3-fluoropyrazinyl) | N | CH | —CF$_3$ |
| M17 (a and b) | -3-(4-chloropyridazinyl) | N | CH | —CF$_3$ |
| M18 (a and b) | -3-(4-methylpyridazinyl) | N | CH | —CF$_3$ |
| M19 (a and b) | -3-(4-fluoropyridazinyl) | N | CH | —CF$_3$ |
| M20 (a and b) | -5-(4-chlorothiadiazolyl) | N | CH | —CF$_3$ |
| M21 (a and b) | -5-(4-methylthiadiazolyl) | N | N | —CF$_3$ |
| M22 (a and b) | -5-(4-fluorothiadiazolyl) | N | CH | —CF$_3$ |
| M23 (a and b) | -2-(3-chloropyridyl) | CH | N | —CF$_3$ |
| M24 (a and b) | -2-(3-fluoropyridyl) | CH | N | —CF$_3$ |
| M25 (a and b) | -2-(3-methylpyridyl) | CH | N | —CF$_3$ |
| M26 (a and b) | -2-(3-CF$_3$-pyridyl) | CH | N | —CF$_3$ |
| M27 (a and b) | -2-(3-CHF$_2$-pyridyl) | CH | N | —CF$_3$ |
| M28 (a and b) | -2-(3-hydroxypyridyl) | CH | N | —CF$_3$ |
| M29 (a and b) | -2-(3-nitropyridyl) | CH | N | —CF$_3$ |
| M30 (a and b) | -2-(3-cyanopyridyl) | CH | N | —CF$_3$ |
| M31 (a and b) | -2-(3-bromopyridyl) | CH | N | —CF$_3$ |
| M32 (a and b) | -2-(3-iodopyridyl) | CH | N | —CF$_3$ |
| M33 (a and b) | -4-(5-chloropyrimidinyl) | CH | N | —CF$_3$ |
| M34 (a and b) | -4-(5-methylpyrimidinyl) | CH | N | —CF$_3$ |
| M35 (a and b) | -4-(5-fluoropyrimidinyl) | CH | N | —CF$_3$ |
| M36 (a and b) | -2-(3-chloropyrazinyl) | CH | N | —CF$_3$ |
| M37 (a and b) | -2-(3-methylpyrazinyl) | CH | N | —CF$_3$ |
| M38 (a and b) | -2-(3-fluoropyrazinyl) | CH | N | —CF$_3$ |
| M39 (a and b) | -3-(4-chloropyridazinyl) | CH | N | —CF$_3$ |
| M40 (a and b) | -3-(4-methylpyridazinyl) | CH | N | —CF$_3$ |
| M41 (a and b) | -3-(4-fluoropyridazinyl) | CH | N | —CF$_3$ |
| M42 (a and b) | -5-(4-chlorothiadiazolyl) | CH | N | —CF$_3$ |
| M43 (a and b) | -5-(4-methylthiadiazolyl) | N | N | —CF$_3$ |
| M44 (a and b) | -5-(4-fluorothiadiazolyl) | CH | N | —CF$_3$ |
| M45 (a and b) | -2-(3-chloropyridyl) | N | CH | -tert-butyl |
| M46 (a and b) | -2-(3-fluoropyridyl) | N | CH | -tert-butyl |
| M47 (a and b) | -2-(3-methylpyridyl) | N | CH | -tert-butyl |
| M48 (a and b) | -2-(3-CF$_3$-pyridyl) | N | CH | -tert-butyl |
| M49 (a and b) | -2-(3-CHF$_2$-pyridyl) | N | CH | -tert-butyl |
| M50 (a and b) | -2-(3-hydroxypyridyl) | N | CH | -tert-butyl |
| M51 (a and b) | -2-(3-nitropyridyl) | N | CH | -tert-butyl |
| M52 (a and b) | -2-(3-cyanopyridyl) | N | CH | -tert-butyl |
| M53 (a and b) | -2-(3-bromopyridyl) | N | CH | -tert-butyl |
| M54 (a and b) | -2-(3-iodopyridyl) | N | CH | -tert-butyl |
| M55 (a and b) | -4-(5-chloropyrimidinyl) | N | CH | -tert-butyl |
| M56 (a and b) | -4-(5-methylpyrimidinyl) | N | CH | -tert-butyl |
| M57 (a and b) | -4-(5-fluoropyrimidinyl) | N | CH | -tert-butyl |
| M58 (a and b) | -2-(3-chloropyrazinyl) | N | CH | -tert-butyl |
| M59 (a and b) | -2-(3-methylpyrazinyl) | N | CH | -tert-butyl |
| M60 (a and b) | -2-(3-fluoropyrazinyl) | N | CH | -tert-butyl |
| M61 (a and b) | -3-(4-chloropyridazinyl) | N | CH | -tert-butyl |
| M62 (a and b) | -3-(4-methylpyridazinyl) | N | CH | -tert-butyl |
| M63 (a and b) | -3-(4-fluoropyridazinyl) | N | CH | -tert-butyl |
| M64 (a and b) | -5-(4-chlorothiadiazolyl) | N | CH | -tert-butyl |
| M65 (a and b) | -5-(4-methylthiadiazolyl) | N | N | -tert-butyl |
| M66 (a and b) | -5-(4-fluorothiadiazolyl) | N | CH | -tert-butyl |
| M67 (a and b) | -2-(3-chloropyridyl) | CH | N | -tert-butyl |
| M68 (a and b) | -2-(3-fluoropyridyl) | CH | N | -tert-butyl |
| M69 (a and b) | -2-(3-methylpyridyl) | CH | N | -tert-butyl |
| M70 (a and b) | -2-(3-CF$_3$-pyridyl) | CH | N | -tert-butyl |
| M71 (a and b) | -2-(3-CHF$_2$-pyridyl) | CH | N | -tert-butyl |
| M72 (a and b) | -2-(3-hydroxypyridyl) | CH | N | -tert-butyl |
| M73 (a and b) | -2-(3-nitropyridyl) | CH | N | -tert-butyl |
| M74 (a and b) | -2-(3-cyanopyridyl) | CH | N | -tert-butyl |
| M75 (a and b) | -2-(3-bromopyridyl) | CH | N | -tert-butyl |
| M76 (a and b) | -2-(3-iodopyridyl) | CH | N | -tert-butyl |
| M77 (a and b) | -4-(5-chloropyrimidinyl) | CH | N | -tert-butyl |
| M78 (a and b) | -4-(5-methylpyrimidinyl) | CH | N | -tert-butyl |
| M79 (a and b) | -4-(5-fluoropyrimidinyl) | CH | N | -tert-butyl |
| M80 (a and b) | -2-(3-chloropyrazinyl) | CH | N | -tert-butyl |
| M81 (a and b) | -2-(3-methylpyrazinyl) | CH | N | -tert-butyl |
| M82 (a and b) | -2-(3-fluoropyrazinyl) | CH | N | -tert-butyl |
| M83 (a and b) | -3-(4-chloropyridazinyl) | CH | N | -tert-butyl |
| M84 (a and b) | -3-(4-methylpyridazinyl) | CH | N | -tert-butyl |
| M85 (a and b) | -3-(4-fluoropyridazinyl) | CH | N | -tert-butyl |
| M86 (a and b) | -5-(4-chlorothiadiazolyl) | CH | N | -tert-butyl |
| M87 (a and b) | -5-(4-methylthiadiazolyl) | N | N | -tert-butyl |
| M88 (a and b) | -5-(4-fluorothiadiazolyl) | CH | N | -tert-butyl |
| M89 (a and b) | -2-(3-chloropyridyl) | N | CH | -iso-butyl |
| M90 (a and b) | -2-(3-fluoropyridyl) | N | CH | -iso-butyl |
| M91 (a and b) | -2-(3-methylpyridyl) | N | CH | -iso-butyl |
| M92 (a and b) | -2-(3-CF$_3$-pyridyl) | N | CH | -iso-butyl |
| M93 (a and b) | -2-(3-CHF$_2$-pyridyl) | N | CH | -iso-butyl |
| M94 (a and b) | -2-(3-hydroxypyridyl) | N | CH | -iso-butyl |
| M95 (a and b) | -2-(3-nitropyridyl) | N | CH | -iso-butyl |
| M96 (a and b) | -2-(3-cyanopyridyl) | N | CH | -iso-butyl |
| M97 (a and b) | -2-(3-bromopyridyl) | N | CH | -iso-butyl |
| M98 (a and b) | -2-(3-iodopyridyl) | N | CH | -iso-butyl |
| M99 (a and b) | -4-(5-chloropyrimidinyl) | N | CH | -iso-butyl |
| M100 (a and b) | -4-(5-methylpyrimidinyl) | N | CH | -iso-butyl |
| M101 (a and b) | -4-(5-fluoropyrimidinyl) | N | CH | -iso-butyl |
| M102 (a and b) | -2-(3-chloropyrazinyl) | N | CH | -iso-butyl |
| M103 (a and b) | -2-(3-methylpyrazinyl) | N | CH | -iso-butyl |
| M104 (a and b) | -2-(3-fluoropyrazinyl) | N | CH | -iso-butyl |
| M105 (a and b) | -3-(4-chloropyridazinyl) | N | CH | -iso-butyl |
| M106 (a and b) | -3-(4-methylpyridazinyl) | N | CH | -iso-butyl |
| M107 (a and b) | -3-(4-fluoropyridazinyl) | N | CH | -iso-butyl |
| M108 (a and b) | -5-(4-chlorothiadiazolyl) | N | CH | -iso-butyl |
| M109 (a and b) | -5-(4-methylthiadiazolyl) | N | N | -iso-butyl |
| M110 (a and b) | -5-(4-fluorothiadiazolyl) | N | CH | -iso-butyl |
| M111 (a and b) | -2-(3-chloropyridyl) | CH | N | -iso-butyl |
| M112 (a and b) | -2-(3-fluoropyridyl) | CH | N | -iso-butyl |
| M113 (a and b) | -2-(3-methylpyridyl) | CH | N | -iso-butyl |
| M114 (a and b) | -2-(3-CF$_3$-pyridyl) | CH | N | -iso-butyl |
| M115 (a and b) | -2-(3-CHF$_2$-pyridyl) | CH | N | -iso-butyl |
| M116 (a and b) | -2-(3-hydroxypyridyl) | CH | N | -iso-butyl |
| M117 (a and b) | -2-(3-nitropyridyl) | CH | N | -iso-butyl |
| M118 (a and b) | -2-(3-cyanopyridyl) | CH | N | -iso-butyl |
| M119 (a and b) | -2-(3-bromopyridyl) | CH | N | -iso-butyl |
| M120 (a and b) | -2-(3-iodopyridyl) | CH | N | -iso-butyl |
| M121 (a and b) | -4-(5-chloropyrimidinyl) | CH | N | -iso-butyl |
| M122 (a and b) | -4-(5-methylpyrimidinyl) | CH | N | -iso-butyl |
| M123 (a and b) | -4-(5-fluoropyrimidinyl) | CH | N | -iso-butyl |

TABLE 13-continued

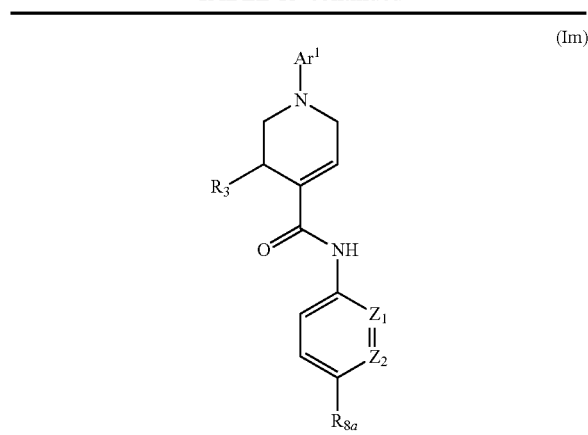

(Im)

and pharmaceutically acceptable salts thereof, wherein:

| Compound | Ar¹ | $Z_1$ | $Z_2$ | $R_{8a}$ |
|---|---|---|---|---|
| M124 (a and b) | -2-(3-chloropyrazinyl) | CH | N | -iso-butyl |
| M125 (a and b) | -2-(3-methylpyrazinyl) | CH | N | -iso-butyl |
| M126 (a and b) | -2-(3-fluoropyrazinyl) | CH | N | -iso-butyl |
| M127 (a and b) | -3-(4-chloropyridazinyl) | CH | N | -iso-butyl |
| M128 (a and b) | -3-(4-methylpyridazinyl) | CH | N | -iso-butyl |
| M129 (a and b) | -3-(4-fluoropyridazinyl) | CH | N | -iso-butyl |
| M130 (a and b) | -5-(4-chlorothiadiazolyl) | CH | N | -iso-butyl |
| M131 (a and b) | -5-(4-methylthiadiazolyl) | N | N | -iso-butyl |
| M132 (a and b) | -5-(4-fluorothiadiazolyl) | CH | N | -iso-butyl |
| M133 (a and b) | -2-(3-chloropyridyl) | N | CH | -sec-butyl |
| M134 (a and b) | -2-(3-fluoropyridyl) | N | CH | -sec-butyl |
| M135 (a and b) | -2-(3-methylpyridyl) | N | CH | -sec-butyl |
| M136 (a and b) | -2-(3-CF$_3$-pyridyl) | N | CH | -sec-butyl |
| M137 (a and b) | -2-(3-CHF$_2$-pyridyl) | N | CH | -sec-butyl |
| M138 (a and b) | -2-(3-hydroxypyridyl) | N | CH | -sec-butyl |
| M139 (a and b) | -2-(3-nitropyridyl) | N | CH | -sec-butyl |
| M140 (a and b) | -2-(3-cyanopyridyl) | N | CH | -sec-butyl |
| M141 (a and b) | -2-(3-bromopyridyl) | N | CH | -sec-butyl |
| M142 (a and b) | -2-(3-iodopyridyl) | N | CH | -sec-butyl |
| M143 (a and b) | -4-(5-chloropyrimidinyl) | N | CH | -sec-butyl |
| M144 (a and b) | -4-(5-methylpyrimidinyl) | N | CH | -sec-butyl |
| M145 (a and b) | -4-(5-fluoropyrimidinyl) | N | CH | -sec-butyl |
| M146 (a and b) | -2-(3-chloropyrazinyl) | N | CH | -sec-butyl |
| M147 (a and b) | -2-(3-methylpyrazinyl) | N | CH | -sec-butyl |
| M148 (a and b) | -2-(3-fluoropyrazinyl) | N | CH | -sec-butyl |
| M149 (a and b) | -3-(4-chloropyridazinyl) | N | CH | -sec-butyl |
| M150 (a and b) | -3-(4-methylpyridazinyl) | N | CH | -sec-butyl |
| M151 (a and b) | -3-(4-fluoropyridazinyl) | N | CH | -sec-butyl |
| M152 (a and b) | -5-(4-chlorothiadiazolyl) | N | CH | -sec-butyl |
| M153 (a and b) | -5-(4-methylthiadiazolyl) | N | N | -sec-butyl |
| M154 (a and b) | -5-(4-fluorothiadiazolyl) | N | CH | -sec-butyl |
| M155 (a and b) | -2-(3-chloropyridyl) | CH | N | -sec-butyl |
| M156 (a and b) | -2-(3-fluoropyridyl) | CH | N | -sec-butyl |
| M157 (a and b) | -2-(3-methylpyridyl) | CH | N | -sec-butyl |
| M158 (a and b) | -2-(3-CF$_3$-pyridyl) | CH | N | -sec-butyl |
| M159 (a and b) | -2-(3-CHF$_2$-pyridyl) | CH | N | -sec-butyl |
| M160 (a and b) | -2-(3-hydroxypyridyl) | CH | N | -sec-butyl |
| M161 (a and b) | -2-(3-nitropyridyl) | CH | N | -sec-butyl |
| M162 (a and b) | -2-(3-cyanopyridyl) | CH | N | -sec-butyl |
| M163 (a and b) | -2-(3-bromopyridyl) | CH | N | -sec-butyl |
| M164 (a and b) | -2-(3-iodopyridyl) | CH | N | -sec-butyl |
| M165 (a and b) | -4-(5-chloropyrimidinyl) | CH | N | -sec-butyl |
| M166 (a and b) | -4-(5-methylpyrimidinyl) | CH | N | -sec-butyl |
| M167 (a and b) | -4-(5-fluoropyrimidinyl) | CH | N | -sec-butyl |
| M168 (a and b) | -2-(3-chloropyrazinyl) | CH | N | -sec-butyl |
| M169 (a and b) | -2-(3-methylpyrazinyl) | CH | N | -sec-butyl |
| M170 (a and b) | -2-(3-fluoropyrazinyl) | CH | N | -sec-butyl |
| M171 (a and b) | -3-(4-chloropyridazinyl) | CH | N | -sec-butyl |
| M172 (a and b) | -3-(4-methylpyridazinyl) | CH | N | -sec-butyl |
| M173 (a and b) | -3-(4-fluoropyridazinyl) | CH | N | -sec-butyl |
| M174 (a and b) | -5-(4-chlorothiadiazolyl) | CH | N | -sec-butyl |
| M175 (a and b) | -5-(4-methylthiadiazolyl) | N | N | -sec-butyl |
| M176 (a and b) | -5-(4-fluorothiadiazolyl) | CH | N | -sec-butyl |
| M177 (a and b) | -2-(3-chloropyridyl) | N | CH | -iso-propyl |
| M178 (a and b) | -2-(3-fluoropyridyl) | N | CH | -iso-propyl |
| M179 (a and b) | -2-(3-methylpyridyl) | N | CH | -iso-propyl |
| M180 (a and b) | -2-(3-CF$_3$-pyridyl) | N | CH | -iso-propyl |
| M181 (a and b) | -2-(3-CHF$_2$-pyridyl) | N | CH | -iso-propyl |
| M182 (a and b) | -2-(3-hydroxypyridyl) | N | CH | -iso-propyl |
| M183 (a and b) | -2-(3-nitropyridyl) | N | CH | -iso-propyl |
| M184 (a and b) | -2-(3-cyanopyridyl) | N | CH | -iso-propyl |
| M185 (a and b) | -2-(3-bromopyridyl) | N | CH | -iso-propyl |
| M186 (a and b) | -2-(3-iodopyridyl) | N | CH | -iso-propyl |
| M187 (a and b) | -4-(5-chloropyrimidinyl) | N | CH | -iso-propyl |
| M188 (a and b) | -4-(5-methylpyrimidinyl) | N | CH | -iso-propyl |
| M189 (a and b) | -4-(5-fluoropyrimidinyl) | N | CH | -iso-propyl |
| M190 (a and b) | -2-(3-chloropyrazinyl) | N | CH | -iso-propyl |
| M191 (a and b) | -2-(3-methylpyrazinyl) | N | CH | -iso-propyl |
| M192 (a and b) | -2-(3-fluoropyrazinyl) | N | CH | -iso-propyl |
| M193 (a and b) | -3-(4-chloropyridazinyl) | N | CH | -iso-propyl |
| M194 (a and b) | -3-(4-methylpyridazinyl) | N | CH | -iso-propyl |
| M195 (a and b) | -3-(4-fluoropyridazinyl) | N | CH | -iso-propyl |
| M196 (a and b) | -5-(4-chlorothiadiazolyl) | N | CH | -iso-propyl |
| M197 (a and b) | -5-(4-methylthiadiazolyl) | N | N | -iso-propyl |
| M198 (a and b) | -5-(4-fluorothiadiazolyl) | N | CH | -iso-propyl |
| M199 (a and b) | -2-(3-chloropyridyl) | CH | N | -iso-propyl |
| M200 (a and b) | -2-(3-fluoropyridyl) | CH | N | -iso-propyl |
| M201 (a and b) | -2-(3-methylpyridyl) | CH | N | -iso-propyl |
| M202 (a and b) | -2-(3-CF$_3$-pyridyl) | CH | N | -iso-propyl |
| M203 (a and b) | -2-(3-CHF$_2$-pyridyl) | CH | N | -iso-propyl |
| M204 (a and b) | -2-(3-hydroxypyridyl) | CH | N | -iso-propyl |
| M205 (a and b) | -2-(3-nitropyridyl) | CH | N | -iso-propyl |
| M206 (a and b) | -2-(3-cyanopyridyl) | CH | N | -iso-propyl |
| M207 (a and b) | -2-(3-bromopyridyl) | CH | N | -iso-propyl |
| M208 (a and b) | -2-(3-iodopyridyl) | CH | N | -iso-propyl |
| M209 (a and b) | -4-(5-chloropyrimidinyl) | CH | N | -iso-propyl |
| M210 (a and b) | -4-(5-methylpyrimidinyl) | CH | N | -iso-propyl |
| M211 (a and b) | -4-(5-fluoropyrimidinyl) | CH | N | -iso-propyl |
| M212 (a and b) | -2-(3-chloropyrazinyl) | CH | N | -iso-propyl |
| M213 (a and b) | -2-(3-methylpyrazinyl) | CH | N | -iso-propyl |
| M214 (a and b) | -2-(3-fluoropyrazinyl) | CH | N | -iso-propyl |
| M215 (a and b) | -3-(4-chloropyridazinyl) | CH | N | -iso-propyl |
| M216 (a and b) | -3-(4-methylpyridazinyl) | CH | N | -iso-propyl |
| M217 (a and b) | -3-(4-fluoropyridazinyl) | CH | N | -iso-propyl |
| M218 (a and b) | -5-(4-chlorothiadiazolyl) | CH | N | -iso-propyl |
| M219 (a and b) | -5-(4-methylthiadiazolyl) | N | N | -iso-propyl |
| M220 (a and b) | -5-(4-fluorothiadiazolyl) | CH | N | -iso-propyl |
| M221 (a and b) | -2-(3-chloropyridyl) | N | CH | -cyclohexyl |
| M222 (a and b) | -2-(3-fluoropyridyl) | N | CH | -cyclohexyl |
| M223 (a and b) | -2-(3-methylpyridyl) | N | CH | -cyclohexyl |
| M224 (a and b) | -2-(3-CF$_3$-pyridyl) | N | CH | -cyclohexyl |
| M225 (a and b) | -2-(3-CHF$_2$-pyridyl) | N | CH | -cyclohexyl |
| M226 (a and b) | -2-(3-hydroxypyridyl) | N | CH | -cyclohexyl |
| M227 (a and b) | -2-(3-nitropyridyl) | N | CH | -cyclohexyl |
| M228 (a and b) | -2-(3-cyanopyridyl) | N | CH | -cyclohexyl |
| M229 (a and b) | -2-(3-bromopyridyl) | N | CH | -cyclohexyl |
| M230 (a and b) | -2-(3-iodopyridyl) | N | CH | -cyclohexyl |
| M231 (a and b) | -4-(5-chloropyrimidinyl) | N | CH | -cyclohexyl |
| M232 (a and b) | -4-(5-methylpyrimidinyl) | N | CH | -cyclohexyl |
| M233 (a and b) | -4-(5-fluoropyrimidinyl) | N | CH | -cyclohexyl |

TABLE 13-continued

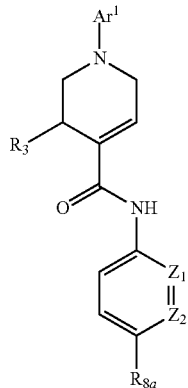

(Im)

and pharmaceutically acceptable salts thereof, wherein:

| Compound | Ar¹ | $Z_1$ | $Z_2$ | $R_{8a}$ |
|---|---|---|---|---|
| M234 (a and b) | -2-(3-chloropyrazinyl) | N | CH | -cyclohexyl |
| M235 (a and b) | -2-(3-methylpyrazinyl) | N | CH | -cyclohexyl |
| M236 (a and b) | -2-(3-fluoropyrazinyl) | N | CH | -cyclohexyl |
| M237 (a and b) | -3-(4-chloropyridazinyl) | N | CH | -cyclohexyl |
| M238 (a and b) | -3-(4-methylpyridazinyl) | N | CH | -cyclohexyl |
| M239 (a and b) | -3-(4-fluoropyridazinyl) | N | CH | -cyclohexyl |
| M240 (a and b) | -5-(4-chlorothiadiazolyl) | N | CH | -cyclohexyl |
| M241 (a and b) | -5-(4-methylthiadiazolyl) | N | N | -cyclohexyl |
| M242 (a and b) | -5-(4-fluorothiadiazolyl) | N | CH | -cyclohexyl |
| M243 (a and b) | -2-(3-chloropyridyl) | CH | N | -cyclohexyl |
| M244 (a and b) | -2-(3-fluoropyridyl) | CH | N | -cyclohexyl |
| M245 (a and b) | -2-(3-methylpyridyl) | CH | N | -cyclohexyl |
| M246 (a and b) | -2-(3-CF₃-pyridyl) | CH | N | -cyclohexyl |
| M247 (a and b) | -2-(3-CHF₂-pyridyl) | CH | N | -cyclohexyl |
| M248 (a and b) | -2-(3-hydroxypyridyl) | CH | N | -cyclohexyl |
| M249 (a and b) | -2-(3-nitropyridyl) | CH | N | -cyclohexyl |
| M250 (a and b) | -2-(3-cyanopyridyl) | CH | N | -cyclohexyl |
| M251 (a and b) | -2-(3-bromopyridyl) | CH | N | -cyclohexyl |
| M252 (a and b) | -2-(3-iodopyridyl) | CH | N | -cyclohexyl |
| M253 (a and b) | -4-(5-chloropyrimidinyl) | CH | N | -cyclohexyl |
| M254 (a and b) | -4-(5-methylpyrimidinyl) | CH | N | -cyclohexyl |
| M255 (a and b) | -4-(5-fluoropyrimidinyl) | CH | N | -cyclohexyl |
| M256 (a and b) | -2-(3-chloropyrazinyl) | CH | N | -cyclohexyl |
| M257 (a and b) | -2-(3-methylpyrazinyl) | CH | N | -cyclohexyl |
| M258 (a and b) | -2-(3-fluoropyrazinyl) | CH | N | -cyclohexyl |
| M259 (a and b) | -3-(4-chloropyridazinyl) | CH | N | -cyclohexyl |
| M260 (a and b) | -3-(4-methylpyridazinyl) | CH | N | -cyclohexyl |
| M261 (a and b) | -3-(4-fluoropyridazinyl) | CH | N | -cyclohexyl |
| M262 (a and b) | -5-(4-chlorothiadiazolyl) | CH | N | -cyclohexyl |
| M263 (a and b) | -5-(4-methylthiadiazolyl) | N | N | -cyclohexyl |
| M264 (a and b) | -5-(4-fluorothiadiazolyl) | CH | N | -cyclohexyl |
| M265 (a and b) | -2-(3-chloropyridyl) | N | CH | —CH₂CF₃ |
| M266 (a and b) | -2-(3-fluoropyridyl) | N | CH | —CH₂CF₃ |
| M267 (a and b) | -2-(3-methylpyridyl) | N | CH | —CH₂CF₃ |
| M268 (a and b) | -2-(3-CF₃-pyridyl) | N | CH | —CH₂CF₃ |
| M269 (a and b) | -2-(3-CHF₂-pyridyl) | N | CH | —CH₂CF₃ |
| M270 (a and b) | -2-(3-hydroxypyridyl) | N | CH | —CH₂CF₃ |
| M271 (a and b) | -2-(3-nitropyridyl) | N | CH | —CH₂CF₃ |
| M272 (a and b) | -2-(3-cyanopyridyl) | N | CH | —CH₂CF₃ |
| M273 (a and b) | -2-(3-bromopyridyl) | N | CH | —CH₂CF₃ |
| M274 (a and b) | -2-(3-iodopyridyl) | N | CH | —CH₂CF₃ |
| M275 (a and b) | -4-(5-chloropyrimidinyl) | N | CH | —CH₂CF₃ |
| M276 (a and b) | -4-(5-methylpyrimidinyl) | N | CH | —CH₂CF₃ |
| M277 (a and b) | -4-(5-fluoropyrimidinyl) | N | CH | —CH₂CF₃ |
| M278 (a and b) | -2-(3-chloropyrazinyl) | N | CH | —CH₂CF₃ |
| M279 (a and b) | -2-(3-methylpyrazinyl) | N | CH | —CH₂CF₃ |
| M280 (a and b) | -2-(3-fluoropyrazinyl) | N | CH | —CH₂CF₃ |
| M281 (a and b) | -3-(4-chloropyridazinyl) | N | CH | —CH₂CF₃ |
| M282 (a and b) | -3-(4-methylpyridazinyl) | N | CH | —CH₂CF₃ |
| M283 (a and b) | -3-(4-fluoropyridazinyl) | N | CH | —CH₂CF₃ |
| M284 (a and b) | -5-(4-chlorothiadiazolyl) | N | CH | —CH₂CF₃ |
| M285 (a and b) | -5-(4-methylthiadiazolyl) | N | N | —CH₂CF₃ |
| M286 (a and b) | -5-(4-fluorothiadiazolyl) | N | CH | —CH₂CF₃ |
| M287 (a and b) | -2-(3-chloropyridyl) | CH | N | —CH₂CF₃ |
| M288 (a and b) | -2-(3-fluoropyridyl) | CH | N | —CH₂CF₃ |
| M289 (a and b) | -2-(3-methylpyridyl) | CH | N | —CH₂CF₃ |
| M290 (a and b) | -2-(3-CF₃-pyridyl) | CH | N | —CH₂CF₃ |
| M291 (a and b) | -2-(3-CHF₂-pyridyl) | CH | N | —CH₂CF₃ |
| M292 (a and b) | -2-(3-hydroxypyridyl) | CH | N | —CH₂CF₃ |
| M293 (a and b) | -2-(3-nitropyridyl) | CH | N | —CH₂CF₃ |
| M294 (a and b) | -2-(3-cyanopyridyl) | CH | N | —CH₂CF₃ |
| M295 (a and b) | -2-(3-bromopyridyl) | CH | N | —CH₂CF₃ |
| M296 (a and b) | -2-(3-iodopyridyl) | CH | N | —CH₂CF₃ |
| M297 (a and b) | -4-(5-chloropyrimidinyl) | CH | N | —CH₂CF₃ |
| M298 (a and b) | -4-(5-methylpyrimidinyl) | CH | N | —CH₂CF₃ |
| M299 (a and b) | -4-(5-fluoropyrimidinyl) | CH | N | —CH₂CF₃ |
| M300 (a and b) | -2-(3-chloropyrazinyl) | CH | N | —CH₂CF₃ |
| M301 (a and b) | -2-(3-methylpyrazinyl) | CH | N | —CH₂CF₃ |
| M302 (a and b) | -2-(3-fluoropyrazinyl) | CH | N | —CH₂CF₃ |
| M303 (a and b) | -3-(4-chloropyridazinyl) | CH | N | —CH₂CF₃ |
| M304 (a and b) | -3-(4-methylpyridazinyl) | CH | N | —CH₂CF₃ |
| M305 (a and b) | -3-(4-fluoropyridazinyl) | CH | N | —CH₂CF₃ |
| M306 (a and b) | -5-(4-chlorothiadiazolyl) | CH | N | —CH₂CF₃ |
| M307 (a and b) | -5-(4-methylthiadiazolyl) | N | N | —CH₂CF₃ |
| M308 (a and b) | -5-(4-fluorothiadiazolyl) | CH | N | —CH₂CF₃ |
| M309 (a and b) | -2-(3-chloropyridyl) | N | CH | —OCF₃ |
| M310 (a and b) | -2-(3-fluoropyridyl) | N | CH | —OCF₃ |
| M311 (a and b) | -2-(3-methylpyridyl) | N | CH | —OCF₃ |
| M312 (a and b) | -2-(3-CF₃-pyridyl) | N | CH | —OCF₃ |
| M313 (a and b) | -2-(3-CHF₂-pyridyl) | N | CH | —OCF₃ |
| M314 (a and b) | -2-(3-hydroxypyridyl) | N | CH | —OCF₃ |
| M315 (a and b) | -2-(3-nitropyridyl) | N | CH | —OCF₃ |
| M316 (a and b) | -2-(3-cyanopyridyl) | N | CH | —OCF₃ |
| M317 (a and b) | -2-(3-bromopyridyl) | N | CH | —OCF₃ |
| M318 (a and b) | -2-(3-iodopyridyl) | N | CH | —OCF₃ |
| M319 (a and b) | -4-(5-chloropyrimidinyl) | N | CH | —OCF₃ |
| M320 (a and b) | -4-(5-methylpyrimidinyl) | N | CH | —OCF₃ |
| M321 (a and b) | -4-(5-fluoropyrimidinyl) | N | CH | —OCF₃ |
| M322 (a and b) | -2-(3-chloropyrazinyl) | N | CH | —OCF₃ |
| M323 (a and b) | -2-(3-methylpyrazinyl) | N | CH | —OCF₃ |
| M324 (a and b) | -2-(3-fluoropyrazinyl) | N | CH | —OCF₃ |
| M325 (a and b) | -3-(4-chloropyridazinyl) | N | CH | —OCF₃ |
| M326 (a and b) | -3-(4-methylpyridazinyl) | N | CH | —OCF₃ |
| M327 (a and b) | -3-(4-fluoropyridazinyl) | N | CH | —OCF₃ |
| M328 (a and b) | -5-(4-chlorothiadiazolyl) | N | CH | —OCF₃ |
| M329 (a and b) | -5-(4-methylthiadiazolyl) | N | N | —OCF₃ |
| M330 (a and b) | -5-(4-fluorothiadiazolyl) | N | CH | —OCF₃ |
| M331 (a and b) | -2-(3-chloropyridyl) | CH | N | —OCF₃ |
| M332 (a and b) | -2-(3-fluoropyridyl) | CH | N | —OCF₃ |
| M333 (a and b) | -2-(3-methylpyridyl) | CH | N | —OCF₃ |
| M334 (a and b) | -2-(3-CF₃-pyridyl) | CH | N | —OCF₃ |
| M335 (a and b) | -2-(3-CHF₂-pyridyl) | CH | N | —OCF₃ |
| M336 (a and b) | -2-(3-hydroxypyridyl) | CH | N | —OCF₃ |
| M337 (a and b) | -2-(3-nitropyridyl) | CH | N | —OCF₃ |
| M338 (a and b) | -2-(3-cyanopyridyl) | CH | N | —OCF₃ |
| M339 (a and b) | -2-(3-bromopyridyl) | CH | N | —OCF₃ |
| M340 (a and b) | -2-(3-iodopyridyl) | CH | N | —OCF₃ |
| M341 (a and b) | -4-(5-chloropyrimidinyl) | CH | N | —OCF₃ |
| M342 (a and b) | -4-(5-methylpyrimidinyl) | CH | N | —OCF₃ |
| M343 (a and b) | -4-(5-fluoropyrimidinyl) | CH | N | —OCF₃ |

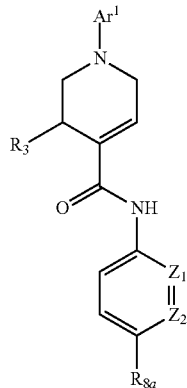

TABLE 13-continued (Im)

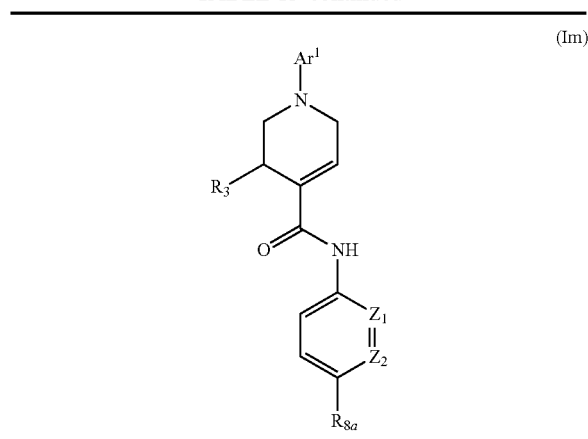

and pharmaceutically acceptable salts thereof, wherein:

| Compound | Ar¹ | $Z_1$ | $Z_2$ | $R_{8a}$ |
|---|---|---|---|---|
| M344 (a and b) | -2-(3-chloropyrazinyl) | CH | N | —OCF₃ |
| M345 (a and b) | -2-(3-methylpyrazinyl) | CH | N | —OCF₃ |
| M346 (a and b) | -2-(3-fluoropyrazinyl) | CH | N | —OCF₃ |
| M347 (a and b) | -3-(4-chloropyridazinyl) | CH | N | —OCF₃ |
| M348 (a and b) | -3-(4-methylpyridazinyl) | CH | N | —OCF₃ |
| M349 (a and b) | -3-(4-fluoropyridazinyl) | CH | N | —OCF₃ |
| M350 (a and b) | -5-(4-chlorothiadiazolyl) | CH | N | —OCF₃ |
| M351 (a and b) | -5-(4-methylthiadiazolyl) | N | N | —OCF₃ |
| M352 (a and b) | -5-(4-fluorothiadiazolyl) | CH | N | —OCF₃ |
| M353 (a and b) | -2-(3-chloropyridyl) | N | CH | —SCF₃ |
| M354 (a and b) | -2-(3-fluoropyridyl) | N | CH | —SCF₃ |
| M355 (a and b) | -2-(3-methylpyridyl) | N | CH | —SCF₃ |
| M356 (a and b) | -2-(3-CF₃-pyridyl) | N | CH | —SCF₃ |
| M357 (a and b) | -2-(3-CHF₂-pyridyl) | N | CH | —SCF₃ |
| M358 (a and b) | -2-(3-hydroxypyridyl) | N | CH | —SCF₃ |
| M359 (a and b) | -2-(3-nitropyridyl) | N | CH | —SCF₃ |
| M360 (a and b) | -2-(3-cyanopyridyl) | N | CH | —SCF₃ |
| M361 (a and b) | -2-(3-bromopyridyl) | N | CH | —SCF₃ |
| M362 (a and b) | -2-(3-iodopyridyl) | N | CH | —SCF₃ |
| M363 (a and b) | -4-(5-chloropyrimidinyl) | N | CH | —SCF₃ |
| M364 (a and b) | -4-(5-methylpyrimidinyl) | N | CH | —SCF₃ |
| M365 (a and b) | -4-(5-fluoropyrimidinyl) | N | CH | —SCF₃ |
| M366 (a and b) | -2-(3-chloropyrazinyl) | N | CH | —SCF₃ |
| M367 (a and b) | -2-(3-methylpyrazinyl) | N | CH | —SCF₃ |
| M368 (a and b) | -2-(3-fluoropyrazinyl) | N | CH | —SCF₃ |
| M369 (a and b) | -3-(4-chloropyridazinyl) | N | CH | —SCF₃ |
| M370 (a and b) | -3-(4-methylpyridazinyl) | N | CH | —SCF₃ |
| M371 (a and b) | -3-(4-fluoropyridazinyl) | N | CH | —SCF₃ |
| M372 (a and b) | -5-(4-chlorothiadiazolyl) | N | CH | —SCF₃ |
| M373 (a and b) | -5-(4-methylthiadiazolyl) | N | N | —SCF₃ |
| M374 (a and b) | -5-(4-fluorothiadiazolyl) | N | CH | —SCF₃ |
| M375 (a and b) | -2-(3-chloropyridyl) | CH | N | —SCF₃ |
| M376 (a and b) | -2-(3-fluoropyridyl) | CH | N | —SCF₃ |
| M377 (a and b) | -2-(3-methylpyridyl) | CH | N | —SCF₃ |
| M378 (a and b) | -2-(3-CF₃-pyridyl) | CH | N | —SCF₃ |
| M379 (a and b) | -2-(3-CHF₂-pyridyl) | CH | N | —SCF₃ |
| M380 (a and b) | -2-(3-hydroxypyridyl) | CH | N | —SCF₃ |
| M381 (a and b) | -2-(3-nitropyridyl) | CH | N | —SCF₃ |
| M382 (a and b) | -2-(3-cyanopyridyl) | CH | N | —SCF₃ |
| M383 (a and b) | -2-(3-bromopyridyl) | CH | N | —SCF₃ |
| M384 (a and b) | -2-(3-iodopyridyl) | CH | N | —SCF₃ |
| M385 (a and b) | -4-(5-chloropyrimidinyl) | CH | N | —SCF₃ |
| M386 (a and b) | -4-(5-methylpyrimidinyl) | CH | N | —SCF₃ |
| M387 (a and b) | -4-(5-fluoropyrimidinyl) | CH | N | —SCF₃ |
| M388 (a and b) | -2-(3-chloropyrazinyl) | CH | N | —SCF₃ |
| M389 (a and b) | -2-(3-methylpyrazinyl) | CH | N | —SCF₃ |
| M390 (a and b) | -2-(3-fluoropyrazinyl) | CH | N | —SCF₃ |
| M391 (a and b) | -3-(4-chloropyridazinyl) | CH | N | —SCF₃ |
| M392 (a and b) | -3-(4-methylpyridazinyl) | CH | N | —SCF₃ |
| M393 (a and b) | -3-(4-fluoropyridazinyl) | CH | N | —SCF₃ |
| M394 (a and b) | -5-(4-chlorothiadiazolyl) | CH | N | —SCF₃ |
| M395 (a and b) | -5-(4-methylthiadiazolyl) | N | N | —SCF₃ |
| M396 (a and b) | -5-(4-fluorothiadiazolyl) | CH | N | —SCF₃ |
| M397 (a and b) | -2-(3-chloropyridyl) | N | CH | —H |
| M398 (a and b) | -2-(3-fluoropyridyl) | N | CH | —H |

TABLE 13-continued (Im)

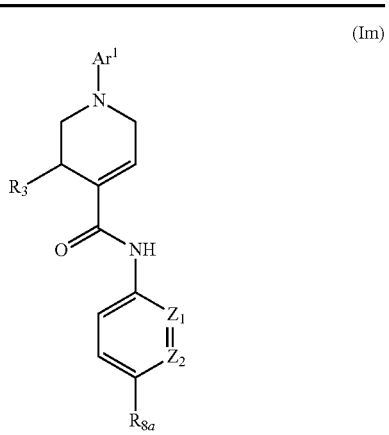

and pharmaceutically acceptable salts thereof, wherein:

| Compound | Ar¹ | $Z_1$ | $Z_2$ | $R_{8a}$ |
|---|---|---|---|---|
| M399 (a and b) | -2-(3-methylpyridyl) | N | CH | —H |
| M400 (a and b) | -2-(3-CF₃-pyridyl) | N | CH | —H |
| M401 (a and b) | -2-(3-CHF₂-pyridyl) | N | CH | —H |
| M402 (a and b) | -2-(3-hydroxypyridyl) | N | CH | —H |
| M403 (a and b) | -2-(3-nitropyridyl) | N | CH | —H |
| M404 (a and b) | -2-(3-cyanopyridyl) | N | CH | —H |
| M405 (a and b) | -2-(3-bromopyridyl) | N | CH | —H |
| M406 (a and b) | -2-(3-iodopyridyl) | N | CH | —H |
| M407 (a and b) | -4-(5-chloropyrimidinyl) | N | CH | —H |
| M408 (a and b) | -4-(5-methylpyrimidinyl) | N | CH | —H |
| M409 (a and b) | -4-(5-fluoropyrimidinyl) | N | CH | —H |
| M410 (a and b) | -2-(3-chloropyrazinyl) | N | CH | —H |
| M411 (a and b) | -2-(3-methylpyrazinyl) | N | CH | —H |
| M412 (a and b) | -2-(3-fluoropyrazinyl) | N | CH | —H |
| M413 (a and b) | -3-(4-chloropyridazinyl) | N | CH | —H |
| M414 (a and b) | -3-(4-methylpyridazinyl) | N | CH | —H |
| M415 (a and b) | -3-(4-fluoropyridazinyl) | N | CH | —H |
| M416 (a and b) | -5-(4-chlorothiadiazolyl) | N | CH | —H |
| M417 (a and b) | -5-(4-methylthiadiazolyl) | N | N | —H |
| M418 (a and b) | -5-(4-fluorothiadiazolyl) | N | CH | —H |
| M419 (a and b) | -2-(3-chloropyridyl) | CH | N | —H |
| M420 (a and b) | -2-(3-fluoropyridyl) | CH | N | —H |
| M421 (a and b) | -2-(3-methylpyridyl) | CH | N | —H |
| M422 (a and b) | -2-(3-CF₃-pyridyl) | CH | N | —H |
| M423 (a and b) | -2-(3-CHF₂-pyridyl) | CH | N | —H |
| M424 (a and b) | -2-(3-hydroxypyridyl) | CH | N | —H |
| M425 (a and b) | -2-(3-nitropyridyl) | CH | N | —H |
| M426 (a and b) | -2-(3-cyanopyridyl) | CH | N | —H |
| M427 (a and b) | -2-(3-bromopyridyl) | CH | N | —H |
| M428 (a and b) | -2-(3-iodopyridyl) | CH | N | —H |
| M429 (a and b) | -4-(5-chloropyrimidinyl) | CH | N | —H |
| M430 (a and b) | -4-(5-methylpyrimidinyl) | CH | N | —H |
| M431 (a and b) | -4-(5-fluoropyrimidinyl) | CH | N | —H |
| M432 (a and b) | -2-(3-chloropyrazinyl) | CH | N | —H |
| M433 (a and b) | -2-(3-methylpyrazinyl) | CH | N | —H |
| M434 (a and b) | -2-(3-fluoropyrazinyl) | CH | N | —H |
| M435 (a and b) | -3-(4-chloropyridazinyl) | CH | N | —H |
| M436 (a and b) | -3-(4-methylpyridazinyl) | CH | N | —H |
| M437 (a and b) | -3-(4-fluoropyridazinyl) | CH | N | —H |
| M438 (a and b) | -5-(4-chlorothiadiazolyl) | CH | N | —H |
| M439 (a and b) | -5-(4-methylthiadiazolyl) | N | N | —H |
| M440 (a and b) | -5-(4-fluorothiadiazolyl) | CH | N | —H |

(a) means that R₃ is —H.
(b) means that R₃ is —CH₃.

TABLE 14

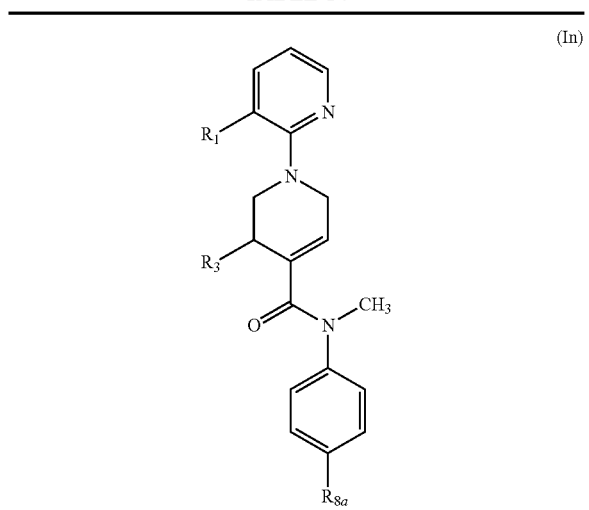

and pharmaceutically acceptable salts thereof, wherein:

| Compound | R₁ | R₈ₐ |
|---|---|---|
| N1 (a and b) | —H | —H |
| N2 (a and b) | —H | -tert-butyl |
| N3 (a and b) | —H | -iso-butyl |
| N4 (a and b) | —H | -sec-butyl |
| N5 (a and b) | —H | -iso-propyl |
| N6 (a and b) | —H | -n-propyl |
| N7 (a and b) | —H | -cyclohexyl |
| N8 (a and b) | —H | -tert-butoxy |
| N9 (a and b) | —H | -isopropoxy |
| N10 (a and b) | —H | —CF₃ |
| N11 (a and b) | —H | —CH₂CF₃ |
| N12 (a and b) | —H | —OCF₃ |
| N13 (a and b) | —H | —Cl |
| N14 (a and b) | —H | —Br |
| N15 (a and b) | —H | —I |
| N16 (a and b) | —H | -n-butyl |
| N17 (a and b) | —H | —CH₃ |
| N18 (a and b) | —H | —SCF₃ |
| N19 (a and b) | —H | —N(CH₂CH₃)₂ |
| N20 (a and b) | —H | —OCF₂CHF₂ |
| N21 (a and b) | —H | —C(OH)(CF₃)₂ |
| N22 (a and b) | —H | -(1,1-dimethyl-pentyl) |
| N23 (a and b) | —H | -(1,1-dimethyl-acetic acid) ethyl ester |
| N24 (a and b) | —H | —N-piperidinyl |
| N25 (a and b) | —Cl | —H |
| N26 (a and b) | —Cl | -tert-butyl |
| N27 (a and b) | —Cl | -iso-butyl |
| N28 (a and b) | —Cl | -sec-butyl |
| N29 (a and b) | —Cl | -iso-propyl |
| N30 (a and b) | —Cl | -n-propyl |
| N31 (a and b) | —Cl | -cyclohexyl |
| N32 (a and b) | —Cl | -tert-butoxy |
| N33 (a and b) | —Cl | -isopropoxy |
| N34 (a and b) | —Cl | —CF₃ |
| N35 (a and b) | —Cl | —CH₂CF₃ |
| N36 (a and b) | —Cl | —OCF₃ |
| N37 (a and b) | —Cl | —Cl |
| N38 (a and b) | —Cl | —Br |
| N39 (a and b) | —Cl | —I |
| N40 (a and b) | —Cl | -n-butyl |
| N41 (a and b) | —Cl | —CH₃ |
| N42 (a and b) | —Cl | —SCF₃ |
| N43 (a and b) | —Cl | —N(CH₂CH₃)₂ |
| N44 (a and b) | —Cl | —OCF₂CHF₂ |
| N45 (a and b) | —Cl | —C(OH)(CF₃)₂ |
| N46 (a and b) | —Cl | -(1,1-dimethyl-pentyl) |
| N47 (a and b) | —Cl | -(1,1-dimethyl-acetic acid) ethyl ester |
| N48 (a and b) | —Cl | —N-piperidinyl |
| N49 (a and b) | —F | —H |
| N50 (a and b) | —F | -tert-butyl |
| N51 (a and b) | —F | -iso-butyl |
| N52 (a and b) | —F | -sec-butyl |
| N53 (a and b) | —F | -iso-propyl |
| N54 (a and b) | —F | -n-propyl |
| N55 (a and b) | —F | -cyclohexyl |
| N56 (a and b) | —F | -tert-butoxy |
| N57 (a and b) | —F | -isopropoxy |
| N58 (a and b) | —F | —CF₃ |
| N59 (a and b) | —F | —CH₂CF₃ |
| N60 (a and b) | —F | —OCF₃ |
| N61 (a and b) | —F | —Cl |
| N62 (a and b) | —F | —Br |
| N63 (a and b) | —F | —I |
| N64 (a and b) | —F | -n-butyl |
| N65 (a and b) | —F | —CH₃ |
| N66 (a and b) | —F | —SCF₃ |
| N67 (a and b) | —F | —N(CH₂CH₃)₂ |
| N68 (a and b) | —F | —OCF₂CHF₂ |
| N69 (a and b) | —F | —C(OH)(CF₃)₂ |
| N70 (a and b) | —F | -(1,1-dimethyl-pentyl) |
| N71 (a and b) | —F | -(1,1-dimethyl-acetic acid) ethyl ester |
| N72 (a and b) | —F | —N-piperidinyl |
| N73 (a and b) | —CH₃ | —H |
| N74 (a and b) | —CH₃ | -iso-butyl |
| N75 (a and b) | —CH₃ | -tert-butyl |
| N76 (a and b) | —CH₃ | -sec-butyl |
| N77 (a and b) | —CH₃ | -iso-propyl |
| N78 (a and b) | —CH₃ | -n-propyl |
| N79 (a and b) | —CH₃ | -cyclohexyl |
| N80 (a and b) | —CH₃ | -tert-butoxy |
| N81 (a and b) | —CH₃ | -isopropoxy |
| N82 (a and b) | —CH₃ | —CF₃ |
| N83 (a and b) | —CH₃ | —CH₂CF₃ |
| N84 (a and b) | —CH₃ | —OCF₃ |
| N85 (a and b) | —CH₃ | —Cl |
| N86 (a and b) | —CH₃ | —Br |
| N87 (a and b) | —CH₃ | —I |
| N88 (a and b) | —CH₃ | -n-butyl |
| N89 (a and b) | —CH₃ | —CH₃ |
| N90 (a and b) | —CH₃ | —SCF₃ |
| N91 (a and b) | —CH₃ | —N(CH₂CH₃)₂ |
| N92 (a and b) | —CH₃ | —OCF₂CHF₂ |
| N93 (a and b) | —CH₃ | —C(OH)(CF₃)₂ |
| N94 (a and b) | —CH₃ | -(1,1-dimethyl-pentyl) |
| N95 (a and b) | —CH₃ | -(1,1-dimethyl-acetic acid) ethyl ester |
| N96 (a and b) | —CH₃ | —N-piperidinyl |
| N97 (a and b) | —CF₃ | —H |
| N98 (a and b) | —CF₃ | -tert-butyl |
| N99 (a and b) | —CF₃ | -iso-butyl |
| N100 (a and b) | —CF₃ | -sec-butyl |

TABLE 14-continued

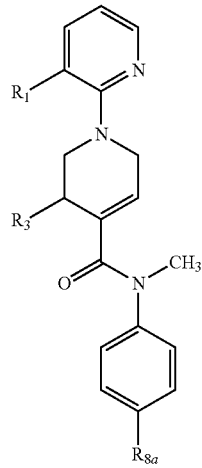

and pharmaceutically acceptable salts thereof, wherein:

| Compound | $R_1$ | $R_{8a}$ |
|---|---|---|
| N101 (a and b) | —$CF_3$ | -iso-propyl |
| N102 (a and b) | —$CF_3$ | -n-propyl |
| N103 (a and b) | —$CF_3$ | -cyclohexyl |
| N104 (a and b) | —$CF_3$ | -tert-butoxy |
| N105 (a and b) | —$CF_3$ | -isopropoxy |
| N106 (a and b) | —$CF_3$ | —$CF_3$ |
| N107 (a and b) | —$CF_3$ | —$CH_2CF_3$ |
| N108 (a and b) | —$CF_3$ | —$OCF_3$ |
| N109 (a and b) | —$CF_3$ | —Cl |
| N110 (a and b) | —$CF_3$ | —Br |
| N111 (a and b) | —$CF_3$ | —I |
| N112 (a and b) | —$CF_3$ | -n-butyl |
| N113 (a and b) | —$CF_3$ | —$CH_3$ |
| N114 (a and b) | —$CF_3$ | —$SCF_3$ |
| N115 (a and b) | —$CF_3$ | —$N(CH_2CH_3)_2$ |
| N116 (a and b) | —$CF_3$ | —$OCF_2CHF_2$ |
| N117 (a and b) | —$CF_3$ | —$C(OH)(CF_3)_2$ |
| N118 (a and b) | —$CF_3$ | -(1,1-dimethyl-pentyl) |
| N119 (a and b) | —$CF_3$ | -(1,1-dimethyl-acetic acid) ethyl ester |
| N120 (a and b) | —$CF_3$ | —N-piperidinyl |
| N121 (a and b) | —$CHF_2$ | -tert-butyl |
| N122 (a and b) | —$CHF_2$ | —H |
| N123 (a and b) | —$CHF_2$ | -iso-butyl |
| N124 (a and b) | —$CHF_2$ | -sec-butyl |
| N125 (a and b) | —$CHF_2$ | -iso-propyl |
| N126 (a and b) | —$CHF_2$ | -n-propyl |
| N127 (a and b) | —$CHF_2$ | -cyclohexyl |
| N128 (a and b) | —$CHF_2$ | -tert-butoxy |
| N129 (a and b) | —$CHF_2$ | -isopropoxy |
| N130 (a and b) | —$CHF_2$ | —$CF_3$ |
| N131 (a and b) | —$CHF_2$ | —$CH_2CF_3$ |
| N132 (a and b) | —$CHF_2$ | —$OCF_3$ |
| N133 (a and b) | —$CHF_2$ | —Cl |
| N134 (a and b) | —$CHF_2$ | —Br |
| N135 (a and b) | —$CHF_2$ | —I |
| N136 (a and b) | —$CHF_2$ | -n-butyl |
| N137 (a and b) | —$CHF_2$ | —$CH_3$ |
| N138 (a and b) | —$CHF_2$ | —$SCF_3$ |
| N139 (a and b) | —$CHF_2$ | —$N(CH_2CH_3)_2$ |
| N140 (a and b) | —$CHF_2$ | —$OCF_2CHF_2$ |
| N141 (a and b) | —$CHF_2$ | —$C(OH)(CF_3)_2$ |
| N142 (a and b) | —$CHF_2$ | -(1,1-dimethyl-pentyl) |
| N143 (a and b) | —$CHF_2$ | -(1,1-dimethyl-acetic acid) ethyl ester |
| N144 (a and b) | —$CHF_2$ | —N-piperidinyl |
| N145 (a and b) | —OH | —H |
| N146 (a and b) | —OH | -tert-butyl |
| N147 (a and b) | —OH | -iso-butyl |
| N148 (a and b) | —OH | -sec-butyl |
| N149 (a and b) | —OH | -iso-propyl |
| N150 (a and b) | —OH | -n-propyl |

TABLE 14-continued

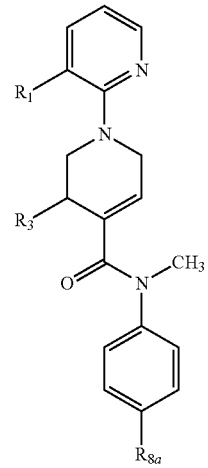

and pharmaceutically acceptable salts thereof, wherein:

| Compound | $R_1$ | $R_{8a}$ |
|---|---|---|
| N151 (a and b) | —OH | -cyclohexyl |
| N152 (a and b) | —OH | -tert-butoxy |
| N153 (a and b) | —OH | -isopropoxy |
| N154 (a and b) | —OH | —$CF_3$ |
| N155 (a and b) | —OH | —$CH_2CF_3$ |
| N156 (a and b) | —OH | —$OCF_3$ |
| N157 (a and b) | —OH | —Cl |
| N158 (a and b) | —OH | —Br |
| N159 (a and b) | —OH | —I |
| N160 (a and b) | —OH | -n-butyl |
| N161 (a and b) | —OH | —$CH_3$ |
| N162 (a and b) | —OH | —$SCF_3$ |
| N163 (a and b) | —OH | —$N(CH_2CH_3)_2$ |
| N164 (a and b) | —OH | —$OCF_2CHF_2$ |
| N165 (a and b) | —OH | —$C(OH)(CF_3)_2$ |
| N166 (a and b) | —OH | -(1,1-dimethyl-pentyl) |
| N167 (a and b) | —OH | -(1,1-dimethyl-acetic acid) ethyl ester |
| N168 (a and b) | —OH | —N-piperidinyl |
| N169 (a and b) | —$NO_2$ | —H |
| N170 (a and b) | —$NO_2$ | -tert-butyl |
| N171 (a and b) | —$NO_2$ | -iso-butyl |
| N172 (a and b) | —$NO_2$ | -sec-butyl |
| N173 (a and b) | —$NO_2$ | -iso-propyl |
| N174 (a and b) | —$NO_2$ | -n-propyl |
| N175 (a and b) | —$NO_2$ | -cyclohexyl |
| N176 (a and b) | —$NO_2$ | -tert-butoxy |
| N177 (a and b) | —$NO_2$ | -isopropoxy |
| N178 (a and b) | —$NO_2$ | —$CF_3$ |
| N179 (a and b) | —$NO_2$ | —$CH_2CF_3$ |
| N180 (a and b) | —$NO_2$ | —$OCF_3$ |
| N181 (a and b) | —$NO_2$ | —Cl |
| N182 (a and b) | —$NO_2$ | —Br |
| N183 (a and b) | —$NO_2$ | —I |
| N184 (a and b) | —$NO_2$ | -n-butyl |
| N185 (a and b) | —$NO_2$ | —$CH_3$ |
| N186 (a and b) | —$NO_2$ | —$SCF_3$ |
| N187 (a and b) | —$NO_2$ | —$N(CH_2CH_3)_2$ |
| N188 (a and b) | —$NO_2$ | —$OCF_2CHF_2$ |
| N189 (a and b) | —$NO_2$ | —$C(OH)(CF_3)_2$ |
| N190 (a and b) | —$NO_2$ | -(1,1-dimethyl-pentyl) |
| N191 (a and b) | —$NO_2$ | -(1,1-dimethyl-acetic acid) ethyl ester |
| N192 (a and b) | —$NO_2$ | —N-piperidinyl |
| N193 (a and b) | —CN | —H |
| N194 (a and b) | —CN | -tert-butyl |
| N195 (a and b) | —CN | -iso-butyl |
| N196 (a and b) | —CN | -sec-butyl |
| N197 (a and b) | —CN | -iso-propyl |
| N198 (a and b) | —CN | -n-propyl |
| N199 (a and b) | —CN | -cyclohexyl |
| N200 (a and b) | —CN | -tert-butoxy |

TABLE 14-continued

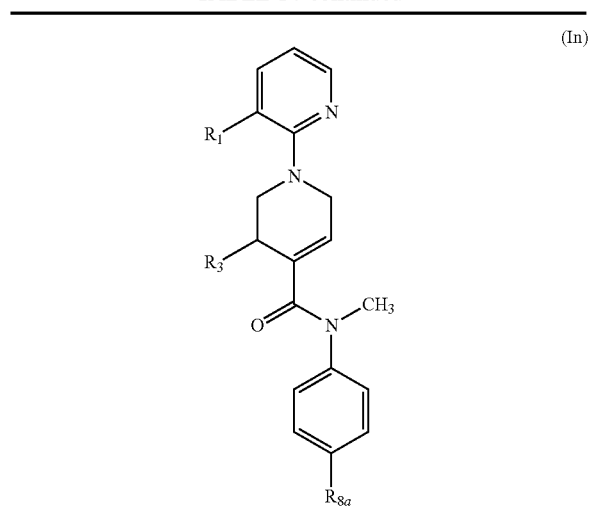

(In)

and pharmaceutically acceptable salts thereof, wherein:

| Compound | $R_1$ | $R_{8a}$ |
|---|---|---|
| N201 (a and b) | —CN | -isopropoxy |
| N202 (a and b) | —CN | —$CF_3$ |
| N203 (a and b) | —CN | —$CH_2CF_3$ |
| N204 (a and b) | —CN | —$OCF_3$ |
| N205 (a and b) | —CN | —Cl |
| N206 (a and b) | —CN | —Br |
| N207 (a and b) | —CN | —I |
| N208 (a and b) | —CN | -n-butyl |
| N209 (a and b) | —CN | —$CH_3$ |
| N210 (a and b) | —CN | —$SCF_3$ |
| N211 (a and b) | —CN | —$N(CH_2CH_3)_2$ |
| N212 (a and b) | —CN | —$OCF_2CHF_2$ |
| N213 (a and b) | —CN | —$C(OH)(CF_3)_2$ |
| N214 (a and b) | —CN | -(1,1-dimethyl-pentyl) |
| N215 (a and b) | —CN | -(1,1-dimethyl-acetic acid) ethyl ester |
| N216 (a and b) | —CN | —N-piperidinyl |
| N217 (a and b) | —Br | —H |
| N218 (a and b) | —Br | -tert-butyl |
| N219 (a and b) | —Br | -iso-butyl |
| N220 (a and b) | —Br | -sec-butyl |
| N221 (a and b) | —Br | -iso-propyl |
| N222 (a and b) | —Br | -n-propyl |
| N223 (a and b) | —Br | -cyclohexyl |
| N224 (a and b) | —Br | -tert-butoxy |
| N225 (a and b) | —Br | -isopropoxy |
| N226 (a and b) | —Br | —$CF_3$ |
| N227 (a and b) | —Br | —$CH_2CF_3$ |
| N228 (a and b) | —Br | —$OCF_3$ |
| N229 (a and b) | —Br | —Cl |
| N230 (a and b) | —Br | —Br |
| N231 (a and b) | —Br | —I |
| N232 (a and b) | —Br | -n-butyl |
| N233 (a and b) | —Br | —$CH_3$ |
| N234 (a and b) | —Br | —$SCF_3$ |
| N235 (a and b) | —Br | —$N(CH_2CH_3)_2$ |
| N236 (a and b) | —Br | —$OCF_2CHF_2$ |
| N237 (a and b) | —Br | —$C(OH)(CF_3)_2$ |
| N238 (a and b) | —Br | -(1,1-dimethyl-pentyl) |
| N239 (a and b) | —Br | -(1,1-dimethyl-acetic acid) ethyl ester |
| N240 (a and b) | —Br | —N-piperidinyl |
| N241 (a and b) | —I | -tert-butyl |
| N242 (a and b) | —I | —H |
| N243 (a and b) | —I | -iso-butyl |
| N244 (a and b) | —I | -sec-butyl |
| N245 (a and b) | —I | -iso-propyl |
| N246 (a and b) | —I | -n-propyl |
| N247 (a and b) | —I | -cyclohexyl |
| N248 (a and b) | —I | -tert-butoxy |
| N249 (a and b) | —I | -isopropoxy |
| N250 (a and b) | —I | —$CF_3$ |

TABLE 14-continued

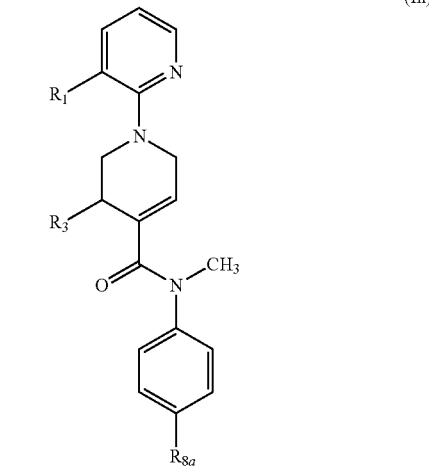

(In)

and pharmaceutically acceptable salts thereof, wherein:

| Compound | $R_1$ | $R_{8a}$ |
|---|---|---|
| N251 (a and b) | —I | —$CH_2CF_3$ |
| N252 (a and b) | —I | —$OCF_3$ |
| N253 (a and b) | —I | —Cl |
| N254 (a and b) | —I | —Br |
| N255 (a and b) | —I | —I |
| N256 (a and b) | —I | -n-butyl |
| N257 (a and b) | —I | —$CH_3$ |
| N258 (a and b) | —I | —$SCF_3$ |
| N259 (a and b) | —I | —$N(CH_2CH_3)_2$ |
| N260 (a and b) | —I | —$OCF_2CHF_2$ |
| N261 (a and b) | —I | —$C(OH)(CF_3)_2$ |
| N262 (a and b) | —I | -(1,1-dimethyl-pentyl) |
| N263 (a and b) | —I | -(1,1-dimethyl-acetic acid) ethyl ester |
| N264 (a and b) | —I | —N-piperidinyl |

(a) means that $R_3$ is —H.
(b) means that $R_3$ is —$CH_3$.

TABLE 15

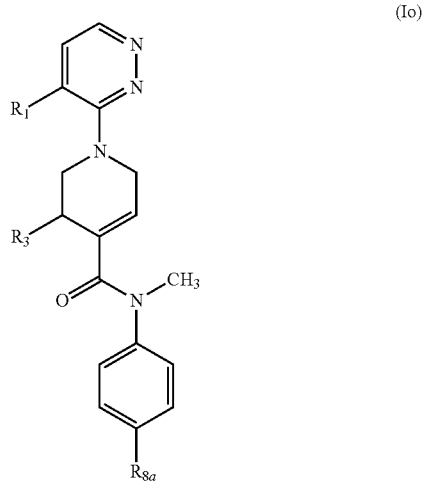

(Io)

and pharmaceutically acceptable salts thereof, wherein:

| Compound | $R_1$ | $R_{8a}$ |
|---|---|---|
| O1 (a and b) | —H | —H |
| O2 (a and b) | —H | -tert-butyl |

TABLE 15-continued

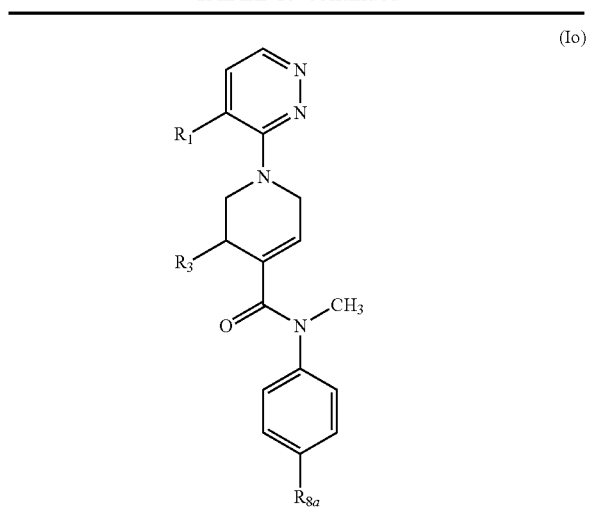

(Io)

and pharmaceutically acceptable salts thereof, wherein:

| Compound | $R_1$ | $R_{8a}$ |
|---|---|---|
| O3 (a and b) | —H | -iso-butyl |
| O4 (a and b) | —H | -sec-butyl |
| O5 (a and b) | —H | -iso-propyl |
| O6 (a and b) | —H | -n-propyl |
| O7 (a and b) | —H | -cyclohexyl |
| O8 (a and b) | —H | -tert-butoxy |
| O9 (a and b) | —H | -isopropoxy |
| O10 (a and b) | —H | —$CF_3$ |
| O11 (a and b) | —H | —$CH_2CF_3$ |
| O12 (a and b) | —H | —$OCF_3$ |
| O13 (a and b) | —H | —Cl |
| O14 (a and b) | —H | —Br |
| O15 (a and b) | —H | —I |
| O16 (a and b) | —H | -n-butyl |
| O17 (a and b) | —H | —$CH_3$ |
| O18 (a and b) | —H | —$SCF_3$ |
| O19 (a and b) | —H | —$N(CH_2CH_3)_2$ |
| O20 (a and b) | —H | —$OCF_2CHF_2$ |
| O21 (a and b) | —H | —$C(OH)(CF_3)_2$ |
| O22 (a and b) | —H | -(1,1-dimethyl-pentyl) |
| O23 (a and b) | —H | -(1,1-dimethyl-acetic acid) ethyl ester |
| O24 (a and b) | —H | —N-piperidinyl |
| O25 (a and b) | —Cl | —H |
| O26 (a and b) | —Cl | -tert-butyl |
| O27 (a and b) | —Cl | -iso-butyl |
| O28 (a and b) | —Cl | -sec-butyl |
| O29 (a and b) | —Cl | -iso-propyl |
| O30 (a and b) | —Cl | -n-propyl |
| O31 (a and b) | —Cl | -cyclohexyl |
| O32 (a and b) | —Cl | -tert-butoxy |
| O33 (a and b) | —Cl | -isopropoxy |
| O34 (a and b) | —Cl | —$CF_3$ |
| O35 (a and b) | —Cl | —$CH_2CF_3$ |
| O36 (a and b) | —Cl | —$OCF_3$ |
| O37 (a and b) | —Cl | —Cl |
| O38 (a and b) | —Cl | —Br |
| O39 (a and b) | —Cl | —I |
| O40 (a and b) | —Cl | -n-butyl |
| O41 (a and b) | —Cl | —$CH_3$ |
| O42 (a and b) | —Cl | —$SCF_3$ |
| O43 (a and b) | —Cl | —$N(CH_2CH_3)_2$ |
| O44 (a and b) | —Cl | —$OCF_2CHF_2$ |
| O45 (a and b) | —Cl | —$C(OH)(CF_3)_2$ |
| O46 (a and b) | —Cl | -(1,1-dimethyl-pentyl) |
| O47 (a and b) | —Cl | -(1,1-dimethyl-acetic acid) ethyl ester |
| O48 (a and b) | —Cl | —N-piperidinyl |
| O49 (a and b) | —F | —H |
| O50 (a and b) | —F | -tert-butyl |
| O51 (a and b) | —F | -iso-butyl |
| O52 (a and b) | —F | -sec-butyl |

TABLE 15-continued

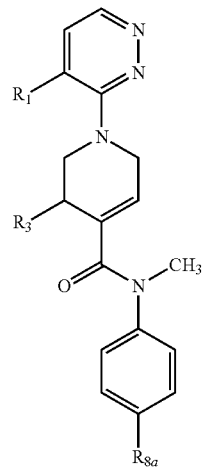

(Io)

and pharmaceutically acceptable salts thereof, wherein:

| Compound | $R_1$ | $R_{8a}$ |
|---|---|---|
| O53 (a and b) | —F | -iso-propyl |
| O54 (a and b) | —F | -n-propyl |
| O55 (a and b) | —F | -cyclohexyl |
| O56 (a and b) | —F | -tert-butoxy |
| O57 (a and b) | —F | -isopropoxy |
| O58 (a and b) | —F | —$CF_3$ |
| O59 (a and b) | —F | —$CH_2CF_3$ |
| O60 (a and b) | —F | —$OCF_3$ |
| O61 (a and b) | —F | —Cl |
| O62 (a and b) | —F | —Br |
| O63 (a and b) | —F | —I |
| O64 (a and b) | —F | -n-butyl |
| O65 (a and b) | —F | —$CH_3$ |
| O66 (a and b) | —F | —$SCF_3$ |
| O67 (a and b) | —F | —$N(CH_2CH_3)_2$ |
| O68 (a and b) | —F | —$OCF_2CHF_2$ |
| O69 (a and b) | —F | —$C(OH)(CF_3)_2$ |
| O70 (a and b) | —F | -(1,1-dimethyl-pentyl) |
| O71 (a and b) | —F | -(1,1-dimethyl-acetic acid) ethyl ester |
| O72 (a and b) | —F | —N-piperidinyl |
| O73 (a and b) | —$CH_3$ | —H |
| O74 (a and b) | —$CH_3$ | -iso-butyl |
| O75 (a and b) | —$CH_3$ | -tert-butyl |
| O76 (a and b) | —$CH_3$ | -sec-butyl |
| O77 (a and b) | —$CH_3$ | -iso-propyl |
| O78 (a and b) | —$CH_3$ | -n-propyl |
| O79 (a and b) | —$CH_3$ | -cyclohexyl |
| O80 (a and b) | —$CH_3$ | -tert-butoxy |
| O81 (a and b) | —$CH_3$ | -isopropoxy |
| O82 (a and b) | —$CH_3$ | —$CF_3$ |
| O83 (a and b) | —$CH_3$ | —$CH_2CF_3$ |
| O84 (a and b) | —$CH_3$ | —$OCF_3$ |
| O85 (a and b) | —$CH_3$ | —Cl |
| O86 (a and b) | —$CH_3$ | —Br |
| O87 (a and b) | —$CH_3$ | —I |
| O88 (a and b) | —$CH_3$ | -n-butyl |
| O89 (a and b) | —$CH_3$ | —$CH_3$ |
| O90 (a and b) | —$CH_3$ | —$SCF_3$ |
| O91 (a and b) | —$CH_3$ | —$N(CH_2CH_3)_2$ |
| O92 (a and b) | —$CH_3$ | —$OCF_2CHF_2$ |
| O93 (a and b) | —$CH_3$ | —$C(OH)(CF_3)_2$ |
| O94 (a and b) | —$CH_3$ | -(1,1-dimethyl-pentyl) |
| O95 (a and b) | —$CH_3$ | -(1,1-dimethyl-acetic acid) ethyl ester |
| O96 (a and b) | —$CH_3$ | —N-piperidinyl |
| O97 (a and b) | —$CF_3$ | —H |
| O98 (a and b) | —$CF_3$ | -tert-butyl |
| O99 (a and b) | —$CF_3$ | -iso-butyl |
| O100 (a and b) | —$CF_3$ | -sec-butyl |
| O101 (a and b) | —$CF_3$ | -iso-propyl |
| O102 (a and b) | —$CF_3$ | -n-propyl |

TABLE 15-continued (Io)

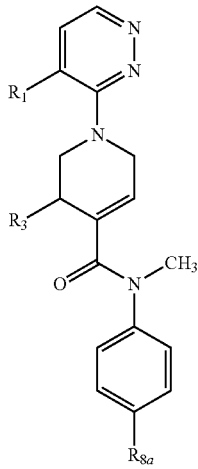

and pharmaceutically acceptable salts thereof, wherein:

| Compound | $R_1$ | $R_{8a}$ |
|---|---|---|
| O103 (a and b) | —$CF_3$ | -cyclohexyl |
| O104 (a and b) | —$CF_3$ | -tert-butoxy |
| O105 (a and b) | —$CF_3$ | -isopropoxy |
| O106 (a and b) | —$CF_3$ | —$CF_3$ |
| O107 (a and b) | —$CF_3$ | —$CH_2CF_3$ |
| O108 (a and b) | —$CF_3$ | —$OCF_3$ |
| O109 (a and b) | —$CF_3$ | —Cl |
| O110 (a and b) | —$CF_3$ | —Br |
| O111 (a and b) | —$CF_3$ | —I |
| O112 (a and b) | —$CF_3$ | -n-butyl |
| O113 (a and b) | —$CF_3$ | —$CH_3$ |
| O114 (a and b) | —$CF_3$ | —$SCF_3$ |
| O115 (a and b) | —$CF_3$ | —$N(CH_2CH_3)_2$ |
| O116 (a and b) | —$CF_3$ | —$OCF_2CHF_2$ |
| O117 (a and b) | —$CF_3$ | —$C(OH)(CF_3)_2$ |
| O118 (a and b) | —$CF_3$ | -(1,1-dimethyl-pentyl) |
| O119 (a and b) | —$CF_3$ | -(1,1-dimethyl-acetic acid) ethyl ester |
| O120 (a and b) | —$CF_3$ | —N-piperidinyl |
| O121 (a and b) | —$CHF_2$ | -tert-butyl |
| O122 (a and b) | —$CHF_2$ | —H |
| O123 (a and b) | —$CHF_2$ | -iso-butyl |
| O124 (a and b) | —$CHF_2$ | -sec-butyl |
| O125 (a and b) | —$CHF_2$ | -iso-propyl |
| O126 (a and b) | —$CHF_2$ | -n-propyl |
| O127 (a and b) | —$CHF_2$ | -cyclohexyl |
| O128 (a and b) | —$CHF_2$ | -tert-butoxy |
| O129 (a and b) | —$CHF_2$ | -isopropoxy |
| O130 (a and b) | —$CHF_2$ | —$CF_3$ |
| O131 (a and b) | —$CHF_2$ | —$CH_2CF_3$ |
| O132 (a and b) | —$CHF_2$ | —$OCF_3$ |
| O133 (a and b) | —$CHF_2$ | —Cl |
| O134 (a and b) | —$CHF_2$ | —Br |
| O135 (a and b) | —$CHF_2$ | —I |
| O136 (a and b) | —$CHF_2$ | -n-butyl |
| O137 (a and b) | —$CHF_2$ | —$CH_3$ |
| O138 (a and b) | —$CHF_2$ | —$SCF_3$ |
| O139 (a and b) | —$CHF_2$ | —$N(CH_2CH_3)_2$ |
| O140 (a and b) | —$CHF_2$ | —$OCF_2CHF_2$ |
| O141 (a and b) | —$CHF_2$ | —$C(OH)(CF_3)_2$ |
| O142 (a and b) | —$CHF_2$ | -(1,1-dimethyl-pentyl) |
| O143 (a and b) | —$CHF_2$ | -(1,1-dimethyl-acetic acid) ethyl ester |
| O144 (a and b) | —$CHF_2$ | —N-piperidinyl |
| O145 (a and b) | —OH | —H |
| O146 (a and b) | —OH | -tert-butyl |
| O147 (a and b) | —OH | -iso-butyl |
| O148 (a and b) | —OH | -sec-butyl |
| O149 (a and b) | —OH | -iso-propyl |
| O150 (a and b) | —OH | -n-propyl |
| O151 (a and b) | —OH | -cyclohexyl |
| O152 (a and b) | —OH | -tert-butoxy |

TABLE 15-continued (Io)

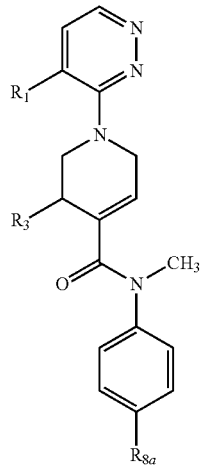

and pharmaceutically acceptable salts thereof, wherein:

| Compound | $R_1$ | $R_{8a}$ |
|---|---|---|
| O153 (a and b) | —OH | -isopropoxy |
| O154 (a and b) | —OH | —$CF_3$ |
| O155 (a and b) | —OH | —$CH_2CF_3$ |
| O156 (a and b) | —OH | —$OCF_3$ |
| O157 (a and b) | —OH | —Cl |
| O158 (a and b) | —OH | —Br |
| O159 (a and b) | —OH | —I |
| O160 (a and b) | —OH | -n-butyl |
| O161 (a and b) | —OH | —$CH_3$ |
| O162 (a and b) | —OH | —$SCF_3$ |
| O163 (a and b) | —OH | —$N(CH_2CH_3)_2$ |
| O164 (a and b) | —OH | —$OCF_2CHF_2$ |
| O165 (a and b) | —OH | —$C(OH)(CF_3)_2$ |
| O166 (a and b) | —OH | -(1,1-dimethyl-pentyl) |
| O167 (a and b) | —OH | -(1,1-dimethyl-acetic acid) ethyl ester |
| O168 (a and b) | —OH | —N-piperidinyl |
| O169 (a and b) | —$NO_2$ | —H |
| O170 (a and b) | —$NO_2$ | -tert-butyl |
| O171 (a and b) | —$NO_2$ | -iso-butyl |
| O172 (a and b) | —$NO_2$ | -sec-butyl |
| O173 (a and b) | —$NO_2$ | -iso-propyl |
| O174 (a and b) | —$NO_2$ | -n-propyl |
| O175 (a and b) | —$NO_2$ | -cyclohexyl |
| O176 (a and b) | —$NO_2$ | -tert-butoxy |
| O177 (a and b) | —$NO_2$ | -isopropoxy |
| O178 (a and b) | —$NO_2$ | —$CF_3$ |
| O179 (a and b) | —$NO_2$ | —$CH_2CF_3$ |
| O180 (a and b) | —$NO_2$ | —$OCF_3$ |
| O181 (a and b) | —$NO_2$ | —Cl |
| O182 (a and b) | —$NO_2$ | —Br |
| O183 (a and b) | —$NO_2$ | —I |
| O184 (a and b) | —$NO_2$ | -n-butyl |
| O185 (a and b) | —$NO_2$ | —$CH_3$ |
| O186 (a and b) | —$NO_2$ | —$SCF_3$ |
| O187 (a and b) | —$NO_2$ | —$N(CH_2CH_3)_2$ |
| O188 (a and b) | —$NO_2$ | —$OCF_2CHF_2$ |
| O189 (a and b) | —$NO_2$ | —$C(OH)(CF_3)_2$ |
| O190 (a and b) | —$NO_2$ | -(1,1-dimethyl-pentyl) |
| O191 (a and b) | —$NO_2$ | -(1,1-dimethyl-acetic acid) ethyl ester |
| O192 (a and b) | —$NO_2$ | —N-piperidinyl |
| O193 (a and b) | —CN | —H |
| O194 (a and b) | —CN | -tert-butyl |
| O195 (a and b) | —CN | -iso-butyl |
| O196 (a and b) | —CN | -sec-butyl |
| O197 (a and b) | —CN | -iso-propyl |
| O198 (a and b) | —CN | -n-propyl |
| O199 (a and b) | —CN | -cyclohexyl |
| O200 (a and b) | —CN | -tert-butoxy |
| O201 (a and b) | —CN | -isopropoxy |
| O202 (a and b) | —CN | —$CF_3$ |

TABLE 15-continued (Io)

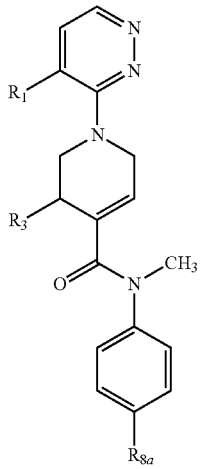

and pharmaceutically acceptable salts thereof, wherein:

| Compound | $R_1$ | $R_{8a}$ |
|---|---|---|
| O203 (a and b) | —CN | —CH$_2$CF$_3$ |
| O204 (a and b) | —CN | —OCF$_3$ |
| O205 (a and b) | —CN | —Cl |
| O206 (a and b) | —CN | —Br |
| O207 (a and b) | —CN | —I |
| O208 (a and b) | —CN | -n-butyl |
| O209 (a and b) | —CN | —CH$_3$ |
| O210 (a and b) | —CN | —SCF$_3$ |
| O211 (a and b) | —CN | —N(CH$_2$CH$_3$)$_2$ |
| O212 (a and b) | —CN | —OCF$_2$CHF$_2$ |
| O213 (a and b) | —CN | —C(OH)(CF$_3$)$_2$ |
| O214 (a and b) | —CN | -(1,1-dimethyl-pentyl) |
| O215 (a and b) | —CN | -(1,1-dimethyl-acetic acid) ethyl ester |
| O216 (a and b) | —CN | —N-piperidinyl |
| O217 (a and b) | —Br | —H |
| O218 (a and b) | —Br | -tert-butyl |
| O219 (a and b) | —Br | -iso-butyl |
| O220 (a and b) | —Br | -sec-butyl |
| O221 (a and b) | —Br | -iso-propyl |
| O222 (a and b) | —Br | -n-propyl |
| O223 (a and b) | —Br | -cyclohexyl |
| O224 (a and b) | —Br | -tert-butoxy |
| O225 (a and b) | —Br | -isopropoxy |
| O226 (a and b) | —Br | —CF$_3$ |
| O227 (a and b) | —Br | —CH$_2$CF$_3$ |
| O228 (a and b) | —Br | —OCF$_3$ |
| O229 (a and b) | —Br | —Cl |
| O230 (a and b) | —Br | —Br |
| O231 (a and b) | —Br | —I |
| O232 (a and b) | —Br | -n-butyl |
| O233 (a and b) | —Br | —CH$_3$ |
| O234 (a and b) | —Br | —SCF$_3$ |
| O235 (a and b) | —Br | —N(CH$_2$CH$_3$)$_2$ |
| O236 (a and b) | —Br | —OCF$_2$CHF$_2$ |
| O237 (a and b) | —Br | —C(OH)(CF$_3$)$_2$ |
| O238 (a and b) | —Br | -(1,1-dimethyl-pentyl) |
| O239 (a and b) | —Br | -(1,1-dimethyl-acetic acid) ethyl ester |
| O240 (a and b) | —Br | —N-piperidinyl |
| O241 (a and b) | —I | -tert-butyl |
| O242 (a and b) | —I | —H |
| O243 (a and b) | —I | -iso-butyl |
| O244 (a and b) | —I | -sec-butyl |
| O245 (a and b) | —I | -iso-propyl |
| O246 (a and b) | —I | -n-propyl |
| O247 (a and b) | —I | -cyclohexyl |
| O248 (a and b) | —I | -tert-butoxy |
| O249 (a and b) | —I | -isopropoxy |
| O250 (a and b) | —I | —CF$_3$ |
| O251 (a and b) | —I | —CH$_2$CF$_3$ |
| O252 (a and b) | —I | —OCF$_3$ |

TABLE 15-continued (Io)

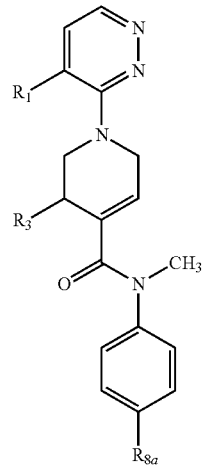

and pharmaceutically acceptable salts thereof, wherein:

| Compound | $R_1$ | $R_{8a}$ |
|---|---|---|
| O253 (a and b) | —I | —Cl |
| O254 (a and b) | —I | —Br |
| O255 (a and b) | —I | —I |
| O256 (a and b) | —I | -n-butyl |
| O257 (a and b) | —I | —CH$_3$ |
| O258 (a and b) | —I | —SCF$_3$ |
| O259 (a and b) | —I | —N(CH$_2$CH$_3$)$_2$ |
| O260 (a and b) | —I | —OCF$_2$CHF$_2$ |
| O261 (a and b) | —I | —C(OH)(CF$_3$)$_2$ |
| O262 (a and b) | —I | -(1,1-dimethyl-pentyl) |
| O263 (a and b) | —I | -(1,1-dimethyl-acetic acid) ethyl ester |
| O264 (a and b) | —I | —N-piperidinyl |

(a) means that $R_3$ is —H.
(b) means that $R_3$ is —CH$_3$.

TABLE 16

(Ip)

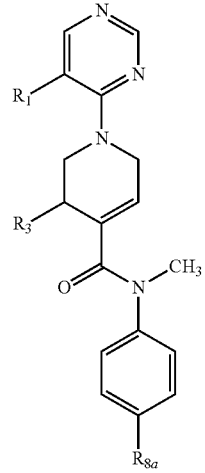

and pharmaceutically acceptable salts thereof, wherein:

| Compound | $R_1$ | $R_{8a}$ |
|---|---|---|
| P1 (a and b) | —H | —H |
| P2 (a and b) | —H | -tert-butyl |
| P3 (a and b) | —H | -iso-butyl |

TABLE 16-continued

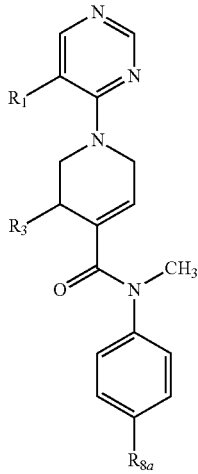

(Ip)

and pharmaceutically acceptable salts thereof, wherein:

| Compound | R₁ | R₈ₐ |
|---|---|---|
| P4 (a and b) | —H | -sec-butyl |
| P5 (a and b) | —H | -iso-propyl |
| P6 (a and b) | —H | -n-propyl |
| P7 (a and b) | —H | -cyclohexyl |
| P8 (a and b) | —H | -tert-butoxy |
| P9 (a and b) | —H | -isopropoxy |
| P10 (a and b) | —H | —CF₃ |
| P11 (a and b) | —H | —CH₂CF₃ |
| P12 (a and b) | —H | —OCF₃ |
| P13 (a and b) | —H | —Cl |
| P14 (a and b) | —H | —Br |
| P15 (a and b) | —H | —I |
| P16 (a and b) | —H | -n-butyl |
| P17 (a and b) | —H | —CH₃ |
| P18 (a and b) | —H | —SCF₃ |
| P19 (a and b) | —H | —N(CH₂CH₃)₂ |
| P20 (a and b) | —H | —OCF₂CHF₂ |
| P21 (a and b) | —H | —C(OH)(CF₃)₂ |
| P22 (a and b) | —H | -(1,1-dimethyl-pentyl) |
| P23 (a and b) | —H | -(1,1-dimethyl-acetic acid) ethyl ester |
| P24 (a and b) | —H | —N-piperidinyl |
| P25 (a and b) | —Cl | —H |
| P26 (a and b) | —Cl | -tert-butyl |
| P27 (a and b) | —Cl | -iso-butyl |
| P28 (a and b) | —Cl | -sec-butyl |
| P29 (a and b) | —Cl | -iso-propyl |
| P30 (a and b) | —Cl | -n-propyl |
| P31 (a and b) | —Cl | -cyclohexyl |
| P32 (a and b) | —Cl | -tert-butoxy |
| P33 (a and b) | —Cl | -isopropoxy |
| P34 (a and b) | —Cl | —CF₃ |
| P35 (a and b) | —Cl | —CH₂CF₃ |
| P36 (a and b) | —Cl | —OCF₃ |
| P37 (a and b) | —Cl | —Cl |
| P38 (a and b) | —Cl | —Br |
| P39 (a and b) | —Cl | —I |
| P40 (a and b) | —Cl | -n-butyl |
| P41 (a and b) | —Cl | —CH₃ |
| P42 (a and b) | —Cl | —SCF₃ |
| P43 (a and b) | —Cl | —N(CH₂CH₃)₂ |
| P44 (a and b) | —Cl | —OCF₂CHF₂ |
| P45 (a and b) | —Cl | —C(OH)(CF₃)₂ |
| P46 (a and b) | —Cl | -(1,1-dimethyl-pentyl) |
| P47 (a and b) | —Cl | -(1,1-dimethyl-acetic acid) ethyl ester |
| P48 (a and b) | —Cl | —N-piperidinyl |
| P49 (a and b) | —F | —H |
| P50 (a and b) | —F | -tert-butyl |
| P51 (a and b) | —F | -iso-butyl |
| P52 (a and b) | —F | -sec-butyl |
| P53 (a and b) | —F | -iso-propyl |

TABLE 16-continued

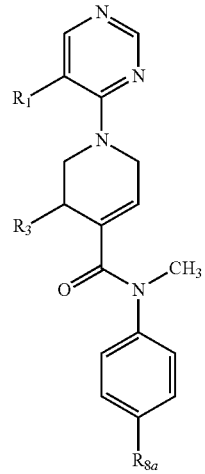

(Ip)

and pharmaceutically acceptable salts thereof, wherein:

| Compound | R₁ | R₈ₐ |
|---|---|---|
| P54 (a and b) | —F | -n-propyl |
| P55 (a and b) | —F | -cyclohexyl |
| P56 (a and b) | —F | -tert-butoxy |
| P57 (a and b) | —F | -isopropoxy |
| P58 (a and b) | —F | —CF₃ |
| P59 (a and b) | —F | —CH₂CF₃ |
| P60 (a and b) | —F | —OCF₃ |
| P61 (a and b) | —F | —Cl |
| P62 (a and b) | —F | —Br |
| P63 (a and b) | —F | —I |
| P64 (a and b) | —F | -n-butyl |
| P65 (a and b) | —F | —CH₃ |
| P66 (a and b) | —F | —SCF₃ |
| P67 (a and b) | —F | —N(CH₂CH₃)₂ |
| P68 (a and b) | —F | —OCF₂CHF₂ |
| P69 (a and b) | —F | —C(OH)(CF₃)₂ |
| P70 (a and b) | —F | -(1,1-dimethyl-pentyl) |
| P71 (a and b) | —F | -(1,1-dimethyl-acetic acid) ethyl ester |
| P72 (a and b) | —F | —N-piperidinyl |
| P73 (a and b) | —CH₃ | —H |
| P74 (a and b) | —CH₃ | -iso-butyl |
| P75 (a and b) | —CH₃ | -tert-butyl |
| P76 (a and b) | —CH₃ | -sec-butyl |
| P77 (a and b) | —CH₃ | -iso-propyl |
| P78 (a and b) | —CH₃ | -n-propyl |
| P79 (a and b) | —CH₃ | -cyclohexyl |
| P80 (a and b) | —CH₃ | -tert-butoxy |
| P81 (a and b) | —CH₃ | -isopropoxy |
| P82 (a and b) | —CH₃ | —CF₃ |
| P83 (a and b) | —CH₃ | —CH₂CF₃ |
| P84 (a and b) | —CH₃ | —OCF₃ |
| P85 (a and b) | —CH₃ | —Cl |
| P86 (a and b) | —CH₃ | —Br |
| P87 (a and b) | —CH₃ | —I |
| P88 (a and b) | —CH₃ | -n-butyl |
| P89 (a and b) | —CH₃ | —CH₃ |
| P90 (a and b) | —CH₃ | —SCF₃ |
| P91 (a and b) | —CH₃ | —N(CH₂CH₃)₂ |
| P92 (a and b) | —CH₃ | —OCF₂CHF₂ |
| P93 (a and b) | —CH₃ | —C(OH)(CF₃)₂ |
| P94 (a and b) | —CH₃ | -(1,1-dimethyl-pentyl) |
| P95 (a and b) | —CH₃ | -(1,1-dimethyl-acetic acid) ethyl ester |
| P96 (a and b) | —CH₃ | —N-piperidinyl |
| P97 (a and b) | —CF₃ | —H |
| P98 (a and b) | —CF₃ | -tert-butyl |
| P99 (a and b) | —CF₃ | -iso-butyl |
| P100 (a and b) | —CF₃ | -sec-butyl |
| P101 (a and b) | —CF₃ | -iso-propyl |
| P102 (a and b) | —CF₃ | -n-propyl |
| P103 (a and b) | —CF₃ | -cyclohexyl |

TABLE 16-continued

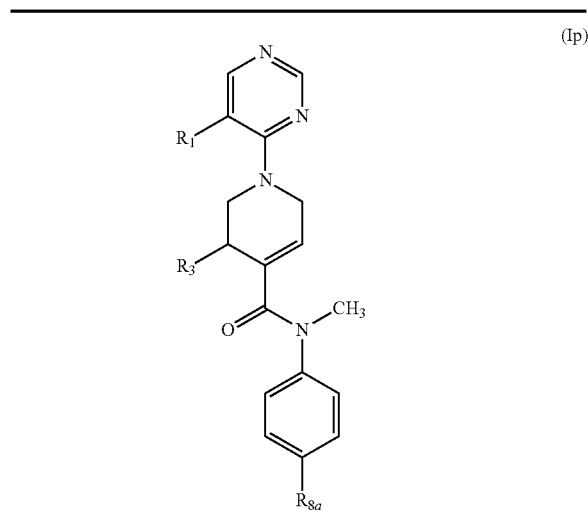

(Ip)

and pharmaceutically acceptable salts thereof, wherein:

| Compound | $R_1$ | $R_{8a}$ |
|---|---|---|
| P104 (a and b) | —$CF_3$ | -tert-butoxy |
| P105 (a and b) | —$CF_3$ | -isopropoxy |
| P106 (a and b) | —$CF_3$ | —$CF_3$ |
| P107 (a and b) | —$CF_3$ | —$CH_2CF_3$ |
| P108 (a and b) | —$CF_3$ | —$OCF_3$ |
| P109 (a and b) | —$CF_3$ | —Cl |
| P110 (a and b) | —$CF_3$ | —Br |
| P111 (a and b) | —$CF_3$ | —I |
| P112 (a and b) | —$CF_3$ | -n-butyl |
| P113 (a and b) | —$CF_3$ | —$CH_3$ |
| P114 (a and b) | —$CF_3$ | —$SCF_3$ |
| P115 (a and b) | —$CF_3$ | —$N(CH_2CH_3)_2$ |
| P116 (a and b) | —$CF_3$ | —$OCF_2CHF_2$ |
| P117 (a and b) | —$CF_3$ | —$C(OH)(CF_3)_2$ |
| P118 (a and b) | —$CF_3$ | -(1,1-dimethyl-pentyl) |
| P119 (a and b) | —$CF_3$ | -(1,1-dimethyl-acetic acid) ethyl ester |
| P120 (a and b) | —$CF_3$ | —N-piperidinyl |
| P121 (a and b) | —$CHF_2$ | -tert-butyl |
| P122 (a and b) | —$CHF_2$ | —H |
| P123 (a and b) | —$CHF_2$ | -iso-butyl |
| P124 (a and b) | —$CHF_2$ | -sec-butyl |
| P125 (a and b) | —$CHF_2$ | -iso-propyl |
| P126 (a and b) | —$CHF_2$ | -n-propyl |
| P127 (a and b) | —$CHF_2$ | -cyclohexyl |
| P128 (a and b) | —$CHF_2$ | -tert-butoxy |
| P129 (a and b) | —$CHF_2$ | -isopropoxy |
| P130 (a and b) | —$CHF_2$ | —$CF_3$ |
| P131 (a and b) | —$CHF_2$ | —$CH_2CF_3$ |
| P132 (a and b) | —$CHF_2$ | —$OCF_3$ |
| P133 (a and b) | —$CHF_2$ | —Cl |
| P134 (a and b) | —$CHF_2$ | —Br |
| P135 (a and b) | —$CHF_2$ | —I |
| P136 (a and b) | —$CHF_2$ | -n-butyl |
| P137 (a and b) | —$CHF_2$ | —$CH_3$ |
| P138 (a and b) | —$CHF_2$ | —$SCF_3$ |
| P139 (a and b) | —$CHF_2$ | —$N(CH_2CH_3)_2$ |
| P140 (a and b) | —$CHF_2$ | —$OCF_2CHF_2$ |
| P141 (a and b) | —$CHF_2$ | —$C(OH)(CF_3)_2$ |
| P142 (a and b) | —$CHF_2$ | -(1,1-dimethyl-pentyl) |
| P143 (a and b) | —$CHF_2$ | -(1,1-dimethyl-acetic acid) ethyl ester |
| P144 (a and b) | —$CHF_2$ | —N-piperidinyl |
| P145 (a and b) | —OH | —H |
| P146 (a and b) | —OH | -tert-butyl |
| P147 (a and b) | —OH | -iso-butyl |
| P148 (a and b) | —OH | -sec-butyl |
| P149 (a and b) | —OH | -iso-propyl |
| P150 (a and b) | —OH | -n-propyl |
| P151 (a and b) | —OH | -cyclohexyl |
| P152 (a and b) | —OH | -tert-butoxy |
| P153 (a and b) | —OH | -isopropoxy |

TABLE 16-continued

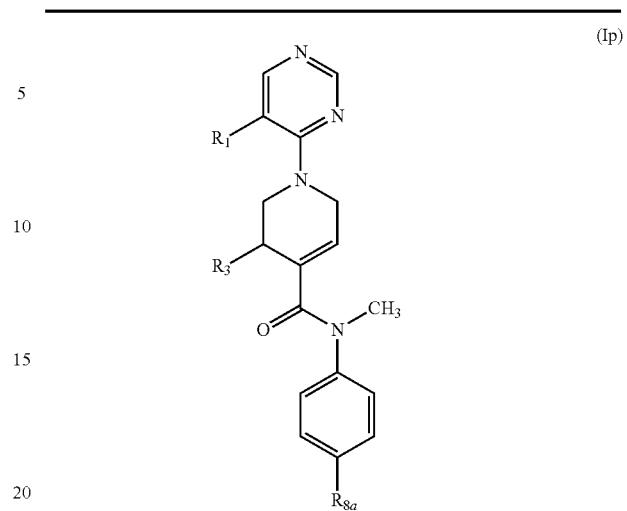

(Ip)

and pharmaceutically acceptable salts thereof, wherein:

| Compound | $R_1$ | $R_{8a}$ |
|---|---|---|
| P154 (a and b) | —OH | —$CF_3$ |
| P155 (a and b) | —OH | —$CH_2CF_3$ |
| P156 (a and b) | —OH | —$OCF_3$ |
| P157 (a and b) | —OH | —Cl |
| P158 (a and b) | —OH | —Br |
| P159 (a and b) | —OH | —I |
| P160 (a and b) | —OH | -n-butyl |
| P161 (a and b) | —OH | —$CH_3$ |
| P162 (a and b) | —OH | —$SCF_3$ |
| P163 (a and b) | —OH | —$N(CH_2CH_3)_2$ |
| P164 (a and b) | —OH | —$OCF_2CHF_2$ |
| P165 (a and b) | —OH | —$C(OH)(CF_3)_2$ |
| P166 (a and b) | —OH | -(1,1-dimethyl-pentyl) |
| P167 (a and b) | —OH | -(1,1-dimethyl-acetic acid) ethyl ester |
| P168 (a and b) | —OH | —N-piperidinyl |
| P169 (a and b) | —$NO_2$ | —H |
| P170 (a and b) | —$NO_2$ | -tert-butyl |
| P171 (a and b) | —$NO_2$ | -iso-butyl |
| P172 (a and b) | —$NO_2$ | -sec-butyl |
| P173 (a and b) | —$NO_2$ | -iso-propyl |
| P174 (a and b) | —$NO_2$ | -n-propyl |
| P175 (a and b) | —$NO_2$ | -cyclohexyl |
| P176 (a and b) | —$NO_2$ | -tert-butoxy |
| P177 (a and b) | —$NO_2$ | -isopropoxy |
| P178 (a and b) | —$NO_2$ | —$CF_3$ |
| P179 (a and b) | —$NO_2$ | —$CH_2CF_3$ |
| P180 (a and b) | —$NO_2$ | —$OCF_3$ |
| P181 (a and b) | —$NO_2$ | —Cl |
| P182 (a and b) | —$NO_2$ | —Br |
| P183 (a and b) | —$NO_2$ | —I |
| P184 (a and b) | —$NO_2$ | -n-butyl |
| P185 (a and b) | —$NO_2$ | —$CH_3$ |
| P186 (a and b) | —$NO_2$ | —$SCF_3$ |
| P187 (a and b) | —$NO_2$ | —$N(CH_2CH_3)_2$ |
| P188 (a and b) | —$NO_2$ | —$OCF_2CHF_2$ |
| P189 (a and b) | —$NO_2$ | —$C(OH)(CF_3)_2$ |
| P190 (a and b) | —$NO_2$ | -(1,1-dimethyl-pentyl) |
| P191 (a and b) | —$NO_2$ | -(1,1-dimethyl-acetic acid) ethyl ester |
| P192 (a and b) | —$NO_2$ | —N-piperidinyl |
| P193 (a and b) | —CN | —H |
| P194 (a and b) | —CN | -tert-butyl |
| P195 (a and b) | —CN | -iso-butyl |
| P196 (a and b) | —CN | -sec-butyl |
| P197 (a and b) | —CN | -iso-propyl |
| P198 (a and b) | —CN | -n-propyl |
| P199 (a and b) | —CN | -cyclohexyl |
| P200 (a and b) | —CN | -tert-butoxy |
| P201 (a and b) | —CN | -isopropoxy |
| P202 (a and b) | —CN | —$CF_3$ |
| P203 (a and b) | —CN | —$CH_2CF_3$ |

TABLE 16-continued (Ip)

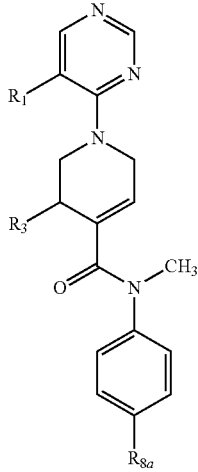

and pharmaceutically acceptable salts thereof, wherein:

| Compound | $R_1$ | $R_{8a}$ |
|---|---|---|
| P204 (a and b) | —CN | —OCF$_3$ |
| P205 (a and b) | —CN | —Cl |
| P206 (a and b) | —CN | —Br |
| P207 (a and b) | —CN | —I |
| P208 (a and b) | —CN | -n-butyl |
| P209 (a and b) | —CN | —CH$_3$ |
| P210 (a and b) | —CN | —SCF$_3$ |
| P211 (a and b) | —CN | —N(CH$_2$CH$_3$)$_2$ |
| P212 (a and b) | —CN | —OCF$_2$CHF$_2$ |
| P213 (a and b) | —CN | —C(OH)(CF$_3$)$_2$ |
| P214 (a and b) | —CN | -(1,1-dimethyl-pentyl) |
| P215 (a and b) | —CN | -(1,1-dimethyl-acetic acid) ethyl ester |
| P216 (a and b) | —CN | —N-piperidinyl |
| P217 (a and b) | —Br | —H |
| P218 (a and b) | —Br | -tert-butyl |
| P219 (a and b) | —Br | -iso-butyl |
| P220 (a and b) | —Br | -sec-butyl |
| P221 (a and b) | —Br | -iso-propyl |
| P222 (a and b) | —Br | -n-propyl |
| P223 (a and b) | —Br | -cyclohexyl |
| P224 (a and b) | —Br | -tert-butoxy |
| P225 (a and b) | —Br | -isopropoxy |
| P226 (a and b) | —Br | —CF$_3$ |
| P227 (a and b) | —Br | —CH$_2$CF$_3$ |
| P228 (a and b) | —Br | —OCF$_3$ |
| P229 (a and b) | —Br | —Cl |
| P230 (a and b) | —Br | —Br |
| P231 (a and b) | —Br | —I |
| P232 (a and b) | —Br | -n-butyl |
| P233 (a and b) | —Br | —CH$_3$ |
| P234 (a and b) | —Br | —SCF$_3$ |
| P235 (a and b) | —Br | —N(CH$_2$CH$_3$)$_2$ |
| P236 (a and b) | —Br | —OCF$_2$CHF$_2$ |
| P237 (a and b) | —Br | —C(OH)(CF$_3$)$_2$ |
| P238 (a and b) | —Br | -(1,1-dimethyl-pentyl) |
| P239 (a and b) | —Br | -(1,1-dimethyl-acetic acid) ethyl ester |
| P240 (a and b) | —Br | —N-piperidinyl |
| P241 (a and b) | —I | -tert-butyl |
| P242 (a and b) | —I | —H |
| P243 (a and b) | —I | -iso-butyl |
| P244 (a and b) | —I | -sec-butyl |
| P245 (a and b) | —I | -iso-propyl |
| P246 (a and b) | —I | -n-propyl |
| P247 (a and b) | —I | -cyclohexyl |
| P248 (a and b) | —I | -tert-butoxy |
| P249 (a and b) | —I | -isopropoxy |
| P250 (a and b) | —I | —CF$_3$ |
| P251 (a and b) | —I | —CH$_2$CF$_3$ |
| P252 (a and b) | —I | —OCF$_3$ |
| P253 (a and b) | —I | —Cl |

TABLE 16-continued (Ip)

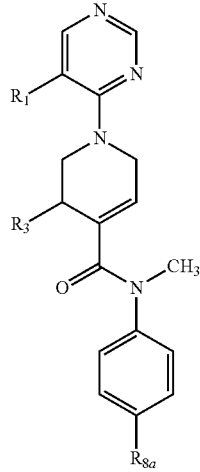

and pharmaceutically acceptable salts thereof, wherein:

| Compound | $R_1$ | $R_{8a}$ |
|---|---|---|
| P254 (a and b) | —I | —Br |
| P255 (a and b) | —I | —I |
| P256 (a and b) | —I | -n-butyl |
| P257 (a and b) | —I | —CH$_3$ |
| P258 (a and b) | —I | —SCF$_3$ |
| P259 (a and b) | —I | —N(CH$_2$CH$_3$)$_2$ |
| P260 (a and b) | —I | —OCF$_2$CHF$_2$ |
| P261 (a and b) | —I | —C(OH)(CF$_3$)$_2$ |
| P262 (a and b) | —I | -(1,1-dimethyl-pentyl) |
| P263 (a and b) | —I | -(1,1-dimethyl-acetic acid) ethyl ester |
| P264 (a and b) | —I | —N-piperidinyl |

(a) means that $R_3$ is —H.
(b) means that $R_3$ is —CH$_3$.

TABLE 17

(Iq)

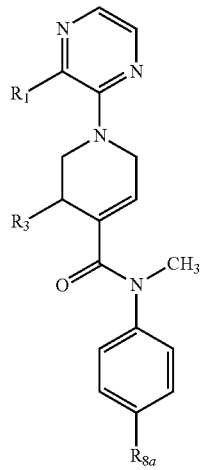

and pharmaceutically acceptable salts thereof, wherein:

| Compound | $R_1$ | $R_{8a}$ |
|---|---|---|
| Q1 (a and b) | —H | —H |
| Q2 (a and b) | —H | -tert-butyl |
| Q3 (a and b) | —H | -iso-butyl |
| Q4 (a and b) | —H | -sec-butyl |

TABLE 17-continued (Iq)

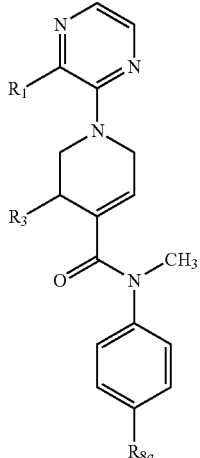

and pharmaceutically acceptable salts thereof, wherein:

| Compound | $R_1$ | $R_{8a}$ |
|---|---|---|
| Q5 (a and b) | —H | -iso-propyl |
| Q6 (a and b) | —H | -n-propyl |
| Q7 (a and b) | —H | -cyclohexyl |
| Q8 (a and b) | —H | -tert-butoxy |
| Q9 (a and b) | —H | -isopropoxy |
| Q10 (a and b) | —H | —$CF_3$ |
| Q11 (a and b) | —H | —$CH_2CF_3$ |
| Q12 (a and b) | —H | —$OCF_3$ |
| Q13 (a and b) | —H | —Cl |
| Q14 (a and b) | —H | —Br |
| Q15 (a and b) | —H | —I |
| Q16 (a and b) | —H | -n-butyl |
| Q17 (a and b) | —H | —$CH_3$ |
| Q18 (a and b) | —H | —$SCF_3$ |
| Q19 (a and b) | —H | —$N(CH_2CH_3)_2$ |
| Q20 (a and b) | —H | —$OCF_2CHF_2$ |
| Q21 (a and b) | —H | —$C(OH)(CF_3)_2$ |
| Q22 (a and b) | —H | -(1,1-dimethyl-pentyl) |
| Q23 (a and b) | —H | -(1,1-dimethyl-acetic acid) ethyl ester |
| Q24 (a and b) | —H | —N-piperidinyl |
| Q25 (a and b) | —Cl | —H |
| Q26 (a and b) | —Cl | -tert-butyl |
| Q27 (a and b) | —Cl | -iso-butyl |
| Q28 (a and b) | —Cl | -sec-butyl |
| Q29 (a and b) | —Cl | -iso-propyl |
| Q30 (a and b) | —Cl | -n-propyl |
| Q31 (a and b) | —Cl | -cyclohexyl |
| Q32 (a and b) | —Cl | -tert-butoxy |
| Q33 (a and b) | —Cl | -isopropoxy |
| Q34 (a and b) | —Cl | —$CF_3$ |
| Q35 (a and b) | —Cl | —$CH_2CF_3$ |
| Q36 (a and b) | —Cl | —$OCF_3$ |
| Q37 (a and b) | —Cl | —Cl |
| Q38 (a and b) | —Cl | —Br |
| Q39 (a and b) | —Cl | —I |
| Q40 (a and b) | —Cl | -n-butyl |
| Q41 (a and b) | —Cl | —$CH_3$ |
| Q42 (a and b) | —Cl | —$SCF_3$ |
| Q43 (a and b) | —Cl | —$N(CH_2CH_3)_2$ |
| Q44 (a and b) | —Cl | —$OCF_2CHF_2$ |
| Q45 (a and b) | —Cl | —$C(OH)(CF_3)_2$ |
| Q46 (a and b) | —Cl | -(1,1-dimethyl-pentyl) |
| Q47 (a and b) | —Cl | -(1,1-dimethyl-acetic acid) ethyl ester |
| Q48 (a and b) | —Cl | —N-piperidinyl |
| Q49 (a and b) | —F | —H |
| Q50 (a and b) | —F | -tert-butyl |
| Q51 (a and b) | —F | -iso-butyl |
| Q52 (a and b) | —F | -sec-butyl |
| Q53 (a and b) | —F | -iso-propyl |
| Q54 (a and b) | —F | -n-propyl |

TABLE 17-continued (Iq)

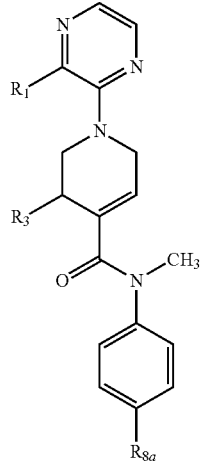

and pharmaceutically acceptable salts thereof, wherein:

| Compound | $R_1$ | $R_{8a}$ |
|---|---|---|
| Q55 (a and b) | —F | -cyclohexyl |
| Q56 (a and b) | —F | -tert-butoxy |
| Q57 (a and b) | —F | -isopropoxy |
| Q58 (a and b) | —F | —$CF_3$ |
| Q59 (a and b) | —F | —$CH_2CF_3$ |
| Q60 (a and b) | —F | —$OCF_3$ |
| Q61 (a and b) | —F | —Cl |
| Q62 (a and b) | —F | —Br |
| Q63 (a and b) | —F | —I |
| Q64 (a and b) | —F | -n-butyl |
| Q65 (a and b) | —F | —$CH_3$ |
| Q66 (a and b) | —F | —$SCF_3$ |
| Q67 (a and b) | —F | —$N(CH_2CH_3)_2$ |
| Q68 (a and b) | —F | —$OCF_2CHF_2$ |
| Q69 (a and b) | —F | —$C(OH)(CF_3)_2$ |
| Q70 (a and b) | —F | -(1,1-dimethyl-pentyl) |
| Q71 (a and b) | —F | -(1,1-dimethyl-acetic acid) ethyl ester |
| Q72 (a and b) | —F | —N-piperidinyl |
| Q73 (a and b) | —$CH_3$ | —H |
| Q74 (a and b) | —$CH_3$ | -iso-butyl |
| Q75 (a and b) | —$CH_3$ | -tert-butyl |
| Q76 (a and b) | —$CH_3$ | -sec-butyl |
| Q77 (a and b) | —$CH_3$ | -iso-propyl |
| Q78 (a and b) | —$CH_3$ | -n-propyl |
| Q79 (a and b) | —$CH_3$ | -cyclohexyl |
| Q80 (a and b) | —$CH_3$ | -tert-butoxy |
| Q81 (a and b) | —$CH_3$ | -isopropoxy |
| Q82 (a and b) | —$CH_3$ | —$CF_3$ |
| Q83 (a and b) | —$CH_3$ | —$CH_2CF_3$ |
| Q84 (a and b) | —$CH_3$ | —$OCF_3$ |
| Q85 (a and b) | —$CH_3$ | —Cl |
| Q86 (a and b) | —$CH_3$ | —Br |
| Q87 (a and b) | —$CH_3$ | —I |
| Q88 (a and b) | —$CH_3$ | -n-butyl |
| Q89 (a and b) | —$CH_3$ | —$CH_3$ |
| Q90 (a and b) | —$CH_3$ | —$SCF_3$ |
| Q91 (a and b) | —$CH_3$ | —$N(CH_2CH_3)_2$ |
| Q92 (a and b) | —$CH_3$ | —$OCF_2CHF_2$ |
| Q93 (a and b) | —$CH_3$ | —$C(OH)(CF_3)_2$ |
| Q94 (a and b) | —$CH_3$ | -(1,1-dimethyl-pentyl) |
| Q95 (a and b) | —$CH_3$ | -(1,1-dimethyl-acetic acid) ethyl ester |
| Q96 (a and b) | —$CH_3$ | —N-piperidinyl |
| Q97 (a and b) | —$CF_3$ | —H |
| Q98 (a and b) | —$CF_3$ | -tert-butyl |
| Q99 (a and b) | —$CF_3$ | -iso-butyl |
| Q100 (a and b) | —$CF_3$ | -sec-butyl |
| Q101 (a and b) | —$CF_3$ | -iso-propyl |
| Q102 (a and b) | —$CF_3$ | -n-propyl |
| Q103 (a and b) | —$CF_3$ | -cyclohexyl |
| Q104 (a and b) | —$CF_3$ | -tert-butoxy |

TABLE 17-continued

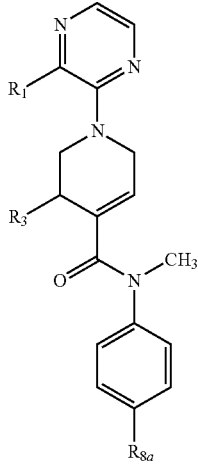

(Iq)

and pharmaceutically acceptable salts thereof, wherein:

| Compound | $R_1$ | $R_{8a}$ |
|---|---|---|
| Q105 (a and b) | —CF$_3$ | -isopropoxy |
| Q106 (a and b) | —CF$_3$ | —CF$_3$ |
| Q107 (a and b) | —CF$_3$ | —CH$_2$CF$_3$ |
| Q108 (a and b) | —CF$_3$ | —OCF$_3$ |
| Q109 (a and b) | —CF$_3$ | —Cl |
| Q110 (a and b) | —CF$_3$ | —Br |
| Q111 (a and b) | —CF$_3$ | —I |
| Q112 (a and b) | —CF$_3$ | -n-butyl |
| Q113 (a and b) | —CF$_3$ | —CH$_3$ |
| Q114 (a and b) | —CF$_3$ | —SCF$_3$ |
| Q115 (a and b) | —CF$_3$ | —N(CH$_2$CH$_3$)$_2$ |
| Q116 (a and b) | —CF$_3$ | —OCF$_2$CHF$_2$ |
| Q117 (a and b) | —CF$_3$ | —C(OH)(CF$_3$)$_2$ |
| Q118 (a and b) | —CF$_3$ | -(1,1-dimethyl-pentyl) |
| Q119 (a and b) | —CF$_3$ | -(1,1-dimethyl-acetic acid) ethyl ester |
| Q120 (a and b) | —CF$_3$ | —N-piperidinyl |
| Q121 (a and b) | —CHF$_2$ | -tert-butyl |
| Q122 (a and b) | —CHF$_2$ | —H |
| Q123 (a and b) | —CHF$_2$ | -iso-butyl |
| Q124 (a and b) | —CHF$_2$ | -sec-butyl |
| Q125 (a and b) | —CHF$_2$ | -iso-propyl |
| Q126 (a and b) | —CHF$_2$ | -n-propyl |
| Q127 (a and b) | —CHF$_2$ | -cyclohexyl |
| Q128 (a and b) | —CHF$_2$ | -tert-butoxy |
| Q129 (a and b) | —CHF$_2$ | -isopropoxy |
| Q130 (a and b) | —CHF$_2$ | —CF$_3$ |
| Q131 (a and b) | —CHF$_2$ | —CH$_2$CF$_3$ |
| Q132 (a and b) | —CHF$_2$ | —OCF$_3$ |
| Q133 (a and b) | —CHF$_2$ | —Cl |
| Q134 (a and b) | —CHF$_2$ | —Br |
| Q135 (a and b) | —CHF$_2$ | —I |
| Q136 (a and b) | —CHF$_2$ | -n-butyl |
| Q137 (a and b) | —CHF$_2$ | —CH$_3$ |
| Q138 (a and b) | —CHF$_2$ | —SCF$_3$ |
| Q139 (a and b) | —CHF$_2$ | —N(CH$_2$CH$_3$)$_2$ |
| Q140 (a and b) | —CHF$_2$ | —OCF$_2$CHF$_2$ |
| Q141 (a and b) | —CHF$_2$ | —C(OH)(CF$_3$)$_2$ |
| Q142 (a and b) | —CHF$_2$ | -(1,1-dimethyl-pentyl) |
| Q143 (a and b) | —CHF$_2$ | -(1,1-dimethyl-acetic acid) ethyl ester |
| Q144 (a and b) | —CHF$_2$ | —N-piperidinyl |
| Q145 (a and b) | —OH | —H |
| Q146 (a and b) | —OH | -tert-butyl |
| Q147 (a and b) | —OH | -iso-butyl |
| Q148 (a and b) | —OH | -sec-butyl |
| Q149 (a and b) | —OH | -iso-propyl |
| Q150 (a and b) | —OH | -n-propyl |
| Q151 (a and b) | —OH | -cyclohexyl |
| Q152 (a and b) | —OH | -tert-butoxy |
| Q153 (a and b) | —OH | -isopropoxy |
| Q154 (a and b) | —OH | —CF$_3$ |

TABLE 17-continued

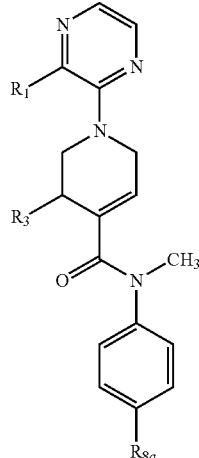

(Iq)

and pharmaceutically acceptable salts thereof, wherein:

| Compound | $R_1$ | $R_{8a}$ |
|---|---|---|
| Q155 (a and b) | —OH | —CH$_2$CF$_3$ |
| Q156 (a and b) | —OH | —OCF$_3$ |
| Q157 (a and b) | —OH | —Cl |
| Q158 (a and b) | —OH | —Br |
| Q159 (a and b) | —OH | —I |
| Q160 (a and b) | —OH | -n-butyl |
| Q161 (a and b) | —OH | —CH$_3$ |
| Q162 (a and b) | —OH | —SCF$_3$ |
| Q163 (a and b) | —OH | —N(CH$_2$CH$_3$)$_2$ |
| Q164 (a and b) | —OH | —OCF$_2$CHF$_2$ |
| Q165 (a and b) | —OH | —C(OH)(CF$_3$)$_2$ |
| Q166 (a and b) | —OH | -(1,1-dimethyl-pentyl) |
| Q167 (a and b) | —OH | -(1,1-dimethyl-acetic acid) ethyl ester |
| Q168 (a and b) | —OH | —N-piperidinyl |
| Q169 (a and b) | —NO$_2$ | —H |
| Q170 (a and b) | —NO$_2$ | -tert-butyl |
| Q171 (a and b) | —NO$_2$ | -iso-butyl |
| Q172 (a and b) | —NO$_2$ | -sec-butyl |
| Q173 (a and b) | —NO$_2$ | -iso-propyl |
| Q174 (a and b) | —NO$_2$ | -n-propyl |
| Q175 (a and b) | —NO$_2$ | -cyclohexyl |
| Q176 (a and b) | —NO$_2$ | -tert-butoxy |
| Q177 (a and b) | —NO$_2$ | -isopropoxy |
| Q178 (a and b) | —NO$_2$ | —CF$_3$ |
| Q179 (a and b) | —NO$_2$ | —CH$_2$CF$_3$ |
| Q180 (a and b) | —NO$_2$ | —OCF$_3$ |
| Q181 (a and b) | —NO$_2$ | —Cl |
| Q182 (a and b) | —NO$_2$ | —Br |
| Q183 (a and b) | —NO$_2$ | —I |
| Q184 (a and b) | —NO$_2$ | -n-butyl |
| Q185 (a and b) | —NO$_2$ | —CH$_3$ |
| Q186 (a and b) | —NO$_2$ | —SCF$_3$ |
| Q187 (a and b) | —NO$_2$ | —N(CH$_2$CH$_3$)$_2$ |
| Q188 (a and b) | —NO$_2$ | —OCF$_2$CHF$_2$ |
| Q189 (a and b) | —NO$_2$ | —C(OH)(CF$_3$)$_2$ |
| Q190 (a and b) | —NO$_2$ | -(1,1-dimethyl-pentyl) |
| Q191 (a and b) | —NO$_2$ | -(1,1-dimethyl-acetic acid) ethyl ester |
| Q192 (a and b) | —NO$_2$ | —N-piperidinyl |
| Q193 (a and b) | —CN | —H |
| Q194 (a and b) | —CN | -tert-butyl |
| Q195 (a and b) | —CN | -iso-butyl |
| Q196 (a and b) | —CN | -sec-butyl |
| Q197 (a and b) | —CN | -iso-propyl |
| Q198 (a and b) | —CN | -n-propyl |
| Q199 (a and b) | —CN | -cyclohexyl |
| Q200 (a and b) | —CN | -tert-butoxy |
| Q201 (a and b) | —CN | -isopropoxy |
| Q202 (a and b) | —CN | —CF$_3$ |
| Q203 (a and b) | —CN | —CH$_2$CF$_3$ |
| Q204 (a and b) | —CN | —OCF$_3$ |

TABLE 17-continued (Iq)

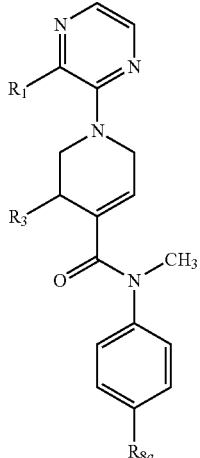

and pharmaceutically acceptable salts thereof, wherein:

| Compound | $R_1$ | $R_{8a}$ |
|---|---|---|
| Q205 (a and b) | —CN | —Cl |
| Q206 (a and b) | —CN | —Br |
| Q207 (a and b) | —CN | —I |
| Q208 (a and b) | —CN | -n-butyl |
| Q209 (a and b) | —CN | —CH$_3$ |
| Q210 (a and b) | —CN | —SCF$_3$ |
| Q211 (a and b) | —CN | —N(CH$_2$CH$_3$)$_2$ |
| Q212 (a and b) | —CN | —OCF$_2$CHF$_2$ |
| Q213 (a and b) | —CN | —C(OH)(CF$_3$)$_2$ |
| Q214 (a and b) | —CN | -(1,1-dimethyl-pentyl) |
| Q215 (a and b) | —CN | -(1,1-dimethyl-acetic acid) ethyl ester |
| Q216 (a and b) | —CN | —N-piperidinyl |
| Q217 (a and b) | —Br | —H |
| Q218 (a and b) | —Br | -tert-butyl |
| Q219 (a and b) | —Br | -iso-butyl |
| Q220 (a and b) | —Br | -sec-butyl |
| Q221 (a and b) | —Br | -iso-propyl |
| Q222 (a and b) | —Br | -n-propyl |
| Q223 (a and b) | —Br | -cyclohexyl |
| Q224 (a and b) | —Br | -tert-butoxy |
| Q225 (a and b) | —Br | -isopropoxy |
| Q226 (a and b) | —Br | —CF$_3$ |
| Q227 (a and b) | —Br | —CH$_2$CF$_3$ |
| Q228 (a and b) | —Br | —OCF$_3$ |
| Q229 (a and b) | —Br | —Cl |
| Q230 (a and b) | —Br | —Br |
| Q231 (a and b) | —Br | —I |
| Q232 (a and b) | —Br | -n-butyl |
| Q233 (a and b) | —Br | —CH$_3$ |
| Q234 (a and b) | —Br | —SCF$_3$ |
| Q235 (a and b) | —Br | —N(CH$_2$CH$_3$)$_2$ |
| Q236 (a and b) | —Br | —OCF$_2$CHF$_2$ |
| Q237 (a and b) | —Br | —C(OH)(CF$_3$)$_2$ |
| Q238 (a and b) | —Br | -(1,1-dimethyl-pentyl) |
| Q239 (a and b) | —Br | -(1,1-dimethyl-acetic acid) ethyl ester |
| Q240 (a and b) | —Br | —N-piperidinyl |
| Q241 (a and b) | —I | -tert-butyl |
| Q242 (a and b) | —I | —H |
| Q243 (a and b) | —I | -iso-butyl |
| Q244 (a and b) | —I | -sec-butyl |
| Q245 (a and b) | —I | -iso-propyl |
| Q246 (a and b) | —I | -n-propyl |
| Q247 (a and b) | —I | -cyclohexyl |
| Q248 (a and b) | —I | -tert-butoxy |
| Q249 (a and b) | —I | -isopropoxy |
| Q250 (a and b) | —I | —CF$_3$ |
| Q251 (a and b) | —I | —CH$_2$CF$_3$ |
| Q252 (a and b) | —I | —OCF$_3$ |
| Q253 (a and b) | —I | —Cl |
| Q254 (a and b) | —I | —Br |

TABLE 17-continued (Iq)

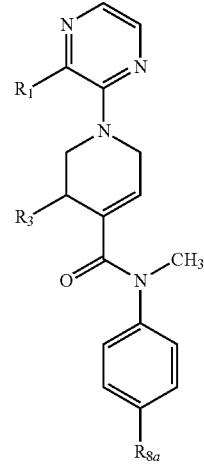

and pharmaceutically acceptable salts thereof, wherein:

| Compound | $R_1$ | $R_{8a}$ |
|---|---|---|
| Q255 (a and b) | —I | —I |
| Q256 (a and b) | —I | -n-butyl |
| Q257 (a and b) | —I | —CH$_3$ |
| Q258 (a and b) | —I | —SCF$_3$ |
| Q259 (a and b) | —I | —N(CH$_2$CH$_3$)$_2$ |
| Q260 (a and b) | —I | —OCF$_2$CHF$_2$ |
| Q261 (a and b) | —I | —C(OH)(CF$_3$)$_2$ |
| Q262 (a and b) | —I | -(1,1-dimethyl-pentyl) |
| Q263 (a and b) | —I | -(1,1-dimethyl-acetic acid) ethyl ester |
| Q264 (a and b) | —I | —N-piperidinyl |

(a) means that $R_3$ is —H.
(b) means that $R_3$ is —CH$_3$.

TABLE 18

(Ir)

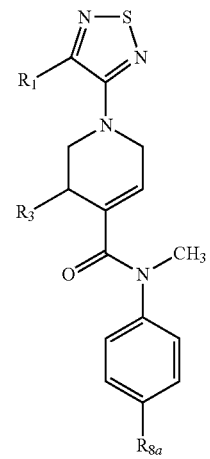

and pharmaceutically acceptable salts thereof, wherein:

| Compound | $R_1$ | $R_{8a}$ |
|---|---|---|
| R1 (a and b) | —H | —H |
| R2 (a and b) | —H | -tert-butyl |
| R3 (a and b) | —H | -iso-butyl |
| R4 (a and b) | —H | -sec-butyl |
| R5 (a and b) | —H | -iso-propyl |
| R6 (a and b) | —H | -n-propyl |

TABLE 18-continued

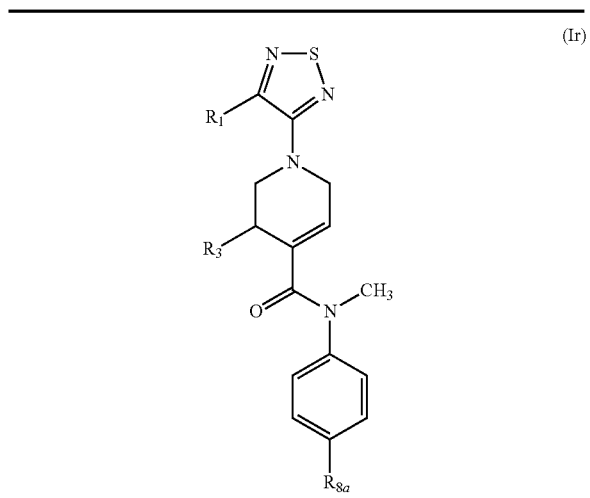

(Ir)

and pharmaceutically acceptable salts thereof, wherein:

| Compound | $R_1$ | $R_{8a}$ |
|---|---|---|
| R7 (a and b) | —H | -cyclohexyl |
| R8 (a and b) | —H | -tert-butoxy |
| R9 (a and b) | —H | -isopropoxy |
| R10 (a and b) | —H | —$CF_3$ |
| R11 (a and b) | —H | —$CH_2CF_3$ |
| R12 (a and b) | —H | —$OCF_3$ |
| R13 (a and b) | —H | —Cl |
| R14 (a and b) | —H | —Br |
| R15 (a and b) | —H | —I |
| R16 (a and b) | —H | -n-butyl |
| R17 (a and b) | —H | —$CH_3$ |
| R18 (a and b) | —H | —$SCF_3$ |
| R19 (a and b) | —H | —$N(CH_2CH_3)_2$ |
| R20 (a and b) | —H | —$OCF_2CHF_2$ |
| R21 (a and b) | —H | —$C(OH)(CF_3)_2$ |
| R22 (a and b) | —H | -(1,1-dimethyl-pentyl) |
| R23 (a and b) | —H | -(1,1-dimethyl-acetic acid) ethyl ester |
| R24 (a and b) | —H | —N-piperidinyl |
| R25 (a and b) | —Cl | —H |
| R26 (a and b) | —Cl | -tert-butyl |
| R27 (a and b) | —Cl | -iso-butyl |
| R28 (a and b) | —Cl | -sec-butyl |
| R29 (a and b) | —Cl | -iso-propyl |
| R30 (a and b) | —Cl | -n-propyl |
| R31 (a and b) | —Cl | -cyclohexyl |
| R32 (a and b) | —Cl | -tert-butoxy |
| R33 (a and b) | —Cl | -isopropoxy |
| R34 (a and b) | —Cl | —$CF_3$ |
| R35 (a and b) | —Cl | —$CH_2CF_3$ |
| R36 (a and b) | —Cl | —$OCF_3$ |
| R37 (a and b) | —Cl | —Cl |
| R38 (a and b) | —Cl | —Br |
| R39 (a and b) | —Cl | —I |
| R40 (a and b) | —Cl | -n-butyl |
| R41 (a and b) | —Cl | —$CH_3$ |
| R42 (a and b) | —Cl | —$SCF_3$ |
| R43 (a and b) | —Cl | —$N(CH_2CH_3)_2$ |
| R44 (a and b) | —Cl | —$OCF_2CHF_2$ |
| R45 (a and b) | —Cl | —$C(OH)(CF_3)_2$ |
| R46 (a and b) | —Cl | -(1,1-dimethyl-pentyl) |
| R47 (a and b) | —Cl | -(1,1-dimethyl-acetic acid) ethyl ester |
| R48 (a and b) | —Cl | —N-piperidinyl |
| R49 (a and b) | —F | —H |
| R50 (a and b) | —F | -tert-butyl |
| R51 (a and b) | —F | -iso-butyl |
| R52 (a and b) | —F | -sec-butyl |
| R53 (a and b) | —F | -iso-propyl |
| R54 (a and b) | —F | -n-propyl |
| R55 (a and b) | —F | -cyclohexyl |
| R56 (a and b) | —F | -tert-butoxy |

TABLE 18-continued

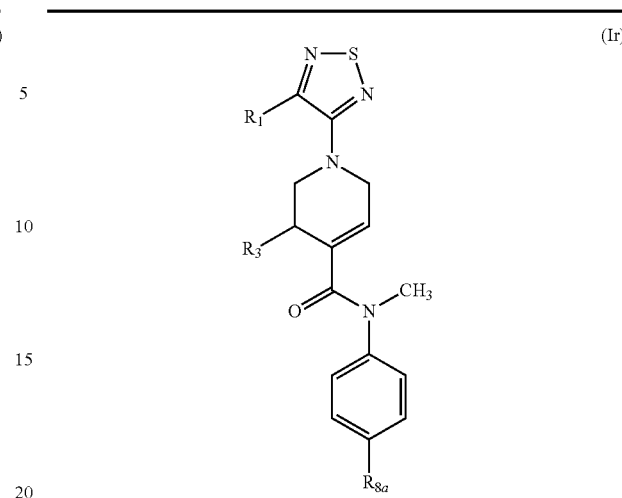

(Ir)

and pharmaceutically acceptable salts thereof, wherein:

| Compound | $R_1$ | $R_{8a}$ |
|---|---|---|
| R57 (a and b) | —F | -isopropoxy |
| R58 (a and b) | —F | —$CF_3$ |
| R59 (a and b) | —F | —$CH_2CF_3$ |
| R60 (a and b) | —F | —$OCF_3$ |
| R61 (a and b) | —F | —Cl |
| R62 (a and b) | —F | —Br |
| R63 (a and b) | —F | —I |
| R64 (a and b) | —F | -n-butyl |
| R65 (a and b) | —F | —$CH_3$ |
| R66 (a and b) | —F | —$SCF_3$ |
| R67 (a and b) | —F | —$N(CH_2CH_3)_2$ |
| R68 (a and b) | —F | —$OCF_2CHF_2$ |
| R69 (a and b) | —F | —$C(OH)(CF_3)_2$ |
| R70 (a and b) | —F | -(1,1-dimethyl-pentyl) |
| R71 (a and b) | —F | -(1,1-dimethyl-acetic acid) ethyl ester |
| R72 (a and b) | —F | —N-piperidinyl |
| R73 (a and b) | —$CH_3$ | —H |
| R74 (a and b) | —$CH_3$ | -iso-butyl |
| R75 (a and b) | —$CH_3$ | -tert-butyl |
| R76 (a and b) | —$CH_3$ | -sec-butyl |
| R77 (a and b) | —$CH_3$ | -iso-propyl |
| R78 (a and b) | —$CH_3$ | -n-propyl |
| R79 (a and b) | —$CH_3$ | -cyclohexyl |
| R80 (a and b) | —$CH_3$ | -tert-butoxy |
| R81 (a and b) | —$CH_3$ | -isopropoxy |
| R82 (a and b) | —$CH_3$ | —$CF_3$ |
| R83 (a and b) | —$CH_3$ | —$CH_2CF_3$ |
| R84 (a and b) | —$CH_3$ | —$OCF_3$ |
| R85 (a and b) | —$CH_3$ | —Cl |
| R86 (a and b) | —$CH_3$ | —Br |
| R87 (a and b) | —$CH_3$ | —I |
| R88 (a and b) | —$CH_3$ | -n-butyl |
| R89 (a and b) | —$CH_3$ | —$CH_3$ |
| R90 (a and b) | —$CH_3$ | —$SCF_3$ |
| R91 (a and b) | —$CH_3$ | —$N(CH_2CH_3)_2$ |
| R92 (a and b) | —$CH_3$ | —$OCF_2CHF_2$ |
| R93 (a and b) | —$CH_3$ | —$C(OH)(CF_3)_2$ |
| R94 (a and b) | —$CH_3$ | -(1,1-dimethyl-pentyl) |
| R95 (a and b) | —$CH_3$ | -(1,1-dimethyl-acetic acid) ethyl ester |
| R96 (a and b) | —$CH_3$ | —N-piperidinyl |
| R97 (a and b) | —$CF_3$ | —H |
| R98 (a and b) | —$CF_3$ | -tert-butyl |
| R99 (a and b) | —$CF_3$ | -iso-butyl |
| R100 (a and b) | —$CF_3$ | -sec-butyl |
| R101 (a and b) | —$CF_3$ | -iso-propyl |
| R102 (a and b) | —$CF_3$ | -n-propyl |
| R103 (a and b) | —$CF_3$ | -cyclohexyl |
| R104 (a and b) | —$CF_3$ | -tert-butoxy |
| R105 (a and b) | —$CF_3$ | -isopropoxy |
| R106 (a and b) | —$CF_3$ | —$CF_3$ |

TABLE 18-continued

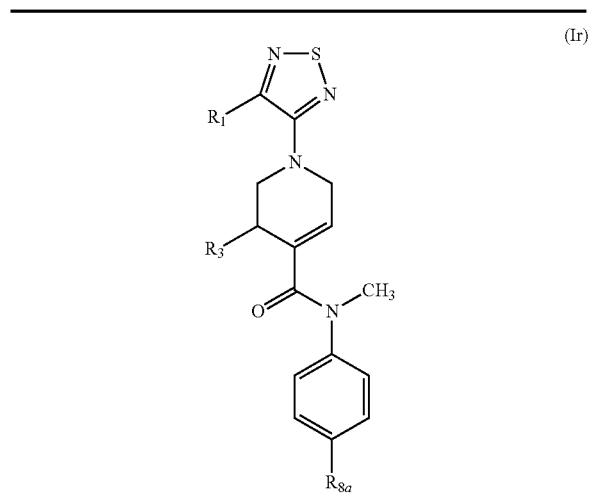

(Ir)

and pharmaceutically acceptable salts thereof, wherein:

| Compound | R$_1$ | R$_{8a}$ |
|---|---|---|
| R107 (a and b) | —CF$_3$ | —CH$_2$CF$_3$ |
| R108 (a and b) | —CF$_3$ | —OCF$_3$ |
| R109 (a and b) | —CF$_3$ | —Cl |
| R110 (a and b) | —CF$_3$ | —Br |
| R111 (a and b) | —CF$_3$ | —I |
| R112 (a and b) | —CF$_3$ | -n-butyl |
| R113 (a and b) | —CF$_3$ | —CH$_3$ |
| R114 (a and b) | —CF$_3$ | —SCF$_3$ |
| R115 (a and b) | —CF$_3$ | —N(CH$_2$CH$_3$)$_2$ |
| R116 (a and b) | —CF$_3$ | —OCF$_2$CHF$_2$ |
| R117 (a and b) | —CF$_3$ | —C(OH)(CF$_3$)$_2$ |
| R118 (a and b) | —CF$_3$ | -(1,1-dimethyl-pentyl) |
| R119 (a and b) | —CF$_3$ | -(1,1-dimethyl-acetic acid) ethyl ester |
| R120 (a and b) | —CF$_3$ | —N-piperidinyl |
| R121 (a and b) | —CHF$_2$ | -tert-butyl |
| R122 (a and b) | —CHF$_2$ | —H |
| R123 (a and b) | —CHF$_2$ | -iso-butyl |
| R124 (a and b) | —CHF$_2$ | -sec-butyl |
| R125 (a and b) | —CHF$_2$ | -iso-propyl |
| R126 (a and b) | —CHF$_2$ | -n-propyl |
| R127 (a and b) | —CHF$_2$ | -cyclohexyl |
| R128 (a and b) | —CHF$_2$ | -tert-butoxy |
| R129 (a and b) | —CHF$_2$ | -isopropoxy |
| R130 (a and b) | —CHF$_2$ | —CF$_3$ |
| R131 (a and b) | —CHF$_2$ | —CH$_2$CF$_3$ |
| R132 (a and b) | —CHF$_2$ | —OCF$_3$ |
| R133 (a and b) | —CHF$_2$ | —Cl |
| R134 (a and b) | —CHF$_2$ | —Br |
| R135 (a and b) | —CHF$_2$ | —I |
| R136 (a and b) | —CHF$_2$ | -n-butyl |
| R137 (a and b) | —CHF$_2$ | —CH$_3$ |
| R138 (a and b) | —CHF$_2$ | —SCF$_3$ |
| R139 (a and b) | —CHF$_2$ | —N(CH$_2$CH$_3$)$_2$ |
| R140 (a and b) | —CHF$_2$ | —OCF$_2$CHF$_2$ |
| R141 (a and b) | —CHF$_2$ | —C(OH)(CF$_3$)$_2$ |
| R142 (a and b) | —CHF$_2$ | -(1,1-dimethyl-pentyl) |
| R143 (a and b) | —CHF$_2$ | -(1,1-dimethyl-acetic acid) ethyl ester |
| R144 (a and b) | —CHF$_2$ | —N-piperidinyl |
| R145 (a and b) | —OH | —H |
| R146 (a and b) | —OH | -tert-butyl |
| R147 (a and b) | —OH | -iso-butyl |
| R148 (a and b) | —OH | -sec-butyl |
| R149 (a and b) | —OH | -iso-propyl |
| R150 (a and b) | —OH | -n-propyl |
| R151 (a and b) | —OH | -cyclohexyl |
| R152 (a and b) | —OH | -tert-butoxy |
| R153 (a and b) | —OH | -isopropoxy |
| R154 (a and b) | —OH | —CF$_3$ |
| R155 (a and b) | —OH | —CH$_2$CF$_3$ |
| R156 (a and b) | —OH | —OCF$_3$ |

TABLE 18-continued

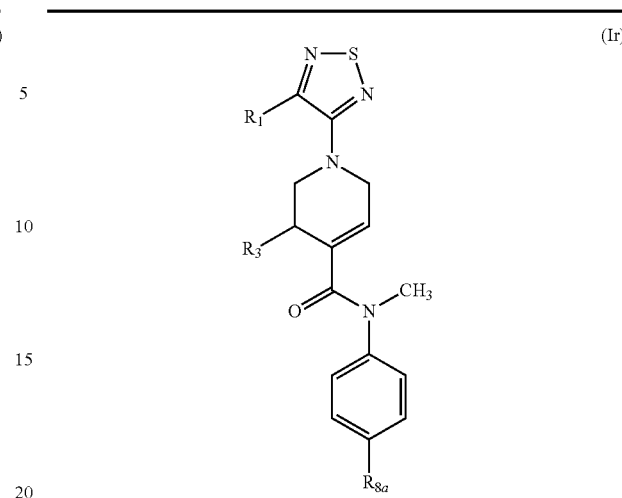

(Ir)

and pharmaceutically acceptable salts thereof, wherein:

| Compound | R$_1$ | R$_{8a}$ |
|---|---|---|
| R157 (a and b) | —OH | —Cl |
| R158 (a and b) | —OH | —Br |
| R159 (a and b) | —OH | —I |
| R160 (a and b) | —OH | -n-butyl |
| R161 (a and b) | —OH | —CH$_3$ |
| R162 (a and b) | —OH | —SCF$_3$ |
| R163 (a and b) | —OH | —N(CH$_2$CH$_3$)$_2$ |
| R164 (a and b) | —OH | —OCF$_2$CHF$_2$ |
| R165 (a and b) | —OH | —C(OH)(CF$_3$)$_2$ |
| R166 (a and b) | —OH | -(1,1-dimethyl-pentyl) |
| R167 (a and b) | —OH | -(1,1-dimethyl-acetic acid) ethyl ester |
| R168 (a and b) | —OH | —N-piperidinyl |
| R169 (a and b) | —NO$_2$ | —H |
| R170 (a and b) | —NO$_2$ | -tert-butyl |
| R171 (a and b) | —NO$_2$ | -iso-butyl |
| R172 (a and b) | —NO$_2$ | -sec-butyl |
| R173 (a and b) | —NO$_2$ | -iso-propyl |
| R174 (a and b) | —NO$_2$ | -n-propyl |
| R175 (a and b) | —NO$_2$ | -cyclohexyl |
| R176 (a and b) | —NO$_2$ | -tert-butoxy |
| R177 (a and b) | —NO$_2$ | -isopropoxy |
| R178 (a and b) | —NO$_2$ | —CF$_3$ |
| R179 (a and b) | —NO$_2$ | —CH$_2$CF$_3$ |
| R180 (a and b) | —NO$_2$ | —OCF$_3$ |
| R181 (a and b) | —NO$_2$ | —Cl |
| R182 (a and b) | —NO$_2$ | —Br |
| R183 (a and b) | —NO$_2$ | —I |
| R184 (a and b) | —NO$_2$ | -n-butyl |
| R185 (a and b) | —NO$_2$ | —CH$_3$ |
| R186 (a and b) | —NO$_2$ | —SCF$_3$ |
| R187 (a and b) | —NO$_2$ | —N(CH$_2$CH$_3$)$_2$ |
| R188 (a and b) | —NO$_2$ | —OCF$_2$CHF$_2$ |
| R189 (a and b) | —NO$_2$ | —C(OH)(CF$_3$)$_2$ |
| R190 (a and b) | —NO$_2$ | -(1,1-dimethyl-pentyl) |
| R191 (a and b) | —NO$_2$ | -(1,1-dimethyl-acetic acid) ethyl ester |
| R192 (a and b) | —NO$_2$ | —N-piperidinyl |
| R193 (a and b) | —CN | —H |
| R194 (a and b) | —CN | -tert-butyl |
| R195 (a and b) | —CN | -iso-butyl |
| R196 (a and b) | —CN | -sec-butyl |
| R197 (a and b) | —CN | -iso-propyl |
| R198 (a and b) | —CN | -n-propyl |
| R199 (a and b) | —CN | -cyclohexyl |
| R200 (a and b) | —CN | -tert-butoxy |
| R201 (a and b) | —CN | -isopropoxy |
| R202 (a and b) | —CN | —CF$_3$ |
| R203 (a and b) | —CN | —CH$_2$CF$_3$ |
| R204 (a and b) | —CN | —OCF$_3$ |
| R205 (a and b) | —CN | —Cl |
| R206 (a and b) | —CN | —Br |

TABLE 18-continued

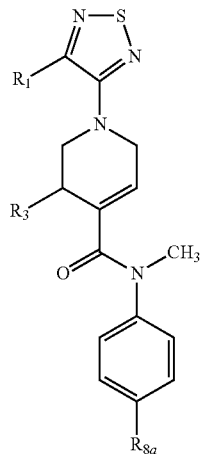

(Ir)

and pharmaceutically acceptable salts thereof, wherein:

| Compound | R₁ | R₈ₐ |
|---|---|---|
| R207 (a and b) | —CN | —I |
| R208 (a and b) | —CN | -n-butyl |
| R209 (a and b) | —CN | —CH₃ |
| R210 (a and b) | —CN | —SCF₃ |
| R211 (a and b) | —CN | —N(CH₂CH₃)₂ |
| R212 (a and b) | —CN | —OCF₂CHF₂ |
| R213 (a and b) | —CN | —C(OH)(CF₃)₂ |
| R214 (a and b) | —CN | -(1,1-dimethyl-pentyl) |
| R215 (a and b) | —CN | -(1,1-dimethyl-acetic acid) ethyl ester |
| R216 (a and b) | —CN | —N-piperidinyl |
| R217 (a and b) | —Br | —H |
| R218 (a and b) | —Br | -tert-butyl |
| R219 (a and b) | —Br | -iso-butyl |
| R220 (a and b) | —Br | -sec-butyl |
| R221 (a and b) | —Br | -iso-propyl |
| R222 (a and b) | —Br | -n-propyl |
| R223 (a and b) | —Br | -cyclohexyl |
| R224 (a and b) | —Br | -tert-butoxy |
| R225 (a and b) | —Br | -isopropoxy |
| R226 (a and b) | —Br | —CF₃ |
| R227 (a and b) | —Br | —CH₂CF₃ |
| R228 (a and b) | —Br | —OCF₃ |
| R229 (a and b) | —Br | —Cl |
| R230 (a and b) | —Br | —Br |
| R231 (a and b) | —Br | —I |
| R232 (a and b) | —Br | -n-butyl |
| R233 (a and b) | —Br | —CH₃ |
| R234 (a and b) | —Br | —SCF₃ |
| R235 (a and b) | —Br | —N(CH₂CH₃)₂ |
| R236 (a and b) | —Br | —OCF₂CHF₂ |
| R237 (a and b) | —Br | —C(OH)(CF₃)₂ |
| R238 (a and b) | —Br | -(1,1-dimethyl-pentyl) |
| R239 (a and b) | —Br | -(1,1-dimethyl-acetic acid) ethyl ester |
| R240 (a and b) | —Br | —N-piperidinyl |
| R241 (a and b) | —I | -tert-butyl |
| R242 (a and b) | —I | —H |
| R243 (a and b) | —I | -iso-butyl |
| R244 (a and b) | —I | -sec-butyl |
| R245 (a and b) | —I | -iso-propyl |
| R246 (a and b) | —I | -n-propyl |
| R247 (a and b) | —I | -cyclohexyl |
| R248 (a and b) | —I | -tert-butoxy |
| R249 (a and b) | —I | -isopropoxy |
| R250 (a and b) | —I | —CF₃ |
| R251 (a and b) | —I | —CH₂CF₃ |
| R252 (a and b) | —I | —OCF₃ |
| R253 (a and b) | —I | —Cl |
| R254 (a and b) | —I | —Br |
| R255 (a and b) | —I | —I |
| R256 (a and b) | —I | -n-butyl |

TABLE 18-continued

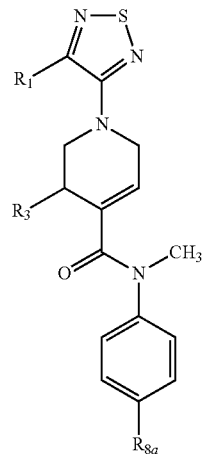

(Ir)

and pharmaceutically acceptable salts thereof, wherein:

| Compound | R₁ | R₈ₐ |
|---|---|---|
| R257 (a and b) | —I | —CH₃ |
| R258 (a and b) | —I | —SCF₃ |
| R259 (a and b) | —I | —N(CH₂CH₃)₂ |
| R260 (a and b) | —I | —OCF₂CHF₂ |
| R261 (a and b) | —I | —C(OH)(CF₃)₂ |
| R262 (a and b) | —I | -(1,1-dimethyl-pentyl) |
| R263 (a and b) | —I | -(1,1-dimethyl-acetic acid) ethyl ester |
| R264 (a and b) | —I | —N-piperidinyl |

(a) means that R₃ is —H.
(b) means that R₃ is —CH₃.

TABLE 19

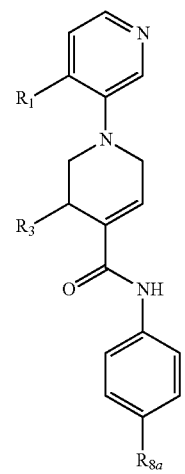

(Is)

and pharmaceutically acceptable salts thereof, wherein:

| Compound | R₁ | R₈ₐ |
|---|---|---|
| S1 (a and b) | —H | —H |
| S2 (a and b) | —H | -tert-butyl |
| S3 (a and b) | —H | -iso-butyl |
| S4 (a and b) | —H | -sec-butyl |
| S5 (a and b) | —H | -iso-propyl |
| S6 (a and b) | —H | -n-propyl |
| S7 (a and b) | —H | -cyclohexyl |
| S8 (a and b) | —H | -tert-butoxy |

TABLE 19-continued

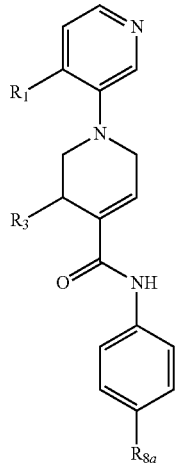

(Is)

and pharmaceutically acceptable salts thereof, wherein:

| Compound | $R_1$ | $R_{8a}$ |
|---|---|---|
| S9 (a and b) | —H | -isopropoxy |
| S10 (a and b) | —H | —$CF_3$ |
| S11 (a and b) | —H | —$CH_2CF_3$ |
| S12 (a and b) | —H | —$OCF_3$ |
| S13 (a and b) | —H | —Cl |
| S14 (a and b) | —H | —Br |
| S15 (a and b) | —H | —I |
| S16 (a and b) | —H | -n-butyl |
| S17 (a and b) | —H | —$CH_3$ |
| S18 (a and b) | —H | —$SCF_3$ |
| S19 (a and b) | —H | —$N(CH_2CH_3)_2$ |
| S20 (a and b) | —H | —$OCF_2CHF_2$ |
| S21 (a and b) | —H | —$C(OH)(CF_3)_2$ |
| S22 (a and b) | —H | -(1,1-dimethyl-pentyl) |
| S23 (a and b) | —H | -(1,1-dimethyl-acetic acid) ethyl ester |
| S24 (a and b) | —H | —N-piperidinyl |
| S25 (a and b) | —Cl | —H |
| S26 (a and b) | —Cl | -tert-butyl |
| S27 (a and b) | —Cl | -iso-butyl |
| S28 (a and b) | —Cl | -sec-butyl |
| S29 (a and b) | —Cl | -iso-propyl |
| S30 (a and b) | —Cl | -n-propyl |
| S31 (a and b) | —Cl | -cyclohexyl |
| S32 (a and b) | —Cl | -tert-butoxy |
| S33 (a and b) | —Cl | -isopropoxy |
| S34 (a and b) | —Cl | —$CF_3$ |
| S35 (a and b) | —Cl | —$CH_2CF_3$ |
| S36 (a and b) | —Cl | —$OCF_3$ |
| S37 (a and b) | —Cl | —Cl |
| S38 (a and b) | —Cl | —Br |
| S39 (a and b) | —Cl | —I |
| S40 (a and b) | —Cl | -n-butyl |
| S41 (a and b) | —Cl | —$CH_3$ |
| S42 (a and b) | —Cl | —$SCF_3$ |
| S43 (a and b) | —Cl | —$N(CH_2CH_3)_2$ |
| S44 (a and b) | —Cl | —$OCF_2CHF_2$ |
| S45 (a and b) | —Cl | —$C(OH)(CF_3)_2$ |
| S46 (a and b) | —Cl | -(1,1-dimethyl-pentyl) |
| S47 (a and b) | —Cl | -(1,1-dimethyl-acetic acid) ethyl ester |
| S48 (a and b) | —Cl | —N-piperidinyl |
| S49 (a and b) | —F | —H |
| S50 (a and b) | —F | -tert-butyl |
| S51 (a and b) | —F | -iso-butyl |
| S52 (a and b) | —F | -sec-butyl |
| S53 (a and b) | —F | -iso-propyl |
| S54 (a and b) | —F | -n-propyl |
| S55 (a and b) | —F | -cyclohexyl |
| S56 (a and b) | —F | -tert-butoxy |
| S57 (a and b) | —F | -isopropoxy |
| S58 (a and b) | —F | —$CF_3$ |
| S59 (a and b) | —F | —$CH_2CF_3$ |
| S60 (a and b) | —F | —$OCF_3$ |
| S61 (a and b) | —F | —Cl |
| S62 (a and b) | —F | —Br |
| S63 (a and b) | —F | —I |
| S64 (a and b) | —F | -n-butyl |
| S65 (a and b) | —F | —$CH_3$ |
| S66 (a and b) | —F | —$SCF_3$ |
| S67 (a and b) | —F | —$N(CH_2CH_3)_2$ |
| S68 (a and b) | —F | —$OCF_2CHF_2$ |
| S69 (a and b) | —F | —$C(OH)(CF_3)_2$ |
| S70 (a and b) | —F | -(1,1-dimethyl-pentyl) |
| S71 (a and b) | —F | -(1,1-dimethyl-acetic acid) ethyl ester |
| S72 (a and b) | —F | —N-piperidinyl |
| S73 (a and b) | —$CH_3$ | —H |
| S74 (a and b) | —$CH_3$ | -iso-butyl |
| S75 (a and b) | —$CH_3$ | -tert-butyl |
| S76 (a and b) | —$CH_3$ | -sec-butyl |
| S77 (a and b) | —$CH_3$ | -iso-propyl |
| S78 (a and b) | —$CH_3$ | -n-propyl |
| S79 (a and b) | —$CH_3$ | -cyclohexyl |
| S80 (a and b) | —$CH_3$ | -tert-butoxy |
| S81 (a and b) | —$CH_3$ | -isopropoxy |
| S82 (a and b) | —$CH_3$ | —$CF_3$ |
| S83 (a and b) | —$CH_3$ | —$CH_2CF_3$ |
| S84 (a and b) | —$CH_3$ | —$OCF_3$ |
| S85 (a and b) | —$CH_3$ | —Cl |
| S86 (a and b) | —$CH_3$ | —Br |
| S87 (a and b) | —$CH_3$ | —I |
| S88 (a and b) | —$CH_3$ | -n-butyl |
| S89 (a and b) | —$CH_3$ | —$CH_3$ |
| S90 (a and b) | —$CH_3$ | —$SCF_3$ |
| S91 (a and b) | —$CH_3$ | —$N(CH_2CH_3)_2$ |
| S92 (a and b) | —$CH_3$ | —$OCF_2CHF_2$ |
| S93 (a and b) | —$CH_3$ | —$C(OH)(CF_3)_2$ |
| S94 (a and b) | —$CH_3$ | -(1,1-dimethyl-pentyl) |
| S95 (a and b) | —$CH_3$ | -(1,1-dimethyl-acetic acid) ethyl ester |
| S96 (a and b) | —$CH_3$ | —N-piperidinyl |
| S97 (a and b) | —$CF_3$ | —H |
| S98 (a and b) | —$CF_3$ | -tert-butyl |
| S99 (a and b) | —$CF_3$ | -iso-butyl |
| S100 (a and b) | —$CF_3$ | -sec-butyl |
| S101 (a and b) | —$CF_3$ | -iso-propyl |
| S102 (a and b) | —$CF_3$ | -n-propyl |
| S103 (a and b) | —$CF_3$ | -cyclohexyl |
| S104 (a and b) | —$CF_3$ | -tert-butoxy |
| S105 (a and b) | —$CF_3$ | -isopropoxy |
| S106 (a and b) | —$CF_3$ | —$CF_3$ |
| S107 (a and b) | —$CF_3$ | —$CH_2CF_3$ |
| S108 (a and b) | —$CF_3$ | —$OCF_3$ |

TABLE 19-continued

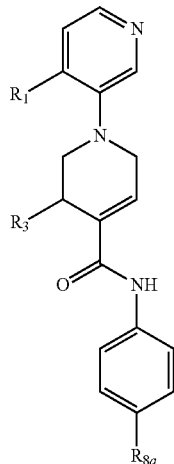

(Is)

and pharmaceutically acceptable salts thereof, wherein:

| Compound | $R_1$ | $R_{8a}$ |
|---|---|---|
| S109 (a and b) | —CF$_3$ | —Cl |
| S110 (a and b) | —CF$_3$ | —Br |
| S111 (a and b) | —CF$_3$ | —I |
| S112 (a and b) | —CF$_3$ | -n-butyl |
| S113 (a and b) | —CF$_3$ | —CH$_3$ |
| S114 (a and b) | —CF$_3$ | —SCF$_3$ |
| S115 (a and b) | —CF$_3$ | —N(CH$_2$CH$_3$)$_2$ |
| S116 (a and b) | —CF$_3$ | —OCF$_2$CHF$_2$ |
| S117 (a and b) | —CF$_3$ | —C(OH)(CF$_3$)$_2$ |
| S118 (a and b) | —CF$_3$ | -(1,1-dimethyl-pentyl) |
| S119 (a and b) | —CF$_3$ | -(1,1-dimethyl-acetic acid) ethyl ester |
| S120 (a and b) | —CF$_3$ | —N-piperidinyl |
| S121 (a and b) | —CHF$_2$ | -tert-butyl |
| S122 (a and b) | —CHF$_2$ | —H |
| S123 (a and b) | —CHF$_2$ | -iso-butyl |
| S124 (a and b) | —CHF$_2$ | -sec-butyl |
| S125 (a and b) | —CHF$_2$ | -iso-propyl |
| S126 (a and b) | —CHF$_2$ | -n-propyl |
| S127 (a and b) | —CHF$_2$ | -cyclohexyl |
| S128 (a and b) | —CHF$_2$ | -tert-butoxy |
| S129 (a and b) | —CHF$_2$ | -isopropoxy |
| S130 (a and b) | —CHF$_2$ | —CF$_3$ |
| S131 (a and b) | —CHF$_2$ | —CH$_2$CF$_3$ |
| S132 (a and b) | —CHF$_2$ | —OCF$_3$ |
| S133 (a and b) | —CHF$_2$ | —Cl |
| S134 (a and b) | —CHF$_2$ | —Br |
| S135 (a and b) | —CHF$_2$ | —I |
| S136 (a and b) | —CHF$_2$ | -n-butyl |
| S137 (a and b) | —CHF$_2$ | —CH$_3$ |
| S138 (a and b) | —CHF$_2$ | —SCF$_3$ |
| S139 (a and b) | —CHF$_2$ | —N(CH$_2$CH$_3$)$_2$ |
| S140 (a and b) | —CHF$_2$ | —OCF$_2$CHF$_2$ |
| S141 (a and b) | —CHF$_2$ | —C(OH)(CF$_3$)$_2$ |
| S142 (a and b) | —CHF$_2$ | -(1,1-dimethyl-pentyl) |
| S143 (a and b) | —CHF$_2$ | -(1,1-dimethyl-acetic acid) ethyl ester |
| S144 (a and b) | —CHF$_2$ | —N-piperidinyl |
| S145 (a and b) | —OH | —H |
| S146 (a and b) | —OH | -tert-butyl |
| S147 (a and b) | —OH | -iso-butyl |
| S148 (a and b) | —OH | -sec-butyl |
| S149 (a and b) | —OH | -iso-propyl |
| S150 (a and b) | —OH | -n-propyl |
| S151 (a and b) | —OH | -cyclohexyl |
| S152 (a and b) | —OH | -tert-butoxy |
| S153 (a and b) | —OH | -isopropoxy |
| S154 (a and b) | —OH | —CF$_3$ |
| S155 (a and b) | —OH | —CH$_2$CF$_3$ |
| S156 (a and b) | —OH | —OCF$_3$ |
| S157 (a and b) | —OH | —Cl |
| S158 (a and b) | —OH | —Br |

TABLE 19-continued

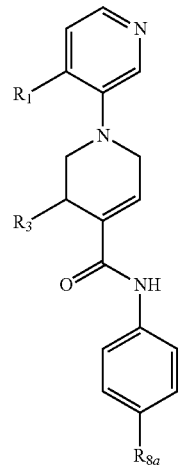

(Is)

and pharmaceutically acceptable salts thereof, wherein:

| Compound | $R_1$ | $R_{8a}$ |
|---|---|---|
| S159 (a and b) | —OH | —I |
| S160 (a and b) | —OH | -n-butyl |
| S161 (a and b) | —OH | —CH$_3$ |
| S162 (a and b) | —OH | —SCF$_3$ |
| S163 (a and b) | —OH | —N(CH$_2$CH$_3$)$_2$ |
| S164 (a and b) | —OH | —OCF$_2$CHF$_2$ |
| S165 (a and b) | —OH | —C(OH)(CF$_3$)$_2$ |
| S166 (a and b) | —OH | -(1,1-dimethyl-pentyl) |
| S167 (a and b) | —OH | -(1,1-dimethyl-acetic acid) ethyl ester |
| S168 (a and b) | —OH | —N-piperidinyl |
| S169 (a and b) | —NO$_2$ | —H |
| S170 (a and b) | —NO$_2$ | -tert-butyl |
| S171 (a and b) | —NO$_2$ | -iso-butyl |
| S172 (a and b) | —NO$_2$ | -sec-butyl |
| S173 (a and b) | —NO$_2$ | -iso-propyl |
| S174 (a and b) | —NO$_2$ | -n-propyl |
| S175 (a and b) | —NO$_2$ | -cyclohexyl |
| S176 (a and b) | —NO$_2$ | -tert-butoxy |
| S177 (a and b) | —NO$_2$ | -isopropoxy |
| S178 (a and b) | —NO$_2$ | —CF$_3$ |
| S179 (a and b) | —NO$_2$ | —CH$_2$CF$_3$ |
| S180 (a and b) | —NO$_2$ | —OCF$_3$ |
| S181 (a and b) | —NO$_2$ | —Cl |
| S182 (a and b) | —NO$_2$ | —Br |
| S183 (a and b) | —NO$_2$ | —I |
| S184 (a and b) | —NO$_2$ | -n-butyl |
| S185 (a and b) | —NO$_2$ | —CH$_3$ |
| S186 (a and b) | —NO$_2$ | —SCF$_3$ |
| S187 (a and b) | —NO$_2$ | —N(CH$_2$CH$_3$)$_2$ |
| S188 (a and b) | —NO$_2$ | —OCF$_2$CHF$_2$ |
| S189 (a and b) | —NO$_2$ | —C(OH)(CF$_3$)$_2$ |
| S190 (a and b) | —NO$_2$ | -(1,1-dimethyl-pentyl) |
| S191 (a and b) | —NO$_2$ | -(1,1-dimethyl-acetic acid) ethyl ester |
| S192 (a and b) | —NO$_2$ | —N-piperidinyl |
| S193 (a and b) | —CN | —H |
| S194 (a and b) | —CN | -tert-butyl |
| S195 (a and b) | —CN | -iso-butyl |
| S196 (a and b) | —CN | -sec-butyl |
| S197 (a and b) | —CN | -iso-propyl |
| S198 (a and b) | —CN | -n-propyl |
| S199 (a and b) | —CN | -cyclohexyl |
| S200 (a and b) | —CN | -tert-butoxy |
| S201 (a and b) | —CN | -isopropoxy |
| S202 (a and b) | —CN | —CF$_3$ |
| S203 (a and b) | —CN | —CH$_2$CF$_3$ |
| S204 (a and b) | —CN | —OCF$_3$ |
| S205 (a and b) | —CN | —Cl |
| S206 (a and b) | —CN | —Br |
| S207 (a and b) | —CN | —I |
| S208 (a and b) | —CN | -n-butyl |

TABLE 19-continued

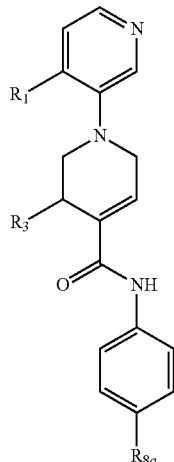

(Is)

and pharmaceutically acceptable salts thereof, wherein:

| Compound | $R_1$ | $R_{8a}$ |
|---|---|---|
| S209 (a and b) | —CN | —CH$_3$ |
| S210 (a and b) | —CN | —SCF$_3$ |
| S211 (a and b) | —CN | —N(CH$_2$CH$_3$)$_2$ |
| S212 (a and b) | —CN | —OCF$_2$CHF$_2$ |
| S213 (a and b) | —CN | —C(OH)(CF$_3$)$_2$ |
| S214 (a and b) | —CN | -(1,1-dimethyl-pentyl) |
| S215 (a and b) | —CN | -(1,1-dimethyl-acetic acid) ethyl ester |
| S216 (a and b) | —CN | —N-piperidinyl |
| S217 (a and b) | —Br | —H |
| S218 (a and b) | —Br | -tert-butyl |
| S219 (a and b) | —Br | -iso-butyl |
| S220 (a and b) | —Br | -sec-butyl |
| S221 (a and b) | —Br | -iso-propyl |
| S222 (a and b) | —Br | -n-propyl |
| S223 (a and b) | —Br | -cyclohexyl |
| S224 (a and b) | —Br | -tert-butoxy |
| S225 (a and b) | —Br | -isopropoxy |
| S226 (a and b) | —Br | —CF$_3$ |
| S227 (a and b) | —Br | —CH$_2$CF$_3$ |
| S228 (a and b) | —Br | —OCF$_3$ |
| S229 (a and b) | —Br | —Cl |
| S230 (a and b) | —Br | —Br |
| S231 (a and b) | —Br | —I |
| S232 (a and b) | —Br | -n-butyl |
| S233 (a and b) | —Br | —CH$_3$ |
| S234 (a and b) | —Br | —SCF$_3$ |
| S235 (a and b) | —Br | —N(CH$_2$CH$_3$)$_2$ |
| S236 (a and b) | —Br | —OCF$_2$CHF$_2$ |
| S237 (a and b) | —Br | —C(OH)(CF$_3$)$_2$ |
| S238 (a and b) | —Br | -(1,1-dimethyl-pentyl) |
| S239 (a and b) | —Br | -(1,1-dimethyl-acetic acid) ethyl ester |
| S240 (a and b) | —Br | —N-piperidinyl |
| S241 (a and b) | —I | -tert-butyl |
| S242 (a and b) | —I | —H |
| S243 (a and b) | —I | -iso-butyl |
| S244 (a and b) | —I | -sec-butyl |
| S245 (a and b) | —I | -iso-propyl |
| S246 (a and b) | —I | -n-propyl |
| S247 (a and b) | —I | -cyclohexyl |
| S248 (a and b) | —I | -tert-butoxy |
| S249 (a and b) | —I | -isopropoxy |
| S250 (a and b) | —I | —CF$_3$ |
| S251 (a and b) | —I | —CH$_2$CF$_3$ |
| S252 (a and b) | —I | —OCF$_3$ |
| S253 (a and b) | —I | —Cl |
| S254 (a and b) | —I | —Br |
| S255 (a and b) | —I | —I |
| S256 (a and b) | —I | -n-butyl |
| S257 (a and b) | —I | —CH$_3$ |
| S258 (a and b) | —I | —SCF$_3$ |

TABLE 19-continued

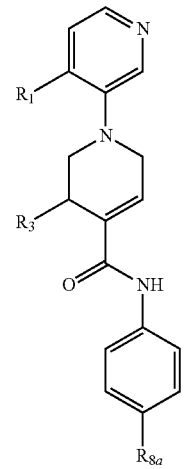

(Is)

and pharmaceutically acceptable salts thereof, wherein:

| Compound | $R_1$ | $R_{8a}$ |
|---|---|---|
| S259 (a and b) | —I | —N(CH$_2$CH$_3$)$_2$ |
| S260 (a and b) | —I | —OCF$_2$CHF$_2$ |
| S261 (a and b) | —I | —C(OH)(CF$_3$)$_2$ |
| S262 (a and b) | —I | -(1,1-dimethyl-pentyl) |
| S263 (a and b) | —I | -(1,1-dimethyl-acetic acid) ethyl ester |
| S264 (a and b) | —I | —N-piperidinyl |

(a) means that $R_3$ is —H.
(b) means that $R_3$ is —CH$_3$.

TABLE 20

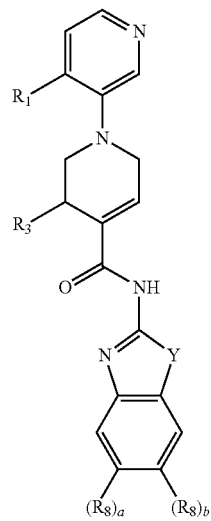

(It)

and pharmaceutically acceptable salts thereof, wherein:

| Compound | Y | $R_1$ | $(R_8)_a$ | $(R_8)_b$ |
|---|---|---|---|---|
| T1 (a and b) | S | —H | —Cl | —H |
| T2 (a and b) | S | —H | —Br | —H |
| T3 (a and b) | S | —H | —F | —H |
| T4 (a and b) | S | —H | —CH$_3$ | —H |
| T5 (a and b) | S | —H | —CF$_3$ | —H |
| T6 (a and b) | S | —H | —OCH$_3$ | —H |
| T7 (a and b) | S | —H | —OCH$_2$CH$_3$ | —H |

TABLE 20-continued

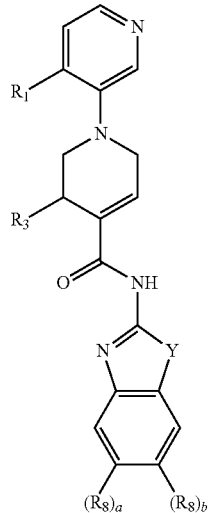

(It)

and pharmaceutically acceptable salts thereof, wherein:

| Compound | Y | $R_1$ | $(R_8)_a$ | $(R_8)_b$ |
|---|---|---|---|---|
| T8 (a and b) | S | —H | —OCF$_3$ | —H |
| T9 (a and b) | S | —H | -tert-butyl | —H |
| T10 (a and b) | S | —H | -iso-propyl | —H |
| T11 (a and b) | S | —H | —CH$_3$ | —CH$_3$ |
| T12 (a and b) | S | —H | —H | —H |
| T13 (a and b) | S | —H | —H | —Cl |
| T14 (a and b) | S | —H | —H | —Br |
| T15 (a and b) | S | —H | —H | —F |
| T16 (a and b) | S | —H | —H | —CH$_3$ |
| T17 (a and b) | S | —H | —H | —CF$_3$ |
| T18 (a and b) | S | —H | —H | —OCH$_3$ |
| T19 (a and b) | S | —H | —H | —OCH$_2$CH$_3$ |
| T20 (a and b) | S | —H | —H | —OCF$_3$ |
| T21 (a and b) | S | —H | —H | -tert-butyl |
| T22 (a and b) | S | —H | —H | -iso-propyl |
| T23 (a and b) | S | —Cl | —Cl | —H |
| T24 (a and b) | S | —Cl | —Br | —H |
| T25 (a and b) | S | —Cl | —F | —H |
| T26 (a and b) | S | —Cl | —CH$_3$ | —H |
| T27 (a and b) | S | —Cl | —CF$_3$ | —H |
| T28 (a and b) | S | —Cl | —OCH$_3$ | —H |
| T29 (a and b) | S | —Cl | —OCH$_2$CH$_3$ | —H |
| T30 (a and b) | S | —Cl | —OCF$_3$ | —H |
| T31 (a and b) | S | —Cl | -tert-butyl | —H |
| T32 (a and b) | S | —Cl | -iso-propyl | —H |
| T33 (a and b) | S | —Cl | —CH$_3$ | —CH$_3$ |
| T34 (a and b) | S | —Cl | —H | —H |
| T35 (a and b) | S | —Cl | —H | —Cl |
| T36 (a and b) | S | —Cl | —H | —Br |
| T37 (a and b) | S | —Cl | —H | —F |
| T38 (a and b) | S | —Cl | —H | —CH$_3$ |
| T39 (a and b) | S | —Cl | —H | —CF$_3$ |
| T40 (a and b) | S | —Cl | —H | —OCH$_3$ |
| T41 (a and b) | S | —Cl | —H | —OCH$_2$CH$_3$ |
| T42 (a and b) | S | —Cl | —H | —OCF$_3$ |
| T43 (a and b) | S | —Cl | —H | -tert-butyl |
| T44 (a and b) | S | —Cl | —H | -iso-propyl |
| T45 (a and b) | S | —Cl | —H | —OCF$_3$ |
| T46 (a and b) | S | —Cl | —H | -tert-butyl |
| T47 (a and b) | S | —Cl | —H | -iso-propyl |
| T48 (a and b) | S | —CH$_3$ | —Cl | —H |
| T49 (a and b) | S | —CH$_3$ | —Br | —H |
| T50 (a and b) | S | —CH$_3$ | —F | —H |
| T51 (a and b) | S | —CH$_3$ | —CH$_3$ | —H |
| T52 (a and b) | S | —CH$_3$ | —CF$_3$ | —H |
| T53 (a and b) | S | —CH$_3$ | —OCH$_3$ | —H |
| T54 (a and b) | S | —CH$_3$ | —OCH$_2$CH$_3$ | —H |
| T55 (a and b) | S | —CH$_3$ | —OCF$_3$ | —H |
| T56 (a and b) | S | —CH$_3$ | -tert-butyl | —H |
| T57 (a and b) | S | —CH$_3$ | -iso-propyl | —H |
| T58 (a and b) | S | —CH$_3$ | —CH$_3$ | —CH$_3$ |
| T59 (a and b) | S | —CH$_3$ | —H | —H |
| T60 (a and b) | S | —CH$_3$ | —H | —Cl |
| T61 (a and b) | S | —CH$_3$ | —H | —Br |
| T62 (a and b) | S | —CH$_3$ | —H | —F |
| T63 (a and b) | S | —CH$_3$ | —H | —CH$_3$ |
| T64 (a and b) | S | —CH$_3$ | —H | —CF$_3$ |
| T65 (a and b) | S | —CH$_3$ | —H | —OCH$_3$ |
| T66 (a and b) | S | —CH$_3$ | —H | —OCH$_2$CH$_3$ |
| T67 (a and b) | S | —CH$_3$ | —H | —OCF$_3$ |
| T68 (a and b) | S | —CH$_3$ | —H | -tert-butyl |
| T69 (a and b) | S | —CH$_3$ | —H | -iso-propyl |
| T70 (a and b) | S | —CF$_3$ | —Cl | —H |
| T71 (a and b) | S | —CF$_3$ | —Br | —H |
| T72 (a and b) | S | —CF$_3$ | —F | —H |
| T73 (a and b) | S | —CF$_3$ | —CH$_3$ | —H |
| T74 (a and b) | S | —CF$_3$ | —CF$_3$ | —H |
| T75 (a and b) | S | —CF$_3$ | —OCH$_3$ | —H |
| T76 (a and b) | S | —CF$_3$ | —OCH$_2$CH$_3$ | —H |
| T77 (a and b) | S | —CF$_3$ | —OCF$_3$ | —H |
| T78 (a and b) | S | —CF$_3$ | -tert-butyl | —H |
| T79 (a and b) | S | —CF$_3$ | -iso-propyl | —H |
| T80 (a and b) | S | —CF$_3$ | —CH$_3$ | —CH$_3$ |
| T81 (a and b) | S | —CF$_3$ | —H | —H |
| T82 (a and b) | S | —CF$_3$ | —H | —Cl |
| T83 (a and b) | S | —CF$_3$ | —H | —Br |
| T84 (a and b) | S | —CF$_3$ | —H | —F |
| T85 (a and b) | S | —CF$_3$ | —H | —CH$_3$ |
| T86 (a and b) | S | —CF$_3$ | —H | —CF$_3$ |
| T87 (a and b) | S | —CF$_3$ | —H | —OCH$_3$ |
| T88 (a and b) | S | —CF$_3$ | —H | —OCH$_2$CH$_3$ |
| T89 (a and b) | S | —CF$_3$ | —H | —OCF$_3$ |
| T90 (a and b) | S | —CF$_3$ | —H | -tert-butyl |
| T91 (a and b) | S | —CF$_3$ | —H | -iso-propyl |
| T92 (a and b) | S | —CHF$_2$ | —Cl | —H |
| T93 (a and b) | S | —CHF$_2$ | —Br | —H |
| T94 (a and b) | S | —CHF$_2$ | —F | —H |
| T95 (a and b) | S | —CHF$_2$ | —CH$_3$ | —H |
| T96 (a and b) | S | —CHF$_2$ | —CF$_3$ | —H |
| T97 (a and b) | S | —CHF$_2$ | —OCH$_3$ | —H |
| T98 (a and b) | S | —CHF$_2$ | —OCH$_2$CH$_3$ | —H |
| T99 (a and b) | S | —CHF$_2$ | —OCF$_3$ | —H |
| T100 (a and b) | S | —CHF$_2$ | -tert-butyl | —H |
| T101 (a and b) | S | —CHF$_2$ | -iso-propyl | —H |
| T102 (a and b) | S | —CHF$_2$ | —CH$_3$ | —CH$_3$ |
| T103 (a and b) | S | —CHF$_2$ | —H | —H |
| T104 (a and b) | S | —CHF$_2$ | —H | —Cl |
| T105 (a and b) | S | —CHF$_2$ | —H | —Br |

TABLE 20-continued

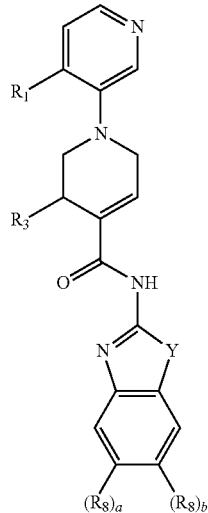

(It)

and pharmaceutically acceptable salts thereof, wherein:

| Compound | Y | R$_1$ | (R$_8$)$_a$ | (R$_8$)$_b$ |
|---|---|---|---|---|
| T106 (a and b) | S | —CHF$_2$ | —H | —F |
| T107 (a and b) | S | —CHF$_2$ | —H | —CH$_3$ |
| T108 (a and b) | S | —CHF$_2$ | —H | —CF$_3$ |
| T109 (a and b) | S | —CHF$_2$ | —H | —OCH$_3$ |
| T110 (a and b) | S | —CHF$_2$ | —H | —OCH$_2$CH$_3$ |
| T111 (a and b) | S | —CHF$_2$ | —H | —OCF$_3$ |
| T112 (a and b) | S | —CHF$_2$ | —H | -tert-butyl |
| T113 (a and b) | S | —CHF$_2$ | —H | -iso-propyl |
| T114 (a and b) | S | —OH | —Cl | —H |
| T115 (a and b) | S | —OH | —Br | —H |
| T116 (a and b) | S | —OH | —F | —H |
| T117 (a and b) | S | —OH | —CH$_3$ | —H |
| T118 (a and b) | S | —OH | —CF$_3$ | —H |
| T119 (a and b) | S | —OH | —OCH$_3$ | —H |
| T120 (a and b) | S | —OH | —OCH$_2$CH$_3$ | —H |
| T121 (a and b) | S | —OH | —OCF$_3$ | —H |
| T122 (a and b) | S | —OH | -tert-butyl | —H |
| T123 (a and b) | S | —OH | -iso-propyl | —H |
| T124 (a and b) | S | —OH | —CH$_3$ | —CH$_3$ |
| T125 (a and b) | S | —OH | —H | —H |
| T126 (a and b) | S | —OH | —H | —Cl |
| T127 (a and b) | S | —OH | —H | —Br |
| T128 (a and b) | S | —OH | —H | —F |
| T129 (a and b) | S | —OH | —H | —CH$_3$ |
| T130 (a and b) | S | —OH | —H | —CF$_3$ |
| T131 (a and b) | S | —OH | —H | —OCH$_3$ |
| T132 (a and b) | S | —OH | —H | —OCH$_2$CH$_3$ |
| T133 (a and b) | S | —OH | —H | —OCF$_3$ |
| T134 (a and b) | S | —OH | —H | -tert-butyl |
| T135 (a and b) | S | —OH | —H | -iso-propyl |
| T136 (a and b) | S | —NO$_2$ | —Cl | —H |
| T137 (a and b) | S | —NO$_2$ | —F | —H |
| T139 (a and b) | S | —NO$_2$ | —CH$_3$ | —H |
| T140 (a and b) | S | —NO$_2$ | —CF$_3$ | —H |
| T141 (a and b) | S | —NO$_2$ | —OCH$_3$ | —H |
| T142 (a and b) | S | —NO$_2$ | —OCH$_2$CH$_3$ | —H |
| T143 (a and b) | S | —NO$_2$ | —OCF$_3$ | —H |
| T144 (a and b) | S | —NO$_2$ | -tert-butyl | —H |
| T145 (a and b) | S | —NO$_2$ | -iso-propyl | —H |
| T146 (a and b) | S | —NO$_2$ | —CH$_3$ | —CH$_3$ |
| T147 (a and b) | S | —NO$_2$ | —H | —H |
| T148 (a and b) | S | —NO$_2$ | —H | —Cl |
| T149 (a and b) | S | —NO$_2$ | —H | —Br |
| T150 (a and b) | S | —NO$_2$ | —H | —F |
| T151 (a and b) | S | —NO$_2$ | —H | —CH$_3$ |
| T152 (a and b) | S | —NO$_2$ | —H | —CF$_3$ |
| T153 (a and b) | S | —NO$_2$ | —H | —OCH$_3$ |
| T154 (a and b) | S | —NO$_2$ | —H | —OCH$_2$CH$_3$ |
| T155 (a and b) | S | —NO$_2$ | —H | —OCF$_3$ |

TABLE 20-continued

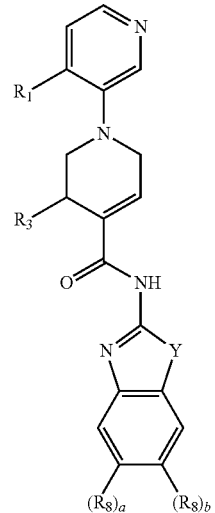

(It)

and pharmaceutically acceptable salts thereof, wherein:

| Compound | Y | R$_1$ | (R$_8$)$_a$ | (R$_8$)$_b$ |
|---|---|---|---|---|
| T156 (a and b) | S | —NO$_2$ | —H | -tert-butyl |
| T157 (a and b) | S | —NO$_2$ | —H | -iso-propyl |
| T158 (a and b) | S | —CN | —Br | —H |
| T159 (a and b) | S | —CN | —Cl | —H |
| T160 (a and b) | S | —CN | —F | —H |
| T161 (a and b) | S | —CN | —CH$_3$ | —H |
| T162 (a and b) | S | —CN | —CF$_3$ | —H |
| T163 (a and b) | S | —CN | —OCH$_3$ | —H |
| T164 (a and b) | S | —CN | —OCH$_2$CH$_3$ | —H |
| T165 (a and b) | S | —CN | —OCF$_3$ | —H |
| T166 (a and b) | S | —CN | -tert-butyl | —H |
| T167 (a and b) | S | —CN | -iso-propyl | —H |
| T168 (a and b) | S | —CN | —CH$_3$ | —CH$_3$ |
| T169 (a and b) | S | —CN | —H | —H |
| T170 (a and b) | S | —CN | —H | —Cl |
| T171 (a and b) | S | —CN | —H | —Br |
| T172 (a and b) | S | —CN | —H | —F |
| T173 (a and b) | S | —CN | —H | —CH$_3$ |
| T174 (a and b) | S | —CN | —H | —CF$_3$ |
| T175 (a and b) | S | —CN | —H | —OCH$_3$ |
| T176 (a and b) | S | —CN | —H | —OCH$_2$CH$_3$ |
| T177 (a and b) | S | —CN | —H | —OCF$_3$ |
| T178 (a and b) | S | —CN | —H | -tert-butyl |
| T179 (a and b) | S | —CN | —H | -iso-propyl |
| T180 (a and b) | S | —Br | —Br | —H |
| T181 (a and b) | S | —Br | —Cl | —H |
| T182 (a and b) | S | —Br | —F | —H |
| T183 (a and b) | S | —Br | —CH$_3$ | —H |
| T184 (a and b) | S | —Br | —CF$_3$ | —H |
| T185 (a and b) | S | —Br | —OCH$_3$ | —H |
| T186 (a and b) | S | —Br | —OCH$_2$CH$_3$ | —H |
| T187 (a and b) | S | —Br | —OCF$_3$ | —H |
| T188 (a and b) | S | —Br | -tert-butyl | —H |
| T189 (a and b) | S | —Br | -iso-propyl | —H |
| T190 (a and b) | S | —Br | —CH$_3$ | —CH$_3$ |
| T191 (a and b) | S | —Br | —H | —H |
| T192 (a and b) | S | —Br | —H | —Cl |
| T193 (a and b) | S | —Br | —H | —Br |
| T194 (a and b) | S | —Br | —H | —F |
| T195 (a and b) | S | —Br | —H | —CH$_3$ |
| TI96 (a and b) | S | —Br | —H | —CF$_3$ |
| T197 (a and b) | S | —Br | —H | —OCH$_3$ |
| TI98 (a and b) | S | —Br | —H | —OCH$_2$CH$_3$ |
| T199 (a and b) | S | —Br | —H | —OCF$_3$ |
| T200 (a and b) | S | —Br | —H | -tert-butyl |
| T201 (a and b) | S | —Br | —H | -iso-propyl |
| T202 (a and b) | S | —I | —Cl | —H |
| T203 (a and b) | S | —I | —Br | —H |
| T204 (a and b) | S | —I | —F | —H |

TABLE 20-continued

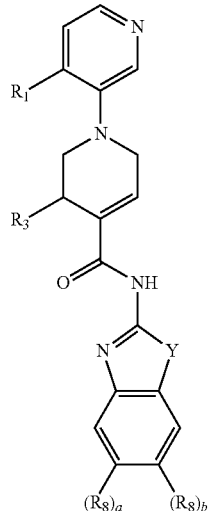

(It)

and pharmaceutically acceptable salts thereof, wherein:

| Compound | Y | R₁ | (R₈)ₐ | (R₈)ᵦ |
|---|---|---|---|---|
| T205 (a and b) | S | —I | —CH₃ | —H |
| T206 (a and b) | S | —I | —CF₃ | —H |
| T207 (a and b) | S | —I | —OCH₃ | —H |
| T208 (a and b) | S | —I | —OCH₂CH₃ | —H |
| T209 (a and b) | S | —I | —OCF₃ | —H |
| T210 (a and b) | S | —I | -tert-butyl | —H |
| T211 (a and b) | S | —I | -iso-propyl | —H |
| T212 (a and b) | S | —I | —CH₃ | —CH₃ |
| T213 (a and b) | S | —I | —H | —H |
| T214 (a and b) | S | —I | —H | —Cl |
| T215 (a and b) | S | —I | —H | —Br |
| T216 (a and b) | S | —I | —H | —F |
| T217 (a and b) | S | —I | —H | —CH₃ |
| T218 (a and b) | S | —I | —H | —CF₃ |
| T219 (a and b) | S | —I | —H | —OCH₃ |
| T220 (a and b) | S | —I | —H | —OCH₂CH₃ |
| T221 (a and b) | S | —I | —H | —OCF₃ |
| T222 (a and b) | S | —I | —H | -tert-butyl |
| T223 (a and b) | S | —I | —H | -iso-propyl |
| T224 (a and b) | O | —H | —Cl | —H |
| T225 (a and b) | O | —H | —Br | —H |
| T226 (a and b) | O | —H | —F | —H |
| T227 (a and b) | O | —H | —CH₃ | —H |
| T228 (a and b) | O | —H | —CF₃ | —H |
| T229 (a and b) | O | —H | —OCH₃ | —H |
| T230 (a and b) | O | —H | —OCH₂CH₃ | —H |
| T231 (a and b) | O | —H | —OCF₃ | —H |
| T232 (a and b) | O | —H | -tert-butyl | —H |
| T233 (a and b) | O | —H | -iso-propyl | —H |
| T234 (a and b) | O | —H | —CH₃ | —CH₃ |
| T235 (a and b) | O | —H | —H | —H |
| T236 (a and b) | O | —H | —H | —Cl |
| T237 (a and b) | O | —H | —H | —Br |
| T238 (a and b) | O | —H | —H | —F |
| T239 (a and b) | O | —H | —H | —CH₃ |
| T240 (a and b) | O | —H | —H | —CF₃ |
| T241 (a and b) | O | —H | —H | —OCH₃ |
| T242 (a and b) | O | —H | —H | —OCH₂CH₃ |
| T243 (a and b) | O | —H | —H | —OCF3 |
| T244 (a and b) | O | —H | —H | -tert-butyl |
| T245 (a and b) | O | —H | —H | -iso-propyl |
| T246 (a and b) | O | —Cl | —Cl | —H |
| T247 (a and b) | O | —Cl | —Br | —H |
| T248 (a and b) | O | —Cl | —F | —H |
| T249 (a and b) | O | —Cl | —CH₃ | —H |
| T250 (a and b) | O | —Cl | —CF₃ | —H |
| T251 (a and b) | O | —Cl | —OCH₃ | —H |
| T252 (a and b) | O | —Cl | —OCH₂CH₃ | —H |
| T253 (a and b) | O | —Cl | —OCF₃ | —H |
| T254 (a and b) | O | —Cl | -tert-butyl | —H |
| T255 (a and b) | O | —Cl | -iso-propyl | —H |
| T256 (a and b) | O | —Cl | —CH₃ | —CH₃ |
| T257 (a and b) | O | —Cl | —H | —H |
| T258 (a and b) | O | —Cl | —H | —CH₃ |
| T259 (a and b) | O | —Cl | —H | —Cl |
| T260 (a and b) | O | —Cl | —H | —Br |
| T261 (a and b) | O | —Cl | —H | —F |
| T262 (a and b) | O | —Cl | —H | —CF₃ |
| T263 (a and b) | O | —Cl | —H | —OCH₃ |
| T264 (a and b) | O | —Cl | —H | —OCH₂CH₃ |
| T265 (a and b) | O | —Cl | —H | —OCF₃ |
| T266 (a and b) | O | —Cl | —H | -tert-butyl |
| T267 (a and b) | O | —Cl | —H | -iso-propyl |
| T268 (a and b) | O | —Cl | —H | —OCF₃ |
| T269 (a and b) | O | —Cl | —H | -tert-butyl |
| T270 (a and b) | O | —Cl | —H | -iso-propyl |
| T271 (a and b) | O | —CH₃ | —Cl | —H |
| T272 (a and b) | O | —CH₃ | —Br | —H |
| T273 (a and b) | O | —CH₃ | —F | —H |
| T274 (a and b) | O | —CH₃ | —CH₃ | —H |
| T275 (a and b) | O | —CH₃ | —CF₃ | —H |
| T276 (a and b) | O | —CH₃ | —OCH₃ | —H |
| T277 (a and b) | O | —CH₃ | —OCH₂CH₃ | —H |
| T278 (a and b) | O | —CH₃ | —OCF₃ | —H |
| T279 (a and b) | O | —CH₃ | -tert-butyl | —H |
| T280 (a and b) | O | —CH₃ | -iso-propyl | —H |
| T281 (a and b) | O | —CH₃ | —CH₃ | —CH₃ |
| T282 (a and b) | O | —CH₃ | —H | —H |
| T283 (a and b) | O | —CH₃ | —H | —Cl |
| T284 (a and b) | O | —CH₃ | —H | —Br |
| T285 (a and b) | O | —CH₃ | —H | —F |
| T286 (a and b) | O | —CH₃ | —H | —CH₃ |
| T287 (a and b) | O | —CH₃ | —H | —CF₃ |
| T288 (a and b) | O | —CH₃ | —H | —OCH₃ |
| T289 (a and b) | O | —CH₃ | —H | —OCH₂CH₃ |
| T290 (a and b) | O | —CH₃ | —H | —OCF₃ |
| T291 (a and b) | O | —CH₃ | —H | -tert-butyl |
| T292 (a and b) | O | —CH₃ | —H | -iso-propyl |
| T293 (a and b) | O | —CF₃ | —Cl | —H |
| T294 (a and b) | O | —CF₃ | —Br | —H |
| T295 (a and b) | O | —CF₃ | —F | —H |
| T296 (a and b) | O | —CF₃ | —CH₃ | —H |
| T297 (a and b) | O | —CF₃ | —CF₃ | —H |
| T298 (a and b) | O | —CF₃ | —OCH₃ | —H |
| T299 (a and b) | O | —CF₃ | —OCH₂CH₃ | —H |
| T300 (a and b) | O | —CF₃ | —OCF₃ | —H |
| T301 (a and b) | O | —CF₃ | -tert-butyl | —H |
| T302 (a and b) | O | —CF₃ | -iso-propyl | —H |

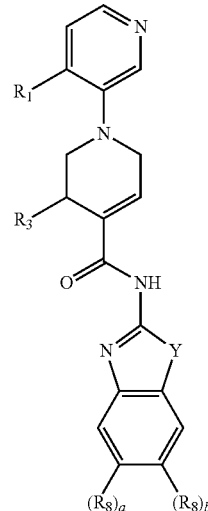

TABLE 20-continued (It)

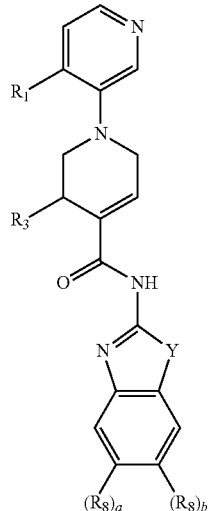

and pharmaceutically acceptable salts thereof, wherein:

| Compound | Y | $R_1$ | $(R_8)_a$ | $(R_8)_b$ |
|---|---|---|---|---|
| T303 (a and b) | O | —$CF_3$ | —$CH_3$ | —$CH_3$ |
| T304 (a and b) | O | —$CF_3$ | —H | —H |
| T305 (a and b) | O | —$CF_3$ | —H | —Cl |
| T306 (a and b) | O | —$CF_3$ | —H | —Br |
| T307 (a and b) | O | —$CF_3$ | —H | —F |
| T308 (a and b) | O | —$CF_3$ | —H | —$CH_3$ |
| T309 (a and b) | O | —$CF_3$ | —H | —$CF_3$ |
| T310 (a and b) | O | —$CF_3$ | —H | —$OCH_3$ |
| T311 (a and b) | O | —$CF_3$ | —H | —$OCH_2CH_3$ |
| T312 (a and b) | O | —$CF_3$ | —H | —$OCF_3$ |
| T313 (a and b) | O | —$CF_3$ | —H | -tert-butyl |
| T314 (a and b) | O | —$CF_3$ | —H | -iso-propyl |
| T315 (a and b) | O | —$CHF_2$ | —Cl | —H |
| T316 (a and b) | O | —$CHF_2$ | —Br | —H |
| T317 (a and b) | O | —$CHF_2$ | —F | —H |
| T318 (a and b) | O | —$CHF_2$ | —$CH_3$ | —H |
| T319 (a and b) | O | —$CHF_2$ | —$CF_3$ | —H |
| T320 (a and b) | O | —$CHF_2$ | —$OCH_3$ | —H |
| T321 (a and b) | O | —$CHF_2$ | —$OCH_2CH_3$ | —H |
| T322 (a and b) | O | —$CHF_2$ | —$OCF_3$ | —H |
| T323 (a and b) | O | —$CHF_2$ | -tert-butyl | —H |
| T324 (a and b) | O | —$CHF_2$ | -iso-propyl | —H |
| T325 (a and b) | O | —$CHF_2$ | —$CH_3$ | —$CH_3$ |
| T326 (a and b) | O | —$CHF_2$ | —H | —H |
| T327 (a and b) | O | —$CHF_2$ | —H | —Cl |
| T328 (a and b) | O | —$CHF_2$ | —H | —Br |
| T329 (a and b) | O | —$CHF_2$ | —H | —F |
| T330 (a and b) | O | —$CHF_2$ | —H | —$CH_3$ |
| T331 (a and b) | O | —$CHF_2$ | —H | —$CF_3$ |
| T332 (a and b) | O | —$CHF_2$ | —H | —$OCH_3$ |
| T333 (a and b) | O | —$CHF_2$ | —H | —$OCH_2CH_3$ |
| T334 (a and b) | O | —$CHF_2$ | —H | —$OCF_3$ |
| T335 (a and b) | O | —$CHF_2$ | —H | -tert-butyl |
| T336 (a and b) | O | —$CHF_2$ | —H | -iso-propyl |
| T337 (a and b) | O | —OH | —Cl | —H |
| T338 (a and b) | O | —OH | —Br | —H |
| T339 (a and b) | O | —OH | —F | —H |
| T340 (a and b) | O | —OH | —$CH_3$ | —H |
| T341 (a and b) | O | —OH | —$CF_3$ | —H |
| T342 (a and b) | O | —OH | —$OCH_3$ | —H |
| T343 (a and b) | O | —OH | —$OCH_2CH_3$ | —H |
| T344 (a and b) | O | —OH | —$OCF_3$ | —H |
| T345 (a and b) | O | —OH | -tert-butyl | —H |
| T346 (a and b) | O | —OH | -iso-propyl | —H |
| T347 (a and b) | O | —OH | —$CH_3$ | —$CH_3$ |
| T348 (a and b) | O | —OH | —H | —H |
| T349 (a and b) | O | —OH | —H | —Cl |
| T350 (a and b) | O | —OH | —H | —Br |
| T351 (a and b) | O | —OH | —H | —F |

TABLE 20-continued (It)

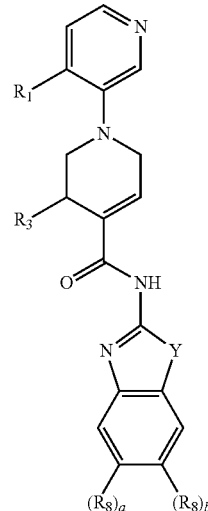

and pharmaceutically acceptable salts thereof, wherein:

| Compound | Y | $R_1$ | $(R_8)_a$ | $(R_8)_b$ |
|---|---|---|---|---|
| T352 (a and b) | O | —OH | —H | —$CH_3$ |
| T353 (a and b) | O | —OH | —H | —$CF_3$ |
| T354 (a and b) | O | —OH | —H | —$OCH_3$ |
| T355 (a and b) | O | —OH | —H | —$OCH_2CH_3$ |
| T356 (a and b) | O | —OH | —H | —$OCF_3$ |
| T357 (a and b) | O | —OH | —H | -tert-butyl |
| T358 (a and b) | O | —OH | —H | -iso-propyl |
| T359 (a and b) | O | —$NO_2$ | —Cl | —H |
| T360 (a and b) | O | —$NO_2$ | —Br | —H |
| T361 (a and b) | O | —$NO_2$ | —F | —H |
| T362 (a and b) | O | —$NO_2$ | —$CH_3$ | —H |
| T363 (a and b) | O | —$NO_2$ | —$CF_3$ | —H |
| T364 (a and b) | O | —$NO_2$ | —$OCH_3$ | —H |
| T365 (a and b) | O | —$NO_2$ | —$OCH_2CH_3$ | —H |
| T366 (a and b) | O | —$NO_2$ | —$OCF_3$ | —H |
| T367 (a and b) | O | —$NO_2$ | -tert-butyl | —H |
| T368 (a and b) | O | —$NO_2$ | -iso-propyl | —H |
| T369 (a and b) | O | —$NO_2$ | —$CH_3$ | —$CH_3$ |
| T370 (a and b) | O | —$NO_2$ | —H | —H |
| T371 (a and b) | O | —$NO_2$ | —H | —Cl |
| T372 (a and b) | O | —$NO_2$ | —H | —Br |
| T373 (a and b) | O | —$NO_2$ | —H | —F |
| T374 (a and b) | O | —$NO_2$ | —H | —$CH_3$ |
| T375 (a and b) | O | —$NO_2$ | —H | —$CF_3$ |
| T376 (a and b) | O | —$NO_2$ | —H | —$OCH_3$ |
| T377 (a and b) | O | —$NO_2$ | —H | —$OCH_2CH_3$ |
| T378 (a and b) | O | —$NO_2$ | —H | —$OCF_3$ |
| T379 (a and b) | O | —$NO_2$ | —H | -tert-butyl |
| T380 (a and b) | O | —$NO_2$ | —H | -iso-propyl |
| T381 (a and b) | O | —CN | —Br | —H |
| T382 (a and b) | O | —CN | —Cl | —H |
| T383 (a and b) | O | —CN | —F | —H |
| T384 (a and b) | O | —CN | —$CH_3$ | —H |
| T385 (a and b) | O | —CN | —$CF_3$ | —H |
| T386 (a and b) | O | —CN | —$OCH_3$ | —H |
| T387 (a and b) | O | —CN | —$OCH_2CH_3$ | —H |
| T388 (a and b) | O | —CN | —$OCF_3$ | —H |
| T389 (a and b) | O | —CN | -tert-butyl | —H |
| T390 (a and b) | O | —CN | -iso-propyl | —H |
| T391 (a and b) | O | —CN | —$CH_3$ | —$CH_3$ |
| T392 (a and b) | O | —CN | —H | —H |
| T393 (a and b) | O | —CN | —H | —Cl |
| T394 (a and b) | O | —CN | —H | —Br |
| T395 (a and b) | O | —CN | —H | —F |
| T396 (a and b) | O | —CN | —H | —$CH_3$ |
| T397 (a and b) | O | —CN | —H | —$CF_3$ |
| T398 (a and b) | O | —CN | —H | —$OCH_3$ |
| T399 (a and b) | O | —CN | —H | —$OCH_2CH_3$ |
| T400 (a and b) | O | —CN | —H | —$OCF_3$ |

TABLE 20-continued

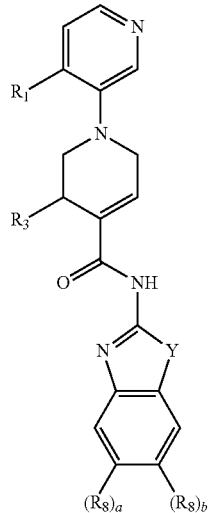

(It)

and pharmaceutically acceptable salts thereof, wherein:

| Compound | Y | R$_1$ | (R$_8$)$_a$ | (R$_8$)$_b$ |
|---|---|---|---|---|
| T401 (a and b) | O | —CN | —H | -tert-butyl |
| T402 (a and b) | O | —CN | —H | -iso-propyl |
| T403 (a and b) | O | —Br | —Br | —H |
| T404 (a and b) | O | —Br | —Cl | —H |
| T405 (a and b) | O | —Br | —F | —H |
| T406 (a and b) | O | —Br | —CH$_3$ | —H |
| T407 (a and b) | O | —Br | —CF$_3$ | —H |
| T408 (a and b) | O | —Br | —OCH$_3$ | —H |
| T409 (a and b) | O | —Br | —OCH$_2$CH$_3$ | —H |
| T410 (a and b) | O | —Br | —OCF$_3$ | —H |
| T411 (a and b) | O | —Br | -tert-butyl | —H |
| T412 (a and b) | O | —Br | -iso-propyl | —H |
| T413 (a and b) | O | —Br | —CH$_3$ | —CH$_3$ |
| T414 (a and b) | O | —Br | —H | —H |
| T415 (a and b) | O | —Br | —H | —Cl |
| T416 (a and b) | O | —Br | —H | —Br |
| T417 (a and b) | O | —Br | —H | —F |
| T418 (a and b) | O | —Br | —H | —CH$_3$ |
| T419 (a and b) | O | —Br | —H | —CF$_3$ |
| T420 (a and b) | O | —Br | —H | —OCH$_3$ |
| T421 (a and b) | O | —Br | —H | —OCH$_2$CH$_3$ |
| T422 (a and b) | O | —Br | —H | —OCF$_3$ |
| T423 (a and b) | O | —Br | —H | -tert-butyl |
| T424 (a and b) | O | —Br | —H | -iso-propyl |
| T425 (a and b) | O | —I | —Cl | —H |
| T426 (a and b) | O | —I | —Br | —H |
| T427 (a and b) | O | —I | —F | —H |
| T428 (a and b) | O | —I | —CH$_3$ | —H |
| T429 (a and b) | O | —I | —CF$_3$ | —H |
| T430 (a and b) | O | —I | —OCH$_3$ | —H |
| T431 (a and b) | O | —I | —OCH$_2$CH$_3$ | —H |
| T432 (a and b) | O | —I | —OCF$_3$ | —H |
| T433 (a and b) | O | —I | -tert-butyl | —H |
| T434 (a and b) | O | —I | -iso-propyl | —H |
| T435 (a and b) | O | —I | —CH$_3$ | —CH$_3$ |
| T436 (a and b) | O | —I | —H | —H |
| T437 (a and b) | O | —I | —H | —Cl |
| T438 (a and b) | O | —I | —H | —Br |
| T439 (a and b) | O | —I | —H | —F |
| T440 (a and b) | O | —I | —H | —CH$_3$ |
| T441 (a and b) | O | —I | —H | —CF$_3$ |
| T442 (a and b) | O | —I | —H | —OCH$_3$ |
| T443 (a and b) | O | —I | —H | —OCH$_2$CH$_3$ |
| T444 (a and b) | O | —I | —H | —OCF$_3$ |
| T445 (a and b) | O | —I | —H | -tert-butyl |
| T446 (a and b) | O | —I | —H | -iso-propyl |
| T447 (a and b) | NH | —H | —Cl | —H |
| T448 (a and b) | NH | —H | —Br | —H |
| T449 (a and b) | NH | —H | —F | —H |
| T450 (a and b) | NH | —H | —CH$_3$ | —H |
| T451 (a and b) | NH | —H | —CF$_3$ | —H |
| T452 (a and b) | NH | —H | —OCH$_3$ | —H |
| T453 (a and b) | NH | —H | —OCH$_2$CH$_3$ | —H |
| T454 (a and b) | NH | —H | —OCF$_3$ | —H |
| T455 (a and b) | NH | —H | -tert-butyl | —H |
| T456 (a and b) | NH | —H | -iso-propyl | —H |
| T457 (a and b) | NH | —H | —CH$_3$ | —CH$_3$ |
| T458 (a and b) | NH | —H | —H | —H |
| T459 (a and b) | NH | —H | —H | —Cl |
| T460 (a and b) | NH | —H | —H | —Br |
| T461 (a and b) | NH | —H | —H | —F |
| T462 (a and b) | NH | —H | —H | —CH$_3$ |
| T463 (a and b) | NH | —H | —H | —CF$_3$ |
| T464 (a and b) | NH | —H | —H | —OCH$_3$ |
| T465 (a and b) | NH | —H | —H | —OCH$_2$CH$_3$ |
| T466 (a and b) | NH | —H | —H | —OCF$_3$ |
| T467 (a and b) | NH | —H | —H | -tert-butyl |
| T468 (a and b) | NH | —H | —H | -iso-propyl |
| T469 (a and b) | NH | —Cl | —Cl | —H |
| T470 (a and b) | NH | —Cl | —Br | —H |
| T471 (a and b) | NH | —Cl | —F | —H |
| T472 (a and b) | NH | —Cl | —CH$_3$ | —H |
| T473 (a and b) | NH | —Cl | —CF$_3$ | —H |
| T474 (a and b) | NH | —Cl | —OCH$_3$ | —H |
| T475 (a and b) | NH | —Cl | —OCH$_2$CH$_3$ | —H |
| T476 (a and b) | NH | —Cl | —OCF$_3$ | —H |
| T477 (a and b) | NH | —Cl | -tert-butyl | —H |
| T478 (a and b) | NH | —Cl | -iso-propyl | —H |
| T479 (a and b) | NH | —Cl | —CH$_3$ | —CH$_3$ |
| T480 (a and b) | NH | —Cl | —H | —H |
| T481 (a and b) | NH | —Cl | —H | —CH$_3$ |
| T482 (a and b) | NH | —Cl | —H | —Cl |
| T483 (a and b) | NH | —Cl | —H | —Br |
| T484 (a and b) | NH | —Cl | —H | —F |
| T485 (a and b) | NH | —Cl | —H | —CF$_3$ |
| T486 (a and b) | NH | —Cl | —H | —OCH$_3$ |
| T487 (a and b) | NH | —Cl | —H | —OCH$_2$CH$_3$ |
| T488 (a and b) | NH | —Cl | —H | —OCF$_3$ |
| T489 (a and b) | NH | —Cl | —H | -tert-butyl |
| T490 (a and b) | NH | —Cl | —H | -iso-propyl |
| T491 (a and b) | NH | —Cl | —H | —OCF$_3$ |
| T492 (a and b) | NH | —Cl | —H | -tert-butyl |
| T493 (a and b) | NH | —Cl | —H | -iso-propyl |
| T494 (a and b) | NH | —CH$_3$ | —Cl | —H |
| T495 (a and b) | NH | —CH$_3$ | —Br | —H |
| T496 (a and b) | NH | —CH$_3$ | —F | —H |
| T497 (a and b) | NH | —CH$_3$ | —CH$_3$ | —H |
| T498 (a and b) | NH | —CH$_3$ | —CF$_3$ | —H |

TABLE 20-continued (It)

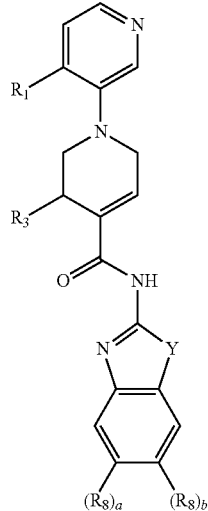

and pharmaceutically acceptable salts thereof, wherein:

| Compound | Y | R₁ | (R₈)ₐ | (R₈)ᵦ |
|---|---|---|---|---|
| T499 (a and b) | NH | —CH₃ | —OCH₃ | —H |
| T500 (a and b) | NH | —CH₃ | —OCH₂CH₃ | —H |
| T501 (a and b) | NH | —CH₃ | —OCF₃ | —H |
| T502 (a and b) | NH | —CH₃ | -tert-butyl | —H |
| T503 (a and b) | NH | —CH₃ | -iso-propyl | —H |
| T504 (a and b) | NH | —CH₃ | —CH₃ | —CH₃ |
| T505 (a and b) | NH | —CH₃ | —H | —H |
| T506 (a and b) | NH | —CH₃ | —H | —Cl |
| T507 (a and b) | NH | —CH₃ | —H | —Br |
| T508 (a and b) | NH | —CH₃ | —H | —F |
| T509 (a and b) | NH | —CH₃ | —H | —CH₃ |
| T510 (a and b) | NH | —CH₃ | —H | —CF₃ |
| T511 (a and b) | NH | —CH₃ | —H | —OCH₃ |
| T512 (a and b) | NH | —CH₃ | —H | —OCH₂CH₃ |
| T513 (a and b) | NH | —CH₃ | —H | —OCF₃ |
| T514 (a and b) | NH | —CH₃ | —H | -tert-butyl |
| T515 (a and b) | NH | —CH₃ | —H | -iso-propyl |
| T516 (a and b) | NH | —CF₃ | —Cl | —H |
| T517 (a and b) | NH | —CF₃ | —Br | —H |
| T518 (a and b) | NH | —CF₃ | —F | —H |
| T519 (a and b) | NH | —CF₃ | —CH₃ | —H |
| T520 (a and b) | NH | —CF₃ | —CF₃ | —H |
| T521 (a and b) | NH | —CF₃ | —OCH₃ | —H |
| T522 (a and b) | NH | —CF₃ | —OCH₂CH₃ | —H |
| T523 (a and b) | NH | —CF₃ | —OCF₃ | —H |
| T524 (a and b) | NH | —CF₃ | -tert-butyl | —H |
| T525 (a and b) | NH | —CF₃ | -iso-propyl | —H |
| T526 (a and b) | NH | —CF₃ | —CH₃ | —CH₃ |
| T527 (a and b) | NH | —CF₃ | —H | —H |
| T528 (a and b) | NH | —CF₃ | —H | —Cl |
| T529 (a and b) | NH | —CF₃ | —H | —Br |
| T530 (a and b) | NH | —CF₃ | —H | —F |
| T531 (a and b) | NH | —CF₃ | —H | —CH₃ |
| T532 (a and b) | NH | —CF₃ | —H | —CF₃ |
| T533 (a and b) | NH | —CF₃ | —H | —OCH₃ |
| T534 (a and b) | NH | —CF₃ | —H | —OCH₂CH₃ |
| T535 (a and b) | NH | —CF₃ | —H | —OCF₃ |
| T536 (a and b) | NH | —CF₃ | —H | -tert-butyl |
| T537 (a and b) | NH | —CF₃ | —H | -iso-propyl |
| T538 (a and b) | NH | —CHF₂ | —Cl | —H |
| T539 (a and b) | NH | —CHF₂ | —Br | —H |
| T540 (a and b) | NH | —CHF₂ | —F | —H |
| T541 (a and b) | NH | —CHF₂ | —CH₃ | —H |
| T542 (a and b) | NH | —CHF₂ | —CF₃ | —H |
| T543 (a and b) | NH | —CHF₂ | —OCH₃ | —H |
| T544 (a and b) | NH | —CHF₂ | —OCH₂CH₃ | —H |
| T545 (a and b) | NH | —CHF₂ | —OCF₃ | —H |
| T546 (a and b) | NH | —CHF₂ | -tert-butyl | —H |
| T547 (a and b) | NH | —CHF₂ | -iso-propyl | —H |

TABLE 20-continued (It)

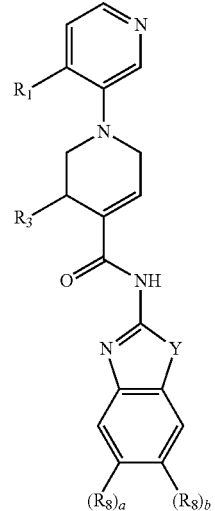

and pharmaceutically acceptable salts thereof, wherein:

| Compound | Y | R₁ | (R₈)ₐ | (R₈)ᵦ |
|---|---|---|---|---|
| T548 (a and b) | NH | —CHF₂ | —CH₃ | —CH₃ |
| T549 (a and b) | NH | —CHF₂ | —H | —H |
| T550 (a and b) | NH | —CHF₂ | —H | —Cl |
| T551 (a and b) | NH | —CHF₂ | —H | —Br |
| T552 (a and b) | NH | —CHF₂ | —H | —F |
| T553 (a and b) | NH | —CHF₂ | —H | —CH₃ |
| T554 (a and b) | NH | —CHF₂ | —H | —CF₃ |
| T555 (a and b) | NH | —CHF₂ | —H | —OCH₃ |
| T556 (a and b) | NH | —CHF₂ | —H | —OCH₂CH₃ |
| T557 (a and b) | NH | —CHF₂ | —H | —OCF₃ |
| T558 (a and b) | NH | —CHF₂ | —H | -tert-butyl |
| T559 (a and b) | NH | —CHF₂ | —H | -iso-propyl |
| T560 (a and b) | NH | —OH | —Cl | —H |
| T561 (a and b) | NH | —OH | —Br | —H |
| T562 (a and b) | NH | —OH | —F | —H |
| T563 (a and b) | NH | —OH | —CH₃ | —H |
| T564 (a and b) | NH | —OH | —CF₃ | —H |
| T565 (a and b) | NH | —OH | —OCH₃ | —H |
| T566 (a and b) | NH | —OH | —OCH₂CH₃ | —H |
| T567 (a and b) | NH | —OH | —OCF₃ | —H |
| T568 (a and b) | NH | —OH | -tert-butyl | —H |
| T569 (a and b) | NH | —OH | -iso-propyl | —H |
| T570 (a and b) | NH | —OH | —CH₃ | —CH₃ |
| T571 (a and b) | NH | —OH | —H | —H |
| T572 (a and b) | NH | —OH | —H | —Cl |
| T573 (a and b) | NH | —OH | —H | —Br |
| T574 (a and b) | NH | —OH | —H | —F |
| T575 (a and b) | NH | —OH | —H | —CH₃ |
| T576 (a and b) | NH | —OH | —H | —CF₃ |
| T577 (a and b) | NH | —OH | —H | —OCH₃ |
| T578 (a and b) | NH | —OH | —H | —OCH₂CH₃ |
| T579 (a and b) | NH | —OH | —H | —OCF₃ |
| T580 (a and b) | NH | —OH | —H | -tert-butyl |
| T581 (a and b) | NH | —OH | —H | -iso-propyl |
| T582 (a and b) | NH | —NO₂ | —Cl | —H |
| T583 (a and b) | NH | —NO₂ | —Br | —H |
| T584 (a and b) | NH | —NO₂ | —F | —H |
| T585 (a and b) | NH | —NO₂ | —CH₃ | —H |
| T586 (a and b) | NH | —NO₂ | —CF₃ | —H |
| T587 (a and b) | NH | —NO₂ | —OCH₃ | —H |
| T588 (a and b) | NH | —NO₂ | —OCH₂CH₃ | —H |
| T589 (a and b) | NH | —NO₂ | —OCF₃ | —H |
| T590 (a and b) | NH | —NO₂ | -tert-butyl | —H |
| T591 (a and b) | NH | —NO₂ | -iso-propyl | —H |
| T592 (a and b) | NH | —NO₂ | —CH₃ | —CH₃ |
| T593 (a and b) | NH | —NO₂ | —H | —H |
| T594 (a and b) | NH | —NO₂ | —H | —Cl |
| T595 (a and b) | NH | —NO₂ | —H | —Br |
| T596 (a and b) | NH | —NO₂ | —H | —F |

TABLE 20-continued

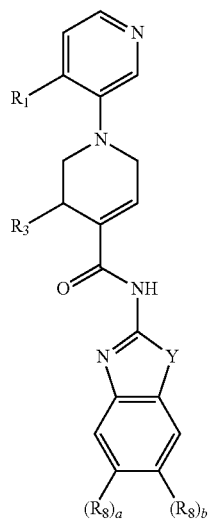

(It)

and pharmaceutically acceptable salts thereof, wherein:

| Compound | Y | R₁ | (R₈)ₐ | (R₈)ᵦ |
|---|---|---|---|---|
| T597 (a and b) | NH | —NO₂ | —H | —CH₃ |
| T598 (a and b) | NH | —NO₂ | —H | —CF₃ |
| T599 (a and b) | NH | —NO₂ | —H | —OCH₃ |
| T600 (a and b) | NH | —NO₂ | —H | —OCH₂CH₃ |
| T601 (a and b) | NH | —NO₂ | —H | —OCF₃ |
| T602 (a and b) | NH | —NO₂ | —H | -tert-butyl |
| T603 (a and b) | NH | —NO₂ | —H | -iso-propyl |
| T604 (a and b) | NH | —CN | —Br | —H |
| T605 (a and b) | NH | —CN | —Cl | —H |
| T606 (a and b) | NH | —CN | —F | —H |
| T607 (a and b) | NH | —CN | —CH₃ | —H |
| T608 (a and b) | NH | —CN | —CF₃ | —H |
| T609 (a and b) | NH | —CN | —OCH₃ | —H |
| T610 (a and b) | NH | —CN | —OCH₂CH₃ | —H |
| T611 (a and b) | NH | —CN | —OCF₃ | —H |
| T612 (a and b) | NH | —CN | -tert-butyl | —H |
| T613 (a and b) | NH | —CN | -iso-propyl | —H |
| T614 (a and b) | NH | —CN | —CH₃ | —CH₃ |
| T615 (a and b) | NH | —CN | —H | —H |
| T616 (a and b) | NH | —CN | —H | —Cl |
| T617 (a and b) | NH | —CN | —H | —Br |
| T618 (a and b) | NH | —CN | —H | —F |
| T619 (a and b) | NH | —CN | —H | —CH₃ |
| T620 (a and b) | NH | —CN | —H | —CF₃ |
| T621 (a and b) | NH | —CN | —H | —OCH₃ |
| T622 (a and b) | NH | —CN | —H | —OCH₂CH₃ |
| T623 (a and b) | NH | —CN | —H | —OCF₃ |
| T624 (a and b) | NH | —CN | —H | -tert-butyl |
| T625 (a and b) | NH | —CN | —H | -iso-propyl |
| T626 (a and b) | NH | —Br | —Br | —H |
| T627 (a and b) | NH | —Br | —Cl | —H |
| T628 (a and b) | NH | —Br | —F | —H |
| T629 (a and b) | NH | —Br | —CH₃ | —H |
| T630 (a and b) | NH | —Br | —CF₃ | —H |
| T631 (a and b) | NH | —Br | —OCH₃ | —H |
| T632 (a and b) | NH | —Br | —OCH₂CH₃ | —H |
| T633 (a and b) | NH | —Br | —OCF₃ | —H |
| T634 (a and b) | NH | —Br | -tert-butyl | —H |
| T635 (a and b) | NH | —Br | -iso-propyl | —H |
| T636 (a and b) | NH | —Br | —CH₃ | —CH₃ |
| T637 (a and b) | NH | —Br | —H | —H |
| T638 (a and b) | NH | —Br | —H | —Cl |
| T639 (a and b) | NH | —Br | —H | —Br |
| T640 (a and b) | NH | —Br | —H | —F |
| T641 (a and b) | NH | —Br | —H | —CH₃ |

TABLE 20-continued

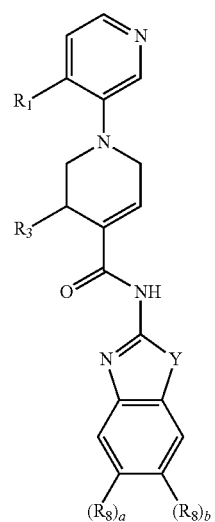

(It)

and pharmaceutically acceptable salts thereof, wherein:

| Compound | Y | R₁ | (R₈)ₐ | (R₈)ᵦ |
|---|---|---|---|---|
| T642 (a and b) | NH | —Br | —H | —CF₃ |
| T643 (a and b) | NH | —Br | —H | —OCH₃ |
| T644 (a and b) | NH | —Br | —H | —OCH₂CH₃ |
| T645 (a and b) | NH | —Br | —H | —OCF₃ |
| T646 (a and b) | NH | —Br | —H | -tert-butyl |
| T647 (a and b) | NH | —Br | —H | -iso-propyl |
| T648 (a and b) | NH | —I | —Cl | —H |
| T649 (a and b) | NH | —I | —Br | —H |
| T650 (a and b) | NH | —I | —F | —H |
| T651 (a and b) | NH | —I | —CH₃ | —H |
| T652 (a and b) | NH | —I | —CF₃ | —H |
| T653 (a and b) | NH | —I | —OCH₃ | —H |
| T654 (a and b) | NH | —I | —OCH₂CH₃ | —H |
| T655 (a and b) | NH | —I | —OCF₃ | —H |
| T656 (a and b) | NH | —I | -tert-butyl | —H |
| T657 (a and b) | NH | —I | -iso-propyl | —H |
| T658 (a and b) | NH | —I | —CH₃ | —CH₃ |
| T659 (a and b) | NH | —I | —H | —H |
| T660 (a and b) | NH | —I | —H | —Cl |
| T661 (a and b) | NH | —I | —H | —Br |
| T662 (a and b) | NH | —I | —H | —F |
| T663 (a and b) | NH | —I | —H | —CH₃ |
| T664 (a and b) | NH | —I | —H | —CF₃ |
| T665 (a and b) | NH | —I | —H | —OCH₃ |
| T666 (a and b) | NH | —I | —H | —OCH₂CH₃ |
| T667 (a and b) | NH | —I | —H | —OCF₃ |
| T668 (a and b) | NH | —I | —H | -tert-butyl |
| T669 (a and b) | NH | —I | —H | -iso-propyl |

(a) means that R₃ is —H.
(b) means that R₃ is —CH₃.

TABLE 21

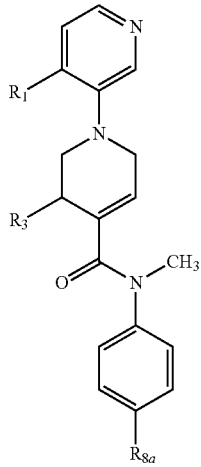

(Iu)

and pharmaceutically acceptable salts thereof, wherein:

| Compound | $R_1$ | $R_{8a}$ |
|---|---|---|
| U1 (a and b) | —H | —H |
| U2 (a and b) | —H | -tert-butyl |
| U3 (a and b) | —H | -iso-butyl |
| U4 (a and b) | —H | -sec-butyl |
| U5 (a and b) | —H | -iso-propyl |
| U6 (a and b) | —H | -n-propyl |
| U7 (a and b) | —H | -cyclohexyl |
| U8 (a and b) | —H | -tert-butoxy |
| U9 (a and b) | —H | -isopropoxy |
| U10 (a and b) | —H | —$CF_3$ |
| U11 (a and b) | —H | —$CH_2CF_3$ |
| U12 (a and b) | —H | —$OCF_3$ |
| U13 (a and b) | —H | —Cl |
| U14 (a and b) | —H | —Br |
| U15 (a and b) | —H | —I |
| U16 (a and b) | —H | -n-butyl |
| U17 (a and b) | —H | —$CH_3$ |
| U18 (a and b) | —H | —$SCF_3$ |
| U19 (a and b) | —H | —$N(CH_2CH_3)_2$ |
| U20 (a and b) | —H | —$OCF_2CHF_2$ |
| U21 (a and b) | —H | —$C(OH)(CF_3)_2$ |
| U22 (a and b) | —H | -(1,1-dimethyl-pentyl) |
| U23 (a and b) | —H | -(1,1-dimethyl-acetic acid) ethyl ester |
| U24 (a and b) | —H | —N-piperidinyl |
| U25 (a and b) | —Cl | —H |
| U26 (a and b) | —Cl | -tert-butyl |
| U27 (a and b) | —Cl | -iso-butyl |
| U28 (a and b) | —Cl | -sec-butyl |
| U29 (a and b) | —Cl | -iso-propyl |
| U30 (a and b) | —Cl | -n-propyl |
| U31 (a and b) | —Cl | -cyclohexyl |
| U32 (a and b) | —Cl | -tert-butoxy |
| U33 (a and b) | —Cl | -isopropoxy |
| U34 (a and b) | —Cl | —$CF_3$ |
| U35 (a and b) | —Cl | —$CH_2CF_3$ |
| U36 (a and b) | —Cl | —$OCF_3$ |
| U37 (a and b) | —Cl | —Cl |
| U38 (a and b) | —Cl | —Br |
| U39 (a and b) | —Cl | —I |
| U40 (a and b) | —Cl | -n-butyl |
| U41 (a and b) | —Cl | —$CH_3$ |
| U42 (a and b) | —Cl | —$SCF_3$ |
| U43 (a and b) | —Cl | —$N(CH_2CH_3)_2$ |
| U44 (a and b) | —Cl | —$OCF_2CHF_2$ |
| U45 (a and b) | —Cl | —$C(OH)(CF_3)_2$ |
| U46 (a and b) | —Cl | -(1,1-dimethyl-pentyl) |
| U47 (a and b) | —Cl | -(1,1-dimethyl-acetic acid) ethyl ester |
| U48 (a and b) | —Cl | —N-piperidinyl |
| U49 (a and b) | —F | —H |
| U50 (a and b) | —F | -tert-butyl |

TABLE 21-continued

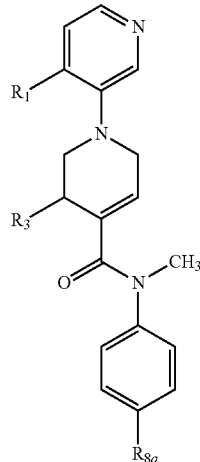

(Iu)

and pharmaceutically acceptable salts thereof, wherein:

| Compound | $R_1$ | $R_{8a}$ |
|---|---|---|
| U51 (a and b) | —F | -iso-butyl |
| U52 (a and b) | —F | -sec-butyl |
| U53 (a and b) | —F | -iso-propyl |
| U54 (a and b) | —F | -n-propyl |
| U55 (a and b) | —F | -cyclohexyl |
| U56 (a and b) | —F | -tert-butoxy |
| U57 (a and b) | —F | -isopropoxy |
| U58 (a and b) | —F | —$CF_3$ |
| U59 (a and b) | —F | —$CH_2CF_3$ |
| U60 (a and b) | —F | —$OCF_3$ |
| U61 (a and b) | —F | —Cl |
| U62 (a and b) | —F | —Br |
| U63 (a and b) | —F | —I |
| U64 (a and b) | —F | -n-butyl |
| U65 (a and b) | —F | —$CH_3$ |
| U66 (a and b) | —F | —$SCF_3$ |
| U67 (a and b) | —F | —$N(CH_2CH_3)_2$ |
| U68 (a and b) | —F | —$OCF_2CHF_2$ |
| U69 (a and b) | —F | —$C(OH)(CF_3)_2$ |
| U70 (a and b) | —F | -(1,1-dimethyl-pentyl) |
| U71 (a and b) | —F | -(1,1-dimethyl-acetic acid) ethyl ester |
| U72 (a and b) | —F | —N-piperidinyl |
| U73 (a and b) | —$CH_3$ | —H |
| U74 (a and b) | —$CH_3$ | -iso-butyl |
| U75 (a and b) | —$CH_3$ | -tert-butyl |
| U76 (a and b) | —$CH_3$ | -sec-butyl |
| U77 (a and b) | —$CH_3$ | -iso-propyl |
| U78 (a and b) | —$CH_3$ | -n-propyl |
| U79 (a and b) | —$CH_3$ | -cyclohexyl |
| U80 (a and b) | —$CH_3$ | -tert-butoxy |
| U81 (a and b) | —$CH_3$ | -isopropoxy |
| U82 (a and b) | —$CH_3$ | —$CF_3$ |
| U83 (a and b) | —$CH_3$ | —$CH_2CF_3$ |
| U84 (a and b) | —$CH_3$ | —$OCF_3$ |
| U85 (a and b) | —$CH_3$ | —Cl |
| U86 (a and b) | —$CH_3$ | —Br |
| U87 (a and b) | —$CH_3$ | —I |
| U88 (a and b) | —$CH_3$ | -n-butyl |
| U89 (a and b) | —$CH_3$ | —$CH_3$ |
| U90 (a and b) | —$CH_3$ | —$SCF_3$ |
| U91 (a and b) | —$CH_3$ | —$N(CH_2CH_3)_2$ |
| U92 (a and b) | —$CH_3$ | —$OCF_2CHF_2$ |
| U93 (a and b) | —$CH_3$ | —$C(OH)(CF_3)_2$ |
| U94 (a and b) | —$CH_3$ | -(1,1-dimethyl-pentyl) |
| U95 (a and b) | —$CH_3$ | -(1,1-dimethyl-acetic acid) ethyl ester |
| U96 (a and b) | —$CH_3$ | —N-piperidinyl |
| U97 (a and b) | —$CF_3$ | —H |
| U98 (a and b) | —$CF_3$ | -tert-butyl |
| U99 (a and b) | —$CF_3$ | -iso-butyl |
| U100 (a and b) | —$CF_3$ | -sec-butyl |

TABLE 21-continued

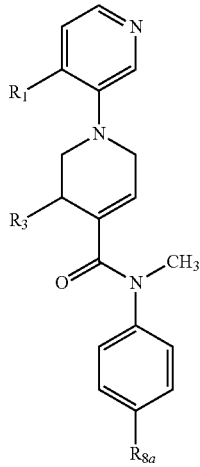

(Iu)

and pharmaceutically acceptable salts thereof, wherein:

| Compound | $R_1$ | $R_{8a}$ |
|---|---|---|
| U101 (a and b) | —$CF_3$ | -iso-propyl |
| U102 (a and b) | —$CF_3$ | -n-propyl |
| U103 (a and b) | —$CF_3$ | -cyclohexyl |
| U104 (a and b) | —$CF_3$ | -tert-butoxy |
| U105 (a and b) | —$CF_3$ | -isopropoxy |
| U106 (a and b) | —$CF_3$ | —$CF_3$ |
| U107 (a and b) | —$CF_3$ | —$CH_2CF_3$ |
| U108 (a and b) | —$CF_3$ | —$OCF_3$ |
| U109 (a and b) | —$CF_3$ | —Cl |
| U110 (a and b) | —$CF_3$ | —Br |
| U111 (a and b) | —$CF_3$ | —I |
| U112 (a and b) | —$CF_3$ | -n-butyl |
| U113 (a and b) | —$CF_3$ | —$CH_3$ |
| U114 (a and b) | —$CF_3$ | —$SCF_3$ |
| U115 (a and b) | —$CF_3$ | —$N(CH_2CH_3)_2$ |
| U116 (a and b) | —$CF_3$ | —$OCF_2CHF_2$ |
| U117 (a and b) | —$CF_3$ | —$C(OH)(CF_3)_2$ |
| U118 (a and b) | —$CF_3$ | -(1,1-dimethyl-pentyl) |
| U119 (a and b) | —$CF_3$ | -(1,1-dimethyl-acetic acid) ethyl ester |
| U120 (a and b) | —$CF_3$ | —N-piperidinyl |
| U121 (a and b) | —$CHF_2$ | -tert-butyl |
| U122 (a and b) | —$CHF_2$ | —H |
| U123 (a and b) | —$CHF_2$ | -iso-butyl |
| U124 (a and b) | —$CHF_2$ | -sec-butyl |
| U125 (a and b) | —$CHF_2$ | -iso-propyl |
| U126 (a and b) | —$CHF_2$ | -n-propyl |
| U127 (a and b) | —$CHF_2$ | -cyclohexyl |
| U128 (a and b) | —$CHF_2$ | -tert-butoxy |
| U129 (a and b) | —$CHF_2$ | -isopropoxy |
| U130 (a and b) | —$CHF_2$ | —$CF_3$ |
| U131 (a and b) | —$CHF_2$ | —$CH_2CF_3$ |
| U132 (a and b) | —$CHF_2$ | —$OCF_3$ |
| U133 (a and b) | —$CHF_2$ | —Cl |
| U134 (a and b) | —$CHF_2$ | —Br |
| U135 (a and b) | —$CHF_2$ | —I |
| U136 (a and b) | —$CHF_2$ | -n-butyl |
| U137 (a and b) | —$CHF_2$ | —$CH_3$ |
| U138 (a and b) | —$CHF_2$ | —$SCF_3$ |
| U139 (a and b) | —$CHF_2$ | —$N(CH_2CH_3)_2$ |
| U140 (a and b) | —$CHF_2$ | —$OCF_2CHF_2$ |
| U141 (a and b) | —$CHF_2$ | —$C(OH)(CF_3)_2$ |
| U142 (a and b) | —$CHF_2$ | -(1,1-dimethyl-pentyl) |
| U143 (a and b) | —$CHF_2$ | -(1,1-dimethyl-acetic acid) ethyl ester |
| U144 (a and b) | —$CHF_2$ | —N-piperidinyl |
| U145 (a and b) | —OH | —H |
| U146 (a and b) | —OH | -tert-butyl |
| U147 (a and b) | —OH | -iso-butyl |
| U148 (a and b) | —OH | -sec-butyl |
| U149 (a and b) | —OH | -iso-propyl |
| U150 (a and b) | —OH | -n-propyl |

TABLE 21-continued

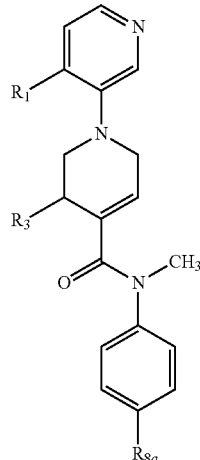

(Iu)

and pharmaceutically acceptable salts thereof, wherein:

| Compound | $R_1$ | $R_{8a}$ |
|---|---|---|
| U151 (a and b) | —OH | -cyclohexyl |
| U152 (a and b) | —OH | -tert-butoxy |
| U153 (a and b) | —OH | -isopropoxy |
| U154 (a and b) | —OH | —$CF_3$ |
| U155 (a and b) | —OH | —$CH_2CF_3$ |
| U156 (a and b) | —OH | —$OCF_3$ |
| U157 (a and b) | —OH | —Cl |
| U158 (a and b) | —OH | —Br |
| U159 (a and b) | —OH | —I |
| U160 (a and b) | —OH | -n-butyl |
| U161 (a and b) | —OH | —$CH_3$ |
| U162 (a and b) | —OH | —$SCF_3$ |
| U163 (a and b) | —OH | —$N(CH_2CH_3)_2$ |
| U164 (a and b) | —OH | —$OCF_2CHF_2$ |
| U165 (a and b) | —OH | —$C(OH)(CF_3)_2$ |
| U166 (a and b) | —OH | -(1,1-dimethyl-pentyl) |
| U167 (a and b) | —OH | -(1,1-dimethyl-acetic acid) ethyl ester |
| U168 (a and b) | —OH | —N-piperidinyl |
| U169 (a and b) | —$NO_2$ | —H |
| U170 (a and b) | —$NO_2$ | -tert-butyl |
| U171 (a and b) | —$NO_2$ | -iso-butyl |
| U172 (a and b) | —$NO_2$ | -sec-butyl |
| U173 (a and b) | —$NO_2$ | -iso-propyl |
| U174 (a and b) | —$NO_2$ | -n-propyl |
| U175 (a and b) | —$NO_2$ | -cyclohexyl |
| U176 (a and b) | —$NO_2$ | -tert-butoxy |
| U177 (a and b) | —$NO_2$ | -isopropoxy |
| U178 (a and b) | —$NO_2$ | —$CF_3$ |
| U179 (a and b) | —$NO_2$ | —$CH_2CF_3$ |
| U180 (a and b) | —$NO_2$ | —$OCF_3$ |
| U181 (a and b) | —$NO_2$ | —Cl |
| U182 (a and b) | —$NO_2$ | —Br |
| U183 (a and b) | —$NO_2$ | —I |
| U184 (a and b) | —$NO_2$ | -n-butyl |
| U185 (a and b) | —$NO_2$ | —$CH_3$ |
| U186 (a and b) | —$NO_2$ | —$SCF_3$ |
| U187 (a and b) | —$NO_2$ | —$N(CH_2CH_3)_2$ |
| U188 (a and b) | —$NO_2$ | —$OCF_2CHF_2$ |
| U189 (a and b) | —$NO_2$ | —$C(OH)(CF_3)_2$ |
| U190 (a and b) | —$NO_2$ | -(1,1-dimethyl-pentyl) |
| U191 (a and b) | —$NO_2$ | -(1,1-dimethyl-acetic acid) ethyl ester |
| U192 (a and b) | —$NO_2$ | —N-piperidinyl |
| U193 (a and b) | —CN | —H |
| U194 (a and b) | —CN | -tert-butyl |
| U195 (a and b) | —CN | -iso-butyl |
| U196 (a and b) | —CN | -sec-butyl |
| U197 (a and b) | —CN | -iso-propyl |
| U198 (a and b) | —CN | -n-propyl |
| U199 (a and b) | —CN | -cyclohexyl |
| U200 (a and b) | —CN | -tert-butoxy |

TABLE 21-continued

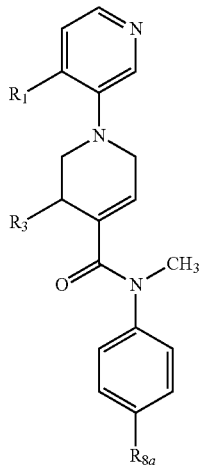

(Iu)

and pharmaceutically acceptable salts thereof, wherein:

| Compound | $R_1$ | $R_{8a}$ |
|---|---|---|
| U201 (a and b) | —CN | -isopropoxy |
| U202 (a and b) | —CN | —$CF_3$ |
| U203 (a and b) | —CN | —$CH_2CF_3$ |
| U204 (a and b) | —CN | —$OCF_3$ |
| U205 (a and b) | —CN | —Cl |
| U206 (a and b) | —CN | —Br |
| U207 (a and b) | —CN | —I |
| U208 (a and b) | —CN | -n-butyl |
| U209 (a and b) | —CN | —$CH_3$ |
| U210 (a and b) | —CN | —$SCF_3$ |
| U211 (a and b) | —CN | —$N(CH_2CH_3)_2$ |
| U212 (a and b) | —CN | —$OCF_2CHF_2$ |
| U213 (a and b) | —CN | —$C(OH)(CF_3)_2$ |
| U214 (a and b) | —CN | -(1,1-dimethyl-pentyl) |
| U215 (a and b) | —CN | -(1,1-dimethyl-acetic acid) ethyl ester |
| U216 (a and b) | —CN | —N-piperidinyl |
| U217 (a and b) | —Br | —H |
| U218 (a and b) | —Br | -tert-butyl |
| U219 (a and b) | —Br | -iso-butyl |
| U220 (a and b) | —Br | -sec-butyl |
| U221 (a and b) | —Br | -iso-propyl |
| U222 (a and b) | —Br | -n-propyl |
| U223 (a and b) | —Br | -cyclohexyl |
| U224 (a and b) | —Br | -tert-butoxy |
| U225 (a and b) | —Br | -isopropoxy |
| U226 (a and b) | —Br | —$CF_3$ |
| U227 (a and b) | —Br | —$CH_2CF_3$ |
| U228 (a and b) | —Br | —$OCF_3$ |
| U229 (a and b) | —Br | —Cl |
| U230 (a and b) | —Br | —Br |
| U231 (a and b) | —Br | —I |
| U232 (a and b) | —Br | -n-butyl |
| U233 (a and b) | —Br | —$CH_3$ |
| U234 (a and b) | —Br | —$SCF_3$ |
| U235 (a and b) | —Br | —$N(CH_2CH_3)_2$ |
| U236 (a and b) | —Br | —$OCF_2CHF_2$ |
| U237 (a and b) | —Br | —$C(OH)(CF_3)_2$ |
| U238 (a and b) | —Br | -(1,1-dimethyl-pentyl) |
| U239 (a and b) | —Br | -(1,1-dimethyl-acetic acid) ethyl ester |
| U240 (a and b) | —Br | —N-piperidinyl |
| U241 (a and b) | —I | -tert-butyl |
| U242 (a and b) | —I | —H |
| U243 (a and b) | —I | -iso-butyl |
| U244 (a and b) | —I | -sec-butyl |
| U245 (a and b) | —I | -iso-propyl |
| U246 (a and b) | —I | -n-propyl |
| U247 (a and b) | —I | -cyclohexyl |
| U248 (a and b) | —I | -tert-butoxy |
| U249 (a and b) | —I | -isopropoxy |
| U250 (a and b) | —I | —$CF_3$ |

TABLE 21-continued

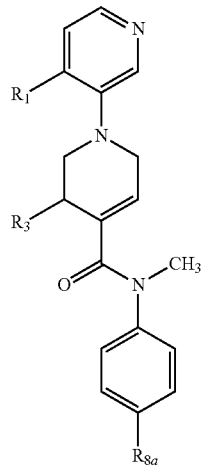

(Iu)

and pharmaceutically acceptable salts thereof, wherein:

| Compound | $R_1$ | $R_{8a}$ |
|---|---|---|
| U251 (a and b) | —I | —$CH_2CF_3$ |
| U252 (a and b) | —I | —$OCF_3$ |
| U253 (a and b) | —I | —Cl |
| U254 (a and b) | —I | —Br |
| U255 (a and b) | —I | —I |
| U256 (a and b) | —I | -n-butyl |
| U257 (a and b) | —I | —$CH_3$ |
| U258 (a and b) | —I | —$SCF_3$ |
| U259 (a and b) | —I | —$N(CH_2CH_3)_2$ |
| U260 (a and b) | —I | —$OCF_2CHF_2$ |
| U261 (a and b) | —I | —$C(OH)(CF_3)_2$ |
| U262 (a and b) | —I | -(1,1-dimethyl-pentyl) |
| U263 (a and b) | —I | -(1,1-dimethyl-acetic acid) ethyl ester |
| U264 (a and b) | —I | —N-piperidinyl |

(a) means that $R_3$ is —H.
(b) means that $R_3$ is —$CH_3$.

TABLE 22

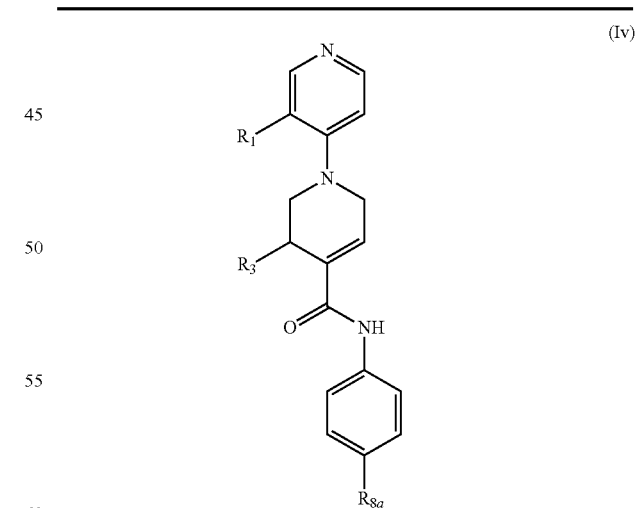

(Iv)

and pharmaceutically acceptable salts thereof, wherein:

| Compound | $R_1$ | $R_{8a}$ |
|---|---|---|
| V1 (a and b) | —H | —H |
| V2 (a and b) | —H | -tert-butyl |
| V3 (a and b) | —H | -iso-butyl |

TABLE 22-continued

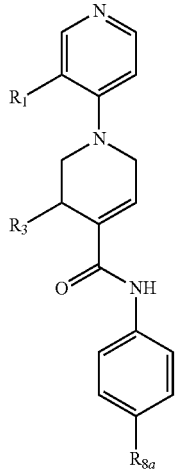

(Iv)

and pharmaceutically acceptable salts thereof, wherein:

| Compound | $R_1$ | $R_{8a}$ |
|---|---|---|
| V4 (a and b) | —H | -sec-butyl |
| V5 (a and b) | —H | -iso-propyl |
| V6 (a and b) | —H | -n-propyl |
| V7 (a and b) | —H | -cyclohexyl |
| V8 (a and b) | —H | -tert-butoxy |
| V9 (a and b) | —H | -isopropoxy |
| V10 (a and b) | —H | —$CF_3$ |
| V11 (a and b) | —H | —$CH_2CF_3$ |
| V12 (a and b) | —H | —$OCF_3$ |
| V13 (a and b) | —H | —Cl |
| V14 (a and b) | —H | —Br |
| V15 (a and b) | —H | —I |
| V16 (a and b) | —H | -n-butyl |
| V17 (a and b) | —H | —$CH_3$ |
| V18 (a and b) | —H | —$SCF_3$ |
| V19 (a and b) | —H | —$N(CH_2CH_3)_2$ |
| V20 (a and b) | —H | —$OCF_2CHF_2$ |
| V21 (a and b) | —H | —$C(OH)(CF_3)_2$ |
| V22 (a and b) | —H | -(1,1-dimethyl-pentyl) |
| V23 (a and b) | —H | -(1,1-dimethyl-acetic acid) ethyl ester |
| V24 (a and b) | —H | —N-piperidinyl |
| V25 (a and b) | —Cl | —H |
| V26 (a and b) | —Cl | -tert-butyl |
| V27 (a and b) | —Cl | -iso-butyl |
| V28 (a and b) | —Cl | -sec-butyl |
| V29 (a and b) | —Cl | -iso-propyl |
| V30 (a and b) | —Cl | -n-propyl |
| V31 (a and b) | —Cl | -cyclohexyl |
| V32 (a and b) | —Cl | -tert-butoxy |
| V33 (a and b) | —Cl | -isopropoxy |
| V34 (a and b) | —Cl | —$CF_3$ |
| V35 (a and b) | —Cl | —$CH_2CF_3$ |
| V36 (a and b) | —Cl | —$OCF_3$ |
| V37 (a and b) | —Cl | —Cl |
| V38 (a and b) | —Cl | —Br |
| V39 (a and b) | —Cl | —I |
| V40 (a and b) | —Cl | -n-butyl |
| V41 (a and b) | —Cl | —$CH_3$ |
| V42 (a and b) | —Cl | —$SCF_3$ |
| V43 (a and b) | —Cl | —$N(CH_2CH_3)_2$ |
| V44 (a and b) | —Cl | —$OCF_2CHF_2$ |
| V45 (a and b) | —Cl | —$C(OH)(CF_3)_2$ |
| V46 (a and b) | —Cl | -(1,1-dimethyl-pentyl) |
| V47 (a and b) | —Cl | -(1,1-dimethyl-acetic acid) ethyl ester |
| V48 (a and b) | —Cl | —N-piperidinyl |
| V49 (a and b) | —F | —H |
| V50 (a and b) | —F | -tert-butyl |
| V51 (a and b) | —F | -iso-butyl |
| V52 (a and b) | —F | -sec-butyl |
| V53 (a and b) | —F | -iso-propyl |
| V54 (a and b) | —F | -n-propyl |
| V55 (a and b) | —F | -cyclohexyl |
| V56 (a and b) | —F | -tert-butoxy |
| V57 (a and b) | —F | -isopropoxy |
| V58 (a and b) | —F | —$CF_3$ |
| V59 (a and b) | —F | —$CH_2CF_3$ |
| V60 (a and b) | —F | —$OCF_3$ |
| V61 (a and b) | —F | —Cl |
| V62 (a and b) | —F | —Br |
| V63 (a and b) | —F | —I |
| V64 (a and b) | —F | -n-butyl |
| V65 (a and b) | —F | —$CH_3$ |
| V66 (a and b) | —F | —$SCF_3$ |
| V67 (a and b) | —F | —$N(CH_2CH_3)_2$ |
| V68 (a and b) | —F | —$OCF_2CHF_2$ |
| V69 (a and b) | —F | —$C(OH)(CF_3)_2$ |
| V70 (a and b) | —F | -(1,1-dimethyl-pentyl) |
| V71 (a and b) | —F | -(1,1-dimethyl-acetic acid) ethyl ester |
| V72 (a and b) | —F | —N-piperidinyl |
| V73 (a and b) | —$CH_3$ | —H |
| V74 (a and b) | —$CH_3$ | -iso-butyl |
| V75 (a and b) | —$CH_3$ | -tert-butyl |
| V76 (a and b) | —$CH_3$ | -sec-butyl |
| V77 (a and b) | —$CH_3$ | -iso-propyl |
| V78 (a and b) | —$CH_3$ | -n-propyl |
| V79 (a and b) | —$CH_3$ | -cyclohexyl |
| V80 (a and b) | —$CH_3$ | -tert-butoxy |
| V81 (a and b) | —$CH_3$ | -isopropoxy |
| V82 (a and b) | —$CH_3$ | —$CF_3$ |
| V83 (a and b) | —$CH_3$ | —$CH_2CF_3$ |
| V84 (a and b) | —$CH_3$ | —$OCF_3$ |
| V85 (a and b) | —$CH_3$ | —Cl |
| V86 (a and b) | —$CH_3$ | —Br |
| V87 (a and b) | —$CH_3$ | —I |
| V88 (a and b) | —$CH_3$ | -n-butyl |
| V89 (a and b) | —$CH_3$ | —$CH_3$ |
| V90 (a and b) | —$CH_3$ | —$SCF_3$ |
| V91 (a and b) | —$CH_3$ | —$N(CH_2CH_3)_2$ |
| V92 (a and b) | —$CH_3$ | —$OCF_2CHF_2$ |
| V93 (a and b) | —$CH_3$ | —$C(OH)(CF_3)_2$ |
| V94 (a and b) | —$CH_3$ | -(1,1-dimethyl-pentyl) |
| V95 (a and b) | —$CH_3$ | -(1,1-dimethyl-acetic acid) ethyl ester |
| V96 (a and b) | —$CH_3$ | —N-piperidinyl |
| V97 (a and b) | —$CF_3$ | —H |
| V98 (a and b) | —$CF_3$ | -tert-butyl |
| V99 (a and b) | —$CF_3$ | -iso-butyl |
| V100 (a and b) | —$CF_3$ | -sec-butyl |
| V101 (a and b) | —$CF_3$ | -iso-propyl |

TABLE 22-continued

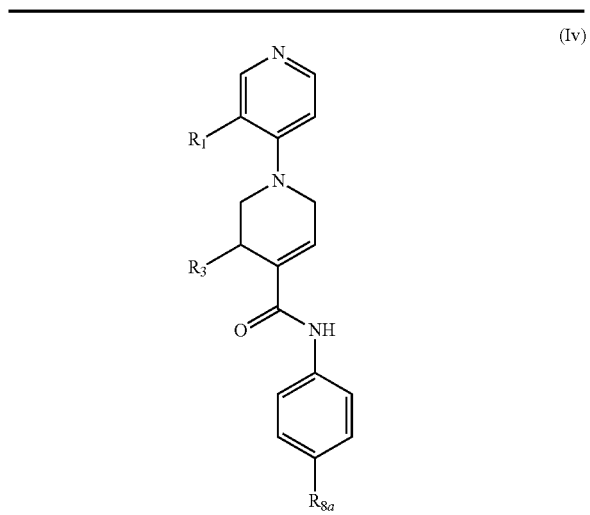

(Iv)

and pharmaceutically acceptable salts thereof, wherein:

| Compound | $R_1$ | $R_{8a}$ |
|---|---|---|
| V102 (a and b) | —$CF_3$ | -n-propyl |
| V103 (a and b) | —$CF_3$ | -cyclohexyl |
| V104 (a and b) | —$CF_3$ | -tert-butoxy |
| V105 (a and b) | —$CF_3$ | -isopropoxy |
| V106 (a and b) | —$CF_3$ | —$CF_3$ |
| V107 (a and b) | —$CF_3$ | —$CH_2CF_3$ |
| V108 (a and b) | —$CF_3$ | —$OCF_3$ |
| V109 (a and b) | —$CF_3$ | —Cl |
| V110 (a and b) | —$CF_3$ | —Br |
| V111 (a and b) | —$CF_3$ | —I |
| V112 (a and b) | —$CF_3$ | -n-butyl |
| V113 (a and b) | —$CF_3$ | —$CH_3$ |
| V114 (a and b) | —$CF_3$ | —$SCF_3$ |
| V115 (a and b) | —$CF_3$ | —$N(CH_2CH_3)_2$ |
| V116 (a and b) | —$CF_3$ | —$OCF_2CHF_2$ |
| V117 (a and b) | —$CF_3$ | —$C(OH)(CF_3)_2$ |
| V118 (a and b) | —$CF_3$ | -(1,1-dimethyl-pentyl) |
| V119 (a and b) | —$CF_3$ | -(1,1-dimethyl-acetic acid) ethyl ester |
| V120 (a and b) | —$CF_3$ | —N-piperidinyl |
| V121 (a and b) | —$CHF_2$ | -tert-butyl |
| V122 (a and b) | —$CHF_2$ | —H |
| V123 (a and b) | —$CHF_2$ | -iso-butyl |
| V124 (a and b) | —$CHF_2$ | -sec-butyl |
| V125 (a and b) | —$CHF_2$ | -iso-propyl |
| V126 (a and b) | —$CHF_2$ | -n-propyl |
| V127 (a and b) | —$CHF_2$ | -cyclohexyl |
| V128 (a and b) | —$CHF_2$ | -tert-butoxy |
| V129 (a and b) | —$CHF_2$ | -isopropoxy |
| V130 (a and b) | —$CHF_2$ | —$CF_3$ |
| V131 (a and b) | —$CHF_2$ | —$CH_2CF_3$ |
| V132 (a and b) | —$CHF_2$ | —$OCF_3$ |
| V133 (a and b) | —$CHF_2$ | —Cl |
| V134 (a and b) | —$CHF_2$ | —Br |
| V135 (a and b) | —$CHF_2$ | —I |
| V136 (a and b) | —$CHF_2$ | -n-butyl |
| V137 (a and b) | —$CHF_2$ | —$CH_3$ |
| V138 (a and b) | —$CHF_2$ | —$SCF_3$ |
| V139 (a and b) | —$CHF_2$ | —$N(CH_2CH_3)_2$ |
| V140 (a and b) | —$CHF_2$ | —$OCF_2CHF_2$ |
| V141 (a and b) | —$CHF_2$ | —$C(OH)(CF_3)_2$ |
| V142 (a and b) | —$CHF_2$ | -(1,1-dimethyl-pentyl) |
| V143 (a and b) | —$CHF_2$ | -(1,1-dimethyl-acetic acid) ethyl ester |
| V144 (a and b) | —$CHF_2$ | —N-piperidinyl |
| V145 (a and b) | —OH | —H |
| V146 (a and b) | —OH | -tert-butyl |
| V147 (a and b) | —OH | -iso-butyl |
| V148 (a and b) | —OH | -sec-butyl |
| V149 (a and b) | —OH | -iso-propyl |
| V150 (a and b) | —OH | -n-propyl |

TABLE 22-continued

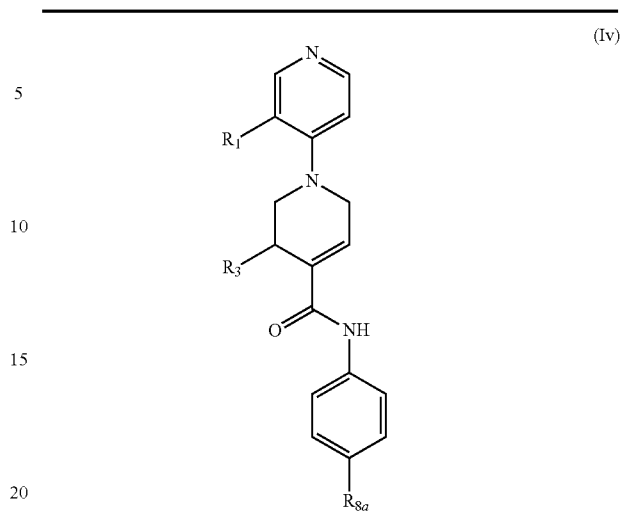

(Iv)

and pharmaceutically acceptable salts thereof, wherein:

| Compound | $R_1$ | $R_{8a}$ |
|---|---|---|
| V151 (a and b) | —OH | -cyclohexyl |
| V152 (a and b) | —OH | -tert-butoxy |
| V153 (a and b) | —OH | -isopropoxy |
| V154 (a and b) | —OH | —$CF_3$ |
| V155 (a and b) | —OH | —$CH_2CF_3$ |
| V156 (a and b) | —OH | —$OCF_3$ |
| V157 (a and b) | —OH | —Cl |
| V158 (a and b) | —OH | —Br |
| V159 (a and b) | —OH | —I |
| V160 (a and b) | —OH | -n-butyl |
| V161 (a and b) | —OH | —$CH_3$ |
| V162 (a and b) | —OH | —$SCF_3$ |
| V163 (a and b) | —OH | —$N(CH_2CH_3)_2$ |
| V164 (a and b) | —OH | —$OCF_2CHF_2$ |
| V165 (a and b) | —OH | —$C(OH)(CF_3)_2$ |
| V166 (a and b) | —OH | -(1,1-dimethyl-pentyl) |
| V167 (a and b) | —OH | -(1,1-dimethyl-acetic acid) ethyl ester |
| V168 (a and b) | —OH | —N-piperidinyl |
| V169 (a and b) | —$NO_2$ | —H |
| V170 (a and b) | —$NO_2$ | -tert-butyl |
| V171 (a and b) | —$NO_2$ | -iso-butyl |
| V172 (a and b) | —$NO_2$ | -sec-butyl |
| V173 (a and b) | —$NO_2$ | -iso-propyl |
| V174 (a and b) | —$NO_2$ | -n-propyl |
| V175 (a and b) | —$NO_2$ | -cyclohexyl |
| V176 (a and b) | —$NO_2$ | -tert-butoxy |
| V177 (a and b) | —$NO_2$ | -isopropoxy |
| V178 (a and b) | —$NO_2$ | —$CF_3$ |
| V179 (a and b) | —$NO_2$ | —$CH_2CF_3$ |
| V180 (a and b) | —$NO_2$ | —$OCF_3$ |
| V181 (a and b) | —$NO_2$ | —Cl |
| V182 (a and b) | —$NO_2$ | —Br |
| V183 (a and b) | —$NO_2$ | —I |
| V184 (a and b) | —$NO_2$ | -n-butyl |
| V185 (a and b) | —$NO_2$ | —$CH_3$ |
| V186 (a and b) | —$NO_2$ | —$SCF_3$ |
| V187 (a and b) | —$NO_2$ | —$N(CH_2CH_3)_2$ |
| V188 (a and b) | —$NO_2$ | —$OCF_2CHF_2$ |
| V189 (a and b) | —$NO_2$ | —$C(OH)(CF_3)_2$ |
| V190 (a and b) | —$NO_2$ | -(1,1-dimethyl-pentyl) |
| V191 (a and b) | —$NO_2$ | -(1,1-dimethyl-acetic acid) ethyl ester |
| V192 (a and b) | —$NO_2$ | —N-piperidinyl |
| V193 (a and b) | —CN | —H |
| V194 (a and b) | —CN | -tert-butyl |
| V195 (a and b) | —CN | -iso-butyl |
| V196 (a and b) | —CN | -sec-butyl |
| V197 (a and b) | —CN | -iso-propyl |
| V198 (a and b) | —CN | -n-propyl |
| V199 (a and b) | —CN | -cyclohexyl |

TABLE 22-continued

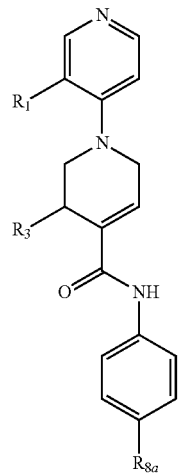

(Iv)

and pharmaceutically acceptable salts thereof, wherein:

| Compound | $R_1$ | $R_{8a}$ |
|---|---|---|
| V200 (a and b) | —CN | -tert-butoxy |
| V201 (a and b) | —CN | -isopropoxy |
| V202 (a and b) | —CN | —$CF_3$ |
| V203 (a and b) | —CN | —$CH_2CF_3$ |
| V204 (a and b) | —CN | —$OCF_3$ |
| V205 (a and b) | —CN | —Cl |
| V206 (a and b) | —CN | —Br |
| V207 (a and b) | —CN | —I |
| V208 (a and b) | —CN | -n-butyl |
| V209 (a and b) | —CN | —$CH_3$ |
| V210 (a and b) | —CN | —$SCF_3$ |
| V211 (a and b) | —CN | —$N(CH_2CH_3)_2$ |
| V212 (a and b) | —CN | —$OCF_2CHF_2$ |
| V213 (a and b) | —CN | —$C(OH)(CF_3)_2$ |
| V214 (a and b) | —CN | -(1,1-dimethyl-pentyl) |
| V215 (a and b) | —CN | -(1,1-dimethyl-acetic acid) ethyl ester |
| V216 (a and b) | —CN | —N-piperidinyl |
| V217 (a and b) | —Br | —H |
| V218 (a and b) | —Br | -tert-butyl |
| V219 (a and b) | —Br | -iso-butyl |
| V220 (a and b) | —Br | -sec-butyl |
| V221 (a and b) | —Br | -iso-propyl |
| V222 (a and b) | —Br | -n-propyl |
| V223 (a and b) | —Br | -cyclohexyl |
| V224 (a and b) | —Br | -tert-butoxy |
| V225 (a and b) | —Br | -isopropoxy |
| V226 (a and b) | —Br | —$CF_3$ |
| V227 (a and b) | —Br | —$CH_2CF_3$ |
| V228 (a and b) | —Br | —$OCF_3$ |
| V229 (a and b) | —Br | —Cl |
| V230 (a and b) | —Br | —Br |
| V231 (a and b) | —Br | —I |
| V232 (a and b) | —Br | -n-butyl |
| V233 (a and b) | —Br | —$CH_3$ |
| V234 (a and b) | —Br | —$SCF_3$ |
| V235 (a and b) | —Br | —$N(CH_2CH_3)_2$ |
| V236 (a and b) | —Br | —$OCF_2CHF_2$ |
| V237 (a and b) | —Br | —$C(OH)(CF_3)_2$ |
| V238 (a and b) | —Br | -(1,1-dimethyl-pentyl) |
| V239 (a and b) | —Br | -(1,1-dimethyl-acetic acid) ethyl ester |

TABLE 22-continued

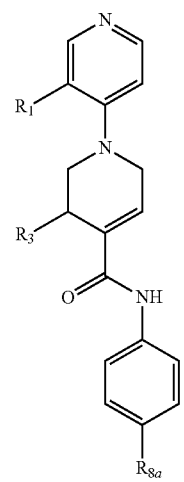

(Iv)

and pharmaceutically acceptable salts thereof, wherein:

| Compound | $R_1$ | $R_{8a}$ |
|---|---|---|
| V240 (a and b) | —Br | —N-piperidinyl |
| V241 (a and b) | —I | -tert-butyl |
| V242 (a and b) | —I | —H |
| V243 (a and b) | —I | -iso-butyl |
| V244 (a and b) | —I | -sec-butyl |
| V245 (a and b) | —I | -iso-propyl |
| V246 (a and b) | —I | -n-propyl |
| V247 (a and b) | —I | -cyclohexyl |
| V248 (a and b) | —I | -tert-butoxy |
| V249 (a and b) | —I | -isopropoxy |
| V250 (a and b) | —I | —$CF_3$ |
| V251 (a and b) | —I | —$CH_2CF_3$ |
| V252 (a and b) | —I | —$OCF_3$ |
| V253 (a and b) | —I | —Cl |
| V254 (a and b) | —I | —Br |
| V255 (a and b) | —I | —I |
| V256 (a and b) | —I | -n-butyl |
| V257 (a and b) | —I | —$CH_3$ |
| V258 (a and b) | —I | —$SCF_3$ |
| V259 (a and b) | —I | —$N(CH_2CH_3)_2$ |
| V260 (a and b) | —I | —$OCF_2CHF_2$ |
| V261 (a and b) | —I | —$C(OH)(CF_3)_2$ |
| V262 (a and b) | —I | -(1,1-dimethyl-pentyl) |
| V263 (a and b) | —I | -(1,1-dimethyl-acetic acid) ethyl ester |
| V264 (a and b) | —I | —N-piperidinyl |

(a) means that $R_3$ is —H.
(b) means that $R_3$ is —$CH_3$.

TABLE 23

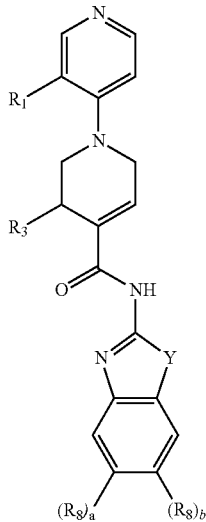

(Iw)

and pharmaceutically acceptable salts thereof, wherein:

| Compound | Y | R₁ | (R₈)ₐ | (R₈)_b |
|---|---|---|---|---|
| W1 (a and b) | S | —H | —Cl | —H |
| W2 (a and b) | S | —H | —Br | —H |
| W3 (a and b) | S | —H | —F | —H |
| W4 (a and b) | S | —H | —CH₃ | —H |
| W5 (a and b) | S | —H | —CF₃ | —H |
| W6 (a and b) | S | —H | —OCH₃ | —H |
| W7 (a and b) | S | —H | —OCH₂CH₃ | —H |
| W8 (a and b) | S | —H | —OCF₃ | —H |
| W9 (a and b) | S | —H | -tert-butyl | —H |
| W10 (a and b) | S | —H | -iso-propyl | —H |
| W11 (a and b) | S | —H | —CH₃ | —CH₃ |
| W12 (a and b) | S | —H | —H | —H |
| W13 (a and b) | S | —H | —H | —Cl |
| W14 (a and b) | S | —H | —H | —Br |
| W15 (a and b) | S | —H | —H | —F |
| W16 (a and b) | S | —H | —H | —CH₃ |
| W17 (a and b) | S | —H | —H | —CF₃ |
| W18 (a and b) | S | —H | —H | —OCH₃ |
| W19 (a and b) | S | —H | —H | —OCH₂CH₃ |
| W20 (a and b) | S | —H | —H | —OCF₃ |
| W21 (a and b) | S | —H | —H | -tert-butyl |
| W22 (a and b) | S | —H | —H | -iso-propyl |
| W23 (a and b) | S | —Cl | —Cl | —H |
| W24 (a and b) | S | —Cl | —Br | —H |
| W25 (a and b) | S | —Cl | —F | —H |
| W26 (a and b) | S | —Cl | —CH₃ | —H |
| W27 (a and b) | S | —Cl | —CF₃ | —H |
| W28 (a and b) | S | —Cl | —OCH₃ | —H |
| W29 (a and b) | S | —Cl | —OCH₂CH₃ | —H |
| W30 (a and b) | S | —Cl | —OCF₃ | —H |
| W31 (a and b) | S | —Cl | -tert-butyl | —H |
| W32 (a and b) | S | —Cl | -iso-propyl | —H |
| W33 (a and b) | S | —Cl | —CH₃ | —CH₃ |
| W34 (a and b) | S | —Cl | —H | —H |
| W35 (a and b) | S | —Cl | —H | —Cl |
| W36 (a and b) | S | —Cl | —H | —Br |
| W37 (a and b) | S | —Cl | —H | —F |
| W38 (a and b) | S | —Cl | —H | —CH₃ |
| W39 (a and b) | S | —Cl | —H | —CF₃ |
| W40 (a and b) | S | —Cl | —H | —OCH₃ |
| W41 (a and b) | S | —Cl | —H | —OCH₂CH₃ |
| W42 (a and b) | S | —Cl | —H | —OCF₃ |
| W43 (a and b) | S | —Cl | —H | -tert-butyl |
| W44 (a and b) | S | —Cl | —H | -iso-propyl |
| W45 (a and b) | S | —Cl | —H | —OCF₃ |
| W46 (a and b) | S | —Cl | —H | -tert-butyl |
| W47 (a and b) | S | —Cl | —H | -iso-propyl |
| W48 (a and b) | S | —CH₃ | —Cl | —H |
| W49 (a and b) | S | —CH₃ | —Br | —H |
| W50 (a and b) | S | —CH₃ | —F | —H |
| W51 (a and b) | S | —CH₃ | —CH₃ | —H |
| W52 (a and b) | S | —CH₃ | —CF₃ | —H |
| W53 (a and b) | S | —CH₃ | —OCH₃ | —H |
| W54 (a and b) | S | —CH₃ | —OCH₂CH₃ | —H |
| W55 (a and b) | S | —CH₃ | —OCF₃ | —H |
| W56 (a and b) | S | —CH₃ | -tert-butyl | —H |
| W57 (a and b) | S | —CH₃ | -iso-propyl | —H |
| W58 (a and b) | S | —CH₃ | —CH₃ | —CH₃ |
| W59 (a and b) | S | —CH₃ | —H | —H |
| W60 (a and b) | S | —CH₃ | —H | —Cl |
| W61 (a and b) | S | —CH₃ | —H | —Br |
| W62 (a and b) | S | —CH₃ | —H | —F |
| W63 (a and b) | S | —CH₃ | —H | —CH₃ |
| W64 (a and b) | S | —CH₃ | —H | —CF₃ |
| W65 (a and b) | S | —CH₃ | —H | —OCH₃ |
| W66 (a and b) | S | —CH₃ | —H | —OCH₂CH₃ |
| W67 (a and b) | S | —CH₃ | —H | —OCF₃ |
| W68 (a and b) | S | —CH₃ | —H | -tert-butyl |
| W69 (a and b) | S | —CH₃ | —H | -iso-propyl |
| W70 (a and b) | S | —CF₃ | —Cl | —H |
| W71 (a and b) | S | —CF₃ | —Br | —H |
| W72 (a and b) | S | —CF₃ | —F | —H |
| W73 (a and b) | S | —CF₃ | —CH₃ | —H |
| W74 (a and b) | S | —CF₃ | —CF₃ | —H |
| W75 (a and b) | S | —CF₃ | —OCH₃ | —H |
| W76 (a and b) | S | —CF₃ | —OCH₂CH₃ | —H |
| W77 (a and b) | S | —CF₃ | —OCF₃ | —H |
| W78 (a and b) | S | —CF₃ | -tert-butyl | —H |
| W79 (a and b) | S | —CF₃ | -iso-propyl | —H |
| W80 (a and b) | S | —CF₃ | —CH₃ | —CH₃ |
| W81 (a and b) | S | —CF₃ | —H | —H |
| W82 (a and b) | S | —CF₃ | —H | —Cl |
| W83 (a and b) | S | —CF₃ | —H | —Br |
| W84 (a and b) | S | —CF₃ | —H | —F |
| W85 (a and b) | S | —CF₃ | —H | —CH₃ |
| W86 (a and b) | S | —CF₃ | —H | —CF₃ |
| W87 (a and b) | S | —CF₃ | —H | —OCH₃ |
| W88 (a and b) | S | —CF₃ | —H | —OCH₂CH₃ |
| W89 (a and b) | S | —CF₃ | —H | —OCF₃ |
| W90 (a and b) | S | —CF₃ | —H | -tert-butyl |
| W91 (a and b) | S | —CF₃ | —H | -iso-propyl |
| W92 (a and b) | S | —CHF₂ | —Cl | —H |
| W93 (a and b) | S | —CHF₂ | —Br | —H |
| W94 (a and b) | S | —CHF₂ | —F | —H |
| W95 (a and b) | S | —CHF₂ | —CH₃ | —H |
| W96 (a and b) | S | —CHF₂ | —CF₃ | —H |
| W97 (a and b) | S | —CHF₂ | —OCH₃ | —H |
| W98 (a and b) | S | —CHF₂ | —OCH₂CH₃ | —H |

TABLE 23-continued

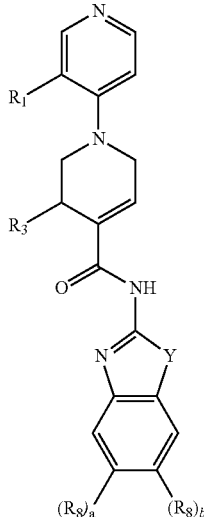

(Iw)

and pharmaceutically acceptable salts thereof, wherein:

| Compound | Y | R₁ | (R₈)ₐ | (R₈)ᵦ |
|---|---|---|---|---|
| W99 (a and b) | S | —CHF₂ | —OCF₃ | —H |
| W100 (a and b) | S | —CHF₂ | -tert-butyl | —H |
| W101 (a and b) | S | —CHF₂ | -iso-propyl | —H |
| W102 (a and b) | S | —CHF₂ | —CH₃ | —CH₃ |
| W103 (a and b) | S | —CHF₂ | —H | —H |
| W104 (a and b) | S | —CHF₂ | —H | —Cl |
| W105 (a and b) | S | —CHF₂ | —H | —Br |
| W106 (a and b) | S | —CHF₂ | —H | —F |
| W107 (a and b) | S | —CHF₂ | —H | —CH₃ |
| W108 (a and b) | S | —CHF₂ | —H | —CF₃ |
| W109 (a and b) | S | —CHF₂ | —H | —OCH₃ |
| W110 (a and b) | S | —CHF₂ | —H | —OCH₂CH₃ |
| W111 (a and b) | S | —CHF₂ | —H | —OCF₃ |
| W112 (a and b) | S | —CHF₂ | —H | -tert-butyl |
| W113 (a and b) | S | —CHF₂ | —H | -iso-propyl |
| W114 (a and b) | S | —OH | —Cl | —H |
| W115 (a and b) | S | —OH | —Br | —H |
| W116 (a and b) | S | —OH | —F | —H |
| W117 (a and b) | S | —OH | —CH₃ | —H |
| W118 (a and b) | S | —OH | —CF₃ | —H |
| W119 (a and b) | S | —OH | —OCH₃ | —H |
| W120 (a and b) | S | —OH | —OCH₂CH₃ | —H |
| W121 (a and b) | S | —OH | —OCF₃ | —H |
| W122 (a and b) | S | —OH | -tert-butyl | —H |
| W123 (a and b) | S | —OH | -iso-propyl | —H |
| W124 (a and b) | S | —OH | —CH₃ | —CH₃ |
| W125 (a and b) | S | —OH | —H | —H |
| W126 (a and b) | S | —OH | —H | —Cl |
| W127 (a and b) | S | —OH | —H | —Br |
| W128 (a and b) | S | —OH | —H | —F |
| W129 (a and b) | S | —OH | —H | —CH₃ |
| W130 (a and b) | S | —OH | —H | —CF₃ |
| W131 (a and b) | S | —OH | —H | —OCH₃ |
| W132 (a and b) | S | —OH | —H | —OCH₂CH₃ |
| W133 (a and b) | S | —OH | —H | —OCF₃ |
| W134 (a and b) | S | —OH | —H | -tert-butyl |
| W135 (a and b) | S | —OH | —H | -iso-propyl |
| W136 (a and b) | S | —NO₂ | —Cl | —H |
| W137 (a and b) | S | —NO₂ | —Br | —H |
| W138 (a and b) | S | —NO₂ | —F | —H |
| W139 (a and b) | S | —NO₂ | —CH₃ | —H |
| W140 (a and b) | S | —NO₂ | —CF₃ | —H |
| W141 (a and b) | S | —NO₂ | —OCH₃ | —H |
| W142 (a and b) | S | —NO₂ | —OCH₂CH₃ | —H |
| W143 (a and b) | S | —NO₂ | —OCF₃ | —H |
| W144 (a and b) | S | —NO₂ | -tert-butyl | —H |
| W145 (a and b) | S | —NO₂ | -iso-propyl | —H |
| W146 (a and b) | S | —NO₂ | —CH₃ | —CH₃ |
| W147 (a and b) | S | —NO₂ | —H | —H |

TABLE 23-continued

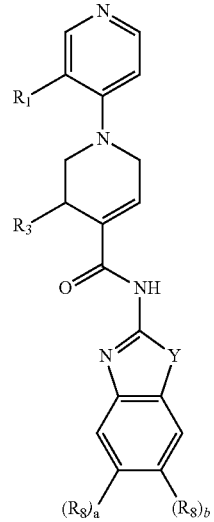

(Iw)

and pharmaceutically acceptable salts thereof, wherein:

| Compound | Y | R₁ | (R₈)ₐ | (R₈)ᵦ |
|---|---|---|---|---|
| W148 (a and b) | S | —NO₂ | —H | —Cl |
| W149 (a and b) | S | —NO₂ | —H | —Br |
| W150 (a and b) | S | —NO₂ | —H | —F |
| W151 (a and b) | S | —NO₂ | —H | —CH₃ |
| W152 (a and b) | S | —NO₂ | —H | —CF₃ |
| W153 (a and b) | S | —NO₂ | —H | —OCH₃ |
| W154 (a and b) | S | —NO₂ | —H | —OCH₂CH₃ |
| W155 (a and b) | S | —NO₂ | —H | —OCF₃ |
| W156 (a and b) | S | —NO₂ | —H | -tert-butyl |
| W157 (a and b) | S | —NO₂ | —H | -iso-propyl |
| W158 (a and b) | S | —CN | —Br | —H |
| W159 (a and b) | S | —CN | —Cl | —H |
| W160 (a and b) | S | —CN | —F | —H |
| W161 (a and b) | S | —CN | —CH₃ | —H |
| W162 (a and b) | S | —CN | —CF₃ | —H |
| W163 (a and b) | S | —CN | —OCH₃ | —H |
| W164 (a and b) | S | —CN | —OCH₂CH₃ | —H |
| W165 (a and b) | S | —CN | —OCF₃ | —H |
| W166 (a and b) | S | —CN | -tert-butyl | —H |
| W167 (a and b) | S | —CN | -iso-propyl | —H |
| W168 (a and b) | S | —CN | —CH₃ | —CH₃ |
| W169 (a and b) | S | —CN | —H | —H |
| W170 (a and b) | S | —CN | —H | —Cl |
| W171 (a and b) | S | —CN | —H | —Br |
| W172 (a and b) | S | —CN | —H | —F |
| W173 (a and b) | S | —CN | —H | —CH₃ |
| W174 (a and b) | S | —CN | —H | —CF₃ |
| W175 (a and b) | S | —CN | —H | —OCH₃ |
| W176 (a and b) | S | —CN | —H | —OCH₂CH₃ |
| W177 (a and b) | S | —CN | —H | —OCF₃ |
| W178 (a and b) | S | —CN | —H | -tert-butyl |
| W179 (a and b) | S | —CN | —H | -iso-propyl |
| W180 (a and b) | S | —Br | —Br | —H |
| W181 (a and b) | S | —Br | —Cl | —H |
| W182 (a and b) | S | —Br | —F | —H |
| W183 (a and b) | S | —Br | —CH₃ | —H |
| W184 (a and b) | S | —Br | —CF₃ | —H |
| W185 (a and b) | S | —Br | —OCH₃ | —H |
| W186 (a and b) | S | —Br | —OCH₂CH₃ | —H |
| W187 (a and b) | S | —Br | —OCF₃ | —H |
| W188 (a and b) | S | —Br | -tert-butyl | —H |
| W189 (a and b) | S | —Br | -iso-propyl | —H |
| W190 (a and b) | S | —Br | —CH₃ | —CH₃ |
| W191 (a and b) | S | —Br | —H | —H |
| W192 (a and b) | S | —Br | —H | —Cl |
| W193 (a and b) | S | —Br | —H | —Br |
| W194 (a and b) | S | —Br | —H | —F |
| W195 (a and b) | S | —Br | —H | —CH₃ |
| W196 (a and b) | S | —Br | —H | —CF₃ |

TABLE 23-continued

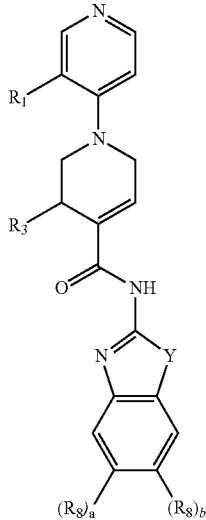

(Iw)

and pharmaceutically acceptable salts thereof, wherein:

| Compound | Y | R₁ | (R₈)ₐ | (R₈)ᵦ |
|---|---|---|---|---|
| W197 (a and b) | S | —Br | —H | —OCH₃ |
| W198 (a and b) | S | —Br | —H | —OCH₂CH₃ |
| W199 (a and b) | S | —Br | —H | —OCF₃ |
| W200 (a and b) | S | —Br | —H | -tert-butyl |
| W201 (a and b) | S | —Br | —H | -iso-propyl |
| W202 (a and b) | S | —I | —Cl | —H |
| W203 (a and b) | S | —I | —Br | —H |
| W204 (a and b) | S | —I | —F | —H |
| W205 (a and b) | S | —I | —CH₃ | —H |
| W206 (a and b) | S | —I | —CF₃ | —H |
| W207 (a and b) | S | —I | —OCH₃ | —H |
| W208 (a and b) | S | —I | —OCH₂CH₃ | —H |
| W209 (a and b) | S | —I | —OCF₃ | —H |
| W210 (a and b) | S | —I | -tert-butyl | —H |
| W211 (a and b) | S | —I | -iso-propyl | —H |
| W212 (a and b) | S | —I | —CH₃ | —CH₃ |
| W213 (a and b) | S | —I | —H | —H |
| W214 (a and b) | S | —I | —H | —Cl |
| W215 (a and b) | S | —I | —H | —Br |
| W216 (a and b) | S | —I | —H | —F |
| W217 (a and b) | S | —I | —H | —CH₃ |
| W218 (a and b) | S | —I | —H | —CF₃ |
| W219 (a and b) | S | —I | —H | —OCH₃ |
| W220 (a and b) | S | —I | —H | —OCH₂CH₃ |
| W221 (a and b) | S | —I | —H | —OCF₃ |
| W222 (a and b) | S | —I | —H | -tert-butyl |
| W223 (a and b) | S | —I | —H | -iso-propyl |
| W224 (a and b) | O | —H | —Cl | —H |
| W225 (a and b) | O | —H | —Br | —H |
| W226 (a and b) | O | —H | —F | —H |
| W227 (a and b) | O | —H | —CH₃ | —H |
| W228 (a and b) | O | —H | —CF₃ | —H |
| W229 (a and b) | O | —H | —OCH₃ | —H |
| W230 (a and b) | O | —H | —OCH₂CH₃ | —H |
| W231 (a and b) | O | —H | —OCF₃ | —H |
| W232 (a and b) | O | —H | -tert-butyl | —H |
| W233 (a and b) | O | —H | -iso-propyl | —H |
| W234 (a and b) | O | —H | —CH₃ | —CH₃ |
| W235 (a and b) | O | —H | —H | —H |
| W236 (a and b) | O | —H | —H | —Cl |
| W237 (a and b) | O | —H | —H | —Br |
| W238 (a and b) | O | —H | —H | —F |
| W239 (a and b) | O | —H | —H | —CH₃ |
| W240 (a and b) | O | —H | —H | —CF₃ |
| W241 (a and b) | O | —H | —H | —OCH₃ |
| W242 (a and b) | O | —H | —H | —OCH₂CH₃ |
| W243 (a and b) | O | —H | —H | —OCF₃ |
| W244 (a and b) | O | —H | —H | -tert-butyl |
| W245 (a and b) | O | —H | —H | -iso-propyl |

TABLE 23-continued

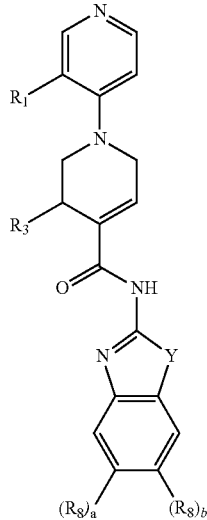

(Iw)

and pharmaceutically acceptable salts thereof, wherein:

| Compound | Y | R₁ | (R₈)ₐ | (R₈)ᵦ |
|---|---|---|---|---|
| W246 (a and b) | O | —Cl | —Cl | —H |
| W247 (a and b) | O | —Cl | —Br | —H |
| W248 (a and b) | O | —Cl | —F | —H |
| W249 (a and b) | O | —Cl | —CH₃ | —H |
| W250 (a and b) | O | —Cl | —CF₃ | —H |
| W251 (a and b) | O | —Cl | —OCH₃ | —H |
| W252 (a and b) | O | —Cl | —OCH₂CH₃ | —H |
| W253 (a and b) | O | —Cl | —OCF₃ | —H |
| W254 (a and b) | O | —Cl | -tert-butyl | —H |
| W255 (a and b) | O | —Cl | -iso-propyl | —H |
| W256 (a and b) | O | —Cl | —CH₃ | —CH₃ |
| W257 (a and b) | O | —Cl | —H | —H |
| W258 (a and b) | O | —Cl | —H | —CH₃ |
| W259 (a and b) | O | —Cl | —H | —Cl |
| W260 (a and b) | O | —Cl | —H | —Br |
| W261 (a and b) | O | —Cl | —H | —F |
| W262 (a and b) | O | —Cl | —H | —CF₃ |
| W263 (a and b) | O | —Cl | —H | —OCH₃ |
| W264 (a and b) | O | —Cl | —H | —OCH₂CH₃ |
| W265 (a and b) | O | —Cl | —H | —OCF₃ |
| W266 (a and b) | O | —Cl | —H | -tert-butyl |
| W267 (a and b) | O | —Cl | —H | -iso-propyl |
| W268 (a and b) | O | —Cl | —H | —OCF₃ |
| W269 (a and b) | O | —Cl | —H | -tert-butyl |
| W270 (a and b) | O | —Cl | —H | -iso-propyl |
| W271 (a and b) | O | —CH₃ | —Cl | —H |
| W272 (a and b) | O | —CH₃ | —Br | —H |
| W273 (a and b) | O | —CH₃ | —F | —H |
| W274 (a and b) | O | —CH₃ | —CH₃ | —H |
| W275 (a and b) | O | —CH₃ | —CF₃ | —H |
| W276 (a and b) | O | —CH₃ | —OCH₃ | —H |
| W277 (a and b) | O | —CH₃ | —OCH₂CH₃ | —H |
| W278 (a and b) | O | —CH₃ | —OCF₃ | —H |
| W279 (a and b) | O | —CH₃ | -tert-butyl | —H |
| W280 (a and b) | O | —CH₃ | -iso-propyl | —H |
| W281 (a and b) | O | —CH₃ | —CH₃ | —CH₃ |
| W282 (a and b) | O | —CH₃ | —H | —H |
| W283 (a and b) | O | —CH₃ | —H | —Cl |
| W284 (a and b) | O | —CH₃ | —H | —Br |
| W285 (a and b) | O | —CH₃ | —H | —F |
| W286 (a and b) | O | —CH₃ | —H | —CH₃ |
| W287 (a and b) | O | —CH₃ | —H | —CF₃ |
| W288 (a and b) | O | —CH₃ | —H | —OCH₃ |
| W289 (a and b) | O | —CH₃ | —H | —OCH₂CH₃ |
| W290 (a and b) | O | —CH₃ | —H | —OCF₃ |
| W291 (a and b) | O | —CH₃ | —H | -tert-butyl |
| W292 (a and b) | O | —CH₃ | —H | -iso-propyl |
| W293 (a and b) | O | —CF₃ | —Cl | —H |
| W294 (a and b) | O | —CF₃ | —Br | —H |

TABLE 23-continued (Iw)

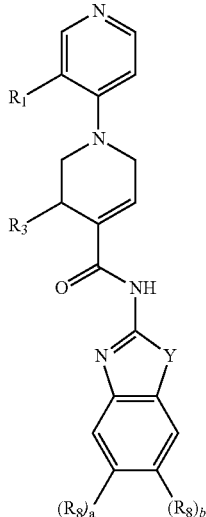

and pharmaceutically acceptable salts thereof, wherein:

| Compound | Y | R₁ | (R₈)ₐ | (R₈)ᵦ |
|---|---|---|---|---|
| W295 (a and b) | O | —CF₃ | —F | —H |
| W296 (a and b) | O | —CF₃ | —CH₃ | —H |
| W297 (a and b) | O | —CF₃ | —CF₃ | —H |
| W298 (a and b) | O | —CF₃ | —OCH₃ | —H |
| W299 (a and b) | O | —CF₃ | —OCH₂CH₃ | —H |
| W300 (a and b) | O | —CF₃ | —OCF₃ | —H |
| W301 (a and b) | O | —CF₃ | -tert-butyl | —H |
| W302 (a and b) | O | —CF₃ | -iso-propyl | —H |
| W303 (a and b) | O | —CF₃ | —CH₃ | —CH₃ |
| W304 (a and b) | O | —CF₃ | —H | —H |
| W305 (a and b) | O | —CF₃ | —H | —Cl |
| W306 (a and b) | O | —CF₃ | —H | —Br |
| W307 (a and b) | O | —CF₃ | —H | —F |
| W308 (a and b) | O | —CF₃ | —H | —CH₃ |
| W309 (a and b) | O | —CF₃ | —H | —CF₃ |
| W310 (a and b) | O | —CF₃ | —H | —OCH₃ |
| W311 (a and b) | O | —CF₃ | —H | —OCH₂CH₃ |
| W312 (a and b) | O | —CF₃ | —H | —OCF₃ |
| W313 (a and b) | O | —CF₃ | —H | -tert-butyl |
| W314 (a and b) | O | —CF₃ | —H | -iso-propyl |
| W315 (a and b) | O | —CHF₂ | —Cl | —H |
| W316 (a and b) | O | —CHF₂ | —Br | —H |
| W317 (a and b) | O | —CHF₂ | —F | —H |
| W318 (a and b) | O | —CHF₂ | —CH₃ | —H |
| W319 (a and b) | O | —CHF₂ | —CF₃ | —H |
| W320 (a and b) | O | —CHF₂ | —OCH₃ | —H |
| W321 (a and b) | O | —CHF₂ | —OCH₂CH₃ | —H |
| W322 (a and b) | O | —CHF₂ | —OCF₃ | —H |
| W323 (a and b) | O | —CHF₂ | -tert-butyl | —H |
| W324 (a and b) | O | —CHF₂ | -iso-propyl | —H |
| W325 (a and b) | O | —CHF₂ | —CH₃ | —CH₃ |
| W326 (a and b) | O | —CHF₂ | —H | —H |
| W327 (a and b) | O | —CHF₂ | —H | —Cl |
| W328 (a and b) | O | —CHF₂ | —H | —Br |
| W329 (a and b) | O | —CHF₂ | —H | —F |
| W330 (a and b) | O | —CHF₂ | —H | —CH₃ |
| W331 (a and b) | O | —CHF₂ | —H | —CF₃ |
| W332 (a and b) | O | —CHF₂ | —H | —OCH₃ |
| W333 (a and b) | O | —CHF₂ | —H | —OCH₂CH₃ |
| W334 (a and b) | O | —CHF₂ | —H | —OCF₃ |
| W335 (a and b) | O | —CHF₂ | —H | -tert-butyl |
| W336 (a and b) | O | —CHF₂ | —H | -iso-propyl |
| W337 (a and b) | O | —OH | —Cl | —H |
| W338 (a and b) | O | —OH | —Br | —H |
| W339 (a and b) | O | —OH | —F | —H |
| W340 (a and b) | O | —OH | —CH₃ | —H |
| W341 (a and b) | O | —OH | —CF₃ | —H |
| W342 (a and b) | O | —OH | —OCH₃ | —H |
| W343 (a and b) | O | —OH | —OCH₂CH₃ | —H |
| W344 (a and b) | O | —OH | —OCF₃ | —H |
| W345 (a and b) | O | —OH | -tert-butyl | —H |
| W346 (a and b) | O | —OH | -iso-propyl | —H |
| W347 (a and b) | O | —OH | —CH₃ | —CH₃ |
| W348 (a and b) | O | —OH | —H | —H |
| W349 (a and b) | O | —OH | —H | —Cl |
| W350 (a and b) | O | —OH | —H | —Br |
| W351 (a and b) | O | —OH | —H | —F |
| W352 (a and b) | O | —OH | —H | —CH₃ |
| W353 (a and b) | O | —OH | —H | —CF₃ |
| W354 (a and b) | O | —OH | —H | —OCH₃ |
| W355 (a and b) | O | —OH | —H | —OCH₂CH₃ |
| W356 (a and b) | O | —OH | —H | —OCF₃ |
| W357 (a and b) | O | —OH | —H | -tert-butyl |
| W358 (a and b) | O | —OH | —H | -iso-propyl |
| W359 (a and b) | O | —NO₂ | —Cl | —H |
| W360 (a and b) | O | —NO₂ | —Br | —H |
| W361 (a and b) | O | —NO₂ | —F | —H |
| W362 (a and b) | O | —NO₂ | —CH₃ | —H |
| W363 (a and b) | O | —NO₂ | —CF₃ | —H |
| W364 (a and b) | O | —NO₂ | —OCH₃ | —H |
| W365 (a and b) | O | —NO₂ | —OCH₂CH₃ | —H |
| W366 (a and b) | O | —NO₂ | —OCF₃ | —H |
| W367 (a and b) | O | —NO₂ | -tert-butyl | —H |
| W368 (a and b) | O | —NO₂ | -iso-propyl | —H |
| W369 (a and b) | O | —NO₂ | —CH₃ | —CH₃ |
| W370 (a and b) | O | —NO₂ | —H | —H |
| W371 (a and b) | O | —NO₂ | —H | —Cl |
| W372 (a and b) | O | —NO₂ | —H | —Br |
| W373 (a and b) | O | —NO₂ | —H | —F |
| W374 (a and b) | O | —NO₂ | —H | —CH₃ |
| W375 (a and b) | O | —NO₂ | —H | —CF₃ |
| W376 (a and b) | O | —NO₂ | —H | —OCH₃ |
| W377 (a and b) | O | —NO₂ | —H | —OCH₂CH₃ |
| W378 (a and b) | O | —NO₂ | —H | —OCF₃ |
| W379 (a and b) | O | —NO₂ | —H | -tert-butyl |
| W380 (a and b) | O | —NO₂ | —H | -iso-propyl |
| W381 (a and b) | O | —CN | —Br | —H |
| W382 (a and b) | O | —CN | —Cl | —H |
| W383 (a and b) | O | —CN | —F | —H |
| W384 (a and b) | O | —CN | —CH₃ | —H |
| W385 (a and b) | O | —CN | —CF₃ | —H |
| W386 (a and b) | O | —CN | —OCH₃ | —H |
| W387 (a and b) | O | —CN | —OCH₂CH₃ | —H |
| W388 (a and b) | O | —CN | —OCF₃ | —H |
| W389 (a and b) | O | —CN | -tert-butyl | —H |
| W390 (a and b) | O | —CN | -iso-propyl | —H |
| W391 (a and b) | O | —CN | —CH₃ | —CH₃ |
| W392 (a and b) | O | —CN | —H | —H |

TABLE 23-continued (Iw)

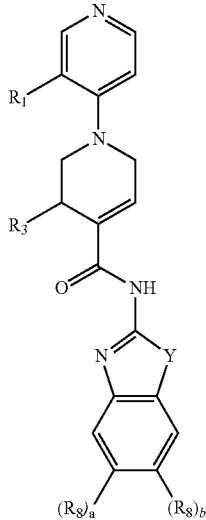

and pharmaceutically acceptable salts thereof, wherein:

| Compound | Y | R₁ | (R₈)ₐ | (R₈)ᵦ |
|---|---|---|---|---|
| W393 (a and b) | O | —CN | —H | —Cl |
| W394 (a and b) | O | —CN | —H | —Br |
| W395 (a and b) | O | —CN | —H | —F |
| W396 (a and b) | O | —CN | —H | —CH₃ |
| W397 (a and b) | O | —CN | —H | —CF₃ |
| W398 (a and b) | O | —CN | —H | —OCH₃ |
| W399 (a and b) | O | —CN | —H | —OCH₂CH₃ |
| W400 (a and b) | O | —CN | —H | —OCF₃ |
| W401 (a and b) | O | —CN | —H | -tert-butyl |
| W402 (a and b) | O | —CN | —H | -iso-propyl |
| W403 (a and b) | O | —Br | —Br | —H |
| W404 (a and b) | O | —Br | —Cl | —H |
| W405 (a and b) | O | —Br | —F | —H |
| W406 (a and b) | O | —Br | —CH₃ | —H |
| W407 (a and b) | O | —Br | —CF₃ | —H |
| W408 (a and b) | O | —Br | —OCH₃ | —H |
| W409 (a and b) | O | —Br | —OCH₂CH₃ | —H |
| W410 (a and b) | O | —Br | —OCF₃ | —H |
| W411 (a and b) | O | —Br | -tert-butyl | —H |
| W412 (a and b) | O | —Br | -iso-propyl | —H |
| W413 (a and b) | O | —Br | —CH₃ | —CH₃ |
| W414 (a and b) | O | —Br | —H | —H |
| W415 (a and b) | O | —Br | —H | —Cl |
| W416 (a and b) | O | —Br | —H | —Br |
| W417 (a and b) | O | —Br | —H | —F |
| W418 (a and b) | O | —Br | —H | —CH₃ |
| W419 (a and b) | O | —Br | —H | —CF₃ |
| W420 (a and b) | O | —Br | —H | —OCH₃ |
| W421 (a and b) | O | —Br | —H | —OCH₂CH₃ |
| W422 (a and b) | O | —Br | —H | —OCF₃ |
| W423 (a and b) | O | —Br | —H | -tert-butyl |
| W424 (a and b) | O | —Br | —H | -iso-propyl |
| W425 (a and b) | O | —I | —Cl | —H |
| W426 (a and b) | O | —I | —Br | —H |
| W427 (a and b) | O | —I | —F | —H |
| W428 (a and b) | O | —I | —CH₃ | —H |
| W429 (a and b) | O | —I | —CF₃ | —H |
| W430 (a and b) | O | —I | —OCH₃ | —H |
| W431 (a and b) | O | —I | —OCH₂CH₃ | —H |
| W432 (a and b) | O | —I | —OCF₃ | —H |
| W433 (a and b) | O | —I | -tert-butyl | —H |
| W434 (a and b) | O | —I | -iso-propyl | —H |
| W435 (a and b) | O | —I | —CH₃ | —CH₃ |
| W436 (a and b) | O | —I | —H | —H |
| W437 (a and b) | O | —I | —H | —Cl |
| W438 (a and b) | O | —I | —H | —Br |
| W439 (a and b) | O | —I | —H | —F |
| W440 (a and b) | O | —I | —H | —CH₃ |
| W441 (a and b) | O | —I | —H | —CF₃ |
| W442 (a and b) | O | —I | —H | —OCH₃ |
| W443 (a and b) | O | —I | —H | —OCH₂CH₃ |
| W444 (a and b) | O | —I | —H | —OCF₃ |
| W445 (a and b) | O | —I | —H | -tert-butyl |
| W446 (a and b) | O | —I | —H | -iso-propyl |
| W447 (a and b) | NH | —H | —Cl | —H |
| W448 (a and b) | NH | —H | —Br | —H |
| W449 (a and b) | NH | —H | —F | —H |
| W450 (a and lo) | NH | —H | —CH₃ | —H |
| W451 (a and b) | NH | —H | —CF₃ | —H |
| W452 (a and b) | NH | —H | —OCH₃ | —H |
| W453 (a and b) | NH | —H | —OCH₂CH₃ | —H |
| W454 (a and b) | NH | —H | —OCF₃ | —H |
| W455 (a and b) | NH | —H | -tert-butyl | —H |
| W456 (a and b) | NH | —H | -iso-propyl | —H |
| W457 (a and b) | NH | —H | —CH₃ | —CH₃ |
| W458 (a and b) | NH | —H | —H | —H |
| W459 (a and b) | NH | —H | —H | —Cl |
| W460 (a and b) | NH | —H | —H | —Br |
| W461 (a and b) | NH | —H | —H | —F |
| W462 (a and b) | NH | —H | —H | —CH₃ |
| W463 (a and b) | NH | —H | —H | —CF₃ |
| W464 (a and b) | NH | —H | —H | —OCH₃ |
| W465 (a and b) | NH | —H | —H | —OCH₂CH₃ |
| W466 (a and b) | NH | —H | —H | —OCF₃ |
| W467 (a and b) | NH | —H | —H | -tert-butyl |
| W468 (a and b) | NH | —H | —H | -iso-propyl |
| W469 (a and b) | NH | —Cl | —Cl | —H |
| W470 (a and b) | NH | —Cl | —Br | —H |
| W471 (a and b) | NH | —Cl | —F | —H |
| W472 (a and b) | NH | —Cl | —CH₃ | —H |
| W473 (a and b) | NH | —Cl | —CF₃ | —H |
| W474 (a and b) | NH | —Cl | —OCH₃ | —H |
| W475 (a and b) | NH | —Cl | —OCH₂CH₃ | —H |
| W476 (a and b) | NH | —Cl | —OCF₃ | —H |
| W477 (a and b) | NH | —Cl | -tert-butyl | —H |
| W478 (a and b) | NH | —Cl | -iso-propyl | —H |
| W479 (a and b) | NH | —Cl | —CH₃ | —CH₃ |
| W480 (a and b) | NH | —Cl | —H | —H |
| W481 (and b) | NH | —Cl | —H | —CH₃ |
| W482 (a and b) | NH | —Cl | —H | —Cl |
| W483 (a and b) | NH | —Cl | —H | —Br |
| W484 (a and b) | NH | —Cl | —H | —F |
| W485 (a and b) | NH | —Cl | —H | —CF₃ |
| W486 (a and b) | NH | —Cl | —H | —OCH₃ |
| W487 (a and b) | NH | —Cl | —H | —OCH₂CH₃ |
| W488 (a and b) | NH | —Cl | —H | —OCF₃ |
| W489 (a and b) | NH | —Cl | —H | -tert-butyl |
| W490 (a and b) | NH | —Cl | —H | -iso-propyl |

TABLE 23-continued

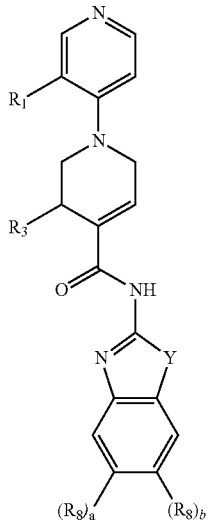

(Iw)

and pharmaceutically acceptable salts thereof, wherein:

| Compound | Y | R₁ | (R₈)ₐ | (R₈)ᵦ |
|---|---|---|---|---|
| W491 (a and b) | NH | —Cl | —H | —OCF₃ |
| W492 (a and b) | NH | —Cl | —H | -tert-butyl |
| W493 (a and b) | NH | —Cl | —H | -iso-propyl |
| W494 (a and b) | NH | —CH₃ | —Cl | —H |
| W495 (a and b) | NH | —CH₃ | —Br | —H |
| W496 (a and b) | NH | —CH₃ | —F | —H |
| W497 (a and b) | NH | —CH₃ | —CH₃ | —H |
| W498 (a and b) | NH | —CH₃ | —CF₃ | —H |
| W499 (a and b) | NH | —CH₃ | —OCH₃ | —H |
| W500 (a and b) | NH | —CH₃ | —OCH₂CH₃ | —H |
| W501 (a and b) | NH | —CH₃ | —OCF₃ | —H |
| W502 (a and b) | NH | —CH₃ | -tert-butyl | —H |
| W503 (a and b) | NH | —CH₃ | -iso-propyl | —H |
| W504 (a and b) | NH | —CH₃ | —CH₃ | —CH₃ |
| W505 (a and b) | NH | —CH₃ | —H | —H |
| W506 (a and b) | NH | —CH₃ | —H | —Cl |
| W507 (a and b) | NH | —CH₃ | —H | —Br |
| W508 (a and b) | NH | —CH₃ | —H | —F |
| W509 (a and b) | NH | —CH₃ | —H | —CH₃ |
| W510 (a and b) | NH | —CH₃ | —H | —CF₃ |
| W511 (a and b) | NH | —CH₃ | —H | —OCH₃ |
| W512 (a and b) | NH | —CH₃ | —H | —OCH₂CH₃ |
| W513 (a and b) | NH | —CH₃ | —H | —OCF₃ |
| W514 (a and b) | NH | —CH₃ | —H | -tert-butyl |
| W515 (a and b) | NH | —CH₃ | —H | -iso-propyl |
| W516 (a and b) | NH | —CF₃ | —Cl | —H |
| W517 (a and b) | NH | —CF₃ | —Br | —H |
| W518 (a and b) | NH | —CF₃ | —F | —H |
| W519 (a and b) | NH | —CF₃ | —CH₃ | —H |
| W520 (a and b) | NH | —CF₃ | —CF₃ | —H |
| W521 (a and b) | NH | —CF₃ | —OCH₃ | —H |
| W522 (a and b) | NH | —CF₃ | —OCH₂CH₃ | —H |
| W523 (a and b) | NH | —CF₃ | —OCF₃ | —H |
| W524 (a and b) | NH | —CF₃ | -tert-butyl | —H |
| W525 (a and b) | NH | —CF₃ | -iso-propyl | —H |
| W526 (a and b) | NH | —CF₃ | —CH₃ | —CH₃ |
| W527 (a and b) | NH | —CF₃ | —H | —H |
| W528 (a and b) | NH | —CF₃ | —H | —Cl |
| W529 (a and b) | NH | —CF₃ | —H | —Br |
| W530 (a and b) | NH | —CF₃ | —H | —F |
| W531 (a and b) | NH | —CF₃ | —H | —CH₃ |
| W532 (a and b) | NH | —CF₃ | —H | —CF₃ |
| W533 (a and b) | NH | —CF₃ | —H | —OCH₃ |
| W534 (a and b) | NH | —CF₃ | —H | —OCH₂CH₃ |
| W535 (a and b) | NH | —CF₃ | —H | —OCF₃ |
| W536 (a and b) | NH | —CF₃ | —H | -tert-butyl |
| W537 (a and b) | NH | —CF₃ | —H | -iso-propyl |
| W538 (a and b) | NH | —CHF₂ | —Cl | —H |
| W539 (a and b) | NH | —CHF₂ | —Br | —H |
| W540 (a and b) | NH | —CHF₂ | —F | —H |
| W541 (a and b) | NH | —CHF₂ | —CH₃ | —H |
| W542 (a and b) | NH | —CHF₂ | —CF₃ | —H |
| W543 (a and b) | NH | —CHF₂ | —OCH₃ | —H |
| W544 (a and b) | NH | —CHF₂ | —OCH₂CH₃ | —H |
| W545 (a and b) | NH | —CHF₂ | —OCF₃ | —H |
| W546 (a and b) | NH | —CHF₂ | -tert-butyl | —H |
| W547 (a and b) | NH | —CHF₂ | -iso-propyl | —H |
| W548 (a and b) | NH | —CHF₂ | —CH₃ | —CH₃ |
| W549 (a and b) | NH | —CHF₂ | —H | —H |
| W550 (a and b) | NH | —CHF₂ | —H | —Cl |
| W551 (a and b) | NH | —CHF₂ | —H | —Br |
| W552 (a and b) | NH | —CHF₂ | —H | —F |
| W553 (a and b) | NH | —CHF₂ | —H | —CH₃ |
| W554 (a and b) | NH | —CHF₂ | —H | —CF₃ |
| W555 (a and b) | NH | —CHF₂ | —H | —OCH₃ |
| W556 (a and b) | NH | —CHF₂ | —H | —OCH₂CH₃ |
| W557 (a and b) | NH | —CHF₂ | —H | —OCF₃ |
| W558 (a and b) | NH | —CHF₂ | —H | -tert-butyl |
| W559 (a and b) | NH | —CHF₂ | —H | -iso-propyl |
| W560 (a and b) | NH | —OH | —Cl | —H |
| W561 (a and b) | NH | —OH | —Br | —H |
| W562 (a and b) | NH | —OH | —F | —H |
| W563 (a and b) | NH | —OH | —CH₃ | —H |
| W564 (a and b) | NH | —OH | —CF₃ | —H |
| W565 (a and b) | NH | —OH | —OCH₃ | —H |
| W566 (a and b) | NH | —OH | —OCH₂CH₃ | —H |
| W567 (a and b) | NH | —OH | —OCF₃ | —H |
| W568 (a and b) | NH | —OH | -tert-butyl | —H |
| W569 (a and b) | NH | —OH | -iso-propyl | —H |
| W570 (a and b) | NH | —OH | —CH₃ | —CH₃ |
| W571 (a and b) | NH | —OH | —H | —H |
| W572 (a and b) | NH | —OH | —H | —Cl |
| W573 (a and b) | NH | —OH | —H | —Br |
| W574 (a and b) | NH | —OH | —H | —F |
| W575 (a and b) | NH | —OH | —H | —CH₃ |
| W576 (a and b) | NH | —OH | —H | —CF₃ |
| W577 (a and b) | NH | —OH | —H | —OCH₃ |
| W578 (a and b) | NH | —OH | —H | —OCH₂CH₃ |
| W579 (a and b) | NH | —OH | —H | —OCF₃ |
| W580 (a and b) | NH | —OH | —H | -tert-butyl |
| W581 (a and b) | NH | —OH | —H | -iso-propyl |
| W582 (a and b) | NH | —NO₂ | —Cl | —H |
| W583 (a and b) | NH | —NO₂ | —Br | —H |
| W584 (a and b) | NH | —NO₂ | —F | —H |
| W585 (a and b) | NH | —NO₂ | —CH₃ | —H |
| W586 (a and b) | NH | —NO₂ | —CF₃ | —H |
| W587 (a and b) | NH | —NO₂ | —OCH₃ | —H |
| W588 (a and b) | NH | —NO₂ | —OCH₂CH₃ | —H |

TABLE 23-continued

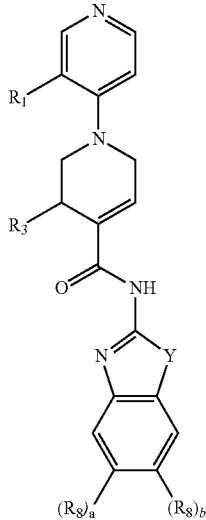

(Iw)

and pharmaceutically acceptable salts thereof, wherein:

| Compound | Y | $R_1$ | $(R_8)_a$ | $(R_8)_b$ |
|---|---|---|---|---|
| W589 (a and b) | NH | —NO$_2$ | —OCF$_3$ | —H |
| W590 (a and b) | NH | —NO$_2$ | -tert-butyl | —H |
| W591 (a and b) | NH | —NO$_2$ | -iso-propyl | —H |
| W592 (a and b) | NH | —NO$_2$ | —CH$_3$ | —CH$_3$ |
| W593 (a and b) | NH | —NO$_2$ | —H | —H |
| W594 (a and b) | NH | —NO$_2$ | —H | —Cl |
| W595 (a and b) | NH | —NO$_2$ | —H | —Br |
| W596 (a and b) | NH | —NO$_2$ | —H | —F |
| W597 (a and b) | NH | —NO$_2$ | —H | —CH$_3$ |
| W598 (a and b) | NH | —NO$_2$ | —H | —CF$_3$ |
| W599 (a and b) | NH | —NO$_2$ | —H | —OCH$_3$ |
| W600 (a and b) | NH | —NO$_2$ | —H | —OCH$_2$CH$_3$ |
| W601 (a and b) | NH | —NO$_2$ | —H | —OCF$_3$ |
| W602 (a and b) | NH | —NO$_2$ | —H | -tert-butyl |
| W603 (a and b) | NH | —NO$_2$ | —H | -iso-propyl |
| W604 (a and b) | NH | —CN | —Br | —H |
| W605 (a and b) | NH | —CN | —Cl | —H |
| W606 (a and b) | NH | —CN | —F | —H |
| W607 (a and b) | NH | —CN | —CH$_3$ | —H |
| W608 (a and b) | NH | —CN | —CF$_3$ | —H |
| W609 (a and b) | NH | —CN | —OCH$_3$ | —H |
| W610 (a and b) | NH | —CN | —OCH$_2$CH$_3$ | —H |
| W611 (a and b) | NH | —CN | —OCF$_3$ | —H |
| W612 (a and b) | NH | —CN | -tert-butyl | —H |
| W613 (a and b) | NH | —CN | -iso-propyl | —H |
| W614 (a and b) | NH | —CN | —CH$_3$ | —CH$_3$ |
| W615 (a and b) | NH | —CN | —H | —H |
| W616 (a and b) | NH | —CN | —H | —Cl |
| W617 (a and b) | NH | —CN | —H | —Br |
| W618 (a and b) | NH | —CN | —H | —F |
| W619 (a and b) | NH | —CN | —H | —CH$_3$ |
| W620 (a and b) | NH | —CN | —H | —CF$_3$ |
| W621 (a and b) | NH | —CN | —H | —OCH$_3$ |
| W622 (a and b) | NH | —CN | —H | —OCH$_2$CH$_3$ |
| W623 (a and b) | NH | —CN | —H | —OCF$_3$ |
| W624 (a and b) | NH | —CN | —H | -tert-butyl |
| W625 (a and b) | NH | —CN | —H | -iso-propyl |
| W626 (a and b) | NH | —Br | —Br | —H |
| W627 (a and b) | NH | —Br | —Cl | —H |
| W628 (a and b) | NH | —Br | —F | —H |
| W629 (a and b) | NH | —Br | —CH$_3$ | —H |
| W630 (a and b) | NH | —Br | —CF$_3$ | —H |
| W631 (a and b) | NH | —Br | —OCH$_3$ | —H |
| W632 (a and b) | NH | —Br | —OCH$_2$CH$_3$ | —H |
| W633 (a and b) | NH | —Br | —OCF$_3$ | —H |
| W634 (a and b) | NH | —Br | -tert-butyl | —H |
| W635 (a and b) | NH | —Br | -iso-propyl | —H |
| W636 (a and b) | NH | —Br | —CH$_3$ | —CH$_3$ |
| W637 (a and b) | NH | —Br | —H | —H |

TABLE 23-continued

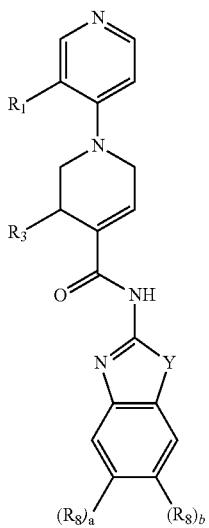

(Iw)

and pharmaceutically acceptable salts thereof, wherein:

| Compound | Y | $R_1$ | $(R_8)_a$ | $(R_8)_b$ |
|---|---|---|---|---|
| W638 (a and b) | NH | —Br | —H | —Cl |
| W639 (a and b) | NH | —Br | —H | —Br |
| W640 (a and b) | NH | —Br | —H | —F |
| W641 (a and b) | NH | —Br | —H | —CH$_3$ |
| W642 (a and b) | NH | —Br | —H | —CF$_3$ |
| W643 (a and b) | NH | —Br | —H | —OCH$_3$ |
| W644 (a and b) | NH | —Br | —H | —OCH$_2$CH$_3$ |
| W645 (a and b) | NH | —Br | —H | —OCF$_3$ |
| W646 (a and b) | NH | —Br | —H | -tert-butyl |
| W647 (a and b) | NH | —Br | —H | -iso-propyl |
| W648 (a and b) | NH | —I | —Cl | —H |
| W649 (a and b) | NH | —I | —Br | —H |
| W650 (a and b) | NH | —I | —F | —H |
| W651 (a and b) | NH | —I | —CH$_3$ | —H |
| W652 (a and b) | NH | —I | —CF$_3$ | —H |
| W653 (a and b) | NH | —I | —OCH$_3$ | —H |
| W654 (a and b) | NH | —I | —OCH$_2$CH$_3$ | —H |
| W655 (a and b) | NH | —I | —OCF$_3$ | —H |
| W656 (a and b) | NH | —I | -tert-butyl | —H |
| W657 (a and b) | NH | —I | -iso-propyl | —H |
| W658 (a and b) | NH | —I | —CH$_3$ | —CH$_3$ |
| W659 (a and b) | NH | —H | —H | |
| W660 (a and b) | NH | —I | —H | —Cl |
| W661 (a and b) | NH | —I | —H | —Br |
| W662 (a and b) | NH | —I | —H | —F |
| W663 (a and b) | NH | —I | —H | —CH$_3$ |
| W664 (a and b) | NH | —I | —H | —CF$_3$ |
| W665 (a and b) | NH | —I | —H | —OCH$_3$ |
| W666 (a and b) | NH | —I | —H | —OCH$_2$CH$_3$ |
| W667 (a and b) | NH | —I | —H | —OCF$_3$ |
| W668 (a and b) | NH | —I | —H | -tert-butyl |
| W669 (a and b) | NH | —I | —H | -iso-propyl |

(a) means that $R_3$ is —H.
(b) means that $R_3$ is —CH$_3$.

TABLE 24

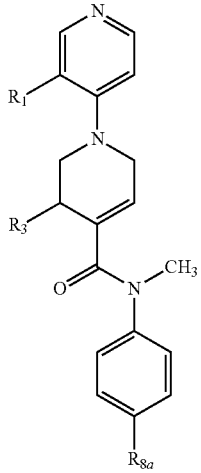

(Ix)

and pharmaceutically acceptable salts thereof, wherein:

| Compound | $R_1$ | $R_{8a}$ |
|---|---|---|
| X1 (a and b) | —H | —H |
| X2 (a and b) | —H | -tert-butyl |
| X3 (a and b) | —H | -iso-butyl |
| X4 (a and b) | —H | -sec-butyl |
| X5 (a and b) | —H | -iso-propyl |
| X6 (a and b) | —H | -n-propyl |
| X7 (a and b) | —H | -cyclohexyl |
| X8 (a and b) | —H | -tert-butoxy |
| X9 (a and b) | —H | -isopropoxy |
| X10 (a and b) | —H | —$CF_3$ |
| X11 (a and b) | —H | —$CH_2CF_3$ |
| X12 (a and b) | —H | —$OCF_3$ |
| X13 (a and b) | —H | —Cl |
| X14 (a and b) | —H | —Br |
| X15 (a and b) | —H | —I |
| X16 (a and b) | —H | -n-butyl |
| X17 (a and b) | —H | —$CH_3$ |
| X18 (a and b) | —H | —$SCF_3$ |
| X19 (a and b) | —H | —$N(CH_2CH_3)_2$ |
| X20 (a and b) | —H | —$OCF_2CHF_2$ |
| X21 (a and b) | —H | —$C(OH)(CF_3)_2$ |
| X22 (a and b) | —H | -(1,1-dimethyl-pentyl) |
| X23 (a and b) | —H | -(1,1-dimethyl-acetic acid) ethyl ester |
| X24 (a and b) | —H | —N-piperidinyl |
| X25 (a and b) | —Cl | —H |
| X26 (a and b) | —Cl | -tert-butyl |
| X27 (a and b) | —Cl | -iso-butyl |
| X28 (a and b) | —Cl | -sec-butyl |
| X29 (a and b) | —Cl | -iso-propyl |
| X30 (a and b) | —Cl | -n-propyl |
| X31 (a and b) | —Cl | -cyclohexyl |
| X32 (a and b) | —Cl | -tert-butoxy |
| X33 (a and b) | —Cl | -isopropoxy |
| X34 (a and b) | —Cl | —$CF_3$ |
| X35 (a and b) | —Cl | —$CH_2CF_3$ |
| X36 (a and b) | —Cl | —$OCF_3$ |
| X37 (a and b) | —Cl | —Cl |
| X38 (a and b) | —Cl | —Br |
| X39 (a and b) | —Cl | —I |
| X40 (a and b) | —Cl | -n-butyl |
| X41 (a and b) | —Cl | —$CH_3$ |
| X42 (a and b) | —Cl | —$SCF_3$ |
| X43 (a and b) | —Cl | —$N(CH_2CH_3)_2$ |
| X44 (a and b) | —Cl | —$OCF_2CHF_2$ |
| X45 (a and b) | —Cl | —$C(OH)(CF_3)_2$ |
| X46 (a and b) | —Cl | -(1,1-dimethyl-pentyl) |
| X47 (a and b) | —Cl | -(1,1-dimethyl-acetic acid) ethyl ester |
| X48 (a and b) | —Cl | —N-piperidinyl |
| X49 (a and b) | —F | —H |
| X50 (a and b) | —F | -tert-butyl |
| X51 (a and b) | —F | -iso-butyl |
| X52 (a and b) | —F | -sec-butyl |

TABLE 24-continued

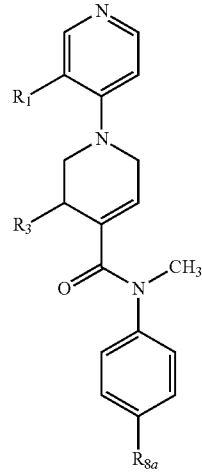

(Ix)

and pharmaceutically acceptable salts thereof, wherein:

| Compound | $R_1$ | $R_{8a}$ |
|---|---|---|
| X53 (a and b) | —F | -iso-propyl |
| X54 (a and b) | —F | -n-propyl |
| X55 (a and b) | —F | -cyclohexyl |
| X56 (a and b) | —F | -tert-butoxy |
| X57 (a and b) | —F | -isopropoxy |
| X58 (a and b) | —F | —$CF_3$ |
| X59 (a and b) | —F | —$CH_2CF_3$ |
| X60 (a and b) | —F | —$OCF_3$ |
| X61 (a and b) | —F | —Cl |
| X62 (a and b) | —F | —Br |
| X63 (a and b) | —F | —I |
| X64 (a and b) | —F | -n-butyl |
| X65 (a and b) | —F | —$CH_3$ |
| X66 (a and b) | —F | —$SCF_3$ |
| X67 (a and b) | —F | —$N(CH_2CH_3)_2$ |
| X68 (a and b) | —F | —$OCF_2CHF_2$ |
| X69 (a and b) | —F | —$C(OH)(CF_3)_2$ |
| X70 (a and b) | —F | -(1,1-dimethyl-pentyl) |
| X71 (a and b) | —F | -(1,1-dimethyl-acetic acid) ethyl ester |
| X72 (a and b) | —F | —N-piperidinyl |
| X73 (a and b) | —$CH_3$ | —H |
| X74 (a and b) | —$CH_3$ | -iso-butyl |
| X75 (a and b) | —$CH_3$ | -tert-butyl |
| X76 (a and b) | —$CH_3$ | -sec-butyl |
| X77 (a and b) | —$CH_3$ | -iso-propyl |
| X78 (a and b) | —$CH_3$ | -n-propyl |
| X79 (a and b) | —$CH_3$ | -cyclohexyl |
| X80 (a and b) | —$CH_3$ | -tert-butoxy |
| X81 (a and b) | —$CH_3$ | -isopropoxy |
| X82 (a and b) | —$CH_3$ | —$CF_3$ |
| X83 (a and b) | —$CH_3$ | —$CH_2CF_3$ |
| X84 (a and b) | —$CH_3$ | —$OCF_3$ |
| X85 (a and b) | —$CH_3$ | —Cl |
| X86 (a and b) | —$CH_3$ | —Br |
| X87 (a and b) | —$CH_3$ | —I |
| X88 (a and b) | —$CH_3$ | -n-butyl |
| X89 (a and b) | —$CH_3$ | —$CH_3$ |
| X90 (a and b) | —$CH_3$ | —$SCF_3$ |
| X91 (a and b) | —$CH_3$ | —$N(CH_2CH_3)_2$ |
| X92 (a and b) | —$CH_3$ | —$OCF_2CHF_2$ |
| X93 (a and b) | —$CH_3$ | —$C(OH)(CF_3)_2$ |
| X94 (a and b) | —$CH_3$ | -(1,1-dimethyl-pentyl) |
| X95 (a and b) | —$CH_3$ | -(1,1-dimethyl-acetic acid) ethyl ester |
| X96 (a and b) | —$CH_3$ | —N-piperidinyl |
| X97 (a and b) | —$CF_3$ | —H |
| X98 (a and b) | —$CF_3$ | -tert-butyl |
| X99 (a and b) | —$CF_3$ | -iso-butyl |
| X100 (a and b) | —$CF_3$ | -sec-butyl |
| X101 (a and b) | —$CF_3$ | -iso-propyl |
| X102 (a and b) | —$CF_3$ | -n-propyl |
| X103 (a and b) | —$CF_3$ | -cyclohexyl |
| X104 (a and b) | —$CF_3$ | -tert-butoxy |

TABLE 24-continued

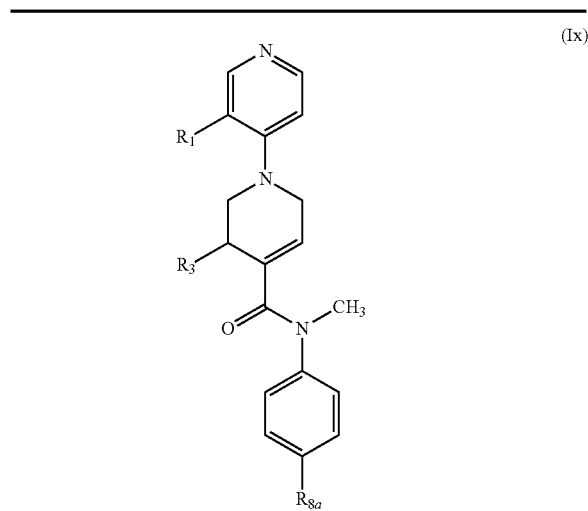

(Ix)

and pharmaceutically acceptable salts thereof, wherein:

| Compound | $R_1$ | $R_{8a}$ |
|---|---|---|
| X105 (a and b) | —$CF_3$ | -isopropoxy |
| X106 (a and b) | —$CF_3$ | —$CF_3$ |
| X107 (a and b) | —$CF_3$ | —$CH_2CF_3$ |
| X108 (a and b) | —$CF_3$ | —$OCF_3$ |
| X109 (a and b) | —$CF_3$ | —Cl |
| X110 (a and b) | —$CF_3$ | —Br |
| X111 (a and b) | —$CF_3$ | —I |
| X112 (a and b) | —$CF_3$ | -n-butyl |
| X113 (a and b) | —$CF_3$ | —$CH_3$ |
| X114 (a and b) | —$CF_3$ | —$SCF_3$ |
| X115 (a and b) | —$CF_3$ | —$N(CH_2CH_3)_2$ |
| X116 (a and b) | —$CF_3$ | —$OCF_2CHF_2$ |
| X117 (a and b) | —$CF_3$ | —$C(OH)(CF_3)_2$ |
| X118 (a and b) | —$CF_3$ | -(1,1-dimethyl-pentyl) |
| X119 (a and b) | —$CF_3$ | -(1,1-dimethyl-acetic acid) ethyl ester |
| X120 (a and b) | —$CF_3$ | —N-piperidinyl |
| X121 (a and b) | —$CHF_2$ | -tert-butyl |
| X122 (a and b) | —$CHF_2$ | —H |
| X123 (a and b) | —$CHF_2$ | -iso-butyl |
| X124 (a and b) | —$CHF_2$ | -sec-butyl |
| X125 (a and b) | —$CHF_2$ | -iso-propyl |
| X126 (a and b) | —$CHF_2$ | -n-propyl |
| X127 (a and b) | —$CHF_2$ | -cyclohexyl |
| X128 (a and b) | —$CHF_2$ | -tert-butoxy |
| X129 (a and b) | —$CHF_2$ | -isopropoxy |
| X130 (a and b) | —$CHF_2$ | —$CF_3$ |
| X131 (a and b) | —$CHF_2$ | —$CH_2CF_3$ |
| X132 (a and b) | —$CHF_2$ | —$OCF_3$ |
| X133 (a and b) | —$CHF_2$ | —Cl |
| X134 (a and b) | —$CHF_2$ | —Br |
| X135 (a and b) | —$CHF_2$ | —I |
| X136 (a and b) | —$CHF_2$ | -n-butyl |
| X137 (a and b) | —$CHF_2$ | —$CH_3$ |
| X138 (a and b) | —$CHF_2$ | —$SCF_3$ |
| X139 (a and b) | —$CHF_2$ | —$N(CH_2CH_3)_2$ |
| X140 (a and b) | —$CHF_2$ | —$OCF_2CHF_2$ |
| X141 (a and b) | —$CHF_2$ | —$C(OH)(CF_3)_2$ |
| X142 (a and b) | —$CHF_2$ | -(1,1-dimethyl-pentyl) |
| X143 (a and b) | —$CHF_2$ | -(1,1-dimethyl-acetic acid) ethyl ester |
| X144 (a and b) | —$CHF_2$ | —N-piperidinyl |
| X145 (a and b) | —OH | —H |
| X146 (a and b) | —OH | -tert-butyl |
| X147 (a and b) | —OH | -iso-butyl |
| X148 (a and b) | —OH | -sec-butyl |
| X149 (a and b) | —OH | -iso-propyl |
| X150 (a and b) | —OH | -n-propyl |
| X151 (a and b) | —OH | -cyclohexyl |
| X152 (a and b) | —OH | -tert-butoxy |
| X153 (a and b) | —OH | -isopropoxy |
| X154 (a and b) | —OH | —$CF_3$ |
| X155 (a and b) | —OH | —$CH_2CF_3$ |
| X156 (a and b) | —OH | —$OCF_3$ |

TABLE 24-continued

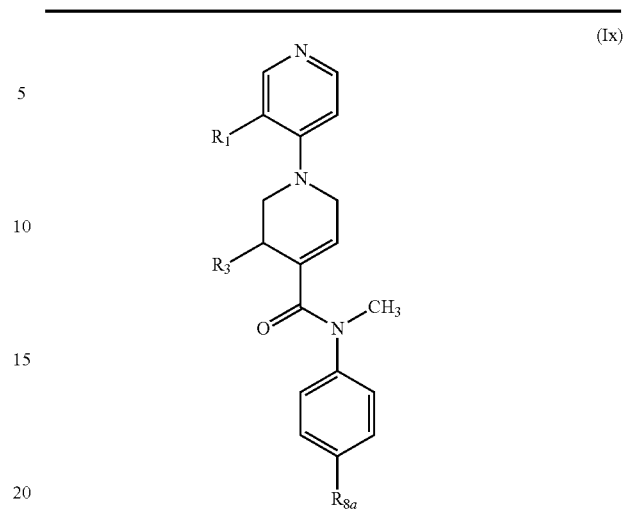

(Ix)

and pharmaceutically acceptable salts thereof, wherein:

| Compound | $R_1$ | $R_{8a}$ |
|---|---|---|
| X157 (a and b) | —OH | —Cl |
| X158 (a and b) | —OH | —Br |
| X159 (a and b) | —OH | —I |
| X160 (a and b) | —OH | -n-butyl |
| X161 (a and b) | —OH | —$CH_3$ |
| X162 (a and b) | —OH | —$SCF_3$ |
| X163 (a and b) | —OH | —$N(CH_2CH_3)_2$ |
| X164 (a and b) | —OH | —$OCF_2CHF_2$ |
| X165 (a and b) | —OH | —$C(OH)(CF_3)_2$ |
| X166 (a and b) | —OH | -(1,1-dimethyl-pentyl) |
| X167 (a and b) | —OH | -(1,1-dimethyl-acetic acid) ethyl ester |
| X168 (a and b) | —OH | —N-piperidinyl |
| X169 (a and b) | —$NO_2$ | —H |
| X170 (a and b) | —$NO_2$ | -tert-butyl |
| X171 (a and b) | —$NO_2$ | -iso-butyl |
| X172 (a and b) | —$NO_2$ | -sec-butyl |
| X173 (a and b) | —$NO_2$ | -iso-propyl |
| X174 (a and b) | —$NO_2$ | -n-propyl |
| X175 (a and b) | —$NO_2$ | -cyclohexyl |
| X176 (a and b) | —$NO_2$ | -tert-butoxy |
| X177 (a and b) | —$NO_2$ | -isopropoxy |
| X178 (a and b) | —$NO_2$ | —$CF_3$ |
| X179 (a and b) | —$NO_2$ | —$CH_2CF_3$ |
| X180 (a and b) | —$NO_2$ | —$OCF_3$ |
| X181 (a and b) | —$NO_2$ | —Cl |
| X182 (a and b) | —$NO_2$ | —Br |
| X183 (a and b) | —$NO_2$ | —I |
| X184 (a and b) | —$NO_2$ | -n-butyl |
| X185 (a and b) | —$NO_2$ | —$CH_3$ |
| X186 (a and b) | —$NO_2$ | —$SCF_3$ |
| X187 (a and b) | —$NO_2$ | —$N(CH_2CH_3)_2$ |
| X188 (a and b) | —$NO_2$ | —$OCF_2CHF_2$ |
| X189 (a and b) | —$NO_2$ | —$C(OH)(CF_3)_2$ |
| X190 (a and b) | —$NO_2$ | -(1,1-dimethyl-pentyl) |
| X191 (a and b) | —$NO_2$ | -(1,1-dimethyl-acetic acid) ethyl ester |
| X192 (a and b) | —$NO_2$ | —N-piperidinyl |
| X193 (a and b) | —CN | —H |
| X194 (a and b) | —CN | -tert-butyl |
| X195 (a and b) | —CN | -iso-butyl |
| X196 (a and b) | —CN | -sec-butyl |
| X197 (a and b) | —CN | -iso-propyl |
| X198 (a and b) | —CN | -n-propyl |
| X199 (a and b) | —CN | -cyclohexyl |
| X200 (a and b) | —CN | -tert-butoxy |
| X201 (a and b) | —CN | -isopropoxy |
| X202 (a and b) | —CN | —$CF_3$ |
| X203 (a and b) | —CN | —$CH_2CF_3$ |
| X204 (a and b) | —CN | —$OCF_3$ |
| X205 (a and b) | —CN | —Cl |
| X206 (a and b) | —CN | —Br |
| X207 (a and b) | —CN | —I |
| X208 (a and b) | —CN | -n-butyl |

TABLE 24-continued (Ix)

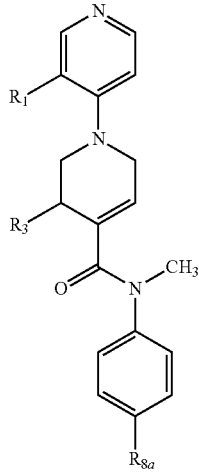

and pharmaceutically acceptable salts thereof, wherein:

| Compound | R₁ | R₈ₐ |
|---|---|---|
| X209 (a and b) | —CN | —CH₃ |
| X210 (a and b) | —CN | —SCF₃ |
| X211 (a and b) | —CN | —N(CH₂CH₃)₂ |
| X212 (a and b) | —CN | —OCF₂CHF₂ |
| X213 (a and b) | —CN | —C(OH)(CF₃)₂ |
| X214 (a and b) | —CN | -(1,1-dimethyl-pentyl) |
| X215 (a and b) | —CN | -(1,1-dimethyl-acetic acid) ethyl ester |
| X216 (a and b) | —CN | —N-piperidinyl |
| X217 (a and b) | —Br | —H |
| X218 (a and b) | —Br | -tert-butyl |
| X219 (a and b) | —Br | -iso-butyl |
| X220 (a and b) | —Br | -sec-butyl |
| X221 (a and b) | —Br | -iso-propyl |
| X222 (a and b) | —Br | -n-propyl |
| X223 (a and b) | —Br | -cyclohexyl |
| X224 (a and b) | —Br | -tert-butoxy |
| X225 (a and b) | —Br | -isopropoxy |
| X226 (a and b) | —Br | —CF₃ |
| X227 (a and b) | —Br | —CH₂CF₃ |
| X228 (a and b) | —Br | —OCF₃ |
| X229 (a and b) | —Br | —Cl |
| X230 (a and b) | —Br | —Br |
| X231 (a and b) | —Br | —I |
| X232 (a and b) | —Br | -n-butyl |
| X233 (a and b) | —Br | —CH₃ |
| X234 (a and b) | —Br | —SCF₃ |
| X235 (a and b) | —Br | —N(CH₂CH₃)₂ |
| X236 (a and b) | —Br | —OCF₂CHF₂ |
| X237 (a and b) | —Br | —C(OH)(CF₃)₂ |
| X238 (a and b) | —Br | -(1,1-dimethyl-pentyl) |
| X239 (a and b) | —Br | -(1,1-dimethyl-acetic acid) ethyl ester |
| X240 (a and b) | —Br | —N-piperidinyl |
| X241 (a and b) | —I | -tert-butyl |
| X242 (a and b) | —I | —H |
| X243 (a and b) | —I | -iso-butyl |
| X244 (a and b) | —I | -sec-butyl |
| X245 (a and b) | —I | -iso-propyl |
| X246 (a and b) | —I | -n-propyl |
| X247 (a and b) | —I | -cyclohexyl |
| X248 (a and b) | —I | -tert-butoxy |
| X249 (a and b) | —I | -isopropoxy |
| X250 (a and b) | —I | —CF₃ |
| X251 (a and b) | —I | —CH₂CF₃ |
| X252 (a and b) | —I | —OCF₃ |
| X253 (a and b) | —I | —Cl |
| X254 (a and b) | —I | —Br |
| X255 (a and b) | —I | —I |
| X256 (a and b) | —I | -n-butyl |
| X257 (a and b) | —I | —CH₃ |
| X258 (a and b) | —I | —SCF₃ |
| X259 (a and b) | —I | —N(CH₂CH₃)₂ |
| X260 (a and b) | —I | —OCF₂CHF₂ |

TABLE 24-continued (Ix)

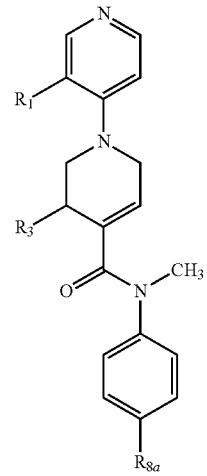

and pharmaceutically acceptable salts thereof, wherein:

| Compound | R₁ | R₈ₐ |
|---|---|---|
| X261 (a and b) | —I | —C(OH)(CF₃)₂ |
| X262 (a and b) | —I | -(1,1-dimethyl-pentyl) |
| X263 (a and b) | —I | -(1,1-dimethyl-acetic acid) ethyl ester |
| X264 (a and b) | —I | —N-piperidinyl |

(a) means that R₃ is —H.
(b) means that R₃ is —CH₃.

TABLE 25

(Iy)

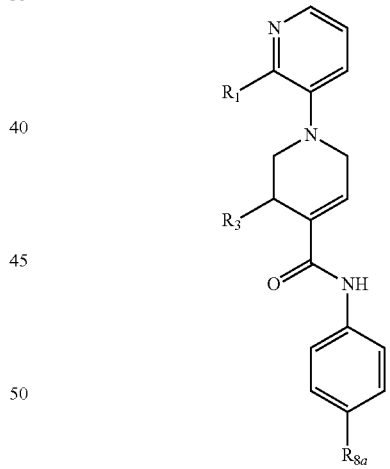

and pharmaceutically acceptable salts thereof, wherein:

| Compound | R₁ | R₈ₐ |
|---|---|---|
| Y1 (a and b) | —H | —H |
| Y2 (a and b) | —H | -tert-butyl |
| Y3 (a and b) | —H | -iso-butyl |
| Y4 (a and b) | —H | -sec-butyl |
| Y5 (a and b) | —H | -iso-propyl |
| Y6 (a and b) | —H | -n-propyl |
| Y7 (a and b) | —H | -cyclohexyl |
| Y8 (a and b) | —H | -tert-butoxy |
| Y9 (a and b) | —H | -isopropoxy |
| Y10 (a and b) | —H | —CF₃ |
| Y11 (a and b) | —H | —CH₂CF₃ |
| Y12 (a and b) | —H | —OCF₃ |

TABLE 25-continued

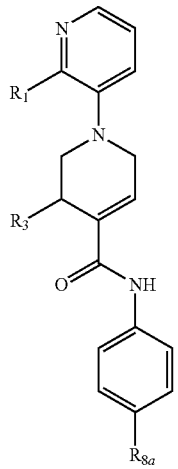

(Iy)

and pharmaceutically acceptable salts thereof, wherein:

| Compound | R₁ | R₈ₐ |
|---|---|---|
| Y13 (a and b) | —H | —Cl |
| Y14 (a and b) | —H | —Br |
| Y15 (a and b) | —H | —I |
| Y16 (a and b) | —H | -n-butyl |
| Y17 (a and b) | —H | —CH₃ |
| Y18 (a and b) | —H | —SCF₃ |
| Y19 (a and b) | —H | —N(CH₂CH₃)₂ |
| Y20 (a and b) | —H | —OCF₂CHF₂ |
| Y21 (a and b) | —H | —C(OH)(CF₃)₂ |
| Y22 (a and b) | —H | -(1,1-dimethyl-pentyl) |
| Y23 (a and b) | —H | -(1,1-dimethyl-acetic acid) ethyl ester |
| Y24 (a and b) | —H | —N-piperidinyl |
| Y25 (a and b) | —Cl | —H |
| Y26 (a and b) | —Cl | -tert-butyl |
| Y27 (a and b) | —Cl | -iso-butyl |
| Y28 (a and b) | —Cl | -sec-butyl |
| Y29 (a and b) | —Cl | -iso-propyl |
| Y30 (a and b) | —Cl | -n-propyl |
| Y31 (a and b) | —Cl | -cyclohexyl |
| Y32 (a and b) | —Cl | -tert-butoxy |
| Y33 (a and b) | —Cl | -isopropoxy |
| Y34 (a and b) | —Cl | —CF₃ |
| Y35 (a and b) | —Cl | —CH₂CF₃ |
| Y36 (a and b) | —Cl | —OCF₃ |
| Y37 (a and b) | —Cl | —Cl |
| Y38 (a and b) | —Cl | —Br |
| Y39 (a and b) | —Cl | —I |
| Y40 (a and b) | —Cl | -n-butyl |
| Y41 (a and b) | —Cl | —CH₃ |
| Y42 (a and b) | —Cl | —SCF₃ |
| Y43 (a and b) | —Cl | —N(CH₂CH₃)₂ |
| Y44 (a and b) | —Cl | —OCF₂CHF₂ |
| Y45 (a and b) | —Cl | —C(OH)(CF₃)₂ |
| Y46 (a and b) | —Cl | -(1,1-dimethyl-pentyl) |
| Y47 (a and b) | —Cl | -(1,1-dimethyl-acetic acid) ethyl ester |
| Y48 (a and b) | —Cl | —N-piperidinyl |
| Y49 (a and b) | —F | —H |
| Y50 (a and b) | —F | -tert-butyl |
| Y51 (a and b) | —F | -iso-butyl |
| Y52 (a and b) | —F | -sec-butyl |
| Y53 (a and b) | —F | -iso-propyl |
| Y54 (a and b) | —F | -n-propyl |
| Y55 (a and b) | —F | -cyclohexyl |
| Y56 (a and b) | —F | -tert-butoxy |
| Y57 (a and b) | —F | -isopropoxy |
| Y58 (a and b) | —F | —CF₃ |
| Y59 (a and b) | —F | —CH₂CF₃ |
| Y60 (a and b) | —F | —OCF₃ |
| Y61 (a and b) | —F | —Cl |
| Y62 (a and b) | —F | —Br |
| Y63 (a and b) | —F | —I |
| Y64 (a and b) | —F | -n-butyl |

TABLE 25-continued

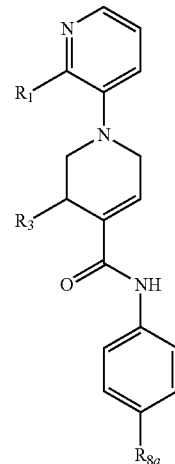

(Iy)

and pharmaceutically acceptable salts thereof, wherein:

| Compound | R₁ | R₈ₐ |
|---|---|---|
| Y65 (a and b) | —F | —CH₃ |
| Y66 (a and b) | —F | —SCF₃ |
| Y67 (a and b) | —F | —N(CH₂CH₃)₂ |
| Y68 (a and b) | —F | —OCF₂CHF₂ |
| Y69 (a and b) | —F | —C(OH)(CF₃)₂ |
| Y70 (a and b) | —F | -(1,1-dimethyl-pentyl) |
| Y71 (a and b) | —F | -(1,1-dimethyl-acetic acid) ethyl ester |
| Y72 (a and b) | —F | —N-piperidinyl |
| Y73 (a and b) | —CH₃ | —H |
| Y74 (a and b) | —CH₃ | -iso-butyl |
| Y75 (a and b) | —CH₃ | -tert-butyl |
| Y76 (a and b) | —CH₃ | -sec-butyl |
| Y77 (a and b) | —CH₃ | -iso-propyl |
| Y78 (a and b) | —CH₃ | -n-propyl |
| Y79 (a and b) | —CH₃ | -cyclohexyl |
| Y80 (a and b) | —CH₃ | -tert-butoxy |
| Y81 (a and b) | —CH₃ | -isopropoxy |
| Y82 (a and b) | —CH₃ | —CF₃ |
| Y83 (a and b) | —CH₃ | —CH₂CF₃ |
| Y84 (a and b) | —CH₃ | —OCF₃ |
| Y85 (a and b) | —CH₃ | —Cl |
| Y86 (a and b) | —CH₃ | —Br |
| Y87 (a and b) | —CH₃ | —I |
| Y88 (a and b) | —CH₃ | -n-butyl |
| Y89 (a and b) | —CH₃ | —CH₃ |
| Y90 (a and b) | —CH₃ | —SCF₃ |
| Y91 (a and b) | —CH₃ | —N(CH₂CH₃)₂ |
| Y92 (a and b) | —CH₃ | —OCF₂CHF₂ |
| Y93 (a and b) | —CH₃ | —C(OH)(CF₃)₂ |
| Y94 (a and b) | —CH₃ | -(1,1-dimethyl-pentyl) |
| Y95 (a and b) | —CH₃ | -(1,1-dimethyl-acetic acid) ethyl ester |
| Y96 (a and b) | —CH₃ | —N-piperidinyl |
| Y97 (a and b) | —CF₃ | —H |
| Y98 (a and b) | —CF₃ | -tert-butyl |
| Y99 (a and b) | —CF₃ | -iso-butyl |
| Y100 (a and b) | —CF₃ | -sec-butyl |
| Y101 (a and b) | —CF₃ | -iso-propyl |
| Y102 (a and b) | —CF₃ | -n-propyl |
| Y103 (a and b) | —CF₃ | -cyclohexyl |
| Y104 (a and b) | —CF₃ | -tert-butoxy |
| Y105 (a and b) | —CF₃ | -isopropoxy |
| Y106 (a and b) | —CF₃ | —CF₃ |
| Y107 (a and b) | —CF₃ | —CH₂CF₃ |
| Y108 (a and b) | —CF₃ | —OCF₃ |
| Y109 (a and b) | —CF₃ | —Cl |
| Y110 (a and b) | —CF₃ | —Br |
| Y111 (a and b) | —CF₃ | —I |
| Y112 (a and b) | —CF₃ | -n-butyl |
| Y113 (a and b) | —CF₃ | —CH₃ |
| Y114 (a and b) | —CF₃ | —SCF₃ |
| Y115 (a and b) | —CF₃ | —N(CH₂CH₃)₂ |
| Y116 (a and b) | —CF₃ | —OCF₂CHF₂ |

TABLE 25-continued

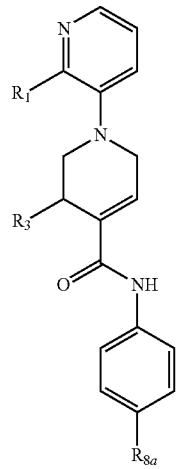

(Iy)

and pharmaceutically acceptable salts thereof, wherein:

| Compound | $R_1$ | $R_{8a}$ |
|---|---|---|
| Y117 (a and b) | —$CF_3$ | —C(OH)($CF_3$)$_2$ |
| Y118 (a and b) | —$CF_3$ | -(1,1-dimethyl-pentyl) |
| Y119 (a and b) | —$CF_3$ | -(1,1-dimethyl-acetic acid) ethyl ester |
| Y120 (a and b) | —$CF_3$ | —N-piperidinyl |
| Y121 (a and b) | —$CHF_2$ | -tert-butyl |
| Y122 (a and b) | —$CHF_2$ | —H |
| Y123 (a and b) | —$CHF_2$ | -iso-butyl |
| Y124 (a and b) | —$CHF_2$ | -sec-butyl |
| Y125 (a and b) | —$CHF_2$ | -iso-propyl |
| Y126 (a and b) | —$CHF_2$ | -n-propyl |
| Y127 (a and b) | —$CHF_2$ | -cyclohexyl |
| Y128 (a and b) | —$CHF_2$ | -tert-butoxy |
| Y129 (a and b) | —$CHF_2$ | -isopropoxy |
| Y130 (a and b) | —$CHF_2$ | —$CF_3$ |
| Y131 (a and b) | —$CHF_2$ | —$CH_2CF_3$ |
| Y132 (a and b) | —$CHF_2$ | —$OCF_3$ |
| Y133 (a and b) | —$CHF_2$ | —Cl |
| Y134 (a and b) | —$CHF_2$ | —Br |
| Y135 (a and b) | —$CHF_2$ | —I |
| Y136 (a and b) | —$CHF_2$ | -n-butyl |
| Y137 (a and b) | —$CHF_2$ | —$CH_3$ |
| Y138 (a and b) | —$CHF_2$ | —$SCF_3$ |
| Y139 (a and b) | —$CHF_2$ | —N($CH_2CH_3$)$_2$ |
| Y140 (a and b) | —$CHF_2$ | —$OCF_2CHF_2$ |
| Y141 (a and b) | —$CHF_2$ | —C(OH)($CF_3$)$_2$ |
| Y142 (a and b) | —$CHF_2$ | -(1,1-dimethyl-pentyl) |
| Y143 (a and b) | —$CHF_2$ | -(1,1-dimethyl-acetic acid) ethyl ester |
| Y144 (a and b) | —$CHF_2$ | —N-piperidinyl |
| Y145 (a and b) | —OH | —H |
| Y146 (a and b) | —OH | -tert-butyl |
| Y147 (a and b) | —OH | -iso-butyl |
| Y148 (a and b) | —OH | -sec-butyl |
| Y149 (a and b) | —OH | -iso-propyl |
| Y150 (a and b) | —OH | -n-propyl |
| Y151 (a and b) | —OH | -cyclohexyl |
| Y152 (a and b) | —OH | -tert-butoxy |
| Y153 (a and b) | —OH | -isopropoxy |
| Y154 (a and b) | —OH | —$CF_3$ |
| Y155 (a and b) | —OH | —$CH_2CF_3$ |
| Y156 (a and b) | —OH | —$OCF_3$ |
| Y157 (a and b) | —OH | —Cl |
| Y158 (a and b) | —OH | —Br |
| Y159 (a and b) | —OH | —I |
| Y160 (a and b) | —OH | -n-butyl |
| Y161 (a and b) | —OH | —$CH_3$ |
| Y162 (a and b) | —OH | —$SCF_3$ |
| Y163 (a and b) | —OH | —N($CH_2CH_3$)$_2$ |
| Y164 (a and b) | —OH | —$OCF_2CHF_2$ |
| Y165 (a and b) | —OH | —C(OH)($CF_3$)$_2$ |
| Y166 (a and b) | —OH | -(1,1-dimethyl-pentyl) |
| Y167 (a and b) | —OH | -(1,1-dimethyl-acetic acid) ethyl ester |
| Y168 (a and b) | —OH | —N-piperidinyl |

TABLE 25-continued

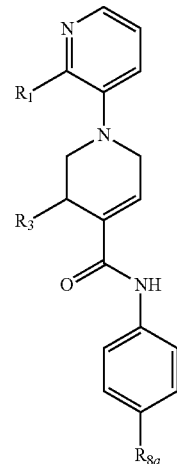

(Iy)

and pharmaceutically acceptable salts thereof, wherein:

| Compound | $R_1$ | $R_{8a}$ |
|---|---|---|
| Y169 (a and b) | —$NO_2$ | —H |
| Y170 (a and b) | —$NO_2$ | -tert-butyl |
| Y171 (a and b) | —$NO_2$ | -iso-butyl |
| Y172 (a and b) | —$NO_2$ | -sec-butyl |
| Y173 (a and b) | —$NO_2$ | -iso-propyl |
| Y174 (a and b) | —$NO_2$ | -n-propyl |
| Y175 (a and b) | —$NO_2$ | -cyclohexyl |
| Y176 (a and b) | —$NO_2$ | -tert-butoxy |
| Y177 (a and b) | —$NO_2$ | -isopropoxy |
| Y178 (a and b) | —$NO_2$ | —$CF_3$ |
| Y179 (a and b) | —$NO_2$ | —$CH_2CF_3$ |
| Y180 (a and b) | —$NO_2$ | —$OCF_3$ |
| Y181 (a and b) | —$NO_2$ | —Cl |
| Y182 (a and b) | —$NO_2$ | —Br |
| Y183 (a and b) | —$NO_2$ | —I |
| Y184 (a and b) | —$NO_2$ | -n-butyl |
| Y185 (a and b) | —$NO_2$ | —$CH_3$ |
| Y186 (a and b) | —$NO_2$ | —$SCF_3$ |
| Y187 (a and b) | —$NO_2$ | —N($CH_2CH_3$)$_2$ |
| Y188 (a and b) | —$NO_2$ | —$OCF_2CHF_2$ |
| Y189 (a and b) | —$NO_2$ | —C(OH)($CF_3$)$_2$ |
| Y190 (a and b) | —$NO_2$ | -(1,1-dimethyl-pentyl) |
| Y191 (a and b) | —$NO_2$ | -(1,1-dimethyl-acetic acid) ethyl ester |
| Y192 (a and b) | —$NO_2$ | —N-piperidinyl |
| Y193 (a and b) | —CN | —H |
| Y194 (a and b) | —CN | -tert-butyl |
| Y195 (a and b) | —CN | -iso-butyl |
| Y196 (a and b) | —CN | -sec-butyl |
| Y197 (a and b) | —CN | -iso-propyl |
| Y198 (a and b) | —CN | -n-propyl |
| Y199 (a and b) | —CN | -cyclohexyl |
| Y200 (a and b) | —CN | -tert-butoxy |
| Y201 (a and b) | —CN | -isopropoxy |
| Y202 (a and b) | —CN | —$CF_3$ |
| Y203 (a and b) | —CN | —$CH_2CF_3$ |
| Y204 (a and b) | —CN | —$OCF_3$ |
| Y205 (a and b) | —CN | —Cl |
| Y206 (a and b) | —CN | —Br |
| Y207 (a and b) | —CN | —I |
| Y208 (a and b) | —CN | -n-butyl |
| Y209 (a and b) | —CN | —$CH_3$ |
| Y210 (a and b) | —CN | —$SCF_3$ |
| Y211 (a and b) | —CN | —N($CH_2CH_3$)$_2$ |
| Y212 (a and b) | —CN | —$OCF_2CHF_2$ |
| Y213 (a and b) | —CN | —C(OH)($CF_3$)$_2$ |
| Y214 (a and b) | —CN | -(1,1-dimethyl-pentyl) |
| Y215 (a and b) | —CN | -(1,1-dimethyl-acetic acid) ethyl ester |
| Y216 (a and b) | —CN | —N-piperidinyl |
| Y217 (a and b) | —Br | —H |
| Y218 (a and b) | —Br | -tert-butyl |
| Y219 (a and b) | —Br | -iso-butyl |
| Y220 (a and b) | —Br | -sec-butyl |

TABLE 25-continued

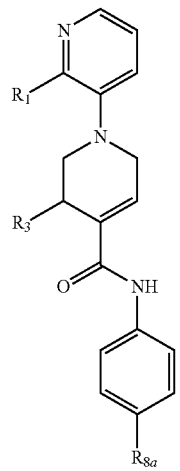

(Iy)

and pharmaceutically acceptable salts thereof, wherein:

| Compound | $R_1$ | $R_{8a}$ |
|---|---|---|
| Y221 (a and b) | —Br | -iso-propyl |
| Y222 (a and b) | —Br | -n-propyl |
| Y223 (a and b) | —Br | -cyclohexyl |
| Y224 (a and b) | —Br | -tert-butoxy |
| Y225 (a and b) | —Br | -isopropoxy |
| Y226 (a and b) | —Br | —$CF_3$ |
| Y227 (a and b) | —Br | —$CH_2CF_3$ |
| Y228 (a and b) | —Br | —$OCF_3$ |
| Y229 (a and b) | —Br | —Cl |
| Y230 (a and b) | —Br | —Br |
| Y231 (a and b) | —Br | —I |
| Y232 (a and b) | —Br | -n-butyl |
| Y233 (a and b) | —Br | —$CH_3$ |
| Y234 (a and b) | —Br | —$SCF_3$ |
| Y235 (a and b) | —Br | —$N(CH_2CH_3)_2$ |
| Y236 (a and b) | —Br | —$OCF_2CHF_2$ |
| Y237 (a and b) | —Br | —$C(OH)(CF_3)_2$ |
| Y238 (a and b) | —Br | -(1,1-dimethyl-pentyl) |
| Y239 (a and b) | —Br | -(1,1-dimethyl-acetic acid) ethyl ester |
| Y240 (a and b) | —Br | —N-piperidinyl |
| Y241 (a and b) | —I | -tert-butyl |
| Y242 (a and b) | —I | —H |
| Y243 (a and b) | —I | -iso-butyl |
| Y244 (a and b) | —I | -sec-butyl |
| Y245 (a and b) | —I | -iso-propyl |
| Y246 (a and b) | —I | -n-propyl |
| Y247 (a and b) | —I | -cyclohexyl |
| Y248 (a and b) | —I | -tert-butoxy |
| Y249 (a and b) | —I | -isopropoxy |
| Y250 (a and b) | —I | —$CF_3$ |
| Y251 (a and b) | —I | —$CH_2CF_3$ |
| Y252 (a and b) | —I | —$OCF_3$ |
| Y253 (a and b) | —I | —Cl |
| Y254 (a and b) | —I | —Br |
| Y255 (a and b) | —I | —I |
| Y256 (a and b) | —I | -n-butyl |
| Y257 (a and b) | —I | —$CH_3$ |
| Y258 (a and b) | —I | —$SCF_3$ |
| Y259 (a and b) | —I | —$N(CH_2CH_3)_2$ |
| Y260 (a and b) | —I | —$OCF_2CHF_2$ |
| Y261 (a and b) | —I | —$C(OH)(CF_3)_2$ |
| Y262 (a and b) | —I | -(1,1-dimethyl-pentyl) |
| Y263 (a and b) | —I | -(1,1-dimethyl-acetic acid) ethyl ester |
| Y264 (a and b) | —I | —N-piperidinyl |

(a) means that $R_3$ is —H.
(b) means that $R_3$ is —$CH_3$.

TABLE 26

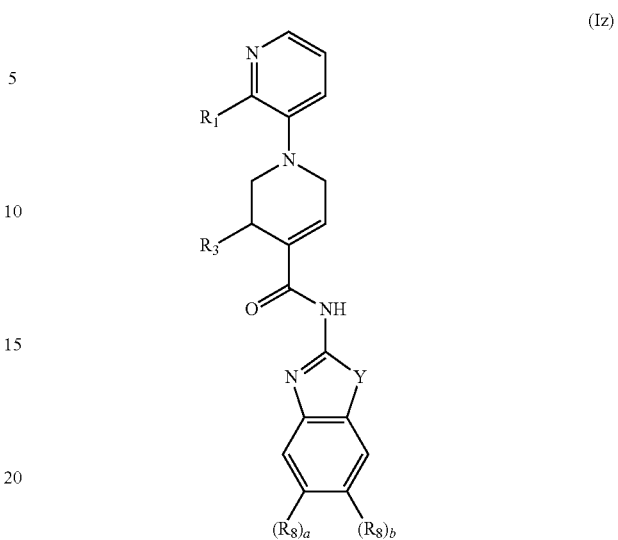

(Iz)

and pharmaceutically acceptable salts thereof, wherein:

| Compound | Y | $R_1$ | $(R_8)_a$ | $(R_8)_b$ |
|---|---|---|---|---|
| Z1 (a and b) | S | —H | —Cl | —H |
| Z2 (a and b) | S | —H | —Br | —H |
| Z3 (a and b) | S | —H | —F | —H |
| Z4 (a and b) | S | —H | —$CH_3$ | —H |
| Z5 (a and b) | S | —H | —$CF_3$ | —H |
| Z6 (a and b) | S | —H | —$OCH_3$ | —H |
| Z7 (a and b) | S | —H | —$OCH_2CH_3$ | —H |
| Z8 (a and b) | S | —H | —$OCF_3$ | —H |
| Z9 (a and b) | S | —H | -tert-butyl | —H |
| Z10 (a and b) | S | —H | -iso-propyl | —H |
| Z11 (a and b) | S | —H | —$CH_3$ | —$CH_3$ |
| Z12 (a and b) | S | —H | —H | —H |
| Z13 (a and b) | S | —H | —H | —Cl |
| Z14 (a and b) | S | —H | —H | —Br |
| Z15 (a and b) | S | —H | —H | —F |
| Z16 (a and b) | S | —H | —H | —$CH_3$ |
| Z17 (a and b) | S | —H | —H | —$CF_3$ |
| Z18 (a and b) | S | —H | —H | —$OCH_3$ |
| Z19 (a and b) | S | —H | —H | —$OCH_2CH_3$ |
| Z20 (a and b) | S | —H | —H | —$OCF_3$ |
| Z21 (a and b) | S | —H | —H | -tert-butyl |
| Z22 (a and b) | S | —H | —H | -iso-propyl |
| Z23 (a and b) | S | —Cl | —Cl | —H |
| Z24 (a and b) | S | —Cl | —Br | —H |
| Z25 (a and b) | S | —Cl | —F | —H |
| Z26 (a and b) | S | —Cl | —$CH_3$ | —H |
| Z27 (a and b) | S | —Cl | —$CF_3$ | —H |
| Z28 (a and b) | S | —Cl | —$OCH_3$ | —H |
| Z29 (a and b) | S | —Cl | —$OCH_2CH_3$ | —H |
| Z30 (a and b) | S | —Cl | —$OCF_3$ | —H |
| Z31 (a and b) | S | —Cl | -tert-butyl | —H |
| Z32 (a and b) | S | —Cl | -iso-propyl | —H |
| Z33 (a and b) | S | —Cl | —$CH_3$ | —$CH_3$ |
| Z34 (a and b) | S | —Cl | —H | —H |
| Z35 (a and b) | S | —Cl | —H | —Cl |
| Z36 (a and b) | S | —Cl | —H | —Br |
| Z37 (a and b) | S | —Cl | —H | —F |
| Z38 (a and b) | S | —Cl | —H | —$CH_3$ |
| Z39 (a and b) | S | —Cl | —H | —$CF_3$ |
| Z40 (a and b) | S | —Cl | —H | —$OCH_3$ |
| Z41 (a and b) | S | —Cl | —H | —$OCH_2CH_3$ |
| Z42 (a and b) | S | —Cl | —H | —$OCF_3$ |
| Z43 (a and b) | S | —Cl | —H | -tert-butyl |
| Z44 (a and b) | S | —Cl | —H | -iso-propyl |
| Z45 (a and b) | S | —Cl | —H | —$OCF_3$ |
| Z46 (a and b) | S | —Cl | —H | -tert-butyl |
| Z47 (a and b) | S | —Cl | —H | -iso-propyl |
| Z48 (a and b) | S | —$CH_3$ | —Cl | —H |
| Z49 (a and b) | S | —$CH_3$ | —Br | —H |

TABLE 26-continued (Iz)

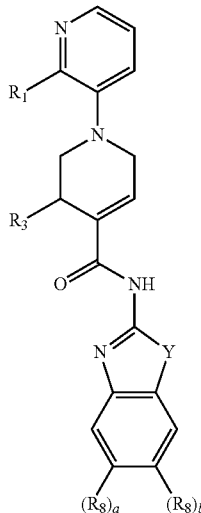

and pharmaceutically acceptable salts thereof, wherein:

| Compound | Y | R₁ | (R₈)ₐ | (R₈)ᵦ |
|---|---|---|---|---|
| Z50 (a and b) | S | —CH₃ | —F | —H |
| Z51 (a and b) | S | —CH₃ | —CH₃ | —H |
| Z52 (a and b) | S | —CH₃ | —CF₃ | —H |
| Z53 (a and b) | S | —CH₃ | —OCH₃ | —H |
| Z54 (a and b) | S | —CH₃ | —OCH₂CH₃ | —H |
| Z55 (a and b) | S | —CH₃ | —OCF₃ | —H |
| Z56 (a and b) | S | —CH₃ | -tert-butyl | —H |
| Z57 (a and b) | S | —CH₃ | -iso-propyl | —H |
| Z58 (a and b) | S | —CH₃ | —CH₃ | —CH₃ |
| Z59 (a and b) | S | —CH₃ | —H | —H |
| Z60 (a and b) | S | —CH₃ | —H | —Cl |
| Z61 (a and b) | S | —CH₃ | —H | —Br |
| Z62 (a and b) | S | —CH₃ | —H | —F |
| Z63 (a and b) | S | —CH₃ | —H | —CH₃ |
| Z64 (a and b) | S | —CH₃ | —H | —CF₃ |
| Z65 (a and b) | S | —CH₃ | —H | —OCH₃ |
| Z66 (a and b) | S | —CH₃ | —H | —OCH₂CH₃ |
| Z67 (a and b) | S | —CH₃ | —H | —OCF₃ |
| Z68 (a and b) | S | —CH₃ | —H | -tert-butyl |
| Z69 (a and b) | S | —CH₃ | —H | -iso-propyl |
| Z70 (a and b) | S | —CF₃ | —Cl | —H |
| Z71 (a and b) | S | —CF₃ | —Br | —H |
| Z72 (a and b) | S | —CF₃ | —F | —H |
| Z73 (a and b) | S | —CF₃ | —CH₃ | —H |
| Z74 (a and b) | S | —CF₃ | —CF₃ | —H |
| Z75 (a and b) | S | —CF₃ | —OCH₃ | —H |
| Z76 (a and b) | S | —CF₃ | —OCH₂CH₃ | —H |
| Z77 (a and b) | S | —CF₃ | —OCF₃ | —H |
| Z78 (a and b) | S | —CF₃ | -tert-butyl | —H |
| Z79 (a and b) | S | —CF₃ | -iso-propyl | —H |
| Z80 (a and b) | S | —CF₃ | —CH₃ | —CH₃ |
| Z81 (a and b) | S | —CF₃ | —H | —H |
| Z82 (a and b) | S | —CF₃ | —H | —Cl |
| Z83 (a and b) | S | —CF₃ | —H | —Br |
| Z84 (a and b) | S | —CF₃ | —H | —F |
| Z85 (a and b) | S | —CF₃ | —H | —CH₃ |
| Z86 (a and b) | S | —CF₃ | —H | —CF₃ |
| Z87 (a and b) | S | —CF₃ | —H | —OCH₃ |
| Z88 (a and b) | S | —CF₃ | —H | —OCH₂CH₃ |
| Z89 (a and b) | S | —CF₃ | —H | —OCF₃ |
| Z90 (a and b) | S | —CF₃ | —H | -tert-butyl |
| Z91 (a and b) | S | —CF₃ | —H | -iso-propyl |
| Z92 (a and b) | S | —CHF₂ | —Cl | —H |
| Z93 (a and b) | S | —CHF₂ | —Br | —H |
| Z94 (a and b) | S | —CHF₂ | —F | —H |
| Z95 (a and b) | S | —CHF₂ | —CH₃ | —H |
| Z96 (a and b) | S | —CHF₂ | —CF₃ | —H |
| Z97 (a and b) | S | —CHF₂ | —OCH₃ | —H |
| Z98 (a and b) | S | —CHF₂ | —OCH₂CH₃ | —H |

TABLE 26-continued (Iz)

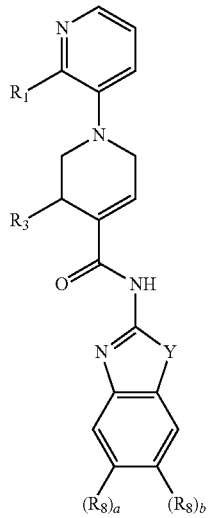

and pharmaceutically acceptable salts thereof, wherein:

| Compound | Y | R₁ | (R₈)ₐ | (R₈)ᵦ |
|---|---|---|---|---|
| Z99 (a and b) | S | —CHF₂ | —OCF₃ | —H |
| Z100 (a and b) | S | —CHF₂ | -tert-butyl | —H |
| Z101 (a and b) | S | —CHF₂ | -iso-propyl | —H |
| Z102 (a and b) | S | —CHF₂ | —CH₃ | —CH₃ |
| Z103 (a and b) | S | —CHF₂ | —H | —H |
| Z104 (a and b) | S | —CHF₂ | —H | —Cl |
| Z105 (a and b) | S | —CHF₂ | —H | —Br |
| Z106 (a and b) | S | —CHF₂ | —H | —F |
| Z107 (a and b) | S | —CHF₂ | —H | —CH₃ |
| Z108 (a and b) | S | —CHF₂ | —H | —CF₃ |
| Z109 (a and b) | S | —CHF₂ | —H | —OCH₃ |
| Z110 (a and b) | S | —CHF₂ | —H | —OCH₂CH₃ |
| Z111 (a and b) | S | —CHF₂ | —H | —OCF₃ |
| Z112 (a and b) | S | —CHF₂ | —H | -tert-butyl |
| Z113 (a and b) | S | —CHF₂ | —H | -iso-propyl |
| Z114 (a and b) | S | —OH | —Cl | —H |
| Z115 (a and b) | S | —OH | —Br | —H |
| Z116 (a and b) | S | —OH | —F | —H |
| Z117 (a and b) | S | —OH | —CH₃ | —H |
| Z118 (a and b) | S | —OH | —CF₃ | —H |
| Z119 (a and b) | S | —OH | —OCH₃ | —H |
| Z120 (a and b) | S | —OH | —OCH₂CH₃ | —H |
| Z121 (a and b) | S | —OH | —OCF₃ | —H |
| Z122 (a and b) | S | —OH | -tert-butyl | —H |
| Z123 (a and b) | S | —OH | -iso-propyl | —H |
| Z124 (a and b) | S | —OH | —CH₃ | —CH₃ |
| Z125 (a and b) | S | —OH | —H | —H |
| Z126 (a and b) | S | —OH | —H | —Cl |
| Z127 (a and b) | S | —OH | —H | —Br |
| Z128 (a and b) | S | —OH | —H | —F |
| Z129 (a and b) | S | —OH | —H | —CH₃ |
| Z130 (a and b) | S | —OH | —H | —CF₃ |
| Z131 (a and b) | S | —OH | —H | —OCH₃ |
| Z132 (a and b) | S | —OH | —H | —OCH₂CH₃ |
| Z133 (a and b) | S | —OH | —H | —OCF₃ |
| Z134 (a and b) | S | —OH | —H | -tert-butyl |
| Z135 (a and b) | S | —OH | —H | -iso-propyl |
| Z136 (a and b) | S | —NO₂ | —Cl | —H |
| Z137 (a and b) | S | —NO₂ | —Br | —H |
| Z138 (a and b) | S | —NO₂ | —F | —H |
| Z139 (a and b) | S | —NO₂ | —CH₃ | —H |
| Z140 (a and b) | S | —NO₂ | —CF₃ | —H |
| Z141 (a and b) | S | —NO₂ | —OCH₃ | —H |
| Z142 (a and b) | S | —NO₂ | —OCH₂CH₃ | —H |
| Z143 (a and b) | S | —NO₂ | —OCF₃ | —H |
| Z144 (a and b) | S | —NO₂ | -tert-butyl | —H |
| Z145 (a and b) | S | —NO₂ | -iso-propyl | —H |
| Z146 (a and b) | S | —NO₂ | —CH₃ | —CH₃ |
| Z147 (a and b) | S | —NO₂ | —H | —H |

TABLE 26-continued

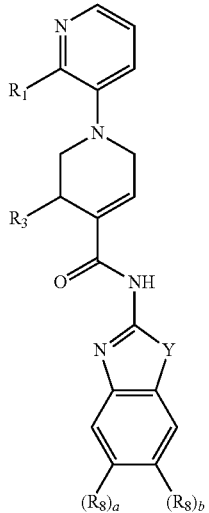

(Iz)

and pharmaceutically acceptable salts thereof, wherein:

| Compound | Y | $R_1$ | $(R_8)_a$ | $(R_8)_b$ |
|---|---|---|---|---|
| Z148 (a and b) | S | —$NO_2$ | —H | —Cl |
| Z149 (a and b) | S | —$NO_2$ | —H | —Br |
| Z150 (a and b) | S | —$NO_2$ | —H | —F |
| Z151 (a and b) | S | —$NO_2$ | —H | —$CH_3$ |
| Z152 (a and b) | S | —$NO_2$ | —H | —$CF_3$ |
| Z153 (a and b) | S | —$NO_2$ | —H | —$OCH_3$ |
| Z154 (a and b) | S | —$NO_2$ | —H | —$OCH_2CH_3$ |
| Z155 (a and b) | S | —$NO_2$ | —H | —$OCF_3$ |
| Z156 (a and b) | S | —$NO_2$ | —H | -tert-butyl |
| Z157 (a and b) | S | —$NO_2$ | —H | -iso-propyl |
| Z158 (a and b) | S | —CN | —Br | —H |
| Z159 (a and b) | S | —CN | —Cl | —H |
| Z160 (a and b) | S | —CN | —F | —H |
| Z161 (a and b) | S | —CN | —$CH_3$ | —H |
| Z162 (a and b) | S | —CN | —$CF_3$ | —H |
| Z163 (a and b) | S | —CN | —$OCH_3$ | —H |
| Z164 (a and b) | S | —CN | —$OCH_2CH_3$ | —H |
| Z165 (a and b) | S | —CN | —$OCF_3$ | —H |
| Z166 (a and b) | S | —CN | -tert-butyl | —H |
| Z167 (a and b) | S | —CN | -iso-propyl | —H |
| Z168 (a and b) | S | —CN | —$CH_3$ | —$CH_3$ |
| Z169 (a and b) | S | —CN | —H | —H |
| Z170 (a and b) | S | —CN | —H | —Cl |
| Z171 (a and b) | S | —CN | —H | —Br |
| Z172 (a and b) | S | —CN | —H | —F |
| Z173 (a and b) | S | —CN | —H | —$CH_3$ |
| Z174 (a and b) | S | —CN | —H | —$CF_3$ |
| Z175 (a and b) | S | —CN | —H | —$OCH_3$ |
| Z176 (a and b) | S | —CN | —H | —$OCH_2CH_3$ |
| Z177 (a and b) | S | —CN | —H | —$OCF_3$ |
| Z178 (a and b) | S | —CN | —H | -tert-butyl |
| Z179 (a and b) | S | —CN | —H | -iso-propyl |
| Z180 (a and b) | S | —Br | —Br | —H |
| Z181 (a and b) | S | —Br | —Cl | —H |
| Z182 (a and b) | S | —Br | —F | —H |
| Z183 (a and b) | S | —Br | —$CH_3$ | —H |
| Z184 (a and b) | S | —Br | —$CF_3$ | —H |
| Z185 (a and b) | S | —Br | —$OCH_3$ | —H |
| Z186 (a and b) | S | —Br | —$OCH_2CH_3$ | —H |
| Z187 (a and b) | S | —Br | —$OCF_3$ | —H |
| Z188 (a and b) | S | —Br | -tert-butyl | —H |
| Z189 (a and b) | S | —Br | -iso-propyl | —H |
| Z190 (a and b) | S | —Br | —$CH_3$ | —$CH_3$ |
| Z191 (a and b) | S | —Br | —H | —H |
| Z192 (a and b) | S | —Br | —H | —Cl |
| Z193 (a and b) | S | —Br | —H | —Br |
| Z194 (a and b) | S | —Br | —H | —F |
| Z195 (a and b) | S | —Br | —H | —$CH_3$ |
| Z196 (a and b) | S | —Br | —H | —$CF_3$ |

TABLE 26-continued

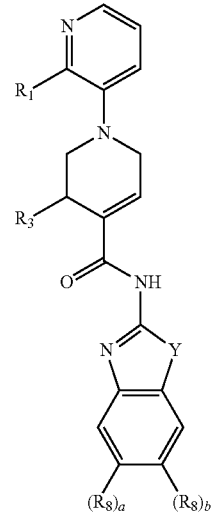

(Iz)

and pharmaceutically acceptable salts thereof, wherein:

| Compound | Y | $R_1$ | $(R_8)_a$ | $(R_8)_b$ |
|---|---|---|---|---|
| Z197 (a and b) | S | —Br | —H | —$OCH_3$ |
| Z198 (a and b) | S | —Br | —H | —$OCH_2CH_3$ |
| Z199 (a and b) | S | —Br | —H | —$OCF_3$ |
| Z200 (a and b) | S | —Br | —H | -tert-butyl |
| Z201 (a and b) | S | —Br | —H | -iso-propyl |
| Z202 (a and b) | S | —I | —Cl | —H |
| Z203 (a and b) | S | —I | —Br | —H |
| Z204 (a and b) | S | —I | —F | —H |
| Z205 (a and b) | S | —I | —$CH_3$ | —H |
| Z206 (a and b) | S | —I | —$CF_3$ | —H |
| Z207 (a and b) | S | —I | —$OCH_3$ | —H |
| Z208 (a and b) | S | —I | —$OCH_2CH_3$ | —H |
| Z209 (a and b) | S | —I | —$OCF_3$ | —H |
| Z210 (a and b) | S | —I | -tert-butyl | —H |
| Z211 (a and b) | S | —I | -iso-propyl | —H |
| Z212 (a and b) | S | —I | —$CH_3$ | —$CH_3$ |
| Z213 (a and b) | S | —I | —H | —H |
| Z214 (a and b) | S | —I | —H | —Cl |
| Z215 (a and b) | S | —I | —H | —Br |
| Z216 (a and b) | S | —I | —H | —F |
| Z217 (a and b) | S | —I | —H | —$CH_3$ |
| Z218 (a and b) | S | —I | —H | —$CF_3$ |
| Z219 (a and b) | S | —I | —H | —$OCH_3$ |
| Z220 (a and b) | S | —I | —H | —$OCH_2CH_3$ |
| Z221 (a and b) | S | —I | —H | —$OCF_3$ |
| Z222 (a and b) | S | —I | —H | -tert-butyl |
| Z223 (a and b) | S | —I | —H | -iso-propyl |
| Z224 (a and b) | O | —H | —Cl | —H |
| Z225 (a and b) | O | —H | —Br | —H |
| Z226 (a and b) | O | —H | —F | —H |
| Z227 (a and b) | O | —H | —$CH_3$ | —H |
| Z228 (a and b) | O | —H | —$CF_3$ | —H |
| Z229 (a and b) | O | —H | —$OCH_3$ | —H |
| Z230 (a and b) | O | —H | —$OCH_2CH_3$ | —H |
| Z231 (a and b) | O | —H | —$OCF_3$ | —H |
| Z232 (a and b) | O | —H | -tert-butyl | —H |
| Z233 (a and b) | O | —H | -iso-propyl | —H |
| Z234 (a and b) | O | —H | —$CH_3$ | —$CH_3$ |
| Z235 (a and b) | O | —H | —H | —H |
| Z236 (a and b) | O | —H | —H | —Cl |
| Z237 (a and b) | O | —H | —H | —Br |
| Z238 (a and b) | O | —H | —H | —F |
| Z239 (a and b) | O | —H | —H | —$CH_3$ |
| Z240 (a and b) | O | —H | —H | —$CF_3$ |
| Z241 (a and b) | O | —H | —H | —$OCH_3$ |
| Z242 (a and b) | O | —H | —H | —$OCH_2CH_3$ |
| Z243 (a and b) | O | —H | —H | —$OCF_3$ |
| Z244 (a and b) | O | —H | —H | -tert-butyl |
| Z245 (a and b) | O | —H | —H | -iso-propyl |

TABLE 26-continued (Iz)

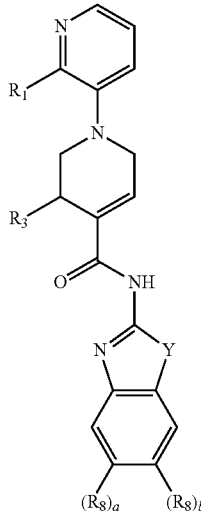

and pharmaceutically acceptable salts thereof, wherein:

| Compound | Y | R₁ | (R₈)ₐ | (R₈)ᵦ |
|---|---|---|---|---|
| Z246 (a and b) | O | —Cl | —Cl | —H |
| Z247 (a and b) | O | —Cl | —Br | —H |
| Z248 (a and b) | O | —Cl | —F | —H |
| Z249 (a and b) | O | —Cl | —CH₃ | —H |
| Z250 (a and b) | O | —Cl | —CF₃ | —H |
| Z251 (a and b) | O | —Cl | —OCH₃ | —H |
| Z252 (a and b) | O | —Cl | —OCH₂CH₃ | —H |
| Z253 (a and b) | O | —Cl | —OCF₃ | —H |
| Z254 (a and b) | O | —Cl | -tert-butyl | —H |
| Z255 (a and b) | O | —Cl | -iso-propyl | —H |
| Z256 (a and b) | O | —Cl | —CH₃ | —CH₃ |
| Z257 (a and b) | O | —Cl | —H | —H |
| Z258 (a and b) | O | —Cl | —H | —CH₃ |
| Z259 (a and b) | O | —Cl | —H | —Cl |
| Z260 (a and b) | O | —Cl | —H | —Br |
| Z261 (a and b) | O | —Cl | —H | —F |
| Z262 (a and b) | O | —Cl | —H | —CF₃ |
| Z263 (a and b) | O | —Cl | —H | —OCH₃ |
| Z264 (a and b) | O | —Cl | —H | —OCH₂CH₃ |
| Z265 (a and b) | O | —Cl | —H | —OCF₃ |
| Z266 (a and b) | O | —Cl | —H | -tert-butyl |
| Z267 (a and b) | O | —Cl | —H | -iso-propyl |
| Z268 (a and b) | O | —Cl | —H | —OCF₃ |
| Z269 (a and b) | O | —Cl | —H | -tert-butyl |
| Z270 (a and b) | O | —Cl | —H | -iso-propyl |
| Z271 (a and b) | O | —CH₃ | —Cl | —H |
| Z272 (a and b) | O | —CH₃ | —Br | —H |
| Z273 (a and b) | O | —CH₃ | —F | —H |
| Z274 (a and b) | O | —CH₃ | —CH₃ | —H |
| Z275 (a and b) | O | —CH₃ | —CF₃ | —H |
| Z276 (a and b) | O | —CH₃ | —OCH₃ | —H |
| Z277 (a and b) | O | —CH₃ | —OCH₂CH₃ | —H |
| Z278 (a and b) | O | —CH₃ | —OCF₃ | —H |
| Z279 (a and b) | O | —CH₃ | -tert-butyl | —H |
| Z280 (a and b) | O | —CH₃ | -iso-propyl | —H |
| Z281 (a and b) | O | —CH₃ | —CH₃ | —CH₃ |
| Z282 (a and b) | O | —CH₃ | —H | —H |
| Z283 (a and b) | O | —CH₃ | —H | —Cl |
| Z284 (a and b) | O | —CH₃ | —H | —Br |
| Z285 (a and b) | O | —CH₃ | —H | —F |
| Z286 (a and b) | O | —CH₃ | —H | —CH₃ |
| Z287 (a and b) | O | —CH₃ | —H | —CF₃ |
| Z288 (a and b) | O | —CH₃ | —H | —OCH₃ |
| Z289 (a and b) | O | —CH₃ | —H | —OCH₂CH₃ |
| Z290 (a and b) | O | —CH₃ | —H | —OCF₃ |
| Z291 (a and b) | O | —CH₃ | —H | -tert-butyl |
| Z292 (a and b) | O | —CH₃ | —H | -iso-propyl |
| Z293 (a and b) | O | —CF₃ | —Cl | —H |
| Z294 (a and b) | O | —CF₃ | —Br | —H |
| Z295 (a and b) | O | —CF₃ | —F | —H |
| Z296 (a and b) | O | —CF₃ | —CH₃ | —H |
| Z297 (a and b) | O | —CF₃ | —CF₃ | —H |
| Z298 (a and b) | O | —CF₃ | —OCH₃ | —H |
| Z299 (a and b) | O | —CF₃ | —OCH₂CH₃ | —H |
| Z300 (a and b) | O | —CF₃ | —OCF₃ | —H |
| Z301 (a and b) | O | —CF₃ | -tert-butyl | —H |
| Z302 (a and b) | O | —CF₃ | -iso-propyl | —H |
| Z303 (a and b) | O | —CF₃ | —CH₃ | —CH₃ |
| Z304 (a and b) | O | —CF₃ | —H | —H |
| Z305 (a and b) | O | —CF₃ | —H | —Cl |
| Z306 (a and b) | O | —CF₃ | —H | —Br |
| Z307 (a and b) | O | —CF₃ | —H | —F |
| Z308 (a and b) | O | —CF₃ | —H | —CH₃ |
| Z309 (a and b) | O | —CF₃ | —H | —CF₃ |
| Z310 (a and b) | O | —CF₃ | —H | —OCH₃ |
| Z311 (a and b) | O | —CF₃ | —H | —OCH₂CH₃ |
| Z312 (a and b) | O | —CF₃ | —H | —OCF₃ |
| Z313 (a and b) | O | —CF₃ | —H | -tert-butyl |
| Z314 (a and b) | O | —CF₃ | —H | -iso-propyl |
| Z315 (a and b) | O | —CHF₂ | —Cl | —H |
| Z316 (a and b) | O | —CHF₂ | —Br | —H |
| Z317 (a and b) | O | —CHF₂ | —F | —H |
| Z318 (a and b) | O | —CHF₂ | —CH₃ | —H |
| Z319 (a and b) | O | —CHF₂ | —CF₃ | —H |
| Z320 (a and b) | O | —CHF₂ | —OCH₃ | —H |
| Z321 (a and b) | O | —CHF₂ | —OCH₂CH₃ | —H |
| Z322 (a and b) | O | —CHF₂ | —OCF₃ | —H |
| Z323 (a and b) | O | —CHF₂ | -tert-butyl | —H |
| Z324 (a and b) | O | —CHF₂ | -iso-propyl | —H |
| Z325 (a and b) | O | —CHF₂ | —CH₃ | —CH₃ |
| Z326 (a and b) | O | —CHF₂ | —H | —H |
| Z327 (a and b) | O | —CHF₂ | —H | —Cl |
| Z328 (a and b) | O | —CHF₂ | —H | —Br |
| Z329 (a and b) | O | —CHF₂ | —H | —F |
| Z330 (a and b) | O | —CHF₂ | —H | —CH₃ |
| Z331 (a and b) | O | —CHF₂ | —H | —CF₃ |
| Z332 (a and b) | O | —CHF₂ | —H | —OCH₃ |
| Z333 (a and b) | O | —CHF₂ | —H | —OCH₂CH₃ |
| Z334 (a and b) | O | —CHF₂ | —H | —OCF₃ |
| Z335 (a and b) | O | —CHF₂ | —H | -tert-butyl |
| Z336 (a and b) | O | —CHF₂ | —H | -iso-propyl |
| Z337 (a and b) | O | —OH | —Cl | —H |
| Z338 (a and b) | O | —OH | —Br | —H |
| Z339 (a and b) | O | —OH | —F | —H |
| Z340 (a and b) | O | —OH | —CH₃ | —H |
| Z341 (a and b) | O | —OH | —CF₃ | —H |
| Z342 (a and b) | O | —OH | —OCH₃ | —H |
| Z343 (a and b) | O | —OH | —OCH₂CH₃ | —H |

TABLE 26-continued (Iz)

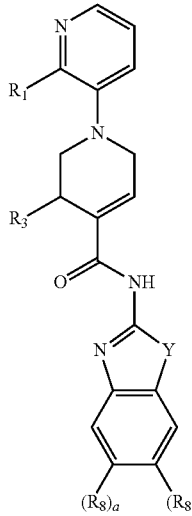

and pharmaceutically acceptable salts thereof, wherein:

| Compound | Y | R₁ | (R₈)ₐ | (R₈)ᵦ |
|---|---|---|---|---|
| Z344 (a and b) | O | —OH | —OCF₃ | —H |
| Z345 (a and b) | O | —OH | -tert-butyl | —H |
| Z346 (a and b) | O | —OH | -iso-propyl | —H |
| Z347 (a and b) | O | —OH | —CH₃ | —CH₃ |
| Z348 (a and b) | O | —OH | —H | —H |
| Z349 (a and b) | O | —OH | —H | —Cl |
| Z350 (a and b) | O | —OH | —H | —Br |
| Z351 (a and b) | O | —OH | —H | —F |
| Z352 (a and b) | O | —OH | —H | —CH₃ |
| Z353 (a and b) | O | —OH | —H | —CF₃ |
| Z354 (a and b) | O | —OH | —H | —OCH₃ |
| Z355 (a and b) | O | —OH | —H | —OCH₂CH₃ |
| Z356 (a and b) | O | —OH | —H | —OCF₃ |
| Z357 (a and b) | O | —OH | —H | -tert-butyl |
| Z358 (a and b) | O | —OH | —H | -iso-propyl |
| Z359 (a and b) | O | —NO₂ | —Cl | —H |
| Z360 (a and b) | O | —NO₂ | —Br | —H |
| Z361 (a and b) | O | —NO₂ | —F | —H |
| Z362 (a and b) | O | —NO₂ | —CH₃ | —H |
| Z363 (a and b) | O | —NO₂ | —CF₃ | —H |
| Z364 (a and b) | O | —NO₂ | —OCH₃ | —H |
| Z365 (a and b) | O | —NO₂ | —OCH₂CH₃ | —H |
| Z366 (a and b) | O | —NO₂ | —OCF₃ | —H |
| Z367 (a and b) | O | —NO₂ | -tert-butyl | —H |
| Z368 (a and b) | O | —NO₂ | -iso-propyl | —H |
| Z369 (a and b) | O | —NO₂ | —CH₃ | —CH₃ |
| Z370 (a and b) | O | —NO₂ | —H | —H |
| Z371 (a and b) | O | —NO₂ | —H | —Cl |
| Z372 (a and b) | O | —NO₂ | —H | —Br |
| Z373 (a and b) | O | —NO₂ | —H | —F |
| Z374 (a and b) | O | —NO₂ | —H | —CH₃ |
| Z375 (a and b) | O | —NO₂ | —H | —CF₃ |
| Z376 (a and b) | O | —NO₂ | —H | —OCH₃ |
| Z377 (a and b) | O | —NO₂ | —H | —OCH₂CH₃ |
| Z378 (a and b) | O | —NO₂ | —H | —OCF₃ |
| Z379 (a and b) | O | —NO₂ | —H | -tert-butyl |
| Z380 (a and b) | O | —NO₂ | —H | -iso-propyl |
| Z381 (a and b) | O | —CN | —Br | —H |
| Z382 (a and b) | O | —CN | —Cl | —H |
| Z383 (a and b) | O | —CN | —F | —H |
| Z384 (a and b) | O | —CN | —CH₃ | —H |
| Z385 (a and b) | O | —CN | —CF₃ | —H |
| Z386 (a and b) | O | —CN | —OCH₃ | —H |
| Z387 (a and b) | O | —CN | —OCH₂CH₃ | —H |
| Z388 (a and b) | O | —CN | —OCF₃ | —H |
| Z389 (a and b) | O | —CN | -tert-butyl | —H |
| Z390 (a and b) | O | —CN | -iso-propyl | —H |
| Z391 (a and b) | O | —CN | —CH₃ | —CH₃ |
| Z392 (a and b) | O | —CN | —H | —H |

TABLE 26-continued (Iz)

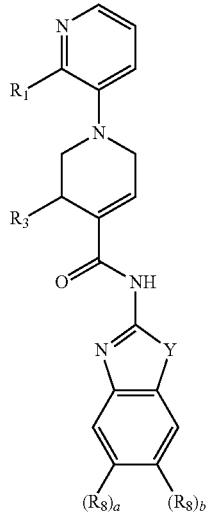

and pharmaceutically acceptable salts thereof, wherein:

| Compound | Y | R₁ | (R₈)ₐ | (R₈)ᵦ |
|---|---|---|---|---|
| Z393 (a and b) | O | —CN | —H | —Cl |
| Z394 (a and b) | O | —CN | —H | —Br |
| Z395 (a and b) | O | —CN | —H | —F |
| Z396 (a and b) | O | —CN | —H | —CH₃ |
| Z397 (a and b) | O | —CN | —H | —CF₃ |
| Z398 (a and b) | O | —CN | —H | —OCH₃ |
| Z399 (a and b) | O | —CN | —H | —OCH₂CH₃ |
| Z400 (a and b) | O | —CN | —H | —OCF₃ |
| Z401 (a and b) | O | —CN | —H | -tert-butyl |
| Z402 (a and b) | O | —CN | —H | -iso-propyl |
| Z403 (a and b) | O | —Br | —Br | —H |
| Z404 (a and b) | O | —Br | —Cl | —H |
| Z405 (a and b) | O | —Br | —F | —H |
| Z406 (a and b) | O | —Br | —CH₃ | —H |
| Z407 (a and b) | O | —Br | —CF₃ | —H |
| Z408 (a and b) | O | —Br | —OCH₃ | —H |
| Z409 (a and b) | O | —Br | —OCH₂CH₃ | —H |
| Z410 (a and b) | O | —Br | —OCF₃ | —H |
| Z411 (a and b) | O | —Br | -tert-butyl | —H |
| Z412 (a and b) | O | —Br | -iso-propyl | —H |
| Z413 (a and b) | O | —Br | —CH₃ | —CH₃ |
| Z414 (a and b) | O | —Br | —H | —H |
| Z415 (a and b) | O | —Br | —H | —Cl |
| Z416 (a and b) | O | —Br | —H | —Br |
| Z417 (a and b) | O | —Br | —H | —F |
| Z418 (a and b) | O | —Br | —H | —CH₃ |
| Z419 (a and b) | O | —Br | —H | —CF₃ |
| Z420 (a and b) | O | —Br | —H | —OCH₃ |
| Z421 (a and b) | O | —Br | —H | —OCH₂CH₃ |
| Z422 (a and b) | O | —Br | —H | —OCF₃ |
| Z423 (a and b) | O | —Br | —H | -tert-butyl |
| Z424 (a and b) | O | —Br | —H | -iso-propyl |
| Z425 (a and b) | O | —I | —Cl | —H |
| Z426 (a and b) | O | —I | —Br | —H |
| Z427 (a and b) | O | —I | —F | —H |
| Z428 (a and b) | O | —I | —CH₃ | —H |
| Z429 (a and b) | O | —I | —CF₃ | —H |
| Z430 (a and b) | O | —I | —OCH₃ | —H |
| Z431 (a and b) | O | —I | —OCH₂CH₃ | —H |
| Z432 (a and b) | O | —I | —OCF₃ | —H |
| Z433 (a and b) | O | —I | -tert-butyl | —H |
| Z434 (a and b) | O | —I | -iso-propyl | —H |
| Z435 (a and b) | O | —I | —CH₃ | —CH₃ |
| Z436 (a and b) | O | —I | —H | —H |
| Z437 (a and b) | O | —I | —H | —Cl |
| Z438 (a and b) | O | —I | —H | —Br |
| Z439 (a and b) | O | —I | —H | —F |
| Z440 (a and b) | O | —I | —H | —CH₃ |
| Z441 (a and b) | O | —I | —H | —CF₃ |

TABLE 26-continued (Iz)

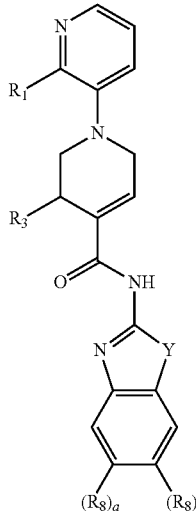

and pharmaceutically acceptable salts thereof, wherein:

| Compound | Y | R₁ | (R₈)ₐ | (R₈)ᵦ |
|---|---|---|---|---|
| Z442 (a and b) | O | —I | —H | —OCH₃ |
| Z443 (a and b) | O | —I | —H | —OCH₂CH₃ |
| Z444 (a and b) | O | —I | —H | —OCF₃ |
| Z445 (a and b) | O | —I | —H | -tert-butyl |
| Z446 (a and b) | O | —I | —H | -iso-propyl |
| Z447 (a and b) | NH | —H | —Cl | —H |
| Z448 (a and b) | NH | —H | —Br | —H |
| Z449 (a and b) | NH | —H | —F | —H |
| Z450 (a and b) | NH | —H | —CH₃ | —H |
| Z451 (a and b) | NH | —H | —CF₃ | —H |
| Z452 (a and b) | NH | —H | —OCH₃ | —H |
| Z453 (a and b) | NH | —H | —OCH₂CH₃ | —H |
| Z454 (a and b) | NH | —H | —OCF₃ | —H |
| Z455 (a and b) | NH | —H | -tert-butyl | —H |
| Z456 (a and b) | NH | —H | -iso-propyl | —H |
| Z457 (a and b) | NH | —H | —CH₃ | —CH₃ |
| Z458 (a and b) | NH | —H | —H | —H |
| Z459 (a and b) | NH | —H | —H | —Cl |
| Z460 (a and b) | NH | —H | —H | —Br |
| Z461 (a and b) | NH | —H | —H | —F |
| Z462 (a and b) | NH | —H | —H | —CH₃ |
| Z463 (a and b) | NH | —H | —H | —CF₃ |
| Z464 (a and b) | NH | —H | —H | —OCH₃ |
| Z465 (a and b) | NH | —H | —H | —OCH₂CH₃ |
| Z466 (a and b) | NH | —H | —H | —OCF₃ |
| Z467 (a and b) | NH | —H | —H | -tert-butyl |
| Z468 (a and b) | NH | —H | —H | -iso-propyl |
| Z469 (a and b) | NH | —Cl | —Cl | —H |
| Z470 (a and b) | NH | —Cl | —Br | —H |
| Z471 (a and b) | NH | —Cl | —F | —H |
| Z472 (a and b) | NH | —Cl | —CH₃ | —H |
| Z473 (a and b) | NH | —Cl | —CF₃ | —H |
| Z474 (a and b) | NH | —Cl | —OCH₃ | —H |
| Z475 (a and b) | NH | —Cl | —OCH₂CH₃ | —H |
| Z476 (a and b) | NH | —Cl | —OCF₃ | —H |
| Z477 (a and b) | NH | —Cl | -tert-butyl | —H |
| Z478 (a and b) | NH | —Cl | -iso-propyl | —H |
| Z479 (a and b) | NH | —Cl | —CH₃ | —CH₃ |
| Z480 (a and b) | NH | —Cl | —H | —H |
| Z481 (a and b) | NH | —Cl | —H | —CH₃ |
| Z482 (a and b) | NH | —Cl | —H | —Cl |
| Z483 (a and b) | NH | —Cl | —H | —Br |
| Z484 (a and b) | NH | —Cl | —H | —F |
| Z485 (a and b) | NH | —Cl | —H | —CF₃ |
| Z486 (a and b) | NH | —Cl | —H | —OCH₃ |
| Z487 (a and b) | NH | —Cl | —H | —OCH₂CH₃ |
| Z488 (a and b) | NH | —Cl | —H | —OCF₃ |
| Z489 (a and b) | NH | —Cl | —H | -tert-butyl |
| Z490 (a and b) | NH | —Cl | —H | -iso-propyl |

TABLE 26-continued (Iz)

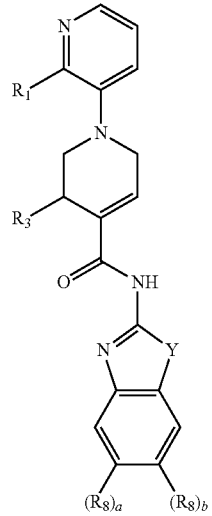

and pharmaceutically acceptable salts thereof, wherein:

| Compound | Y | R₁ | (R₈)ₐ | (R₈)ᵦ |
|---|---|---|---|---|
| Z491 (a and b) | NH | —Cl | —H | —OCF₃ |
| Z492 (a and b) | NH | —Cl | —H | -tert-butyl |
| Z493 (a and b) | NH | —Cl | —H | -iso-propyl |
| Z494 (a and b) | NH | —CH₃ | —Cl | —H |
| Z495 (a and b) | NH | —CH₃ | —Br | —H |
| Z496 (a and b) | NH | —CH₃ | —F | —H |
| Z497 (a and b) | NH | —CH₃ | —CH₃ | —H |
| Z498 (a and b) | NH | —CH₃ | —CF₃ | —H |
| Z499 (a and b) | NH | —CH₃ | —OCH₃ | —H |
| Z500 (a and b) | NH | —CH₃ | —OCH₂CH₃ | —H |
| Z501 (a and b) | NH | —CH₃ | —OCF₃ | —H |
| Z502 (a and b) | NH | —CH₃ | -tert-butyl | —H |
| Z503 (a and b) | NH | —CH₃ | -iso-propyl | —H |
| Z504 (a and b) | NH | —CH₃ | —CH₃ | —CH₃ |
| Z505 (a and b) | NH | —CH₃ | —H | —H |
| Z506 (a and b) | NH | —CH₃ | —H | —Cl |
| Z507 (a and b) | NH | —CH₃ | —H | —Br |
| Z508 (a and b) | NH | —CH₃ | —H | —F |
| Z509 (a and b) | NH | —CH₃ | —H | —CH₃ |
| Z510 (a and b) | NH | —CH₃ | —H | —CF₃ |
| Z511 (a and b) | NH | —CH₃ | —H | —OCH₃ |
| Z512 (a and b) | NH | —CH₃ | —H | —OCH₂CH₃ |
| Z513 (a and b) | NH | —CH₃ | —H | —OCF₃ |
| Z514 (a and b) | NH | —CH₃ | —H | -tert-butyl |
| Z515 (a and b) | NH | —CH₃ | —H | -iso-propyl |
| Z516 (a and b) | NH | —CF₃ | —Cl | —H |
| Z517 (a and b) | NH | —CF₃ | —Br | —H |
| Z518 (a and b) | NH | —CF₃ | —F | —H |
| Z519 (a and b) | NH | —CF₃ | —CH₃ | —H |
| Z520 (a and b) | NH | —CF₃ | —CF₃ | —H |
| Z521 (a and b) | NH | —CF₃ | —OCH₃ | —H |
| Z522 (a and b) | NH | —CF₃ | —OCH₂CH₃ | —H |
| Z523 (a and b) | NH | —CF₃ | —OCF₃ | —H |
| Z524 (a and b) | NH | —CF₃ | -tert-butyl | —H |
| Z525 (a and b) | NH | —CF₃ | -iso-propyl | —H |
| Z526 (a and b) | NH | —CF₃ | —CH₃ | —CH₃ |
| Z527 (a and b) | NH | —CF₃ | —H | —H |
| Z528 (a and b) | NH | —CF₃ | —H | —Cl |
| Z529 (a and b) | NH | —CF₃ | —H | —Br |
| Z530 (a and b) | NH | —CF₃ | —H | —F |
| Z531 (a and b) | NH | —CF₃ | —H | —CH₃ |
| Z532 (a and b) | NH | —CF₃ | —H | —CF₃ |
| Z533 (a and b) | NH | —CF₃ | —H | —OCH₃ |
| Z534 (a and b) | NH | —CF₃ | —H | —OCH₂CH₃ |
| Z535 (a and b) | NH | —CF₃ | —H | —OCF₃ |
| Z536 (a and b) | NH | —CF₃ | —H | -tert-butyl |
| Z537 (a and b) | NH | —CF₃ | —H | -iso-propyl |
| Z538 (a and b) | NH | —CHF₂ | —Cl | —H |
| Z539 (a and b) | NH | —CHF₂ | —Br | —H |

TABLE 26-continued

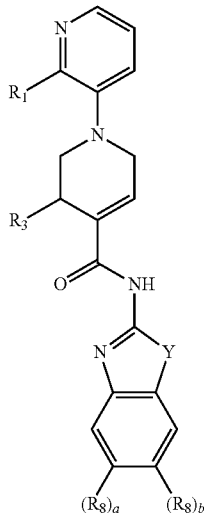

(Iz)

and pharmaceutically acceptable salts thereof, wherein:

| Compound | Y | $R_1$ | $(R_8)_a$ | $(R_8)_b$ |
|---|---|---|---|---|
| Z540 (a and b) | NH | —$CHF_2$ | —F | —H |
| Z541 (a and b) | NH | —$CHF_2$ | —$CH_3$ | —H |
| Z542 (a and b) | NH | —$CHF_2$ | —$CF_3$ | —H |
| Z543 (a and b) | NH | —$CHF_2$ | —$OCH_3$ | —H |
| Z544 (a and b) | NH | —$CHF_2$ | —$OCH_2CH_3$ | —H |
| Z545 (a and b) | NH | —$CHF_2$ | —$OCF_3$ | —H |
| Z546 (a and b) | NH | —$CHF_2$ | -tert-butyl | —H |
| Z547 (a and b) | NH | —$CHF_2$ | -iso-propyl | —H |
| Z548 (a and b) | NH | —$CHF_2$ | —$CH_3$ | —$CH_3$ |
| Z549 (a and b) | NH | —$CHF_2$ | —H | —H |
| Z550 (a and b) | NH | —$CHF_2$ | —H | —Cl |
| Z551 (a and b) | NH | —$CHF_2$ | —H | —Br |
| Z552 (a and b) | NH | —$CHF_2$ | —H | —F |
| Z553 (a and b) | NH | —$CHF_2$ | —H | —$CH_3$ |
| Z554 (a and b) | NH | —$CHF_2$ | —H | —$CF_3$ |
| Z555 (a and b) | NH | —$CHF_2$ | —H | —$OCH_3$ |
| Z556 (a and b) | NH | —$CHF_2$ | —H | —$OCH_2CH_3$ |
| Z557 (a and b) | NH | —$CHF_2$ | —H | —$OCF_3$ |
| Z558 (a and b) | NH | —$CHF_2$ | —H | -tert-butyl |
| Z559 (a and b) | NH | —$CHF_2$ | —H | -iso-propyl |
| Z560 (a and b) | NH | —OH | —Cl | —H |
| Z561 (a and b) | NH | —OH | —Br | —H |
| Z562 (a and b) | NH | —OH | —F | —H |
| Z563 (a and b) | NH | —OH | —$CH_3$ | —H |
| Z564 (a and b) | NH | —OH | —$CF_3$ | —H |
| Z565 (a and b) | NH | —OH | —$OCH_3$ | —H |
| Z566 (a and b) | NH | —OH | —$OCH_2CH_3$ | —H |
| Z567 (a and b) | NH | —OH | —$OCF_3$ | —H |
| Z568 (a and b) | NH | —OH | -tert-butyl | —H |
| Z569 (a and b) | NH | —OH | -iso-propyl | —H |
| Z570 (a and b) | NH | —OH | —$CH_3$ | —$CH_3$ |
| Z571 (a and b) | NH | —OH | —H | —H |
| Z572 (a and b) | NH | —OH | —H | —Cl |
| Z573 (a and b) | NH | —OH | —H | —Br |
| Z574 (a and b) | NH | —OH | —H | —F |
| Z575 (a and b) | NH | —OH | —H | —$CH_3$ |
| Z576 (a and b) | NH | —OH | —H | —$CF_3$ |
| Z577 (a and b) | NH | —OH | —H | —$OCH_3$ |
| Z578 (a and b) | NH | —OH | —H | —$OCH_2CH_3$ |
| Z579 (a and b) | NH | —OH | —H | —$OCF_3$ |
| Z580 (a and b) | NH | —OH | —H | -tert-butyl |
| Z581 (a and b) | NH | —OH | —H | -iso-propyl |
| Z582 (a and b) | NH | —$NO_2$ | —Cl | —H |
| Z583 (a and b) | NH | —$NO_2$ | —Br | —H |
| Z584 (a and b) | NH | —$NO_2$ | —F | —H |
| Z585 (a and b) | NH | —$NO_2$ | —$CH_3$ | —H |
| Z586 (a and b) | NH | —$NO_2$ | —$CF_3$ | —H |
| Z587 (a and b) | NH | —$NO_2$ | —$OCH_3$ | —H |
| Z588 (a and b) | NH | —$NO_2$ | —$OCH_2CH_3$ | —H |
| Z589 (a and b) | NH | —$NO_2$ | —$OCF_3$ | —H |
| Z590 (a and b) | NH | —$NO_2$ | -tert-butyl | —H |
| Z591 (a and b) | NH | —$NO_2$ | -iso-propyl | —H |
| Z592 (a and b) | NH | —$NO_2$ | —$CH_3$ | —$CH_3$ |
| Z593 (a and b) | NH | —$NO_2$ | —H | —H |
| Z594 (a and b) | NH | —$NO_2$ | —H | —Cl |
| Z595 (a and b) | NH | —$NO_2$ | —H | —Br |
| Z596 (a and b) | NH | —$NO_2$ | —H | —F |
| Z597 (a and b) | NH | —$NO_2$ | —H | —$CH_3$ |
| Z598 (a and b) | NH | —$NO_2$ | —H | —$CF_3$ |
| Z599 (a and b) | NH | —$NO_2$ | —H | —$OCH_3$ |
| Z600 (a and b) | NH | —$NO_2$ | —H | —$OCH_2CH_3$ |
| Z601 (a and b) | NH | —$NO_2$ | —H | —$OCF_3$ |
| Z602 (a and b) | NH | —$NO_2$ | —H | -tert-butyl |
| Z603 (a and b) | NH | —$NO_2$ | —H | -iso-propyl |
| Z604 (a and b) | NH | —CN | —Br | —H |
| Z605 (a and b) | NH | —CN | —Cl | —H |
| Z606 (a and b) | NH | —CN | —F | —H |
| Z607 (a and b) | NH | —CN | —$CH_3$ | —H |
| Z608 (a and b) | NH | —CN | —$CF_3$ | —H |
| Z609 (a and b) | NH | —CN | —$OCH_3$ | —H |
| Z610 (a and b) | NH | —CN | —$OCH_2CH_3$ | —H |
| Z611 (a and b) | NH | —CN | —$OCF_3$ | —H |
| Z612 (a and b) | NH | —CN | -tert-butyl | —H |
| Z613 (a and b) | NH | —CN | -iso-propyl | —H |
| Z614 (a and b) | NH | —CN | —$CH_3$ | —$CH_3$ |
| Z615 (a and b) | NH | —CN | —H | —H |
| Z616 (a and b) | NH | —CN | —H | —Cl |
| Z617 (a and b) | NH | —CN | —H | —Br |
| Z618 (a and b) | NH | —CN | —H | —F |
| Z619 (a and b) | NH | —CN | —H | —$CH_3$ |
| Z620 (a and b) | NH | —CN | —H | —$CF_3$ |
| Z621 (a and b) | NH | —CN | —H | —$OCH_3$ |
| Z622 (a and b) | NH | —CN | —H | —$OCH_2CH_3$ |
| Z623 (a and b) | NH | —CN | —H | —$OCF_3$ |
| Z624 (a and b) | NH | —CN | —H | -tert-butyl |
| Z625 (a and b) | NH | —CN | —H | -iso-propyl |
| Z626 (a and b) | NH | —Br | —Br | —H |
| Z627 (a and b) | NH | —Br | —Cl | —H |
| Z628 (a and b) | NH | —Br | —F | —H |
| Z629 (a and b) | NH | —Br | —$CH_3$ | —H |
| Z630 (a and b) | NH | —Br | —$CF_3$ | —H |
| Z631 (a and b) | NH | —Br | —$OCH_3$ | —H |
| Z632 (a and b) | NH | —Br | —$OCH_2CH_3$ | —H |
| Z633 (a and b) | NH | —Br | —$OCF_3$ | —H |
| Z634 (a and b) | NH | —Br | -tert-butyl | —H |
| Z635 (a and b) | NH | —Br | -iso-propyl | —H |
| Z636 (a and b) | NH | —Br | —$CH_3$ | —$CH_3$ |
| Z637 (a and b) | NH | —Br | —H | —H |

TABLE 26-continued

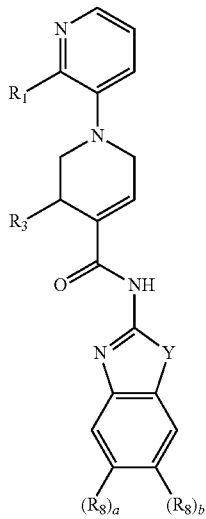

(Iz)

and pharmaceutically acceptable salts thereof, wherein:

| Compound | Y | R₁ | (R₈)ₐ | (R₈)ᵦ |
|---|---|---|---|---|
| Z638 (a and b) | NH | —Br | —H | —Cl |
| Z639 (a and b) | NH | —Br | —H | —Br |
| Z640 (a and b) | NH | —Br | —H | —F |
| Z641 (a and b) | NH | —Br | —H | —CH₃ |
| Z642 (a and b) | NH | —Br | —H | —CF₃ |
| Z643 (a and b) | NH | —Br | —H | —OCH₃ |
| Z644 (a and b) | NH | —Br | —H | —OCH₂CH₃ |
| Z645 (a and b) | NH | —Br | —H | —OCF₃ |
| Z646 (a and b) | NH | —Br | —H | -tert-butyl |
| Z647 (a and b) | NH | —Br | —H | -iso-propyl |
| Z648 (a and b) | NH | —I | —Cl | —H |
| Z649 (a and b) | NH | —I | —Br | —H |
| Z650 (a and b) | NH | —I | —F | —H |
| Z651 (a and b) | NH | —I | —CH₃ | —H |
| Z652 (a and b) | NH | —I | —CF₃ | —H |
| Z653 (a and b) | NH | —I | —OCH₃ | —H |
| Z654 (a and b) | NH | —I | —OCH₂CH₃ | —H |
| Z655 (a and b) | NH | —I | —OCF₃ | —H |
| Z656 (a and b) | NH | —I | -tert-butyl | —H |
| Z657 (a and b) | NH | —I | -iso-propyl | —H |
| Z658 (a and b) | NH | —I | —CH₃ | —CH₃ |
| Z659 (a and b) | NH | —I | —H | —H |
| Z660 (a and b) | NH | —I | —H | —Cl |
| Z661 (a and b) | NH | —I | —H | —Br |
| Z662 (a and b) | NH | —I | —H | —F |
| Z663 (a and b) | NH | —I | —H | —CH₃ |
| Z664 (a and b) | NH | —I | —H | —CF₃ |
| Z665 (a and b) | NH | —I | —H | —OCH₃ |
| Z666 (a and b) | NH | —I | —H | —OCH₂CH₃ |
| Z667 (a and b) | NH | —I | —H | —OCF₃ |
| Z668 (a and b) | NH | —I | —H | -tert-butyl |
| Z669 (a and b) | NH | —I | —H | -iso-propyl |

(a) means that R₃ is —H.
(b) means that R₃ is —CH₃.

TABLE 27

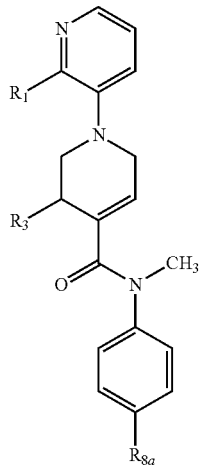

(Iaa)

and pharmaceutically acceptable salts thereof, wherein:

| Compound | R₁ | R₈ₐ |
|---|---|---|
| AA1 (a and b) | —H | —H |
| AA2 (a and b) | —H | -tert-butyl |
| AA3 (a and b) | —H | -iso-butyl |
| AA4 (a and b) | —H | -sec-butyl |
| AA5 (a and b) | —H | -iso-propyl |
| AA6 (a and b) | —H | -n-propyl |
| AA7 (a and b) | —H | -cyclohexyl |
| AA8 (a and b) | —H | -tert-butoxy |
| AA9 (a and b) | —H | -isopropoxy |
| AA10 (a and b) | —H | —CF₃ |
| AA11 (a and b) | —H | —CH₂CF₃ |
| AA12 (a and b) | —H | —OCF₃ |
| AA13 (a and b) | —H | —Cl |
| AA14 (a and b) | —H | —Br |
| AA15 (a and b) | —H | —I |
| AA16 (a and b) | —H | -n-butyl |
| AA17 (a and b) | —H | —CH₃ |
| AA18 (a and b) | —H | —SCF₃ |
| AA19 (a and b) | —H | —N(CH₂CH₃)₂ |
| AA20 (a and b) | —H | —OCF₂CHF₂ |
| AA21 (a and b) | —H | —C(OH)(CF₃)₂ |
| AA22 (a and b) | —H | -(1,1-dimethyl-pentyl) |
| AA23 (a and b) | —H | -(1,1-dimethyl-acetic acid) ethyl ester |
| AA24 (a and b) | —H | —N-piperidinyl |
| AA25 (a and b) | —Cl | —H |
| AA26 (a and b) | —Cl | -tert-butyl |
| AA27 (a and b) | —Cl | -iso-butyl |
| AA28 (a and b) | —Cl | -sec-butyl |
| AA29 (a and b) | —Cl | -iso-propyl |
| AA30 (a and b) | —Cl | -n-propyl |
| AA31 (a and b) | —Cl | -cyclohexyl |
| AA32 (a and b) | —Cl | -tert-butoxy |
| AA33 (a and b) | —Cl | -isopropoxy |
| AA34 (a and b) | —Cl | —CF₃ |
| AA35 (a and b) | —Cl | —CH₂CF₃ |
| AA36 (a and b) | —Cl | —OCF₃ |
| AA37 (a and b) | —Cl | —Cl |
| AA38 (a and b) | —Cl | —Br |
| AA39 (a and b) | —Cl | —I |
| AA40 (a and b) | —Cl | -n-butyl |
| AA41 (a and b) | —Cl | —CH₃ |
| AA42 (a and b) | —Cl | —SCF₃ |
| AA43 (a and b) | —Cl | —N(CH₂CH₃)₂ |
| AA44 (a and b) | —Cl | —OCF₂CHF₂ |
| AA45 (a and b) | —Cl | —C(OH)(CF₃)₂ |
| AA46 (a and b) | —Cl | -(1,1-dimethyl-pentyl) |
| AA47 (a and b) | —Cl | -(1,1-dimethyl-acetic acid) ethyl ester |
| AA48 (a and b) | —Cl | —N-piperidinyl |
| AA49 (a and b) | —F | —H |
| AA50 (a and b) | —F | -tert-butyl |
| AA51 (a and b) | —F | -iso-butyl |
| AA52 (a and b) | —F | -sec-butyl |

TABLE 27-continued

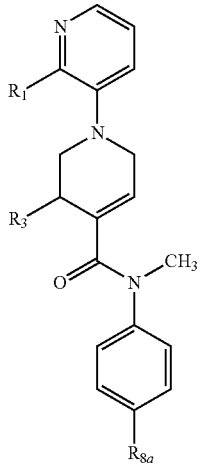

(Iaa)

and pharmaceutically acceptable salts thereof, wherein:

| Compound | R₁ | R₈ₐ |
|---|---|---|
| AA53 (a and b) | —F | -iso-propyl |
| AA54 (a and b) | —F | -n-propyl |
| AA55 (a and b) | —F | -cyclohexyl |
| AA56 (a and b) | —F | -tert-butoxy |
| AA57 (a and b) | —F | -isopropoxy |
| AA58 (a and b) | —F | —CF₃ |
| AA59 (a and b) | —F | —CH₂CF₃ |
| AA60 (a and b) | —F | —OCF₃ |
| AA61 (a and b) | —F | —Cl |
| AA62 (a and b) | —F | —Br |
| AA63 (a and b) | —F | —I |
| AA64 (a and b) | —F | -n-butyl |
| AA65 (a and b) | —F | —CH₃ |
| AA66 (a and b) | —F | —SCF₃ |
| AA67 (a and b) | —F | —N(CH₂CH₃)₂ |
| AA68 (a and b) | —F | —OCF₂CHF₂ |
| AA69 (a and b) | —F | —C(OH)(CF₃)₂ |
| AA70 (a and b) | —F | -(1,1-dimethyl-pentyl) |
| AA71 (a and b) | —F | -(1,1-dimethyl-acetic acid) ethyl ester |
| AA72 (a and b) | —F | —N-piperidinyl |
| AA73 (a and b) | —CH₃ | —H |
| AA74 (a and b) | —CH₃ | -iso-butyl |
| AA75 (a and b) | —CH₃ | -tert-butyl |
| AA76 (a and b) | —CH₃ | -sec-butyl |
| AA77 (a and b) | —CH₃ | -iso-propyl |
| AA78 (a and b) | —CH₃ | -n-propyl |
| AA79 (a and b) | —CH₃ | -cyclohexyl |
| AA80 (a and b) | —CH₃ | -tert-butoxy |
| AA81 (a and b) | —CH₃ | -isopropoxy |
| AA82 (a and b) | —CH₃ | —CF₃ |
| AA83 (a and b) | —CH₃ | —CH₂CF₃ |
| AA84 (a and b) | —CH₃ | —OCF₃ |
| AA85 (a and b) | —CH₃ | —Cl |
| AA86 (a and b) | —CH₃ | —Br |
| AA87 (a and b) | —CH₃ | —I |
| AA88 (a and b) | —CH₃ | -n-butyl |
| AA89 (a and b) | —CH₃ | —CH₃ |
| AA90 (a and b) | —CH₃ | —SCF₃ |
| AA91 (a and b) | —CH₃ | —N(CH₂CH₃)₂ |
| AA92 (a and b) | —CH₃ | —OCF₂CHF₂ |
| AA93 (a and b) | —CH₃ | —C(OH)(CF₃)₂ |
| AA94 (a and b) | —CH₃ | -(1,1-dimethyl-pentyl) |
| AA95 (a and b) | —CH₃ | -(1,1-dimethyl-acetic acid) ethyl ester |
| AA96 (a and b) | —CH₃ | —N-piperidinyl |
| AA97 (a and b) | —CF₃ | —H |
| AA98 (a and b) | —CF₃ | -tert-butyl |
| AA99 (a and b) | —CF₃ | -iso-butyl |
| AA100 (a and b) | —CF₃ | -sec-butyl |
| AA101 (a and b) | —CF₃ | -iso-propyl |
| AA102 (a and b) | —CF₃ | -n-propyl |
| AA103 (a and b) | —CF₃ | -cyclohexyl |
| AA104 (a and b) | —CF₃ | -tert-butoxy |
| AA105 (a and b) | —CF₃ | -isopropoxy |
| AA106 (a and b) | —CF₃ | —CF₃ |
| AA107 (a and b) | —CF₃ | —CH₂CF₃ |
| AA108 (a and b) | —CF₃ | —OCF₃ |
| AA109 (a and b) | —CF₃ | —Cl |
| AA110 (a and b) | —CF₃ | —Br |
| AA111 (a and b) | —CF₃ | —I |
| AA112 (a and b) | —CF₃ | -n-butyl |
| AA113 (a and b) | —CF₃ | —CH₃ |
| AA114 (a and b) | —CF₃ | —SCF₃ |
| AA115 (a and b) | —CF₃ | —N(CH₂CH₃)₂ |
| AA116 (a and b) | —CF₃ | —OCF₂CHF₂ |
| AA117 (a and b) | —CF₃ | —C(OH)(CF₃)₂ |
| AA118 (a and b) | —CF₃ | -(1,1-dimethyl-pentyl) |
| AA119 (a and b) | —CF₃ | -(1,1-dimethyl-acetic acid) ethyl ester |
| AA120 (a and b) | —CF₃ | —N-piperidinyl |
| AA121 (a and b) | —CHF₂ | -tert-butyl |
| AA122 (a and b) | —CHF₂ | —H |
| AA123 (a and b) | —CHF₂ | -iso-butyl |
| AA124 (a and b) | —CHF₂ | -sec-butyl |
| AA125 (a and b) | —CHF₂ | -iso-propyl |
| AA126 (a and b) | —CHF₂ | -n-propyl |
| AA127 (a and b) | —CHF₂ | -cyclohexyl |
| AA128 (a and b) | —CHF₂ | -tert-butoxy |
| AA129 (a and b) | —CHF₂ | -isopropoxy |
| AA130 (a and b) | —CHF₂ | —CF₃ |
| AA131 (a and b) | —CHF₂ | —CH₂CF₃ |
| AA132 (a and b) | —CHF₂ | —OCF₃ |
| AA133 (a and b) | —CHF₂ | —Cl |
| AA134 (a and b) | —CHF₂ | —Br |
| AA135 (a and b) | —CHF₂ | —I |
| AA136 (a and b) | —CHF₂ | -n-butyl |
| AA137 (a and b) | —CHF₂ | —CH₃ |
| AA138 (a and b) | —CHF₂ | —SCF₃ |
| AA139 (a and b) | —CHF₂ | —N(CH₂CH₃)₂ |
| AA140 (a and b) | —CHF₂ | —OCF₂CHF₂ |
| AA141 (a and b) | —CHF₂ | —C(OH)(CF₃)₂ |
| AA142 (a and b) | —CHF₂ | -(1,1-dimethyl-pentyl) |
| AA143 (a and b) | —CHF₂ | -(1,1-dimethyl-acetic acid) ethyl ester |
| AA144 (a and b) | —CHF₂ | —N-piperidinyl |
| AA145 (a and b) | —OH | —H |
| AA146 (a and b) | —OH | -tert-butyl |
| AA147 (a and b) | —OH | -iso-butyl |
| AA148 (a and b) | —OH | -sec-butyl |
| AA149 (a and b) | —OH | -iso-propyl |
| AA150 (a and b) | —OH | -n-propyl |
| AA151 (a and b) | —OH | -cyclohexyl |
| AA152 (a and b) | —OH | -tert-butoxy |
| AA153 (a and b) | —OH | -isopropoxy |
| AA154 (a and b) | —OH | —CF₃ |
| AA155 (a and b) | —OH | —CH₂CF₃ |
| AA156 (a and b) | —OH | —OCF₃ |

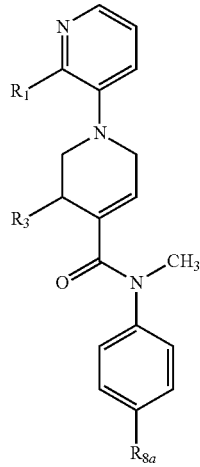

TABLE 27-continued

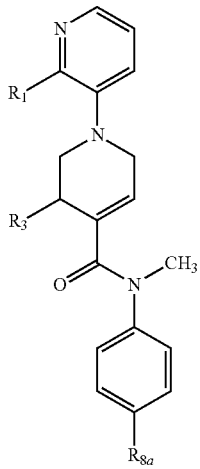

(Iaa)

and pharmaceutically acceptable salts thereof, wherein:

| Compound | $R_1$ | $R_{8a}$ |
|---|---|---|
| AA157 (a and b) | —OH | —Cl |
| AA158 (a and b) | —OH | —Br |
| AA159 (a and b) | —OH | —I |
| AA160 (a and b) | —OH | -n-butyl |
| AA161 (a and b) | —OH | —CH$_3$ |
| AA162 (a and b) | —OH | —SCF$_3$ |
| AA163 (a and b) | —OH | —N(CH$_2$CH$_3$)$_2$ |
| AA164 (a and b) | —OH | —OCF$_2$CHF$_2$ |
| AA165 (a and b) | —OH | —C(OH)(CF$_3$)$_2$ |
| AA166 (a and b) | —OH | -(1,1-dimethyl-pentyl) |
| AA167 (a and b) | —OH | -(1,1-dimethyl-acetic acid) ethyl ester |
| AA168 (a and b) | —OH | —N-piperidinyl |
| AA169 (a and b) | —NO$_2$ | —H |
| AA170 (a and b) | —NO$_2$ | -tert-butyl |
| AA171 (a and b) | —NO$_2$ | -iso-butyl |
| AA172 (a and b) | —NO$_2$ | -sec-butyl |
| AA173 (a and b) | —NO$_2$ | -iso-propyl |
| AA174 (a and b) | —NO$_2$ | -n-propyl |
| AA175 (a and b) | —NO$_2$ | -cyclohexyl |
| AA176 (a and b) | —NO$_2$ | -tert-butoxy |
| AA177 (a and b) | —NO$_2$ | -isopropoxy |
| AA178 (a and b) | —NO$_2$ | —CF$_3$ |
| AA179 (a and b) | —NO$_2$ | —CH$_2$CF$_3$ |
| AA180 (a and b) | —NO$_2$ | —OCF$_3$ |
| AA181 (a and b) | —NO$_2$ | —Cl |
| AA182 (a and b) | —NO$_2$ | —Br |
| AA183 (a and b) | —NO$_2$ | —I |
| AA184 (a and b) | —NO$_2$ | -n-butyl |
| AA185 (a and b) | —NO$_2$ | —CH$_3$ |
| AA186 (a and b) | —NO$_2$ | —SCF$_3$ |
| AA187 (a and b) | —NO$_2$ | —N(CH$_2$CH$_3$)$_2$ |
| AA188 (a and b) | —NO$_2$ | —OCF$_2$CHF$_2$ |
| AA189 (a and b) | —NO$_2$ | —C(OH)(CF$_3$)$_2$ |
| AA190 (a and b) | —NO$_2$ | -(1,1-dimethyl-pentyl) |
| AA191 (a and b) | —NO$_2$ | -(1,1-dimethyl-acetic acid) ethyl ester |
| AA192 (a and b) | —NO$_2$ | —N-piperidinyl |
| AA193 (a and b) | —CN | —H |
| AA194 (a and b) | —CN | -tert-butyl |
| AA195 (a and b) | —CN | -iso-butyl |
| AA196 (a and b) | —CN | -sec-butyl |
| AA197 (a and b) | —CN | -iso-propyl |
| AA198 (a and b) | —CN | -n-propyl |
| AA199 (a and b) | —CN | -cyclohexyl |
| AA200 (a and b) | —CN | -tert-butoxy |
| AA201 (a and b) | —CN | -isopropoxy |
| AA202 (a and b) | —CN | —CF$_3$ |
| AA203 (a and b) | —CN | —CH$_2$CF$_3$ |
| AA204 (a and b) | —CN | —OCF$_3$ |
| AA205 (a and b) | —CN | —Cl |
| AA206 (a and b) | —CN | —Br |
| AA207 (a and b) | —CN | —I |
| AA208 (a and b) | —CN | -n-butyl |

TABLE 27-continued

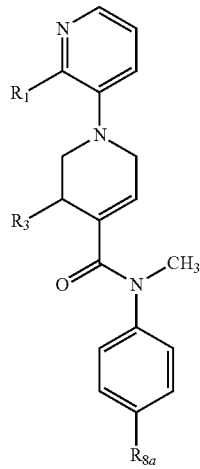

(Iaa)

and pharmaceutically acceptable salts thereof, wherein:

| Compound | $R_1$ | $R_{8a}$ |
|---|---|---|
| AA209 (a and b) | —CN | —CH$_3$ |
| AA210 (a and b) | —CN | —SCF$_3$ |
| AA211 (a and b) | —CN | —N(CH$_2$CH$_3$)$_2$ |
| AA212 (a and b) | —CN | —OCF$_2$CHF$_2$ |
| AA213 (a and b) | —CN | —C(OH)(CF$_3$)$_2$ |
| AA214 (a and b) | —CN | -(1,1-dimethyl-pentyl) |
| AA215 (a and b) | —CN | -(1,1-dimethyl-acetic acid) ethyl ester |
| AA216 (a and b) | —CN | —N-piperidinyl |
| AA217 (a and b) | —Br | —H |
| AA218 (a and b) | —Br | -tert-butyl |
| AA219 (a and b) | —Br | -iso-butyl |
| AA220 (a and b) | —Br | -sec-butyl |
| AA221 (a and b) | —Br | -iso-propyl |
| AA222 (a and b) | —Br | -n-propyl |
| AA223 (a and b) | —Br | -cyclohexyl |
| AA224 (a and b) | —Br | -tert-butoxy |
| AA225 (a and b) | —Br | -isopropoxy |
| AA226 (a and b) | —Br | —CF$_3$ |
| AA227 (a and b) | —Br | —CH$_2$CF$_3$ |
| AA228 (a and b) | —Br | —OCF$_3$ |
| AA229 (a and b) | —Br | —Cl |
| AA230 (a and b) | —Br | —Br |
| AA231 (a and b) | —Br | —I |
| AA232 (a and b) | —Br | -n-butyl |
| AA233 (a and b) | —Br | —CH$_3$ |
| AA234 (a and b) | —Br | —SCF$_3$ |
| AA235 (a and b) | —Br | —N(CH$_2$CH$_3$)$_2$ |
| AA236 (a and b) | —Br | —OCF$_2$CHF$_2$ |
| AA237 (a and b) | —Br | —C(OH)(CF$_3$)$_2$ |
| AA238 (a and b) | —Br | -(1,1-dimethyl-pentyl) |
| AA239 (a and b) | —Br | -(1,1-dimethyl-acetic acid) ethyl ester |
| AA240 (a and b) | —Br | —N-piperidinyl |
| AA241 (a and b) | —I | -tert-butyl |
| AA242 (a and b) | —I | —H |
| AA243 (a and b) | —I | -iso-butyl |
| AA244 (a and b) | —I | -sec-butyl |
| AA245 (a and b) | —I | -iso-propyl |
| AA246 (a and b) | —I | -n-propyl |
| AA247 (a and b) | —I | -cyclohexyl |
| AA248 (a and b) | —I | -tert-butoxy |
| AA249 (a and b) | —I | -isopropoxy |
| AA250 (a and b) | —I | —CF$_3$ |
| AA251 (a and b) | —I | —CH$_2$CF$_3$ |
| AA252 (a and b) | —I | —OCF$_3$ |
| AA253 (a and b) | —I | —Cl |
| AA254 (a and b) | —I | —Br |
| AA255 (a and b) | —I | —I |
| AA256 (a and b) | —I | -n-butyl |
| AA257 (a and b) | —I | —CH$_3$ |
| AA258 (a and b) | —I | —SCF$_3$ |
| AA259 (a and b) | —I | —N(CH$_2$CH$_3$)$_2$ |
| AA260 (a and b) | —I | —OCF$_2$CHF$_2$ |

TABLE 27-continued

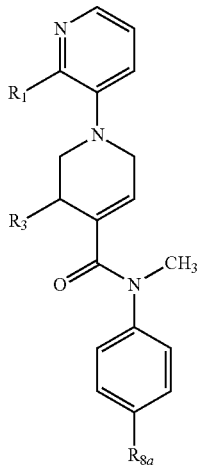

(Iaa)

and pharmaceutically acceptable salts thereof, wherein:

| Compound | $R_1$ | $R_{8a}$ |
|---|---|---|
| AA261 (a and b) | —I | —C(OH)(CF$_3$)$_2$ |
| AA262 (a and b) | —I | -(1,1-dimethyl-pentyl) |
| AA263 (a and b) | —I | -(1,1-dimethyl-acetic acid) ethyl ester |
| AA264 (a and b) | —I | —N-piperidinyl |

(a) means that $R_3$ is —H.
(b) means that $R_3$ is —CH$_3$.

4.2 Definitions

As used in connection with the Cyclo(hetero)alkenyl Compounds herein, the terms used above having following meaning:

"—(C$_1$-C$_{10}$)alkyl" means a straight chain or branched non-cyclic hydrocarbon having from 1 to 10 carbon atoms. Representative straight chain —(C$_1$-C$_{10}$)alkyls include -methyl, -ethyl, -n-propyl, -n-butyl, -n-pentyl, -n-hexyl, -n-heptyl, -n-octyl, -n-nonyl, and -n-decyl. Representative branched —(C$_1$-C$_{10}$)alkyls include -iso-propyl, -sec-butyl, -iso-butyl, -tert-butyl, -iso-pentyl, -neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-methylhexyl, 2-methylhexyl, 3-methylhexyl, 4-methylhexyl, 5-methylhexyl, 1,2-dimethylpentyl, 1,3-dimethylpentyl, 1,2-dimethylhexyl, 1,3-dimethylhexyl, 3,3-dimethylhexyl, 1,2-dimethylheptyl, 1,3-dimethylheptyl, and 3,3-dimethylheptyl.

"—(C$_1$-C$_6$)alkyl" means a straight chain or branched non-cyclic hydrocarbon having from 1 to 6 carbon atoms. Representative straight chain —(C$_1$-C$_6$)alkyls include -methyl, -ethyl, -n-propyl, -n-butyl, -n-pentyl, and -n-hexyl. Representative branched —(C$_1$-C$_6$)alkyls include -iso-propyl, -sec-butyl, -iso-butyl, -tert-butyl, -iso-pentyl, -neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, and 3,3-dimethylbutyl.

"—(C$_1$-C$_4$)alkyl" means a straight chain or branched non-cyclic hydrocarbon having from 1 to 4 carbon atoms. Representative straight chain —(C$_1$-C$_4$)alkyls include -methyl, -ethyl, -n-propyl, and -n-butyl. Representative branched —(C$_1$-C$_4$)alkyls include -iso-propyl, -sec-butyl, -iso-butyl, and -tert-butyl.

"—(C$_2$-C$_{10}$)alkenyl" means a straight chain or branched non-cyclic hydrocarbon having from 2 to 10 carbon atoms and including at least one carbon-carbon double bond. Representative straight chain and branched (C$_2$-C$_{10}$)alkenyls include -vinyl, -allyl, -1-butenyl, -2-butenyl, -iso-butylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl, -1-nonenyl, -2-nonenyl, -3-nonenyl, -1-decenyl, -2-decenyl, -3-decenyl and the like.

"—(C$_2$-C$_6$)alkenyl" means a straight chain or branched non-cyclic hydrocarbon having from 2 to 6 carbon atoms and including at least one carbon-carbon double bond. Representative straight chain and branched (C$_2$-C$_6$)alkenyls include -vinyl, -allyl, -1-butenyl, -2-butenyl, -iso-butylenyl, -1-pentenyl, -2-pentenyl, -3-methyl-1-butenyl, -2-methyl-2-butenyl, -2,3-dimethyl-2-butenyl, -1-hexenyl, 2-hexenyl, 3-hexenyl and the like.

"—(C$_2$-C$_{10}$)alkynyl" means a straight chain or branched non-cyclic hydrocarbon having from 2 to 10 carbon atoms and including at least one carbon-carbon triple bond. Representative straight chain and branched —(C$_2$-C$_{10}$)alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, -1-heptynyl, -2-heptynyl, -6-heptynyl, -1-octynyl, -2-octynyl, -7-octynyl, -1-nonynyl, -2-nonynyl, -8-nonynyl, -1-decynyl, -2-decynyl, -9-decynyl and the like.

"—(C$_2$-C$_6$)alkynyl" means a straight chain or branched non-cyclic hydrocarbon having from 2 to 6 carbon atoms and including at least one carbon-carbon triple bond. Representative straight chain and branched (C$_2$-C$_6$)alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl and the like.

"—(C$_3$-C$_{10}$)cycloalkyl" means a saturated cyclic hydrocarbon having from 3 to 10 carbon atoms. Representative (C$_3$-C$_{10}$)cycloalkyls are -cyclopropyl, -cyclobutyl, -cyclopentyl, -cyclohexyl, -cycloheptyl, -cyclooctyl, -cyclononyl, and -cyclodecyl.

"—(C$_3$-C$_8$)cycloalkyl" means a saturated cyclic hydrocarbon having from 3 to 8 carbon atoms. Representative (C$_3$-C$_8$) cycloalkyls include -cyclopropyl, -cyclobutyl, -cyclopentyl, -cyclohexyl, -cycloheptyl, and -cyclooctyl.

"—(C$_8$-C$_{14}$)bicycloalkyl" means a bi-cyclic hydrocarbon ring system having from 8 to 14 carbon atoms and at least one saturated cyclic alkyl ring. Representative —(C$_8$-C$_{14}$)bicycloalkyls include -indanyl, -1,2,3,4-tetrahydronaphthyl, -5,6,7,8-tetrahydronaphthyl, -perhydronaphthyl and the like.

"—(C$_8$-C$_{14}$)tricycloalkyl" means a tri-cyclic hydrocarbon ring system having from 8 to 14 carbon atoms and at least one saturated cyclic alkyl ring. Representative —(C$_8$-C$_{14}$)tricycloalkyls include -pyrenyl, -1,2,3,4-tetrahydroanthracenyl, -perhydroanthracenyl -aceanthreneyl, -1,2,3,4-tetrahydropenanthrenyl, -5,6,7,8-tetrahydrophenanthrenyl, -perhydrophenanthrenyl and the like.

"—(C$_5$-C$_{10}$)cycloalkenyl" means a cyclic non-aromatic hydrocarbon having at least one carbon-carbon double bond in the cyclic system and from 5 to 10 carbon atoms. Representative (C$_5$-C$_{10}$)cycloalkenyls include -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl, -cyclononenyl, -cyclononadienyl, -cyclodecenyl, -cyclodecadienyl and the like.

"—$(C_5$-$C_8)$cycloalkenyl" means a cyclic non-aromatic hydrocarbon having at least one carbon-carbon double bond in the cyclic system and from 5 to 8 carbon atoms. Representative (C8-C14)cycloalkenyls include -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl and the like.

"—$(C_8$-$C_{14})$bicycloalkenyl" means a bi-cyclic hydrocarbon ring system having at least one carbon-carbon double bond in each ring and from 8 to 14 carbon atoms. Representative —$(C_8$-$C_{14})$bicycloalkenyls include -indenyl, -pentalenyl, -naphthalenyl, -azulenyl, -heptalenyl, -1,2,7,8-tetrahydronaphthalenyl and the like.

"—$(C_8$-$C_{14})$tricycloalkenyl" means a tri-cyclic hydrocarbon ring system having at least one carbon-carbon double bond in each ring and from 8 to 14 carbon atoms. Representative —$(C_8$-$C_{14})$tricycloalkenyls include -anthracenyl, -phenanthrenyl, -phenalenyl, -acenaphthalenyl, as-indacenyl, s-indacenyl and the like.

"-(3- to 7-membered)heterocycle" or "-(3- to 7-membered) heterocyclo" means a 3- to 7-membered monocyclic heterocyclic ring which is either saturated, unsaturated non-aromatic, or aromatic. A 3- or a 4-membered heterocycle can contain up to 3 heteroatoms, a 5-membered heterocycle can contain up to 4 heteroatoms, a 6-membered heterocycle can contain up to 6 heteroatoms, and a 7-membered heterocycle can contain up to 7 heteroatoms. Each heteroatom is independently selected from nitrogen, which can be quaternized; oxygen; and sulfur, including sulfoxide and sulfone. The -(3- to 7-membered)heterocycle can be attached via a nitrogen or carbon atom. Representative -(3- to 7-membered)heterocycles include pyridyl, furyl, thiophenyl, pyrrolyl, oxazolyl, imidazolyl, thiazolyl, thiadiazolyl, isoxazolyl, pyrazolyl, isothiazolyl, pyridazinyl, pyrimidinyl, pyrimidinyl, triazinyl, morpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyrindinyl, tetrahydropyrimidinyl, tetrahydrothiophenyl, tetrahydrothiopyranyl and the like.

"-(3- to 5-membered)heterocycle" or "-(3- to 5-membered) heterocyclo" means a 3- to 5-membered monocyclic heterocyclic ring which is either saturated, unsaturated non-aromatic, or aromatic. A 3- or 4-membered heterocycle can contain up to 3 heteroatoms and a 5-membered heterocycle can contain up to 4 heteroatoms. Each heteroatom is independently selected from nitrogen, which can be quaternized; oxygen; and sulfur, including sulfoxide and sulfone. The -(3- to 5-membered)heterocycle can be attached via a nitrogen or carbon atom. Representative -(3- to 5-membered)heterocycles include furyl, thiophenyl, pyrrolyl, oxazolyl, imidazolyl, thiazolyl, isoxazolyl, pyrazolyl, isothiazolyl, triazinyl, pyrrolidinonyl, pyrrolidinyl, hydantoinyl, oxiranyl, oxetanyl, tetrahydrofuranyl, tetrahydrothiophenyl and the like.

"-(7- to 10-membered)bicycloheterocycle" or "-(7- to 10-membered)bicycloheterocyclo" means a 7- to 10-membered bicyclic, heterocyclic ring which is either saturated, unsaturated non-aromatic, or aromatic. A -(7- to 10-membered)bicycloheterocycle contains from 1 to 4 heteroatoms independently selected from nitrogen, which can be quaternized; oxygen; and sulfur, including sulfoxide and sulfone. The -(7- to 10-membered)bicycloheterocycle can be attached via a nitrogen or carbon atom. Representative -(7- to 10-membered)bicycloheterocycles include -quinolinyl, -isoquinolinyl, -chromonyl, -coumarinyl, -indolyl, -indolizinyl, -benzo[b]furanyl, -benzo[b]thiophenyl, -indazolyl, -purinyl, -4H-quinolizinyl, -isoquinolyl, -quinolyl, -phthalazinyl, -naphthyridinyl, -carbazolyl, -3-carbolinyl and the like.

"—$(C_{14})$aryl" means a 14-membered aromatic carbocyclic moiety such as -anthryl or -phenanthryl.

"-(5- to 10-membered)heteroaryl" means an aromatic heterocycle ring of 5 to 10 members, including both mono- and bicyclic ring systems, wherein at least one carbon atom of one or both of the rings is replaced with a heteroatom independently selected from nitrogen, oxygen, and sulfur. In one embodiment one of the -(5- to 10-membered)heteroaryl's rings contain at least one carbon atom. In another embodiment both of the -(5- to 10-membered)heteroaryl's rings contain at least one carbon atom. Representative -(5- to 10-membered)heteroaryls include pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrimidinyl, thiadiazolyl, triazinyl, cinnolinyl, phthalazinyl, and quinazolinyl.

"—$CH_2$(halo)" means a methyl group wherein one of the hydrogens of the methyl group has been replaced with a halogen. Representative —$CH_2$(halo) groups include —$CH_2F$, —$CH_2Cl$, —$CH_2Br$, and —$CHI_2$.

"—CH(halo)$_2$" means a methyl group wherein two of the hydrogens of the methyl group have been replaced with a halogen. Representative —CH(halo)$_2$ groups include —$CHF_2$, —$CHCl_2$, —$CHBr_2$, —CHBrCl, —CHClI, and —$CHI_2$.

"—C(halo)$_3$" means a methyl group wherein each of the hydrogens of the methyl group has been replaced with a halogen. Representative —C(halo)$_3$ groups include —$CF_3$, —$CCl_3$, —$CBr_3$, and —$CI_3$.

"-Halogen" or "-Halo" means —F, —Cl, —Br, or —I.

The phrase "pyridyl group" means

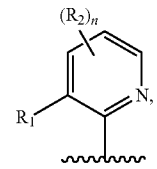

wherein $R_1$, $R_2$, and n are defined above for the Cyclo(hetero)alkenyl Compounds of Formula (I).

The phrase "pyrazinyl group" means,

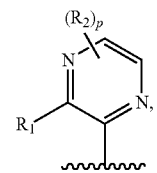

wherein $R_1$, $R_2$, and p are defined above for the Cyclo(hetero)alkenyl Compounds of Formula (I).

The phrase "pyrimidinyl group" means

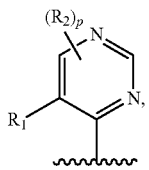

wherein $R_1$, $R_2$, and p are defined above for the Cyclo(hetero)alkenyl Compounds of Formula (I).

The phrase "pyridazinyl group" means

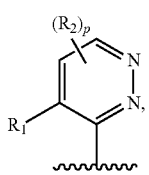

wherein $R_1$, $R_2$, and p are defined above for the Cyclo(hetero)alkenyl Compounds of Formula (I).

The phrase "thiadiazolyl group" means

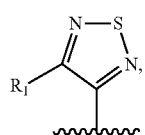

wherein $R_1$ is defined above for the Cyclo(hetero)alkenyl Compounds of Formula (I).

The phrase "benzoimidazolyl group" means

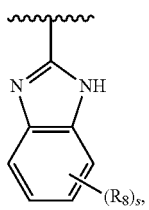

wherein $R_8$ and s are defined above for the Cyclo(hetero)alkenyl Compounds of Formula (I).

The phrase "benzothiazolyl group" means

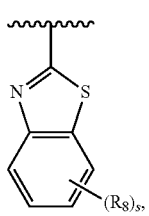

wherein $R_8$ and s are defined above for the Cyclo(hetero)alkenyl Compounds of Formula (I).

The phrase "benzooxazolyl group" means

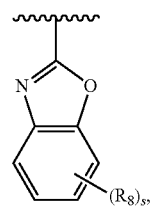

wherein $R_8$ and s are defined above for the Cyclo(hetero)alkenyl Compounds of Formula (I).

The phrase "5-benzodioxolyl group" means

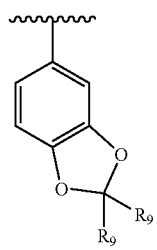

where each $R_9$ is independently —H, -halo, or —($C_1$-$C_6$) alkyl.

The phrase "5-benzodithiolyl group" means

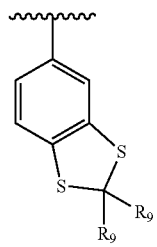

where each $R_9$ is independently —H, -halo, or —($C_1$-$C_6$) alkyl.

The phrase "5-dihydroindenyl group" means

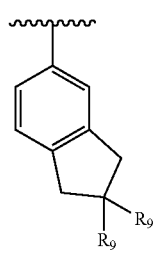

where each $R_9$ is independently —H, -halo, or —($C_1$-$C_6$) alkyl.

The phrase "5-dihydrobenzoimidazolyl group" means

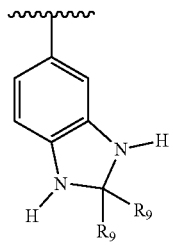

where each R₉ is independently —H, -halo, or —(C₁-C₆) alkyl.

The phrase "6-dihydrobenzofuranyl group" means

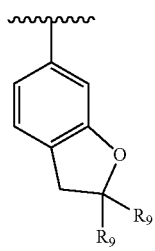

where each R₉ is independently —H, -halo, or —(C₁-C₆) alkyl.

The phrase "5-dihydrobenzofuranyl group" means

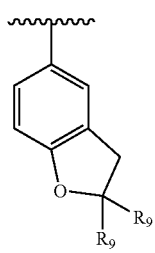

where each R₉ is independently —H, -halo, or —(C₁-C₆) alkyl.

The phrase "6-indolinyl group" means

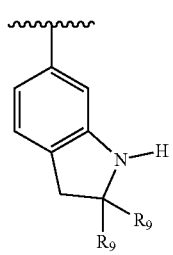

where each R₉ is independently —H, -halo, or —(C₁-C₆) alkyl.

The phrase "5-indolinyl group" means

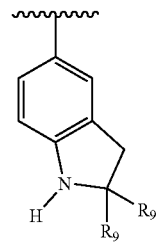

where each R₉ is independently —H, -halo, or —(C₁-C₆) alkyl.

The phrase "6-dihydrobenzothiopheneyl group" means

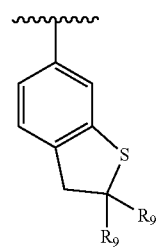

where each R₉ is independently —H, -halo, or —(C₁-C₆) alkyl.

The phrase "5-dihydrobenzothiopheneyl group" means

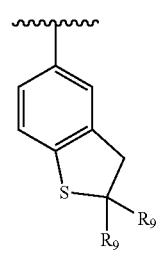

where each R₉ is independently —H, -halo, or —(C₁-C₆) alkyl.

The phrase "5-dihydrobenzooxazolyl group" means

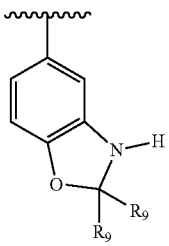

where each R₉ is independently —H, -halo, or —(C₁-C₆) alkyl.

The phrase "6-dihydrobenzooxazolyl group" means

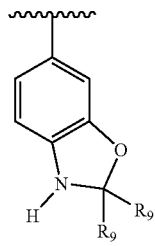

where each $R_9$ is independently —H, -halo, or —$(C_1$-$C_6)$ alkyl.

The phrase "5-dihydrobenzothiazolyl group" means

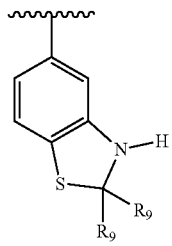

where each $R_9$ is independently —H, -halo, or —$(C_1$-$C_6)$ alkyl.

The phrase "6-dihydrobenzothiazolyl group" means

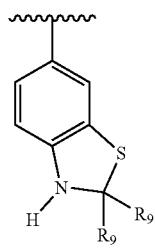

where each $R_9$ is independently —H, -halo, or —$(C_1$-$C_6)$ alkyl.

The phrase "2-(3-chloropyridyl)" means

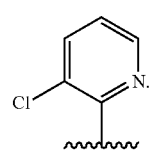

The phrase "2-(3-fluoropyridyl)" means

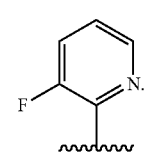

The phrase "2-(3-methylpyridyl)" means

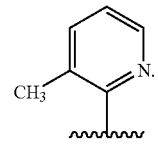 [SMILES: *c1ncccc1C]

The phrase "2-(3-$CF_3$-pyridyl)" means

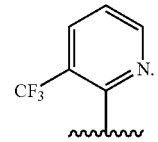

The phrase "2-(3-$CHF_2$-pyridyl)" means

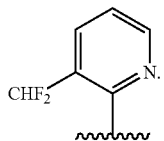

The phrase "2-(3-hydroxypyridyl)" means

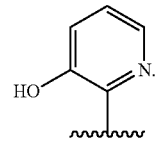

The phrase "2-(3-nitropyridyl)" means

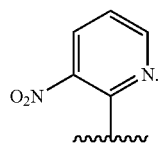 [SMILES: *c1ncccc1[N+](=O)[O-]]

The phrase "2-(3-cyanopyridyl)" means

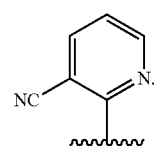 [SMILES: *c1ncccc1C#N]

The phrase "2-(3-bromopyridyl)" means

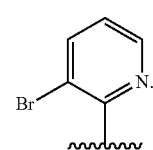

The phrase "2-(3-iodopyridyl)" means

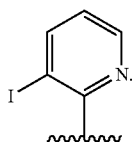

The phrase "4-(5-chloropyrimidinyl)" means

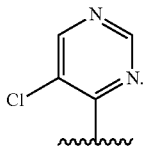

The phrase "4-(5-methylpyrimidinyl)" means

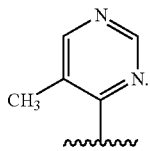 [SMILES: *c1ncncc1C]

The phrase "4-(5-fluoropyrimidinyl)" means

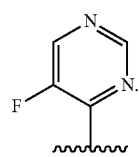

The phrase "2-(3-chloropyrazinyl)" means

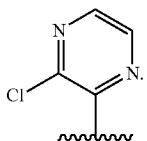

The phrase "2-(3-methylpyrazinyl)" means

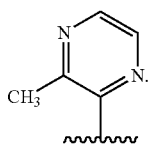 [SMILES: *c1nccnc1C]

The phrase "2-(3-fluoropyrazinyl)" means

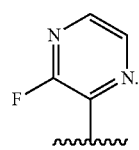

The phrase "3-(4-chloropyridazinyl)" means

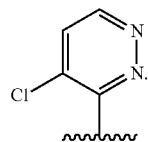

The phrase "3-(4-methylpyridazinyl)" means

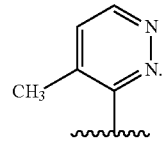

The phrase "3-(4-fluoropyridazinyl)" means

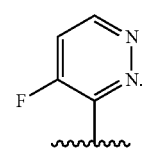

The phrase "5-(4-chlorothiadiazolyl)" means

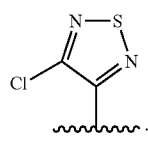

The phrase "5-(4-methylthiadiazolyl)" means

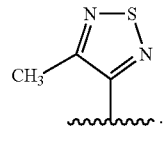

The phrase "5-(4-fluorothiadiazolyl)" means

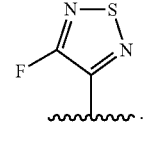

The phrase "-(1,1-dimethyl-pentyl)" means

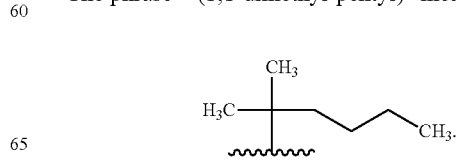

The phrases "-(1,1-dimethyl-acetic acid) ethyl ester" and "2-methylpropionic acid ethyl ester" mean

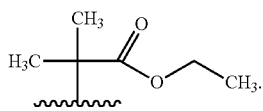

The phrases "-(N-piperidinyl)" and "(piperidin-1-yl)-" mean

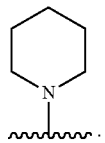

The phrase "cyclo(hetero)alkenyl ring" means

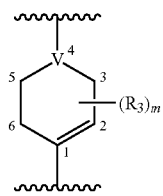

wherein V, $R_3$ and m are defined above and the numbers designate the position of each atom of the cyclo(hetero)alkenyl ring. The language "(hetero)" means that V is either: N, in which case the cyclo(hetero)alkenyl ring is a tetrahydropyridyl ring; or CH, in which case the cyclo(hetero)alkenyl ring is a cycloalkenyl ring.

The term "animal," includes, but is not limited to, a cow, monkey, baboon, chimpanzee, horse, sheep, pig, chicken, turkey, quail, cat, dog, mouse, rat, rabbit, guinea pig, and human.

The phrase "pharmaceutically acceptable salt," as used herein, is any pharmaceutically acceptable salt that can be prepared from a Cyclo(hetero)alkenyl Compound, including a salt formed from an acid and a basic functional group, such as a nitrogen group, of one of the Cyclo(hetero)alkenyl Compounds. Illustrative salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucoronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The term "pharmaceutically acceptable salt" also includes a salt prepared from a Cyclo(hetero)alkenyl Compound having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N,-dimethyl-N-(2-hydroxyethyl)amine, or tri-(2-hydroxyethyl)amine; N-methyl-D-glucamine; and amino acids such as arginine, lysine and the like.

The phrase "effective amount," when used in connection with a Cyclo(hetero)alkenyl Compound means an amount effective for: (a) treating or preventing a Condition; or (b) inhibiting VR1, mGluR1, or mGluR5 function in a cell.

The phrase "effective amount," when used in connection with another therapeutic agent means an amount for providing the therapeutic effect of the other therapeutic agent.

When a first group is "substituted with one or more" second groups, one or more hydrogen atoms of the first group is replaced with a corresponding number of second groups. When the number of second groups is two or greater, each second group can be the same or different. In one embodiment, the number of second groups is one or two. In another embodiment, the number of second groups is one.

The term "THF" means tetrahydrofuran.
The term "DCM" means dichloromethane.
The term "DCE" means dichloroethane, e.g., 1,1-dichloroethane, 1,2-dichloroethane, or mixtures thereof.
The term "DMF" means dimethylformamide.
The term "DMSO" means dimethyl sulfoxide.
The term "DIEA" means diisopropylethylamine.
The term "TFA" means trifluoroacetic acid.
The term "EtOAc" means ethyl acetate.
The term "Dppp" means 1,3-bis(diphenylphosphino)propane.
The term "Pd(OAc)$_2$" means palladium acetate.
The term "IBD" means inflammatory-bowel disease.
The term "IBS" means irritable-bowel syndrome.
The term "ALS" means amyotrophic lateral sclerosis.
The term "LiHMDS" means lithium hexamethyldisilazide.

The phrases "treatment of," "treating" and the like include the amelioration or cessation of a Condition or a symptom thereof.

In one embodiment, treating includes inhibiting, for example, decreasing the overall frequency of episodes of a Condition or a symptom thereof.

The phrases "prevention of," "preventing" and the like include the avoidance of the onset of a Condition or a symptom thereof.

4.3 Methods for Making the Cyclo(Hetero)Alkenyl Compounds

The Cyclo(hetero)alkenyl Compounds can be made using conventional organic synthesis or by the following illustrative methods shown in the schemes below.

4.3.1 Methods for Making the Cyclo(hetero)alkenyl Compounds Where V is N

In one embodiment, the present invention relates to methods for making the Cyclo(hetero)alkenyl Compounds where V is N by the following non-limiting illustrative method shown below in Scheme A.
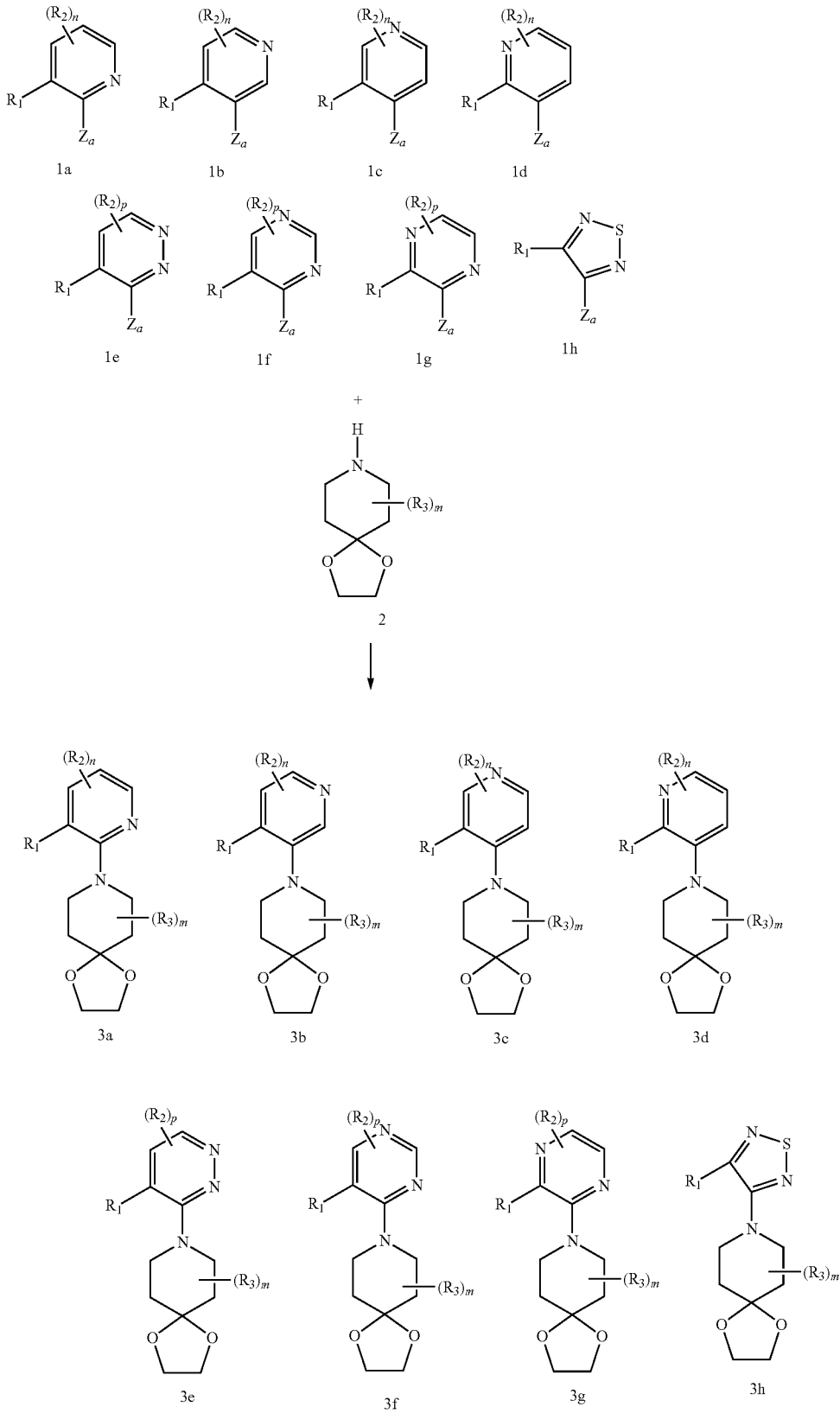

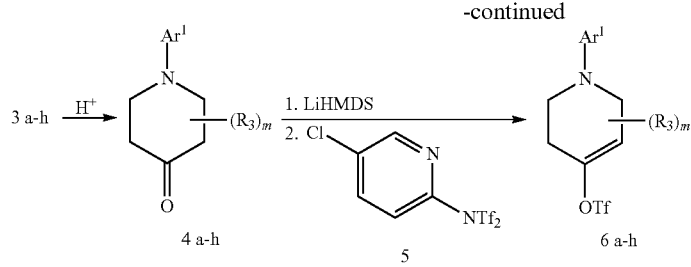

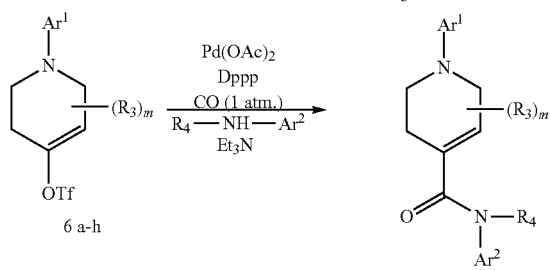

(II) Cyclo(hetero)alkenyl Compound
Where V is N where $R_1$, $R_2$, $R_3$, $R_4$, $Ar^1$, $Ar^2$, m, n and p are defined above and $Z_a$ is a halogen.

About 1 eq. of a Compound of Formula 1a-h (1M) and 1 eq. of a Compound of Formula 2 are heated in DMSO in the presence of about 1 eq. of DIEA at a temperature of from about 125° C. to about 140° C. for about 12 h. The resulting reaction mixture is cooled to about 25° C. and the solvent removed, e.g., under reduced pressure, to provide an 8-heteroaromatic-1,4-dioxa-8-aza-spiro[4.5]decane Compound of Formula 3a-h. A Compound of Formula 3a-h is useful, e.g., as an intermediate for the synthesis of a Cyclo(hetero)alkenyl Compound.

The Compound of Formula 3a-h can also be obtained by dissolving about 1 equivalent of a Compound of Formula 1a-h (1.5M), a Compound of Formula 2 (about 1.2 eq.), and the sodium salt of 2-methylpropan-2-ol ("NaOtBu", 1.5 eq.) in glyme and degassing the resulting solution by bubbling nitrogen through the solution. After the solution is degassed, tris-(dibenzylideneacetone)dipalladium (0) catalyst (0.02 eq.) and 0.02 eq. of the ligand depicted below

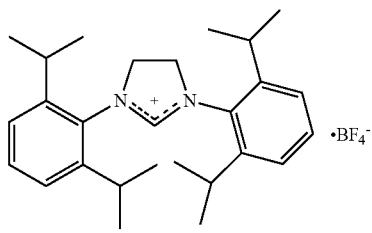

is added to the solution and the resulting reaction mixture is heated at a temperature of about 50° C. for about 4.5 h. The reaction mixture is cooled to about 25° C. and solids removed by filtering over CELITE. The solvent is then removed, e.g., under reduced pressure, to provide a residue. The resulting residue can be purified, e.g., using a silica gel column eluted with 6:1 hexane:ethyl acetate.

The Compound of Formula 3a-h can also be obtained by dissolving, e.g., in toluene, about 1 equivalent of a Compound of Formula 1a-h (1.2M), adding to the solution a Compound of Formula 2 (about 1.1 eq.), followed by the addition of NaOtBu (about 1.1 eq.), Pd(OAc)$_2$ (about 0.05 eq.), and 0.05 eq. Dppp (about 0.05 eq.) to form a reaction mixture. The atmosphere in contact with the reaction mixture is replaced by nitrogen. The reaction mixture is stirred and heated to a temperature of from about 25° C. to about the boiling point of the solvent, alternately from about 50° C. to about 100° C., for about 3 h. The reaction mixture is cooled to about 25° C. and worked-up, e.g., as described above, to provide the Compound of Formula 3a-h.

The Compound of Formula 3a-h is then reacted with an acid to provide a Compound of Formula 4a-h. In one embodiment, the present invention relates to a method for making a Cyclo(hetero)alkenyl Compound comprising allowing a Compound of Formula 3a-h to react with an acid. In another embodiment, the acid is an organic acid, such as TFA, an inorganic acid, such as hydrochloric acid, or their mixtures. For example, the Compound of Formula 3a-h (0.25M) is reacted with 30% TFA in DCM at a temperature of from about 25° C. to about the boiling point of the solvent. Alternatively, the Compound of Formula 3a-h (0.25M) is reacted with about 4N HCl in THF at a temperature of about 50° C. for about 16 hours. Either resulting reaction mixture is cooled to about 25° C. and neutralized with aqueous Na$_2$CO$_3$ such that separate aqueous and organic layers form. The organic layer is separated from the aqueous layer. The aqueous layer is then extracted with DCM and the organic layer and the post-extraction DCM are combined and dried, e.g., with MgSO$_4$ or Na$_2$SO$_4$. The solvent is removed, e.g., under reduced pressure, to provide a 1-heteroaromatic-piperidin-4-one Compound of Formula 4 a-h. The Compound of Formula 4a-h can be purified, e.g., using a silica gel column eluted with 15:1 hexane:ethyl acetate. A Compound of Formula 4a-h is useful, e.g., as an intermediate for the synthesis of a Cyclo(hetero) alkenyl Compound.

In one embodiment, the present invention relates to a method for making a Cyclo(hetero)alkenyl Compound comprising allowing a Compound of Formula 4a-h to react with LiHMDS and then an excess triflimide. For example, the Compound of Formula 4a-h (1 eq.) is reacted with 1.25 eq. of LiHMDS at about −78° C. and the resulting reaction mixture allowed to stir at about −78° C. for about 2 h. After stirring for about 2 h, an excess of N-(5-chloro-2-pyridyl)triflimide 5 (1.05 eq. in one embodiment, 3 eq. in another embodiment) is added to the reaction mixture at a temperature of about −78° C. The reaction mixture is stirred for about 2.5 h at a temperature of about −78° C. and then allowed to warm to about 25° C. The solvent is removed, e.g., under reduced pressure, to provide a residue that can be purified, e.g., using a silica gel column eluted with 10:1 hexane:ethyl acetate to provide a Compound of Formula 6a-h. A Compound of Formula 6a-h is useful, e.g., as an intermediate for the synthesis of a Cyclo(hetero)alkenyl Compound.

In one embodiment, the present invention relates to a method for making a Cyclo(hetero)alkenyl Compound comprising allowing a Compound of Formula 6a-h to react with a compound of formula $Ar^2$—$NHR_4$. In another embodiment, the reaction in the presence of an organic base, e.g., a trialkylamine. In another embodiment, the reaction in the presence of $Pd(OAc)_2$ and Dppp. In another embodiment, the reaction in the presence of a carbon monoxide atmosphere. For example, about 1 equivalent of the Compound of Formula 6a-h (about 1M), an excess of a compound of formula $Ar^2$—$NHR_4$ (about 2 eq.), and a trialkylamine, e.g., triethylamine (from about 1.1 to about 20 eq., about 2.2 eq. in one embodiment), are dissolved in DMF or THF and the resulting solution is degassed by bubbling nitrogen through the solution. $Pd(OAc)_2$ and Dppp (about 0.2-0.3 eq. of each) are added to the solution and the nitrogen atmosphere is replaced with carbon monoxide at a pressure of about 1 atm. The reaction mixture is then heated to about 70° C. for about 2 h. The reaction mixture is cooled to about 25° C. and the solvent removed, e.g., under reduced pressure, to provide a residue. The resulting residue can be purified, e.g., using a silica gel column eluted with 10:1 hexane:ethyl acetate. Where m=1, a mixture of Cyclo(hetero)alkenyl Compounds is generally obtained. The mixture can be separated by conventional methods, for example, column chromatography.

Compounds of formula 2 are commercially available or can be prepared by methods known to those skilled in the art.

The Compound of Formula (I) where X is S (i.e., the Compound of Formula (II′)) can be made by, e.g., reacting a Compound of Formula (II) (i.e., where X is O) with Lawesson's reagent (i.e., 2,4-bis(4-methoxyphenyl)-1,3-dithia-2,4-diphosphetane-2,4-disulfide) according to the procedures described in *Chem. Let.* 8:713-4 (1995) or *Chem. Let.* 12:1398-9 (2000). In one embodiment, the Compound of Formula (I) where X is S can be made by reacting a Compound of Formula (II) (where X is O) with Lawesson's reagent in a nonpolar solvent such as THF or toluene at a temperature of about 100° C. for about 2-3 hours, as shown below:

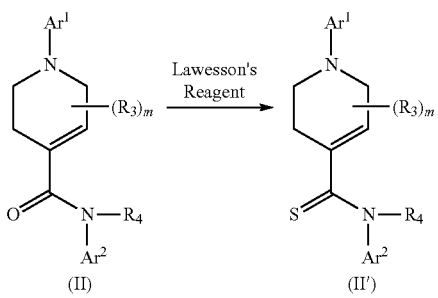

In another embodiment, the present invention relates to methods for making the Cyclo(hetero)alkenyl Compounds where V is N from the 8-heteroaromatic-1,4-dioxa-8-azaspiro[4.5]decane Compounds of Formula 3a-h by the following non-limiting illustrative method shown below in Scheme B.

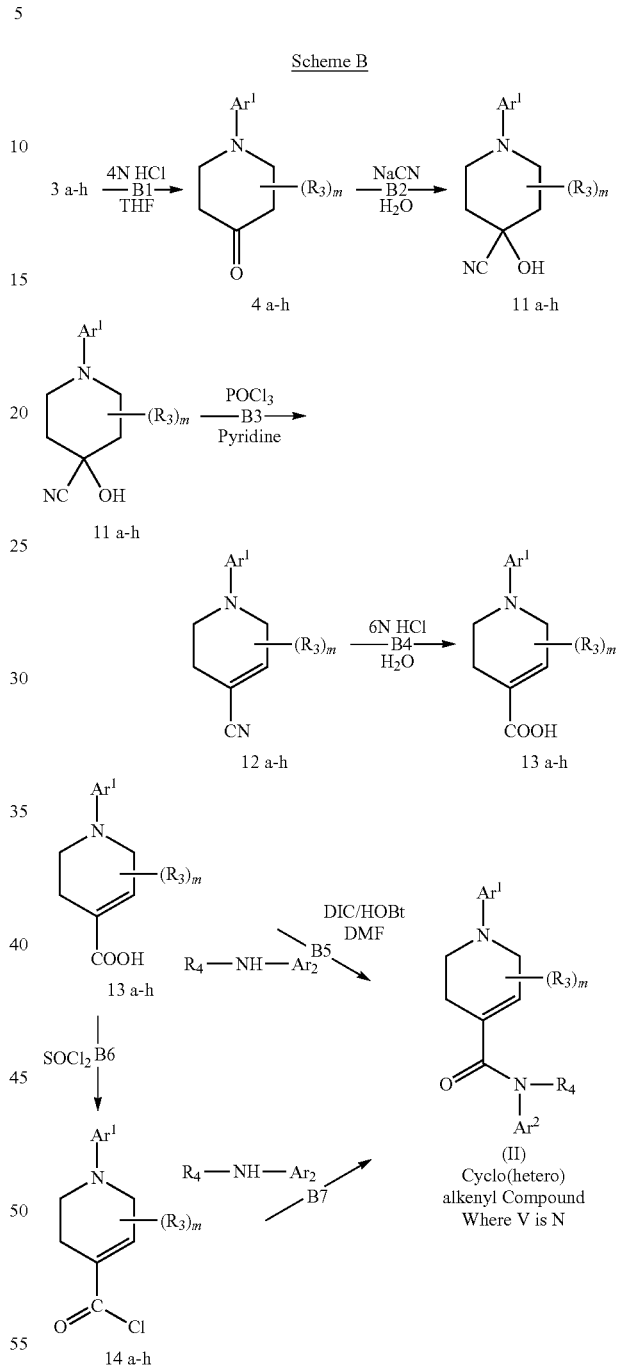

where $R_3$, $R_4$, $Ar^1$, $Ar^2$, and m are defined above.

In Step B1 of Scheme B, the Compound of Formula 3a-h, which can be obtained, e.g., as described in Scheme A, is reacted with a ketone-forming reagent, e.g., an inorganic acid such as HCl or $H_2SO_4$, or an organic acid, such as trifluoroacetic acid. In one embodiment, the present invention relates to a method for making a Cyclo(hetero)alkenyl Compound comprising allowing a Compound of Formula 3a-h to react with a ketone-forming reagent. In another embodiment, the ketone-forming reagent is HCl, $H_2SO_4$, trifluoroacetic acid or a mixture thereof. In another embodiment, the ketone-forming reagent is HCl. In another embodiment, the ketone-forming reagent is $H_2SO_4$. In another embodiment, the ketone-forming reagent is trifluoroacetic acid.

In certain embodiments, the ketone-forming reagent is present in the reaction in Step B1 at an initial concentration within the range of from about 1N to about 12N, or at an initial concentration within the range of from about 2N to about 6N. In a specific embodiment, the ketone-forming reagent is present in the reaction at an initial concentration of about 4N.

In certain embodiments, the Compound of Formula 3a-h is present in the reaction in Step B1 at an initial concentration within the range of from about 0.05M to about 10M, or at an initial concentration within the range of from about 0.1M to about 1M. In a specific embodiment, the Compound of Formula 3a-h is present in the reaction at an initial concentration of about 0.25M.

In certain embodiments, the reaction in Step B1 is carried out at a temperature within the range of from about 0° C. to about the boiling point of the solvent; at a temperature within the range of from about 15° C. to about 100° C.; or at a temperature within the range of from about 45° C. to about 55° C.

In certain embodiments, the reaction in Step B1 is carried out in a nonpolar solvent, e.g., hexane, heptane, benzene, diethyl ether, THF, pyridine, DCM, DCE, chloroform, carbon tetrachloride and combinations thereof. In one embodiment, the nonpolar solvent is THF, chloroform or combinations thereof. In another embodiment, the nonpolar solvent is THF. In another embodiment, the nonpolar solvent is chloroform.

In certain embodiments, the Compound of Formula 3a-h is provided as a salt, e.g., the hydrochloride salt, which can be converted to the free amine, using procedures known in the art, prior to reaction with the ketone-forming reagent. For example, the hydrochloride salt of the Compound of Formula 3a-h is dissolved in a suitable organic solvent, such as but not limited to chloroform, to provide a solution that is extracted with, e.g., a saturated aqueous solution of $Na_2CO_3$. The organic layer is recovered and the aqueous layer back-extracted with an additional volume of the organic solvent. The organic solvent layers are combined, extracted with water, dried, e.g., over anhydrous sodium sulfate, and then the liquid is removed, such as by evaporation under reduced pressure, e.g., with a rotary evaporator, to provide the Compound of Formula 3a-h as the free amine.

The reaction in Step B1 can be carried out at reduced pressure, atmospheric pressure or elevated pressure, i.e., greater than atmospheric pressure. In one embodiment, the reaction is carried out at atmospheric pressure. In certain embodiments, the reaction in Step B1 is carried out in an air atmosphere. In certain embodiments, the reaction in Step B1 is carried out in an inert atmosphere. In one non-limiting aspect of this embodiment, the reaction in Step B1 is carried out under a nitrogen atmosphere. In another non-limiting aspect of this embodiment, the reaction in Step B1 is carried out under an argon atmosphere.

Progress of the reaction in Step B1 can be monitored using conventional analytical techniques, including but not limited to infrared spectroscopy ("IR"), liquid chromatography ("LC"), mass spectrometry ("MS"), liquid chromatography in conjunction with mass spectrometry ("LCMS"), thin-layer chromatography ("TLC"), high-performance liquid chromatography ("HPLC"), gas chromatography ("GC"), gas-liquid chromatography ("GLC"), and/or nuclear magnetic resonance spectroscopy ("NMR"), such as $^1H$ and $^{13}C$ NMR. The reaction according to Step B1 is carried out, in one embodiment, until a starting material is consumed or, in another embodiment, until the ratio of product, a Compound of Formula 4a-h, to starting material, the Compound of Formula 3a-h, remains essentially constant. Typically, a time sufficient for the reaction in Step B1 is within the range of from about 0.5 hours to about 48 hours, from about 1 hour to about 24 hours, or from about 6 hours to about 18 hours. In a specific embodiment, the reaction according to Step B1 is carried out for about 16 hours.

In another embodiment, the reaction according to Step B1 is carried out as described in Scheme A. In another embodiment, the reaction according to Step B1 is carried out in THF with the Compound of Formula 3a-h present at an initial concentration of about 0.35M, with about a 4N initial concentration of HCl, at a temperature of about 50° C., and for a period of about 16 hours with stirring.

The resulting reaction mixture is cooled to about 25° C. and neutralized, e.g., with aqueous $Na_2CO_3$, such that separate aqueous and organic layers form. The organic layer is separated from the aqueous layer. The aqueous layer is then extracted, e.g., with ethyl acetate. The organic layer and the post-extraction aliquot(s) are combined and dried, e.g., with $MgSO_4$ or $Na_2SO_4$, and the solvent is removed, e.g., under reduced pressure, to provide a 1-heteroaromatic-piperidin-4-one Compound of Formula 4a-h which can be used without further purification or, if desired, can be purified, e.g., using a silica gel column eluted with 3:1 hexane:ethyl acetate.

In Step B2 of Scheme B, the 1-heteroaromatic-piperidin-4-one Compound of Formula 4a-h is reacted with a cyanation reagent, e.g., a cyanide salt such as NaCN, KCN or LiCN. In one embodiment, the present invention relates to a method for making a Cyclo(hetero)alkenyl Compound comprising allowing a 1-heteroaromatic-piperidin-4-one Compound of Formula 4a-h to react with a cyanation reagent. In another embodiment, the cyanide salt is NaCN, KCN, LiCN or a mixture thereof. In another embodiment, the cyanide salt is KCN. In another embodiment, the cyanide salt is NaCN. In another embodiment, the cyanide salt is LiCN. Cyanide salts are commercially available from, e.g., Aldrich Chemical Co., Milwaukee, Wis., or can be prepared by methods known to those skilled in the art.

In certain embodiments, the reaction in Step B2 is carried out with an initial amount of cyanation reagent within the range of from about 1 to about 4 equivalents, or within the range of from about 1.1 to about 2 equivalents, on a molar basis, relative to the Compound of Formula 4a-h. In another embodiment, this reaction is carried out with about 1.2 equivalents, on a molar basis, of cyanation reagent, relative to the Compound of Formula 4a-h.

In certain embodiments, the Compound of Formula 4a-h is present in the reaction in Step B2 at an initial concentration within the range of from about 0.05M to about 10M, or at an initial concentration within the range of from about 0.1M to about 5M. In a specific embodiment, the Compound of Formula 4a-h is present in the reaction at an initial concentration of about 0.3M.

In certain embodiments, the reaction in Step B2 is carried out at a temperature within the range of from about 0° C. to about 100° C.; at a temperature within the range of from about 0° C. to about 60° C.; or at a temperature within the range of from about 0° C. to about 25° C.

In certain embodiments, the reaction in Step B2 is carried out in a polar protic solvent, such as water, an alcohol, e.g., methanol, an organic acid, e.g., acetic acid, an amide, e.g., formamide, or combinations thereof. In one embodiment, the polar protic solvent is water, methanol or combinations thereof. In another embodiment, the polar protic solvent is water. In another embodiment, the polar protic solvent is methanol. In other embodiments, the solvent comprises a mixture of water and a suitable aprotic solvent or solvents, such as acetone, MEK, ethyl acetate, acetonitrile, dioxane, N-methyl-pyrrolidone, DMF, DMAc, DMSO, pyridine, and combinations thereof. In such embodiments the ratio of water to aprotic solvent can be within the range of from about 10:1 to about 1:1 (water:aprotic solvent). In certain embodiments, the aprotic solvent mixed with water is selected from acetone, MEK, ethyl acetate, acetonitrile, dioxane, N-methyl-pyrrolidone, DMF, DMAc, DMSO, pyridine, and combinations thereof.

In certain embodiments, the Compound of Formula 4a-h is provided as a salt, e.g., the hydrochloride salt, which can be converted to the free amine, using procedures known in the art, prior to reaction with the cyanide salt. For example, the hydrochloride salt of the Compound of Formula 4a-h is dissolved in a suitable organic solvent, such as but not limited to chloroform, to provide a solution that is extracted with, e.g., a saturated aqueous solution of $Na_2CO_3$. The organic layer is recovered and the aqueous layer back-extracted with an additional volume of the organic solvent. The organic solvent layers are combined, extracted with water, dried, e.g., over anhydrous sodium sulfate, and then the liquid is removed to provide the Compound of Formula 4a-h as the free amine.

The reaction in Step B2 can be carried out at reduced pressure, atmospheric pressure or elevated pressure, i.e., greater than atmospheric pressure. In one embodiment, the reaction is carried out at atmospheric pressure. In certain embodiments, the reaction in Step B2 is carried out in an air atmosphere. In certain embodiments, the reaction in Step B2 is carried out in an inert atmosphere. In one non-limiting aspect of this embodiment, the reaction in Step B2 is carried out under a nitrogen atmosphere. In another non-limiting aspect of this embodiment, the reaction in Step B2 is carried out under an argon atmosphere.

Progress of the reaction in Step B2 can be monitored using conventional analytical techniques, including but not limited to IR, LC, MS, LCMS, TLC, HPLC, GC, GLC and/or NMR. The reaction according to Step B2 is carried out, in one embodiment, until a starting material is consumed or, in another embodiment, until the ratio of product, a Compound of Formula 11a-h, to starting material, the Compound of Formula 4a-h, remains essentially constant. Typically, a time sufficient for the reaction in Step B2 is within the range of from about 0.5 hours to about 36 hours, from about 1 hour to about 24 hours, or from about 4 hours to about 16 hours. In a specific embodiment, the reaction according to Step B2 is carried out for about 12 hours.

In another embodiment, the reaction according to Step B2 is carried out in water with about 1.2 equivalents, on a molar basis, of a cyanide salt, relative to the Compound of Formula 4a-h, at a temperature within the range of from about 0° C. to about 25° C. for a period of about 12 hours with stirring.

Thereafter, the solvent is removed, e.g., under reduced pressure, to provide a residue that can be purified, e.g., using a silica gel column eluted with 3:1 hexane:ethyl acetate, to provide a 1-heteroaromatic-4-hydroxy-piperidine-4-carbonitrile Compound of Formula 11a-h. A Compound of Formula 11a-h is useful, e.g., as an intermediate for the synthesis of a Cyclo(hetero)alkenyl Compound.

In Step B3 of Scheme B, the 1-heteroaromatic-4-hydroxy-piperidine-4-carbonitrile Compound of Formula 11a-h is reacted with a dehydrogenation agent, e.g., $POCl_3$, $PSCl_3$, $PCl_5$, $SOCl_2$ or $COCl_2$. In one embodiment, the present invention relates to a method for making a Cyclo(hetero) alkenyl Compound comprising allowing a 1-heteroaromatic-4-hydroxy-piperidine-4-carbonitrile Compound of Formula 11a-h to react with a dehydrogenation agent. In another embodiment, the dehydrogenation agent is $POCl_3$, $PSCl_3$, $PCl_5$, $SOCl_2$, $COCl_2$ or a mixture thereof. In another embodiment, the dehydrogenation agent is $POCl_3$, $PSCl_3$, $SOCl_2$ or a mixture thereof. In another embodiment, the dehydrogenation agent is $POCl_3$, $PSCl_3$ or a mixture thereof. In another embodiment, the dehydrogenation agent is $POCl_3$. In another embodiment, the dehydrogenation agent is $PSCl_3$. In another embodiment, the dehydrogenation agent is $SOCl_2$. In another embodiment, the dehydrogenation agent is $COCl_2$.

Such dehydrogenation agents are commercially available from, e.g., Aldrich Chemical Co., or can be prepared by methods known to those skilled in the art.

In certain embodiments, the reaction in Step B3 is carried out with an initial amount of dehydrogenation agent within the range of from about 1 to about 10 equivalents, or within the range of from about 1.5 to about 4 equivalents, on a molar basis, relative to the Compound of Formula 11a-h. In another embodiment, this reaction is carried out with about 2.2 equivalents, on a molar basis, of dehydrogenation agent, relative to the Compound of Formula 11a-h.

In certain embodiments, the Compound of Formula 11a-h is present in the reaction in Step B3 at an initial concentration within the range of from about 0.05M to about 10M, or at an initial concentration within the range of from about 0.1M to about 2M. In a specific embodiment, the Compound of Formula 11a-h is present in the reaction at an initial concentration of about 0.25M.

In certain embodiments, the reaction in Step B3 is carried out at a temperature within the range of from about 0° C. to about 100° C.; at a temperature within the range of from about 0° C. to about 60° C.; or at a temperature within the range of from about 15° C. to about 30° C.

In certain embodiments, the reaction in Step B3 is carried out in an aprotic solvent, e.g., acetone, MEK, ethyl acetate, acetonitrile, dioxane, N-methyl-pyrrolidone, DMF, DMAc, DMSO, pyridine, and combinations thereof. In one embodiment, the aprotic solvent is pyridine, dioxane or combinations thereof. In another embodiment, the aprotic solvent is pyridine. In another embodiment, the aprotic solvent is dioxane.

In certain embodiments, the Compound of Formula 11a-h is provided as a salt, e.g., the hydrochloride salt, which can be converted to the free amine, using procedures known in the art, prior to reaction with the dehydrogenation agent. For example, the hydrochloride salt of the Compound of Formula 11a-h is dissolved in a suitable organic solvent, such as but not limited to chloroform, to provide a solution that is extracted with, e.g., a saturated aqueous solution of $Na_2CO_3$. The organic layer is recovered and the aqueous layer back-extracted with an additional volume of the organic solvent. The organic solvent layers are combined, extracted with water, dried, e.g., over anhydrous sodium sulfate, and then the liquid is removed to provide the Compound of Formula 11 a-h as the free amine.

The reaction in Step B3 can be carried out at reduced pressure, atmospheric pressure or elevated pressure, i.e., greater than atmospheric pressure. In one embodiment, the reaction is carried out at atmospheric pressure. In certain embodiments, the reaction in Step B3 is carried out in an inert atmosphere. In one non-limiting aspect of this embodiment, the reaction in Step B3 is carried out under a nitrogen atmosphere. In another non-limiting aspect of this embodiment, the reaction in Step B3 is carried out under an argon atmosphere.

Progress of the reaction in Step B3 can be monitored using conventional analytical techniques, including but not limited to IR, LC, MS, LCMS, TLC, HPLC, GC, GLC and/or NMR.

The reaction according to Step B3 is carried out, in one embodiment, until a starting material is consumed or, in another embodiment, until the ratio of product, a Compound of Formula 12a-h, to starting material, the Compound of Formula 11a-h, remains essentially constant. Typically, a time sufficient for the reaction in Step B3 is within the range of from about 0.5 hours to about 48 hours, from about 2 hours to about 36 hours, or from about 4 hours to about 24 hours. In a specific embodiment, the reaction according to Step B3 is carried out for about 22 hours.

In another embodiment, the reaction according to Step B3 is carried out in pyridine with about 2.2 equivalents, on a molar basis, of a dehydrogenation agent, relative to the Compound of Formula 11a-h, at a temperature within the range of from about 20° C. to about 25° C. for a period of about 22 hours with stirring.

Thereafter, the solvent is removed, e.g., under reduced pressure, to provide a residue that can be purified, e.g., using a silica gel column eluted with 5:1 hexane:ethyl acetate, to provide a 1-heteroaromatic-1,2,3,6-tetrahydro-pyridine-4-carbonitrile Compound of Formula 12a-h. A Compound of Formula 12a-h is useful, e.g., as an intermediate for the synthesis of a Cyclo(hetero)alkenyl Compound.

In Step B4 of Scheme B, the 1-heteroaromatic-1,2,3,6-tetrahydro-pyridine-4-carbonitrile Compound of Formula 12a-h is reacted with an acidifying reagent, e.g., an inorganic acid such as HCl or $H_2SO_4$, or an organic acid, such as phthalic acid or tetrahalophthalic acid. In one embodiment, the present invention relates to a method for making a Cyclo(hetero)alkenyl Compound comprising allowing a 1-heteroaromatic-1,2,3,6-tetrahydro-pyridine-4-carbonitrile Compound of Formula 12a-h to react with an acidifying reagent. In another embodiment, the acidifying reagent is HCl, $H_2SO_4$, phthalic acid, tetrahalophthalic acid or a mixture thereof. In another embodiment, the acidifying reagent is HCl. In another embodiment, the acidifying reagent is $H_2SO_4$. In another embodiment, the acidifying reagent is phthalic acid. In another embodiment, the acidifying reagent is tetrahalophthalic acid.

In certain embodiments, the acidifying reagent is present in the reaction in Step B4 at an initial concentration within the range of from about 0.5N to about 12N, or at an initial concentration within the range of from about 1N to about 8N. In a specific embodiment, the acidifying reagent is present in the reaction at an initial concentration of about 6N.

In certain embodiments, the Compound of Formula 12a-h is present in the reaction in Step B4 at an initial concentration within the range of from about 0.05M to about 10M, or at an initial concentration within the range of from about 0.1M to about 5M. In a specific embodiment, the Compound of Formula 12a-h is present in the reaction at an initial concentration of about 0.5M.

In certain embodiments, the reaction in Step B4 is carried out at a temperature within the range of from about 0° C. to about 120° C.; at a temperature within the range of from about 25° C. to about 120° C.; or at a temperature within the range of from about 95° C. to about 105° C.

In certain embodiments, the reaction in Step B4 is carried out in a polar protic solvent or in combinations of such solvents; polar protic solvents have been described above. In one embodiment, the polar protic solvent is water, an organic acid, e.g., formic acid (see U.S. Pat. No. 5,206,392) or combinations thereof. In another embodiment, the polar protic solvent is water. In other embodiments, the solvent comprises a mixture of water and a suitable aprotic solvent or solvents. In such embodiments the ratio of water to aprotic solvent can be within the range of from about 10:1 to about 1:1 (water: aprotic solvent). In certain embodiments, the aprotic solvent mixed with water is selected from acetone, MEK, ethyl acetate, acetonitrile, dioxane, N-methyl-pyrrolidone, DMF, DMAc, DMSO, pyridine, and combinations thereof.

In certain embodiments, the Compound of Formula 12a-h is provided as a salt, e.g., the hydrochloride salt, which can be converted to the free amine, using procedures known in the art, prior to reaction with the acidifying reagent. For example, the hydrochloride salt of the Compound of Formula 12a-h is dissolved in a suitable organic solvent, such as but not limited to chloroform, to provide a solution that is extracted with, e.g., a saturated aqueous solution of $Na_2CO_3$. The organic layer is recovered and the aqueous layer back-extracted with an additional volume of the organic solvent. The organic solvent layers are combined, extracted with water, dried, e.g., over anhydrous sodium sulfate, and then the liquid is removed to provide the Compound of Formula 12 a-h as the free amine.

The reaction in Step B4 can be carried out at reduced pressure, atmospheric pressure or elevated pressure, i.e., greater than atmospheric pressure. In one embodiment, the reaction is carried out at atmospheric pressure. In certain embodiments, the reaction in Step B4 is carried out in an inert atmosphere. In one non-limiting aspect of this embodiment, the reaction in Step B4 is carried out under a nitrogen atmosphere. In another non-limiting aspect of this embodiment, the reaction in Step B4 is carried out under an argon atmosphere.

Progress of the reaction in Step B4 can be monitored using conventional analytical techniques, including but not limited to IR, LC, MS, LCMS, TLC, HPLC, GC, GLC and/or NMR. The reaction according to Step B4 is carried out, in one embodiment, until a starting material is consumed or, in another embodiment, until the ratio of product, a Compound of Formula 13a-h, to starting material, the Compound of Formula 12a-h, remains essentially constant. Typically, a time sufficient for the reaction in Step B4 is within the range of from about 0.5 hours to about 36 hours, from about 1 hour to about 24 hours, or from about 4 hours to about 16 hours. In a specific embodiment, the reaction according to Step B4 is carried out for about 12 hours.

In another embodiment, the reaction according to Step B4 is carried out in water with about a 6N initial concentration of HCl, at a temperature within the range of from about 95° C. to about 105° C., and for a period of about 12 hours with refluxing.

The resulting reaction mixture is cooled to about 25° C. and the solvent is removed, e.g., under reduced pressure, to provide a 1-heteroaromatic-1,2,3,6-tetrahydro-pyridine-4-carboxylic acid Compound of Formula 13a-h, which can be used without further purification or, if desired, can be purified using methods known to those skilled in the art. A Compound of Formula 13a-h is useful, e.g., as an intermediate for the synthesis of a Cyclo(hetero)alkenyl Compound.

In Step B5 of Scheme B, the 1-heteroaromatic-1,2,3,6-tetrahydro-pyridine-4-carboxylic acid Compound of Formula 13a-h is reacted in a single step procedure with a compound of formula $Ar^2$—$NHR_4$. In one embodiment, the present invention relates to a method for making a Cyclo(hetero)alkenyl Compound comprising allowing a 1-heteroaromatic-1,2,3,6-tetrahydro-pyridine-4-carboxylic acid Compound of Formula 13 a-h to react with a compound of formula $Ar^2$—$NHR_4$. In another embodiment, this reaction is in a single step. In another embodiment, the compound of formula $Ar^2$—$NHR_4$ is 4-trifluoromethyl-aniline. In another embodiment, the compound of formula $Ar^2$—$NHR_4$ is 5-trifluoromethyl-pyridin-2-ylamine. In another embodiment, the compound of formula $Ar^2$—$NHR_4$ is 2,2-difluoro-benzo[1, 3]dioxol-5-ylamine. $Ar^2$—$NHR_4$ compounds are commercially available from, e.g., Aldrich Chemical Co., or can be prepared by methods known to those skilled in the art.

In certain embodiments, the reaction in Step B5 is carried out with an initial amount of the a compound of formula $Ar^2$—$NHR_4$ within the range of from about 1 to about 5 equivalents, or within the range of from about 1 to about 2 equivalents, on a molar basis, relative to the Compound of Formula 13a-h. In another embodiment, this reaction is carried out with about 1 equivalent, on a molar basis, of the compound of formula $Ar^2$—$NHR_4$, relative to the Compound of Formula 13a-h.

In certain embodiments, the reaction in Step B5 is carried out to include an initial amount of 1-hydroxybenzotriazole (HOBt) within the range of from about 0.1 to about 3 equivalents, or within the range of from about 0.2 to about 1.5 equivalents, on a molar basis, relative to the Compound of Formula 13a-h. In another embodiment, this reaction is carried out with about 1.25 equivalents, on a molar basis, of HOBt, relative to the Compound of Formula 13a-h.

In certain embodiments, the reaction in Step B5 is carried out to include an initial amount of DIC within the range of from about 0.1 to about 3 equivalents, or within the range of from about 0.2 to about 1.5 equivalents, on a molar basis, relative to the Compound of Formula 13a-h. In another embodiment, this reaction is carried out with about 1.25 equivalents, on a molar basis, of DIC, relative to the Compound of Formula 13 a-h. In another embodiment, this reaction is carried out to include an initial amount of DIC about identical with the initial amount of HOBt, each on a molar basis relative to the Compound of Formula 13a-h. HOBt and DIC are commercially available from, e.g., Aldrich Chemical Co., or can be prepared by methods known to those skilled in the art.

In certain embodiments, the Compound of Formula 13a-h is present in the reaction in Step B5 at an initial concentration within the range of from about 0.05M to about 10M, or at an initial concentration within the range of from about 0.1M to about 1M. In a specific embodiment, the Compound of Formula 13a-h is present in the reaction at an initial concentration of about 0.35M.

In certain embodiments, the reaction in Step B5 is carried out at a temperature within the range of from about 0° C. to about 100° C.; at a temperature within the range of from about 0° C. to about 60° C.; or at a temperature within the range of from about 15° C. to about 30° C.

In certain embodiments, the reaction in Step B5 is carried out in an aprotic solvent or in combinations of such solvents; aprotic solvents have been described above. In one embodiment, the aprotic solvent is pyridine, DMF or combinations thereof. In another embodiment, the aprotic solvent is DMF. In another embodiment, the aprotic solvent is pyridine.

In certain embodiments, the Compound of Formula 13a-h is provided as a salt, e.g., the hydrochloride salt, which can be converted to the free amine, using procedures known in the art, prior to reaction with the compound of formula $Ar^2$—$NHR_4$. For example, the hydrochloride salt of the Compound of Formula 13a-h is dissolved in a suitable organic solvent, such as but not limited to chloroform, to provide a solution that is extracted with, e.g., a saturated aqueous solution of $Na_2CO_3$. The organic layer is recovered and the aqueous layer back-extracted with an additional volume of the organic solvent. The organic solvent layers are combined, extracted with water, dried, e.g., over anhydrous sodium sulfate, and then the liquid is removed to provide the Compound of Formula 13a-h as the free amine.

The reaction in Step B5 can be carried out at reduced pressure, atmospheric pressure or elevated pressure, i.e., greater than atmospheric pressure. In one embodiment, the reaction is carried out at atmospheric pressure. In certain embodiments, the reaction in Step B5 is carried out in an inert atmosphere. In one non-limiting aspect of this embodiment, the reaction in Step B5 is carried out under a nitrogen atmosphere. In another non-limiting aspect of this embodiment, the reaction in Step B5 is carried out under an argon atmosphere.

Progress of the reaction in Step B5 can be monitored using conventional analytical techniques, including but not limited to IR, LC, MS, LCMS, TLC, HPLC, GC, GLC and/or NMR. The reaction according to Step B5 is carried out, in one embodiment, until a starting material is consumed or, in another embodiment, until the ratio of product, the Cyclo(hetero)alkenyl Compound, to starting material, the Compound of Formula 13a-h, remains essentially constant. Typically, a time sufficient for the reaction in Step B5 is within the range of from about 0.5 hours to about 36 hours, from about 1 hour to about 24 hours, or from about 4 hours to about 16 hours. In a specific embodiment, the reaction according to Step B5 is carried out for about 12 hours.

In another embodiment, the reaction according to Step B5 is carried out in DMF with about 1 equivalent of a compound of formula $Ar^2$—$NHR_4$, 1-hydroxybenzotriazole (HOBt, about 1.25 eq.), and DIC (about 1.25 eq.) relative to the Compound of Formula 13a-h (present at an initial concentration of about 0.35M), at a temperature within the range of from about 20° C. to about 25° C. for a period of about 12 hours with stirring.

Thereafter, the solvent is removed, e.g., under reduced pressure, to provide a residue that can be purified, e.g., using a silica gel column eluted with 10:1 hexane:ethyl acetate, to provide a Cyclo(hetero)alkenyl Compound where V is N. Where m=1, a mixture of Cyclo(hetero)alkenyl Compounds where V is N is generally obtained. The mixture can be separated by conventional methods, for example, column chromatography.

A Cyclo(hetero)alkenyl Compound where V is N can also be obtained from a Compound of Formula 13a-h by a two-step procedure, e.g., Step B6 followed by Step B7. In one embodiment, the present invention relates to a method for making a Cyclo(hetero)alkenyl Compound comprising allowing a 1-heteroaromatic-1,2,3,6-tetrahydro-pyridine-4-carboxylic acid Compound of Formula 13a-h to react, in a plurality of steps; in one step the reacting is with a compound of formula $Ar^2$—$NHR_4$.

In Step B6 of Scheme B, the 1-heteroaromatic-1,2,3,6-tetrahydro-pyridine-4-carboxylic acid Compound of Formula 13a-h is reacted with an excess of a Lewis acid comprising chlorine, such as $SOCl_2$, $COCl_2$, $PSCl_3$, $PCl_5$ or $POCl_3$, which serves as a reagent and can also serve as a solvent. In one embodiment, the present invention relates to a method for making a Cyclo(hetero)alkenyl Compound comprising allowing a 1-heteroaromatic-1,2,3,6-tetrahydro-pyridine-4-carboxylic acid Compound of Formula 13 a-h to react with an excess of a Lewis acid comprising chlorine. In another embodiment, the Lewis acid comprising chlorine is $POCl_3$, $PSCl_3$, $PCl_5$, $SOCl_2$, $COCl_2$ or a mixture thereof. In another embodiment, the Lewis acid comprising chlorine is $SOCl_2$, $COCl_2$ or a mixture thereof. In another embodiment, the Lewis acid comprising chlorine is $SOCl_2$. In another embodiment, the Lewis acid comprising chlorine is $POCl_3$. In another embodiment, the Lewis acid comprising chlorine is $COCl_2$.

In certain embodiments, the reaction in Step B6 is carried out with an initial amount of the Lewis acid within the range of from about 1 to about 100 equivalents, or within the range of from about 1 to about 50 equivalents, on a molar basis, relative to the Compound of Formula 13a-h. In another embodiment, this reaction is carried out with about 24 equivalents, on a molar basis, of the Lewis acid, relative to the Compound of Formula 13a-h.

In certain embodiments, the Compound of Formula 13a-h is present in the reaction in Step B6 at an initial concentration within the range of from about 0.05M to about 10M, or at an initial concentration within the range of from about 0.1M to about 5M. In a specific embodiment, the Compound of Formula 13a-h is present in the reaction at an initial concentration of about 0.6M.

In certain embodiments, the reaction in Step B6 is carried out at a temperature within the range of from about 0° C. to about 100° C.; at a temperature within the range of from about 10° C. to about 60° C.; or at a temperature within the range of from about 15° C. to about 30° C.

In certain embodiments, the reaction in Step B6 is carried out in a nonpolar solvent, e.g., THF, an aprotic solvent or in combinations of such solvents; nonpolar solvents and aprotic solvents have been described above. In certain embodiments, the reaction in Step B6 is carried out without a solvent, i.e., the Lewis acid serves as the solvent. In another embodiment, the solvent is THF. In another embodiment, the solvent is $SOCl_2$. In another embodiment, the solvent is $POCl_3$. In another embodiment, the solvent is $COCl_2$.

In certain embodiments, the Compound of Formula 13a-h is provided as a salt, e.g., the hydrochloride salt, which can be converted to the free amine, using procedures known in the art, prior to reaction with the Lewis acid. For example, the hydrochloride salt of the Compound of Formula 13a-h is dissolved in a suitable organic solvent, such as but not limited to chloroform, to provide a solution that is extracted with, e.g., a saturated aqueous solution of $Na_2CO_3$. The organic layer is recovered and the aqueous layer back-extracted with an additional volume of the organic solvent. The organic solvent layers are combined, extracted with water, dried, e.g., over anhydrous sodium sulfate, and then the liquid is removed to provide the Compound of Formula 13a-h as the free amine.

The reaction in Step B6 can be carried out at reduced pressure, atmospheric pressure or elevated pressure, i.e., greater than atmospheric pressure. In one embodiment, the reaction is carried out at atmospheric pressure. In certain embodiments, the reaction in Step B6 is carried out in an inert atmosphere. In one non-limiting aspect of this embodiment, the reaction in Step B6 is carried out under a nitrogen atmosphere. In another non-limiting aspect of this embodiment, the reaction in Step B6 is carried out under an argon atmosphere.

Progress of the reaction in Step B6 can be monitored using conventional analytical techniques, including but not limited to IR, LC, MS, LCMS, TLC, HPLC, GC, GLC and/or NMR. The reaction according to Step B6 is carried out, in one embodiment, until a starting material is consumed or, in another embodiment, until the ratio of product, a Compound of Formula 14a-h, to starting material, the Compound of Formula 13a-h, remains essentially constant. Typically, a time sufficient for the reaction in Step B6 is within the range of from about 0.5 hours to about 36 hours, from about 1 hour to about 24 hours, or from about 4 hours to about 19 hours. In a specific embodiment, the reaction according to Step B6 is carried out for about 12 hours. In a specific embodiment, the reaction according to Step B6 is carried out for about 17 hours.

In another embodiment, the reaction according to Step B6 is carried out by reacting the Compound of Formula 13a-h (about 1 eq.) with an excess of a Lewis acid comprising chlorine (about 24 eq.), at a temperature of about 25° C. for a period of about 12 hours with stirring to provide a 1-heteroaromatic-1,2,3,6-tetrahydro-pyridine-4-carbonyl chloride Compound of Formula 14a-h, which can be used without further purification or, if desired, can be purified using methods known to those skilled in the art. A Compound of Formula 14a-h is useful, e.g., as an intermediate for the synthesis of a Cyclo(hetero)alkenyl Compound.

In Step B7 of Scheme B, the 1-heteroaromatic-1,2,3,6-tetrahydro-pyridine-4-carbonyl chloride Compound of Formula 14a-h is reacted with a compound of formula $Ar^2$—$NHR_4$. In one embodiment, the present invention relates to a method for making a Cyclo(hetero)alkenyl Compound comprising allowing a 1-heteroaromatic-1,2,3,6-tetrahydro-pyridine-4-carbonyl chloride Compound of Formula 14a-h to react with a compound of formula $Ar^2$—$NHR_4$. In another embodiment, the compound of formula $Ar^2$ $NHR_4$ is 4-trifluoromethyl-aniline. In another embodiment, the compound of formula $Ar^2$—$NHR_4$ is 5-trifluoromethyl-pyridin-2-ylamine. In another embodiment, the compound of formula $Ar^2$—$NHR_4$ is 2,2-difluoro-benzo[1,3]dioxol-5-ylamine.

In certain embodiments, the reaction in Step B7 is carried out with an initial amount of the a compound of formula $Ar^2$—$NHR_4$ within the range of from about 1 to about 10 equivalents, or within the range of from about 1 to about 5 equivalents, on a molar basis, relative to the Compound of Formula 14a-h. In another embodiment, this reaction is carried out with about 1.5 equivalents, on a molar basis, of the compound of formula $Ar^2$—$NHR_4$, relative to the Compound of Formula 14a-h. In another embodiment, this reaction is carried out with about 1.2 equivalents, on a molar basis, of the compound of formula $Ar^2$—$NHR_4$, relative to the Compound of Formula 14a-h. In another embodiment, this reaction is carried out with about 1.1 equivalents, on a molar basis, of the compound of formula $Ar^2$—$NHR_4$, relative to the Compound of Formula 14 a-h.

In certain embodiments, the reaction in Step B7 is carried out to include an initial amount of an organic base, an inorganic base or a mixture thereof. In certain embodiments, the reaction in Step B7 is carried out to include an initial amount of an organic base, e.g., pyridine or a trialkylamine, such as triethylamine, trimethylamine, methyl diethylamine or diisopropyl ethylamine, within the range of from about 1 to about 5 equivalents, or within the range of from about 1 to about 2 equivalents, on a molar basis, relative to the Compound of Formula 14a-h. In another embodiment, this reaction is carried out with about 1.25 equivalents, on a molar basis, of organic base, e.g., trialkylamine, relative to the Compound of Formula 14a-h. In one embodiment, the trialkylamine is triethylamine, trimethylamine, methyl diethylamine, diisopropyl ethylamine or combinations thereof. In another embodiment, the trialkylamine is triethylamine. Trialkylamines are commercially available from, e.g., Aldrich Chemical Co., or can be prepared by methods known to those skilled in the art.

In certain embodiments, the reaction in Step B7 is carried out to include an initial amount of an inorganic base, such as sodium bicarbonate, within the range of from about 1 to about 10 equivalents, or within the range of from about 1 to about 5 equivalents, on a molar basis, relative to the Compound of Formula 14a-h. In another embodiment, this reaction is carried out with about 3 equivalents, on a molar basis, of inorganic base, relative to the Compound of Formula 14a-h. In one embodiment, the inorganic base is sodium bicarbonate, sodium carbonate, potassium bicarbonate, potassium carbonate or combinations thereof. In another embodiment, the inorganic base is sodium bicarbonate. In another embodiment, the inorganic base is potassium carbonate.

In certain embodiments, the Compound of Formula 14a-h is present in the reaction in Step B7 at an initial concentration within the range of from about 0.05M to about 10M, at an initial concentration within the range of from about 0.1M to about 5M, at an initial concentration within the range of from about 0.1M to about 2M. In a specific embodiment, the Compound of Formula 14a-h is present in the reaction at an initial concentration of about 0.2M. In a specific embodiment, the Compound of Formula 14 a-h is present in the reaction at an initial concentration of about 0.3M. In a specific embodiment, the Compound of Formula 14a-h is present in the reaction at an initial concentration of about 0.5M.

In certain embodiments, the reaction in Step B7 is carried out at a temperature within the range of from about 0° C. to about the boiling point of the solvent; at a temperature within the range of from about 0° C. to about 115° C.; at a temperature within the range of from about 0° C. to about 100° C.; at a temperature within the range of from about 0° C. to about 80° C.; at a temperature within the range of from about 40° C. to about 80° C.; or at a temperature within the range of from about 15° C. to about 30° C.

In certain embodiments, the reaction in Step B7 is carried out in an aprotic solvent or in combinations of such solvents; aprotic solvents have been described above. In one embodiment, the aprotic solvent is DCM, DCE, THF, pyridine or combinations thereof. In another embodiment, the aprotic solvent is DCM. In another embodiment, the aprotic solvent is DCE. In another embodiment, the aprotic solvent is THF. In another embodiment, the aprotic solvent is pyridine. As pyridine can serve in a dual role, i.e., simultaneously serve as a solvent and as an organic base, as discussed above, if such a dual-role organic base is present then the reaction in Step B7 is carried out, in certain embodiments, with an initial amount of the dual-role organic base within the range of from about 1 to about 100 equivalents, or within the range of from about 1 to about 50 equivalents, on a molar basis, relative to the Compound of Formula 14a-h.

In certain embodiments, the Compound of Formula 14a-h is provided as a salt, e.g., the hydrochloride salt, which can be converted to the free amine, using procedures known in the art, prior to reaction with the compound of formula $Ar^2$—$NHR_4$. For example, the hydrochloride salt of the Compound of Formula 14a-h is dissolved in a suitable organic solvent, such as but not limited to chloroform, to provide a solution that is extracted with, e.g., a saturated aqueous solution of $Na_2CO_3$. The organic layer is recovered and the aqueous layer back-extracted with an additional volume of the organic solvent. The organic solvent layers are combined, extracted with water, dried, e.g., over anhydrous sodium sulfate, and then the liquid is removed to provide the Compound of Formula 14a-h as the free amine.

The reaction in Step B7 can be carried out at reduced pressure, atmospheric pressure or elevated pressure, i.e., greater than atmospheric pressure. In one embodiment, the reaction is carried out at atmospheric pressure. In certain embodiments, the reaction in Step B7 is carried out in an inert atmosphere. In one non-limiting aspect of this embodiment, the reaction in Step B7 is carried out under a nitrogen atmosphere. In another non-limiting aspect of this embodiment, the reaction in Step B7 is carried out under an argon atmosphere.

Progress of the reaction in Step B7 can be monitored using conventional analytical techniques, including but not limited to IR, LC, MS, LCMS, TLC, HPLC, GC, GLC and/or NMR.

The reaction according to Step B7 is carried out, in one embodiment, until a starting material is consumed or, in another embodiment, until the ratio of product, the Cyclo(hetero)alkenyl Compound, to starting material, the Compound of Formula 14a-h, remains essentially constant. Typically, a time sufficient for the reaction in Step B7 is within the range of from about 0.5 hours to about 24 hours; from about 1 hour to about 19 hours; or from about 1 hour to about 17 hours. In a specific embodiment, the reaction according to Step B7 is carried out for about 1.6 hours. In a specific embodiment, the reaction according to Step B7 is carried out for about 4 hours. In a specific embodiment, the reaction according to Step B7 is carried out for about 16 hours.

In another specific embodiment, the reaction according to Step B7 is carried out in DCM with about 1.5 equivalents of a compound of formula $Ar^2$—$NHR_4$ and a trialkylamine, such as triethylamine, trimethylamine, methyl diethylamine or diisopropyl ethylamine (about 2.0 eq.) relative to the Compound of Formula 14a-h (present at an initial concentration of about 0.2M). The resulting solution is degassed by bubbling nitrogen through the solution. The reaction mixture is kept at a temperature within the range of from about 20° C. to about 25° C. for a period of about 4 hours with stirring.

In another specific embodiment, the reaction according to Step B7 is carried out in pyridine with about 1.2 equivalents of a compound of formula $Ar^2$—$NHR_4$ relative to the Compound of Formula 14a-h (present at an initial concentration of about 0.5M). For example, a 0.5M suspension of the Compound of Formula 14a-h in pyridine can be added to a 0.5M solution of a compound of formula $Ar^2$—$NHR_4$ in pyridine about 25° C. to form a reaction mixture and the reaction mixture is kept at a temperature of about 70° C. for a period of about 16 hours with stirring.

In another specific embodiment, the reaction according to Step B7 is carried out in THF at about 0° C. with about 1.1 equivalents of a compound of formula $Ar^2$—$NHR_4$ and a base, such as sodium bicarbonate (about 3.0 eq.) relative to the Compound of Formula 14 a-h (present at an initial concentration of about 0.3M). The resulting solution is stirred at 0° C. for about 5 min, warmed to about 25° C. over a period of about 30 min with stirring, and kept at about 65° C. for 1 hour with stirring. Thereafter, the solvent is removed, e.g., under reduced pressure, to provide a residue that suspended in ethyl acetate and washed with aqueous 3N HCl such that separate aqueous and organic layers form. The layers can be separated and the aqueous layer extracted with ethyl acetate as required. The organic layer can be combined with the post-extraction ethyl acetate aliquot(s) and the combination dried, e.g., with $Na_2SO_4$.

Thereafter, in any of these specific embodiments for conducting the reaction according to Step B7, the solvent is removed, e.g., under reduced pressure, to provide a residue that can be purified, e.g., using a silica gel column eluted with 10:1 hexane:ethyl acetate or using flash chromatography on a silica gel column with 1:1 (by volume) ethyl acetate:hexane as an eluent, to provide a Cyclo(hetero)alkenyl Compound where V is N. As discussed above, if a mixture of Cyclo(hetero)alkenyl Compounds is obtained where m=1, the mixture can be separated by conventional methods, for example, column chromatography.

The Compound of Formula (I) where X is S can be made by, e.g., reacting a Compound of Formula (II) (i.e., where X is O) with Lawesson's reagent as described in connection with Scheme A. In another embodiment, the Compound of Formula (I) where X is S can be made by forming a dithio acid from the Compound of Formula 13a-h, e.g., according to the procedure described in *Helvetica Chimica Acta* 3:824-33 (1920). The dithio acid can be reacted according to Step B5 of Scheme B or according to the two-step procedure of Scheme B, e.g., Step B6 followed by Step B7, as described above.

Thus, in another embodiment, a method for preparing a Cyclo(hetero)alkenyl Compound comprises allowing a 1-heteroaromatic-1,2,3,6-tetrahydro-pyridine-4-carboxylic acid compound to react with a compound of formula $Ar^2$—$NHR_4$ to provide the Cyclo(hetero)alkenyl Compound.

In another embodiment, a method for preparing a Cyclo (hetero)alkenyl Compound comprises forming the Cyclo (hetero)alkenyl Compound from the 1-heteroaromatic-1,2,3, 6-tetrahydro-pyridine-4-carboxylic acid compound in one step.

In another embodiment, a method for preparing a Cyclo (hetero)alkenyl Compound comprises forming the Cyclo (hetero)alkenyl Compound from the 1-heteroaromatic-1,2,3, 6-tetrahydro-pyridine-4-carboxylic acid compound in a plurality of steps.

In another embodiment, a method for preparing a Cyclo (hetero)alkenyl Compound comprises:

(i) allowing a 1-heteroaromatic-1,2,3,6-tetrahydro-pyridine-4-carboxylic acid compound to react with a Lewis acid comprising chlorine in a first step to provide a 1-heteroaromatic-1,2,3,6-tetrahydro-pyridine-4-carbonyl chloride compound; and (ii) allowing the 1-heteroaromatic-1,2,3,6-tetrahydro-pyridine-4-carbonyl chloride compound to react with the compound of formula $Ar^2$—$NHR_4$ in a second step to provide a Cyclo(hetero)alkenyl Compound.

In another embodiment, a method for preparing a Cyclo (hetero)alkenyl Compound comprises allowing a 1-heteroaromatic-1,2,3,6-tetrahydro-pyridine-4-carbonitrile compound to react with an acidifying reagent to provide a 1-heteroaromatic-1,2,3,6-tetrahydro-pyridine-4-carboxylic acid compound.

In another embodiment, a method for preparing a Cyclo (hetero)alkenyl Compound comprises allowing a 1-heteroaromatic-4-hydroxy-piperidine-4-carbonitrile compound to react with a dehydrogenation agent to provide a 1-heteroaromatic-1,2,3,6-tetrahydro-pyridine-4-carbonitrile compound.

In another embodiment, a method for preparing a Cyclo (hetero)alkenyl Compound comprises allowing a 1-heteroaromatic-piperidin-4-one compound to react with a cyanation reagent to provide the 1-heteroaromatic-4-hydroxy-piperidine-4-carbonitrile compound.

In another embodiment, a method for preparing a Cyclo (hetero)alkenyl Compound comprises allowing a 8-heteroaromatic-1,4-dioxa-8-aza-spiro[4.5]decane compound to react with a ketone-forming reagent to provide a 1-heteroaromatic-piperidin-4-one compound.

In another embodiment, a method for preparing a Cyclo (hetero)alkenyl Compound comprises allowing a 8-heteroaromatic-1,4-dioxa-8-aza-spiro[4.5]decane compound to react with a ketone-forming reagent to provide the 1-heteroaromatic-piperidin-4-one compound.

In another embodiment, the present invention relates to a compound of formula 4 a-h

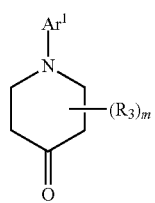

4 a-h or a pharmaceutically acceptable salt thereof, where:
$Ar^1$ is

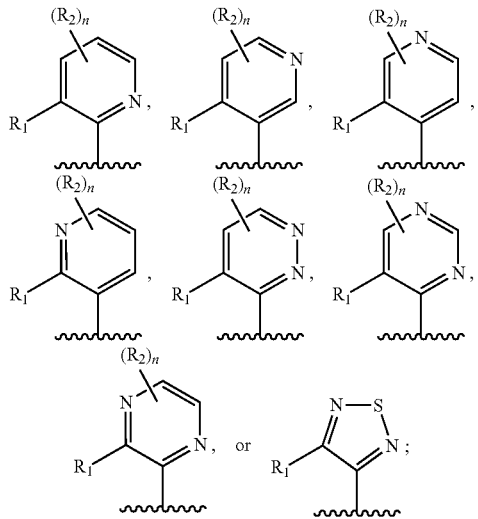

$R_1$ is —H, -halo, —$CH_3$, —$NO_2$, —CN, —OH, —$OCH_3$, —$NH_2$, —C(halo)$_3$, —CH(halo)$_2$, or —$CH_2$(halo);

each $R_2$ is independently:
(a) -halo, —CN, —OH, —$NO_2$, or —$NH_2$,
(b) —($C_1$-$C_{10}$)alkyl, —($C_2$-$C_{10}$)alkenyl, —($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle, or -(7- to 10-membered)bicycloheterocycle, each of which is unsubstituted or substituted with one or more $R_5$ groups, or
(c) -phenyl, -naphthyl, —($C_{14}$)aryl or -(5- to 10-membered)heteroaryl, each of which is unsubstituted or substituted with one or more $R_6$ groups;

each $R_3$ is independently:
(a) -halo, —CN, —OH, —$NO_2$, or —$NH_2$,
(b) —($C_1$-$C_{10}$)alkyl, —($C_2$-$C_{10}$)alkenyl, —($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle, or -(7- to 10-membered)bicycloheterocycle, each of which is unsubstituted or substituted with one or more $R_5$ groups, or
(c) -phenyl, -naphthyl, —($C_{14}$)aryl or -(5- to 10-membered) heteroaryl, each of which is unsubstituted or substituted with one or more $R_6$ groups;

each $R_5$ is independently —CN, —OH, —($C_1$-$C_6$)alkyl, —($C_2$-$C_6$)alkenyl, —($C_2$-$C_6$)alkynyl, -halo, —$N_3$, —$NO_2$, —$N(R_7)_2$, —CH═$NR_7$, —$NR_7$OH, —$OR_7$, —$COR_7$, —C(O)$OR_7$, —OC(O)$R_7$, —OC(O)$OR_7$, —$SR_7$, —S(O)$R_7$, or —S(O)$_2R_7$;

each $R_6$ is independently —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, -(3- to 5-membered)heterocycle, —C(halo)$_3$, —CH(halo)$_2$, —$CH_2$(halo), —CN, —OH, -halo, —$N_3$, —$NO_2$, —$N(R_7)_2$, —CH═$NR_7$, —$NR_7$OH, —$OR_7$, —$COR_7$, —C(O)$OR_7$, —OC(O)$R_7$, —OC(O)$OR_7$, —$SR_7$, —S(O)$R_7$, or —S(O)$_2R_7$;

each $R_7$ is independently —H, —($C_1$-$C_6$)alkyl, —($C_2$-$C_6$) alkenyl, —($C_2$-$C_6$)alkynyl, —($C_3$-$C_8$)cycloalkyl, —($C_5$-$C_8$) cycloalkenyl, -phenyl, -(3- to 5-membered)heterocycle, —C(halo)$_3$, —CH(halo)$_2$, or $CH_2$(halo);

each halo is independently —F, —Cl, —Br, or —I;

m is 0 or 1 and when m is 1, $R_3$ is attached to the 2-, 3-, 5-, or 6-position of the cyclo(hetero)alkenyl ring;

n is an integer ranging from 0 to 3; and p is an integer ranging from 0 to 2.

In another embodiment, the present invention relates to a compound of formula 11 a-h

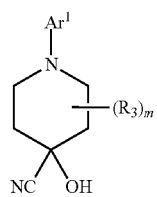

11 a-h or a pharmaceutically acceptable salt thereof, where:
$Ar^1$ is

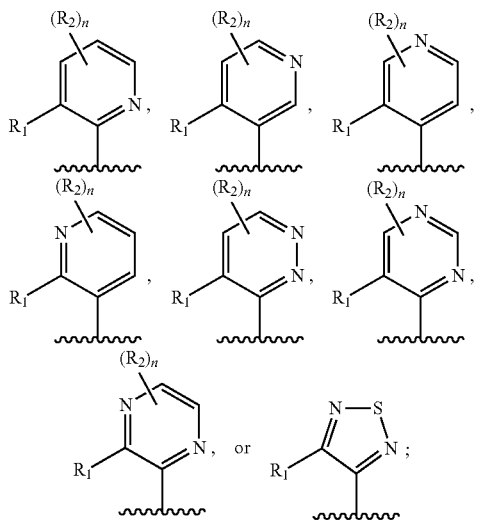

$R_1$ is —H, -halo, —$CH_3$, —$NO_2$, —CN, —OH, —$OCH_3$, —$NH_2$, —C(halo)$_3$, —CH(halo)$_2$, or —$CH_2$(halo);

each $R_2$ is independently:
(a) -halo, —CN, —OH, —$NO_2$, or —$NH_2$,
(b) —($C_1$-$C_{10}$)alkyl, —($C_2$-$C_{10}$)alkenyl, —($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle, or -(7- to 10-membered)bicycloheterocycle, each of which is unsubstituted or substituted with one or more $R_5$ groups, or
(c) -phenyl, -naphthyl, —($C_{14}$)aryl or -(5- to 10-membered)heteroaryl, each of which is unsubstituted or substituted with one or more $R_6$ groups;

each $R_3$ is independently:
(a) -halo, —CN, —OH, —$NO_2$, or —$NH_2$,
(b) —($C_1$-$C_{10}$)alkyl, —($C_2$-$C_{10}$)alkenyl, —($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle, or -(7- to 10-membered)bicycloheterocycle, each of which is unsubstituted or substituted with one or more $R_5$ groups, or
(c) -phenyl, -naphthyl, —($C_{14}$)aryl or -(5- to 10-membered)heteroaryl, each of which is unsubstituted or substituted with one or more $R_6$ groups;

each $R_5$ is independently —CN, —OH, —($C_1$-$C_6$)alkyl, —($C_2$-$C_6$)alkenyl, —($C_2$-$C_6$)alkynyl, -halo, —$N_3$, —$NO_2$, —$N(R_7)_2$, —CH=$NR_7$, —$NR_7OH$, —$OR_7$, —$COR_7$, —C(O)$OR_7$, —OC(O)$R_7$, —OC(O)$OR_7$, —$SR_7$, —S(O)$R_7$, or —S(O)$_2R_7$;

each $R_6$ is independently —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, -(3- to 5-membered)heterocycle, —C(halo)$_3$, —CH(halo)$_2$, —$CH_2$(halo), —CN, —OH, -halo, —$N_3$, —$NO_2$, —$N(R_7)_2$, —CH=$NR_7$, —$NR_7OH$, —$OR_7$, —$COR_7$, —C(O)$OR_7$, —OC(O)$R_7$, —OC(O)$OR_7$, —$SR_7$, —S(O)$R_7$, or —S(O)$_2R_7$;

each $R_7$ is independently —H, —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, -(3- to 5-membered)heterocycle, —C(halo)$_3$, —CH(halo)$_2$, or —$CH_2$(halo);

each halo is independently —F, —Cl, —Br, or —I;

m is 0 or 1 and when m is 1, $R_3$ is attached to the 2-, 3-, 5-, or 6-position of the cyclo(hetero)alkenyl ring;

n is an integer ranging from 0 to 3; and p is an integer ranging from 0 to 2.

In another embodiment, the present invention relates to a compound of formula 12 a-h

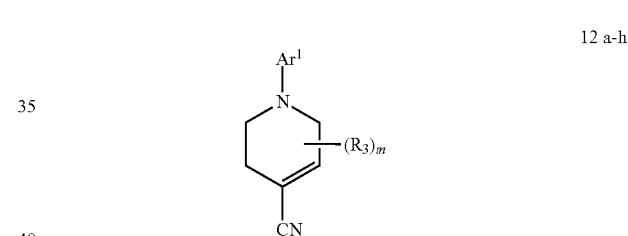

12 a-h or a pharmaceutically acceptable salt thereof, where:
$Ar^1$ is

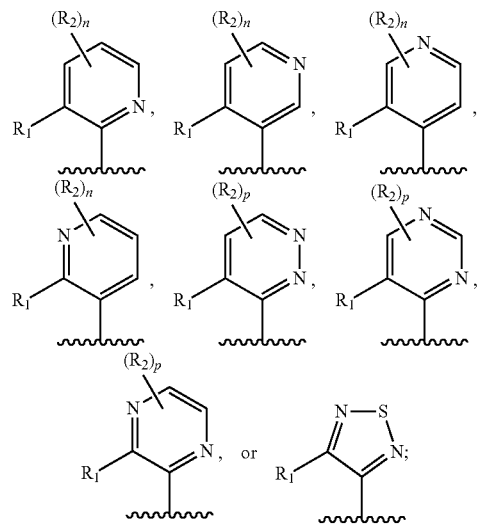

$R_1$ is H, -halo, —$CH_3$, —$NO_2$, —CN, —OH, —$OCH_3$, —$NH_2$, —C(halo)$_3$, —CH(halo)$_2$, or —$CH_2$(halo);

each $R_2$ is independently:
(a) -halo, —CN, —OH, —$NO_2$, or —$NH_2$, —
(b) —($C_1$-$C_{10}$)alkyl, —($C_2$-$C_{10}$)alkenyl, —($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle, or -(7- to 10-membered)bicycloheterocycle, each of which is unsubstituted or substituted with one or more $R_5$ groups, or
(c) -phenyl, -naphthyl, —($C_{14}$)aryl or -(5- to 10-membered)heteraryl, each of which is unsubstituted or substituted with one or more $R_6$ groups;

each $R_3$ is independently:
(a) -halo, —CN, —OH, —$NO_2$, or —$NH_2$,
(b) —($C_1$-$C_{10}$)alkyl, —($C_2$-$C_{10}$)alkenyl, —($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —($C_3$-$C_{10}$)cycloalkenyl, —($C_8$-$C_{14}$)bicycloalkenyl, —($C_8$-$C_{14}$)tricycloalkenyl, -(3- to 7-membered)heterocycle, or -(7- to 10-membered)bicycloheterocycle, each of which is unsubstituted or substituted with one or more $R_5$ groups, or
(c) -phenyl, -naphthyl, —($C_{14}$)aryl or -(5- to 10-membered) heteroaryl, each of which is unsubstituted or substituted with one or more $R_6$ groups;

each $R_5$ is independently —CN, —OH, —($C_1$-$C_6$)alkyl, —($C_2$-$C_6$)alkenyl, —($C_2$-$C_6$)alkynyl, -halo, —$N_3$, —$NO_2$, —N($R_7$)$_2$, —CH=$NR_7$, —$NR_7$OH, —$OR_7$, —$COR_7$, —C(O)$OR_7$, —OC(O)$R_7$, —OC(O)$OR_7$, —$SR_7$, —S(O)$R_7$, or —S(O)$_2R_7$;

each $R_6$ is independently —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, -(3- to 5-membered)heterocycle, —C(halo)$_3$, —CH(halo)$_2$, —$CH_2$(halo), —CN, —OH, -halo, —$N_3$, —$NO_2$, —N($R_7$)$_2$, —CH=$NR_7$, —$NR_7$OH, —$OR_7$, —$COR_7$, —C(O)$OR_7$, —OC(O)$R_7$, —OC(O)$OR_7$, —$SR_7$, —S(O)$R_7$, or —S(O)$_2R_7$;

each $R_7$ is independently —H, —($C_1$-$C_6$)alkyl, —($C_2$-$C_6$)alkenyl, —($C_2$-$C_6$)alkynyl, —($C_3$-$C_8$)cycloalkyl, —($C_5$-$C_8$) cycloalkenyl, -phenyl, -(3- to 5-membered)heterocycle, —C(halo)$_3$, —CH(halo)$_2$, or $CH_2$(halo);

each halo is independently —F, —Cl, —Br, or —I;

m is 0 or 1 and when m is 1, $R_3$ is attached to the 2-, 3-, 5-, or 6-position of the cyclo(hetero)alkenyl ring;

n is an integer ranging from 0 to 3; and p is an integer ranging from 0 to 2.

In another embodiment, the present invention relates to a compound of formula 13 a-h

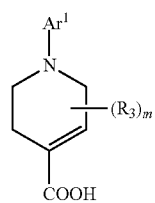

13 a-h or a pharmaceutically acceptable salt thereof, where:
$Ar^1$ is

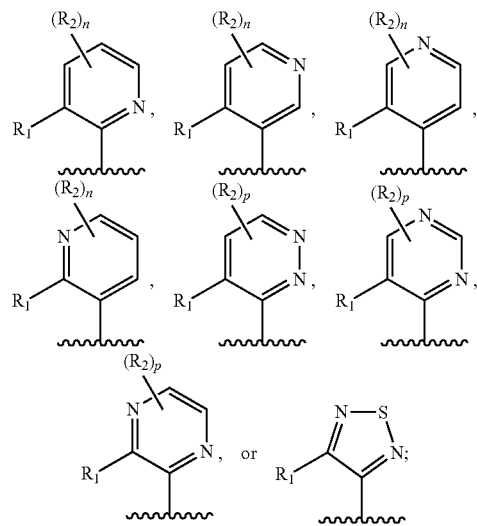

$R_1$ is —H, -halo, —$CH_3$, —$NO_2$, —CN, —OH, —$OCH_3$, —$NH_2$, —C(halo)$_3$, —CH(halo)$_2$, or —$CH_2$(halo);

each $R_2$ is independently:
(a) -halo, —CN, —OH, —$NO_2$, or —$NH_2$,
(b) —($C_1$-$C_{10}$)alkyl, —($C_2$-$C_{10}$)alkenyl, —($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle, or -(7- to 10-membered)bicycloheterocycle, each of which is unsubstituted or substituted with one or more $R_5$ groups, or
(c) -phenyl, -naphthyl, —($C_{14}$)aryl or -(5- to 10-membered)heteraryl, each of which is unsubstituted or substituted with one or more $R_6$ groups;

each $R_3$ is independently:
(a) -halo, —CN, —OH, —$NO_2$, or —$NH_2$,
(b) —($C_1$-$C_{10}$)alkyl, —($C_2$-$C_{10}$)alkenyl, —($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle, or -(7- to 10-membered)bicycloheterocycle, each of which is unsubstituted or substituted with one or more $R_5$ groups, or
(c) -phenyl, napthyl, —($C_{14}$)aryl or -(5- to 10-membered) heteroaryl, each of which is unsubstituted or substituted with one or more $R_6$ groups;

each $R_5$ is independently —CN, —OH, —($C_1$-$C_6$)alkyl, —($C_2$-$C_6$)alkenyl, —($C_2$-$C_6$)alkynyl, -halo, —$N_3$, —$NO_2$, —N($R_7$)$_2$, —CH=$NR_7$, —$NR_7$OH, —$OR_7$, —$COR_7$, —C(O)$OR_7$, —OC(O)$R_7$, —OC(O)$OR_7$, —$SR_7$, —S(O)$R_7$, or —S(O)$_2R_7$;

each $R_6$ is independently —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, -(3- to 5-membered)heterocycle, —C(halo)$_3$, —CH(halo)$_2$, —$CH_2$(halo), —CN, —OH, -halo, —$N_3$, —$NO_2$, —N($R_7$)$_2$, —CH=$NR_7$, —$NR_7$OH, —$OR_7$, —$COR_7$, —C(O)$OR_7$, —OC(O)$R_7$, —OC(O)$OR_7$, —$SR_7$, —S(O)$R_7$, or —S(O)$_2R_7$;

each $R_7$ is independently —H, —($C_1$-$C_6$)alkyl, —($C_2$-$C_6$) alkenyl, —($C_2$-$C_6$)alkynyl, —($C_3$-$C_8$)cycloalkyl, —($C_5$-$C_8$) cycloalkenyl, -phenyl, -(3- to 5-membered)heterocycle, —C(halo)$_3$, —CH(halo)$_2$, or $CH_2$(halo);

each halo is independently —F, —Cl, —Br, or —I;

m is 0 or 1 and when m is 1, $R_3$ is attached to the 2-, 3-, 5-, or 6-position of the cyclo(hetero)alkenyl ring;

n is an integer ranging from 0 to 3; and p is an integer ranging from 0 to 2.

In another embodiment, the present invention relates to a compound of formula 14 a-h

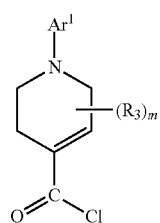

14 a-h or a pharmaceutically acceptable salt thereof, where:
Ar$^1$ is

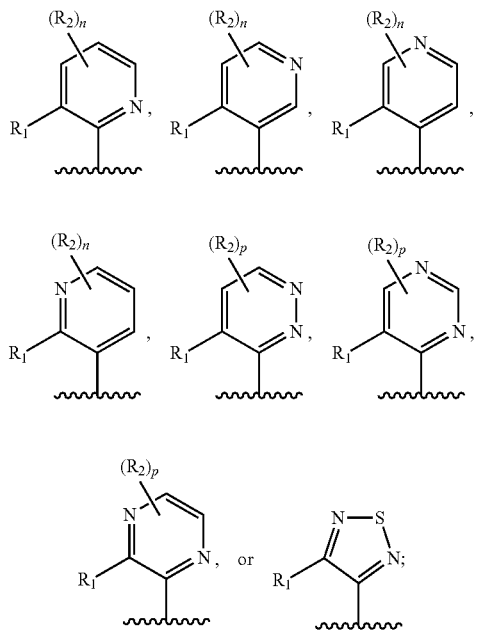

$R_1$ is —H, -halo, —CH$_3$, —NO$_2$, —CN, —OH, —OCH$_3$, —NH$_2$, —C(halo)$_3$, —CH(halo)$_2$, or —CH$_2$(halo);

each $R_2$ is independently:
(a) -halo, —CN, —OH, —NO$_2$, or —NH$_2$,
(b) —(C$_1$-C$_{10}$)alkyl, —(C$_2$-C$_{10}$)alkenyl, —(C$_2$-C$_{10}$)alkynyl, —(C$_3$-C$_{10}$)cycloalkyl, —(C$_8$-C$_{14}$)bicycloalkyl, —(C$_8$-C$_{14}$)tricycloalkyl, —(C$_5$-C$_{10}$)cycloalkenyl, —(C$_8$-C$_{14}$)bicycloalkenyl, —(C$_8$-C$_{14}$)tricycloalkenyl, -(3- to 7-membered)heterocycle, or -(7- to 10-membered)bicycloheterocycle, each of which is unsubstituted or substituted with one or more $R_5$ groups, or
(c) -phenyl, -naphthyl, —(C$_{14}$)aryl or -(5- to 10-membered)heteroaryl, each of which is unsubstituted or substituted with one or more $R_6$ groups;

each $R_3$ is independently:
(a) -halo, —CN, —OH, —NO$_2$, or —NH$_2$,
(b) —(C$_1$-C$_{10}$)alkyl, —(C$_2$-C$_{10}$)alkenyl, —(C$_2$-C$_{10}$)alkynyl, —(C$_3$-C$_{10}$)cycloalkyl, —(C$_8$-C$_{14}$)bicycloalkyl, —(C$_8$-C$_{14}$)tricycloalkyl, —(C$_5$-C$_{10}$)cycloalkenyl, —(C$_8$-C$_{14}$)bicycloalkenyl, —(C$_8$-C$_{14}$)tricycloalkenyl, -(3- to 7-membered)heterocycle, or -(7- to 10-membered)bicycloheterocycle, each of which is unsubstituted or substituted with one or more $R_5$ groups, or
(c) -phenyl, -naphthyl, —(C$_{14}$)aryl or -(5- to 10-membered) heteroaryl, each of which is unsubstituted or substituted with one or more $R_6$ groups;

each $R_5$ is independently —CN, —OH, —(C$_1$-C$_6$)alkyl, —(C$_2$-C$_6$)alkenyl, —(C$_2$-C$_6$)alkynyl, -halo, —N$_3$, —NO$_2$, —N(R$_7$)$_2$, —CH=NR$_7$, —NR$_7$OH, —OR$_7$, —COR$_7$, —C(O)OR$_7$, —OC(O)R$_7$, —OC(O)OR$_7$, —SR$_7$, —S(O)R$_7$, or —S(O)$_2$R$_7$;

each $R_6$ is independently —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, -(3- to 5-membered)heterocycle, —C(halo)$_3$, CH(halo)$_2$, —CH$_2$(halo), —CN, —OH, -halo, —N$_3$, —NO$_2$, —N(R$_7$)$_2$, —CH=NR$_7$, —NR$_7$OH, —OR$_7$, —COR$_7$, —C(O)OR$_7$, —OC(O)R$_7$, —OC(O)OR$_7$, —SR$_7$, —S(O)R$_7$, or —S(O)$_2$R$_7$;

each $R_7$ is independently —H, —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, -(3- to 5-membered)heterocycle, —C(halo)$_3$, —CH(halo)$_2$, or CH$_2$(halo);

each halo is independently —F, —Cl, —Br, or —I;

m is 0 or 1 and when m is 1, $R_3$ is attached to the 2-, 3-, 5-, or 6-position of the cyclo(hetero)alkenyl ring;

n is an integer ranging from 0 to 3; and p is an integer ranging from 0 to 2.

In another embodiment, the present invention relates to methods for making the Cyclo(hetero)alkenyl Compounds where V is N from the amino Compounds of Formula 17a-l and the isonicotinoyl chloride Compounds of Formula 16 by the following non-limiting illustrative method shown below in Scheme C.

Scheme C

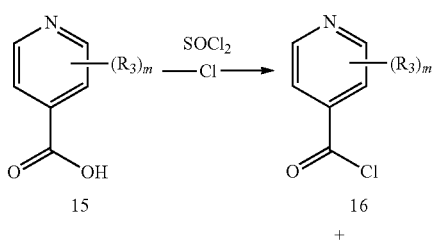

15      16

+

-continued
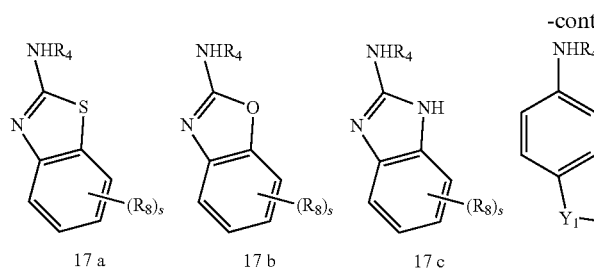
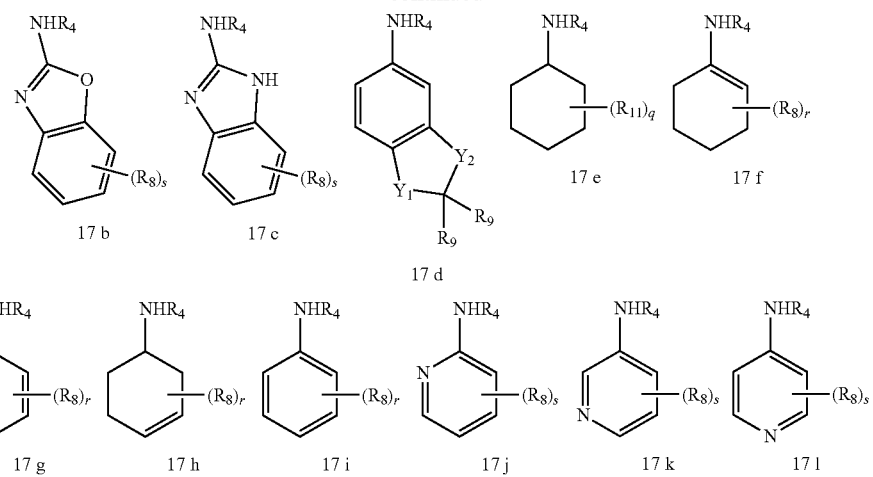
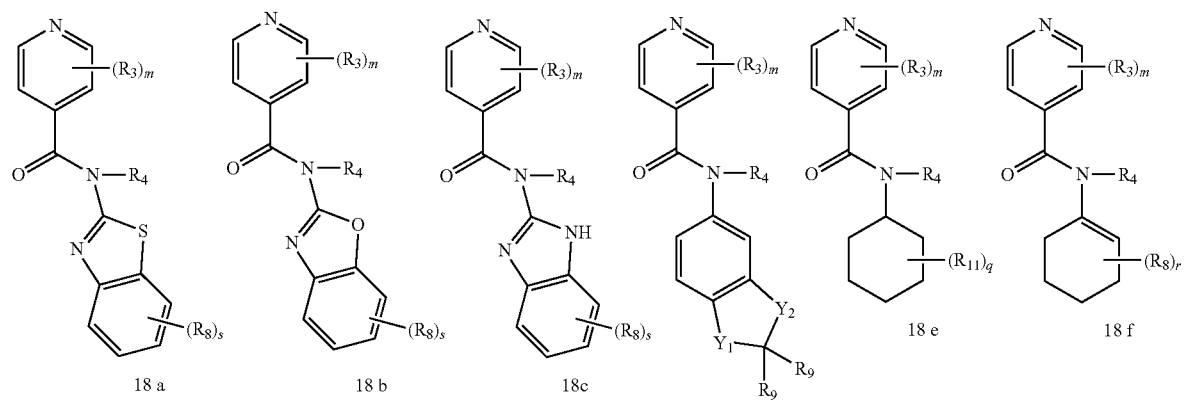
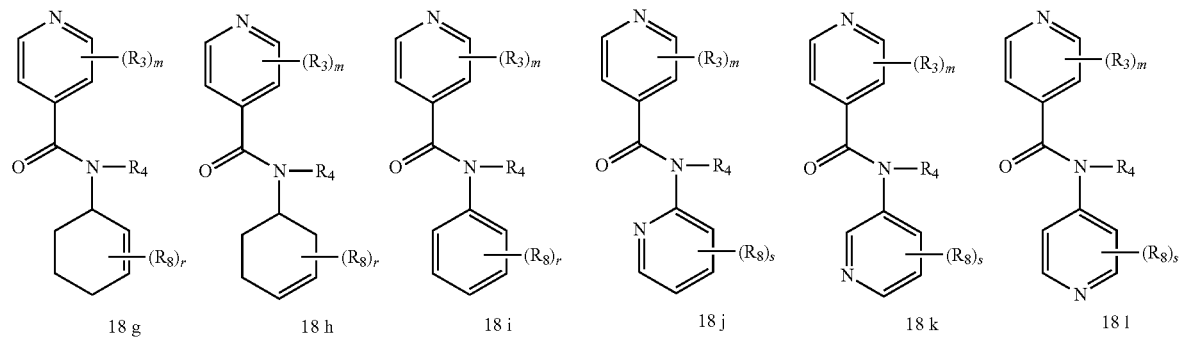
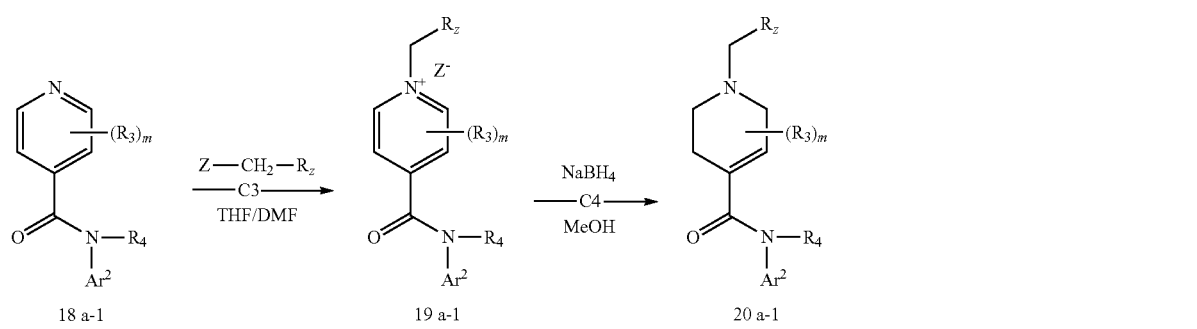

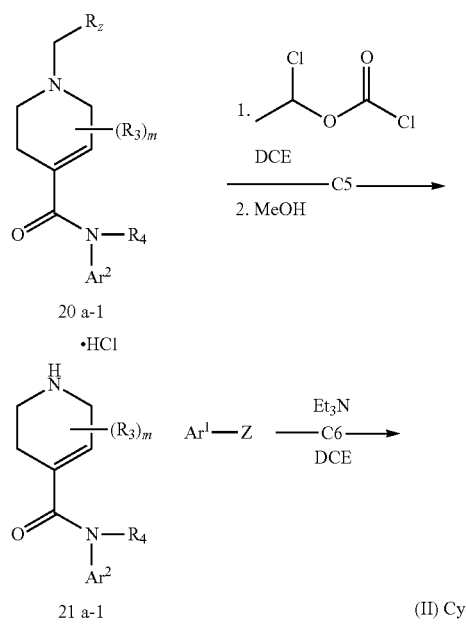
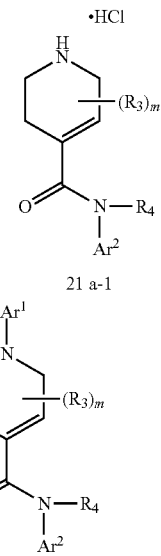

where $R_3$, $R_4$, $R_8$, $R_9$, Y, $Ar^1$, $Ar^2$, m, q, r and s are defined above and Z is Cl, Br or I.

In Step C of Scheme C, the isonicotinic acid Compound of Formula 15, which can be obtained, for example, commercially from, e.g., Aldrich Chemical Co., or can be prepared by methods known to those skilled in the art, is reacted with an excess of a Lewis acid comprising chlorine, such as $SOCl_2$, $COCl_2$, $PSCl_3$, $PCl_5$ or $POCl_3$, which serves as a reagent and can also serve as a solvent. In one embodiment, the present invention relates to a method for making a Cyclo(hetero)alkenyl Compound comprising allowing an isonicotinic acid Compound of Formula 15 to react with an excess of a Lewis acid comprising chlorine. In another embodiment, the Lewis acid comprising chlorine is $POCl_3$, $PSCl_3$, $PCl_5$, $SOCl_2$, $COCl_2$ or a mixture thereof. In another embodiment, the Lewis acid comprising chlorine is $SOCl_2$, $COCl_2$ or a mixture thereof. In another embodiment, the Lewis acid comprising chlorine is $SOCl_2$. In another embodiment, the Lewis acid comprising chlorine is $POCl_3$. In another embodiment, the Lewis acid comprising chlorine is $COCl_2$.

In certain embodiments, the reaction in Step C1 is carried out with an initial amount of the Lewis acid within the range of from about 1 to about 30 equivalents, or within the range of from about 1 to about 20 equivalents, on a molar basis, relative to the Compound of Formula 15. In another embodiment, this reaction is carried out with about 11 equivalents, on a molar basis, of the Lewis acid, relative to the Compound of Formula 15.

In certain embodiments, the Compound of Formula 15 is present in the reaction in Step C1 at an initial concentration within the range of from about LM to about 4M, or at an initial concentration within the range of from about 1M to about 2M. In a specific embodiment, the Compound of Formula 15 is present in the reaction at an initial concentration of about 1.2M.

In certain embodiments, the reaction in Step C1 is carried out at a temperature within the range of from about 10° C. to about 45° C.; at a temperature within the range of from about 10° C. to about 40° C.; or at a temperature within the range of from about 15° C. to about 30° C.

In certain embodiments, the reaction in Step C1 is carried out in an aprotic solvent, e.g., acetone, MEK, ethyl acetate, acetonitrile, dioxane, N-methyl-pyrrolidone, DMF, DMAc, DMSO, pyridine, DCM, DCE and combinations thereof. In certain embodiments, the reaction in Step C1 is carried out without a solvent, i.e., the Lewis acid serves as the solvent. In another embodiment, the solvent is $SOCl_2$.

In certain embodiments, the Compound of Formula 15 is provided as a salt, e.g., the hydrochloride salt, which can be converted to the free amine, using procedures known in the art, prior to reaction with the Lewis acid. For example, the hydrochloride salt of the Compound of Formula 15 is dissolved in a suitable organic solvent, such as but not limited to chloroform, to provide a solution that is extracted with, e.g., a saturated aqueous solution of $Na_2CO_3$. The organic layer is recovered and the aqueous layer back-extracted with an additional volume of the organic solvent. The organic solvent layers are combined, extracted with water, dried, e.g., over anhydrous sodium sulfate, and then the liquid is removed to provide the Compound of Formula 15 as the free amine.

The reaction in Step C1 can be carried out at reduced pressure, atmospheric pressure or elevated pressure, i.e., greater than atmospheric pressure. In one embodiment, the reaction is carried out at atmospheric pressure. In certain embodiments, the reaction in Step C1 is carried out in an air atmosphere. In certain embodiments, the reaction in Step C1 is carried out in an inert atmosphere. In one non-limiting aspect of this embodiment, the reaction in Step C1 is carried out under a nitrogen atmosphere. In another non-limiting aspect of this embodiment, the reaction in Step C is carried out under an argon atmosphere.

Progress of the reaction in Step C1 can be monitored using conventional analytical techniques, including but not limited to IR, LC, MS, LCMS, TLC, HPLC, GC, GLC and/or NMR. The reaction according to Step C1 is carried out, in one embodiment, until a starting material is consumed or, in another embodiment, until the ratio of product, a Compound of Formula 16, to starting material, the Compound of Formula 15, remains essentially constant. Typically, a time sufficient for the reaction in Step C1 is within the range of from about 1 hour to about 48 hours, from about 5 hours to about 36 hours, or from about 10 hours to about 24 hours. In a specific embodiment, the reaction according to Step C1 is carried out for about 17 hours.

In another embodiment, the reaction according to Step C1 is carried out by reacting the Compound of Formula 15 (about 1 eq.) with an excess of a Lewis acid comprising chlorine (about 11 eq.), at a temperature of about 25° C. for a period of about 17 hours with stirring to provide an isonicotinolyl chloride Compound of Formula 16, which, after the Lewis acid comprising chlorine is removed, e.g., under reduced pressure, can be used without further purification or, if desired, can be purified. For example, THF can be used to dissolve the Compound of Formula 16 and the solvent can be removed, e.g., under reduced pressure, to provide a purified Compound of Formula 16.

In Step C2 of Scheme C, the isonicotinolyl chloride Compound of Formula 16 is reacted with a compound of formula $Ar^2$—$NHR_4$, e.g., a Compound of Formula 17 a-l. In one embodiment, the present invention relates to a method for making a Cyclo(hetero)alkenyl Compound comprising allowing an isonicotinolyl chloride Compound of Formula 16 to react with a compound of formula $Ar^2$—$NHR_4$. In another embodiment, the compound of formula $Ar^2$—$NHR_4$ is 4-trifluoromethyl-aniline. In another embodiment, the compound of formula $Ar^2$—$NHR_4$ is 5-trifluoromethyl-pyridin-2-ylamine. In another embodiment, the compound of formula $Ar^2$—$NHR_4$ is 2,2-difluoro-benzo[1,3]dioxol-5-ylamine. In another embodiment, the compound of formula $Ar^2$—$NHR_4$ is 6-fluoro-benzothiazol-2-ylamine.

In certain embodiments, the reaction in Step C2 is carried out with an initial amount of the a compound of formula $Ar^2$—$NHR_4$ within the range of from about 1 to about 2 equivalents, or within the range of from about 1 to about 1.5 equivalents, on a molar basis, relative to the Compound of Formula 16. In another embodiment, this reaction is carried out with about 1.1 equivalents, on a molar basis, of the compound of formula $Ar^2$—$NHR_4$, relative to the Compound of Formula 16.

In certain embodiments, the Compound of Formula 16 is present in the reaction in Step C2 at an initial concentration within the range of from about 0.05M to about 2M, or at an initial concentration within the range of from about 0.1M to about 1M. In a specific embodiment, the Compound of Formula 16 is present in the reaction at an initial concentration of about 0.3M.

In certain embodiments, the reaction in Step C2 is carried out to include an initial amount of a base, such as an inorganic base, e.g., sodium bicarbonate, within the range of from about 1 to about 10 equivalents, or within the range of from about 1 to about 5 equivalents, on a molar basis, relative to the Compound of Formula 16. In another embodiment, this reaction is carried out with about 3 equivalents, on a molar basis, of base, relative to the Compound of Formula 16. In one embodiment, the inorganic base is sodium bicarbonate, sodium carbonate, potassium bicarbonate, potassium carbonate or combinations thereof. In another embodiment, the base is sodium bicarbonate. In another embodiment, the base is potassium carbonate.

In certain embodiments, the reaction in Step C2 is carried out at a temperature within the range of from about −10° C. to about 80° C.; at a temperature within the range of from about −10° C. to about 65° C.; or at a temperature within the range of from about 0° C. to about 65° C.

In certain embodiments, the reaction in Step C2 is carried out in a nonpolar solvent, e.g., hexane, heptane, benzene, diethyl ether, THF, DCM, DCE, chloroform, carbon tetrachloride and combinations thereof. In one embodiment, the nonpolar solvent is THF, DCM, DCE or combinations thereof. In another embodiment, the nonpolar solvent is THF. In another embodiment, the nonpolar solvent is DCM.

In certain embodiments, the Compound of Formula 17 a-l is provided as a salt, e.g., the hydrochloride salt, which can be converted to the free amine, using procedures known in the art, prior to reaction in Step C2. For example, the hydrochloride salt of the Compound of Formula 17 a-l is dissolved in a suitable organic solvent, such as but not limited to chloroform, to provide a solution that is extracted with, e.g., a saturated aqueous solution of $Na_2CO_3$. The organic layer is recovered and the aqueous layer back-extracted with an additional volume of the organic solvent. The organic solvent layers are combined, extracted with water, dried, e.g., over anhydrous sodium sulfate, and then the liquid is removed to provide the Compound of Formula 17 a-l as the free amine.

The reaction in Step C2 can be carried out at reduced pressure, atmospheric pressure or elevated pressure, i.e., greater than atmospheric pressure. In one embodiment, the reaction is carried out at atmospheric pressure. In certain embodiments, the reaction in Step C2 is carried out in an air atmosphere. In certain embodiments, the reaction in Step C2 is carried out in an inert atmosphere. In one non-limiting aspect of this embodiment, the reaction in Step C2 is carried out under a nitrogen atmosphere. In another non-limiting aspect of this embodiment, the reaction in Step C2 is carried out under an argon atmosphere.

Progress of the reaction in Step C2 can be monitored using conventional analytical techniques, including but not limited to IR, LC, MS, LCMS, TLC, HPLC, GC, GLC and/or NMR. The reaction according to Step C2 is carried out, in one embodiment, until a starting material is consumed or, in another embodiment, until the ratio of product, the isonicotinamide Compound of Formula 18 a-l, to starting material, the Compound of Formula 16, remains essentially constant. Typically, a time sufficient for the reaction in Step C2 is within the range of from about 5 minutes to about 5 hours, from about 5 minutes to about 3 hours, or from about 15 minutes to about 3 hours. In a specific embodiment, the reaction according to Step C2 is carried out for about 1.6 hours.

In another embodiment, the reaction according to Step C2 is carried out in THF with about 1.1 equivalents of a compound of formula $Ar^2$—$NHR_4$ and a base, such as sodium bicarbonate (about 3 eq.), each relative to the Compound of Formula 16 (present at an initial concentration of about 0.3M). The reaction mixture is kept at a temperature of about 0° C. for about 5 min with stirring, warmed to about 25° C. over about 30 min, then heated to about 65° C. and kept at that temperature for about 1 h to provide an isonicotinamide Compound of Formula 18 a-l, which, after the THF is removed, e.g., under reduced pressure, can be used without further purification or, if desired, can be purified. For example, the Compound of Formula 18 a-l can be suspended in ethyl acetate and washed with aqueous 3N HCl such that separate aqueous and organic layers form. The layers can be separated and the aqueous layer extracted with ethyl acetate as required. The organic layer can be combined with the post-extraction ethyl acetate aliquot(s), the combination dried, e.g., with $Na_2SO_4$, and the solvent removed, e.g., under reduced pressure, to provide a purified Compound of Formula 18 a-l. A Compound of Formula 18 a-l is useful, e.g., as an intermediate for the synthesis of a Cyclo(hetero)alkenyl Compound.

In Step C3 of Scheme C, the isonicotinamide Compound of Formula 18 a-l is reacted with an alkylating reagent of the formula Z—CH$_2$—R$_z$, where Z is Cl, Br or I, and R$_z$ is —H; —(C$_1$-C$_6$)alkyl; —(C$_3$-C$_8$)cycloalkyl or -(3- to 7-membered) heterocyclo, each of which is optionally substituted with one or more R$_5$ groups; or -phenyl, -naphthyl, —(C$_{14}$)aryl or -(5- to 10-membered)heteroaryl, each of which is optionally substituted with one or more R$_6$ groups; where R$_5$ and R$_6$ are defined above in connection with the Cyclo(hetero)alkenyl Compounds of Formula (I). In one embodiment, the present invention relates to a method for making a Cyclo(hetero)alkenyl Compound comprising allowing an isonicotinamide Compound of Formula 18 a-l to react with an alkylating reagent of the formula Z—CH$_2$—R$_z$. In another embodiment, R$_z$ is —H; —(C$_1$-C$_6$)alkyl; or -phenyl, which is optionally substituted with one or more R$_6$ groups. In another embodiment, R$_z$ is —H, —(C$_1$-C$_4$)alkyl, or -phenyl which is unsubstituted. In another embodiment, R$_z$ is -phenyl which is unsubstituted. Exemplary alkylating reagents include methyl iodide, methyl bromide, ethyl iodide, ethyl bromide, benzyl bromide, benzyl iodide, benzyl chloride, 4-methoxybenzyl bromide, and 4-methoxybenzyl iodide. In another embodiment, the alkylating reagent is a benzylating reagent, i.e., comprises a benzyl group. Exemplary benzylating reagents include benzyl bromide, benzyl iodide, benzyl chloride, 4-methoxybenzyl bromide, 4-methoxybenzyl iodide, 4-methoxybenzyl chloride, or a mixture thereof. In another embodiment, the benzylating reagent is benzyl bromide, benzyl iodide, benzyl chloride or a mixture thereof. In another embodiment, the benzylating reagent is benzyl bromide. In another embodiment, the benzylating reagent is benzyl iodide. In another embodiment, the benzylating reagent is benzyl chloride. In another embodiment, sodium iodide, potassium iodide, tetrabutylammonium iodide, or combinations thereof is present with an alkylating reagent comprising chlorine.

In certain embodiments, the alkylating reagent is present in the reaction in Step C3 at an initial concentration within the range of from about 0.05M to about 2M, or at an initial concentration within the range of from about 0.1M to about 2M. In a specific embodiment, the Compound of Formula 18 a-l is present in the reaction at an initial concentration of about 0.35M.

In certain embodiments, the Compound of Formula 18 a-l is present in the reaction in Step C3 at an initial concentration within the range of from about 0.05M to about 5M, or at an initial concentration within the range of from about 0.1M to about 2M. In a specific embodiment, the Compound of Formula 18 a-l is present in the reaction at an initial concentration of about 0.24M.

In certain embodiments, the reaction in Step C3 is carried out at a temperature within the range of from about 60° C. to about the boiling point of the solvent; at a temperature within the range of from about 65° C. to about 100° C.; or at a temperature within the range of from about 75° C. to about 85° C.

In certain embodiments, the reaction in Step C3 is carried out in a nonpolar solvent, e.g., hexane, heptane, benzene, diethyl ether, THF, DCM, DCE, chloroform, carbon tetrachloride and combinations thereof. In one embodiment, the nonpolar solvent is THF, DMF or combinations thereof. In another embodiment, the nonpolar solvent is a mixture of THF and DMF. In another embodiment, the mixture of THF:DMF is from about 8:1 to about 1:1, or from about 5:1 to about 1:1 by volume. In another embodiment, the mixture of THF:DMF is about 4:1 by volume.

In certain embodiments, the Compound of Formula 18 a-l is provided as a salt, e.g., the hydrochloride salt, which can be converted to the free amine, using procedures known in the art prior to reaction with the alkylating reagent. For example, the hydrochloride salt of the Compound of Formula 18 a-l is dissolved in a suitable organic solvent, such as but not limited to chloroform, to provide a solution that is extracted with, e.g., a saturated aqueous solution of Na$_2$CO$_3$. The organic layer is recovered and the aqueous layer back-extracted with an additional volume of the organic solvent. The organic solvent layers are combined, extracted with water, dried, e.g., over anhydrous sodium sulfate, and then the liquid is removed, such as by evaporation under reduced pressure, e.g., with a rotary evaporator, to provide the Compound of Formula 18 a-l as the free amine.

The reaction in Step C3 can be carried out at reduced pressure, atmospheric pressure or elevated pressure, i.e., greater than atmospheric pressure. In one embodiment, the reaction is carried out at atmospheric pressure. In certain embodiments, the reaction in Step C3 is carried out in an air atmosphere. In certain embodiments, the reaction in Step C3 is carried out in an inert atmosphere. In one non-limiting aspect of this embodiment, the reaction in Step C3 is carried out under a nitrogen atmosphere. In another non-limiting aspect of this embodiment, the reaction in Step C3 is carried out under an argon atmosphere.

Progress of the reaction in Step C3 can be monitored using conventional analytical techniques, including but not limited to IR, LC, MS, LCMS, TLC, HPLC, GC, GLC and/or NMR. The reaction according to Step C3 is carried out, in one embodiment, until a starting material is consumed or, in another embodiment, until the ratio of product, a 1-alkylated-isonicotinamide Compound of Formula 19 a-l, to starting material, the Compound of Formula 18 a-l, remains essentially constant. Typically, a time sufficient for the reaction in Step C3 is within the range of from about 1 hour to about 48 hours, from about 3 hours to about 48 hours, or from about 10 hours to about 36 hours. In a specific embodiment, the reaction according to Step C3 is carried out for about 24 hours.

In another embodiment, the reaction according to Step C3 is carried out in 4:1 THF:DMF by volume with the Compound of Formula 18 a-l present at an initial concentration of about 0.24M, with about a 0.35M initial concentration of benzyl bromide, at a temperature of about 80° C., and for a period of about 24 hours under reflux. Thereafter, the 1-alkylated-isonicotinamide Compound of Formula 19 a-l is recovered using methods known to those skilled in the art. For example, the reaction mixture can be cooled to about 25° C. and the resulting solid can be filtered off. A majority of the THF can be removed from the filtrate, e.g., under reduced pressure. Diethyl ether can be added to cause a precipitate to form from the DMF-enriched solution. The resulting solid can be filtered off and the solids can be combined and dried to provide the 1-alkylated-isonicotinamide Compound of Formula 19 a-l. A Compound of Formula 19 a-l is useful, e.g., as an intermediate for the synthesis of a Cyclo(hetero)alkenyl Compound.

In Step C4 of Scheme C, the 1-alkylated-isonicotinamide Compound of Formula 19 a-l is reacted with a hydrogenation agent, e.g., NaBH$_4$ or LiBH$_4$. In one embodiment, the present invention relates to a method for making a Cyclo(hetero)alkenyl Compound comprising allowing a 1-alkylated-isonicotinamide Compound of Formula 19 a-l to react with a hydrogenation agent. In another embodiment, the hydrogenation agent is NaBH$_4$, LiBH$_4$ or a mixture thereof. In another embodiment, the hydrogenation agent is NaBH$_4$. Hydrogenation agents are commercially available from, e.g., Aldrich Chemical Co., or can be prepared by methods known to those skilled in the art.

In certain embodiments, the reaction in Step C4 is carried out with an initial amount of hydrogenation agent within the range of from about 1 to about 10 equivalents, or within the range of from about 1 to about 6 equivalents, on a molar basis, relative to the Compound of Formula 19 a-l. In another embodiment, this reaction is carried out with about 3.2 equivalents, on a molar basis, of hydrogenation agent, relative to the Compound of Formula 19 a-l.

In certain embodiments, the Compound of Formula 19 a-l is present in the reaction in Step C4 at an initial concentration within the range of from about 0.01M to about 5M, or at an initial concentration within the range of from about 0.05M to about 2M. In a specific embodiment, the Compound of Formula 19 a-l is present in the reaction at an initial concentration of about 0.18M.

In certain embodiments, the reaction in Step C4 is carried out at a temperature within the range of from about −10° C. to about 50° C.; at a temperature within the range of from about −10° C. to about 40° C.; or at a temperature within the range of from about 0° C. to about 30° C.

In certain embodiments, the reaction in Step C4 is carried out in a polar protic nonaqueous solvent, such as an alcohol, e.g., methanol, ethanol, a dialkylamide, e.g., dimethyl formamide, dimethyl formamide, methyl ethyl formamide, or combinations thereof. In one embodiment, the polar protic nonaqueous solvent is an alcohol, a dialkylamide or combinations thereof. In another embodiment, the polar protic nonaqueous solvent is methanol, ethanol, isopropanol or combinations thereof. In another embodiment, the polar protic nonaqueous solvent is methanol. In another embodiment, the polar protic nonaqueous solvent is dimethyl formamide, dimethyl formamide, methyl ethyl formamide or combinations thereof. In another embodiment, the polar protic nonaqueous solvent is dimethyl formamide.

The reaction in Step C4 can be carried out at reduced pressure, atmospheric pressure or elevated pressure, i.e., greater than atmospheric pressure. In one embodiment, the reaction is carried out at atmospheric pressure. In certain embodiments, the reaction in Step C4 is carried out in an air atmosphere. In certain embodiments, the reaction in Step C4 is carried out in an inert atmosphere. In one non-limiting aspect of this embodiment, the reaction in Step C4 is carried out under a nitrogen atmosphere. In another non-limiting aspect of this embodiment, the reaction in Step C4 is carried out under an argon atmosphere.

Progress of the reaction in Step C4 can be monitored using conventional analytical techniques, including but not limited to IR, LC, MS, LCMS, TLC, HPLC, GC, GLC and/or NMR. The reaction according to Step C4 is carried out, in one embodiment, until a starting material is consumed or, in another embodiment, until the ratio of product, a 1-alkylated-1,2,3,6-tetrahydro-pyridine-4-carboxylic acid amide Compound of Formula 20 a-l, to starting material, the Compound of Formula 19 a-l, remains essentially constant. Typically, a time sufficient for the reaction in Step C4 is within the range of from about 5 minutes to about 10 hours, from about 5 minutes to about 5 hours, or from about 15 minutes to about 5 hours. In a specific embodiment, the reaction according to Step C4 is carried out for about 3.5 hours.

In another embodiment, the reaction according to Step C4 is carried out at about 0° C. in an alcohol with about 3.2 equivalents, on a molar basis, of a hydrogenation agent, relative to the Compound of Formula 19 a-l, added portion-wise over a period of about 30 min. Thereafter, the reaction mixture can be stirred for about 1 h at about 0° C. and warmed to about 25° C. over about a 2 hour period to provide a 1-alkylated-1,2,3,6-tetrahydro-pyridine-4-carboxylic acid amide Compound of Formula 20 a-l, which, after the alcohol is removed, e.g., under reduced pressure, can be used without further purification or, if desired, can be purified. For example, the Compound of Formula 20 a-l can be diluted with brine and ethyl acetate such that separate aqueous and organic layers form. The layers can be separated and the aqueous layer washed with ethyl acetate as required. The organic layer can be combined with the post-washing ethyl acetate aliquot (s), the combination dried, e.g., with $Na_2SO_4$, and the solvent removed, e.g., under reduced pressure, to provide purified Compound of Formula 20 a-l which can be used without additional purification or, if desired, can be further purified. For example, the purified Compound of Formula 20 a-l can be dissolved in DCM and precipitated by adding hexane to the DCM solution. The resulting solid can be filtered off and dried to provide further purified Compound of Formula 20 a-l. A Compound of Formula 20 a-l is useful, e.g., as an intermediate for the synthesis of a Cyclo(hetero)alkenyl Compound.

In Step C5 of Scheme C, the 1-alkylated-1,2,3,6-tetrahydro-pyridine-4-carboxylic acid amide Compound of Formula 20 a-l is reacted with a dealkylating reagent, e.g., α-chloroethylchloroformate. In one embodiment, the present invention relates to a method for making a Cyclo(hetero)alkenyl Compound comprising allowing a 1-alkylated-1,2,3,6-tetrahydro-pyridine-4-carboxylic acid amide Compound of Formula 20 a-l to react with a dealkylating reagent. In another embodiment, the dealkylating reagent is α-chloroethylchloroformate, 2,2,2-trichloroethylchloroformate or a mixture thereof. In another embodiment, the dealkylating reagent is α-chloroethylchloroformate. In another embodiment, the dealkylating reagent is 2,2,2-trichloroethylchloroformate. Dealkylating reagents are commercially available from, e.g., Aldrich Chemical Co., or can be prepared by methods known to those skilled in the art.

In certain embodiments, the dealkylating reagent is present in the reaction in Step C5 at an initial concentration within the range of from about 0.05M to about 4M, or at an initial concentration within the range of from about 0.06M to about 4M. In a specific embodiment, the dealkylating reagent is present in the reaction at an initial concentration of about 0.32M.

In certain embodiments, the Compound of Formula 20 a-l is present in the reaction in Step C5 at an initial concentration within the range of from about 0.01M to about 5M, or at an initial concentration within the range of from about 0.05M to about 2M. In a specific embodiment, the Compound of Formula 20 a-l is present in the reaction at an initial concentration of about 0.17M.

In certain embodiments, the reaction in Step C5 is carried out at a temperature within the range of from about 0° C. to about the boiling point of the solvent; at a temperature within the range of from about 0° C. to about 100° C.; or at a temperature within the range of from about 0° C. to about 90° C.

In certain embodiments, the reaction in Step C5 is carried out in a nonpolar solvent, e.g., hexane, heptane, benzene, diethyl ether, THF, DCM, DCE, chloroform, carbon tetrachloride and combinations thereof. In one embodiment, the nonpolar solvent is DCE, THF or combinations thereof. In another embodiment, the nonpolar solvent is DCE. In another embodiment, the nonpolar solvent is THF.

In certain embodiments, the Compound of Formula 20 a-l is provided as a salt, e.g., the hydrochloride salt, which can be converted to the free amine, using procedures known in the art, prior to reaction with the dealkylating reagent. For example, the hydrochloride salt of the Compound of Formula 20 a-l is dissolved in a suitable organic solvent, such as but not limited to chloroform, to provide a solution that is extracted with, e.g., a saturated aqueous solution of $Na_2CO_3$. The organic layer is recovered and the aqueous layer back-extracted with an additional volume of the organic solvent. The organic solvent layers are combined, extracted with water, dried, e.g., over anhydrous sodium sulfate, and then the liquid is removed, such as by evaporation under reduced pressure, e.g., with a rotary evaporator, to provide the Compound of Formula 20 a-l as the free amine.

The reaction in Step C5 can be carried out at reduced pressure, atmospheric pressure or elevated pressure, i.e., greater than atmospheric pressure. In one embodiment, the reaction is carried out at atmospheric pressure. In certain embodiments, the reaction in Step C5 is carried out in an air atmosphere. In certain embodiments, the reaction in Step C5 is carried out in an inert atmosphere. In one non-limiting aspect of this embodiment, the reaction in Step C5 is carried out under a nitrogen atmosphere. In another non-limiting aspect of this embodiment, the reaction in Step C5 is carried out under an argon atmosphere.

Progress of the reaction in Step C5 can be monitored using conventional analytical techniques, including but not limited to IR, LC, MS, LCMS, TLC, HPLC, GC, GLC and/or NMR. The reaction according to Step C5 is carried out, in one embodiment, until a starting material is consumed or, in another embodiment, until the ratio of product, a 1,2,3,6-tetrahydro-pyridine-4-carboxylic acid amide Compound of Formula 21 a-l, to starting material, the Compound of Formula 20 a-l, remains essentially constant. Typically, a time sufficient for the reaction in Step C5 is within the range of from about 0.3 hours to about 48 hours, from about 0.5 hours to about 48 hours, or from about 0.5 hours to about 5 hours. In a specific embodiment, the reaction according to Step C5 is carried out for about 4.75 hours.

In another embodiment, the reaction according to Step C5 is carried out in DCE with the Compound of Formula 20 a-l present at an initial concentration of about 0.17M, with about a 0.32M initial concentration of α-chloroethylchloroformate (after adding drop-wise over a 15 minute period) at a temperature of about 0° C. The reaction mixture can be warmed to about 25° C. over a period of about 30 min then heated to about 83° C. for about 4 hours at that temperature to provide a 1,2,3,6-tetrahydro-pyridine-4-carboxylic acid amide Compound of Formula 21 a-l, which, after the solvent and unreacted α-chloroethylchloroformate are removed, e.g., under reduced pressure, can be used without further purification or, if desired, can be purified. For example, the Compound of Formula 21 a-l can be dissolved in methanol, refluxed for about 3 hours at a temperature of about 65° C., and the methanol removed, e.g., under reduced pressure, to provide purified Compound of Formula 21 a-l which can be used without additional purification or, if desired, can be further purified. For example, the purified Compound of Formula 21 a-l can be dissolved in DCM and precipitated by adding diethyl ether to the DCM solution. The resulting solid can be filtered off and dried to provide further purified Compound of Formula 21 a-l. A Compound of Formula 21 a-l is useful, e.g., as an intermediate for the synthesis of a Cyclo(hetero)alkenyl Compound.

In Step C6 of Scheme C, the 1,2,3,6-tetrahydro-pyridine-4-carboxylic acid amide Compound of Formula 21 a-l is reacted with a compound of formula $Ar^1$—Z, where Z is Cl, Br or I. In one embodiment, the present invention relates to a method for making a Cyclo(hetero)alkenyl Compound comprising allowing a 1,2,3,6-tetrahydro-pyridine-4-carboxylic acid amide Compound of Formula 21 a-l to react with a compound of formula $Ar^1$—Z. In another embodiment, the compound of formula $Ar^1$—Z is 2-chloro-3-nitropyridine. In another embodiment, the compound of formula $Ar^1$—Z is 2,3-dichloropyridine. In another embodiment, the compound of formula $Ar^1$—Z is 2-chloro-3-fluoropyridine.

In certain embodiments, the compound of formula $Ar^1$—Z is present in the reaction in Step C6 at an initial concentration within the range of from about 0.01M to about 5M, or at an initial concentration within the range of from about 0.05M to about 3M. In a specific embodiment, the compound of formula Ar—Z is present in the reaction at an initial concentration of about 0.064M.

In certain embodiments, the Compound of Formula 21 a-l is present in the reaction in Step C6 at an initial concentration within the range of from about 0.01M to about 5M, or at an initial concentration within the range of from about 0.05M to about 3M. In a specific embodiment, the Compound of Formula 21 a-l is present in the reaction at an initial concentration of about 0.068M.

In certain embodiments, a trialkylamine, such as triethylamine, trimethylamine, methyl diethylamine or diisopropyl ethylamine, is present in the reaction in Step C6 at an initial concentration within the range of from about 0.01M to about 5M, or at an initial concentration within the range of from about 0.05M to about 3M. In a specific embodiment, the trialkylamine is present in the reaction at an initial concentration of about 0.27M. In one embodiment, the trialkylamine is triethylamine, trimethylamine, methyl diethylamine, diisopropyl ethylamine or combinations thereof. In another embodiment, the trialkylamine is triethylamine.

In certain embodiments, the reaction in Step C6 is carried out at a temperature within the range of from about 15° C. to about 140° C.; at a temperature within the range of from about 25° C. to about 140° C.; or at a temperature within the range of from about 15° C. to about 30° C.

In certain embodiments, the reaction in Step C6 is carried out in a solvent, e.g., hexane, heptane, benzene, diethyl ether, THF, DCM, DCE, chloroform, carbon tetrachloride, DMF, DMSO, and combinations thereof. In one embodiment, the nonpolar solvent is DCE, THF or combinations thereof. In another embodiment, the nonpolar solvent is DCE.

The reaction in Step C6 can be carried out at reduced pressure, atmospheric pressure or elevated pressure, i.e., greater than atmospheric pressure. In one embodiment, the reaction is carried out at atmospheric pressure. In certain embodiments, the reaction in Step C6 is carried out in an air atmosphere. In certain embodiments, the reaction in Step C6 is carried out in an inert atmosphere. In one non-limiting aspect of this embodiment, the reaction in Step C6 is carried out under a nitrogen atmosphere. In another non-limiting aspect of this embodiment, the reaction in Step C6 is carried out under an argon atmosphere.

Progress of the reaction in Step C6 can be monitored using conventional analytical techniques, including but not limited to IR, LC, MS, LCMS, TLC, HPLC, GC, GLC and/or NMR. The reaction according to Step C6 is carried out, in one embodiment, until a starting material is consumed or, in another embodiment, until the ratio of product, the Cyclo(hetero)alkenyl Compound, to starting material, the Compound of Formula 21 a-l, remains essentially constant. Typically, a time sufficient for the reaction in Step C6 is within the range of from about 0.5 hours to about 48 hours, from about 0.5 hours to about 36 hours, or from about 3 hours to about 24 hours. In a specific embodiment, the reaction according to Step C6 is carried out for about 12 hours.

In another embodiment, the reaction according to Step C6 is carried out in DCE with about 0.064M of a compound of formula $Ar^1$—Z, about 0.068M of a Compound of Formula 21 a-l, and about 0.27M of a trialkylamine, such as triethylamine, trimethylamine, methyl diethylamine or diisopropyl ethylamine. The reaction mixture is kept at a temperature within the range of from about 20° C. to about 30° C. for a period of about 12 hours with stirring. Thereafter, the mixture can be poured into aqueous sodium bicarbonate and DCM such that separate aqueous and organic layers form. The organic layer is separated from the aqueous layer. The organic layer is dried, e.g., with $Na_2SO_4$, and the solvent is removed, e.g., under reduced pressure, to provide a residue that can be used without further purification or, if desired, can be purified to provide a Cyclo(hetero)alkenyl Compound where V is N. For example, the residue can be dissolved in DCM and precipitated by adding hexane to the DCM solution. The resulting solid can be filtered off and dried to provide a purified Cyclo(hetero)alkenyl Compound where V is N. As discussed above, if a mixture of Cyclo(hetero)alkenyl Compounds is obtained where m=1, the mixture can be separated by conventional methods, for example, column chromatography.

The Compound of Formula (I) where X is S (i.e., the Compound of Formula (II')) can be made by, e.g., reacting a Compound of Formula (II) (i.e., where X is O) with Lawesson's reagent as described in connection with Scheme A.

Thus, in another embodiment, a method for preparing a Cyclo(hetero)alkenyl Compound comprises allowing a 1,2,3,6-tetrahydro-pyridine-4-carboxylic acid amide compound to react with a compound of formula $Ar^1$—Z to provide a Cyclo(hetero)alkenyl Compound; where Z is Cl, Br or I.

In another embodiment, a method for preparing a Cyclo(hetero)alkenyl Compound comprises allowing a 1-alkylated-1,2,3,6-tetrahydro-pyridine-4-carboxylic acid amide compound to react with a dealkylating reagent to provide a 1,2,3,6-tetrahydro-pyridine-4-carboxylic acid amide compound.

In another embodiment, a method for preparing a Cyclo(hetero)alkenyl Compound comprises allowing a 1-alkylated-isonicotinamide compound to react with a hydrogenation agent to provide a 1-alkylated-1,2,3,6-tetrahydro-pyridine-4-carboxylic acid amide compound.

In another embodiment, a method for preparing a Cyclo(hetero)alkenyl Compound comprises allowing an isonicotinamide compound to react with an alkylating reagent to provide a 1-alkylated-isonicotinamide compound.

In another embodiment, in method for preparing a Cyclo(hetero)alkenyl Compound, the alkylating reagent is a benzylating reagent selected from benzyl bromide, benzyl iodide, benzyl chloride or a mixture thereof.

In another embodiment, a method for preparing a Cyclo(hetero)alkenyl Compound comprises forming the isonicotinamide compound by allowing an isonicotinolyl chloride compound to react with a compound of formula $Ar^2$—$NHR_4$;

where $R_4$ is —H or —($C_1$-$C_6$)alkyl; and
$Ar^2$ is

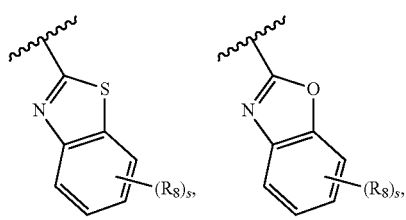

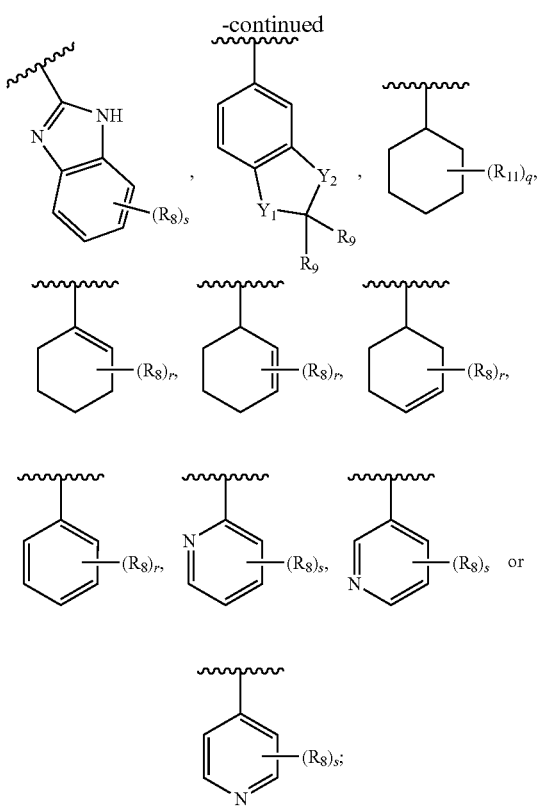

where $Y_1$ and $Y_2$ are —$CH_2$— and —$CH_2$—, —O— and —O—, —NH— and —NH—, —S— and —S—, —$CH_2$— and —O—, —$CH_2$— and —NH—, —$CH_2$— and —S—, —O— and —$CH_2$—, —NH— and —$CH_2$—, —S— and —$CH_2$—, —O— and —NH—, —NH— and —O—, —S— and —NH—, or —NH— and —S— respectively;

each $R_7$ is independently —H, —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, -(3- to 5-membered)heterocycle, —C(halo)$_3$, —CH(halo)$_2$, or $CH_2$(halo);

each $R_8$ is independently —($C_1$-$C_{10}$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, —C(halo)$_3$, —CH(halo)$_2$, —$CH_2$(halo), —CN, —OH, -halo, —$N_3$, —$NO_2$, —N($R_7$)$_2$, —CH=$NR_7$, —$NR_7$OH, —$OR_7$, —$COR_7$, —C(O)$OR_7$, —OC(O)$R_7$, —OC(O)$OR_7$, —$SR_7$, —S(O)$R_7$, —S(O)$_2R_7$, —$R_7OR_7$, —$R_7COR_7$, —$R_7$C(O)$OR_7$, —$R_7$OC(O)$R_7$, —$R_7$OC(O)$OR_7$, —$R_7SR_7$, —$R_7$S(O)$R_7$, —$R_7$S(O)$_2R_7$, —C(halo)$_2$C(halo)$_3$, —C(halo)$_2$CH(halo)$_2$, —CH(C(halo)$_3$)$_2$, —CH(C(halo)$_3$)(CH$_3$), —OC(halo)$_2$C(halo)$_3$, —OC(halo)$_2$CH(halo)$_2$, —OCH(C(halo)$_3$)$_2$, —OCH(C(halo)$_3$)(CH$_3$), —C(OH)(CF$_3$)$_2$, —($C_1$-$C_{10}$)alkyl, or -(3- to 7-membered) heterocycle;

each $R_9$ is independently —H, -halo or —($C_1$-$C_6$)alkyl, each $R_{11}$ is independently —CN, —OH, —($C_1$-$C_6$)alkyl, —($C_2$-$C_6$)alkenyl, —($C_2$-$C_6$)alkynyl, -halo, —$N_3$, —$NO_2$, —N($R_7$)$_2$, —CH=$NR_7$, —$NR_7$OH, —$OR_7$, —$COR_7$, —C(O)$OR_7$, —OC(O)$R_7$, or —OC(O)$OR_7$;

each halo is independently —F, —Cl, —Br, or —I;

q is an integer ranging from 0 to 6;

r is an integer ranging from 0 to 5; and s is an integer ranging from 0 to 4.

In another embodiment, the present invention relates to a compound of formula 18 a-l

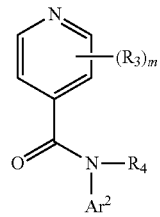

18 a-l or a pharmaceutically acceptable salt thereof, where:
Ar² is

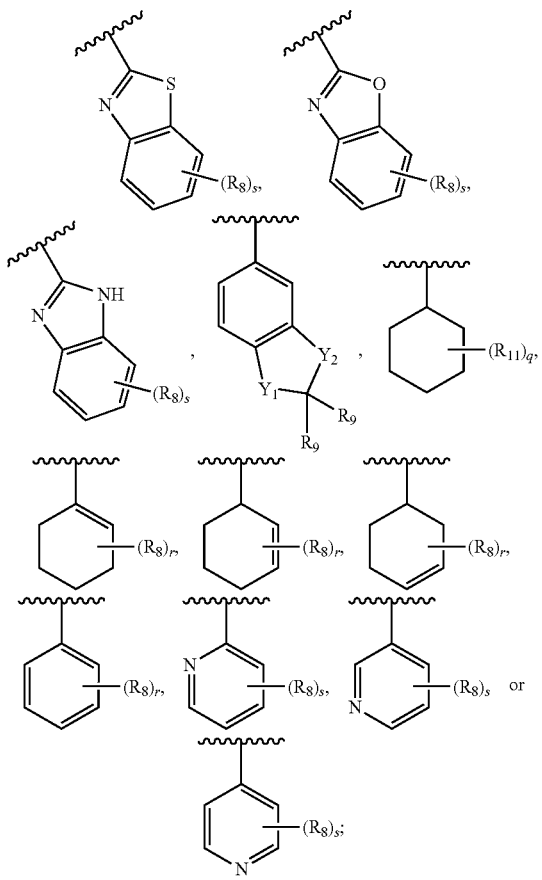

$Y_1$ and $Y_2$ are —$CH_2$— and —$CH_2$—, —O— and —O—, —NH— and —NH—, —S— and —S—, —$CH_2$— and —O—, —$CH_2$— and —NH—, —$CH_2$— and —S—, —O— and —$CH_2$—, —NH— and —$CH_2$—, —S— and —$CH_2$—, —O— and —NH—, —NH— and —O—, —S— and —NH—, or —NH— and —S— respectively;

each $R_3$ is independently:
(a) -halo, —CN, —OH, —$NO_2$, or —$NH_2$,
(b) —($C_1$-$C_{10}$)alkyl, —($C_2$-$C_{10}$)alkenyl, —($C_2$-$C_{10}$)alkynyl, —($C_3$-$C_{10}$)cycloalkyl, -($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle, or -(7- to 10-membered)bicycloheterocycle, each of which is unsubstituted or substituted with one or more $R_5$ groups, or (c) -phenyl, -naphthyl, —($C_{14}$)aryl or -(5- to 10-membered) heteroaryl, each of which is unsubstituted or substituted with one or more $R_6$ groups;

$R_4$ is —H or —($C_1$-$C_6$)alkyl;

each $R_5$ is independently —CN, —OH, —($C_1$-$C_6$)alkyl, —($C_2$-$C_6$)alkenyl, —($C_2$-$C_6$)alkynyl, -halo, —$N_3$, —$NO_2$, —$N(R_7)_2$, —CH=$NR_7$, —$NR_7$OH, —$OR_7$, —$COR_7$, —C(O)$OR_7$, —OC(O)$R_7$, —OC(O)$OR_7$, —$SR_7$, —S(O)$R_7$, or —S(O)$_2R_7$;

each $R_6$ is independently —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, -(3- to 5-membered)heterocycle, —C(halo)$_3$, —CH(halo)$_2$, —$CH_2$(halo), —CN, —OH, -halo, —$N_3$, —$NO_2$, —$N(R_7)_2$, —CH=$NR_7$, —$NR_7$OH, —$OR_7$, —$COR_7$, —C(O)$OR_7$, —OC(O)$R_7$, —OC(O)$OR_7$, —$SR_7$, —S(O)$R_7$, or —S(O)$_2R_7$;

each $R_7$ is independently —H, —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, -(3- to 5-membered)heterocycle, —C(halo)$_3$, —CH(halo)$_2$, or $CH_2$(halo);

each $R_8$ is independently —($C_1$-$C_{10}$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, —C(halo)$_3$, —CH(halo)$_2$, —$CH_2$(halo), —CN, —OH, -halo, —$N_3$, —$NO_2$, —$N(R_7)_2$, —CH=$NR_7$, —$NR_7$OH, —$OR_7$, —$COR_7$, —C(O)$OR_7$, —OC(O)$R_7$, —OC(O)$OR_7$, —$SR_7$, —S(O)$R_7$, —S(O)$_2R_7$, —$R_7OR_7$, —$R_7COR_7$, —$R_7$C(O)$OR_7$, —$R_7$OC(O)$R_7$, —$R_7$OC(O)$OR_7$, —$R_7SR_7$, —$R_7$S(O)$R_7$, —$R_7$S(O)$_2R_7$, —C(halo)$_2$C(halo)$_3$, —C(halo)$_2$CH(halo)$_2$, —CH(C(halo)$_3$)$_2$, —CH(C(halo)$_3$)(CH$_3$), —OC(halo)$_2$C(halo)$_3$, —OC(halo)$_2$CH(halo)$_2$, —OCH(C(halo)$_3$)$_2$, —OCH(C(halo)$_3$)(CH$_3$), —C(OH)(CF$_3$)$_2$, —($C_1$-$C_{10}$)alkyl, or -(3- to 7-membered) heterocycle;

each $R_9$ is independently —H, -halo or —($C_1$-$C_6$)alkyl;

each $R_{11}$ is independently —CN, —OH, —($C_1$-$C_6$)alkyl, —($C_2$-$C_6$)alkenyl, —($C_2$-$C_6$)alkynyl, -halo, —$N_3$, —$NO_2$, —$N(R_7)_2$, —CH=$NR_7$, —$NR_7$OH, —$OR_7$, —$COR_7$, —C(O)$OR_7$, —OC(O)$R_7$, or —OC(O)$OR_7$;

each halo is independently —F, —Cl, —Br, or —I;

m is 0 or 1 and when m is 1, $R_3$ is attached to the 2-, 3-, 5-, or 6-position of the cyclo(hetero)alkenyl ring;

q is an integer ranging from 0 to 6;

r is an integer ranging from 0 to 5; and s is an integer ranging from 0 to 4.

In another embodiment, the present invention relates to a compound of formula 19 a-l

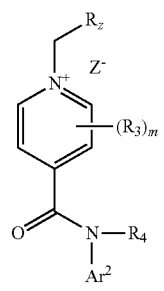

19 a-l or a pharmaceutically acceptable salt thereof, where:
Ar² is

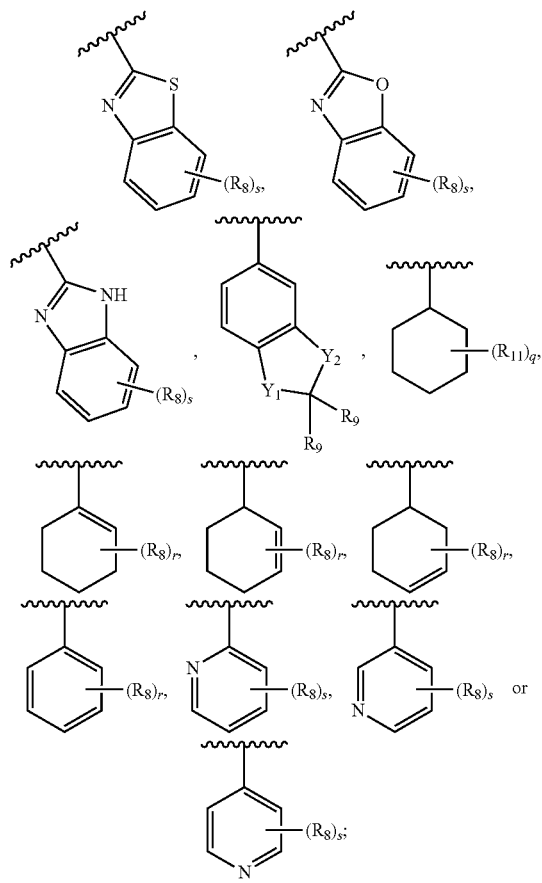

Y₁ and Y₂ are —CH₂— and —CH₂—, —O— and —O—, —NH— and —NH—, —S— and —S—, —CH₂— and —O—, —CH₂— and —NH—, —CH₂— and —S—, —O— and —CH₂—, —NH— and —CH₂—, —S— and —CH₂—, —O— and —NH—, —NH— and —O—, —S— and —NH—, or —NH— and —S— respectively each $R_3$ is independently:

(a) -halo, —CN, —OH, —NO₂, or —NH₂,
(b) —(C₁-C₁₀)alkyl, —(C₂-C₁₀)alkenyl, —(C₂-C₁₀)alkynyl, —(C₃-C₁₀)cycloalkyl, —(C₈-C₁₄)bicycloalkyl, —(C₈-C₁₄)tricycloalkyl, —(C₅-C₁₀)cycloalkenyl, —(C₈-C₁₄)bicycloalkenyl, —(C₈-C₁₄)tricycloalkenyl, -(3- to 7-membered)heterocycle, or -(7- to 10-membered)bicycloheterocycle, each of which is unsubstituted or substituted with one or more $R_5$ groups, or
(c) -phenyl, -naphthyl, —(C₁₄)aryl or -(5- to 10-membered) heteroaryl, each of which is unsubstituted or substituted with one or more $R_6$ groups;

$R_4$ is —H or —(C₁-C₆)alkyl;

each $R_5$ is independently —CN, —OH, —(C₁-C₆)alkyl, —(C₂-C₆)alkenyl, —(C₂-C₆)alkynyl, -halo, —N₃, —NO₂, —N(R₇)₂, —CH=NR₇, —NR₇OH, —OR₇, —COR₇, —C(O)OR₇, —OC(O)R₇, —OC(O)OR₇, —SR₇, —S(O)R₇, or —S(O)₂R₇;

each $R_6$ is independently —(C₁-C₆)alkyl, —(C₂-C₆)alkenyl, —(C₂-C₆)alkynyl, —(C₃-C₈)cycloalkyl, —(C₅-C₈)cycloalkenyl, -phenyl, -(3- to 5-membered)heterocycle, —C(halo)₃, —CH(halo)₂, —CH₂(halo), —CN, —OH, -halo, —N₃, —NO₂, —N(R₇)₂, —CH=NR₇, —NR₇OH, —OR₇, —COR₇, —C(O)OR₇, —OC(O)R₇, —OC(O)OR₇, —SR₇, —S(O)R₇, or —S(O)₂R₇;

each $R_7$ is independently —H, —(C₁-C₆)alkyl, —(C₂-C₆)alkenyl, —(C₂-C₆)alkynyl, —(C₃-C₈)cycloalkyl, —(C₅-C₈)cycloalkenyl, -phenyl, -(3- to 5-membered)heterocycle, —C(halo)₃, —CH(halo)₂, or —CH₂(halo);

each $R_8$ is independently —(C₁-C₁₀)alkyl, —(C₂-C₆)alkenyl, —(C₂-C₆)alkynyl, —(C₃-C₈)cycloalkyl, —(C₅-C₈)cycloalkenyl, -phenyl, —C(halo)₃, —CH(halo)₂, —CH₂(halo), —CN, —OH, -halo, —N₃, —NO₂, —N(R₇)₂, —CH=NR₇, —NR₇OH, —OR₇, —COR₇, —C(O)OR₇, —OC(O)R₇, —OC(O)OR₇, —SR₇, —S(O)R₇, —S(O)₂R₇, —R₇OR₇, —R₇COR₇, —R₇C(O)OR₇, —R₇OC(O)R₇, —R₇OC(O)OR₇, —R₇SR₇, —R₇S(O)R₇, —R₇S(O)₂R₇, —C(halo)₂C(halo)₃, —C(halo)₂CH(halo)₂, —CH(C(halo)₃)₂, —CH(C(halo)₃)(CH₃), —OC(halo)₂C(halo)₃, —OC(halo)₂CH(halo)₂, —OCH(C(halo)₃)₂, —OCH(C(halo)₃)(CH₃), —C(OH)(CF₃)₂, —(C₁-C₁₀)alkyl, or -(3- to 7-membered)heterocycle;

each $R_9$ is independently —H, -halo or —(C₁-C₆)alkyl;

each $R_{11}$ is independently —CN, —OH, —(C₁-C₆)alkyl, —(C₂-C₆)alkenyl, —(C₂-C₆)alkynyl, -halo, —N₃, —NO₂, —N(R₇)₂, —CH=NR₇, —NR₇OH, —OR₇, —COR₇, —C(O)OR₇, —OC(O)R₇, or —OC(O)OR₇;

each halo is independently —F, —Cl, —Br, or —I;

m is 0 or 1 and when m is 1, $R_3$ is attached to the 2-, 3-, 5-, or 6-position of the cyclo(hetero)alkenyl ring;

q is an integer ranging from 0 to 6;

r is an integer ranging from 0 to 5;

s is an integer ranging from 0 to 4;

$R_z$ is -phenyl which is optionally substituted with one or more $R_6$ groups, —H or —(C₁-C₆)alkyl; and Z is Cl, Br or I.

In another embodiment, the present invention relates to a compound of formula 20 a-1

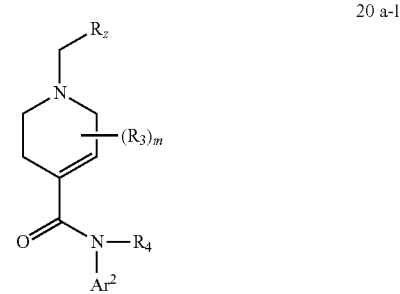

20 a-1 or a pharmaceutically acceptable salt thereof, where:
Ar² is

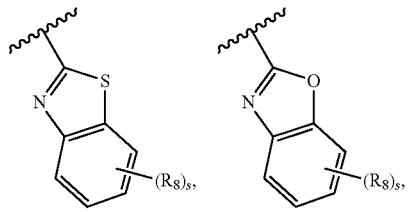

-continued

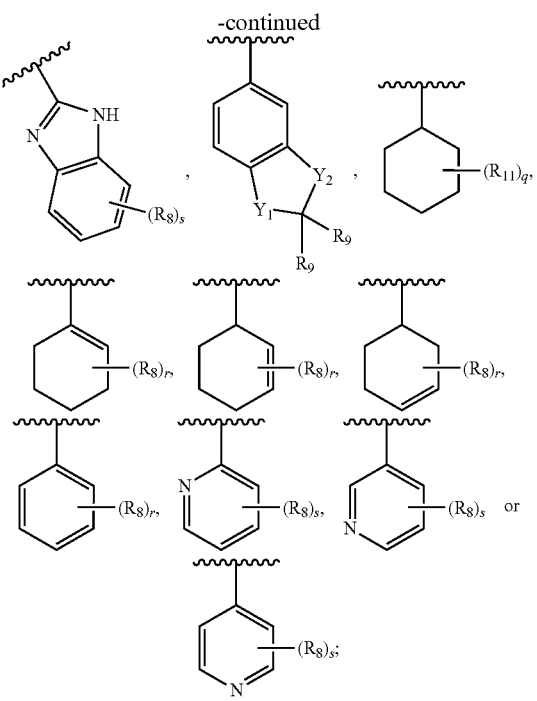

$Y_1$ and $Y_2$ are —CH$_2$— and —CH$_2$—, —O— and —O—, —NH— and —NH—, —S— and —S—, —CH$_2$— and —O—, —CH$_2$— and —NH—, —CH$_2$— and —S—, —O— and —CH$_2$—, —NH— and —CH$_2$—, —S— and —CH$_2$—, —O— and —NH—, —NH— and —O—, —S— and —NH—, or —NH— and —S— respectively;

each $R_3$ is independently:
(a) -halo, —CN, —OH, —NO$_2$, or —NH$_2$,
(b) —(C$_1$-C$_{10}$)alkyl, —(C$_2$-C$_{10}$)alkenyl, —(C$_2$-C$_{10}$)alkynyl, —(C$_3$-C$_{10}$)cycloalkyl, —(C$_8$-C$_{14}$)bicycloalkyl, —(C$_8$-C$_{14}$)tricycloalkyl, —(C$_5$-C$_{10}$)cycloalkenyl, —(C$_8$-C$_{14}$)bicycloalkenyl, —(C$_8$-C$_{14}$)tricycloalkenyl, -(3- to 7-membered)heterocycle, or -(7- to 10-membered)bicycloheterocycle, each of which is unsubstituted or substituted with one or more $R_5$ groups, or
(c) -phenyl, -naphthyl, —(C$_{14}$)aryl or -(5- to 10-membered) heteroaryl, each of which is unsubstituted or substituted with one or more $R_6$ groups;

$R_4$ is —H or —(C$_1$-C$_6$)alkyl;

each $R_5$ is independently —CN, —OH, —(C$_1$-C$_6$)alkyl, —(C$_2$-C$_6$)alkenyl, —(C$_2$-C$_6$)alkynyl, -halo, —N$_3$, —NO$_2$, —N(R$_7$)$_2$, —CH=NR$_7$, —NR$_7$OH, —OR$_7$, —COR$_7$, —C(O)OR$_7$, —OC(O)R$_7$, —OC(O)OR$_7$, —SR$_7$, —S(O)R$_7$, or —S(O)$_2$R$_7$;

each $R_6$ is independently —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, -(3- to 5-membered)heterocycle, —C(halo)$_3$, —CH(halo)$_2$, —CH$_2$(halo), —CN, —OH, -halo, —N$_3$, —NO$_2$, —N(R$_7$)$_2$, —CH=NR$_7$, —NR$_7$OH, —OR$_7$, —COR$_7$, —C(O)OR$_7$, —OC(O)R$_7$, —OC(O)OR$_7$, —SR$_7$, —S(O)R$_7$, or —S(O)$_2$R$_7$;

each $R_7$ is independently —H, —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, -(3- to 5-membered)heterocycle, —C(halo)$_3$, —CH(halo)$_2$, or —CH$_2$(halo);

each $R_8$ is independently —(C$_1$-C$_{10}$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, —C(halo)$_3$, —CH(halo)$_2$, —CH$_2$(halo), —CN, —OH, -halo, —N$_3$, —NO$_2$, —N(R$_7$)$_2$, —CH=NR$_7$, —NR$_7$OH, —OR$_7$, —COR$_7$, —C(O)OR$_7$, —OC(O)R$_7$, —OC(O)OR$_7$, —SR$_7$, —S(O)R$_7$, —S(O)$_2$R$_7$, —R$_7$OR$_7$, —R$_7$COR$_7$, —R$_7$C(O)OR$_7$, —R$_7$OC(O)R$_7$, —R$_7$OC(O)OR$_7$, —R$_7$SR$_7$, —R$_7$S(O)R$_7$, —R$_7$S(O)$_2$R$_7$, —C(halo)$_2$C(halo)$_3$, —C(halo)$_2$CH(halo)$_2$, —CH(C(halo)$_3$)$_2$, —CH(C(halo)$_3$)(CH$_3$), —OC(halo)$_2$C(halo)$_3$, —OC(halo)$_2$CH(halo)$_2$, —OCH(C(halo)$_3$)$_2$, —OCH(C(halo)$_3$)(CH$_3$), —C(OH)(CF$_3$)$_2$, —(C$_1$-C$_{10}$)alkyl, or -(3- to 7-membered) heterocycle;

each $R_9$ is independently —H, -halo or —(C$_1$-C$_6$)alkyl;

each $R_{11}$ is independently —CN, —OH, —(C$_1$-C$_6$)alkyl, —(C$_2$-C$_6$)alkenyl, —(C$_2$-C$_6$)alkynyl, -halo, —N$_3$, —NO$_2$, —N(R$_7$)$_2$, —CH=NR$_7$, —NR$_7$OH, —OR$_7$, —COR$_7$, —C(O)OR$_7$, —OC(O)R$_7$, or —OC(O)OR$_7$;

each halo is independently —F, —Cl, —Br, or —I;

m is 0 or 1 and when m is 1, $R_3$ is attached to the 2-, 3-, 5-, or 6-position of the cyclo(hetero)alkenyl ring;

q is an integer ranging from 0 to 6;

r is an integer ranging from 0 to 5;

s is an integer ranging from 0 to 4; and $R_z$ is -phenyl which is optionally substituted with one or more $R_6$ groups, —H or —(C$_1$-C$_6$)alkyl.

In another embodiment, the present invention relates to a compound of formula 21 a-1

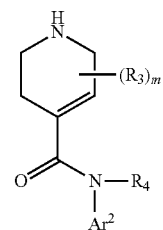

21 a-1 or a pharmaceutically acceptable salt thereof, where:

$Ar^2$ is

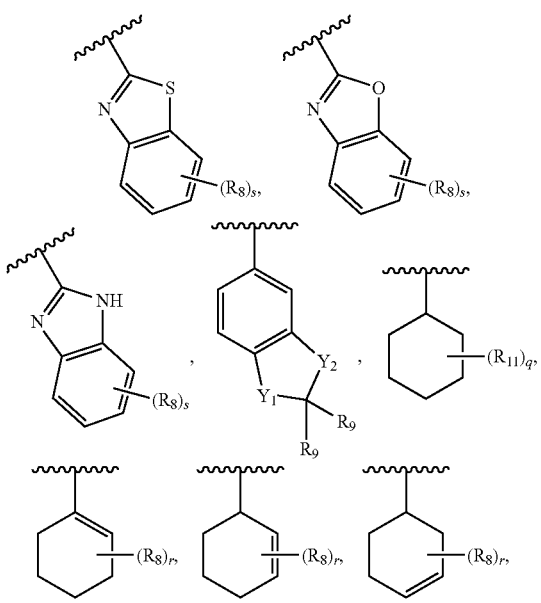

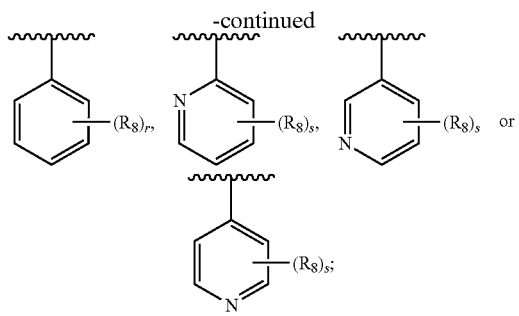

$Y_1$ and $Y_2$ are —$CH_2$— and —$CH_2$—, —O— and —O—, —NH— and —NH—, —S— and —S—, —$CH_2$— and —O—, —$CH_2$— and —NH—, —$CH_2$— and —S—, —O— and —$CH_2$—, —NH— and —$CH_2$—, —S— and —$CH_2$—, —O— and —NH—, —NH— and —O—, —S— and —NH—, or —NH— and —S— respectively;

each $R_3$ is independently:
(a) -halo, —CN, —OH, —$NO_2$, or —$NH_2$,
(b) —($C_1$-$C_{10}$)alkyl, —($C_2$-$C_{10}$)alkenyl, —($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle, or -(7- to 10-membered)bicycloheterocycle, each of which is unsubstituted or substituted with one or more $R_5$ groups, or
(c) -phenyl, -naphthyl, —($C_{14}$)aryl or -(5- to 10-membered) heteroaryl, each of which is unsubstituted or substituted with one or more $R_6$ groups;

$R_4$ is —H or —($C_1$-$C_6$)alkyl;

each $R_5$ is independently —CN, —OH, —($C_1$-$C_6$)alkyl, —($C_2$-$C_6$)alkenyl, —($C_2$-$C_6$)alkynyl, -halo, —$N_3$, —$NO_2$, —$N(R_7)_2$, —CH=$NR_7$, —$NR_7OH$, —$OR_7$, —$COR_7$, —C(O)$OR_7$, —OC(O)$R_7$, —OC(O)$OR_7$, —$SR_7$, —S(O)$R_7$, or —S(O)$_2R_7$;

each $R_6$ is independently —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, -(3- to 5-membered)heterocycle, —C(halo)$_3$, —CH(halo)$_2$, —$CH_2$(halo), —CN, —OH, -halo, —$N_3$, —$NO_2$, —$N(R_7)_2$, —CH=$NR_7$, —$NR_7OH$, —$OR_7$, —$COR_7$, —C(O)$OR_7$, —OC(O)$R_7$, —OC(O)$OR_7$, —$SR_7$, —S(O)$R_7$, or —S(O)$_2R_7$;

each $R_7$ is independently —H, —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, -(3- to 5-membered)heterocycle, —C(halo)$_3$, —CH(halo)$_2$, or $CH_2$(halo);

each $R_8$ is independently —($C_1$-$C_{10}$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, —C(halo)$_3$, —CH(halo)$_2$, —$CH_2$(halo), —CN, —OH, -halo, —$N_3$, —$NO_2$, —$N(R_7)_2$, —CH=$NR_7$, —$NR_7OH$, —$OR_7$, —$COR_7$, —C(O)$OR_7$, —OC(O)$R_7$, —OC(O)$OR_7$, —$SR_7$, —S(O)$R_7$, —S(O)$_2R_7$, —$R_7OR_7$, —$R_7COR_7$, —$R_7C(O)OR_7$, —$R_7OC(O)R_7$, —$R_7OC(O)OR_7$, —$R_7SR_7$, —$R_7S(O)R_7$, —$R_7S(O)_2R_7$, —C(halo)$_2$C(halo)$_3$, —C(halo)$_2$CH(halo)$_2$, —CH(C(halo)$_3$)$_2$, —CH(C(halo)$_3$)(CH$_3$), —OC(halo)$_2$C(halo)$_3$, —OC(halo)$_2$CH(halo)$_2$, —OCH(C(halo)$_3$)$_2$, —OCH(C(halo)$_3$)(CH$_3$), —C(OH)(CF$_3$)$_2$, —($C_1$-$C_{10}$)alkyl, or -(3- to 7-membered) heterocycle;

each $R_9$ is independently —H, -halo or —($C_1$-$C_6$)alkyl;

each $R_{11}$ is independently —CN, —OH, —($C_1$-$C_6$)alkyl, —($C_2$-$C_6$)alkenyl, —($C_2$-$C_6$)alkynyl, -halo, —$N_3$, —$NO_2$, —$N(R_7)_2$, —CH=$NR_7$, —$NR_7OH$, —$OR_7$, —$COR_7$, —C(O)$OR_7$, —OC(O)$R_7$, or —OC(O)$OR_7$;

each halo is independently —F, —Cl, —Br, or —I;

m is 0 or 1 and when m is 1, $R_3$ is attached to the 2-, 3-, 5-, or 6-position of the cyclo(hetero)alkenyl ring;

q is an integer ranging from 0 to 6;

r is an integer ranging from 0 to 5; and s is an integer ranging from 0 to 4.

4.3.2 Methods for Making the Cyclo(hetero)alkenyl Compounds Where V is CH

In another embodiment, the present invention relates to methods for making the Cyclo(hetero)alkenyl Compounds where V is CH by the following non-limiting illustrative method shown below in Scheme D.

Scheme D

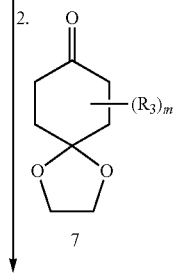

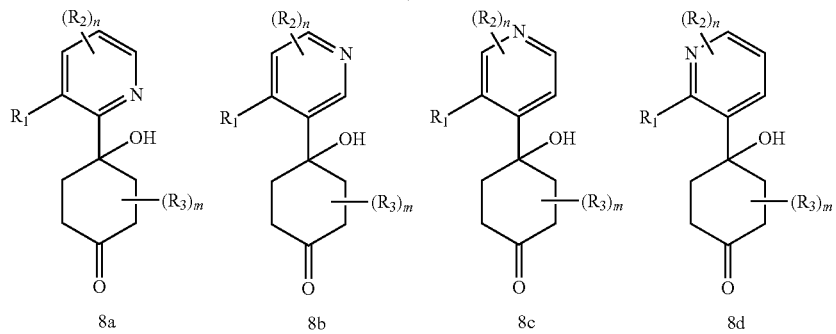

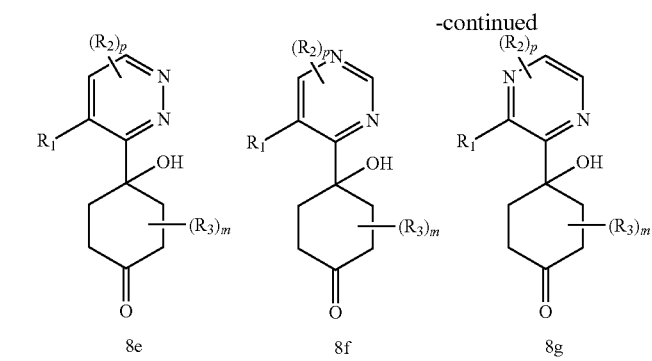

8e  8f  8g  8h

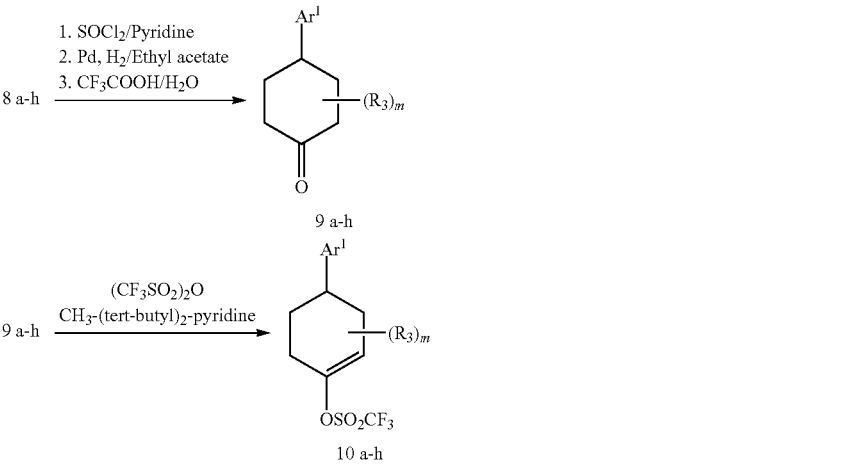

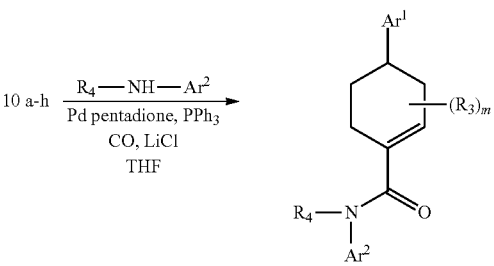

(III) Cyclo(hetero)alkenyl Compound
Where V is CH where $R_1$, $R_2$, $R_3$, $R_4$, $Ar^1$, $Ar^2$, m, n and p are defined above.

A Compound of Formula 1a-h is reacted with butyl lithium in diethyl ether/THF and then with a Compound of Formula 7 according to the procedure described in *J. Med. Chem.* 32(2):351-7 (1989) to provide a Compound of Formula 8a-h. In one embodiment, the present invention relates to a method for making a Cyclo(hetero)alkenyl Compound comprising allowing a Compound of Formula 1a-h to react with butyl lithium and then with a Compound of Formula 7. A Compound of Formula 8a-h is useful, e.g., as an intermediate for the synthesis of a Cyclo(hetero)alkenyl Compound.

The Compound of Formula 8a-h is then reacted with a Lewis acid, e.g., $SOCl_2$/pyridine, hydrogenated using a Pd catalyst in ethyl acetate, and reacted with trifluoroacetic acid in water according to the procedure described in *J. Med. Chem.* 32(2):351-7 (1989) to provide a Compound of Formula 9a-h. In one embodiment, the present invention relates to a method for making a Cyclo(hetero)alkenyl Compound comprising allowing a Compound of Formula 8a-h to react with a Lewis acid, then hydrogenating the product, and allowing the hydrogenated product to react with trifluoroacetic acid. A Compound of Formula 9a-h is useful, e.g., as an intermediate for the synthesis of a Cyclo(hetero)alkenyl Compound.

The Compound of Formula 9a-h is then reacted with $(CF_3SO_2)_2O$ in the presence of methyl-di-(tert-butyl)-pyridine in DCM according to the procedure described in *J. Org. Chem.* 54(12):2886-9 (1989) or *Organic Syntheses* 68:116-29 (1980) to provide a Compound of Formula 10a-h. In one embodiment, the present invention relates to a method for making a Cyclo (hetero)alkenyl Compound comprising allowing a Compound of Formula 9a-h to react with $(CF_3SO_2)_2O$. In another embodiment, this reaction is in the presence of methyl-di-(tert-butyl)-pyridine. A Compound of Formula 10a-h is useful, e.g., as an intermediate for the synthesis of a Cyclo (hetero)alkenyl Compound.

The Compound of Formula 10a-h is then reacted with an amine of formula $Ar^2$—$NHR_4$ in the presence of palladium pentadione, triphenylphosphine, and lithium chloride in THF under an atmosphere of carbon monoxide according to the procedure described in *Tetrahedron Letters* 33(9): 1181-4 (1992) to provide the Cyclo(hetero)alkenyl Compound where V is CH. In one embodiment, the present invention relates to a method for making a Cyclo(hetero)alkenyl Compound comprising allowing a Compound of Formula 10a-h to react with an amine of formula $Ar^2$—$NHR_4$. In another embodiment, this reaction is in the presence of palladium pentadione, triphenylphosphine, and lithium chloride. In another embodiment, this reaction is under an atmosphere of carbon monoxide.

Compounds of formula 7 are commercially available or can be prepared by methods known to those skilled in the art.

Where m=1, a mixture of Cyclo(hetero)alkenyl Compounds is generally obtained. The mixture can be separated by conventional methods, for example, column chromatography.

The Compound of Formula (I) where X is S (i.e., the Compound of Formula (III')) can be made by, e.g., reacting a Compound of Formula (III) (i.e., where X is O) with Lawesson's reagent as described in connection with Scheme A. This reaction is illustrated below:

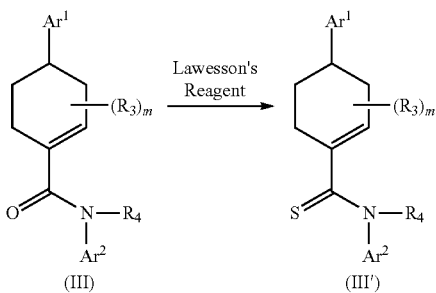

Certain Cyclo(hetero)alkenyl Compounds can have asymmetric centers and therefore exist in different enantiomeric and diastereomeric forms. A Cyclo(hetero)alkenyl Compound can be in the form of an optical isomer or a diastereomer. Accordingly, the invention encompasses Cyclo(hetero)alkenyl Compounds and their uses as described herein in the form of their optical isomers, diasteriomers and mixtures thereof, including a racemic mixture. Optical isomers of the Cyclo(hetero)alkenyl Compounds can be obtained by known techniques such as chiral chromatography or formation of diastereomeric salts from an optically active acid or base.

In addition, one or more hydrogen, carbon or other atoms of a Cyclo(hetero)alkenyl Compound can be replaced by an isotope of the hydrogen, carbon or other atoms. Such compounds, which are encompassed by the present invention, are useful as research and diagnostic tools in metabolism pharmacokinetic studies and in binding assays.

4.4 Therapeutic Uses of the Cyclo(Hetero)Alkenyl Compounds

In accordance with the invention, the Cyclo(hetero)alkenyl Compounds are administered to an animal in need of treatment or prevention of a Condition.

In one embodiment, an effective amount of a Cyclo(hetero)alkenyl Compound can be used to treat or prevent any condition treatable or preventable by inhibiting VR1. Examples of conditions that are treatable or preventable by inhibiting VR1 include, but are not limited to, pain, UI, an ulcer, IBD, and IBS.

In another embodiment, an effective amount of a Cyclo(hetero)alkenyl Compound can be used to treat or prevent any condition treatable or preventable by inhibiting mGluR5. Examples of conditions that are treatable or preventable by inhibiting mGluR5 include, but are not limited to, pain, an addictive disorder, Parkinson's disease, parkinsonism, anxiety, a pruritic condition, and psychosis.

In another embodiment, an effective amount of a Cyclo(hetero)alkenyl Compound can be used to treat or prevent any condition treatable or preventable by inhibiting mGluR1. Examples of conditions that are treatable or preventable by inhibiting mGluR1 include, but are not limited to, pain, UI, an addictive disorder, Parkinson's disease, parkinsonism, anxiety, epilepsy, stroke, a seizure, a pruritic condition, psychosis, a cognitive disorder, a memory deficit, restricted brain function, Huntington's chorea, ALS, dementia, retinopathy, a muscle spasm, a migraine, vomiting, dyskinesia, and depression.

The Cyclo(hetero)alkenyl Compounds can be used to treat or prevent acute or chronic pain. Examples of pain treatable or preventable using the Cyclo(hetero)alkenyl Compounds include, but are not limited to, cancer pain, labor pain, myocardial infarction pain, pancreatic pain, colic pain, post-operative pain, headache pain, muscle pain, arthritic pain, and pain associated with a periodontal disease, including gingivitis and periodontitis.

The Cyclo(hetero)alkenyl Compounds can also be used for treating or preventing pain associated with inflammation or with an inflammatory disease in an animal. Such pain can arise where there is an inflammation of the body tissue which can be a local inflammatory response and/or a systemic inflammation. For example, the Cyclo(hetero)alkenyl Compounds can be used to treat or prevent pain associated with inflammatory diseases including, but not limited to: organ transplant rejection; reoxygenation injury resulting from organ transplantation (see Grupp et al., *J. Mol. Cell. Cardiol.* 31:297-303 (1999)) including, but not limited to, transplantation of the heart, lung, liver, or kidney; chronic inflammatory diseases of the joints, including arthritis, rheumatoid arthritis, osteoarthritis and bone diseases associated with increased bone resorption; inflammatory lung diseases, such as asthma, adult respiratory distress syndrome, and chronic obstructive airway disease; inflammatory diseases of the eye, including corneal dystrophy, trachoma, onchocerciasis, uveitis, sympathetic ophthalmitis and endophthalmitis; chronic inflammatory diseases of the gum, including gingivitis and periodontitis; tuberculosis; leprosy; inflammatory diseases of the kidney, including uremic complications, glomerulonephritis and nephrosis; inflammatory diseases of the skin, including sclerodermatitis, psoriasis and eczema; inflammatory diseases of the central nervous system, including chronic demyelinating diseases of the nervous system, multiple sclerosis, AIDS-related neurodegeneration and Alzheimer s disease, infectious meningitis, encephalomyelitis, Parkinson's disease, Huntington's disease, amyotrophic lateral sclerosis and viral or autoimmune encephalitis; autoimmune diseases, including Type I and Type II diabetes mellitus; diabetic complications, including, but not limited to, diabetic cataract, glaucoma, retinopathy, nephropathy (such as microaluminuria and progressive diabetic nephropathy), polyneuropathy, mononeuropathies, autonomic neuropathy, gangrene of the feet, atherosclerotic coronary arterial disease, peripheral arterial disease, nonketotic hyperglycemic-hyperosmolar coma, foot ulcers, joint problems, and a skin or mucous membrane complication (such as an infection, a shin spot, a candidal infection or necrobiosis lipoidica diabeticorum); immune-complex vasculitis, and systemic lupus erythematosus (SLE); inflammatory diseases of the heart, such as cardiomyopathy, ischemic heart disease hypercholesterolemia, and atherosclerosis; as well as various other diseases that can have significant inflammatory components, including preeclampsia, chronic liver failure, brain and spinal cord trauma, and cancer. The Cyclo(hetero)alkenyl Compounds can also be used for treating or preventing pain associated with inflammatory disease that can, for example, be a systemic inflammation of the body, exemplified by gram-positive or gram negative shock, hemorrhagic or anaphylactic shock, or shock induced by cancer chemotherapy in response to pro-inflammatory cytokines, e.g., shock associated with pro-inflammatory cytokines. Such shock can be induced, e.g., by a chemotherapeutic agent that is administered as a treatment for cancer.

The Cyclo(hetero)alkenyl Compounds can be used to treat or prevent UI. Examples of UI treatable or preventable using the Cyclo(hetero)alkenyl Compounds include, but are not limited to, urge incontinence, stress incontinence, overflow incontinence, neurogenic incontinence, and total incontinence.

The Cyclo(hetero)alkenyl Compounds can be used to treat or prevent an ulcer. Examples of ulcers treatable or preventable using the Cyclo(hetero)alkenyl Compounds include, but are not limited to, a duodenal ulcer, a gastric ulcer, a marginal ulcer, an esophageal ulcer, or a stress ulcer.

The Cyclo(hetero)alkenyl Compounds can be used to treat or prevent IBD, including Crohn's disease and ulcerative colitis.

The Cyclo(hetero)alkenyl Compounds can be used to treat or prevent IBS. Examples of IBS treatable or preventable using the Cyclo(hetero)alkenyl Compounds include, but are not limited to, spastic-colon-type IBS and constipation-predominant IBS.

The Cyclo(hetero)alkenyl Compounds can be used to treat or prevent an addictive disorder, including but not limited to, an eating disorder, an impulse-control disorder, an alcohol-related disorder, a nicotine-related disorder, an amphetamine-related disorder, a *cannabis*-related disorder, a cocaine-related disorder, an hallucinogen-related disorder, an inhalant-related disorders, and an opioid-related disorder, all of which are further sub-classified as listed below.

Eating disorders include, but are not limited to, Bulimia Nervosa, Nonpurging Type; Bulimia Nervosa, Purging Type; Anorexia; and Eating Disorder not otherwise specified (NOS).

Impulse control disorders include, but are not limited to, Intermittent Explosive Disorder, Kleptomania, Pyromania, Pathological Gambling, Trichotillomania, and Impulse Control Disorder not otherwise specified (NOS).

Alcohol-related disorders include, but are not limited to, Alcohol-Induced Psychotic Disorder with delusions, Alcohol Abuse, Alcohol Intoxication, Alcohol Withdrawal, Alcohol Intoxication Delirium, Alcohol Withdrawal Delirium, Alcohol-Induced Persisting Dementia, Alcohol-Induced Persisting Amnestic Disorder, Alcohol Dependence, Alcohol-Induced Psychotic Disorder with hallucinations, Alcohol-Induced Mood Disorder, Alcohol-Induced Anxiety Disorder, Alcohol-Induced Sexual Dysfunction, Alcohol-Induced Sleep Disorder, and Alcohol-Related Disorder not otherwise specified (NOS).

Nicotine-related disorders include, but are not limited to, Nicotine Dependence, Nicotine Withdrawal, and Nicotine-Related Disorder not otherwise specified (NOS).

Amphetamine-related disorders include, but are not limited to, Amphetamine Dependence, Amphetamine Abuse, Amphetamine Intoxication, Amphetamine Withdrawal, Amphetamine Intoxication Delirium, Amphetamine-Induced Psychotic Disorder with delusions, Amphetamine-Induced Psychotic Disorders with hallucinations, Amphetamine-Induced Mood Disorder, Amphetamine-Induced Anxiety Disorder, Amphetamine-Induced Sexual Dysfunction, Amphetamine-Induced Sleep Disorder, Amphetamine Related Disorder not otherwise specified (NOS), Amphetamine Intoxication, and Amphetamine Withdrawal.

*Cannabis*-related disorders include, but are not limited to, *Cannabis* Dependence, *Cannabis* Abuse, *Cannabis* Intoxication, *Cannabis* Intoxication Delirium, *Cannabis*-Induced Psychotic Disorder with delusions, *Cannabis*-Induced Psychotic Disorder with hallucinations, *Cannabis*-Induced Anxiety Disorder, *Cannabis* Related Disorder not otherwise specified (NOS), and *Cannabis* Intoxication.

Cocaine-related disorders include, but are not limited to, Cocaine Dependence, Cocaine Abuse, Cocaine Intoxication, Cocaine Withdrawal, Cocaine Intoxication Delirium, Cocaine-Induced Psychotic Disorder with delusions, Cocaine-Induced Psychotic Disorders with hallucinations, Cocaine-Induced Mood Disorder, Cocaine-Induced Anxiety Disorder, Cocaine-Induced Sexual Dysfunction, Cocaine-Induced Sleep Disorder, Cocaine Related Disorder not otherwise specified (NOS), Cocaine Intoxication, and Cocaine Withdrawal.

Hallucinogen-related disorders include, but are not limited to, Hallucinogen Dependence, Hallucinogen Abuse, Hallucinogen Intoxication, Hallucinogen Withdrawal, Hallucinogen Intoxication Delirium, Hallucinogen-Induced Psychotic Disorder with delusions, Hallucinogen-Induced Psychotic Disorders with hallucinations, Hallucinogen-Induced Mood Disorder, Hallucinogen-Induced Anxiety Disorder, Hallucinogen-Induced Sexual Dysfunction, Hallucinogen-Induced Sleep Disorder, Hallucinogen Related Disorder not otherwise specified (NOS), Hallucinogen Intoxication, and Hallucinogen Persisting Perception Disorder (Flashbacks).

Inhalant-related disorders include, but are not limited to, Inhalant Dependence, Inhalant Abuse, Inhalant Intoxication, Inhalant Intoxication Delirium, Inhalant-Induced Psychotic Disorder with delusions, Inhalant-Induced Psychotic Disorder with hallucinations, Inhalant-Induced Anxiety Disorder, Inhalant Related Disorder not otherwise specified (NOS), and Inhalant Intoxication.

Opioid-related disorders include, but are not limited to, Opioid Dependence, Opioid Abuse, Opioid Intoxication, Opioid Intoxication Delirium, Opioid-Induced Psychotic Disorder with delusions, Opioid-Induced Psychotic Disorder with hallucinations, Opioid-Induced Anxiety Disorder, Opioid Related Disorder not otherwise specified (NOS), Opioid Intoxication, and Opioid Withdrawal.

The Cyclo(hetero)alkenyl Compounds can be used to treat or prevent Parkinson's disease and parkinsonism and the symptoms associated with Parkinson's disease and parkinsonism, including but not limited to, bradykinesia, muscular rigidity, resting tremor, and impairment of postural balance.

The Cyclo(hetero)alkenyl Compounds can be used to treat or prevent generalized anxiety or severe anxiety and the symptoms associated with anxiety, including but not limited to, restlessness; tension; tachycardia; dyspnea; depression, including chronic "neurotic" depression; panic disorder; agoraphobia and other specific phobias; eating disorders; and personality disorders.

The Cyclo(hetero)alkenyl Compounds can be used to treat or prevent epilepsy, including but not limited to, partial epilepsy, generalized epilepsy, and the symptoms associated with epilepsy, including but not limited to, simple partial seizures, jacksonian seizures, complex partial (psychomotor)

seizures, convulsive seizures (grand mal or tonic-clonic seizures), petit mal (absence) seizures, and status epilepticus.

The Cyclo(hetero)alkenyl Compounds can be used to treat or prevent strokes, including but not limited to, ischemic strokes and hemorrhagic strokes.

The Cyclo(hetero)alkenyl Compounds can be used to treat or prevent a seizure, including but not limited to, infantile spasms, febrile seizures, and epileptic seizures.

The Cyclo(hetero)alkenyl Compounds can be used to treat or prevent a pruritic condition, including but not limited to, pruritus caused by dry skin, scabies, dermatitis, herpetiformis, atopic dermatitis, pruritus vulvae et ani, miliaria, insect bites, pediculosis, contact dermatitis, drug reactions, urticaria, urticarial eruptions of pregnancy, psoriasis, lichen planus, lichen simplex chronicus, exfoliative dermatitis, folliculitis, bullous pemphigoid, or fiberglass dermatitis.

The Cyclo(hetero)alkenyl Compounds can be used to treat or prevent psychosis, including but not limited to, schizophrenia, including paranoid schizophrenia, hebephrenic or disorganized schizophrenia, catatonic schizophrenia, undifferentiated schizophrenia, negative or deficit subtype schizophrenia, and non-deficit schizophrenia; a delusional disorder, including erotomanic subtype delusional disorder, grandiose subtype delusional disorder, jealous subtype delusional disorder, persecutory subtype delusional disorder, and somatic subtype delusional disorder; and brief psychosis.

The Cyclo(hetero)alkenyl Compounds can be used to treat or prevent a cognitive disorder, including but not limited to, delirium and dementia such as multi-infarct dementia, dementia pugilistica, dementia caused by AIDS, and dementia caused by Alzheimer's disease.

The Cyclo(hetero)alkenyl Compounds can be used to treat or prevent a memory deficiency, including but not limited to, dissociative amnesia and dissociative fugue.

The Cyclo(hetero)alkenyl Compounds can be used to treat or prevent restricted brain function, including but not limited to, that caused by surgery or an organ transplant, restricted blood supply to the brain, a spinal cord injury, a head injury, hypoxia, cardiac arrest, or hypoglycemia.

The Cyclo(hetero)alkenyl Compounds can be used to treat or prevent Huntington's chorea.

The Cyclo(hetero)alkenyl Compounds can be used to treat or prevent ALS.

The Cyclo(hetero)alkenyl Compounds can be used to treat or prevent retinopathy, including but not limited to, arteriosclerotic retinopathy, diabetic arteriosclerotic retinopathy, hypertensive retinopathy, non-proliferative retinopathy, and proliferative retinopathy.

The Cyclo(hetero)alkenyl Compounds can be used to treat or prevent a muscle spasm.

The Cyclo(hetero)alkenyl Compounds can be used to treat or prevent a migraine.

The Cyclo(hetero)alkenyl Compounds can be used to treat or prevent vomiting, including but not limited to, nausea vomiting, dry vomiting (retching), and regurgitation.

The Cyclo(hetero)alkenyl Compounds can be used to treat or prevent dyskinesia, including but not limited to, tardive dyskinesia and biliary dyskinesia.

The Cyclo(hetero)alkenyl Compounds can be used to treat or prevent depression, including but not limited to, major depression and bipolar disorder.

Applicants believe that the Cyclo(hetero)alkenyl Compounds are antagonists for VR1.

The invention relates to methods for inhibiting VR1 function in a cell comprising contacting a cell capable of expressing VR1 with an effective amount of a Cyclo(hetero)alkenyl Compound. This method can be used in vitro, for example, as an assay to select cells that express VR1 and, accordingly, are useful as part of an assay to select compounds useful for treating or preventing pain, UI, an ulcer, IBD, or IBS. The method is also useful for inhibiting VR1 function in a cell in vivo, in an animal, a human in one embodiment, by contacting a cell, in an animal, with an effective amount of a Cyclo(hetero)alkenyl Compound. In one embodiment, the method is useful for treating or preventing pain in an animal. In another embodiment, the method is useful for treating or preventing UI in an animal. In another embodiment, the method is useful for treating or preventing an ulcer in an animal. In another embodiment, the method is useful for treating or preventing IBD in an animal. In another embodiment, the method is useful for treating or preventing IBS in an animal.

Examples of tissue comprising cells capable of expressing VR1 include, but are not limited to, neuronal, brain, kidney, urothelium, and bladder tissue. Methods for assaying cells that express VR1 are known in the art.

Applicants believe that the Cyclo(hetero)alkenyl Compounds are antagonists for mGluR5.

The invention relates to methods for inhibiting mGluR5 function in a cell comprising contacting a cell capable of expressing mGluR5 with an amount of a Cyclo(hetero)alkenyl Compound effective to inhibit mGluR5 function in the cell. This method can be used in vitro, for example, as an assay to select cells that express mGluR5 and, accordingly, are useful as part of an assay to select compounds useful for treating or preventing pain, an addictive disorder, Parkinson's disease, parkinsonism, anxiety, a pruritic condition, or psychosis. The method is also useful for inhibiting mGluR5 function in a cell in vivo, in an animal, a human in one embodiment, by contacting a cell, in an animal, with an amount of a Cyclo(hetero)alkenyl Compound effective to inhibit mGluR5 function in the cell. In one embodiment, the method is useful for treating or preventing pain in an animal in need thereof. In another embodiment, the method is useful for treating or preventing an addictive disorder in an animal in need thereof. In another embodiment, the method is useful for treating or preventing Parkinson's disease in an animal in need thereof. In another embodiment, the method is useful for treating or preventing parkinsonism in an animal in need thereof. In another embodiment, the method is useful for treating or preventing anxiety in an animal in need thereof. In another embodiment, the method is useful for treating or preventing a pruritic condition in an animal in need thereof. In another embodiment, the method is useful for treating or preventing psychosis in an animal in need thereof.

Examples of cells capable of expressing mGluR5 are neuronal and glial cells of the central nervous system, particularly the brain, especially in the nucleus accumbens. Methods for assaying cells that express mGluR5 are known in the art.

Applicants believe that the Cyclo(hetero)alkenyl Compounds are antagonists for mGluR1.

The invention relates to methods for inhibiting mGluR1 function in a cell comprising contacting a cell capable of expressing mGluR1 with an amount of a Cyclo(hetero)alkenyl Compound effective to inhibit mGluR1 function in the cell. This method can be used in vitro, for example, as an assay to select cells that express mGluR1 and, accordingly, are useful as part of an assay to select compounds useful for treating or preventing pain, UI, an addictive disorder, Parkinson's disease, parkinsonism, anxiety, epilepsy, stroke, a seizure, a pruritic condition, psychosis, a cognitive disorder, a memory deficit, restricted brain function, Huntington's chorea, ALS, dementia, retinopathy, a muscle spasm, a migraine, vomiting, dyskinesia, or depression. The method is also useful for inhibiting mGluR1 function in a cell in vivo, in an animal, a human in one embodiment, by contacting a cell, in an animal, with an amount of a Cyclo(hetero)alkenyl Compound effective to inhibit mGluR1 function in the cell. In one embodiment, the method is useful for treating or preventing pain in an animal in need thereof. In another embodiment, the method is useful for treating or preventing UI in an animal in need thereof. In another embodiment, the method is useful for treating or preventing an addictive disorder in an animal in need thereof. In another embodiment, the method is useful for treating or preventing Parkinson's disease in an animal in need thereof. In another embodiment, the method is useful for treating or preventing parkinsonism in an animal in need thereof. In another embodiment, the method is useful for treating or preventing anxiety in an animal in need thereof. In another embodiment, the method is useful for treating or preventing epilepsy in an animal in need thereof. In another embodiment, the method is useful for treating or preventing stroke in an animal in need thereof. In another embodiment, the method is useful for treating or preventing a seizure in an animal in need thereof. In another embodiment, the method is useful for treating or preventing a pruritic condition in an animal in need thereof. In another embodiment, the method is useful for treating or preventing psychosis in an animal in need thereof. In another embodiment, the method is useful for treating or preventing a cognitive disorder in an animal in need thereof. In another embodiment, the method is useful for treating or preventing a memory deficit in an animal in need thereof. In another embodiment, the method is useful for treating or preventing restricted brain function in an animal in need thereof. In another embodiment, the method is useful for treating or preventing Huntington's chorea in an animal in need thereof. In another embodiment, the method is useful for treating or preventing ALS in an animal in need thereof. In another embodiment, the method is useful for treating or preventing dementia in an animal in need thereof. In another embodiment, the method is useful for treating or preventing retinopathy in an animal in need thereof. In another embodiment, the method is useful for treating or preventing a muscle spasm in an animal in need thereof. In another embodiment, the method is useful for treating or preventing a migraine in an animal in need thereof. In another embodiment, the method is useful for treating or preventing vomiting in an animal in need thereof. In another embodiment, the method is useful for treating or preventing dyskinesia in an animal in need thereof. In another embodiment, the method is useful for treating or preventing depression in an animal in need thereof.

Examples of cells capable of expressing mGluR1 include, but are not limited to, cerebellar Purkinje neuron cells, Purkinje cell bodies (punctate), cells of spine(s) of the cerebellum; neurons and neurophil cells of olfactory-bulb glomeruli; cells of the superficial layer of the cerebral cortex; hippocampus cells; thalamus cells; superior colliculus cells; and spinal trigeminal nucleus cells. Methods for assaying cells that express mGluR1 are known in the art.

4.5 Therapeutic/Prophylactic Administration and Compositions of the Invention Due to their activity, the Cyclo(hetero)alkenyl Compounds are advantageously useful in veterinary and human medicine. As described above, the Cyclo(hetero)alkenyl Compounds are useful for treating or preventing a condition in an animal in need thereof.

When administered to an animal, the Cyclo(hetero)alkenyl Compounds are administered as a component of a composition that comprises a pharmaceutically acceptable carrier or excipient. The present compositions, which comprise a Cyclo(hetero)alkenyl Compound, can be administered orally. The Cyclo(hetero)alkenyl Compounds of the invention can also be administered by any other convenient route, for example, by infusion or bolus injection, by absorption through epithelial or mucocutaneous linings (e.g., oral, rectal, and intestinal mucosa, etc.) and can be administered together with another therapeutically active agent. Administration can be systemic or local. Various delivery systems are known, e.g., encapsulation in liposomes, microparticles, microcapsules, capsules, etc., and can be used to administer the Cyclo(hetero)alkenyl Compound.

Methods of administration include, but are not limited to, intradermal, intramuscular, intraperitoneal, intravenous, subcutaneous, intranasal, epidural, oral, sublingual, intracerebral, intravaginal, transdermal, rectal, by inhalation, or topical, particularly to the ears, nose, eyes, or skin. The mode of administration is left to the discretion of the practitioner. In most instances, administration will result in the release of the Cyclo(hetero)alkenyl Compounds into the bloodstream.

In specific embodiments, it can be desirable to administer the Cyclo(hetero)alkenyl Compounds locally. This can be achieved, for example, and not by way of limitation, by local infusion during surgery, topical application, e.g., in conjunction with a wound dressing after surgery, by injection, by means of a catheter, by means of a suppository or enema, or by means of an implant, said implant being of a porous, non-porous, or gelatinous material, including membranes, such as sialastic membranes, or fibers.

In certain embodiments, it can be desirable to introduce the Cyclo(hetero)alkenyl Compounds into the central nervous system or gastrointestinal tract by any suitable route, including intraventricular, intrathecal, and epidural injection, and enema. Intraventricular injection can be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, the Cyclo(hetero)alkenyl Compounds can be formulated as a suppository, with traditional binders and excipients such as triglycerides.

In another embodiment, the Cyclo(hetero)alkenyl Compounds can be delivered in a vesicle, in particular a liposome (see Langer, *Sci.* 249:1527-1533 (1990) and Treat et al., *Liposomes in the Therapy of Infectious Disease and Cancer* 317-327 and 353-365 (1989)).

In yet another embodiment, the Cyclo(hetero)alkenyl Compounds can be delivered in a controlled-release system or sustained-release system (see, e.g., Goodson, in Medical Applications of Controlled Release, supra, vol. 2, pp. 115-138 (1984)). Other controlled- or sustained-release systems discussed in the review by Langer, *Sci.* 249:1527-1533 (1990) can be used. In one embodiment, a pump can be used (Langer, *Sci.* 249:1527-1533 (1990); Sefton, *CRC Crit. Ref Biomed. Eng.* 14:201 (1987); Buchwald et al., *Surgery* 88:507 (1980); and Saudek et al., *N. Engl. J. Med.* 321:574 (1989)). In another embodiment, polymeric materials can be used (see Medical Applications of Controlled Release (Langer and Wise eds., 1974); Controlled Drug Bioavailability, Drug Product Design and Performance (Smolen and Ball eds., 1984); Ranger and Peppas, *J. Macromol. Sci. Rev. Macromol. Chem.* 23:61 (1983); Levy et al., *Sci.* 228:190 (1985); During et al., *Ann. Neurol.* 25:351 (1989); and Howard et al., *J. Neurosurg.* 71:105 (1989)). In yet another embodiment, a controlled- or sustained-release system can be placed in proximity of a target of the Cyclo(hetero)alkenyl Compounds, e.g., the spinal column, brain, or gastrointestinal tract, thus requiring only a fraction of the systemic dose.

The present compositions can optionally comprise a suitable amount of a pharmaceutically acceptable excipient so as to provide the form for proper administration to the animal.

Such pharmaceutical excipients can be liquids, such as water and oils, including those of petroleum, animal, vegetable, or synthetic origin, such as peanut oil, soybean oil, mineral oil, sesame oil and the like. The pharmaceutical excipients can be saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipients are sterile when administered to an animal. Water is a particularly useful excipient when the Cyclo(hetero)alkenyl Compound is administered intravenously. Saline solutions and aqueous dextrose and glycerol solutions can also be employed as liquid excipients, particularly for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The present compositions can take the form of solutions, suspensions, emulsions, tablets, pills, pellets, capsules, capsules containing liquids, powders, sustained-release formulations, suppositories, aerosols, sprays, suspensions, or any other form suitable for use. In one embodiment, the composition is in the form of a capsule (see e.g., U.S. Pat. No. 5,698,155). Other examples of suitable pharmaceutical excipients are described in *Remington's Pharmaceutical Sci.* 1447-1676 (Alfonso R. Gennaro ed., 19th ed. 1995), incorporated herein by reference.

In one embodiment, the Cyclo(hetero)alkenyl Compounds are formulated in accordance with routine procedures as a composition adapted for oral administration to human beings. Compositions for oral delivery can be in the form of tablets, lozenges, aqueous or oily suspensions, granules, powders, emulsions, capsules, syrups, or elixirs, for example. Orally administered compositions can contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include standard excipients such as mannitol, lactose, starch, magnesium stearate, sodium saccharin, cellulose, and magnesium carbonate. In one embodiment, the excipients are of pharmaceutical grade.

In another embodiment, the Cyclo(hetero)alkenyl Compounds can be formulated for intravenous administration. Typically, compositions for intravenous administration comprise sterile isotonic aqueous buffer. Where necessary, the compositions can also include a solubilizing agent. Compositions for intravenous administration can optionally include a local anesthetic such as lidocaine to lessen pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the Cyclo(hetero)alkenyl Compounds are to be administered by infusion, they can be dispensed, for example, with an infusion bottle containing sterile pharmaceutical grade water or saline. Where the Cyclo(hetero)alkenyl Compounds are administered by injection, an ampule of sterile water for injection or saline can be provided so that the ingredients can be mixed prior to administration.

The Cyclo(hetero)alkenyl Compounds can be administered by controlled-release or sustained-release means or by delivery devices that are known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566, each of which is incorporated herein by reference. Such dosage forms can be used to provide controlled- or sustained-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled- or sustained-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled- or sustained-release.

Controlled- or sustained-release pharmaceutical compositions can have a common goal of improving drug therapy over that achieved by their non-controlled or non-sustained counterparts. In one embodiment, a controlled- or sustained-release composition comprises a minimal amount of a Cyclo (hetero)alkenyl Compound to cure or control the condition in a minimum amount of time. Advantages of controlled- or sustained-release compositions include extended activity of the drug, reduced dosage frequency, and increased patient compliance. In addition, controlled- or sustained-release compositions can favorably affect the time of onset of action or other characteristics, such as blood levels of the Cyclo (hetero)alkenyl Compound, and can thus reduce the occurrence of adverse side effects.

Controlled- or sustained-release compositions can initially release an amount of a Cyclo(hetero)alkenyl Compound that promptly produces the desired therapeutic or prophylactic effect, and gradually and continually release other amounts of the Cyclo(hetero)alkenyl Compound to maintain this level of therapeutic or prophylactic effect over an extended period of time. To maintain a constant level of the Cyclo(hetero)alkenyl Compound in the body, the Cyclo(hetero)alkenyl Compound can be released from the dosage form at a rate that will replace the amount of Cyclo(hetero)alkenyl Compound being metabolized and excreted from the body. Controlled- or sustained-release of an active ingredient can be stimulated by various conditions, including but not limited to, changes in pH, changes in temperature, concentration or availability of enzymes, concentration or availability of water, or other physiological conditions or compounds.

In another embodiment, a composition is prepared by admixing a Cyclo(hetero)alkenyl Compound or a pharmaceutically acceptable salt thereof and a pharmaceutically acceptable carrier or excipient. Admixing can be accomplished using methods known for admixing a compound (or a salt) and a pharmaceutically acceptable carrier or excipient. In another embodiment, the Cyclo(hetero)alkenyl Compound or a pharmaceutically acceptable salt thereof is present in an effective amount.

The amount of the Cyclo(hetero)alkenyl Compound that is effective in the treatment or prevention of a condition can be determined by standard clinical techniques. In addition, in vitro or in vivo assays can optionally be employed to help identify optimal dosage ranges. The precise dose to be employed will also depend on the route of administration, and the seriousness of the Condition and can be decided according to the judgment of a practitioner and/or each animal's circumstances. Suitable effective dosage amounts, however, range from about 0.01 mg/kg of body weight to about 2500 mg/kg of body weight, although they are typically about 100 mg/kg of body weight or less. In one embodiment, the effective dosage amount ranges from about 0.01 mg/kg of body weight to about 100 mg/kg of body weight of a Cyclo(hetero)alkenyl Compound, in another embodiment, about 0.02 mg/kg of body weight to about 50 mg/kg of body weight, and in another embodiment, about 0.025 mg/kg of body weight to about 20 mg/kg of body weight. In one embodiment, an effective dosage amount is administered about every 24 h until the Condition is abated. In another embodiment, an effective dosage amount is administered about every 12 h until the Condition is abated. In another embodiment, an effective dosage amount is administered about every 8 h until the Condition is abated. In another embodiment, an effective dosage amount is administered about every 6 h until the Condition is abated. In another embodiment, an effective dosage amount is administered about every 4 h until the Condition is abated. The effective dosage amounts described herein refer to total amounts administered; that is, if more than one Cyclo(hetero)alkenyl Compound is administered, the effective dosage amounts correspond to the total amount administered.

Where a cell capable of expressing VR1, mGluR5 or mGluR1 is contacted with a Cyclo(hetero)alkenyl Compound in vitro, the amount effective for inhibiting the VR1, mGluR5 or mGluR1 receptor function in a cell will typically range from about 0.01 µg/L to about 5 mg/L, in one embodiment, from about 0.01 µg/L to about 2.5 mg/L, in another embodiment, from about 0.01 µg/L to about 0.5 mg/L, and in another embodiment, from about 0.01 µg/L to about 0.25 mg/L of a solution or suspension of a pharmaceutically acceptable carrier or excipient. In one embodiment, the volume of solution or suspension comprising the Cyclo(hetero)alkenyl Compound is from about 0.01 µL to about 1 mL. In another embodiment, the volume of solution or suspension is about 200 µL.

Where a cell capable of expressing VR1, mGluR5, or mGluR1 is contacted with a Cyclo(hetero)alkenyl Compound in vivo, the amount effective for inhibiting the receptor function in a cell will typically range from about 0.01 mg/kg of body weight to about 100 mg/kg of body weight, although it typically ranges from about 100 mg/kg of body weight or less. In one embodiment, the effective dosage amount ranges from about 0.01 mg/kg of body weight to about 100 mg/kg of body weight of a Cyclo(hetero)alkenyl Compound, in another embodiment, about 0.020 mg/kg of body weight to about 50 mg/kg of body weight, and in another embodiment, about 0.025 mg/kg of body weight to about 20 mg/kg of body weight. In one embodiment, an effective dosage amount is administered about every 24 h. In another embodiment, an effective dosage amount is administered about every 12 h. In another embodiment, an effective dosage amount is administered about every 8 h. In another embodiment, an effective dosage amount is administered about every 6 h. In another embodiment, an effective dosage amount is administered about every 4 h.

The Cyclo(hetero)alkenyl Compounds can be assayed in vitro or in vivo for the desired therapeutic or prophylactic activity prior to use in humans. Animal model systems can be used to demonstrate safety and efficacy.

The present methods for treating or preventing a Condition in an animal in need thereof can further comprise administering another therapeutic agent to the animal being administered a Cyclo(hetero)alkenyl Compound. In one embodiment, the other therapeutic agent is administered in an effective amount.

The present methods for inhibiting VR1 function in a cell capable of expressing VR1 can further comprise contacting the cell with an effective amount of another therapeutic agent.

The present methods for inhibiting mGluR5 function in a cell capable of expressing mGluR5 can further comprise contacting the cell with an effective amount of another therapeutic agent.

The present methods for inhibiting mGluR1 function in a cell capable of expressing mGluR1 can further comprise contacting the cell with an effective amount of another therapeutic agent.

Effective amounts of the other therapeutic agents are known to those skilled in the art. However, it is well within the skilled artisan's purview to determine the other therapeutic agent's optimal effective-amount range. In one embodiment of the invention, where another therapeutic agent is administered to an animal, the effective amount of the Cyclo(hetero)alkenyl Compound is less than its effective amount would be where the other therapeutic agent is not administered. In this case, without being bound by theory, it is believed that the Cyclo(hetero)alkenyl Compounds and the other therapeutic agent act synergistically to treat or prevent a Condition.

The other therapeutic agent can be, but is not limited to, an opioid agonist, a non-opioid analgesic, a non-steroidal anti-inflammatory agent, an antimigraine agent, a Cox-II inhibitor, an antiemetic, a β-adrenergic blocker, an anticonvulsant, an antidepressant, a $Ca^{2+}$-channel blocker, an anticancer agent, an agent for treating or preventing UI, an agent for treating or preventing an ulcer, an agent for treating or preventing IBD, an agent for treating or preventing IBS, an agent for treating addictive disorder, an agent for treating Parkinson's disease and parkinsonism, an agent for treating anxiety, an agent for treating epilepsy, an agent for treating a stroke, an agent for treating a seizure, an agent for treating a pruritic condition, an agent for treating psychosis, an agent for treating Huntington's chorea, an agent for treating ALS, an agent for treating a cognitive disorder, an agent for treating a migraine, an agent for treating vomiting, an agent for treating dyskinesia, or an agent for treating depression, and mixtures thereof.

Examples of useful opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papavereturn, pentazocine, phenadoxone, phenomorphan, phenazocine, phennneridine, piminndine, piritramide, prnheptazine, promedol, properidine, propiram, propoxyphene, sufentanil, tilidine, tramadol, pharmaceutically acceptable salts thereof, and mixtures thereof.

In certain embodiments, the opioid agonist is selected from codeine, hydromorphone, hydrocodone, oxycodone, dihydrocodeine, dihydromorphine, morphine, tramadol, oxymorphone, pharmaceutically acceptable salts thereof, and mixtures thereof.

Examples of useful non-opioid analgesics include non-steroidal anti-inflammatory agents, such as aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, and pharmaceutically acceptable salts thereof, and mixtures thereof. Other suitable non-opioid analgesics include the following, non-limiting, chemical classes of analgesic, antipyretic, nonsteroidal anti-inflammatory drugs: salicylic acid derivatives, including aspirin, sodium salicylate, choline magnesium trisalicylate, salsalate, diflunisal, salicylsalicylic acid, sulfasalazine, and olsalazin; para-aminophenol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid and meclofenamic acid; enolic acids, including oxicams (piroxicam, tenoxicam), and pyrazolidinediones (phenylbutazone, oxyphenthartazone); and alkanones, including nabumetone. For a more detailed description of the NSAIDs, see Paul A. Insel, *Analgesic-Antipyretic and Anti-inflammatory Agents and Drugs Employed in the Treatment of Gout*, in *Goodman & Gilman's The Pharmacological Basis of Therapeutics* 617-57 (Perry B. Molinhoff and Raymond W. Ruddon eds., 9$^{th}$ ed 1996) and Glen R. Hanson, *Analgesic, Antipyretic and Anti-Inflammatory Drugs* in *Remington: The Science and Practice of Pharmacy* Vol II 1196-1221 (A. R. Gennaro ed. 19th ed. 1995) which are hereby incorporated by reference in their entireties.

Examples of useful Cox-II inhibitors and 5-lipoxygenase inhibitors, as well as combinations thereof, are described in U.S. Pat. No. 6,136,839, which is hereby incorporated by reference in its entirety. Examples of useful Cox-II inhibitors include, but are not limited to, rofecoxib and celecoxib.

Examples of useful antimigraine agents include, but are not limited to, alpiropride, bromocriptine, dihydroergotamine, dolasetron, ergocornine, ergocorninine, ergocryptine, ergonovine, ergot, ergotamine, flumedroxone acetate, fonazine, ketanserin, lisuride, lomerizine, methylergonovine, methysergide, metoprolol, naratriptan, oxetorone, pizotyline, propranolol, risperidone, rizatriptan, sumatriptan, timolol, trazodone, zolmitriptan, and mixtures thereof.

The other therapeutic agent can alternatively be an agent useful for reducing any potential side effects of a Cyclo(hetero)alkenyl Compounds. For example, the other therapeutic agent can be an antiemetic agent. Examples of useful antiemetic agents include, but are not limited to, metoclopromide, domperidone, prochlorperazine, promethazine, chlorpromazine, trimethobenzamide, odansteron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, and mixtures thereof.

Examples of useful β-adrenergic blockers include, but are not limited to, acebutolol, alprenolol, amosulabol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol, indenolol, labetalol, levobunolol, mepindolol, metipranolol, metoprolol, moprolol, nadolol, nadoxolol, nebivalol, nifenalol, nipradilol, oxprenolol, penbutolol, pindolol, practolol, pronethalol, propranolol, sotalol, sulfinalol, talinolol, tertatolol, tilisolol, timolol, toliprolol, and xibenolol.

Examples of useful anticonvulsants include, but are not limited to, acetylpheneturide, albutoin, aloxidone, aminoglutethimide, 4-amino-3-hydroxybutyric acid, atrolactamide, beclamide, buramate, calcium bromide, carbamazepine, cinromide, clomethiazole, clonazepam, decimemide, diethadione, dimethadione, doxenitroin, eterobarb, ethadione, ethosuximide, ethotoin, felbamate, fluoresone, gabapentin, 5-hydroxytryptophan, lamotrigine, magnesium bromide, magnesium sulfate, mephenyloin, mephobarbital, metharbital, methetoin, methsuximide, 5-methyl-5-(3-phenanthryl)-hydantoin, 3-methyl-5-phenylhydantoin, narcobarbital, nimetazepam, nitrazepam, oxcarbazepine, paramethadione, phenacemide, phenetharbital, pheneturide, phenobarbital, phensuximide, phenylmethylbarbituric acid, phenyloin, phethenylate sodium, potassium bromide, pregabaline, primidone, progabide, sodium bromide, *solanum*, strontium bromide, suclofenide, sulthiame, tetrantoin, tiagabine, topiramate, trimethadione, valproic acid, valpromide, vigabatrin, and zonisamide.

Examples of useful antidepressants include, but are not limited to, binedaline, caroxazone, citalopram, (S)-citalopram, dimethazan, fencamine, indalpine, indeloxazine hydrocholoride, nefopam, nomifensine, oxitriptan, oxypertine, paroxetine, sertraline, thiazesim, trazodone, benmoxine, iproclozide, iproniazid, isocarboxazid, nialamide, octamoxin, phenelzine, cotinine, rolicyprine, rolipram, maprotiline, metralindole, mianserin, mirtazepine, adinazolam, amitriptyline, amitriptylinoxide, amoxapine, butriptyline, clomipramine, demexiptiline, desipramine, dibenzepin, dimetacrine, dothiepin, doxepin, fluacizine, imipramine, imipramine N-oxide, iprindole, lofepramine, melitracen, metapramine, nortriptyline, noxiptilin, opipramol, pizotyline, propizepine, protriptyline, quinupramine, tianeptine, trimipramine, adrafinil, benactyzine, bupropion, butacetin, dioxadrol, duloxetine, etoperidone, febarbamate, femoxetine, fenpentadiol, fluoxetine, fluvoxamine, hematoporphyrin, hypericin, levophacetoperane, medifoxamine, milnacipran, minaprine, moclobemide, nefazodone, oxaflozane, piberaline, prolintane, pyrisuccideanol, ritanserin, roxindole, rubidium chloride, sulpiride, tandospirone, thozalinone, tofenacin, toloxatone, tranylcypromine, L-tryptophan, venlafaxine, viloxazine, and zimelidine.

Examples of useful Ca$^{2+}$-channel blockers include, but are not limited to, bepridil, clentiazem, diltiazem, fendiline, gallopamil, mibefradil, prenylamine, semotiadil, terodiline, verapamil, amlodipine, aranidipine, barnidipine, benidipine, cilnidipine, efonidipine, elgodipine, felodipine, isradipine, lacidipine, lercanidipine, manidipine, nicardipine, nifedipine, nilvadipine, nimodipine, nisoldipine, nitrendipine, cinnarizine, flunarizine, lidoflazine, lomerizine, bencyclane, etafenone, fantofarone, and perhexyline.

Examples of useful anticancer agents include, but are not limited to, acivicin, aclarubicin, acodazole hydrochloride, acronine, adozelesin, aldesleukin, altretamine, amhmycin, ameptntrnn acetate, aminogutethimide, amsacrine, anastrozole, anthramycin, asparaginase, asperlin, azacitidine, azetepa, azotomycin, batimastat, benzodepa, bicalutamide, bisantrene hydrochloride, bisnafide dimesylate, bizelesin, bleomycin sulfate, brequinar sodium, bropirimine, busulfan, cactinomycin, calusterone, caracemide, carbetimer, carboplatin, carmustine, carubicin hydrochloride, carzelesin, cedefingol, chlorambucil, cirolemycin, cisplatin, cladribine, crisnatol mesylate, cyclophosphamide, cytarabine, dacarbazine, dactinomycin, daunorubicin hydrochloride, decitabine, dexormaplatin, dezaguanine, dezaguanine mesylate, diaziquone, docetaxel, doxorubicin, doxorubicin hydrochloride, droloxifene, droloxifene citrate, dromostanolone propionate, duazomycin, edatrexate, eflornithine hydrochloride, elsamitrucin, enloplatin, enpromate, epipropidine, epirubicin hydrochloride, erbulozole, esorubicin hydrochloride, estramustine, estramustine phosphate sodium, etanidazole, etoposide, etoposide phosphate, etoprine, fadrozole hydrochloride, fazarabine, fenretinide, floxuridine, fludarabine phosphate, fluorouracil, fluorocitabine, fosquidone, fostriecin sodium, gemcitabine, gemcitabine hydrochloride, hydroxyurea, idarubicin hydrochloride, ifosfamide, ilmofosine, interleukin II (including recombinant interleukin II or rIL2), interferon alpha-2a, interferon alpha-2b, interferon alpha-n1, interferon alpha-n3, interferon beta-I a, interferon gamma-I b, iproplatin, irinotecan hydrochloride, lanreotide acetate, letrozole, leuprolide acetate, liarozole hydrochloride, lometrexol sodium, lomustine, losoxantrone hydrochloride, masoprocol, maytansine, mechlorethamine hydrochloride, megestrol acetate, melengestrol acetate, melphalan, menogaril, mercaptopurine, methotrexate, methotrexate sodium, metoprine, meturedepa, mitindomide, mitocarcin, mitocromin, mitogillin, mitomalcin, mitomycin, mitosper, mitotane, mitoxantrone hydrochloride, mycophenolic acid, nocodazole, nogalamycin, ormaplatin, oxisuran, paclitaxel, pegaspargase, peliomycin, pentamustine, peplomycin sulfate, perfosfamide, pipobroman, piposulfan, piroxantrone hydrochloride, plicamycin, plomestane, porfimer sodium, porfiromycin, prednimustine, procarbazine hydrochloride, puromycin, puromycin hydrochloride, pyrazofurin, riboprine, rogletimide, safingol, safingol hydrochloride, semustine, simtrazene, sparfosate sodium, sparsomycin, spirogermanium hydrochloride, spiromustine, spiroplatin, streptonigrin, streptozotocin, sulofenur, talisomycin, tecogalan sodium, tegafur, teloxantrone hydrochloride, temoporfin, teniposide, teroxirone, testolactone, thiamiprine, thioguanine, thiotepa, tiazofurin, tirapazamine, toremifene citrate, trestolone acetate, triciribine phosphate, trimetrexate, trimetrexate glucuronate, triptorelin, tubulnozole hydrochloride, uracil mustard, uredepa, vapreotide, verteporfin, vinblastine sulfate, vincristine sulfate, vindesine, vindesine sulfate, vinepidine sulfate, vinglycinate sulfate, vinleurosine sulfate, vinorelbine tartrate, vinrosidine sulfate, vinzolidine sulfate, vorozole, zeniplatin, zinostatin, zorubicin hydrochloride.

Examples of other anti-cancer drugs include, but are not limited to, 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; odansteron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; $R_{11}$ retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Examples of useful therapeutic agents for treating or preventing UI include, but are not limited to, propantheline, imipramine, hyoscyamine, oxybutynin, and dicyclomine.

Examples of useful therapeutic agents for treating or preventing an ulcer include, antacids such as aluminum hydroxide, magnesium hydroxide, sodium bicarbonate, and calcium bicarbonate; sucraflate; bismuth compounds such as bismuth subsalicylate and bismuth subcitrate; $H_2$ antagonists such as cimetidine, ranitidine, famotidine, and nizatidine; $H^+$, $K^+$-ATPase inhibitors such as omeprazole, iansoprazole, and lansoprazole; carbenoxolone; misprostol; and antibiotics such as tetracycline, metronidazole, timidazole, clarithromycin, and amoxicillin.

Examples of useful therapeutic agents for treating or preventing IBD include, but are not limited to, anticholinergic drugs; diphenoxylate; loperamide; deodorized opium tincture; codeine; broad-spectrum antibiotics such as metronidazole; sulfasalazine; olsalazine; mesalamine; prednisone; azathioprine; mercaptopurine; and methotrexate.

Examples of useful therapeutic agents for treating or preventing IBS include, but are not limited to, propantheline; muscarine receptor antagonists such as pirenzapine, methoctramine, ipratropium, tiotropium, scopolamine, methscopolamine, homatropine, homatropine methylbromide, and methantheline; and antidiarrheal drugs such as diphenoxylate and loperamide.

Examples of useful therapeutic agents for treating or preventing an addictive disorder include, but are not limited to, methadone, desipramine, amantadine, fluoxetine, buprenorphine, an opiate agonist, 3-phenoxypyridine, levomethadyl acetate hydrochloride, and serotonin antagonists.

Examples of useful therapeutic agents for treating or preventing Parkinson's disease and parkinsonism include, but are not limited to, carbidopa/levodopa, pergolide, bromocriptine, ropinirole, pramipexole, entacapone, tolcapone, selegiline, amantadine, and trihexyphenidyl hydrochloride.

Examples of useful therapeutic agents for treating or preventing anxiety include, but are not limited to, benzodiazepines, such as alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, temazepam, and triazolam; non-benzodiazepine agents, such as buspirone, gepirone, ipsapirone, tiospirone, zolpicone, zolpidem, and zaleplon; tranquilizers, such as barbituates, e.g., amobarbital, aprobarbital, butabarbital, butalbital, mephobarbital, methohexital, pentobarbital, phenobarbital, secobarbital, and thiopental; and propanediol carbamates, such as meprobamate and tybamate.

Examples of useful therapeutic agents for treating or preventing epilepsy include, but are not limited to, carbamazepine, ethosuximide, gabapentin, lamotrigine, phenobarbital, phenyloin, primidone, valproic acid, trimethadione, benzodiazepines, γ-vinyl GABA, acetazolamide, and felbamate.

Examples of useful therapeutic agents for treating or preventing stroke include, but are not limited to, anticoagulants such as heparin, agents that break up clots such as streptokinase or tissue plasminogen activator, agents that reduce swelling such as mannitol or corticosteroids, and acetylsalicylic acid.

Examples of useful therapeutic agents for treating or preventing a seizure include, but are not limited to, carbamazepine, ethosuximide, gabapentin, lamotrigine, phenobarbital, phenyloin, primidone, valproic acid, trimethadione, benzodiazepines, gabapentin, lamotrigine, γ-vinyl GABA, acetazolamide, and felbamate.

Examples of useful therapeutic agents for treating or preventing a pruritic condition include, but are not limited to, naltrexone; nalmefene; danazol; tricyclics such as amitriptyline, imipramine, and doxepin; antidepressants such as those given below, menthol; camphor; phenol; pramoxine; capsaicin; tar; steroids; and antihistamines.

Examples of useful therapeutic agents for treating or preventing psychosis include, but are not limited to, phenothiazines such as chlorpromazine hydrochloride, mesoridazine besylate, and thoridazine hydrochloride; thioxanthenes such as chloroprothixene and thiothixene hydrochloride; clozapine; risperidone; olanzapine; quetiapine; quetiapine fumarate; haloperidol; haloperidol decanoate; loxapine succinate; molindone hydrochloride; pimozide; and ziprasidone.

Examples of useful therapeutic agents for treating or preventing Huntington's chorea include, but are not limited to, haloperidol and pimozide.

Examples of useful therapeutic agents for treating or preventing ALS include, but are not limited to, baclofen, neurotrophic factors, riluzole, tizanidine, benzodiazepines such as clonazepan and dantrolene.

Examples of useful therapeutic agents for treating or preventing cognitive disorders include, but are not limited to, agents for treating or preventing dementia such as tacrine; donepezil; ibuprofen; antipsychotic drugs such as thioridazine and haloperidol; and antidepressant drugs such as those given below.

Examples of useful therapeutic agents for treating or preventing a migraine include, but are not limited to, sumatriptan; methysergide; ergotamine; caffeine; and beta-blockers such as propranolol, verapamil, and divalproex.

Examples of useful therapeutic agents for treating or preventing vomiting include, but are not limited to, 5-HT$_3$ receptor antagonists such as odansteron, dolasetron, granisetron, and tropisetron; dopamine receptor antagonists such as prochlorperazine, thiethylperazine, chlorpromazin, metoclopramide, and domperidone; glucocorticoids such as dexamethasone; and benzodiazepines such as lorazepam and alprazolam.

Examples of useful therapeutic agents for treating or preventing dyskinesia include, but are not limited to, reserpine and tetrabenazine.

Examples of useful therapeutic agents for treating or preventing depression include, but are not limited to, tricyclic antidepressants such as amitryptyline, amoxapine, bupropion, clomipramine, desipramine, doxepin, imipramine, maprotiline, nefazadone, nortriptyline, protriptyline, trazodone, trimipramine, and venlafaxine; selective serotonin reuptake inhibitors such as citalopram, (S)-citalopram, fluoxetine, fluvoxamine, paroxetine, and setraline; monoamine oxidase inhibitors such as isocarboxazid, pargyline, phenelzine, and tranylcypromine; and psychostimulants such as dextroamphetamine and methylphenidate.

A Cyclo(hetero)alkenyl Compound and the other therapeutic agent can act additively or in one embodiment, synergistically. In one embodiment, a Cyclo(hetero)alkenyl Compound is administered concurrently with another therapeutic agent, for example, a composition comprising an effective amount of a Cyclo(hetero)alkenyl Compound, an effective amount of another therapeutic agent can be administered. Alternatively, a composition comprising an effective amount of a Cyclo(hetero)alkenyl Compound and a different composition comprising an effective amount of another therapeutic agent can be concurrently administered. In another embodiment, an effective amount of a Cyclo(hetero)alkenyl Compound is administered prior or subsequent to administration of an effective amount of another therapeutic agent. In this embodiment, the Cyclo(hetero)alkenyl Compound is administered while the other therapeutic agent exerts its therapeutic effect, or the other therapeutic agent is administered while the Cyclo(hetero)alkenyl Compound exerts its preventative or therapeutic effect for treating or a Condition.

A composition of the invention is prepared by a method comprising admixing a Cyclo(hetero)alkenyl Compound or pharmaceutically acceptable salt and a pharmaceutically acceptable carrier or excipient. Admixing can be accomplished using methods well known for admixing a compound (or salt) and a pharmaceutically acceptable carrier or excipient. In one embodiment the composition is prepared such that the Cyclo(hetero)alkenyl Compound is present in the composition in an effective amount.

4.6 Kits

The invention encompasses kits that can simplify the administration of a Cyclo(hetero)alkenyl Compound to an animal.

A typical kit of the invention comprises a unit dosage form of a Cyclo(hetero)alkenyl Compound. In one embodiment, the unit dosage form is a container, which can be sterile, containing an effective amount of a Cyclo(hetero)alkenyl Compound and a pharmaceutically acceptable carrier or excipient. The kit can further comprise a label or printed instructions instructing the use of the Cyclo(hetero)alkenyl Compound to treat or prevent a Condition. The kit can also further comprise a unit dosage form of another therapeutic agent, for example, a second container containing an effective amount of the other therapeutic agent and a pharmaceutically acceptable carrier or excipient. In another embodiment, the kit comprises a container containing an effective amount of a Cyclo(hetero)alkenyl Compound, an effective amount of another therapeutic agent and a pharmaceutically acceptable carrier or excipient. Examples of other therapeutic agents include, but are not limited to, those listed above.

Kits of the invention can further comprise a device that is useful for administering the unit dosage forms. Examples of such a device include, but are not limited to, a syringe, a drip bag, a patch, an inhaler, and an enema bag.

The following examples are set forth to assist in understanding the invention and should not be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

5. EXAMPLES

5.1 Example 1

Synthesis of a Cyclo(Hetero)Alkenyl Compound of Formula A26(a)

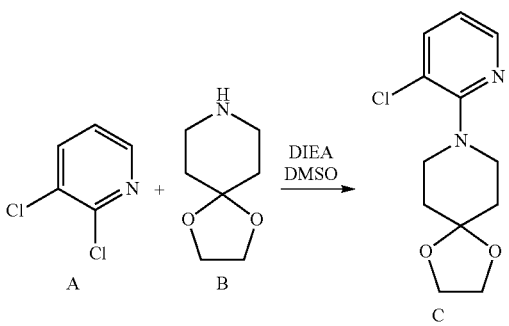

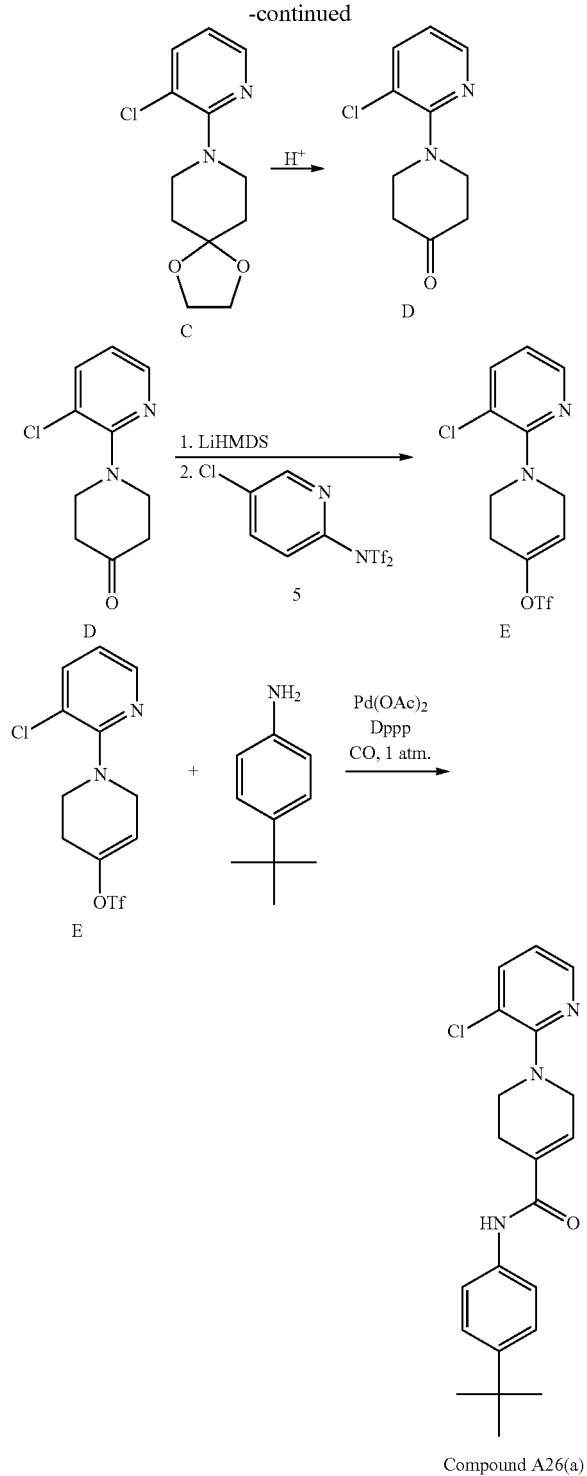

aq. Na$_2$CO$_3$, and the organic layer separated from the aqueous layer. The aqueous layer was then extracted with DCM, the organic layers combined and dried (MgSO$_4$), and the solvent removed under reduced pressure to provide a Compound of Formula D. The Compound of Formula D was purified using a silica gel column eluted with 15:1 hexane-ethyl acetate.

The Compound of Formula D (1 eq.) was reacted with 1.25 eq. of LiHMDS at about −78° C. and the resulting reaction mixture allowed to stir at about −78° C. for about 2 h. After stirring for about 2 h, 3 eq. of N-(5-chloro-2-pyridyl)triflimide 5 was added to the reaction mixture at a temperature of about −78° C. The reaction mixture was then stirred for about 2.5 h at a temperature of about −78° C. and then allowed to warm to about 25° C. The solvent was removed under reduced pressure and the resulting residue purified using a silica gel column eluted with 20:1 hexane-ethyl acetate provide a Compound of Formula E.

The Compound of Formula E (about 1 eq.), 4-(tert-butyl) aniline (about 2 eq.), and triethylamine (about 2.2 eq.) were dissolved in DMF (about 1 mL/mmol) and the resulting solution was degassed by bubbling N$_2$ through the solution. Pd(OAc)$_2$ and Dppp (about 0.3 eq. of each) were added to the solution and the nitrogen atmosphere was replaced with CO at a pressure of about 1 atm. The reaction mixture was then heated to about 70° C. for about 2 h. The reaction mixture was cooled to about 25° C. and the solvent removed under reduced pressure to provide a residue. The resulting residue was purified using silica gel column chromatography eluted with 5:1 hexane-ethyl acetate to provide Cyclo(hetero)alkenyl Compound A26(a).

The structure of Cyclo(hetero)alkenyl Compound A26(a) was confirmed by $^1$H NMR and liquid chromatography-mass spectrometry (LCMS).

Compound of Formula A26(a): $^1$H-NMR (CDCl$_3$): 1.33 (s, 9H), 2.71 (m, 2H), 3.60 (t, 2H, J=5.73 Hz), 4.12 (m, 2H), 6.80 (m, 1H), 6.88 (dd, 1H, J=4.9, 7.6 Hz), 7.38 (m, 2H), 7.42 (m, 1H), 7.5 (m, 2H), 7.64 (dd, 1H, J=1.84, 2.02 Hz), 8.21 (dd, 1H, J=1.83, 4.88 Hz); LCMS: 370 (M+1).

5.2 Example 2

Synthesis of a Cyclo(Hetero)Alkenyl Compound of Formula A98(a)

Cyclo(hetero)alkenyl Compound A98(a) was obtained by a method analogous to that used to obtain Cyclo(hetero) alkenyl Compound A26(a) as described in Example 1 except that 2-chloro-3-(trifluoromethyl)pyridine was used in place of 2,3-dichloropyridine.

The structure of Cyclo(hetero)alkenyl Compound A98(a) was confirmed by $^1$H NMR and liquid chromatography-mass spectrometry.

Compound of Formula A98(a): $^1$H NMR (400 MHz, CDCl$_3$): δ ppm: 1.31 (s, 9H), 2.66 (m, 2H), 3.51 (t, 2H), 4.05 (dd, 2H), 6.75 (m, 1H), 6.97 (dd, 1H), 7.36 (d, 2H), 7.47 (t, 3H), 7.87 (dd, 1H), 8.41 (dd, 1H); LCMS (M+1): 404.2.

5.3 Example 3

Synthesis of a Cyclo(Hetero)Alkenyl Compound of Formula A34(a)

Cyclo(hetero)alkenyl Compound A34(a) was obtained by a method analogous to that used to obtain Cyclo(hetero) alkenyl Compound A26(a) as described in Example 1 except that 4-(trifluoromethyl)aniline was used in place of 4-(tert-butyl)aniline.

About 1 eq. of 2,3-dichloropyridine A and 1 eq. of a Compound of Formula B were heated in DMSO (1 ml/mmol) in the presence of about 1 eq. of DIEA at a temperature of about 125° C. for about 12 h. The resulting reaction mixture was cooled to about 25° C. and the solvent was removed under reduced pressure to provide a Compound of Formula C.

The Compound of Formula C was then reacted with 30% TFA in DCM (5 mL/mmol) at a temperature of from about 25° C. to about the boiling point of the solvent. The resulting reaction mixture was cooled to about 25° C., neutralized with The structure of Cyclo(hetero)alkenyl Compound A34(a) was confirmed by ¹H NMR and liquid chromatography-mass spectrometry.

Compound of Formula A34(a): ¹H NMR (400 MHz, CDCl₃) 2.72 (m, 2H), 3.60 (t, 2H, J=5.47 Hz), 4.14 (m, 2H), 6.85 (m, 1H), 6.89 (dd, 1H, J—=4.58, 7.69 Hz), 7.62 (d, 2H, J=8.8 Hz), 7.66 (m, 2H), 7.72 (d, 2H, J=8.3 Hz), 8.21 (m, 1H); LCMS: 382 (M+1).

5.4 Example 4

Synthesis of a Cyclo(Hetero)Alkenyl Compound of Formula A29(a)

Cyclo(hetero)alkenyl Compound A29(a) was obtained by a method analogous to that used to obtain Cyclo(hetero)alkenyl Compound A26(a) as described in Example 1 except that 4-(iso-propyl)aniline was used in place of 4-(tert-butyl)aniline.

Cyclo(hetero)alkenyl Compound A29(a) was confirmed by ¹H NMR and liquid chromatography-mass spectrometry.

Compound of Formula A29(a): ¹H NMR (400 MHz, CD₃OD): δ ppm: 1.21 (bs, 6H), 2.61 (bs, 2H), 2.75 (bm, 1H), 3.55 (bs, 2H), 4.12 (bs, 2H), 6.70 (s, 1H), 6.82 (m, 1H), 7.21 (t, 2H), 7.40 (s, 1H), 7.45 (t, 2H), 7.77 (t, 1H), 8.25 (s, 1H); LCMS: 382 (M+1).

5.5 Example 5

Synthesis of a Cyclo(Hetero)Alkenyl Compound of Formula A75(a)

Cyclo(hetero)alkenyl Compound A75(a) was obtained by a method analogous to that used to obtain the Cyclo(hetero)alkenyl Compound A26(a) as described in Example 1 except that 2-chloro-3-methylpyridine was used in place of 2,3-dichloropyridine and the Compound of Formula C was obtained by the following method: 2-chloro-3-methyl pyridine (about 1 eq.), a Compound of Formula B (about 1.2 eq.), and sodium tert-butoxide (1.5 eq.) were dissolved in glyme (0.66 mL/mmol), and the resulting solution was degassed by bubbling N₂ through the solution.

After the solution was degassed, 0.02 eq. of tris-(dibenzylideneacetone)dipalladium (0) catalyst and 0.02 eq. of the ligand depicted below

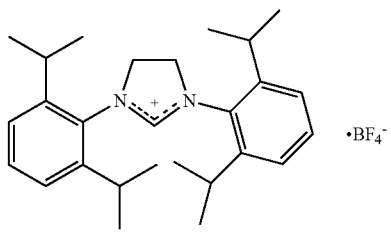

were added to the solution and the resulting reaction mixture was heated at a temperature of about 50° C. for about 4.5 h. The reaction mixture was cooled to about 25° C. and solids removed by filtering over CELITE. The solvent was then removed under reduced pressure to provide a residue. The resulting residue was purified by column chromatography using a silica gel column eluted with 6:1 hexane-ethyl acetate to provide the Cyclo(hetero)alkenyl Compound A75(a).

The structure of Cyclo(hetero)alkenyl Compound A75(a) was confirmed by ¹H NMR and liquid chromatography-mass spectrometry.

Compound of Formula A75(a): ¹H NMR (400 MHz, CDCl₃): 1.33 (s, 9H), 2.33 (s, 3H), 2.67 (m, 2H), 3.33 (t, 2H), 3.99 (m, 2H), 6.81 (m, 1H), 6.89 (m, 1H), 7.38 (m, 2H), 7.46 (m, 2H), 7.50 (m, 2H), 8.19 (m, 1H); LCMS: 350 (M+1).

5.6 Example 6

Synthesis of a Cyclo(Hetero)Alkenyl Compound of Formula A81(a)

Cyclo(hetero)alkenyl Compound A81(a) was obtained by a method analogous to that used to obtain the Cyclo(hetero)alkenyl Compound A75(a) as described in Example except that 4-(isopropoxy)aniline was used in place of 4-(tert-butyl)aniline.

The structure of Cyclo(hetero)alkenyl Compound A81(a) was confirmed by ¹H NMR and liquid chromatography-mass spectrometry.

Compound of Formula A81(a): ¹H NMR (400 MHz, CD₃OD): 1.32 (d, 6H, J=5.98 Hz), 2.35 (s, 3H), 2.62 (m, 2H), 3.32 (m, 2H), 3.92 (m, 2H), 4.58 (m, 2H), 6.80 (m, 1H), 6.89 (m, 2H), 6.97 (m, 1H), 7.48 (m, 2H), 7.58 (m, 1H), 8.1 (m, 1H); LCMS: 351 (M⁺).

5.7 Example 7

Synthesis of a Cyclo(Hetero)Alkenyl Compound of Formula A77(a)

Cyclo(hetero)alkenyl Compound A77(a) was obtained by a method analogous to that used to obtain Cyclo(hetero)alkenyl Compound A75(a) as described in Example 5 except that 4-(iso-propyl)aniline was used in place of 4-(tert-butyl)aniline.

The structure of Cyclo(hetero)alkenyl Compound A77(a) was confirmed by ¹H NMR and mass spectrometry (MS).

Compound of Formula A77(a): ¹H NMR (400 MHz, CD₃OD): δ ppm: 1.25 (bd, 6H), 2.22 (s, 3H), 2.61 (bs, 2H), 2.75 (m, 1H), 3.27 (m, 2H), 3.92 (s, 2H), 6.71 (s, 1H), 6.85 (m, 1H), 7.23 (t, 2H), 7.52 (bm, 4H), 8.15 (s, 1H); MS (EI): m/z 335 (M+1).

5.8 Example 8

Synthesis of a Cyclo(Hetero)Alkenyl Compound of Formula A82(a)

Cyclo(hetero)alkenyl Compound A82(a) was obtained by a method analogous to that used to obtain Cyclo(hetero)alkenyl Compound A75(a) as described in Example 5 except that (4-trifluoromethyl)aniline was used in place of 4-(tert-butyl)aniline.

The structure of Cyclo(hetero)alkenyl Compound A82(a) was confirmed by ¹H NMR and liquid chromatography-mass spectrometry.

Compound of Formula A82(a): ¹H NMR (400 MHz, CDCl₃): 2.33 (s, 3H), 2.67 (m, 2H), 3.34 (t, 2H, J=5.48 Hz), 4.01 (dd, 2H, J=2.88, 6.16 Hz), 6.86 (m, 1H), 6.91 (dd, 1H, J=5.09, 7.5 Hz), 7.46 (m, 1H), 7.62 (d, 2H, J=8.47), 7.65 (b, 1H), 7.73 (d, 2H, J=8.5 Hz), 8.18 (m, 1H); LCMS: 362 (M+1).

5.9 Example 9

Synthesis of a Cyclo(Hetero)Alkenyl Compound of Formula A170(a)

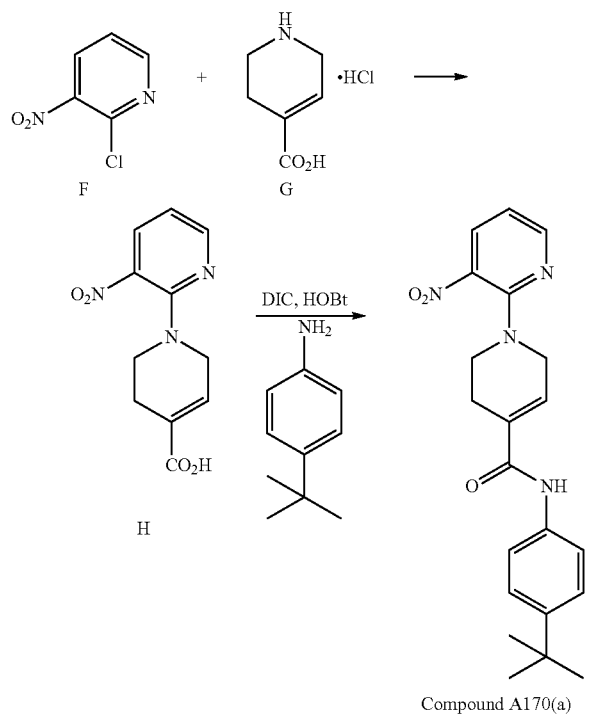

Compound A170(a)

A Compound of Formula F (about 1 eq.), a Compound of Formula 2 (about 1 eq.) (commercially available from Sigma-Aldrich, St. Louis, Mo. (www.sigma-aldrich.com)), and triethylamine (about 2.2 eq.) were dissolved in DMF (5 mL/mmol) and the resulting solution was stirred at about 25° C. for about 5 h. The solvent was then removed under reduced pressure to provide a yellow residue. The residue was dissolved in methylene chloride and filtered through CELITE. The solvent was then removed from the resulting filtrate under reduced pressure to provide a Compound of Formula H which was used without further purification. The Compound of Formula H (about 1 eq.), 4-tert-butyl aniline (about 5 eq.), 1-hydroxybenzotriazole (HOBt, about 1 eq.), and DIC (about 1 eq.) were dissolved in DCM and the resulting solution was stirred at about 25° C. for about 2 days. The solvent was removed under reduced pressure and the resulting residue was purified using silica gel column chromatography eluted with 10:1 hexane-ethyl acetate to provide Cyclo(hetero)alkenyl Compound A170(a) as a yellow solid.

The structure of Cyclo(hetero)alkenyl Compound A170(a) was confirmed by $^1$H NMR and mass spectrometry.

Compound of Formula A170(a): $^1$H NMR (400 MHz, CD$_3$OD): δ ppm: 1.25 (bd, 6H), 2.22 (s, 3H), 2.61 (bs, 2H), 2.75 (m, 1H), 3.27 (m, 2H), 3.92 (s, 2H), 6.71 (s, 1H), 6.85 (m, 1H), 7.23 (t, 2H), 7.52 (bm, 4H), 8.15 (s, 1H); MS (EI): m/z 335 (M+1).

5.10 Example 10

Synthesis of a Cyclo(Hetero)Alkenyl Compound of Formula B38(a)

Cyclo(hetero)alkenyl Compound B38(a) was obtained by a method analogous to that used to obtain the Cyclo(hetero)alkenyl Compound A26(a) as described in Example 1 except that 0.2 eq. of 2-amino-6-methylbenzothiazole was used in place of 0.3 eq. 4-(tert-butyl)aniline.

The structure of Cyclo(hetero)alkenyl Compound B38(a) was confirmed by $^1$H NMR and liquid chromatography-mass spectrometry.

Compound of Formula B38(a): $^1$H NMR (400 MHz, CDCl$_3$): δ ppm: 11.25 (s, 1H), 8.15 (dd, 1H), 7.62 (m, 3H), 7.12 (dd, 1H), 6.87 (dd, 1H), 6.81 (m, 1H), 3.83 (m, 2H), 3.57 (t, 2H), 2.78 (m, 2H), 2.40 (s, 3H); LCMS (M+H$^+$): 385.

5.11 Example 11

Synthesis of a Cyclo(Hetero)Alkenyl Compound of Formula B37(a)

Cyclo(hetero)alkenyl Compound B37(a) was obtained by a method analogous to that used to obtain Cyclo(hetero)alkenyl Compound B38(a) as described in Example 10 except that 2-amino-6-fluorobenzothiazole was used in place of 2-amino-6-methylbenzothiazole.

The structure of Cyclo(hetero)alkenyl Compound B37(a) was confirmed by $^1$H NMR and mass spectrometry.

Compound of Formula B37(a): $^1$H NMR (400 MHz, DMSO): δ ppm: 2.61 (s, 2H), 3.50 (s, 2H), 4.05 (s, 2H), 7.10 (m, 1H), 7.20 (s, 1H), 7.35 (m, 1H), 7.75 (m, 1H), 7.80 (t, 1H), 7.92 (m, 1H), 8.23 (s, 1H), 12.20 (s, 1H); MS (EI): m/z 389 (M+1).

5.12 Example 12

Synthesis of a Cyclo(Hetero)Alkenyl Compound of Formula B85(a) AND B84(a)

Cyclo(hetero)alkenyl Compound B85(a) was obtained by a method analogous to that used to obtain Cyclo(hetero)alkenyl Compound B38(a) as described in Example 10 except that 2-chloro-3-(trifluoromethyl)pyridine was used in place 2,3-dichloropyridine.

Cyclo(hetero)alkenyl Compound B84(a) was obtained by a method analogous to that used to obtain Cyclo(hetero)alkenyl Compound B38(a) as described in Example 10 except that 2-chloro-3-(trifluoromethyl)pyridine was used in place 2,3-dichloropyridine, and 2-amino-6-fluorobenzothiazole was used in place of 2-amino-6-methylbenzothiazole.

The structure of Cyclo(hetero)alkenyl Compound B85(a) was confirmed by $^1$H NMR and mass spectrometry.

Compound of Formula B85(a): $^1$H NMR (CDCl$_3$): 2.46 (s, 3H), 2.74 (m, 2H), 3.54 (t, 2H, J=5.49 Hz), 4.00 (dd, 2H, J=2.86, 6.16 Hz), 6.92 (m, 1H), 7.02 (dd, 1H, J=4.16, 8.36 Hz), 7.20 (m, 1H), 7.63 (m, 2H), 7.91 (dd, 1H, J=2, 7.96 Hz), 8.44 (m, 1H), 9.90 (b, 1H); MS: 419 (M+1).

The structure of Cyclo(hetero)alkenyl Compound B84(a) was confirmed by $^1$H NMR and mass spectrometry.

Compound of Formula B84(a): $^1$H NMR (400 MHz, CDCl$_3$): δ ppm: 2.73 (m, 2H), 3.52 (t, 2H), 3.95 (d, 2H), 6.90 (s, 1H), 7.06 (m, 2H), 7.51 (dd, 1H), 7.65 (dd, 1H), 7.91 (d, 1H), 8.41 (dd, 1H), 10.27 (broad s, 1H); MS: 423.1 (M+1).

5.13 Example 13

Synthesis of a Cyclo(Hetero)Alkenyl Compounds of FORMULA B62(a) AND B63(a)

Cyclo(hetero)alkenyl Compound B62(a) was obtained by a method analogous to that used to obtain Cyclo(hetero)

alkenyl Compound A75(a) as described in Example 5 except that 2-amino-6-fluorobenzothiazole was used in place 4-(tert-butyl)aniline.

Cyclo(hetero)alkenyl Compound B63(a) was obtained by a method analogous to that used to obtain the Cyclo(hetero)alkenyl Compound A75(a) as described in Example except that 2-amino-6-methylbenzothiazole was used in place 4-(tert-butyl)aniline.

The structure of Cyclo(hetero)alkenyl Compound B62(a) was confirmed by $^1$H NMR and mass spectrometry.

Compound of Formula B62(a): $^1$H NMR (CDCl$_3$): 9.82 (br, 1H), 8.17 (dd, 1H, J=1.9 and 4.8 Hz), 7.71 (dd, 1H, J=4.8 and 8.7 Hz), 7.54 (dd, 1H, J=2.6 and 8.1 Hz), 7.46 (d, 1H, J=7.2 Hz), 7.15 (ddd, 1H, J=2.3, 6.4 and 8.7 Hz), 7.0-7.04 (m, 1H), 6.91 (dd, 1H, J=4.8 and 7.4 Hz), 3.95 (dd, 2H, J=2.8 and 6.4 Hz), 3.35 (dd, 2H, J=5.4 and 5.8 Hz), 2.68-2.74 (m, 2H), 2.31 (s, 3H); MS: 369 (M+1).

The structure of Cyclo(hetero)alkenyl Compound B63(a) was confirmed by $^1$H NMR and mass spectrometry.

Compound of Formula B63(a): $^1$H NMR (CDCl$_3$): 9.80 (br, 1H), 8.19 (dd, 1H, J=1.3 and 4.8 Hz), 7.64-7.66 (m, 2H), 7.45 (d, 1H, J=7.2 Hz), 7.23 (dd, 1H, J=1.9 and 8.3 Hz), 6.99-7.0 (m, 1H), 6.85 (dd, 1H, J=4.8 and 7.2 Hz), 3.92-3.95 (m, 2H), 3.34 (dd, 2H, 5.4 and 5.5 Hz), 2.68-2.72 (m, 2H), 2.48 (s, 3H), 2.31 (s, 3H); MS: 365 (M+1).

5.14 Example 14

Synthesis of a Cyclo(Hetero)Alkenyl Compound of Formula K1(a)

Cyclo(hetero)alkenyl Compound K1(a) was obtained by a method analogous to that used to obtain Cyclo(hetero)alkenyl Compound A26(a) as described in Example 1 except that 2,2-difluoro-5-aminobenzodioxole (commercially available from Lancaster Synthesis of Windam, N.H.) was used in place of tert-butyl aniline.

The structure of Cyclo(hetero)alkenyl Compound K1(a) was confirmed by $^1$H NMR.

Compound of Formula K1(a): $^1$H NMR (400 MHz, CDCl$_3$): δ ppm: 8.20-8.17 (m 1H), 6.68-7.65 (m, 1H), 7.64-7.61 (m, 1H), 7.43 (bs, 1H), 7.02-6.99 (m, 2H), 6.89-6.85 (m, 1H), 6.83-6.78 (m, 1H), 4.14-4.08 (m, 2H), 3.61-3.55 (m, 2H), 2.72-2.65 (m, 2H).

5.15 Example 15

Synthesis of a Cyclo(Hetero)Alkenyl Compound of Formula A34(a)

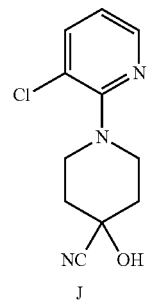

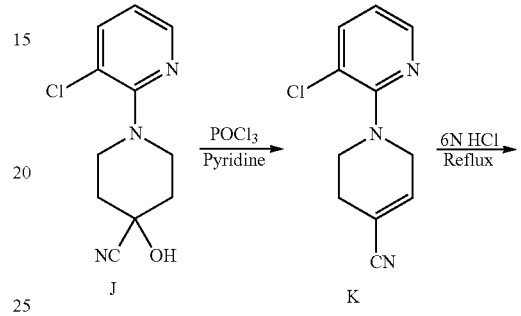

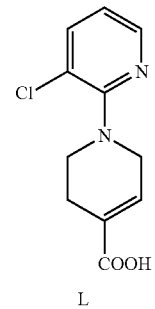

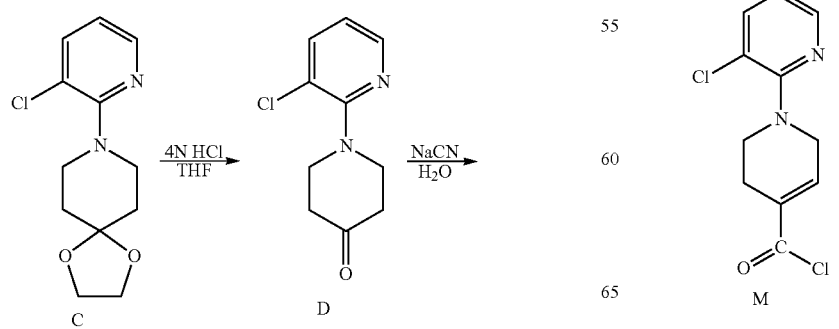

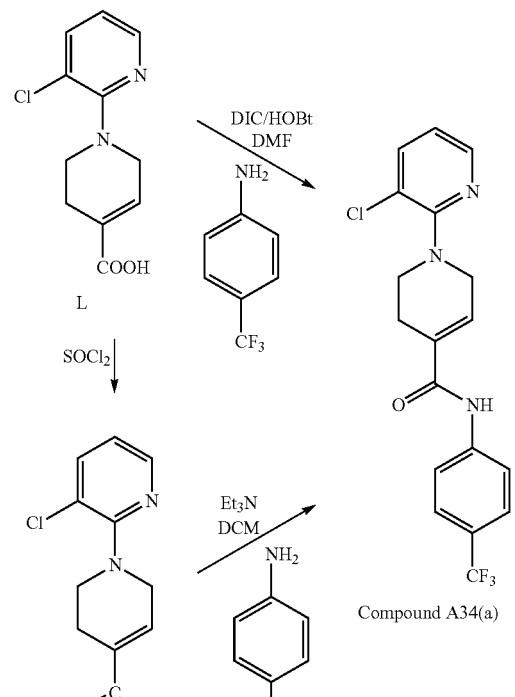

Compound A34(a)

A Compound of Formula C was obtained, in one method, by a method analogous to that described in Example 1 except that the heating was at a temperature of about 140° C. for about 12 hours.

A Compound of Formula C was obtained, in another method, by adding at a temperature of about 25° C. the Compound of Formula A (51.9 g, 350 mmol) to a suspension of the Compound of Formula B (50.3 g. 350 mmol) and $K_2CO_3$ (120 g, 875 mmol) in DMSO to form a reaction mixture. The reaction mixture was stirred at 150° C. for about 16 hours. Thereafter, the reaction mixture was cooled to about 25° C. and quenched with water. The resulting liquid was extracted 3 times with EtOAc (300 mL per extraction), the organic layers combined and dried ($Na_2SO_4$), and the solvent removed to provide the Compound of Formula C (92.5% yield) with a purity of >90%, as determined by LCMS.

The Compound of Formula C (about 0.25 mmol/mL) was reacted with 4N HCl in THF at a temperature of about 50° C. for about 16 hours. The resulting reaction mixture was cooled to about 25° C. and neutralized with aqueous $Na_2CO_3$. Separate aqueous and organic layers formed. The organic layer was separated from the aqueous layer. The aqueous layer was then extracted with about 150-300 mL of ethyl acetate. The organic layer was combined with the post-extraction ethyl acetate and the combination was dried with $MgSO_4$. The solvent was removed under reduced pressure to provide a Compound of Formula D. The Compound of Formula D was purified using a silica gel column eluted with 3:1 hexane:ethyl acetate (80% yield).

The Compound of Formula D (1 eq., about 0.3 mmol/mL) was reacted with 1.2 eq. of aqueous NaCN within the temperature range of from 0° C. to 25° C. for about 12 hours. The solvent was removed under reduced pressure and the resulting residue was purified using a silica gel column eluted with 3:1 hexane:ethyl acetate provide a Compound of Formula J (99% yield).

The Compound of Formula J (about 1 eq., about 0.25 mmol/mL) was reacted with 2.2 eq. of $POCl_3$ in pyridine at a temperature of about 25° C. for about 22 hours. The solvent was removed under reduced pressure and the resulting residue was purified using a silica gel column eluted with 5:1 hexane:ethyl acetate provide a Compound of Formula K (91% yield).

The Compound of Formula K (about 0.5 mmol/mL) was refluxed in 6N aqueous HCl at a temperature of about 100° C. for about 12 hours. The resulting reaction mixture was cooled to about 25° C. and the solvent was removed under reduced pressure to provide a Compound of Formula L which was used without further purification (92% yield).

In a single step procedure, the Compound of Formula L (about 1 eq.), 4-trifluoromethyl-aniline (about 1 eq., obtained from Aldrich Chemical Co., Milwaukee, Wis.), 1-hydroxybenzotriazole (HOBt, about 1.25 eq.), and DIC (about 1.25 eq.) were dissolved in DMF (about 0.35 mmol/mL) and the resulting solution was stirred at a temperature of about 25° C. for about 12 hours. The solvent was removed under reduced pressure and the resulting residue was purified using silica gel column chromatography eluted with 10:1 hexane:ethyl acetate to provide 0.37 equivalents of Cyclo(hetero)alkenyl Compound A34(a) (37% yield).

In a two-step procedure, the Compound of Formula L (about 1 eq., about 0.6 mmol/mL) was reacted with excess $SOCl_2$ (about 24 eq.) at a temperature of about 25° C. for about 12 hours in a first step to provide a Compound of Formula M, which was used without further purification. Then, in a second step, about 1 equivalent of the Compound of Formula M (about 1 mmol/5.0 mL), 4-trifluoromethyl-aniline (about 1.5 eq.), and triethylamine (about 2.0 eq.) were dissolved in DCM and the resulting solution was degassed by bubbling nitrogen through the solution. The reaction mixture was kept at about 25° C. for about 4 hours. The solvent was removed under reduced pressure to provide a residue. The resulting residue was purified using a silica gel column and eluted with 10:1 hexane:ethyl acetate to provide 0.63 equivalents of Cyclo(hetero)alkenyl Compound A34(a) (63% yield for the two-step procedure).

The structure of Cyclo(hetero)alkenyl Compound A34(a) was confirmed by $^1$H-NMR and mass spectrometry.

Compound of Formula A34(a): $^1$H-NMR (CDCl$_3$): 8.19 (dd, 1H, J=1.6, 7.7 Hz), 7.73 (d, 2H, J=10.1 Hz), 7.67-7.59 (m, 4H), 6.87 (dd, 1H, J=4.8, 7.7 Hz), 6.82 (m, 1H), 4.12 (dd, 2H, J=2.9, 6.3 Hz), 3.58 (t, 2H, J=5.5 Hz), 2.70 (m, 2H); MS: 382.1 (M+1).

5.16 Example 16

Synthesis of a Cyclo(Hetero)Alkenyl Compound of Formula A178(a)

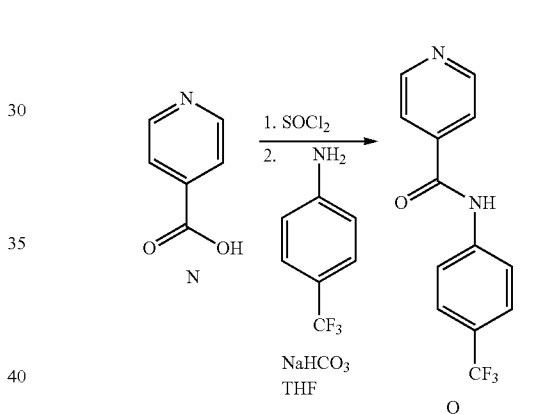

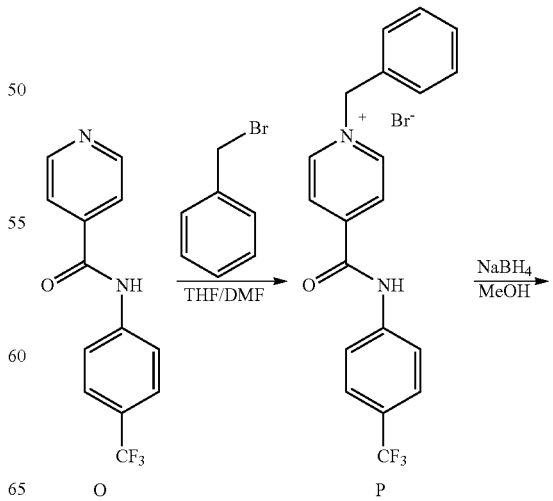

613
-continued

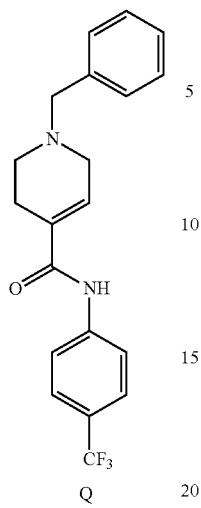

Q

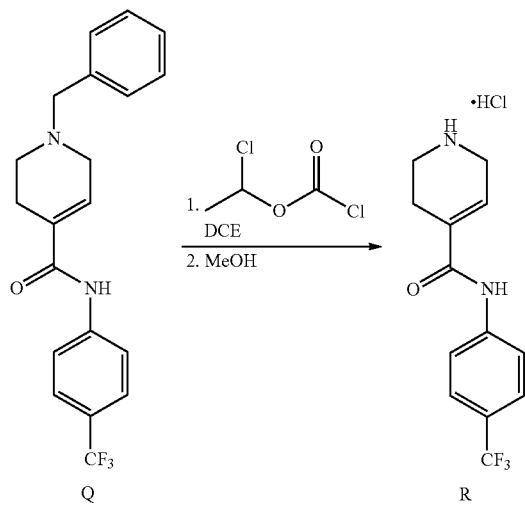

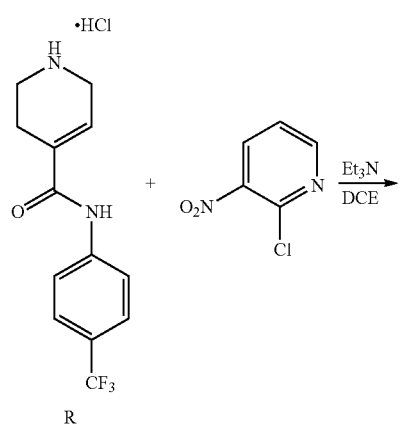

614
-continued

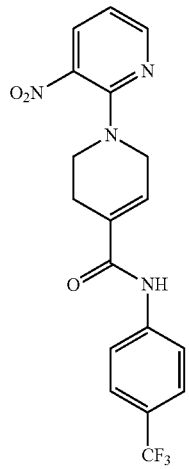

Compound A178(a)

Isonicotinic acid N (15 g, 121.8 mmol, obtained from Aldrich Chemical Co.) was added to about 100 mL of thionyl chloride and the reaction mixture was stirred for about 17 h at about 25° C. After this period, excess $SOCl_2$ was removed under reduced pressure to provide a white solid. About 400 mL of THF was added to the resulting solid and the solvent was removed under reduced pressure to provide isonicotinic acid chloride as a white powder. The white powder was dissolved in about 400 mL of THF. The solution was cooled to about 0° C. and 4-trifluoromethyl-aniline (21.6 g, 134.0 mmol, 1.1 eq., obtained from Aldrich Chemical Co.) and sodium bicarbonate (30 g, 365.4 mmol, 3.0 eq.) were added. The reaction mixture was stirred for about 5 min at about 0° C., warmed to about 25° C. over about 30 min, then heated to about 65° C. and kept at that temperature for about 1 h. After this period, the reaction mixture was cooled to about 25° C. and the THF was removed under reduced pressure. The residue was suspended in about 800 mL of ethyl acetate and washed with about 600 mL of aqueous 3N HCl. Separate aqueous and organic layers formed. The layers were separated and the aqueous layer was extracted three times with about 600 mL of ethyl acetate per extraction. The organic layer was combined with the post-extraction ethyl acetate aliquots. The combination was dried with $Na_2SO_4$ and the solvent was removed under reduced pressure to provide 32 g of the Compound of Formula O as a white solid (99% yield).

The structure of the Compound of Formula O was confirmed by $^1$H-NMR and mass spectrometry.

Compound of Formula O: $^1$H-NMR (CD$_3$OD) δ: 9.14-9.08 (m, 2H), 8.60-8.53 (m, 2H), 8.06-7.98 (m, 2H), 7.77-7.69 (m, 2H); MS: m/z=267.1.

The Compound of Formula O (31 g, 118.1 mmol) was suspended in a mixture of THF (400 mL) and DMF (100 mL) at about 25° C. and benzyl bromide (30.3 g, 177.1 mmol, obtained from Aldrich Chemical Co.) was added. The resulting reaction mixture was refluxed for about 24 hours at a temperature of about 80° C. After this period, the reaction mixture was cooled to about 25° C. and the resulting solid was filtered off. A majority of the THF was removed from the filtrate under reduced pressure. A precipitate formed when about 400 mL of diethyl ether was added to the DMF-enriched solution. The resulting solid was filtered off. The solids were combined and dried to provide 51 g of the Compound of Formula P (99% yield).

The structure of the Compound of Formula P was confirmed by $^1$H-NMR and mass spectrometry.

Compound of Formula P: $^1$H-NMR (CD$_3$OD) δ: 9.29-9.23 (m, 2H), 8.58-8.51 (m, 2H), 7.98-7.92 (m, 2H), 7.72-7.65 (m, 2H), 7.56-7.51 (m, 2H), 7.49-7.43 (m, 2H), 5.91 (s, 2H); MS: m/z=357.1.

The Compound of Formula P (48 g, 109.8 mmol) was suspended in about 600 mL of methanol, cooled to about 0° C., and sodium borohydride (13.3 g, 351.2 mmol) was added in several portions of about 1 g each over a period of about 30 min. The reaction mixture was stirred for about 1 h at about 0° C. and warmed to about 25° C. over about a 2 hour period. After this period, the methanol was removed under reduced pressure. The residue was diluted with about 800 mL of brine and about 1.5 L of ethyl acetate. Separate aqueous and organic layers formed. The layers were separated and the aqueous layer was washed twice with about 600 mL of ethyl acetate per wash. The organic layer was combined with the post-washing ethyl acetate aliquots. The combination was dried with Na$_2$SO$_4$ and the solvent was removed under reduced pressure to provide a brown residue. The residue was dissolved in about 200 mL of DCM. A precipitate formed when about 200 mL of hexane was added to the DCM solution. The resulting solid was filtered off. The solid was dried to provide 39 g of the Compound of Formula Q (98% yield).

The structure of the Compound of Formula Q was confirmed by $^1$H-NMR and mass spectrometry.

Compound of Formula Q: $^1$H-NMR (CDCl$_3$) δ: 7.70-7.64 (m, 2H), 7.62-7.56 (m, 4H), 7.48 (bs, 1H), 7.38-7.27 (m, 5H), 6.69-6.64 (m, 1H), 3.64 (s, 2H), 3.21-3.16 (m, 2H), 2.72-2.66 (m, 2H), 2.56-2.48 (m, 2H); MS: m/z=361.1.

Under a dry nitrogen atmosphere, α-chloroethylchloroformate (16 mL, 22.6 g, 158.1 mmol, obtained from Aldrich Chemical Co.) was added drop wise to a solution of the Compound of Formula Q (30 g, 83.2 mmol) in about 500 mL of DCE over a period of about 15 min at about 0° C. The reaction mixture was then warmed to about 25° C. over a period of about 30 min. The reaction mixture was then heated to about 83° C. and refluxed for about 4 hours at that temperature. After this period, the solvent and unreacted α-chloroethylchloroformate were removed under reduced pressure. The resulting residue was dissolved in about 500 mL of methanol. The methanol solution was refluxed for about 3 hours at a temperature of about 65° C. After this, the methanol was removed to provide 31.3 g of brown residue. The residue was dissolved in about 500 mL of DCM. A precipitate formed when about 300 mL of diethyl ether was added to the DCM solution. The resulting solid was filtered off. The solid was dried to provide 26 g of the Compound of Formula R as white solid. The $^1$H-NMR and LCMS analyses of the white solid showed that the sample was about 92-95% pure; therefore, the yield (based on the starting weight of compound Q used) was determined to be about 94-97%.

The structure of the Compound of Formula R was confirmed by $^1$H-NMR and mass spectrometry.

Compound of Formula R: $^1$H-NMR (CD$_3$OD) δ: 7.79-7.71 (m, 2H), 7.60-7.49 (m, 2H), 6.65-6.59 (m, 1H), 3.84-3.76 (m, 2H), 3.36-3.28 (m, 2H), 2.68-2.59 (m, 2H); LCMS: m/z=271.1.

The Compound of Formula R (10.5 g, 34.2 mmol), 2-chloro-3-nitropyridine (5.1 g, 32.2 mmol, obtained from Aldrich Chemical Co.) and triethylamine (19 mL, 13.8 g, 136.8 mmol) were mixed in about 500 mL of DCE at about 25° C. and kept for about 12 hours at about 25° C. After this period the mixture was poured into about 800 mL of aqueous sodium bicarbonate and about 800 mL of DCM. Separate aqueous and organic layers formed. The organic layer was separated from the aqueous layer. The organic layer was dried with Na$_2$SO$_4$ and the solvent was removed under reduced pressure to provide 14.2 g of crude product. The crude product was dissolved in about 300 mL of DCM. A precipitate formed when about 600 mL of hexane was added to the DCM solution. The resulting solid was filtered off and dried to provide 12.5 g of Cyclo(hetero)alkenyl Compound A178(a) as a yellow solid (99% yield).

The structure of Cyclo(hetero)alkenyl Compound A178(a) was confirmed by $^1$H-NMR and mass spectrometry.

Compound of Formula A178(a): $^1$H-NMR (CDCl$_3$) δ: 8.38-8.35 (m, 1H), 8.21-8.16 (m, 2H), 7.73-7.66 (m, 1H), 7.64-7.57 (m, 1H), 7.52 (bs, 1H), 6.84-6.79 (m, 1H), 6.75-6.71 (m, 1H), 4.06-4.01 (m, 2H), 3.76-3.70 (m, 2H), 2.74-2.67 (m, 2H); MS: m/z=393.1.

5.17 Example 17

Synthesis of a Cyclo(Hetero)Alkenyl Compound of Formula AAA

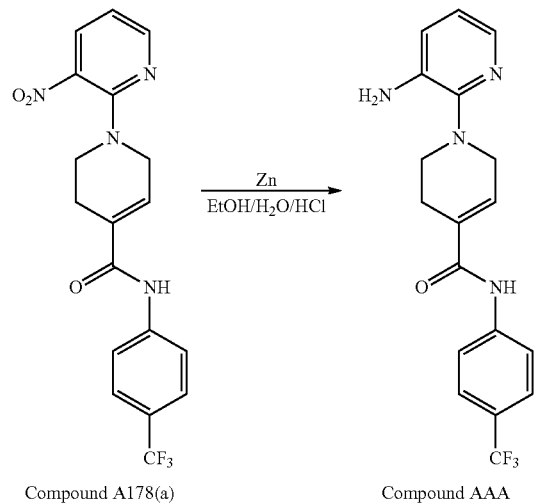

Compound A178(a)  Compound AAA

A mixture of zinc granules (13.9 g, 212.3 mmol) in ethanol (160 mL), water (40 mL), and HCl (10 mL) was cooled to about 0° C. A solution of Cyclo(hetero)alkenyl Compound A178(a) in about 120 mL of ethanol was added to the mixture. The resulting reaction mixture was stirred for about 1.5 h at about 0° C. After this period, the mixture was filtered and the solvent was removed from the filtrate under reduced pressure to provide a dark brown residue. The residue was dissolved in about 1 L of DCM and neutralized with 1N aqueous KOH to a pH of about 10. Separate aqueous and organic layers formed. The organic layer was separated from the aqueous layer. The organic layer was dried with Na$_2$SO$_4$ and the solvent was removed under reduced pressure to provide 9.2 g of a brown oil. The $^1$H-NMR and LCMS analyses of the oil showed that the sample was about 80-85% pure; therefore, the yield (based on the starting weight of Cyclo(hetero)alkenyl Compound AAA) of the Cyclo(hetero)alkenyl Compound AAA was determined to be about 96-100%.

The structure of Cyclo(hetero)alkenyl Compound AAA was confirmed by $^1$H-NMR and mass spectrometry.

Compound of Formula AAA: $^1$H-NMR (CDCl$_3$) δ: 7.82-7.79 (m, 1H), 7.73-7.68 (m, 2H), 7.63-7.57 (m, 3H), 7.01-

6.96 (m, 1H), 6.91-6.83 (m, 2H), 3.95-3.89 (m, 2H), 3.83-3.75 (m, 2H), 3.35-3.29 (m, 2H), 2.68-2.60 (m, 2-1); LCMS: m/z 363.2.

5.18 Example 18

Synthesis of a Cyclo(Hetero)Alkenyl Compound of Formula A34(a)

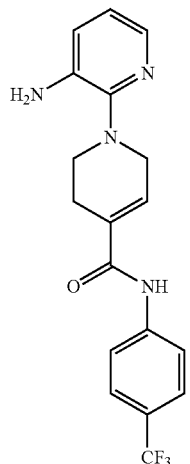 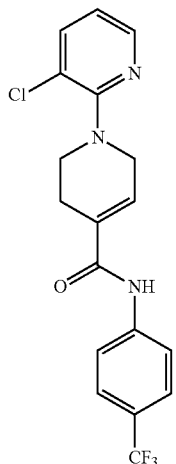

Compound AAA → Compound A34(a)

Cyclo(hetero)alkenyl Compound AAA (1.77 g, 4.88 mmol) was suspended in about 100 mL of 6N aqueous HCl, cooled to about 0° C., and treated with a solution of $NaNO_2$ (0.34 g, 4.88 mmol) in about 40 mL of water with stirring. The resulting solution was stirred for about 30 minutes at about 0° C. Thereafter, a solution of $(CuCl)_2$ (0.58 g, 5.86 mmol, obtained from Aldrich Chemical Co.) in about 50 mL of water was added. The resulting mixture was stirred for about 30 minutes at about 0° C., allowed to warm to about 25° C., then stirred for about 1 h at about 25° C. After this period, the mixture was diluted with about 300 mL of water and extracted twice with about 700 mL of ethyl acetate used per extraction. The post-extraction ethyl acetate aliquots were combined, dried with $Na_2SO_4$ and the solvent was removed to provide 1.8 g of a dark brown oil. This oil was purified by flash chromatography on a silica gel column, using a gradient of from 5:95 to 80:20 (by volume) ethyl acetate:hexane as an eluent, to provide 0.82 g of the Cyclo(hetero)alkenyl Compound A34(a) as tan solid (45% yield).

The structure of Cyclo(hetero)alkenyl Compound A34(a) was confirmed by $^1$H-NMR and mass spectrometry.

Compound of Formula A34(a): $^1$H-NMR (CDCl$_3$) δ: 8.19 (dd, 1H, J=1.54, 4.82 Hz), 7.73-7.67 (m, 2H), 7.65-7.56 (m, 4H), 6.87 (dd, 1H, J=4.6, 7.45 Hz), 6.85-6.82 (m, 1H), 4.14-4.09 (m, 2H), 3.58 (t, 2H, J=5.7 Hz), 2.74-2.66 (m, 2H); MS: m/z=382.1.

5.19 Example 19

Synthesis of a Cyclo(Hetero)Alkenyl Compound of Formula A36(a)

Compound A36(a) was prepared according to Example 1, except that 4-trifluoromethoxyphenyl amine was used in place of 4-(tert-butyl)aniline.

5.20 Example 20

Synthesis of a Cyclo(Hetero)Alkenyl Compound of Formula L1(a)

Compound L1(a) was prepared according to Example 1, except that 4-chloro-3-trifluoromethylphenyl amine was used in place of 4-(tert-butyl)aniline.

5.21 Example 21

Synthesis of a Cyclo(Hetero)Alkenyl Compound of Formula A106(a)

Compound A106(a) was prepared according to Example 3, except that 2-chloro-3-trifluoropyridine was used in place of 2,3-dichloropyridine.

5.22 Example 22

Synthesis of a Cyclo(Hetero)Alkenyl Compound of Formula L3(a)

Compound L3(a) was prepared according to Example 1, except that 4-methyl-3-trifluoromethylphenyl amine was used in place of 4-(tert-butyl)aniline.

5.23 Example 23

Synthesis of a Cyclo(Hetero)Alkenyl Compound of Formula L4(a)

Compound L4(a) was prepared according to Example 1, except that 3-chloro-4-(trifluoromethylthio)benzenamine was used in place of 4-(tert-butyl)aniline.

5.24 Example 24

Synthesis of a Cyclo(Hetero)Alkenyl Compound of Formula L5(a)

Compound L5(a) was prepared according to Example 1, except that 4-fluoro-3-trifluoromethylphenyl amine was used in place of 4-(tert-butyl)aniline.

5.25 Example 25

Synthesis of a Cyclo(Hetero)Alkenyl Compound of Formula L7(a)

Compound L7(a) was prepared according to Example 1, except that 4-amino-2-trifluoromethylbenzonitrile was used in place of 4-(tert-butyl)aniline.

5.26 Example 26

Synthesis of a Cyclo(Hetero)Alkenyl Compound of Formula A44(a)

Compound A44(a) was prepared according to Example 1, except that 4-(1,1,2,2-tetrafluoroethoxy)benzenamine was used in place of 4-(tert-butyl)aniline.

5.27 Example 27

Synthesis of a Cyclo(Hetero)Alkenyl Compound of Formula A43(a)

Compound A43(a) was prepared according to Example 1, except that N,N-diethylbenzene-1,4-diamine was used in place of 4-(tert-butyl)aniline.

5.28 Example 28

Synthesis of a Cyclo(Hetero)Alkenyl Compound of Formula A34(b)

Compound A34(b) was prepared according to Example 1, except that 4-trifluoromethylphenyl amine was used in place of 4-(tert-butyl)aniline and 1-(3-chloropyridin-2-yl)-3-methylpiperidin-4-one, the reaction product of 3-methylpiperidin-4-one with 2,3-dichloropyridine (Compound of Formula A), was used in place of the Compound of Formula D.

3-Methylpiperidin-4-one was prepared by debenzylating 1-benzyl-3-methylpiperidin-4-one as follows. 70 g (344.3 mmol) of 1-benzyl-3-methylpiperidin-4-one (available from Across Organics, Piscataway, N.J.) was dissolved in methanol (400 mL) under a nitrogen atmosphere. 5.6 g of a Pd/C catalyst was added to form a reaction mixture. The nitrogen atmosphere was replaced by a hydrogen atmosphere. The reaction mixture was stirred at 25° C. for 48 hours and then filtered through a pad of CELITE (about 200 g). The filtrate was concentrated by removing the solvent under reduced pressure to provide 38 g of 3-methylpiperidin-4-one.

1-(3-Chloropyridin-2-yl)-3-methylpiperidin-4-one was prepared by dissolving 19.2 g 3-methylpiperidin-4-one (168.9 mmol) and 25 g of Compound of Formula A (168.9 mmol) in DMSO (400 mL) under a nitrogen atmosphere to form a reaction mixture. The reaction mixture was stirred at 85° C. for 12 hours. Thereafter, the solvent was removed under reduced pressure. The residue was purified by column chromatography on a silica gel column, using a gradient of from 10:90 to 98:2 (by volume) ethyl acetate:hexane as an eluent, to provide 9 g of 1-(3-chloropyridin-2-yl)-3-methylpiperidin-4-one.

The structure of Cyclo(hetero)alkenyl Compound A34(b) was confirmed by $^1$H-NMR.

Compound of Formula A34(b): $^1$H NMR (400 MHz, CDCl$_3$): δ ppm: 8.20 (dd, 1H, J=4.82, 1.53 Hz), 7.74-7.69 (m, 2H), 7.64-7.58 (m, 4H), 6.87 (dd, 1H, J=7.45, 4.82 Hz), 6.61 (bt, 1H, J=3.29 Hz), 4.17-4.09 (m, 1H), 3.99 (td, 1H, J=19.1, 2.85 Hz), 3.64 (dd, 1H, J=12.49, 3.94 Hz), 3.34 (dd, 1H, J=12.71, 4.38 Hz), 3.13-3.04 (m, 1H), 1.29 (d, 3H, J=6.79 Hz).

5.29 Example 29

Synthesis of a Cyclo(Hetero)Alkenyl Compound of Formula K4(a)

Compound K4(a) was prepared according to Example 21, except that 2,2-difluoro-5-aminobenzodioxole was used in place of 4-(trifluoromethyl)aniline.

5.30 Example 30

Synthesis of a Cyclo(Hetero)Alkenyl Compound of Formula A42(a)

Compound A42(a) was prepared according to Example 1, except that 4-(trifluoromethylthio)benzenamine was used in place of 4-(tert-butyl)aniline.

5.31 Example 31

Synthesis of a Cyclo(Hetero)Alkenyl Compound of Formula M1(a)

Compound M1(a) was prepared according to Example 1, except that 5-trifluoromethylpyridin-2-yl amine was used in place of 4-(tert-butyl)aniline.

5.32 Example 32

Synthesis of a Cyclo(Hetero)Alkenyl Compound of Formula M23(a)

Compound M23(a) was prepared according to Example 1, except that 6-trifluoromethylpyridin-3-yl amine was used in place of 4-(tert-butyl)aniline.

5.33 Example 33

Synthesis of a Cyclo(Hetero)Alkenyl Compound of Formula M4(a)

Compound M4(a) was prepared according to Example 31, except that 2-chloro-3-trifluoromethylpyridine was used in place of 2,3-dichloropyridine.

5.34 Example 34

Synthesis of a Cyclo(Hetero)Alkenyl Compound of Formula M26(a)

Compound M26(a) was prepared according to Example 33, except that 6-trifluoromethylpyridin-3-yl amine was used in place of 5-trifluoromethylpyridin-2-yl amine.

5.35 Example 35

Synthesis of a Cyclo(Hetero)Alkenyl Compound of Formula E34(a)

Compound E34(a) was prepared according to Example 3, except that 2,3-dichloropyrazine was used in place of 2,3-dichloropyridine.

5.36 Example 36

Synthesis of a Cyclo(Hetero)Alkenyl Compound of Formula A58(a)

Compound A58(a) was prepared according to Example 3, except that 2-chloro-3-fluoropyridine was used in place of 2,3-dichloropyridine.

5.37 Example 37

Synthesis of a Cyclo(Hetero)Alkenyl Compound of Formula M2(a)

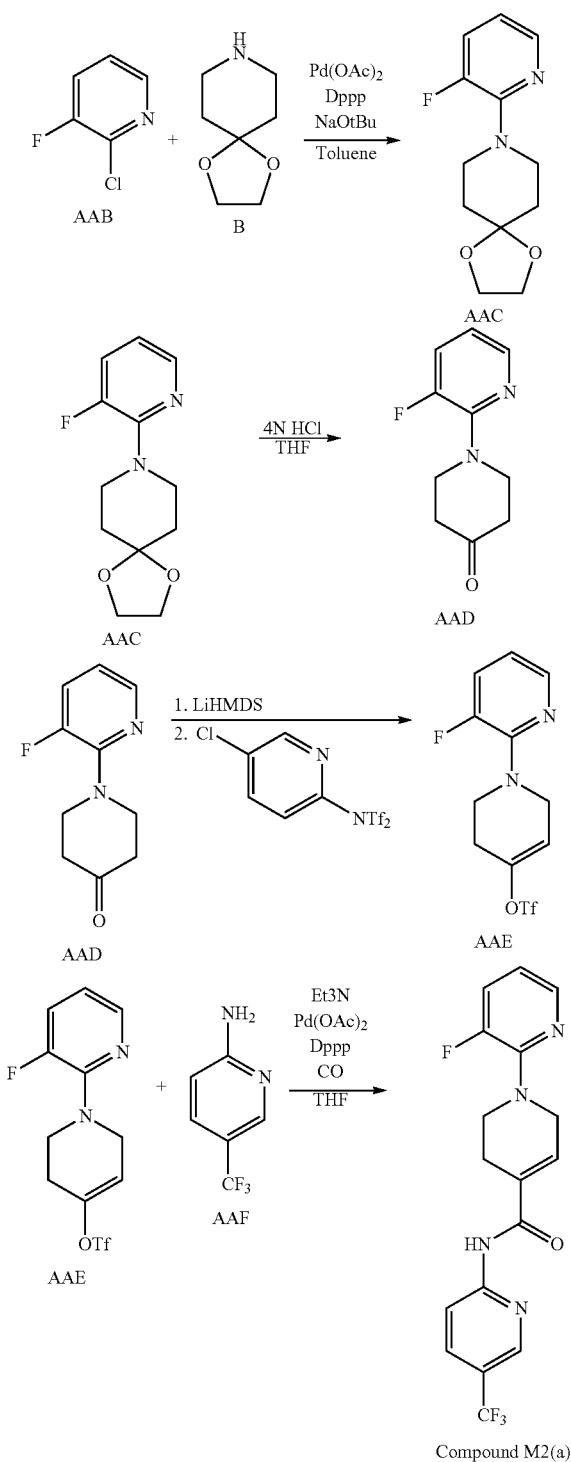

1.1 eq. of the piperidinyl ketal 1,4-dioxa-8-azaspiro[4.5]-decane (B) was added to a 1.2M solution of 2-chloro-3-fluoropyridine (AAB, 1 eq.) in toluene (96 mL), followed by the addition of 1.1 eq. of the sodium salt of 2-methylpropan-2-ol ("NaOtBu"), 0.05 eq. Pd(OAc)$_2$, and 0.05 eq. Dppp to form a reaction mixture. The atmosphere in contact with the reaction mixture was replaced by nitrogen. The reaction mixture was stirred with a magnetic stirring bar and heated to 65° C. The reaction mixture was stirred at this temperature for 3 h. The reaction mixture was then cooled to about 25° C. and filtered through about 200 g of CELITE powder that had been prewetted with about 200 mL of EtOAc. The solvent was partially removed under reduced pressure to provide a residue. The residue was purified by passing through a silica gel pad with a solution of 50% EtOAc in hexane by volume. This provided the Compound of Formula AAC as a yellow oil (94% yield) which was shown, by LC/MS, to be about 99% pure. The structure of the Compound of Formula AAC was confirmed by $^1$H-NMR spectrometry.

Compound of Formula AAC: $^1$H-NMR (CDCl$_3$) δ: 8.01-7.97 (m, 1H), 7.25-7.17 (m, 1H), 6.75-6.69 (m, 1H), 4.02 (s, 4H), 3.64-3.57 (m, 4H), 1.86-1.80 (m, 4H).

The Compound of Formula AAC, prepared as described above, was used without further purification. 1 eq. of the Compound of Formula AAC was dissolved in 60 mL THF. Thereafter, an equal volume of 4N aqueous HCl was added to form a reaction mixture. The reaction mixture was stirred while heating to 60° C. and stirred at this temperature for 3 h. The reaction mixture was then to cooled to about 25° C. The solution was made basic by adding aqueous K$_2$CO$_3$, extracted with EtOAc, dried over Na$_2$SO$_4$, and the solvent was removed under reduced pressure to provide a residue. The residue was purified by chromatography on a silica gel column, using a gradient of from 0:100 to 5:95 (by volume) methanol:(10% diethyl ether in hexane by volume) as an eluent, to provide, after removing the solvent under reduced pressure, the ketone Compound of Formula AAD as a yellow oil (82% yield). The structure of the Compound of Formula AAD was confirmed by $^1$H-NMR spectrometry.

Compound of Formula AAD: $^1$H-NMR (CDCl$_3$) δ: 8.06-8.01 (m, 1H), 7.33-7.25 (m, 1H), 6.85-6.78 (m, 1H), 3.90-3.79 (m, 4H), 2.62-2.51 (m, 4H).

Under a nitrogen atmosphere, the Compound of Formula AAD (5.6 g, 26.6 mmol) was dissolved in THF (500 mL) at a temperature of about 25° C. The resulting solution was cooled to −78° C. and LiHMDS (35 mL, 34.6 mmol, 1M in THF) was added to form a reaction mixture. The reaction mixture was stirred at −78° C. for 1.5 h and a THF (100 mL) solution of N-(5-chloro-2-pyridyl)triflimide (also known as Comins' reagent, 10.5 g, 26.6 mmol) was added. The resulting reaction mixture was stirred at −78° C. for 1 h. The reaction mixture was then warmed to about 25° C. over a 1 h period and stirred for an additional 4 h at about 25° C. After this period, the solvent was removed under reduced pressure to provide a residue. The residue was purified by column chromatography on a silica gel column, using a gradient of from 2:98 to 50:50 (by volume) EtOAc:hexane as an eluent, to provide 5.75 g of the triflate Compound of Formula AAE as light yellow oil.

The structure of the Compound of Formula AAE was confirmed by $^1$H-NMR and mass spectrometry.

Compound of Formula AAE: $^1$H-NMR (CDCl$_3$) δ: 8.03-7.97 (m, 1H), 7.31-7.22 (m, 1H+CHCl$_3$), 6.83-6.75 (m, 1H), 5.92-5.87 (m, 1H), 4.17-4.12 (m, 2H), 3.77-3.71 (m, 2H), 2.64-2.58 (m, 2H); MS: 327 (M+1).

Under a nitrogen atmosphere, the Compound of Formula AAE (2.1 g, 6.4 mmol), 5-trifluoromethyl-pyridin-2-ylamine (AAF, 2.1 g, 12.8 mmol), and triethylamine (1.96 mL, 1.42 g, 14.2 mmol) were dissolved in THF (30 mL) at a temperature of about 25. The resulting solution was stirred for 2 min. Thereafter, Pd(OAc)$_2$ (287 mg, 1.28 mmol) and Dppp (528 mg, 1.28 mmol) were added to form a reaction mixture. The reaction mixture was flushed with nitrogen gas. The nitrogen atmosphere was removed and replaced by a carbon monoxide atmosphere. The reaction mixture was stirred while heating to 72° C. and stirred at this temperature for 35 minutes. The reaction mixture was then to cooled to about 25° C. The solvent was removed under reduced pressure to provide a residue. The residue was purified by column chromatography on a silica gel column, using a gradient of from 2:98 to 99:1 (by volume) EtOAc:hexane as an eluent, to provide 1.2 g of Cyclo(hetero)alkenyl Compound M2(a) as a white solid.

The structure of Cyclo(hetero)alkenyl Compound M2(a) was confirmed by $^1$H-NMR and mass spectrometry.

Cyclo(hetero)alkenyl Compound M2(a): $^1$H-NMR (CD$_3$OD) δ: 8.66-8.60 (m, 1H), 8.40-8.33 (m, 1H), 8.12-7.96 (m, 2H), 7.47-7.36 (m, 1H), 6.95-6.82 (m, 2H), 4.26-4.18 (m, 2H), 3.73-3.64 (m, 2H), 2.68-2.57 (m, 2H); MS: m/z=367.

5.38 Example 38

Synthesis of a Cyclo(Hetero)Alkenyl Compound of Formula Y34(a)

Compound Y34(a) was prepared according to Example 3, except that 2-chloro-3-fluoropyridine was used in place of 2,3-dichloropyridine.

5.39 Example 39

Synthesis of a Cyclo(Hetero)Alkenyl Compound of Formula N34(a)

Compound N34(a) was prepared according to Example 1, except that 4-(trifluoromethyl)-N-methylbenzenamine was used in place of 4-(tert-butyl)aniline.

5.40 Example 40

Synthesis of a Cyclo(Hetero)Alkenyl Compound of Formula A45(a)

Compound A45(a) was prepared according to Example 1, except that 2-(4-aminophenyl)-1,1,1,3,3,3-hexafluoropropan-2-ol was used in place of 4-(tert-butyl)aniline.

5.41 Example 41

Synthesis of a Cyclo(Hetero)Alkenyl Compound of Formula A226(a)

Compound A226(a) was prepared according to Example 3, except that 2-chloro-3-bromopyridine was used in place of 2,3-dichloropyridine.

5.42 Example 42

Synthesis of a Cyclo(Hetero)Alkenyl Compound of Formula L8(a)

Compound L8(a) was prepared according to Example 1, except that 3-chloro-4-trifluoromethoxy aniline was used in place of 4-(tert-butyl)aniline.

5.43 Example 43

Synthesis of a Cyclo(Hetero)Alkenyl Compound of Formula A116(a)

Compound A116(a) was prepared according to Example 33, except that 4-(1,1,2,2-tetrafluoroethoxy)phenyl amine was used in place of 5-trifluoromethylpyridin-2-yl amine.

5.44 Example 44

Synthesis of a Cyclo(Hetero)Alkenyl Compound of Formula A118(a)

Compound A118(a) was prepared according to Example 1, except that 4-(1,1-dimethyl-pentyl)phenyl amine was used in place of 4-(tert-butyl)aniline.

5.45 Example 45

Synthesis of a Cyclo(Hetero)Alkenyl Compound of Formula A120(a)

Compound A120(a) was prepared according to Example 1, except that 4-(piperidin-1-yl)benzenamine was used in place of 4-(tert-butyl)aniline.

5.46 Example 46

Synthesis of a Cyclo(Hetero)Alkenyl Compound of Formula L6(a)

Compound L6(a) was prepared according to Example 1, except that 3-fluoro-4-trifluoromethylphenyl amine was used in place of 4-(tert-butyl)aniline.

5.47 Example 47

Synthesis of a Cyclo(Hetero)Alkenyl Compound of Formula A47(a)

Compound A47(a) was prepared according to Example 1, except that 2-(4-aminophenyl)-2-methylpropionic acid ethyl ester was used in place of 4-(tert-butyl)aniline.

5.48 Example 48

Binding of Cyclo(Hetero)Alkenyl Compounds to mGluR5

The following assay can be used to demonstrate that Cyclo (hetero)alkenyl Compounds bind to and modulate the activity of mGluR5.

Cell Cultures:

Primary glial cultures are prepared from cortices of Sprague-Dawley 18 days old embryos. The cortices are dissected and then dissociated by trituration. The resulting cell homogenate is plated onto poly-D-lysine precoated T175 flasks (BIOCOAT, commercially available from Becton Dickinson and Company Inc. of Franklin Lakes, N.J.) in Dulbecco's Modified Eagle's Medium ("DMEM," pH 7.4), buffered with 25 mM HEPES, and supplemented with 15% fetal calf serum ("FCS," commercially available from Hyclone Laboratories Inc. of Omaha, Nebr.), and incubated at 37° C. and 5% CO$_2$. After 24 hours, FCS supplementation is reduced to 10%. On day six, oligodendrocytes and microglia are removed by strongly tapping the sides of the flasks. One day following this purification step, secondary astrocyte cultures are established by subplating onto 96 poly-D-lysine precoated T175 flasks (BIOCOAT) at a density of 65,000 cells/well in DMEM and 10% FCS. After 24 hours, the astrocytes are washed with serum free medium and then cultured in DMEM, without glutamate, supplemented with 0.5% FCS, 20 mM HEPES, 10 ng/mL epidermal growth factor ("EGF"), 1 mM sodium pyruvate, and LX penicillin/streptomycin at pH 7.5 for 3 to 5 days at 37° C. and 5% $CO_2$. The procedure allows the expression of the mGluR5 receptor by astrocytes, as demonstrated by S. Miller et al., *J. Neurosci.* 15(9):6103-6109 (1995).

Assay Protocol:

After 3-5 days incubation with EGF, the astrocytes are washed with 127 mM NaCl, 5 mM KCl, 2 mM $MgCl_2$, 700 mM $NaH_2PO_4$, 2 mM $CaCl_2$, 5 mM $NaHCO_3$, 8 mM HEPES, 10 mM Glucose at pH 7.4 ("Assay Buffer") and loaded with the dye Fluo-4 (commercially available from Molecular Probes Inc. of Eugene, Oreg.) using 0.1 mL of Assay Buffer containing Fluo-4 (3 mM final). After 90 minutes of dye loading, the cells are then washed twice with 0.2 mL Assay Buffer and resuspended in 0.1 mL of Assay Buffer. The plates containing the astrocytes are then transferred to a Fluorometric Imaging Plate reader (commercially available from Molecular Devices Corporation of Sunnyvale, Calif.) for the assessment of calcium mobilization flux in the presence of glutamate and in the presence or absence of antagonist. After monitoring fluorescence for 15 seconds to establish a baseline, DMSO solutions containing various concentrations of a Cyclo(hetero)alkenyl Compound diluted in Assay Buffer (0.05 mL of 4x dilutions for competition curves) are added to the cell plate and fluorescence is monitored for 2 minutes. 0.05 mL of a 4x glutamate solution (agonist) is then added to each well to provide a final glutamate concentration in each well of 10 mM. Plate fluorescence is then monitored for an additional 60 seconds after agonist addition. The final DMSO concentration in the assay s is 1.0%. In each experiment, fluorescence is monitored as a function of time and the data analyzed using Microsoft Excel and GraphPad Prism. Dose-response curves are fit using a non-linear regression to determine $IC_{50}$ value. In each experiment, each data point is determined two times.

5.49 Example 49

In Vivo Assays for Prevention Or Treatment of Pain

Test Animals:

Each experiment uses rats weighing between 200-260 g at the start of the experiment. The rats are group-housed and have free access to food and water at all times, except prior to oral administration of a Cyclo(hetero)alkenyl Compound when food is removed for 16 hours before dosing. A control group acts as a comparison to rats treated with a Cyclo(hetero)alkenyl Compound. The control group is administered the carrier for the Cyclo(hetero)alkenyl Compound. The volume of carrier administered to the control group is the same as the volume of carrier and Cyclo(hetero)alkenyl Compound administered to the test group.

Acute Pain:

To assess the actions of the Cyclo(hetero)alkenyl Compounds for the treatment or prevention of acute pain the rat tail flick test can be used. Rats are gently restrained by hand and the tail exposed to a focused beam of radiant heat at a point 5 cm from the tip using a tail flick unit (Model 7360, commercially available from Ugo Basile of Italy). Tail flick latencies are defined as the interval between the onset of the thermal stimulus and the flick of the tail. Animals not responding within 20 seconds are removed from the tail flick unit and assigned a withdrawal latency of 20 seconds. Tail flick latencies are measured immediately before (pre-treatment) and 1, 3, and 5 hours following administration of a Cyclo(hetero)alkenyl Compound. Data are expressed as tail flick latency(s) and the percentage of the maximal possible effect (% MPE), i.e., 15 seconds, is calculated as follows:

$$\% MPE = \frac{[(\text{post administration latency}) - (\text{pre-administration latency})]}{(20 \text{ s pre-administration latency})} \times 100$$

The rat tail flick test is described in F. E. D'Amour et al., "A Method for Determining Loss of Pain Sensation," *J. Pharmacol. Exp. Ther.* 72:74-79 (1941).

Acute pain can also be assessed by measuring the animal's response to noxious mechanical stimuli by determining the paw withdrawal threshold ("PWT"), as described below.

Inflammatory Pain:

To assess the actions of the Cyclo(hetero)alkenyl Compounds for the treatment or prevention of inflammatory pain the Freund's complete adjuvant ("FCA") model of inflammatory pain is used. FCA-induced inflammation of the rat hind paw is associated with the development of persistent inflammatory mechanical hyperalgesia and provides reliable prediction of the anti-hyperalgesic action of clinically useful analgesic drugs (L. Bartho et al., "Involvement of Capsaicin-sensitive Neurones in Hyperalgesia and Enhanced Opioid Antinociception in Inflammation," *Naunyn-Schmiedeberg's Archives of Pharmacol.* 342:666-670 (1990)). The left hind paw of each animal is administered a 50 μL intraplantar injection of 50% FCA. 24 hour post injection, the animal is assessed for response to noxious mechanical stimuli by determining the PWT, as described below. Rats are then administered a single injection of 1, 3, 10 or 30 mg/Kg of either a Cyclo(hetero)alkenyl Compound; 30 mg/Kg of a control selected from Celebrex, indomethacin or naproxen; or carrier. Responses to noxious mechanical stimuli are then determined 1, 3, 5 and 24 hours post administration. Percentage reversal of hyperalgesia for each animal is defined as:

$$\% \text{ Reversal} = \frac{[(\text{post administration } PWT) - (\text{pre-administration } PWT)]}{[(\text{baseline } PWT) - (\text{pre-administration } PWT)]} \times 100$$

Neuropathic Pain:

To assess the actions of the Cyclo(hetero)alkenyl Compounds for the treatment or prevention of neuropathic pain either the Seltzer model or the Chung model can be used.

In the Seltzer model, the partial sciatic nerve ligation model of neuropathic pain is used to produce neuropathic hyperalgesia in rats (Z. Seltzer et al., "A Novel Behavioral Model of Neuropathic Pain Disorders Produced in Rats by Partial Sciatic Nerve Injury," *Pain* 43:205-218 (1990)). Partial ligation of the left sciatic nerve is performed under isoflurane/$O_2$ inhalation anaesthesia. Following induction of anesthesia, the left thigh of the rat is shaved and the sciatic nerve exposed at high thigh level through a small incision and is carefully cleared of surrounding connective tissues at a site near the trocanther just distal to the point at which the posterior biceps semitendinosus nerve branches off of the common sciatic nerve. A 7-0 silk suture is inserted into the nerve with a ⅜ curved, reversed-cutting mini-needle and tightly ligated so that the dorsal ⅓ to ½ of the nerve thickness is held within the ligature. The wound is closed with a single muscle suture (4-0 nylon (Vicryl)) and vetbond tissue glue. Following surgery, the wound area is dusted with antibiotic powder. Sham-treated rats undergo an identical surgical procedure except that the sciatic nerve is not manipulated. Following surgery, animals are weighed and placed on a warm pad until they recover from anesthesia. Animals are then returned to their home cages until behavioral testing begins. The animal is assessed for response to noxious mechanical stimuli by determining PWT, as described below, prior to surgery (baseline), then immediately prior to and 1, 3, and 5 hours after drug administration for rear paw of the animal. Percentage reversal of neuropathic hyperalgesia is defined as:

$$\% \text{ Reversal} = \frac{[(\text{post administration } PWT) - (\text{pre-administration } PWT)]}{[(\text{baseline } PWT) - (\text{pre-administration } PWT)]} \times 100$$

In the Chung model, the spinal nerve ligation model of neuropathic pain is used to produce mechanical hyperalgesia, thermal hyperalgesia and tactile allodynia in rats. Surgery is performed under isoflurane/$O_2$ inhalation anaesthesia. Following induction of anaesthesia a 3 cm incision is made and the left paraspinal muscles are separated from the spinous process at the $L_4$-$S_2$ levels. The L transverse process is carefully removed with a pair of small rongeurs to identify visually the $L_4$-$L_6$ spinal nerves. The left $L_5$ (or $L_5$ and $L_6$) spinal nerve(s) is isolated and tightly ligated with silk thread. A complete hemostasis is confirmed and the wound is sutured using non-absorbable sutures, such as nylon sutures or stainless steel staples. Sham-treated rats undergo an identical surgical procedure except that the spinal nerve(s) is not manipulated. Following surgery animals are weighed, administered a subcutaneous (s.c.) injection of saline or ringers lactate, the wound area is dusted with antibiotic powder and they are kept on a warm pad until they recover from the anesthesia. Animals are then be returned to their home cages until behavioral testing begins. The animals are assessed for response to noxious mechanical stimuli by determining PWT, as described below, prior to surgery (baseline), then immediately prior to and 1, 3, and 5 hours after being administered a Cyclo(hetero) alkenyl Compound for the left rear paw of the animal. The animal can also be assessed for response to noxious thermal stimuli or for tactile allodynia, as described below. The Chung model for neuropathic pain is described in S. H. Kim, "An Experimental Model for Peripheral Neuropathy Produced by Segmental Spinal Nerve Ligation in the Rat," *Pain* 50(3):355-363 (1992).

Response to Mechanical Stimuli as an Assessment of Mechanical Hyperalgesia:

The paw pressure assay can be used to assess mechanical hyperalgesia. For this assay, hind paw withdrawal thresholds (PWT) to a noxious mechanical stimulus are determined using an analgesymeter (Model 7200, commercially available from Ugo Basile of Italy) as described in C. Stein, "Unilateral Inflammation of the Hindpaw in Rats as a Model of Prolonged Noxious Stimulation: Alterations in Behavior and Nociceptive Thresholds," *Pharmacol. Biochem. and Behavior* 31:451-455 (1988). The maximum weight that can be applied to the hind paw is set at 250 g and the end point is taken as complete withdrawal of the paw. PWT is determined once for each rat at each time point and only the affected (ipsilateral) paw is tested.

Response to Thermal Stimuli as an Assessment of Thermal Hyperalgesia:

The plantar test can be used to assess thermal hyperalgesia. For this test, hind paw withdrawal latencies to a noxious thermal stimulus are determined using a plantar test apparatus (commercially available from Ugo Basile of Italy) following the technique described by K. Hargreaves et al., "A New and Sensitive Method for Measuring Thermal Nociception in Cutaneous Hyperalgesia," *Pain* 32(1):77-88 (1988). The maximum exposure time is set at 32 seconds to avoid tissue damage and any directed paw withdrawal from the heat source is taken as the end point. Three latencies are determined at each time point and averaged. Only the affected (ipsilateral) paw is tested.

Assessment of Tactile Allodynia:

To assess tactile allodynia, rats are placed in clear, plexiglass compartments with a wire mesh floor and allowed to habituate for a period of at least 15 minutes. After habituation, a series of von Frey monofilaments are presented to the plantar surface of the left (operated) foot of each rat. The series of von Frey monofilaments consists of six monofilaments of increasing diameter, with the smallest diameter fiber presented first. Five trials are conducted with each filament with each trial separated by approximately 2 minutes. Each presentation lasts for a period of 4-8 seconds or until a nociceptive withdrawal behavior is observed. Flinching, paw withdrawal or licking of the paw are considered nociceptive behavioral responses.

5.50 Example 50

In Vivo Assays for Prevention or Treatment of Anxiety

The elevated plus maze test or the shock-probe burying test can be used to assess the anxiolytic activity of Cyclo(hetero) alkenyl Compounds in rats or mice.

The Elevated Plus Maze Test:

The elevated plus maze consists of a platform with 4 arms, two open and two closed (50×10×50 cm enclosed with an open roof). Rats (or mice) are placed in the center of the platform, at the crossroad of the 4 arms, facing one of the closed arms. Time spent in the open arms vs the closed arms and number of open arm entries during the testing period are recorded. This test is conducted prior to drug administration and again after drug administration. Test results are expressed as the mean time spent in open arms and the mean number of entries into open arms. Known anxiolytic drugs increase both the time spent in open arms and number of open arm entries. The elevated plus maze test is described in D. Treit, "Animal Models for the Study of Anti-anxiety Agents: A Review," *Neurosci. & Biobehavioral Reviews* 9(2):203-222 (1985).

The Shock-Probe Burying Test:

For the shock-probe burying test the testing apparatus consists of a plexiglass box measuring 40×30×40 cm, evenly covered with approximately 5 cm of bedding material (odor absorbent kitty litter) with a small hole in one end through which a shock probe (6.5 cm long and 0.5 cm in diameter) is inserted. The plexiglass shock probe is helically wrapped with two copper wires through which an electric current is administered. The current is set at 2 mA. Rats are habituated to the testing apparatus for 30 min on 4 consecutive days without the shock probe in the box. On test day, rats are placed in one corner of the test chamber following drug administration. The probe is not electrified until the rat touches it with its snout or fore paws, at which point the rat receives a brief 2 mA shock. The 15 min testing period begins once the rat receives its first shock and the probe remains electrified for the remainder of the testing period. The shock elicits burying behavior by the rat. Following the first shock, the duration of time the rat spends spraying bedding material toward or over the probe with its snout or fore paws (burying behavior) is measured as well as the number of contact-induced shocks the rat receives from the probe. Known anxiolytic drugs reduce the amount of burying behavior. In addition, an index of the rat's reactivity to each shock is scored on a 4 point scale. The total time spent immobile during the 15 min testing period is used as an index of general activity. The shock-probe burying test is described in D. Treit, 1985, supra.

5.51 Example 51

In Vivo Assays for Prevention or Treatment of an Addictive Disorder

The conditioned place preference test or drug self-administration test can be used to assess the ability of Cyclo(hetero) alkenyl Compounds to attenuate the rewarding properties of known drugs of abuse.

The Conditioned Place Preference Test:

The apparatus for the conditioned place preference test consists of two large compartments (45×45×30 cm) made of wood with a plexiglass front wall. These two large compartments are distinctly different. Doors at the back of each large compartment lead to a smaller box (36×18×20 cm) box made of wood, painted grey, with a ceiling of wire mesh. The two large compartments differ in terms of shading (white vs black), level of illumination (the plexiglass door of the white compartment is covered with aluminum foil except for a window of 7×7 cm), texture (the white compartment has a 3 cm thick floor board (40×40 cm) with nine equally spaced 5 cm diameter holes and the black has a wire mesh floor), and olfactory cues (saline in the white compartment and 1 mL of 10% acetic acid in the black compartment). On habituation and testing days, the doors to the small box remain open, giving the rat free access to both large compartments.

The first session that a rat is placed in the apparatus is a habituation session and entrances to the smaller grey compartment remain open giving the rat free access to both large compartments. During habituation, rats generally show no preference for either compartment. Following habituation, rats are given 6 conditioning sessions. Rats are divided into 4 groups: carrier pre-treatment+carrier (control group), Cyclo (hetero)alkenyl Compound pre-treatment+carrier, carrier pre-treatment+morphine, Cyclo(hetero)alkenyl Compound pre-treatment+morphine. During each conditioning session the rat is injected with one of the drug combinations and confined to one compartment for 30 min. On the following day, the rat receives a carrier+carrier treatment and is confined to the other large compartment. Each rat receives three conditioning sessions consisting of 3 drug combination-compartment and 3 carrier-compartment pairings. The order of injections and the drug/compartment pairings are counterbalanced within groups. On the test day, rats are injected prior to testing (30 min to 1 hour) with either morphine or carrier and the rat is placed in the apparatus, the doors to the grey compartment remain open and the rat is allowed to explore the entire apparatus for 20 min. The time spent in each compartment is recorded. Known drugs of abuse increase the time spent in the drug-paired compartment during the testing session. If the Cyclo(hetero)alkenyl Compound blocks the acquisition of morphine conditioned place preference (reward), there will be no difference in time spent in each side in rats pre-treated with a Cyclo(hetero)alkenyl Compound and the group will not be different from the group of rats that was given carrier+carrier in both compartments. Data will be analyzed as time spent in each compartment (drug combination-paired vs carrier-paired). Generally, the experiment is repeated with a minimum of 3 doses of a Cyclo(hetero)alkenyl Compound.

The Drug Self-Administration Test:

The apparatus for the drug self-administration test is a standard commercially available operant conditioning chamber. Before drug trials begin rats are trained to press a lever for a food reward. After stable lever pressing behavior is acquired, rats are tested for acquisition of lever pressing for drug reward. Rats are implanted with chronically indwelling jugular catheters for i.v. administration of compounds and are allowed to recover for 7 days before training begins. Experimental sessions are conducted daily for 5 days in 3 hour sessions. Rats are trained to self-administer a known drug of abuse, such as morphine. Rats are then presented with two levers, an "active" lever and an "inactive" lever. Pressing of the active lever results in drug infusion on a fixed ratio 1 (FR1) schedule (i.e., one lever press gives an infusion) followed by a 20 second time out period (signaled by illumination of a light above the levers). Pressing of the inactive lever results in infusion of excipient. Training continues until the total number of morphine infusions stabilizes to within ±10% per session. Trained rats are then used to evaluate the effect of Cyclo(hetero)alkenyl Compounds pre-treatment on drug self-administration. On test day, rats are pre-treated with a Cyclo(hetero)alkenyl Compound or excipient and then are allowed to self-administer drug as usual. If the Cyclo(hetero) alkenyl Compound blocks the rewarding effects of morphine, rats pre-treated with the Cyclo(hetero)alkenyl Compound will show a lower rate of responding compared to their previous rate of responding and compared to excipient pre-treated rats. Data is analyzed as the change in number of drug infusions per testing session (number of infusions during test session−number of infusions during training session).

5.52 Example 52

Functional Assay for Characterizing mGluR1 Antagonistic Properties

Functional assays for the characterization of mGluR1 antagonistic properties are well known in the art. For example, the following procedure can be used.

A CHO-rat mGluR1 cell line is generated using cDNA encoding rat mGluR1 receptor (M. Masu and S, Nakanishi, *Nature* 349:760-765 (1991)). The cDNA encoding rat mGluR1 receptor can be obtained from, e.g., Prof. S, Nakanishi (Kyoto, Japan).

40,000 CHO-rat mGluR1 cells/well are plated into a COSTAR 3409, black, clear bottom, 96 well, tissue culture treated plate (commercially available from Fisher Scientific of Chicago, Ill.) and are incubated in Dulbecco's Modified Eagle's Medium (DMEM, pH 7.4) supplemented with glutamine, 10% FBS, 1% Pen/Strep, and 500 μg/mL Geneticin for about 12 h. The CHO-rat mGluR1 cells are then washed and treated with OPTIMEM medium (commercially available from Invitrogen, Carlsbad, Calif.) and incubated for a time period ranging from 1 to 4 hours prior to loading the cells with the dye FLUO-4 (commercially available from Molecular Probes Inc., Eugene, Oreg.). After incubation, the cell plates are washed with loading buffer (127 mM NaCl, 5 mM KCl, 2 mM MgCl$_2$, 700 µM, NaH$_2$PO$_4$, 2 mM CaCl$_2$, 5 mMNaHCO$_3$, 8 mM HEPES, and 10 mM glucose, pH 7.4) and incubated with 3 µM FLUO-4 in 0.1 mL loading buffer for 90 min. The cells are then washed twice with 0.2 mL loading buffer, resuspended in 0.1 mL of loading buffer, and transferred to a Fluorometric Imaging Plate Reader ("FLIPR") (commercially available from Molecular Devices Corp., Sunnyvale, Calif.) for measurement of calcium mobilization flux in the presence of glutamate and in the presence or absence of a Cyclo(hetero)alkenyl Compound.

To measure calcium mobilization flux, fluoresence is monitored for about 15 s to establish a baseline and DMSO solutions containing various concentrations of a Cyclo(hetero)alkenyl Compound ranging from about 50 µM to about 0.8 nM diluted in loading buffer (0.05 mL of a 4× dilution) are added to the cell plate and fluoresence is monitored for about 2 min. 0.05 mL of a 4× glutamate solution (agonist) is then added to each well to provide a final glutamate concentration in each well of 10 µM and fluoresence is monitored for about 1 additional min. The final DMSO concentration in the assay is 1%. In each experiment fluoresence is monitored as a function of time and the data is analyzed using a non-linear regression to determine the IC$_{50}$ value. In each experiment each data point is determined twice.

5.53 Example 53

Binding of Cyclo(Hetero)Alkenyl Compounds TO VR1

Methods for demonstrating a compound's ability to inhibit VR1 are known to those skilled in the art, for example, those methods disclosed in U.S. Pat. No. 6,239,267 to Duckworth et al.; U.S. Pat. No. 6,406,908 to McIntyre et al.; or U.S. Pat. No. 6,335,180 to Julius et al.

Binding of Compound A77(a) to VR1: Assay Protocol
Human VR1 Cloning.

Human spinal cord RNA (commercially available from Clontech, Palo Alto, Calif.) was used. Reverse transcription was conducted on 1.0 µg total RNA using Thermoscript Reverse Transcriptase (commercially available from Invitrogen, Carlsbad, Calif.) and oligo dT primers as detailed in its product description. Reverse transcription reactions were incubated at 55° C. for 1 h, heat-inactivated at 85° C. for 5 min, and RNase H-treated at 37° C. for 20 min.

Human VR1 cDNA sequence was obtained by comparison of the human genomic sequence, prior to annotation, to the published rat sequence. Intron sequences were removed and flanking exonic sequences were joined to generate the hypothetical human cDNA. Primers flanking the coding region of human VR1 were designed as follows:

```
forward primer,
AAGATCTTCGCTGGTTGCACACTGGGCCACA (SEQ ID NO: 1); and reverse primer,
GAAGATCTTCGGGGACAGTGACGGTTGGATGT (SEQ ID NO: 2).
```

PCR of VR1 was performed on one tenth of the Reverse transcription reaction mixture using Expand Long Template Polymerase and Expand Buffer 2 in a final volume of 50 µL according to the manufacturer's instructions (Roche Applied Sciences, Indianapolis, Ind.). After denaturation at 94° C. for 2 min PCR amplification was performed for 25 cycles at 94° C. for 15 sec, 58° C. for 30 sec, and 68° C. for 3 min followed by a final incubation at 72° C. for 7 min to complete the amplification. A PCR product of ~2.8 kb was gel-isolated using a 1.0% agarose, Tris-Acetate gel containing 1.6 g/mL of crystal violet and purified with a S.N.A.P. UV-Free Gel Purification Kit (commercially available from Invitrogen). The VR1 PCR product was cloned into the pIND/V5-His-TOPO vector (commercially available from Invitrogen) according to the manufacturer's instructions. DNA preparations, restriction enzyme digestions, and preliminary DNA sequencing were performed according to standard protocols. Full-length sequencing confirmed the identity of the human VR1.

Generation of Inducible Cell Lines.

Unless noted otherwise, cell culture reagents were purchased from Life Technologies of Rockville, Md. HEK293-EcR cells expressing the ecdysone receptor (commercially available from Invitrogen) were cultured in Growth Medium (Dulbecco's Modified Eagles Medium containing 10% fetal bovine serum (commercially available from HYCLONE, Logan, Utah), 1× penicillin/streptomycin, 1× glutamine, 1 mM sodium pyruvate and 400 µg/mL Zeocin (commercially available from Invitrogen)). The VR1-pIND constructs were transfected into the HEK293-EcR cell line using Fugene transfection reagent (commercially available from Roche Applied Sciences, Basel, Switzerland). After 48 h, cells were transferred to Selection Medium (Growth Medium containing 300 µg/mL G418 (commercially available from Invitrogen)). Approximately 3 weeks later individual Zeocin/G418 resistant colonies were isolated and expanded. To identify functional clones, multiple colonies were plated into 96-well plates and expression was induced for 48 h using Selection Medium supplemented with 5 µM ponasterone A ("PonA") (commercially available from Invitrogen). On the day of assay, cells were loaded with Fluo-4 (a calcium-sensitive dye that is commercially available from Molecular Probes, Eugene, Oreg.) and CAP-mediated calcium influx was measured using a FLIPR as described below. Functional clones were re-assayed, expanded, and cryopreserved.

pH-Based Assay. Two days prior to performing this assay, cells were seeded on poly-D-lysine-coated 96-well clear-bottom black plates (commercially available from Becton-Dickinson) at 75,000 cells/well in growth media containing 5 µM PonA (commercially available from Invitrogen) to induce expression. On the day of the assay, the plates were washed with 0.2 mL 1× Hank's Balanced Salt Solution (commercially available from Life Technologies) containing 1.6 mM CaCl$_2$ and 20 mM HEPES, pH 7.4 ("wash buffer"), and loaded using 0.1 mL of wash buffer containing Fluo-4 (3 µM final concentration, commercially available from Molecular Probes). After 1 h, the cells were washed twice with 0.2 mL wash buffer and resuspended in 0.05 mL 1× Hank's Balanced Salt Solution (commercially available from Life Technologies) containing 3.5 mM CaCl$_2$ and 10 mM Citrate, pH 7.4 ("assay buffer"). Plates were then transferred to a FLIPR for assay. Compound A77(a) was diluted in assay buffer, and 50 mL of the resultant solution were added to the cell plates and the solution monitored for two minutes. The final concentration of Compound A77(a) ranged from about 50 µM to about 3 M. Agonist buffer (wash buffer titrated with 1N HCl to provide a solution having a pH of 5.5 when mixed 1:1 with assay buffer) (0.1 mL) was then added to each well, and the plates were incubated for 1 additional min. Data were collected over the entire time course and analyzed using Excel and Graph Pad Prism. Compound A77(a) when assayed according to this protocol had an IC$_{50}$ of 148.1 nM.

Capsaicin-Based Assay.

Two days prior to performing this assay, cells were seeded in poly-D-lysine-coated 96-well clear-bottom black plates (50,000 cells/well) in growth media containing 5 µM PonA (commercially available from Invitrogen) to induce expression. On the day of the assay, the plates were washed with 0.2 mL 1× Hank's Balanced Salt Solution (commercially available from Life Technologies) containing 1 mM CaCl$_2$ and 20 mM HEPES, pH 7.4, and cells were loaded using 0.1 mL of wash buffer containing Fluo-4 (3 µM final). After one h, the cells were washed twice with 0.2 mL of wash buffer and resuspended in 0.1 mL of wash buffer. The plates were transferred to a FLIPR for assay. 50 µL of Compound A77(a)

diluted with assay buffer were added to the cell plates and incubated for 2 min. The final concentration of Compound A77(a) ranged from about 50 pM to about 3 μM. Human VR1 was activated by the addition of 50 μL of capsaicin (400 nM), and the plates were incubated for an additional 3 min. Data were collected over the entire time course and analyzed using Excel and GraphPad Prism. Compound A77(a) when assayed according to this protocol had an $IC_{50}$ of 4.4 nM.

The results of the pH-based assay and the capsaicin-based assay demonstrate that Compound A77(a), an illustrative Cyclo(hetero)alkenyl Compound, binds to and modulates the activity of human VR1 and, accordingly, is useful for treating or preventing pain, UI, an ulcer, IBD or IBS.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited, the entire disclosures of which are incorporated herein by reference.

or a pharmaceutically acceptable salt thereof, wherein $Ar^1$ is

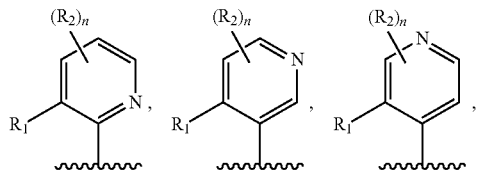

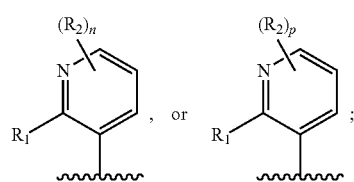

What is claimed is:

1. A compound of formula:

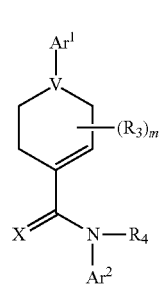

(I)

$Ar^2$ is

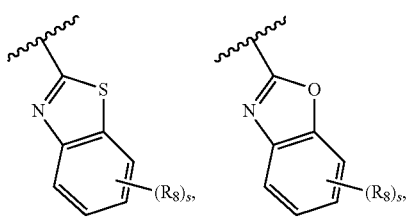

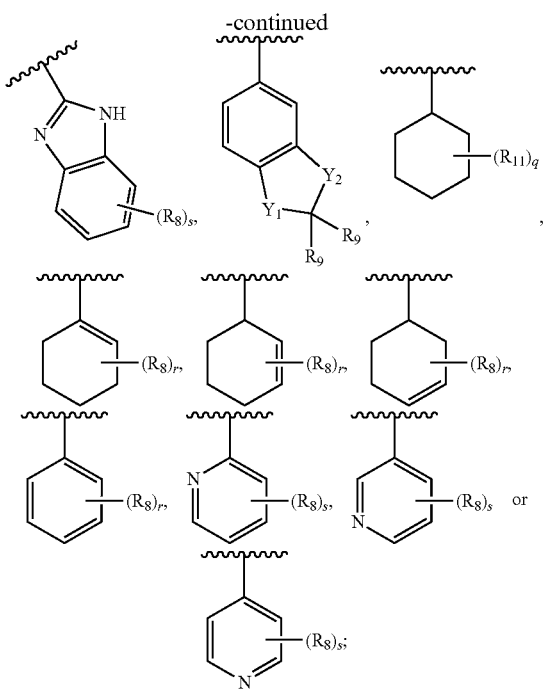

V is N;

X is O or S;

$Y_1$ and $Y_2$ are —$CH_2$— and —$CH_2$—, —O— and —O—, —NH— and —NH—, —S— and —S—, —$CH_2$— and —O—, —$CH_2$— and —NH—, —$CH_2$— and —S—, —O— and —$CH_2$—, —NH— and —$CH_2$—, —S— and —$CH_2$—, —O— and —NH—, —NH— and —O—, —S— and —NH—, or —NH— and —S— respectively;

$R_1$ is —H, -halo, —($C_1$-$C_4$)alkyl, —$NO_2$, —CN, —OH, —$OCH_3$, —$NH_2$, C(halo)$_3$, —CH(halo)$_2$, or —$CH_2$(halo);

each $R_2$ is independently:
(a) -halo, —CN, —OH, —$NO_2$, or —$NH_2$,
(b) —($C_1$-$C_{10}$)alkyl, —($C_2$-$C_{10}$)alkenyl, —($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle, or -(7- to 10-membered)bicycloheterocycle, each of which is unsubstituted or substituted with one or more $R_5$ groups, or
(c) -phenyl, -naphthyl, —($C_{14}$)aryl or -(5- to 10-membered)heteroaryl, each of which is unsubstituted or substituted with one or more $R_6$ groups;

each $R_3$ is independently:
(a) -halo, —CN, —OH, —$NO_2$, or —$NH_2$,
(b) —($C_1$-$C_{10}$)alkyl, —($C_2$-$C_{10}$)alkenyl, —($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle, or -(7- to 10-membered)bicycloheterocycle, each of which is unsubstituted or substituted with one or more $R_5$ groups, or
(c) -phenyl, -naphthyl, —($C_{14}$)aryl or -(5- to 10-membered) heteroaryl, each of which is unsubstituted or substituted with one or more $R_6$ groups;

$R_4$ is —H or —($C_1$-$C_6$)alkyl;

each $R_5$ is independently —CN, —OH, —($C_1$-$C_6$)alkyl, —($C_2$-$C_6$)alkenyl, —($C_2$-$C_6$)alkynyl, -halo, —$N_3$, —$NO_2$, —N($R_7$)$_2$, —CH=$NR_7$, —$NR_7$OH, —$OR_7$, —$COR_7$, —C(O)$OR_7$, —OC(O)$R_7$, —OC(O)$OR_7$, —$SR_7$, —S(O)$R_7$, or —S(O)$_2R_7$;

each $R_6$ is independently —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, -(3- to 5-membered)heterocycle, —C(halo)$_3$, —CH(halo)$_2$, —$CH_2$(halo), —CN, —OH, -halo, —$N_3$, —$NO_2$, —N($R_7$)$_2$, —CH=$NR_7$, —$NR_7$OH, —$OR_7$, —$COR_7$, —C(O)$OR_7$, —OC(O)$R_7$, —OC(O)$OR_7$, —$SR_7$, —S(O)$R_7$, or —S(O)$_2R_7$;

each $R_7$ is independently —H, —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, -(3- to 5-membered) heterocycle, —C(halo)$_3$, —CH(halo)$_2$, or $CH_2$(halo);

each $R_8$ is independently —H, —($C_1$-$C_{10}$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, —C(halo)$_3$, —CH(halo)$_2$, —$CH_2$(halo), —CN, —OH, -halo, —$N_3$, —$NO_2$, —N($R_7$)$_2$, —CH=$NR_7$, —$NR_7$OH, —$OR_7$, —$COR_7$, —C(O)$OR_7$, —OC(O)$R_7$, —OC(O)$OR_7$, —$SR_7$, —S(O)$R_7$, —S(O)$_2R_7$, —$R_7OR_7$, —$R_7COR_7$, —$R_7$C(O)$OR_7$, —$R_7$OC(O)$R_7$, —$R_7$OC(O)$OR_7$, —$R_7SR_7$, —$R_7$S(O)$R_7$, —$R_7$S(O)$_2R_7$, —C(halo)$_2$C(halo)$_3$, —C(halo)$_2$CH(halo)$_2$, —CH(C(halo)$_3$)$_2$, —CH(C(halo)$_3$)(CH$_3$), —OC(halo)$_2$C(halo)$_3$, —OC(halo)$_2$CH(halo)$_2$, —OCH(C(halo)$_3$)$_2$, —OCH(C(halo)$_3$)(CH$_3$), —C(OH)(CF$_3$)$_2$, —($C_1$-$C_{10}$)alkyl, or -(3- to 7-membered)heterocycle;

each $R_9$ is independently —H, -halo or —($C_1$-$C_6$)alkyl;

each $R_{11}$ is independently —CN, —OH, —($C_1$-$C_6$)alkyl, —($C_2$-$C_6$)alkenyl, —($C_2$-$C_6$)alkynyl, -halo, —$N_3$, —$NO_2$, —N($R_7$)$_2$, —CH=$NR_7$, —$NR_7$OH, —$OR_7$, —$COR_7$, —C(O)$OR_7$, —OC(O)$R_7$, or —OC(O)$OR_7$;

each halo is independently —F, —Cl, —Br, or —I;

m is 0 or 1 and when m is 1, $R_3$ is attached to the 2-, 3-, 5-, or 6-position of the cyclo(hetero)alkenyl ring;

n is an integer ranging from 0 to 3;

p is an integer ranging from 0 to 2;

q is an integer ranging from 0 to 6;

r is an integer ranging from 0 to 5; and s is an integer ranging from 0 to 4.

2. The compound of claim 1, wherein $Ar^2$ is

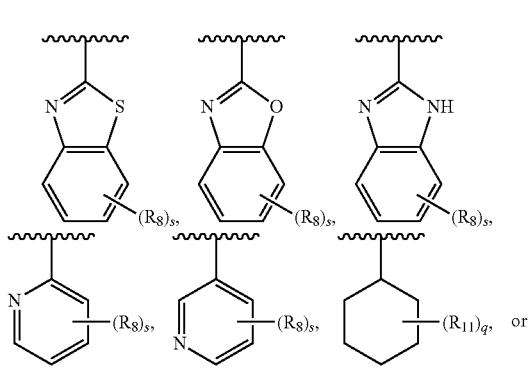

-continued

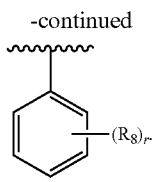

3. The compound of claim 1, wherein Ar¹ is

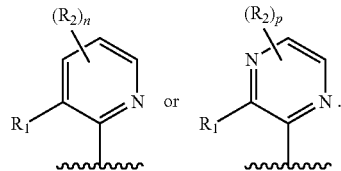

4. The compound of claim 1, wherein each $R_8$ is independently —$(C_1\text{-}C_6)$alkyl, —$(C_2\text{-}C_6)$alkenyl, —$(C_2\text{-}C_6)$alkynyl, —$(C_3\text{-}C_8)$cycloalkyl, —$(C_5\text{-}C_8)$cycloalkenyl, -phenyl, —C(halo)$_3$, —CH(halo)$_2$, —CH$_2$(halo), —CN, —OH, -halo, —N$_3$, —NO$_2$, —N(R$_7$)$_2$, —CH=NR$_7$, —NR$_7$OH, —OR$_7$, —COR$_7$, —C(O)OR$_7$, —OC(O)R$_7$, —OC(O)OR$_7$, —SR$_7$, —S(O)R$_7$, or —S(O)$_2$R$_7$.

5. The compound of claim 3, wherein each $R_8$ is independently -$(C_1\text{-}C_6)$alkyl, —$(C_2\text{-}C_6)$alkenyl, —$(C_2\text{-}C_6)$alkynyl, —$(C_3\text{-}C_8)$cycloalkyl, —$(C_5\text{-}C_8)$cycloalkenyl, -phenyl, —C(halo)$_3$, —CH(halo)$_2$, —CH$_2$(halo), —CN, —OH, -halo, —N$_3$, —NO$_2$, —N(R$_7$)$_2$, —CH=NR$_7$, —NR$_7$OH, —OR$_7$, —COR$_7$, —C(O)OR$_7$, —OC(O)R$_7$, —OC(O)OR$_7$, —SR$_7$, —S(O)R$_7$, or —S(O)$_2$R$_7$.

6. The compound of claim 1, wherein $R_4$ is —H; $R_1$ is —H, -halo, —CH$_3$, —NO$_2$, —CN, —OH, —OCH$_3$, —NH$_2$, —C(halo)$_3$, —CH(halo)$_2$, or —CH$_2$(halo); and each $R_8$ is independently —$(C_1\text{-}C_6)$alkyl, —$(C_2\text{-}C_6)$alkenyl, —$(C_2\text{-}C_6)$alkynyl, —$(C_3\text{-}C_8)$cycloalkyl, —$(C_5\text{-}C_8)$cycloalkenyl, -phenyl, —C(halo)$_3$, —CH(halo)$_2$, —CH$_2$(halo), —CN, —OH, -halo, —N$_3$, —NO$_2$, —N(R$_7$)$_2$, —CH=NR$_7$, —NR$_7$OH, —OR$_7$, —COR$_7$, —C(O)OR$_7$, —OC(O)R$_7$, —OC(O)OR$_7$, —SR$_7$, —S(O)R$_7$, or —S(O)$_2$R$_7$.

7. The compound of claim 6, wherein n or p is 1 and $R_2$ is —$(C_1\text{-}C_{10})$alkyl, —$(C_2\text{-}C_{10})$alkenyl, —$(C_2\text{-}C_{10})$alkynyl, —$(C_3\text{-}C_{10})$cycloalkyl, —$(C_8\text{-}C_{14})$bicycloalkyl, —$(C_8\text{-}C_{14})$tricycloalkyl, —$(C_8\text{-}C_{10})$cycloalkenyl, —$(C_8\text{-}C_{14})$bicycloalkenyl, —$(C_8\text{-}C_{14})$tricycloalkenyl, -(3- to 7-membered)heterocycle, or -(7- to 10-membered)bicycloheterocycle, each of which is unsubstituted or substituted with one or more $R_5$ groups.

8. The compound of claim 6, wherein X is O.

9. The compound of claim 8, wherein Ar¹ is pyridyl; n is 1 and $R_2$ is —$(C_1\text{-}C_{10})$alkyl, —$(C_2\text{-}C_{10})$alkenyl, —$(C_2\text{-}C_{10})$alkynyl, —$(C_3\text{-}C_{10})$cycloalkyl, —$(C_8\text{-}C_{14})$bicycloalkyl, —$(C_8\text{-}C_{14})$tricycloalkyl, —$(C_8\text{-}C_{10})$cycloalkenyl, —$(C_8\text{-}C_{14})$bicycloalkenyl, —$(C_8\text{-}C_{14})$tricycloalkenyl, -(3- to 7-membered)heterocycle, or -(7- to 10-membered)bicycloheterocycle, each of which is unsubstituted or substituted with one or more $R_5$ groups.

10. The compound of claim 8, wherein m is 0; n is 0; and Ar¹ is

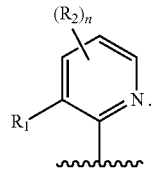

11. The compound of claim 10, wherein $R_1$ is Cl and Ar² is

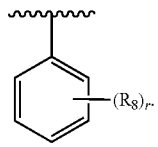

12. The compound of claim 11, wherein r is 1 and $R_8$ is halo or —$(C_1\text{-}C_6)$alkyl.

13. The compound of claim 12, wherein Ar² is substituted in the 4-position.

14. The compound of claim 13, wherein the —$(C_1\text{-}C_6)$alkyl is tert-butyl group.

15. The compound of claim 13, wherein $R_8$ is halo.

16. The compound of claim 8, wherein n is 0, m is 1, $R_1$ is —CH$_3$, and Ar¹ is pyridyl.

17. The compound of claim 16, wherein Ar² is

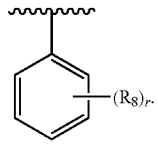

18. The compound of claim 17, wherein r is 1 and $R_8$ is halo or —$(C_1\text{-}C_6)$alkyl.

19. The compound of claim 17, wherein the —$(C_1\text{-}C_6)$alkyl is tert-butyl group and Ar² is substituted at 4-position.

20. The compound of claim 17, wherein $R_8$ is halo.

21. The compound of claim 8, wherein Ar¹ is

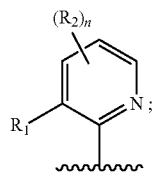

Ar² is

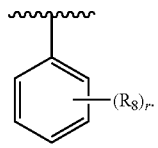

22. The compound of claim 21, wherein n is 1 and $R_2$ is —$(C_1\text{-}C_{10})$alkyl, —$(C_2\text{-}C_{10})$alkenyl, —$(C_2\text{-}C_{10})$alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle, or -(7- to 10-membered)bicycloheterocycle, each of which is unsubstituted or substituted with one or more $R_5$ groups.

23. The compound of claim 21, wherein $R_1$ is —F, —Cl, —Br, or —I; n is 0; r is 1 and $R_8$ is -halo.

24. The compound of claim 21, wherein $R_1$ is —F, —Cl, —Br, or —I; n is 0; r is 1 and $R_8$ is —$CF_3$.

25. The compound of claim 21, wherein $R_1$ is —F, —Cl, —Br, or —I; n is 0; r is 1 and $R_8$ is -tert-butyl.

26. The compound of claim 21, wherein $R_1$ is —$CF_3$, n is 0; r is 1 and $R_8$ is -tert-butyl.

27. The compound of claim 21, wherein $R_1$ is —$CH_3$; n is 0; r is 1 and $R_8$ is -halo.

28. The compound of claim 21, wherein $R_1$ is —$CF_3$; n is 0; r is 1 and $R_8$ is -halo.

29. The compound of claim 21, wherein $R_1$ is —$CF_3$; n is 0; r is 1 and $R_8$ is —$CH_3$.

30. The compound of claim 21, wherein n is 0; m is 0; $R_1$ is —$CH_3$; r is 1 and $R_8$ is —$CF_3$.

31. The compound of claim 21, wherein $R_1$ is —$CF_3$; n is 0; r is 1 and $R_8$ is —$CF_3$.

32. The compound of claim 21, wherein $R_1$ is —$CH_3$; n is 0; r is 1 and $R_8$ is -tert-butyl.

33. The compound of claim 1, wherein m is 0; n is 0, $Ar^1$ is

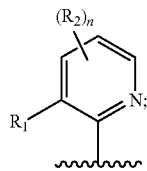

and $R_1$ is —Cl or —$CH_3$.

34. The compound of claim 33, wherein $R_1$ is —Cl.

35. The compound of claim 34, wherein $Ar^2$ is

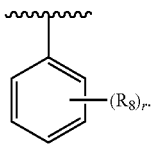

36. The compound of claim 35, wherein r is 1 and $R_8$ is -halo or a —($C_1$-$C_6$)alkyl.

37. The compound of claim 36, wherein the $Ar^2$ is substituted in the 4-position.

38. The compound of claim 37, wherein the —($C_1$-$C_6$)alkyl group is a tert-butyl group.

39. The compound of claim 37, wherein $R_8$ is -halo.

40. The compound of claim 39, wherein $R_8$ is —F.

41. The compound of claim 8, wherein $Ar^1$ is

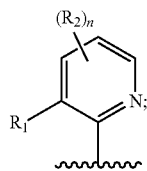

$Ar^2$ is

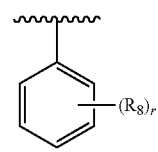

wherein r is 1, n is zero, m is zero, $R_1$ is H, halo, $CH_3$, $CF_3$, $CHF_2$, OH, $NO_2$, or CN; $R_8$ is H, Cl, Br, I, $CH_3$, $C_{3-4}$ alkyl, $C_{3-4}$ alkoxy, cyclohexyl, $CF_3$, $CH_2CF_3$, or $OCF_3$; and $R_8$ is connected at the 4-position of the phenyl ring.

42. The compound of claim 8, wherein $Ar^1$ is

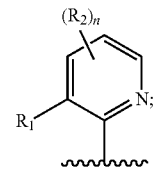

and $Ar^2$ is

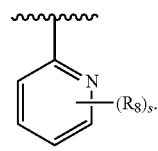

43. The compound of claim 42, wherein n is 1 and $R_2$ is —($C_1$-$C_{10}$)alkyl, —($C_2$-$C_{10}$)alkenyl, —($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle, or -(7- to 10-membered)bicycloheterocycle, each of which is unsubstituted or substituted with one or more $R_5$ groups.

44. The compound of claim 42, wherein $R_1$ is —F, —Cl, —Br, or —I; n is 0; s is 1 and $R_8$ is -halo.

45. The compound of claim 42, wherein $R_1$ is —$CH_3$; n is 0; s is 1 and $R_8$ is -halo.

46. The compound of claim 42, wherein $R_1$ is —$CF_3$; n is 0; s is 1 and $R_8$ is -halo.

47. The compound of claim 42, wherein $R_1$ is —F, —Cl, —Br, or —I; n is 0; s is 1 and $R_1$ is —$CH_3$.

48. The compound of claim 42, wherein $R_1$ is —$CH_3$; n is 0; s is 1 and R is —$CH_3$.

49. The compound of claim 42, wherein $R_1$ is —$CF_3$; n is 0; s is 1 and $R_8$ is —$CH_3$.

50. The compound of claim 42, wherein $R_1$ is —F, —Cl, —Br, or —I; n is 0; s is 1 and $R_8$ is —$CF_3$.

51. The compound of claim 42, wherein $R_1$ is —$CH_3$; n is 0; s is 1 and $R_8$ is —$CF_3$.

52. The compound of claim 42, wherein $R_1$ is —$CF_3$; n is 0; s is 1 and $R_8$ is —$CF_3$.

53. The compound of claim 42, wherein $R_1$ is —F, —Cl, —Br, or —I; n is 0; s is 1 and $R_8$ is —$CH_2CF_3$.

54. The compound of claim 42, wherein $R_1$ is —$CH_3$; n is 0; s is 1 and $R_8$ is —$CH_2CF_3$.

55. The compound of claim 42, wherein $R_1$ is —$CF_3$; n is 0; s is 1 and $R_8$ is —$CH_2CF_3$.

56. The compound of claim 42, wherein $R_1$ is —F, —Cl, —Br, or —I; n is 0; s is 1 and $R_8$ is -tert-butyl.

57. The compound of claim 42, wherein $R_1$ is —$CF_3$; n is 0; s is 1 and $R_8$ is -tert-butyl.

58. The compound of claim 10, wherein $Ar^2$ is

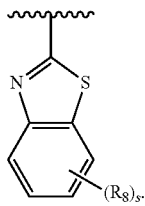

59. The compound of claim 58, wherein $R_1$ is —F, —Cl, —Br, or —I; s is 1 and $R_8$ is -halo.
60. The compound of claim 58, wherein $R_1$ is —F, —Cl, —Br, or —I; s is 1 and $R_8$ is —$CF_3$.
61. The compound of claim 58, wherein $R_1$ is —F, —Cl, —Br, or —I; and $R_8$ is -tert-butyl.
62. The compound of claim 58, wherein $R_1$ is —$CF_3$; s is 1 and $R_8$ is -halo.
63. The compound of claim 58, wherein $R_1$ is —$CF_3$; s is 1 and $R_8$ is —$CF_3$.
64. The compound of claim 58, wherein $R_1$ is —$CF_3$; s is 1 and $R_8$ is -tert-butyl.
65. The compound of claim 58, wherein $R_1$ is —$CH_3$; s is 1 and $R_8$ is -halo.
66. The compound of claim 58, wherein $R_1$ is —$CF_3$; s is 1 and $R_8$ is —$CH_3$.
67. The compound of claim 58, wherein $R_1$ is —$CH_3$; s is 1 and $R_8$ is —$CF_3$.
68. The compound of claim 58, wherein $R_1$ is —$CH_3$; s is 1 and $R_8$ is -tert-butyl.
69. The compound of claim 8, wherein $Ar^1$ is

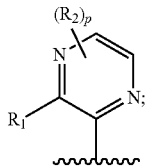

$Ar^2$ is

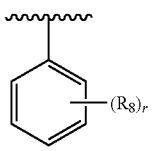

wherein r is 1, p is zero, $R_1$ is H, halo, $CH_3$, $CF_3$, $CHF_2$, OH, $NO_2$, or CN; $R_8$ is H, Cl, Br, I, $CH_3$, $C_{3-4}$ alkyl, $C_{3-4}$ alkoxy, cyclohexyl, $CF_3$, $CH_2CF_3$, or $OCF_3$; and $R_8$ is connected at the 4-position of the phenyl ring.

70. The compound of claim 1, wherein m is 0.
71. The compound of claim 1, wherein $Ar^1$ is a pyridyl group.
72. The compound of claim 1, wherein $Ar^2$ is

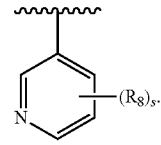

73. The compound of claim 72, wherein s is 0 or 1.
74. The compound of claim 1, wherein $Ar^2$ is

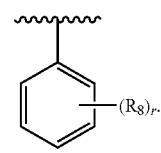

75. The compound of claim 74, wherein r is 0 or 1.
76. The compound of claim 1, wherein $Ar^2$ is

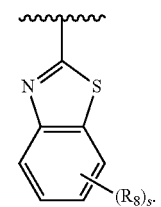

77. The compound of claim 76, wherein each $R_8$ is independently —H, halo, —($C_1$-$C_6$)alkyl, —O($C_1$-$C_6$)alkyl, —C(halo)$_3$, —CH(halo)$_2$, or —$CH_2$(halo).
78. The compound of claim 77, wherein s is 0, 1 or 2.
79. A composition comprising the compound or a pharmaceutically acceptable salt of the compound of claim 1 and a pharmaceutically acceptable carrier or excipient.
80. A method for treating pain in an animal, comprising administering to an animal in need thereof an effective amount of the compound or a pharmaceutically acceptable salt of the compound of claim 1.
81. A method for making the cyclo(hetero)alkenyl compound of claim 6, comprising allowing a 1-heteroaromatic-1,2,3,6-tetrahydro-pyridine-4-carboxylic acid compound to react with a compound of formula $Ar^2$—$NHR_4$ to provide the cyclo(hetero)alkenyl compound.
82. A method for making the cyclo(hetero)alkenyl compound of claim 6, comprising allowing a 1,2,3,6-tetrahydro-pyridine-4-carboxylic acid amide compound to react with a compound of formula $Ar^1$—Z to provide the cyclo(hetero)alkenyl compound; wherein Z is Cl, Br or I.

* * * * *

SEQUENCE LISTING

```
<160> NUMBER OF SEQ ID NOS: 2

<210> SEQ ID NO 1
<211> LENGTH: 31
<212> TYPE: DNA
<213> ORGANISM: Artificial Sequence
<220> FEATURE:
<223> OTHER INFORMATION: VR1 Forward Primer

<400> SEQUENCE: 1
aagatcttcg ctggttgcac actgggccac a                              31

<210> SEQ ID NO 2
<211> LENGTH: 32
<212> TYPE: DNA
<213> ORGANISM: Artificial Sequence
<220> FEATURE:
<223> OTHER INFORMATION: VR1 Reverse Primer

<400> SEQUENCE: 2
gaagatcttc ggggacagtg acggttggat gt                             32
```